(12) United States Patent
Myers et al.

(10) Patent No.: US 11,634,449 B2
(45) Date of Patent: Apr. 25, 2023

(54) MACROLIDES AND METHODS OF THEIR PREPARATION AND USE

(71) Applicant: President and Fellows of Harvard College, Cambridge, MA (US)

(72) Inventors: Andrew G. Myers, Cambridge, MA (US); Ian Bass Seiple, Cambridge, MA (US); Ziyang Zhang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/112,743

(22) Filed: Dec. 4, 2020

(65) Prior Publication Data

US 2022/0332747 A1 Oct. 20, 2022

Related U.S. Application Data

(63) Continuation of application No. 15/946,658, filed on Apr. 5, 2018, now Pat. No. 10,913,764, which is a continuation of application No. 14/781,719, filed as application No. PCT/US2014/033025 on Apr. 4, 2014, now Pat. No. 9,982,005.

(60) Provisional application No. 61/946,604, filed on Feb. 28, 2014, provisional application No. 61/832,639, filed on Jun. 7, 2013, provisional application No. 61/808,441, filed on Apr. 4, 2013.

(51) Int. Cl.
| | | |
|---|---|---|
| *C07H 17/00* | (2006.01) | |
| *C07D 498/04* | (2006.01) | |
| *C07C 231/12* | (2006.01) | |
| *C07D 307/54* | (2006.01) | |
| *C07D 317/30* | (2006.01) | |
| *C07F 7/18* | (2006.01) | |
| *C07H 17/08* | (2006.01) | |

(52) U.S. Cl.
CPC .......... *C07H 17/00* (2013.01); *C07C 231/12* (2013.01); *C07D 307/54* (2013.01); *C07D 317/30* (2013.01); *C07D 498/04* (2013.01); *C07F 7/1892* (2013.01); *C07H 17/08* (2013.01)

(58) Field of Classification Search
None
See application file for complete search history.

(56) References Cited

U.S. PATENT DOCUMENTS

| | | | |
|---|---|---|---|
| 5,599,954 A | 2/1997 | Mitsuhashi et al. | |
| 5,656,607 A | 8/1997 | Roussel et al. | |
| 6,262,030 B1 | 7/2001 | Wu et al. | |
| 6,399,582 B1 | 6/2002 | Hlasta et al. | |
| 6,458,771 B1 | 10/2002 | Hlasta et al. | |
| 6,777,543 B2 | 8/2004 | Wu et al. | |
| 6,939,861 B2 | 9/2005 | Gary et al. | |
| 7,601,695 B2 | 10/2009 | Liang et al. | |
| 7,767,797 B1 | 8/2010 | Gutke et al. | |
| 8,012,943 B2 | 9/2011 | Liang et al. | |
| 8,063,021 B2 | 11/2011 | Li et al. | |
| 8,343,936 B2 | 1/2013 | Duffield et al. | |
| 8,759,500 B2 | 6/2014 | Pereira et al. | |
| 8,791,080 B2 | 7/2014 | Fernandes | |
| 8,796,232 B2 | 8/2014 | Fernandes et al. | |
| 8,796,474 B1 | 8/2014 | Williams et al. | |
| 9,982,005 B2 | 5/2018 | Myers et al. | |
| 10,633,407 B2 | 4/2020 | Myers et al. | |
| 10,640,528 B2 | 5/2020 | Myers et al. | |
| 10,913,764 B2 | 2/2021 | Myers et al. | |
| 2002/0013281 A1 | 1/2002 | Agouridas et al. | |
| 2002/0128212 A1 | 9/2002 | Or et al. | |
| 2003/0199458 A1 | 10/2003 | Kosan et al. | |
| 2005/0090461 A1 | 4/2005 | Leadlay et al. | |
| 2006/0096158 A1 | 5/2006 | Robinson | |
| 2006/0100164 A1 | 5/2006 | Liang et al. | |
| 2006/0141589 A1 | 6/2006 | Okuda et al. | |
| 2008/0021226 A1 | 1/2008 | Kanada et al. | |
| 2008/0287376 A1 | 11/2008 | Das et al. | |
| 2009/0170790 A1 | 7/2009 | Das et al. | |
| 2009/0209547 A1 | 8/2009 | Kim et al. | |
| 2010/0035832 A1 | 2/2010 | Heggelund et al. | |
| 2010/0216731 A1 | 8/2010 | Pereira et al. | |
| 2011/0195920 A1 | 8/2011 | Fernandes | |
| 2011/0201566 A1 | 8/2011 | Fernandes et al. | |

(Continued)

FOREIGN PATENT DOCUMENTS

| | | |
|---|---|---|
| CN | 1259955 A | 7/2000 |
| CN | 1333782 A | 1/2002 |

(Continued)

OTHER PUBLICATIONS

Comin, Org. Lett., vol. 8, No. 4, 2006. (Year: 2006).*
Evans, J. Org. Chem. 1991, 56, 741-750. (Year: 1991).*
Custar, J. Am. Chem. Soc. 2009, 131, 12406-12414. (Year: 2009).*
Reist, J. Org. Chem. 1962, 27, 5, 1722-1727. (Year: 1962).*
Hikota et al., Stereoselective Synthesis of Erythronolide A via an Extremely Efficient Macrolactonization by the Modified Yamaguchi Method. J Org Chem. 1990; 55(1): 7-9.
Baker et al., An Antimalarial Alkaloid From Hydrangea. IX. Synthesis of 3-[β-Keto-γ-(4-Hydroxy-2-Piperidyl)Propyl]-4-Quinazolone, an Isomer. J Org Chem. 1952; 17( 1): 97-108.

(Continued)

*Primary Examiner* — Layla D Berry
(74) *Attorney, Agent, or Firm* — Wolf, Greenfield & Sacks, P.C.

(57) ABSTRACT

Provided herein are methods of preparing macrolides by the coupling of an eastern and western half, followed by macrocyclization, to provide macrolides, including both known and novel macrolides. Intermediates in the synthesis of macrolides including the eastern and western halves are also provided. Pharmaceutical compositions and methods of treating infectious diseases and inflammatory conditions using the inventive macrolides are also provided. A general diastereoselective aldol methodology used in the synthesis of the western half is further provided.

20 Claims, 4 Drawing Sheets

(56) References Cited

U.S. PATENT DOCUMENTS

| | | |
|---|---|---|
| 2011/0237534 A1 | 9/2011 | Fernandes |
| 2012/0058963 A1 | 3/2012 | Alihoszic et al. |
| 2012/0172323 A1 | 7/2012 | Fernandes |
| 2013/0018008 A1 | 1/2013 | Pereira et al. |
| 2013/0045937 A1 | 2/2013 | Fernandes |
| 2013/0066056 A1 | 3/2013 | Pereira et al. |
| 2013/0172280 A1 | 7/2013 | Pereira et al. |
| 2013/0178429 A1 | 7/2013 | Liu et al. |
| 2013/0345410 A1 | 12/2013 | Liang et al. |
| 2014/0213515 A1 | 7/2014 | Liu et al. |
| 2015/0105339 A1 | 4/2015 | Fernandes et al. |
| 2016/0052951 A1 | 2/2016 | Myers et al. |
| 2017/0305953 A1 | 10/2017 | Myers et al. |
| 2018/0066008 A1 | 3/2018 | Myers et al. |
| 2018/0111956 A1 | 4/2018 | Myers et al. |
| 2018/0298048 A1 | 10/2018 | Myers et al. |
| 2020/0361980 A1 | 11/2020 | Myers et al. |
| 2020/0377542 A1 | 12/2020 | Myers et al. |

FOREIGN PATENT DOCUMENTS

| | | |
|---|---|---|
| CN | 1351608 A | 5/2002 |
| CN | 1373767 A | 10/2002 |
| CN | 1984918 A | 6/2007 |
| CN | 101103039 A | 1/2008 |
| CN | 101142225 A | 3/2008 |
| CN | 101631795 A | 1/2010 |
| CN | 102245022 A | 11/2011 |
| CN | 102690297 A | 9/2012 |
| EP | 1 985 620 A1 | 10/2008 |
| EP | 2988597 A2 | 3/2016 |
| JP | S61-152663 A | 7/1986 |
| JP | H08-198832 A | 8/1996 |
| JP | 2001-247595 A | 9/2001 |
| JP | 2002-542254 A | 12/2002 |
| JP | 2003-507487 A | 2/2003 |
| JP | 2012-506872 A | 3/2012 |
| KR | 10-2009-0105309 A | 10/2009 |
| WO | WO 1994/015617 A1 | 7/1994 |
| WO | WO 98/56801 A1 | 12/1998 |
| WO | WO 1999/00125 A1 | 1/1999 |
| WO | WO 99/21866 A1 | 5/1999 |
| WO | WO 2000/63223 A1 | 10/2000 |
| WO | WO 2001/10879 | 2/2001 |
| WO | WO 2001/14397 A1 | 3/2001 |
| WO | WO 2001/55158 A1 | 8/2001 |
| WO | WO 02/32918 A2 | 4/2002 |
| WO | WO 2003/050132 A1 | 6/2003 |
| WO | WO 2004/065346 A1 | 8/2004 |
| WO | WO 2004/080319 A1 | 9/2004 |
| WO | WO 2004/080391 A2 | 9/2004 |
| WO | WO 2004/101591 A1 | 11/2004 |
| WO | WO 2005/030227 A1 | 4/2005 |
| WO | WO 2006/074962 A2 | 7/2006 |
| WO | WO 2006/087644 A2 | 8/2006 |
| WO | WO 2006/120541 A1 | 11/2006 |
| WO | WO 2007/012464 A1 | 2/2007 |
| WO | WO 2007/034909 A1 | 3/2007 |
| WO | WO 2007/091393 A1 | 8/2007 |
| WO | WO 2008/110918 A2 | 9/2008 |
| WO | WO 2009/055557 A1 | 4/2009 |
| WO | WO 2010/015703 A2 | 2/2010 |
| WO | WO 2010/048599 A1 | 4/2010 |
| WO | WO 2010/048600 A1 | 4/2010 |
| WO | WO 2010/048601 A1 | 4/2010 |
| WO | WO 2011/018510 A1 | 2/2011 |
| WO | WO 2011/032052 A1 | 3/2011 |
| WO | WO 2011/119604 A1 | 9/2011 |
| WO | WO 2011/131749 A1 | 10/2011 |
| WO | WO 2011/146829 A1 | 11/2011 |
| WO | WO 2012/001089 A1 | 1/2012 |
| WO | WO 2012/034058 A1 | 3/2012 |
| WO | WO 2012/051126 A2 | 4/2012 |
| WO | WO 2012/127351 A1 | 9/2012 |
| WO | WO 2013/148891 A1 | 10/2013 |
| WO | WO 2014/145210 A1 | 9/2014 |
| WO | WO 2014/152326 A1 | 9/2014 |
| WO | WO 2014/165792 A2 | 10/2014 |
| WO | WO 2016/154591 A1 | 9/2016 |

OTHER PUBLICATIONS

Baker et al., An Antimalarial Alkaloid From Hydrangea. VIII. Attempted Synthesis of 3-[62 -Keto-γ-(4-Hydroxy-2-Piperidyl)Propyl]-4-Quinazolone by the Diketone Approach. J Org Chem. 1952; 17(1): 77-96.

Gondi et al., Hydrogen bond catalyzed enantioselective vinylogous Mukaiyama aldol reaction. Org Lett. Dec. 8, 2005;7(25):5657-60. doi: 10.1021/ol052301p.

Rentsch et al., The total synthesis of corallopyronin A and myxopyronin B. Angew Chem Int Ed Engl. Nov. 5, 2012;51(45):11381-4. doi: 10.1002/anie.201206560. Epub Oct. 8, 2012.

Roy et al., A Chemoenzymatic Synthesis of the C1-C9 Fragment of Bryostatin. Unusual Diastereoselectivity During a Mukaiyama Aldol Condensation. Synlett 1990; 1990(8): 448-450. DOI: 10.1055/s-1990-21122.

Partial Supplementary European Search Report for Application No. EP 14779590.0, dated Oct. 26, 2016.

Extended European Search Report for EP14779590, dated Feb. 6, 2017.

Summons to Attend Oral Proceedings for Application No. EP 14779590.0 mailed Jul. 8, 2019.

European Office Action in connection with Application No. EP 14779590.0, dated Jul. 16, 2020.

Invitation to Pay Additional Fees for PCT/US2014/033025, dated Aug. 14, 2014.

International Search Report and Written Opinion for PCT/US2014/033025, dated Oct. 28, 2014.

International Preliminary Report on Patentability for PCT/US2014/033025, dated Oct. 15, 2015.

Partial Supplementary European Search Report for Application No. EP 15848340.4 dated Jun. 22, 2018.

Extended European Search Report for EP 15848340, dated Sep. 26, 2018.

International Search Report and Written Opinion for PCT/US2015/054700, dated Jan. 11, 2016.

International Preliminary Report on Patentability for PCT/US2015/054700, dated Apr. 20, 2017.

Partial Supplementary European Search Report for Application No. EP 16769811.7, dated Jul. 17, 2018.

Extended European Search Report for Application No. EP 16769811.7, dated Oct. 24, 2018.

European Office Action in connection with Application No. EP 16769811.7 dated Apr. 9, 2020.

Invitation to Pay Additional Fees for PCT/US2016/024333, dated May 18, 2016.

International Search Report and Written Opinion for PCT/US2016/024333, dated Aug. 5, 2016.

Invitation to Pay Additional Fees for PCT/US2018/030002, dated Sep. 25, 2018.

International Search Report and Written Opinion for PCT/US2019/062030 dated Feb. 26, 2020.

International Search Report and Written Opinion for PCT/US2019/062045 dated Mar. 9, 2020.

[No Author Listed] 2005 Caplus entry for AN 2005:124660 (Romero).
[No Author Listed] 2016 Caplus entry for AN 2016:590903 (Myers).
[No Author Listed] 2005 CAS Registry No. 849407-75-6.
[No Author Listed], PubChem Substance Summary for CID 10839468. Deposit date Oct. 26, 2006.
[No Author Listed] STN Registry: CAS Registrtion No. 1631076 to 29-3. 2014.

Alihodzic et al., Synthesis and antibacterial activity of isomeric 15-membered azalides. J Antibiot (Tokyo). Dec. 2006;59(12):753-69.

Amsden, Anti-inflammatory effects of macrolides—an underappreciated benefit in the treatment of community-acquired respiratory

(56) References Cited

OTHER PUBLICATIONS tract infections and chronic inflammatory pulmonary conditions? Journal of Antimicribial Chemotherapy. 2005;55:10-21.
Asaka et al., Recent developments in macrolide antimicrobial research. Curr Top Med Chem (Sharjah, United Arab Emirates). 2003;961-989.
Baer et al., A Stereospecific Synthesis of L-Desosamine. Canadian Journal of Chemistry. 1974;52(1):122-4.
Baer et al., Reactions of nitro sugars. V. Some reactions with methyl 3-deoxy-3-nitro-a, d-hexopyranoside. Canadian J Chem. 1967;45:983-990.
Bertrand et al., Molecular characterization of off-target activities of telithromycin: a potential role for nicotinic acetylcholine receptors. Antimicrob Agents Chemother. Dec. 2010;54(12):5399-402. doi: 10.1128/AAC.00840-10. Epub Sep. 20, 2010.
Boeckman et al., A new, highly efficient, selective methodology for formation of medium-ring and macrocyclic lactones via intramolecular ketene trapping: an application to a convergent synthesis of (-)-kromycin. J Am Chem Soc. 1989;111:8286-8288.
Breton et al., Total synthesis of erythromycin B. Tetrahedron. Jan. 25, 2007;63(26):5709-29.
Bright et al., Synthesis, in vitro and in vivo activity of novel 9-deoxo-9a-AZA-9a-homoerythromycin A derivatives; a new class of macrolide antibiotics, the azalides. J Antibiot. 1988;41:1029-1047.
Bryskier, Ketolides-telithromycin, an example of a new class of antibacterial agents. Clin Microbiol Infect. Dec. 2000;6(12):661-9.
Bulkley et al., Revisiting the structures of several antibiotics bound to the bacterial ribosome. Proc Natl Acad Sci U.S.A. 2010;107:17158-17163.
Bulman et al., Synthesis of enantiomerically pure tertiary 1,2-aminoalcohols by the highly diastereoselective reductive ring opening of oxazolidines. Tetrahedron. Nov. 2007;63(45):10991-10999.
Burger et al., Synthesis and antibacterial activity of novel C12 ethyl ketolides. Bioorg Med Chem. Aug. 15, 2006;14(16):5592-604. Epub May 11, 2006.
Chen et al., Synthesis and antibacterial activity of novel modified 5-O-desosamine ketolides. Bioorg Med Chem Lett. Dec. 15, 2012;22(24):7402-5. Doi: 10.1016/j.bmcl.2012.10.064. Epub Oct. 23, 2012.
Clark et al., Synthesis and antibacterial activity of novel 6-O-substituted erythromycin A derivatives. Bioorganic & Medicinal Chemistry Letters. 2000;10:815-819.
Cossy et al., Formal total synthesis of methynolide. Tetrahedron. 2002;58:5909-5922.
Davidson et al., Stereoselective synthesis of d-desosamine and related glycals via tungsten-catalyzed alkynol cycloisomerization. Org Lett. May 13, 2004;6(10):1601-3.
Denis et al., Synthesis of 6-O-methyl-azithromycin and its ketolide analogue via Beckmann rearrangement of 9€-6-O-methyl-erythromycin oxime. Bioorg Med Chem Lett. Sep. 22, 1998;8(18):2427-32.
Djokic et al., Erythromycin series. XII. Antibacterial in vitro evaluation of 10-dihydro-10-deoxo-11-azaerythromycin A: synthesis and structure-activity relationship of its acyl derivatives. J Antibiot. 1987;40:1006-1015.
Douthwaite et al., Macrolide-ketolide inhibition of MLS-resistant ribosomes is improved by alternative drug interaction with domain II of 23S rRNA. Mol Microbiol. 2000;36:183-192.
Dunkle et al., Structures of the *Escherichia coli* ribosome with antibiotics bound near the peptidyl transferase center explain spectra of drug action. Proc Natl Acad Sci U.S.A. 2010;107:17152-17157.
Fajdetic et al., Synthesis and structural properties of novel tricyclic 15-membered azilides. Croatia Chemica Acta. 2009;82(4):715-23.
Falzari et al., In vitro and in vivo activities of macrolide derivatives against *Mycobacterium tuberculosis*. Antimicrob Agents Chemother. Apr. 2005;49(4):1447-54.
Farrell et al., The in vitro evaluation of solithromycin (CEM-101) against pathogens isolated in the United States and Europe (2009). J Infect. Dec. 2010;61(6):476-83. doi: 10.1016/j.jinf.2010.08.010. Epub Sep. 8, 2010.
Giguere et al., Enantioselective de novo synthesis of 4-deoxy-D-hexopyranoses via hetero-Diels-Alder cycloadditions: total synthesis of ezoaminuroic acid and neosidomycin. J Org Chem. Dec. 2, 2011;76(23):9687-98. Doi: 10.1021/jo201673w. Epub Nov. 10, 2011.
Girard et al., Pharmacokinetic and in vivo studies with azithromycin (CP-62,993), a new macrolide with an extended half-life and excellent tissue distribution. Antimicrob Agents Chemother. 1987;31:1948-1954.
Griesgraber et al., Anhydrolide macrolides. 2. Synthesis and antibacterial activity of 2,3-anhydro-6-O-methyl 11,12-carbazate erythromycin A analogues. J Med Chem. May 7, 1998;41(10):1660-70.
Gunnes et al., Chemoselective synthesis of erythromycin A ketolides substituted in the C10-methyl group. Bioorganic & Medicinal Chemistry Jan. 2007;15(1):119-129.
Hansen et al., Structures of five antibiotics bound at the peptidyl transferase center of the large ribosomal subunit. J Mol Biol. 2003;330:1061-1075.
Hansen et al., The macrolide-ketolide antibiotic binding site is formed by structures in domains II and V of 23S ribosomal RNA. Mol Microbiol. 1999;31:623-631.
Hansen et al., The structures of four macrolide antibiotics bound to the large ribosomal subunit. Mol Cell. 2002;10:117-128.
He et al., Formation of unusual sugars: mechanistic studies and biosynthetic applications. Annu Rev Biochem. 2002;71:701-54. Epub Nov. 9, 2001.
Hoye et al., Dual macrolactonization/pyran-hemiketal formation via acylketenes: applications to the synthesis of (-)-callipeltoside A and a lyngbyaloside B model system. Angew Chem Int Ed Engl. 2008;47(50):9743-6. doi: 10.1002/anie.200804049.
Hoye et al., Total synthesis of (-)-callipeltoside A. J Org Chem. Nov. 5, 2010;75(21):7052-60. doi: 10.1021/j0101598y.
Jakopovic et al., Novel desosamine-modified 14- and 15-membered macrolides without antibacterial activity. Bioorg Med Chem Lett. May 15, 2012;22(10):3527-30. Doi: 10.1016/j.bmcl.2012.03.076. Epub Mar. 29, 2012.
Jones et al., New macrolide antibiotics. Synthesis of a 14-membered azalide. J Org Chem. 1992;57:4361-4367.
Kanemasa et al., Asymmetric anti-Selective Aldol Reactions of Titanium Z-Enolates Derived from N-Alkylideneglycinamides Bearing a 2,2-Dimethyloxazolidine Chiral Controller. Tetrahedron Letts. Dec. 1993;34(51):8293-96.
Kim et al., Total synthesis of azithromycin. Angew Chem Int Ed Engl. 2009;48(10):1827-9. doi: 10.1002/anie.200805334.
Knapp et al., Synthesis of the Ezomycin Nucleoside Disaccharide. Org. Lett. 2000;2(10):1391-1393.
Kummer et al., Stereocontrolled Alkylative Construction of Quaternary Carbon Centers. J Am Chem Soc. Sep. 13, 2008;130(40):13231-13233.
Kurath et al., Acid degradation of erythromycin A and erythromycin B. Experientia. 1971;27:362.
Leclercq et al., Bacterial resistance to macrolide, lincosamide, and streptogramin antibiotics by target modification. Antimicrob Agents Chemother. 1991;35:1267-1272.
Leclercq et al., Intrinsic and unusual resistance to macrolide, lincosamide, and streptogramin antibiotics in bacteria. Antimicrob Agents Chemother. 1991;35:1273-1276.
Lee et al., Chemistry and biology of macrolide antiparasitic agents. J Med Chem. 2011;54:2792-2804.
Letorneau et al., Synthesis and antibacterial activity of desosamine-modified macrolide derivatives. Bioorg Med Chem Lett. Jul. 15, 2012;22(14):4575-8. Doi: 10.1016/j.bmcl.2012.05.110. Epub Jun. 6, 2012.
Liang et al., Synthesis and biological activity of new 5-O-sugar modified ketolide and 2-fluoro-ketolide antibiotics. Bioorg Med Chem Lett. 2005;15:1307-1310.
Llano-Sotelo et al., Binding and action of CEM-101, a new fluoroketolide antibiotic that inhibits protein synthesis. Antimicrob Agents Chemother. 2010;54:4961-4970.

(56) References Cited

OTHER PUBLICATIONS

Ma et al., Regioselective Synthesis of Bifunctional Macrolides for Probing Ribosomal Binding. Org. Lett. 2002;4(6):987-990.

Ma et al., Significant breakthroughs in search for anti-infectious agents derived from erythromycin A. Curr Med Chem. 2011;18:1993-2015.

Ma et al., Various novel erthyromycin derivatives obtained by different modifications: recent advance in macrolide antibiotics. Mini-Rev Med Chem. 2010;10:272-286.

Mankin, Macrolide myths. Curr Opin Microbiol. 2008;11:414-421.

Martins et al., Antimicrobial activity of chitosan derivatives containing N-quaternized moieties in its backbone: a review. Int J Mol Sci. Nov. 13, 2014;15(11):20800-32. Doi: 10.3390/ijms151120800.

Marusic et al., Novel 9a, 11-bridged azalides: One-pot synthesis of N'-substituted 2-imino-1,3-oxazolidines condensed to an azalide aglycome. Bioorg Med Chem. 2011;19:556-66.

Marusic et al., Novel 9a-carbamoyl-and9a-thiocarbamoyl-3-decladinosyl-6-hydroxy and 6-methoxy derivatives of 15-membered macrolides. Bioorg Med Chem. 2007;15:4498-4510.

Masataka et al., Chiral synthesis of polyketide-derived natural products. 27. Stereoselective synthesis of erythronolide A via an extremely efficient macrolactonization by the modified Yamaguchi method. J. Org. Chem., Jan. 1990;55(1):7-9.

Morales et al., Pseudoephenamine: a practical chiral auxiliary for asymmetric synthesis. Angew Chem Int Ed Engl. May 7, 2012;51(19):4568-71. doi: 10.1002/anie.201200370. Epub Mar. 27, 2012.

Morimoto et al., Chemical modification of erythromycins. I. Synthesis and antibacterial activity of 6-O-methylerythromycins A. J Antibiot (Tokyo). Feb. 1984;37(2):187-9.

Morimoto et al., Chemical modification of erythromycins. II. Synthesis and antibacterial activity of O-alkyl derivatives of erythromycin A. J Antibiot (Tokyo). 1990;43:286-294.

Mutak, Azalides from azithromycin to new azalide derivatives. J Antibiot. 2007;60:85-122.

Myers et al., Greatly Simplified Procedures for the Synthesis of α-Amino Acids by the Direct Alkylation of Pseudoephedrine Glycinamide Hydrate. J Org Chem. Apr. 16, 1999;64(9):3322-27.

Myers et al., Practical Syntheses of Enantiomerically Enriched γ-Lactones and γ-Hydroxy Ketones by the Alkylation of Pseudoephedrine Amides with Epoxides and Their Derivatives. J Org Chem. Apr. 5, 1996;61(7):2428-2420.

Myers et al., Pseudoephedrine as a Practical Chiral Auxiliary for the Synthesis of Highly Enantiomerically Enriched Carboxylic Acids, Alcohols, Aldehydes, and Ketones. J Am Chem Soc. Jul. 16, 1997;119(28):6496-6511.

Myers et al., Synthesis of tertiary alkyl fluoride centers by asymmetric C☐C(F) bond formation. Tetrahedron Letts. Oct. 6, 1997;38(40):7037-40.

Myers et al., Use of Pseudoephedrine as a Practical Chiral Auxiliary for Asymmetric Synthesis. J Am Chem Soc. Oct. 1994; 116(20):9361-62.

Nakasutka et al., Total synthesis of FK506 and an FKBP probe reagent, [C(8),C(9)-13C2]-FK506. J Am Chem Soc. 1990;112:5583-5601.

Nakata et al., Total synthesis of 6-deoxyerythronolide B. J Am Chem Soc. 1981;103:1568.

Newman, Degradation and Synthesis of Desosamine. J Org Chem. 1964;29(6):1461-8.

Oh et al., Total synthesis of methymycin. Org. Biomol Chem. 2009;7:4458-4463.

Paterson et al., Total Synthesis of Denticulatins A and B Using Efficient Methods of Acyclic Stereocontrol. Tetrahedron. 1996;52:1811-1834.

Paterson, Tetrahedron report No. 190: Recent developments in the total synthesis of macrolide antibiotics. Tetrahedron. 1985;41:3569-3624.

Pavlovic et al., Novel hybrids of 15-membered 8a- and 9a-azahomoerythromycin A ketolides and quinolones as potent antibacterials. Bioorg Med Chem. 2010;18:8566-8582.

Pereira et al., Synthesis and antibacterial activity of novel 4-aryl-[1,2,3]-triazole containing macrolides. Bioorg Med Chem Lett. Jan. 1, 2011;21(1):510-3. doi: 10.1016/j.bmcl.2010.10.091. Epub Oct. 25, 2010.

Phan et al., Synthesis and antibacterial activity of a novel class of 4'-substituted 16-membered ring macrolides derived from tylosin. J Med Chem. Jun. 3, 2004;47(12):2965-8.

Prunier et al., Clinical isolates of *Staphylococcus aureus* with ribosomal mutations conferring resistance to macrolides. Antimicrob Agents Chemother. 2002;46:3054-3056.

Putnam et al., Antimicrobial characterisation of solithromycin (CEM-101), a novel fluoroketolide: activity against staphylococci and enterococci. Int J Antimicrob Agents. Jan. 2011;37(1):39-45. doi: 10.1016/j.ijantimicag.2010.08.021.

Retsema et al., Spectrum and mode of action of azithromycin (CP-62,993), a new 15-membered-ring macrolide with improved potency against gram-negative organisms. Antimicrob Agents Chemother. 1987;31:1939-1947.

Richardson, A stereospecific synthesis of desosamine hydrochloride. Proceedings of the Chemical Society. 1963:131.

Romero et al., An efficient entry to new sugar modified ketolide antibiotics. Tetrahedron Lett. 2005;46:1483-1487.

Rück, Asymmetric Alkylation of Amide Enolates with Pseudoephedrine and Ephedrine as Chiral Auxiliaries—Unexpected Influence of Additives? Angewandte Chemie. International Edition. Mar. 7, 1995;34(4):433-35.

Seiple et al., A platform for the discovery of new macrolide antibiotics. Nature. May 18, 2016;533(7603):338-45. doi: 10.1038/nature17967.

Shvekhgeimer et al., Aliphatic nitro alcohols. Synthesis, chemical transformations and applications. Russian Chemical Reviews. 1998;67(1):35-68.

Song et al., Protein Phosphatase 2A-SUR-6/B55 Regulates Centriole Duplication in C. elegans by Controlling the Levels of Centriole Assembly Factors. Dev Cell. Apr. 19, 2011; 20(4): 563-571. doi: [10.1016/j.devcel.2011.03.007].

Sutcliffe et al., *Streptococcus pneumoniae* and *Streptococcus pyogenes* resistant to macrolides but sensitive to clindamycin: a common resistance pattern mediated by an efflux system. Antimicrob Agents Chemother. 1996;40:1817-1824.

Tu et al., Structures of MLSBK antibiotics bound to mutated large ribosomal subunits provide a structural explanation for resistance. Cell. 2005;121:257-270.

Van Summeren et al., New approaches towards the synthesis of the side-chain of mycolactones A and B. J Org Biomol Chem. 2005;3:2524-2533.

Velvadapu et al., Concise syntheses of D-desosamine, 2-thiopyrimidinyl desosamine donors, and methyl desosaminide analogues from D-glucose. Carbohydr Res. 2008;343:145-150.

Velvadupu et al., Total synthesis of (-)-4,8,10-tridesmethyl telithromycin. J Org Chem. Sep. 16, 2011;76(18):7516-27. doi: 10.1021/j0201319b. Epub Aug. 24, 2011.

Vester et al., Macrolide resistance conferred by base substitutions in 23S rRNA. Antimicrob Agents Chemother. 2001;45:1-12.

Vicario et al., Asymmetric aldol reactions using (S,S)-(+)-pseudoephedrine-based amides: stereoselective synthesis of alpha-methyl-beta-hydroxy acids, esters, ketones, and 1,3-Syn and 1,3-anti diols. J Org Chem. Jun. 16, 2000;65(12):3754-60.

Waddell et al., Chimeric azalides with functionalized western portions. Heterocycles. 1996;43(11):2325-2332.

Wagh et al., Desmethyl Macrolides: Synthesis and Evaluation of 4,8-Didesmethyl Telithromycin. ACS Med Chem Lett. Dec. 12, 2012;3(12):1013-1018.

Wang et al., Synthesis of novel 6,11-O-bridged bicyclic ketolides via a palladium-catalyzed bis-allylation. Org Lett. Nov. 25, 2004;6(24):4455-8.

Washington et al., Erythromycin: a microbial and clinical perspective after 30 years of clinical use (1). Mayo Clin Proc. 1985;60:189-203.

Washington et al., Erythromycin: a microbial and clinical perspective after 30 years of clinical use (2). Mayo Clin Proc. 1985;60:271-278.

(56) References Cited

OTHER PUBLICATIONS

Watanabe et al., Chemical modification of erythromycins. IX. Selective methylation at the C-6 hydroxyl group of erythromycin A oxime derivatives and preparation of clarithromycin. J Antibiot (Tokyo). Apr. 1993;46(4):647-60.
Watanabe et al., Chemical modification of erythromycins. XII. A facile synthesis of clarithromycin (6-O-methylerythromycin A) via 2'-silylethers of erythromycin A derivatives. J Antibiot (Tokyo). Jul. 1993;46(7):1163-7.
Watanabe et al., Tetronothiodin, a novel cholecystokinin type-B receptor antagonist produced by *Streptomyces* sp. NR0489.1. Taxonomy, yield improvement and fermentation. J Antibiot (Tokyo). Jan. 1993;46(1):1-10.
Weisblum, Erythromycin resistance by ribosome modification. Antimicrob Agents Chemother. 1995;39:577-585.
Wilkening et al., The synthesis of novel 8a-AZA-8a-homoerythromycin derivatives via the Beckman rearrangement of (9z)-erythrromycin a oxime. Bioorg Med Chem. 1993;3(6):1287-92.
Wondrack et al., Clinical strain of *Staphylococcus aureus* inactivates and causes efflux of macrolides. Antimicrob Agents Chemother. 1996;40:992-998.
Woodward et al., Asymmetric total synthesis of erythromcin. 1. Synthesis of an erythronolide A secoacid derivative via asymmetric induction. J Am Chem Soc. 1981;103(11):3210-3213.
Woodward et al., Asymmetric total synthesis of erythromycin. 2. Synthesis of an erythronolide A lactone system. J Am Chem Soc. 1981;103(11):3213-3215.
Woodward et al., Asymmetric total synthesis of erythromycin. 3. Total synthesis of erythromycin. J Am Chem Soc. 1981;103(11):3215-3217.
Worch et al., Unexpected formation of complex bridged tetrazoles via intramolecular 1,3-dipolar cycloaddition of 1,2-O-cyanoalkylidene derivatives of 3-azido-3-deoxy-D-allose. Carbohydr Res. Aug. 11, 2008;343(12):2118-29. Epub Nov. 6, 2007.
Wright, Molecular mechanisms of antibiotic resistance. Chem Commun. 2011;47:4055-4061.
Wu et al., Recent developments on ketolides and macrolides. Curr Med Chem. Dec. 2001;8(14):1727-58.
Wu, Highlights of semi-synthetic developments from erythromycin A. Curr Pharm Des. 2000;6:181-223.
Zhanel et al., The ketolides: a critical review. Drugs. 2002;62(12):1771-804.
Zhang et al., Synthesis of D-Desosamine and Analogs by Rapid Assembly of 3-Amino Sugars. Angewandte Chemie Int Ed. Jan. 11, 2016;55(2):523-7. Epub Nov. 27, 2015.
Zjndel et al., Synthesis of 3-(trans-2'-Nitrocyclopropyl)alanine, a Constituent of the Natural Peptide-Lactone Hormaomycin. J. Org. Chem. 1995;60(10):2968-73.
Boulard et al., Synthesis of the C1-C13 fragment of (+)-callipeltoside A, Synlett. 2007; 9:1461-1463.
Marinier et al., Synthesis and transannular Diels-Alder reaction of a cis-trans-trans and a trans-cis-cis 13-membered macrocyclic trienone. Canadian Journal of Chemistry. 1989;.67(10):1609-1617.
Singer et al., Catalytic, Enantioselective Dienolate Additions to Aldehydes: Preparation of Optically Active Acetoacetate Aldol Adducts. Journal of the American Chemical Society. 1995;117(49): 12360-12361.
Sugita et al., Use of 1,3-dioxin-4-ones and related compounds in synthesis. Part 39. Enantioselective synthesis of 1,3-dioxin-4-ones having 2,3-dihydroxy- or 2,3,4-trihydroxyalkyl groups at the 6-position: versatile building blocks of polyhydroxylated 4-7 carbon backbones. J Chem Soc Perkin Trans. 1992; 21: 2855-2861.
Venkatraman et al., Total synthesis of narbonolide and biotransformation to pikromycin. J Org Chem. Dec. 22, 2006;71(26):9853-6. doi: 10.1021/jo062047u.
U.S. Appl. No. 14/781,719, filed Oct. 1, 2015, Myers et al.

U.S. Appl. No. 15/946,658, filed Apr. 5, 2018, Myers et al.
U.S. Appl. No. 15/517,843, filed Apr. 7, 2017, Myers et al.
U.S. Appl. No. 16/843,259, filed Apr. 8, 2020, Myers et al.
U.S. Appl. No. 15/558,896, filed Mar. 8, 2018, Myers et al.
U.S. Appl. No. 16/843,017, filed Apr. 8, 2020, Myers et al.
EP 14779590.0, Oct. 26, 2016, Partial Supplementary European Search Report.
EP 14779590.0, Feb. 6, 2017, Extended European Search Report.
EP 14779590.0, Jul. 8, 2019, #Summons to Attend Oral Proceedings.
EP 14779590.0, Jul. 16, 2020, #European Office Action.
PCT/US2014/033025, Aug. 14, 2014, Invitation to Pay Additional Fees.
PCT/US2014/033025, Oct. 28, 2014, International Search Report and Written Opinion.
PCT/US2014/033025, Oct. 15, 2015, International Preliminary Report on Patentability.
EP 15848340.4, Jun. 22, 2018, #Partial Supplementary European Search Report.
EP 15848340.4, Sep. 26, 2018, #Extended European Search Report.
PCT/US2015/054700, Jan. 11, 2016, International Search Report and Written Opinion.
PCT/US2015/054700, Apr. 20, 2017, International Preliminary Report on Patentability.
EP 16769811.7, Jul. 17, 2018, #Partial Supplementary European Search Report.
EP 16769811.7, Oct. 24, 2018, #Extended European Search Report.
EP 16769811.7, Apr. 9, 2020, #European Office Action.
PCT/US2016/024333, May 18, 2016, Invitation to Pay Additional Fees.
PCT/US2016/024333, Aug. 5, 2016, International Search Report and Written Opinion.
PCT/US2018/030002, Sep. 25, 2018, #Invitation to Pay Additional Fees.
PCT/US2019/062030, Feb. 26, 2020, #International Search Report and Written Opinion.
PCT/US2019/062045, Mar. 9, 2020, #International Search Report and Written Opinion.
Database Caplus [Online]; Chemical Abstracts Service, Columbus, Ohio, CAS Registry File RN: 946531-73-3. STN Entry Date: Sep. 10, 2007.
Database Caplus [Online]; Chemical Abstracts Service, Columbus, Ohio, CAS Registry File RN: 182247-81-0. STN Entry Date: Oct. 24, 1996.
Database Caplus [Online]; Chemical Abstracts Service, Columbus, Ohio, CAS Registry File RN: 1452152-89-4. STN Entry Date: Aug. 23, 2013.
Database Caplus [Online]; Chemical Abstracts Service, Columbus, Ohio, CAS Registry File RN: 1428343-12-7. STN Entry Date: Oct. 9, 2012.
Database Caplus [Online]; Chemical Abstracts Service, Columbus, Ohio, CAS Registry File RN: 1361978-80-4. STN Entry Date: Dec. 22, 2011.
Database Caplus [Online]; Chemical Abstracts Service, Columbus, Ohio, CAS Registry File RN: 1314123-87-9. STN Entry Date: Jun. 17, 2011.
Database Caplus [Online]; Chemical Abstracts Service, Columbus, Ohio, CAS Registry File RN: 918961-69-0. STN Entry Date: Nov. 30, 2006.
Database Caplus [Online]; Chemical Abstracts Service, Columbus, Ohio, CAS Registry File RN: 910131-69-0. STN Entry Date: Jul. 25, 2006.
Database Caplus [Online]; Chemical Abstracts Service, Columbus, Ohio, CAS Registry File RN: 182247-84-3. STN Entry Date: Oct. 24, 1996.
Database Caplus [Online]; Chemical Abstracts Service, Columbus, Ohio, CAS Registry File RN: 131149-21-8. STN Entry Date: Jan. 26, 1991.

\* cited by examiner erythromycin (1)
14-membered macrolide

Preparation: fermentation from S. erythraea
US FDA Approval: 1952 clarithromycin (2)
14-membered macrolide
semi-synthesis: 6 steps from erythromycin
1991 azithromycin (3)
15-membered azalide
semi-synthesis: 4 steps from erythromycin
1991 telithromycin (4)
14-membered ketolide
semi-synthesis: 12 steps from erythromycin
2004 solithromycin (5)
14-membered ketolide
semi-synthesis: 16 steps from erythromycin
(Clinic Phase II)

cethromycin (7)
14-membered ketolide
(Clinic Phase III)

tylosin (6)
16-membered macrolide
fermentation from *S. fradiae*
(veterinary medicine)

Pseudoephenamine and Zimmerman Traxler:

Felkin-Ahn:

MACROLIDES AND METHODS OF THEIR PREPARATION AND USE

RELATED APPLICATIONS

The present application is a continuation of and claims priority under 35 U.S.C. § 120 to U.S. application, U.S. Ser. No. 15/946,658, filed Apr. 5, 2018, issued as U.S. Pat. No. 10,913,764 on Feb. 9, 2021, which is a continuation of and claims priority under 35 U.S.C. § 120 to U.S. application, U.S. Ser. No. 14/781,719, filed Oct. 1, 2015, issued as U.S. Pat. No. 9,982,005 on May 29, 2018, which is a national stage filing under 35 U.S.C. § 371 of International PCT application, PCT/US2014/033025, filed Apr. 4, 2014, which claims priority under 35 U.S.C. § 119(e) to U.S. provisional applications, U.S. Ser. No. 61/808,441, filed Apr. 4, 2013, U.S. Ser. No. 61/832,639, filed Jun. 7, 2013, and U.S. Ser. No. 61/946,604, filed Feb. 28, 2014, each of which is incorporated herein by reference.

BACKGROUND OF THE INVENTION

Emerging resistance to existing antibiotics is rapidly developing as a crisis of global proportions, especially for *Staphylococcus aureus, Streptococcus pyogenes*, and *Streptococcus pneumonia* infections. Pathogenic bacteria can transmit genes coding for antibiotic resistance both vertically (to their progeny) and horizontally (to neighboring bacteria of different lineages), and as a result antibiotic resistance can evolve quickly, particularly in nosocomial (hospital) settings. See, e.g., Wright, *Chem. Commun.* (2011) 47:4055-4061. This year, >99,000 people will die in the U.S. from healthcare-associated infections, more than all casualties from car accidents, HIV, and breast cancer combined, creating an estimated burden of up to $45 billion in U.S. healthcare costs. See, e.g., Klevens et al., *Public Health Rep* (2007) 722:160-166. The current crisis is exacerbated by the fact that most major pharmaceutical companies have essentially abandoned research in the development of new antibiotics. See, e.g., Projan *Curr. Opin. Microbiol.* (2003) 6:427-430. The current rate of introduction of new antibiotics does not adequately address growing resistance, and with the ease of international travel and increasing population densities, the need for innovation in the field has never been higher.

The macrolides are one of the few major clinically important classes of antibiotics for which the only practical access has been through semi-synthesis, or chemical manipulation of structurally complex fermentation products, in routes as long as 16 steps. See, e.g., Paterson, *Tetrahedron* (1985) 47:3569-3624; Omura, Ed., *Macrolide Antibiotics: Chemistry, Biology, and Practice*, Second Edition; Academic Press, 2002. The macrolide class of antibiotics has proven safe and effective in the battle against pathogenic bacteria since the discovery of erythromycin over 60 years ago. See, e.g., Wu et al., *Curr. Med. Chem.* (2001) 8, 1727-1758. Erythromycin displays a spectrum of antibacterial activity against Gram-positive bacteria similar to that of penicillin but has a lesser propensity to induce allergic interactions, and has been routinely prescribed for upper and lower respiratory tract infections and urogenital infections. See, e.g., Washington et al., *Mayo. Clin. Proc.* (1985) 60:189-203; Washington et al., *Mayo. Clin. Proc.* (1985) 60:271-278. However, erythromycin is known to undergo acid-promoted internal ketalization (cyclization of the C6 and C12 hydroxyl groups onto the C9 ketone) in the gut, which leads to adverse gastrointestinal events. See, e.g., Kurath et al., *Experientia* (1971) 27:362. Second-generation macrolide antibiotics clarithromycin and azithromycin addressed issues of acid instability and were prepared semi-synthetically in 4-6 steps from erythromycin, which is readily available through large-scale fermentation. See, e.g., Ma et al., *Curr. Med. Chem.* (2011) 78:1993-2015; Wu et al., *Curr. Pharm. Des.* (2000) 6:181-223; Ma et al., *Mini-Rev. Med. Chem.* (2010) 70:272-286; Asaka et al., *Curr. Top. Med. Chem.* (Sharjah, United Arab Emirates) (2003) 3:961-989; Morimoto et al., *J. Antibiot.* (1990) 43:286-294; Morimoto et al., *J. Antibiot.* (1984) 37:187-189; Watanabe et al., *J. Antibiot.* (1993) 46: 1163-1167; Watanabe et al., *J. Antibiot.* (1993) 46:647-660; Bright et al., *J. Antibiot.* (1988) 47: 1029-1047; Djokic et al., *J. Antibiot.* (1987) 40:1006-1015; Mutak et al., *J. Antibiot.* (2007) 60: 85-122; and Retsema et al., *Antimicrob. Agents Chemother.* (1987) 37:1939-1947. Azithromycin has been shown to exhibit markedly improved efficacy against Gram-negative organisms, and has a longer half-life and higher tissue distribution than the other macrolide antibiotics, thought to correlate with its 15-membered ring containing a tertiary amine. See, e.g., Ferweida et al., *J. Antimicrob. Chemother.* (2001) 47:441-446; Girard et al., *Antimicrob. Agents Chemother.* (1987) 37:1948-1954. The natural product tylosin, a 16-membered macrolide used in veterinary medicine, has been shown by X-ray crystallography to occupy the same binding pocket as erythromycin and azithromycin, suggesting that there is a high tolerance for variability in ring size and composition of the macrocycle.

The three primary causes of resistance to macrolides in bacterial organisms are ribosome methylation encoded by erm genes, mutations in ribosomal RNA or peptides, and cell efflux mediated by mef and msr genes. See, e.g., Leclercq et al., *Antimicrob. Agents Chemother.* (1991) 35:1273-1276; Leclercq et al., *Antimicrob. Agents Chemother.* (1991) 35:1267-1272; Weisblum, *Antimicrob. Agents Chemother.* (1995) 39:577-585; Vester et al., *Antimicrob. Agents Chemother.* (2001) 45:1-12; Prunier et al., *Antimicrob. Agents Chemother.* (2002) 46:3054-3056; Li et al., *J. Antimicrob. Chemother.* (2011) 66:1983-1986; Sutcliffe et al., *Antimicrob. Agents Chemother.* (1996) 40:1817-1824; Wondrack et al., *Antimicrob. Agents Chemother.* (1996) 40: 992-998. Ketolides such as telithromycin and solithromycin defeat the efflux mechanism of resistance by replacement of the C3 cladinose sugar with a carbonyl group (hence the name "ketolides"), and are thought to exhibit greatly increased binding by virtue of favorable interactions between the novel aryl-alkyl sidechain and the ribosome. See, e.g., Ma et al., *Curr. Med. Chem.* (2011) 78:1993-2015; Ma et al., *Mini-Rev. Med. Chem.* (2010) 70:272-286. Despite greatly improved ribosomal binding, ketolides such as telithromycin and solithromycin have not addressed several of the newest forms of macrolide resistance that have evolved in nosocomial settings, especially ribosome methylation and RNA point mutations.

SUMMARY OF THE INVENTION

Described herein are methods and intermediates for making macrolides, such as known macrolides, as well as new and improved macrolides, in a practical manner via a fully synthetic route. This practical synthetic methodology includes the coupling of two components, the western half (A), and the eastern half (B), as depicted in Scheme 1, to provide a compound of Formula (C-1):

Scheme 1.

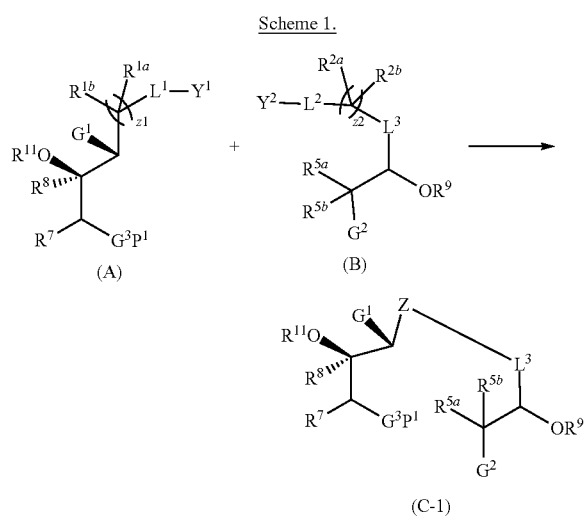

or salt thereof, wherein $G^1$, $R^{1a}$, $R^{1b}$, $R^{2a}$, $R^{2b}$, $R^{5a}$, $R^{5b}$, $R^7$, $R^8$, $R^9$, $R^{11}$, z1, and z2 are as defined herein;

$L^3$ is a group of formula:

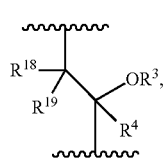
($L^3$-i)

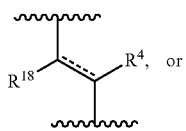
($L^3$-ii)

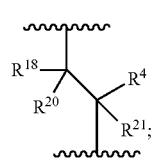
($L^3$-iii)

wherein ═══ $R^3$, $R^4$, $R^{18}$, $R^{19}$, $R^{20}$, and $R^{21}$ are as defined herein;

$G^2$ is a group of formula:

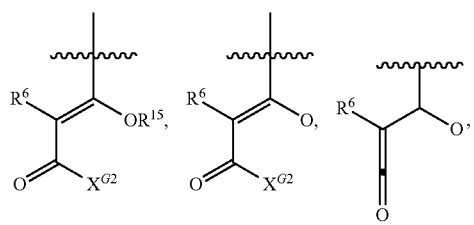

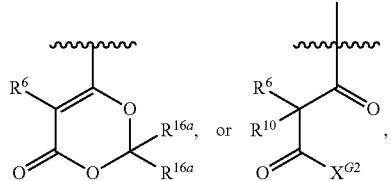

wherein $R^6$, $R^{10}$, $R^{15}$, $R^{16a}$, and $X^{G2}$ are as defined herein;

$P^1$ is hydrogen, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

$G^3$ is —O—, —S—, or —N($R^{G1}$)—, wherein $R^{G1}$ is hydrogen, optionally substituted alkyl, or a nitrogen protecting group; and one of $Y^1$ and $Y^2$ is —$Z^4$H or —$CH_2NO_2$, and the other of $Y^1$ and $Y^2$ is a leaving group (LG), —C(═O)$R^{Z3}$, —C(═O)O$R^{Z3}$, —C(═O)LG, —C(═O)—CH═P($R^{P1}$)($R^{P2}$)($R^{P3}$), or —C(═O)—$CH_2$—P(O)(O$R^{P2}$)(O$R^{P3}$), wherein $Z^4$ is —O—, —S—, or —N$R^{Z2}$—, and wherein the leaving group (LG), $R^{Z3}$, $R^{Z4}$, $R^{P1}$, $R^{P2}$, and $R^{P3}$ are as defined herein, to provide various linkages of formula Z, as defined herein.

For example, in certain embodiments, when $Y^1$ is —C(═O)$R^{Z3}$ and $R^{Z3}$ is hydrogen (aka wherein $Y^1$ is —CHO) and $Y^2$ is —C(═O)—CH═P($R^{P1}$)($R^{P2}$)($R^{P3}$) or —C(═O)—$CH_2$—P(O)(O$R^{P2}$)(O$R^{P3}$), coupling of the eastern and western halves via a Wittig or Homer-Emmons reaction forms the moiety —CH═CH—C(═O)—, and provides a compound of Formula (C-1), wherein Z is an α,β-unsaturated ketone of formula:

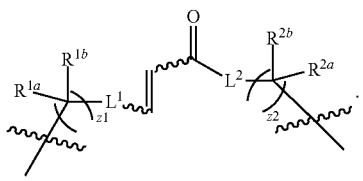

In certain embodiments, when $Y^2$ is —C(═O)$R^{Z3}$ and $R^{Z3}$ is hydrogen (aka wherein $Y^1$ is —CHO) and $Y^1$ is —C(═O)—CH═P($R^{P1}$)($R^{P2}$)($R^{P3}$) or —C(═O)—$CH_2$—P(O)(O$R^{P2}$)(O$R^{P3}$), coupling of the eastern and western halves via a Wittig reaction or Homer-Emmons reaction forms a moiety —C(═O)—CH═CH—, and provides a compound of Formula (C-1), wherein Z is an α,β-unsaturated ketone of formula:

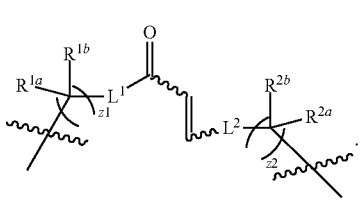

Optional synthetic modification of the moieties —CH═CH—C(═O)— and —C(═O)—CH═CH— is further contemplated herein. For example, the double bond may be reduced to a single bond, and optionally the carbon alpha to the ketone may be substituted by a non-hydrogen group $R^{Za}$. A nucleophile may react with the double bond via 1,4-addition of a non-hydrogen group $R^{Zb}$ optionally followed by alpha substitution via a non-hydrogen group $R^{Za}$. Various synthetic modifications of the α,β-unsaturated ketone formula contemplated herein are thus encompassed by the formulae:

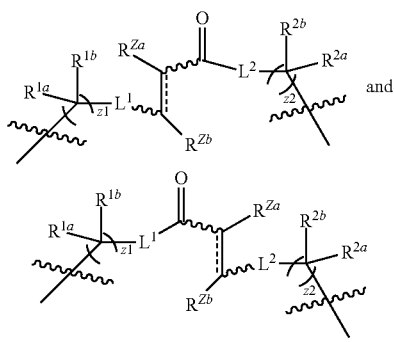

and wherein ---- represents a single or double bond, and $R^{Za}$ and $R^{Zb}$ are each independently hydrogen or a non-hydrogen group, as defined herein.

In certain embodiments, when $Y^1$ is —$Z^4$H and $Y^2$ is a leaving group (LG), or when $Y^2$ is —$Z^4$H and $Y^1$ is a leaving group (LG), coupling of the eastern and western halves by nucleophilic displacement, optionally in the presence of a base, provides a compound of Formula (C-1), wherein Z is an ether, thioether, or amine of formula:

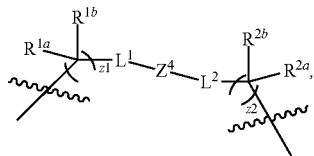

wherein $Z^4$ is —O—, —S—, or —$NR^{Z2}$—, and wherein $R^{Z2}$ is hydrogen or a non-hydrogen group.

In certain embodiments, when $Y^1$ is —$Z^4$H, and $Y^2$ is —C(=O)$OR^{Z3}$ or —C(=O)LG, coupling of the eastern and western halves by 1,2-nucleophilic addition, optionally in the presence of a base, provides a compound of Formula (C-1), wherein Z is an ester, thioester, or amide of formula:

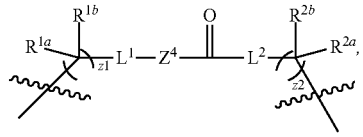

wherein $Z^4$ is —O—, —S—, or —$NR^{Z2}$—, and wherein $R^{Z2}$ is hydrogen or a non-hydrogen group.

Alternatively, in certain embodiments, when $Y^2$ is —$Z^4$H, and $Y^1$ is —C(=O)$OR^{Z3}$ or —C(=O)LG, coupling of the eastern and western halves by 1,2-nucleophilic addition, optionally in the presence of a base, provides a compound of Formula (C-1), wherein Z is an ester, thioester, or amide of formula:

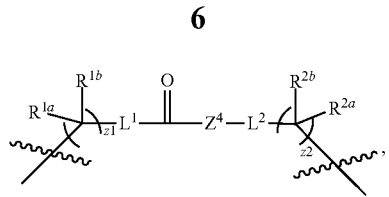

wherein $Z^4$ is —O—, —S—, or —$NR^{Z2}$—, and wherein $R^{Z2}$ is hydrogen or a non-hydrogen group.

In certain embodiments, wherein $Y^1$ is —$NH_2$ or —$NHR^{Z2}$, and $Y^2$ is —C(=O)$R^{Z3}$, coupling of the eastern and western halves by reductive amination, optionally followed by protection of the amine group by a non-hydrogen $R^{Z2}$, provides a compound of Formula (C-1), wherein Z is an amine of formula:

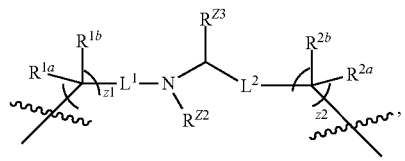

wherein $R^{Z2}$ is hydrogen or a non-hydrogen group.

In certain embodiments, wherein $Y^1$ is —$NH_2$, and $Y^2$ is —C(=O)$R^{Z3}$, coupling of the eastern and western halves by imine formation, optionally followed by addition of a group $R^{Z4}$ to the imine double bond, and optionally followed by protection of the amine group by a non-hydrogen $R^{Z2}$, provides a compound of Formula (C-1), wherein Z is an imine or amine of formula:

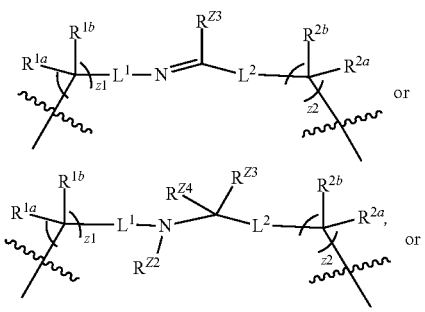

wherein $R^{Z2}$ is hydrogen or a non-hydrogen group.

Alternatively, in certain embodiments, wherein $Y^2$ is —$NH_2$ or —$NHR^{Z2}$ and $Y^1$ is —C(=O)$R^{Z3}$, coupling of the eastern and western halves by reductive amination, optionally followed by protection of the amine group by a non-hydrogen $R^{Z2}$, provides a compound of Formula (C-1), wherein Z is an amine of formula:

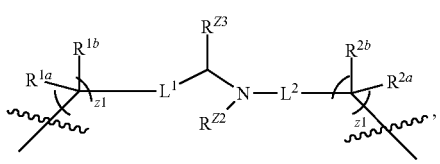

wherein $R^{Z2}$ is hydrogen or a non-hydrogen group.

In certain embodiments, wherein $Y^2$ is —$NH_2$, and $Y^1$ is —C(=O)$R^{Z3}$, coupling of the eastern and western halves by imine formation, optionally followed by addition of a group $R^{Z4}$ to the imine double bond, optionally followed by protection of the amine group by a non-hydrogen $R^{Z2}$, provides a compound of Formula (C-1), wherein Z is an imine or amine of formula:

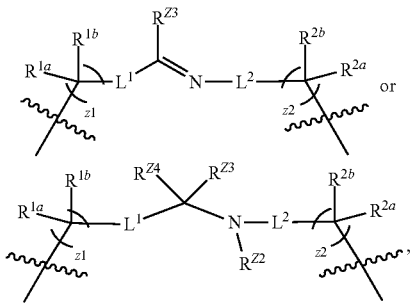

wherein $R^{Z2}$ is hydrogen or a non-hydrogen group.

Further contemplated are nitro-aldol reaction coupling products, and oxidized, reduced, and/or addition products formed therefrom.

For example, in certain embodiments, wherein $Y^1$ is —$CH_2NO_2$, and $Y^2$ is —C(=O)$R^{Z3}$, coupling of the eastern and western halves provides a compound of Formula (C-1), wherein Z is a group of formula:

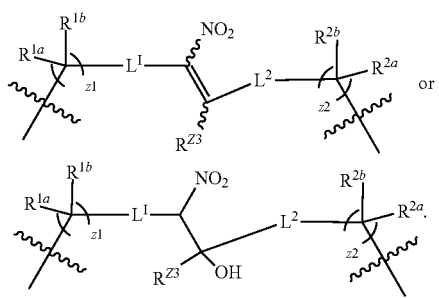

Alternatively, in certain embodiments, wherein $Y^2$ is —$CH_2NO_2$, and $Y^1$ is —C(=O)$R^{Z3}$, coupling of the eastern and western halves provides a compound of Formula (C-1), wherein Z is a group of formula:

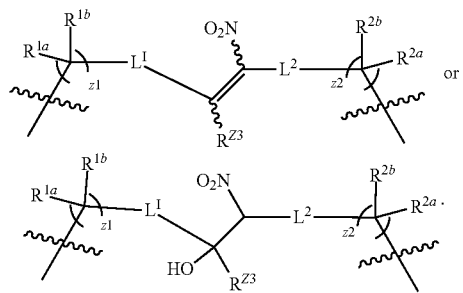

With the nitro-aldol coupling product in hand, the nitro (—$NO_2$) moiety may be manipulated at any stage in the synthesis, e.g., after coupling but before macrocyclization, or after the macrolide has been formed.

For example, reduction of the double bond of the nitro-aldol product of formula:

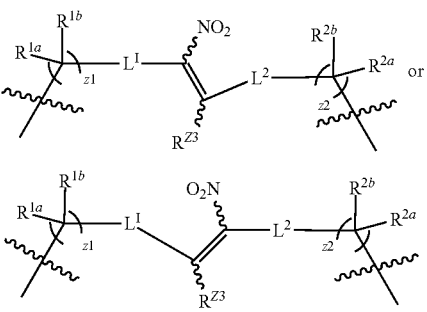

provides a Z group of formula:

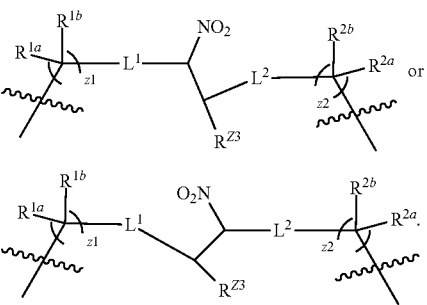

Addition of a group $R^{Z4}$ to the nitro-aldol product of formula:

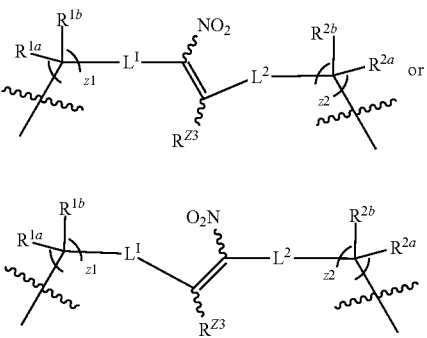

provides a Z group of formula:

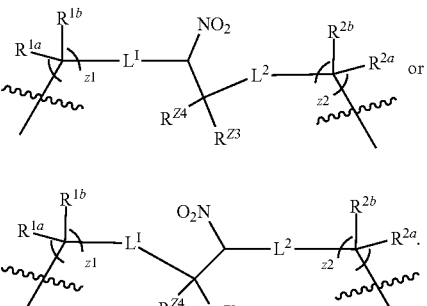

Reduction of the nitro group as provided in formulae:

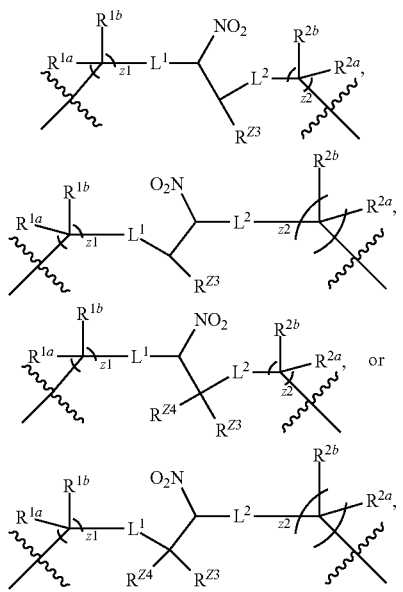

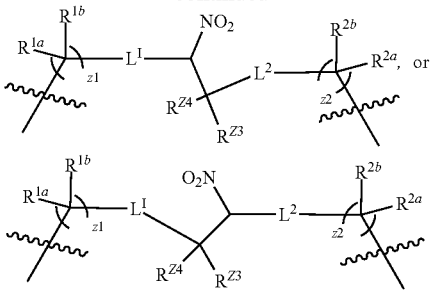

to the free amine, which may be optionally mono- or bis-protected, provides a Z group of formula:

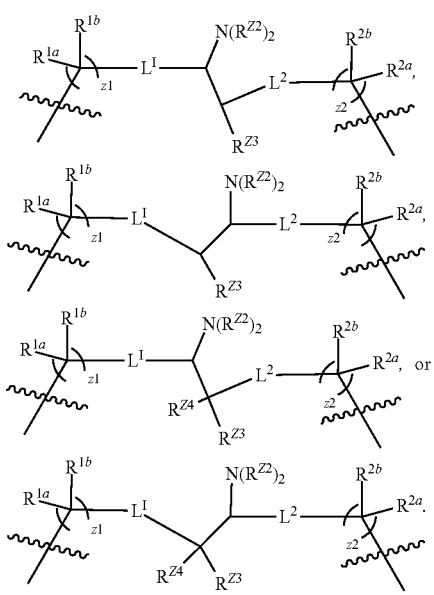

Oxidation of the nitro group as provided in formula:

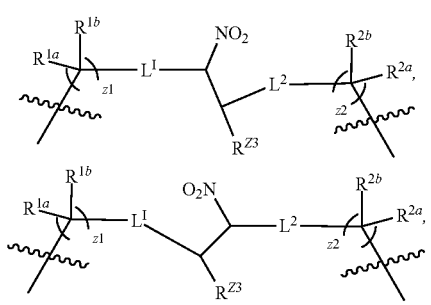

provides the keto (oxo) product of formula:

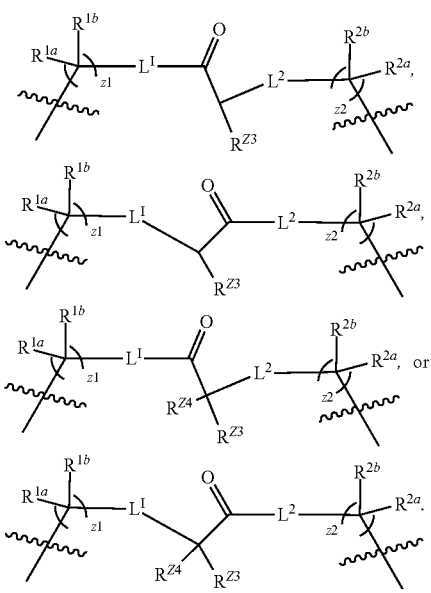

Alternative methods of preparing the above depicted keto (oxo) products are further contemplated herein.

Furthermore, various macrolides may be accessed from the coupled product of Formula (C-1), depending upon the nature of the group $G^2$, upon macrocyclization, e.g. via thermally induced macrocyclization. For example, as depicted in Scheme 2, when $G^2$ is a group of formula:

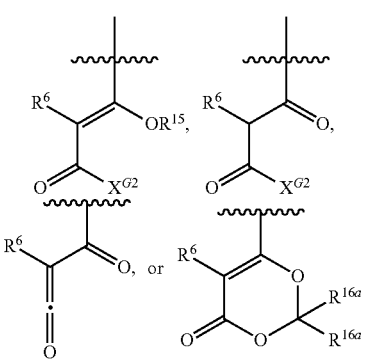

$P^1$ is hydrogen, and a hydrogen or non-hydrogen group, macrocyclization of the compound of Formula (C-1) provides a macrolide of Formula (C-2). Enolization of the macrolide of Formula (C-2) in the presence of a base, followed by addition of a non-hydrogen group $R^{10}$, provides a macrolide of Formula (C-3).

Scheme 2.

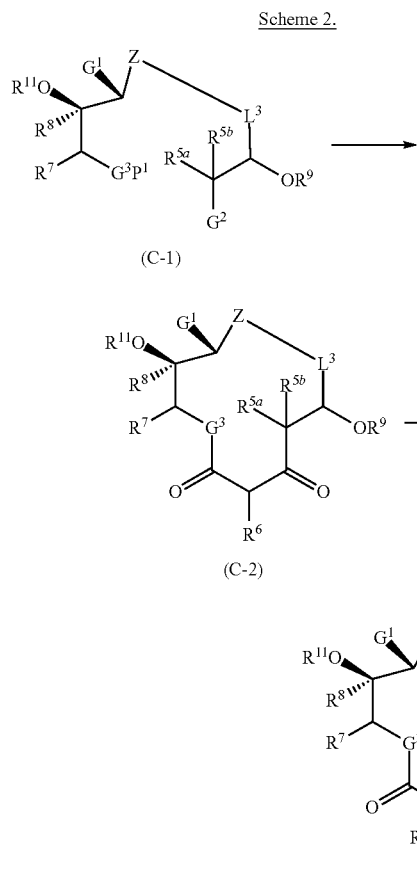

Alternatively, as depicted in Scheme 3, when $G^2$ is a group of formula:

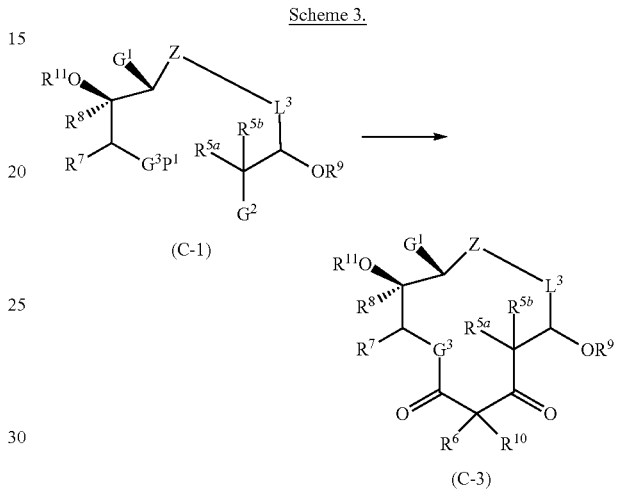

wherein $P^1$ is hydrogen, and each of $R^6$ and $R^{10}$ is independently a hydrogen or non-hydrogen group, macrocyclization of the compound of Formula (C-1) provides a macrolide of Formula (C-3).

Scheme 3.

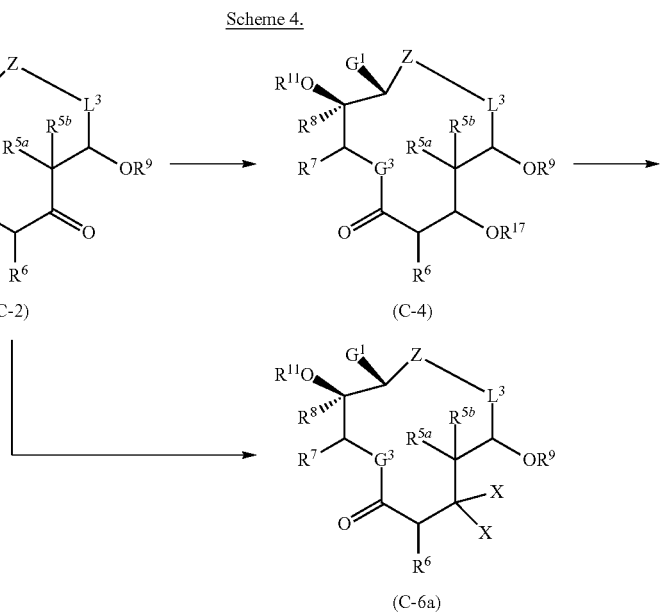

Additional functionalization of the macrolide is contemplated herein. For example, as depicted in Schemes 4 and 5, reduction of the C3 ketone of macrolides (C-2) and (C-3) to a hydroxyl group, optionally followed by protection, provides macrolides (C-4) and (C-5), respectively, wherein $R^{17}$ is as defined herein. Dihalogenation of the C3 ketone of macrolides (C-2) and (C-3), or monohalogenation of macrolides (C-4) and (C-5), providing the products, (C6a/b) and (C7a/b), is further contemplated herein, wherein X is halogen, e.g., fluoro.

Scheme 4.

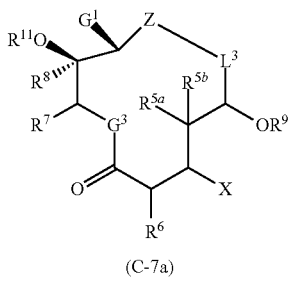

(C-7a)

Scheme 5.

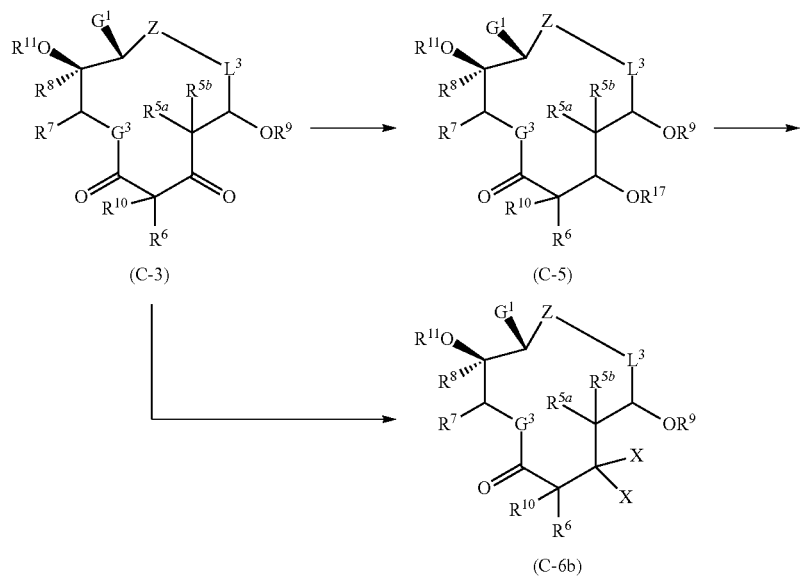

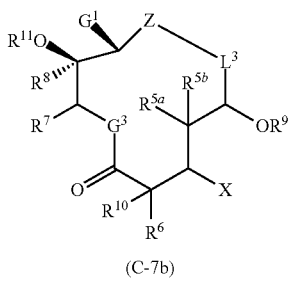

(C-7b)

Formula (C-467) and subgenera thereof as described herein are intended to encompass compounds of Formula (C-2), (C-4), (C6a), and (C7a) and subgenera thereof, wherein $R^{Y1}$ is —$OR^{17}$ and $R^{Y2}$ is hydrogen, or $R^{Y1}$ is halogen and $R^{Y2}$ is hydrogen, or $R^{Y1}$ is halogen and $R^{Y2}$ is halogen. Likewise, Formula (C-567) and subgenera thereof are intended to encompass compounds of Formula (C-3), (C-5), (C6b), and (C7b), wherein $R^{Y1}$ is —$OR^{17}$ and $R^{Y2}$ is hydrogen, or $R^{Y1}$ is halogen and $R^{Y2}$ is hydrogen, or $R^{Y1}$ is halogen and $R^{Y2}$ is halogen, or $R^{Y1}$ and $R^{Y2}$ are joined to form an oxo (=O) group.

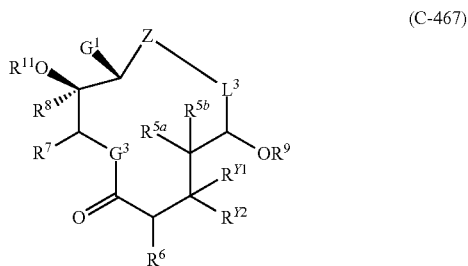

(C-467)

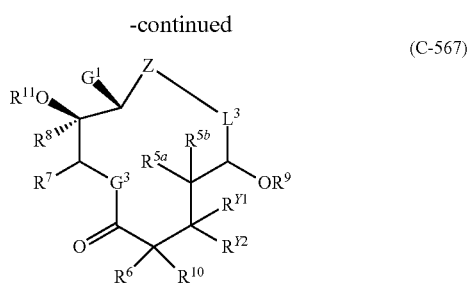

(C-567)

Additional functionalization of the coupled product (C-1) and the macrolides (C-2), (C-3), (C-4), (C-5), (C-6), and (C-7), for example, by addition and synthetic manipulation of a tethered moiety on the eastern or western portion of the molecule, and construction of the eastern and western halves, is also described herein.

Is generally understood that the synthetic methodology as described herein is both useful in the synthesis of known macrolides, such as those depicted in FIG. 1, and in the synthesis and development of new macrolides as described herein. New macrolides synthesized using the inventive methodology, and pharmaceutical compositions thereof, are contemplated to be useful in the treatment of various conditions such as, for example, the treatment of infectious diseases, such as bacterial and parasitic infections, and the treatment of inflammatory conditions.

An additional aspect of the present invention is further described herein. In the construction of the western half (A), it was discovered that pseudoephanamine glycinamide undergoes highly selective addition to aldehydes and ketones to generate products with high diastereoselectivity in a single step. See, e.g., Scheme 7. Such a reaction is considered broadly applicable using other chiral auxiliaries, such as pseudoephedrine glycinamide, in combination with a wide range of aldehydes and ketones.

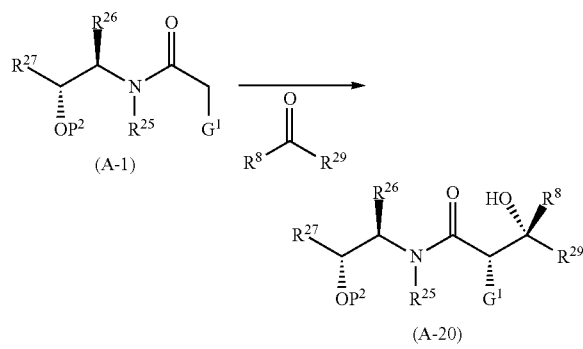

Scheme 7.

The details of certain embodiments of the invention are set forth in the Detailed Description of Certain Embodiments, as described below. Other features, objects, and advantages of the invention will be apparent from the Definitions, Examples, Figures, and Claims.

DEFINITIONS

Chemical Definitions

Figure 1:
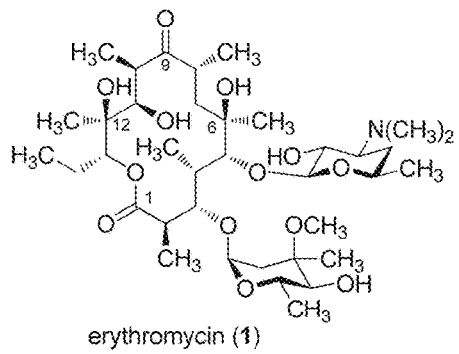
FIG. 1 depicts exemplary 14-, 15-, and 16-membered macrolide antibiotics used in the United States.
Figure 1:
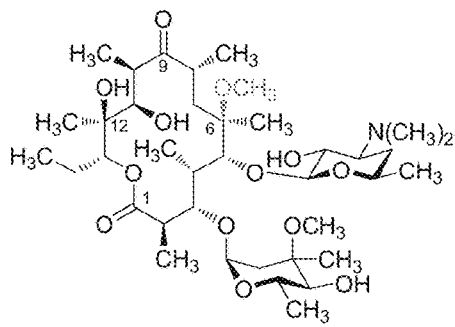
Figure 1:
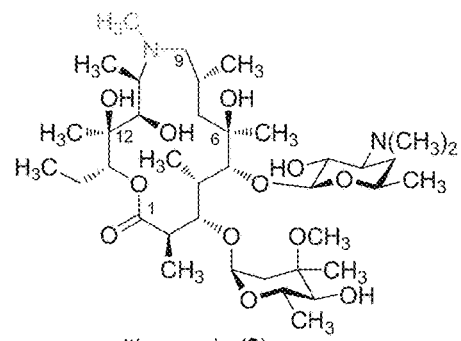
Figure 1:
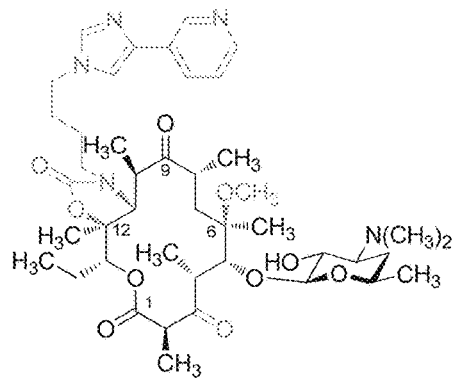
Figure 1:
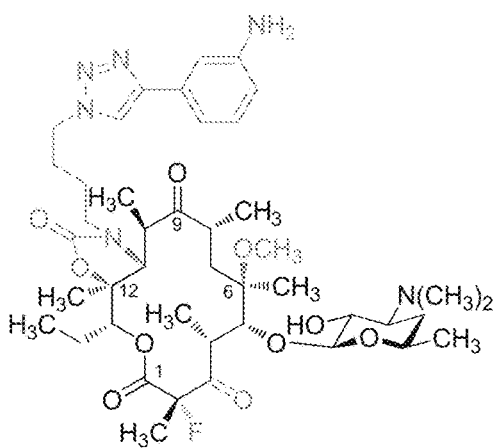
Figure 1:
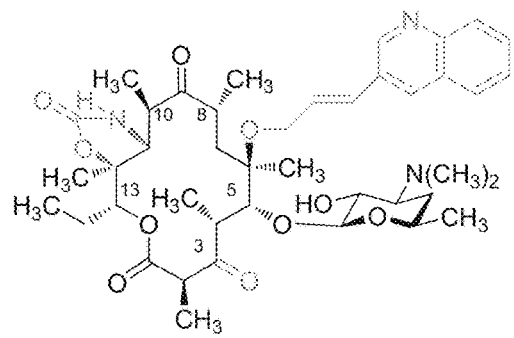
Figure 1:
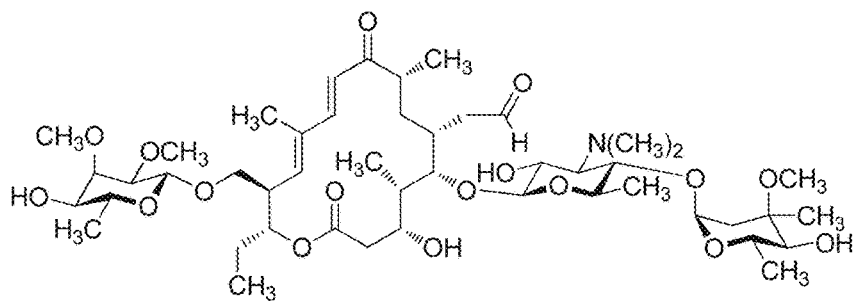

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds and macrolides described herein can comprise one or more asymmetric centers, and thus can exist in various stereoisomeric forms, e.g., enantiomers and/or diastereomers. For example, the compounds and macrolides described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds and macrolides as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 9 ring carbon atoms ("C$_{3-9}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C3-s carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 9 ring carbon atoms ("C$_{3-9}$ cycloalkyl"). In some embodiments, a cycloalkyl group has 3 to 8 ring carbon atoms ("C$_{3-8}$ cycloalkyl"). In some embodiments, a cycloalkyl group has 3 to 7 ring carbon atoms ("C$_{3-6}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("C$_{6-14}$ aryl"). In some embodiments, an aryl group has 6 ring carbon atoms ("C$_6$ aryl"; e.g., phenyl). In some embodiments, an aryl group has 10 ring carbon atoms ("C$_{10}$ aryl"; e.g., naphthyl such as 1-naphthyl and 2-naphthyl). In some embodiments, an aryl group has 14 ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety. An exemplary aralkyl group is —$CH_2$-phenyl (benzyl, Bz), wherein the phenyl moiety may be substituted or unsubstituted.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{1-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, —C(=S)NH(C$_{1-6}$ alkyl), —C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon substituents are selected from the group consisting of halogen, —CN, —NO$_2$, —OH, —OR$^{aa}$, —N(R$^{bb}$)$_2$, —SH, —SR$^{aa}$, —C(=O)R$^{aa}$, —CO$_2$H, —CHO, —CO$_2$R$^{aa}$, —OC(=O)R$^{aa}$, —C(=O)N(R$^{bb}$)$_2$, —OC(=O)N(R$^{bb}$)$_2$, —NR$^{bb}$C(=O)R$^{aa}$, —SO$_2$N(R$^{bb}$)$_2$, —SO$_2$R$^{aa}$, C$_{1-6}$ alkyl, C$_{1-6}$ perhaloalkyl, C$_{2-6}$ alkenyl, C$_{2-6}$ alkynyl, C$_{3-6}$ carbocyclyl, 3-6 membered heterocyclyl, C$_6$ aryl, and 5-6 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "hydroxyl" or "hydroxy" refers to the group —OH. The term "substituted hydroxyl" or "substituted hydroxy," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

As used herein, the term "alkoxyalkyl" refers to an alkyl group as defined herein substituted by a group of formula —OR$^{aa}$ wherein R$^{aa}$ is as defined herein, wherein the point of attachment is on the alkyl group.

As used herein, the term "aminoalkyl" refers to an alkyl group as defined herein substituted by an amino or substituted amino group, as defined herein, wherein the point of attachment is on the alkyl group.

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

As used herein, the term "silyl" refers to the group —Si(R$^{aa}$)$_3$, wherein R$^{aa}$ is as defined herein.

As used herein, the term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propan amide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-f-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, t-amyl carbamate, 5-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-r-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, A-benzylamine, TV-di(4-methoxyphenyl)methylamine, N-5-dibenzosuberylamine, A-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, TV-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), r-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, l-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. See, for example, Smith, March *Advanced*

*Organic Chemistry* 6th ed. (501-502). Exemplary leaving groups include, but are not limited to, halo (e.g., chloro, bromo, iodo), —OR$^{aa}$ (when attached to a carbonyl group, wherein R$^{aa}$ is as defined herein), —O(C=O)R$^{LG}$, or —O(SO)$_2$R$^{LG}$ (e.g., tosyl, mesyl, besyl), wherein R$^{LG}$ is optionally substituted alkyl, optionally substituted aryl, or optionally substituted heteroaryl.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

A "carbohydrate group" or a "carbohydrate" refers to a monosaccharide or a polysaccharide (e.g., a disaccharide or oligosaccharide). Exemplary monosaccharides include, but are not limited to, natural sugars, such as allose, altrose, glucose, mannose, gulose, idose, galactose, talose, ribose, arabinose, xylose, and lyxose. Disaccharides are two joined monosaccharides. Exemplary disaccharides include, but are not limited to, sucrose, maltose, cellobiose, and lactose. Typically, an oligosaccharide includes between three and ten monosaccharide units (e.g., raffinose, stachyose). The carbohydrate group may be a natural sugar or a modified sugar. Exemplary modified sugars include, but are not limited to, sugars where the hydroxyl group is replaced with an amino group and/or alkyl group (e.g., such as desosamine), 2'-deoxyribose wherein a hydroxyl group is removed, 2'-fluororibose wherein a hydroxyl group is replace with a fluorine, or N-acetylglucosamine, or a nitrogen-containing form of glucose (e.g., 2'-fluororibose, deoxyribose, and hexose), and the like. Various carbohydrates are further described below and herein. Carbohydrates may exist in many different forms, for example, conformers, cyclic forms, acyclic forms, stereoisomers, tautomers, anomers, and isomers.

These and other exemplary substituents are described in more detail in the Detailed Description, Examples, and claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the macrolides of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); commercially relevant mammals such as cattle, pigs, horses, sheep, goats, cats, and/or dogs], birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

"Disease," "disorder," and "condition" are used interchangeably herein.

As used herein, and unless otherwise specified, the terms "treat," "treating" and "treatment" contemplate an action that occurs while a subject is suffering from the specified infectious disease or inflammatory condition, which reduces the severity of the infectious disease or inflammatory condition, or retards or slows the progression of the infectious disease or inflammatory condition ("therapeutic treatment"), and also contemplates an action that occurs before a subject begins to suffer from the specified infectious disease or inflammatory condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of an infectious disease or inflammatory condition, or to delay or minimize one or more symptoms associated with the infectious disease or inflammatory condition. A therapeutically effective amount of a compound means an amount of therapeutic agent, alone or in combination with other therapies, which provides a therapeutic benefit in the treatment of the infectious disease or inflammatory condition. The term "therapeutically effective amount" can encompass an amount that improves overall therapy, reduces or avoids symptoms or causes of infectious disease or inflammatory condition, or enhances the therapeutic efficacy of another therapeutic agent.

As used herein, and unless otherwise specified, a "prophylactically effective amount" of a compound is an amount sufficient to prevent an infectious disease or inflammatory condition, or one or more symptoms associated with the infectious disease or inflammatory condition, or prevent its recurrence. A prophylactically effective amount of a compound means an amount of a therapeutic agent, alone or in combination with other agents, which provides a prophylactic benefit in the prevention of the infectious disease or inflammatory condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally understood from the present disclosure, the present invention is, in part, directed to macrolides of the formulae below, constructed from the coupling of an eastern half and western half, followed by macrocyclization and further synthetic manipulation:

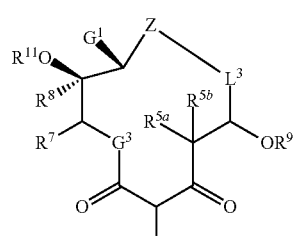
(C-2)

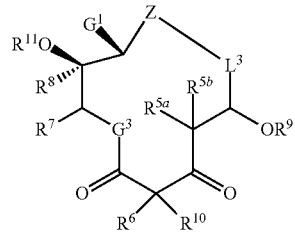
(C-3)

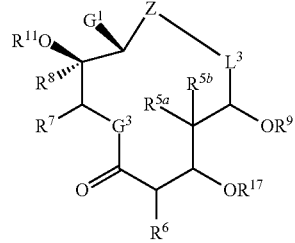
(C-4)

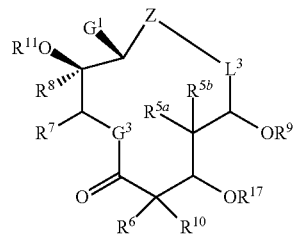
(C-5)

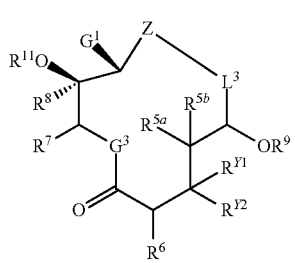
(C-467)

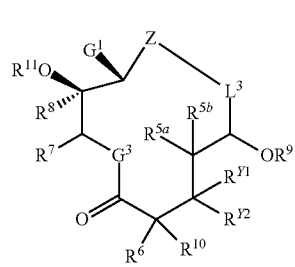
(C-567)

and salts thereof;

wherein:

Z is:

[1] an ether, thioether, or amine of formula:

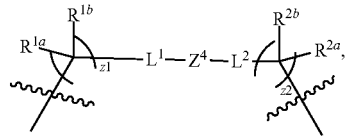

wherein $L^1$ and $L^2$ are each independently a bond or —$CH_2$—; z1 and z2 are each independently 0, 1, or 2 and $Z^4$ is —O—, —S—, or —$NR^{Z2}$—, e.g., to provide a 13-, 14-, 15- or 16-membered ring system, e.g., of formula:

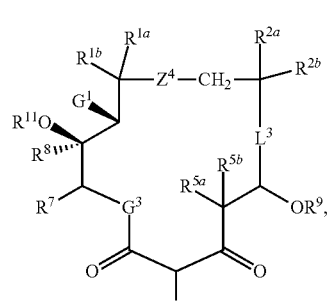
(C-2-ia)

15-membered ring system (C-2-ib)
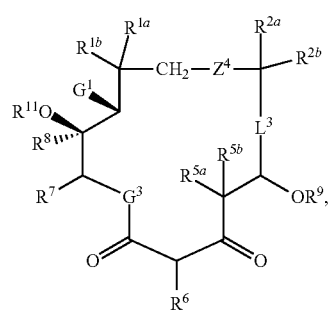
15-membered ring system
(C-2-ic)
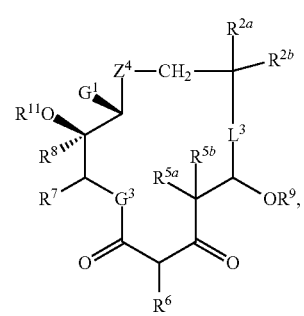
14-membered ring system
(C-2-id)
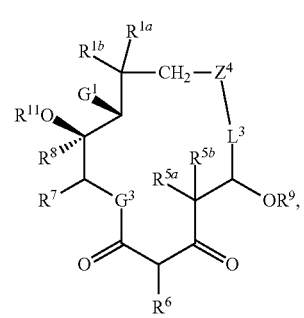
14-membered ring system
(C-2-ie)
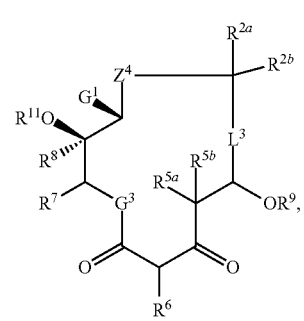
13-membered ring system
(C-2-if)
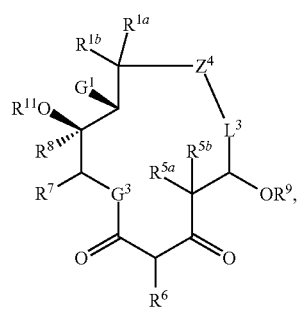
13-membered ring system
(C-3-ia)
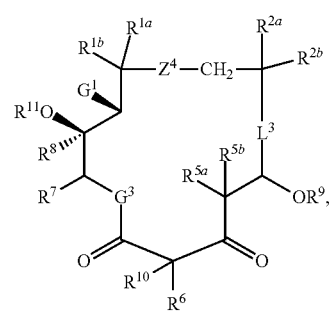
15-membered ring system
(C-3-ib)
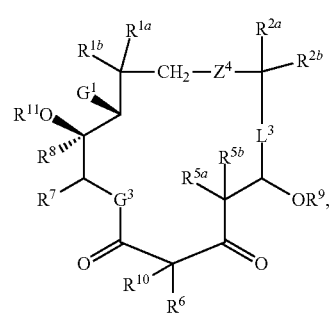
15-membered ring system
(C-3-ic)
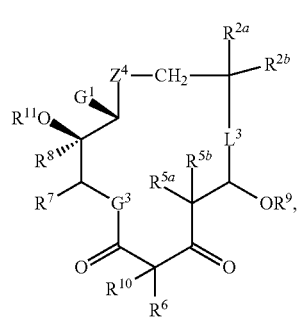
14-membered ring system

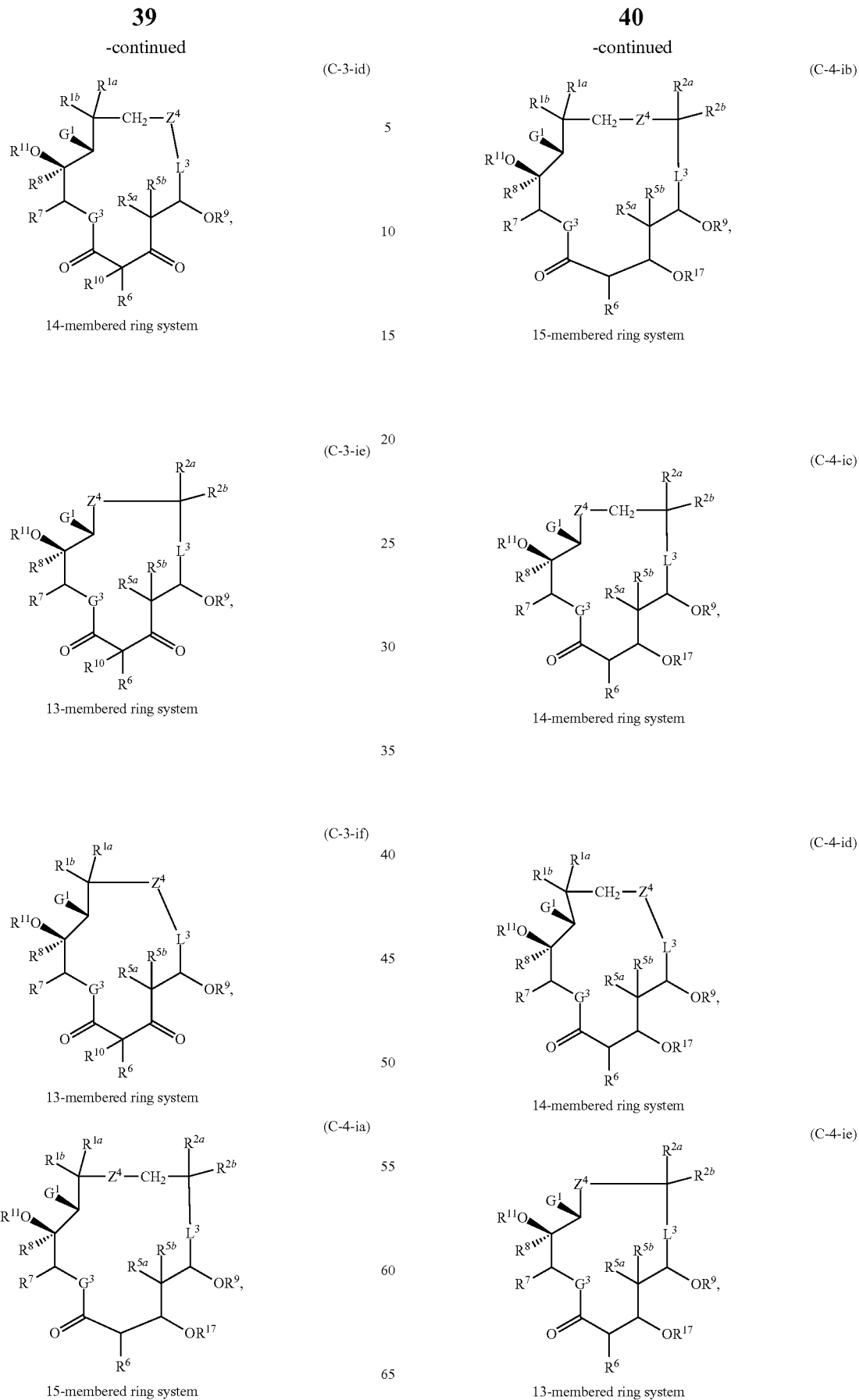

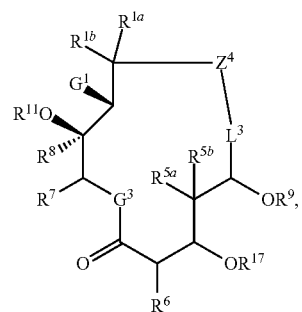
(C-4-if)
13-membered ring system
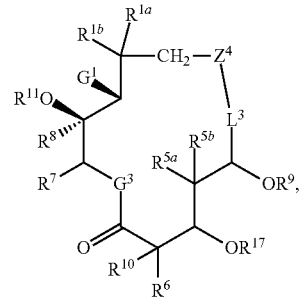
(C-5-id)
14-membered ring system
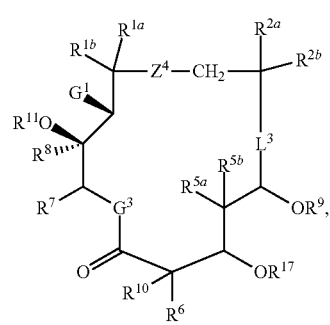
(C-5-ia)
15-membered ring system
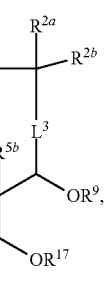
(C-5-ie)
13-membered ring system
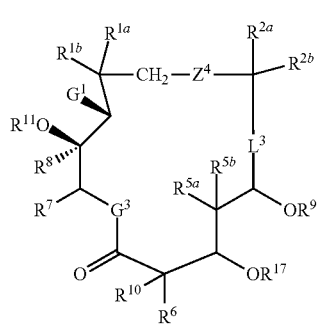
(C-5-ib)
15-membered ring system
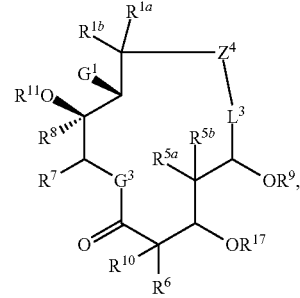
(C-5-if)
13-membered ring system
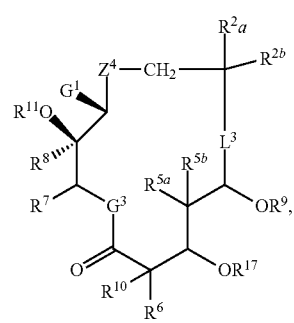
(C-5-ic)
14-membered ring system
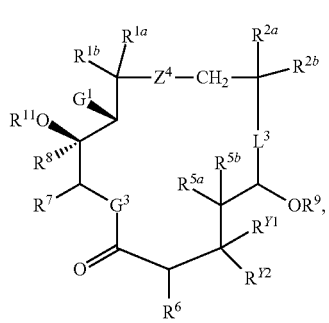
(C-467-ia)
15-membered ring system

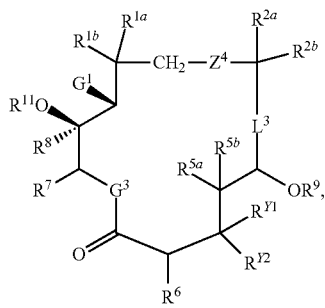
(C-467-ib)
15-membered ring system
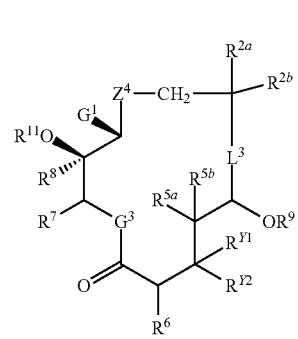
(C-467-ic)
14-membered ring system
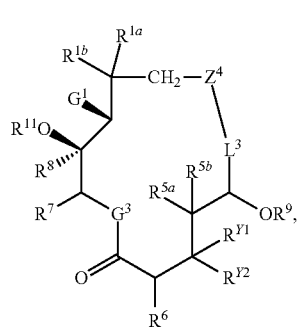
(C-467-id)
14-membered ring system
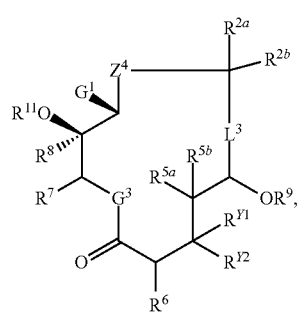
(C-467-ie)
13-membered ring system
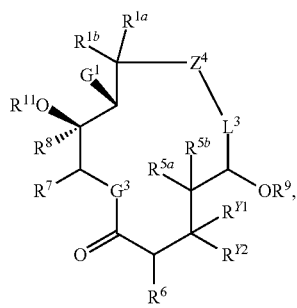
(C-467-if)
13-membered ring system
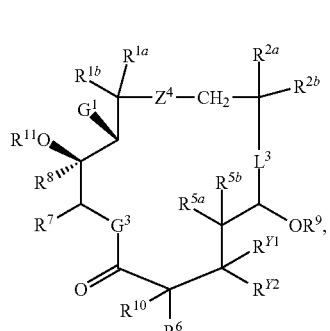
(C-567-ia)
15-membered ring system
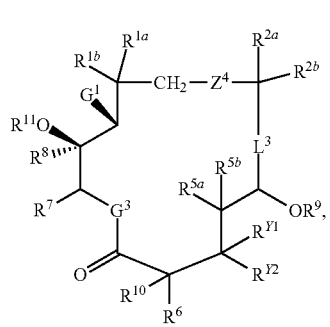
(C-567-ib)
15-membered ring system
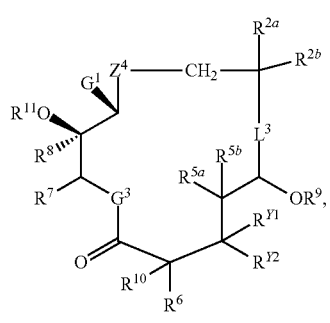
(C-567-ic)
14-membered ring system -continued

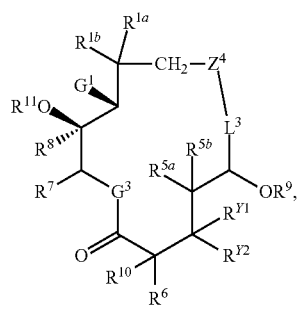
(C-567-id)
14-membered ring system

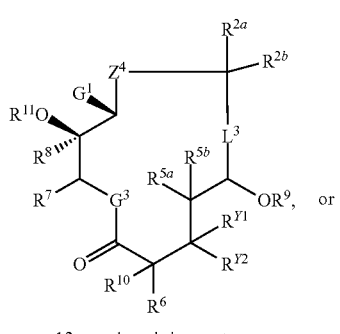
(C-567-ie)
13-membered ring system or

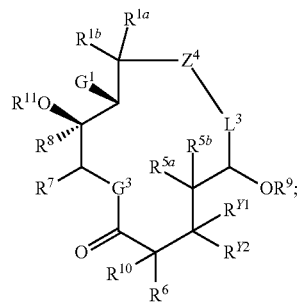
(C-567-if)
13-membered ring system wherein the macrolide is prepared by macrocyclization (e.g., thermally induced macrocyclization) of the coupled precursor of one of the formulae below, optionally followed by further synthetic manipulation, as described herein:

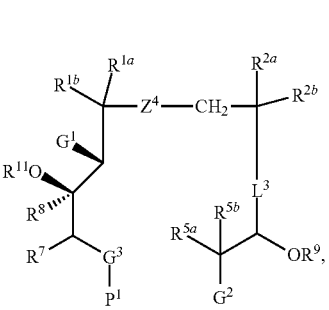
(C-1-ia)

-continued

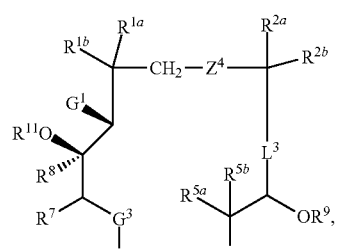
(C-1-ib)

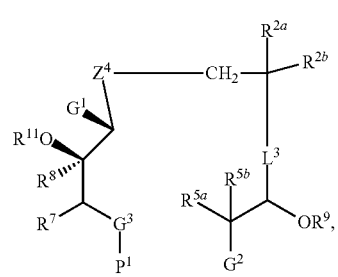
(C-1-ic)

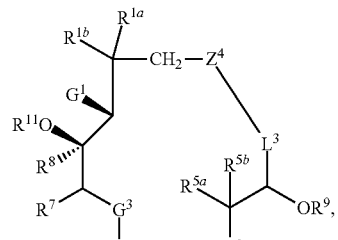
(C-1-id)

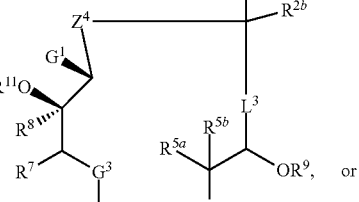
(C-1-ie)

or

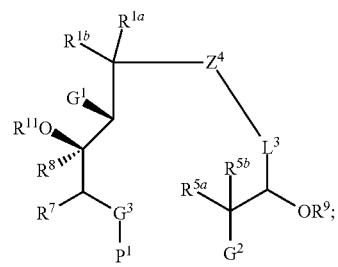
(C-1-if)

[2] an ester, thioester, or amide of formula:

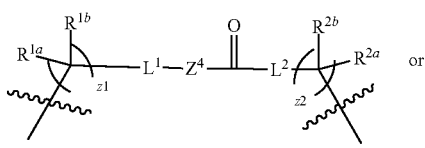

or

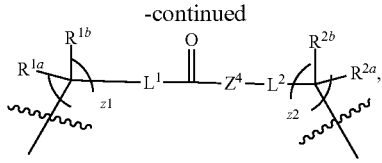
wherein $L^1$ and $L^2$ are each independently a bond or —CH$_2$—; z1 and z2 are each independently 0, 1, or 2, and $Z^4$ is —O—, —S—, or —NR$^{Z2}$—, e.g., to provide a 13-, 14-, 15- or 16-membered ring system, e.g., of formula:
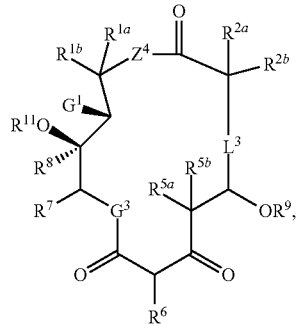
(C-2-iia)
15-membered ring system
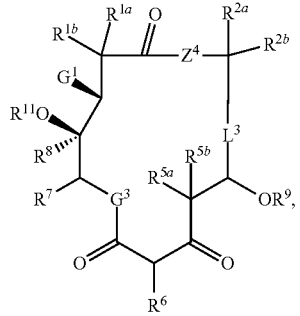
(C-2-iib)
15-membered ring system
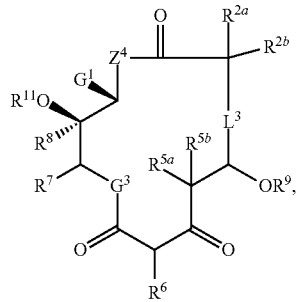
(C-2-iic)
14-membered ring system
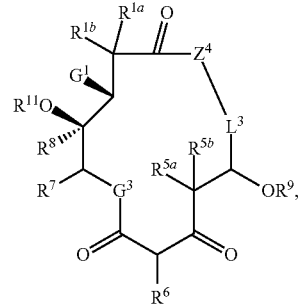
(C-2-iid)
14-membered ring system
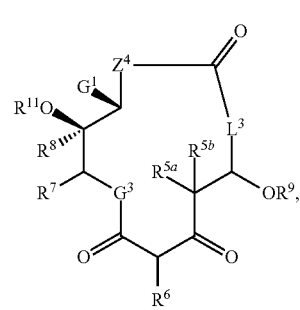
(C-2-iie)
13-membered ring system
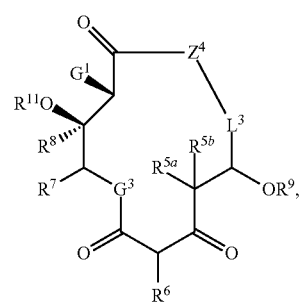
(C-2-iif)
13-membered ring system
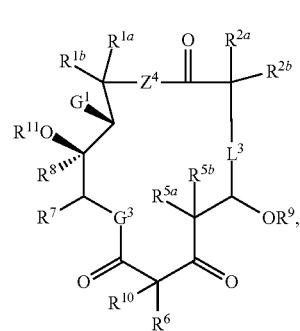
(C-3-iia)
15-membered ring system (C-3-iib)
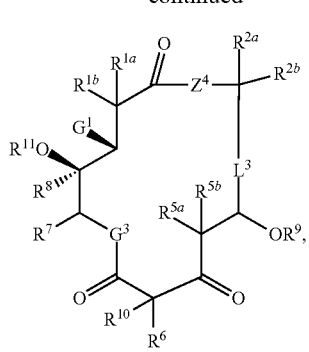
15-membered ring system
(C-3-iic)
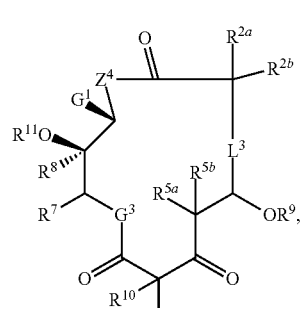
14-membered ring system
(C-3-iid)
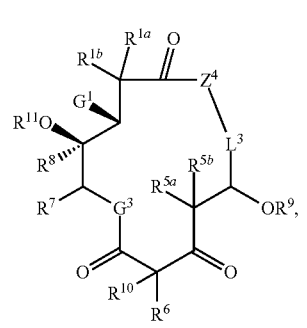
14-membered ring system
(C-3-iie)
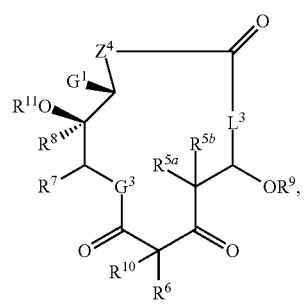
13-membered ring system
(C-3-iif)
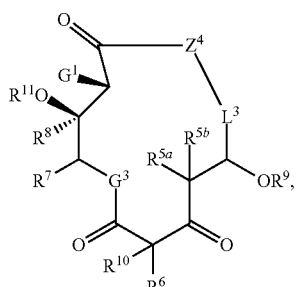
13-membered ring system
(C-4-iia)
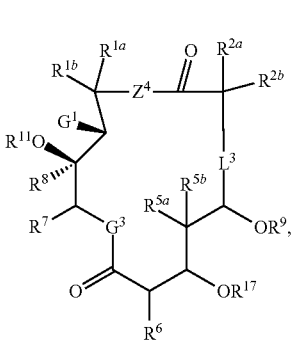
15-membered ring system
(C-4-iib)
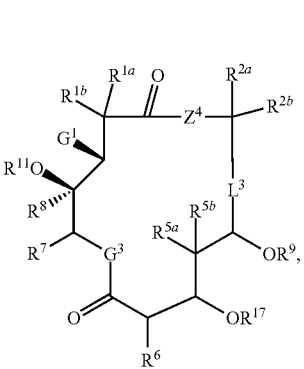
15-membered ring system
(C-4-iic)
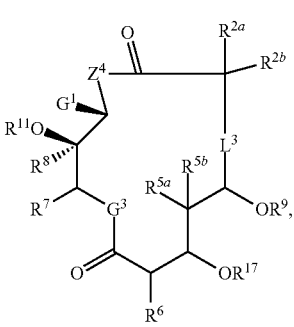
14-membered ring system -continued
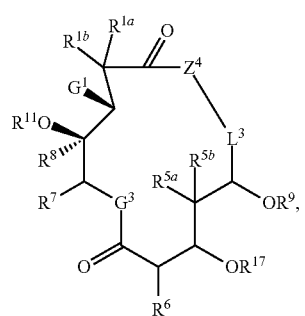
(C-4-iid)
14-membered ring system
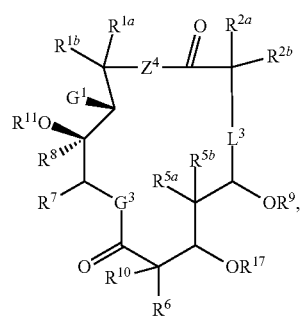
(C-5-iib)
15-membered ring system
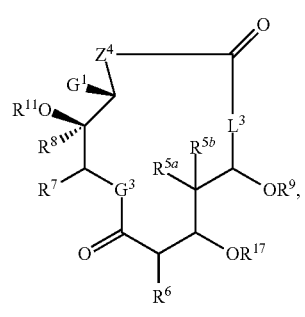
(C-4-iie)
13-membered ring system
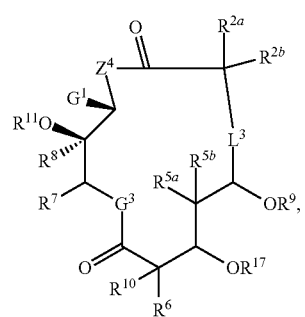
(C-5-iic)
14-membered ring system
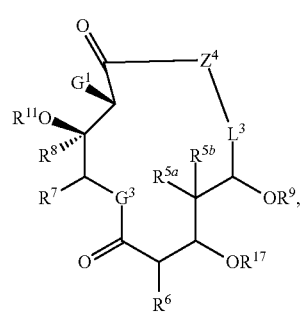
(C-4-iif)
13-membered ring system
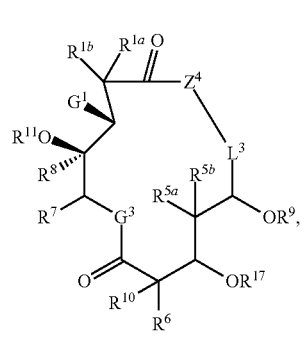
(C-5-iid)
14-membered ring system
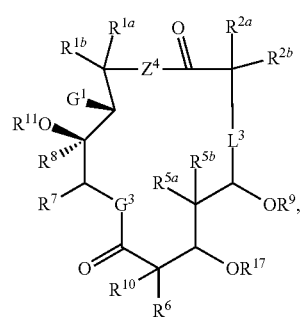
(C-5-iia)
15-membered ring system
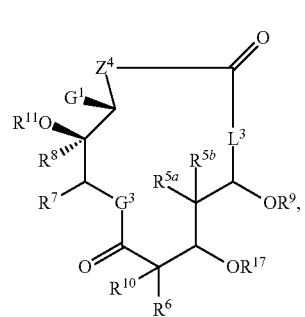
(C-5-iie)
13-membered ring system

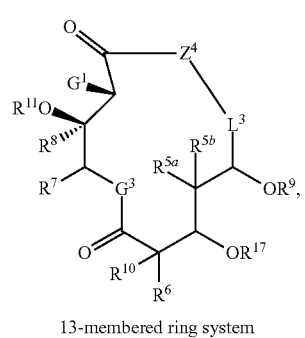
(C-5-iif)
13-membered ring system
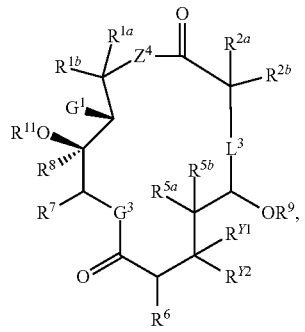
(C-467-iia)
15-membered ring system
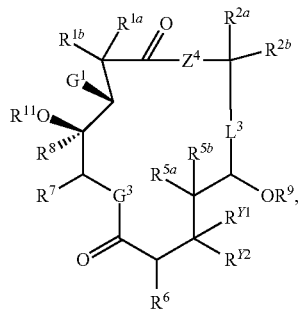
(C-467-iib)
15-membered ring system
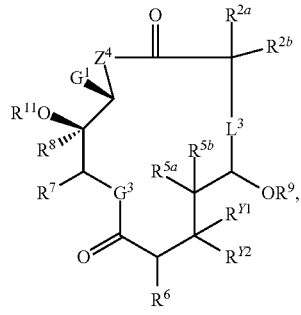
(C-467-iic)
14-membered ring system
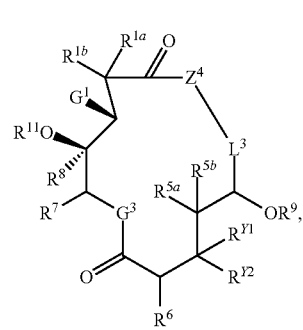
(C-467-iid)
14-membered ring system
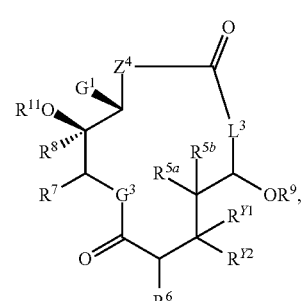
(C-467-iie)
13-membered ring system
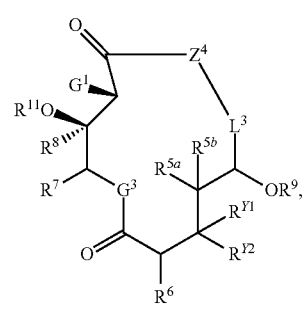
(C-467-iif)
13-membered ring system
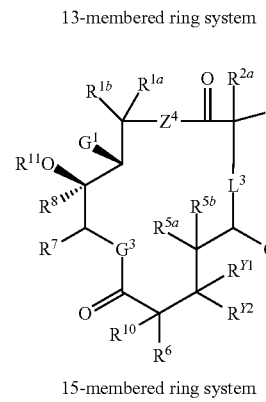
(C-567-iia)
15-membered ring system (C-567-iib)

15-membered ring system (C-567-iic)

14-membered ring system (C-567-iid)

14-membered ring system (C-567-iie)

13-membered ring system (C-567-iif)

13-membered ring system wherein in certain embodiments the macrolide is prepared from macrocyclization (e.g., thermally induced) of the coupled precursor compound of the below formula, optionally followed by further synthetic manipulation, as described herein:

(C-1-iia)

(C-1-iib)

(C-1-iic)

(C-1-iid)

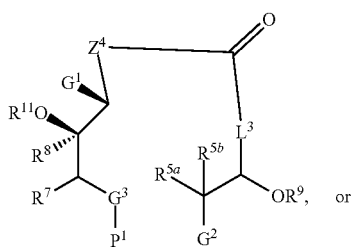
(C-1-iie)
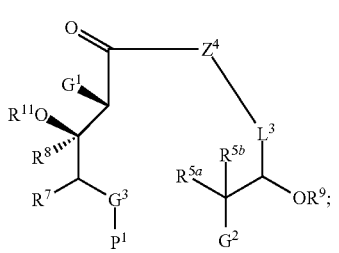
(C-1-iif)
[3] an ester, thioester, or amide of formula:
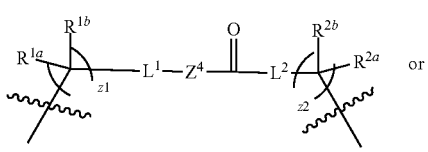
or
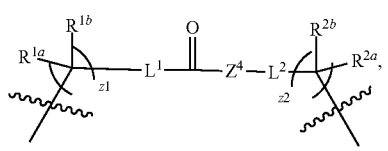
wherein $L^1$ and $L^2$ are each independently a bond or —CH$_2$—; z1 and z2 are each independently 0, 1, or 2, and $Z^4$ is —O—, —S—, or —NR$^{Z2}$—, e.g., to provide a 13-, 14-, 15- or 16-membered ring system, e.g., of formula:
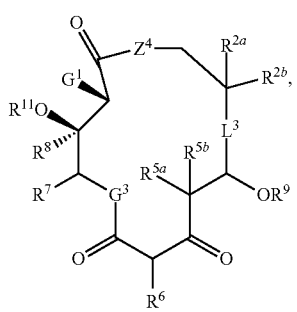
15-membered ring system
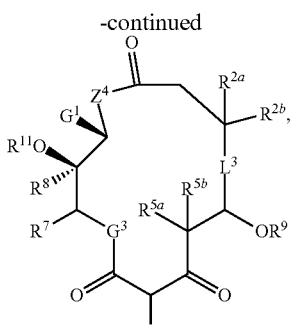
15-membered ring system
(C-2-xxc)
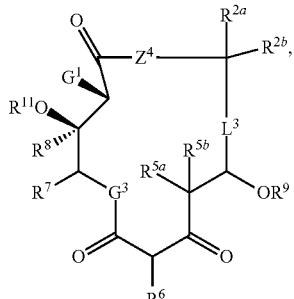
14-membered ring system
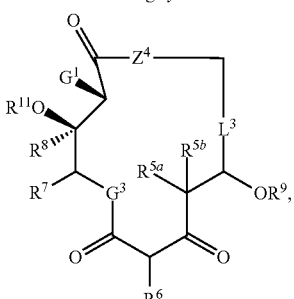
14-membered ring system
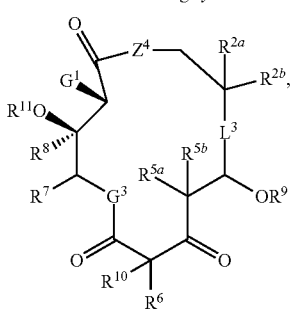
15-membered ring system
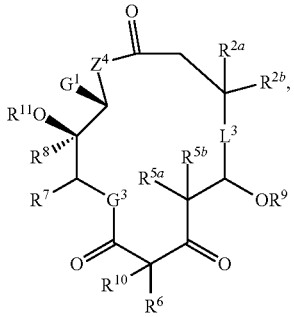
15-membered ring system -continued
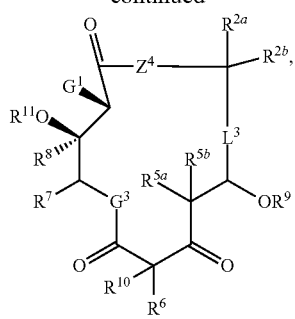
14-membered ring system
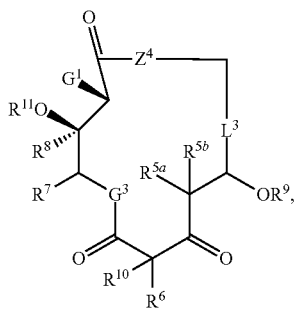
14-membered ring system
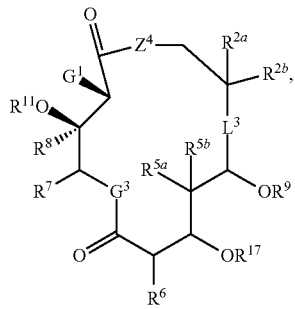
15-membered ring system
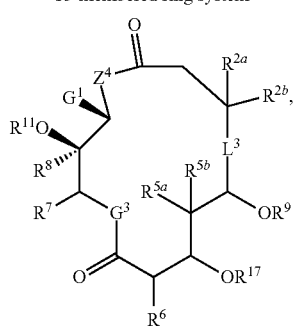
15-membered ring system
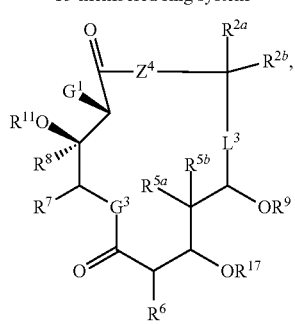
14-membered ring system
-continued
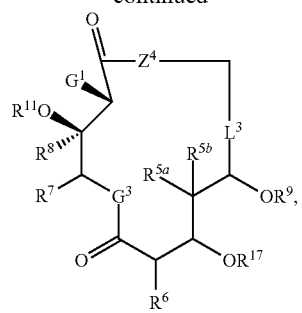
14-membered ring system
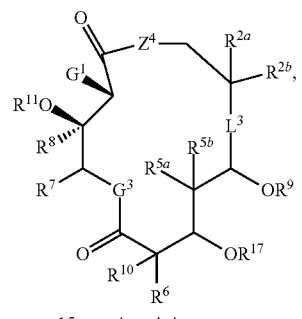
15-membered ring system
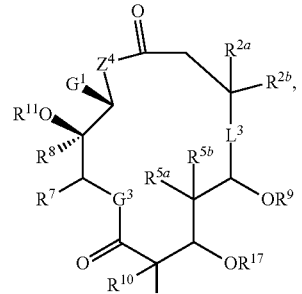
15-membered ring system
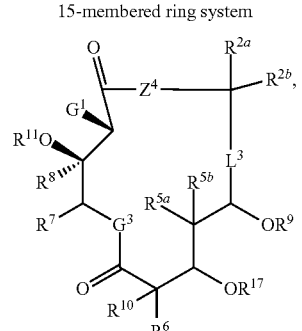
14-membered ring system
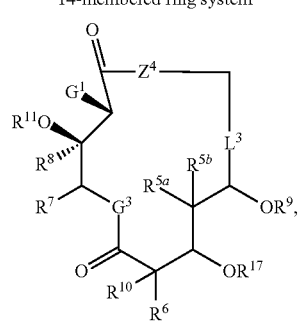
14-membered ring system

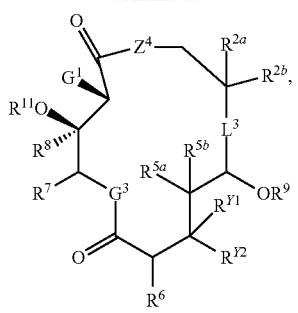

15-membered ring system

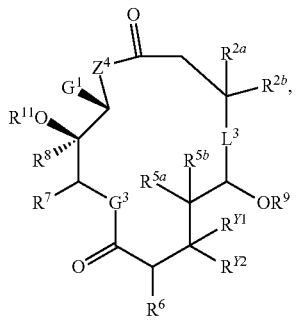

15-membered ring system

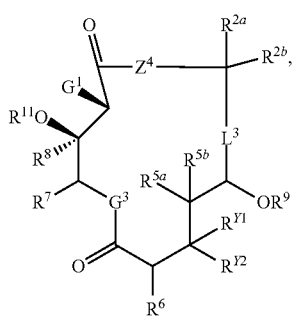

14-membered ring system

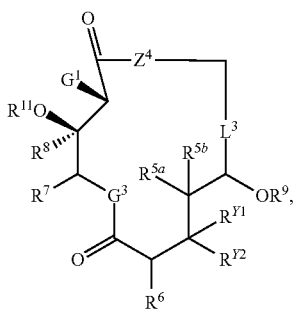

14-membered ring system

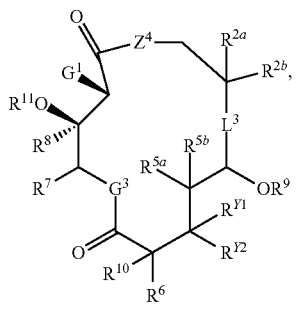

15-membered ring system

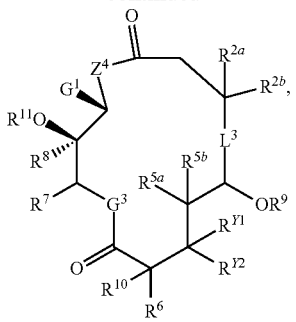

15-membered ring system

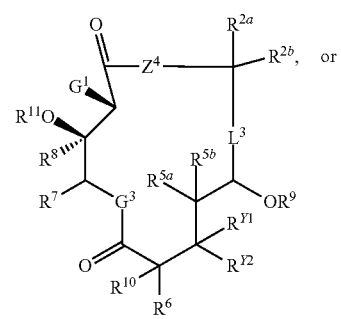

14-membered ring system

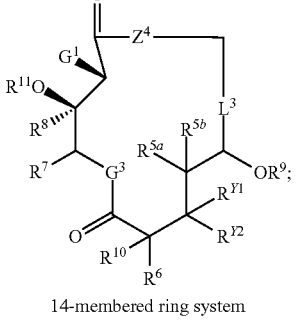

14-membered ring system wherein in certain embodiments the macrolide is prepared from macrocyclization (e.g., thermally induced) of the coupled precursor compound of the below formula, optionally followed by further synthetic manipulation, as described herein:

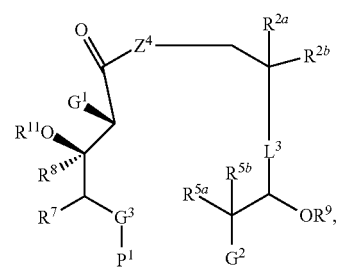

-continued
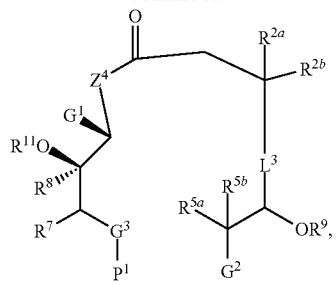
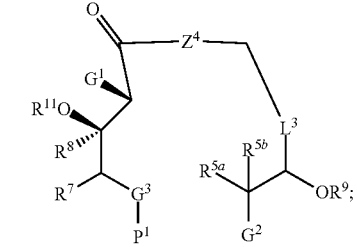
[4] an amine of formula:
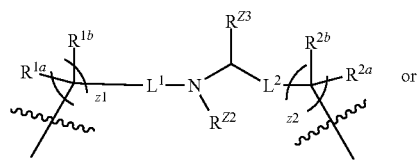
or
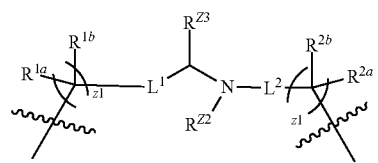
wherein $L^1$ and $L^2$ are each independently a bond or —$CH_2$—; z1 and z2 are 0, 1, or 2, e.g., to provide a 13-, 14-, 15- or 16-membered ring system, e.g., of formula:
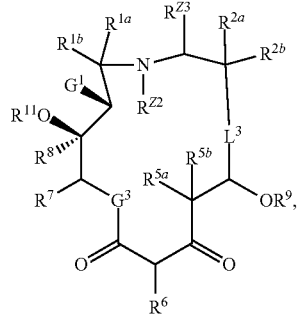
(C-2-iiia)
15-membered ring system
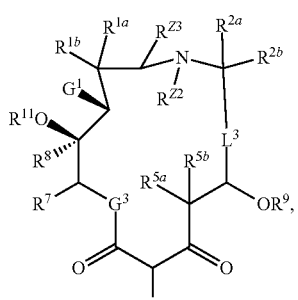
(C-2-iiib)
15-membered ring system
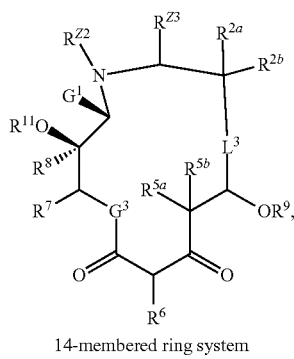
(C-2-iiic)
14-membered ring system
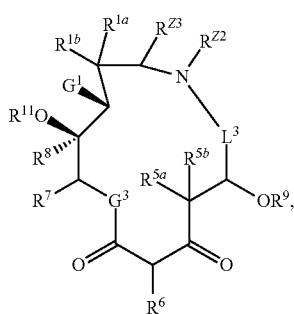
(C-2-iiid)
14-membered ring system

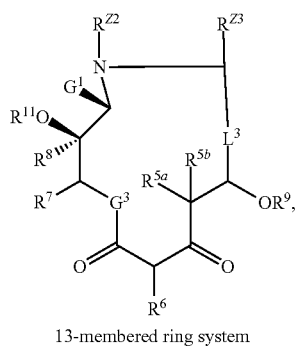
(C-2-iiie)
13-membered ring system
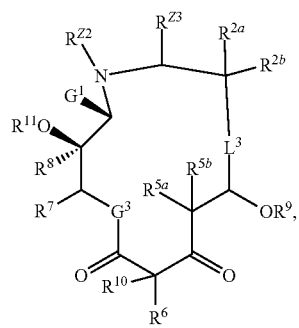
(C-3-iiic)
14-membered ring system
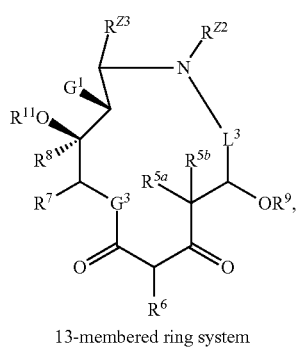
(C-2-iiif)
13-membered ring system
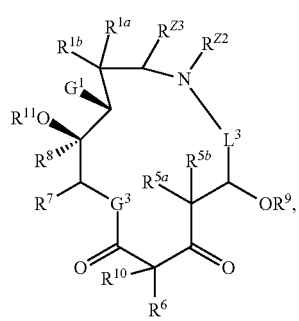
(C-3-iiid)
14-membered ring system
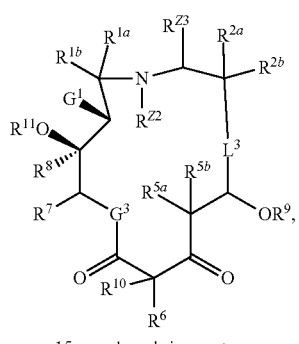
(C-3-iiia)
15-membered ring system
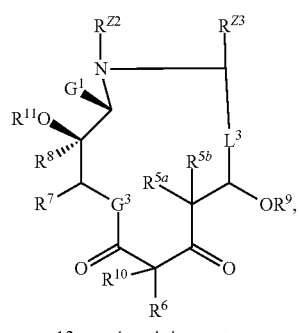
(C-3-iiie)
13-membered ring system
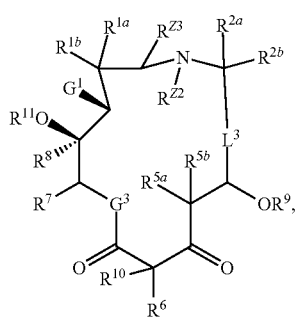
(C-3-iiib)
15-membered ring system
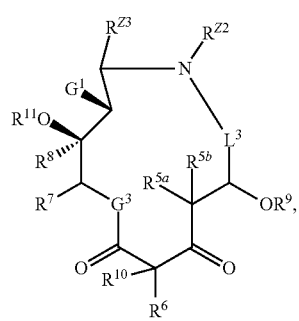
(C-3-iiif)
13-membered ring system -continued
(C-4-iiia)
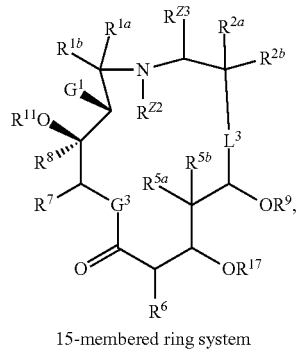
15-membered ring system
(C-4-iiib)
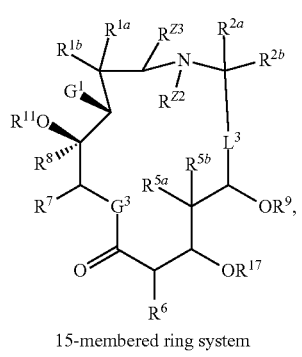
15-membered ring system
(C-4-iiic)
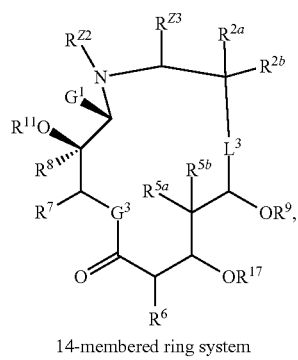
14-membered ring system
(C-4-iiid)
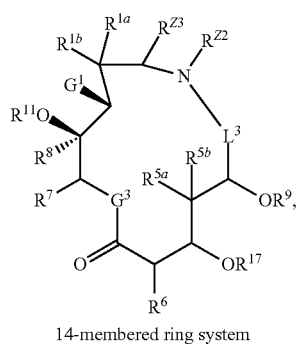
14-membered ring system
(C-4-iiie)
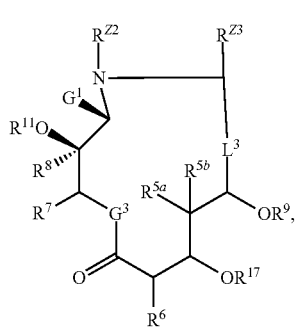
13-membered ring system
(C-4-iiif)
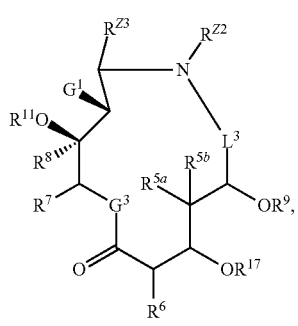
13-membered ring system
(C-5-iiia)
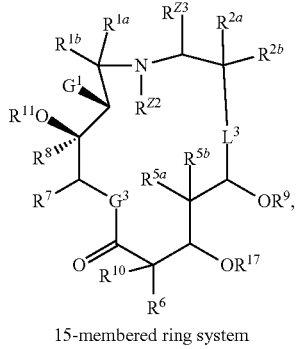
15-membered ring system
(C-5-iiib)
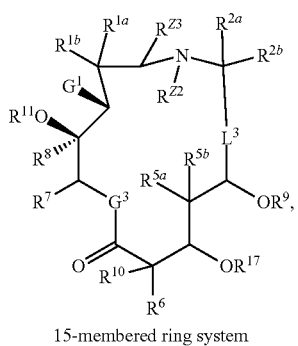
15-membered ring system (C-5-iiic)
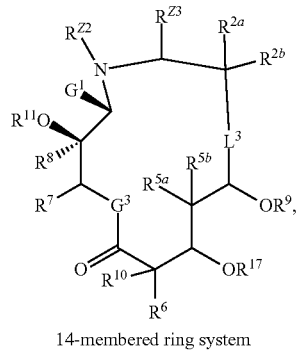
14-membered ring system
(C-5-iiid)
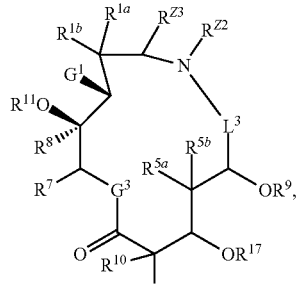
14-membered ring system
(C-5-iiie)
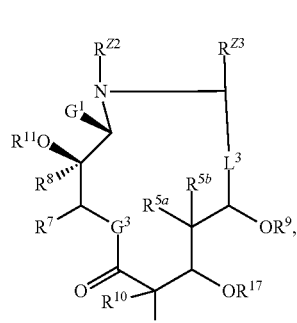
13-membered ring system
(C-5-iiif)
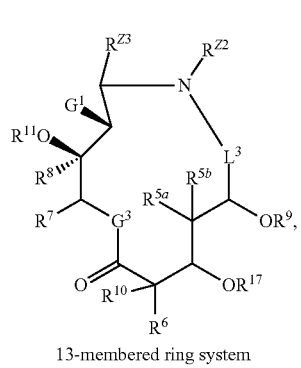
13-membered ring system
(C-467-iiia)
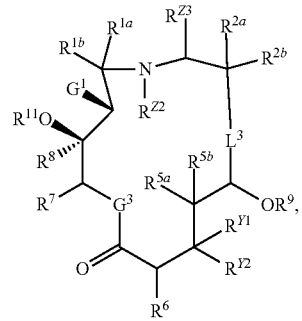
15-membered ring system
(C-467-iiib)
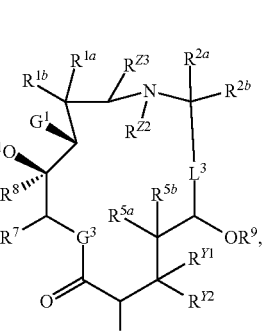
15-membered ring system
(C-467-iiic)
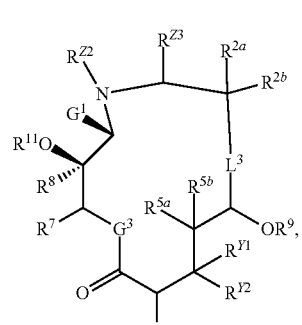
14-membered ring system
(C-467-iiid)
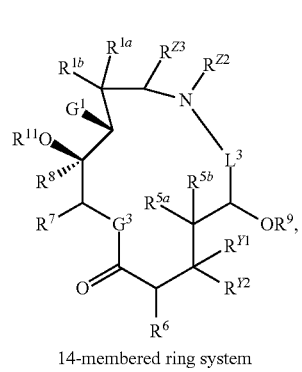
14-membered ring system (C-467-iiie)

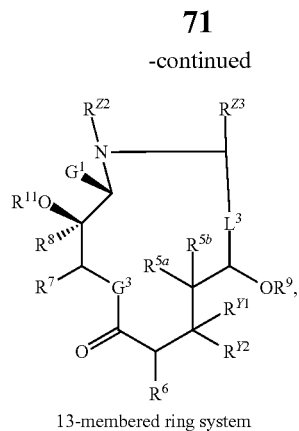

13-membered ring system (C-467-iiif)

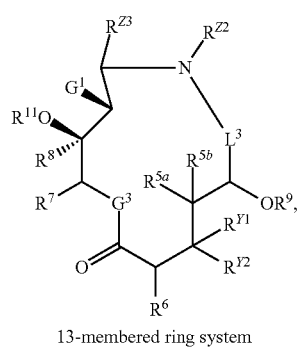

13-membered ring system (C-567-iiia)

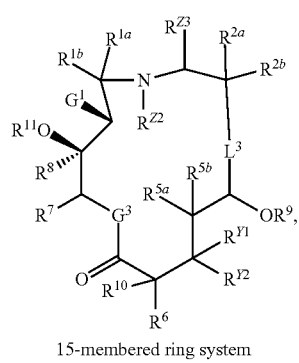

15-membered ring system (C-567-iiib)

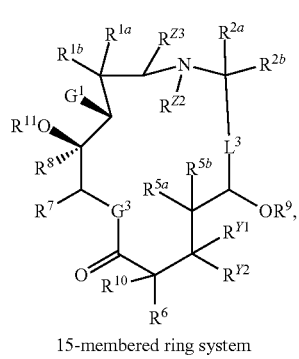

15-membered ring system (C-567-iiic)

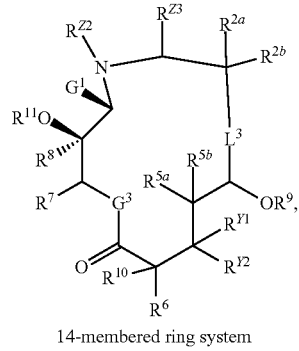

14-membered ring system (C-567-iiid)

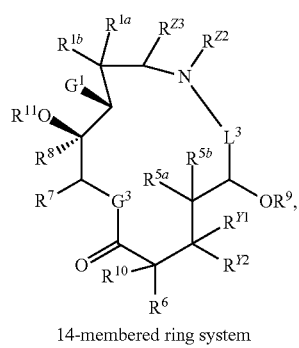

14-membered ring system (C-567-iiie)

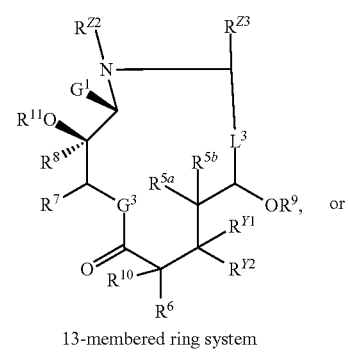

13-membered ring system (C-567-iiif)

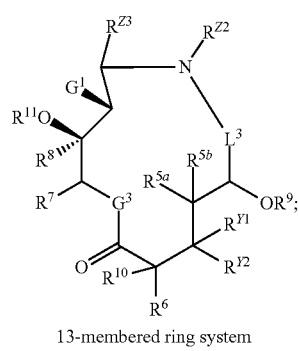

13-membered ring system wherein the macrolide is prepared from macrocyclization (e.g., thermally induced macrocyclization) of the coupled precursor of the below formula, optionally followed by further synthetic manipulation, as described herein:

(C-1-iiia)
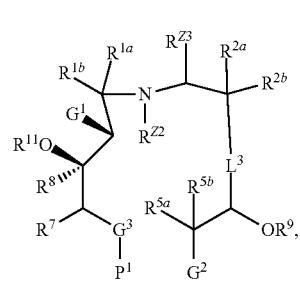
(C-1-iiib)
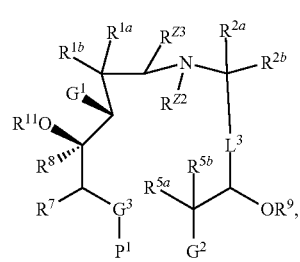
(C-1-iiic)
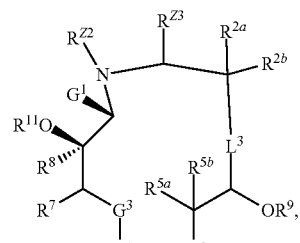
(C-1-iiid)
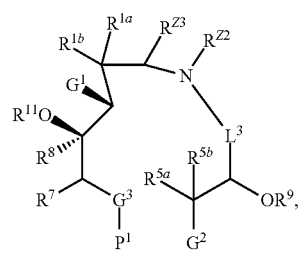
(C-1-iiie)
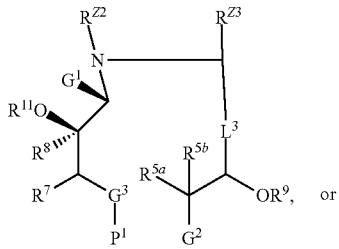
or
(C-1-iiif)
[5] an amine of Formula:
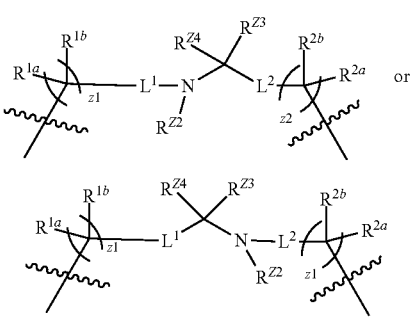
wherein $L^1$ and $L^2$ are each independently a bond or —CH$_2$—; z1 and z2 are each independently 0, 1, or 2, e.g., to provide a 13-, 14-, 15- or 16-membered ring system, e.g., of formula:
(C-2-iva)
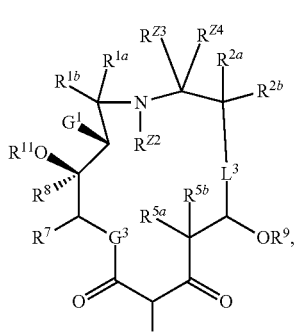
15-membered ring system
(C-2-ivb)
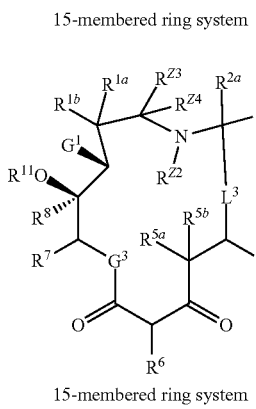
15-membered ring system
(C-2-ivc)
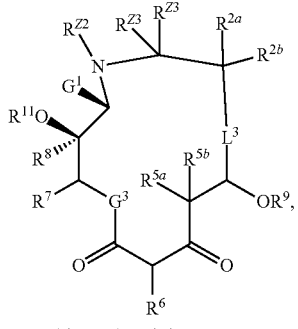
14-membered ring system -continued
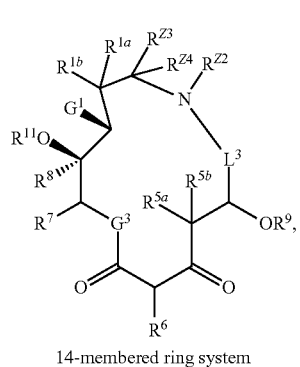
(C-2-ivd)
14-membered ring system
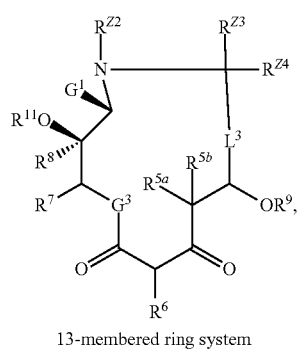
(C-2-ive)
13-membered ring system
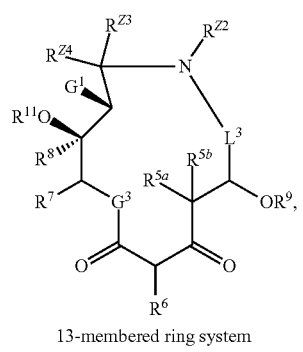
(C-2-ivf)
13-membered ring system
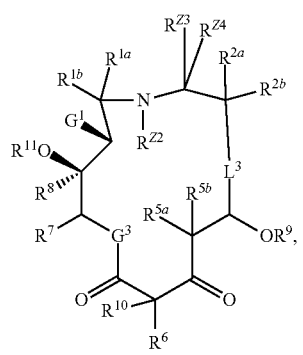
(C-3-iva)
15-membered ring system
-continued
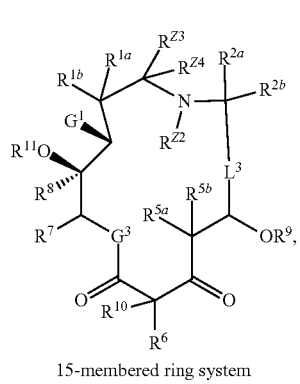
(C-3-ivb)
15-membered ring system
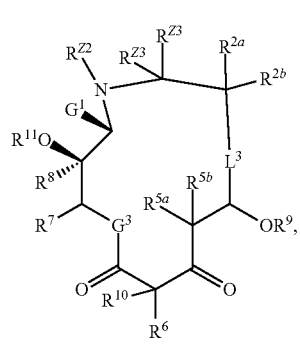
(C-3-ivc)
14-membered ring system
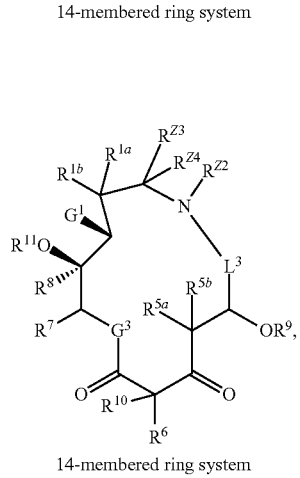
(C-3-ivd)
14-membered ring system
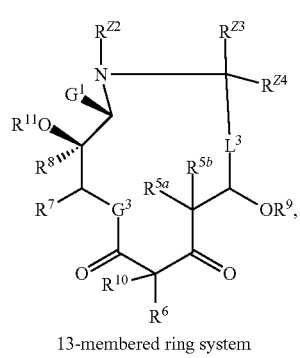
(C-3-ive)
13-membered ring system (C-3-ivf)
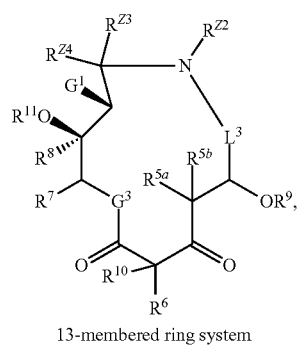
13-membered ring system
(C-4-iva)
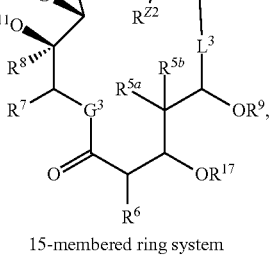
15-membered ring system
(C-4-ivb)
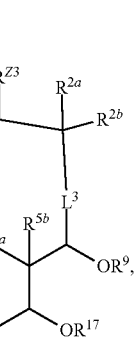
15-membered ring system
(C-4-ivc)
14-membered ring system
(C-4-ivd)
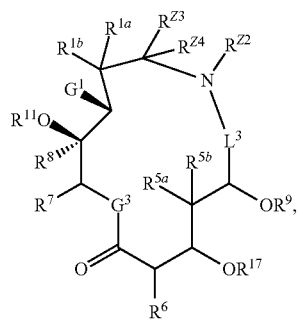
14-membered ring system
(C-4-ive)
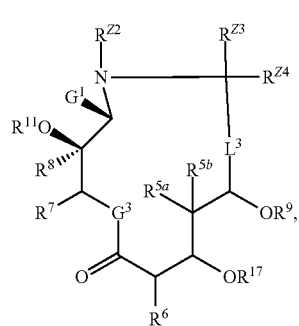
13-membered ring system
(C-4-ivf)
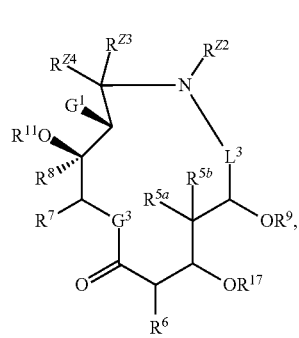
13-membered ring system
(C-5-iva)
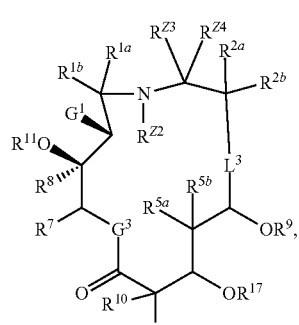
15-membered ring system

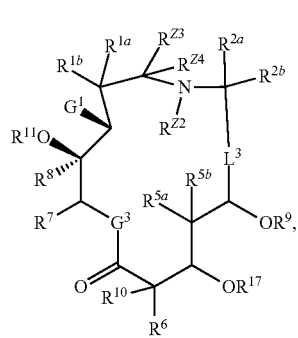
(C-5-ivb)
15-membered ring system
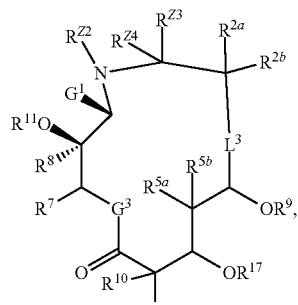
(C-5-ivc)
14-membered ring system
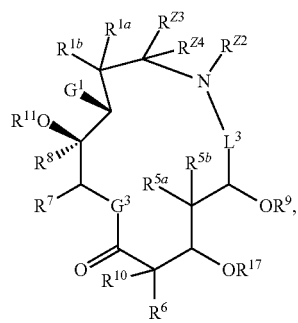
(C-5-ivd)
14-membered ring system
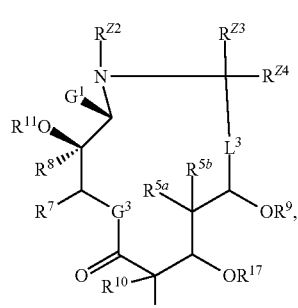
(C-5-ive)
13-membered ring system
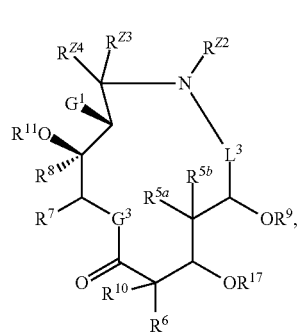
(C-5-ivf)
13-membered ring system
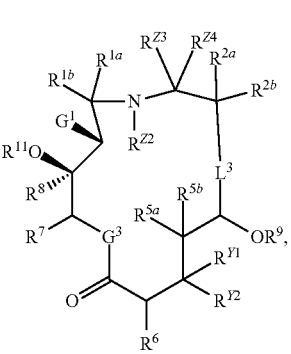
(C-467-iva)
15-membered ring system
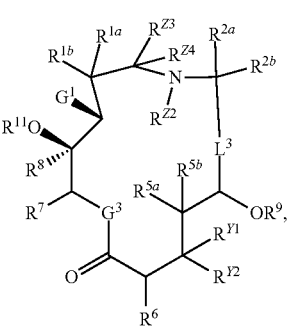
(C-467-ivb)
15-membered ring system
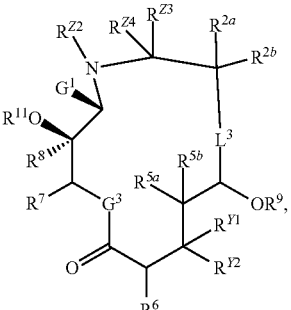
(C-467-ivc)
14-membered ring system

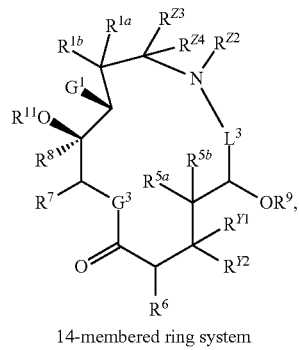
(C-467-ivd)
14-membered ring system
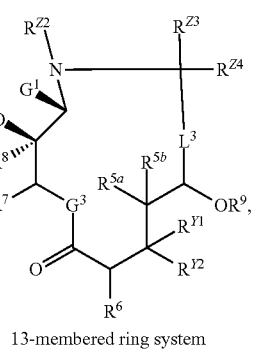
(C-467-ive)
13-membered ring system
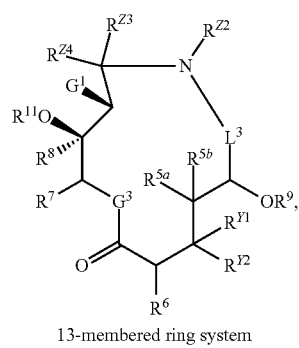
(C-467-ivf)
13-membered ring system
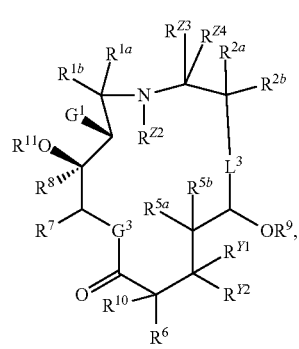
(C-567-iva)
15-membered ring system
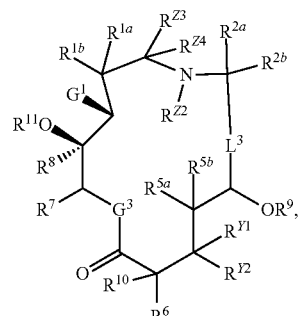
(C-567-ivb)
15-membered ring system
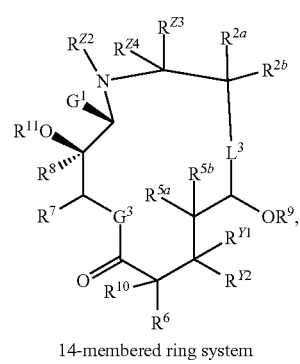
(C-567-ivc)
14-membered ring system
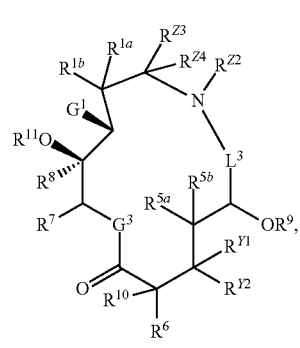
(C-567-ivd)
14-membered ring system
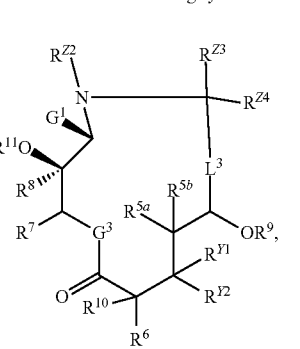
(C-567-ive)
13-membered ring system, or (C-567-ivf)

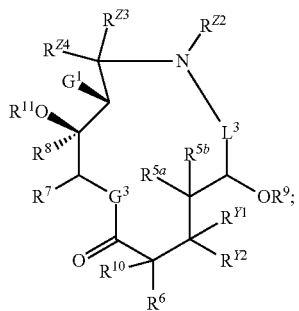
13-membered ring system wherein in certain embodiments the macrolide is prepared, in part, from macrocyclization (e.g., thermally induced macrocyclization) of the coupled precursor compound of the below formula, optionally followed by further synthetic manipulation, as described herein:

(C-1-iva)

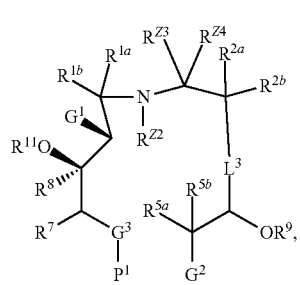

(C-1-ivb)

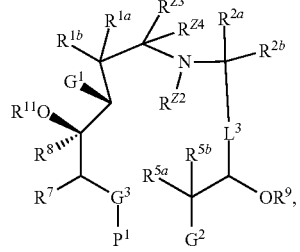

(C-1-ivc)

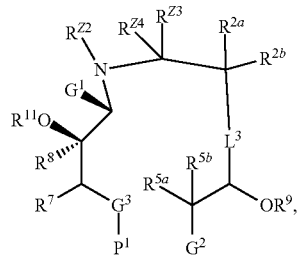

(C-1-ivd)

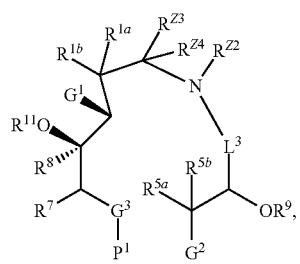

(C-1-ive)

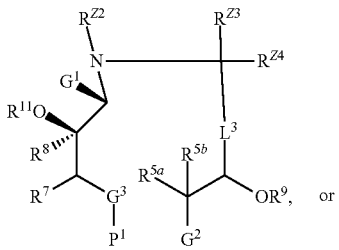

or (C-1-ivf)

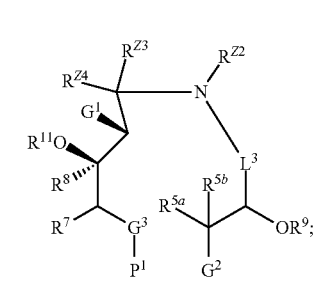

[6] an amine of formula:

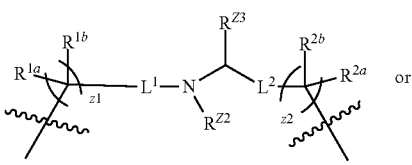

or

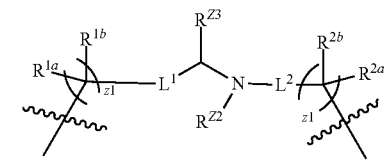

wherein $L^1$ and $L^2$ are each independently a bond and z1 and z2 are 1 or 2, e.g., to provide a ring system of formula:

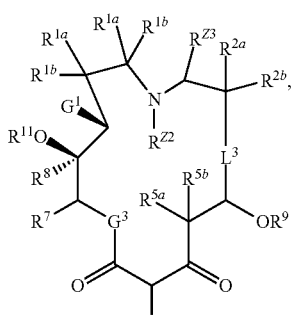
16-membered ring system

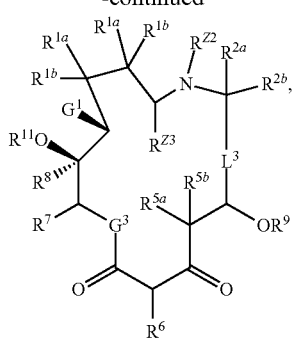
16-membered ring system
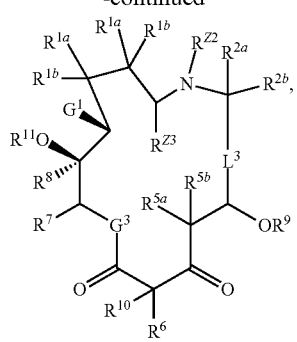
16-membered ring system
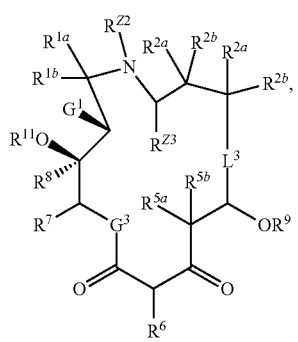
16-membered ring system
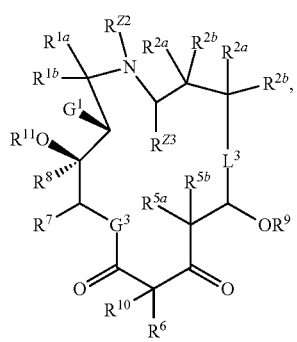
16-membered ring system
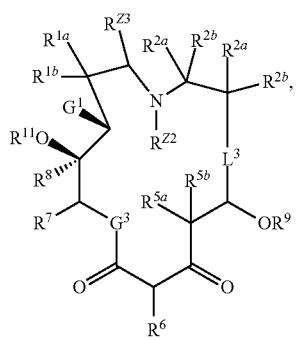
16-membered ring system
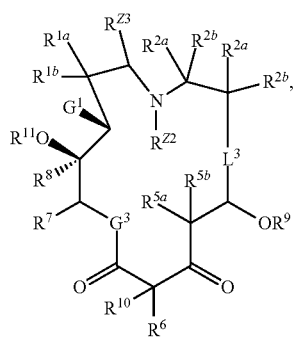
16-membered ring system
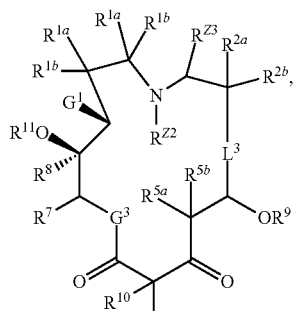
16-membered ring system
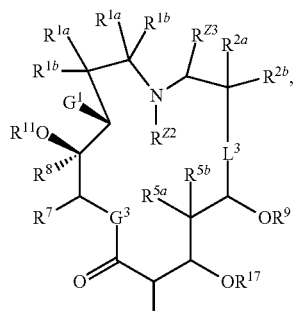
16-membered ring system -continued
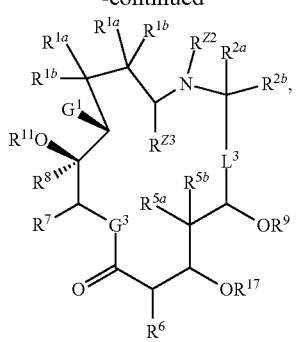
16-membered ring system
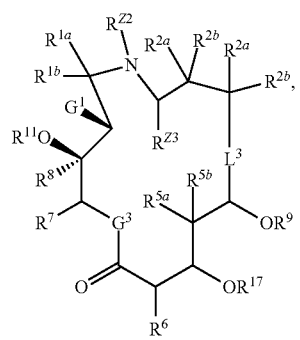
16-membered ring system
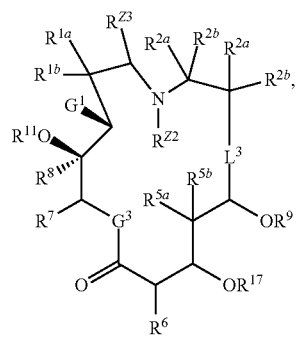
16-membered ring system
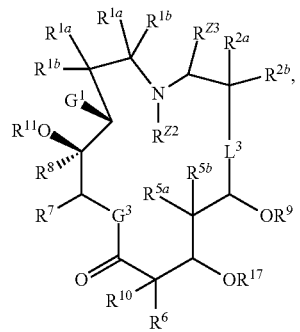
16-membered ring system
-continued
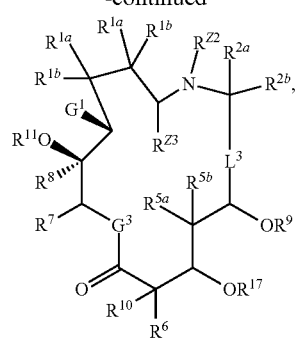
16-membered ring system
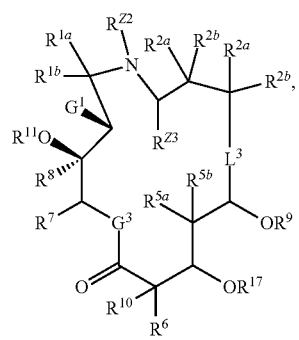
16-membered ring system
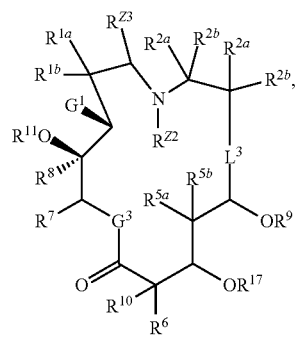
16-membered ring system
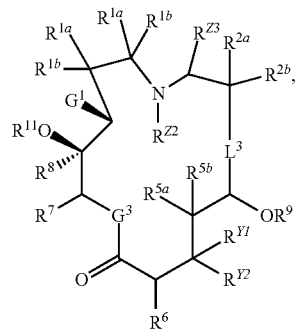
16-membered ring system


16-membered ring system

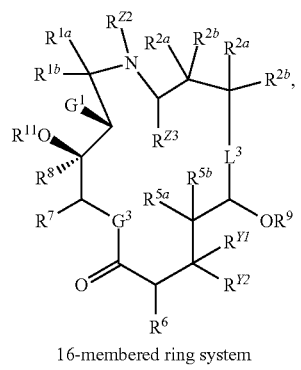

16-membered ring system

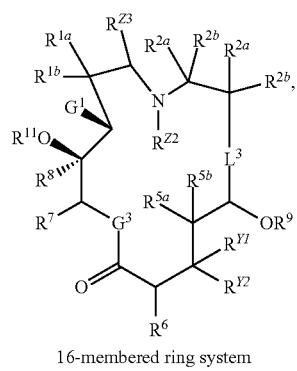

16-membered ring system

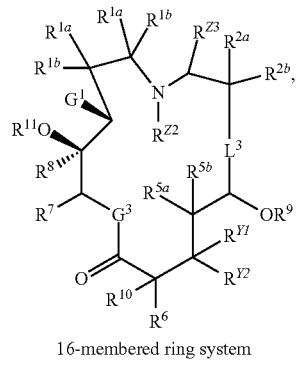

16-membered ring system


16-membered ring system

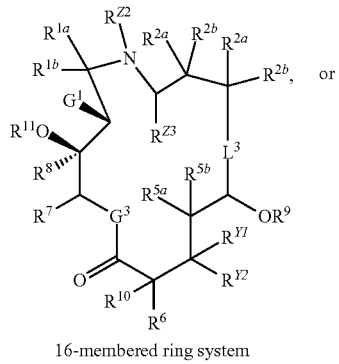

16-membered ring system

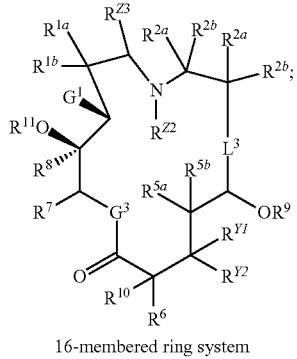

16-membered ring system wherein the macrolide is prepared from macrocyclization (e.g., thermally induced macrocyclization) of the coupled precursor of the below formula, optionally followed by further synthetic manipulation, as described herein:

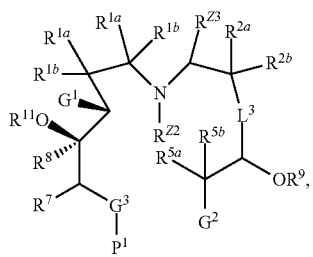

-continued
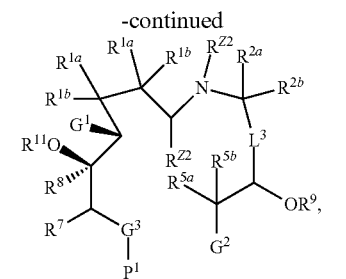
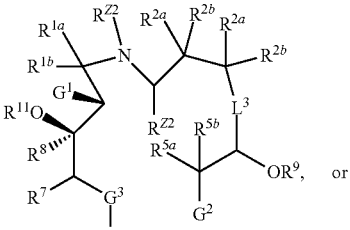
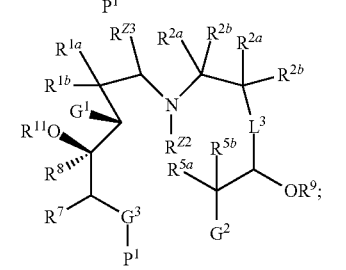
[7] an amine of formula:
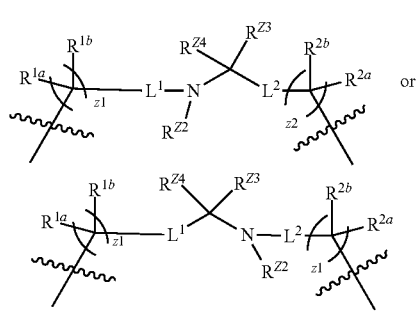
wherein $L^1$ and $L^2$ are each independently a bond and z1 and z2 are each independently 1 or 2 to provide a ring system of formula:
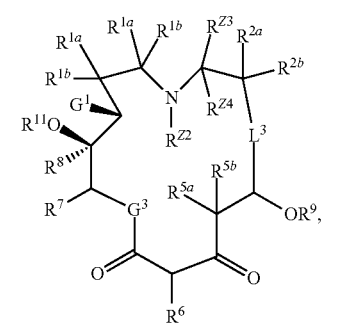
16-membered ring system
-continued
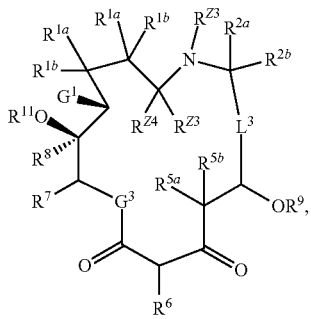
16-membered ring system
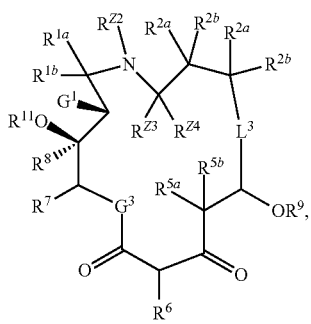
16-membered ring system
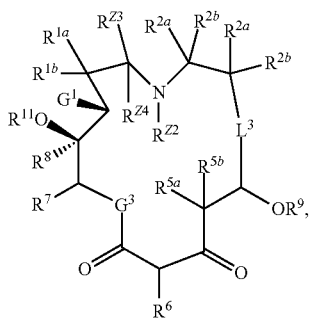
16-membered ring system
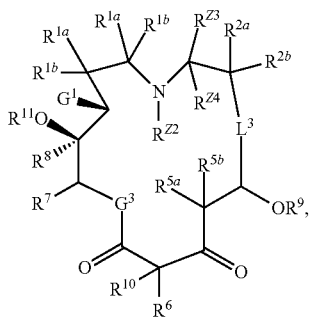
16-membered ring system -continued
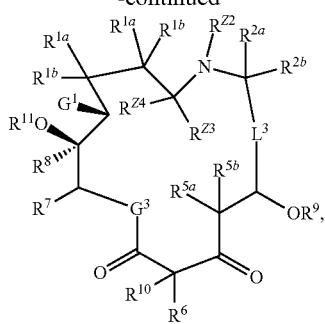
16-membered ring system
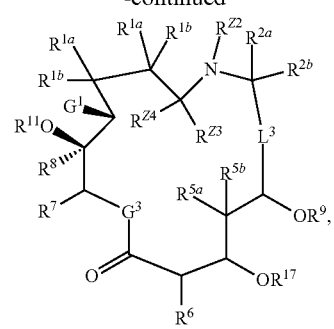
16-membered ring system
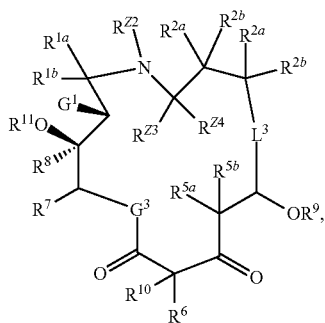
16-membered ring system
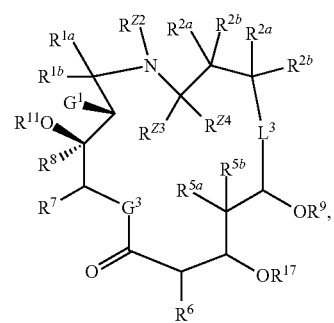
16-membered ring system
16-membered ring system
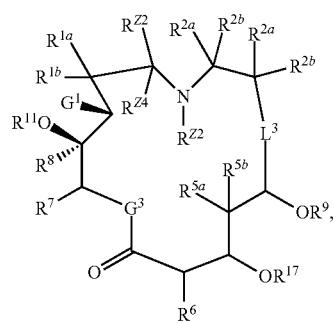
16-membered ring system
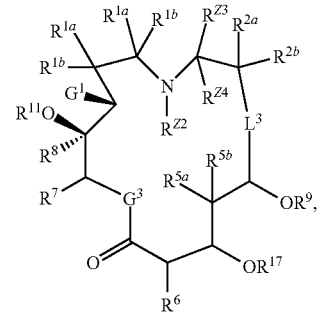
16-membered ring system
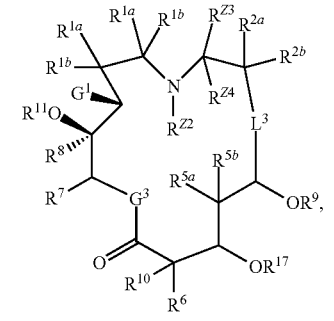
16-membered ring system -continued
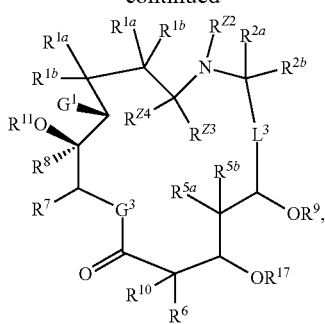
16-membered ring system
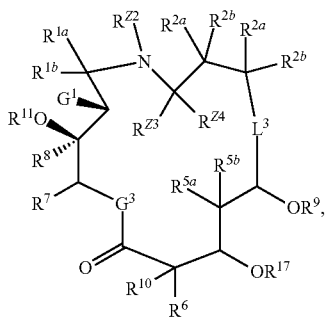
16-membered ring system
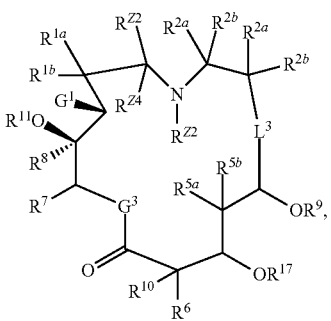
16-membered ring system
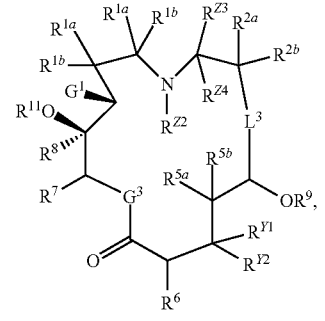
16-membered ring system
-continued
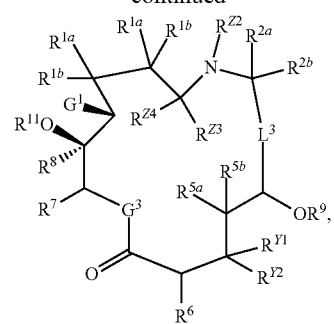
16-membered ring system
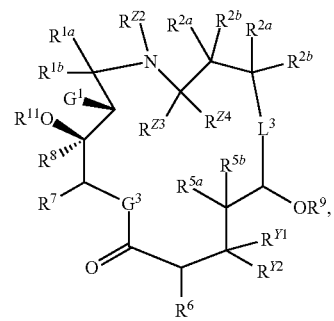
16-membered ring system
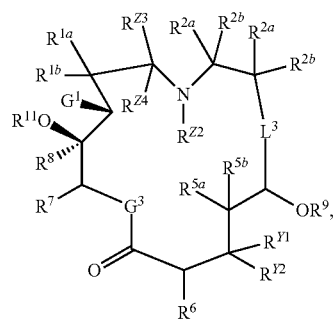
16-membered ring system
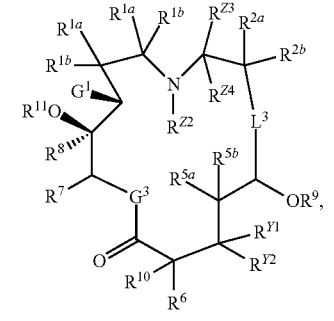
16-membered ring system

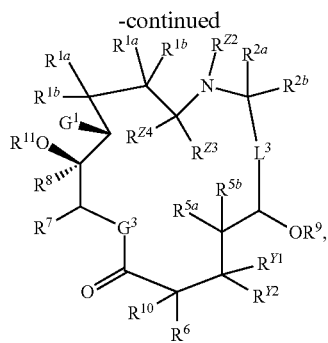

16-membered ring system

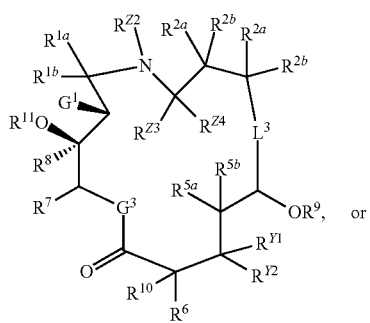

16-membered ring system

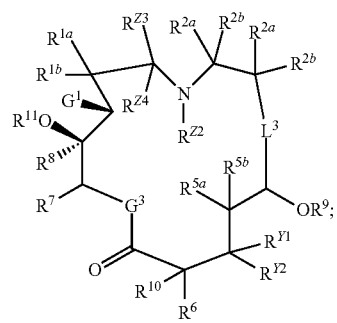

16-membered ring system wherein in certain embodiments the macrolide is prepared, in part, from macrocyclization (e.g., thermally induced macrocyclization) of the coupled precursor compound of the below formula, optionally followed by further synthetic manipulation, as described herein:

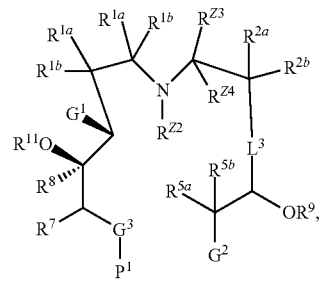

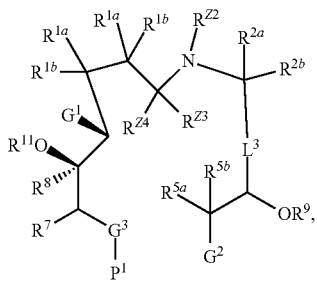

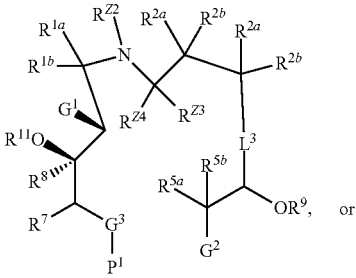

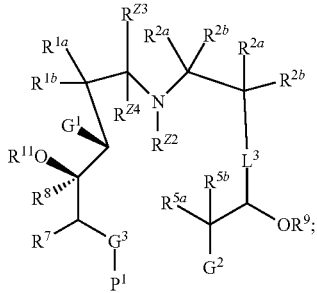

[8] an amine of Formula:

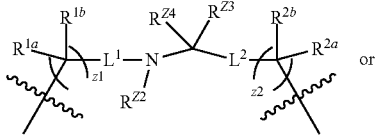

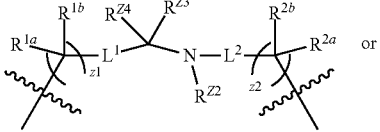

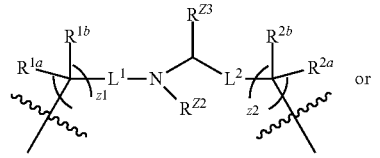

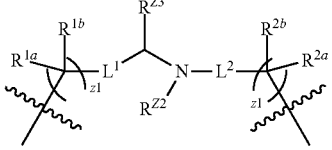

wherein $L^1$ and $L^2$ are each independently a bond or —$CH_2$—; z1 and z2 are each independently 0, 1, or 2, e.g., to provide a ring system of any one of formula:

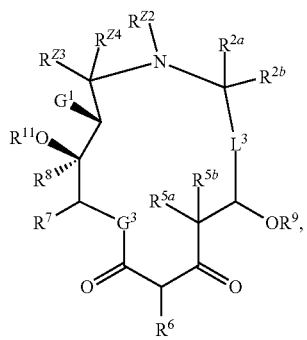
14-membered ring system
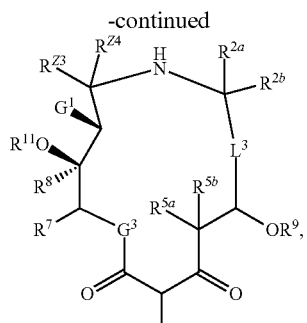
14-membered ring system

-continued

14-membered ring system
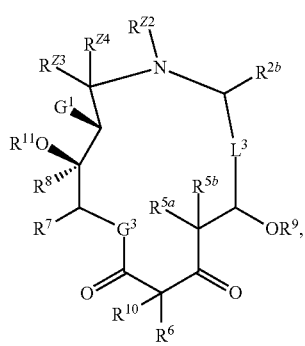
14-membered ring system
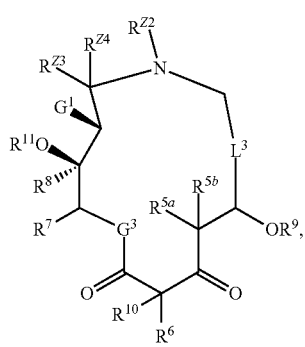
14-membered ring system
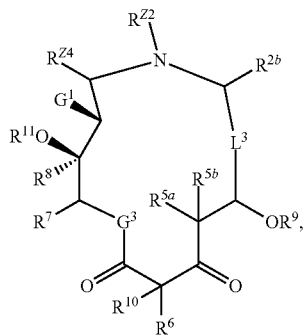
14-membered ring system
-continued
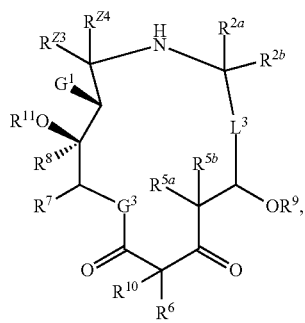
14-membered ring system
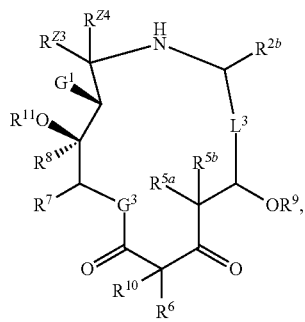
14-membered ring system
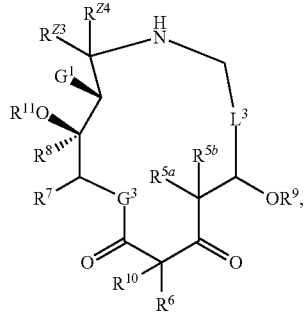
14-membered ring system
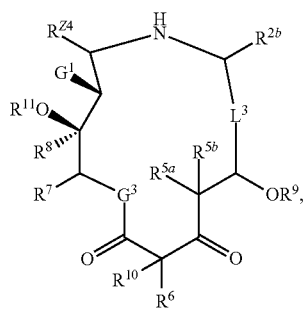
14-membered ring system -continued

14-membered ring system
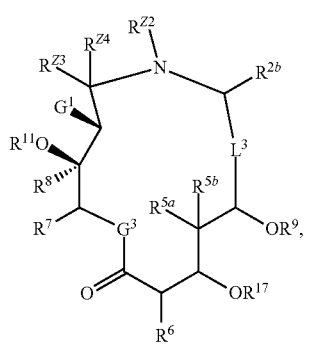
14-membered ring system
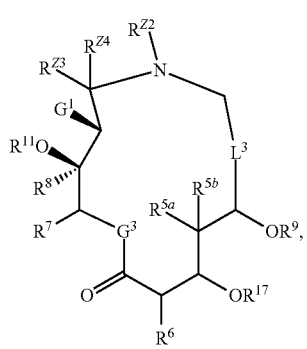
14-membered ring system
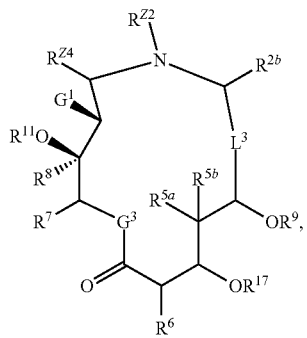
14-membered ring system
-continued
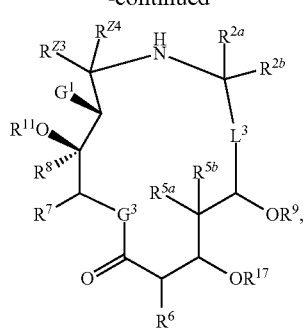
14-membered ring system
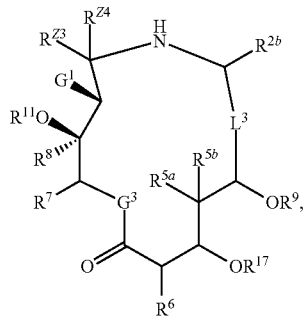
14-membered ring system
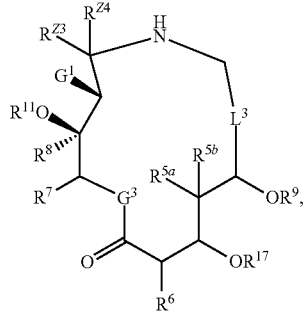
14-membered ring system
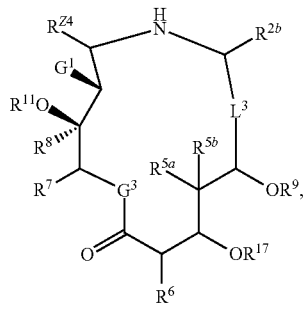
14-membered ring system

14-membered ring system
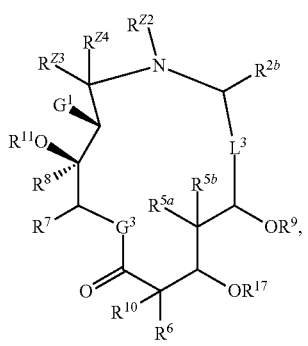
14-membered ring system
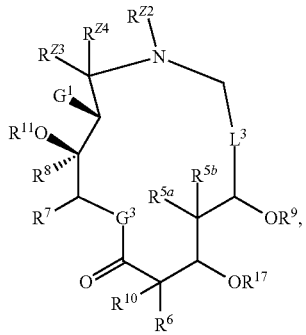
14-membered ring system
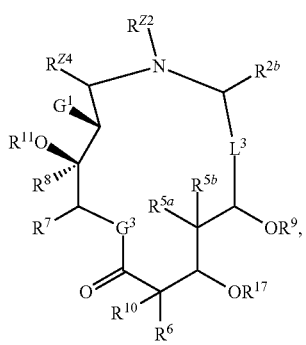
14-membered ring system
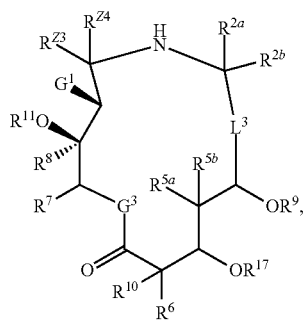
14-membered ring system
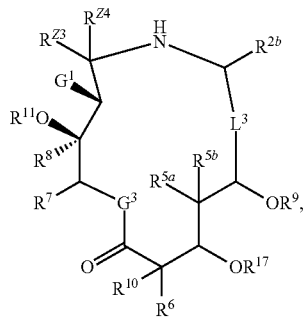
14-membered ring system
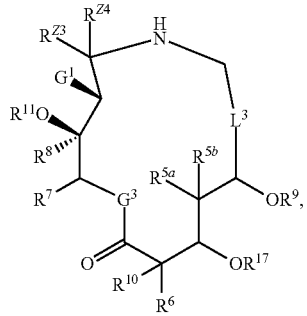
14-membered ring system
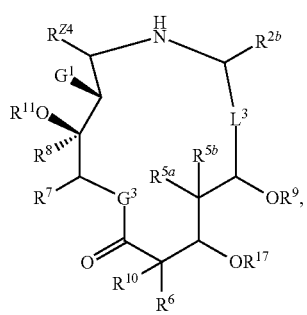
14-membered ring system 107
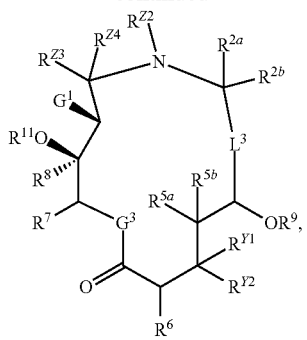
14-membered ring system
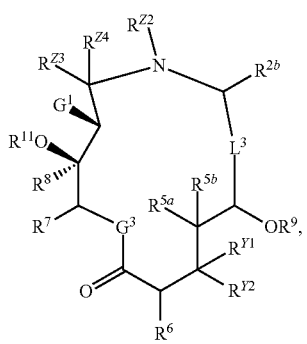
14-membered ring system
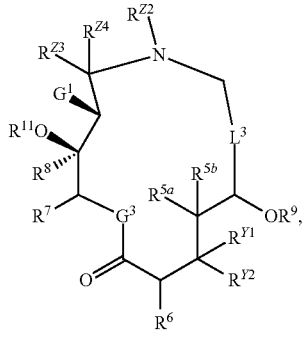
14-membered ring system
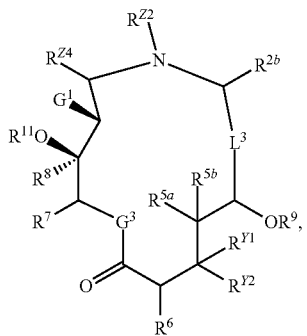
14-membered ring system
108
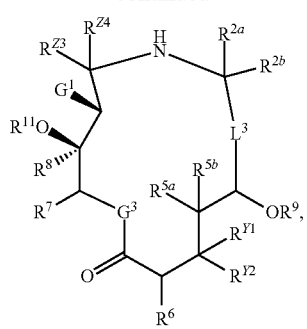
14-membered ring system
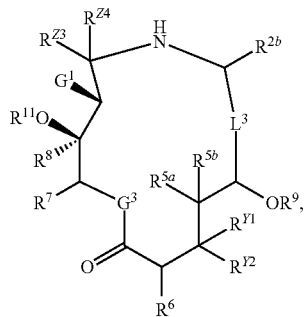
14-membered ring system
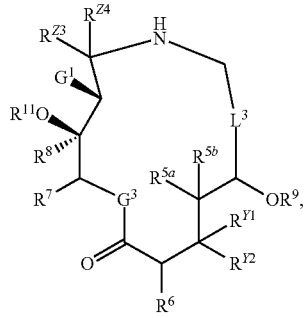
14-membered ring system
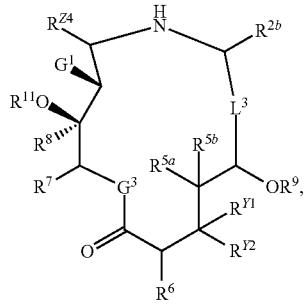
14-membered ring system

109

-continued


14-membered ring system

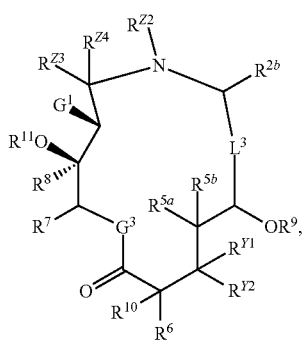

14-membered ring system

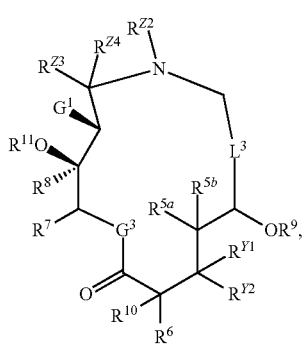

14-membered ring system

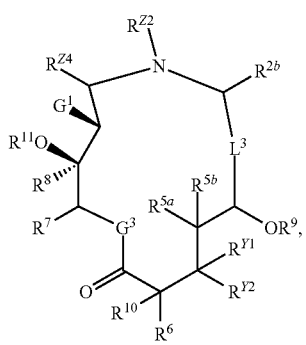

14-membered ring system

110

-continued

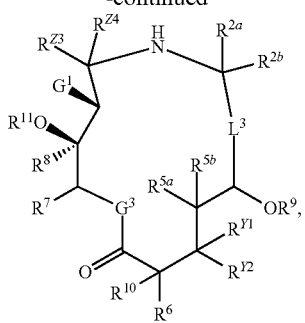

14-membered ring system

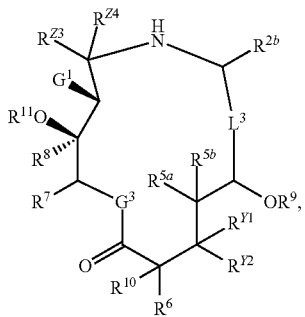

14-membered ring system

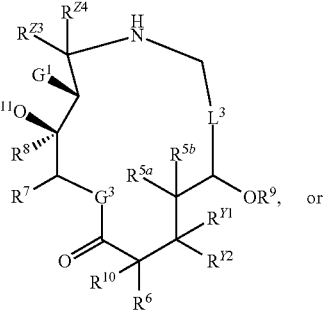

14-membered ring system, or

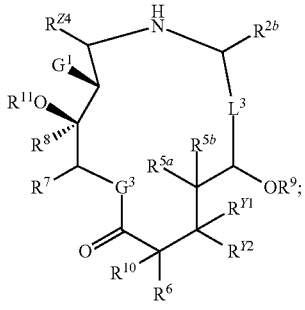

14-membered ring system wherein in certain embodiments the macrolide is prepared, in part, from macrocyclization (e.g., thermally induced macrocyclization) of the coupled precursor compound of the below formula, optionally followed by further synthetic manipulation, as described herein:

111
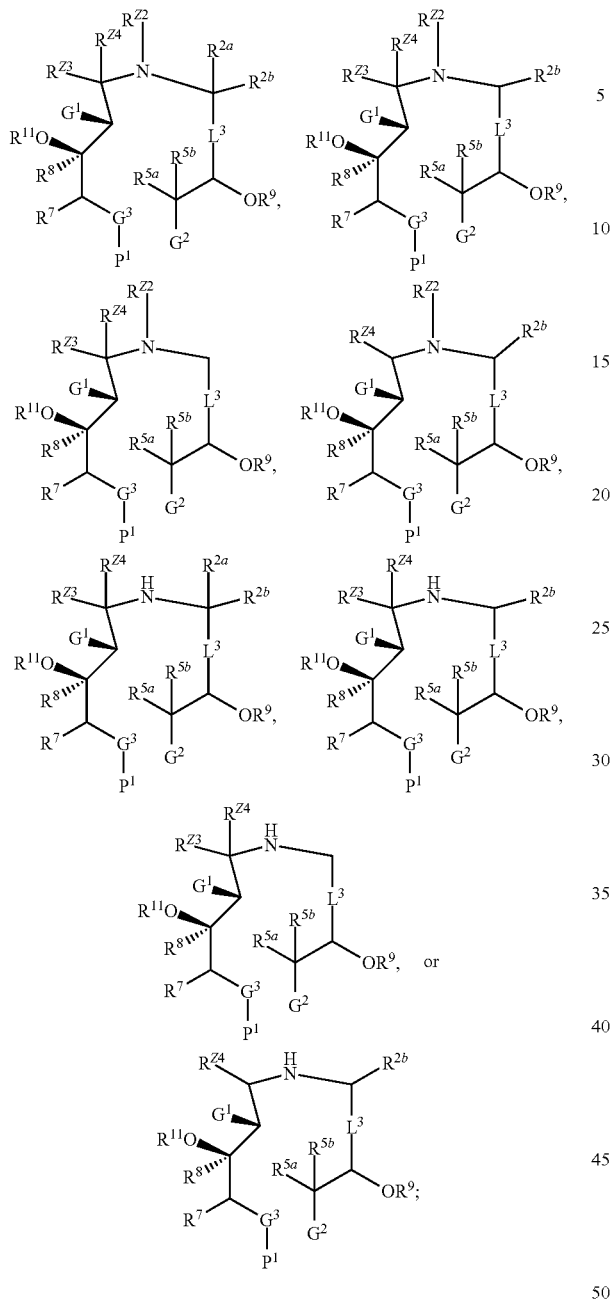
[9] an imine of formula:
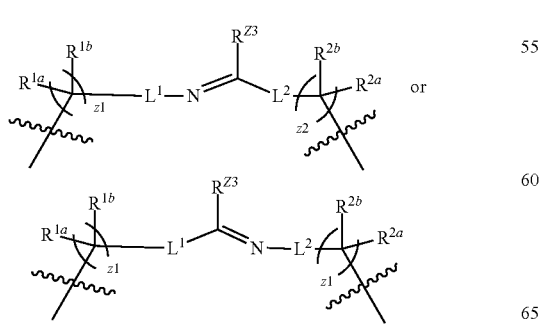
112
wherein $L^1$ and $L^2$ are each independently a bond or —$CH_2$—; z1 and z2 are each independently 0, 1, or 2, e.g., to provide a 13-, 14-, 15- or 16-membered ring system, e.g., of formula:
(C-2-va)
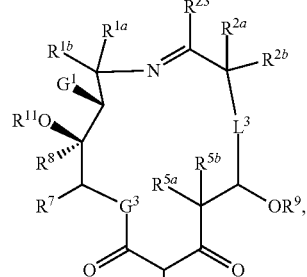
15-membered ring system
(C-2-vb)
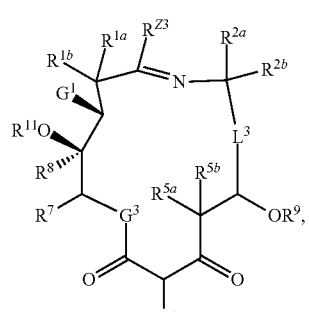
15-membered ring system
(C-2-vc)
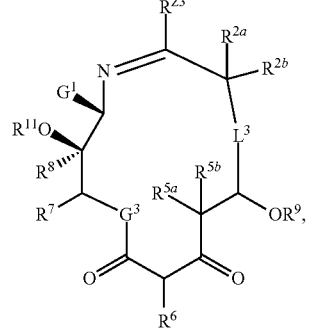
14-membered ring system
(C-2-vd)
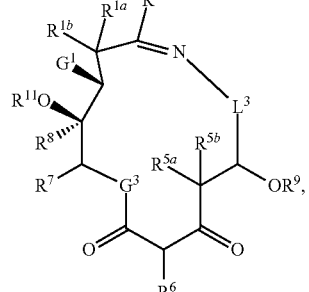
14-membered ring system

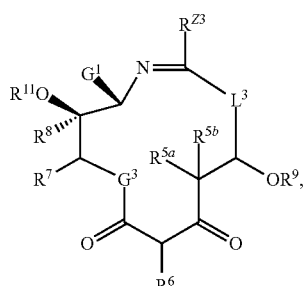
(C-2-ve)
13-membered ring system
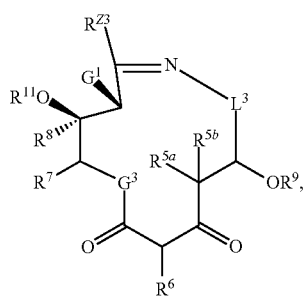
(C-2-vf)
13-membered ring system
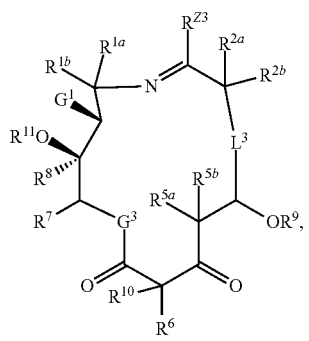
(C-3-va)
15-membered ring system
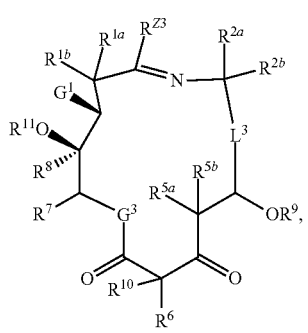
(C-3-vb)
15-membered ring system
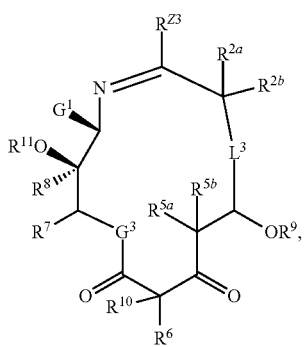
(C-3-vc)
14-membered ring system
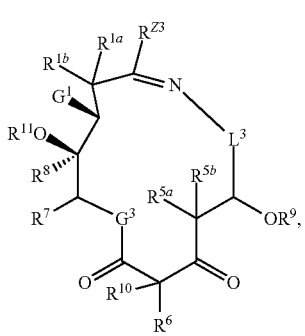
(C-3-vd)
14-membered ring system
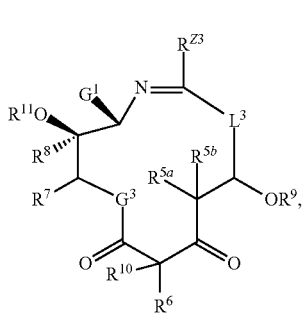
(C-3-ve)
13-membered ring system
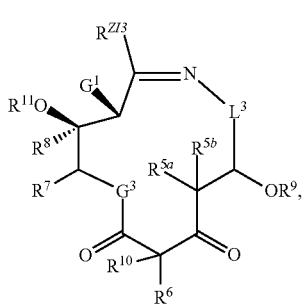
(C-3-vf)
13-membered ring system

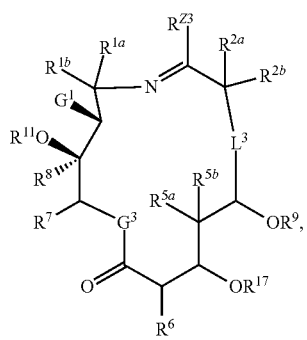
(C-4-va)
15-membered ring system
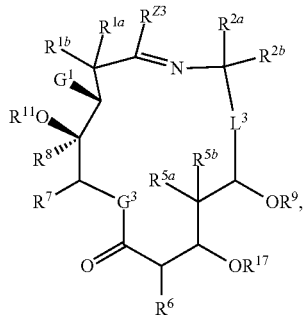
(C-4-vb)
15-membered ring system
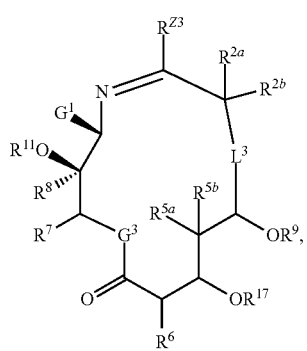
(C-4-vc)
14-membered ring system
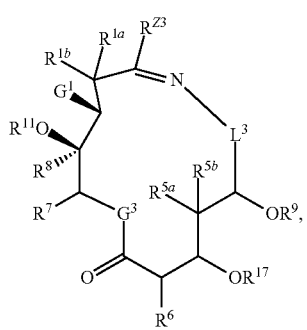
(C-4-vd)
14-membered ring system
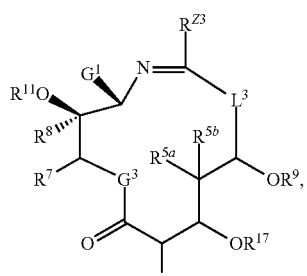
(C-4-ve)
13-membered ring system
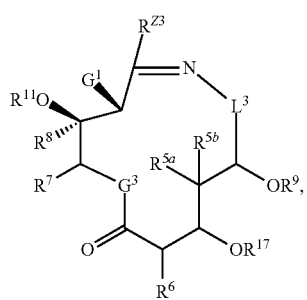
(C-4-vf)
13-membered ring system
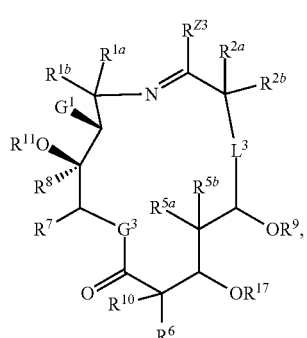
(C-5-va)
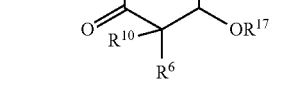
15-membered ring system
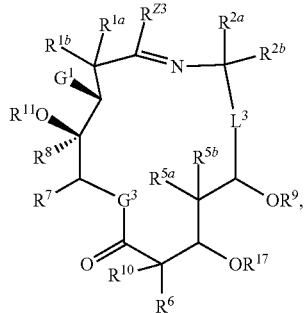
(C-5-vb)
15-membered ring system -continued
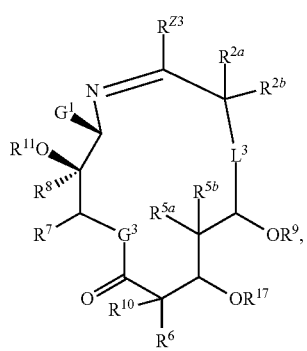
(C-5-vc)
14-membered ring system
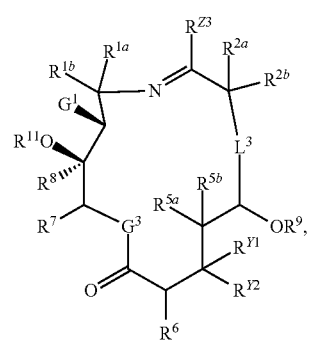
(C-467-va)
15-membered ring system
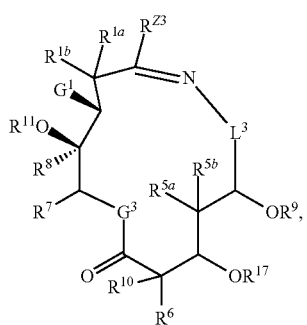
(C-5-vd)
14-membered ring system
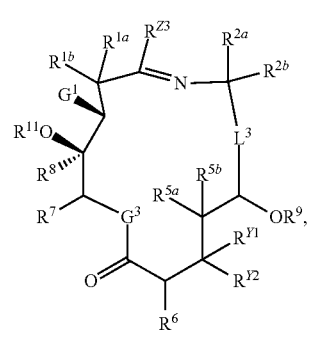
(C-467-vb)
15-membered ring system
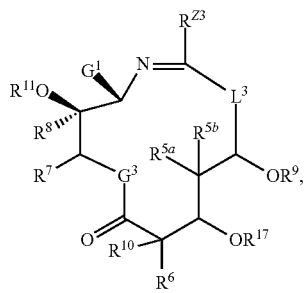
(C-5-ve)
13-membered ring system
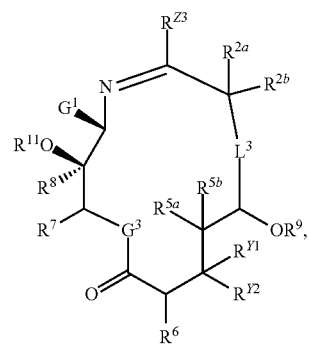
(C-467-vc)
14-membered ring system
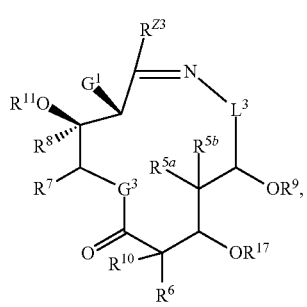
(C-5-vf)
13-membered ring system
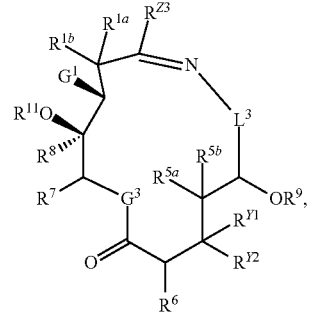
(C-467-vd)
14-membered ring system 119
-continued (C-467-ve)

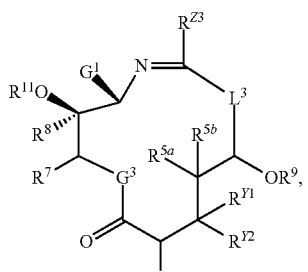

13-membered ring system (C-467-vf)

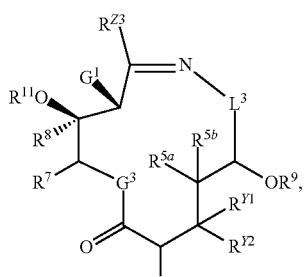

13-membered ring system (C-567-va)

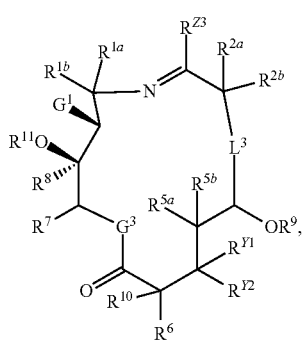

15-membered ring system (C-567-vb)

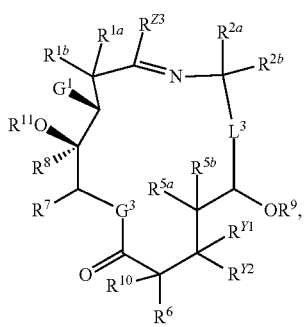

15-membered ring system

120
-continued (C-567-vc)

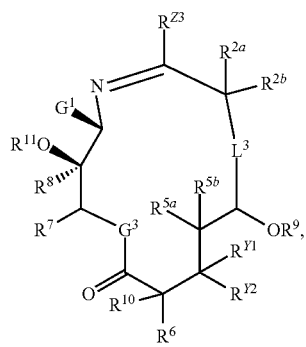

14-membered ring system (C-567-vd)

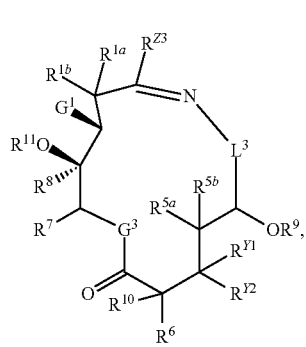

14-membered ring system (C-567-ve)

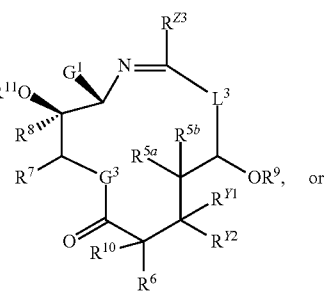

13-membered ring system (C-567-vf)

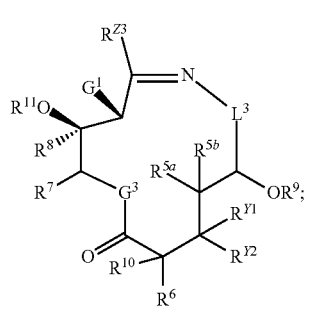

13-membered ring system wherein in certain embodiments the macrolide is prepared from macrocyclization (e.g., thermally induced macrocyclization) of the coupled precursor compound of the below formula, optionally followed by further synthetic manipulation, as described herein:

(C-1-va)
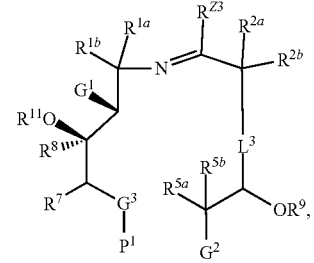
(C-1-vb)
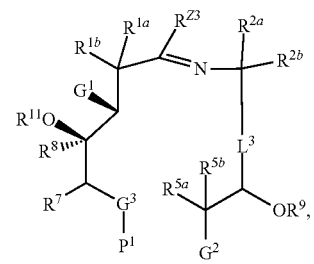
(C-1-vc)
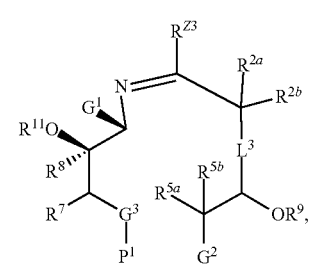
(C-1-vd)
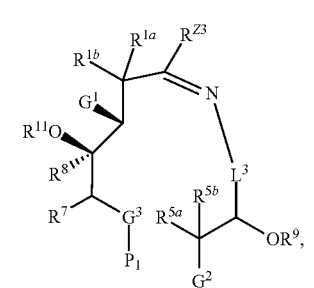
(C-1-ve)
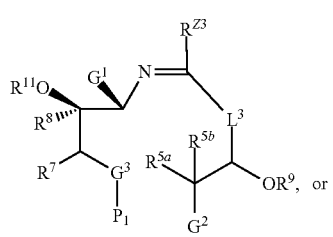
(C-1-vf)
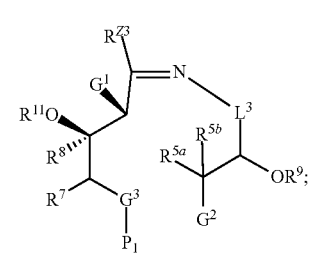
[10] an nitro alkene of formula:
(C-2-va)
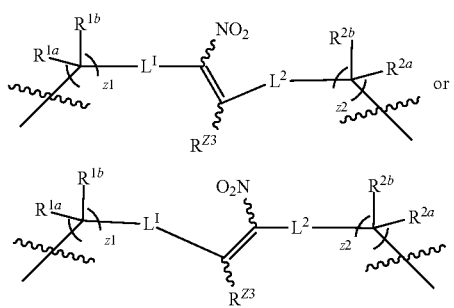
wherein $L^1$ and $L^2$ are each independently a bond or —CH$_2$—; z1 and z2 are 0, 1, or 2, e.g., to provide a 13-, 14-, 15- or 16-membered ring system, e.g., of formula:
(C-2-via)
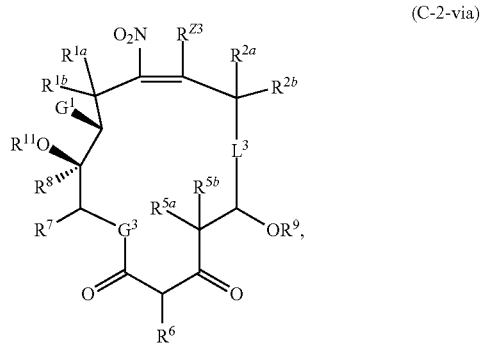
15-membered ring system
(C-2-vib)
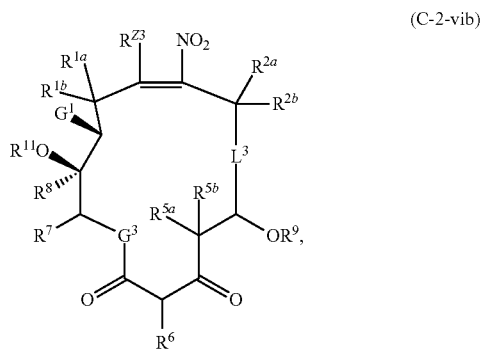
15-membered ring system
(C-2-vic)
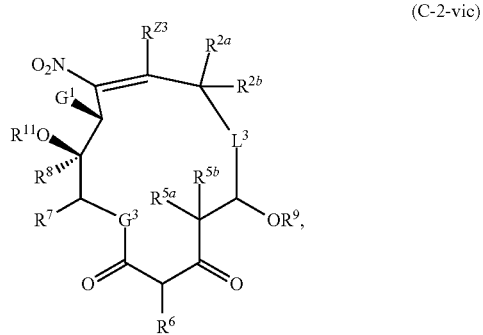
14-membered ring system

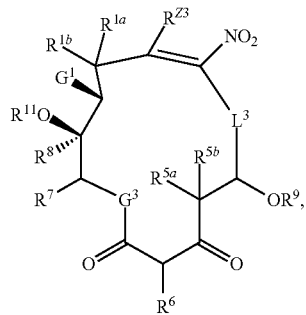
(C-2-vid)
14-membered ring system

(C-2-vie)
13-membered ring system
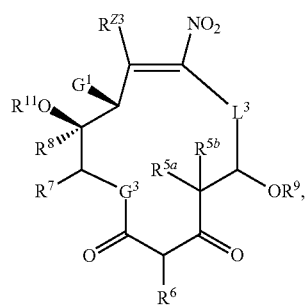
(C-2-vif)
13-membered ring system
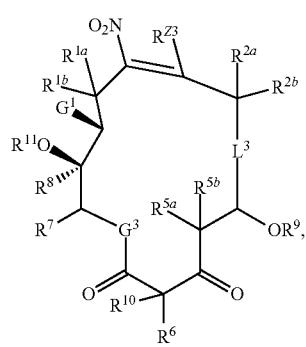
(C-3-via)
15-membered ring system
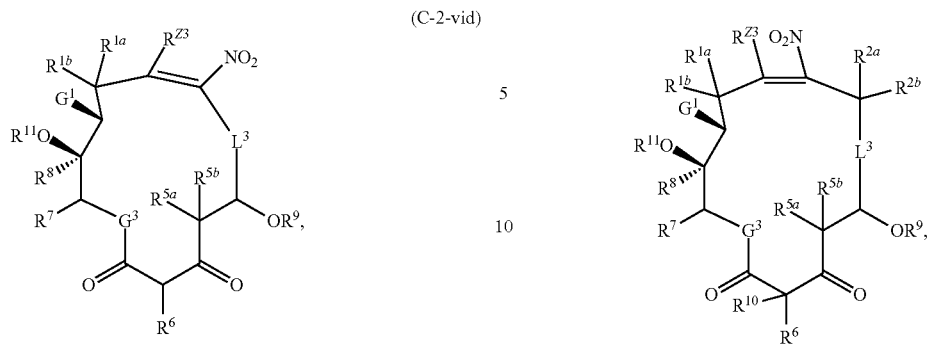
(C-3-vib)
15-membered ring system
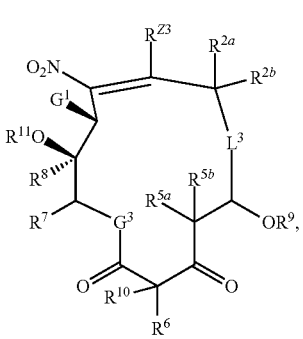
(C-3-vic)
14-membered ring system
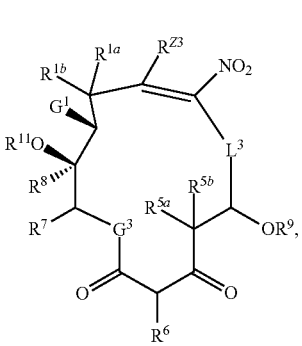
(C-3-vid)
14-membered ring system
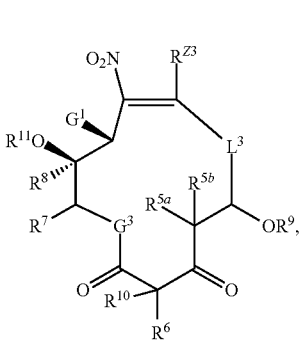
(C-3-vie)
13-membered ring system -continued
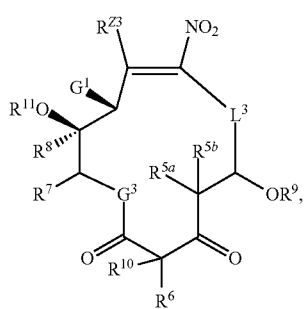
(C-3-vif)
13-membered ring system
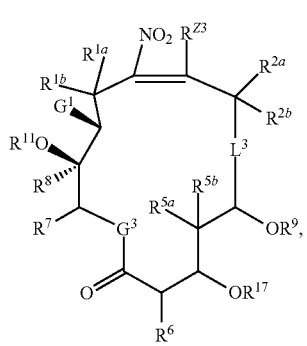
(C-4-via)
15-membered ring system
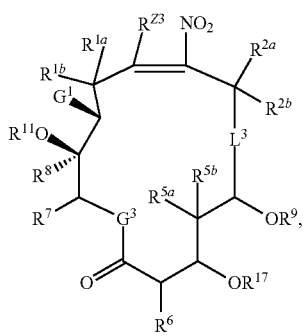
(C-4-vib)
15-membered ring system
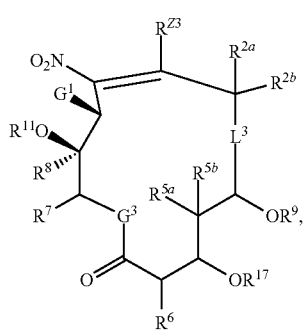
(C-4-vic)
14-membered ring system
-continued
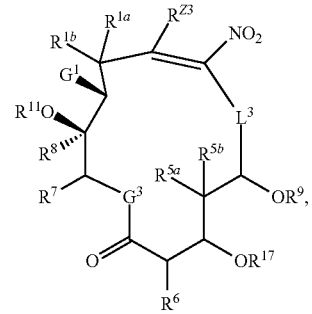
(C-4-vid)
14-membered ring system
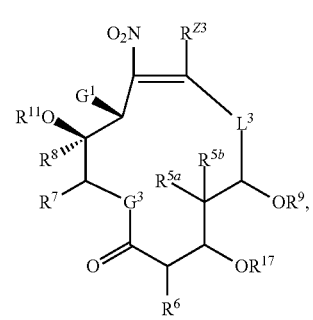
(C-4-vie)
13-membered ring system
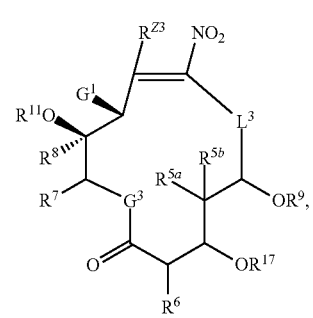
(C-4-vif)
13-membered ring system
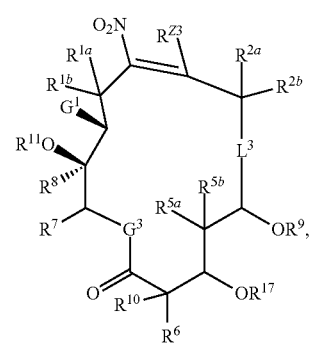
(C-5-via)
15-membered ring system

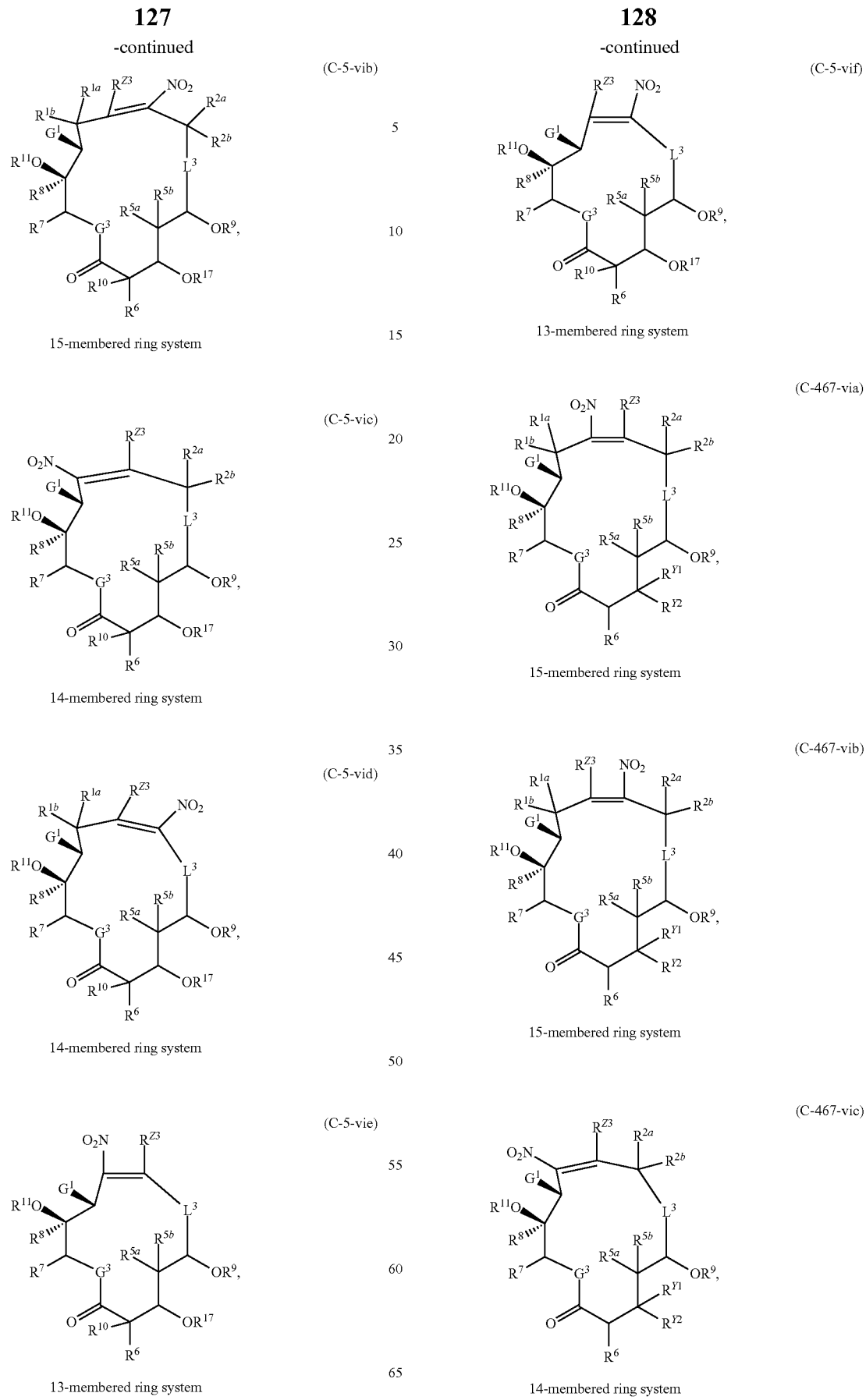

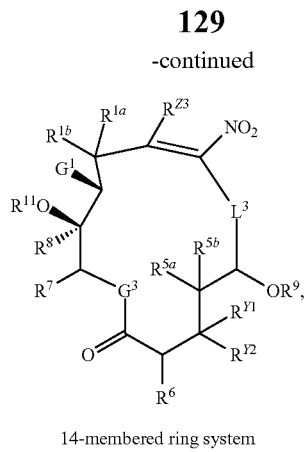
(C-467-vid)
14-membered ring system
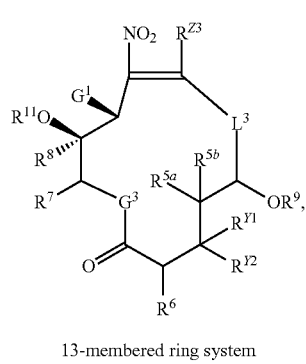
(C-467-vie)
13-membered ring system
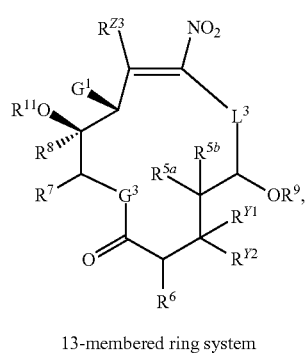
(C-467-vif)
13-membered ring system
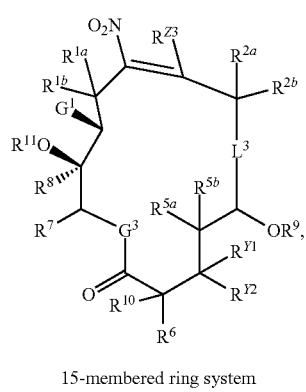
(C-567-via)
15-membered ring system
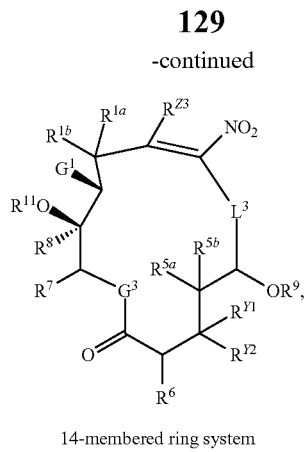
(C-567-vib)
15-membered ring system
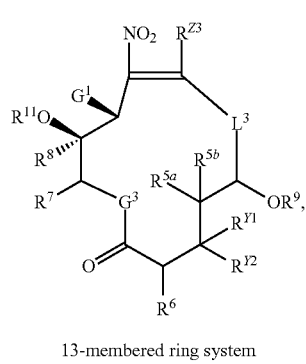
(C-567-vic)
14-membered ring system
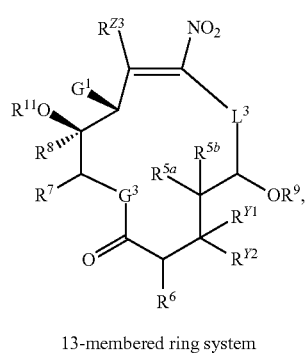
(C-567-vid)
14-membered ring system
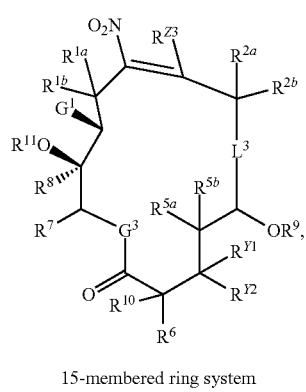
(C-567-vie)
13-membered ring system
or -continued (C-567-vif)

13-membered ring system wherein in certain embodiments the macrolide is prepared from macrocyclization (e.g., thermally induced macrocyclization) of the coupled precursor of one of the formulae, optionally followed by further synthetic manipulation, as described herein:

(C-1-via)

(C-1-vib)

(C-1-vic)

(C-1-vid)

-continued (C-1-vie)

(C-1-vif)

[11] an nitro compound of formula:

wherein $L^1$ and $L^2$ are each independently a bond or —$CH_2$—; z1 and z2 are 0, 1, or 2, e.g., to provide a 13-, 14-, 15- or 16-membered ring system, e.g., of formula:

(C-2-viia)

15-membered ring system

-continued
(C-2-viib)
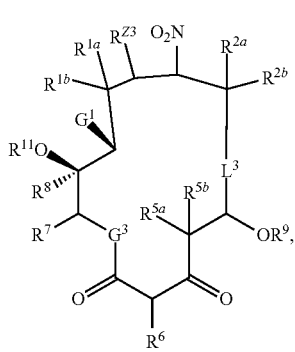
15-membered ring system
(C-2-viic)
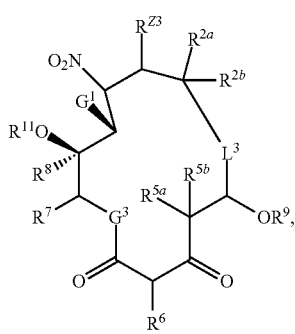
14-membered ring system
(C-2-viid)
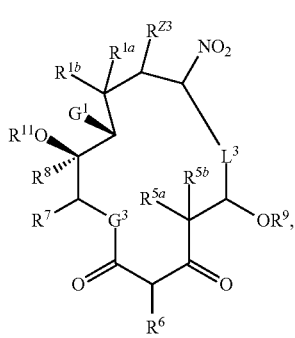
14-membered ring system
(C-2-viie)
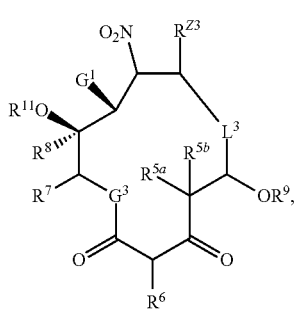
13-membered ring system
-continued
(C-3-viif)
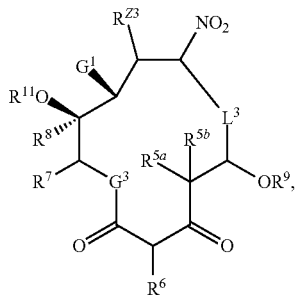
13-membered ring system
(C-3-viia)
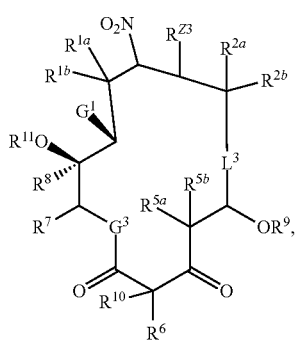
15-membered ring system
(C-3-viib)
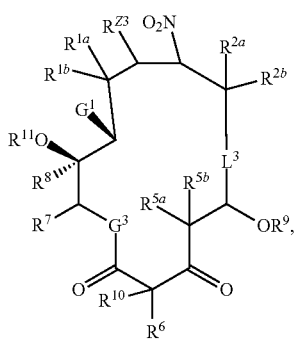
15-membered ring system
(C-3-viic)
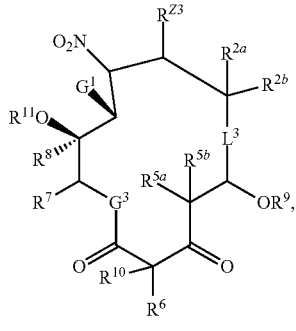
14-membered ring system -continued
(C-3-viid)
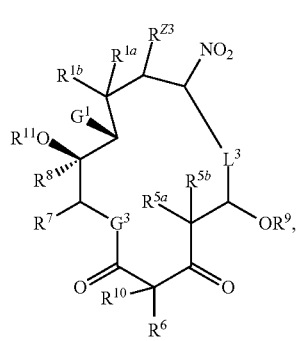
14-membered ring system
(C-3-viie)
13-membered ring system
(C-3-viif)
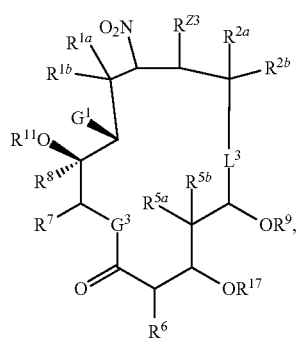
13-membered ring system
(C-4-viia)
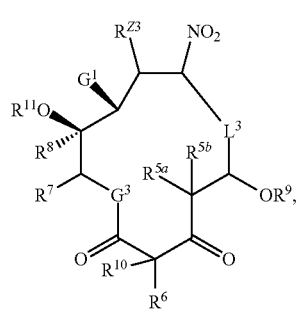
15-membered ring system
-continued
(C-4-viib)
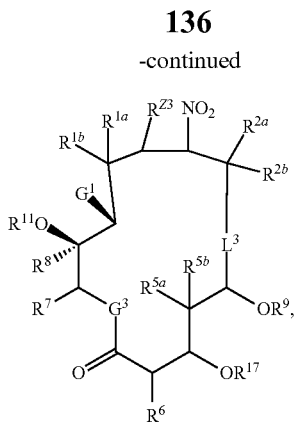
15-membered ring system
(C-4-viic)
14-membered ring system
(C-4-viid)
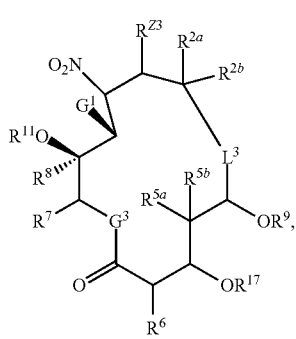
14-membered ring system
(C-4-viie)
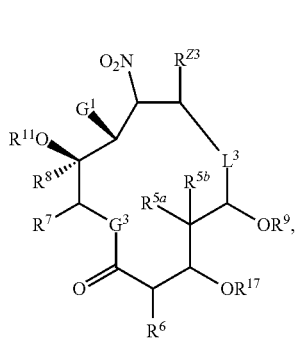
13-membered ring system

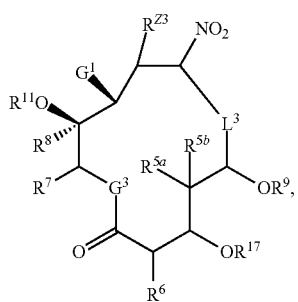
(C-4-viif)
13-membered ring system
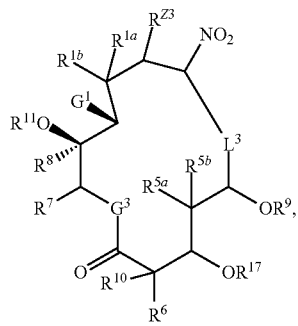
(C-5-viid)
14-membered ring system
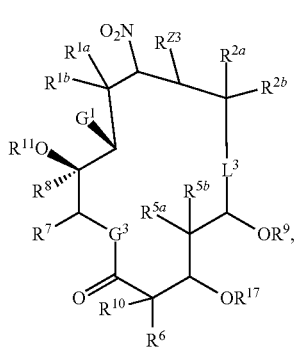
(C-5-viia)
15-membered ring system
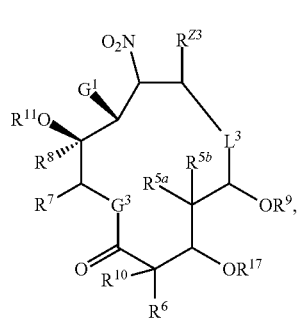
(C-5-viie)
13-membered ring system
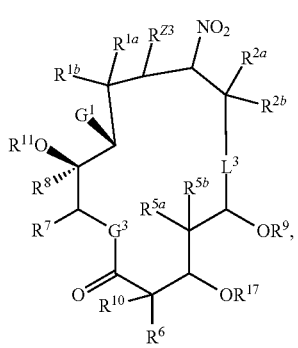
(C-5-viib)
15-membered ring system
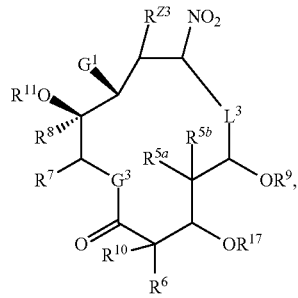
(C-5-viif)
13-membered ring system
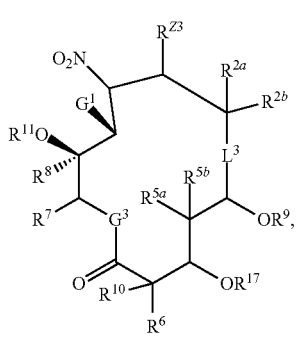
(C-5-viic)
14-membered ring system
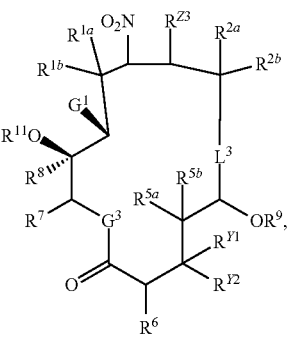
(C-467-viia)
15-membered ring system (C-467-viib)
15-membered ring system (C-467-xif)
14-membered ring system (C-467-viid)
14-membered ring system (C-467-viie)
13-membered ring system (C-467-viif)
13-membered ring system (C-567-viia)
15-membered ring system (C-567-viib)
15-membered ring system (C-567-viic)
14-membered ring system -continued

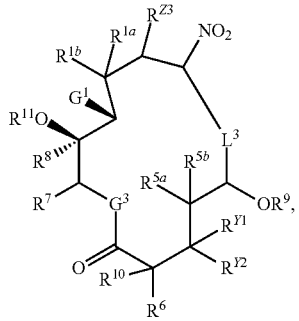
14-membered ring system
(C-567-viid)

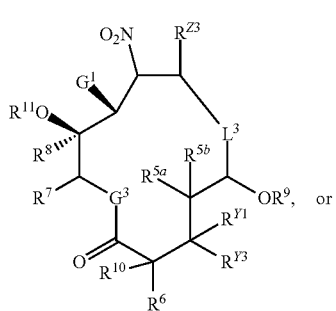
13-membered ring system
(C-567-viie)

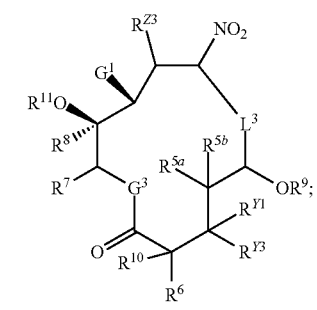
13-membered ring system
(C-567-viif)

wherein in certain embodiments the macrolide is prepared, in part, from macrocyclization (e.g., thermally induced) of the coupled precursor compound of the below formula, optionally followed by further synthetic manipulation, as described herein:

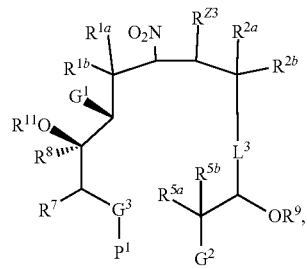
(C-1-viia)

-continued

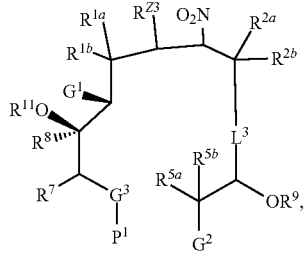
(C-1-viib)

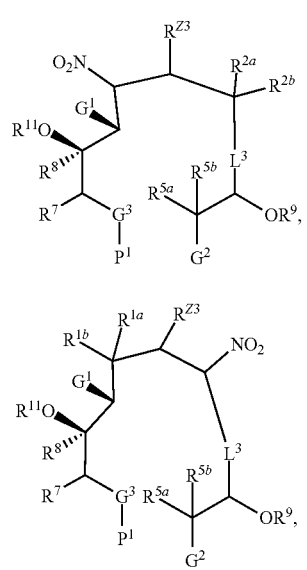
(C-1-viic)

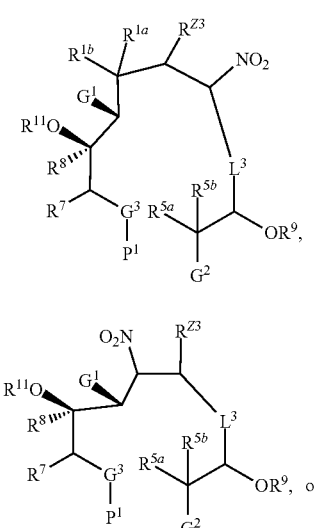
(C-1-viid)

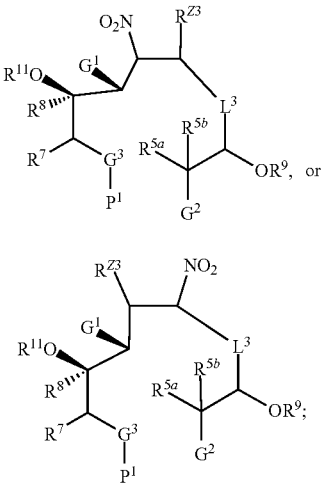
(C-1-viie)

(C-1-viif)

[12] an nitro compound of Formula:

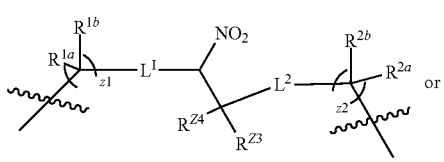

-continued
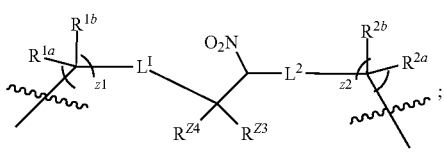
wherein $L^1$ and $L^2$ are each independently a bond or —$CH_2$—; z1 and z2 are 0, 1, or 2, e.g., to provide a 13-, 14-, 15- or 16-membered ring system, e.g., of formula:
(C-2-viiia)
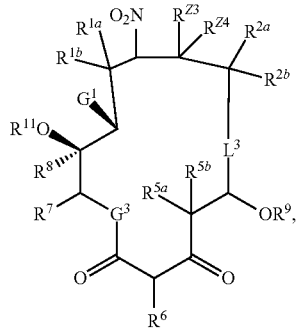
15-membered ring system
(C-2-viiib)
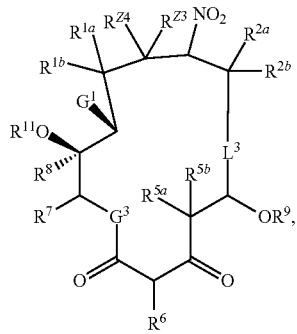
15-membered ring system
(C-2-viiic)
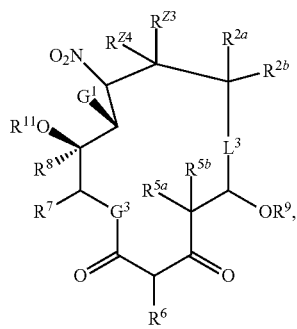
14-membered ring system
(C-2-viiid)
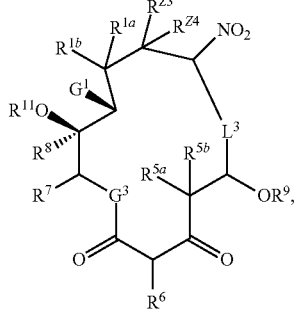
14-membered ring system
(C-2-viiie)
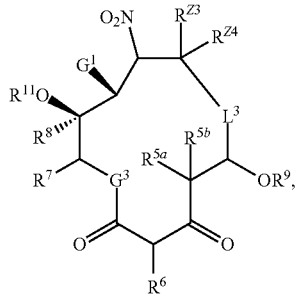
13-membered ring system
(C-2-viiif)
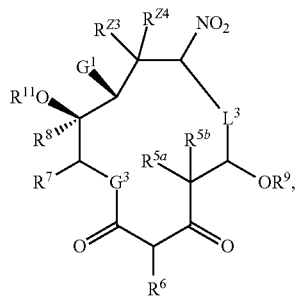
13-membered ring system
(C-3-viiia)
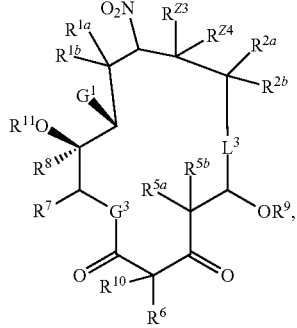
15-membered ring system (C-3-viiib) 15-membered ring system (C-3-viiic) 14-membered ring system (C-3-viiid) 14-membered ring system (C-3-viiie) 13-membered ring system (C-3-viiif) 13-membered ring system (C-4-viiia) 15-membered ring system (C-4-viiib) 15-membered ring system (C-4-viiic) 14-membered ring system

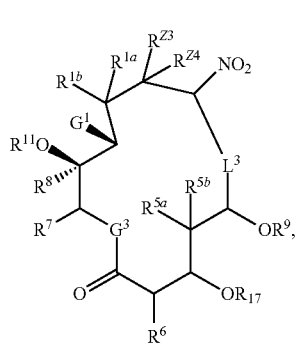
(C-4-viiid)
14-membered ring system
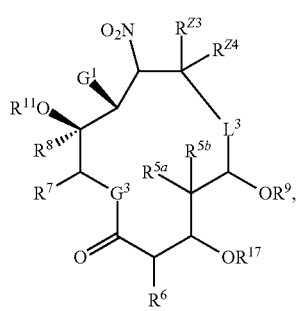
(C-4-viiie)
13-membered ring system
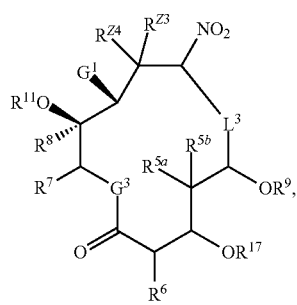
(C-4-viiif)
13-membered ring system
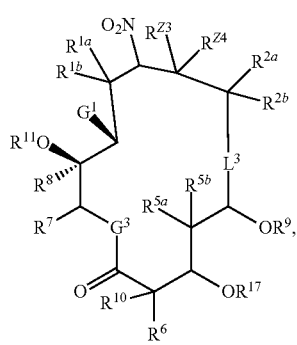
(C-5-viiia)
15-membered ring system
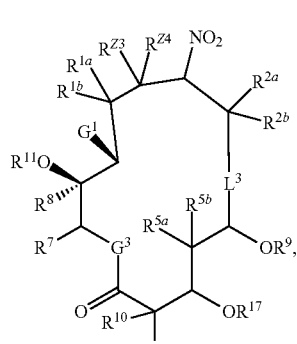
(C-5-viiib)
15-membered ring system
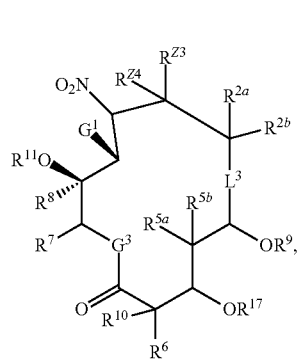
(C-5-viiic)
14-membered ring system
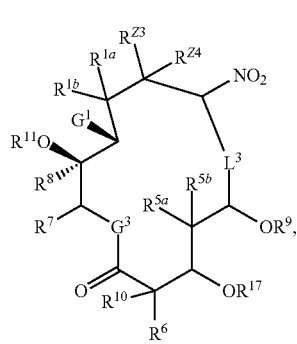
(C-5-viiid)
14-membered ring system
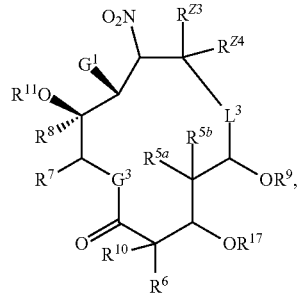
(C-5-viiie)
13-membered ring system 149
-continued
(C-5-viiif)
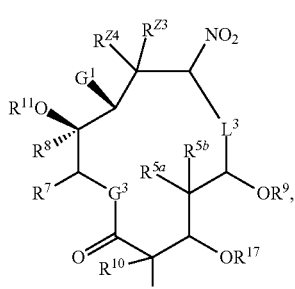
13-membered ring system
(C-467-viiia)
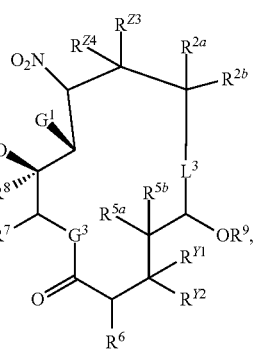
15-membered ring system
(C-467-viiib)
15-membered ring system
(C-467-viiic)
14-membered ring system
150
-continued
(C-467-viiid)
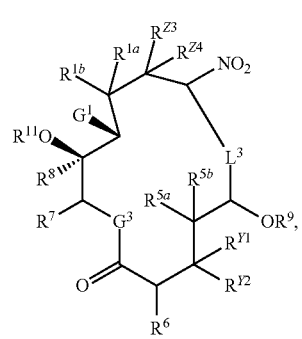
14-membered ring system
(C-467-viiie)
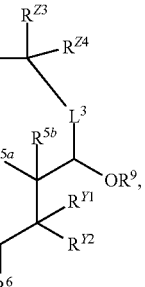
13-membered ring system
(C-467-viiif)
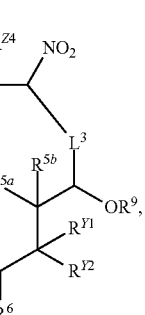
13-membered ring system
(C-567-viiia)
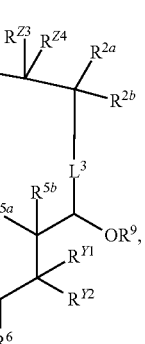
15-membered ring system -continued (C-567-viiib)

15-membered ring system (C-567-viiic)

14-membered ring system (C-567-viiid)

14-membered ring system (C-567-viiie)

13-membered ring system

-continued (C-3-viiif)

13-membered ring system wherein in certain embodiments the macrolide is prepared, in part, from macrocyclization (e.g., thermally induced) of the coupled precursor compound of the below formula, optionally followed by further synthetic manipulation, as described herein:

(C-1-viiia)

(C-1-viiib)

(C-1-viiic)

(C-1-viiid)

-continued (C-1-viiie)

(C-2-ixb)

15-membered ring system (C-1-viiif)

[13] a group of formula:

(C-2-ixc)

14-membered ring system wherein $L^1$ and $L^2$ are each independently a bond or —$CH_2$—; z1 and z2 are 0, 1, or 2, e.g., to provide a 13-, 14-, 15- or 16-membered ring system, e.g., of formula:

(C-2-ixd)

14-membered ring system (C-2-ixa)

(C-2-ixe)

15-membered ring system 13-membered ring system

-continued
(C-2-ixf)
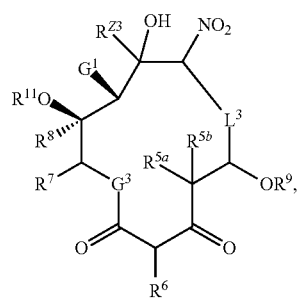
13-membered ring system
(C-3-ixa)
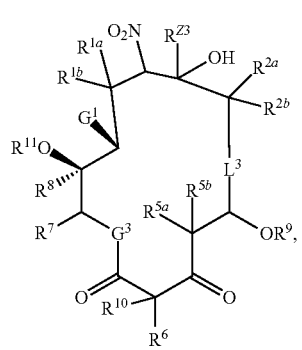
15-membered ring system
(C-3-ixb)
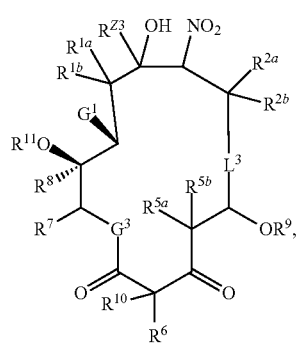
15-membered ring system
(C-3-ixc)
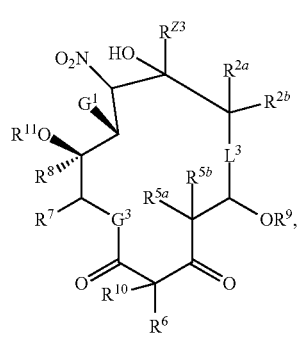
14-membered ring system
(C-3-ixd)
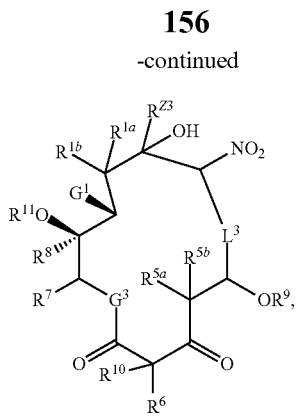
14-membered ring system
(C-3-ixe)
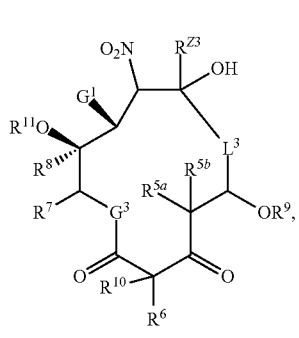
13-membered ring system
(C-3-ixf)
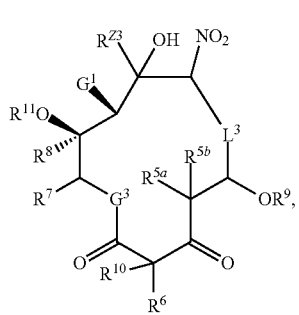
13-membered ring system
(C-4-ixa)
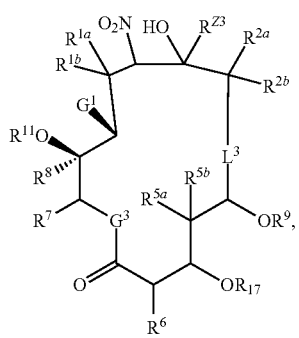
15-membered ring system

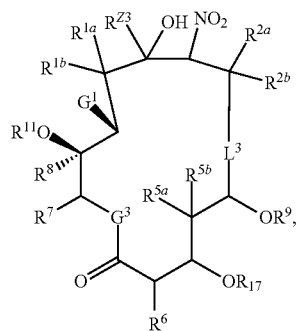
(C-4-ixb)
15-membered ring system
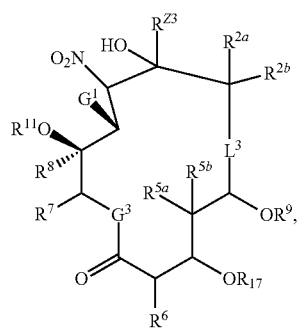
(C-4-ixc)
14-membered ring system
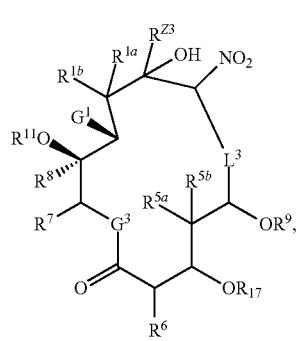
(C-4-ixd)
14-membered ring system
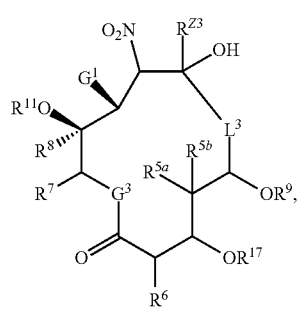
(C-4-ixe)
13-membered ring system
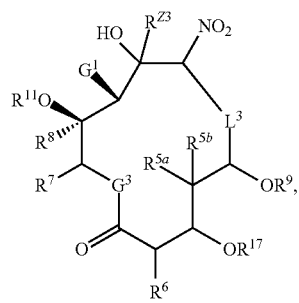
(C-4-ixf)
13-membered ring system
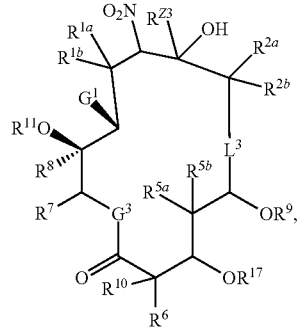
(C-5-ixa)
15-membered ring system
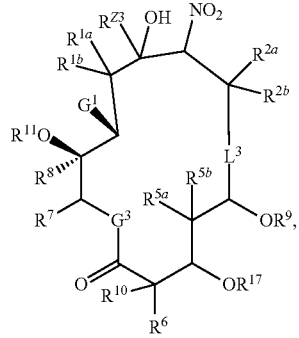
(C-5-ixb)
15-membered ring system
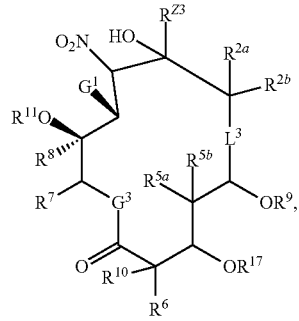
(C-5-ixc)
14-membered ring system -continued
(C-5-ixd)
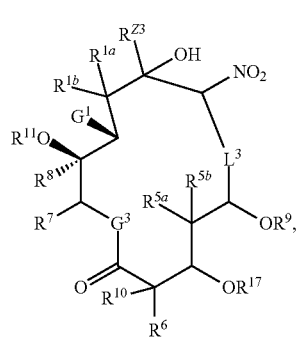
14-membered ring system
(C-5-ixe)
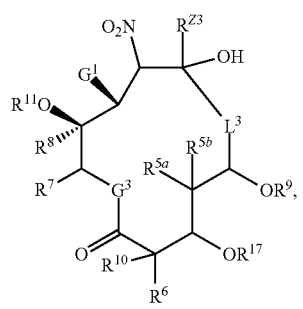
13-membered ring system
(C-5-ixf)
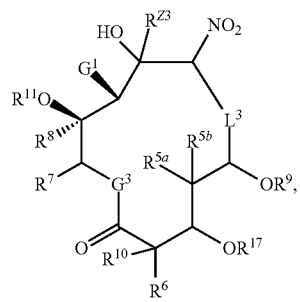
13-membered ring system
(C-467-ixa)
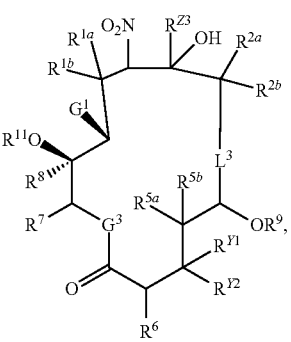
15-membered ring system
(C-467-ixb)
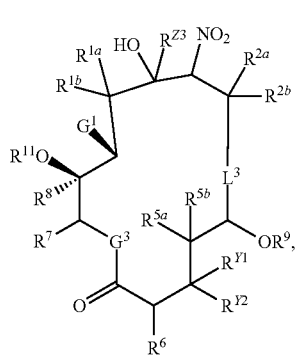
15-membered ring system
(C-467-ixc)
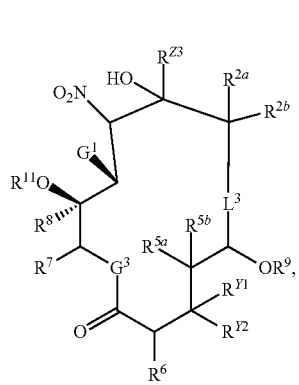
14-membered ring system
(C-467-ixd)
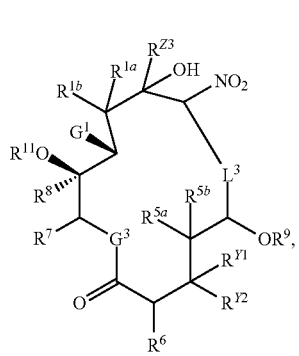
14-membered ring system
(C-467-ixe)
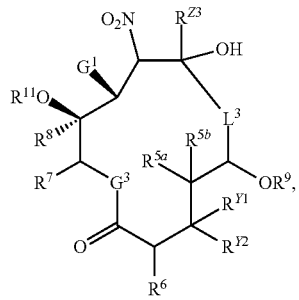
13-membered ring system

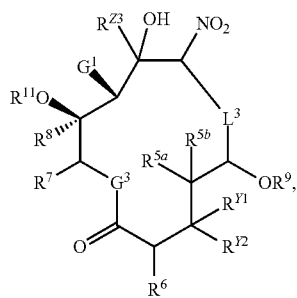

13-membered ring system (C-467-ixf)

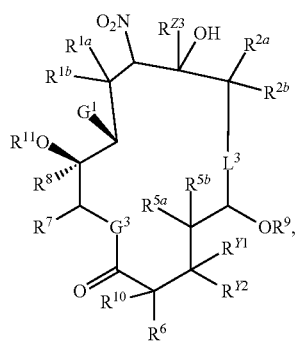

15-membered ring system (C-567-ixa)

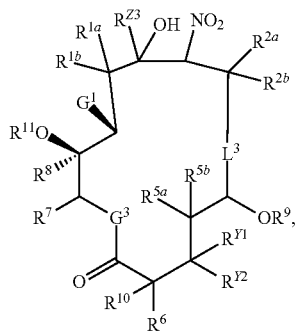

15-membered ring system (C-567-ixb)

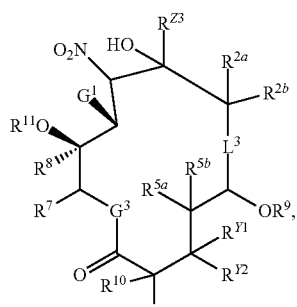

14-membered ring system (C-567-ixc)

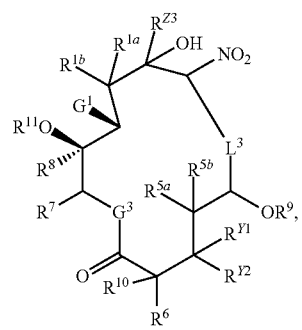

14-membered ring system (C-567-ixd)

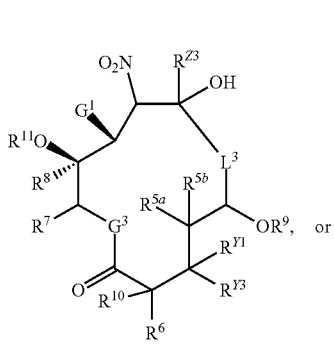

13-membered ring system (C-567-ixe)

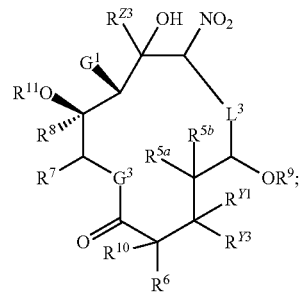

13-membered ring system (C-567-ixf)

wherein in certain embodiments the macrolide is prepared, in part, from macrocyclization (e.g., thermally induced) of the coupled precursor compound of the below formula, optionally followed by further synthetic manipulation, as described herein:

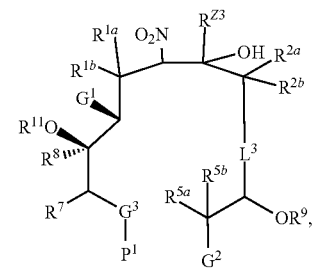

(C-1-ixa)

-continued
(C-1-ixb)
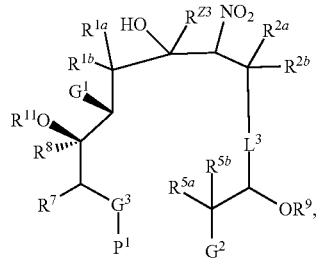
(C-1-ixc)
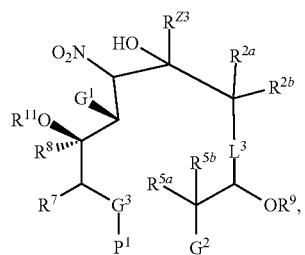
(C-1-ixd)
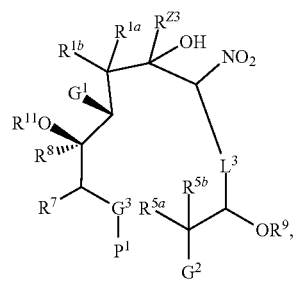
(C-1-ixe)
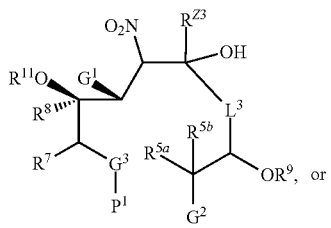
(C-1-ixf)
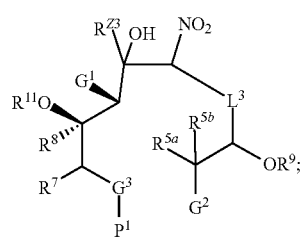
[14] a group of formula:
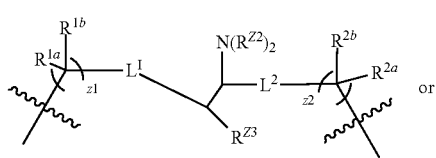 or
-continued
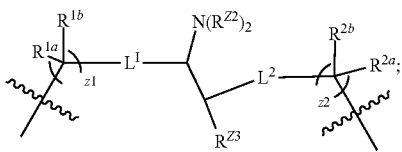
wherein $L^1$ and $L^2$ are each independently a bond or —CH$_2$—; z1 and z2 are 0, 1, or 2 e.g., to provide a 13-, 14-, 15- or 16-membered ring system, e.g., of formula:
(C-2-xa)
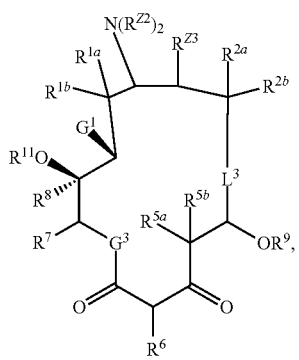
15-membered ring system
(C-2-xb)
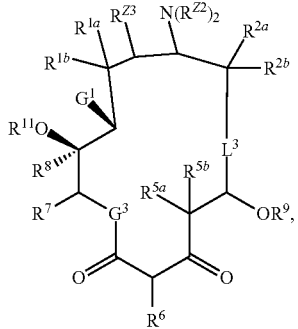
15-membered ring system
(C-2-xc)
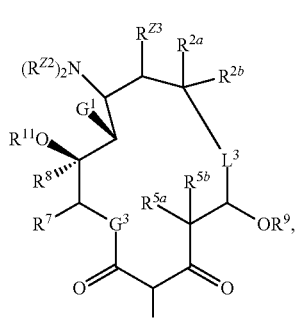
14-membered ring system

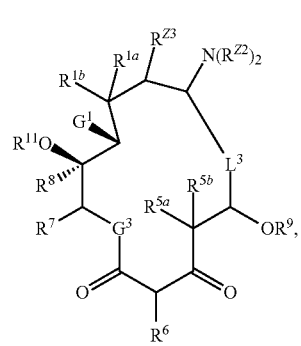
(C-2-xd)
14-membered ring system
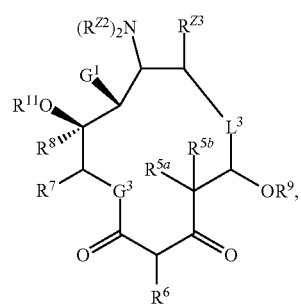
(C-2-xe)
13-membered ring system
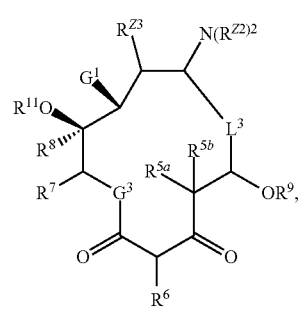
(C-2-xf)
13-membered ring system
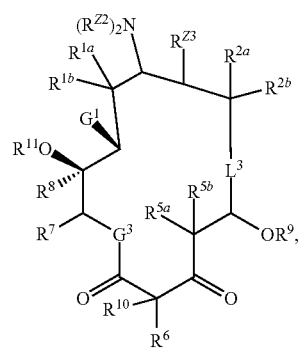
(C-3-xa)
15-membered ring system
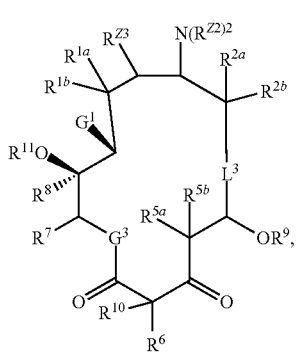
(C-3-xb)
15-membered ring system
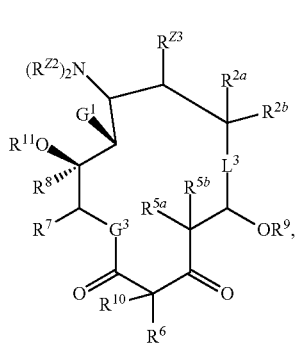
(C-3-xc)
14-membered ring system
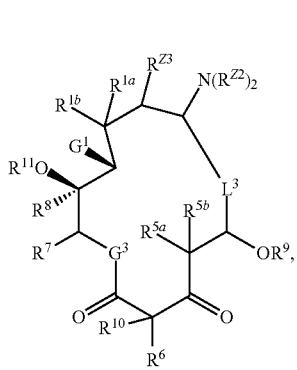
(C-3-xd)
14-membered ring system
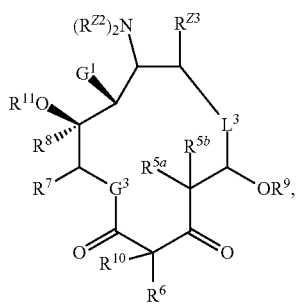
(C-3-xe)
13-membered ring system (C-3-xf)
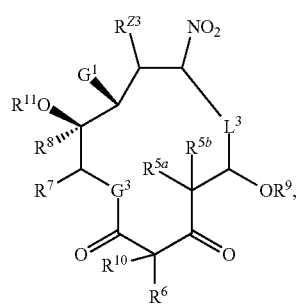
13-membered ring system
(C-4-xa)
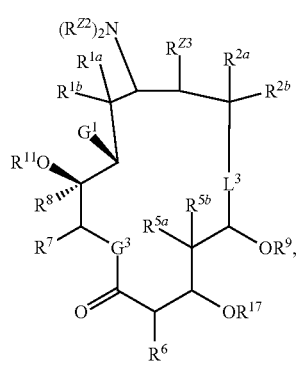
15-membered ring system
(C-4-xb)
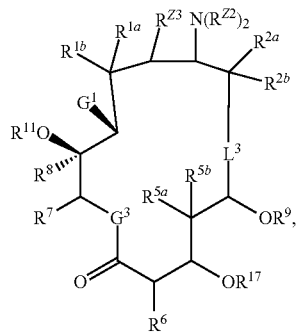
15-membered ring system
(C-4-xc)
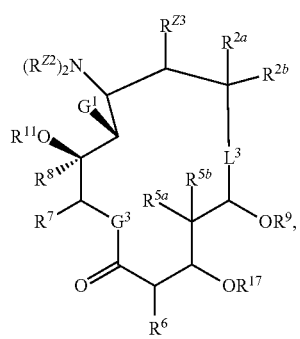
14-membered ring system
(C-4-xd)
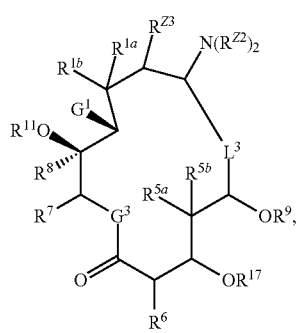
14-membered ring system
(C-4-xe)
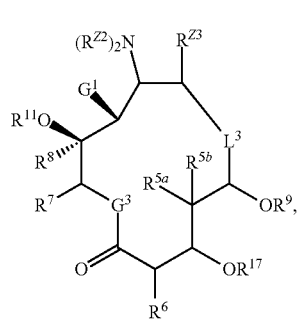
13-membered ring system
(C-4-xf)
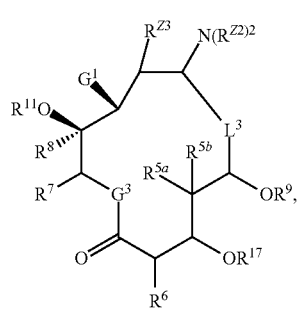
13-membered ring system
(C-5-xa)
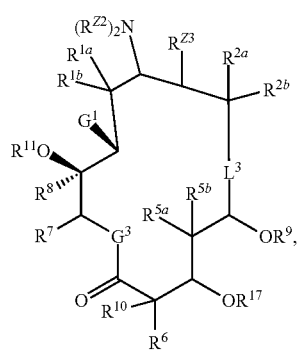
15-membered ring system (C-5-xb) 15-membered ring system (C-5-xc) 14-membered ring system (C-5-xd) 14-membered ring system (C-5-xe) 13-membered ring system (C-5-xf) 13-membered ring system (C-467-xa) 15-membered ring system (C-467-xb) 15-membered ring system (C-467-xc) 15-membered ring system (C-467-xd)
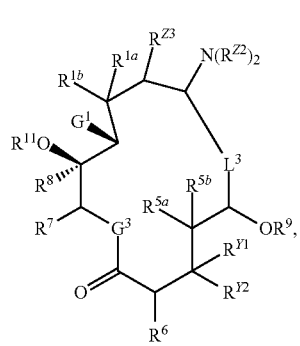
14-membered ring system
(C-467-xe)
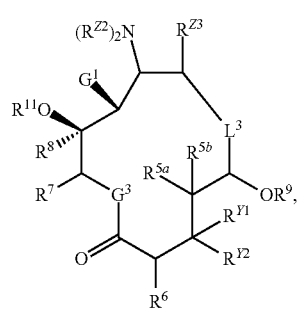
13-membered ring system
(C-467-xf)
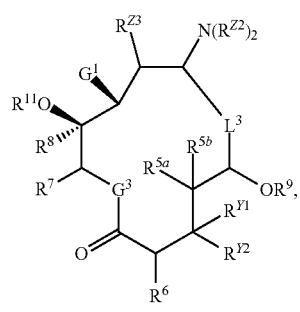
13-membered ring system
(C-567-xa)
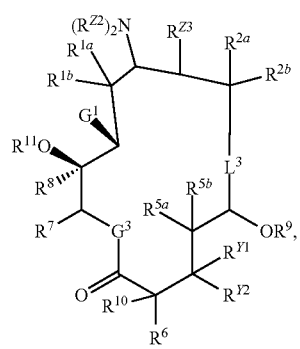
15-membered ring system
(C-567-xb)
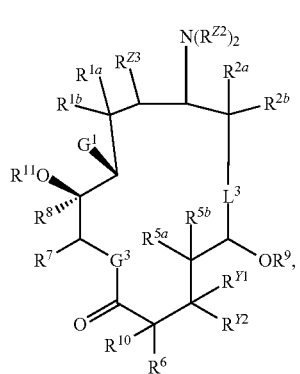
15-membered ring system
(C-567-xc)
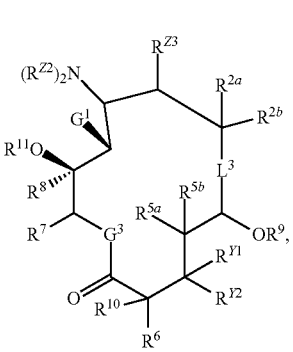
14-membered ring system
(C-567-xd)
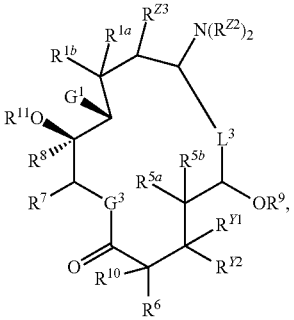
14-membered ring system
(C-567-xe)
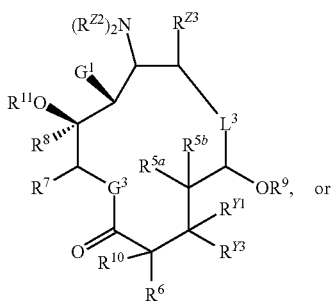
13-membered ring system
or (C-567-xf)

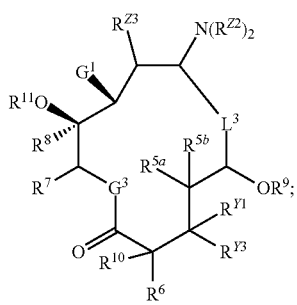

13-membered ring system wherein in certain embodiments the macrolide is prepared, in part, from macrocyclization (e.g., thermally induced macrocyclization) of the coupled precursor compound of the below formula, optionally followed by further synthetic manipulation, as described herein:

(C-1-xa)

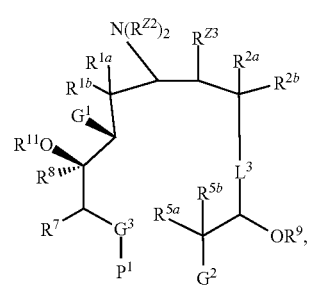

(C-1-xb)

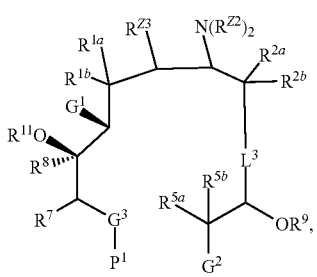

(C-1-xc)

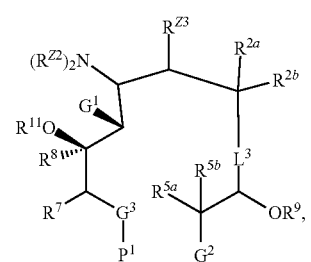

(C-1-xd)

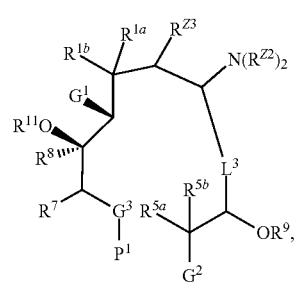

(C-1-xe)

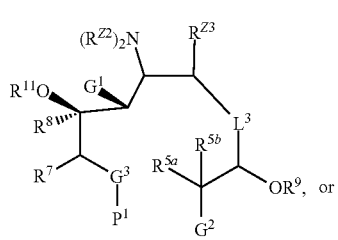

(C-1-xf)

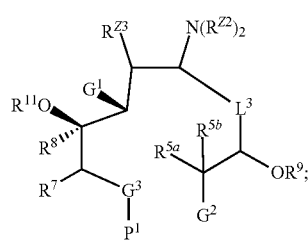

[15] an amino group of formula:

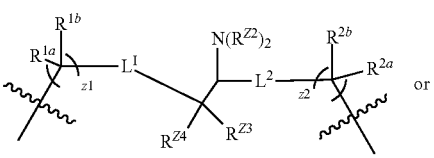

or

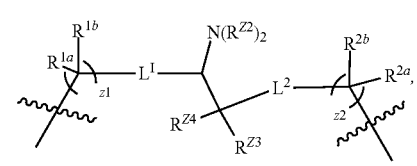

wherein $L^1$ and $L^2$ are each independently a bond or —CH$_2$—; z1 and z2 are 0, 1, or 2, e.g., to provide a 13-, 14-, 15- or 16-membered ring system, e.g., of formula:

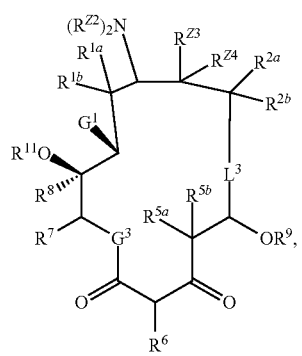
(C-2-xia)
15-membered ring system
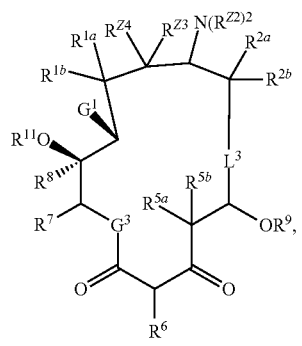
(C-2-xib)
15-membered ring system
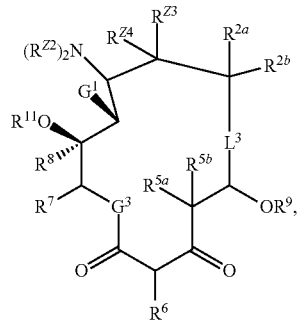
(C-2-xic)
14-membered ring system
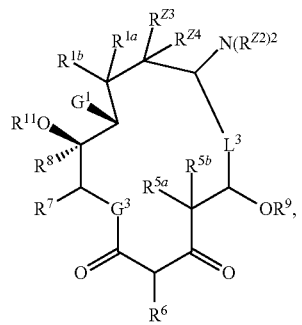
(C-2-xid)
14-membered ring system
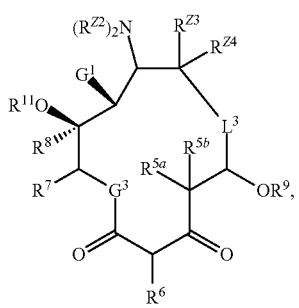
(C-2-xie)
13-membered ring system
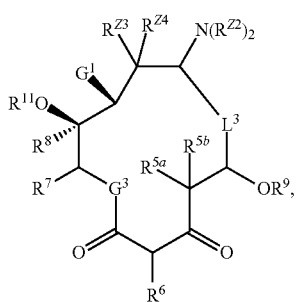
(C-2-xif)
13-membered ring system
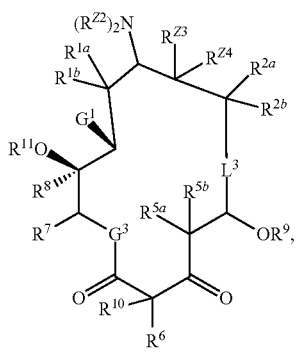
(C-3-xia)
15-membered ring system
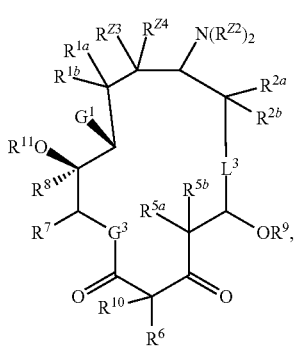
(C-3-xib)
15-membered ring system -continued
(C-3-xic)
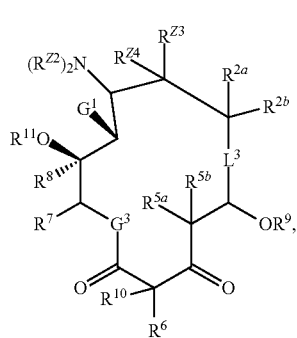
14-membered ring system
(C-3-xid)
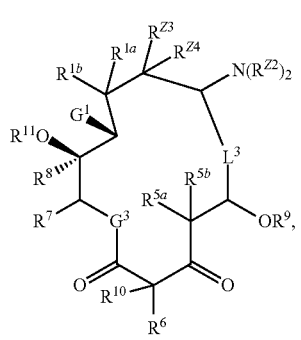
14-membered ring system
(C-3-xie)
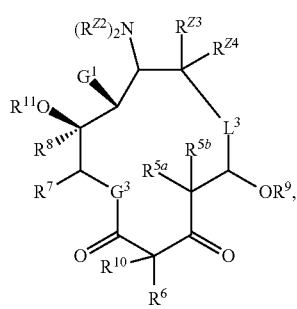
13-membered ring system
(C-3-xif)
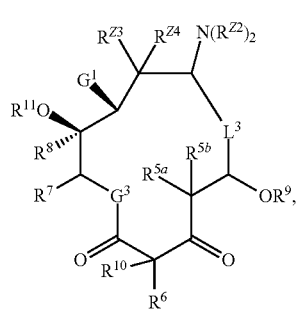
13-membered ring system
-continued
(C-4-xia)
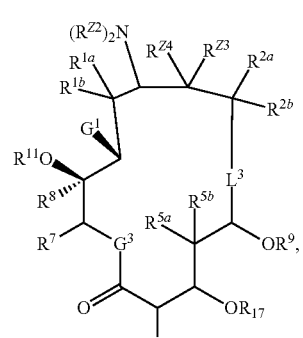
15-membered ring system
(C-4-xib)
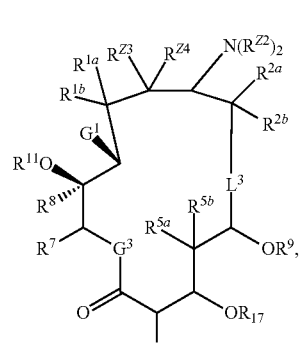
15-membered ring system
(C-4-xic)
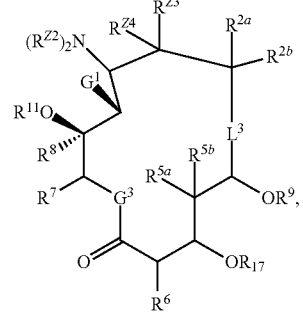
14-membered ring system
(C-4-xid)
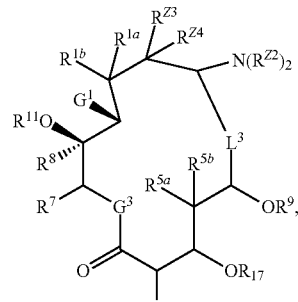
14-membered ring system

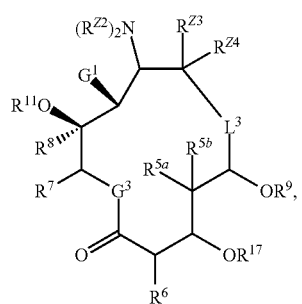
(C-4-xie)
13-membered ring system
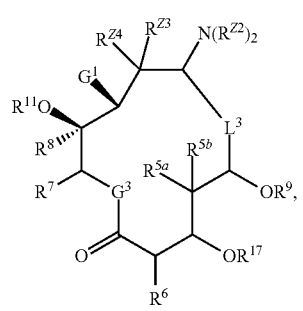
(C-4-xif)
13-membered ring system
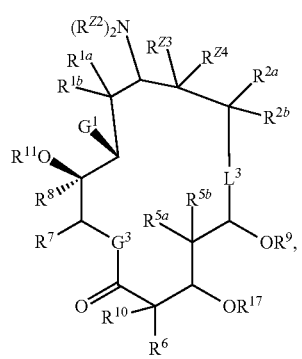
(C-5-xia)
15-membered ring system
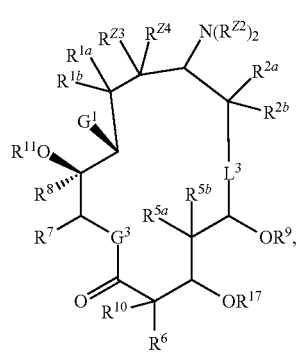
(C-5-xib)
15-membered ring system
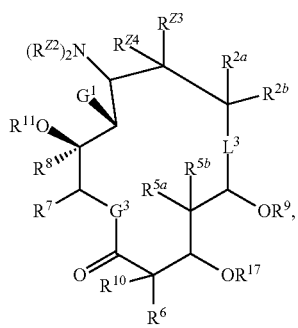
(C-5-xic)
14-membered ring system
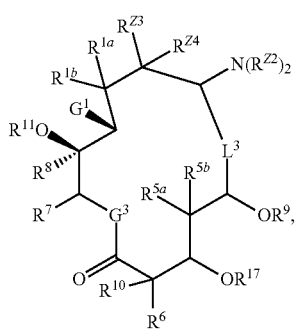
(C-5-xid)
14-membered ring system
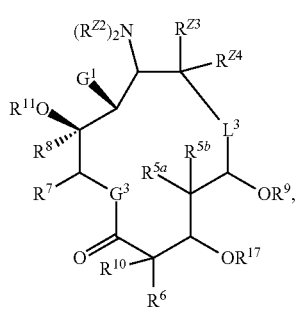
(C-5-xie)
13-membered ring system
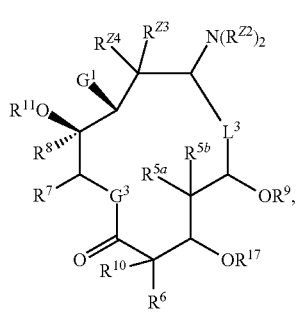
(C-5-xif)
13-membered ring system -continued (C-467-xia)

15-membered ring system (C-467-xib)

15-membered ring system (C-467-xic)

14-membered ring system (C-467-xid)

14-membered ring system (C-467-xie)

13-membered ring system (C-467-xif)

13-membered ring system (C-567-xia)

15-membered ring system (C-567-xib)

15-membered ring system

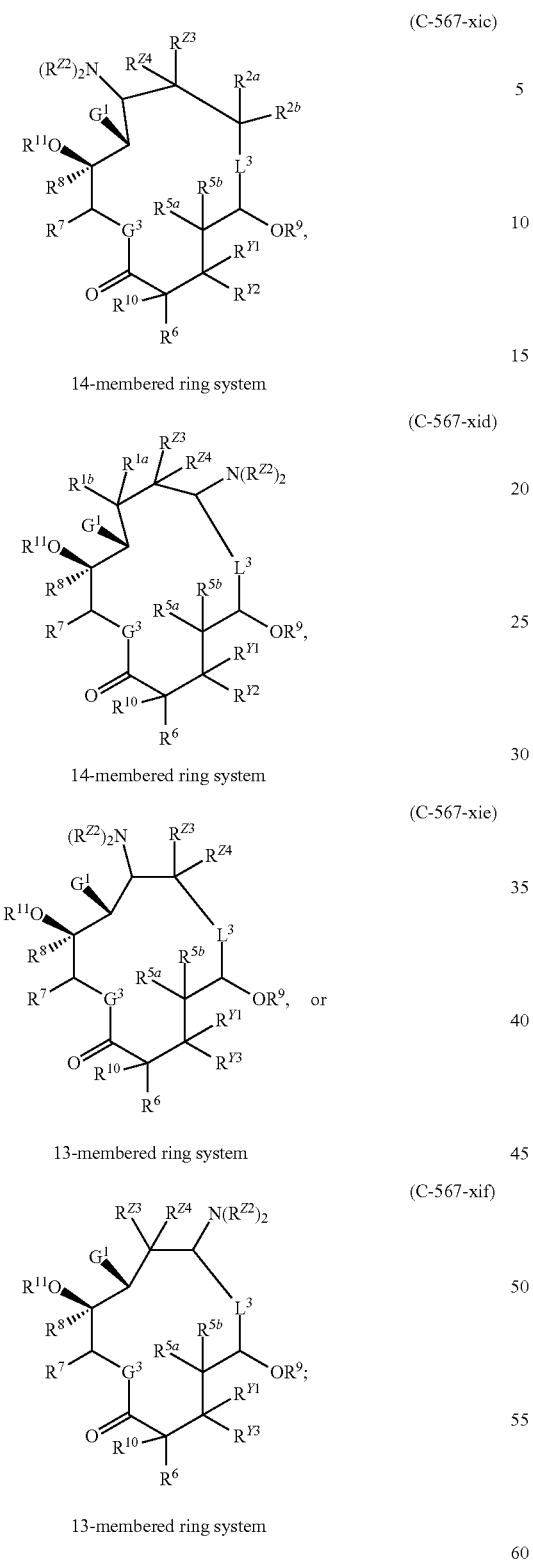

14-membered ring system (C-567-xic)

14-membered ring system (C-567-xid)

13-membered ring system (C-567-xie)

13-membered ring system (C-567-xif)

wherein in certain embodiments the macrolide is prepared, in part, from macrocyclization (e.g., thermally induced) of the coupled precursor compound of the below formula, optionally followed by further synthetic manipulation, as described herein:

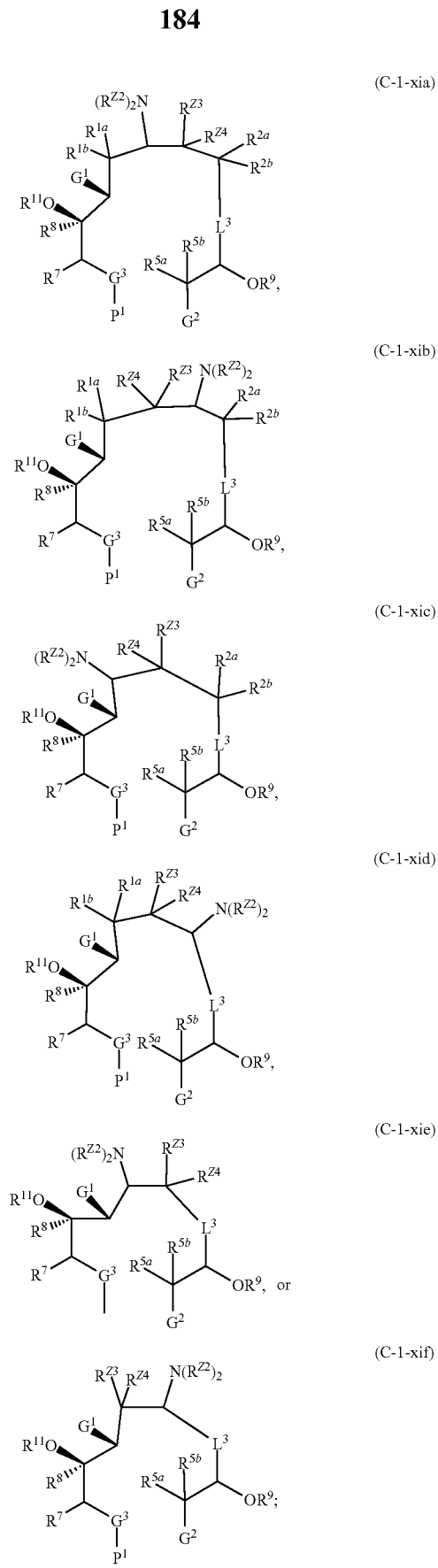

(C-1-xia)

(C-1-xib)

(C-1-xic)

(C-1-xid)

(C-1-xie)

(C-1-xif)

[16] an keto compound of formula:
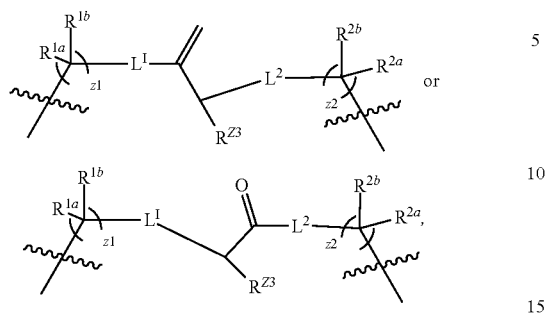
wherein $L^1$ and $L^2$ are each independently a bond or —CH$_2$—; z1 and z2 are 0, 1, or 2, e.g., to provide a 13-, 14-, 15- or 16-membered ring system, e.g., of formula:
(C-2-xiia)
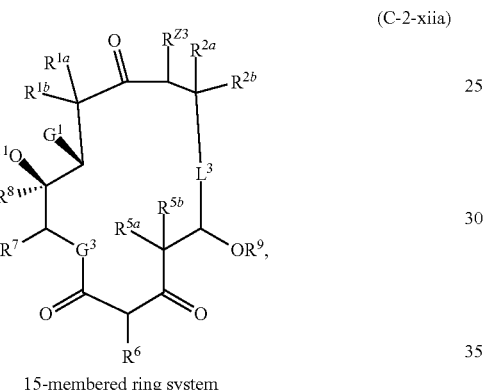
15-membered ring system
(C-2-xiib)
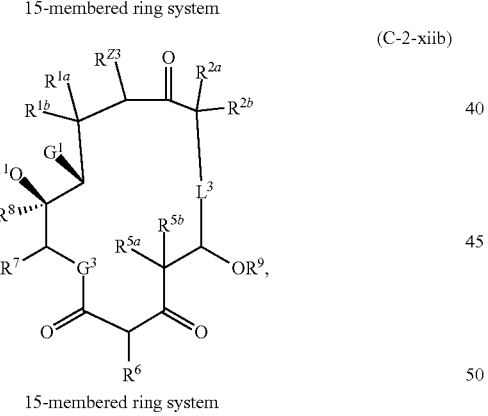
15-membered ring system
(C-2-xiic)
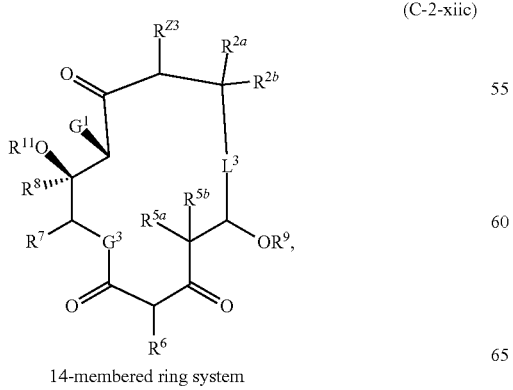
14-membered ring system
(C-2-xiid)
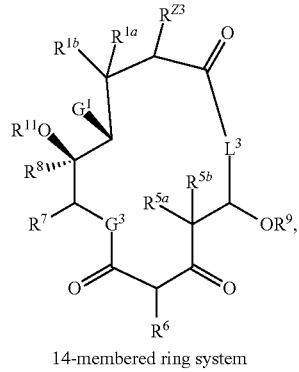
14-membered ring system
(C-2-xiie)
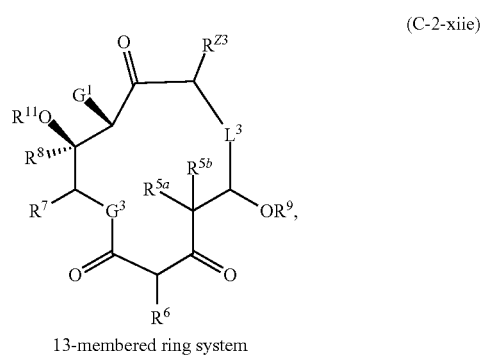
13-membered ring system
(C-2-xiif)
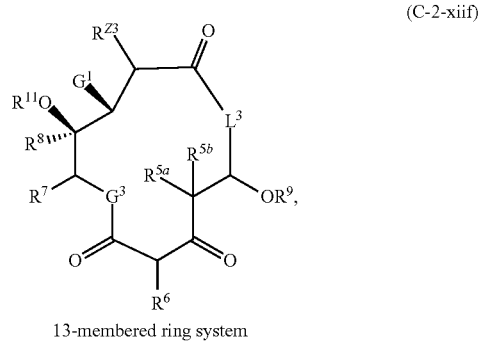
13-membered ring system
(C-3-xiia)
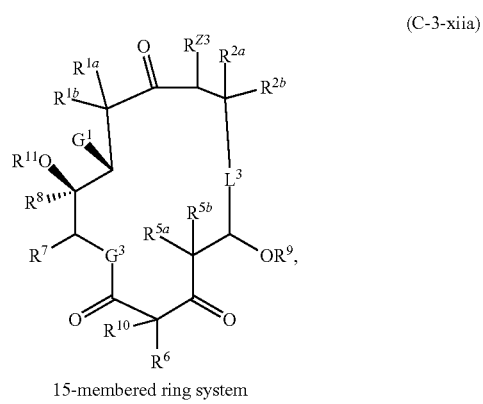
15-membered ring system (C-3-xiib)

15-membered ring system
(C-3-xiic)
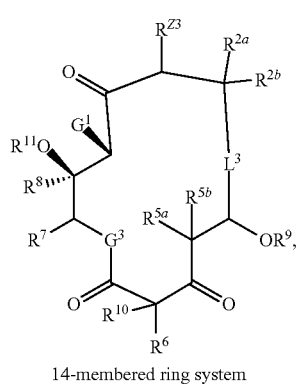
14-membered ring system
(C-3-xiid)
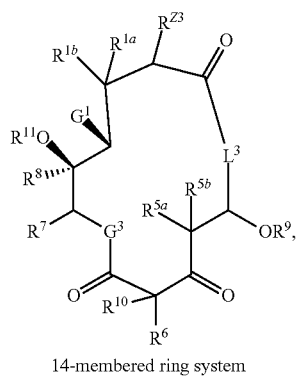
14-membered ring system
(C-3-xiie)
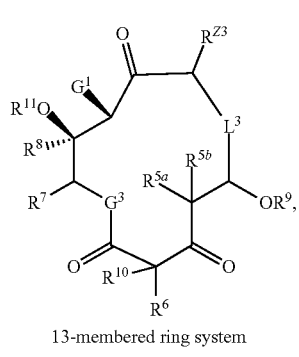
13-membered ring system
(C-3-xiif)
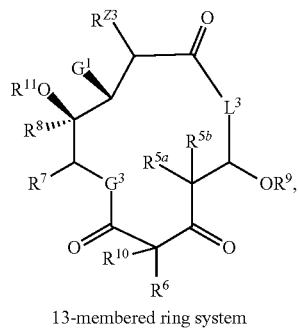
13-membered ring system
(C-4-xiia)
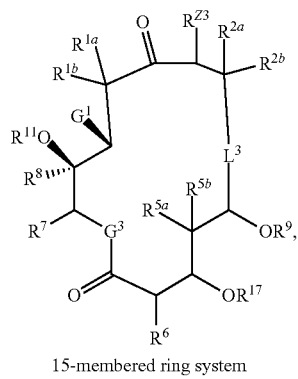
15-membered ring system
(C-4-xiib)
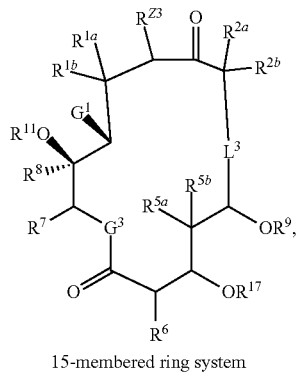
15-membered ring system
(C-4-xiic)
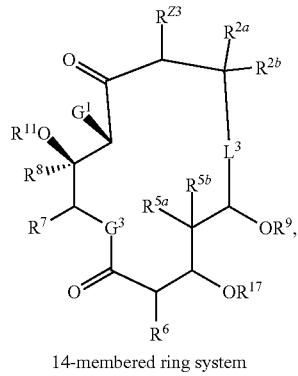
14-membered ring system

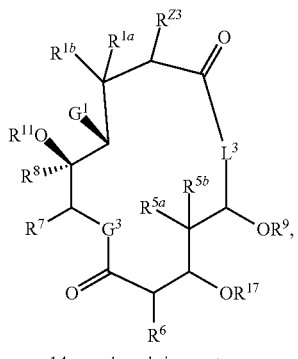
(C-4-xiid)
14-membered ring system
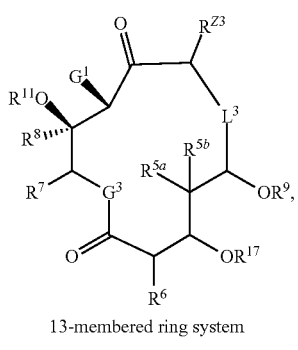
(C-4-xiie)
13-membered ring system
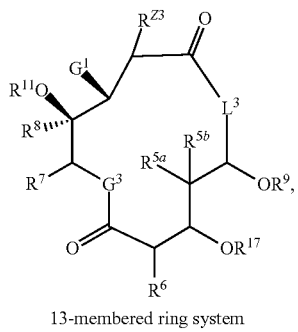
(C-4-xiif)
13-membered ring system
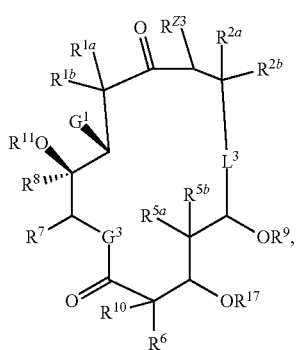
(C-5-xiia)
15-membered ring system
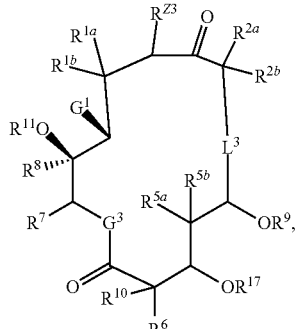
(C-5xiib)
15-membered ring system
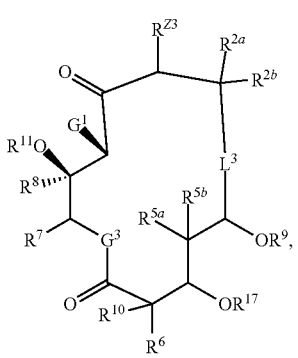
(C-5-xiic)
14-membered ring system
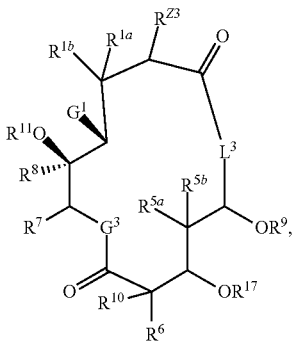
(C-5-xiid)
14-membered ring system
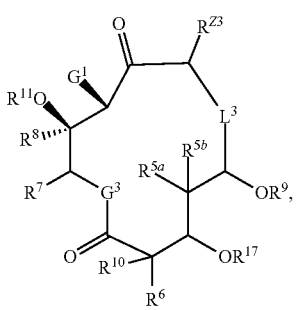
(C-5-xiie)
13-membered ring system -continued
(C-5-xiif)
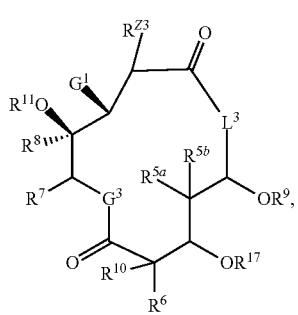
13-membered ring system
(C-467-xiia)
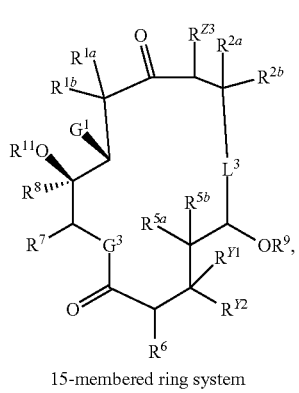
15-membered ring system
(C-467-xiib)
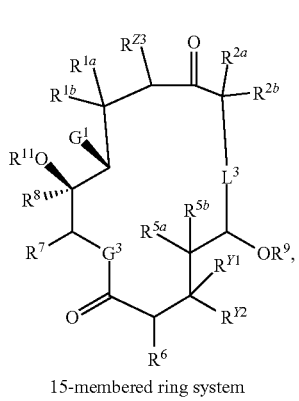
15-membered ring system
(C-467-xiic)
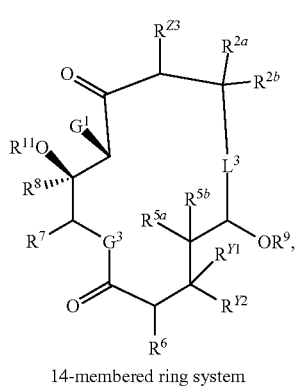
14-membered ring system
-continued
(C-467-xiid)
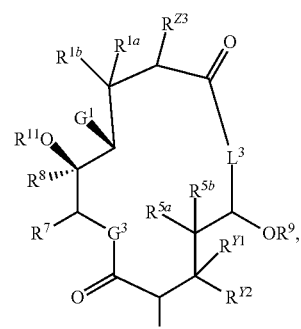
14-membered ring system
(C-467-xiie)
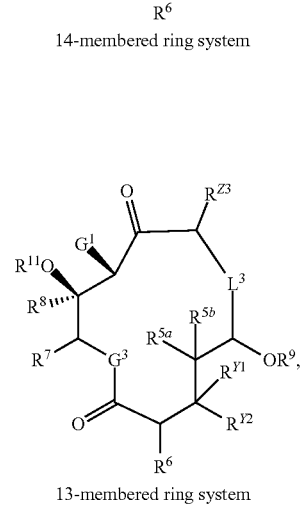
13-membered ring system
(C-467-xiif)
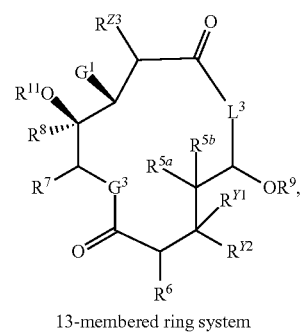
13-membered ring system
(C-567-xiia)
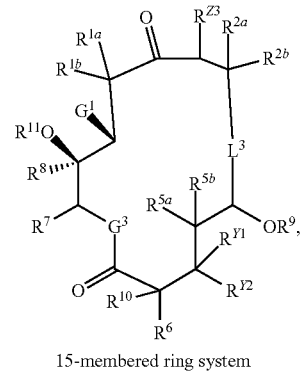
15-membered ring system -continued

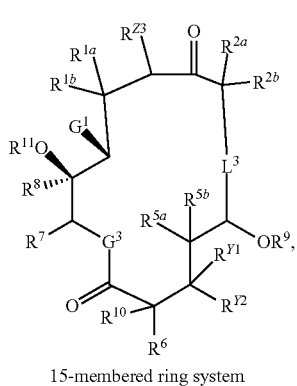
15-membered ring system
(C-567-xiib)

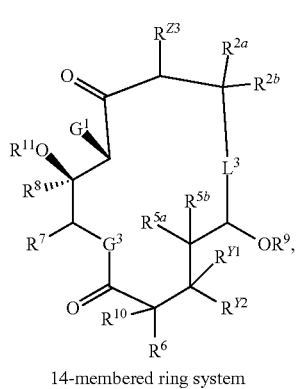
14-membered ring system
(C-567-xiic)

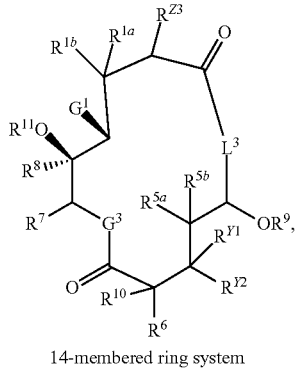
14-membered ring system
(C-567-xiid)

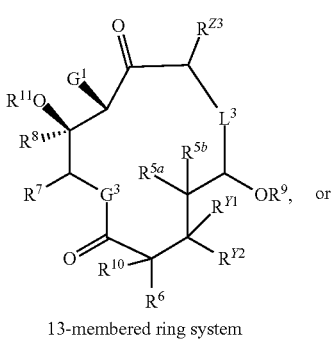
13-membered ring system
(C-567-xiif)

-continued

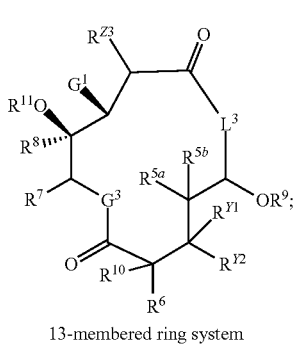
13-membered ring system
(C-567-xiif)

wherein in certain embodiments the macrolide is prepared, in part, from macrocyclization (e.g., thermally induced) of the coupled precursor compound of the below formula, optionally followed by further synthetic manipulation, as described herein:

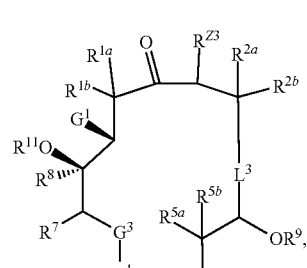
(C-1-xiia)

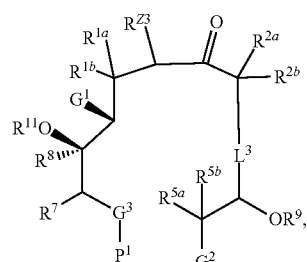
(C-1-xiib)

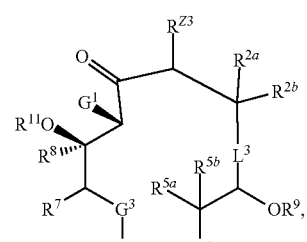
(C-1-xiic)

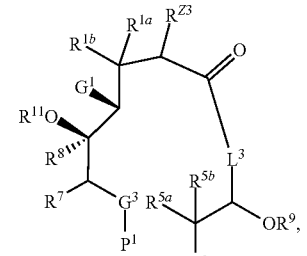
(C-1-xiid)

-continued
(C-1-xiie)
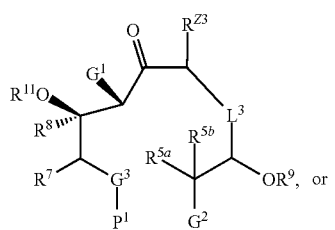
or
(C-1-xiif)
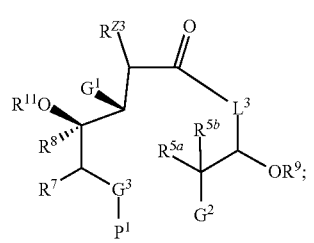
;
[17] an keto group of formula:
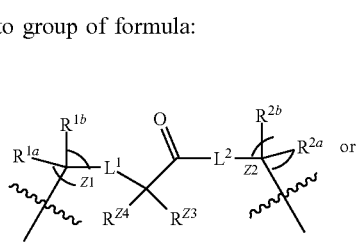
or
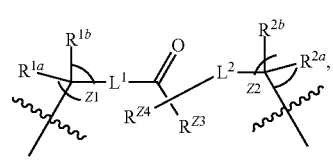
,
wherein $L^1$ and $L^2$ are each independently a bond or —CH$_2$—; z1 and z2 are 0, 1, or 2, e.g., to provide a 13-, 14-, 15- or 16-membered ring system, e.g., of formula:
(C-2-xiiia)
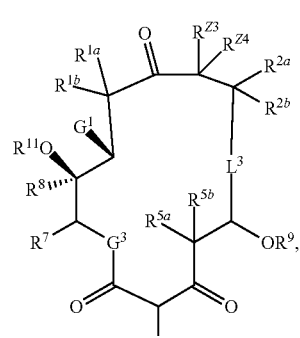
15-membered ring system
-continued
(C-2-xiiib)
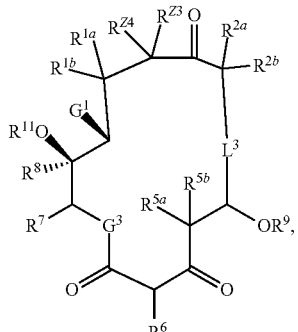
15-membered ring system
(C-2-xiiic)
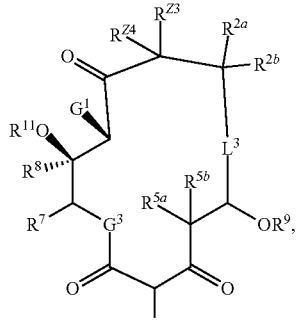
14-membered ring system
(C-2-xiiid)
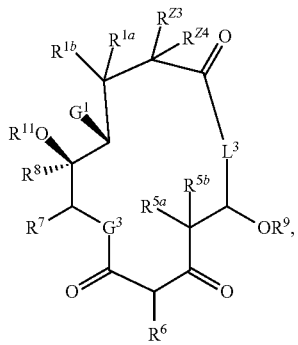
14-membered ring system
(C-2-xiiie)
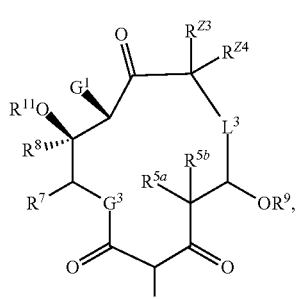
13-membered ring system (C-2-xiiif)
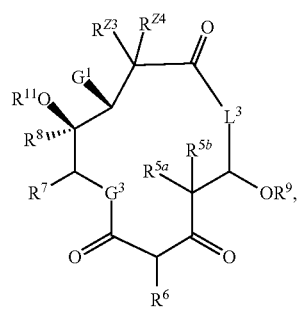
13-membered ring system
(C-3-xiiia)
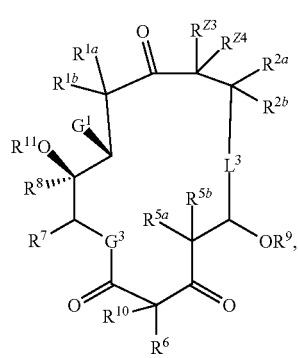
15-membered ring system
(C-3-xiiib)
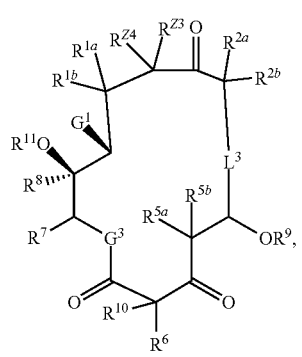
15-membered ring system
(C-3-xiiic)
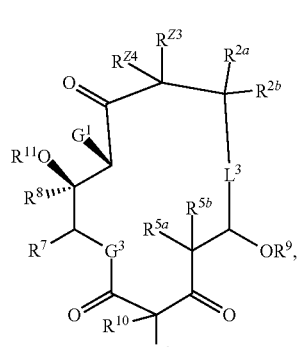
14-membered ring system
(C-3-xiiid)
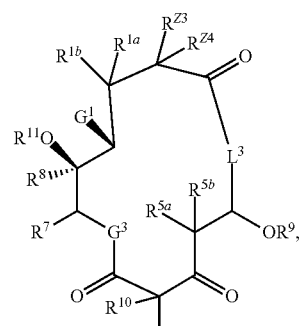
14-membered ring system
(C-3-xiiie)
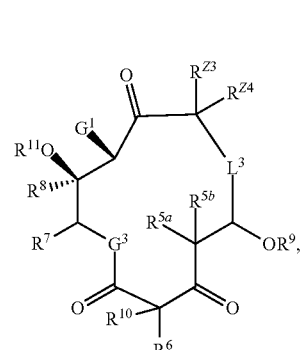
13-membered ring system
(C-3-xiiif)
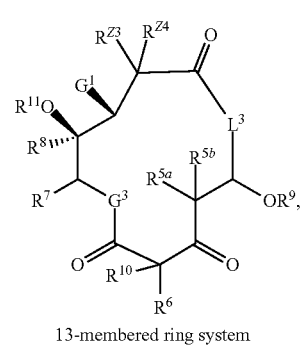
13-membered ring system
(C-4-xiiia)
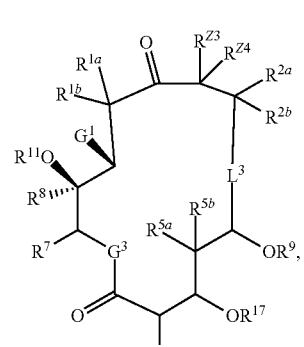
15-membered ring system

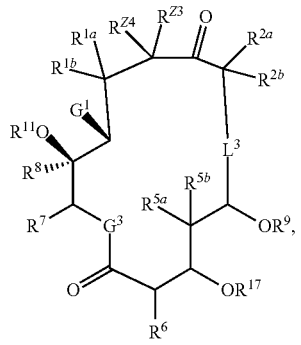
(C-4-xiiib)
15-membered ring system
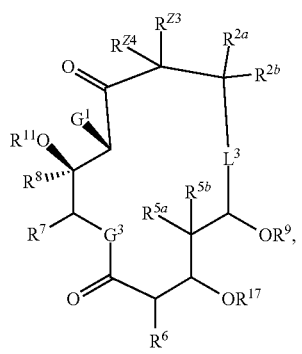
(C-4-xiiic)
14-membered ring system
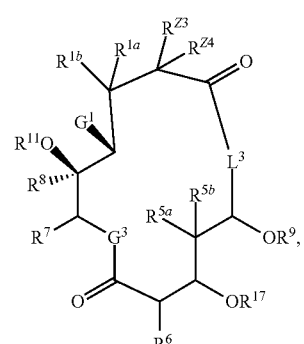
(C-4-xiii)
14-membered ring system
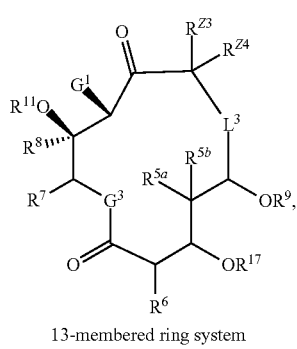
(C-4-xiiie)
13-membered ring system
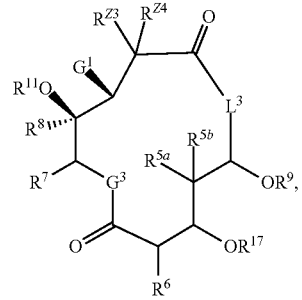
(C-4-xiiif)
13-membered ring system
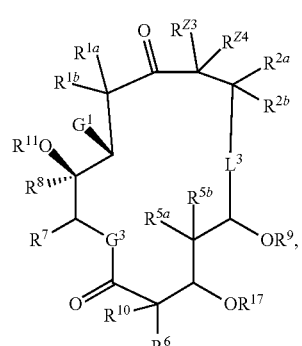
(C-5-xiiia)
15-membered ring system
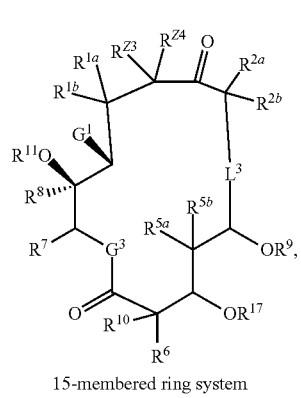
(C-5-xiiib)
15-membered ring system
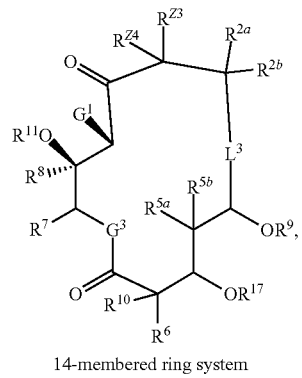
(C-5-xiiic)
14-membered ring system 201
-continued
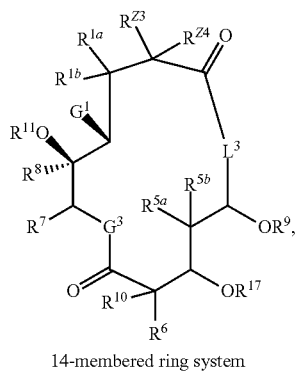
(C-5-xiiid)
14-membered ring system
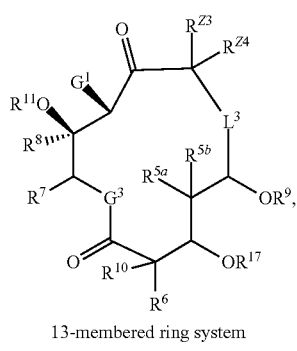
(C-5-xiiie)
13-membered ring system
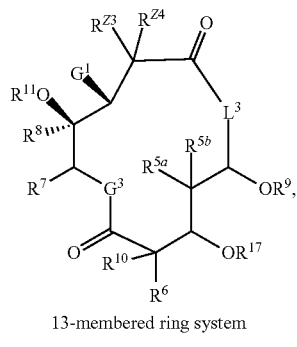
(C-5-xiiif)
13-membered ring system
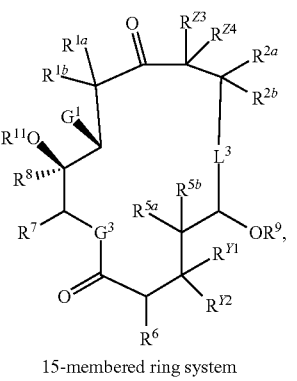
(C-467-xiiia)
15-membered ring system
202
-continued
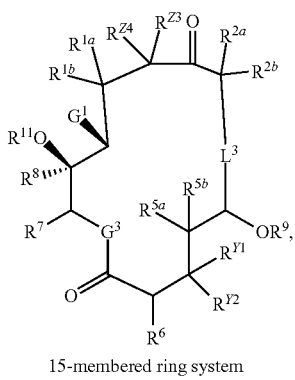
(C-467-xiiib)
15-membered ring system
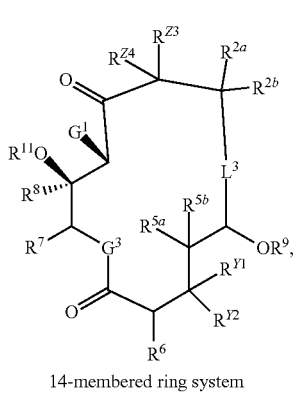
(C-467-xiiic)
14-membered ring system
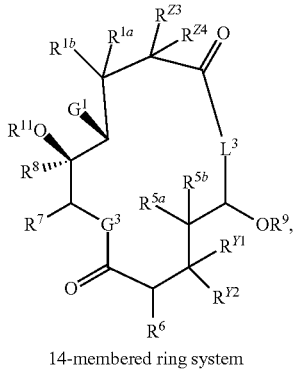
(C-467-xiiid)
14-membered ring system
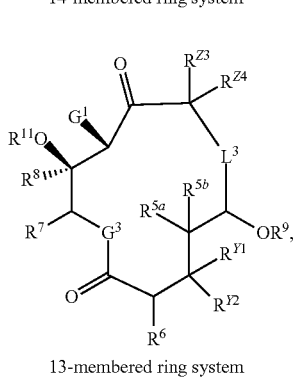
(C-467-xiiie)
13-membered ring system (C-467-xiiif)

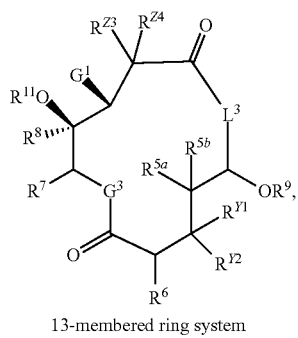
13-membered ring system (C-567-xiiia)

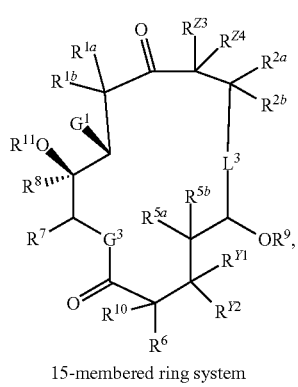
15-membered ring system (C-567-xiiib)

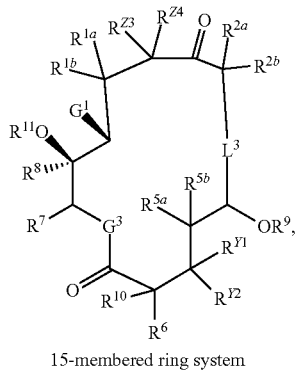
15-membered ring system (C-567-xiiic)

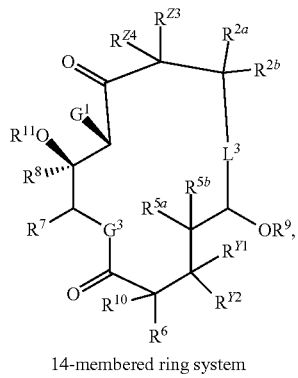
14-membered ring system (C-567-xiiid)

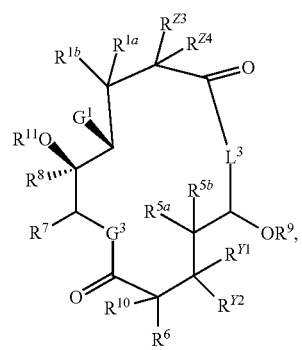
14-membered ring system (C-567-xiiie)

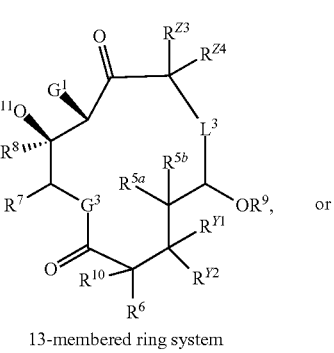
13-membered ring system or (C-567-xiiif)

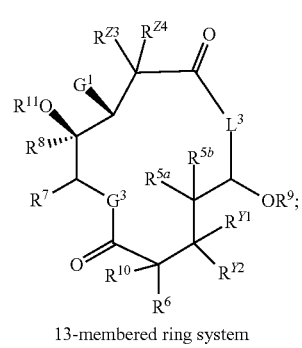
13-membered ring system wherein in certain embodiments the macrolide is prepared, in part, from macrocyclization (e.g., thermally induced) of the coupled precursor compound of the below formula, optionally followed by further synthetic manipulation, as described herein:

(C-1-xiiia)

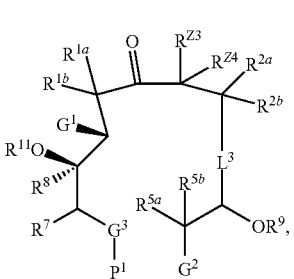

(C-1-xiiib)
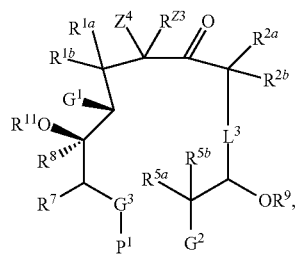
(C-1-xiiic)
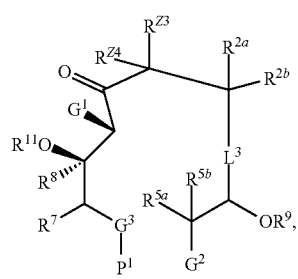
(C-1-xiiid)
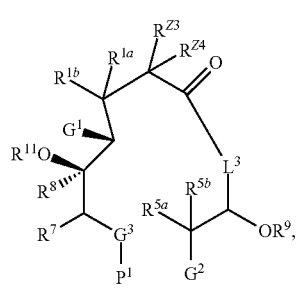
(C-1-xiiie)
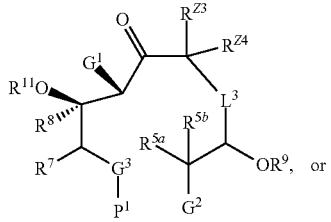
or
(C-2-xiiif)
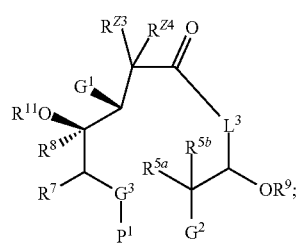
[18] a ketone of formula:
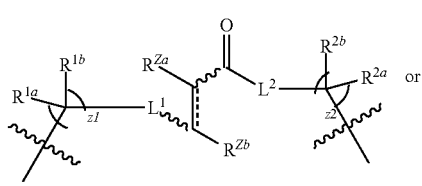 or
(C-1-xiiib)
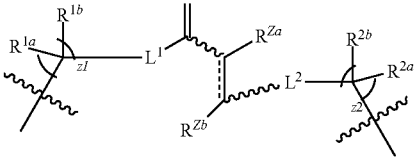
wherein $L^1$ and $L^2$ are each independently a bond or —CH$_2$—; z1 and z2 are each independently 0, 1, or 2, e.g., to provide a 14-, 15- or 16-membered ring system, e.g., of formula:
(C-2-xiva)
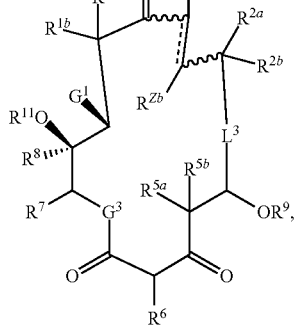
16-membered ring system
(C-2-xivb)
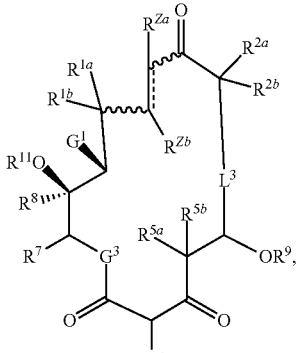
16-membered ring system
(C-2-xivc)
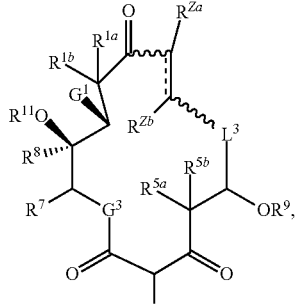
15-membered ring system

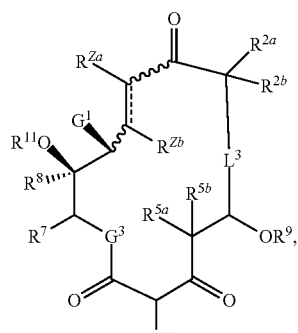
(C-2-xivd)
15-membered ring system
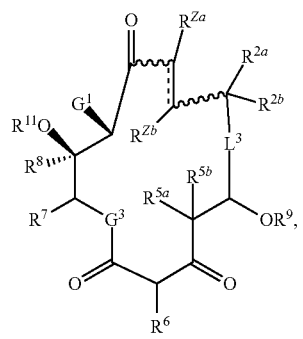
(C-2-xive)
15-membered ring system
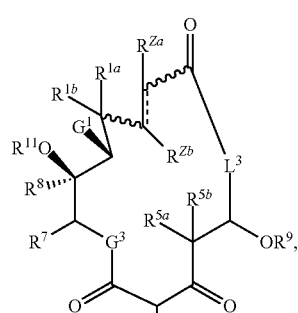
(C-2-xivf)
15-membered ring system
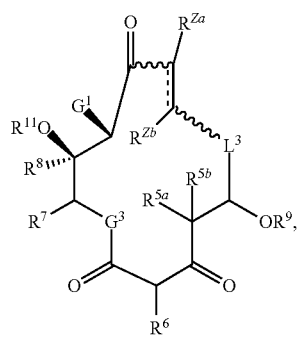
(C-2-xivg)
14-membered ring system
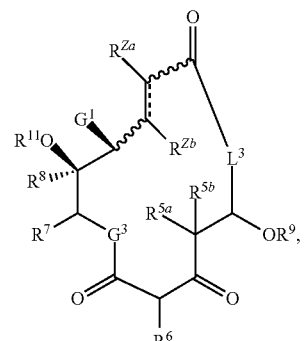
(C-2-xivh)
14-membered ring system
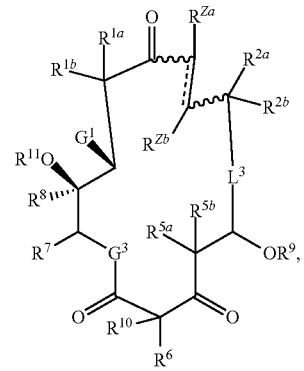
(C-3-xiva)
16-membered ring system
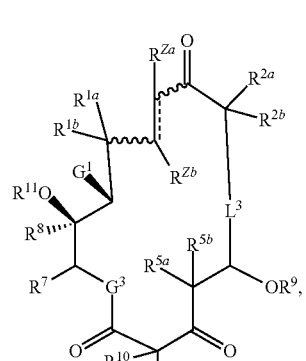
(C-3-xivb)
16-membered ring system
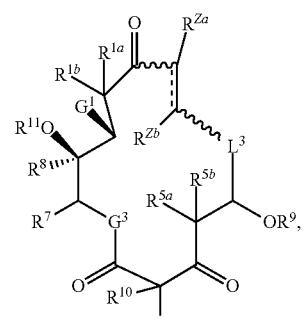
(C-3-xivc)
15-membered ring system -continued
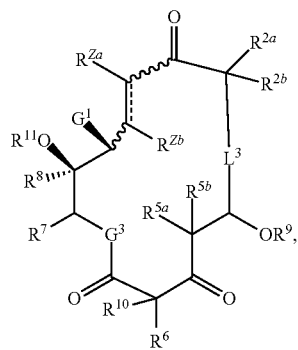
(C-3-xivd)
15-membered ring system
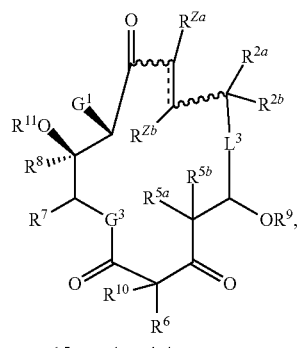
(C-3-xive)
15-membered ring system
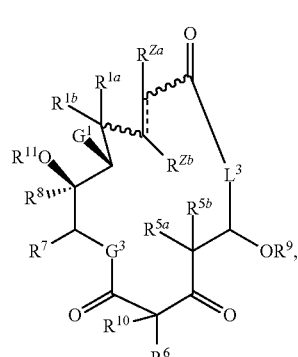
(C-3-xivf)
15-membered ring system
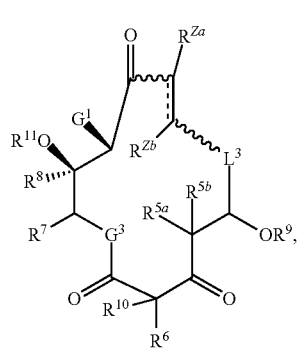
(C-3-xivg)
14-membered ring system
-continued
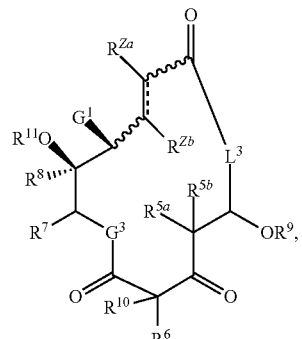
(C-3-xivh)
14-membered ring system
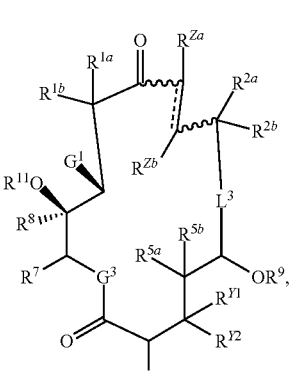
(C-467-xiva)
16-membered ring system
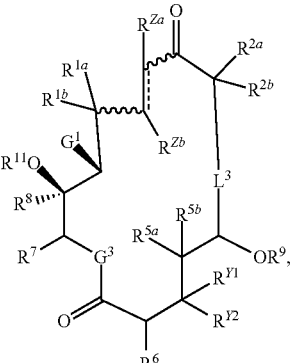
(C-467-xivb)
16-membered ring system
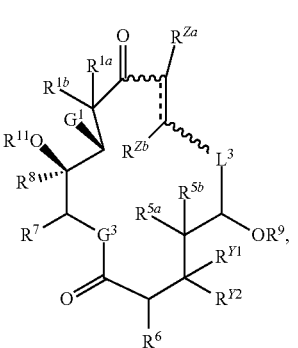
(C-467-xivc)
15-membered ring system (C-467-xivd)
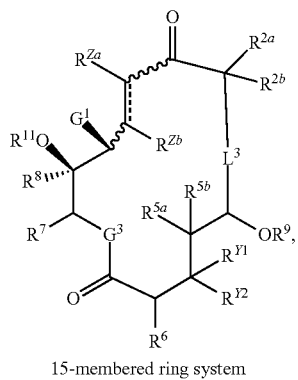
15-membered ring system
(C-467-xive)
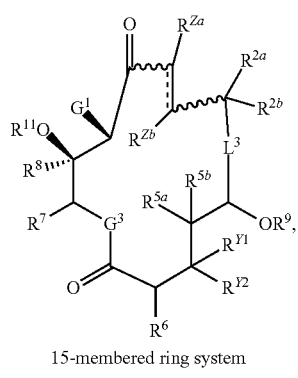
15-membered ring system
(C-467-xivf)
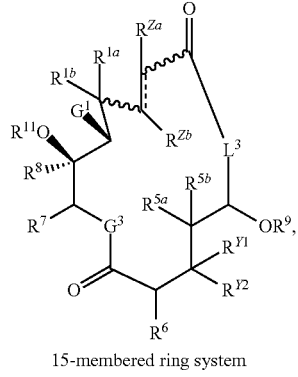
15-membered ring system
(C-467-xivg)
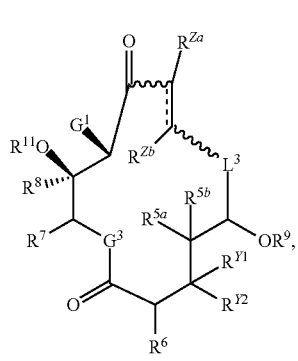
14-membered ring system
(C-467-xivh)
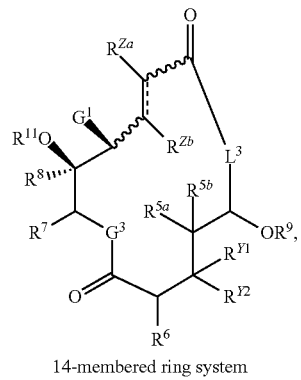
14-membered ring system
(C-567-xiva)
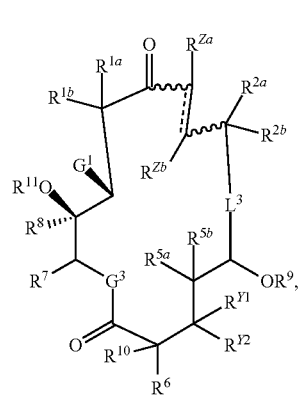
16-membered ring system
(C-567-xivb)
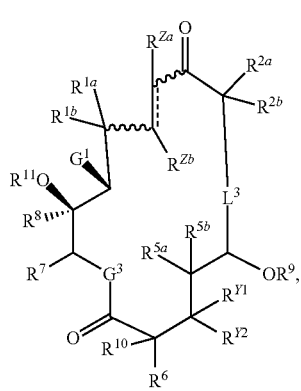
16-membered ring system
(C-567-xivc)
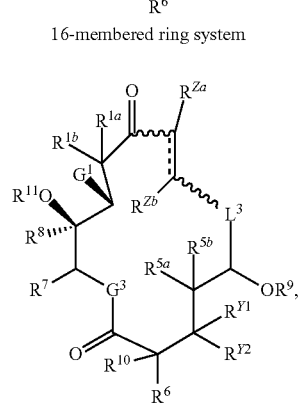
15-membered ring system (C-567-xivd)
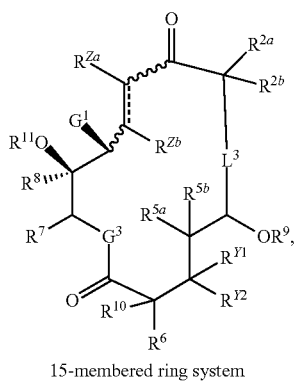
15-membered ring system (C-567-xive)
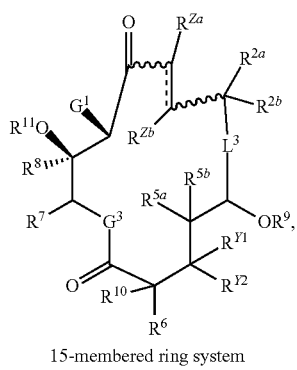
15-membered ring system (C-567-xivf)
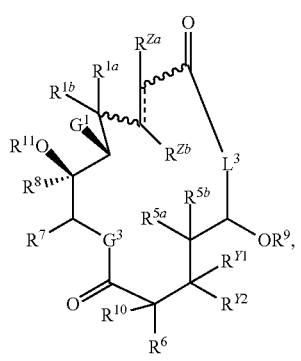
15-membered ring system (C-567-xivg)
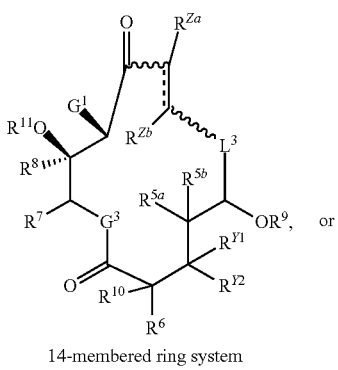
14-membered ring system (C-567-xivh)
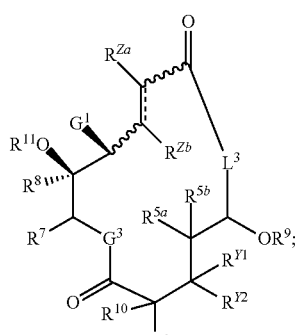
14-membered ring system wherein the macrolide is prepared by macrocyclization (e.g., thermally induced macrocyclization) of the coupled precursor of one of the formulae below, optionally followed by further synthetic manipulation, as described herein:

(C-1-xiva)

(C-1-xivb)

(C-1-xivc)

(C-1-xivd)

(C-1-xive)

(C-1-xivf)

(C-1-xivg)

(C-1-xivh)

wherein:

$R^{Y1}$ is —$OR^{17}$ and $R^{Y2}$ is hydrogen, or $R^{Y1}$ is halogen and $R^{Y2}$ is hydrogen, or $R^{Y1}$ is halogen and $R^{Y2}$ is halogen, or $R^{Y1}$ and $R^{Y2}$ are joined to form an oxo (=O) group;

each instance of $R^{1a}$, $R^{1b}$, $R^{2a}$, and $R^{2b}$ is independently hydrogen, halogen, carbonyl, optionally substituted alkyl, optionally substituted alkenyl, optionally substituted alkynyl, optionally substituted carbocyclyl, optionally substituted heterocylyl, optionally substituted aryl, optionally substituted heteroaryl, or wherein $R^{1a}$ and $R^{1b}$ or $R^{2a}$ and $R^{2b}$ can be taken together to form $R^{Za}$ and $R^{Zb}$ are each independently hydrogen, halogen, hydroxyl, substituted hydroxyl, amino, substituted amino, thiol, substituted thiol, carbonyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{Z2}$ is independently hydrogen, optionally substituted alkyl, optionally substituted alkenyl, optionally substituted alkynyl, optionally substituted carbocyclyl, optionally substituted heterocylyl, optionally substituted aryl, optionally substituted heteroaryl, hydroxyl, substituted hydroxyl, amino, substituted amino, —C(=O)$R^{Z8}$, —C(=O)O$R^{Z8}$, —C(=O)N($R^{Z8}$)$_2$, or a nitrogen protecting group, or two $R^{Z2}$ groups are joined to form an optionally substituted heterocylyl or optionally substituted heteroaryl ring;

$R^{Z3}$ is hydrogen, halogen, optionally substituted alkyl, optionally substituted alkenyl, optionally substituted alkynyl, optionally substituted carbocyclyl, optionally substituted heterocylyl, optionally substituted aryl, or optionally substituted heteroaryl;

$R^{Z4}$ is halogen, optionally substituted alkyl, optionally substituted alkenyl, optionally substituted alkynyl, optionally substituted carbocyclyl, optionally substituted heterocylyl, optionally substituted aryl, or optionally substituted heteroaryl;

or wherein $R^{Z3}$ and $R^{Z4}$ can be taken together to form $L^3$ is a group of formula:

(L3-i)

(L3-ii)

-continued

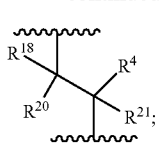
(L3-iii)

---- represents a single or double bond;

$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{Z8}$, —C(=O)O$R^{Z8}$, —C(=O)N($R^{Z8}$)$_2$, an oxygen protecting group, or a group of formula:

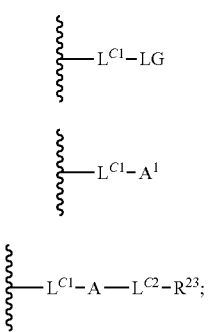

$R^4$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{18}$ and $R^{19}$ independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{20}$ and $R^{21}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, halogen, carbonyl, or $R^{20}$ and $R^{21}$ are joined to form an optionally substituted cyclopropyl or an oxiranyl ring;

each instance of $R^{5a}$ and $R^{5b}$ is independently hydrogen, halogen, silyl, optionally substituted alkyl, optionally substituted carbocyclyl, or optionally substituted heterocyclyl;

$R^6$ is hydrogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl, hydroxyl, substituted hydroxyl, thiol, substituted thiol, amino, substituted amino, carbonyl, silyl, or halogen;

$R^7$ and $R^8$ are each independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^9$ and $R^{17}$ are each independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{Z8}$, —C(=O)O$R^{Z8}$, —C(=O)N($R^{Z8}$)$_2$, an oxygen protecting group, or a carbohydrate;

$R^{10}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, carbonyl, silyl, and halogen;

$G^3$ is —O—, —S—, or —N($R^{G1}$)—, wherein $R^{G1}$ is hydrogen, optionally substituted alkyl, or a nitrogen protecting group;

$P^1$ is hydrogen, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

$G^1$ is —O$R^{12}$ or —N$R^{13}R^{14}$;

provided when $G^1$ is —O$R^{12}$, then:

$R^{11}$ and $R^{12}$ are joined as a group of formula —C(=O)— to provide a cyclic carbonate, or $R^{11}$ and $R^{12}$ are not joined, and $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, and $R^{12}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group, or a group of formula:

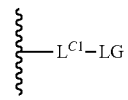
(LC1-i)

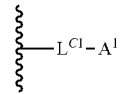
(LC1-ii)

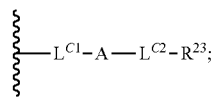
(LC1-iii)

or provided when $G^1$ is —N$R^{13}R^{14}$, then:

$R^{11}$ and $R^{13}$ are joined as a group of formula —C(=O)— to provide a cyclic carbamate, or $R^{11}$ and $R^{13}$ are not joined, $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, $R^{13}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, —C(=O)R$^{Z8}$, or —C(=O)OR$^{Z8}$, or a group of formula:

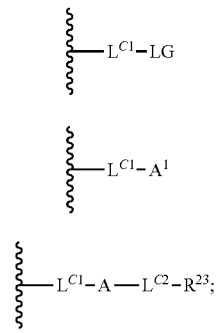

(LC1-i)
(LC1-ii)
(LC1-iii)

or R$^{13}$ and R$^{14}$ are joined to form an optionally substituted heterocyclyl or optionally substituted heteroaryl;

G$^2$ is a group of formula:

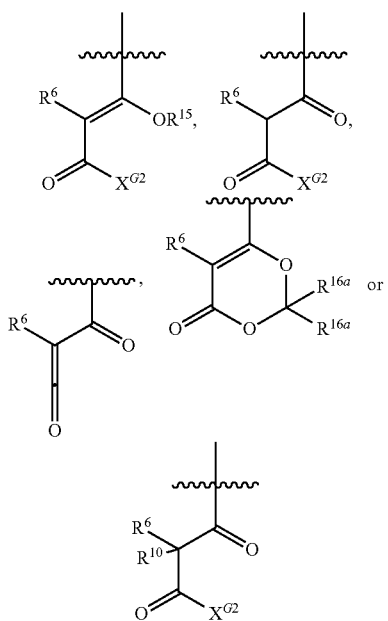

each instance of X$^{G2}$ is —OR$^{15}$, —SR$^{15}$, or —N(R$^{15}$)$_2$;

each instance of R$^{15}$ is independently silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or two R$^{15}$ groups can be taken together to form an optionally substituted heteroaryl or heterocyclic ring;

each instance of R$^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of L$^{C1}$ and L$^{C2}$ is independently a bond, or a linking group selected from the group consisting of optionally substituted alkylene, optionally substituted alkenylene, optionally substituted alkynylene; optionally substituted heteroalkylene, optionally substituted heteroalkenylene, optionally substituted heteroalkynylene, and combinations thereof;

Leaving group (LG) is —Br, —I, —Cl, —O(C=O)R$^{LG}$, or —O(SO)$_2$R$^{LG}$, wherein R$^{LG}$ is optionally substituted alkyl, optionally substituted aryl, or optionally substituted heteroaryl;

each instance of A$^1$ and A$^2$ is independently a leaving group (LG), —SH, —OH, —NH$_2$, —NH—NH$_2$, —N$_3$, —O—NH$_2$, —C(=O)R$^{X1}$,

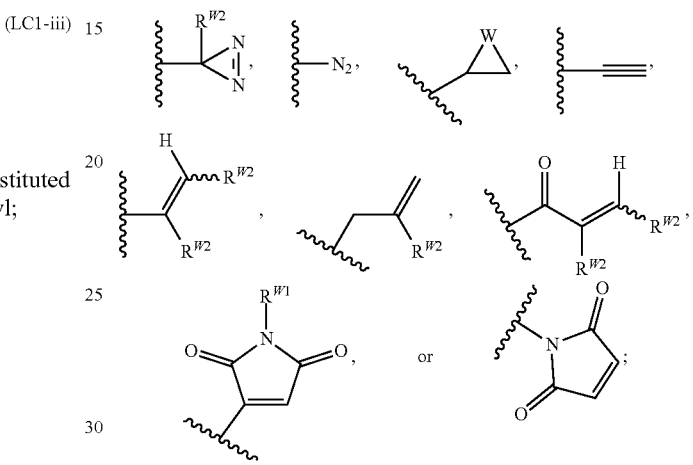

A is —NH—, —NH—NH—, —NH—O—, —O—NH—, —S—, —O—,

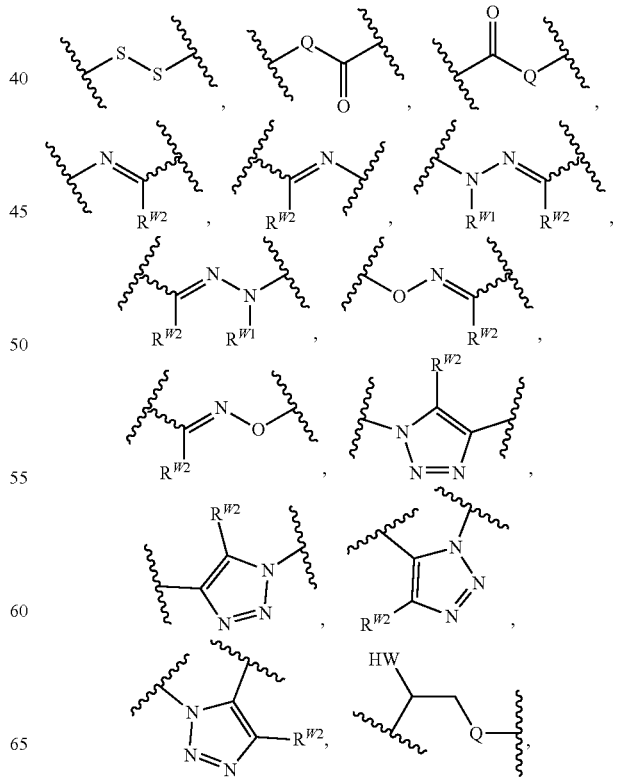

-continued

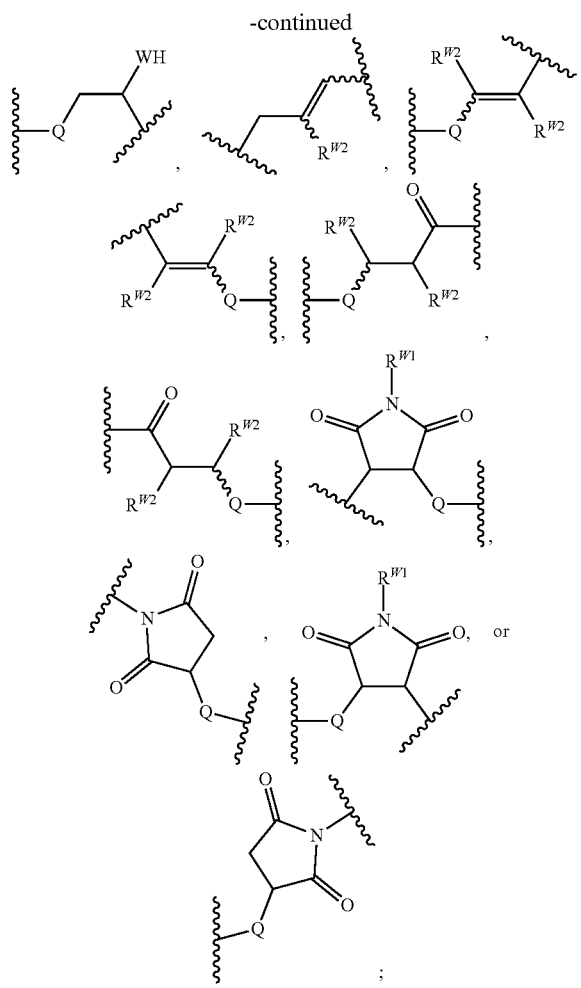

Q is —NH—, —NH—NH—, —O—NH—, —NH—O—, —S— or —O—;

W is O, S, or NR$^{W1}$;

R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

R$^{W2}$ is hydrogen, optionally substituted alkyl; optionally substituted alkenyl; optionally substituted alkynyl; optionally substituted carbocyclyl; optionally substituted heterocyclyl; optionally substituted aryl; or optionally substituted heteroaryl, or two R$^{W2}$ groups are joined to form an optionally substituted cyclic moiety;

R$^{X1}$ is hydrogen, halogen, or —OR$^{X2}$, wherein R$^{X2}$ is hydrogen; optionally substituted alkyl; optionally substituted alkyl; optionally substituted alkenyl; optionally substituted alkynyl; optionally substituted carbocyclyl; optionally substituted heterocyclyl; optionally substituted aryl; optionally substituted heteroaryl; or an oxygen protecting group;

R$^{23}$ is optionally substituted alkyl; optionally substituted alkenyl; optionally substituted alkynyl; optionally substituted carbocyclyl; optionally substituted heterocyclyl; optionally substituted aryl; or optionally substituted heteroaryl; and each instance of R$^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{Z8}$ groups are joined to form an optionally substituted heterocyclyl or optionally substituted heteroaryl ring;

or A is a cyclic moiety selected from the group consisting of optionally substituted carbocyclyl, optionally substituted heterocyclyl, optionally substituted aryl, and optionally substituted heteroaryl.

Coupling and Macrocyclization

As generally described herein, macrolides of the present invention are prepared by coupling of an western half (A) with an eastern half (B) to provide a compound of Formula (C-1), as depicted in Scheme 8:

Scheme 8

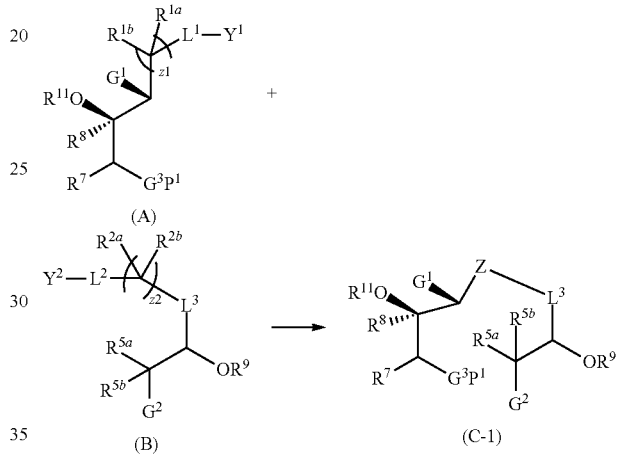

or salt thereof, wherein L$^1$, L$^2$, L$^3$, G$^1$, G$^3$, R$^{1a}$, R$^{1b}$, R$^{2a}$, R$^{2b}$, R$^{5a}$, R$^{5b}$, R$^7$, R$^8$, R$^9$, R$^{11}$, z1, and z2 are as defined herein;

P$^1$ is hydrogen, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

G$^2$ is a group of formula:

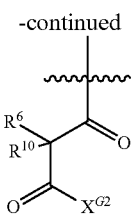

wherein $R^6$ and $R^{10}$ are as defined herein;

each instance of $X^{G2}$ is $-OR^{15}$, $-SR^{15}$, or $-N(R^{15})_2$;

each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or two $R^{15}$ groups can be taken together to form an optionally substituted heteroaryl or heterocyclic ring;

each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and one of $Y^1$ and $Y^2$ is $-Z^4H$ or $-CH_2NO_2$, and the other of $Y^1$ and $Y^2$ is a leaving group (LG), $-C(=O)R^{Z3}$, $-C(=O)OR^{Z3}$, $-C(=O)LG$, $-C(=O)-CH=P(R^{P1})(R^{P2})(R^{P3})$, or $-C(=O)-CH_2-P(O)(OR^{P2})(OR^{P3})$, wherein $Z^4$ is $-O-$, $-S-$, or $-NR^{Z2}-$, and wherein the leaving group (LG), $R^{Z3}$, $R^{Z4}$, $R^{P1}$, $R^{P2}$, and $R^{P3}$ are as defined herein, to provide various linkages of formula Z.

For example, in certain embodiments, when $Y^1$ is $-C(=O)R^{Z3}$ and $R^{Z3}$ is hydrogen (aka wherein $Y^1$ is $-CHO$) and $Y^2$ is $-C(=O)-CH=P(R^{P1})(R^{P2})(R^{P3})$ or $-C(=O)-CH_2-P(O)(OR^{P2})(OR^{P3})$, coupling of the eastern and western halves via a Wittig or Homer-Emmons reaction forms the moiety $-CH=CH-C(=O)-$, and provides a compound of Formula (C-1), wherein Z is an α,β-unsaturated ketone of formula:

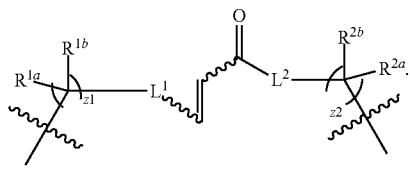

In certain embodiments, the double bond of the above recited formula is provided in the cis-configuration. In certain embodiments, the double bond of the above recited formula is provided in the trans-configuration.

In certain embodiments, when $Y^2$ is $-C(=O)R^{Z3}$ and $R^{Z3}$ is hydrogen (aka wherein $Y^1$ is $-CHO$) and $Y^1$ is $-C(=O)-CH=P(R^{P1})(R^{P2})(R^{P3})$ or $-C(=O)-CH_2-P(O)(OR^{P2})(OR^{P3})$, coupling of the eastern and western halves via a Wittig reaction or Homer-Emmons reaction forms a moiety $-C(=O)-CH=CH-$, and provides a compound of Formula (C-1), wherein Z is an α,β-unsaturated ketone of formula:

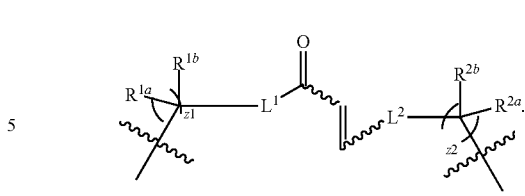

In certain embodiments, the double bond of the above recited formula is provided in the cis-configuration. In certain embodiments, the double bond of the above recited formula is provided in the trans-configuration.

Optional synthetic modification of the moieties $-CH=CH-C(=O)-$ and $-C(=O)-CH=CH-$ is further contemplated herein. For example, the double bond may be reduced to a single bond, and optionally the carbon alpha to the ketone may be substituted by a non-hydrogen group $R^{Za}$. A nucleophile may react with the double bond via 1,4-addition of a non-hydrogen group $R^{Zb}$ optionally followed by alpha substitution via a non-hydrogen group $R^{Za}$. Various synthetic modifications of the α,β-unsaturated ketone formula contemplated herein are thus encompassed by the formulae:

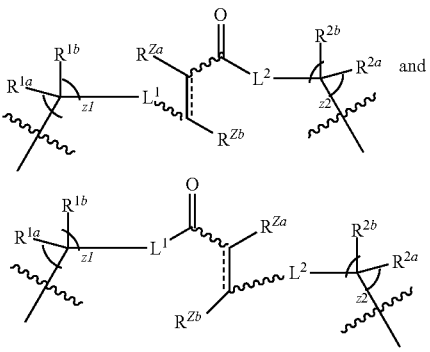

wherein ----- represents a single or double bond, and $R^{Za}$ and $R^{Zb}$ are each independently hydrogen or a non-hydrogen group (e.g., halogen, hydroxyl, substituted hydroxyl, amino, substituted amino, thiol, substituted thiol, carbonyl, optionally substituted alkyl, optionally substituted alkenyl, optionally substituted alkynyl, optionally substituted carbocyclyl, optionally substituted heterocyclyl, optionally substituted aryl, or optionally substituted heteroaryl). The above formulae thus encompass the initial Wittig reaction or Homer-Emmons reaction linkages, i.e., wherein ----- represents a double bond and $R^{Za}$ and $R^{Zb}$ are each hydrogen, as well as additional synthetic modifications of the linkage, e.g., wherein ----- represents a single bond, and $R^{Za}$ and $R^{Zb}$ are each independently hydrogen or a non-hydrogen group, or wherein ----- represents a single bond or double bond, and $R^{Za}$ and $R^{Zb}$ are each independently hydrogen or a non-hydrogen group, provided at least one of $R^{Za}$ and $R^{Zb}$ is a non-hydrogen group. In certain embodiments, wherein ----- represents a double bond, $R^{Za}$ and $R^{Zb}$ are in a cis-configuration. In certain embodiments, wherein ----- represents a double bond, $R^{Za}$ and $R^{Zb}$ are in a trans-configuration.

In certain embodiments, when $Y^1$ is $-Z^4H$ and $Y^2$ is a leaving group (LG), or when $Y^2$ is $-Z^4H$ and $Y^1$ is a leaving group (LG), coupling of the eastern and western halves by nucleophilic displacement (nucleophilic substitution), optionally in the presence of a base, provides a compound of Formula (C-1), wherein Z is an ether, thioether, or amine of formula:

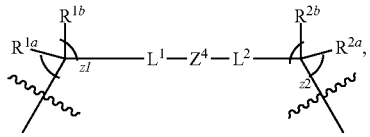

wherein $Z^4$ is —O—, —S—, or —NR$^{Z2}$—, and wherein R$^{Z2}$ hydrogen or a non-hydrogen group. Exemplary bases include, but are not limited to, organic bases (e.g., pyridine, DMAP, Hunig's base) and inorganic bases (e.g., sodium bicarbonate, sodium carbonate). Exemplary leaving groups include bromine, chlorine, iodine, tosylate, triflate, mesylate, and besylate.

In certain embodiments, when $Y^1$ is —$Z^4$H, and $Y^2$ is —C(=O)OR$^{Z3}$ or —C(=O)LG, coupling of the eastern and western halves by 1,2-nucleophilic addition, optionally in the presence of a base, provides a compound of Formula (C-1), wherein Z is an ester, thioester, or amide of formula:

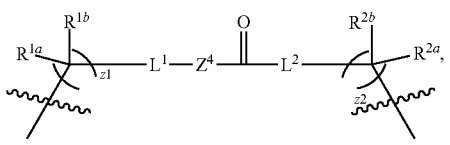

wherein $Z^4$ is —O—, —S—, or —NR$^{Z2}$—, and wherein R$^{Z2}$ is hydrogen or a non-hydrogen group. In certain embodiments, wherein R$^{Z3}$ is hydrogen, the reaction proceeds in the presence of a coupling agent, e.g., a carbodiimide reagent. Exemplary bases include, but are not limited to, organic bases (e.g., pyridine, DMAP, Hunig's base) and inorganic bases (e.g., sodium bicarbonate, sodium carbonate). Exemplary leaving groups include bromine, chlorine, iodine, tosylate, mesylate, triflate, and besylate.

Alternatively, in certain embodiments, when $Y^2$ is —$Z^4$H, and $Y^1$ is —C(=O)OR$^{Z3}$ or —C(=O)LG, coupling of the eastern and western halves by 1,2-nucleophilic addition, optionally in the presence of a base, provides a compound of Formula (C-1), wherein Z is an ester, thioester, or amide of formula:

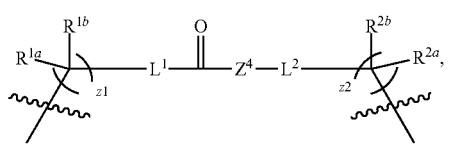

wherein $Z^4$ is —O—, —S—, or —NR$^{Z2}$—, and wherein R$^{Z2}$ is hydrogen or a non-hydrogen group. In certain embodiments, wherein R$^{Z3}$ is hydrogen, the reaction proceeds in the presence of a coupling agent, e.g., a carbodiimide reagent. Exemplary bases include, but are not limited to, organic bases (e.g., pyridine, DMAP, Hunig's base) and inorganic bases (e.g., sodium bicarbonate, sodium carbonate). Exemplary leaving groups include bromine, chlorine, iodine, tosylate, triflate, and besylate.

In certain embodiments, wherein $Y^1$ is —NH$_2$ or —NHR$^{Z2}$, and $Y^2$ is —C(=O)R$^{Z3}$, coupling of the eastern and western halves by reductive amination, optionally followed by protection of the amine group by a non-hydrogen R$^{Z2}$, provides a compound of Formula (C-1), wherein Z is an amine of formula:

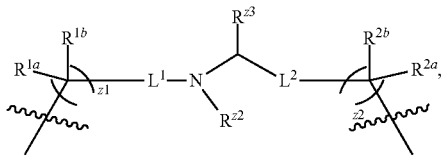

wherein R$^{Z2}$ is hydrogen or a non-hydrogen group. Exemplary reductive amination conditions include, but are not limited to, use of B$_{10}$H$_{14}$, InCl$_3$/Et$_3$SiH, NaBH$_4$, NaBH$_4$/H$_3$BO$_3$, NaBH$_3$CN or NaBH(OAc)$_3$, optionally in the presence of an acid (e.g., AcOH, TFA) or protic solvent (e.g., MeOH). In certain embodiments, R$^{Z2}$ is hydrogen. In certain embodiments, R$^{Z2}$ is methyl. In certain embodiments, R$^{Z2}$ is —C(=O)R$^{Z8}$. In certain embodiments, R$^{Z2}$ is —C(=O)Me. In certain embodiments, R$^{Z2}$ is a nitrogen protecting group.

In certain embodiments, wherein $Y^1$ is —NH$_2$, and $Y^2$ is —C(=O)R$^{Z3}$, coupling of the eastern and western halves by imine formation, optionally followed by addition of a group R$^{Z4}$ to the imine double bond, and optionally followed by protection of the amine group by a non-hydrogen R$^{Z2}$, provides a compound of Formula (C-1), wherein Z is an imine or amine of formula:

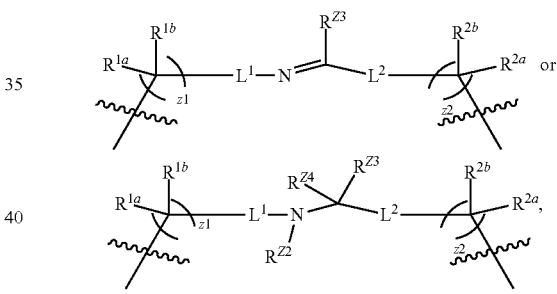

wherein R$^{Z2}$ is hydrogen or a non-hydrogen group. In certain embodiments, R$^{Z2}$ is hydrogen. In certain embodiments, R$^{Z2}$ is protected as methyl, —C(=O)R$^{Z8}$, or a nitrogen protecting group. In certain embodiments, R$^{Z4}$ is added to the imine double bond via a nucleophilic reagent, R$^{Z4}$M, wherein M is an anion, Li, K, CuX, or MgX, wherein X is halogen.

Alternatively, in certain embodiments, wherein $Y^2$ is —NH$_2$ or —NHR$^{Z2}$ and $Y^1$ is —C(=O)R$^{Z3}$, coupling of the eastern and western halves by reductive amination, optionally followed by protection of the amine group by a non-hydrogen R$^{Z2}$, provides a compound of Formula (C-1), wherein Z is an amine of formula:

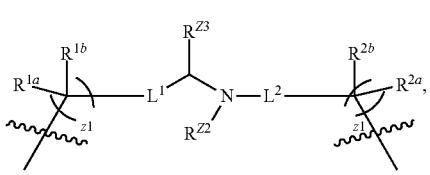

wherein R$^{Z2}$ is hydrogen or a non-hydrogen group. Exemplary reductive amination conditions include, but are not limited to, use of $B_{10}H_{14}$, $InCl_3/Et_3SiH$, $NaBH_4$, $NaBH_4/H_3BO_3$, $NaBH_3CN$ or $NaBH(OAc)_3$, optionally in the presence of an acid (e.g., AcOH, TFA) or protic solvent (e.g., MeOH). In certain embodiments, $R^{Z2}$ is hydrogen. In certain embodiments, $R^{Z2}$ is protected as methyl, —C(=O)$R^{Z8}$, or a nitrogen protecting group.

In certain embodiments, wherein $Y^2$ is —NH$_2$, and $Y^1$ is —C(=O)$R^{Z3}$, coupling of the eastern and western halves by imine formation, optionally followed by addition of a group $R^{Z4}$ to the imine double bond, optionally followed by protection of the amine group by a non-hydrogen $R^{Z2}$, provides a compound of Formula (C-1), wherein Z is an imine or amine of formula:

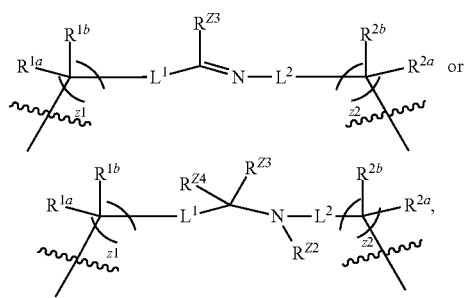

wherein $R^{Z2}$ is hydrogen or a non-hydrogen group. In certain embodiments, $R^{Z2}$ is hydrogen. In certain embodiments, $R^{Z2}$ is protected as methyl, —C(=O)$R^{Z8}$, or a nitrogen protecting group. In certain embodiments, $R^{Z4}$ is added to the imine double bond via a nucleophilic reagent, $R^{Z4}M$, wherein M is an anion, Li, K, CuX, or MgX, wherein X is halogen.

Further contemplated are nitro-aldol reaction (Henry reaction) coupling products, and oxidized, reduced, and/or addition products formed therefrom. The nitro aldol reaction may be catalyzed or promoted by many different sets of conditions, e.g., use of an organic base, inorganic base, quaternary ammonium salt, and/or a catalyst; and use of protic or aprotic solvents and/or use of solventless conditions. See, e.g., Luzzio *Tetrahedron* (2001) 915-945, for a review of various conditions employed in a nitro aldol reaction.

For example, in certain embodiments, wherein $Y^1$ is —CH$_2$NO$_2$, and $Y^2$ is —C(=O)$R^{Z3}$, coupling of the eastern and western halves provides a compound of Formula (C-1), wherein Z is a group of formula:

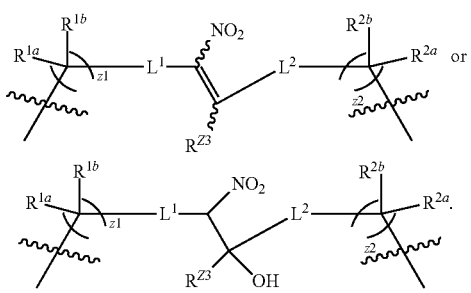

Alternatively, in certain embodiments, wherein $Y^2$ is —CH$_2$NO$_2$, and $Y^1$ is —C(=O)$R^{Z3}$, coupling of the eastern and western halves provides a compound of Formula (C-1), wherein Z is a group of formula:

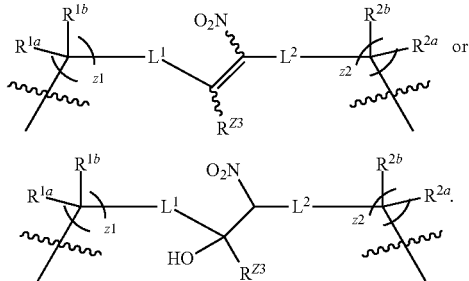

With the nitro-aldol coupling product in hand, the nitro (—NO$_2$) moiety may be manipulated at any stage in the synthesis.

For example, reduction of the double bond of the nitro-aldol product of formula:

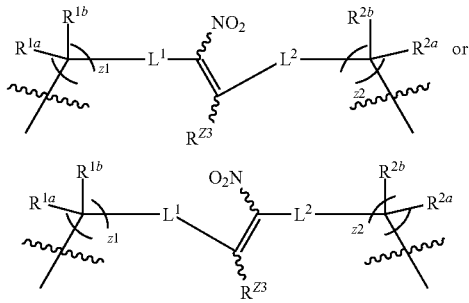

provides a Z group of formula:

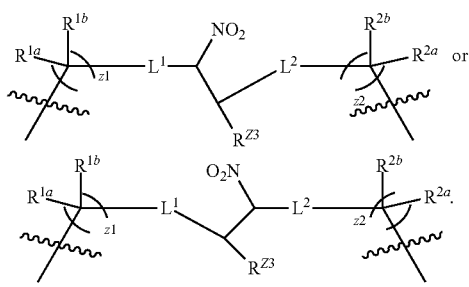

Addition of a group $R^{Z4}$ to the nitro-aldol product of formula:

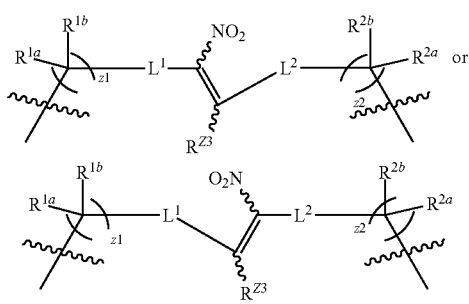

provides a Z group of formula:

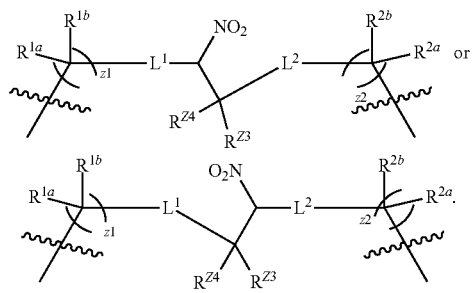

Reduction of the nitro group as provided in formulae:

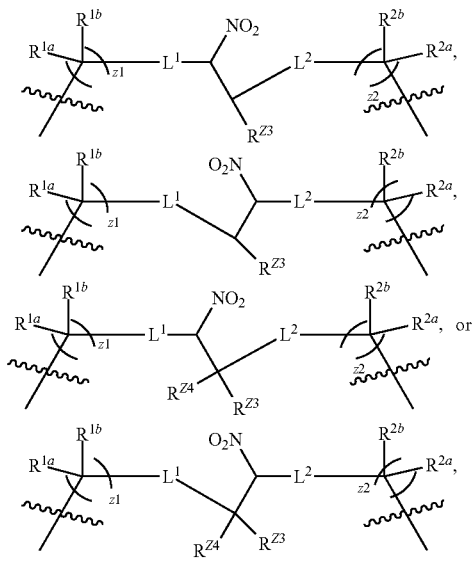

to the free amine, which may be optionally mono- or bis-protected, provides a Z group of formula:

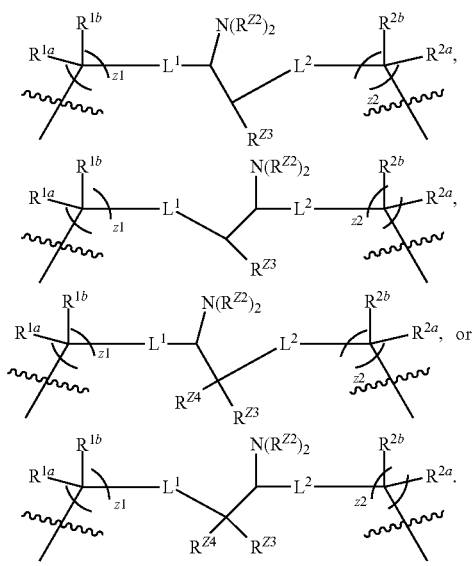

Oxidation of the nitro group as provided in formula:

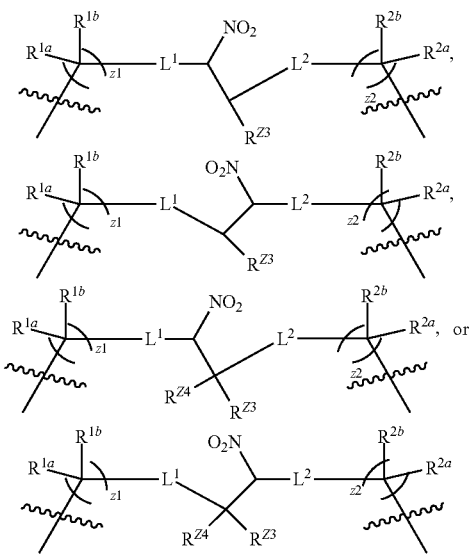

provides the keto (oxo) product of formula:

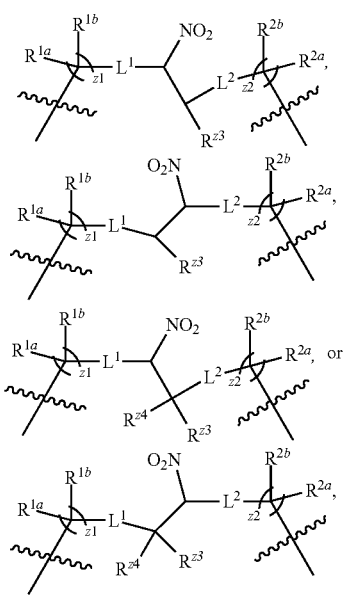

Alternative syntheses to form the keto (oxo) product are further contemplated herein.

Various macrolides may be accessed from these coupled products of Formula (C-1), depending upon the nature of the group $G^2$, upon macrocyclization. For example, as depicted in Scheme 9, when $G^2$ is a group of formula:

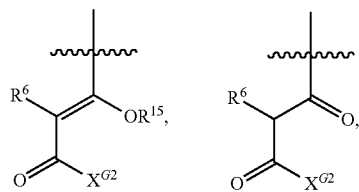

-continued

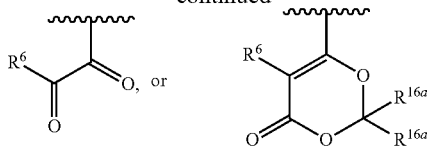

and $R^6$ is a hydrogen or non-hydrogen group, macrocyclization of the compound of Formula (C-1), e.g., wherein $P^1$ is hydrogen, provides a macrolide of Formula (C-2). Enolization of the macrolide of Formula (C-2), followed by addition of a non-hydrogen group $R^{10}$ (e.g., with a base and an $R^{10}$ alkylating agent, e.g., $R^{10}$-LG, or with a halogenating agent if $R^{10}$ is halogen), provides a macrolide of Formula (C-3).

Scheme 9.

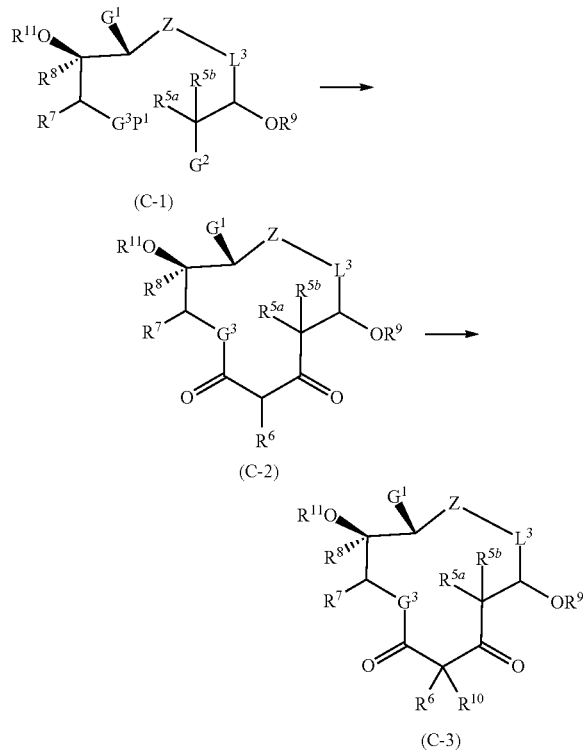

Alternatively, as depicted in Scheme 10, when $G^2$ is a group of formula:

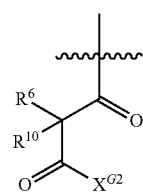

(c-v)

and wherein each of $R^6$ and $R^{10}$ is a hydrogen or non-hydrogen group, macrocyclization of the compound of Formula (C-1) e.g., wherein $P^1$ is hydrogen, provides a macrolide of Formula (C-3).

Scheme 10

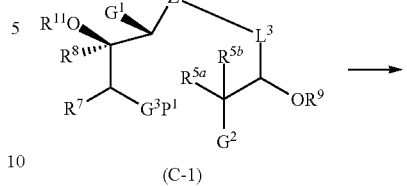

Further functionalization of the macrolide is also contemplated herein. For example, as depicted in Schemes 11 and 12, reduction of the C3 ketone of macrolides (C-2) and (C-3) to a hydroxyl group, optionally followed by protection, provides macrolides (C-4) and (C-5), respectively. Alternatively, the hydroxyl group at C3 can be modified through O-alkylation or acylation as depicted in Schemes 13A-13B, where LG is a leaving group as defined herein. In certain embodiments, $R^{17}$ is —C(=O)$R^{Z8}$, wherein $R^{Z8}$ is optionally substituted alkyl (e.g., optionally substituted aralkyl or optionally substituted heteroaralkyl).

The ability to readily alter the oxidation state of oxygen at C3 enables the protection of this position as a carbonyl group while other free hydroxy groups are modified (e.g. O-alkylation). Therefore, oxidation or reduction of this position at various points along the specific synthetic sequence is contemplated herein.

Scheme 11

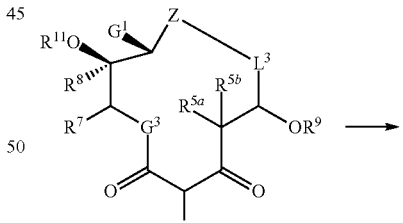

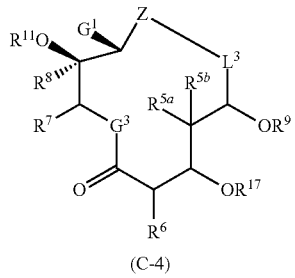

Scheme 12

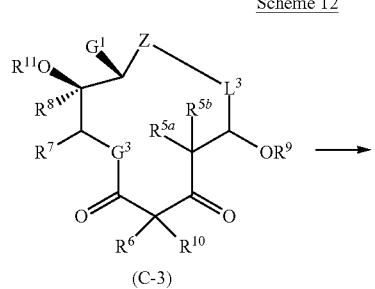

(C-3)

Further modification of the ketone or reduced macrolide is also contemplated herein. For example, as depicted in Schemes 14A-14B, and 15A-15B, the C3 ketone C-2 or C-3, or C-4 or C-5 (e.g., hydroxyl at C3, wherein $R^{17}$ is hydrogen), can be halogenated with an electrophilic halogenating agent (e.g. Deoxo-Fluor) to give geminal dihalides such as C-6, or monohalides such as C-7, respectively, wherein X is a halogen (e.g. fluorine, bromine, iodine).

Scheme 14A

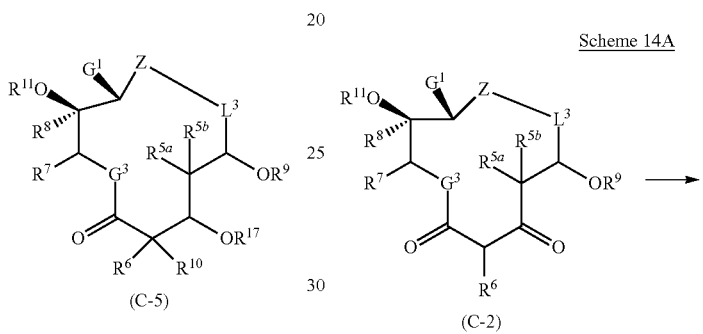

Scheme 13A

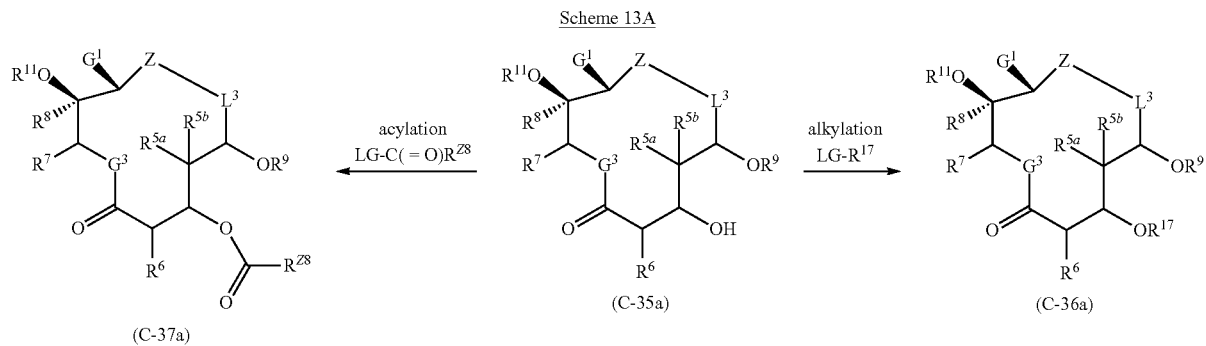

Scheme 13B

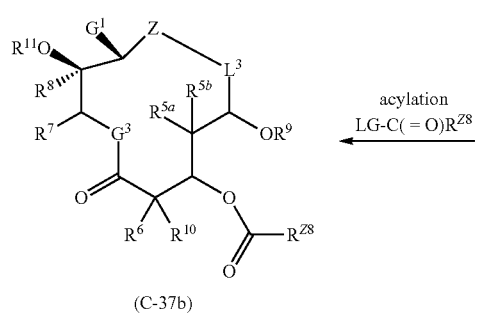

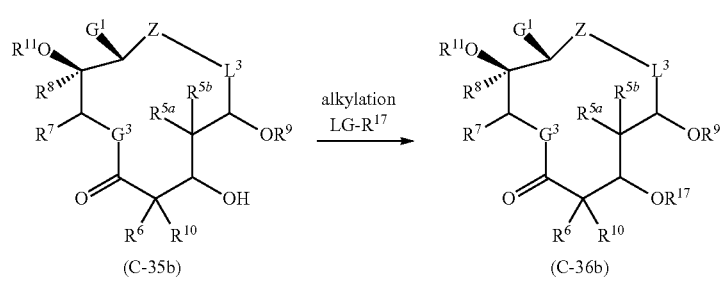

-continued

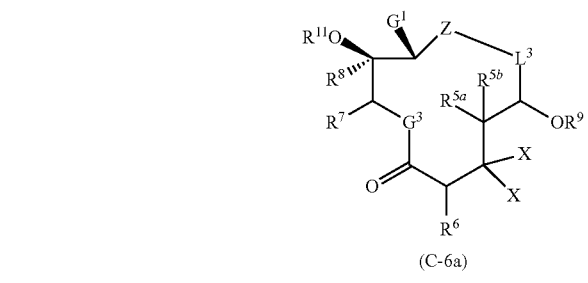

(C-6a)

Scheme 14B

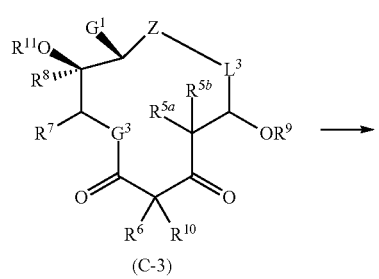

(C-3)

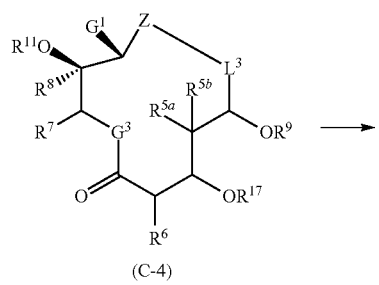

(C-6b)

Scheme 15A

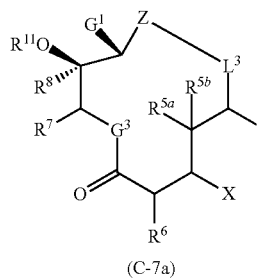

(C-4)

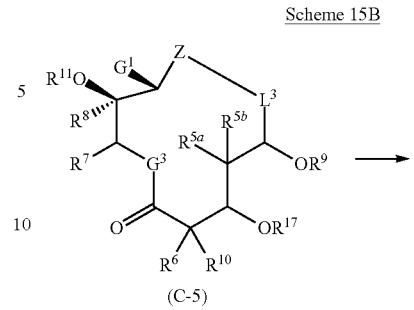

(C-7a)

Scheme 15B

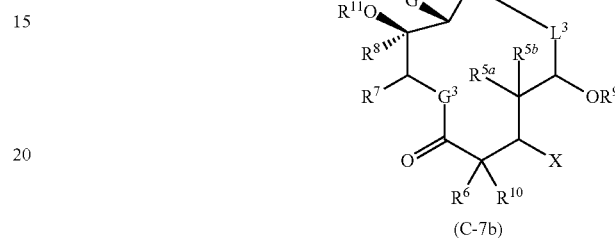

(C-5)

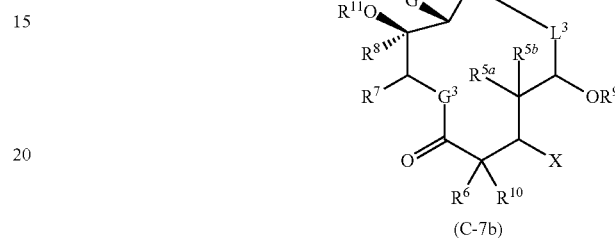

(C-7b)

Instances wherein either $R^3$ or $R^4$ is allyl enable rapid derivitization into novel macrolides as demonstrated in Schemes 16A-16B and 17A-17B. A variety of groups, such as heteroaryl or aryl moieties, may be introduced through a transition metal catalyzed cross coupling (e.g. Heck reaction) or through an olefin metathesis reaction (e.g. cross methathesis using a Grubbs or Schrock metal carbene catalyst) leading to derivatives such as C-9 or C-15. Subsequent manipulation of the olefin (e.g. hydrogenation) can access further structural diversity (e.g. C-10a-b, C-16a-b). Alternatively, the olefin functionality can be oxidatively cleaved to produce a carbonyl functionality (C-11a-b or C-17a-b) that may be further modified through transformations such as reduction, nucleophilic additions (C-13a-b or C-19a-b), or reductive amination (C-12a-b or C-18a-b), wherein each instance of $R^{22}$ is independently hydrogen or optionally substituted alkyl and $R^{24}$ is hydrogen, optionally substituted alkyl, or optionally substituted aryl. In certain embodiments, $R^{22}$ is —$CH_2C(=O)OH$. In certain embodiments, $R^{22}$ is

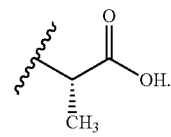

In certain embodiments, $R^{22}$ is

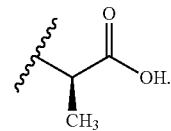

While the modifications as drawn herein are demonstrated in the context of the preformed macrocycle, identical transformations on the macrolide building blocks prior to assembly are contemplated herein.

Scheme 16A
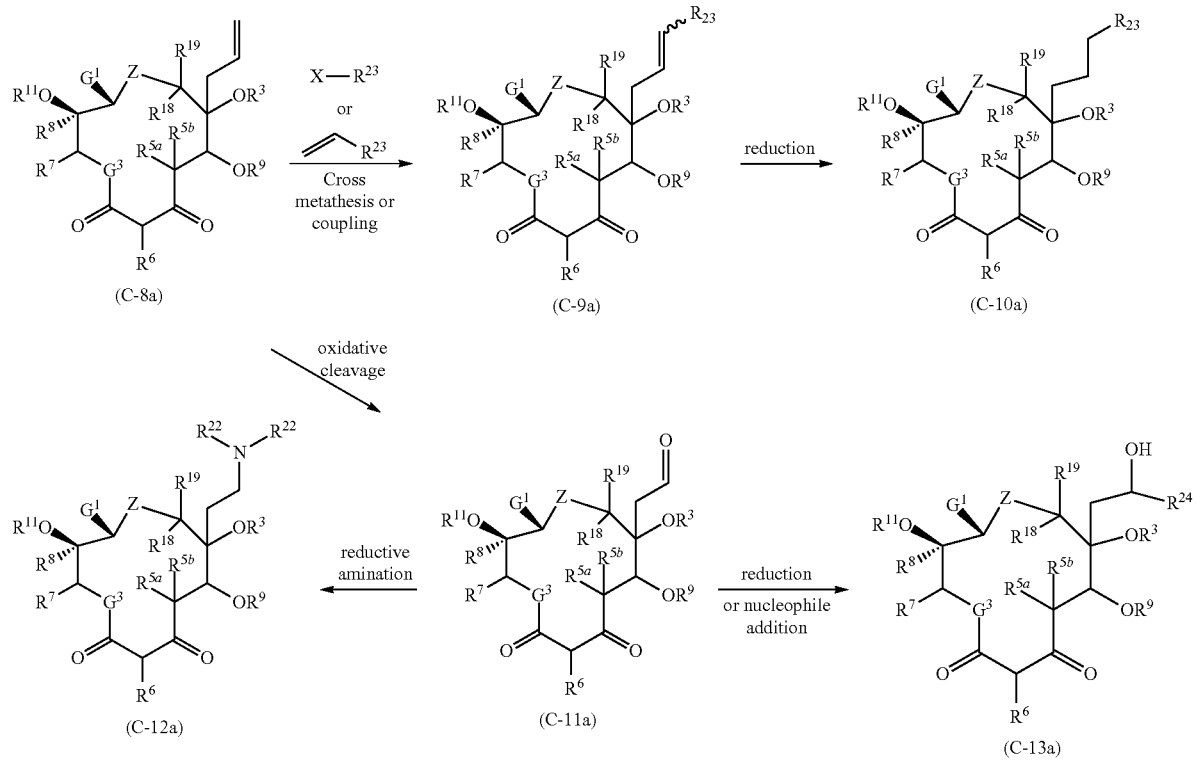
Scheme 16B
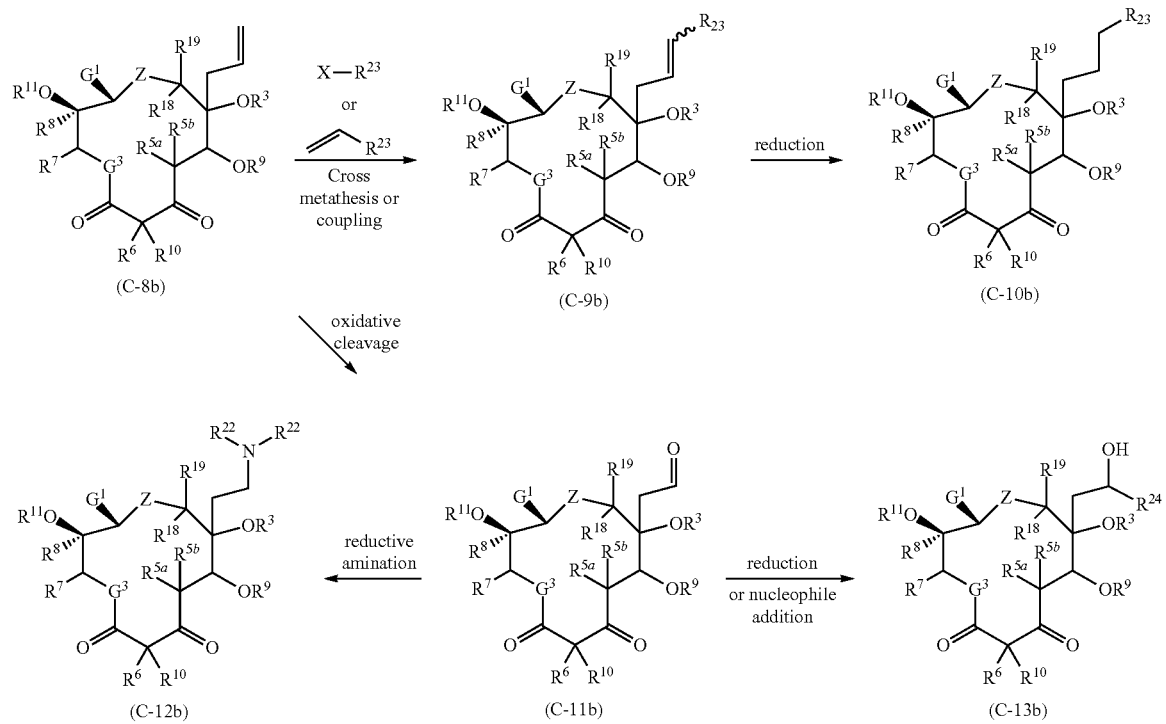

Scheme 17A
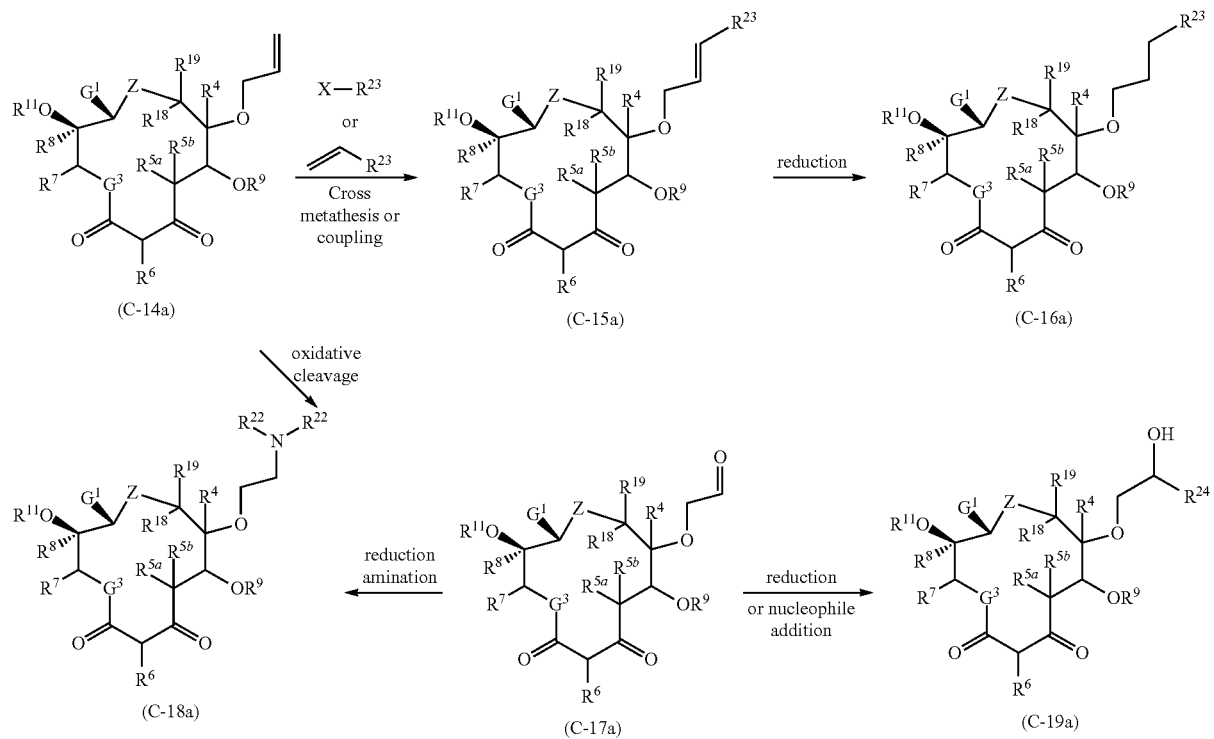
Scheme 17B
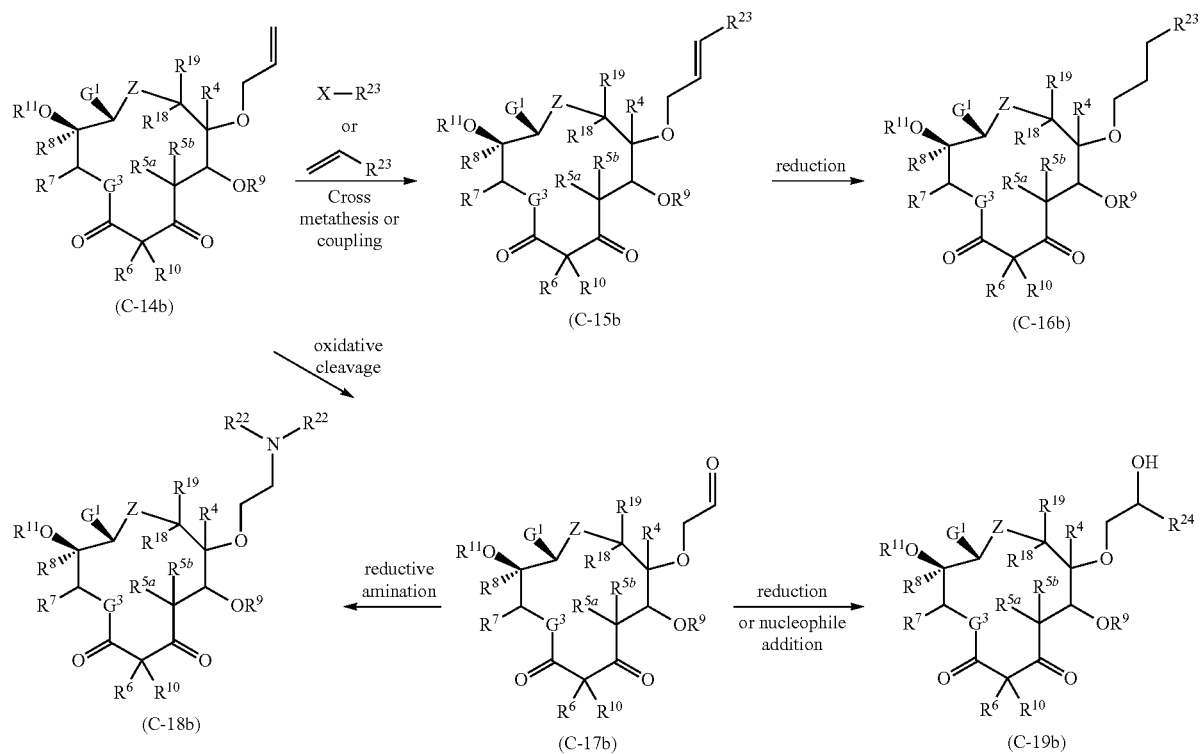

Further derivatization may be carried out using the transformations described herein pre- or post-macrocyclization when any of $R^{1a}$, $R^{1b}$, $R^{2a}$, $R^{2b}$, or $R^{Z3}$ is allyl. While only depicted for macrocycles of C-20a-b in Scheme 18A-B, such modifications are contemplated for any macrocycle wherein at least one of $R^{1a}$, $R^{1b}$, $R^{2a}$, $R^{2b}$, or $R^{Z3}$ is allyl. Derivatives wherein a —$CH_2$— moiety in the chain has been removed may be prepared using the precursor wherein any of $R^{1a}$, $R^{1b}$, $R^{2a}$, $R^{2b}$, or $R^{Z3}$ is vinyl (Scheme 19A-19B). In certain embodiments, $R^{22}$ is —$CH_2C(=O)OH$. In certain embodiments, $R^{22}$ is

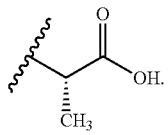

In certain embodiments, $R^{22}$ is

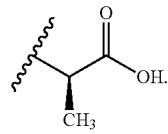

While the modifications as drawn herein are demonstrated in the context of the preformed macrocycle, identical transformations on the macrolide building blocks prior to assembly are contemplated herein.

Scheme 18A

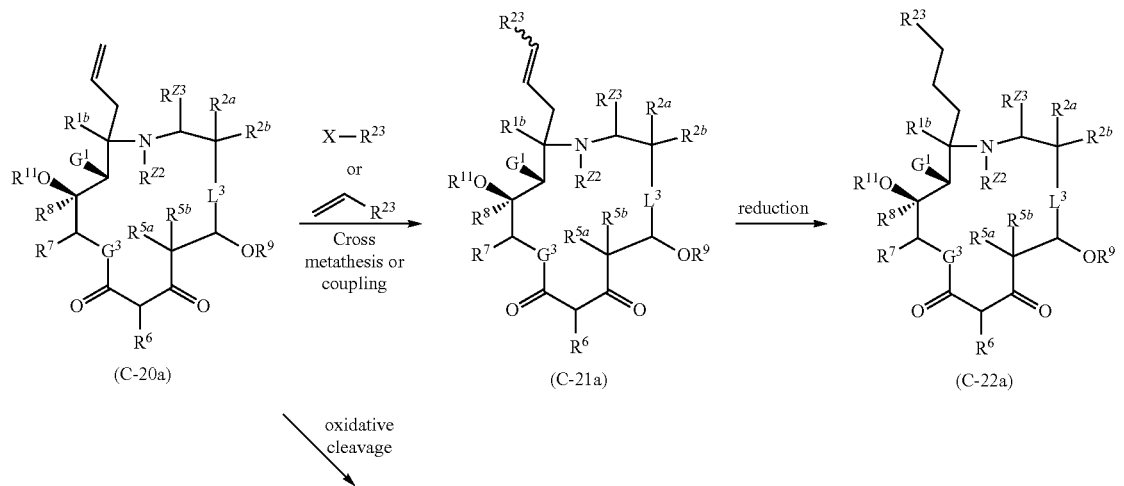

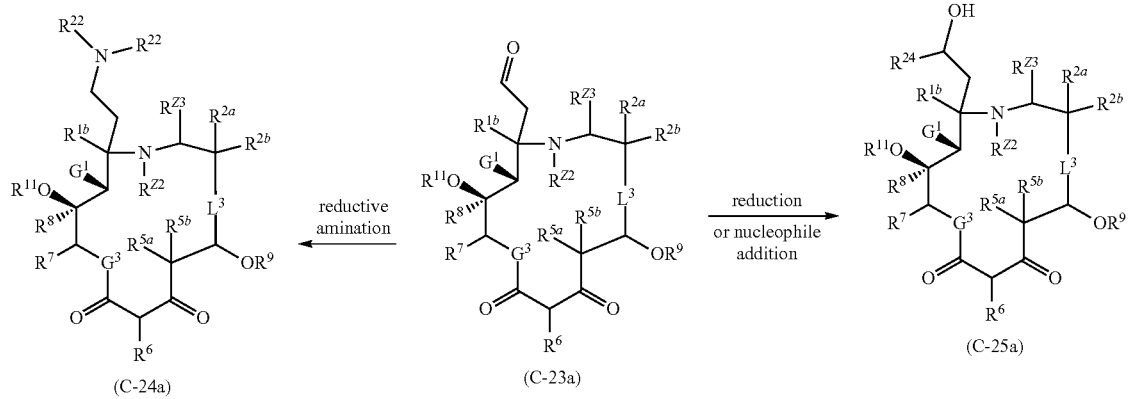

243       244
Scheme 18B
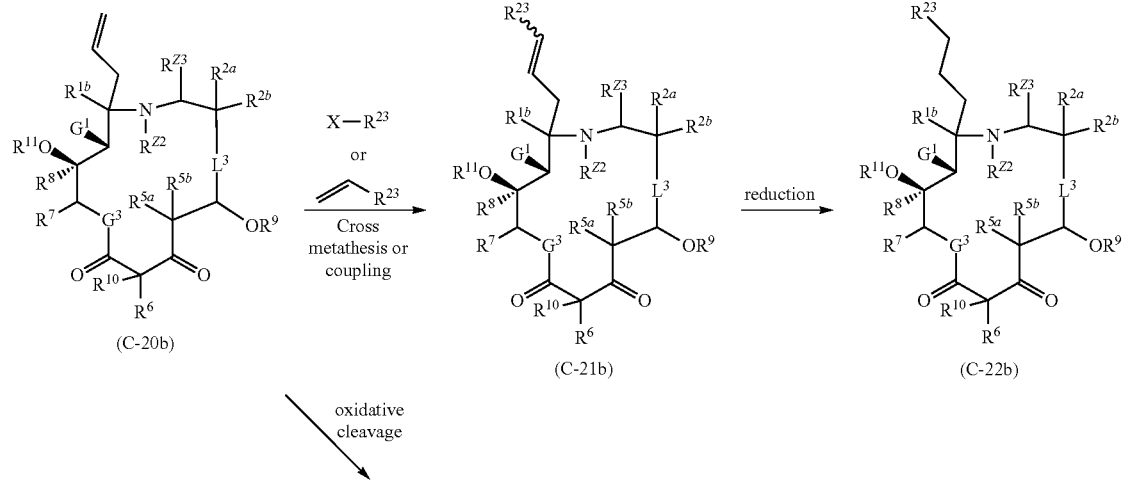
(C-20b)        (C-21b)        (C-22b)
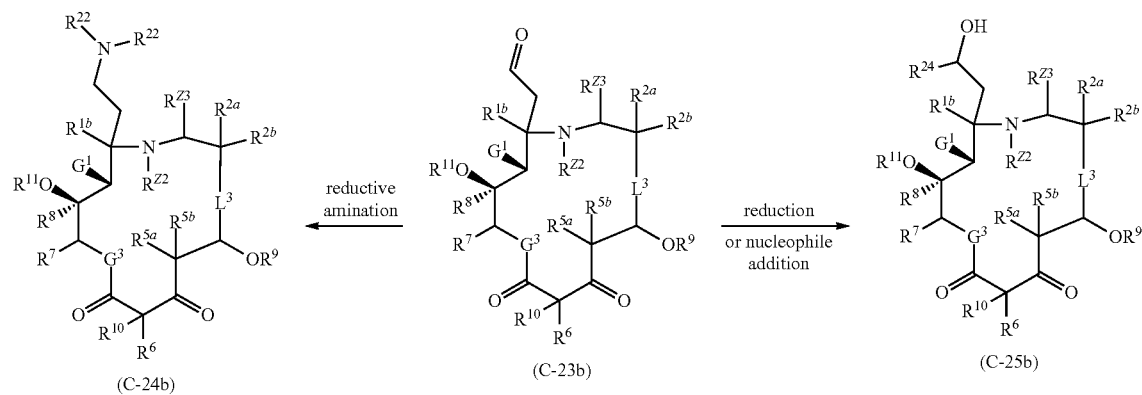
(C-24b)        (C-23b)        (C-25b)
Scheme 19A
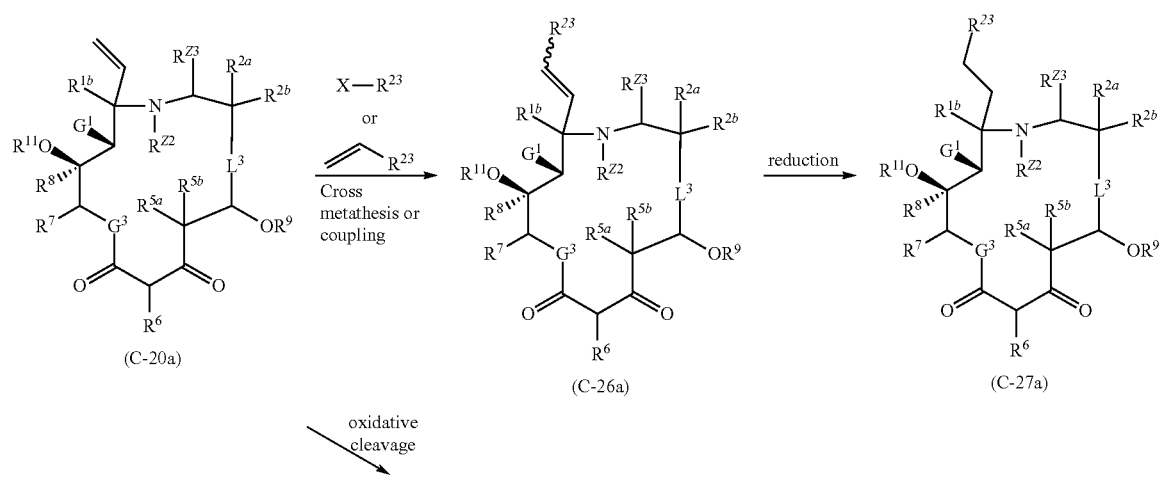
(C-20a)        (C-26a)        (C-27a)

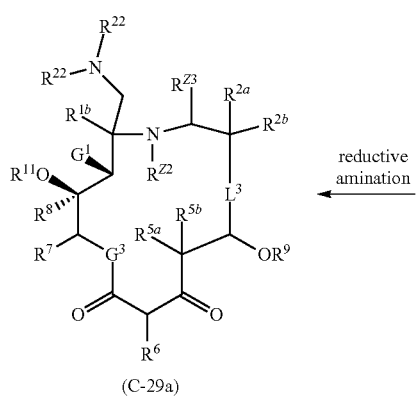
(C-29a)
-continued
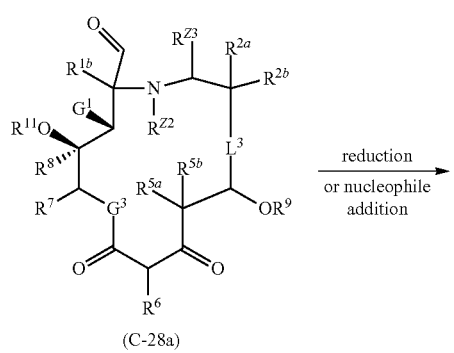
(C-28a)
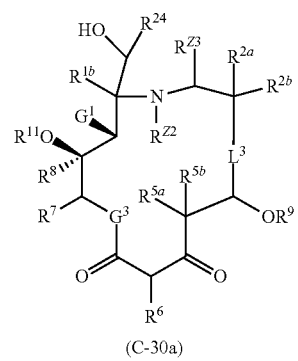
(C-30a)
Scheme 19B
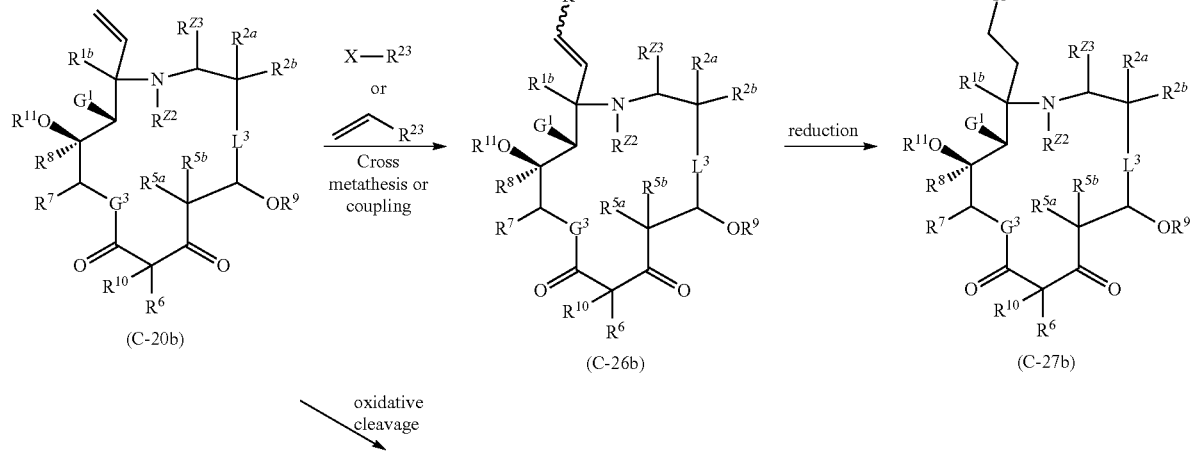
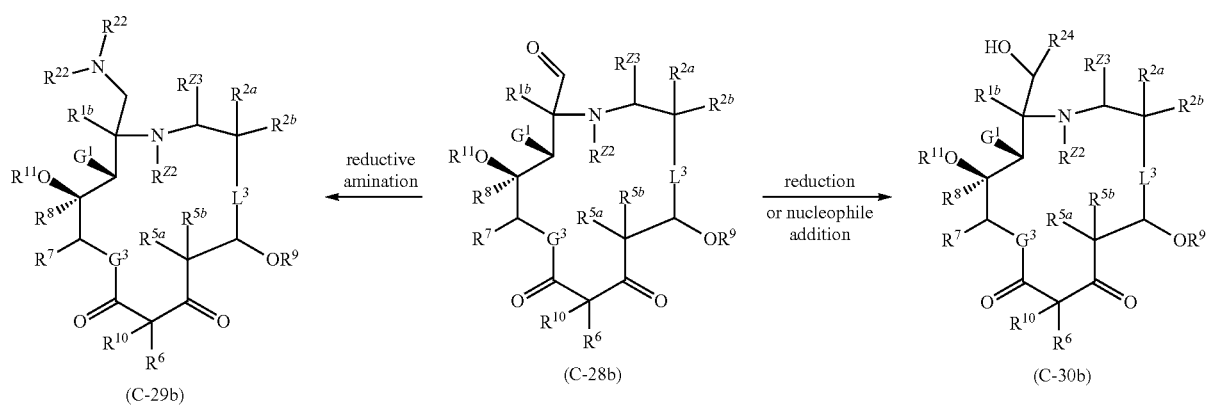

Further derivatization may be carried out using the transformations described herein pre- or post-macrocyclization when $R^{1a}$ and $R^{1b}$ or $R^{2a}$ and $R^{2b}$ can be taken together to form

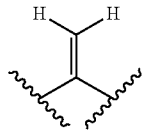

alpha to an oxo (=O) moiety. Conjugate addition reactions using nucleophilic $R^{23}$ species (such as X—$R^{23}$ or M-$R^{23}$, wherein M is an anion, Li, Na, K, CuX, or MgX and wherein X is a halogen) provide compounds of formula C-42a-b. While only depicted for macrocycles of C41a-b in Scheme 20A-20B, such modifications are anticipated for any macrocycle wherein $R^{1a}$ and $R^{1b}$ or $R^{2a}$ and $R^{2b}$ is

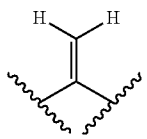

alpha to an oxo (=O) moiety. While the modifications as drawn herein are demonstrated in the context of the preformed macrocycle, identical transformations on the macrolide building blocks prior to assembly are contemplated herein.

Scheme 20A

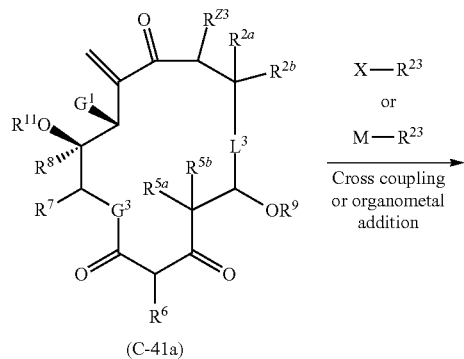

(C-41a)

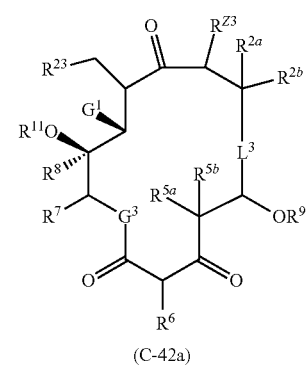

(C-42a)

Scheme 20B

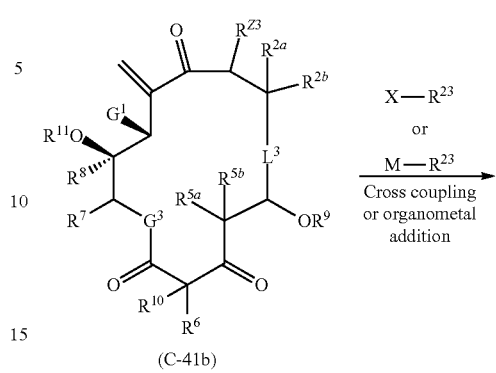

(C-41b)

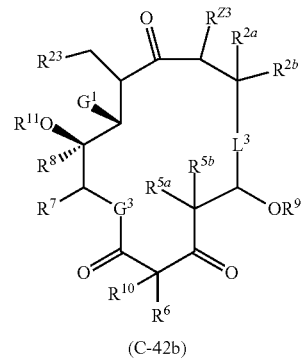

(C-42b)

Further derivatization may be carried out using the transformations described herein pre- or post-macrocyclization when any of $R^{1a}$, $R^{1b}$, $R^{2a}$, $R^{2b}$, or $R^{Z3}$ is hydrogen, attached alpha to an oxo (=O) moiety. Base-mediated deprotonation and nucleophilic addition of the enolate to leaving group conjugates of $R^{1a}$, wherein LG is a leaving group as defined herein, provide alpha-functionalized ketolides of formula C-44a-b. While only depicted for macrocycles of C-43a-b in Scheme 21A-21B, such modifications are anticipated for any macrocycle wherein at least one of $R^{1a}$, $R^{1b}$, $R^{2a}$, $R^{2b}$, or $R^{Z3}$ is hydrogen and Z contains a ketone moiety. While the modifications as drawn herein are demonstrated in the context of the preformed macrocycle, identical transformations on the macrolide building blocks prior to assembly are contemplated herein.

Scheme 21A

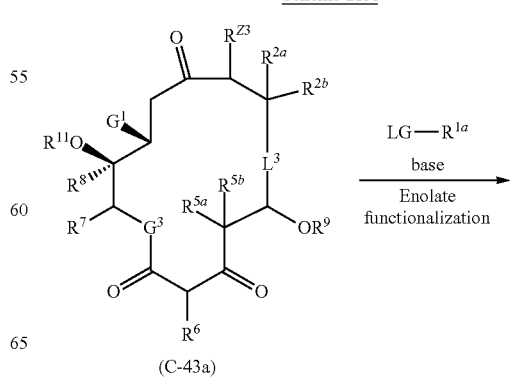

(C-43a)

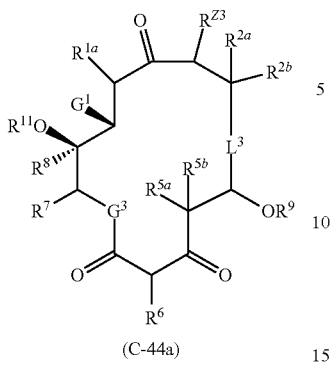

(C-44a)

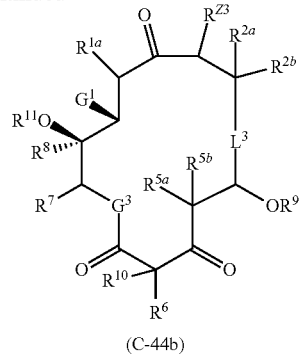

(C-44b)

As depicted in Scheme 22A-2B, the nitrogen of the macrocycle can be further functionalized with $R^{Z2}$ groups. Non-limiting examples of double bond functionalization include:

(i) Amine N-alkylation with leaving group conjugates of $R^{Z2}$ (i.e. C32a-b, $R^{Z2}$-LG, wherein LG is a leaving group as defined herein). In certain embodiments, the leaving group conjugate of $R^{Z2}$ is an organohalide. In certain embodiments, the organohalide is a methyl halide (e.g. methyl iodide).

(ii) Amine acylation with reagents such as carboxylic acids, acid anhydrides, or other acid leaving group conjugates (i.e. C33a-b, $R^{Z2}$(C=O)OH, $R^{Z2}$(C=O)O(C=O)$R^{Z2}$, or $R^{Z2}$(C=O)-LG wherein LG is a leaving group as defined herein). In certain embodiments, the acid anhydride is acetic anhydride.

(iii) Reductive amination with reagents such as aldehydes or ketones (i.e. C34a-b, $R^{Z2}$(C=O)H or $R^{Z2}$(C=O)$R^{Z2}$). In certain embodiments, the aldehyde is formaldehyde. While only depicted for macrocycles of C31a-b in Scheme 21A-B, such modifications are anticipated for any macrocycle wherein Z contains an amine moiety. While the modifications as drawn herein are demonstrated in the context of the preformed macrocycle, identical transformations on the macrolide building blocks prior to assembly are contemplated herein.

Scheme 21B

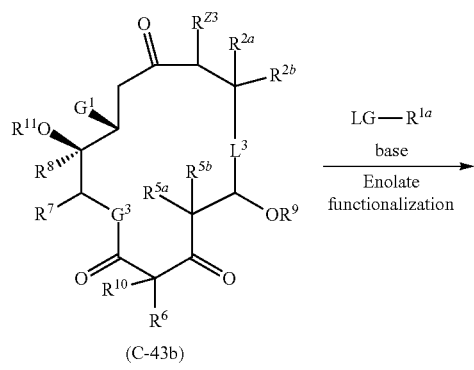

(C-43b)

Scheme 22A

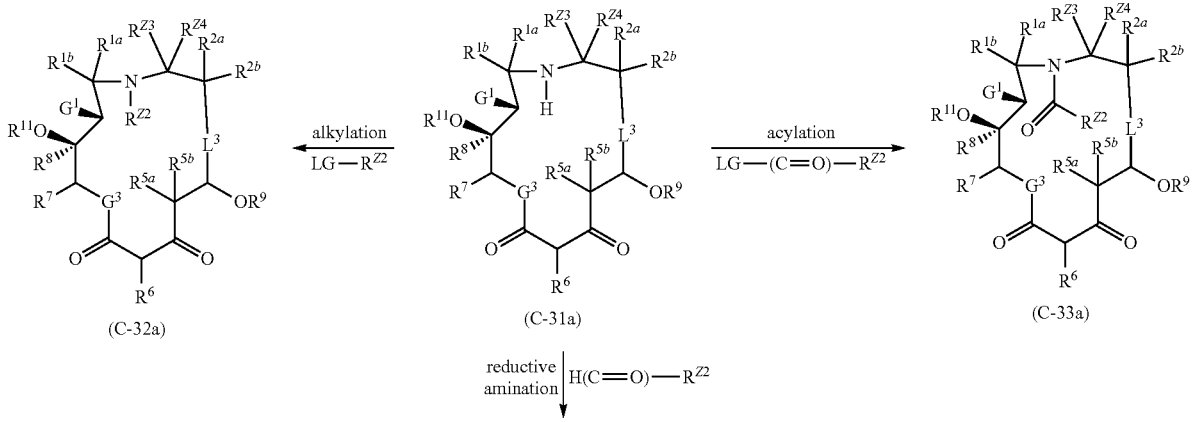

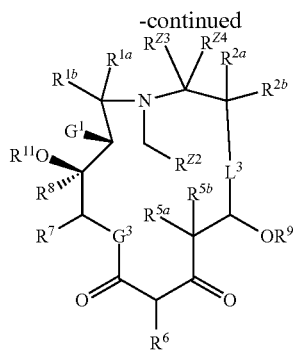

(C-34a)

Scheme 22B

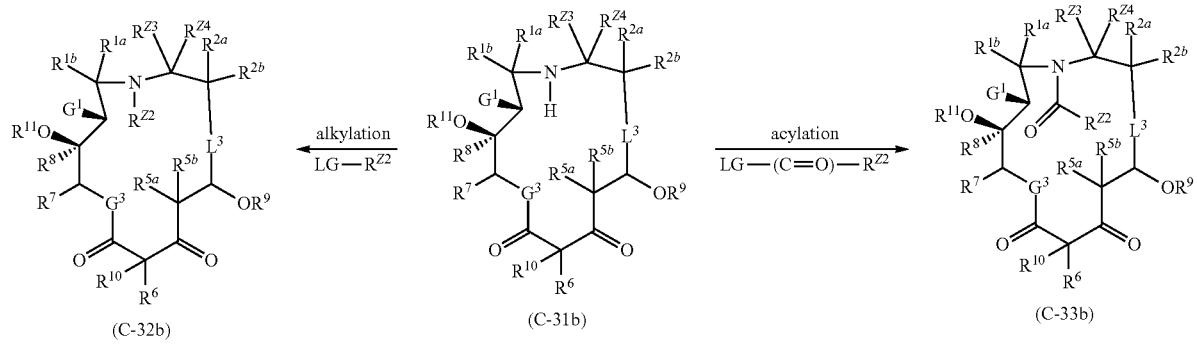

(C-32b)    (C-31b)    (C-33b)

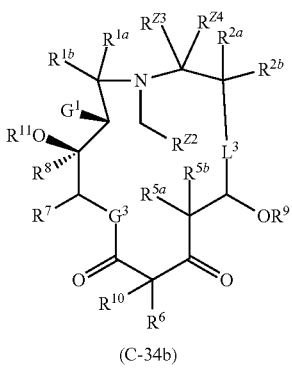

(C-34b)

Furthermore, as depicted in Schemes 23-26, wherein $G^1$ is —$NHR^{13}$, installation of a group of formula ($L^{C1}$-i) by reaction of the alcohol with a compound of formula LG-$L^{C1}$-LG, followed by displacement of the second leaving group with a nucleophilic group $A^1$ to provide a group of formula ($L^{C1}$-ii), followed by reaction of the group $A^1$ and with a compound of formula $A^2$-$L^{C2}$-$R^{23}$ to install a group of formula ($L^{C1}$-iii), is contemplated herein.

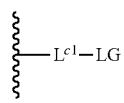

(Lc1-i)

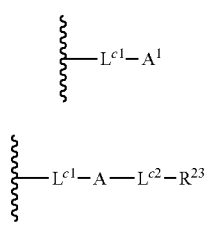
(Lc1-ii)
(Lc1-iii)
Scheme 23
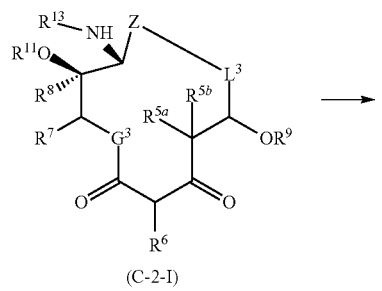
(C-2-I)
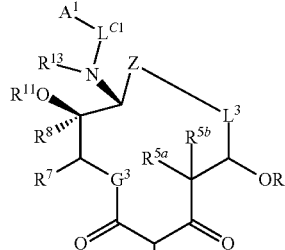
(C-2-II)
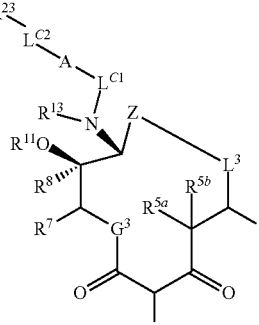
(C-2-III)
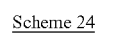
Scheme 24
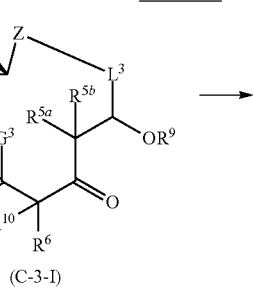
(C-3-I)
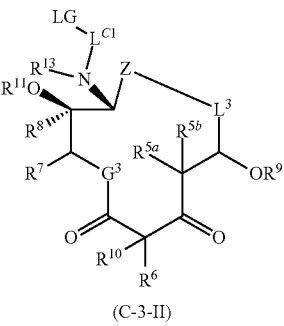
(C-3-II)
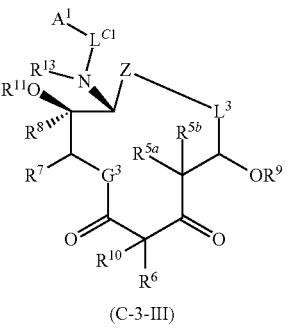
(C-3-III)
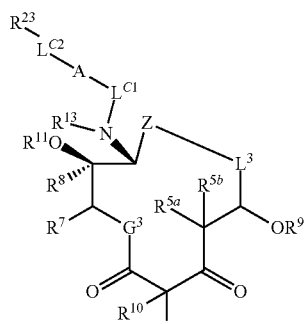
(C-2-IV)
(C-3-IV)

Scheme 25

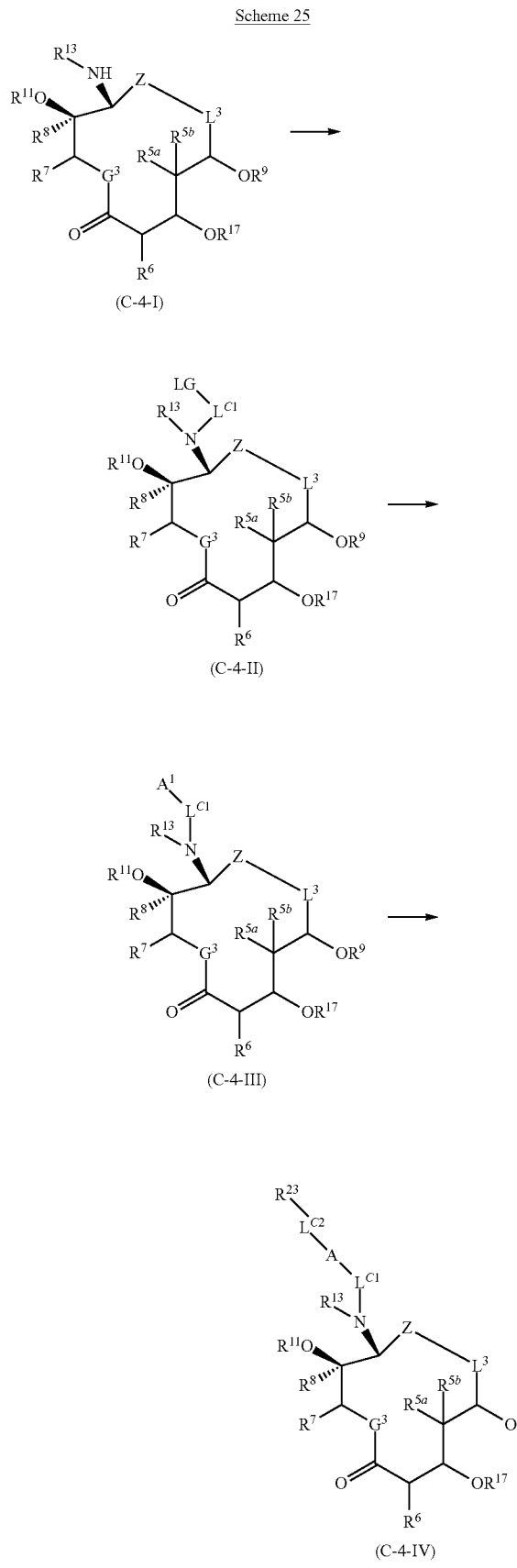

Scheme 26

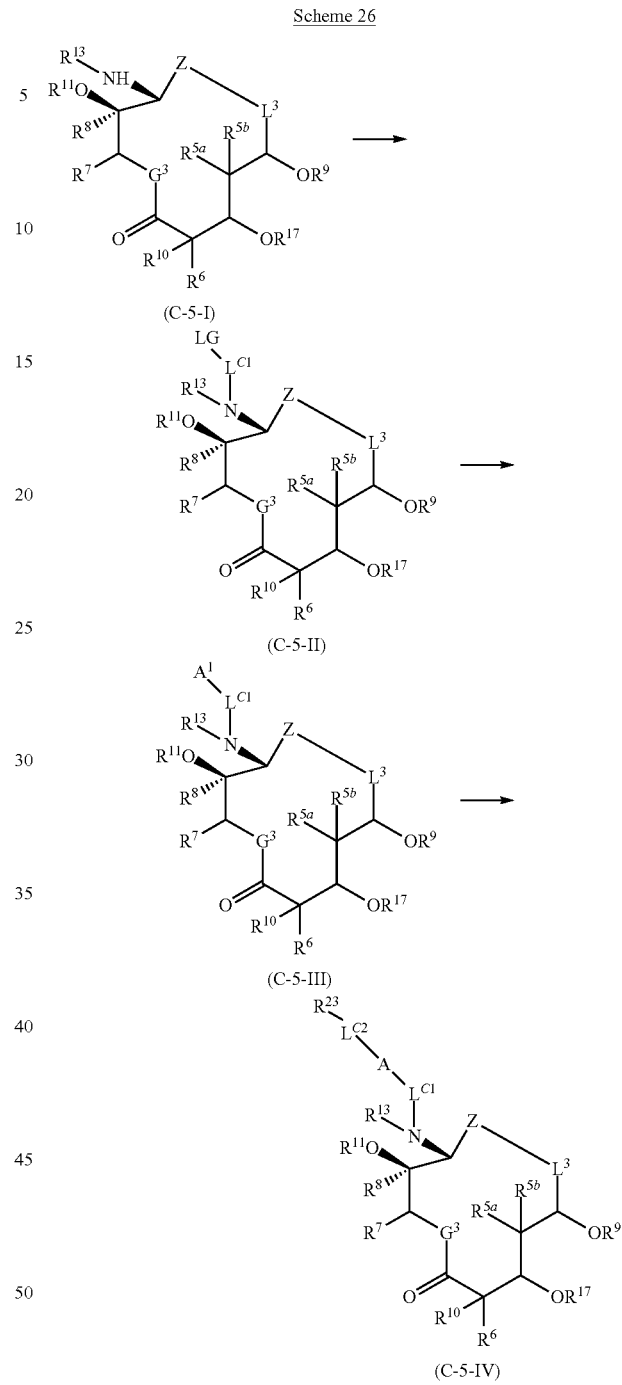

Alternatively, the group -$L^{C1}$-$A^1$ may be installed directly by reaction of the amine with a compound of formula LG-$L^{C1}$-$A^1$. Such reactions are also contemplated wherein $G^1$ is —OH.

Additionally, as depicted in Scheme 27, wherein $L^3$ is a group of formula ($L^3$-i), wherein $R^3$ is hydrogen (referred to as ($L^3$-ia)), installation of a group of formula ($L^{C1}$-i) by reaction of the alcohol with a compound of formula LG-$L^{C1}$-LG, followed by conversion of (e.g., by nucleophilic displacement or other synthetic manipulation) of the second leaving group with a group $A^1$ to provide a group of formula ($L^{C1}$-ii), followed by reaction of the group $A^1$ and with a compound of formula $A^2$-$L^{C2}$-$R^{23}$ to install a group of formula ($L^{C1}$-iii), is also contemplated herein.

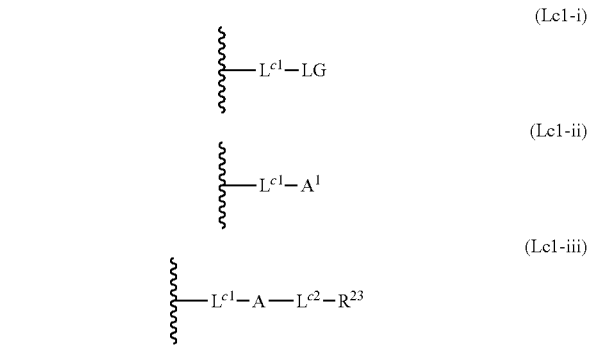

Alternatively, the group -$L^{C1}$-$A^1$ may be installed directly from ($L^3$-ia) to provide ($L^3$-ic) by reaction of the hydroxyl group with a compound of formula LG-$L^{C1}$-$A^*$.

Furthermore, there are many ways of adding a group of formula ($L^{C1}$-iii) which do not involve reaction of $A^1$ and $A^2$ to form A and thus A may be any group, e.g., for example, a cyclic moiety selected from the group consisting of optionally substituted carbocyclyl, optionally substituted heterocyclyl, optionally substituted aryl, and optionally substituted heteroaryl. For example, a group of formula ($L^{C1}$-iii) may be installed by reaction of the group —$OR^{12}$, —$NR^{13}R^{14}$, and/or —$OR^3$, wherein $R^{12}$, $R^{14}$, and/or $R^3$ are hydrogen, with a compound of formula ($L^{C1}$-vii), e.g., by nucleophilic displacement, to provide a group wherein $R^{12}$, $R^{14}$, and/or $R^3$ is of formula ($L^{C1}$-iii). See, e.g., Scheme 28.

Scheme 28.

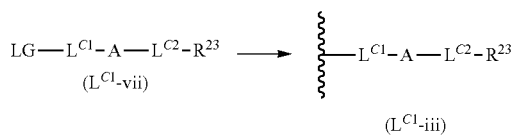

Furthermore, as depicted in Scheme 28, wherein $L^3$ is a group of formula ($L^3$-i), elimination of the group —$OR^3$ provides an alkenyl moiety, which may be reduced (e.g., by hydrogenation), or be further functionalized with groups $R^{20}$ and $R^{21}$, as depicted in Scheme 29. Functionalization of double bonds to provide groups $R^{20}$ and $R^{21}$ are known in the art. See, e.g., *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. Non-limiting examples of double bond functionalization include:

(i) reaction of the double bond with a cyclopropanting reagent to provide a group ($L^3$-iii) wherein $R^{20}$ and $R^{21}$ are joined to form an optionally substituted cyclopropyl ring;

(ii) reaction of the double bond with an epoxidizing reagent to provide a group ($L^3$-iii) wherein $R^{20}$ and $R^{21}$ are joined to form an oxiranyl ring;

(iii) reaction of the double bond with a dihydroxylation reagent (e.g., $OsO_4$), optionally followed by protection of Scheme 27.

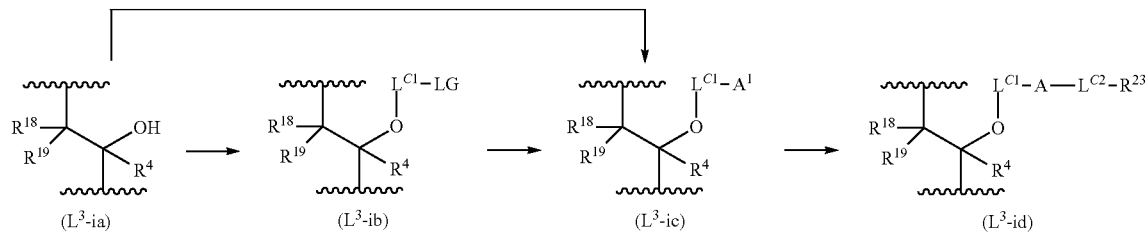

the hydroxyl groups, to provide a group ($L^3$-iii) wherein $R^{20}$ and $R^{21}$ are each independently hydroxyl or substituted hydroxyl;

(iv) HX addition to the double bond, wherein X is a halogen or hydroxyl or substituted hydroxyl, to provide a group ($L^3$-iii) wherein one of $R^{20}$ and $R^{21}$ is halogen or hydroxyl or substituted hydroxyl, and one of $R^{20}$ and $R^{21}$ is hydrogen;

(v) $X_2$ addition to the double bond, wherein X is halogen, to provide a group ($L^3$-iii) wherein $R^{20}$ and $R^{21}$ are each independently halogen;

(vi) $X_2/H_2O$ or $X_2$/alcohol addition to the double bond, wherein X is halogen, to provide a group ($L^3$-iii) wherein one of $R^{20}$ and $R^{21}$ is hydroxyl or substituted hydroxyl, and one of $R^{20}$ and $R^{21}$ is halogen; and (viii) oxidative hydroboration of the double bond to provide a group ($L^3$-iii) wherein one of $R^{20}$ and $R^{21}$ is hydroxyl or substituted hydroxyl, and one of $R^{20}$ and $R^{21}$ is hydrogen.

Scheme 29.

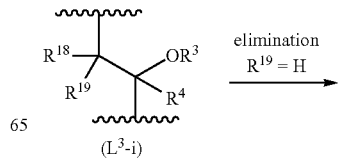

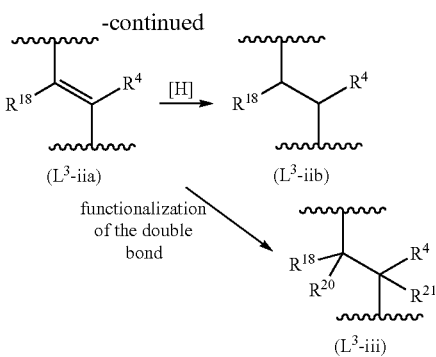

(L³-iia) → [H] → (L³-iib)

functionalization of the double bond → (L³-iii)

For all of the transformations pertaining to functionalization of the pre-formed macrocycle, incorporation of these groups through such general transformations at steps prior to ring formation is contemplated herein. Such reordering of steps as is appropriate to accommodate particular intermediates or functional groups is understood by those skilled in the art.

Alternative Method of Synthesizing Ketolides

As generally described herein, alternative methods of preparing the keto (oxo) product wherein Z is of formula:

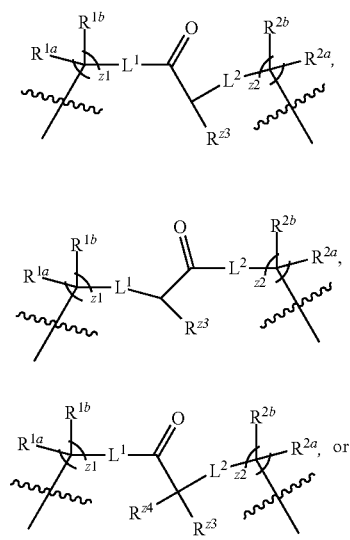

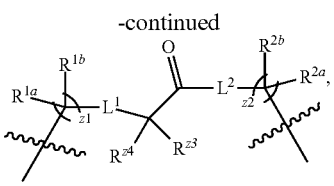

are further contemplated herein.

For example, the above recited Z linkage may be formed via Wittig or Homer Emmons reaction between an aldehyde and a ylide or phosphonate ester to form an α,β-unsaturated keto linked intermediate. See, e.g., Schemes 30 and 31. In certain embodiments, wherein ----- represents a double bond, the ketone moeity and β-substitutent are in a cis-configuration. In certain embodiments, wherein ----- represents a double bond, the ketone moeity and β-substitutent are in a trans-configuration.

The cyclic carbamate, installed prior to macrocyclization (see, e.g., Scheme 30) or after macrocyclization (see, e.g., Scheme 31), may be formed via Michael addition of the amine $NH_2R^{14}$ to the α,β-unsaturated keto moiety, followed by reaction of the attached amino group —$NHR^{14}$ and vicinal hydroxyl group (i.e., $R^{11}$ is hydrogen) with reagent LG-C(=O)-LG, wherein each LG is a leaving group as defined herein (e.g., chloro), substituted hydroxyl (e.g., to provide a carbonate ester), substituted thiol, substituted amino (e.g., imidazolyl). In certain embodiments, the free hydroxyl group is first treated with reagent LG-C(=O)-LG, following which an amine of $NH_2R^{14}$ is added, leading to initial formation of an acyclic carbamate prior to conjugate addition of the intermediate —$NHR^{14}$ group to the unsaturated ketone.

Alternatively, the cyclic carbamate, installed prior to macrocyclization (see, e.g., Scheme 30) or after macrocyclization (see, e.g., Scheme 31), may be formed via reaction of the free hydroxyl group (i.e., $R^{11}$ is hydrogen) with an isocyanate reagent O=C=N—$R^{14}$, followed by conjugate addition of the intermediate —$NHR^{14}$ group to the unsaturated ketone. In certain embodiments, the isocyanate reacts with the free hydroxyl group and —$NHR^{14}$ undergoes the conjugate addition reaction in a single step. In certain embodiments, the intermediate acyclic carbamate is isolated. In certain embodiments, base is added to the isolated acyclic carbamate to promote the conjugate addition reaction.

Scheme 30.

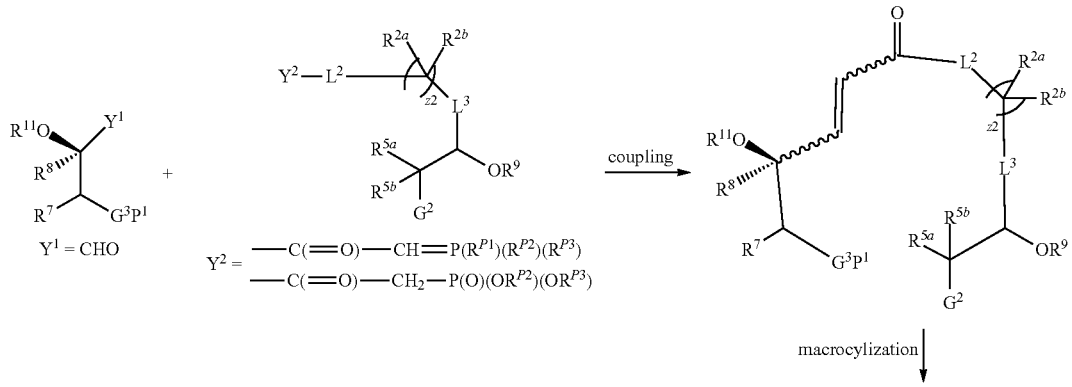

261
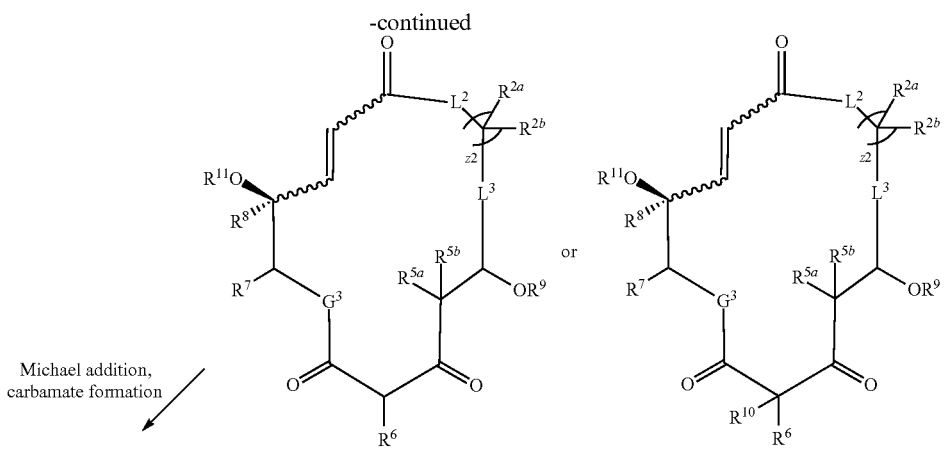
262
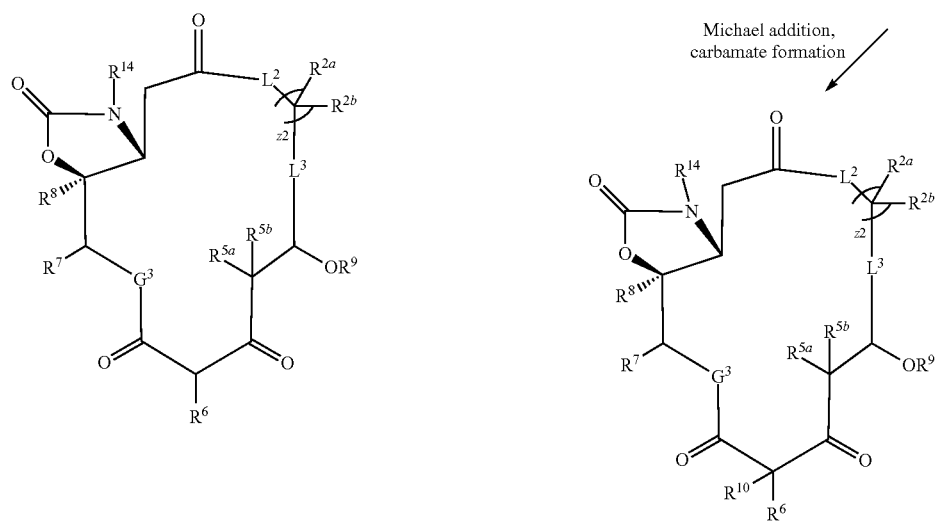
Scheme 31.
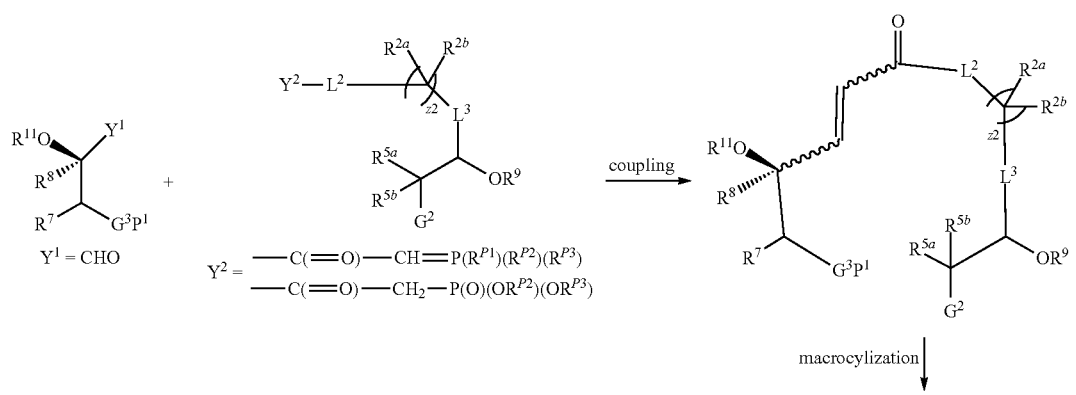

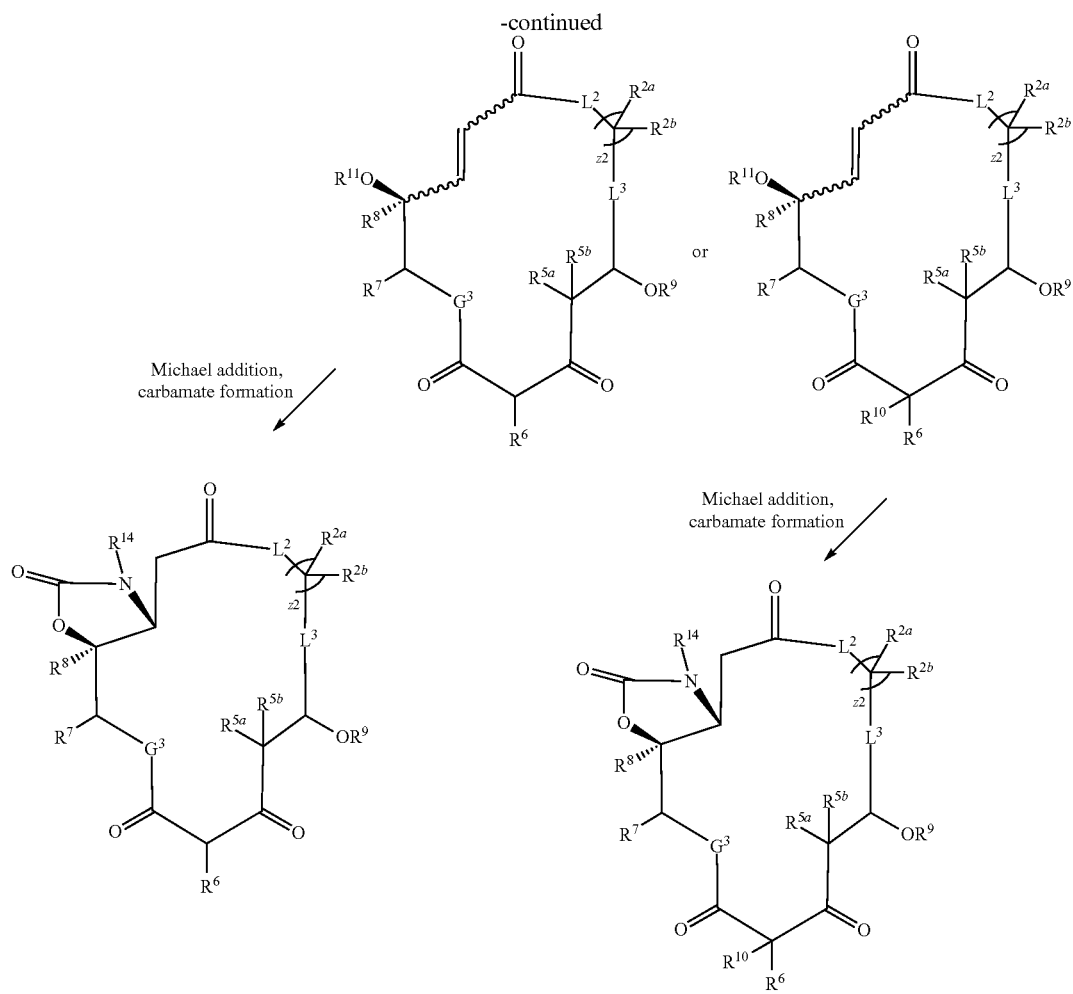

Scheme 32 depicts various synthetic modifications which are contemplated and further described in greater detail elsewhere. For example, after formation of the cyclic carbamate, the carbon alpha to the ketone moiety so installed may be monosubstituted (e.g., wherein $R^{Z3}$ is hydrogen and $R^{Z4}$ is a non-hydrogen) or di-substituted (i.e., wherein both $R^{Z3}$ and $R^{Z4}$ are non-hydrogen groups). Synthetic modification of the C3 ketone by dihalogenation (e.g., wherein each of $R^{Y1}$ and $R^{Y2}$ is halogen (e.g., fluoro)), or by reduction to provide an alcohol wherein $R^{Y1}$ is —$OR^{17}$ and $R^{Y2}$ is hydrogen, followed by monohalogenation to provide a product wherein $R^{Y1}$ is halogen (e.g., fluoro) and $R^{Y2}$ is hydrogen is further contemplated.

Scheme 32.

265 266

-continued

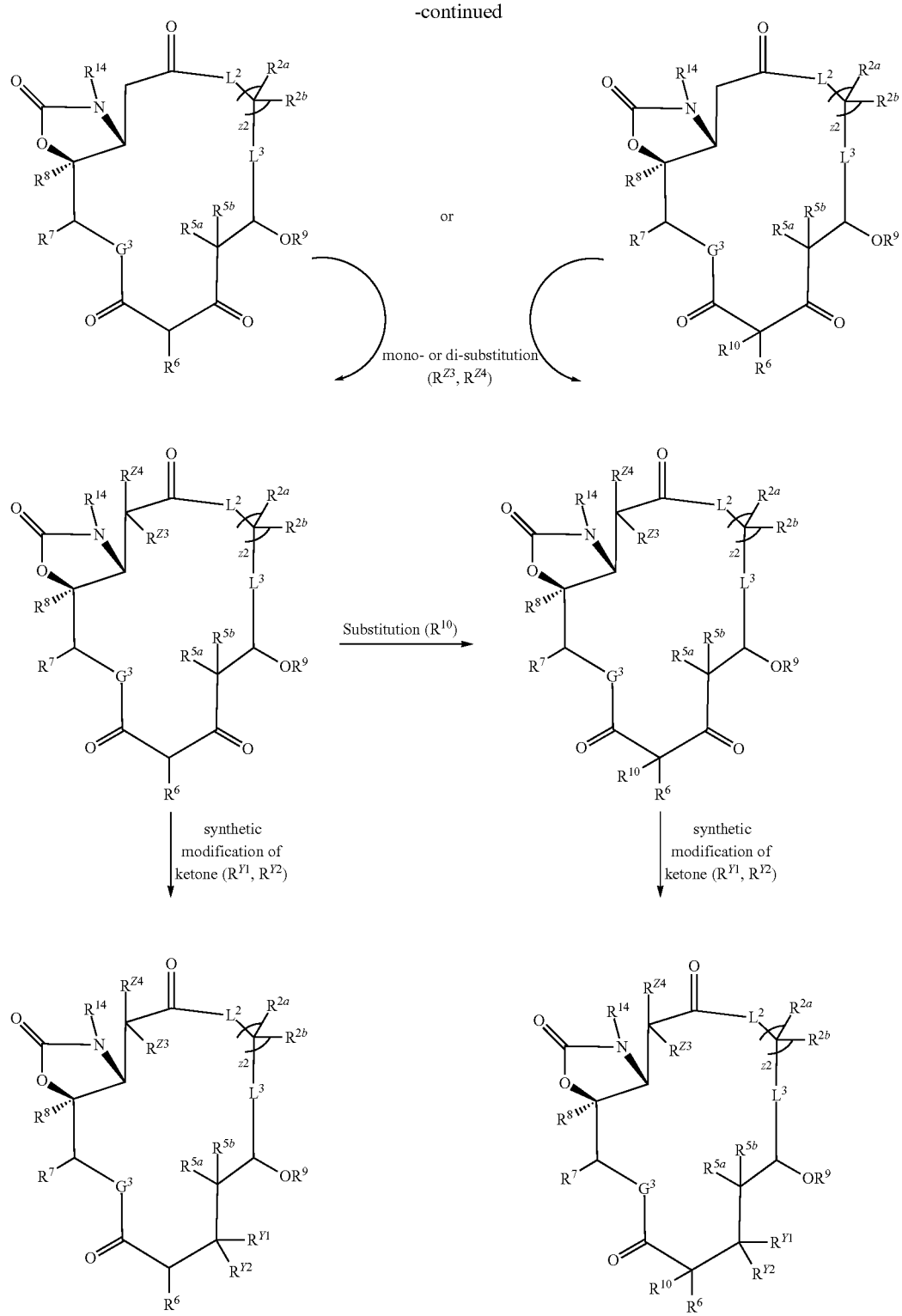

Scheme 33 depicts additional functionalization of ketolides prepared by the methods described herein via an enolate or trapped enolate, wherein PG is an oxygen protecting group as defined herein. In certain embodiments, the trapped enolate is trapped as a protected enol ether using a reagent of formula LG-PG wherein LG is leaving group and PG is protecting group as defined herein. In certain embodiments, either the protected enol ether or the enolate can be utilized to carry out an aldol condensation reaction with aldehydes of formula $R^{23}$—CHO. Alternatively, the protected enol ether can be contacted with iminium salts under suitable conditions to afford amino substituted products. Amines produced via this method can be eliminated to provide exocyclic alkenes.

Scheme 33.

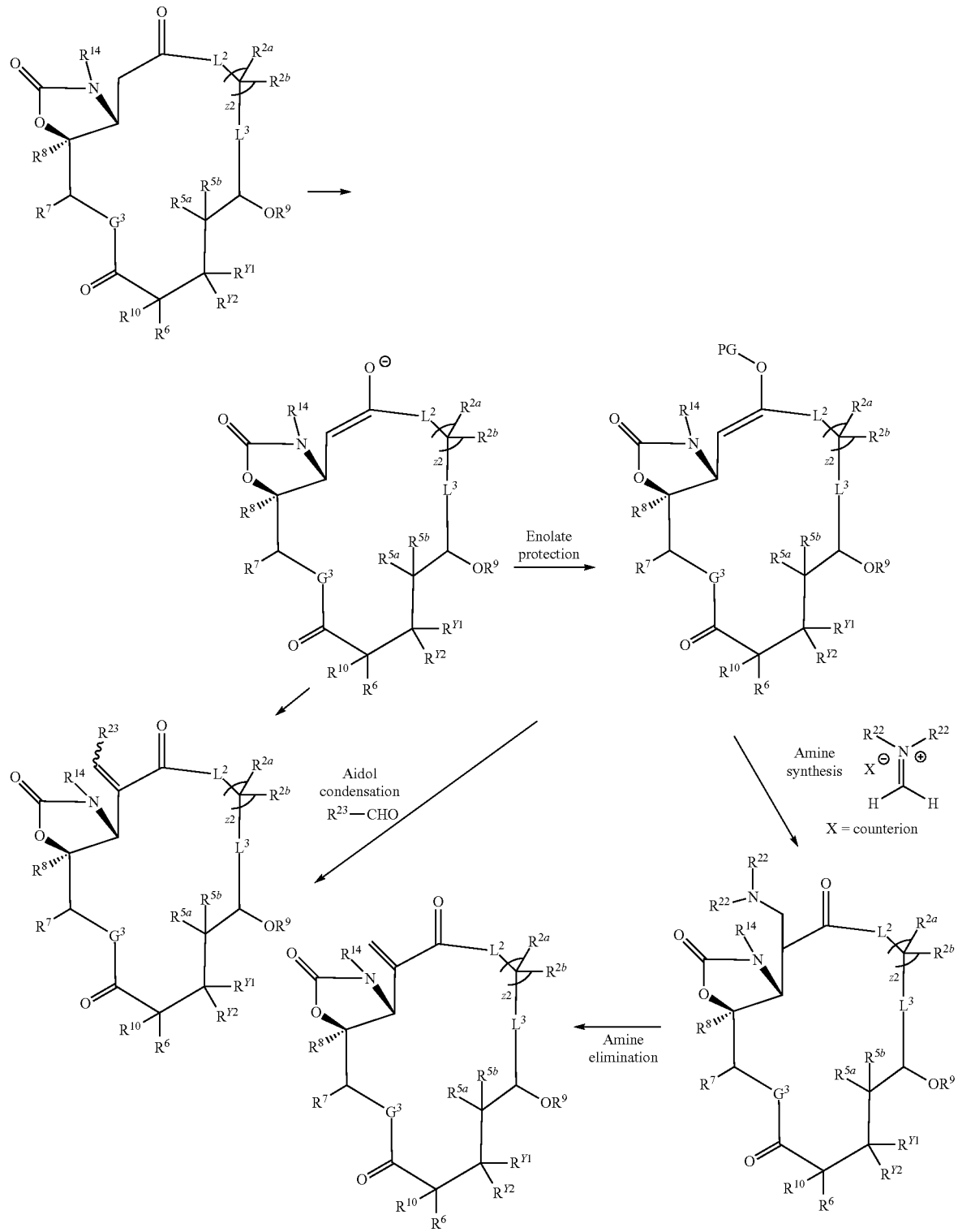

Group $G^1$ and $R^{11}$

As generally defined herein, $G^1$ is —$OR^{12}$ or —$NR^{13}R^{14}$.

In certain embodiments, $G^1$ is —$OR^{12}$, then $R^{11}$ and $R^{12}$ are joined as a group of formula —C(=O)— to provide a cyclic carbonate.

In certain embodiments, $G^1$ is —$OR^{12}$ and $R^{11}$ and $R^{12}$ are not joined to form a cyclic carbonate. In that instance, in certain embodiments, $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, and $R^{12}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group, or a group of formula:

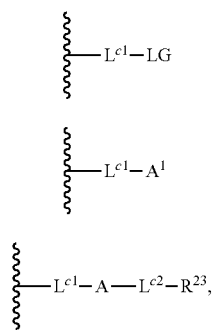

(Lc1-i)

(Lc1-ii)

(Lc1-iii)

as defined herein.

In certain embodiments, wherein $R^{12}$ is not hydrogen, $R^{12}$ is optionally substituted with a non-hydrogen group of formula $R^{23}$ as defined herein.

In certain embodiments, $G^1$ is —$NR^{13}R^{14}$, and $R^{11}$ and $R^{13}$ are joined as a group of formula —C(=O)— to provide a cyclic carbamate.

In certain embodiments, $G^1$ is —$NR^{13}R^{14}$, and $R^{11}$ and $R^{13}$ are not joined to form a cyclic carbamate. In that instance, in certain embodiments, $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, $R^{13}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group.

In certain embodiments, wherein $R^{13}$ is not hydrogen, $R^{13}$ is optionally substituted with a non-hydrogen group of formula $R^{23}$ as defined herein.

In certain embodiments, wherein $G^1$ is —$NR^{13}R^{14}$, $R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, —C(=O)$R^{Z8}$, or —C(=O)O$R^{Z8}$, or a group of formula:

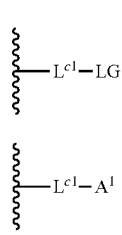

(Lc1-i)

(Lc1-ii)

-continued

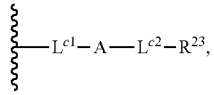

(Lc1-iii)

In certain embodiments, wherein $R^{14}$ is not hydrogen, $R^{14}$ is optionally substituted with a non-hydrogen group of formula $R^{23}$ as defined herein.

In certain embodiments, wherein $G^1$ is —$NR^{13}R^{14}$, $R^{13}$ and $R^{14}$ are joined to form an optionally substituted heterocyclyl or optionally substituted heteroaryl. In certain embodiments, the heterocyclyl or heteroaryl ring system formed from the joining of $R^{13}$ and $R^{14}$ is optionally substituted with a non-hydrogen group of formula $R^{23}$ as defined herein.

Groups $R^{1a}$, $R^{1b}$, $R^{2a}$, and $R^{2b}$

As generally defined herein, each instance of $R^{1a}$, $R^{1b}$, $R^{2a}$, and $R^{2b}$ is independently hydrogen, halogen, carbonyl, optionally substituted alkyl, optionally substituted alkenyl, optionally substituted alkynyl, optionally substituted carbocyclyl, optionally substituted heterocylyl, optionally substituted aryl, optionally substituted heteroaryl, or wherein $R^{1a}$ and $R^{1b}$ or $R^{2a}$ and $R^{2b}$ can be taken together to form

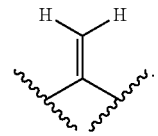 [SMILES: *C(*)=C]

In certain embodiments, the carbon to which $R^{1a}$ and $R^{1b}$ is attached is a stereocenter of the (R)-configuration. In certain embodiments, the carbon to which $R^{1a}$ and $R^{1b}$ is attached is a stereocenter of the (S)-configuration In certain embodiments, at least one of $R^{1a}$ and $R^{1b}$ is hydrogen. In certain embodiments, both $R^{1a}$ and $R^{1b}$ are hydrogen.

In certain embodiments, at least one of $R^{1a}$ and $R^{1b}$ is halogen; e.g. —F, —Cl, —Br, or I. In certain embodiments, both $R^{1a}$ and $R^{1b}$ are halogen; e.g. —F, —Cl, —Br, or I.

In certain embodiments, at least one of $R^{1a}$ and $R^{1b}$ is carbonyl. In certain embodiments, at least one of $R^{1a}$ and $R^{1b}$ is a carboxylic acid. In certain embodiments, at least one of $R^{1a}$ and $R^{1b}$ is a ketone. In certain embodiments, at least one of $R^{1a}$ and $R^{1b}$ is an aldehyde (—CHO).

In certain embodiments, at least one instance of $R^{1a}$ and $R^{1b}$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, at least one instance of $R^{1a}$ and $R^{1b}$ is —$CH_3$. In certain embodiments, both instances of $R^{1a}$ and $R^{1b}$ are —$CH_3$. In certain embodiments, at least one instance of $R^{1a}$ and $R^{1b}$ is alkyl substituted with one or more halogen atoms, e.g., optionally substituted haloalkyl; e.g., —$CF_3$, —$CF_2CF_3$, or —$CF_2H$. In certain embodiments, at least one of $R^{1a}$ and $R^{1b}$ is —$CH_2CHO$.

In certain embodiments, at least one instance of $R^{1a}$ and $R^{1b}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, at least one instance of $R^{1a}$ and $R^{1b}$ is vinyl, allyl, or prenyl.

In certain embodiments, at least one instance of $R^{1a}$ and $R^{1b}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, at least one instance of $R^{1a}$ and $R^{1b}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl. In certain embodiments, at least one instance of $R^{1a}$ and $R^{1b}$ is optionally substituted cyclopropyl. In certain embodiments, at least one instance of $R^{1a}$ and $R^{1b}$ is unsubstituted cyclopropyl. In certain embodiments, at least one instance of $R^{1a}$ and $R^{1b}$ is optionally substituted cyclobutyl. In certain embodiments, at least one instance of $R^{1a}$ and $R^{1b}$ is unsubstituted cyclobutyl. In certain embodiments, at least one instance of $R^{1a}$ and $R^{1b}$ is optionally substituted cyclopentyl. In certain embodiments, at least one instance of $R^{1a}$ and $R^{1b}$ is unsubstituted cyclopentyl. In certain embodiments, at least one instance of $R^{1a}$ and $R^{1b}$ is optionally substituted cyclohexyl. In certain embodiments, at least one instance of $R^{1a}$ and $R^{1b}$ is unsubstituted cyclohexyl.

In certain embodiments, at least one instance of $R^{1a}$ and $R^{1b}$ is optionally substituted heterocylyl, e.g., e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one instance of $R^{1a}$ and $R^{1b}$ is optionally substituted aryl, e.g., optionally substituted phenyl.

In certain embodiments, at least one instance of $R^{1a}$ and $R^{1b}$ is optionally substituted heteroaryl, e.g., optionally substituted 5- to 6-membered heteroaryl.

In certain embodiments, $R^{1a}$ and $R^{1b}$ are taken together to form

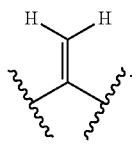 [SMILES: *C(*)=C]

In certain embodiments, the carbon to which $R^{2a}$ and $R^{2b}$ is attached is a stereocenter of the (R)-configuration. In certain embodiments, the carbon to which $R^{2a}$ and $R^{2b}$ is attached is a stereocenter of the (S)-configuration.

In certain embodiments, at least one instance of $R^{2a}$ and $R^{2b}$ is hydrogen. In certain embodiments, both $R^{2a}$ and $R^{2b}$ are hydrogen.

In certain embodiments, at least one of $R^{2a}$ and $R^{2b}$ is halogen; e.g. —F, —Cl, —Br, or I. In certain embodiments, both $R^{2a}$ and $R^{2b}$ are halogen; e.g. —F, —Cl, —Br, or I.

In certain embodiments, at least one of $R^{2a}$ and $R^{2b}$ is carbonyl. In certain embodiments, at least one of $R^{2a}$ and $R^{2b}$ is a carboxylic acid. In certain embodiments, at least one of $R^{2a}$ and $R^{2b}$ is a ketone. In certain embodiments, at least one of $R^{2a}$ and $R^{2b}$ is an aldehyde (—CHO).

In certain embodiments, at least one instance of $R^{2a}$ and $R^{2b}$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, at least one instance of $R^{2a}$ and $R^{2b}$ is —CH$_3$. In certain embodiments, both instances of $R^{2a}$ and $R^{2b}$ are —CH$_3$. In certain embodiments, at least one instance of $R^{2a}$ and $R^{2b}$ is alkyl optionally substituted with one or more halogen atoms, e.g., optionally substituted haloalkyl; e.g., —CF$_3$, —CF$_2$CF$_3$, or —CF$_2$H. In certain embodiments, at least one of $R^{2a}$ and $R^{2b}$ is —CH$_2$CHO.

In certain embodiments, at least one instance of $R^{2a}$ and $R^{2b}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, at least one instance of $R^{2a}$ and $R^{2b}$ is vinyl, allyl, or prenyl.

In certain embodiments, at least one instance of $R^{2a}$ and $R^{2b}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, at least one instance of $R^{2a}$ and $R^{2b}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, at least one instance of $R^{2a}$ and $R^{2b}$ is optionally substituted heterocylyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one instance of $R^{2a}$ and $R^{2b}$ is optionally substituted aryl, e.g., optionally substituted phenyl.

In certain embodiments, at least one instance of $R^{2a}$ and $R^{2b}$ is optionally substituted heteroaryl, e.g., optionally substituted 5- to 6-membered heteroaryl.

In certain embodiments, $R^{2a}$ and $R^{2b}$ are taken together to form

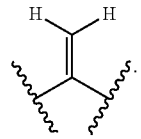 [SMILES: *C(*)=C]

Group $L^3$ and Groups $R^3$, $R^4$, $R^{18}$, $R^{19}$, $R^{20}$, and $R^{21}$

As generally defined herein, $L^3$ is a group of the formula:

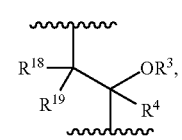

(L$^3$-i)

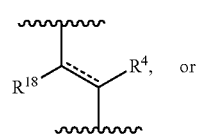

(L$^3$-ii)

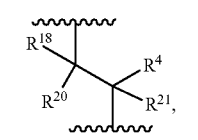

(L$^3$-iii)

═══ represents a single or double bond;

$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^{Z8}$, —C(=O)OR$^{Z8}$, —C(=O)N(R$^{Z8}$)$_2$, an oxygen protecting group, or a group of formula:

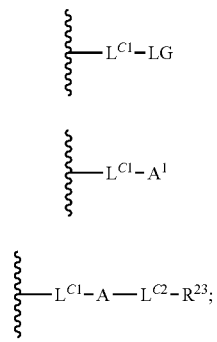

R$^4$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl;

each instance of R$^{18}$ and R$^{19}$ independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each instance of R$^{20}$ and R$^{21}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, halogen, carbonyl, or R$^{20}$ and R$^{21}$ are joined to form an optionally substituted cyclopropyl or an oxiranyl ring.

In certain embodiments, the carbon to which R$^3$ is attached is a stereocenter of the (R)-configuration. In certain embodiments, the carbon to which R$^3$ is attached is a stereocenter of the (S)-configuration.

In certain embodiments, R$^3$ is hydrogen.

In certain embodiments, R$^3$ is optionally substituted alkyl; e.g., optionally substituted C$_{1-6}$alkyl optionally substituted C$_{1-2}$alkyl, optionally substituted C$_{2-3}$alkyl, optionally substituted C$_{3-4}$alkyl, optionally substituted C$_{4-5}$alkyl, or an optionally substituted C$_{5-6}$alkyl. In certain embodiments, R$^3$ is —CH$_3$. In certain embodiments, R$^3$ is —CH$_2$CHO. In certain embodiments, R$^3$ is —CH$_2$N(R$^{22}$)$_2$ wherein each instance of R$^{22}$ is independently hydrogen or optionally substituted alkyl. In certain embodiments, R$^3$ is-CH$_2$NH(R$^{22}$). In certain embodiments, R$^3$ is —CH$_2$NH$_2$. In certain embodiments, R$^3$ is —CH$_2$CH$_2$R$^{24}$ wherein R$^{24}$ is hydrogen, optionally substituted alkyl, or optionally substituted aryl. In certain embodiments, R$^3$ is —CH$_2$CH$_2$OH. In certain embodiments, R$^3$ is —CH$_2$CH$_2$R$^{23}$ wherein R$^{23}$ is as defined herein.

In certain embodiments, R$^3$ is optionally substituted alkenyl; e.g., optionally substituted C$_{2-6}$alkenyl, optionally substituted C$_{2-3}$alkenyl, optionally substituted C$_{3-4}$alkenyl, optionally substituted C$_{4-5}$alkenyl, or optionally substituted C$_{5-6}$alkenyl. In certain embodiments, R$^3$ is vinyl, allyl, or prenyl. In certain embodiments, R$^3$ is optionally substituted allyl, e.g., substituted allyl, e.g.,

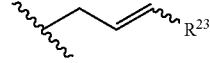

wherein R$^{23}$ is as defined herein, or unsubstituted allyl

In certain embodiments, R$^3$ is optionally substituted vinyl, e.g., substituted vinyl, e.g.,

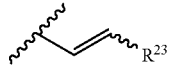

wherein R$^{23}$ is as defined herein, or unsubstituted vinyl

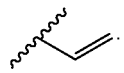

In certain embodiments, R$^3$ is optionally substituted alkynyl, e.g., optionally substituted C$_{2-6}$alkynyl, optionally substituted C$_{2-3}$alkynyl, optionally substituted C$_{3-4}$alkynyl, optionally substituted C$_{4-5}$alkynyl, or optionally substituted C$_{5-6}$alkynyl.

In certain embodiments, R$^3$ is optionally substituted carbocyclyl; e.g., optionally substituted C$_{3-6}$carbocyclyl, optionally substituted C$_{3-4}$carbocyclyl, optionally substituted C$_{4-5}$ carbocyclyl, or optionally substituted C$_{5-6}$ carbocyclyl.

In certain embodiments, R$^3$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, R$^3$ is optionally substituted aryl, e.g., optionally substituted phenyl.

In certain embodiments, R$^3$ is optionally substituted heteroaryl, e.g., optionally substituted 5- to 6-membered heteroaryl.

In certain embodiments, R$^3$ is —C(=O)R$^{Z8}$, —C(=O)OR$^{Z8}$, —C(=)N(R$^{Z8}$)$_2$, or an oxygen protecting group.

In certain embodiments, R$^3$ is or a group of formula:

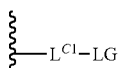

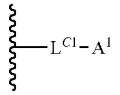

-continued

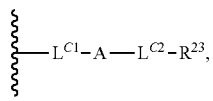

(L^{C1}-iii)

wherein $L^{C1}$, LG, $A^1$, A, $L^{C2}$, and $R^{23}$ are as defined herein.

In certain embodiments, the carbon to which $R^4$ is attached is a stereocenter of the (R)-configuration. In certain embodiments, the carbon to which $R^4$ is attached is a stereocenter of the (S)-configuration.

In certain embodiments, $R^4$ is hydrogen.

In certain embodiments, $R^4$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, $R^4$ is —$CH_3$. In certain embodiments, $R^4$ is —$CH_2CHO$. In certain embodiments, $R^4$ is —$CH_2N(R^{22})_2$ wherein each instance of $R^{22}$ is independently hydrogen or optionally substituted alkyl. In certain embodiments, $R^4$ is -$CH_2NH$($R^{22}$). In certain embodiments, $R^4$ is —$CH_2NH_2$. In certain embodiments, $R^4$ is —$CH_2CH(OH)R^{24}$ wherein $R^{24}$ is hydrogen, optionally substituted alkyl, or optionally substituted aryl. In certain embodiments, $R^4$ is —$CH_2CH_2OH$. In certain embodiments, $R^4$ is —$CH_2CH_2R^{23}$ wherein $R^{23}$ is as defined herein.

In certain embodiments, $R^4$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, $R^4$ is optionally substituted allyl, e.g., substituted allyl, e.g.,

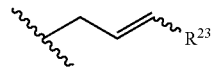

wherein $R^{23}$ is as defined herein, or unsubstituted allyl

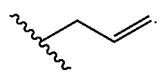 [SMILES: *CC=C]

In certain embodiments, $R^4$ is optionally substituted vinyl, e.g., substituted vinyl, e.g.,

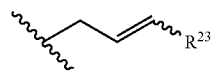

wherein $R^{23}$ is as defined herein, or unsubstituted vinyl

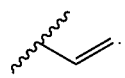

Various combinations of $R^4$ and $R^{21}$ are contemplated herein. For example, in certain embodiments, $R^4$ is optionally substituted $C_{1-3}$alkyl and $R^{21}$ is hydrogen. In certain embodiments, $R^3$ is —$CH_2CHO$, —$CH_2N(R^{22})_2$, —$CH_2CH$(OH)$R^{24}$, or —$CH_2CH_2R^{23}$ and $R^{21}$ is hydrogen. In certain embodiments, $R^4$ is optionally substituted $C_{2-3}$alkenyl, and $R^{21}$ is hydrogen. In certain embodiments, $R^4$ is

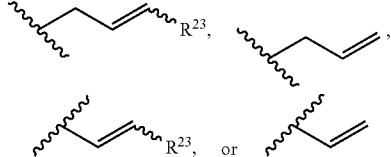

and $R^{21}$ is hydrogen.

In certain embodiments, $R^4$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, $R^4$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^4$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^4$ is optionally substituted aryl, e.g., optionally substituted phenyl.

In certain embodiments, $R^4$ is optionally substituted heteroaryl, e.g., optionally substituted 5- to 6-membered heteroaryl.

In certain embodiments, each instance of $R^{18}$ and $R^{19}$ is independently hydrogen or optionally substituted alkyl, e.g., hydrogen or —$CH_3$. In certain embodiments, the carbon to which $R^{18}$ and $R^{19}$ are attached is a stereocenter in the (R) configuration. In certain embodiments, the carbon to which $R^{18}$ and $R^{19}$ are attached is a stereocenter in the (S) configuration.

In certain embodiments, each instance of $R^{20}$ and $R^{21}$ is independently hydrogen, hydroxyl, substituted hydroxyl, thiol, substituted thiol, amino, substituted amino, halogen, or $R^{20}$ and $R^{21}$ are joined to form an optionally substituted cyclopropyl or an oxiranyl ring. In certain embodiments, $R^{20}$ and $R^{21}$ are syn to each other. In certain embodiments, $R^{20}$ and $R^{21}$ are anti to each other.

In certain embodiments, $L^3$ is:

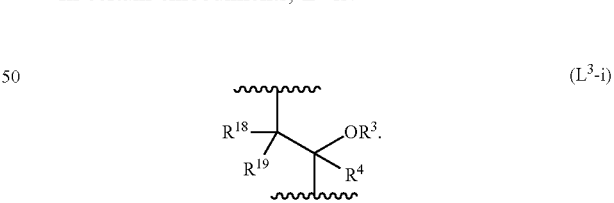

(L^3-i)

In certain embodiments, $L^3$ is:

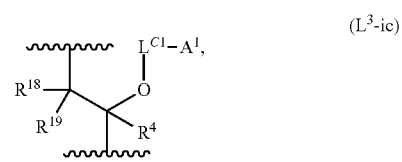

(L^3-ic)

wherein $L^{C1}$ and $A^1$ are as defined herein.

In certain embodiments, $L^3$ is of the formula:

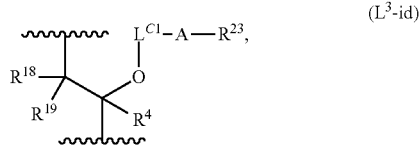

wherein $L^{C1}$, A, $L^{C2}$, and $R^{23}$ are as defined herein.

Groups $R^{5a}$ and $R^{5b}$

As generally defined herein, each instance of $R^{5a}$ and $R^{5b}$ is independently hydrogen, halogen, silyl, optionally substituted alkyl, optionally substituted carbocyclyl, or optionally substituted heterocyclyl.

In certain embodiments, one instance of $R^{5a}$ and $R^{5b}$ is hydrogen, and the other of $R^{5a}$ and $R^{5b}$ is a non-hydrogen group. In certain embodiments, each instance of $R^{5a}$ and $R^{5b}$ is hydrogen. In certain embodiments, each instance of $R^{5a}$ and $R^{5b}$ is a non-hydrogen group, e.g., halogen, optionally substituted alkyl, optionally substituted carbocyclyl, or optionally substituted heterocyclyl.

In certain embodiments, the carbon to which $R^{5a}$ and $R^{5b}$ is attached is a stereocenter of the (R)-configuration. In certain embodiments, the carbon to which $R^{5a}$ and $R^{5b}$ is attached is a stereocenter of the (S)-configuration.

In certain embodiments, at least one instance of $R^{5a}$ and $R^{5b}$ is optionally substituted alkyl, e.g., optionally substituted $C_{1-6}$alkyl, optionally substituted $C_{1-2}$alkyl, optionally substituted $C_{2-3}$alkyl optionally substituted $C_{3-4}$alkyl, optionally substituted $C_{4-5}$alkyl, or optionally substituted $C_{5-6}$alkyl. In certain embodiments, at least one instance of $R^{5a}$ and $R^{5b}$ is —$CH_3$. In certain embodiments, both instances of $R^{5a}$ and $R^{5b}$ are —$CH_3$.

In certain embodiments, at least one instance of $R^{5a}$ and $R^{5b}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, at least one instance of $R^{5a}$ and $R^{5b}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one instance of $R^{5a}$ and $R^{5b}$ is halogen, e.g., bromo, iodo, chloro, or fluoro. In certain embodiments, at least one instance of $R^{5a}$ and $R^{5b}$ is fluoro. In certain embodiments, both instances of $R^{5a}$ and $R^{5b}$ are fluoro. In certain embodiments, one of $R^{5a}$ and $R^{5b}$ is hydrogen and the other of $R^{5a}$ and $R^{5b}$ is fluoro.

In certain embodiments, at least one instance of $R^{5a}$ and $R^{5b}$ is silyl.

Groups $R^6$ and $R^{10}$

As generally defined herein, $R^6$ and/or $R^{10}$ is hydrogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl, hydroxyl, substituted hydroxyl, thiol, substituted thiol, amino, substituted amino, carbonyl, silyl, or halogen.

In certain embodiments, $R^6$ and/or $R^{10}$ is hydrogen. In certain embodiments, $R^6$ is hydrogen. In certain embodiments, $R^{10}$ is hydrogen. In certain embodiments, $R^6$ is hydrogen, and $R^{10}$ is hydrogen. In certain embodiments, both of $R^6$ and $R^{10}$ are non-hydrogen groups.

In certain embodiments, the carbon to which $R^6$ and $R^{10}$ is attached is a stereocenter of the (R)-configuration. In certain embodiments, the carbon to which $R^6$ and $R^{10}$ is attached is a stereocenter of the (S)-configuration.

In certain embodiments, at least one instance of $R^6$ and $R^{10}$ is optionally substituted alkyl; e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, at least one instance of $R^6$ and $R^{10}$ is —$CH_3$. In certain embodiments, at least one instance of $R^6$ and $R^{10}$ is —$CH_3$. In certain embodiments, at least one instance of $R^6$ and $R^{10}$ is —$CH_2CN$. In certain embodiments, at least one instance of $R^6$ and $R^{10}$ is —$CH_2C(=O)OR^{23}$, wherein $R^{32}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl. In certain embodiments, $R^{32}$ is optionally substituted alkyl, e.g. $C_{1-6}$ alkyl. In certain embodiments, $R^{32}$ is unsubstituted $C_{1-6}$ alkyl. In certain embodiments, $R^{32}$ is methyl, ethyl, or propyl. In certain embodiments, $R^{32}$ is substituted $C_{1-6}$ alkyl. In certain embodiments, $R^{32}$ is hydrogen.

In certain embodiments, at least one instance of $R^6$ and $R^{10}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, at least one instance of $R^6$ and $R^{10}$ is substituted or unsubstituted allyl. In certain embodiments, at least one instance of $R^6$ and $R^{10}$ is substituted or unsubstituted vinyl. Such groups are contemplated after the macrocyclization step, converted, for example, from the enolate of the macrolide wherein $R^6$ and/or $R^{10}$ is hydrogen.

In certain embodiments, at least one instance of $R^6$ and $R^{10}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl. Such groups are contemplated after the macrocyclization step, converted, for example, from the enolate of the macrolide wherein $R^6$ and/or $R^{10}$ is hydrogen.

In certain embodiments, at least one instance of $R^6$ and $R^{10}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, at least one instance of $R^6$ and $R^{10}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, at least one instance of $R^6$ and $R^{10}$ is optionally substituted aryl; e.g., optionally substituted phenyl.

In certain embodiments, at least one instance of $R^6$ and $R^{10}$ is optionally substituted aralkyl; e.g., optionally substituted benzyl.

In certain embodiments, at least one instance of $R^6$ and $R^{10}$ is optionally substituted heteroaryl, e.g., optionally substituted 5- to 6-membered heteroaryl.

In certain embodiments, at least one instance of $R^6$ and $R^{10}$ is optionally substituted heteroaralkyl; e.g., optionally substituted pyrazolylalkyl, imidazolylalkyl, thiazolylalkyl, oxazolylalkyl, pyridinylalkyl, pyrimidinylalkyl, or pyrazinylalkyl.

In certain embodiments, at least one instance of $R^6$ and $R^{10}$ is hydroxyl, substituted hydroxyl, thiol, substituted thiol, amino, or substituted amino. Such groups are contemplated after the macrocyclization step, converted, for example, from wherein $R^6$ and/or $R^{10}$ is a halogen.

In certain embodiments, at least one instance of $R^6$ and $R^{10}$ is carbonyl, e.g., acetyl.

In certain embodiments, at least one instance of $R^6$ and $R^{10}$ is silyl. In certain embodiments, $R^6$ is silyl prior to macrocyclization, but is removed after the macrolide is formed and replaced with, for example, hydrogen.

In certain embodiments, at least one instance of $R^6$ and $R^{10}$ is halogen, e.g., fluoro, bromo, chloro, or iodo.

Groups $R^7$ and $R^8$

As generally defined herein, $R^7$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^7$ is hydrogen. However, in certain embodiments, $R^7$ is a non-hydrogen group, and the carbon to which $R^7$ is attached is a stereocenter of the (R)-configuration. In certain embodiments, $R^7$ is a non-hydrogen group, and the carbon to which $R^7$ is attached is a stereocenter of the (S)-configuration.

In certain embodiments, $R^7$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, $R^7$ is —$CH_3$ or —$CH_2CH_3$.

In certain embodiments, $R^7$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, $R^7$ is vinyl, allyl, or prenyl.

In certain embodiments, $R^7$ is optionally substituted alkynyl, e.g., optionally substituted $C_{2-6}$alkynyl, optionally substituted $C_{2-3}$alkynyl, optionally substituted $C_{4-5}$alkynyl, optionally substituted $C_{4-5}$alkynyl, or optionally substituted $C_{5-6}$alkynyl.

In certain embodiments, $R^7$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^7$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^7$ is optionally substituted aryl; e.g., optionally substituted phenyl.

In certain embodiments, $R^7$ is optionally substituted heteroaryl, e.g., optionally substituted 5- to 6-membered heteroaryl.

As generally defined herein, $R^8$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^8$ is hydrogen.

In certain embodiments, $R^8$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, $R^8$ is —$CH_3$ or —$CH_2CH_3$.

In certain embodiments, $R^8$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, $R^8$ is vinyl, allyl, or prenyl In certain embodiments, $R^8$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, $R^8$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^8$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^8$ is optionally substituted aryl, e.g., optionally substituted phenyl.

In certain embodiments, $R^8$ is optionally substituted heteroaryl, e.g., optionally substituted 5- to 6-membered heteroaryl.

Groups $R^{Za}$ and $R^{Zb}$

As generally defined herein, $R^{Za}$ and $R^{Zb}$ are each independently hydrogen, halogen, hydroxyl, substituted hydroxyl, amino, substituted amino, thiol, substituted thiol, carbonyl, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, the bond ==== between the two carbons to which $R^{Za}$ and $R^{Zb}$ are attached represents a double bond, and $R^{Za}$ and $R^{Zb}$ are each independently hydrogen.

In certain embodiments, the bond ==== between the two carbons to which $R^{Za}$ and $R^{Zb}$ are attached represents a single bond (e.g., provided by hydrogenation of the double bond), and $R^{Za}$ and $R^{Zb}$ are each independently hydrogen.

In certain embodiments, at least one of $R^{Za}$ and $R^{Zb}$ is a hydrogen and at least one of $R^{Za}$ and $R^{Zb}$ is a non-hydrogen group, e.g., halogen, hydroxyl, substituted hydroxyl, amino, substituted amino, thiol, substituted thiol, carbonyl, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{Za}$ is hydrogen and $R^{Zb}$ is a non-hydrogen group. In certain embodiments, $R^{Za}$ is a non-hydrogen group and $R^{Zb}$ is hydrogen. In certain embodiments, both of $R^{Za}$ and $R^{Zb}$ are non-hydrogen groups. In any of the above instance, in certain embodiments, the bond ==== between the two carbons to which $R^{Za}$ and $R^{Zb}$ are attached represents a single bond. Alternatively, in any of the above instance, in certain embodiments, the bond ==== between the two carbons to which $R^{Za}$ and $R^{Zb}$ are attached represents a double bond.

In certain embodiments, $R^{Za}$ is hydrogen, $R^{Zb}$ is hydrogen, and the bond ═ between the two carbons to which $R^{Za}$ and $R^{Zb}$ are attached represents a double bond.

In certain embodiments, $R^{Za}$ is halogen (e.g., fluoro) or optionally substituted alkyl (e.g., methyl), $R^{Zb}$ is hydrogen, and the bond ═ between the two carbons to which $R^{Za}$ and $R^{Zb}$ are attached represents a single bond.

In certain embodiments, the bond ═ between the two carbons to which $R^{Za}$ and $R^{Zb}$ are attached represents a double bond and $R^{Za}$ and $R^{Zb}$ are in a cis-configuration. In certain embodiments, the bond ═ between the two carbons to which $R^{Za}$ and $R^{Zb}$ are attached represents a double bond and $R^{Za}$ and $R^{Zb}$ are in a trans-configuration.

Groups $R^{Z2}$, $R^{Z3}$ and $R^{Z4}$

As generally defined herein, each instance of $R^{Z2}$ is independently hydrogen, optionally substituted alkyl, optionally substituted alkenyl, optionally substituted alkynyl, optionally substituted carbocyclyl, optionally substituted heterocylyl, optionally substituted aryl, optionally substituted heteroaryl, hydroxyl, substituted hydroxyl, amino, substituted amino, —C(═O)$R^{Z8}$, —C(═)O$R^{Z8}$, —C(═O)N($R^{Z8}$)$_2$, or a nitrogen protecting group, or two $R^{Z2}$ groups are joined to form an optionally substituted heterocylyl or optionally substituted heteroaryl ring.

In certain embodiments, $R^{Z2}$ is hydrogen.

In certain embodiments, $R^{Z2}$ is optionally substituted alkyl; e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, $R^{Z2}$ is —CH$_3$.

In certain embodiments, $R^{Z2}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl.

In certain embodiments, $R^{Z2}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, $R^{Z2}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^{Z2}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^{Z2}$ is optionally substituted aryl, e.g., optionally substituted phenyl.

In certain embodiments, $R^{Z2}$ is optionally substituted heteroaryl, e.g., optionally substituted 5- to 6-membered heteroaryl.

In certain embodiments, $R^{Z2}$ is hydroxyl, substituted hydroxyl, amino, or substituted amino.

In certain embodiments, $R^{Z2}$ is —C(═O)$R^{Z8}$, —C(═O)O$R^{Z8}$, —C(═O)N($R^{Z8}$)$_2$.

In certain embodiments, $R^{Z2}$ is a nitrogen protecting group.

In certain embodiments, two $R^{Z2}$ groups are joined to form an optionally substituted heterocylyl or optionally substituted heteroaryl ring.

As generally defined herein, $R^{Z3}$ is hydrogen, optionally substituted alkyl, optionally substituted alkenyl, optionally substituted alkynyl, optionally substituted carbocyclyl, optionally substituted heterocylyl, optionally substituted aryl, or optionally substituted heteroaryl.

In certain embodiments, $R^{Z3}$ is hydrogen.

In certain embodiments, $R^{Z3}$ is optionally substituted alkyl; e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, $R^{23}$ is —CH$_3$. In certain embodiments, $R^{23}$ is —CH$_2$CHO. In certain embodiments, $R^{23}$ is —CH$_2$CH$_2$OH. In certain embodiments, $R^{23}$ is —CH$_2$CH$_2$N($R^{22}$)$_2$. In certain embodiments, $R^{23}$ is —CH$_2$CH$_2$N(CH$_3$)$_2$. In certain embodiments, $R^{23}$ is —CH$_2$CH(OH)$R^{24}$. In certain embodiments, $R^{23}$ is alkyl optionally substituted with one or more halogen atoms, e.g., optionally substituted haloalkyl; e.g., —CF$_3$, —CF$_2$CF$_3$, or —CF$_2$H. In certain embodiments, $R^{23}$ is —CF$_3$.

In certain embodiments, $R^{Z3}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, $R^{Z3}$ is optionally substituted vinyl. In certain embodiments, $R^{Z3}$ is unsubstituted vinyl. In certain embodiments, $R^{Z3}$ is optionally substituted allyl. In certain embodiments, $R^{Z3}$ is unsubstituted allyl.

In certain embodiments, $R^{Z3}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, $R^{Z3}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl. In certain embodiments, $R^{Z3}$ is optionally substituted cyclopropyl. In certain embodiments, $R^{Z3}$ is unsubstituted cyclopropyl. In certain embodiments, $R^{Z3}$ is optionally substituted cyclobutyl. In certain embodiments, $R^{Z3}$ is unsubstituted cyclobutyl.

In certain embodiments, $R^{Z3}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^{Z3}$ is optionally substituted aryl, e.g., optionally substituted phenyl.

In certain embodiments, $R^{Z3}$ is optionally substituted aralkyl. In certain embodiments, $R^{Z3}$ is unsubstituted aralkyl. In certain embodiments, $R^{Z3}$ is optionally substituted benzyl. In certain embodiments, $R^{Z3}$ is

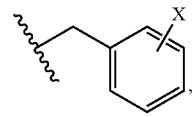

wherein X is halogen. In certain embodiments, $R^{Z3}$ is unsubstituted benzyl.

In certain embodiments, $R^{Z3}$ is optionally substituted heteroaryl, e.g., optionally substituted 5- to 6-membered heteroaryl.

In certain embodiments, $R^{Z3}$ is optionally substituted heteroaralkyl. In certain embodiments, $R^{Z3}$ is unsubstituted heteroaralkyl.

As generally defined herein, $R^{Z4}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^{Z4}$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, $R^{Z4}$ is —CH$_3$. In certain embodiments, $R^{Z4}$ is alkyl optionally substituted with one or more halogen atoms, e.g., optionally substituted haloalkyl; e.g., —CF$_3$, —CF$_2$CF$_3$, or —CF$_2$H.

In certain embodiments, $R^{Z4}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl.

In certain embodiments, $R^{Z4}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, $R^{Z4}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^{Z4}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^{Z4}$ is optionally substituted aryl, e.g., optionally substituted phenyl.

In certain embodiments, $R^{Z4}$ is optionally substituted heteroaryl, e.g., optionally substituted 5- to 6-membered heteroaryl.

In certain embodiments, $R^{Z3}$ and $R^{Z4}$ are taken together to form

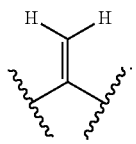

Groups $R^9$ and $R^{17}$, $R^{Y1}$, $R^{Y2}$

As generally defined herein, $R^{Y1}$ is —OR$^{17}$ and $R^{Y2}$ is hydrogen, or $R^{Y1}$ is halogen and $R^{Y2}$ is hydrogen, or $R^{Y1}$ is halogen and $R^{Y2}$ is halogen, or $R^{Y1}$ and $R^{Y2}$ are joined to form an oxo (=O) group.

In certain embodiments, $R^{Y1}$ and $R^{Y2}$ are joined to form an oxo (=O) group.

In certain embodiments, $R^{Y1}$ is —OR$^{17}$ and $R^{Y2}$ is hydrogen.

In certain embodiments, $R^{Y1}$ is halogen (e.g., fluoro) and $R^{Y2}$ is hydrogen.

In certain embodiments, $R^{Y1}$ is halogen (e.g., fluoro) and $R^{Y2}$ is halogen (e.g., fluoro).

As generally defined herein, $R^9$ and/or $R^{17}$ are each independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^{Z8}$, —C(=O)OR$^{Z8}$, —C(=O)N(R$^{Z8}$)$_2$, an oxygen protecting group, or a carbohydrate, wherein each instance of $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups are joined to form an optionally substituted heterocylyl or optionally substituted heteroaryl ring.

In certain embodiments, the carbon to which $R^9$ is attached is of the (R)-configuration. In certain embodiments, the carbon to which $R^9$ is attached is of the (S)-configuration.

In certain embodiments, the carbon to which $R^{17}$ is attached is of the (R)-configuration. In certain embodiments, the carbon to which $R^{17}$ is attached is of the (S)-configuration.

In certain embodiments, $R^9$ is hydrogen. In certain embodiments, $R^{17}$ is hydrogen.

In certain embodiments, $R^9$ and/or $R^{17}$ are each independently optionally substituted alkyl, e.g., optionally substituted $C_{1-6}$alkyl, optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl, e.g., —CH$_3$.

In certain embodiments, $R^9$ is

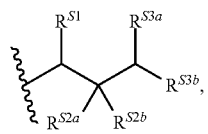

where $R^{S1}$, $R^{S2a}$, $R^{S2b}$, $R^{S3a}$, and $R^{S3b}$ are defined herein. In certain embodiments, $R^9$ is

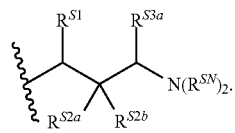

In certain embodiments, $R^9$ is

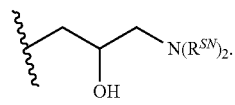

In certain embodiments, $R^9$ is

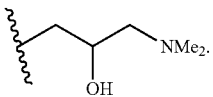

In certain embodiments, $R^9$ and/or $R^{17}$ are each independently optionally substituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl.

In certain embodiments, $R^9$ and/or $R^{17}$ are each independently optionally substituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl.

In certain embodiments, $R^9$ and/or $R^{17}$ are each independently optionally substituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, $R^9$ and/or $R^{17}$ are each independently optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^9$ and/or $R^{17}$ are each independently optionally substituted aryl, e.g., optionally substituted phenyl.

In certain embodiments, $R^9$ and/or $R^{17}$ are each independently optionally substituted heteroaryl, e.g., optionally substituted 5- to 6-membered heteroaryl.

In certain embodiments, $R^9$ and/or $R^{17}$ are each independently —C(=O)$R^{Z8}$, —C(=O)O$R^{Z8}$, or —C(=O)N($R^{Z8}$)$_2$. For example, in certain embodiments, $R^{17}$ is —C(=O)$R^{Z8}$, wherein $R^{Z8}$ is optionally substituted aryl or optionally substituted heteroaryl. In certain embodiments, $R^{17}$ is —C(=O)$R^{Z8}$, wherein $R^{Z8}$ is optionally substituted aralkyl or optionally substituted heteroaralkyl.

In certain embodiments, $R^9$ and/or $R^{17}$ are each independently an oxygen protecting group.

In certain embodiments, $R^9$ and/or $R^{17}$ are each independently a carbohydrate.

In certain embodiments, $R^9$ and/or $R^{17}$ is a group of Formula (s-1), which encompasses carbohydrates, but also encompasses optionally substituted heterocylyl:

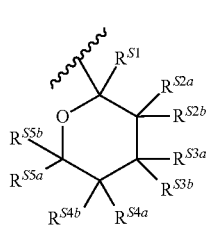

(s-1)

wherein:
each of $R^{S1}$, $R^{S2a}$, $R^{S2b}$, $R^{S3a}$, $R^{S3b}$, $R^{S4a}$, $R^{S4b}$, $R^{S5a}$, and $R^{S5b}$ is independently hydrogen, optionally substituted alkyl, —O$R^{SO}$, —N($R^{SN}$)$_2$, or wherein $R^{S2a}$ or $R^{S2b}$ may be taken together with $R^{S3a}$ or $R^{S3b}$ to form an optionally substituted fused heterocyclic ring;
each instance of $R^{SO}$ is independently hydrogen, optionally substituted alkyl, optionally substituted alkenyl, optionally substituted heterocyclyl, or an oxygen protecting group; and
each instance of $R^{SN}$ is independently hydrogen, optionally substituted alkyl, or a nitrogen protecting group; or optionally two $R^{SN}$ are taken with the intervening atoms to form a heterocyclic ring.

As generally defined herein, each instance of $R^{S1}$ is independently hydrogen, optionally substituted alkyl, —O$R^{SO}$, or —N($R^{SN}$)$_2$.

In certain embodiments, $R^{S1}$ is hydrogen.

In certain embodiments, $R^{S1}$ is optionally substituted alkyl. In certain embodiments, $R^{S1}$ is substituted $C_{1-6}$ alkyl. In certain embodiments, $R^{S1}$ is unsubstituted $C_{1-6}$ alkyl. In certain embodiments, $R^{S1}$ is methyl, ethyl, propyl, butyl, pentyl, or hexyl. In certain embodiments, $R^{S1}$ is isopropyl, isobutyl, or isoamyl. In certain embodiments, $R^{S1}$ is isobutyl. In certain embodiments, $R^{S1}$ is tert-butyl.

In certain embodiments, $R^{S1}$ is —O$R^{SO}$, wherein $R^{SO}$ is independently hydrogen, optionally substituted alkyl, optionally substituted alkenyl, optionally substituted heterocyclyl, or an oxygen protecting group. In certain embodiments, $R^{S1}$ is —OH. In certain embodiments, $R^{S1}$ is —O$R^{SO}$, wherein $R^{SO}$ is optionally substituted alkyl. In certain embodiments, $R^{S1}$ is —O-methyl, —O-ethyl, or —O-propyl. In certain embodiments, $R^{S1}$ is optionally substituted —O-alkyl-aryl. In certain embodiments, $R^{S1}$ is —O-Bz. In certain embodiments, $R^{S1}$ is optionally substituted —O-alky 1-heteroaryl. In certain embodiments, $R^{S1}$ is optionally substituted —O-alkenyl-aryl. In certain embodiments, $R^{S1}$ is optionally substituted —O-alkenyl-heteroaryl. In certain embodiments, $R^{S1}$ is —O$R^{SO}$, wherein $R^{SO}$ is

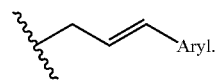

In certain embodiments, $R^{S1}$ is —O$R^{SO}$, wherein $R^{SO}$ is

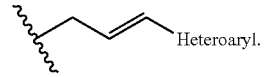

In certain embodiments, $R^{S1}$ is —O$R^{SO}$, wherein $R^{SO}$ is

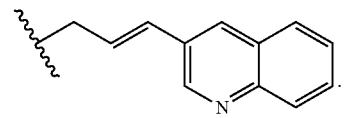 [SMILES: *C/C=C/c1cnc2ccccc2c1]

In certain embodiments, $R^{S1}$ is —O$R^{SO}$, wherein $R^{SO}$ is an oxygen protecting group. In certain embodiments, $R^{S1}$ is —O$R^{SO}$, wherein $R^{SO}$ is carbonyl. In certain embodiments, $R^{S1}$ is —O$R^{SO}$, wherein $R^{SO}$ is acetyl. In certain embodiments, $R^{S1}$ is —O$R^{SO}$, wherein $R^{SO}$ is optionally substituted heterocyclyl.

In certain embodiments, $R^{S1}$ is —N($R^{SN}$)$_2$. In some embodiments, $R^{S1}$ is —N($R^{SN}$)$_2$, wherein each $R^{SN}$ is the same. In some embodiments, $R^{S1}$ is —N($R^{SN}$)$_2$, wherein each $R^{SN}$ is different.

In certain embodiments, $R^{S1}$ is —NH$_2$.

In certain embodiments, $R^{S1}$ is —NH$R^{SN}$. In certain embodiments, $R^{S1}$ is —NH$R^{SN}$, wherein $R^{SN}$ is optionally substituted $C_{1-6}$ alkyl. In certain embodiments, $R^{S1}$ is —NH$R^{SN}$, wherein $R^{SN}$ is unsubstituted $C_{1-6}$ alkyl. In certain embodiments, $R^{S1}$ is —NH$R^{SN}$, wherein $R^{SN}$ is substituted $C_{1-6}$ alkyl. In certain embodiments, $R^{S1}$ is —NH-benzyl.

In certain embodiments, $R^{S1}$ is —$NHR^{SN}$, wherein $R^{SN}$ is a nitrogen protecting group. In certain embodiments, $R^{S1}$ is —NHFmoc. In certain embodiment, $R^{S1}$ is —NHBoc.

In certain embodiments, $R^{S1}$ is —$N(R^{SN})_2$, wherein each $R^{SN}$ is independently optionally substituted $C_{1-6}$ alkyl. In certain embodiments, $R^{S1}$ is —$N(R^{SN})_2$, wherein each $R^{SN}$ is independently unsubstituted $C_{1-6}$ alkyl. In certain embodiments, $R^{S1}$ is —$N(CH_3)R^{SN}$, wherein each $R^{SN}$ is independently optionally substituted $C_{1-6}$ alkyl. In certain embodiments, $R^{S1}$ is —$N(CH_3)R^{SN}$, wherein each $R^{SN}$ is independently unsubstituted $C_{1-6}$ alkyl. In certain embodiments, $R^{S1}$ is —$N(CH_2CH_3)R^{SN}$, wherein each $R^{SN}$ is independently optionally substituted $C_{1-6}$ alkyl. In certain embodiments, $R^{S1}$ is —$N(CH_2CH_3)R^{SN}$, wherein each $R^{SN}$ is independently unsubstituted $C_{1-6}$ alkyl. In certain embodiments, $R^{S1}$ is —$N(R^{SN})_2$, wherein each $R^{SN}$ is independently selected from the group consisting of methyl, ethyl, isopropyl, isobutyl, isoamyl, and benzyl.

In some embodiments, $R^{S1}$ is —$N(R^{SN})_2$, wherein two $R^{SN}$ groups are taken together with the intervening atoms to form an optionally substituted heterocyclic ring. For example, in certain embodiments, $R^{S1}$ is of the formula:

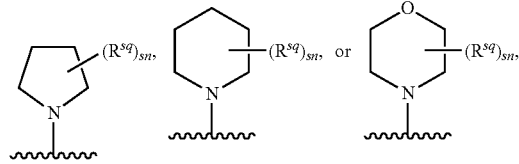

wherein $R^{sq}$ is as defined herein, and sn is 0, 1, 2, or 3.

As generally defined above, each instance of $R^{S2a}$ and $R^{S2b}$ is independently hydrogen, optionally substituted alkyl, —$OR^{SO}$, or —$N(R^{SN})_2$.

In certain embodiments, at least one instance of $R^{S2a}$ and $R^{S2b}$ is hydrogen.

In certain embodiments, at least one instance of $R^{S2a}$ and $R^{S2b}$ is optionally substituted alkyl. In certain embodiments, at least one instance of $R^{S2a}$ and $R^{S2b}$ is substituted $C_{1-6}$ alkyl. In certain embodiments, at least one instance of $R^{S2a}$ and $R^{S2b}$ is unsubstituted $C_{1-6}$ alkyl. In certain embodiments, at least one instance of $R^{S2a}$ and $R^{S2b}$ is methyl, ethyl, propyl, butyl, pentyl, or hexyl. In certain embodiments, at least one instance of $R^{S2a}$ and $R^{S2b}$ is isopropyl, isobutyl, or isoamyl. In certain embodiments, at least one instance of $R^{S2a}$ and $R^{S2b}$ is isobutyl. In certain embodiments, at least one instance of $R^{S2a}$ and $R^{S2b}$ is tert-butyl.

In certain embodiments, at least one instance of $R^{S2a}$ and $R^{S2b}$ is —$OR^{SO}$, wherein $R^{SO}$ is independently hydrogen, optionally substituted alkyl, optionally substituted alkenyl, optionally substituted heterocyclyl, or an oxygen protecting group. In certain embodiments, at least one instance of $R^{S2a}$ and $R^{S2b}$ is —OH. In certain embodiments, at least one instance of $R^{S2a}$ and $R^{S2b}$ is —$OR^{SO}$, wherein $R^{SO}$ is optionally substituted alkyl. In certain embodiments, at least one instance of $R^{S2a}$ and $R^{S2b}$ is —O-methyl, —O-ethyl, or —O-propyl. In certain embodiments, at least one instance of $R^{S2a}$ and $R^{S2b}$ is optionally substituted —O-alkyl-aryl. In certain embodiments, at least one instance of $R^{S2a}$ and $R^{S2b}$ is —O-Bz. In certain embodiments, at least one instance of $R^{S2a}$ and $R^{S2b}$ is —O-alkyl-heteroaryl. In certain embodiments, at least one instance of $R^{S2a}$ and $R^{S2b}$ is optionally substituted —O-alkenyl-aryl. In certain embodiments, at least one instance of $R^{S2a}$ and $R^{S2b}$ is optionally substituted —O-alkenyl-heteroaryl. In certain embodiments, at least one instance of $R^{S2a}$ and $R^{S2b}$ is —$OR^{SO}$, wherein $R^{SO}$ is

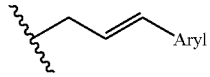

wherein Aryl is an optionally substituted aryl group. In certain embodiments, at least one instance of $R^{S2a}$ and $R^{S2b}$ is —$OR^{SO}$, wherein $R^{SO}$ is

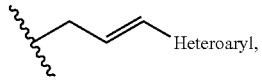

wherein Heteroaryl is an optionally substituted heteroaryl group. In certain embodiments, at least one instance of $R^{S2a}$ and $R^{S2b}$ is —$OR^{SO}$, wherein $R^{SO}$ is

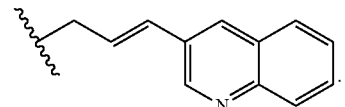

In certain embodiments, at least one instance of $R^{S2a}$ and $R^{S2b}$ is —$OR^{SO}$, wherein $R^{SO}$ is an oxygen protecting group. In certain embodiments, at least one instance of $R^{S2a}$ and $R^{S2b}$ is —$OR^{SO}$, wherein $R^{SO}$ is carbonyl. In certain embodiments, at least one instance of $R^{S2a}$ and $R^{S2b}$ is —$OR^{SO}$, wherein $R^{SO}$ is acetyl. In certain embodiments, at least one instance of $R^{S2a}$ and $R^{S2b}$ is —$OR^{SO}$, wherein $R^{SO}$ is optionally substituted heterocyclyl.

In certain embodiments, at least one instance of $R^{S2a}$ and $R^{S2b}$ is —$N(R^{SN})_2$. In some embodiments, at least one instance of $R^{S2a}$ and $R^{S2b}$ is —$N(R^{SN})_2$, wherein each $R^{SN}$ is the same. In some embodiments, at least one instance of $R^{S2a}$ and $R^{S2b}$ is —$N(R^{SN})_2$, wherein each $R^{SN}$ is different.

In certain embodiments, at least one instance of $R^{S2a}$ and $R^{S2b}$ is —$NH_2$.

In certain embodiments, at least one instance of $R^{S2a}$ and $R^{S2b}$ is —$NHR^{SN}$. In certain embodiments, at least one instance of $R^{S2a}$ and $R^{S2b}$ is —$NHR^{SN}$, wherein $R^{SN}$ is optionally substituted $C_{1-6}$ alkyl. In certain embodiments, at least one instance of $R^{S2a}$ and $R^{S2b}$ is —$NHR^{SN}$, wherein $R^{SN}$ is unsubstituted $C_{1-6}$ alkyl. In certain embodiment, at least one instance of $R^{S2a}$ and $R^{S2b}$ is —$NHR^{SN}$, wherein $R^{SN}$ is substituted $C_{1-6}$ alkyl. In certain embodiments, at least one instance of $R^{S2a}$ and $R^{S2b}$ is —NH-benzyl.

In certain embodiment, at least one instance of $R^{S2a}$ and $R^{S2b}$ is —$NHR^{SN}$, wherein $R^{SN}$ is a nitrogen protecting group. In certain embodiment, at least one instance of $R^{S2a}$ and $R^{S2b}$ is —NHFmoc. In certain embodiment, at least one instance of $R^{S2a}$ and $R^{S2b}$ is —NHBoc.

In certain embodiments, at least one instance of $R^{S2a}$ and $R^{S2b}$ is —$N(R^{SN})_2$, wherein each $R^{SN}$ is independently optionally substituted $C_{1-6}$ alkyl. In certain embodiments, at least one instance of $R^{S2a}$ and $R^{S2b}$ is —$N(R^{SN})_2$, wherein each $R^{SN}$ is independently unsubstituted $C_{1-6}$ alkyl. In certain embodiments, at least one instance of $R^{S2a}$ and $R^{S2b}$ is —$N(CH_3)R^{SN}$, wherein each $R^{SN}$ is independently optionally substituted $C_{1-6}$ alkyl. In certain embodiments, at least one instance of $R^{S2a}$ and $R^{S2b}$ is —$N(CH_3)R^{SN}$, wherein each $R^{SN}$ is independently unsubstituted $C_{1-6}$ alkyl. In certain embodiments, at least one instance of $R^{S2a}$ and $R^{S2b}$ is —N(CH$_2$CH$_3$)$R^{SN}$, wherein each $R^{SN}$ is independently optionally substituted $C_{1-6}$ alkyl. In certain embodiments, at least one instance of $R^{S2a}$ and $R^{S2b}$ is —N(CH$_2$CH$_3$)$R^{SN}$, wherein each $R^{SN}$ is independently unsubstituted $C_{1-6}$ alkyl. In certain embodiments, at least one instance of $R^{S2a}$ and $R^{S2b}$ is —N($R^{SN}$)$_2$, wherein each $R^{SN}$ is independently selected from the group consisting of methyl, ethyl, isopropyl, isobutyl, isoamyl, and benzyl.

In some embodiments, at least one instance of $R^{S2a}$ and $R^{S2b}$ is —N($R^{SN}$)$_2$, wherein two $R^{SN}$ groups are taken together with the intervening atoms to form an optionally substituted heterocyclic ring. For example, in certain embodiments, at least one instance of $R^{S2a}$ and $R^{S2b}$ is of the formula:

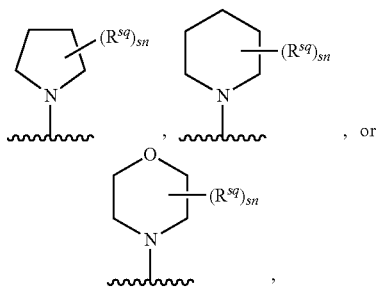

wherein $R^{sq}$ is as defined herein, and sn is 0, 1, 2, or 3.

As generally defined above, each instance of $R^{S3a}$ and $R^{S3b}$ is independently hydrogen, optionally substituted alkyl, —OR$^{SO}$, or —N($R^{SN}$)$_2$.

In certain embodiments, at least one instance of $R^{S3a}$ and $R^{S3b}$ is hydrogen.

In certain embodiments, at least one instance of $R^{S3a}$ and $R^{S3b}$ is optionally substituted alkyl. In certain embodiments, at least one instance of $R^{S3a}$ and $R^{S3b}$ is substituted $C_{1-6}$ alkyl. In certain embodiments, at least one instance of $R^{S3a}$ and $R^{S3b}$ is unsubstituted $C_{1-6}$ alkyl. In certain embodiments, at least one instance of $R^{S3a}$ and $R^{S3b}$ is methyl, ethyl, propyl, butyl, pentyl, or hexyl. In certain embodiments, at least one instance of $R^{S3a}$ and $R^{S3b}$ is isopropyl, isobutyl, or isoamyl. In certain embodiments, at least one instance of $R^{S3a}$ and $R^{S3b}$ is isobutyl. In certain embodiments, at least one instance of $R^{S3a}$ and $R^{S3b}$ is tert-butyl.

In certain embodiments, at least one instance of $R^{S3a}$ and $R^{S3b}$ is —OR$^{SO}$, wherein $R^{SO}$ is independently hydrogen, optionally substituted alkyl, optionally substituted alkenyl, optionally substituted alkyl, optionally substituted heterocyclyl, or an oxygen protecting group. In certain embodiments, at least one instance of $R^{S3a}$ and $R^{S3b}$ is —OH. In certain embodiments, at least one instance of $R^{S3a}$ and $R^{S3b}$ is —OR$^{SO}$, wherein $R^{SO}$ is optionally substituted alkyl. In certain embodiments, at least one instance of $R^{S3a}$ and $R^{S3b}$ is —O-methyl, —O-ethyl, or —O— propyl. In certain embodiments, at least one instance of $R^{S3a}$ and $R^{S3b}$ is optionally substituted —O-alkyl-aryl. In certain embodiments, at least one instance of $R^{S3a}$ and $R^{S3b}$—O-Bz. In certain embodiments, at least one instance of $R^{S3a}$ and $R^{S3b}$ is —O-alky 1-heteroaryl. In certain embodiments, at least one instance of $R^{S3a}$ and $R^{S3b}$ is optionally substituted —O-alkenyl-aryl. In certain embodiments, at least one instance of $R^{S3a}$ and $R^{S3b}$ is optionally substituted —O-alkenyl-heteroaryl. In certain embodiments, at least one instance of $R^{S3a}$ and $R^{S3b}$ is —OR$^{SO}$, wherein $R^{SO}$ is

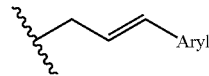

wherein Aryl is an optionally substituted aryl group. In certain embodiments, at least one instance of $R^{S3a}$ and $R^{S3b}$ is —OR$^{SO}$, wherein $R^{SO}$ is

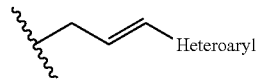

wherein Heteroaryl is an optionally substituted heteroaryl group. In certain embodiments, at least one instance of $R^{S3a}$ and $R^{S3b}$ is —OR$^{SO}$, wherein $R^{SO}$ is

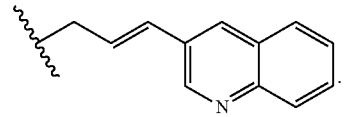 [SMILES: *C/C=C/c1cnc2ccccc2c1]

In certain embodiments, at least one instance of $R^{S3a}$ and $R^{S3b}$ is —OR$^{SO}$, wherein $R^{SO}$ is an oxygen protecting group. In certain embodiments, at least one instance of $R^{S3a}$ and $R^{S3b}$ is —OR$^{SO}$, wherein $R^{SO}$ is carbonyl. In certain embodiments, at least one instance of $R^{S3a}$ and $R^{S3b}$ is —OR$^{SO}$, wherein $R^{SO}$ is acetyl. In certain embodiments, at least one instance of $R^{S3a}$ and $R^{S3b}$ is —OR$^{SO}$, wherein $R^{SO}$ is optionally substituted heterocyclyl.

In certain embodiments, at least one instance of $R^{S3a}$ and $R^{S3b}$ is —N($R^{SN}$)$_2$. In some embodiments, at least one instance of $R^{S3a}$ and $R^{S3b}$ is —N($R^{SN}$)$_2$, wherein each $R^{SN}$ is the same. In some embodiments, at least one instance of $R^{S3a}$ and $R^{S3b}$ is —N($R^{SN}$)$_2$, wherein each $R^{SN}$ is different.

In certain embodiments, at least one instance of $R^{S3a}$ and $R^{S3b}$ is —NH$_2$.

In certain embodiments, at least one instance of $R^{S3a}$ and $R^{S3b}$ is —NHR$^{SN}$. In certain embodiments, at least one instance of $R^{S3a}$ and $R^{S3b}$ is —NHR$^{SN}$, wherein $R^{SN}$ is optionally substituted $C_{1-6}$ alkyl. In certain embodiments, at least one instance of $R^{S3a}$ and $R^{S3b}$ is —NHR$^{SN}$, wherein $R^{SN}$ is unsubstituted $C_{1-6}$ alkyl. In certain embodiment, at least one instance of $R^{S3a}$ and $R^{S3b}$ is —NHR$^{SN}$, wherein $R^{SN}$ is substituted $C_{1-6}$ alkyl. In certain embodiments, at least one instance of $R^{S3a}$ and $R^{S3b}$ is —NH-benzyl.

In certain embodiment, at least one instance of $R^{S3a}$ and $R^{S3b}$ is —NHR$^{SN}$, wherein $R^{SN}$ is a nitrogen protecting group. In certain embodiment, at least one instance of $R^{S3a}$ and $R^{S3b}$ is —NHFmoc. In certain embodiment, at least one instance of $R^{S3a}$ and $R^{S3b}$ is —NHBoc.

In certain embodiments, at least one instance of $R^{S3a}$ and $R^{S3b}$ is —N($R^{SN}$)$_2$, wherein each $R^{SN}$ is independently optionally substituted $C_{1-6}$ alkyl. In certain embodiments, at least one instance of $R^{S3a}$ and $R^{S3b}$ is —N($R^{SN}$)$_2$, wherein each $R^{SN}$ is independently unsubstituted $C_{1-6}$ alkyl. In certain embodiments, at least one instance of $R^{S4a}$ and $R^{S4b}$ is —N(CH$_3$)$R^{SN}$, wherein each $R^{SN}$ is independently optionally substituted $C_{1-6}$ alkyl. In certain embodiments, at least one instance of $R^{S3a}$ and $R^{S3b}$ is —N(CH$_3$)$R^{SN}$, wherein each $R^{SN}$ is independently unsubstituted $C_{1-6}$ alkyl. In certain embodiments, at least one instance of $R^{S3a}$ and $R^{SN}$ is —N(CH$_2$CH$_3$)$R^{SN}$, wherein each $R^{SN}$ is independently optionally substituted $C_{1-6}$ alkyl. In certain embodiments, at least one instance of $R^{S3a}$ and $R^{S3b}$ is —N(CH$_2$CH$_3$)$R^{SN}$, wherein each $R^{SN}$ is independently unsubstituted $C_{1-6}$ alkyl. In certain embodiments, at least one instance of $R^{S3a}$ and $R^{S3b}$ is —N($R^{SN}$)$_2$, wherein each $R^{SN}$ is independently selected from the group consisting of methyl, ethyl, isopropyl, isobutyl, isoamyl, and benzyl.

In some embodiments, at least one instance of $R^{S3a}$ and $R^{S3b}$ is —N($R^{SN}$)$_2$, wherein two $R^{SN}$ groups are taken together with the intervening atoms to form an optionally substituted heterocyclic ring. For example, in certain embodiments, at least one instance of $R^{S3a}$ and $R^{S3b}$ is of the formula:

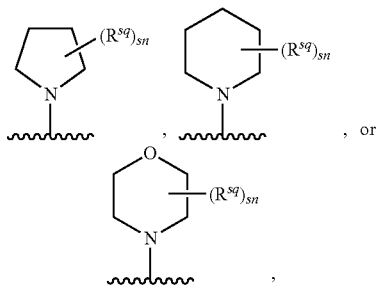

wherein $R^{sq}$ is as defined herein, and sn is 0, 1, 2, or 3.

In certain embodiments, $R^{S2a}$ or $R^{S2b}$ is taken together with $R^{S3a}$ or $R^{S3b}$ to form an optionally substituted fused heterocyclic ring. In certain embodiments, $R^{S2a}$ is taken together with $R^{S3a}$ to form an optionally substituted fused heterocyclic ring. In certain embodiments, $R^{S2b}$ is taken together with $R^{S3b}$ to form an optionally substituted fused heterocyclic ring. In certain embodiments, $R^{S2a}$ is taken together with $R^{S3b}$ to form an optionally substituted fused heterocyclic ring. In certain embodiments, $R^{S2b}$ is taken together with $R^{S3a}$ to form an optionally substituted fused heterocyclic ring.

In certain embodiments, $R^{S2a}$ or $R^{S2b}$ is taken together with $R^{S3a}$ or $R^{S3b}$ to form an optionally substituted fused pyrrolidine. In certain embodiments, $R^{S2a}$ or $R^{82*5}$ is taken together with $R^{S3a}$ or $R^{S3b}$ to form an optionally substituted fused piperidine. In certain embodiments, $R^{S2a}$ or $R^{S2b}$ is taken together with $R^{S3a}$ or $R^{S3b}$ to form an optionally substituted fused piperidinone. In certain embodiments, $R^{S2a}$ or $R^{S2b}$ is taken together with $R^{S3a}$ or $R^{S3b}$ to form an optionally substituted fused piperazine. In certain embodiments, $R^{S2a}$ or $R^{S2b}$ is taken together with $R^{S3a}$ or $R^{S3b}$ to form an optionally substituted fused piperazinone. In certain embodiments, $R^{S2a}$ or $R^{S2b}$ is taken together with $R^{S3a}$ or $R^{S3b}$ to form an optionally substituted fused morpholine. In certain embodiments, $R^{S2a}$ or $R^{S2b}$ is taken together with $R^{S3a}$ or $R^{S3b}$ to form an optionally substituted fused morpholinone.

In certain embodiments, $R^{S2a}$ or $R^{S2b}$ is taken together with $R^{S3a}$ or $R^{S3b}$ to form an optionally substituted fused pyrrolidine; and $R^{SN}$ is methyl. In certain embodiments, $R^{S2a}$ or $R^{S2b}$ is taken together with $R^{S3a}$ or $R^{S3b}$ to form an optionally substituted fused piperidine; and $R^{SN}$ is methyl. In certain embodiments, $R^{S2a}$ or $R^{S2b}$ is taken together with $R^{S3a}$ or $R^{S3b}$ to form an optionally substituted fused piperidinone; and $R^{SN}$ is methyl. In certain embodiments, $R^{S2a}$ or $R^{S2b}$ is taken together with $R^{S3a}$ or $R^{S3b}$ to form an optionally substituted fused piperazine; and $R^{SN}$ is methyl. In certain embodiments, $R^{S2a}$ or $R^{S2b}$ is taken together with $R^{S3a}$ or $R^{S3b}$ to form an optionally substituted fused piperazinone; and $R^{SN}$ is methyl. In certain embodiments, $R^{S2a}$ or $R^{S2b}$ is taken together with $R^{S3a}$ or $R^{S3b}$ to form an optionally substituted fused morpholine; and $R^{SN}$ is methyl. In certain embodiments, $R^{S2a}$ or $R^{S2b}$ is taken together with $R^{S3a}$ or $R^{S3b}$ to form an optionally substituted fused morpholinone; and $R^{SN}$ is methyl.

In certain embodiments, $R^{S2a}$ is taken together with $R^{S3a}$ to form

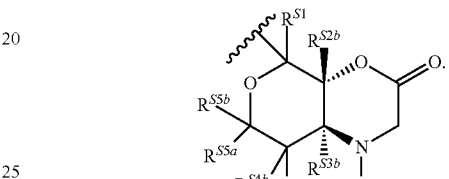

In certain embodiments, $R^{S2a}$ is taken together with $R^{S3a}$ to form

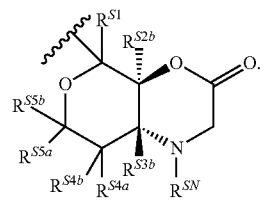

In certain embodiments, $R^{S2a}$ is taken together with $R^{S3a}$ to form

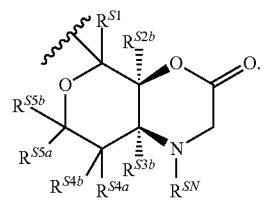

In certain embodiments, $R^{S2a}$ is taken together with $R^{S3a}$ to form

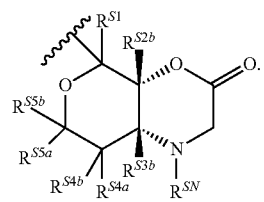

In certain embodiments, $R^{S2a}$ is taken together with $R^{S3a}$ to form

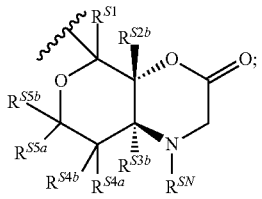

and $R^{SN}$ is methyl.

In certain embodiments, $R^{S2a}$ is taken together with $R^{S3a}$ to form

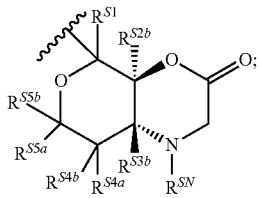

and $R^{SN}$ is methyl.

In certain embodiments, $R^{S2a}$ is taken together with $R^{S3a}$ to form

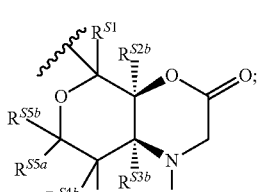

and $R^{SN}$ is methyl.

In certain embodiments, $R^{S2a}$ is taken together with $R^{S3a}$ to form

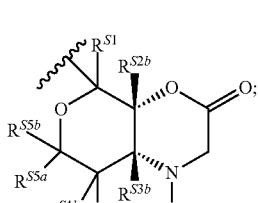

and $R^{SN}$ is methyl.

As generally defined above, each instance of $R^{S4a}$ and $R^{S4b}$ is independently hydrogen, optionally substituted alkyl, —$OR^{SO}$, or —$N(R^{SN})_2$.

In certain embodiments, at least one instance of $R^{S4a}$ and $R^{S4b}$ is hydrogen.

In certain embodiments, at least one instance of $R^{S4a}$ and $R^{S4b}$ is optionally substituted alkyl. In certain embodiments, at least one instance of $R^{S4a}$ and $R^{S4b}$ is substituted $C_{1-6}$ alkyl. In certain embodiments, at least one instance of $R^{S4a}$ and $R^{S4b}$ is unsubstituted $C_{1-6}$ alkyl. In certain embodiments, at least one instance of $R^{S4a}$ and $R^{S4b}$ is methyl, ethyl, propyl, butyl, pentyl, or hexyl. In certain embodiments, at least one instance of $R^{S4a}$ and $R^{S4b}$ is isopropyl, isobutyl, or isoamyl. In certain embodiments, at least one instance of $R^{S4a}$ and $R^{S4b}$ is isobutyl. In certain embodiments, at least one instance of $R^{S4a}$ and $R^{S4b}$ is tert-butyl.

In certain embodiments, at least one instance of $R^{S4a}$ and $R^{S4b}$ is —$OR^{SO}$, wherein $R^{SO}$ is independently hydrogen, optionally substituted alkyl, optionally substituted alkenyl, optionally substituted alkyl, optionally substituted heterocyclyl, or an oxygen protecting group. In certain embodiments, at least one instance of $R^{S4a}$ and $R^{S4b}$ is —OH. In certain embodiments, at least one instance of $R^{S4a}$ and $R^{S4b}$ is —$OR^{SO}$, wherein $R^{SO}$ is optionally substituted alkyl. In certain embodiments, at least one instance of $R^{S4a}$ and $R^{S4b}$ is —O-methyl, —O-ethyl, or —O—propyl. In certain embodiments, at least one instance of $R^{S4a}$ and $R^{S4b}$ is optionally substituted —O-alkyl-aryl. In certain embodiments, at least one instance of $R^{S4a}$ and $R^{S4b}$ is —O-Bz. In certain embodiments, at least one instance of $R^{S4a}$ and $R^{S4b}$ is —$OR^{SO}$, wherein $R^{SO}$ is

wherein Aryl is an optionally substituted aryl group. In certain embodiments, at least one instance of $R^{S4a}$ and $R^{S4b}$ is —$OR^{SO}$, wherein $R^{SO}$ is

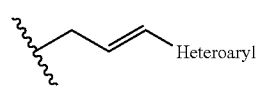

wherein Heteroaryl is an optionally substituted heteroaryl group. In certain embodiments, at least one instance of $R^{S4a}$ and $R^{S4b}$ is —$OR^{SO}$, wherein $R^{SO}$ is

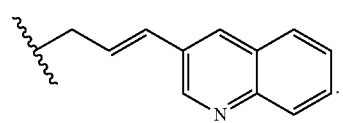 [SMILES: *C/C=C/c1cnc2ccccc2c1]

in certain embodiments, at least one instance of $R^{S4a}$ and $R^{S4b}$ is —$OR^{SO}$, wherein $R^{SO}$ is an oxygen protecting group. In certain embodiments, at least one instance of $R^{S4a}$ and $R^{S4b}$ is —$OR^{SO}$, wherein $R^{SO}$ is carbonyl. In certain embodiments, at least one instance of $R^{S4a}$ and $R^{S4b}$ is —$OR^{SO}$, wherein $R^{SO}$ is acetyl. In certain embodiments, at least one instance of $R^{S4a}$ and $R^{S4b}$ is —$OR^{SO}$, wherein $R^{SO}$ is optionally substituted heterocyclyl.

In certain embodiments, at least one instance of $R^{S4a}$ and $R^{S4b}$ is —$N(R^{SN})_2$. In some embodiments, at least one instance of $R^{S4a}$ and $R^{S4b}$ is —$N(R^{SN})_2$, wherein each $R^{SN}$ is the same. In some embodiments, at least one instance of $R^{S4a}$ and $R^{S4b}$ is —$N(R^{SN})_2$, wherein each $R^{SN}$ is different.

In certain embodiments, at least one instance of $R^{S4a}$ and $R^{S4b}$ is —$NH_2$.

In certain embodiments, at least one instance of $R^{S4a}$ and $R^{S4b}$ is —$NHR^{SN}$. In certain embodiments, at least one instance of $R^{S4a}$ and $R^{S4b}$ is —$NHR^{SN}$, wherein $R^{SN}$ is optionally substituted $C_{1-6}$ alkyl. In certain embodiments, at least one instance of $R^{S4a}$ and $R^{S4b}$ is —$NHR^{SN}$, wherein $R^{SN}$ is unsubstituted $C_{1-6}$ alkyl. In certain embodiment, at least one instance of $R^{S4a}$ and $R^{S4b}$ is —$NHR^{SN}$, wherein $R^{SN}$ is substituted $C_{1-6}$ alkyl. In certain embodiments, at least one instance of $R^{S4a}$ and $R^{S4b}$ is —NH-benzyl.

In certain embodiment, at least one instance of $R^{S4a}$ and $R^{S4b}$ is —NHR$^{SN}$, wherein R$^{SN}$ is a nitrogen protecting group. In certain embodiment, at least one instance of $R^{S4a}$ and $R^{S4b}$ is —NHFmoc. In certain embodiment, at least one instance of $R^{S4a}$ and $R^{S4b}$ is —NHBoc.

In certain embodiments, at least one instance of $R^{S4a}$ and $R^{S4b}$ is —N(R$^{SN}$)$_2$, wherein each R$^{SN}$ is independently optionally substituted $C_{1-6}$ alkyl. In certain embodiments, at least one instance of $R^{S4a}$ and $R^{S4b}$ is —N(R$^{SN}$)$_2$, wherein each R$^{SN}$ is independently unsubstituted $C_{1-6}$ alkyl. In certain embodiments, at least one instance of $R^{S4a}$ and $R^{S4b}$ is —N(CH$_3$)R$^{SN}$, wherein each R$^{SN}$ is independently optionally substituted $C_{1-6}$ alkyl. In certain embodiments, at least one instance of $R^{S4a}$ and $R^{S4b}$ is —N(CH$_3$)R$^{SN}$, wherein each R$^{SN}$ is independently unsubstituted $C_{1-6}$ alkyl. In certain embodiments, at least one instance of $R^{S4a}$ and $R^{S4b}$ is —N(CH$_2$CH$_3$)R$^{SN}$, wherein each R$^{SN}$ is independently optionally substituted $C_{1-6}$ alkyl. In certain embodiments, at least one instance of $R^{S4a}$ and $R^{S4b}$ is —N(CH$_2$CH$_3$)R$^{SN}$, wherein each R$^{SN}$ is independently unsubstituted $C_{1-6}$ alkyl. In certain embodiments, at least one instance of $R^{S4a}$ and $R^{S4b}$ is —N(R$^{SN}$)$_2$, wherein each R$^{SN}$ is independently selected from the group consisting of methyl, ethyl, isopropyl, isobutyl, isoamyl, and benzyl.

In some embodiments, at least one instance of $R^{S4a}$ and $R^{S4b}$ is —N(R$^{SN}$)$_2$, wherein two R$^{SN}$ groups are taken together with the intervening atoms to form an optionally substituted heterocyclic ring. For example, in certain embodiments, at least one instance of $R^{S4a}$ and $R^{S4b}$ is of the formula:

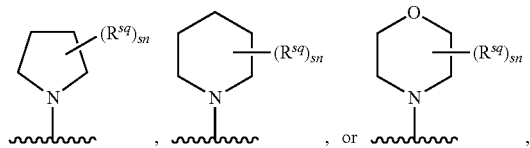

wherein $R^{sq}$ is as defined herein, and sn is 0, 1, 2, or 3.

As generally defined above, each instance of $R^{S5a}$ and $R^{S5b}$ is independently hydrogen, optionally substituted alkyl, —OR$^{SO}$, or —N(R$^{SN}$)$_2$.

In certain embodiments, at least one instance of $R^{S5a}$ and $R^{S5b}$ is hydrogen.

In certain embodiments, at least one instance of $R^{S5a}$ and $R^{S5b}$ is optionally substituted alkyl. In certain embodiments, at least one instance of $R^{S5a}$ and $R^{S5b}$ is substituted $C_{1-6}$ alkyl. In certain embodiments, at least one instance of $R^{S5a}$ and $R^{S5b}$ is unsubstituted $C_{1-6}$ alkyl. In certain embodiments, at least one instance of $R^{S5a}$ and $R^{S5b}$ is methyl, ethyl, propyl, butyl, pentyl, or hexyl. In certain embodiments, at least one instance of $R^{S5a}$ and $R^{S5b}$ is isopropyl, isobutyl, or isoamyl. In certain embodiments, at least one instance of $R^{S5a}$ and $R^{S5b}$ is isobutyl. In certain embodiments, at least one instance of $R^{S5a}$ and $R^{S5b}$ is tert-butyl. In certain embodiments, at least one instance of $R^{S5a}$ and $R^{S5b}$ is alkoxyalkyl, e.g. —CH$_2$OMe, —CH$_2$OEt, or —CH$_2$OBn. In certain embodiments, at least one instance of $R^{S5a}$ and $R^{S5b}$ is —CH$_2$OH. In certain embodiments, at least one instance of $R^{S5a}$ and $R^{S5b}$ is —CH$_2$OBz. In certain embodiments, at least one instance of $R^{S5a}$ and $R^{S5b}$ is —CH$_2$OPG, wherein PG is an oxygen protecting group. In certain embodiments, at least one instance of $R^{S5a}$ and $R^{S5b}$ is aminoalkyl, e.g. —CH$_2$NHMe, —CH$_2$NMe$_2$, or —CH$_2$NHBn. In certain embodiments, at least one instance of $R^{S5a}$ and $R^{S5b}$ is —CH$_2$NH$_2$. In certain embodiments, at least one instance of $R^{S5a}$ and $R^{S5b}$ is —CH$_2$NHPG, wherein PG is an nitrogen protecting group.

In certain embodiments, at least one instance of $R^{S5a}$ and $R^{S5b}$ is —OR$^{SO}$, wherein R$^{SO}$ is independently hydrogen, optionally substituted alkyl, optionally substituted alkenyl, optionally substituted alkyl, optionally substituted heterocyclyl, or an oxygen protecting group. In certain embodiments, at least one instance of $R^{S5a}$ and $R^{S5b}$ is —OH. In certain embodiments, at least one instance of $R^{S5a}$ and $R^{S5b}$ is —OR$^{SO}$, wherein R$^{SO}$ is optionally substituted alkyl. In certain embodiments, at least one instance of $R^{S5a}$ and $R^{S5b}$ is —O-methyl, —O-ethyl, or —O— propyl. In certain embodiments, at least one instance of $R^{S5a}$ and $R^{S5b}$ is optionally substituted —O-alkyl-aryl. In certain embodiments, at least one instance of $R^{S5a}$ and $R^{S5b}$ is —O-Bz. In certain embodiments, at least one instance of $R^{S5a}$ and $R^{S5b}$ is —OR$^{SO}$, wherein R$^{SO}$ is

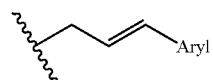

wherein Aryl is an optionally substituted aryl group. In certain embodiments, at least one instance of $R^{S5a}$ and $R^{S5b}$ is —OR$^{SO}$, wherein R$^{SO}$ is

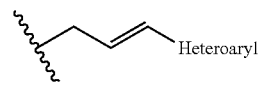

wherein Heteroaryl is an optionally substituted heteroaryl group. In certain embodiments, at least one instance of $R^{S5a}$ and $R^{S5b}$ is —OR$^{SO}$, wherein R$^{SO}$ is

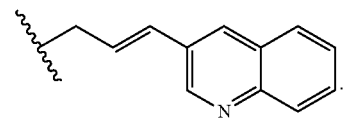 [SMILES: *C/C=C/c1cnc2ccccc2c1]

In certain embodiments, at least one instance of $R^{S5a}$ and $R^{S5b}$ is —OR$^{SO}$, wherein R$^{SO}$ is an oxygen protecting group. In certain embodiments, at least one instance of $R^{S5a}$ and $R^{S5b}$ is —OR$^{SO}$, wherein R$^{SO}$ is carbonyl. In certain embodiments, at least one instance of $R^{S5a}$ and $R^{S5b}$ is —OR$^{SO}$, wherein R$^{SO}$ is acetyl. In certain embodiments, at least one instance of $R^{S5a}$ and $R^{S5b}$ is —OR$^{SO}$, wherein R$^{SO}$ is optionally substituted heterocyclyl.

In certain embodiments, at least one instance of $R^{S5a}$ and $R^{S5b}$ is —N(R$^{SN}$). In some embodiments, at least one instance of $R^{S5a}$ and $R^{S5b}$ is —N(R$^{SN}$)$_2$, wherein each R$^{SN}$ is the same. In some embodiments, at least one instance of $R^{S5a}$ and $R^{S5b}$ is —N(R$^{SN}$)$_2$, wherein each R$^{SN}$ is different.

In certain embodiments, at least one instance of $R^{S5a}$ and $R^{S5b}$ is —NH$_2$.

In certain embodiments, at least one instance of $R^{S5a}$ and $R^{S5b}$ is —NHR$^{SN}$. In certain embodiments, at least one instance of $R^{S5a}$ and $R^{S5b}$ is —NHR$^{SN}$, wherein R$^{SN}$ is optionally substituted $C_{1-6}$ alkyl. In certain embodiments, at least one instance of $R^{S5a}$ and $R^{S5b}$ is —NHR$^{SN}$, wherein R$^{SN}$ is unsubstituted $C_{1-6}$ alkyl. In certain embodiment, at least one instance $R^{S5a}$ and $R^{S5b}$ is —NHR$^{SN}$, wherein R$^{SN}$ is substituted $C_{1-6}$ alkyl. In certain embodiments, at least one instance of $R^{S5a}$ and $R^{S5b}$ is —NH-benzyl.

In certain embodiment, at least one instance of $R^{S5a}$ and $R^{S5b}$ is —NHR$^{SN}$, wherein R$^{SN}$ is a nitrogen protecting group. In certain embodiment, at least one instance of $R^{S4a}$ and $R^{S4b}$ is —NHFmoc. In certain embodiment, at least one instance of $R^{S5a}$ and $R^{S5b}$ is —NHBoc.

In certain embodiments, at least one instance of $R^{S5a}$ and $R^{S5b}$ is —N(R$^{SN}$)$_2$, wherein each R$^{SN}$ is independently optionally substituted $C_{1-6}$ alkyl. In certain embodiments, at least one instance of $R^{S5a}$ and $R^{S5b}$ is —N(R$^{SN}$)$_2$, wherein each R$^{SN}$ is independently unsubstituted $C_{1-6}$ alkyl. In certain embodiments, at least one instance of $R^{S5a}$ and $R^{S5b}$ is —N(CH$_3$)R$^{SN}$, wherein each R$^{SN}$ is independently optionally substituted $C_{1-6}$ alkyl. In certain embodiments, at least one instance of $R^{S5a}$ and $R^{S5b}$ is —N(CH$_3$)R$^{SN}$, wherein each R$^{SN}$ is independently unsubstituted $C_{1-6}$ alkyl. In certain embodiments, at least one instance of $R^{S5a}$ and $R^{S5b}$ is —N(CH$_2$CH$_3$)R$^{SN}$, wherein each R$^{SN}$ is independently optionally substituted $C_{1-6}$ alkyl. In certain embodiments, at least one instance of $R^{S5a}$ and $R^{S5b}$ is —N(CH$_2$CH$_3$)R$^{SN}$, wherein each R$^{SN}$ is independently unsubstituted $C_{1-6}$ alkyl. In certain embodiments, at least one instance of $R^{S5a}$ and $R^{S5b}$ is —N(R$^{SN}$)$_2$, wherein each R$^{SN}$ is independently selected from the group consisting of methyl, ethyl, isopropyl, isobutyl, isoamyl, and benzyl.

In some embodiments, at least one instance of $R^{S5a}$ and $R^{S5b}$ is —N(R$^{SN}$)$_2$, wherein two R$^{SN}$ groups are taken together with the intervening atoms to form an optionally substituted heterocyclic ring. For example, in certain embodiments, at least one instance of $R^{S5a}$ and $R^{S5b}$ is of the formula:

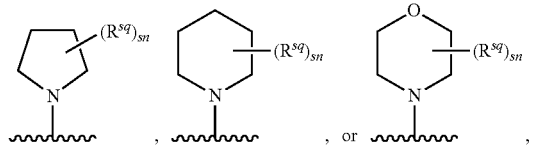

wherein R$^{sq}$ is as defined herein, and sn is 0, 1, 2, or 3.

As used herein, each instance R$^{sq}$ is independently halogen, optionally substituted alkyl, —OR$^{SO1}$, or —N(R$^{SN1}$)$_2$, wherein R$^{SO1}$ is independently hydrogen, optionally substituted alkyl, or an oxygen protecting group; and R$^{SN1}$ is independently hydrogen, optionally substituted alkyl, or a nitrogen protecting group; or optionally two R$^{SN1}$ are taken together with the intervening atoms to form an optionally substituted heterocyclic ring.

As generally defined herein, each instance of R$^{SO}$ is independently hydrogen, optionally substituted alkyl, carbonyl, optionally substituted heterocyclyl, or an oxygen protecting group.

In certain embodiments, R$^{SO}$ is hydrogen. In certain embodiments, R$^{SO}$ is optionally substituted alkyl. In certain embodiments, R$^{SO}$ is optionally substituted $C_{1-6}$ alkyl. In certain embodiments, R$^{SO}$ is methyl, ethyl, or propyl. In certain embodiments, R$^{SO}$ is optionally substituted aralkyl, e.g., optionally substituted benzyl (Bn). In certain embodiments, R$^{SO}$ is optionally substituted heterocyclyl. In certain embodiments, R$^{SO}$ is carbonyl. In certain embodiments, R$^{SO}$ is —C(=O)CH$_3$ (acetyl, Ac). In certain embodiments, R$^{SO}$ is —C(=O)Ph (benzoyl, Bz). In certain embodiments, R$^{SO}$ is

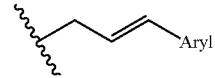

wherein Aryl is an optionally substituted aryl group. In certain embodiments, R$^{SO}$ is

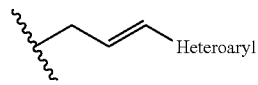

wherein Heteroaryl is an optionally substituted heteroaryl group. In certain embodiments, R$^{SO}$ is

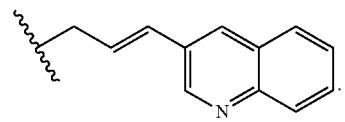 [SMILES: *C/C=C/c1cnc2ccccc2c1]

In certain embodiments, R$^{SO}$ is an oxygen protecting group.

As generally defined herein, each instance of R$^{SN}$ is independently hydrogen, optionally substituted alkyl, optionally substituted heterocyclyl, or a nitrogen protecting group; or optionally two R$^{SN}$ are taken together with the intervening atoms to form an optionally substituted heterocyclic ring. In certain embodiments, R$^{SN}$ is hydrogen. In certain embodiments, R$^{SN}$ is optionally substituted alkyl. In certain embodiments, R$^{SN}$ is optionally substituted $C_{1-6}$ alkyl. In certain embodiments, R$^{SN}$ is methyl, ethyl, or propyl. In certain embodiments, R$^{SN}$ is substituted aralkyl, e.g., optionally substituted benzyl (Bn). In certain embodiments, R$^{SN}$ is optionally substituted heterocyclyl. In certain embodiments, R$^{SN}$ is carbonyl. In certain embodiments, R$^{SN}$ is carbonyl. In certain embodiments, R$^{SN}$ is —C(=O)CH$_3$ (acetyl, Ac). In certain embodiments, R$^{SN}$ is —C(=O)Ph (benzoyl, Bz). In certain embodiments, R$^{SN}$ is a nitrogen protecting group.

In certain embodiments, R$^9$ and/or R$^{17}$ is of Formula (s-2):

(s-2)

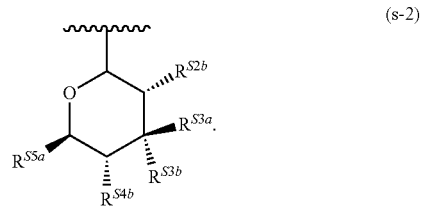

In certain embodiments, $R^9$ and/or $R^{17}$ is of Formula (s-2a):
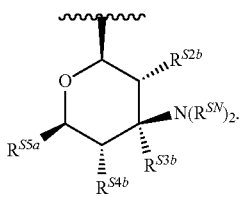
(s-2a)
In certain embodiments, $R^9$ and/or $R^{17}$ is of one of the following formulae:
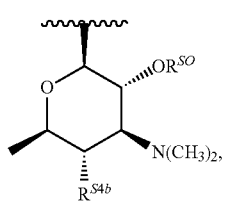
(s-2a-1)
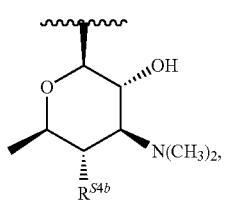
(s-2a-i-1)
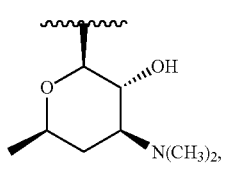
(s-2a-i-2)
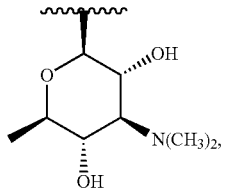
(s-2a-i-3)
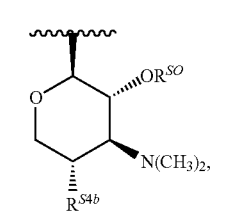
(s-2a-ii)
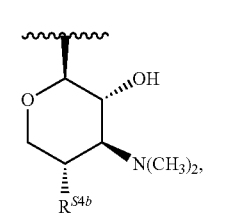
(s-2a-ii-1)
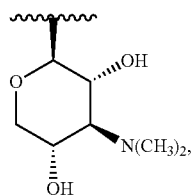
(s-2a-ii-2)
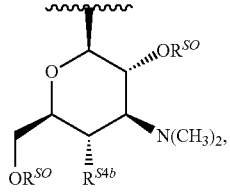
(s-2a-iii)
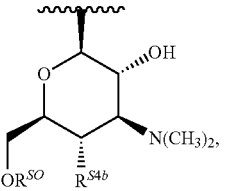
(s-2a-iii-1)
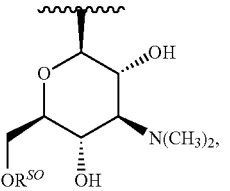
(s-2a-iii-2)
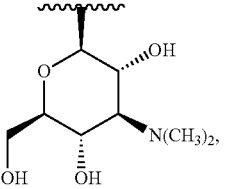
(s-2a-iii-3)
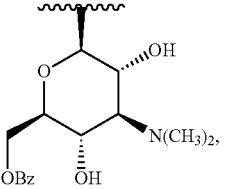
(s-2a-iii-4)
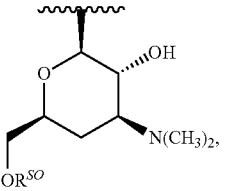
(s-2a-iii-5)
(s-2a-iii-6)

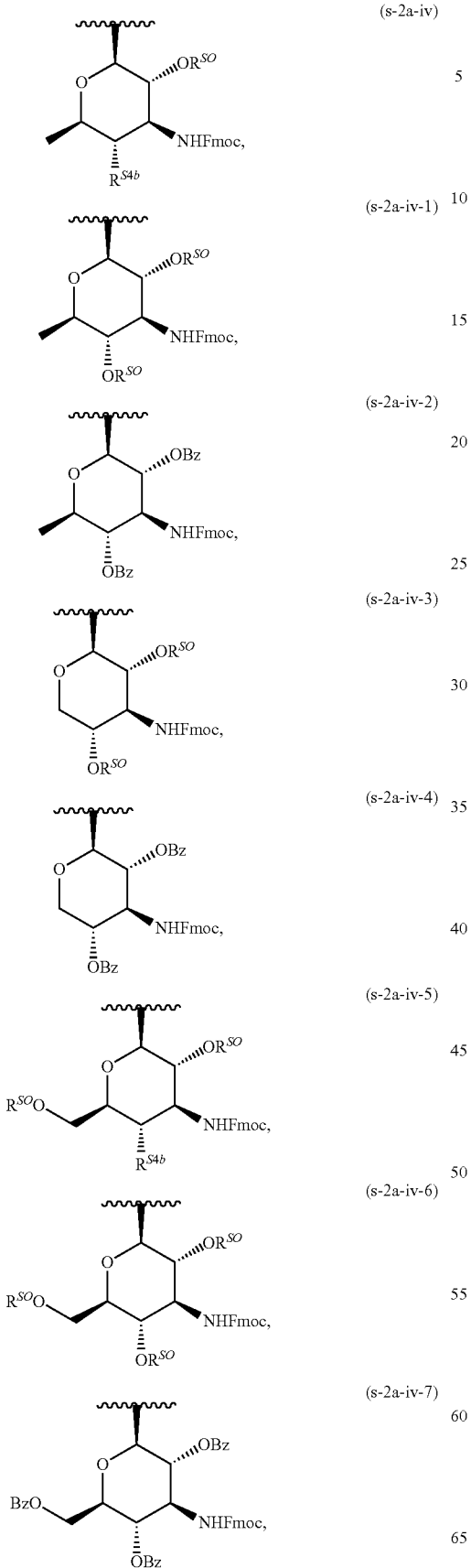
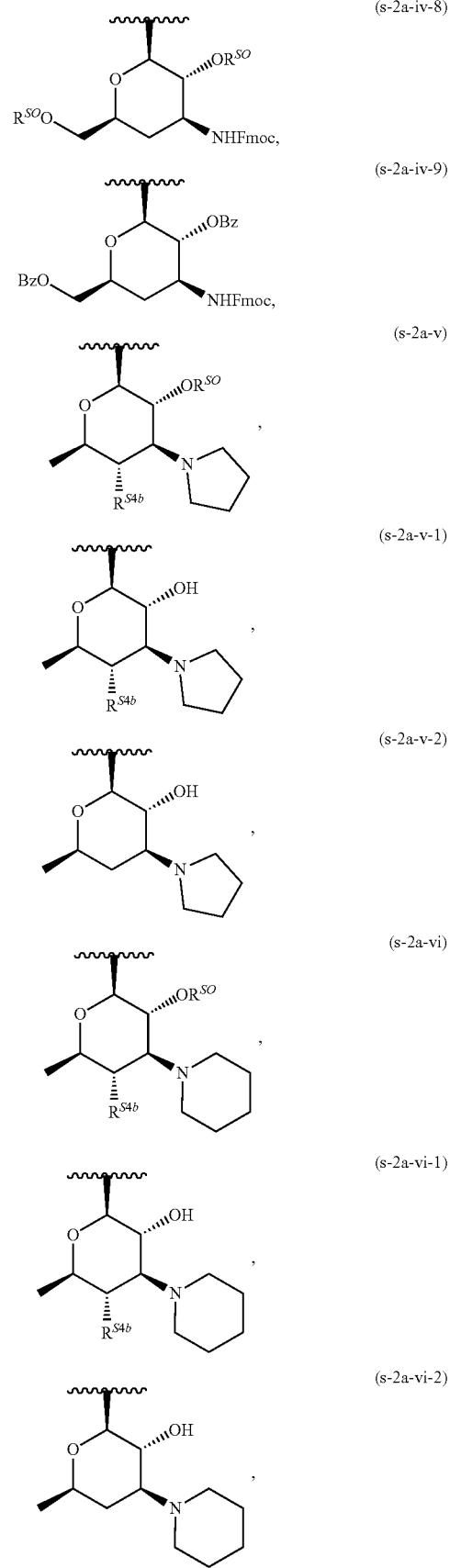

(s-2a-vii)
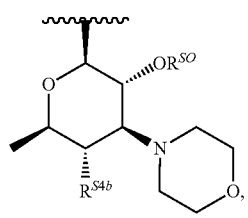
(s-2a-vii-1)
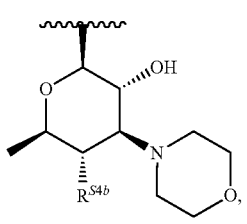
(s-2a-vii-2)
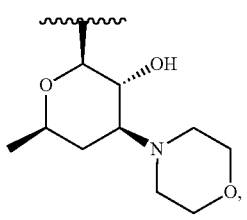
(s-2a-vii-3)
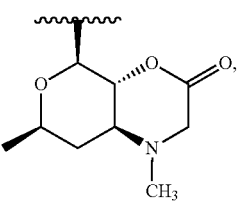
(s-2a-vii-4)
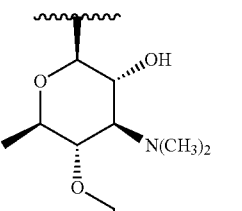
(s-2a-vii-5)
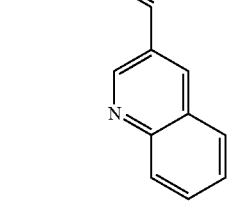
(s-2a-vii-5)
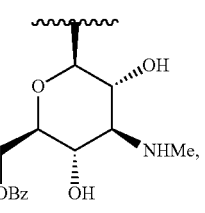
(s-2a-vii-5)
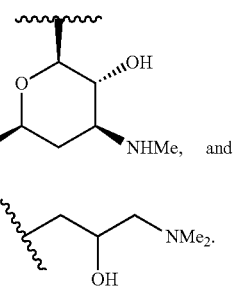
and
(s-2a-vii-5)
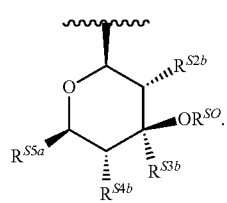
In certain embodiments, $R^9$ and/or $R^{17}$ is of Formula (s-2b):
(s-2b)
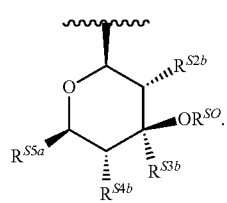
In certain embodiments, $R^9$ and/or $R^{17}$ is of one of the following formulae:
(s-2b-i)
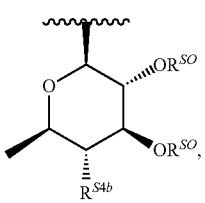
(s-2b-i-1)
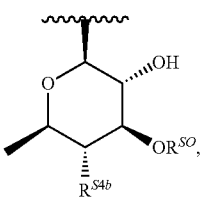
(s-2b-i-2)
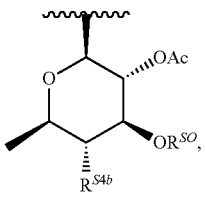

(s-2b-i-3)
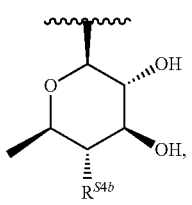
(s-2b-i-4)
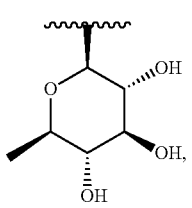
(s-2b-i-5)
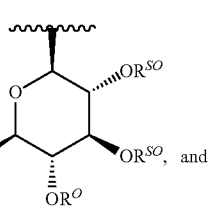
(s-2b-i-5)
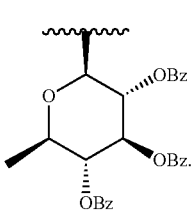
In certain embodiments, $R^9$ and/or $R^{17}$ is of Formula (s 3):
(s-3)
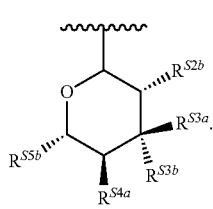
In certain embodiments, $R^9$ and/or $R^{17}$ is of Formula (s-3a):
(s-3a)
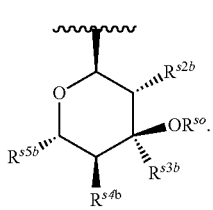
In certain embodiments, $R^9$ and/or $R^{17}$ is one of the following formulae:
(s-3a-i)
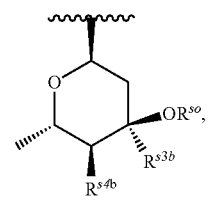
(s-3a-i-1)
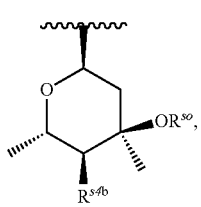
(s-3a-i-2)
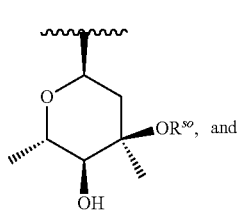
(s-3a-i-3)
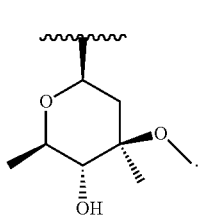
In certain embodiments, $R^{SO}$ is an optionally substituted heterocycyl.
For example, in certain embodiments, $R^{SO}$ is of the formula:
(s-4)
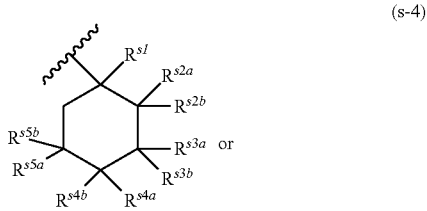
(s-5)
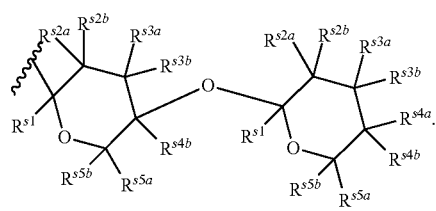

In certain embodiments, $R^{SO}$ is of the formula:

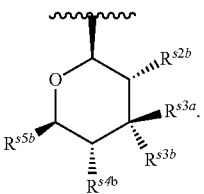

In certain embodiments, $R^{SO}$ is of the formula:

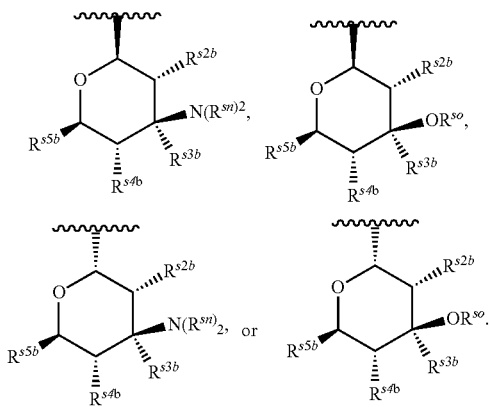

In certain embodiments, $R^{SO}$ is of the formula:

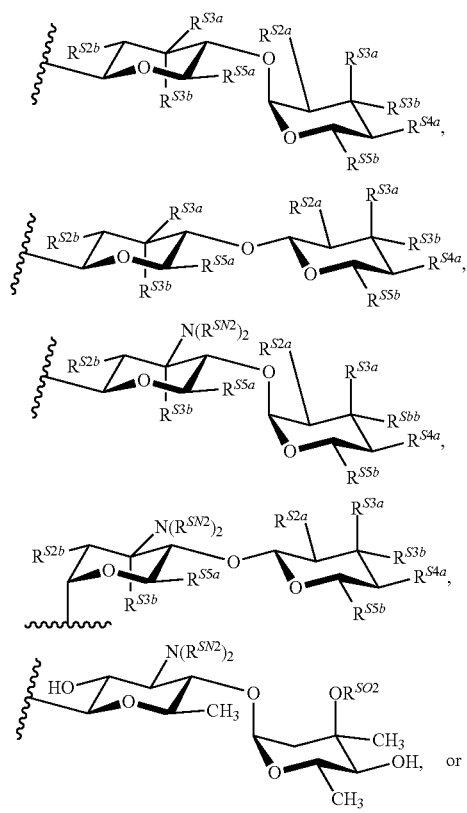

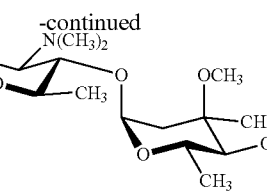

In certain embodiments, $R^9$ and/or $R^{17}$ is of the formula:

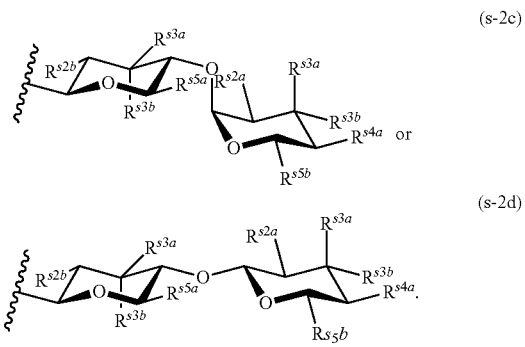

In certain embodiments, $R^9$ and/or $R^{17}$ is one of the following formulae:

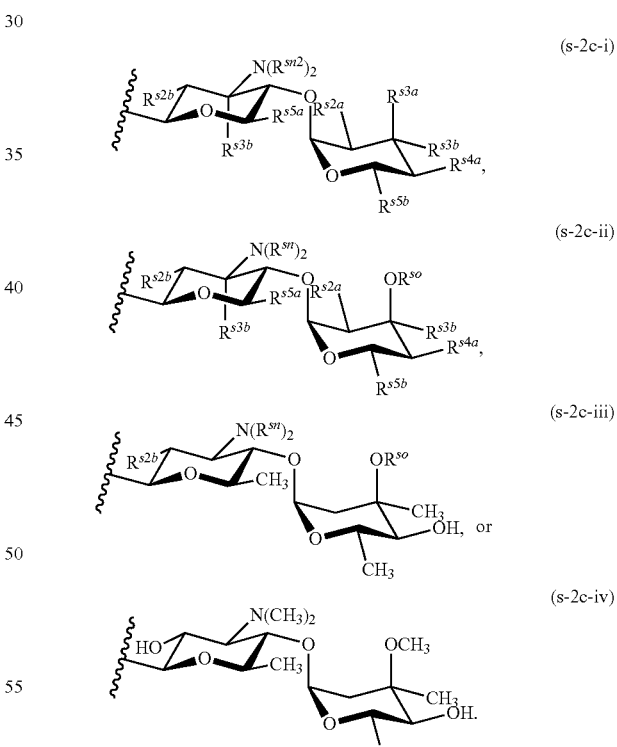

Groups $A^1$, $A^2$, and A

As is generally understood from the above disclosure, in certain embodiments, $R^{12}$, $R^{14}$, and/or $R^3$ is a group of Formula ($L^{C1}$-i), wherein LG is a leaving group as defined herein. In certain embodiments, nucleophilic displacement of the leaving group provides a group of Formula ($L^{C1}$-ii). See Scheme A1. It is generally understood that $A^1$ is a group which is reactive with $A^2$ of a compound of Formula $A^2$-$L^{C2}$-$R^{Z3}$, and reaction between the two halves provides a group of Formula ($L^{C1}$-iii). See, Scheme A1. These reactions, from ($L^{C1}$-i) to ($L^{C1}$-ii), and ($L^{C1}$-ii) to ($L^{C1}$-iii), are envisioned to take place at any stage of the synthesis, for example, during construction of the eastern or western halves, after coupling of the eastern or western halves, or after the macrocyclization step.

Scheme A1.

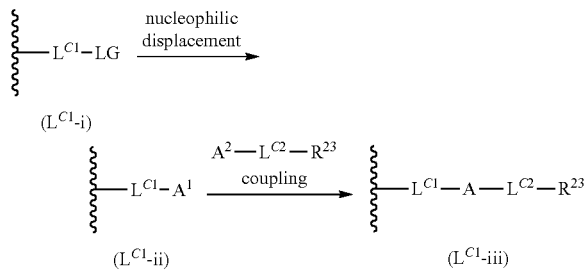

In certain embodiments, the coupling reaction from ($L^{C1}$-ii) to ($L^{C1}$-iii) comprises a reaction typically referred to as "click chemistry." Click chemistry is a chemical approach introduced by Sharpless in 2001 and describes chemistry tailored to generate substances quickly and reliably by joining small units together. See, e.g., Kolb, Finn and Sharpless *Angewandte Chemie International Edition* (2001) 40: 2004-2021; Evans, *Australian Journal of Chemistry* (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition).

In general, for the group ($L^{C1}$-ii), $A^1$ should be complimentary and reactive with the group $A^2$ in order to form the group ($L^{C1}$-iii). For example, if the group $A^2$ of $A^2$-$L^{C2}$-$R^{23}$ is a nucleophilic group, the group $A^1$ must be a electrophilic group. Likewise, if the group $A^2$ of $A^2$-$L^{C2}$-$R^{23}$ is an electrophilic group, the group $A^1$ must be a nucleophilic group. While $A^1$ and $A^2$ are defined the same in the present invention, it is thus understood that such groups are paired complements.

As generally defined herein, $A^1$ and $A^2$ may be selected from the group consisting of a leaving group (LG), —SH, —OH, —NH$_2$, —NH—NH$_2$, —N$_3$, —O—NH$_2$, —C(=O)R$^{X1}$,

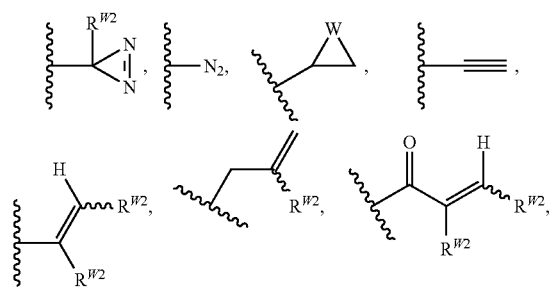

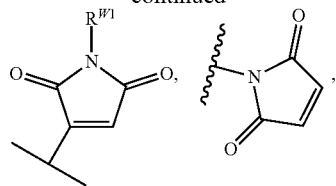

wherein:
$R^{X1}$ is hydrogen, a leaving group, or —OR$^{X2}$, wherein $R^{X2}$ is hydrogen; optionally substituted alkyl; optionally substituted alkyl; optionally substituted alkenyl; optionally substituted alkynyl; optionally substituted carbocyclyl; optionally substituted heterocyclyl; optionally substituted aryl; optionally substituted heteroaryl; an oxygen protecting group;

Leaving group (LG) is —Br, —I, —Cl, —O(C=O)R$^{LG}$, or —O(SO)$_2$R$^{LG}$, wherein R$^{LG}$ is optionally substituted alkyl, optionally substituted aryl, or optionally substituted heteroaryl;

W is O, S, or NR$^{W1}$;

R$^{W1}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl; or a nitrogen protecting group; and R$^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two R$^{W2}$ groups are joined to form a optionally substituted cyclic moiety.

In certain embodiments, $A^2$ is —SH. In certain embodiments, $A^1$ is —SH.

In certain embodiments, $A^2$ is —OH. In certain embodiments, $A^1$ is —OH.

In certain embodiments, $A^2$ is —NH$_2$. In certain embodiments, $A^1$ is —NH$_2$.

In certain embodiments, $A^2$ is —NH—NH$_2$. In certain embodiments, $A^1$ is —NH—NH$_2$.

In certain embodiments, $A^2$ is —O—NH$_2$. In certain embodiments, $A^1$ is —O—NH$_2$.

In certain embodiments, $A^2$ is —N$_3$. In certain embodiments, $A^1$ is —N$_3$.

In certain embodiments, $A^2$ is a leaving group, e.g., —Cl, —Br, or —I. In certain embodiments, $A^1$ is a leaving group, e.g., —Cl, —Br, or —I.

In certain embodiments, $A^2$ is —C(=O)R$^{X1}$, wherein R$^{X1}$ is hydrogen, i.e., to provide $A^2$ as an aldehyde —CHO. In certain embodiments, $A^1$ is —C(=O)R$^{X1}$, wherein R$^{X1}$ is hydrogen, i.e., to provide $A^1$ as an aldehyde —CHO.

In certain embodiments, $A^2$ is —C(=O)R$^{X1}$, wherein R$^{X1}$ is a leaving group (LG).

In certain embodiments, $A^1$ is —C(=O)R$^{X1}$, wherein R$^{X1}$ is a leaving group (LG).

In certain embodiments, $A^2$ is —C(=O)R$^{X1}$, wherein R$^{X1}$ is —OR$^{X2}$, and wherein R$^{20}$ is hydrogen, i.e., to provide $A^2$ as a carboxylic acid —C(=O)OH.

In certain embodiments, $A^1$ is —C(=O)R$^{X1}$, wherein R$^{X1}$ is —OR$^{X2}$, and wherein R$^{20}$ is hydrogen, i.e., to provide $A^1$ as a carboxylic acid —C(=O)OH.

In certain embodiments, $A^2$ is —C(=O)R$^{X1}$, wherein R$^{X1}$ is —OR$^{X2}$, and wherein R$^{20}$ is a non-hydrogen group, i.e., to provide $A^2$ as an ester —C(=O)OR$^{20}$.

In certain embodiments, $A^1$ is —C(=O)$R^{X1}$, wherein $R^{X1}$ is —O$R^{X2}$, and wherein $R^{20}$ is non-hydrogen group, i.e., to provide $A^1$ as an ester —C(=O)O$R^{20}$.

In certain embodiments, $A^2$ is an oxiranyl, thiorenyl, or azirdinyl group of formula:

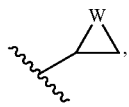

wherein W is O, S, or N$R^{W1}$. In certain embodiments, W is O. In certain embodiments, W is S. In certain embodiments, W is N$R^{W1}$.

In certain embodiments, $A^1$ is an oxiranyl, thiorenyl, or azirdinyl group of formula:

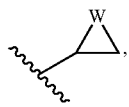

wherein W is O, S, or N$R^{W1}$. In certain embodiments, W is O. In certain embodiments, W is S. In certain embodiments, W is N$R^{W1}$.

In certain embodiments, $A^1$ or $A^2$ is ethynyl:

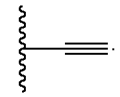 [SMILES: *C#C]

In certain embodiments, $A^1$ or $A^2$ is ethenyl or propenyl:

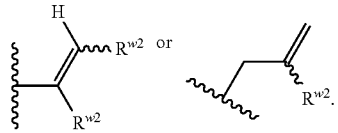

In certain embodiments, $A^1$ or $A^2$ is an α,β-unsaturated carbonyl:

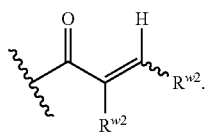

In certain embodiments, $A^1$ or $A^2$ is a maleimide group:

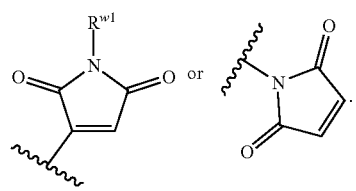

In certain embodiments, $A^1$ or $A^2$ is a group:

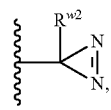

wherein $R^{W2}$ is alkyl, e.g., methyl.

In certain embodiments, $A^1$ or $A^2$ is a group:

Furthermore, as generally defined herein, $A^1$ or $A^2$ react together to form a group A, wherein A is a group of the formula:

—NH—, —NH—NH—, —NH—O—, —O—NH—, —S—, —O—,

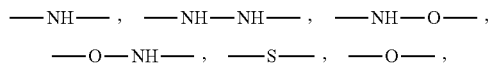

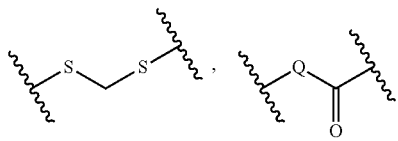

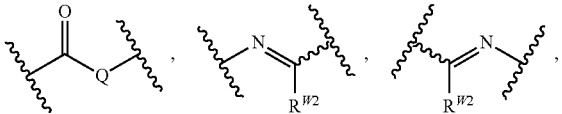

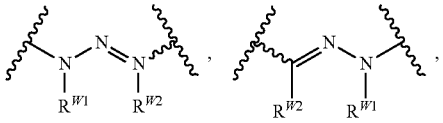

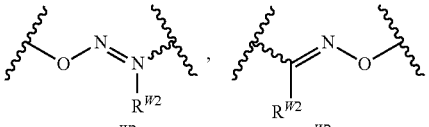

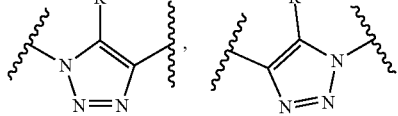

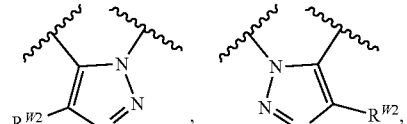

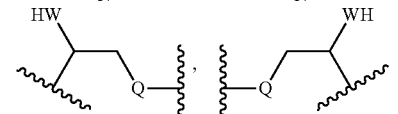

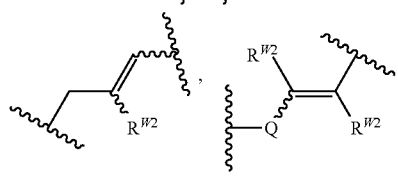

-continued

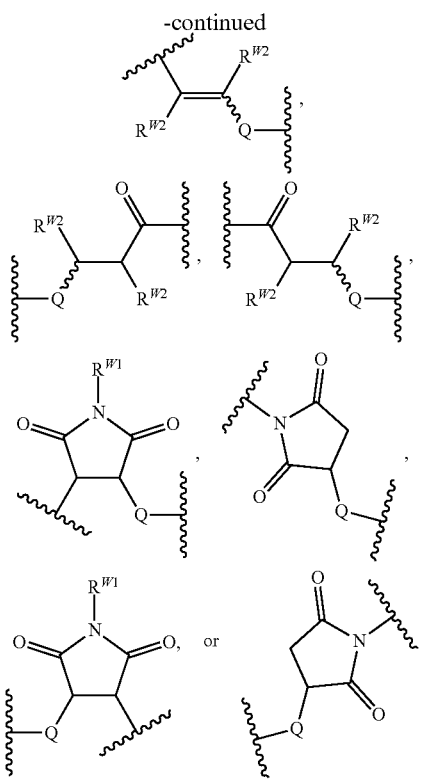

wherein:
Q is —NH—, —NH—NH—, —O—NH—, —NH—O—, —S—, or —O—;
W is O, S, or NR$^{W1}$;
R$^{W1}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl; or a nitrogen protecting group; and
R$^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two R$^{W2}$ groups are joined to form an optionally substituted cyclic moiety.

In certain embodiments, A is —NH—.
In certain embodiments, A is —NH—NH—.
In certain embodiments, A is —S—.
In certain embodiments, A is —O—.
In certain embodiments, A is a disulfide group

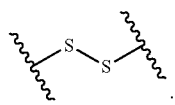

In certain embodiments, A is

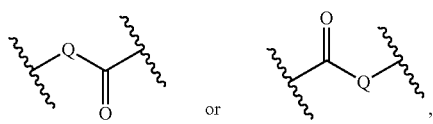

wherein Q is —NH—, —NH—NH—, —O—NH—, —NH—O—, —S—, —O—.

For example, in certain embodiments, wherein Q is —NH—, A is an amide group of the formula:

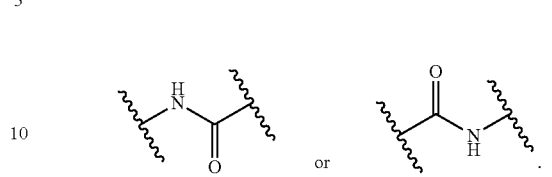

In certain embodiments, wherein Q is —NH—NH—, A is an amide hydrazide group of the formula:

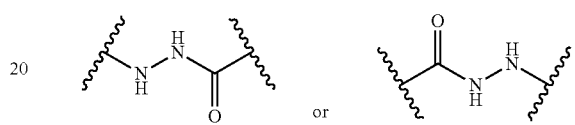

In certain embodiments, wherein Q is —S—, A is an thioester group of the formula:

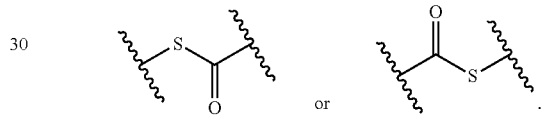

In certain embodiments, wherein Q is —O—, A is an ester group of the formula:

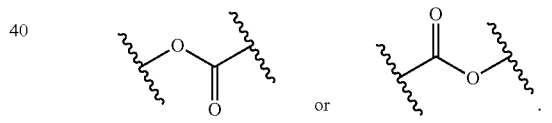

In certain embodiments, A is:

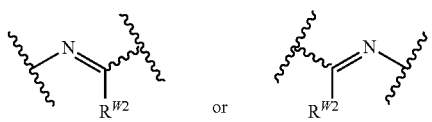

In certain embodiments, R$^{W2}$ is alkyl, e.g., methyl.

In certain embodiments, A is:

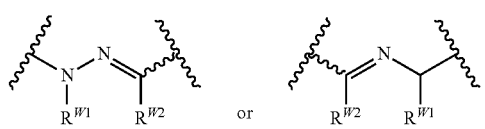

In certain embodiments, R$^{W2}$ is alkyl, e.g., methyl. In certain embodiments, R$^{W1}$ is hydrogen.

In certain embodiments, A is:

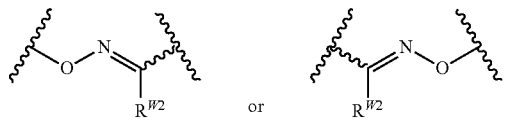

In certain embodiments, $R^{W2}$ is alkyl, e.g., methyl.

In certain embodiments, A is:

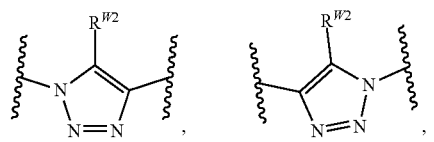

In certain embodiments, A is:

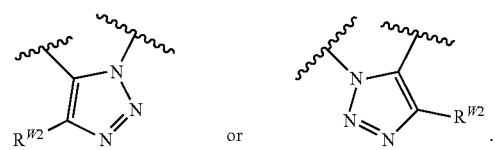

In certain embodiments, A is:

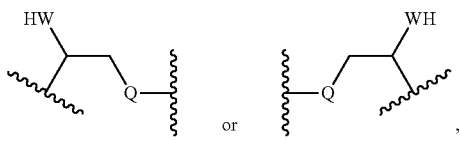

wherein W is O, S, or $NR^{W1}$, $R^{W1}$ is hydrogen, optionally substituted alkyl, or an amino protecting group; and Q is —NH—, —NH—NH—, —O—NH—, —NH—O—, —S—, or —O—. In certain embodiments, W is O. In certain embodiments, W is S. In certain embodiments, W is $NR^{W1}$. In certain embodiments, Q is —NH—. In certain embodiments, Q is —NH—NH—. In certain embodiments, Q is —S—. In certain embodiments, Q is —O—.

In certain embodiments, A is:

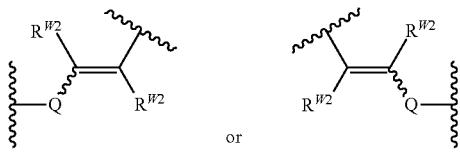

wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments, A is:

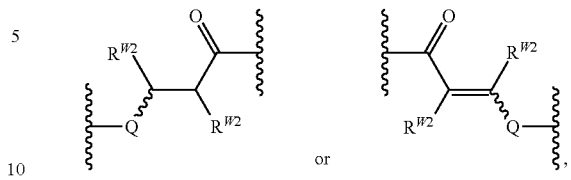

wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments. A is:

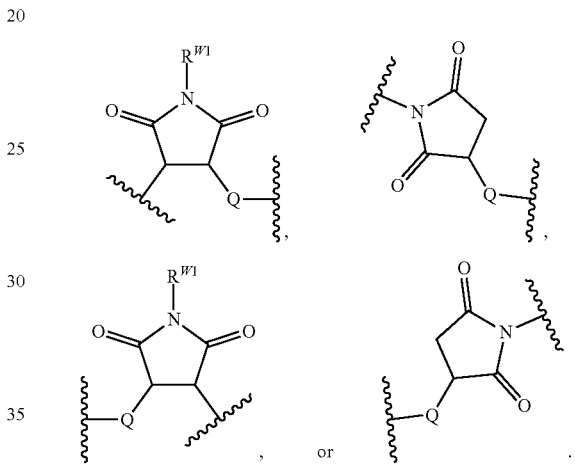

wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments, the method comprises coupling a group of formula ($L^{C1}$-ii) with a compound of formula $A^2$-$L^{C2}$-$R^{Z3}$, wherein one of $A^1$ and $A^2$ is —C(=O)$R^{X1}$, wherein $R^{X1}$ is a leaving group (LG) or —O$R^{X2}$, and the other of $A^1$ and $A^2$ is —SH, —OH, —NH$_2$, or —NH—NH$_2$ to provide a moiety A, wherein A is an amide, thioester, or ester group. See, for example, Scheme A2 and Table A1.

Scheme A2. Preparation via amide, thioester, and ester formation

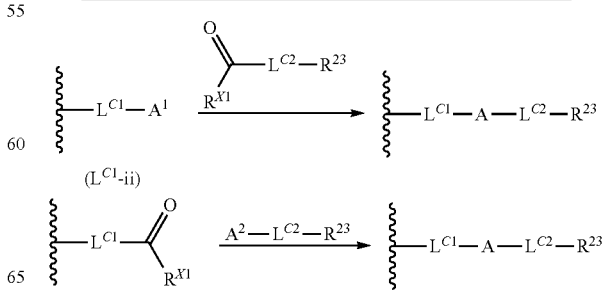

TABLE A1

| $R^{X1}$ | $A^1$ | $A^2$ | A<br>—C(=O)Q-, -QC(=O)— |
|---|---|---|---|
| LG or —OR$^{X2}$ | —SH | — | —C(=O)S— |
| | — | —SH | —SC(=O)— |
| | —OH | — | —C(=O)O— |
| | — | —OH | —OC(=O)— |
| | —NH$_2$ | — | —C(=O)NH— |
| | — | —NH$_2$ | —NHC(=O)— |
| | —NH—NH$_2$ | — | —C(=O)NHNH— |
| | — | —NH—NH$_2$ | —NHNHC(=O)— |

In certain embodiments, the method comprises coupling a group of formula (L$^{C1}$-ii) with a compound of formula A$^2$-L$^{C2}$-R$^{Z3}$, wherein one of A$^1$ and A$^2$ is a leaving group (LG), and the other of A$^1$ and A$^2$ is —SH, —OH, —NH$_2$, or —NH—NH$_2$ to provide a group of formula (L$^{C1}$-iii) wherein A is, respectively, —S—, —O—, —NH—, or —NH—NH—. See, for example, Scheme A3 and Table A2.

Scheme A3. Nucleophilic displacement of a halide or other leaving group

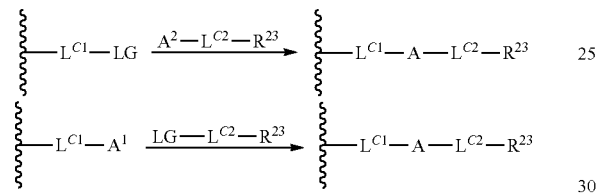

TABLE A2

| $A^1$ | $A^2$ | A |
|---|---|---|
| LG | —SH | —S— |
| | —OH | —O— |
| | —NH$_2$ | —NH— |
| | —NH—NH$_2$ | —NH—NH— |
| | —O—NH$_2$ | —O—NH— |
| —SH | LG | —S— |
| —OH | | —O— |
| —NH$_2$ | | —NH— |
| —NH—NH$_2$ | | —NH—NH— |
| —O—NH$_2$ | | —NH—O— |

In certain embodiments, the method comprises coupling a group of formula (L$^{C1}$-ii) with a compound of formula A$^2$-L$^{C2}$-R$^{Z3}$, wherein one of A$^1$ and A$^2$ is

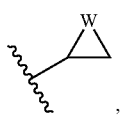, and the other of A$^1$ and A$^2$ is —SH, —OH, —NH$_2$, or —NH—NH$_2$ to provide a group of formula (L$^{C1}$-iii). See, for example, Scheme A4 and Table A3.

Scheme A4. Nucleophilic addition to strained ring systems

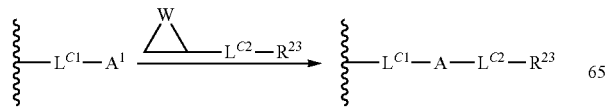

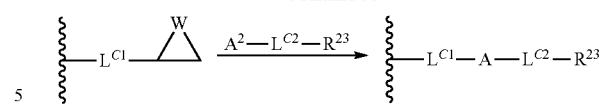

TABLE A3

| W | $A^2$ | $A^1$ | A |
|---|---|---|---|
| O, S, NR$^{W1}$ | —SH | — | 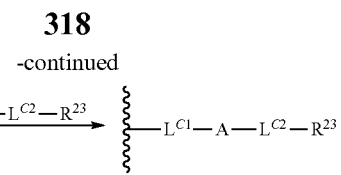 |
| | —OH | — | 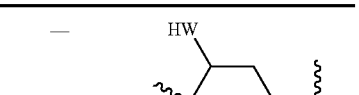 |
| | —NH$_2$ | — | 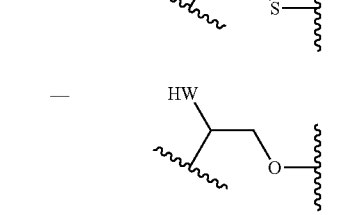 |
| | —NH—NH$_2$ | — | 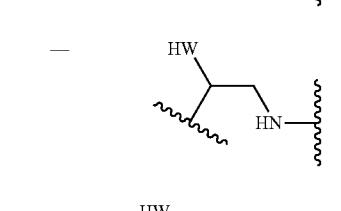 |
| | —O—NH$_2$ | — | 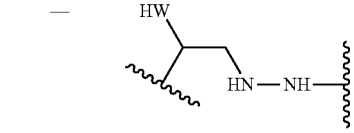 |
| O, S, NR$^{W1}$ | — | —SH | 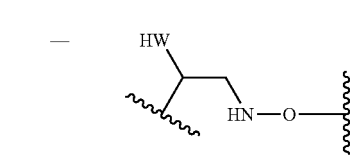 |
| | — | —OH | 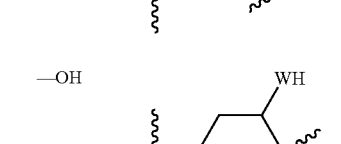 |
| | — | —NH$_2$ | 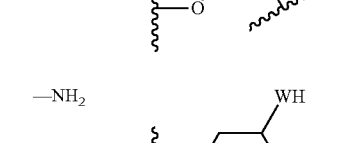 |
| | — | —NH—NH$_2$ | 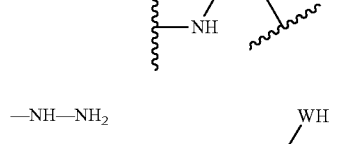 |

TABLE A3-continued

| W | $A^2$ | $A^1$ | A |
|---|---|---|---|
| — | —O—NH$_2$ | | 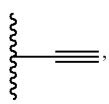 |

In certain embodiments, the method comprises coupling a group of formula ($L^{C1}$-ii) with a compound of formula $A^2$-$L^{C2}$-$R^{Z3}$, wherein one of $A^1$ and $A^2$ is

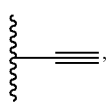

and the other of $A^1$ and $A^2$ is —N$_3$ to provide a group of formula ($L^{C1}$-iii). See, for example, Scheme A5 and Table A4.

Scheme A5. Azide-alkyne Huisgen cycloaddition

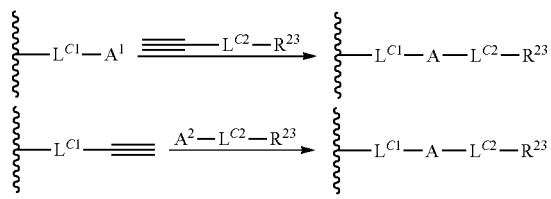

TABLE A4

| | | A | |
|---|---|---|---|
| $A^1$ | $A^2$ | 1,4-adduct | 1,5-adduct |
| — | —N$_3$ | | |
| —N$_3$ | — | | |

In certain embodiments, the method comprises coupling a group of formula ($L^{C1}$-ii) with a compound of formula $A^2$-$L^{C2}$-$R^{Z3}$, wherein one of $A^1$ and $A^2$ is and the other of $A^1$ and $A^2$ is —SH to provide a group of formula ($L^{C1}$-iii). See, for example, Scheme A6 and Table A5.

Scheme A6. Thiol-yne addition

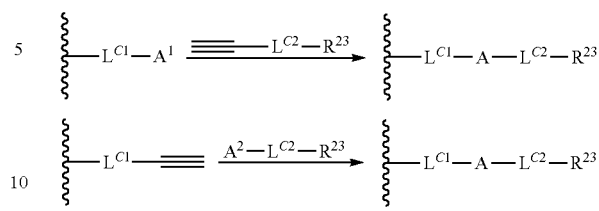

TABLE A5

| $A^1$ | $A^2$ | A |
|---|---|---|
| — | —SH | |
| —SH | — | |

In certain embodiments, the method comprises coupling a group of formula ($L^{C1}$-ii) with a compound of formula $A^2$-$L^{C2}$-$R^{Z3}$, wherein one of $A^1$ and $A^2$ is an aldehyde —CHO or ketone, and the other of $A^1$ and $A^2$ is —NH$_2$, —NH—NH$_2$, or —O—NH$_2$ to provide a group of formula ($L^{C1}$-iii). See, for example, Scheme A7 and Table A6.

Scheme A7. Imine formation

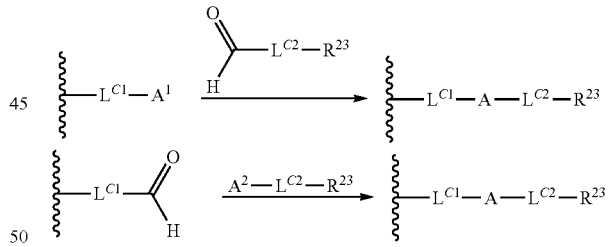

TABLE A6

| $A^1$ | $A^2$ | A |
|---|---|---|
| — | —NH$_2$ | |
| — | —NH—NH$_2$ | |

TABLE A6-continued

| $A^1$ | $A^2$ | A |
|---|---|---|
| — | —O—NH$_2$ | (structure with N—O linkage and $R^{W2}$) |
| —NH$_2$ | — | (imine structure with $R^{W2}$) |
| —NH—NH$_2$ | — | (hydrazone structure with $R^{W1}$, $R^{W2}$) |
| —O—NH$_2$ | — | (oxime structure with $R^{W2}$) |

In certain embodiments, the method comprises coupling a group of formula ($L^{C1}$-ii) with a compound of formula $A^2$-$L^{C2}$-$R^{Z3}$, wherein one of $A^1$ and $A^2$ is an α,β-unsaturated carbonyl, and the other of $A^1$ and $A^2$ is —OH, —SH, —NH$_2$, —NHNH$_2$, or —O—NH$_2$ to provide a group of formula ($L^{C1}$-iii). See, for example, Scheme A8 and Table A7.

Scheme A8. Michael addition

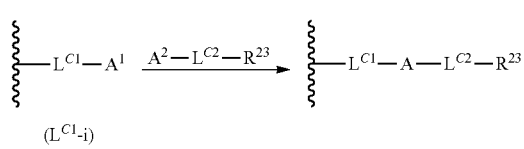

($L^{C1}$-i)

TABLE A7

| $A^1$ | $A^2$ | A |
|---|---|---|
| (α,β-unsaturated carbonyl with $R^{W2}$) | —OH, —SH, —NH$_2$, —NHNH$_2$, —O—NH$_2$ | (Michael adduct with Q, $R^{W2}$) |
| —OH, —SH, —NH$_2$, —NHNH$_2$, —O—NH$_2$ | (α,β-unsaturated carbonyl with $R^{W2}$) | (Michael adduct with Q, $R^{W2}$) |

In certain embodiments, the method comprises coupling a group of formula ($L^{C1}$-ii) with a compound of formula $A^2$-$L^{C2}$-$R^{Z3}$, wherein one of $A^1$ and $A^2$ is a maleimide group, and the other of $A^1$ and $A^2$ is —OH, —SH, —NH$_2$, —NHNH$_2$, or —O—NH$_2$ to provide a group of formula ($L^{C1}$-iii). See, for example, Scheme A9 and Table A8.

Scheme A9. Maleimide addition

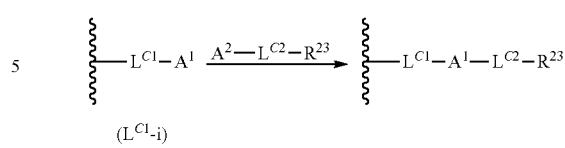

($L^{C1}$-i)

TABLE A8

| $A^1$ | $A^2$ | A |
|---|---|---|
| (N-$R^{W1}$ maleimide) | —OH, —SH, —NH$_2$, —NHNH$_2$, —O—NH$_2$ | (succinimide with $R^{W1}$, Q) |
| (N-linked maleimide) | —OH, —SH, —NH$_2$, —NHNH$_2$, —O—NH$_2$ | (succinimide with Q) |
| —OH, —SH, —NH$_2$, —NHNH$_2$, —O—NH$_2$ | (C-linked maleimide with $R^{W1}$) | (succinimide with $R^{W1}$, Q) |
| —OH, —SH, —NH$_2$, —NHNH$_2$, —O—NH$_2$ | (C-linked maleimide) | (succinimide with Q) |

In certain embodiments, the method comprises coupling (e.g., palladium catalyzed coupling) of a group of formula ($L^{C1}$-ii) with a compound of formula $A^2$-$L^{C2}$-$R^{Z3}$, wherein one of $A^1$ and $A^2$ is an propenyl group, and one of $A^1$ and $A^2$ is a leaving group, to provide a group of formula ($L^{C1}$-iii) upon treatment with a palladium catalyst. See, for example, Table A9.

TABLE A9

| $A^1$ | $A^2$ | A |
|---|---|---|
| (propenyl with $R^{W2}$) | LG | (propenyl with $R^{W2}$) |

TABLE A9-continued

| $A^1$ | $A^2$ | A |
|---|---|---|
| LG | 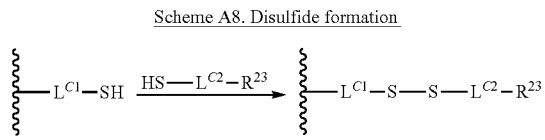 | |

In certain embodiments, the method comprises coupling a group of formula ($L^{C1}$-ii) with a compound of formula $A^2$-$L^{C2}$-$R^{Z3}$, wherein one of $A^1$ and $A^2$ is —SH to provide, upon treatment with an oxidant, a group of formula ($L^{C1}$-iii), wherein A is a disulfide bond. See, for example, Scheme A8.

Scheme A8. Disulfide formation $$\xi\text{—}L^{C1}\text{—SH} \xrightarrow{\text{HS—}L^{C2}\text{—}R^{23}} \xi\text{—}L^{C1}\text{—S—S—}L^{C2}\text{—}R^{23}$$

In certain preferred embodiments, $A^1$ is —$N_3$ and $A^2$ is

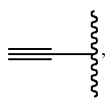

such that the compound of formula $A^2$-$L^{C2}$-$R^{23}$ is of the formula:

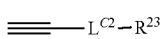

and $A^1$ and $A^2$-$L^{C2}$-$R^{23}$ react together to provide a group of formula:

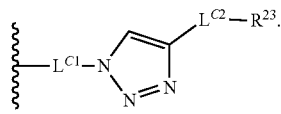

($L^{C1}$-v)

In certain preferred embodiments, $A^1$ is

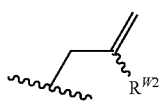

and $A^2$ is a leaving group, and $A^1$ and $A^2$-$L^{C2}$-$R^{23}$ react together (e.g., via palladium catalysis) to provide a group of formula:

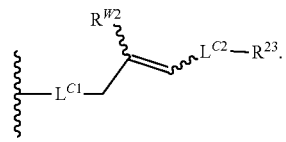

($L^{C1}$-vi)

Furthermore, as described herein, there are many ways of adding a group of formula ($L^{C1}$-iii) which do not involve reaction of $A^1$ and $A^2$ to form A. For example, a group of formula ($L^{C1}$-iii) may be installed by reaction of the group —$OR^{12}$, —$NR^{13}R^{14}$, and/or —$OR^3$, wherein $R^{12}$, $R^{14}$, and/or $R^3$ are hydrogen, with a compound of formula ($L^{C1}$-vii), e.g., by nucleophilic displacement, to provide a group wherein $R^{12}$, $R^{14}$, and/or $R^3$ is of formula ($L^{C1}$-iii). See, e.g., Scheme A9.

Scheme A9.

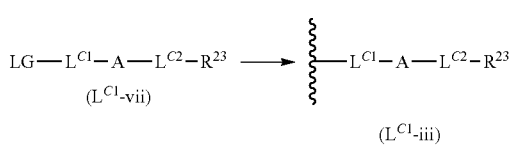

Thus, in certain embodiments, A may be any group as defined above, and further may be any cyclic moiety selected from the group consisting of optionally substituted carbocyclyl, optionally substituted heterocyclyl, optionally substituted aryl, and optionally substituted heteroaryl.

In certain embodiments, A is an optionally substituted heteroaryl, e.g., a 5- to 6-membered optionally substituted heteroaryl.

In certain embodiments, wherein A is a 5-membered optionally substituted heteroaryl, the group of formula ($L^{C1}$-iii) is of the formula ($L^{C1}$-v):

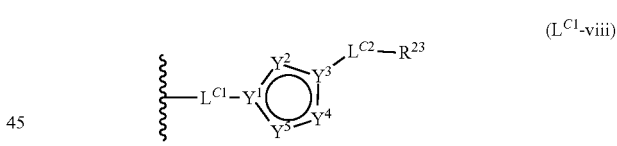

($L^{C1}$-viii)

wherein each instance of $Y^1$, $Y^2$, $Y^3$, $Y^4$, and $Y^5$ is independently $CR^Y$, O, S, N, or $NR^Y$, wherein $R^Y$ is hydrogen or optionally substituted alkyl.

In certain embodiments wherein A is a 5-membered heteroaryl, the group of formula ($L^{C1}$-iii) is selected from:

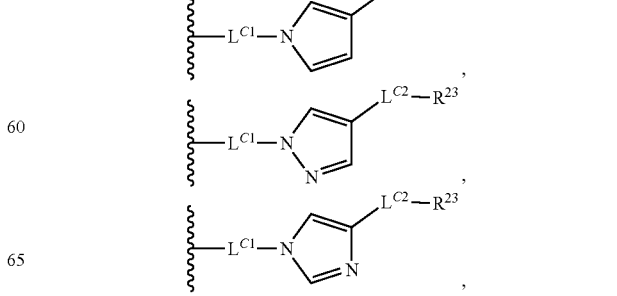

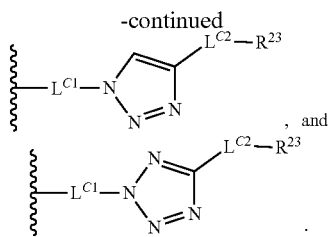

$L^{C1}$, $L^{C2}$ and Group $R^{23}$

As generally defined above, each instance of $L^{C1}$ and $L^{C2}$ is independently a bond, or a linking group selected from the group consisting of optionally substituted alkylene, optionally substituted alkenylene, optionally substituted alkynylene; optionally substituted heteroalkylene, optionally substituted heteroalkenylene, optionally substituted heteroalkynylene, and combinations thereof.

In certain embodiments, $L^{C1}$ is a bond. It is generally understood that if $L^{C1}$ is a bond, then the group -LG, -$A^1$, or -A-$L^{C2}$-$R^{23}$, as described herein, is directly attached to the parent moiety, e.g., the macrolide or intermediate compounds. Furthermore, in certain embodiments, $L^{C2}$ is a bond. It is generally understood that if $L^{C2}$ is a bond, then the group $R^{23}$ is directly attached to A, as described herein.

Alternatively, in certain embodiments, $L^{C1}$ is a linking group. In certain embodiments, $L^{C2}$ is a linking group.

In certain embodiments, $L^{C1}$ and $L^{C2}$ are each optionally and independently linking groups comprising at least one instance of optionally substituted alkylene, e.g., substituted or unsubstituted $C_{1-6}$alkylene, substituted or unsubstituted $C_{2-6}$alkylene, substituted or unsubstituted $C_{3-6}$alkylene, substituted or unsubstituted $C_{1-6}$alkylene, substituted or unsubstituted $C_{5-6}$alkylene, substituted or unsubstituted $C_{2-5}$alkylene, substituted or unsubstituted $C_{2-4}$alkylene, substituted or unsubstituted $C_{2-3}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene. In certain embodiments, $L^{C1}$ and $L^{C2}$ are each optionally and independently an alkylene linking group of the formula —$(CH_2)_n$—, wherein n is 1, 2, 3, 4, 5, 6, 7, 8, 9, or 10.

In certain embodiments, $L^{C1}$ and $L^{C2}$ are each optionally and independently linking groups comprising at least one instance of substituted or unsubstituted alkenylene, e.g., substituted or unsubstituted $C_{2-6}$alkenylene, substituted or unsubstituted $C_{3-6}$alkenylene, substituted or unsubstituted $C_{4-6}$alkenylene, substituted or unsubstituted $C_{5-6}$alkenylene, substituted or unsubstituted $C_{2-5}$alkenylene, substituted or unsubstituted $C_{2-4}$alkenylene, substituted or unsubstituted $C_{2-3}$alkenylene, substituted or unsubstituted $C_2$alkenylene, substituted or unsubstituted $C_3$alkenylene, substituted or unsubstituted $C_4$alkenylene, substituted or unsubstituted $C_5$alkenylene, or substituted or unsubstituted $C_{3-4}$alkenylene.

In certain embodiments, $L^{C1}$ and $L^{C2}$ are each optionally and independently linking groups comprising at least one instance of substituted or unsubstituted alkynylene, e.g., substituted or unsubstituted $C_{2-6}$alkynylene, substituted or unsubstituted $C_{3-6}$alkynylene, substituted or unsubstituted $C_{4-6}$alkynylene, substituted or unsubstituted $C_{5-6}$alkynylene, substituted or unsubstituted $C_{2-5}$alkynylene, substituted or unsubstituted $C_{2-4}$alkynylene, substituted or unsubstituted $C_{2-3}$alkynylene, substituted or unsubstituted $C_2$alkynylene, substituted or unsubstituted $C_3$alkynylene, substituted or unsubstituted $C_4$alkynylene, substituted or unsubstituted $C_5$alkynylene, or substituted or unsubstituted $C_{3-4}$alkynylene.

In certain embodiments, $L^{C1}$ and $L^{C2}$ are each optionally and independently linking groups comprising at least one instance of substituted or unsubstituted heteroalkylene, e.g., substituted or unsubstituted heteroC$_{1-6}$alkylene, substituted or unsubstituted heteroC$_{2-6}$alkylene, substituted or unsubstituted heteroC$_{3-6}$alkylene, substituted or unsubstituted heteroC$_{2-6}$alkylene, substituted or unsubstituted heteroC$_{5-6}$alkylene, substituted or unsubstituted heteroC$_{2-5}$alkylene, substituted or unsubstituted heteroC$_{2-4}$alkylene, substituted or unsubstituted heteroC$_{2-3}$alkylene, substituted or unsubstituted heteroC$_1$alkylene, substituted or unsubstituted heteroC$_2$alkylene, substituted or unsubstituted heteroC$_3$alkylene, substituted or unsubstituted heteroC$_4$alkylene, substituted or unsubstituted heteroC$_5$alkylene, or substituted or unsubstituted heteroC$_6$alkylene.

In certain embodiments, $L^{C1}$ and $L^{C2}$ are each optionally and independently linking groups comprising at least one instance of substituted or unsubstituted heteroalkenylene, e.g., substituted or unsubstituted heteroC$_{2-6}$alkenylene, substituted or unsubstituted heteroC$_{3-6}$alkenylene, substituted or unsubstituted heteroC$_{4-6}$alkenylene, substituted or unsubstituted heteroC$_{5-6}$alkenylene, substituted or unsubstituted heteroC$_{2-5}$alkenylene, substituted or unsubstituted heteroC$_{2-4}$alkenylene, substituted or unsubstituted heteroC$_{2-3}$alkenylene, substituted or unsubstituted heteroC$_2$alkenylene, substituted or unsubstituted heteroC$_3$alkenylene, substituted or unsubstituted heteroC$_4$alkenylene, substituted or unsubstituted heteroC$_5$alkenylene, or substituted or unsubstituted heteroC$_6$alkenylene.

In certain embodiments, $L^{C1}$ and $L^{C2}$ are each optionally and independently linking groups comprising at least one instance of substituted or unsubstituted heteroalkynylene, e.g., substituted or unsubstituted heteroC$_{2-6}$alkynylene, substituted or unsubstituted heteroC$_{3-6}$alkynylene, substituted or unsubstituted heteroC$_{4-6}$alkynylene, substituted or unsubstituted heteroC$_{5-6}$alkynylene, substituted or unsubstituted heteroC$_{2-5}$alkynylene, substituted or unsubstituted heteroC$_{2-4}$alkynylene, substituted or unsubstituted heteroC$_{2-3}$alkynylene, substituted or unsubstituted heteroC$_2$alkynylene, substituted or unsubstituted heteroC$_3$alkynylene, substituted or unsubstituted heteroC$_4$alkynylene, substituted or unsubstituted heteroC$_5$alkynylene, or substituted or unsubstituted heteroC$_6$alkynylene.

In certain embodiments, $L^{C1}$ is an optionally substituted alkylene, and $L^{C2}$ is a bond, e.g., $L^{C1}$ is an optionally substituted alkylene of the formula —$(CH_2)_n$—, wherein n is 1, 2, 3, 4, 5, 6, 7, 8, 9, or 10, and $L^{C2}$ is a bond in groups of formula ($L^{C1}$-v) or ($L^{C1}$-viii) as described herein.

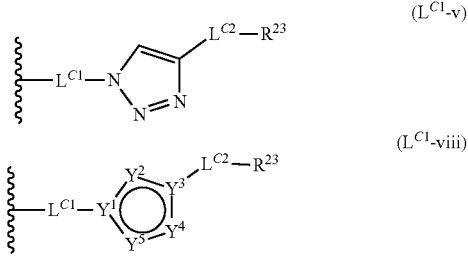

In other embodiments, both of $L^{C1}$ and $L^{C2}$ are bonds, e.g., both of $L^{C1}$ and $L^{C2}$ are bonds in the group of formula ($L^{C1}$-vi) as described herein.

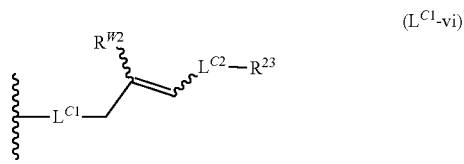

($L^{C1}$-vi)

Furthermore, it is also generally understood that $R^{23}$ may be an acyclic moiety or a cyclic moiety selected from the group consisting of optionally substituted alkyl; optionally substituted alkenyl; optionally substituted alkynyl; optionally substituted carbocyclyl; optionally substituted heterocyclyl; optionally substituted aryl; and optionally substituted heteroaryl.

For example, in certain embodiments, $R^{23}$ is an acyclic moiety selected from the group consisting of optionally substituted alkyl; optionally substituted alkenyl; and optionally substituted alkynyl.

In certain embodiments, $R^{23}$ is optionally substituted alkyl, e.g., optionally substituted $C_{1-6}$alkyl, substituted or unsubstituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. Exemplary $R^{23}$ $C_{1-6}$ alkyl groups include, but are not limited to, optionally substituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

In certain embodiments, $R^{23}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl.

In certain embodiments, $R^{23}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, $R^{23}$ is a cyclic moiety selected from the group consisting of optionally substituted carbocyclyl; optionally substituted heterocyclyl; optionally substituted aryl; and optionally substituted heteroaryl.

In certain embodiments, $R^{23}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl.

In certain embodiments, $R^{23}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^{23}$ is optionally substituted aryl, e.g., optionally substituted monocyclic aryl, optionally substituted 5,6-fused bicyclic aryl, or optionally substituted 6,6-fused aryl. In certain embodiments, $R^{23}$ is optionally substituted phenyl. In certain embodiments, $R^{23}$ is optionally substituted napthyl.

In certain embodiments, $R^{23}$ is optionally substituted heteroaryl, e.g., optionally substituted monocyclic heteroaryl or optionally substituted bicyclic heteroaryl, e.g., optionally substituted 5-6 membered heteroaryl, optionally substituted 5,6 fused-bicyclic heteroaryl, or optionally substituted 6,6 fused-bicyclic heteroaryl.

Specific aryl and heteroaryl $R^{23}$ groups are further contemplated herein. For example, in certain embodiments, $R^{23}$ is an aryl or heteroaryl ring system of formula:

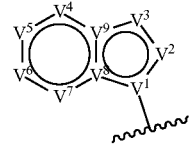

(e-1)

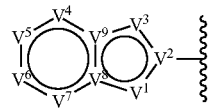

(e-2)

(e-3)

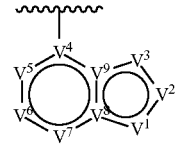

(e-4)

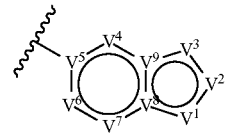

(e-5)

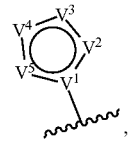

, (e-6)

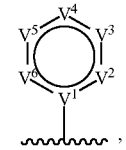

, (e-7)

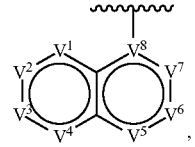

, (e-8)

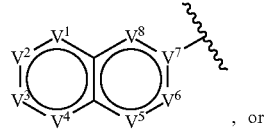

, or (e-9)

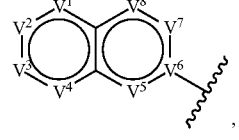

, wherein:
each instance of $V^1$, $V^2$, $V^3$, $V^4$, $V^5$, $V^6$, $V^7$, $V^8$, and $V^9$ may independently be O, S, N, $NR^{23N}$, C, or $CR^{23C}$, as valency permits;

$R^{23N}$ is independently hydrogen, optionally substituted alkyl, optionally substituted aryl, or a nitrogen protecting group; and $R^{23C}$ is hydrogen, halogen, —CN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, amino, substituted amino, thiol, substituted thiol, or carbonyl.

In certain embodiments, $V^1$ is O, S, N or $NR^{23N}$. In certain embodiments, $V^1$ is N or $NR^{23N}$. In certain embodiments, $V^1$ is O. In certain embodiments, $V^1$ is S.

In certain embodiments, $V^2$ is O, S, N or $NR^{23N}$. In certain embodiments, $V^2$ is N or $NR^{23N}$. In certain embodiments, $V^2$ is O. In certain embodiments, $V^2$ is S.

In certain embodiments, $V^3$ is O, S, N or $NR^{23N}$. In certain embodiments, $V^3$ is N or $NR^{23N}$. In certain embodiments, $V^3$ is O. In certain embodiments, $V^3$ is S.

In certain embodiments, $V^4$ is O, S, N or $NR^{23N}$. In certain embodiments, $V^4$ is N or $NR^{23N}$. In certain embodiments, $V^4$ is O. In certain embodiments, $V^4$ is S.

In certain embodiments, $V^5$ is O, S, N or $NR^{23N}$. In certain embodiments, $V^5$ is N or $NR^{23N}$. In certain embodiments, $V^5$ is O. In certain embodiments, $V^5$ is S.

In certain embodiments, $V^6$ is O, S, N or $NR^{23N}$. In certain embodiments, $V^6$ is N or $NR^{23N}$. In certain embodiments, $V^6$ is O. In certain embodiments, $V^6$ is S.

In certain embodiments, $V^7$ is O, S, N or $NR^{23N}$. In certain embodiments, $V^7$ is N or $NR^{23N}$. In certain embodiments, $V^7$ is O. In certain embodiments, $V^7$ is S.

In certain embodiments, $V^8$ is O, S, N or $NR^{23N}$. In certain embodiments, $V^8$ is N or $NR^{23N}$. In certain embodiments, $V^8$ is O. In certain embodiments, $V^8$ is S.

In certain embodiments, $V^9$ is O, S, N or $NR^{23N}$. In certain embodiments, $V^9$ is N or $NR^{23N}$. In certain embodiments, $V^9$ is O. In certain embodiments, $V^9$ is S.

In certain embodiments, only one of $V^1$, $V^2$, $V^3$, $V^4$, $V^5$, $V^6$, $V^7$, $V^8$, and $V^9$ is selected from the group consisting of N and $NR^{23N}$. In certain embodiments, only one of $V^1$, $V^2$, $V^3$, $V^4$, $V^5$, $V^6$, $V^7$, $V^8$, and $V^9$ is O. In certain embodiments, only one of $V^1$, $V^2$, $V^3$, $V^4$, $V^5$, $V^6$, $V^7$, $V^8$, and $V^9$ is S. In any of the above instances, in certain embodiments, the rest of $V^1$, $V^2$, $V^3$, $V^4$, $V^5$, $V^6$, $V^7$, $V^8$, and $V^9$ are independently C or $CR^{23C}$ as valency permits.

In certain embodiments, only two of $V^1$, $V^2$, $V^3$, $V^4$, $V^5$, $V^6$, $V^7$, $V^8$, and $V^9$ are each independently selected from the group consisting of N and $NR^{23N}$. In certain embodiments, only two of $V^1$, $V^2$, $V^3$, $V^4$, $V^5$, $V^6$, $V^7$, $V^8$, and $V^9$ are each independently selected from the group consisting of O, N and $NR^{23N}$. In certain embodiments, only two of $V^1$, $V^2$, $V^3$, $V^4$, $V^5$, $V^6$, $V^7$, $V^8$, and $V^9$ are each independently selected from the group consisting of S, N and $NR^{23N}$. In any of the above instances, in certain embodiments, the rest of $V^1$, $V^2$, $V^3$, $V^4$, $V^5$, $V^6$, $V^7$, $V^8$, and $V^9$ are independently C or $CR^{23C}$ as valency permits.

In certain embodiments, all $V^1$, $V^2$, $V^3$, $V^4$, $V^5$, $V^6$, $V^7$, $V^8$, and $V^9$ are independently C or $CR^{23C}$ as valency permits.

In certain embodiments, $R^{23C}$ is hydrogen, halogen, —CN, hydroxyl, substituted hydroxyl, amino, or substituted amino.

In certain embodiments, $R^{23N}$ is independently hydrogen or optionally substituted alkyl (e.g., —CH$_3$).

In certain embodiments, $R^{23}$ is selected from any one of the following aryl or heteroaryl ring systems:

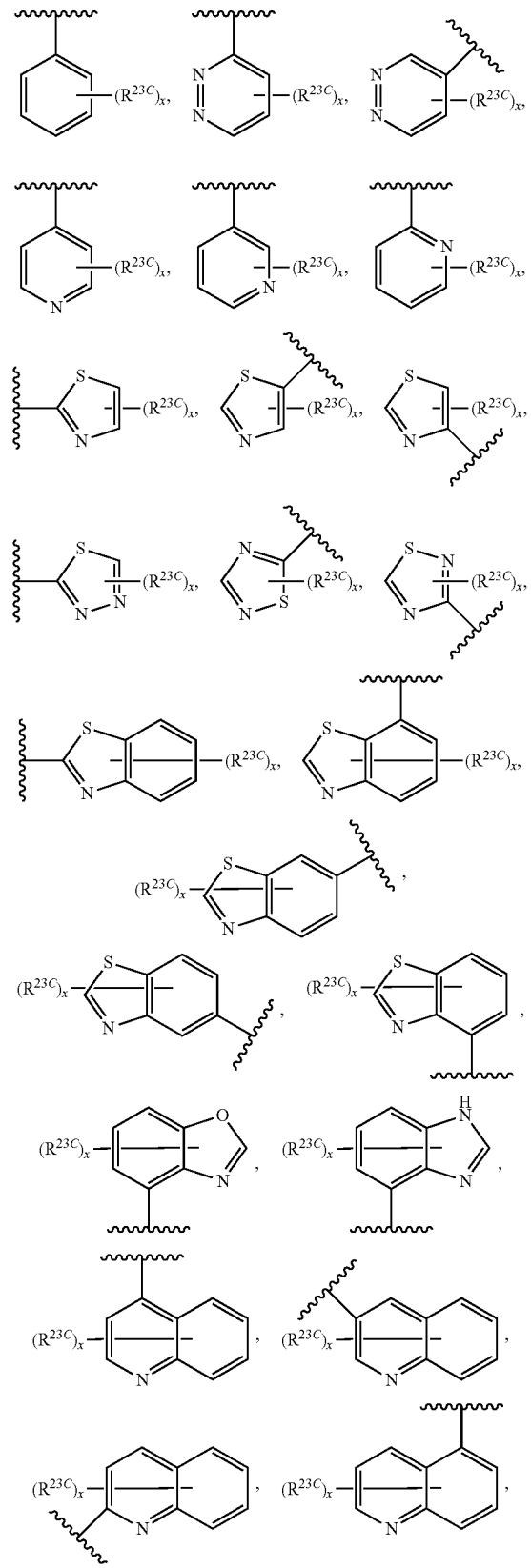

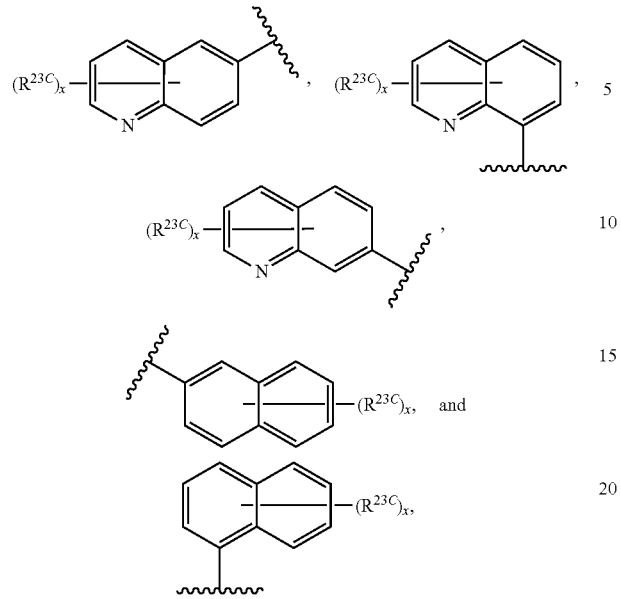
wherein $R^{23C}$ is as defined herein, and x is 0, 1, or 2.
In certain embodiments, $R^{23}$ is selected from any one of the following aryl or heteroaryl ring systems:
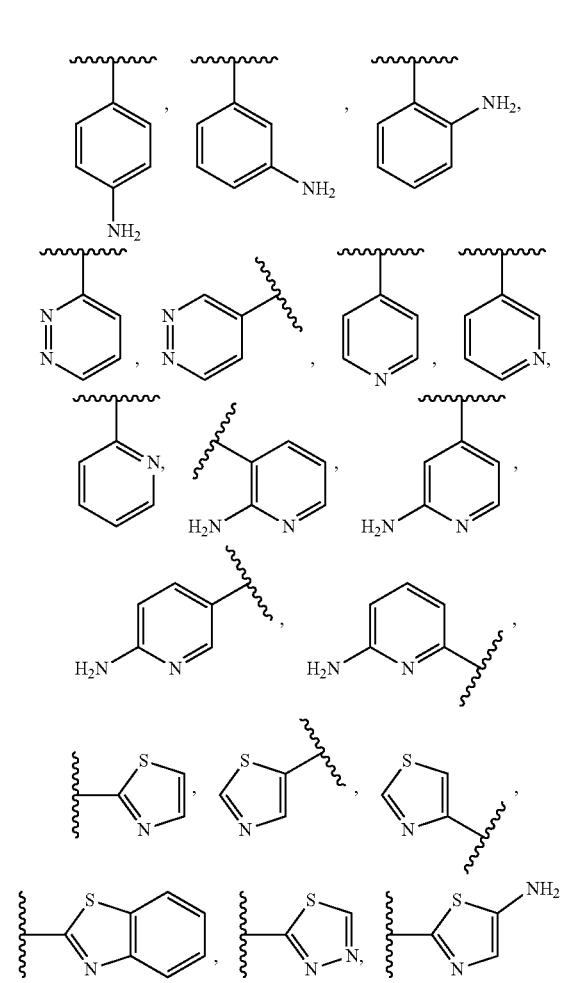
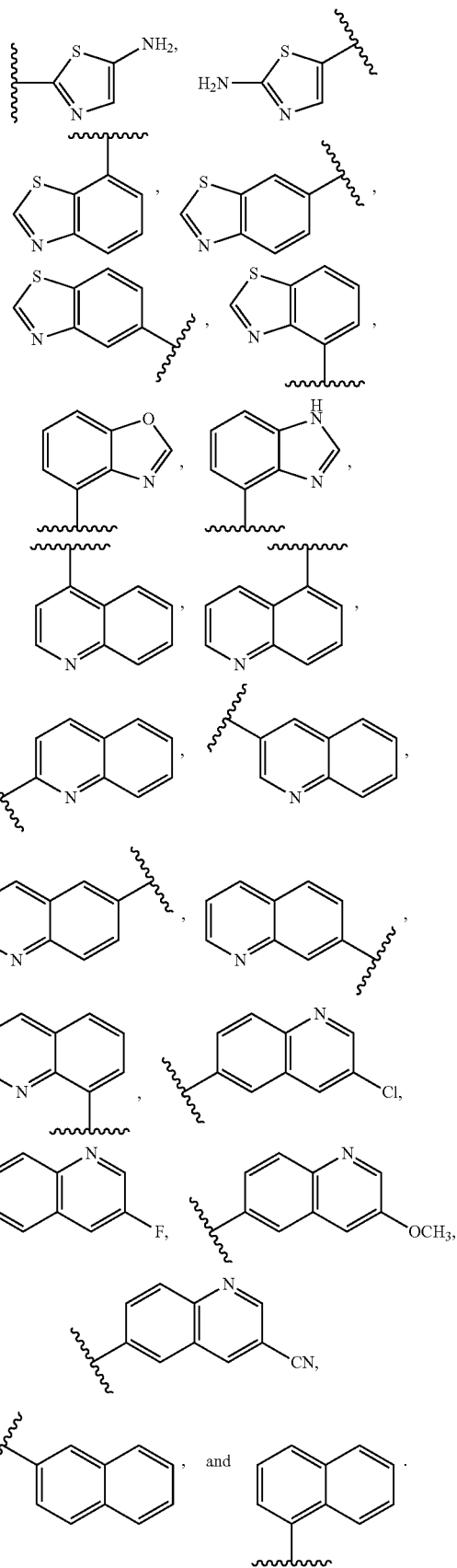

Further Embodiments of the Invention

Various combinations of the above described embodiments are further contemplated herein. For example, in certain embodiments, $G^1$ is —NR$^{13}$NR$^{14}$, to provide a compound or macrolide of formula:

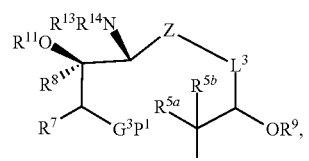
(C-1-A)

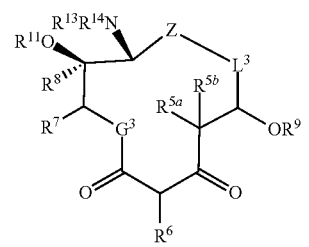
(C-2-A)

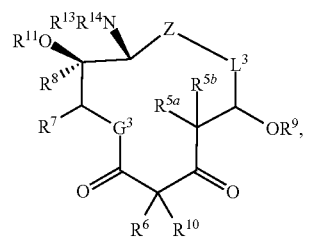
(C-3-A)

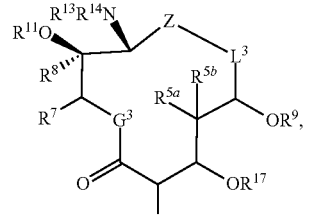
(C-4-A)

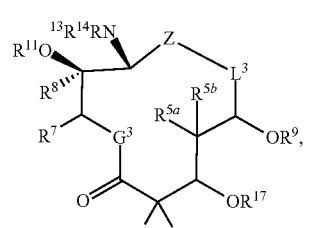
(C-5-A)

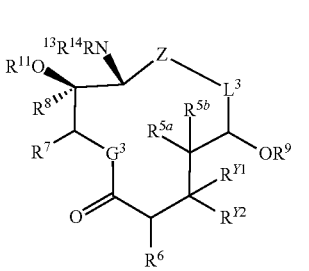
(C-467-A)

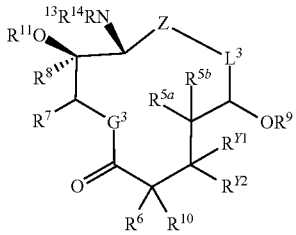
(C-567-A)

or a salt thereof.

In certain embodiments, $G^1$ is —NR$^{13}$NR$^{14}$, and $R^{13}$ and $R^{11}$ are joined to form a carbamate group to provide a compound or macrolide of formula:

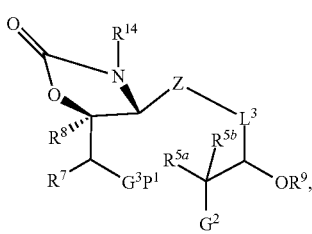
(C-1-B)

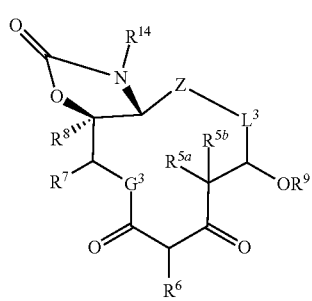
(C-2-B)

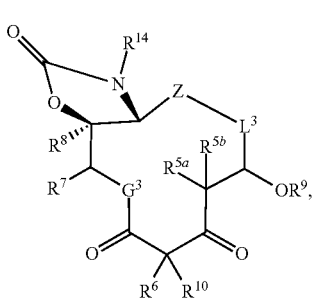
(C-3-B)

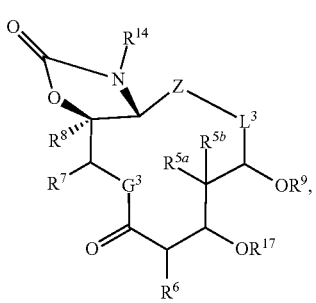
(C-4-B)

-continued
(C-5-B)
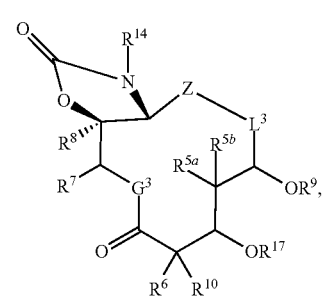
(C-467-B)
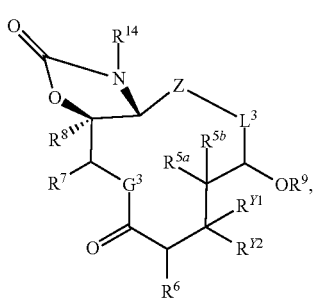
(C-567-B)
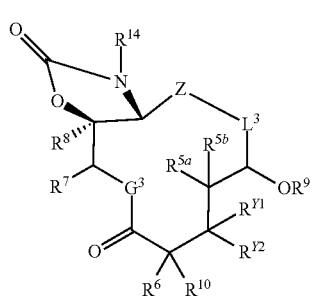
or a salt thereof.
In certain embodiments, $G^1$ is —$NR^{13}NR^{14}$, and $R^{13}$ and $R^{11}$ are joined to form a carbamate group to provide a compound or macrolide having the following stereochemistry:
(C-1-C)
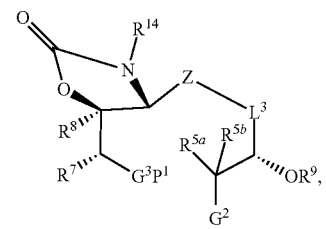
(C-2-C)
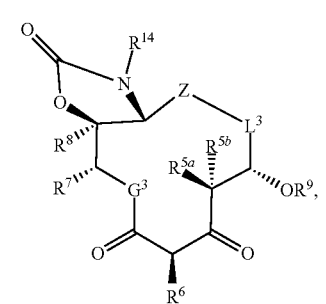
-continued
(C-2-C')
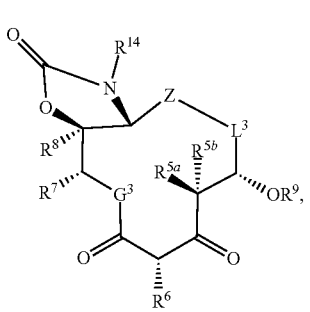
(C-4-C)
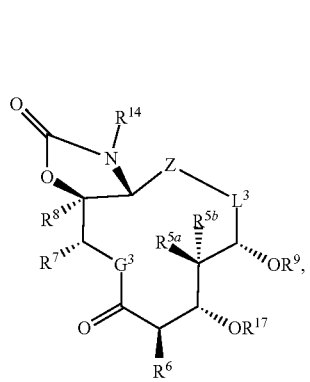
(C-4-C')
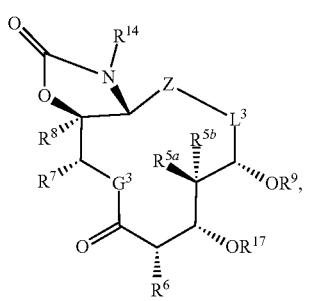
(C-3-C)
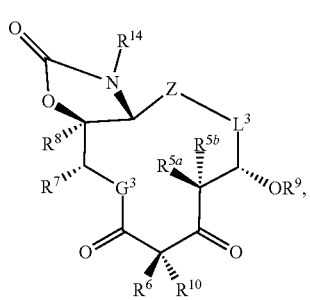
(C-3-C')
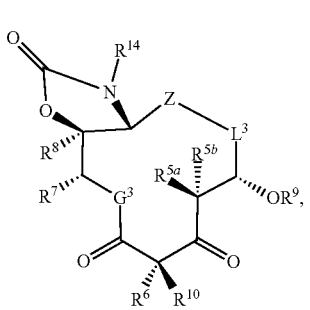

337
-continued (C-5-C)
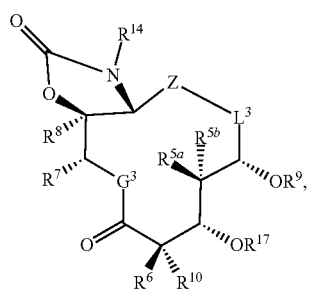

(C-5-C')
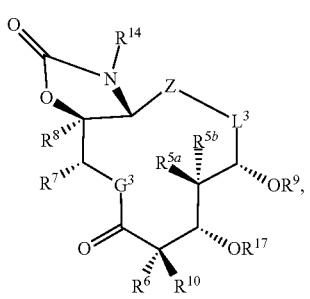

(C-467-C)
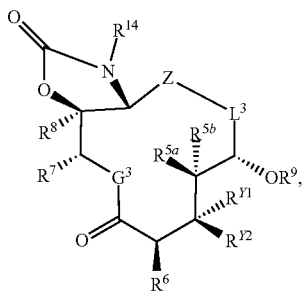

(C-467-C')
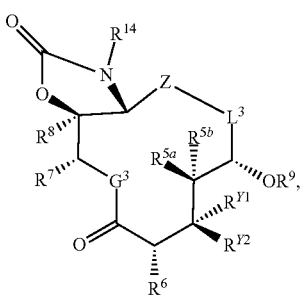

(C-567-C)
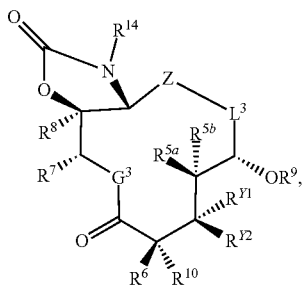

338
-continued (C-567-C')
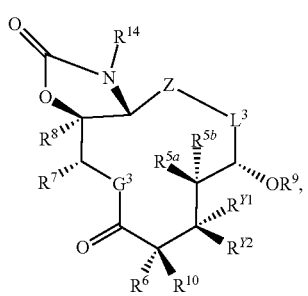

or salts thereof.

Various embodiments are further contemplated in combination with any formulae depicted herein, e.g., for example, any of the above depicted formulae (C-1-A) to (C-567-C').

For example, in certain embodiments of any of the above formulae, Z is of formula:

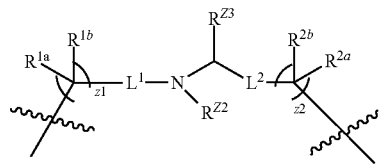

wherein z1 and z2 are 1, $L^1$ and $L^2$ are both a bond, $R^7$ is —$CH_2CH_3$, $R^8$ is —$CH_3$, $G^3$ is —O—, $L^3$ is a group of formula

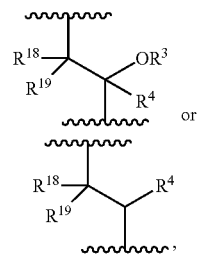

and $R^{18}$ and $R^{19}$ are both hydrogen;

In certain embodiments of any of the above formulae, Z is of formula:

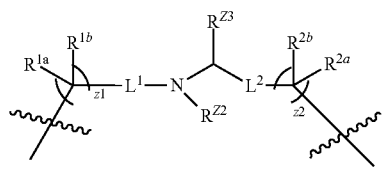

wherein z1 is 1, z2 is 0, $L^1$ and $L^2$ are both a bond, $R^7$ is —$CH_2CH_3$, $R^8$ is —$CH_3$, $G^3$ is —O—, $L^3$ is a group of formula

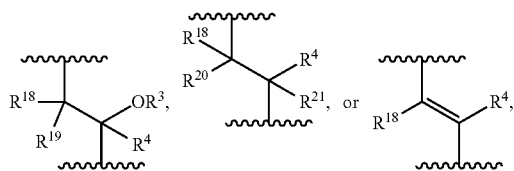

and R$^{18}$ is hydrogen.

In certain embodiments of any of the above formulae, Z is of formula:

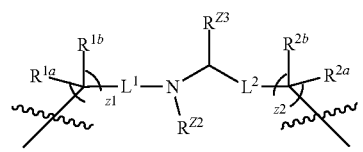

wherein z1 is 1, z2 is 2, L$^1$ and L$^2$ are both a bond, R$^7$ is —CH$_2$CH$_3$, R$^8$ is —CH$_3$, G$^3$ is —O—, L$^3$ is a group of formula

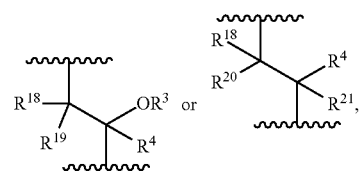

and R$^{18}$ and R$^{19}$ are both hydrogen.

In certain embodiments of any of the above formulae, Z is of formula:

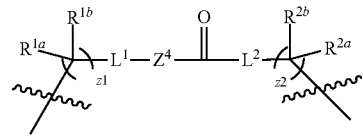

wherein z1 and z2 are 1, L$^1$ and L$^2$ are both a bond, Z$^4$ is —O— or —NH—, R$^7$ is —CH$_2$CH$_3$, R$^8$ is —CH$_3$, G$^3$ is —O—, L$^3$ is a group of formula

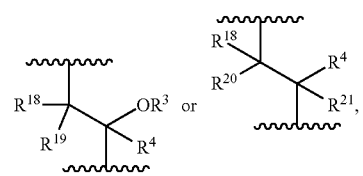

and R$^{18}$ is hydrogen.

In certain embodiments of any of the above formulae, Z is of formula:

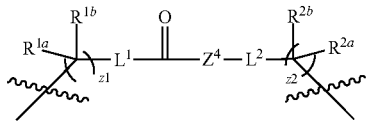

wherein z1 is 0, z2 is 1, L$^1$ is a bond, L$^2$ is —CH$_2$—, Z$^4$ is —O— or —NH—, R$^7$ is —CH$_2$CH$_3$, R$^8$ is —CH$_3$, G$^3$ is —O—, L$^3$ is a group of formula

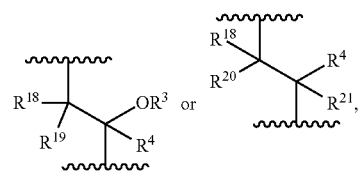

and R$^{18}$ is hydrogen.

In certain embodiments of any of the above formulae, Z is of formula:

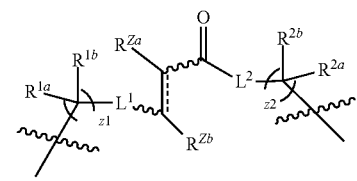

wherein z1 and z2 are 1, L$^1$ and L$^2$ are both a bond, R$^7$ is —CH$_2$CH$_3$, R$^8$ is —CH$_3$, G$^3$ is —O—, L$^3$ is a group of formula

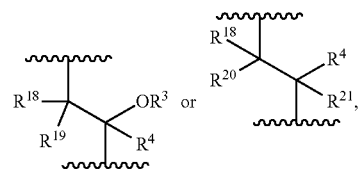

and R$^{18}$ is hydrogen.

In certain embodiments of any of the above formulae, Z is of formula:

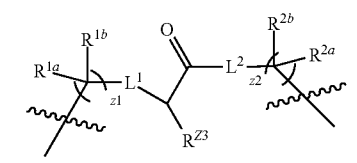

wherein z1 is 0, z2 is 1, L$^1$ and L$^2$ are both a bond, R$^7$ is —CH$_2$CH$_3$, R$^8$ is —CH$_3$, G$^3$ is —O—, and L$^3$ is a group of formula

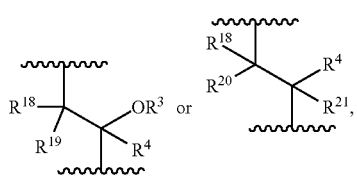

and $R^{18}$ is hydrogen.

In certain aspects of the formulae depicted herein, e.g., for example, any of the above depicted formulae (C-1-A) to (C-567-C'), further specific combinations are contemplated, as provided below.

For example, in certain embodiments, $R^{Z3}$ is hydrogen. In certain embodiments, $R^{Z3}$ is not hydrogen. In certain embodiments, the carbon to which $R^{Z3}$ is attached is a stereocenter of the (R)-configuration. In certain embodiments, the carbon to which $R^{Z3}$ is attached is a stereocenter of the (S)-configuration. In certain embodiments, $R^{Z3}$ is optionally substituted $C_{1-6}$alkyl. In certain embodiments, $R^{Z3}$ is optionally substituted $C_{1-2}$alkyl. In certain embodiments, $R^{Z3}$ is —$CH_3$. In certain embodiments, $R^{Z3}$ is optionally substituted haloalkyl. In certain embodiments, $R^{Z3}$ is —$CF_3$. In certain embodiments, $R^{Z3}$ is —$CH_2CH_2OH$. In certain embodiments, $R^{Z3}$ is —$CH_2CH_2N(R^{22})_2$. In certain embodiments, $R^{Z3}$ is —$CH_2CH_2N(R^{22})_2$. In certain embodiments, $R^{Z3}$ is —$CH_2CH_2NHR^{22}$. In certain embodiments, $R^{Z3}$ is —$CH_2CH_2NHR^{22}$; and $R^{22}$ is —$CH_2C(=O)OH$. In certain embodiments, $R^{23}$ is —$CH_2CH_2NHR^{22}$; and $R^{Z2}$ is

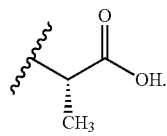

In certain embodiments, $R^{Z3}$ is —$CH_2CH_2NHR^{22}$; and $R^{22}$ is

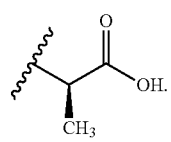

In certain embodiments, $R^{Z3}$ is optionally substituted aralkyl. In certain embodiments, $R^{Z3}$ is optionally substituted benzyl. In certain embodiments, $R^{Z3}$ is unsubstituted benzyl. In certain embodiments, $R^{Z3}$ is substituted benzyl. In certain embodiments, $R^{Z3}$ is monosubstituted benzyl. In certain embodiments, $R^{Z3}$ is benzyl substituted by one instance of halogen. In certain embodiments, $R^{Z3}$ is optionally substituted $C_{2-6}$alkenyl. In certain embodiments, $R^{Z3}$ is optionally substituted vinyl. In certain embodiments, $R^{Z3}$ is unsubstituted vinyl. In certain embodiments, $R^{Z3}$ is optionally substituted allyl. In certain embodiments, $R^{Z3}$ is unsubstituted allyl. In certain embodiments $R^{Z3}$ is optionally substituted carbocyclyl. In certain embodiments, $R^{Z3}$ is optionally substituted $C_{3-6}$carbocyclyl. In certain embodiments, $R^{Z3}$ is optionally substituted cyclopropyl. In certain embodiments, $R^{Z3}$ is unsubstituted cyclopropyl.

In certain embodiments, $R^{Z2}$ is hydrogen. In certain embodiments, $R^{Z2}$ is optionally substituted $C_{1-6}$alkyl. In certain embodiments, $R^{Z2}$ is optionally substituted $C_{1-2}$alkyl. In certain embodiments, $R^{Z2}$ is —$CH_3$. In certain embodiments, $R^{Z2}$ is —$C(=O)R^{Z8}$; and $R^{Z8}$ is optionally substituted alkyl. In certain embodiments, $R^{Z2}$ is acetyl. In certain embodiments, $R^{Z2}$ is a nitrogen protecting group.

In certain embodiments, at least one of $R^{1a}$ and $R^{1b}$ is hydrogen. In certain embodiments, both $R^{1a}$ and $R^{1b}$ are hydrogen. In certain embodiments, neither $R^{1a}$ nor $R^{1b}$ are hydrogen. In certain embodiments, the carbon to which $R^{1a}$ and $R^{1b}$ is attached is a stereocenter of the (R)-configuration. In certain embodiments, the carbon to which $R^{1a}$ and $R^{1b}$ is attached is a stereocenter of the (S)-configuration. In certain embodiments, $R^{1a}$ is optionally substituted $C_{1-6}$alkyl; and $R^{1b}$ is hydrogen. In certain embodiments, $R^{1a}$ is optionally substituted $C_{1-2}$alkyl; and $R^{1b}$ is hydrogen. In certain embodiments, $R^{1a}$ is —$CH_3$; and $R^{1b}$ is hydrogen. In certain embodiments, both $R^{1a}$ and $R^{1b}$ are —$CH_3$. In certain embodiments, $R^{1a}$ is optionally substituted haloalkyl; and $R^{1b}$ is hydrogen. In certain embodiments, $R^{1a}$ is —$CF_3$; and $R^{1b}$ is hydrogen. In certain embodiments, $R^{1a}$ is —$CH_2CH_2OH$; and $R^{1b}$ is hydrogen. In certain embodiments, $R^{1a}$ is —$CH_2CH_2N(R^{22})_2$; and $R^{1b}$ is hydrogen. In certain embodiments, $R^{1a}$ is —$CH_2CH_2N(R^{22})_2$; $R^{22}$ is —$CH_3$; and $R^{1b}$ is hydrogen. In certain embodiments, $R^{1a}$ is —$CH_2CH_2NHR^{22}$; and $R^{1b}$ is hydrogen. In certain embodiments, $R^{1a}$ is —$CH_2CH_2NHR^{22}$; $R^{22}$ is —$CH_2C(=O)OH$; and $R^{1b}$ is hydrogen. In certain embodiments, $R^{1a}$ is —$CH_2CH_2NHR^{22}$; $R^{22}$ is

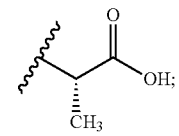

and $R^{1b}$ is hydrogen. In certain embodiments, $R^{1a}$ is —$CH_2CH_2NHR^{22}$; $R^{22}$ is

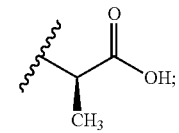

and $R^{1b}$ is hydrogen. In certain embodiments, $R^{1a}$ is optionally substituted aralkyl; and $R^{1b}$ is hydrogen. In certain embodiments, $R^{1a}$ is optionally substituted benzyl; and $R^{1b}$ is hydrogen. In certain embodiments, $R^{1a}$ is unsubstituted benzyl; and $R^{1b}$ is hydrogen. In certain embodiments, $R^{1a}$ is substituted benzyl; and $R^{1b}$ is hydrogen. In certain embodiments, $R^{1a}$ is monosubstituted benzyl; and $R^{1b}$ is hydrogen. In certain embodiments, $R^{1a}$ is benzyl substituted by one instance of halogen; and $R^{1b}$ is hydrogen. In certain embodiments, $R^{1a}$ is optionally substituted $C_{2-6}$alkenyl; and $R^{1b}$ is hydrogen. In certain embodiments, $R^{1a}$ is optionally substituted vinyl; and $R^{1b}$ is hydrogen. In certain embodiments, $R^{1a}$ is unsubstituted vinyl; and $R^{1b}$ is hydrogen. In certain embodiments, $R^{1a}$ is optionally substituted allyl; and $R^{1b}$ is hydrogen. In certain embodiments, $R^{1a}$ is unsubstituted allyl; and $R^{1b}$ is hydrogen. In certain embodiments $R^{1a}$ is optionally substituted carbocyclyl; and $R^{1b}$ is hydrogen. In certain embodiments, $R^{1a}$ is optionally substituted $C_{3-6}$carbocyclyl; and $R^{1b}$ is hydrogen. In certain embodiments, $R^{1a}$ is optionally substituted cyclopropyl; and $R^{1b}$ is hydrogen. In certain embodiments, $R^{1a}$ is unsubstituted cyclopropyl; and $R^{1b}$ is hydrogen.

In certain embodiments, at least one of $R^{2a}$ and $R^{2b}$ is hydrogen. In certain embodiments, both $R^{2a}$ and $R^{2b}$ are hydrogen. In certain embodiments, neither $R^{2a}$ nor $R^{2b}$ are hydrogen. In certain embodiments, $R^{2a}$ is optionally substituted $C_{1-6}$alkyl; and $R^{2b}$ is hydrogen. In certain embodiments, $R^{2a}$ is optionally substituted $C_{1-2}$alkyl; and $R^{2b}$ is hydrogen. In certain embodiments, $R^{Z2}$ is —$CH_3$; and $R^{2b}$ is hydrogen. In certain embodiments, both $R^{2a}$ and $R^{2b}$ are —$CH_3$. In certain embodiments, $R^{2a}$ is optionally substituted haloalkyl; and $R^{2b}$ is hydrogen. In certain embodiments, $R^{2a}$ is —$CF_3$; and $R^{2b}$ is hydrogen. In certain embodiments, $R^{2a}$ is halogen; and $R^{2b}$ is hydrogen. In certain embodiments, $R^{2a}$ is —F; and $R^{2b}$ is hydrogen. In certain embodiments, $R^{2a}$ is halogen; and $R^{2b}$ is $C_{1-6}$alkyl. In certain embodiments, $R^{2a}$ is —F; and $R^{2b}$ is $C_{1-6}$alkyl. In certain embodiments, $R^{2a}$ is halogen; and $R^{2b}$ is —$CH_3$. In certain embodiments, $R^{2a}$ is —F; and $R^{2b}$ is —$CH_3$.

In certain embodiments, the carbon to which $R^4$ is attached is a stereocenter of the (R)-configuration. In certain embodiments, the carbon to which $R^4$ is attached is a stereocenter of the (S)-configuration. In certain embodiments, $R^3$ is hydrogen; and $R^4$ is not hydrogen. In certain embodiments, neither $R^3$ nor $R^4$ are hydrogen. In certain embodiments, $R^3$ is hydrogen. In certain embodiments, $R^3$ is optionally substituted $C_{1-6}$alkyl. In certain embodiments, $R^3$ is optionally substituted $C_{1-2}$alkyl. In certain embodiments, $R^3$ is —$CH_3$. In certain embodiments, $R^3$ is optionally substituted $C_{2-6}$alkenyl. In certain embodiments, $R^3$ is optionally substituted allyl. In certain embodiments, $R^3$ is unsubstituted allyl. In certain embodiments, $R^3$ is allyl substituted with one optionally substituted heteroaryl ring. In certain embodiments, $R^3$ is allyl substituted with one optionally substituted quinoline ring. In certain embodiments, $R^3$ is hydrogen; and $R^4$ is —$CH_3$. In certain embodiments, $R^3$ is optionally substituted $C_{1-6}$alkyl; and $R^4$ is —$CH_3$. In certain embodiments, $R^3$ is optionally substituted $C_{1-2}$alkyl; and $R^4$ is —$CH_3$. In certain embodiments, $R^3$ is —$CH_3$; and $R^4$ is —$CH_3$. In certain embodiments, $R^3$ is optionally substituted $C_{2-6}$alkenyl; and $R^4$ is —$CH_3$. In certain embodiments, $R^3$ is optionally substituted allyl; and $R^4$ is —$CH_3$. In certain embodiments, $R^3$ is unsubstituted allyl; and $R^4$ is —$CH_3$. In certain embodiments, $R^3$ is allyl substituted with one optionally substituted heteroaryl ring; and $R^4$ is —$CH_3$. In certain embodiments, $R^3$ is allyl substituted with one optionally substituted quinoline ring; and $R^4$ is —$CH_3$. In certain embodiments, $R^4$ is optionally substituted $C_{1-6}$alkyl. In certain embodiments, $R^4$ is optionally substituted $C_{1-2}$alkyl. In certain embodiments, $R^4$ is —$CH_3$. In certain embodiments, $R^4$ is optionally substituted $C_{2-6}$alkenyl. In certain embodiments, $R^4$ is optionally substituted allyl. In certain embodiments, $R^4$ is unsubstituted allyl. In certain embodiments, $R^4$ is allyl substituted with one optionally substituted heteroaryl ring. In certain embodiments, $R^4$ is allyl substituted with one optionally substituted quinoline ring. In certain embodiments, $R^4$ is —$CH_2CH_2OH$. In certain embodiments, $R^4$ is —$CH_2CH_2N(R^{22})_2$. In certain embodiments, $R^4$ is —$CH_2CH_2N(R^{22})_2$; and $R^{Z2}$ is —$CH_3$. In certain embodiments, $R^4$ is —$CH_2CHO$. In certain embodiments, $R^4$ is optionally substituted $C_{1-6}$alkyl; and $R^3$ is —$CH_3$. In certain embodiments, $R^4$ is optionally substituted $C_{1-2}$alkyl; and $R^3$ is —$CH_3$. In certain embodiments, $R^4$ is optionally substituted $C_{2-6}$alkenyl; and $R^3$ is —$CH_3$. In certain embodiments, $R^4$ is optionally substituted allyl; and $R^3$ is —$CH_3$. In certain embodiments, $R^4$ is unsubstituted allyl; and $R^3$ is —$CH_3$. In certain embodiments, $R^4$ is allyl substituted with one optionally substituted heteroaryl ring; and $R^3$ is —$CH_3$. In certain embodiments, $R^4$ is allyl substituted with one optionally substituted quinoline ring; and $R^3$ is —$CH_3$. In certain embodiments, $R^4$ is —$CH_2CH_2OH$; and $R^3$ is —$CH_3$. In certain embodiments, $R^4$ is —$CH_2CH_2N(R^{22})_2$; and $R^3$ is —$CH_3$. In certain embodiments, $R^4$ is —$CH_2CH_2N(R^{22})_2$; $R^{Z2}$ is —$CH_3$; and $R^3$ is —$CH_3$. In certain embodiments, $R^4$ is —$CH_2CHO$; and $R^3$ is —$CH_3$. In certain embodiments, $R^4$ is optionally substituted $C_{1-6}$alkyl; and $R^3$ is hydrogen. In certain embodiments, $R^4$ is optionally substituted $C_{1-2}$alkyl; and $R^3$ is hydrogen. In certain embodiments, $R^4$ is optionally substituted $C_{2-6}$alkenyl; and $R^3$ is hydrogen. In certain embodiments, $R^4$ is optionally substituted allyl; and $R^3$ is hydrogen. In certain embodiments, $R^4$ is unsubstituted allyl; and $R^3$ is hydrogen. In certain embodiments, $R^4$ is allyl substituted with one optionally substituted heteroaryl ring; and $R^3$ is hydrogen. In certain embodiments, $R^4$ is allyl substituted with one optionally substituted quinoline ring; and $R^3$ is hydrogen. In certain embodiments, $R^4$ is —$CH_2CH_2OH$; and $R^3$ is hydrogen. In certain embodiments, $R^4$ is —$CH_2CH_2N(R^{22})_2$; and $R^3$ is hydrogen. In certain embodiments, $R^4$ is —$CH_2CH_2N(R^{22})_2$; $R^{Z2}$ is —$CH_3$; and $R^3$ is hydrogen. In certain embodiments, $R^4$ is —$CH_2CHO$; and $R^3$ is hydrogen. In certain embodiments, $R^4$ is optionally substituted $C_{1-6}$alkyl; and $R^{21}$ is hydrogen. In certain embodiments, $R^4$ is optionally substituted $C_{1-2}$alkyl; and $R^{21}$ is hydrogen. In certain embodiments, $R^4$ is optionally substituted $C_{2-6}$alkenyl; and $R^{21}$ is hydrogen. In certain embodiments, $R^4$ is optionally substituted allyl; and $R^{21}$ is hydrogen. In certain embodiments, $R^4$ is unsubstituted allyl; and $R^{21}$ is hydrogen. In certain embodiments, $R^4$ is allyl substituted with one optionally substituted heteroaryl ring; and $R^{21}$ is hydrogen. In certain embodiments, $R^4$ is allyl substituted with one optionally substituted quinoline ring; and $R^{21}$ is hydrogen. In certain embodiments, $R^4$ is —$CH_2CH_2OH$; and $R^{21}$ is hydrogen. In certain embodiments, $R^4$ is —$CH_2CH_2N(R^{22})_2$; and $R^{21}$ is hydrogen. In certain embodiments, $R^4$ is —$CH_2CH_2N(R^{22})_2$; $R^{22}$ is —$CH_3$; and $R^{21}$ is hydrogen. In certain embodiments, $R^4$ is —$CH_2CHO$; and $R^{21}$ is hydrogen.

In certain embodiments, $R^9$ is hydrogen. In certain embodiments, $R^9$ is not hydrogen. In certain embodiments, $R^9$ is an oxygen protecting group. In certain embodiments, $R^9$ is

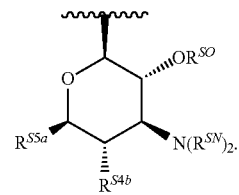

In certain embodiments, $R^{SO}$ is hydrogen. In certain embodiments, $R^{SO}$ is an oxygen protecting group. In certain embodiments, $R^9$ is methyl carbonate. In certain embodiments, at least one $R^{SN}$ is hydrogen. In certain embodiments, at least one $R^{SN}$ is —$CH_3$. In certain embodiments, one $R^{SN}$ is —$CH_3$; and the second $R^{SN}$ is hydrogen. In certain embodiments, both $R^{SN}$ groups are —$CH_3$. In certain embodiments, $R^{S4b}$ is hydrogen. In certain embodiments, $R^{S4b}$ is not hydrogen. In certain embodiments, $R^{S4b}$ is —$OR^{SO}$; and $R^{SO}$ is hydrogen. In certain embodiments, $R^{S4b}$ is —OR$^{SO}$; and R$^{SO}$ is an oxygen protecting group. In certain embodiments, R$^{S5a}$ is optionally substituted alkyl. In certain embodiments, R$^{S5a}$ is alkoxyalkyl. In certain embodiments, R$^{S5a}$ is —CH$_2$OH. In certain embodiments, R$^{S5a}$ is —CH$_2$OBz. In certain embodiments, R$^{S5a}$ is aminoalkyl. In certain embodiments, R$^{S5a}$ is —CH$_2$NH$_2$. In certain embodiments, R$^9$ is

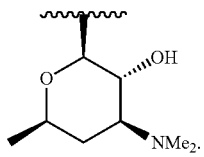 [SMILES: *[C@@H]1O[C@H](C)C[C@H](N(C)C)[C@H]1O]

In certain embodiments, R$^9$ is

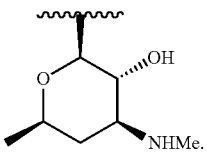 [SMILES: *[C@@H]1O[C@H](C)C[C@H](NC)[C@H]1O]

In certain embodiments, R$^9$ is

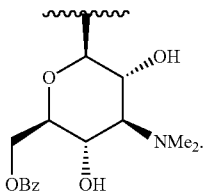

In certain embodiments, R$^9$ is

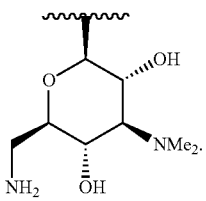 [SMILES: *[C@@H]1O[C@H](CN)[C@@H](O)[C@H](N(C)C)[C@H]1O]

In certain embodiments, R$^9$ is

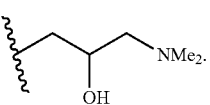

In certain embodiments, the carbon to which R$^{5a}$ and R$^{5b}$ is attached is a stereocenter of the (R)-configuration. In certain embodiments, the carbon to which R$^{5a}$ and R$^{5b}$ is attached is a stereocenter of the (S)-configuration. In certain embodiments, at least one of R$^{5a}$ and R$^{5b}$ is hydrogen. In certain embodiments, both R$^{5a}$ and R$^{5b}$ are hydrogen. In certain embodiments, neither R$^{5a}$ nor R$^{5b}$ are hydrogen. In certain embodiments, at least one instance of R$^{5a}$ and R$^{5b}$ is optionally substituted alkyl. In certain embodiments, at least one instance of R$^{5a}$ and R$^{5b}$ is optionally substituted C$_{1-6}$alkyl. In certain embodiments, at least one instance of R$^{5a}$ and R$^{5b}$ is optionally substituted C$_{1-2}$alkyl. In certain embodiments, at least one instance of R$^{5a}$ and R$^{5b}$ is unsubstituted C$_{1-2}$alkyl. In certain embodiments, at least one instance of R$^{5a}$ and R$^{5b}$ is —CH$_3$. In certain embodiments, R$^{5a}$ is optionally substituted alkyl; and R$^{5b}$ is hydrogen. In certain embodiments, R$^{5a}$ is optionally substituted C$_{1-6}$alkyl; and R$^{5b}$ is hydrogen. In certain embodiments, R$^{5a}$ is optionally substituted C$_{1-2}$alkyl; and is hydrogen. In certain embodiments, R$^{5a}$ is unsubstituted C$_{1-2}$alkyl; and R$^{5b}$ is hydrogen. In certain embodiments, R$^{5a}$ is —CH$_3$; and R$^{5b}$ is hydrogen. In certain embodiments, both instances of R$^{5a}$ and R$^{5b}$ are —CH$_3$. In certain embodiments, neither R$^{5a}$ nor R$^{5b}$ is —CH$_3$.

In certain embodiments, R$^{17}$ is hydrogen. In certain embodiments, R$^{17}$ is not hydrogen. In certain embodiments, R$^{17}$ is an oxygen protecting group. In certain embodiments, R$^{17}$ is —C(=O)R$^{Z8}$.

In certain embodiments, the carbon to which R$^6$ and R$^{10}$ is attached is a stereocenter of the (R)-configuration. In certain embodiments, the carbon to which R$^6$ and R$^{10}$ is attached is a stereocenter of the (S)-configuration. In certain embodiments, at least one of R$^6$ and R$^{10}$ is hydrogen. In certain embodiments, both R$^6$ and R$^{10}$ are hydrogen. In certain embodiments, neither R$^6$ nor R$^{10}$ are hydrogen. In certain embodiments, at least one instance of R$^6$ and R$^{10}$ is optionally substituted alkyl. In certain embodiments, at least one instance of R$^6$ and R$^{10}$ is optionally substituted C$_{1-6}$alkyl. In certain embodiments, at least one instance of R$^6$ and R$^{10}$ is optionally substituted C$_{1-2}$alkyl. In certain embodiments, at least one instance of R$^6$ and R$^{10}$ is —CH$_3$. In certain embodiments, at least one instance of R$^6$ and R$^{10}$ is —CH$_2$CN. In certain embodiments, at least one instance of R$^6$ and R$^{10}$ is —CH$_2$C(=O)OR$^{32}$; and R$^{32}$ is optionally substituted alkyl or hydrogen. In certain embodiments, at least one instance of R$^6$ and R$^{10}$ is optionally substituted heteroaralkyl. In certain embodiments, at least one instance of R$^6$ and R$^{10}$ is optionally substituted pyrazolylalkyl. In certain embodiments, at least one instance of R$^6$ and R$^{10}$ is imidazolylalkyl. In certain embodiments, at least one instance of R$^6$ and R$^{10}$ is thiazolylalkyl. In certain embodiments, at least one instance of R$^6$ and R$^{10}$ is oxazolylalkyl. In certain embodiments, at least one instance of R$^6$ and R$^{10}$ is pyridinylalkyl. In certain embodiments, at least one instance of R$^6$ and R$^{10}$ is pyrimidinylalkyl. In certain embodiments, at least one instance of R$^6$ and R$^{10}$ is pyrazinylalkyl. In certain embodiments, at least one instance of R$^6$ and R$^{10}$ is optionally substituted alkenyl. In certain embodiments, at least one instance of R$^6$ and R$^{10}$ is optionally substituted allyl. In certain embodiments, at least one instance of R$^6$ and R$^{10}$ is unsubstituted allyl. In certain embodiments, at least one instance of R$^6$ and R$^{10}$ is optionally substituted aralkyl. In certain embodiments, at least one instance of R$^6$ and R$^{10}$ is optionally substituted benzyl. In certain embodiments, at least one instance of R$^6$ and R$^{10}$ is unsubstituted benzyl. In certain embodiments, R$^6$ is optionally substituted alkyl; and R$^{10}$ is hydrogen. In certain embodiments, R$^6$ is optionally substituted C$_{1-6}$alkyl; and R$^{10}$ is hydrogen. In certain embodiments, R$^6$ is optionally substituted C$_{1-2}$alkyl; and R$^{10}$ is hydrogen. In certain embodiments, R$^6$ is —CH$_3$; and R$^{10}$ is hydrogen. In certain embodiments, R$^6$ is —CH$_2$CN; and R$^{10}$ is hydrogen. In certain embodiments, R$^6$ is —CH$_2$C(=O)OR$^{32}$; R$^{32}$ is optionally substituted alkyl or hydrogen; and R$^{10}$ is hydrogen. In certain embodiments, R$^6$ is optionally substituted heteroaralkyl; and R$^{10}$ is hydrogen. In certain embodiments, R$^6$ is optionally substituted pyrazolylalkyl; and $R^{10}$ is hydrogen. In certain embodiments, $R^6$ is imidazolylalkyl; and $R^{10}$ is hydrogen. In certain embodiments, $R^6$ is thiazolylalkyl; and $R^{10}$ is hydrogen. In certain embodiments, $R^6$ is oxazolylalkyl; and $R^{10}$ is hydrogen. In certain embodiments, $R^6$ is pyridinylalkyl; and $R^{10}$ is hydrogen. In certain embodiments, $R^6$ is pyrimidinylalkyl; and $R^{10}$ is hydrogen. In certain embodiments, $R^6$ is pyrazinylalkyl; and $R^{10}$ is hydrogen. In certain embodiments, $R^6$ is optionally substituted alkenyl; and $R^{10}$ is hydrogen. In certain embodiments, $R^6$ is optionally substituted allyl; and $R^{10}$ is hydrogen. In certain embodiments, $R^6$ is unsubstituted allyl; and $R^{10}$ is hydrogen. In certain embodiments, $R^6$ is optionally substituted aralkyl; and $R^{10}$ is hydrogen. In certain embodiments, $R^6$ is optionally substituted benzyl; and $R^{10}$ is hydrogen. In certain embodiments, $R^6$ is unsubstituted benzyl; and $R^{10}$ is hydrogen. In certain embodiments, at least one instance of $R^6$ and $R^{10}$ is halogen. In certain embodiments, at least one instance of $R^6$ and $R^{10}$ is fluorine. In certain embodiments, both $R^6$ and $R^{10}$ are halogen. In certain embodiments, both $R^6$ and $R^{10}$ are fluorine. In certain embodiments, $R^6$ is optionally substituted alkyl; and $R^{10}$ is halogen. In certain embodiments, $R^6$ is optionally substituted $C_{1-6}$alkyl; and $R^{10}$ is halogen. In certain embodiments, $R^6$ is optionally substituted $C_{1-2}$alkyl; and $R^{10}$ is halogen. In certain embodiments, $R^6$ is —$CH_3$; and $R^{10}$ is halogen. In certain embodiments, $R^6$ is optionally substituted alkyl; and $R^{10}$ is fluorine. In certain embodiments, $R^6$ is optionally substituted $C_{1-6}$alkyl; and $R^{10}$ is fluorine. In certain embodiments, $R^6$ is optionally substituted $C_{1-2}$alkyl; and $R^{10}$ is fluorine. In certain embodiments, $R^6$ is —$CH_3$; and $R^{10}$ is fluorine.

In certain embodiments, $R^{14}$ is hydrogen. In certain embodiments, $R^{14}$ is not hydrogen. In certain embodiments, $R^{14}$ is

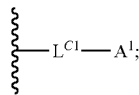

and $A^1$ is —$N_3$. In certain embodiments, $R^{14}$ is

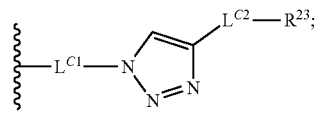

and $L^{C2}$ is a bond. In certain embodiments, $L^{C1}$ is a linking group comprising at least one instance of optionally substituted alkylene. In certain embodiments, $L^{C1}$ is a linking group comprising at least one instance of substituted or unsubstituted $C_{3-6}$alkylene. In certain embodiments, $L^{C1}$ is an alkylene linking group of the formula —$(CH_2)_n$—, wherein n is 3, 4, or 5. In certain embodiments, $L^{C1}$ is a linking group comprising at least one instance of optionally substituted alkenylene. In certain embodiments, $L^{C1}$ is a linking group comprising at least one instance of substituted or unsubstituted $C_{3-6}$alkenylene. In certain embodiments, $L^{C1}$ is a linking group comprising at least one instance of optionally substituted alkynylene. In certain embodiments, $L^{C1}$ is a linking group comprising at least one instance of substituted or unsubstituted $C_{3-6}$alkynylene. In certain embodiments, $R^{23}$ is optionally substituted aryl. In certain embodiments, $R^{23}$ is optionally substituted phenyl. In certain embodiments, $R^{23}$ is optionally substituted 5-6 membered heteroaryl. In certain embodiments, $R^{23}$ is optionally substituted aniline. In certain embodiments, $R^{23}$ is optionally substituted pyridazine. In certain embodiments, $R^{23}$ is optionally substituted pyridine. In certain embodiments, $R^{23}$ is optionally substituted aminopyridine. In certain embodiments, $R^{23}$ is optionally substituted thiazole. In certain embodiments, $R^{23}$ is optionally substituted aminothiazole. In certain embodiments, $R^{23}$ is optionally substituted thiadiazole. In certain embodiments, $R^{23}$ is optionally substituted aminothiadiazole. In certain embodiments, $R^{23}$ is optionally substituted 5,6 fused-bicyclic heteroaryl. In certain embodiments, $R^{23}$ is optionally substituted benzothiazole.

In certain embodiments, known macrolides, such as the macrolides disclosed in FIG. 1, are specifically excluded. Exemplary novel macrolides of the present invention include, but are not limited to, any one of the following macrolides provided in Tables A-L, and salts thereof.

TABLE A

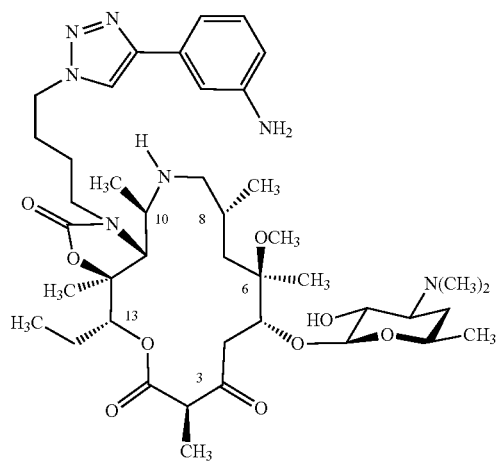

FSM-10781

TABLE A-continued
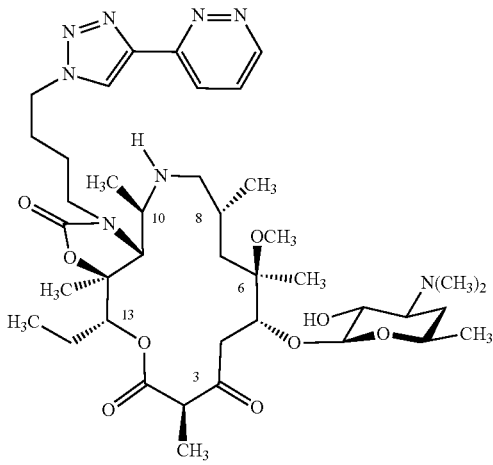
FSM-10785
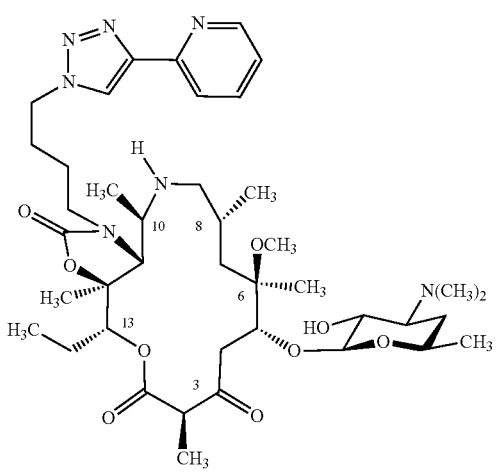
FSM-10786
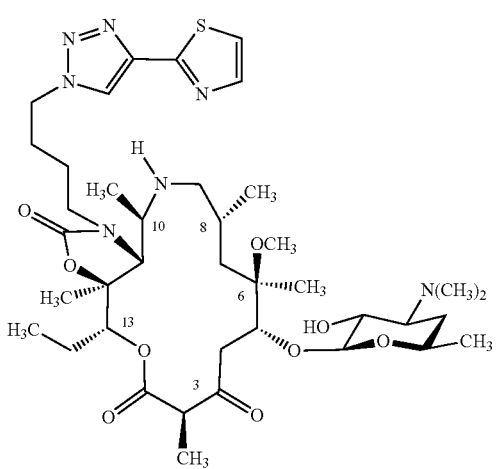
FSM-10787

TABLE A-continued
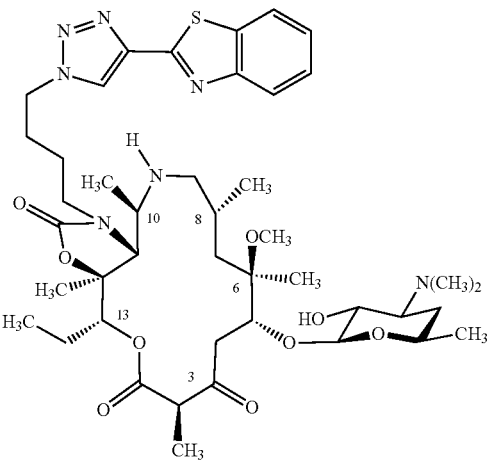
FSM-10788
FSM-10794
FSM-10792

TABLE A-continued
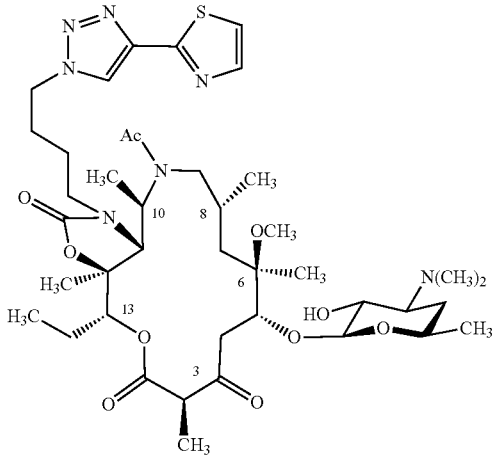
FSM-10790
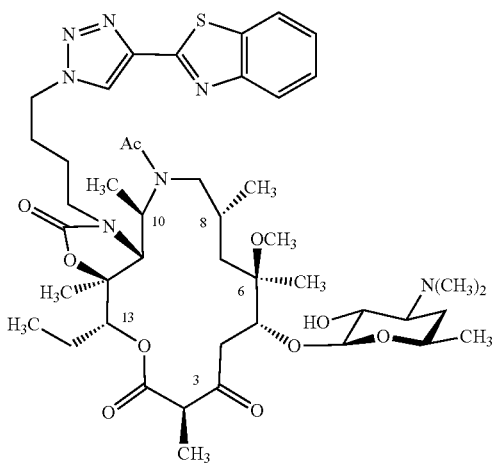
FSM-10791
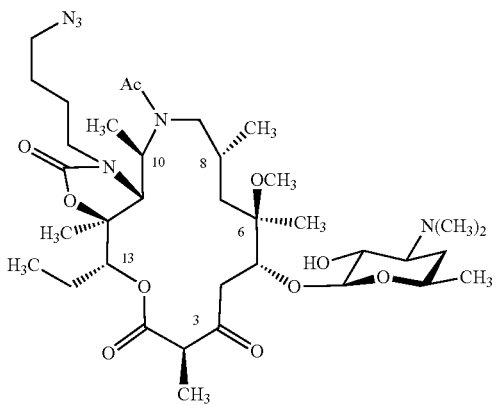
FSM-10789

TABLE A-continued
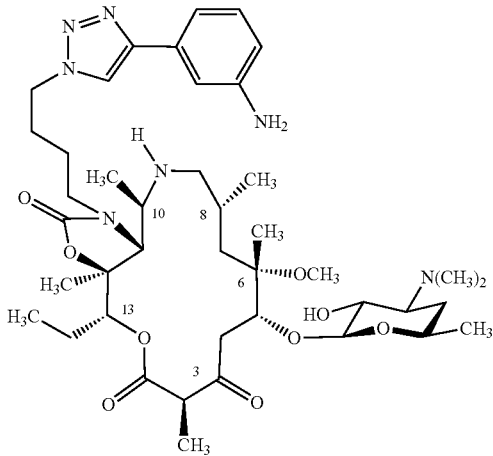
FSM-30502
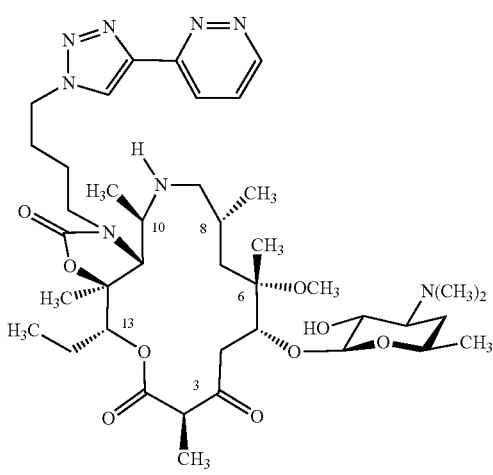
FSM-30506
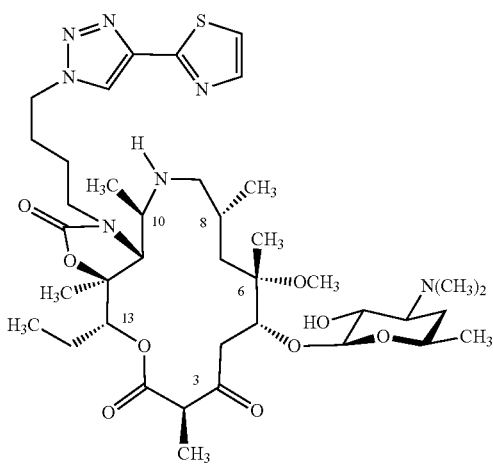
FSM-30501

TABLE A-continued
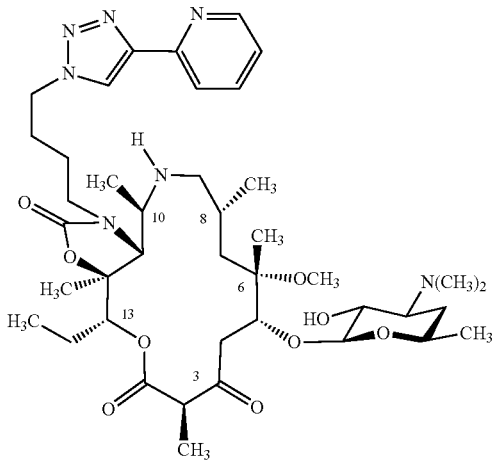
FSM-30517
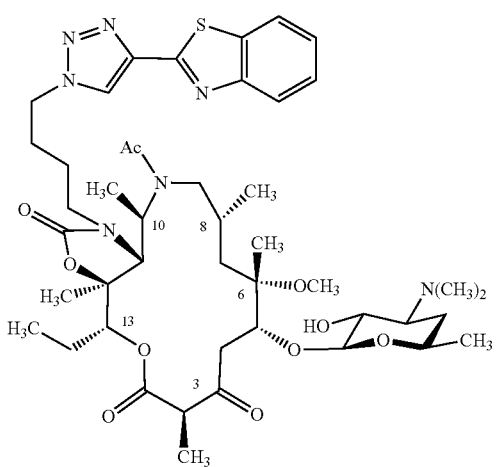
FSM-30514
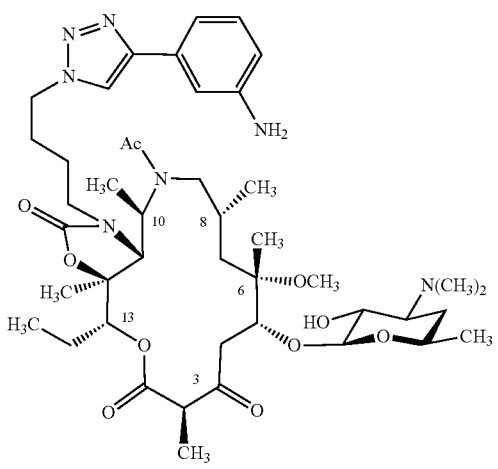
FSM-30512

TABLE A-continued
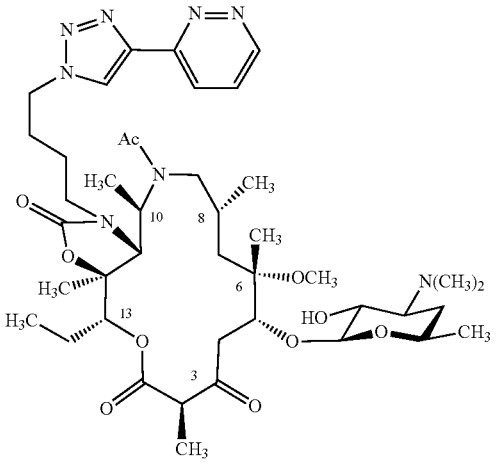
FSM-30513
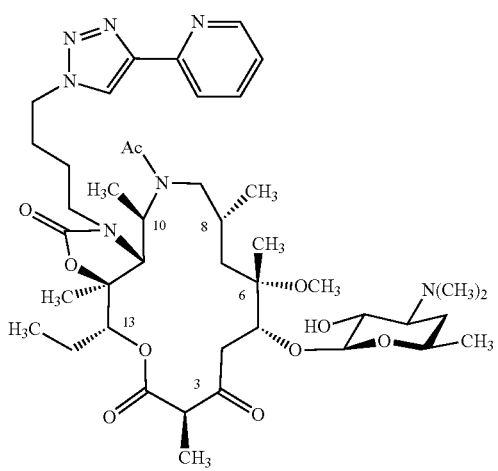
FSM-30515
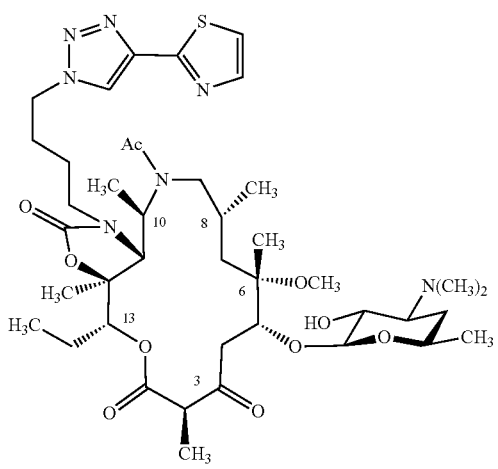
FSM-30503

TABLE A-continued
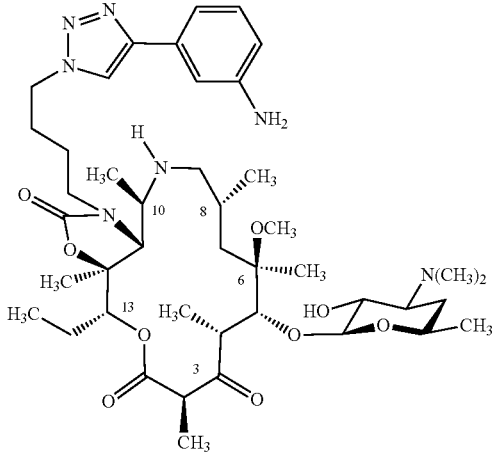
FSM-20707
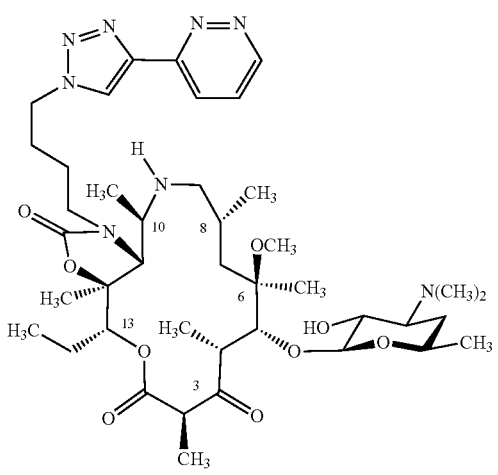
FSM-20710
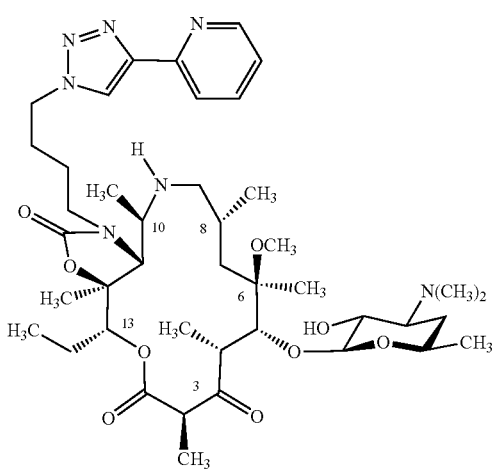
FSM-20706

TABLE A-continued
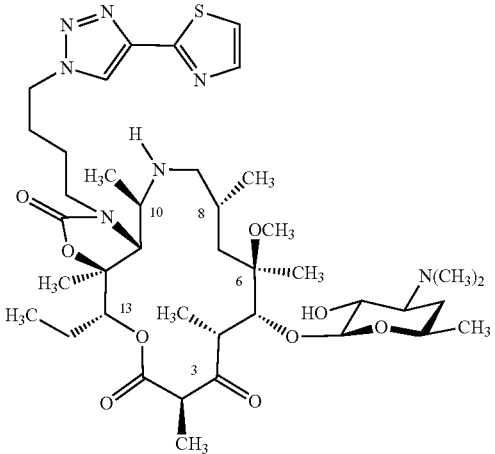
FSM-20708
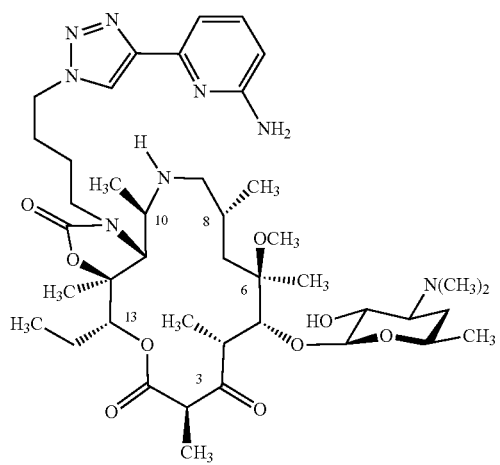
FSM-20715
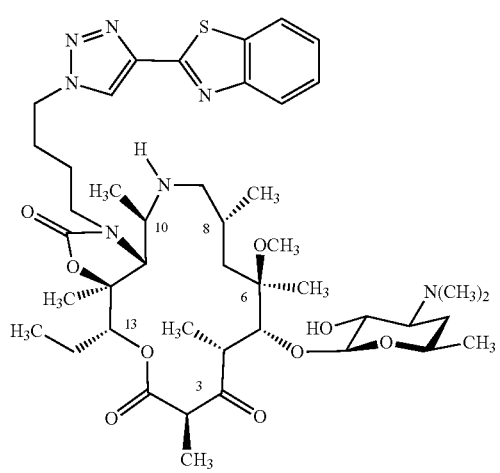
FSM-20711

TABLE A-continued
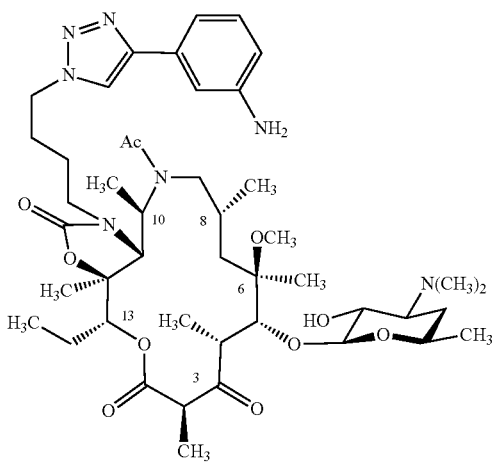
FSM-20767
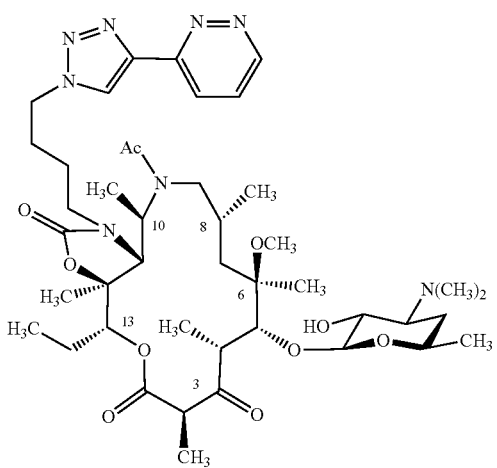
FSM-20764
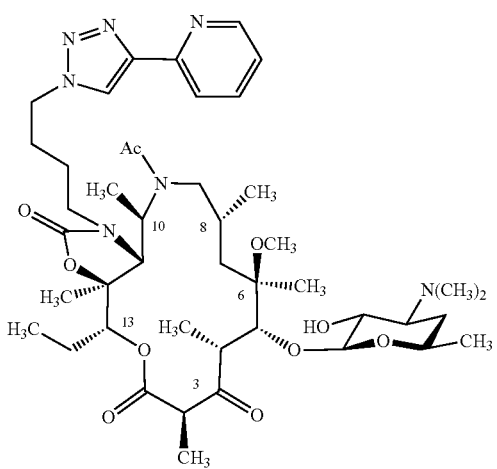
FSM-20766

TABLE A-continued
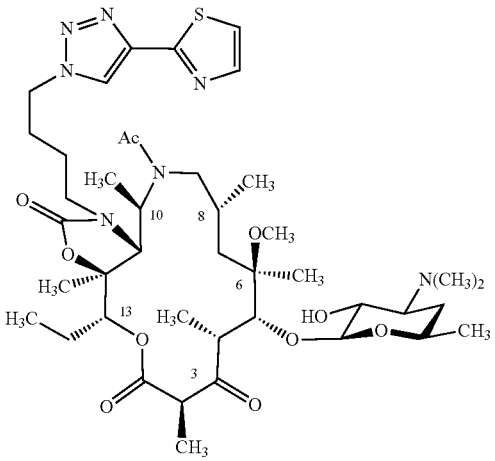
FSM-20763
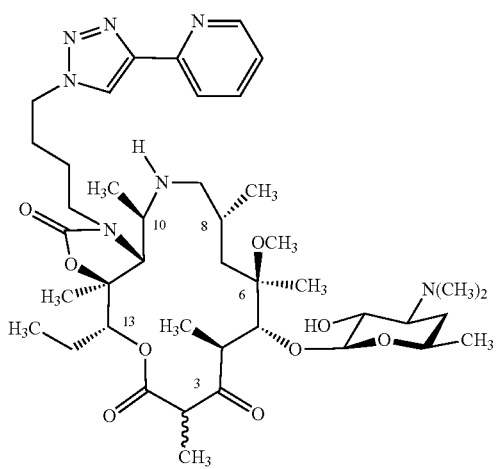
FSM-20754
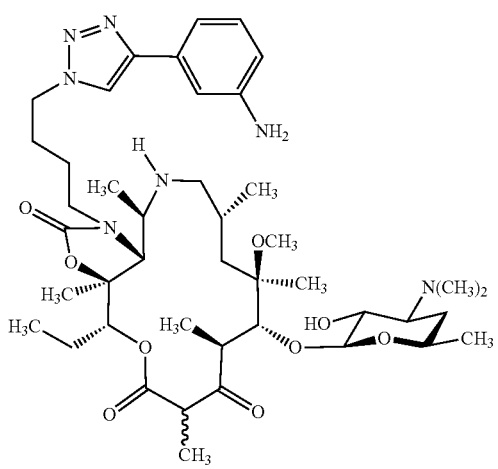
FSM-20789

TABLE A-continued
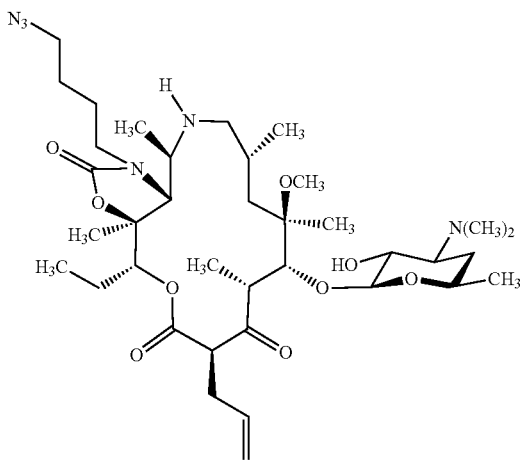
FSM-56131
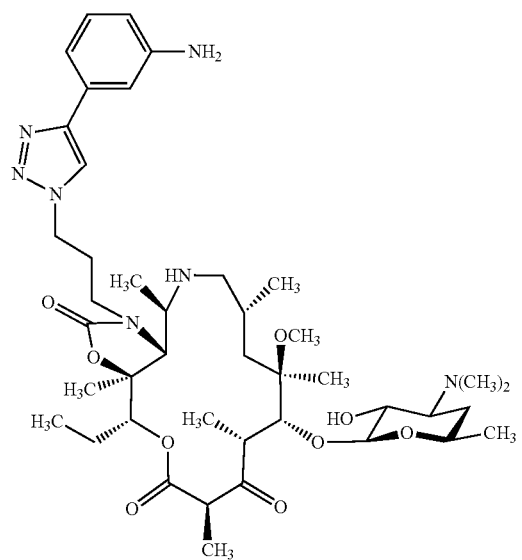
FSM-40347
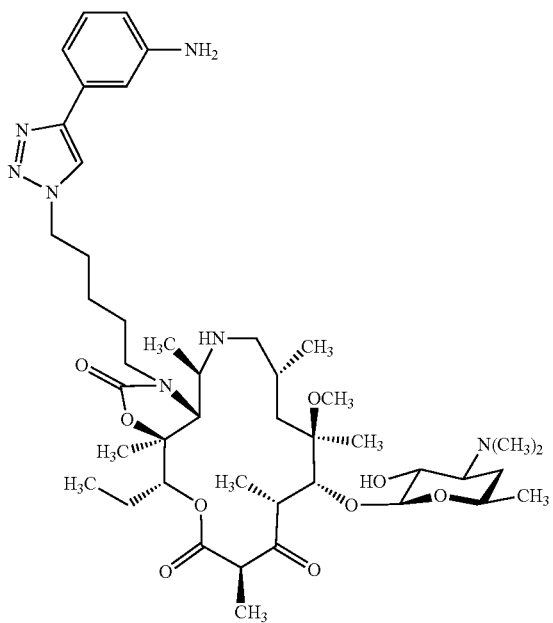
FSM-40349

TABLE A-continued
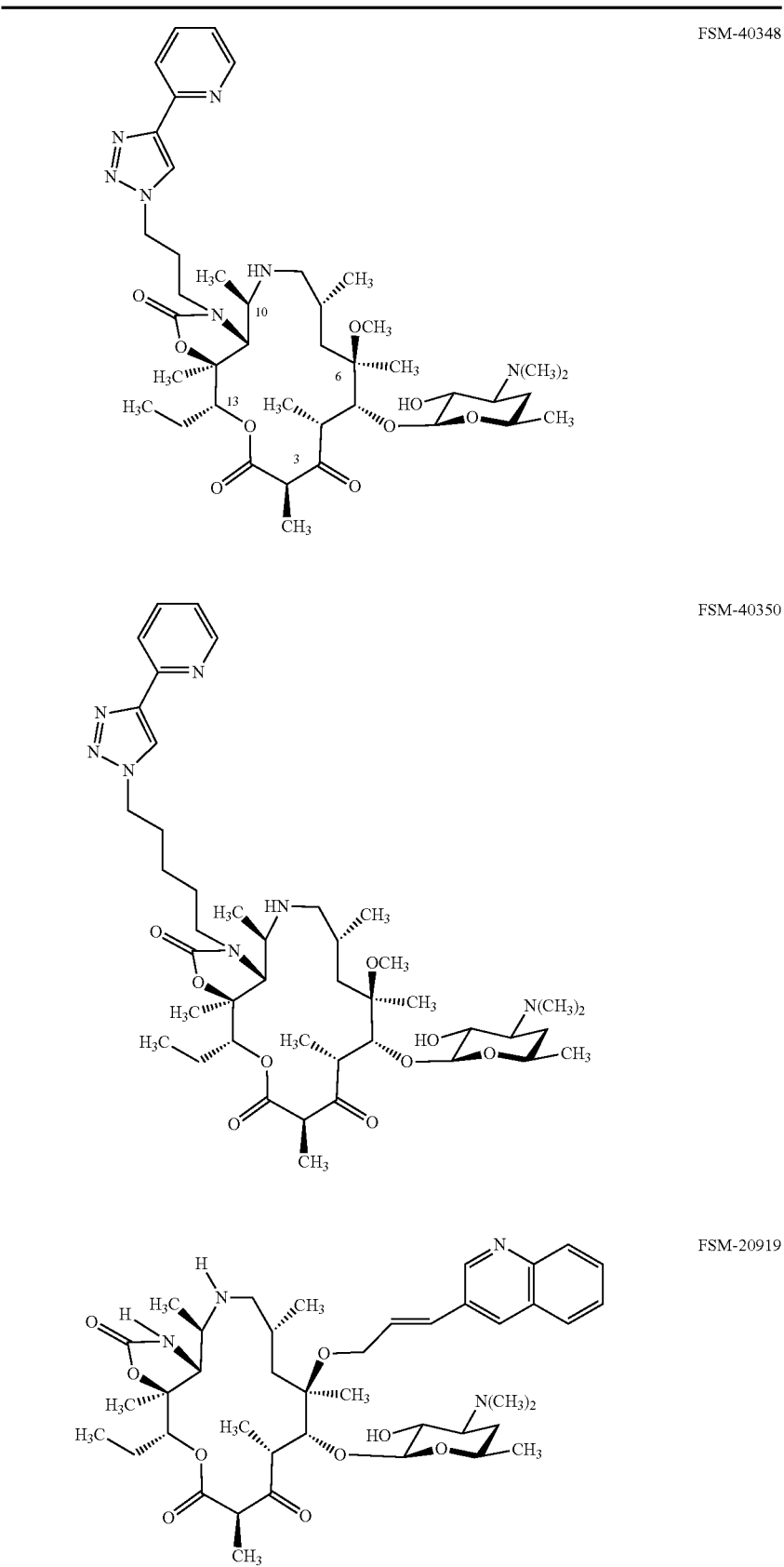

TABLE A-continued
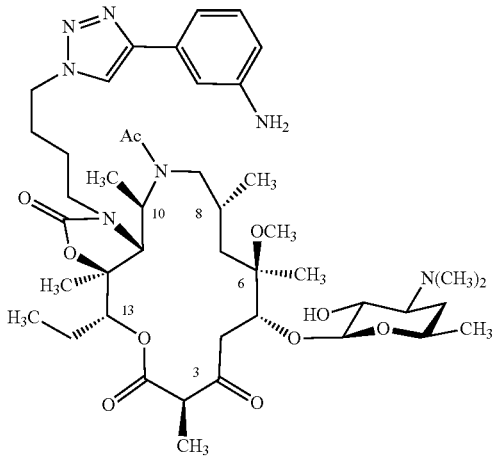
FSM-10793
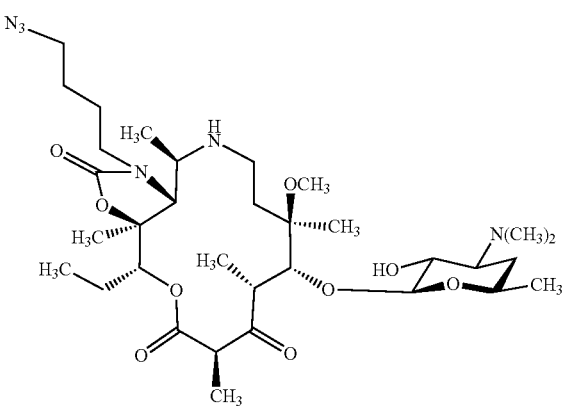
FSM-30604
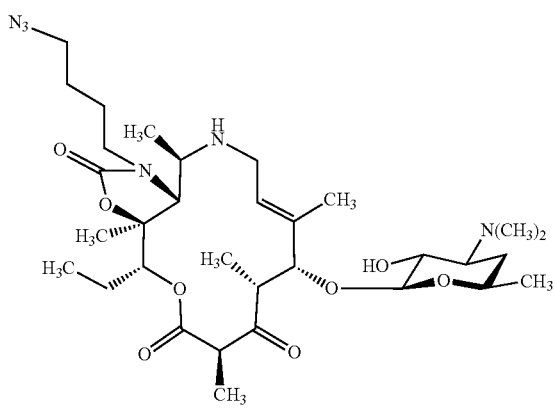
FSM-30608

TABLE A-continued
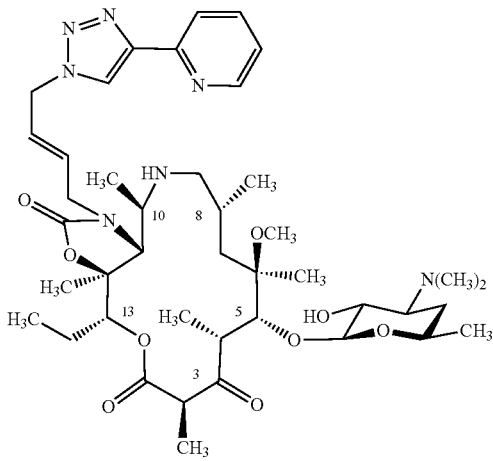
FSM-70153
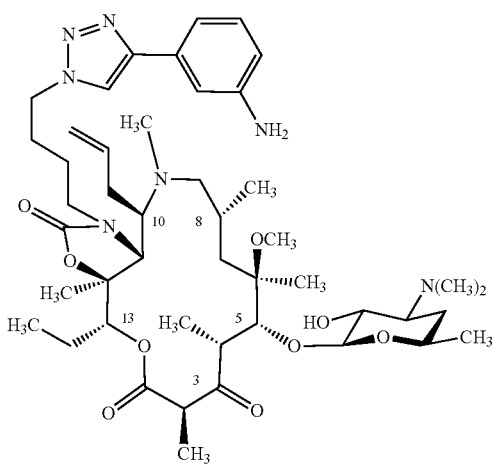
FSM-11094
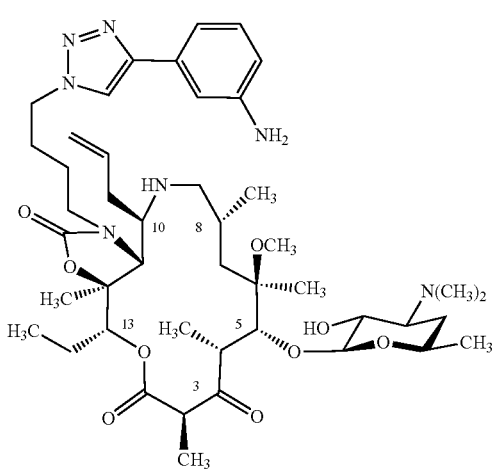
FSM-11044

TABLE A-continued
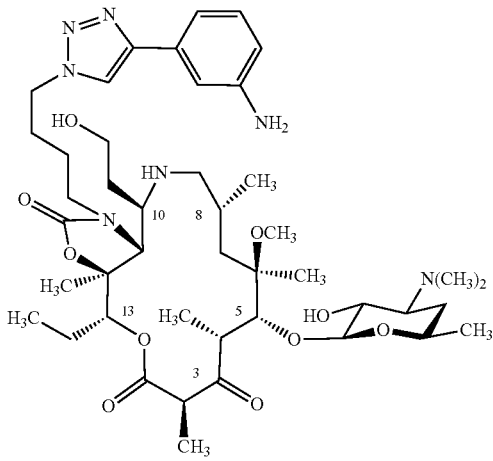
FSM-11056
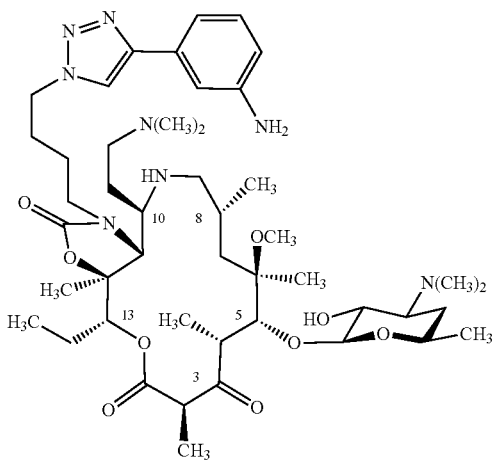
FSM-11052
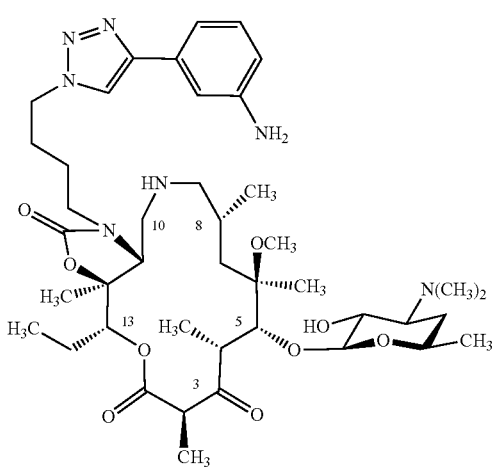
FSM-11031

TABLE A-continued
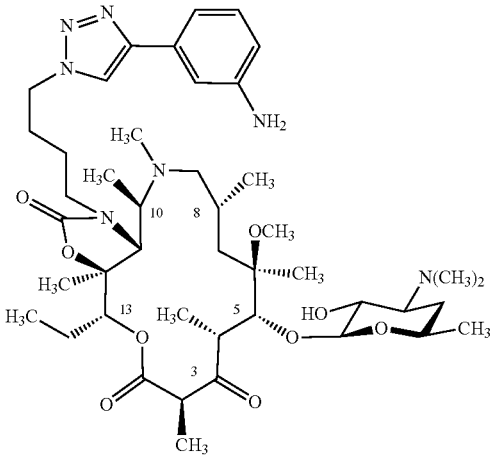
FSM-21339
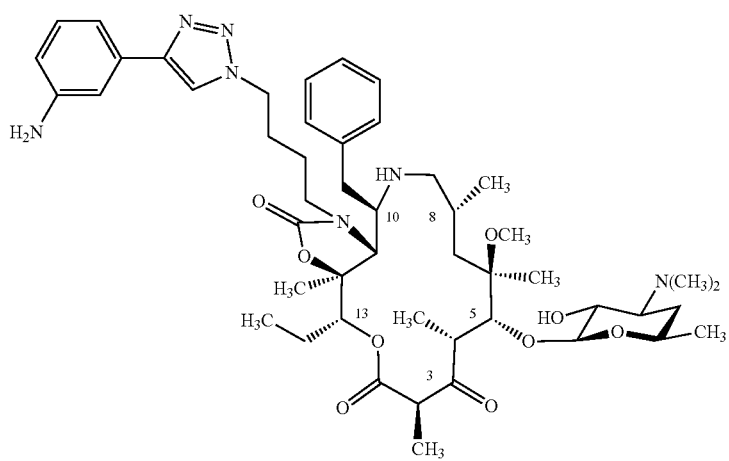
FSM-60353
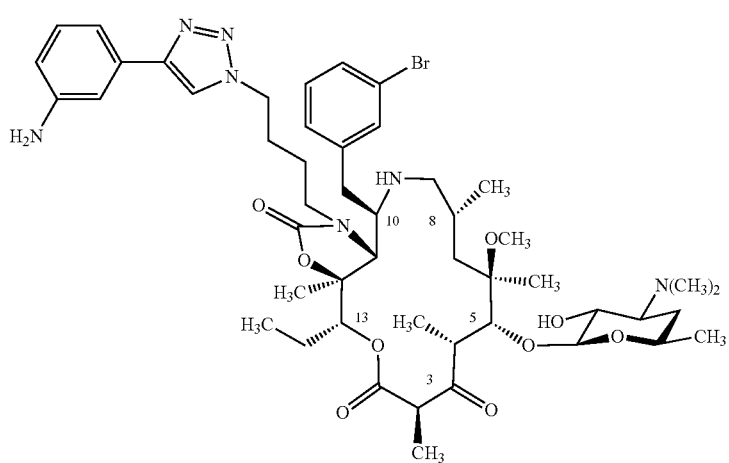
FSM-60415

TABLE A-continued
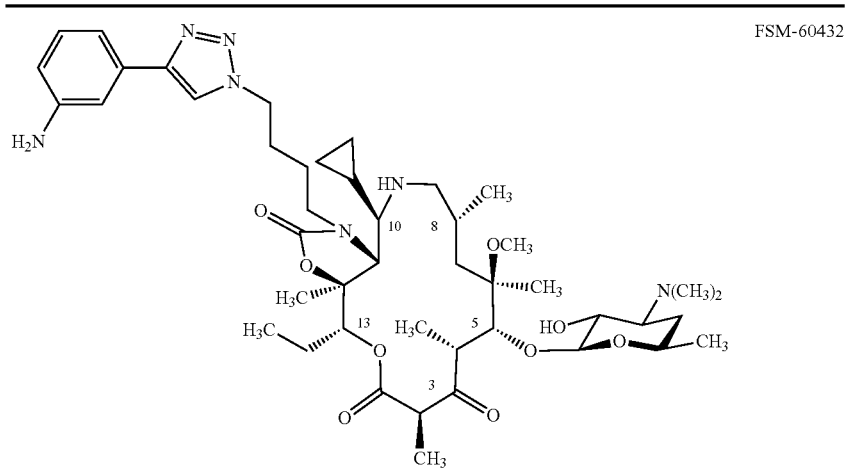
FSM-60432
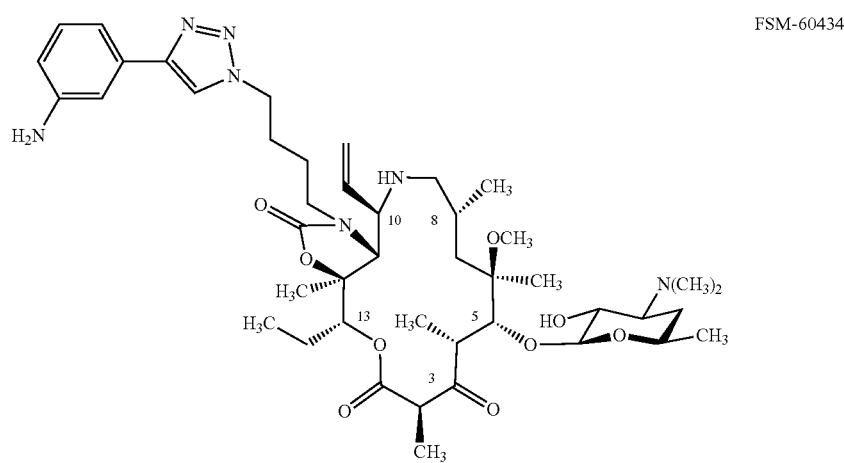
FSM-60434
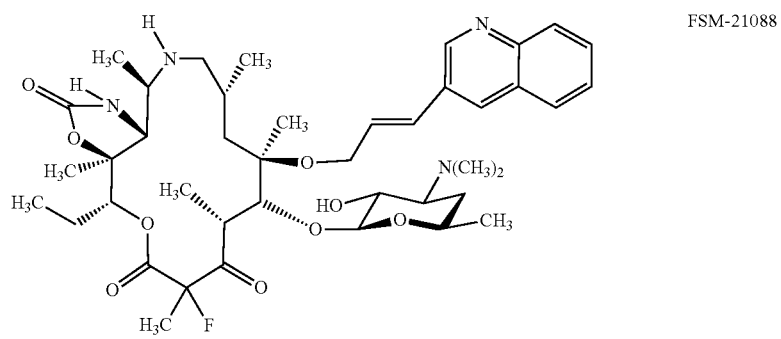
FSM-21088
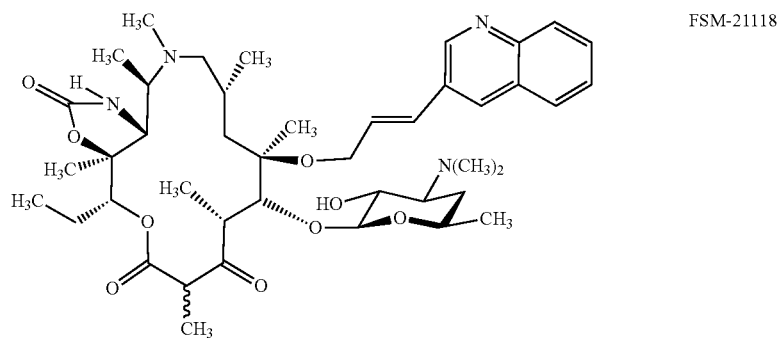
FSM-21118

TABLE A-continued
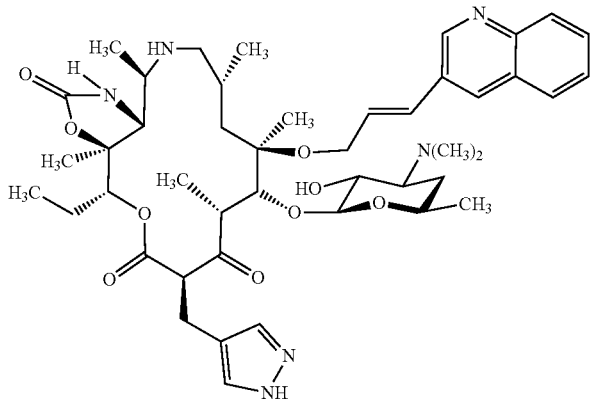
FSM-21064
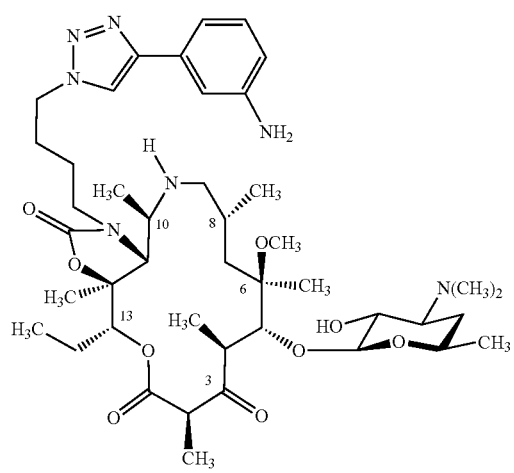
FSM-20707a
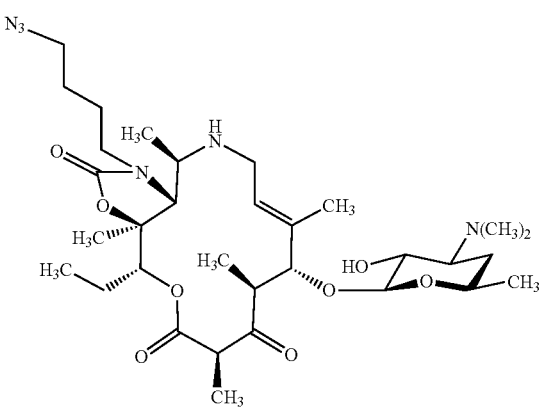
FSM-30608a TABLE A-continued
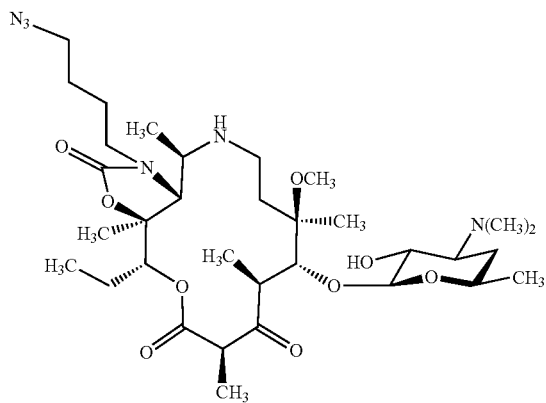
FSM-30604a
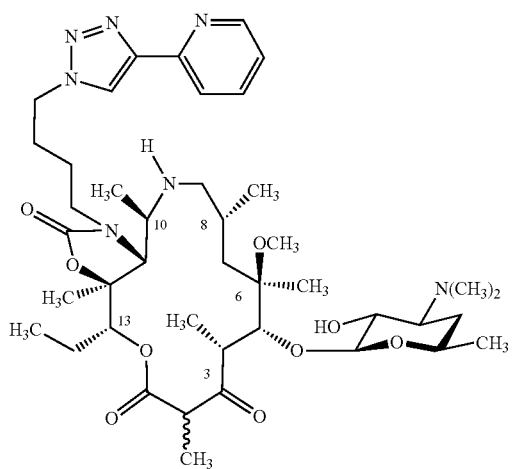
FSM-20754a
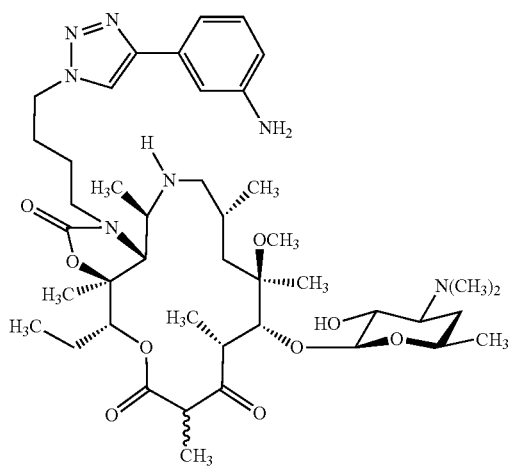
FSM-20789a TABLE A-continued
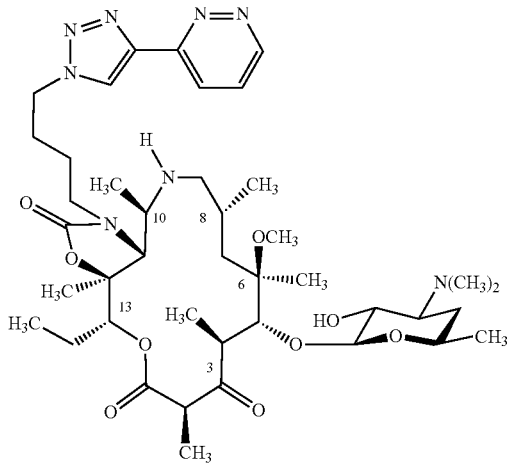
FSM-20710a
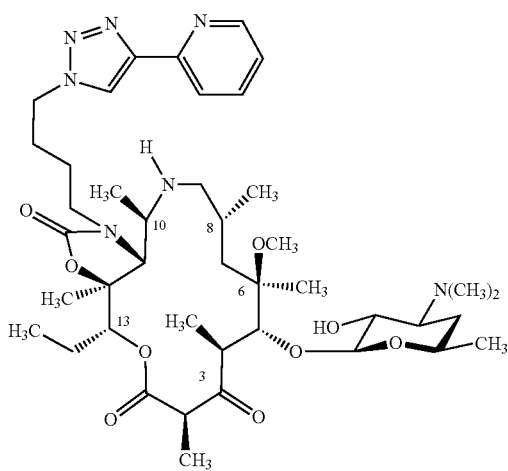
FSM-20706a
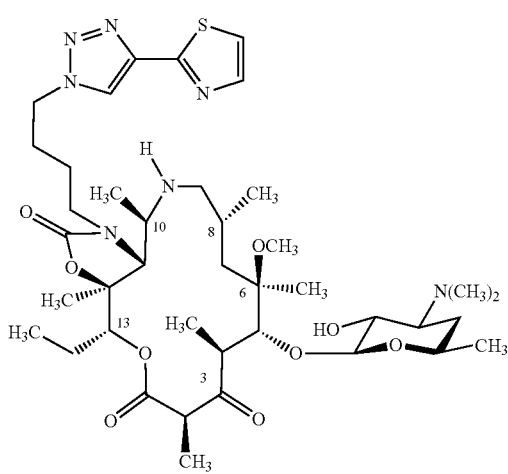
FSM-20708a TABLE A-continued
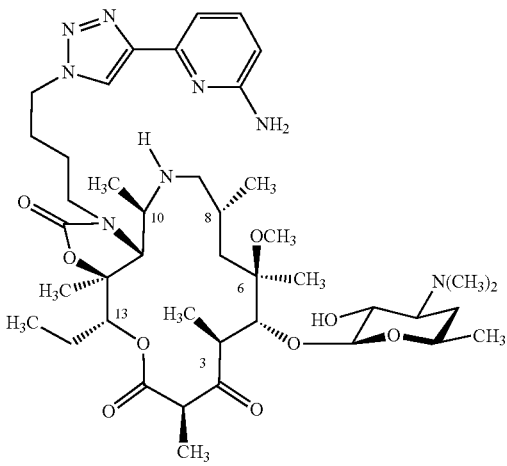
FSM-20715a
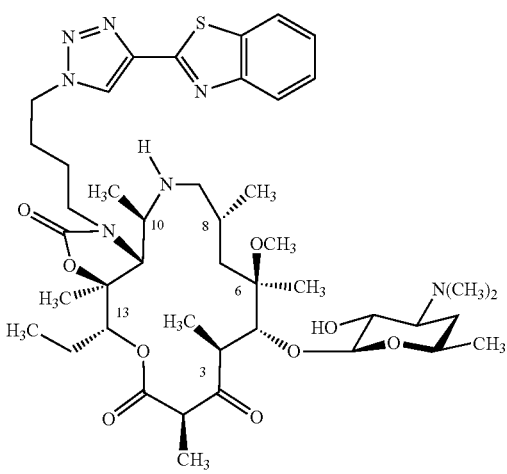
FSM-20711a
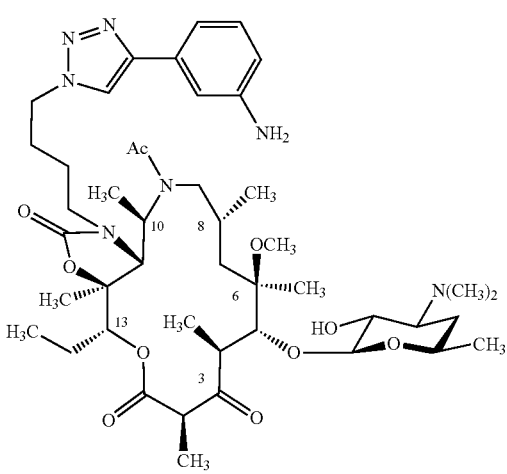
FSM-20767a TABLE A-continued
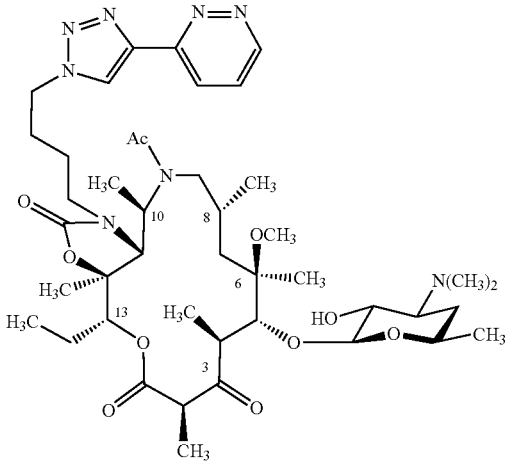
FSM-20764a
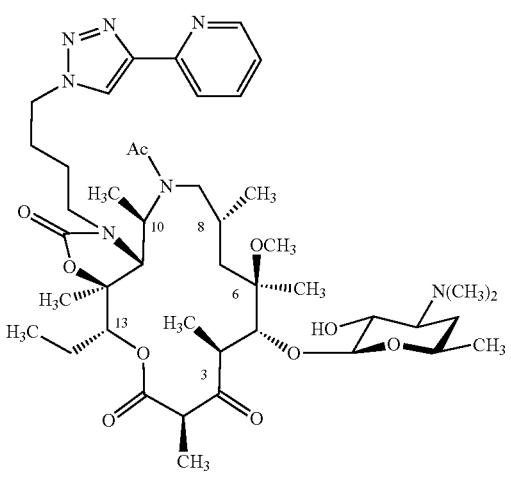
FSM-20766a
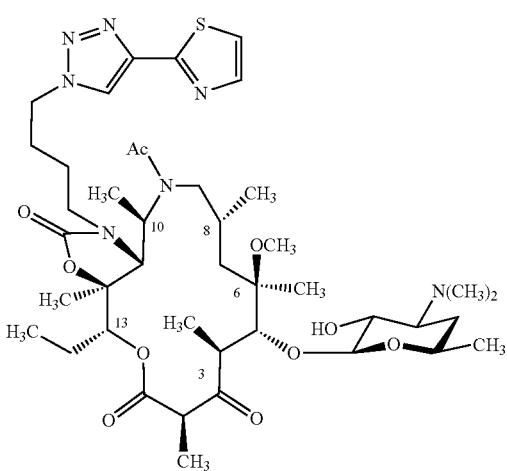
FSM-20763a TABLE A-continued
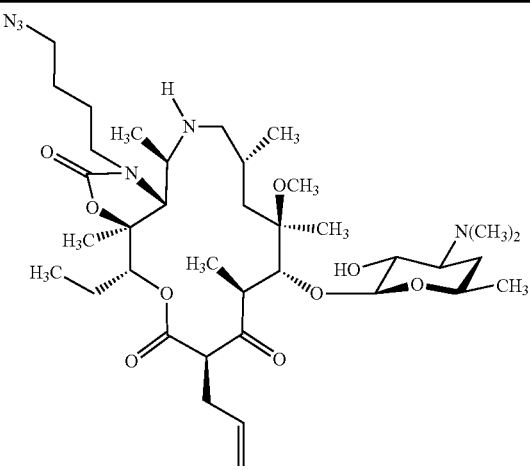
FSM-56131a
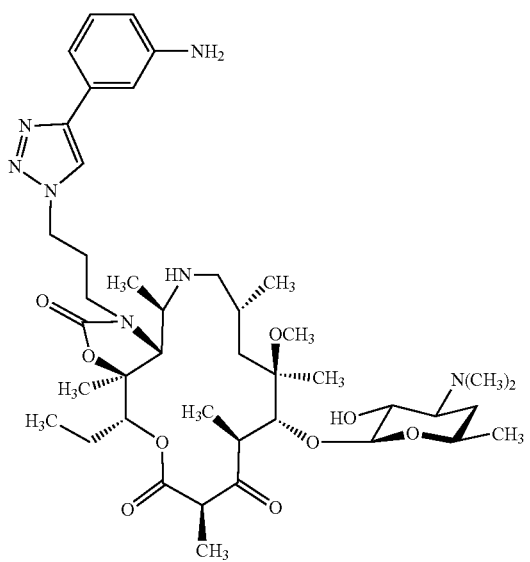
FSM-40347a
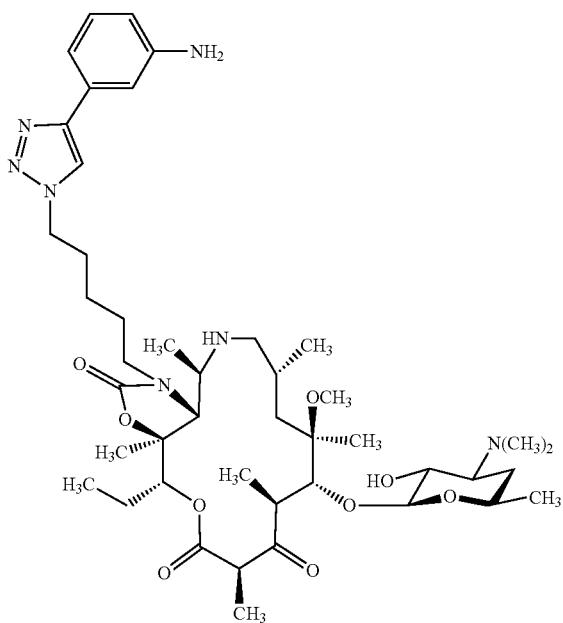
FSM-40349a TABLE A-continued
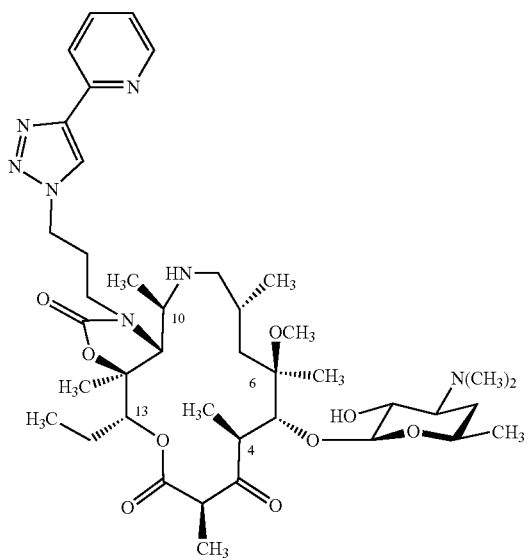
FSM-40348a
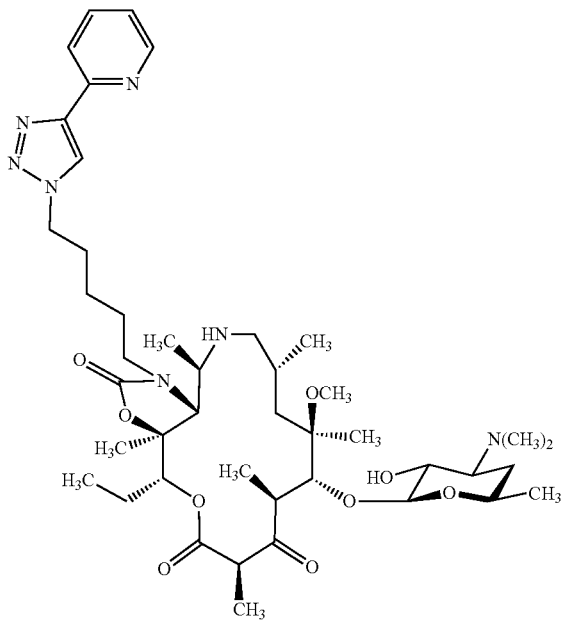
FSM-40350a
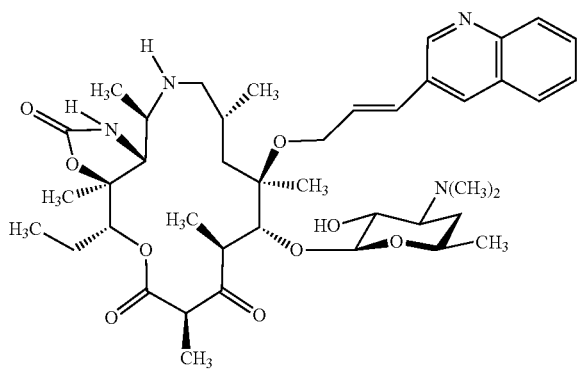
FSM-20919a TABLE B
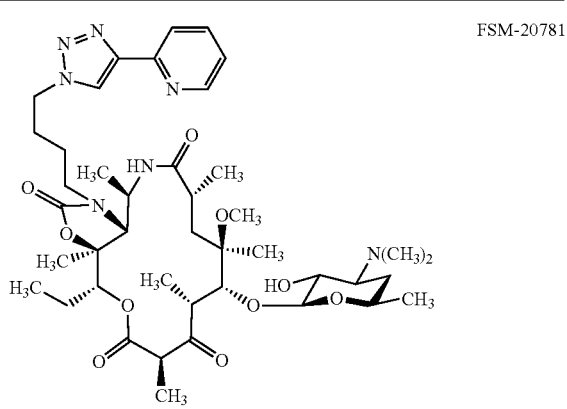
FSM-20781
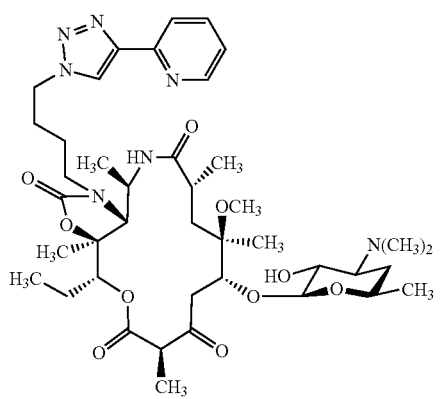
FSM-20739
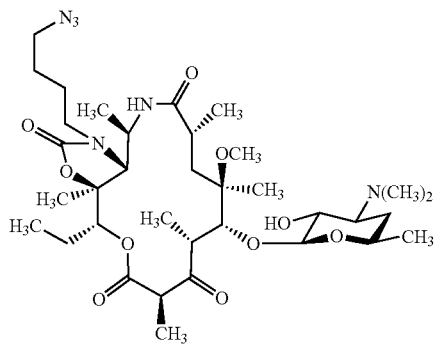
FSM-56077
TABLE B-continued
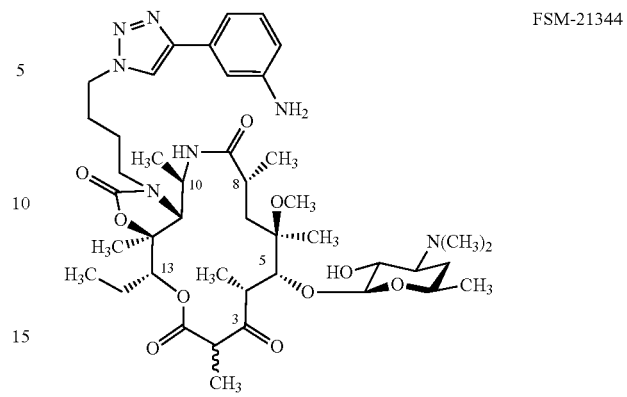
FSM-21344
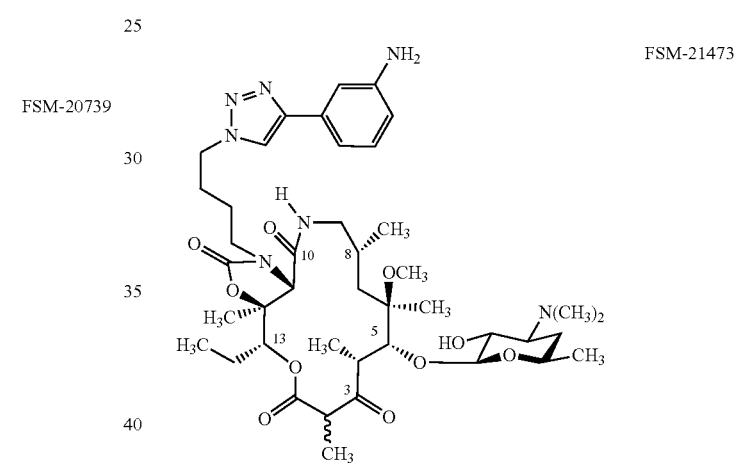
FSM-21473
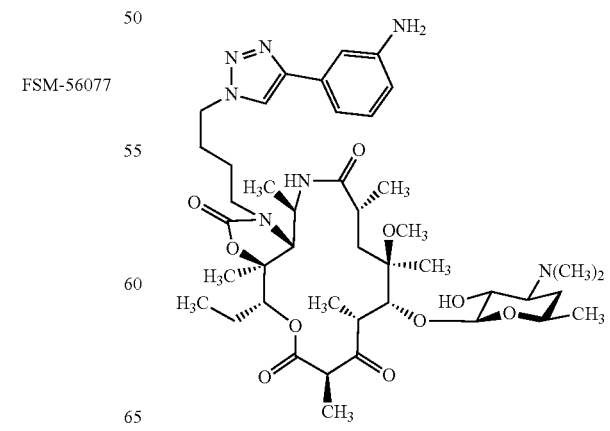

TABLE C
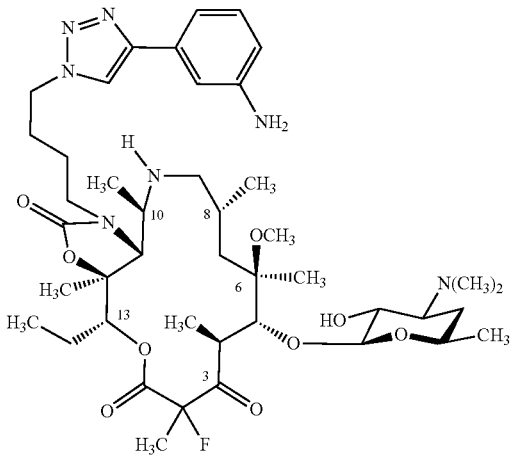
FSM-20720
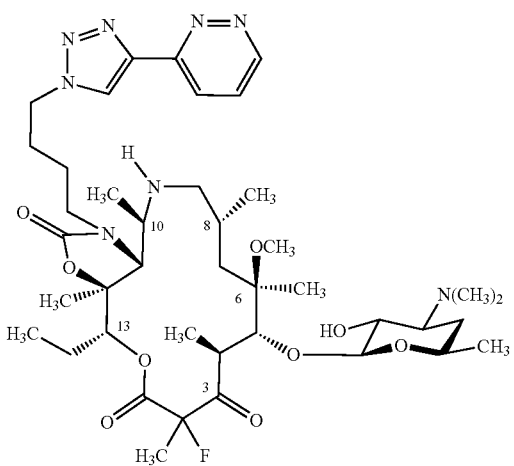
FSM-20717
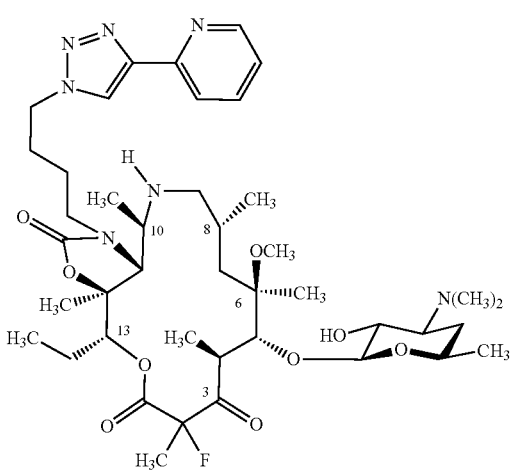
FSM-20716

TABLE C-continued
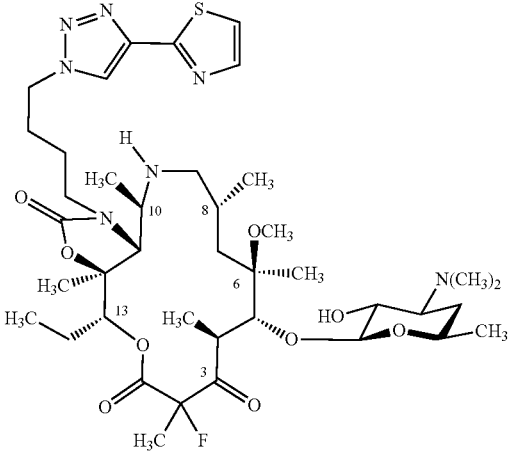
FSM-20721
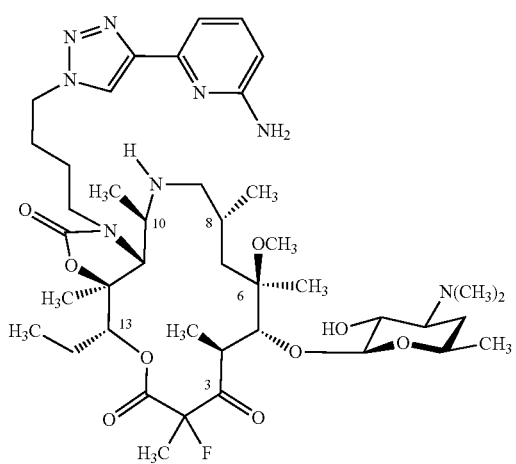
FSM-20718
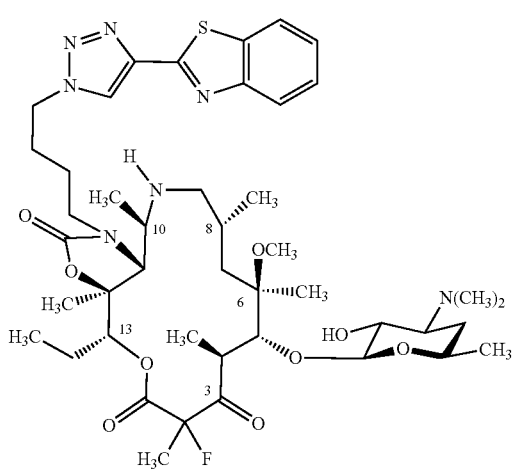
FSM-20722

TABLE C-continued
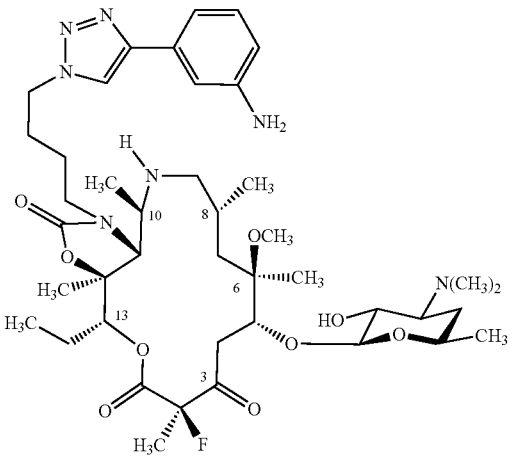
FSM-10661
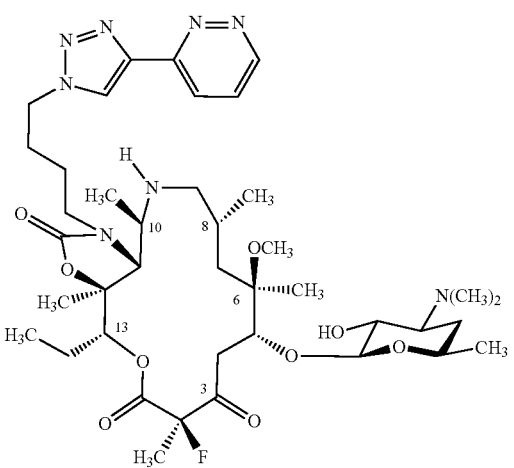
FSM-10667
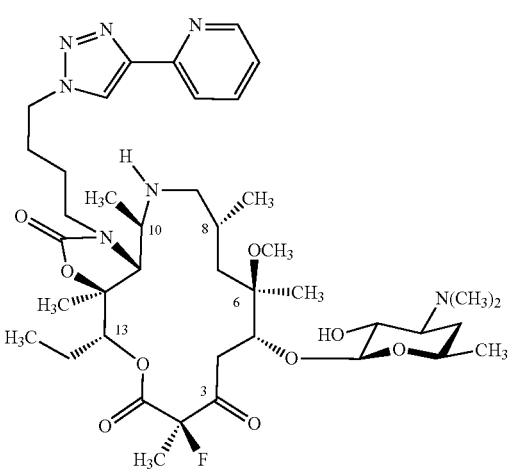
FSM-10662

TABLE C-continued
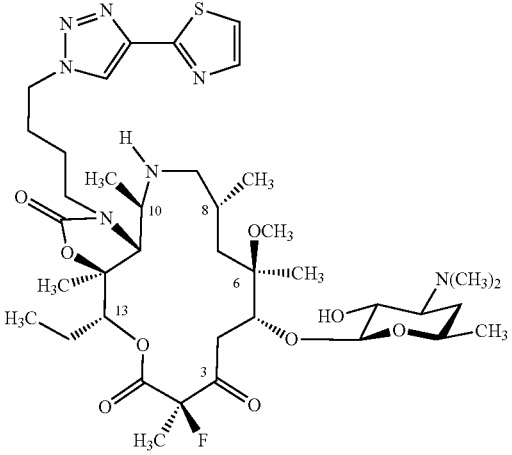
FSM-10666
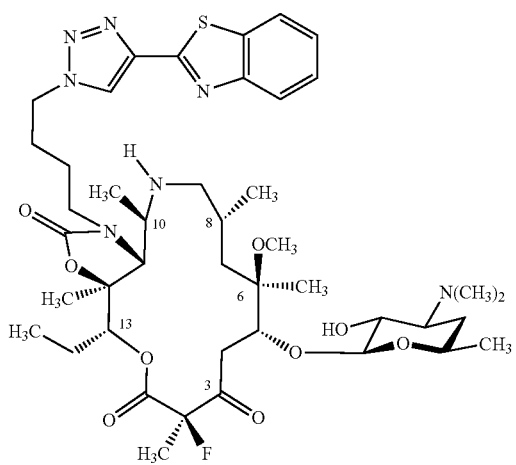
FSM-10671
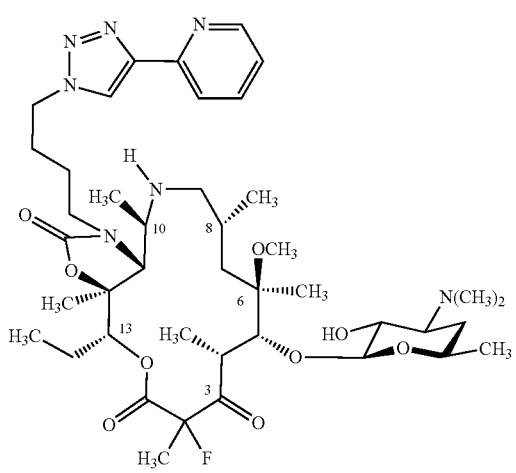
FSM-20738

TABLE C-continued
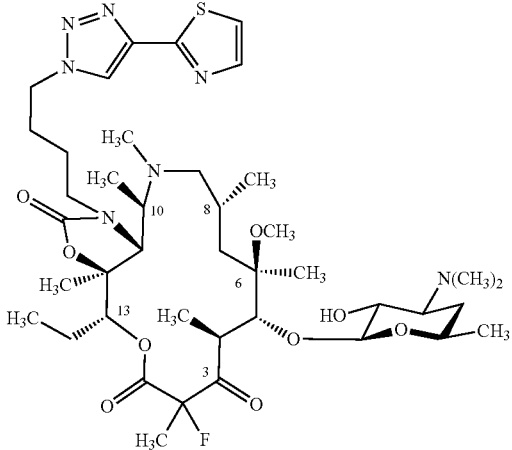
FSM-20705
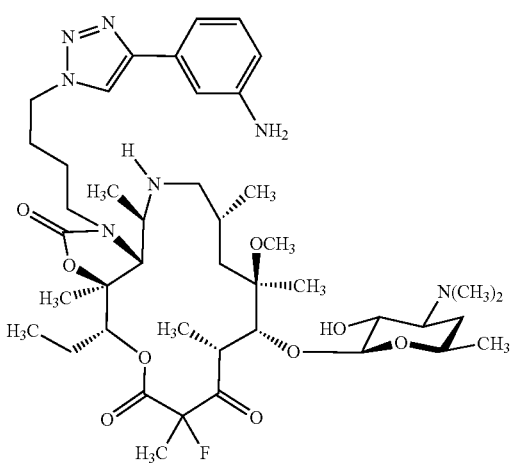
FSM-20795
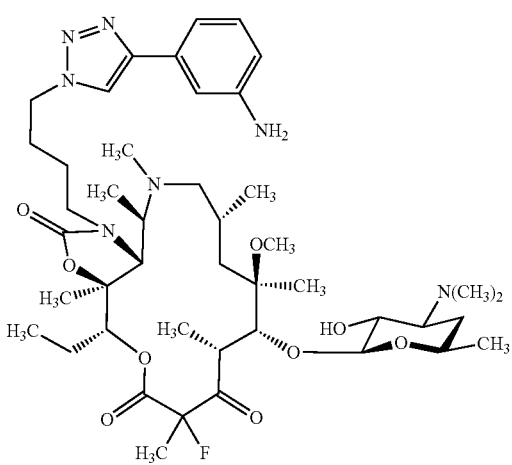
FSM-20797

TABLE C-continued
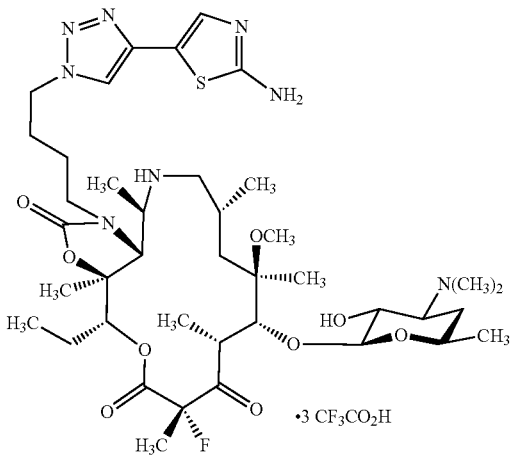
FSM-21760
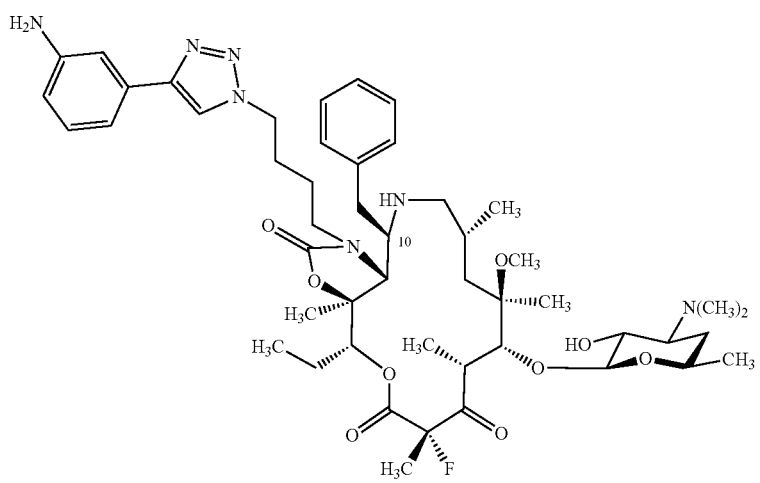
FSM-60506
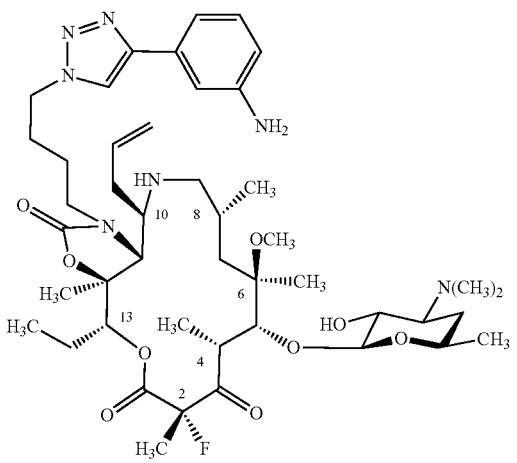
FSM-11203
FSM-11203
Chemical Formula: $C_{45}H_{70}FN_7O_9$

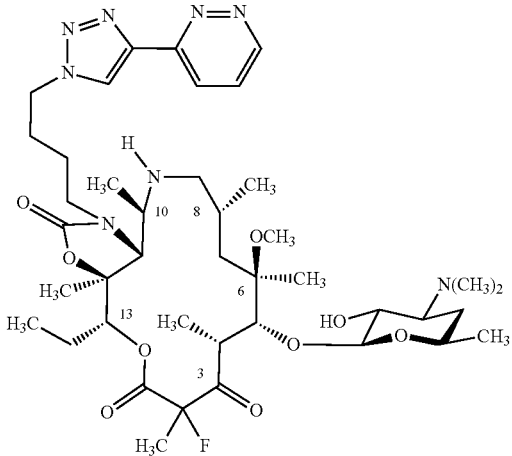
FSM-20717a
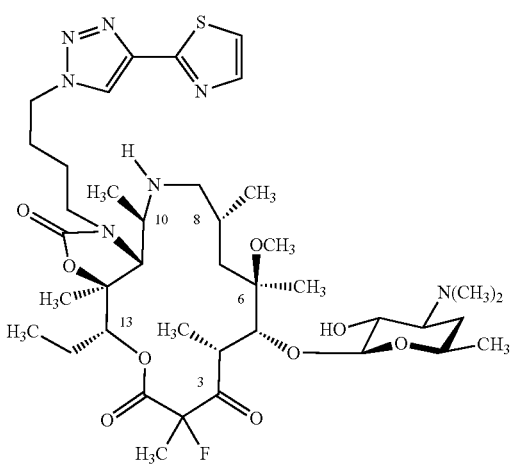
FSM-20721a
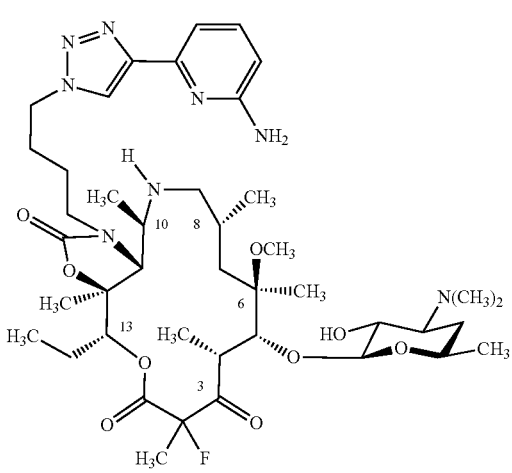
FSM-20718a

TABLE C-continued
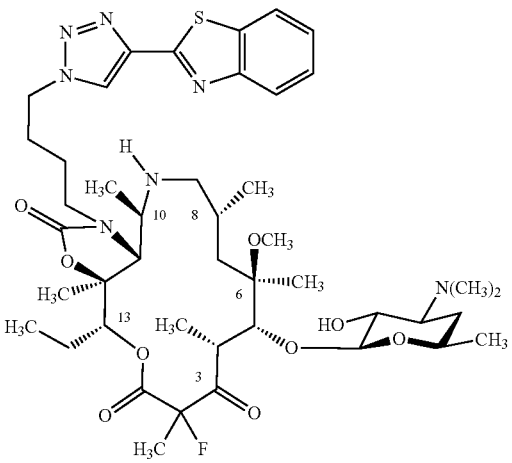
FSM-20722a
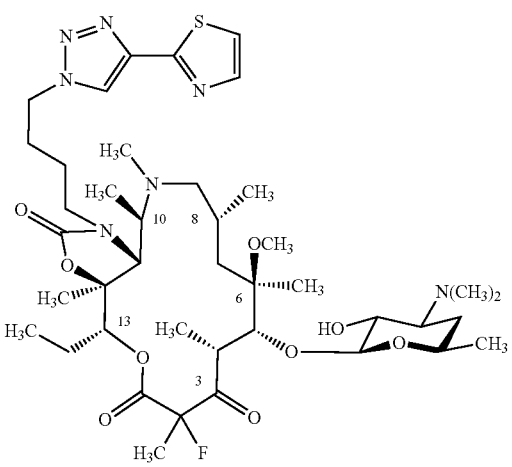
FSM-20705a
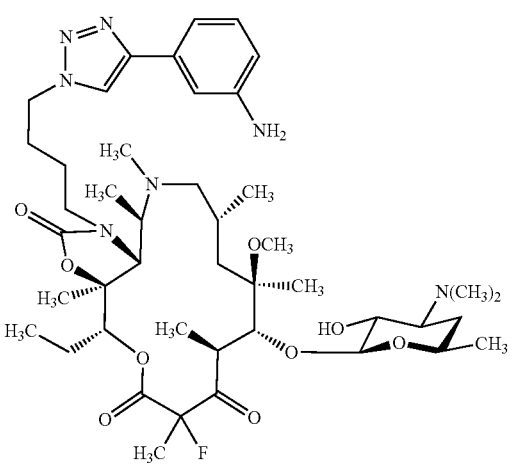
FSM-20797a TABLE D
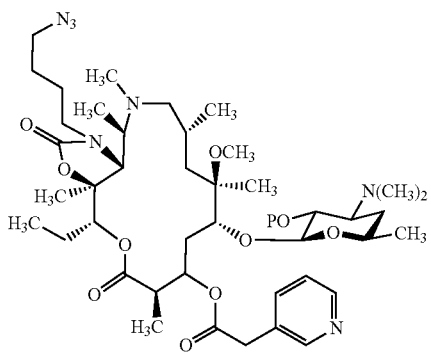
FSM-10809
P = 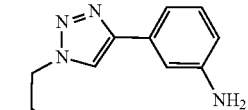
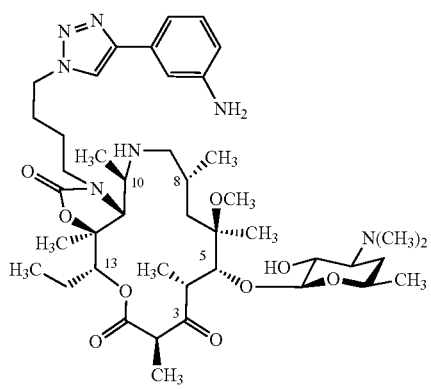
FSM-21340
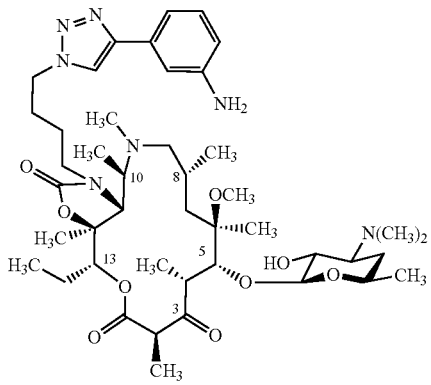
FSM-21335
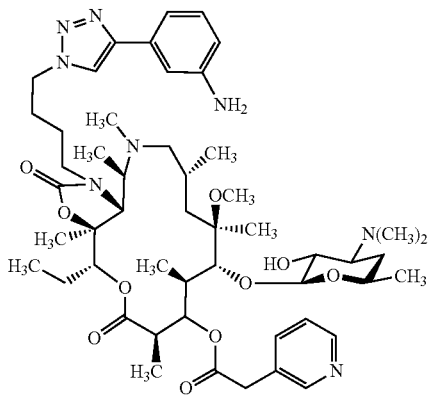
FSM-10809a
TABLE E
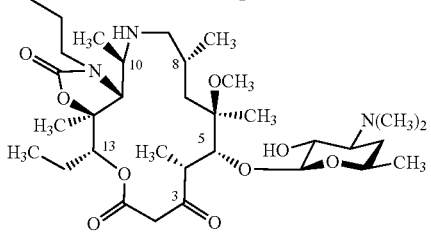
FSM-56133
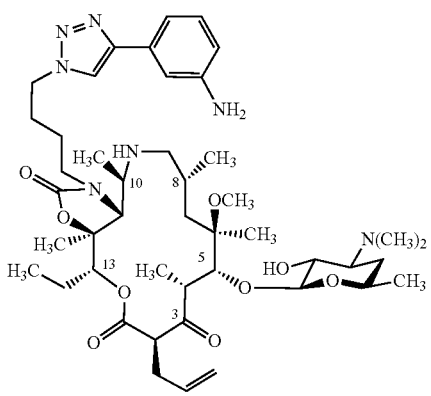
FSM-56156
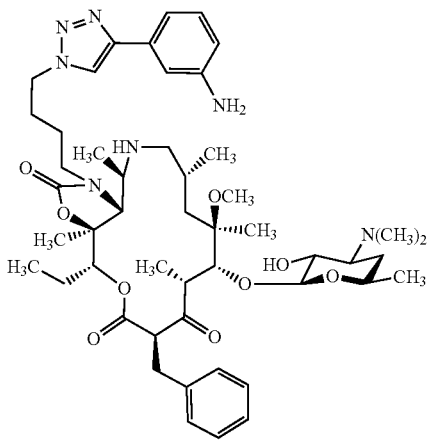
FSM-56158
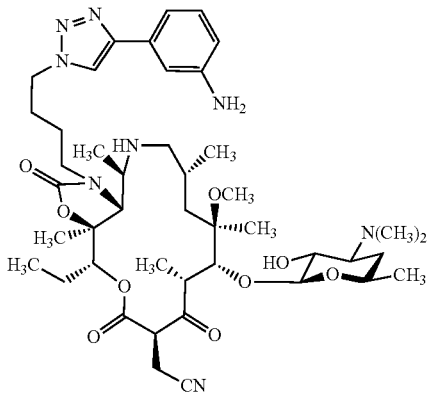
FSM-56160

TABLE E-continued
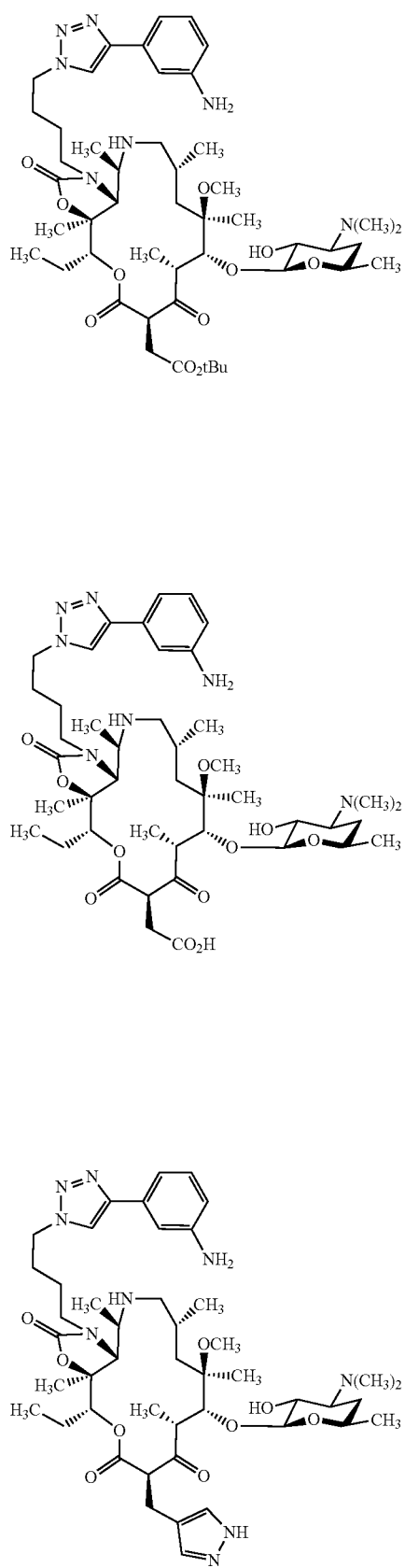
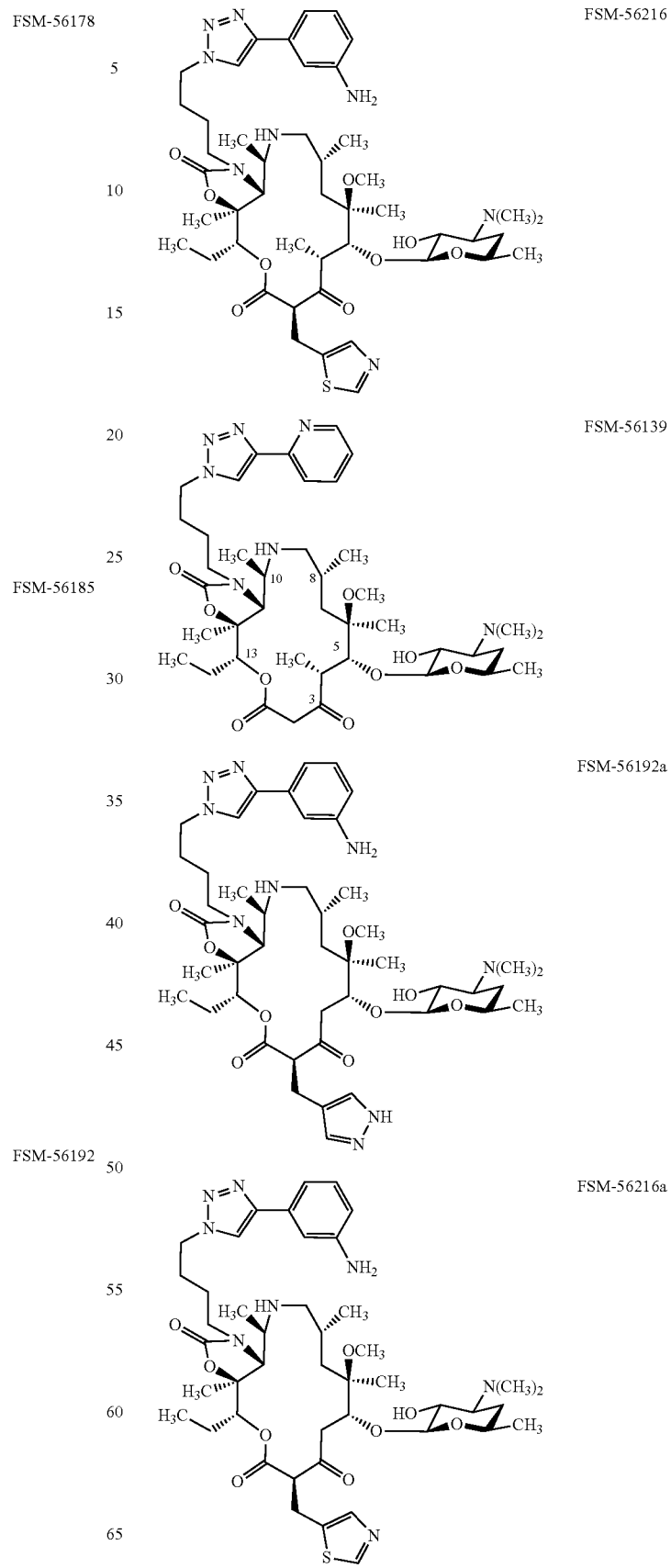

TABLE E-continued
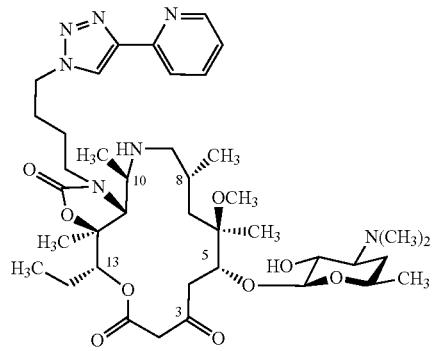
FSM-56139a
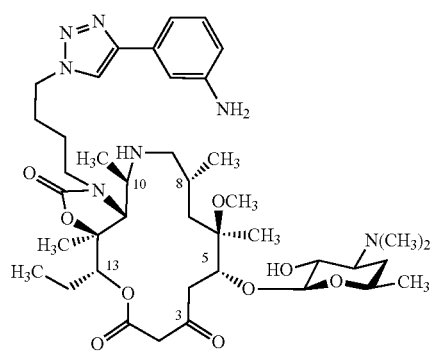
FSM-56133a
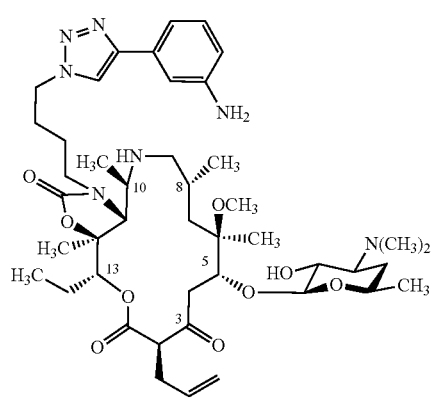
FSM-56156a
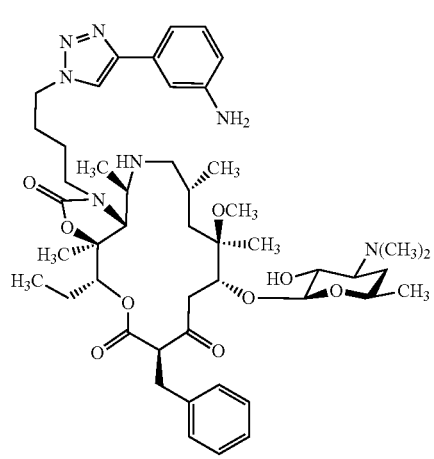
FSM-56158a
TABLE E-continued
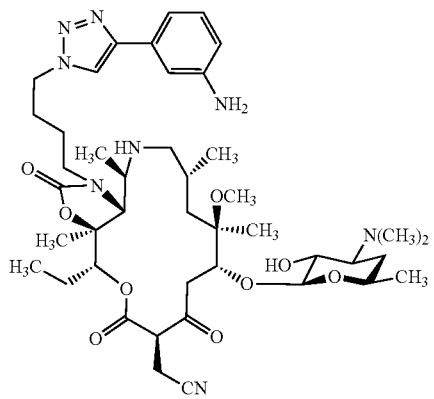
FSM-56160a
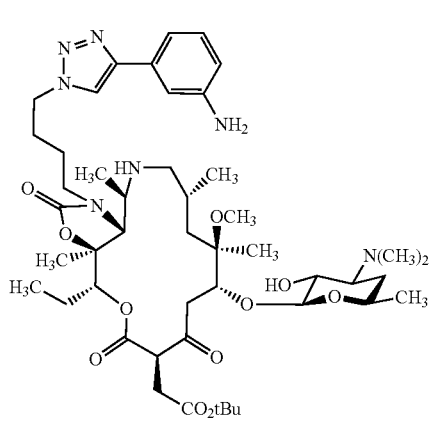
FSM-56178a
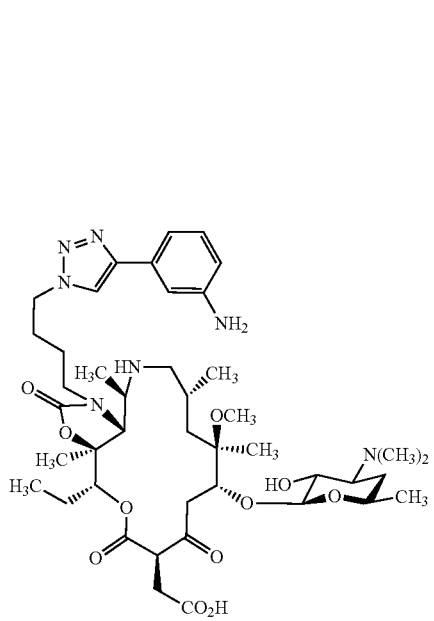
FSM-56185a TABLE F
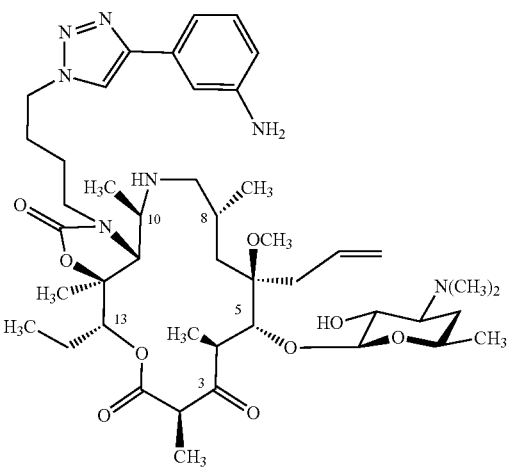
FSM-21368
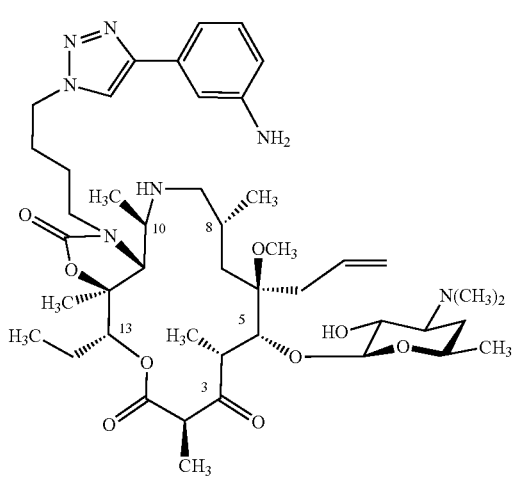
FSM-21367
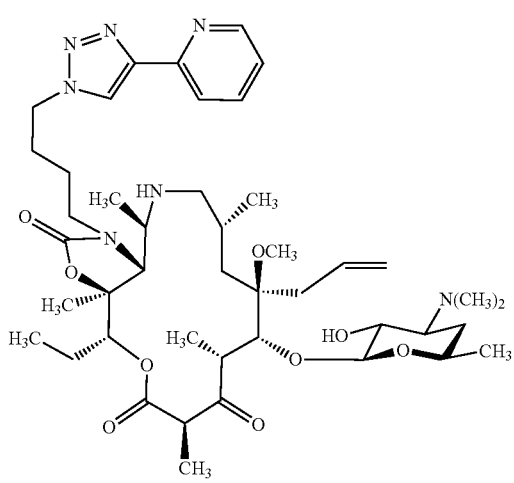
FSM-21423

TABLE F-continued
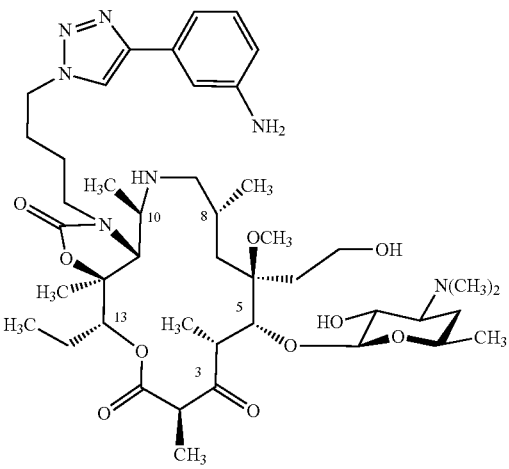
FSM-21422
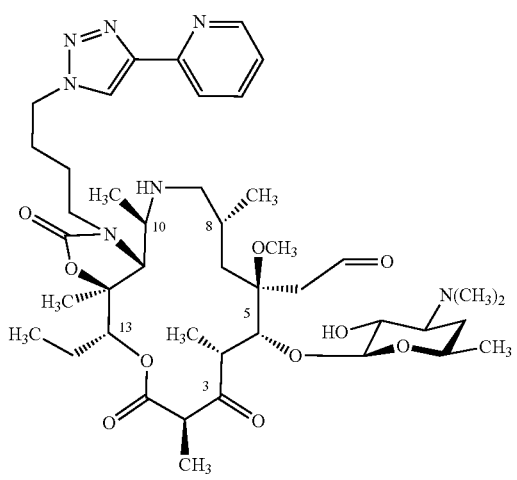
FSM-21428
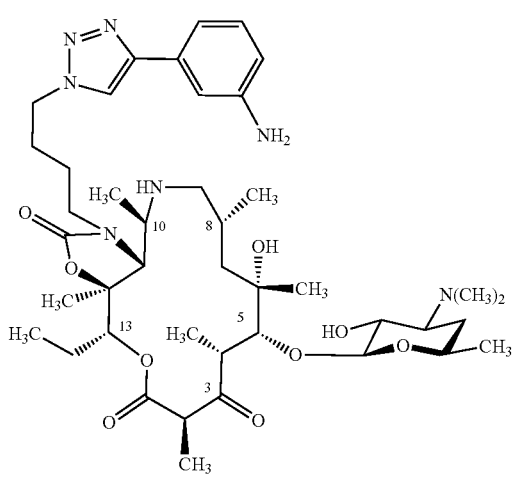

TABLE F-continued
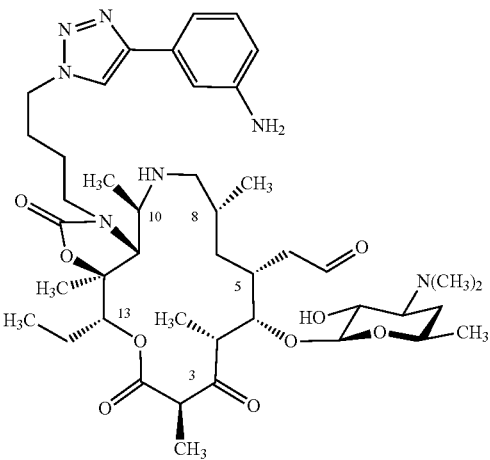
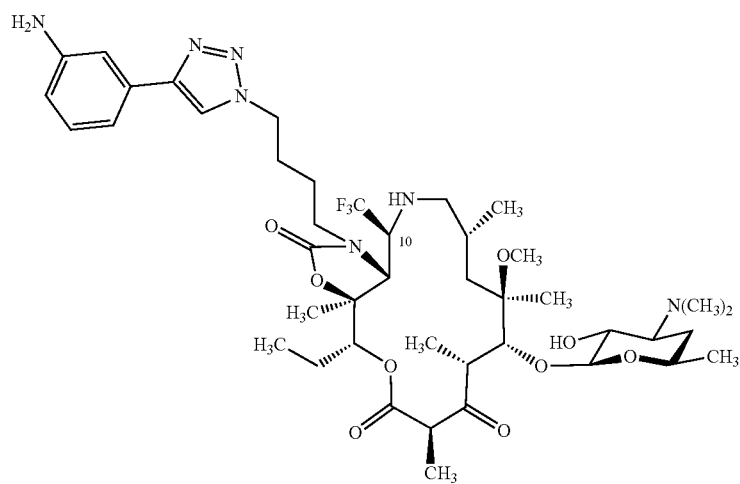
FSM-60546
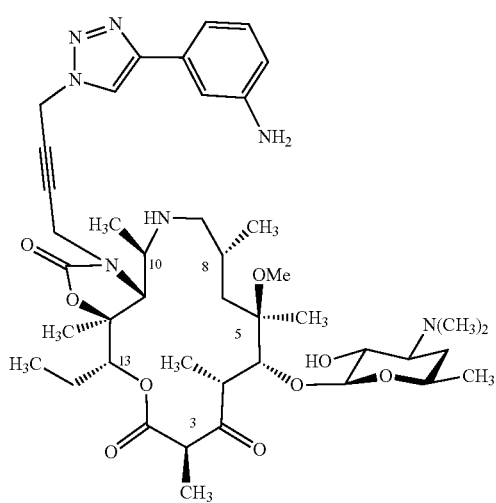

TABLE F-continued
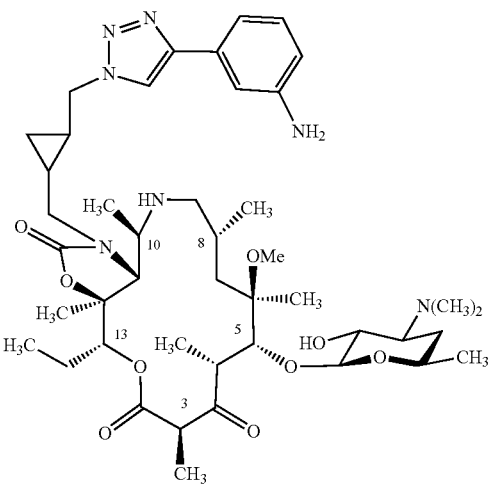
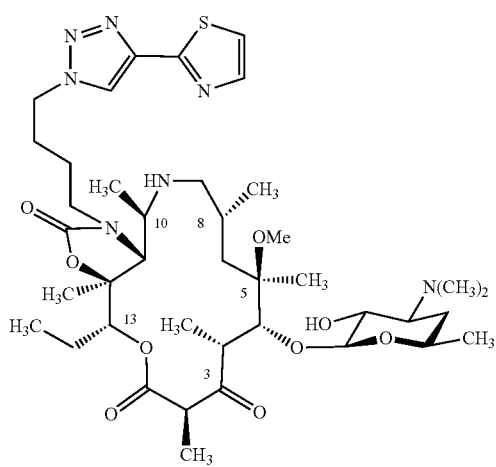
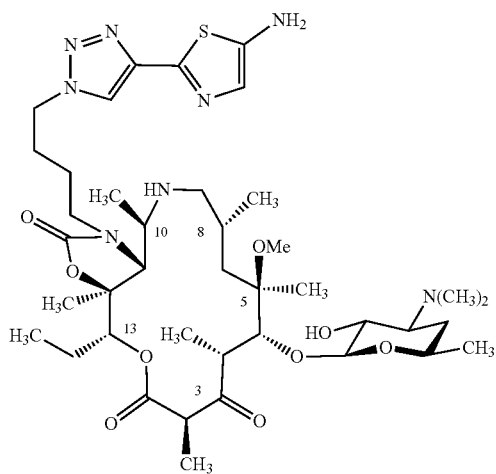

TABLE F-continued
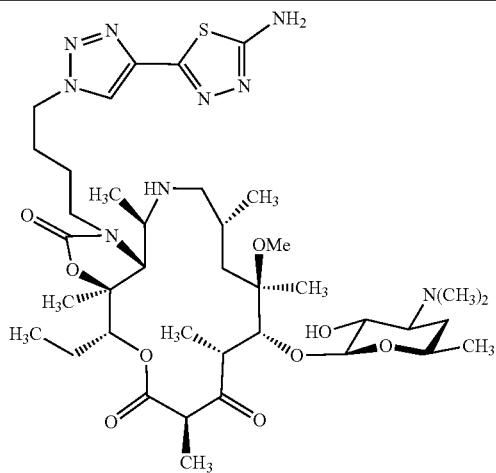
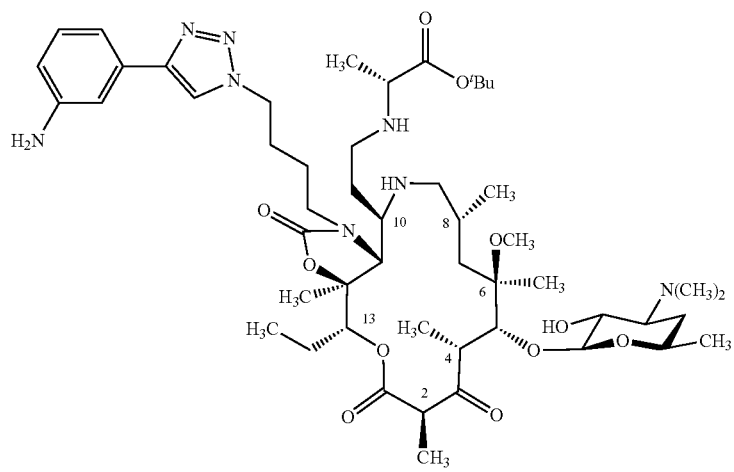
FSM-11238
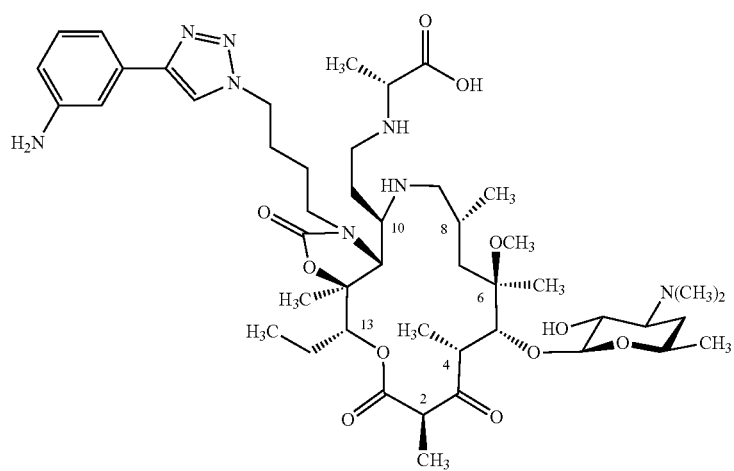
FSM-11258

TABLE F-continued
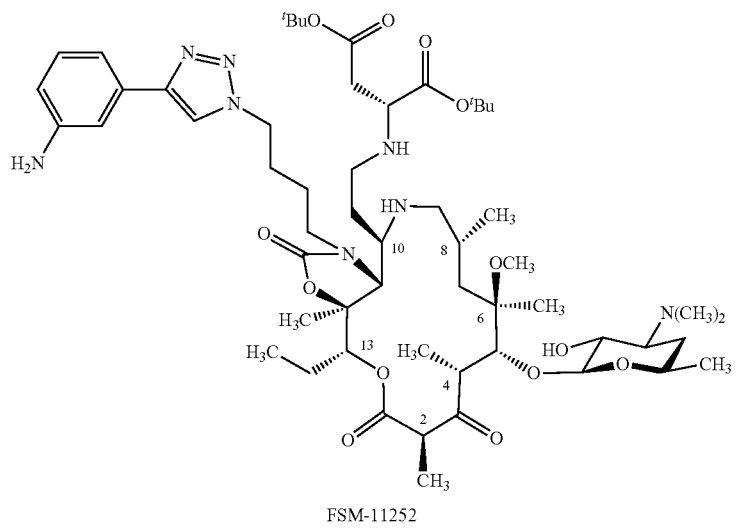
FSM-11252
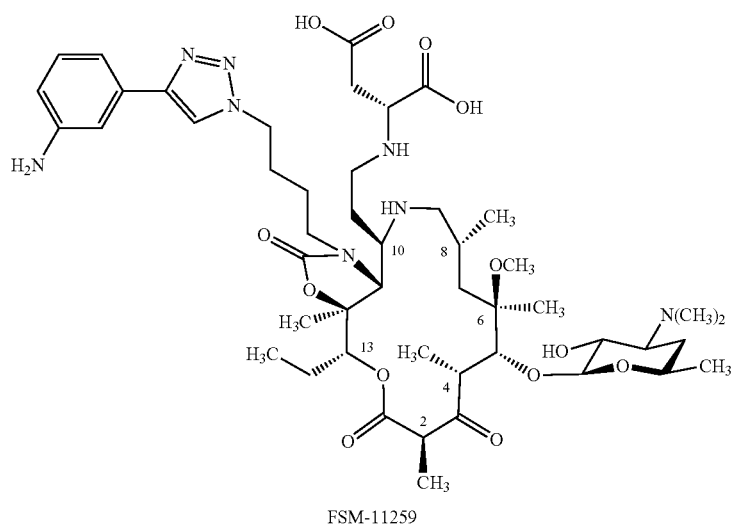
FSM-11259
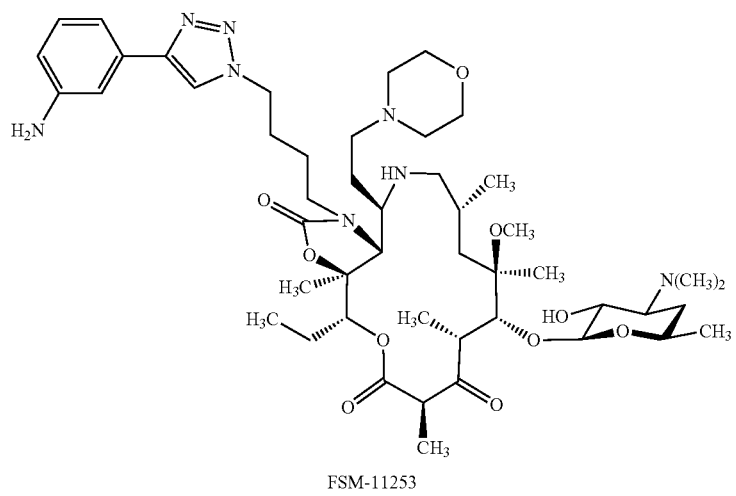
FSM-11253

TABLE F-continued
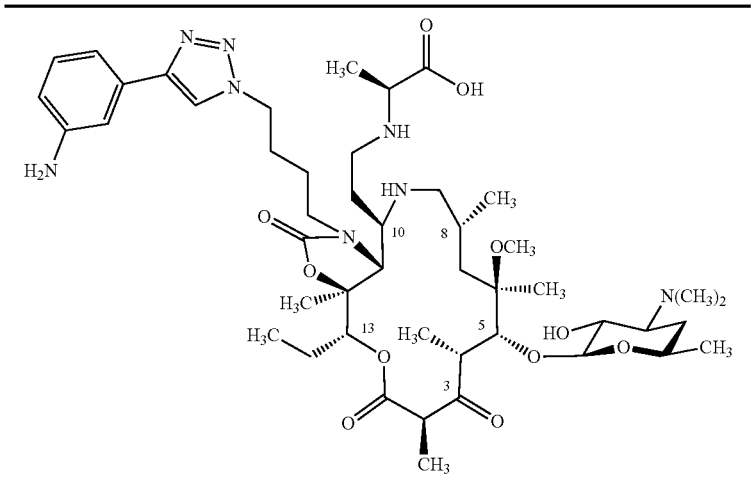
| TABLE G | TABLE H |
|---|---|
| 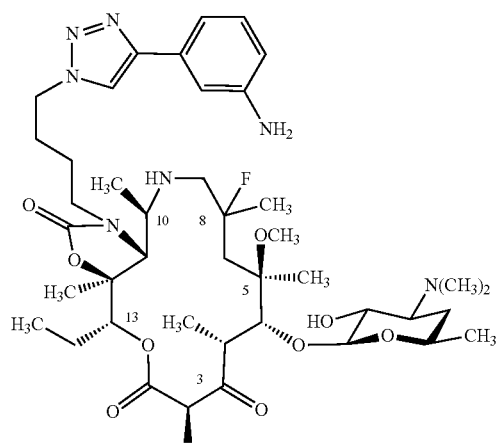 FSM-30686 | 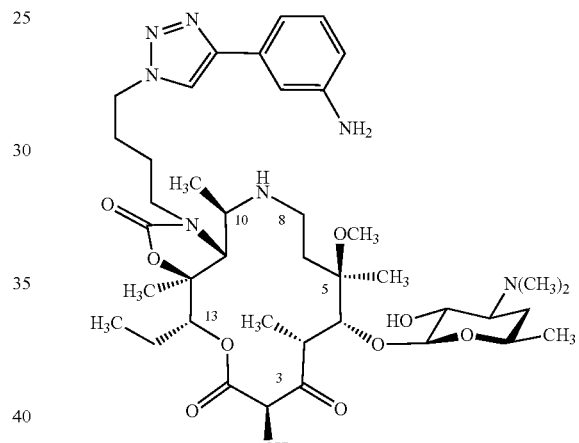 FSM-30622 |
| 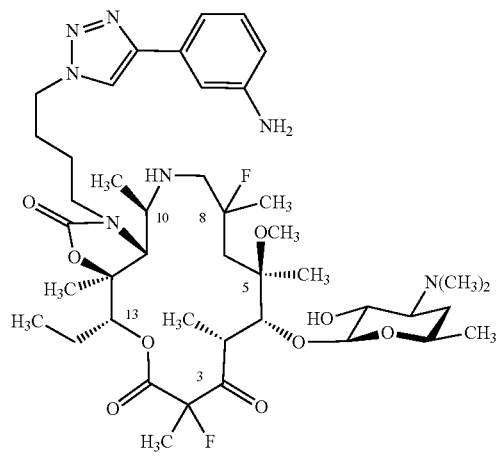 FSM-30704 | 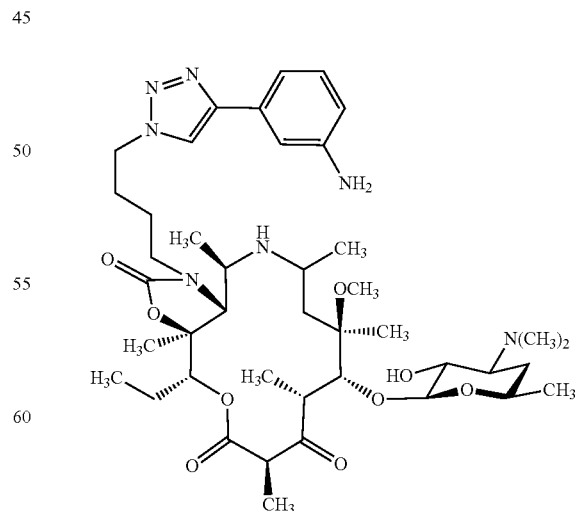 FSM-30690 |

TABLE H-continued
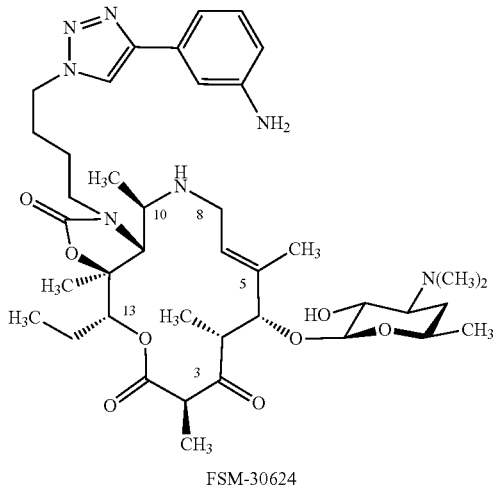
FSM-30624
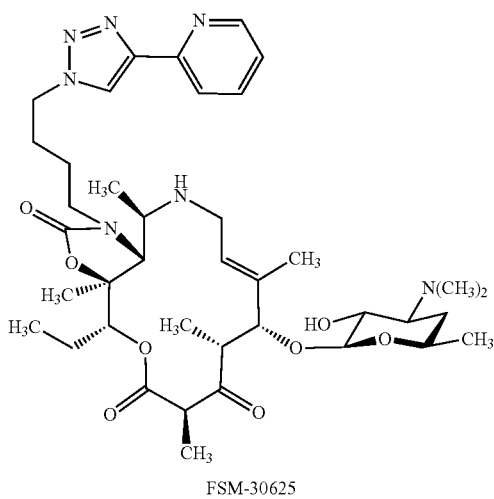
FSM-30625
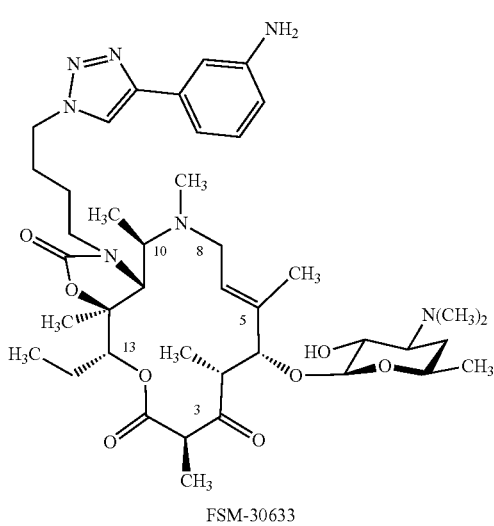
FSM-30633
TABLE H-continued
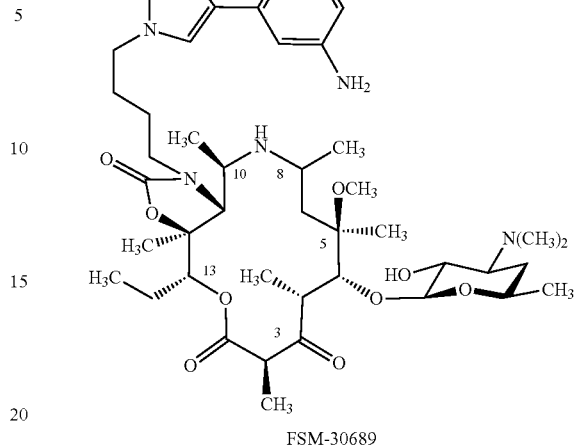
FSM-30689
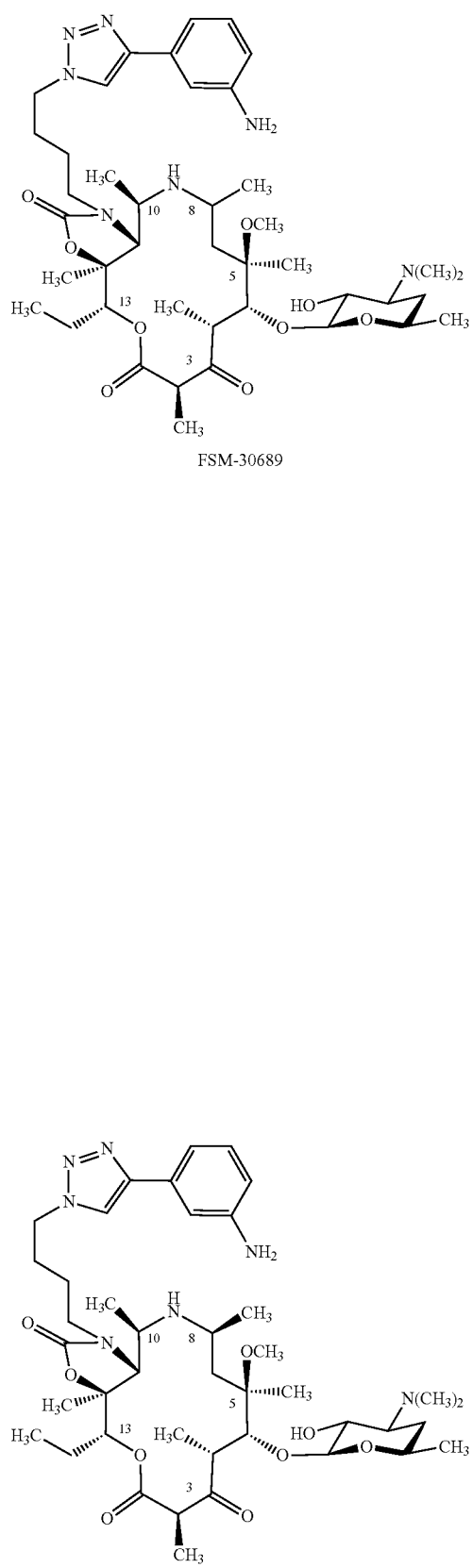

TABLE H-continued
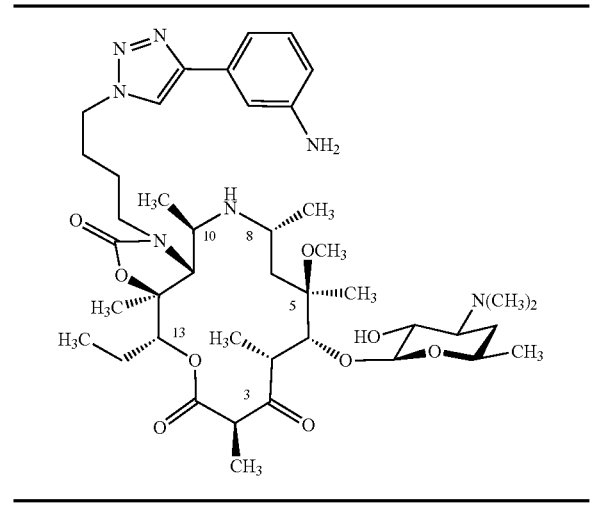
TABLE I
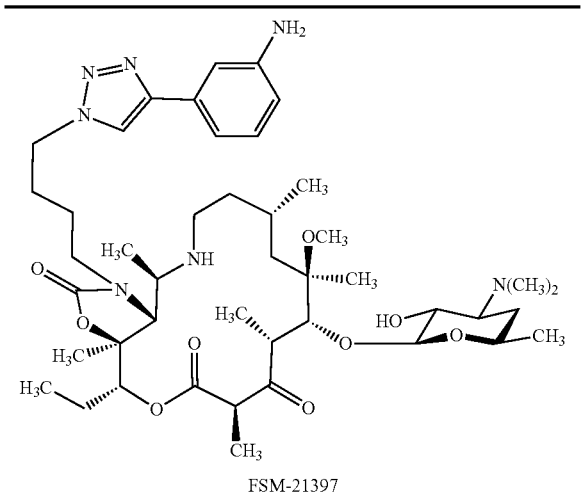
FSM-21397
TABLE J
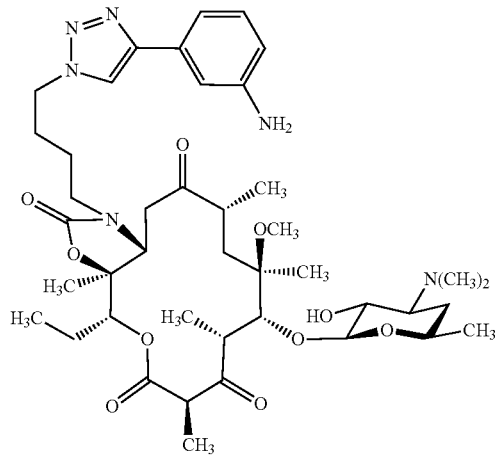
FSM-21535
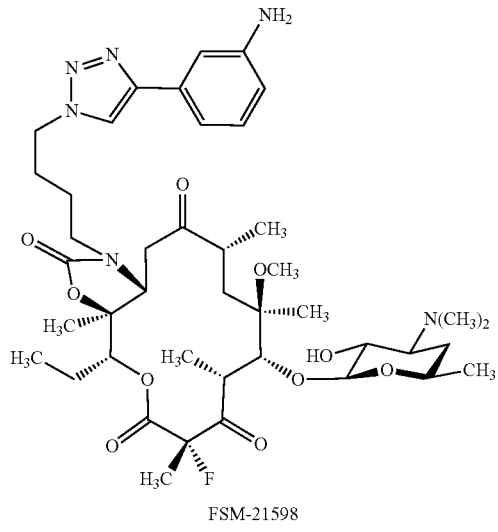
FSM-21598
TABLE K
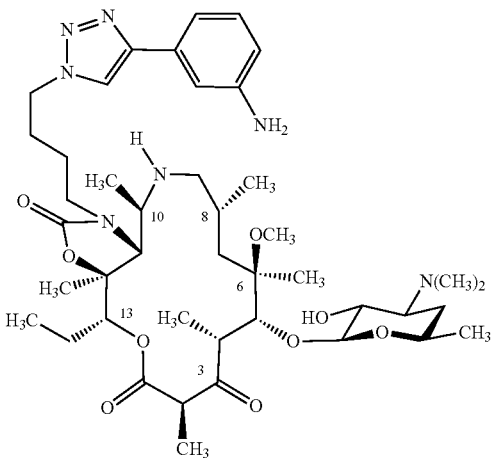

TABLE K-continued
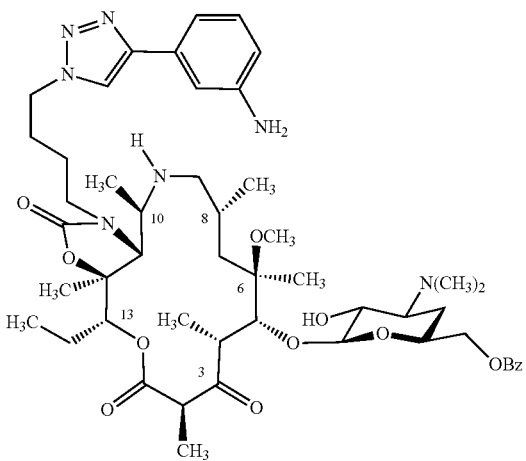
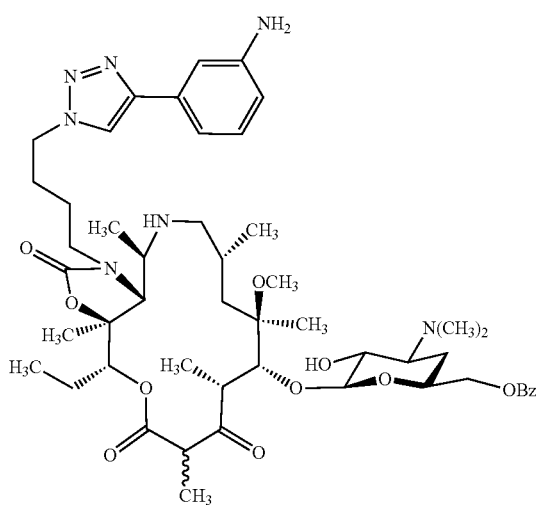
FSM-21797
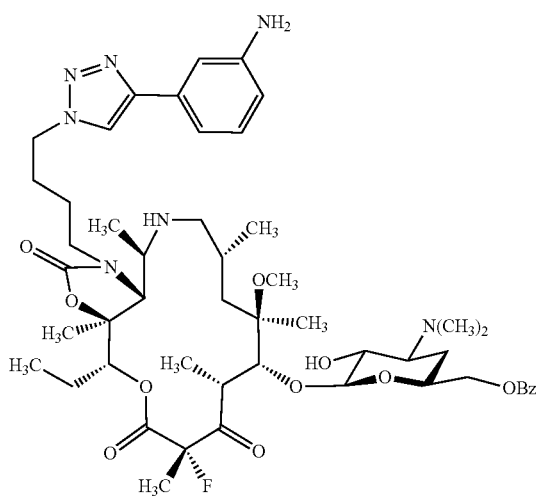
FSM-21798

TABLE K-continued
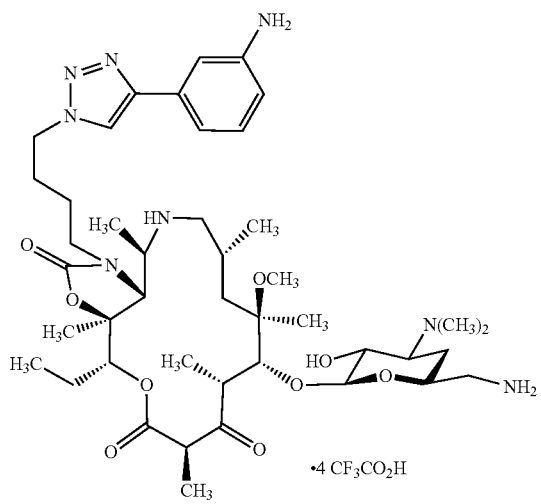
FSM-21700
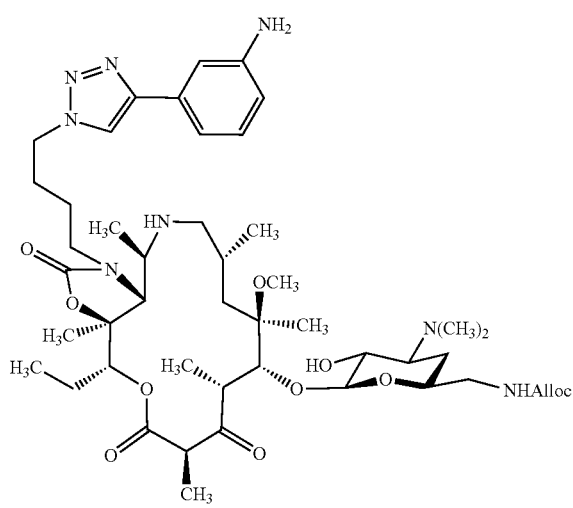
FSM-21795
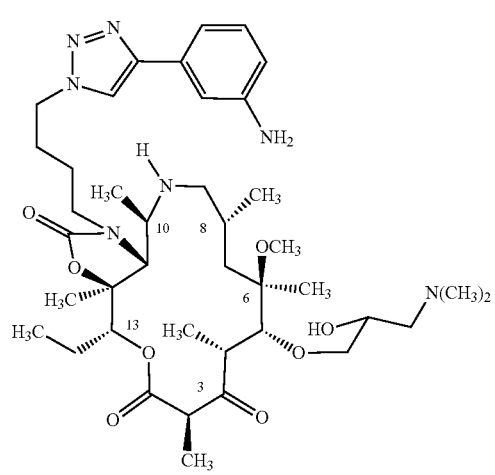

TABLE K-continued
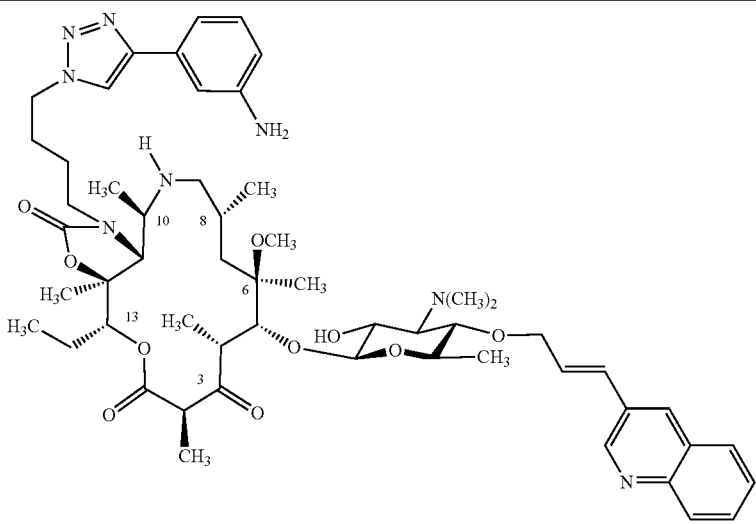
TABLE L
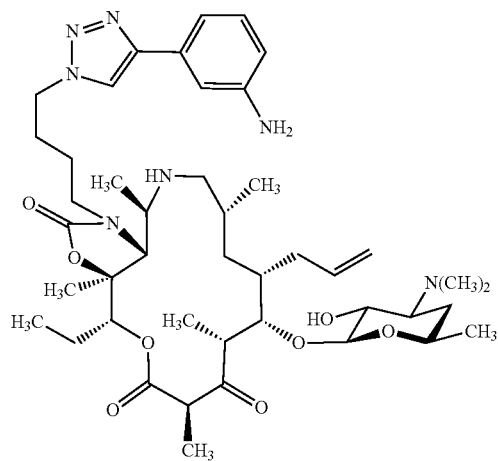
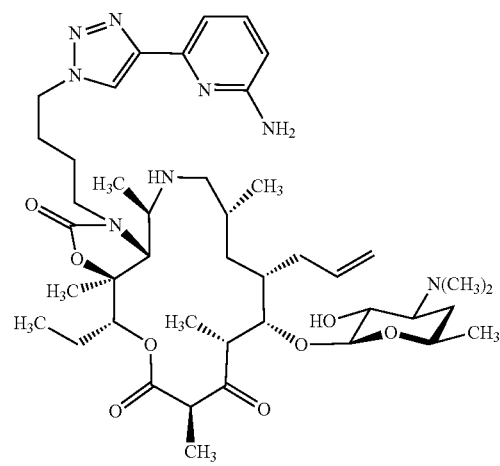
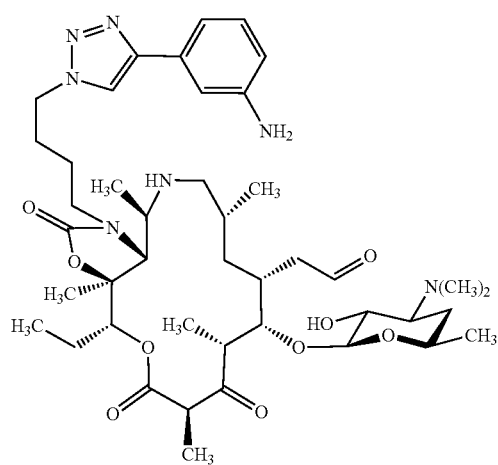
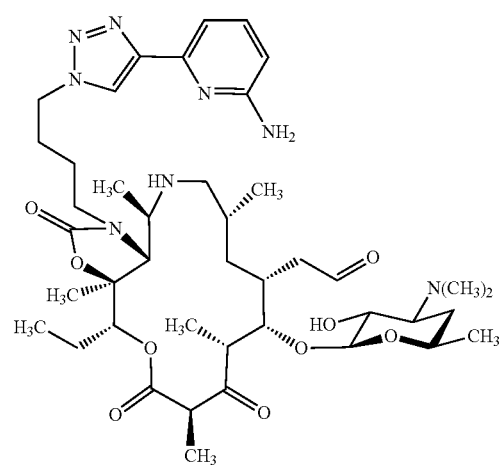

TABLE L-continued
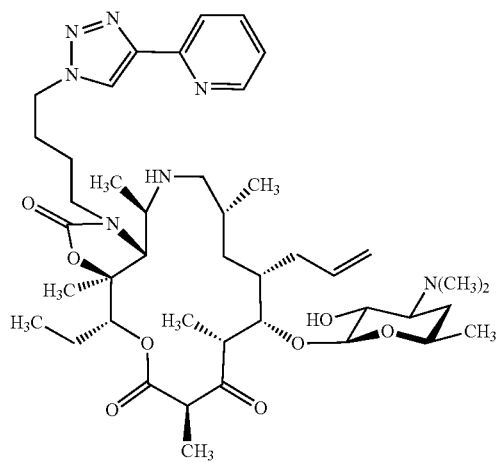
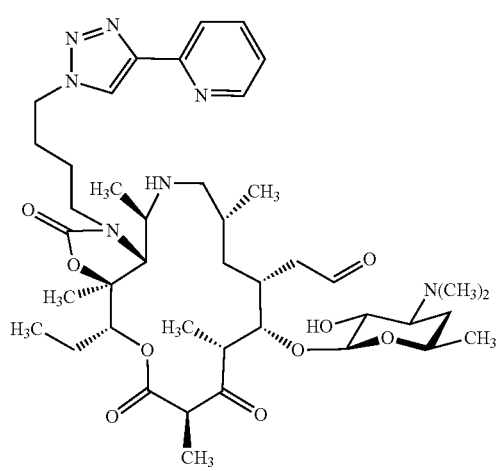
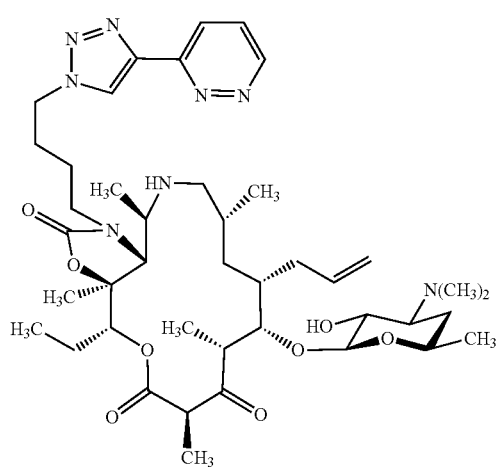
TABLE L-continued
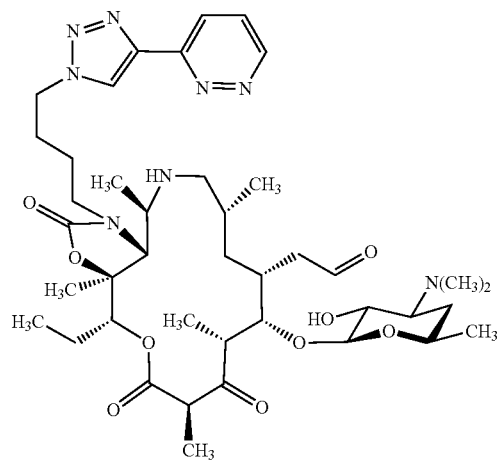
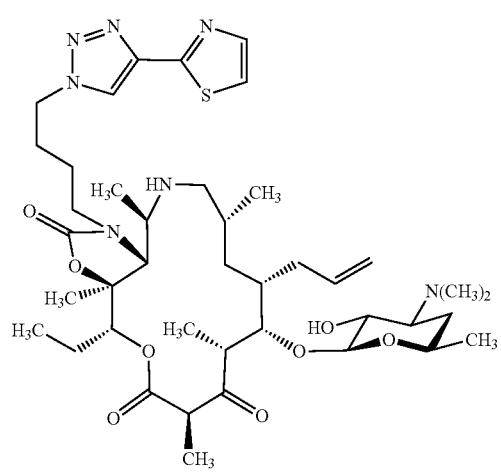
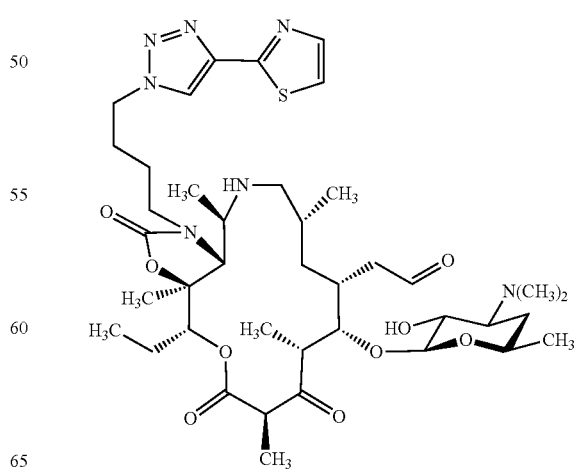

447
TABLE L-continued
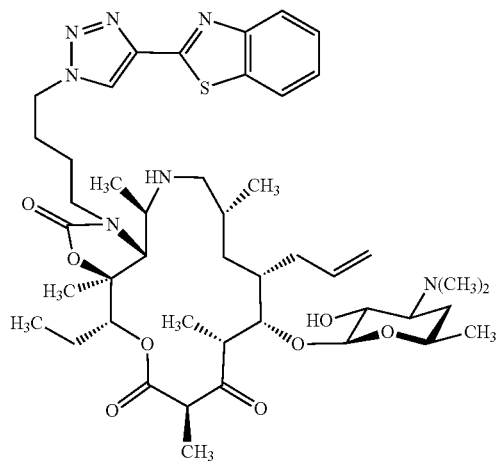
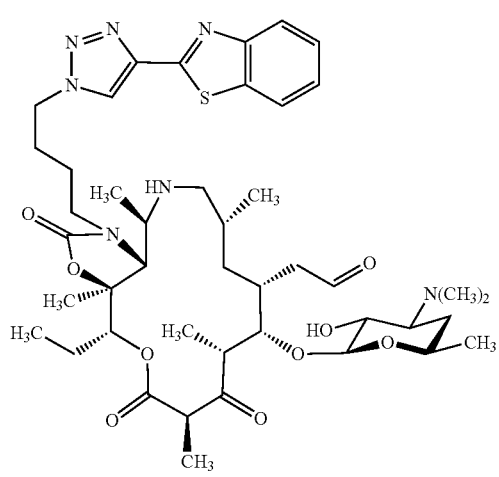
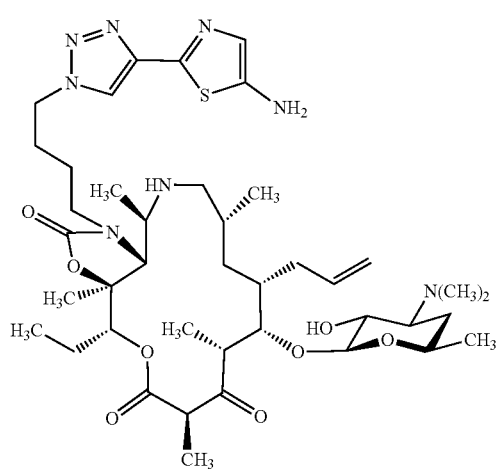
448
TABLE L-continued
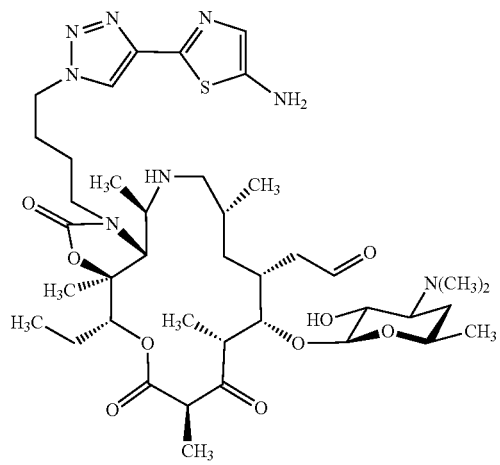
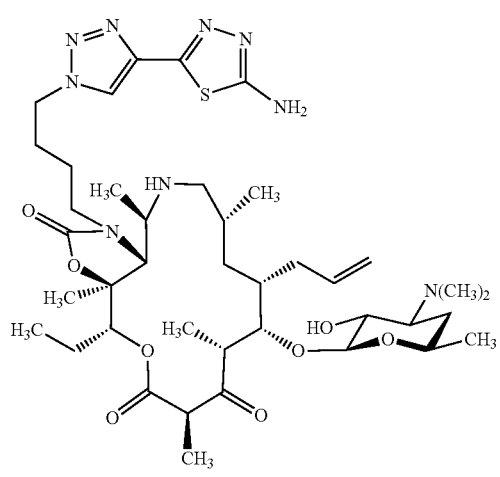
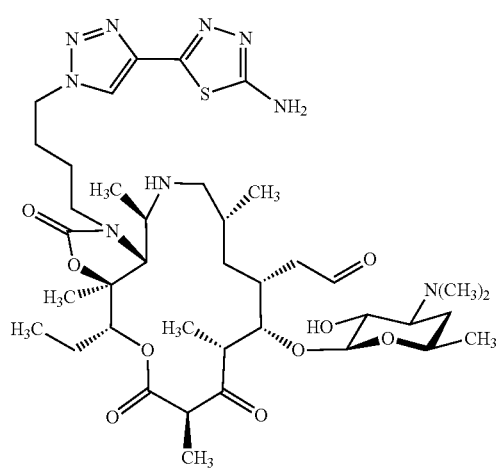

TABLE L-continued

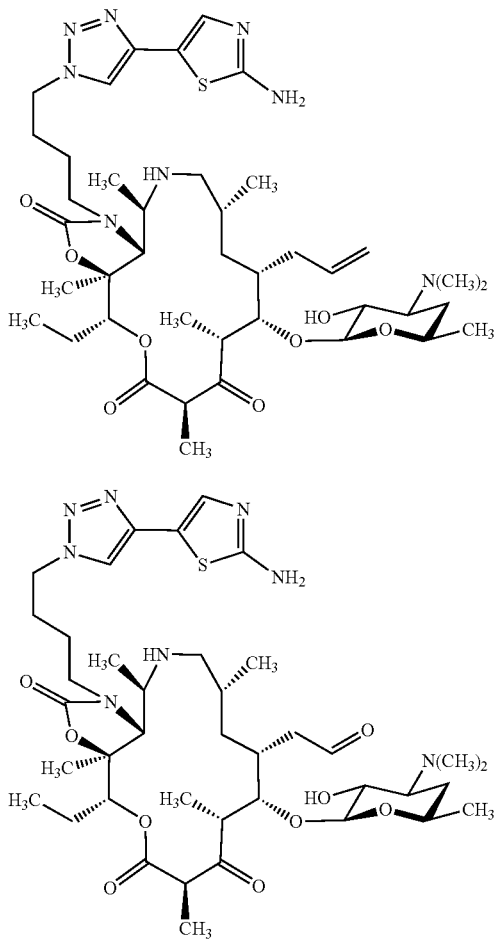

Pharmaceutical Compositions and Administration

The present invention provides pharmaceutical compositions comprising a macrolide as described herein, or a pharmaceutically acceptable salt thereof, and a pharmaceutically acceptable excipient.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Pharmaceutical compositions described herein can be prepared by any method known in the art of pharmacology. In general, such preparatory methods include the steps of bringing the macrolide of the present invention into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the macrolide of the present invention. The amount of the macrolide is generally equal to the dosage of the macrolide which would be administered to a subject and/or a convenient fraction of such a dosage such as, for example, one-half or one-third of such a dosage.

Relative amounts of the macrolide, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) macrolide.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Plutonic F68, Poloxamer 188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the macrolides, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the macrolide.

Solid dosage forms for oral administration include capsules, tablets, pills, powders, and granules. In such solid dosage forms, the macrolide is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the macrolide(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The macrolide can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the macrolide can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the macrolide(s) only, or preferentially, in a certain part of the intestinal tract, optionally, in a delayed manner. Examples of embedding compositions which can be used include polymeric substances and waxes.

Dosage forms for topical and/or transdermal administration of a macrolide of this invention may include ointments, pastes, creams, lotions, gels, powders, solutions, sprays, inhalants and/or patches. Generally, the macrolide is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an macrolide to the body. Such dosage forms can be prepared, for example, by dissolving and/or dispensing the macrolide in the proper medium. Alternatively or additionally, the rate can be controlled by either providing a rate controlling membrane and/or by dispersing the macrolide in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) macrolide, although the concentration of the macrolide can be as high as the solubility limit of the macrolide in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the macrolide and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the macrolide dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the macrolide may constitute 0.1 to 20% (w/w) of the composition. The propellant may further comprise additional ingredients such as a liquid non-ionic and/or solid anionic surfactant and/or a solid diluent (which may have a particle size of the same order as particles comprising the macrolide).

Pharmaceutical compositions of the invention formulated for pulmonary delivery may provide the macrolide in the form of droplets of a solution and/or suspension. Such formulations can be prepared, packaged, and/or sold as aqueous and/or dilute alcoholic solutions and/or suspensions, optionally sterile, comprising the macrolide, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the macrolide and having an average particle from about 0.2 to 500 micrometers. Such a formulation is administered, by rapid inhalation through the nasal passage from a container of the powder held close to the nares.

Formulations for nasal administration may, for example, comprise from about as little as 0.1% (w/w) and as much as 100% (w/w) of the macrolide, and may comprise one or more of the additional ingredients described herein. A pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) macrolide, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the macrolide. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition can be prepared, packaged, and/or sold in a formulation for ophthalmic administration. Such formulations may, for example, be in the form of eye drops including, for example, a 0.1/1.0% (w/w) solution and/or suspension of the macrolide in an aqueous or oily liquid carrier. Such drops may further comprise buffering agents, salts, and/or one or more other of the additional ingredients described herein. Other ophthalmically-administrable formulations which are useful include those which comprise the macrolide in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Macrolides provided herein are typically formulated in dosage unit form for ease of administration and uniformity of dosage. It will be understood, however, that the total daily amount of the macrolide will be decided by the attending physician within the scope of sound medical judgment. The specific therapeutically effective dose level for any particular subject will depend upon a variety of factors including the disease, disorder, or condition being treated and the severity of the disorder, the activity of the specific macrolide employed; the specific composition employed; the age, body weight, general health, sex and diet of the subject; the time of administration, route of administration, and rate of excretion of the specific macrolide employed; the duration of the treatment; drugs used in combination or coincidental with the specific macrolide employed; and like factors well known in the medical arts.

The macrolides and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of administration.

The exact amount of a macrolide required to achieve an effective amount will vary from subject to subject, depending, for example, on species, age, and general condition of a subject, severity of the side effects or disorder, identity of the particular macrolide(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a macrolide for administration one or more times a day to a 70 kg adult human may comprise about 0.1 mg to about 3000 mg, about 0.1 mg to about 2000 mg, about 0.1 mg to about 1000 mg, about 0.1 mg to about 100 mg, about 1 mg to about 100 mg, or about 10 mg to about 100 mg, of a macrolide per unit dosage form.

In certain embodiments, the macrolides of the present invention may be administered at dosage levels sufficient to deliver from about 0.001 mg/kg to about 100 mg/kg, from about 0.01 mg/kg to about 100 mg/kg, from about 0.1 mg/kg to about 100 mg/kg, from about 0.5 mg/kg to about 100 mg/kg, from about 10 mg/kg to about 100 mg/kg, from about 20 mg/kg to about 100 mg/kg, and from about 25 mg/kg to about 100 mg/kg, of subject body weight per day, one or more times a day, to obtain the desired therapeutic effect.

It will be also appreciated that a macrolide or composition, as described herein, can be administered in combination with one or more additional therapeutically active agents. The macrolide or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive macrolide with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In any of the above described methods, one or more additional therapeutic agents (also referred to as the "agent") may be administered concurrently with, prior to, or subsequent to, the macrolide of the present invention, as described herein. The agent may be added at the same time as the macrolide of the present invention (simultaneous administration), before or after administration of the macrolide of the present invention (sequential administration), or any combination thereof. For example, in certain embodiments, the agent is administered first, followed by simultaneous administration of the agent and the macrolide of the present invention. In certain embodiments, the macrolide of the present invention is administered first, followed by simultaneous administration of the agent and the macrolide of the present invention. In any of the above embodiments, either the agent or the macrolide of the present invention may be further administered alone after the simultaneous administration.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutically agent is an antibiotic. Exemplary antibiotics include, but are not limited to, penicillins (e.g., penicillin, amoxicillin), cephalosporins (e.g., cephalexin), macrolides (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, and quinupristin/dalfoprisin (Syndercid™).

Also encompassed by the invention are kits (e.g., pharmaceutical packs). The kits provided may comprise an inventive pharmaceutical composition or macrolide and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or macrolide. In some embodiments, the inventive pharmaceutical composition or macrolide provided in the container and the second container are combined to form one unit dosage form.

Method of Treatment

The present invention contemplates using macrolides of the present invention for the treatment of infectious diseases, for example, fungal, bacterial, viral, or parasitic infections, and for the treatment of inflammatory conditions. Macrolides are known to exhibit anti-bacterial activity as well as anti-parasitic activity. See, for example, Clark et al., *Bioorganic & Medicinal Chemistry* Letters (2000) 10:815-819 (anti-bacterial activity); and Lee et al., *J. Med. Chem.* (2011) 54:2792-2804 (anti-bacterial and anti-parasitic activity). Macrolides are also known to exhibit an anti-inflammatory effect. See, for example, Amsden, *Journal of Antimicrobial Chemotherapy* (2005) 55:10-21 (chronic pulmonary inflammatory syndromes).

Thus, as generally described herein, provided is a method of treating a infectious disease comprising administering an effective amount of a macrolide of the present invention, or a pharmaceutically acceptable salt thereof, to a subject in need thereof. Such a method can be conducted in vivo (i.e., by administration to a subject) or in vitro (e.g., upon contact with the pathogen, tissue, or cell culture). Treating, as used herein, encompasses therapeutic treatment and prophylactic treatment.

In certain embodiments, the effective amount is a therapeutically effective amount. For example, in certain embodiments, the method slows the progress of an infectious disease in the subject. In certain embodiments, the method improves the condition of the subject suffering from an infectious disease. In certain embodiments, the subject has a suspected or confirmed infectious disease.

In certain embodiments, the effective amount is a prophylactically effective amount. For example, in certain embodiments, the method prevents or reduces the likelihood of an infectious disease, e.g., in certain embodiments, the method comprises administering a macrolide of the present invention to a subject in need thereof in an amount sufficient to prevent or reduce the likelihood of an infectious disease. In certain embodiments, the subject is at risk of an infectious disease (e.g., has been exposed to another subject who has a suspected or confirmed infectious disease or has been exposed or thought to be exposed to a pathogen).

In another aspect, provided is an in vitro method of inhibiting pathogenic growth comprising contacting an effective amount of the macrolide of the present invention with a pathogen (e.g., a bacteria, virus, fungus, or parasite) in a cell culture.

As used herein, "infectious disease" and "microbial infection" are used interchangeably, and refer to an infection with a pathogen, such as a fungus, bacteria, virus, or a parasite. In certain embodiments, the infectious disease is caused by a pathogen resistant to other treatments. In certain embodiments, the infectious disease is caused by a pathogen that is multi-drug tolerant or resistant, e.g., the infectious disease is caused by a pathogen that neither grows nor dies in the presence of or as a result of other treatments.

In certain embodiments, the infectious disease is a bacterial infection. For example, in certain embodiments, provided is a method of treating a bacterial infection comprising administering an effective amount of a macrolide of the present invention, or a pharmaceutically acceptable salt thereof, to a subject in need thereof.

In certain embodiments, the macrolide has a mean inhibitory concentration (MIC), with respect to a particular bacteria, of less than 50 µg/mL, less than 25 µg/mL, less than 20 µg/mL, less than 10 µg/mL, less than 5 µg/mL, or less than 1 µg/mL.

In certain embodiments, the bacteria is susceptible (e.g., responds to) or resistant to known commercial macrolides, such as azithromycin, clindamycin, telithromycin, erythromycin, spiramycin, and the like. See also FIG. 1 for a listing of known macrolides. In certain embodiments, the bacteria is resistant to a known macrolide. For example, in certain embodiments, the bacteria is erythromycin resistant (ER).

In certain embodiments, the bacterial infection is resistant to other antibiotics (e.g., non-macrolide) therapy. For example, in certain embodiments, the pathogen is vancomycin resistant (VR). In certain embodiments, the pathogen is a methicillin-resistant (MR), e.g., in certain embodiments, the bacterial infection is an methicillin-resistant *S. aureus* infection (a MRSA infection).

In certain embodiments, the bacteria has an efflux (e.g., mef, msr) genotype. In certain embodiments, the bacteria has a methylase (e.g., erm) genotype. In certain embodiments, the bacteria has a constitutive genotype. In certain embodiments, the bacteria has an inducible genotype.

Exemplary bacterial infections include, but are not limited to, infections with a Gram positive bacteria (e.g., of the phylum Actinobacteria, phylum Firmicutes, or phylum Tenericutes); Gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacterial infection is an infection with a Gram positive bacteria.

In certain embodiments, the Gram positive bacteria is a bacteria of the phylum Firmicutes.

In certain embodiments, the bacteria is a member of the phylum Firmicutes and the genus *Enterococcus*, i.e., the bacterial infection is an *Enterococcus* infection. Exemplary Enterococci bacteria include, but are not limited to, *E. avium, E. durans, E. faecalis, E. faecium, E. gallinarum, E. solitarius, E. casseliflavus*, and *E. raffinosus*.

In certain embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. camous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xyiosus*. In certain embodiments, the *Staphylococcus* infection is an *S. aureus* infection. In certain embodiments, the *S. aureus* has an efflux (e.g., mef, msr) genotype. In certain embodiments, the *S. aureus* has a methylase (e.g., erm) genotype.

In certain embodiments, the bacteria is a member of the phylum Firmicutes and the genus *Bacillus*, i.e., the bacterial infection is a *Bacillus* infection. Exemplary *Bacillus* bacteria include, but are not limited to, *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. globigii, B. infemus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis*, and *B. weihenstephanensis*. In certain embodiments, the *Bacillus* infection is a *B. subtilis* infection. In certain embodiments, the *B. subtilis* has an efflux (e.g., mef, msr) genotype. In certain embodiments, the *B. subtilis* has a methylase (e.g., erm) genotype.

In certain embodiments, the bacteria is a member of the phylum Firmicutes and the genus *Streptococcus*, i.e., the bacterial infection is a *Streptococcus* infection. Exemplary *Streptococcus* bacteria include, but are not limited to, *S. agalactiae, S. anginosus, S. bovis, S. canis, S. constellatus, S. dysgalactiae, S. equinus, S. iniae, S. intermedius, S. mitis,*

*S. mutans, S. oralis, S. parasanguinis, S. peroris, S. pneumoniae, S. pyogenes, S. ratti, S. salivarius, S. thermophilus, S. sanguinis, S. sobrinus, S. suis, S. uberis, S. vestibularis, S. viridans*, and *S. zooepidemicus*. In certain embodiments, the *Streptococcus* infection is an *S. pyogenes* infection. In certain embodiments, the *Streptococcus* infection is an *S. pneumoniae* infection. In certain embodiments, the *S. pneumoniae* has an efflux (e.g., mef, msr) genotype. In certain embodiments, the *S. pneumoniae* has a methylase (e.g., erm) genotype.

In certain embodiments, the bacterial infection is an infection with a Gram negative bacteria.

In certain embodiments, the Gram negative bacteria is a bacteria of the phylum Proteobacteria and the genus *Escherichia*, i.e., the bacterial infection is an *Escherichia* infection. Exemplary *Escherichia* bacteria include, but are not limited to, *E. albertii, E. blattae, E. coli, E. fergusonii, E. hermannii*, and *E. vulneris*. In certain embodiments, the *Escherichia* infection is an *E. coli* infection.

In certain embodiments, the Gram negative bacteria is a bacteria of the phylum Proteobacteria and the genus *Haemophilus*, i.e., the bacterial infection is an *Haemophilus* infection. Exemplary *Haemophilus* bacteria include, but are not limited to, *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis*, and *H. somnus*. In certain embodiments, the *Escherichia* infection is an *H. influenzae* infection.

In certain embodiments, the infectious disease is an infection with a parasitic infection. Thus, in certain embodiments, provided is a method of treating a parasitic infection comprising administering an effective amount of a macrolide of the present invention, or a pharmaceutically acceptable salt thereof, to a subject in need thereof.

In certain embodiments, the macrolide has a $IC_{50}$ (uM) with respect to a particular parasite, of less than 50 uM, less than 25 uM, less than 20 uM, less than 10 uM, less than 5 uM, or less than 1 uM.

Exemplary parasites include, but are not limited to, *Trypanosoma* spp. (e.g., *Trypanosoma cruzi, Trypansosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp. (e.g., *P. flaciparum*), *Crytosporidium* spp., *Isospora* spp., *Balantidium* spp., *Loa loa, Ascaris lumbricoides, Dirofilaria immitis*, and *Toxoplasma* ssp. (e.g. *T. gondii*).

As generally described herein, the present invention further a method of treating an inflammatory condition comprising administering an effective amount of a macrolide of the present invention, or a pharmaceutically acceptable salt thereof, to a subject in need thereof. Such a method can be conducted in vivo (i.e., by administration to a subject) or in vitro (e.g., upon contact with the pathogen, tissue, or cell culture). Treating, as used herein, encompasses therapeutic treatment and prophylactic treatment.

In certain embodiments, the effective amount is a therapeutically effective amount. For example, in certain embodiments, the method slows the progress of an inflammatory condition in the subject. In certain embodiments, the method improves the condition of the subject suffering from an inflammatory condition. In certain embodiments, the subject has a suspected or confirmed inflammatory condition.

In certain embodiments, the effective amount is a prophylactically effective amount. For example, in certain embodiments, the method prevents or reduces the likelihood of an inflammatory condition, e.g., in certain embodiments, the method comprises administering a macrolide of the present invention to a subject in need thereof in an amount sufficient to prevent or reduce the likelihood of an inflammatory condition. In certain embodiments, the subject is at risk to an inflammatory condition.

In another aspect, provided is an in vitro method of treating an inflammatory condition comprising contacting an effective amount of the macrolide of the present invention with an inflammatory cell culture.

The term "inflammatory condition" refers to those diseases, disorders, or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent). Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), chronic pulmonary inflammatory syndromes (e.g., diffuse panbronchiolitis, cystic fibrosis, asthma, bronchiectasis, chronic obstructive pulmonary disease), arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), a gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, scleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo, and Wegener's granulomatosis.

In certain embodiments, the inflammatory condition is an acute inflammatory condition (e.g., for example, inflammation resulting from an infection). In certain embodiments, the inflammatory condition is a chronic inflammatory condition. In certain embodiments, the inflammatory condition is inflammation associated with cancer.

Diastereoselective Aldol Method

During the construction of the western half (A), it was discovered that pseudoephanamine glycinamide undergoes highly selective addition to aldehydes and ketones to generate products with high diastereoselectivity in a single step. See, e.g., Scheme W1. Such a reaction is considered broadly applicable using other chiral auxiliaries, such as pseudoephedrine glycinamide, in combination with a wide range of aldehydes and ketones,

Scheme W1.

wherein:

$R^{25}$ is optionally substituted alkyl, optionally substituted aryl, optionally substituted heteroaryl, or a nitrogen protecting group;

$R^{26}$ and $R^{27}$ are each independently optionally substituted alkyl, optionally substituted aryl, or optionally substituted heteroaryl;

$P^2$ is hydrogen, optionally substituted alkyl, or an oxygen protecting group; and $R^{29}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^8$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

or wherein $R^8$ and $R^{29}$ can be taken together to form an optionally substituted carbocyclyl or optionally substituted heterocyclyl ring;

$G^1$ is —$OR^{12}$ or —$NR^{13}R^{14}$;

$R^{12}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group; and $R^{13}$ and $R^{14}$ are each independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or $R^{13}$ and $R^{14}$ are joined to form a cyclic moiety.

In certain embodiments, $R^{25}$ is optionally substituted $C_{1-6}$ alkyl. In certain embodiments, $R^{25}$ is unsubstituted $C_{1-6}$ alkyl. In certain embodiments, $R^{25}$ is methyl. In certain embodiments, $R^{25}$ is ethyl. In certain embodiments, $R^{25}$ is a nitrogen protecting group.

In certain embodiments, $R^{26}$ and $R^{27}$ are each independently optionally substituted alkyl. In certain embodiments, at least one of $R^{26}$ and $R^{27}$ is independently optionally substituted $C_{1-6}$ alkyl. In certain embodiments, at least one of $R^{26}$ and $R^{27}$ is unsubstituted alkyl. In certain embodiments, at least one of $R^{26}$ and $R^{27}$ is methyl. In certain embodiments, at least one of $R^{26}$ and $R^{27}$ is ethyl.

In certain embodiments, $R^{26}$ and $R^{27}$ are each independently optionally substituted aryl. In certain embodiments, at least one of $R^{26}$ and $R^{27}$ is independently optionally substituted aryl. In certain embodiments, at least one of $R^{26}$ and $R^{27}$ is independently optionally substituted phenyl. In certain embodiments, at least one of $R^{26}$ and $R^{27}$ is independently unsubstituted phenyl. In certain embodiments, both $R^{26}$ and $R^{27}$ are optionally substituted phenyl. In certain embodiments, both $R^{26}$ and $R^{27}$ are unsubstituted phenyl. In certain embodiments, $R^{26}$ is optionally substituted $C_{1-6}$ alkyl and $R^{27}$ is optionally substituted aryl. In certain embodiments, $R^{26}$ is unsubstituted $C_{1-6}$ alkyl and $R^{27}$ is optionally substituted phenyl. In certain embodiments, $R^{26}$ is methyl and $R^{27}$ is phenyl.

In certain embodiments, $R^{26}$ and $R^{27}$ are each independently optionally substituted heteroaryl, e.g., pyridinyl. In certain embodiments, at least one of $R^{26}$ and $R^{27}$ is independently optionally substituted heteroaryl. In certain embodiments, both $R^{26}$ and $R^{27}$ are optionally substituted heteroaryl. In certain embodiments, $R^{26}$ is optionally substituted $C_{1-6}$ alkyl and $R^{27}$ is optionally substituted heteroaryl.

As used herein, $G^1$ is —$OR^{12}$, or —$NR^{14}R^{13}$, wherein $R^{12}$, $R^{13}$, and $R^{14}$ are as defined above. In certain embodiments, $G^1$ is —$NH_2$. In certain embodiments, $G^1$ is —OH.

In certain embodiments, $P^2$ is hydrogen. In certain embodiments, $P^2$ is optionally substituted alkyl, e.g. $C_{1-6}$ alkyl. In certain embodiments, $P^2$ is unsubstituted $C_{1-6}$ alkyl. In certain embodiments, $P^2$ is an oxygen protecting group.

In certain embodiments, $R^8$ and $R^{29}$ are different. In certain embodiments, $R^{29}$ is a larger group (sterically) than $R^8$.

In certain embodiments, at least one of $R^8$ and $R^{29}$ is optionally substituted alkyl, e.g. $C_{1-10}$ alkyl. In certain embodiments, at least one of $R^8$ and $R^{29}$ is unsubstituted $C_{1-10}$ alkyl. In certain embodiments, at least one of $R^8$ and $R^{29}$ is substituted $C_{1-10}$ alkyl.

In certain embodiments, $R^8$ is hydrogen. In certain embodiments, $R^8$ is hydrogen and $R^{29}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^8$ is hydrogen and $R^{29}$ is optionally substituted alkyl, e.g. $C_{1-10}$ alkyl. In certain embodiments, $R^8$ is hydrogen and $R^{29}$ is optionally substituted aryl, e.g. phenyl.

In certain embodiments, $R^8$ is optionally substituted alkyl, e.g., methyl. In certain embodiments, $R^8$ is optionally substituted alkyl and $R^{29}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^8$ is optionally substituted alkyl and $R^{29}$ is optionally substituted alkyl, e.g. $C_{1-10}$ alkyl. In certain embodiments, $R^8$ is optionally substituted alkyl and $R^{29}$ is optionally substituted aryl, e.g. phenyl.

In certain embodiments, $R^8$ and $R^{29}$ are taken together to form an optionally substituted carbocyclyl ring, e.g., cyclopropyl, cyclobutyl, cyclopentyl, or cyclohexyl. In certain embodiments, $R^8$ and $R^{29}$ are taken together to form an optionally substituted heterocyclyl ring, e.g., oxetane, azetidine, tetrahydrofuran, pyrrolidine, pyran, dioxolane, piperidine, piperazine, or morpholine.

In certain embodiments, the compound of Formula (A-1) is of the formula:

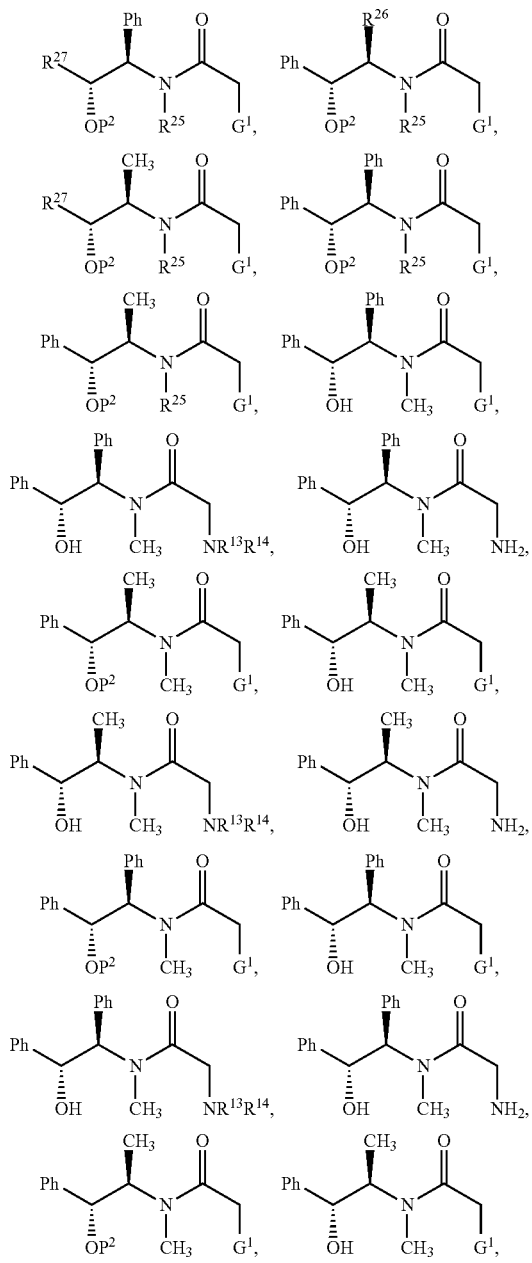

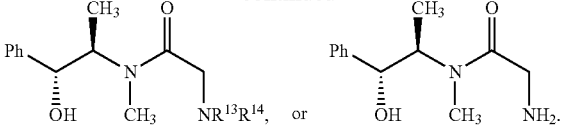

In certain embodiments, an organic base is present in the adol reaction of Scheme W1. In certain embodiments, the organic base is a Group IA or Group IIA hydroxide or alkoxide, organo lithium, organo sodium, or organo magnesium. In certain embodiments, the base is organo lithium. In certain embodiments, the base is LDA. In certain embodiments, the base is LiHMDS. In certain embodiments, the base is NaHMDS. In certain embodiments, a Group IA or Group IIA halide salt is present in the adol reaction of Scheme W1. In certain embodiments, a Group IA or Group IIA halide salt is present with the organic base in the adol reaction of Scheme W1. In certain embodiments, the halide salt is a lithium halide. In certain embodiments, the halide salt is LiCl.

As depicted in Scheme W1, the diastereoselective aldol reaction can provide up to four diastereomeric products upon formation of the two new stereogenic centers. These products are typically enriched in the stereoisomer depicted for formula A-20 over all other stereoisomers. In certain embodiments, the aldol reaction of Scheme W1 provides a ratio of the stereoisomer of formula A-20 over all other stereoisomers of about 1:1 to about 100:1. In certain embodiments, the aldol reaction of Scheme W1 provides a ratio of stereoisomer of formula A-20 over all other stereoisomers of about 1:1 to about 10:1. In certain embodiments, the aldol reaction of Scheme W1 provides a ratio of the stereoisomer of formula A-20 over all other stereoisomers of about 5:1 to about 10:1. In certain embodiments, the aldol reaction of Scheme W1 provides a ratio of the stereoisomer of formula A-20 over all other stereoisomers of about 10:1 to about 100:1. In certain embodiments, the aldol reaction of Scheme W1 provides a ratio of the stereoisomer of formula A-20 over all other stereoisomers of about 30:1 to about 100:1. In certain embodiments, the aldol reaction of Scheme W1 provides a ratio of the stereoisomer of formula A-20 over all other stereoisomers of about 50:1 to about 100:1. In certain embodiments, the aldol reaction of Scheme W1 provides a ratio of the stereoisomer of formula A-20 over all other stereoisomers of about 80:1 to about 100:1. In certain embodiments, the aldol reaction of Scheme W1 provides a ratio of the stereoisomer of formula A-20 over all other stereoisomers of about 90:1 to about 100:1.

The aldol reaction product Formula (A-20) may undergo further transformations to incorporate different functional groups, as shown in Scheme W2. As used herein, $R^{30}$ is optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, or substituted amino. In certain embodiments, $R^{30}$ is optionally substituted alkyl. In certain embodiments, $R^{30}$ is hydroxyl. In certain embodiments, $R^{30}$ is substituted hydroxyl. In certain embodiments, $R^{30}$ is amino. In certain embodiments, $R^{30}$ is substituted amino. In certain embodiments, treating a compound of Formula (A-20) with an organometal complex having a carbon-metal bond provides a compound of Formula (A-21) as a ketone, wherein the metal is Li, Na, K, Mg, or Zn. In certain embodiments, the organometal complex is organolithium. In certain embodiments, the organometal complex is alkyl lithium (e.g. methyl lithium, ethyl lithium). In certain embodiments, the organometal complex is Grignard reagent (e.g. MeMgCl, EtMgCl, MeMgBr).

Scheme W2.

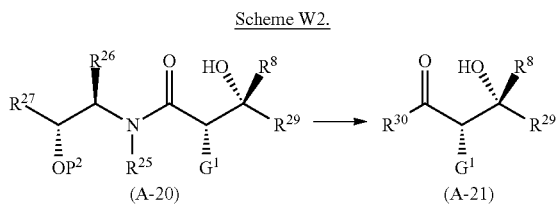

In certain embodiments, heating a compound of Formula (A-20) under a proton-rich condition provides a compound of Formula (A-22) as a carboxylic acid or ester as shown in W3.

Scheme W3.

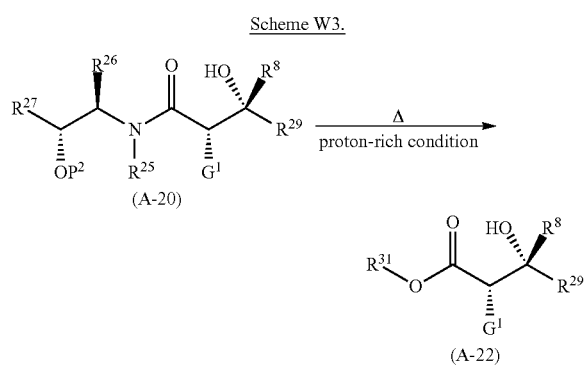

The term "proton-rich condition" as used herein, refers to either a protic solvent, or, a mixture of an aprotic solvent and a proton source. Exemplary protic solvents include, but are not limited to, $H_2O$, methanol, ethanol, propanol, isopropanol, butanol, t-butanol, and the like. Proton source can be either inorganic acid or organic acid. Exemplary inorganic acids include, but are not limited to, hydrobromic acid, hydrochloric acid, hydrofluoric acid, hydroiodic acid, nitric acid, perchloric acid, sulfuric acid, and phosphoric acid. Exemplary organic acids include, but are not limited to, sulfonic acid (methanesulfonic, trifluoromethane sulfonic, ethanesulfonic, benzenesulfonic or p-toluenesulfonic), acetic acid, malic acid, fumaric acid, succinic acid, citric acid, benzoic acid, gluconic acid, lactic acid, mandelic acid, mucic acid, pamoic acid, pantothenic acid, oxalic acid, and maleic acid. In certain embodiments, the proton-rich condition is a mixture of an aprotic solvent and sulfuric acid.

As used herein, $R^{31}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl. In certain embodiments, $R^{31}$ is optionally substituted alkyl, e.g. $C_{1-6}$ alkyl. In certain embodiments, $R^{31}$ is unsubstituted $C_{1-6}$ alkyl. In certain embodiments, $R^{31}$ is methyl, ethyl, or propyl. In certain embodiments, $R^{31}$ is substituted $C_{1-6}$ alkyl. In certain embodiments, $R^{31}$ is hydrogen.

In certain embodiments, a compound of Formula (A-20) is treated with a reducing agent to provide a compound of Formula (A-23) as an aldehyde as shown in W4. An example of a reducing agent to be used in Scheme W4 includes metal hydrides. In certain embodiments, the reducing agent is lithium aluminum hydride, lithium borohydride, sodium borohydride, diisobutyl aluminum hydride, or sodium bis(2-methoxyethoxy)aluminum hydride. The amount of the reducing agent to be used may be selected, as appropriate, in the range from equivalent to excess amount relative to the compound of Formula (A-20).

Scheme W4.

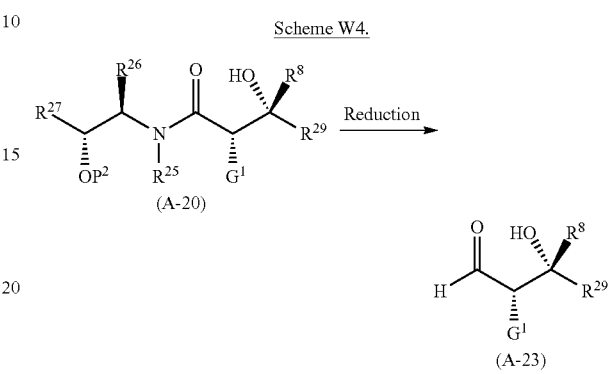

In certain embodiments, a compound of Formula (A-20) is treated with a reducing agent to provide a compound of Formula (A-24) as an alcohol shown in Scheme W5. An example of a reducing agent to be used in Scheme W5 includes metal hydrides. In certain embodiments, the reducing agent is lithium amino borohydride, lithium aluminum hydride, lithium borohydride, sodium borohydride, diisobutyl aluminum hydride, or sodium bis(2-methoxyethoxy)aluminum hydride. The amount of the reducing agent to be used may be selected, as appropriate, in the range from equivalent to excess amount relative to the compound of Formula (A-20). In certain embodiments, the reaction of Scheme W4 is conducted under inert gas such as nitrogen or argon.

Scheme W5.

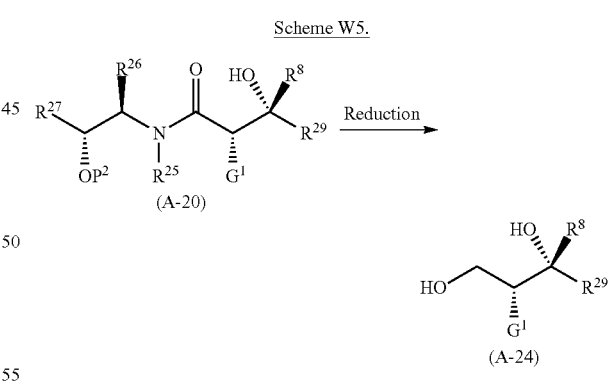

In certain embodiments, a compound of Formula (A-20) is treated with a reducing agent to provide a compound of Formula (A-25) as an amine shown in Scheme W6. An example of a reducing agent to be used in Scheme W6 includes metal hydrides. In certain embodiments, the reducing agent is lithium amino borohydride, lithium aluminum hydride, lithium borohydride, sodium borohydride, diisobutyl aluminum hydride, or sodium bis(2-methoxyethoxy)aluminum hydride. The amount of the reducing agent to be used may be selected, as appropriate, in the range from equivalent to excess amount relative to the compound of Formula (A-20). In certain embodiments, the reaction of Scheme W4 is conducted under inert gas such as nitrogen or argon.

Scheme W6.

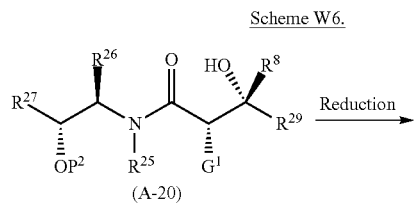

In certain embodiments, a compound of Formula (A-21) or Formula (A-26) is treated with phosphine to provide a compound of Formula (A-27) or Formula (A-28) respectively as shown in Scheme W7. In certain embodiments, an organic amine is present in the reactions of Scheme W7. In certain embodiments, the organic amine is tertiary amine. In certain embodiments, the tertiary amine is $Et_2^iPrN$.

Scheme W7.

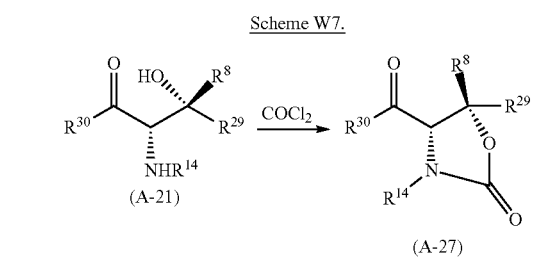

Construction of the Western Half

Construction of the western half (A) (depicted below drawn two different ways) used in the preparation of macrolides of the present invention is contemplated utilizing the inventive diastereoselective aldol method, as described herein. However, the below description of synthesizing the western half using this aldol method is one of many ways of preparing the western half, and should not limit the invention as a whole.

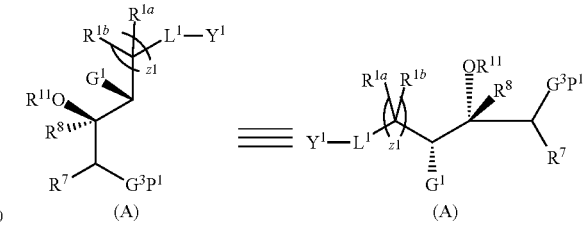

In certain embodiments, the synthesis of the western half proceeds with the treatment of (A-1) or salt thereof, with a base, followed by contacting with a compound of Formula (A-2), or salt thereof, to provide an aldol product of Formula (A-3), or salt thereof, as depicted in Scheme W-8, Scheme W-8.

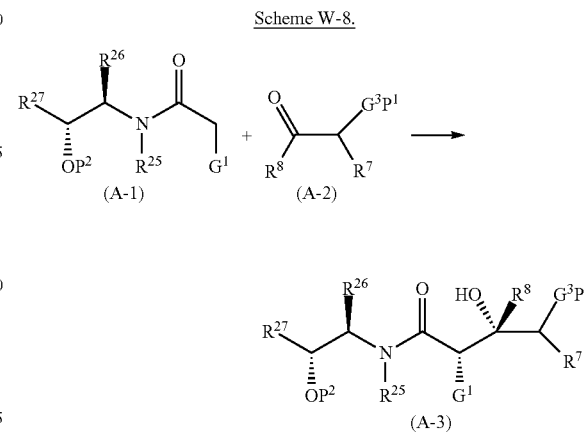

wherein $R^8$, $R^7$, $R^{25}$, $R^{26}$, $R^{27}$, $G^1$, $G^3$, and $P^3$ are as defined herein.

In certain embodiments, the base is LiHMDS. In certain embodiments, the base is LDA. In certain embodiments, the reaction further comprises an additive, such as LiCl.

In certain embodiments, $G^1$ is $-NH_2$, the reaction proceeds to provide an aldol product as depicted in Scheme W-9, or salt thereof.

Scheme W-9.

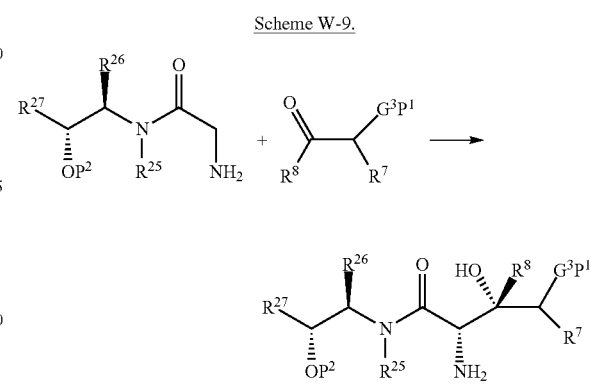

In certain embodiments, $G^1$ is $-NH_2$, and $G^3$ is $-O-$, the reaction to provide an aldol product, or salt thereof, as depicted in Scheme W-10, or salt thereof.

Scheme W-10.

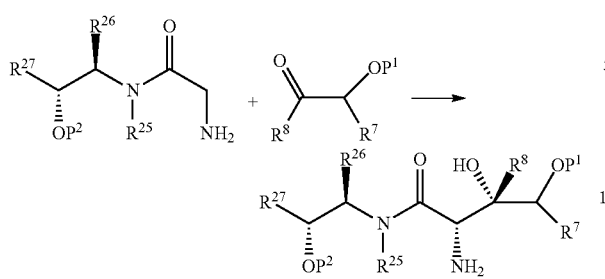

In certain embodiments, $G^1$ is —OH, the reaction to provide an aldol product, or salt thereof, as depicted in Scheme W-11, or salt thereof.

Scheme W-11.

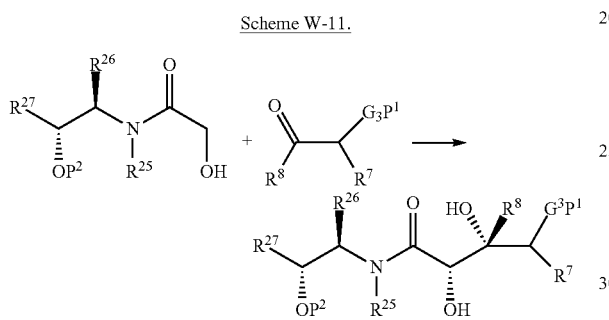

In certain embodiments, $G^1$ is —OH, and $G^3$ is —O—, the reaction to provide an aldol product, or salt thereof, as depicted in Scheme W-12, or salt thereof.

Scheme W-12.

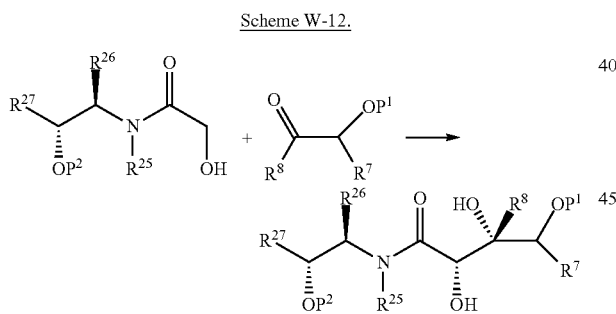

In certain embodiments, wherein $G^1$ is —$OR^{12}$, —$NHR^{13}$, —$NHR^{14}$, or —$NR^{13}R^{14}$, and $R^{12}$, $R^{13}$, and $R^{14}$ are non-hydrogen groups as described herein, protection of the free hydroxyl of Formula (A-3), or salt thereof, provides a compound of Formula (A-4), or salt thereof, as depicted in Scheme W-13, wherein $R^{11}$ is as defined herein.

Scheme W-13.

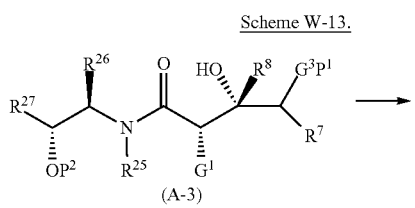

(A-3)

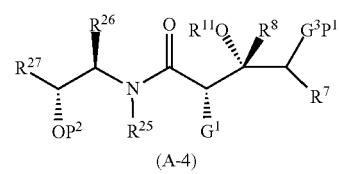

(A-4)

Alternatively, wherein $G^1$ is —$NH_2$, —$NHR^{13}$, or —$NHR^{14}$, the amino group be protected first, followed by protection of the alcohol to provide a compound of Formula (A-4), or salt thereof, wherein $G^1$ is —$NHR^{13}$, —$NHR^{14}$, or —$NR^{13}R^{14}$ as depicted in Scheme W-14.

Scheme W-14.

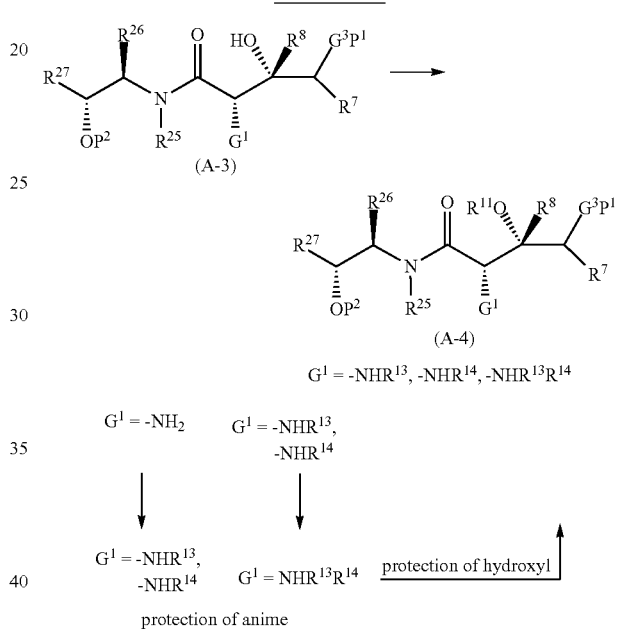

Alternatively, in certain embodiments, wherein $G^1$ is —$NH_2$, —$NHR^{13}$, —$NHR^{14}$, or —OH, the amino and hydroxyl groups are simultaneously protected as a cyclic carbamate or cyclic carbonate, e.g., upon treatment with phosgene, as depicted in Scheme W-15, or salt thereof.

Scheme W-15.

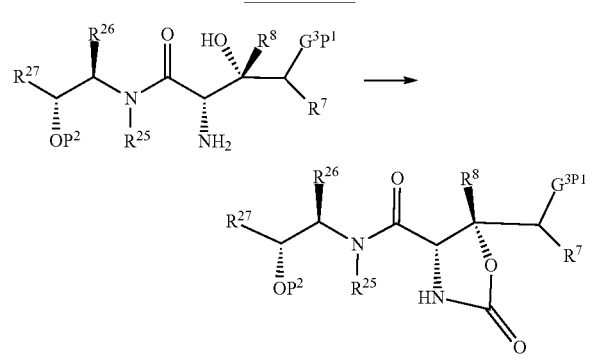

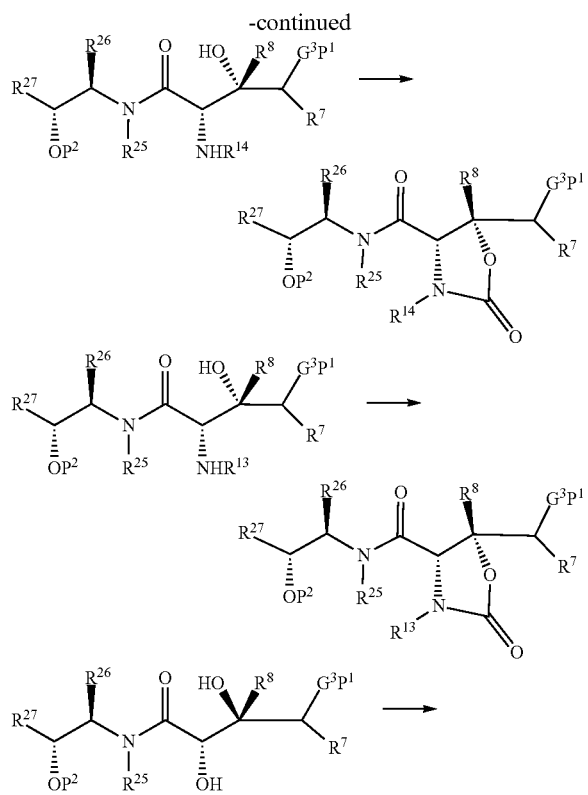

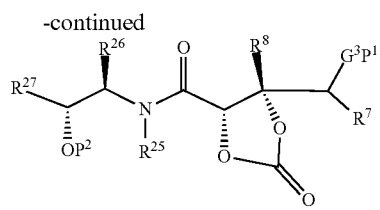

In certain embodiments, treating a compound of Formula (A-4), wherein $R^{11}$ and $G^1$ are as defined herein, and which may be joined or not joined as a carbonate or carbamate, with a nucleophilic $R^{1a}$ reagent, e.g., $R^{1a}M$, wherein M is an anion, Li, Na, K, or MgX wherein X is a halogen, provides the cleavage product of Formula (A-5), or salt thereof, as depicted in Scheme W-16. The resulting compound is a suitable handle for further diversification, such as reduction of the ketone moiety to an alcohol, followed by conversion to a leaving group (LG), optionally followed by conversion to a nitro moiety, amination to an amine or imine, or additional nucleophilic attack of the ketone or imine moiety with a nucleophilic $R^{1b}$ reagent, e.g., $R^{1b}M$, wherein M is an anion, Li, Na, K, or MgX wherein X is a halogen, to provide a tertiary alcohol or amine, wherein $R^{1a}$, $R^{1b}$, $R^8$, $R^7$, $R^{25}$, $R^{26}$, $R^{27}$, $R^{13}$, $R^{14}$, $G^3$, $P^2$, and $P^3$ are as defined herein.

Scheme W-16.

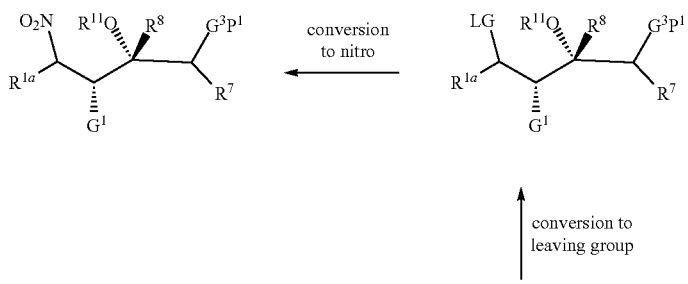

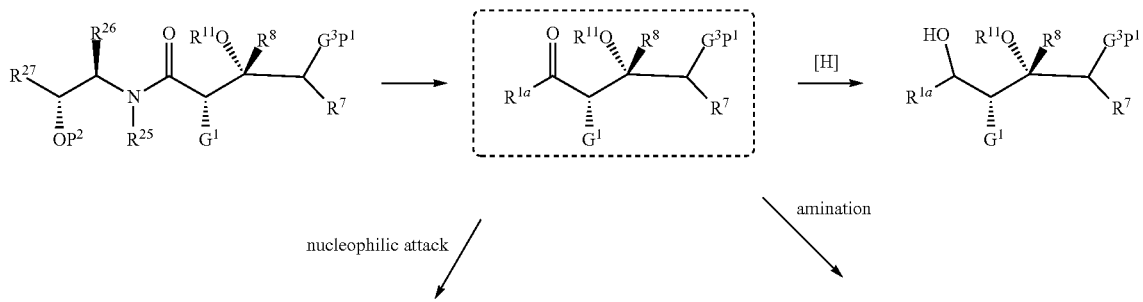

475

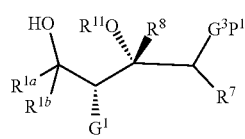

-continued

476

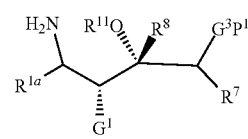

or

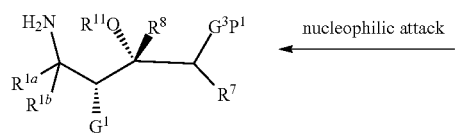

nucleophilic attack

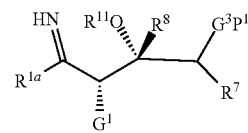

In certain embodiments, reducing a compound of Formula (A-4), wherein $R^{11}$ and $G^1$ are as defined herein, and which may be joined or not joined as a carbonate or carbamate, provides an alcohol, or salt thereof, as depicted in Scheme W-17. The resulting compound is a suitable handle for further diversification, such as oxidation to an aldehyde, or conversion to a leaving group, which optionally is converted to a nitro compound or an amine, wherein LG, $R^{1a}$, $R^{1b}$, $R^8$, $R^7$, $R^{25}$, $R^{26}$, $R^{27}$, $G^1$, $G^3$, $P^2$, and $P^3$ are as defined herein.

-continued

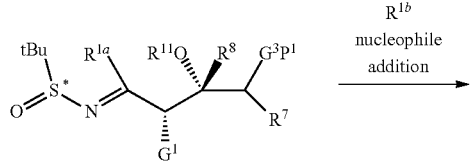

$R^{1b}$ nucleophile addition

Scheme W-17.

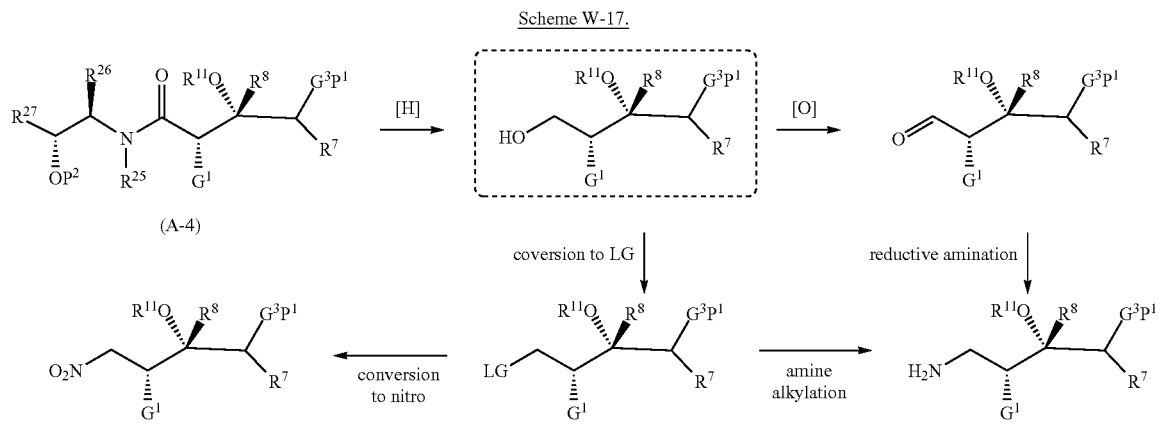

In certain embodiments, the aldehydes or ketones depicted in Scheme W-16 can be converted into substituted amines using the route depicted in Scheme W-18. Formation of the Ellman sulfinimide followed by addition of nucleophiles reagents derived from $R^{1b}$ (e.g., Grignard or organolithium reagents) and subsequent deprotection of the auxiliary produces the desired substituted amines with either relative stereochemistry.

-continued

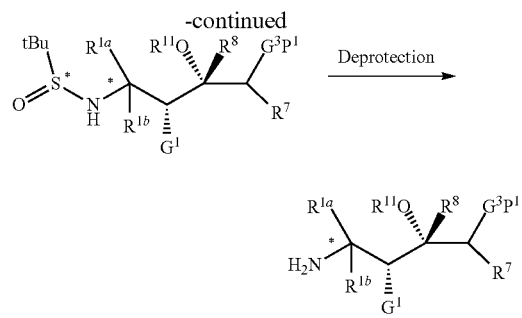

Deprotection

Scheme W-18.

477
-continued

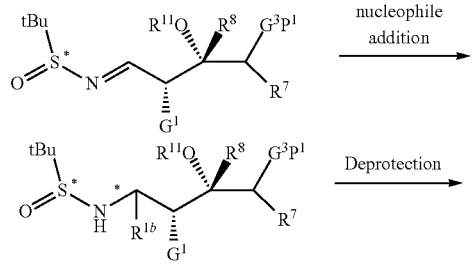

478
-continued

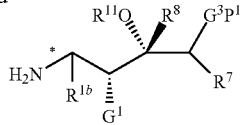

In certain embodiments, the compound of Formula (A-4), wherein $R^{11}$ and $G^1$ are as defined herein, or salt thereof, may be converted to an acid, ester, activated acid or acyl halide, ketone, vinyl iodide, epoxide, or 1-carbon homologated ketone or aldehyde as depicted in Scheme W-18, wherein X, $R^{1a}$, $R^{Z3}$, LG, $R^8$, $R^7$, $R^{25}$, $R^{26}$, $R^{27}$, $G^1$, $G^3$, $P^2$, and $P^3$ are as defined herein.

Scheme W-19.

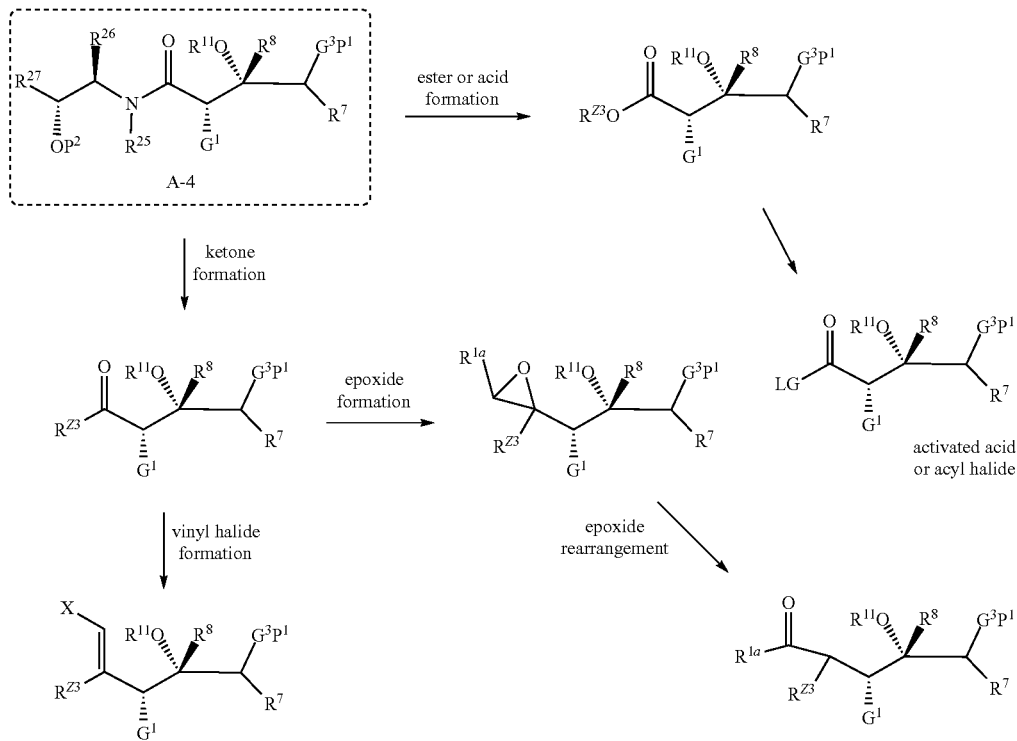

In certain embodiments, phosphonate ester or phosphorous ylides of the western fragment can be prepared to enable linkage to an eastern half carbonyl moiety through an unsaturated ketone linkage (see Scheme W-20). The ester group can be homologated into an intermediate that enables addition of carbon nucleophiles containing the reactive phosphorous moiety.

Scheme W-20

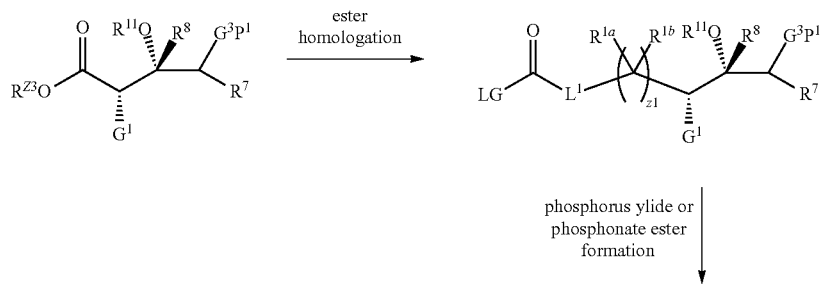

phosphorus ylide or phosphonate ester formation

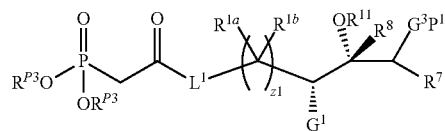 or 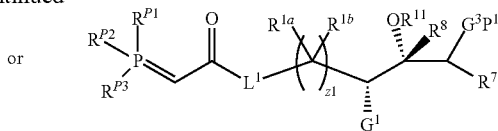

Construction of the Eastern Half

Construction of the eastern half (B) used in the preparation of macrolides of the present invention is further described herein. However, the below description of synthesizing the eastern half is one of many ways of preparing the eastern half, and should not limit the invention as a whole.

(B)

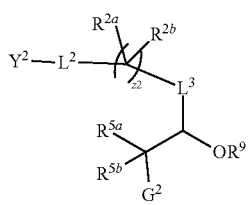

The eastern half (B) is generally described herein, and comprises a group L3 of formula:

(L³-i)

(L³-ii)

(L³-iii)

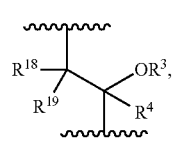

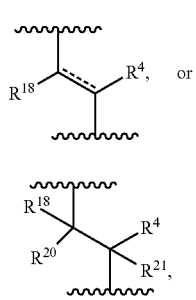

respectively providing a compound of formula:

(B-a)

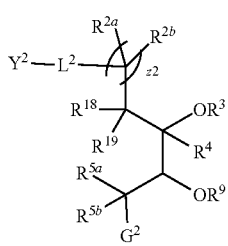

(B-b)

(B-c)

wherein -----, $z2$, $Y^2$, $L^2$, $R^{2a}$, $R^{2b}$, $R^{18}$, $R^{19}$, $R^{20}$, $R^{21}$, $R^{5a}$, $R^{5b}$, $G^2$, and $R^9$ are as defined herein.

It is generally understood that the eastern half encompasses such functionality of formula (L³-i), (L³-ii), and (L³-iii), and that this functionality may be present in the starting material, or may be manipulated at any stage in the synthesis of the eastern half component. For example, as described above and herein, the (L³-i) group may be converted to (L³-ii) and (L³-iii) by elimination of the —OR³ group, and reduction or functionalization of the double bond.

In certain embodiments, preparation of the eastern half comprises installation of a $G^2$ group from the aldehyde (A-1), or salt thereof, with a $G^2$ reagent as defined herein, optionally in the presence of a base, to provide a compound of formula (A-2), or salt thereof, as depicted in Scheme E-1.

Scheme E-1.

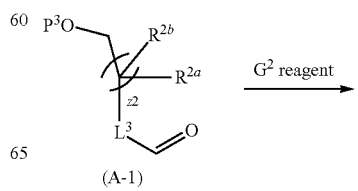

(A-1)

-continued

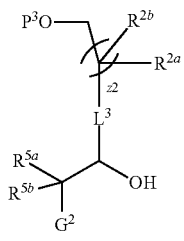

(A-2)

wherein L$^3$, R$^{2*}$, R$^{21*}$, and z2 are as defined herein, the G$^2$ reagent is a compound of formula:

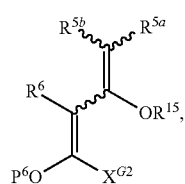

(G-a)

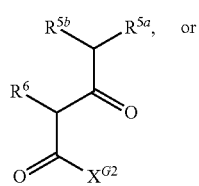

(G-b)

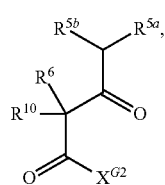

(G-c)

wherein R$^6$, R$^{10}$, R$^{5a}$, and R$^{5b}$ are as defined herein;

each instance of X$^{62}$ is —OR$^{15}$, —SR$^{15}$, or —N(R$^{15}$)$_2$;

each instance of R$^{15}$ is independently silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or two R$^{15}$ groups can be taken together to form an optionally substituted heteroaryl or heterocyclic ring;

each instance of P$^3$ and P$^6$ is independently silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

or two R$^{15}$ groups are joined as a group of formula —C(R$^{16a}$)$_2$— to provide a group G$^2$ of formula:

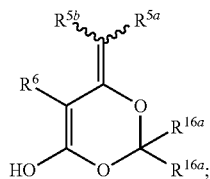

(G-d)

or P$^6$ and R$^{15}$ are joined as a group of formula —Si(R$^{16b}$)$_2$— to provide a group G$^2$ of formula:

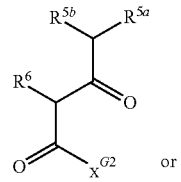

(G-e)

wherein each instance of R$^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and wherein each instance of R$^{16b}$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl; such that reaction with a G$^2$ reagent of formula:

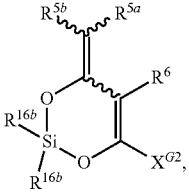

(G-b)

or (G-e)

provides a G$^2$ group of formula:

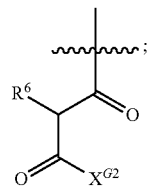

such that reaction with a $G^2$ reagent of formula:

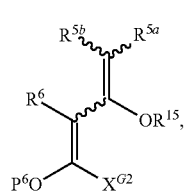

provides a $G^2$ group of formula:

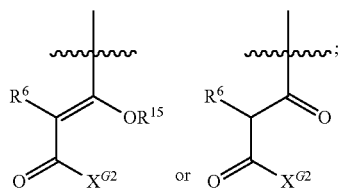

such that reaction with a $G^2$ reagent of formula:

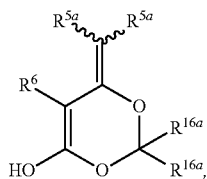

(G-d)

provides a $G^2$ group of formula:

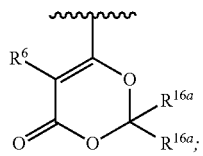

and such that reaction with a $G^2$ reagent of formula:

(G-c)

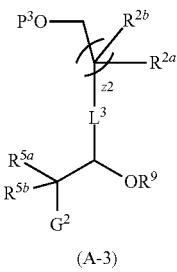

provides a G group of formula:

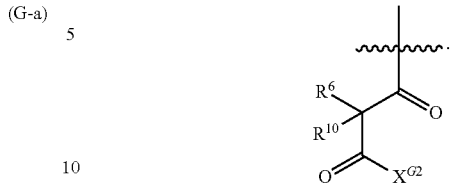

(G-a)

Protection of the alcohol with an $R^9$ group, wherein $R^9$ is as defined herein, using a compound of formula $R^9$-LG, wherein LG is a leaving group as defined herein, or using a thioglycoside compound $R^9$—SAr, when $R^9$ is a carbohydrate as defined herein and wherein Ar is optionally substituted aryl or optionally substituted heteroaryl, provides the protected alcohol of Formula (A-3), as depicted in Scheme E-2, wherein $G^2$, $L^3$, $R^{2a}$, $R^{2b}$, $R^{5a}$, $R^{5b}$, and z2 are as defined herein.

Scheme E-2.

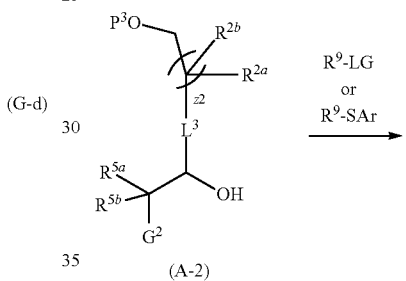

Deprotection of $P^3$ of (A-3) provides the alcohol (A-4), which is a handle for further synthetic manipulation. See, e.g., Scheme E-3. For example, the alcohol may be oxidized to the aldehyde or acid, and the acid may be further converted to the ester or an activated acid or acyl halide. The aldehyde may be converted to the amine by reductive amination, or to the ketone upon addition with a nucleophilic $R^{Z4}$ reagent, e.g., $R^{Z4}M$, wherein M is an anion, Li, Na, K, or MgX wherein X is a halogen, followed by oxidation. The alcohol may also be converted to a leaving group, as defined herein, which may in turn be converted to a nitro compound or an amine.

Scheme E-3.
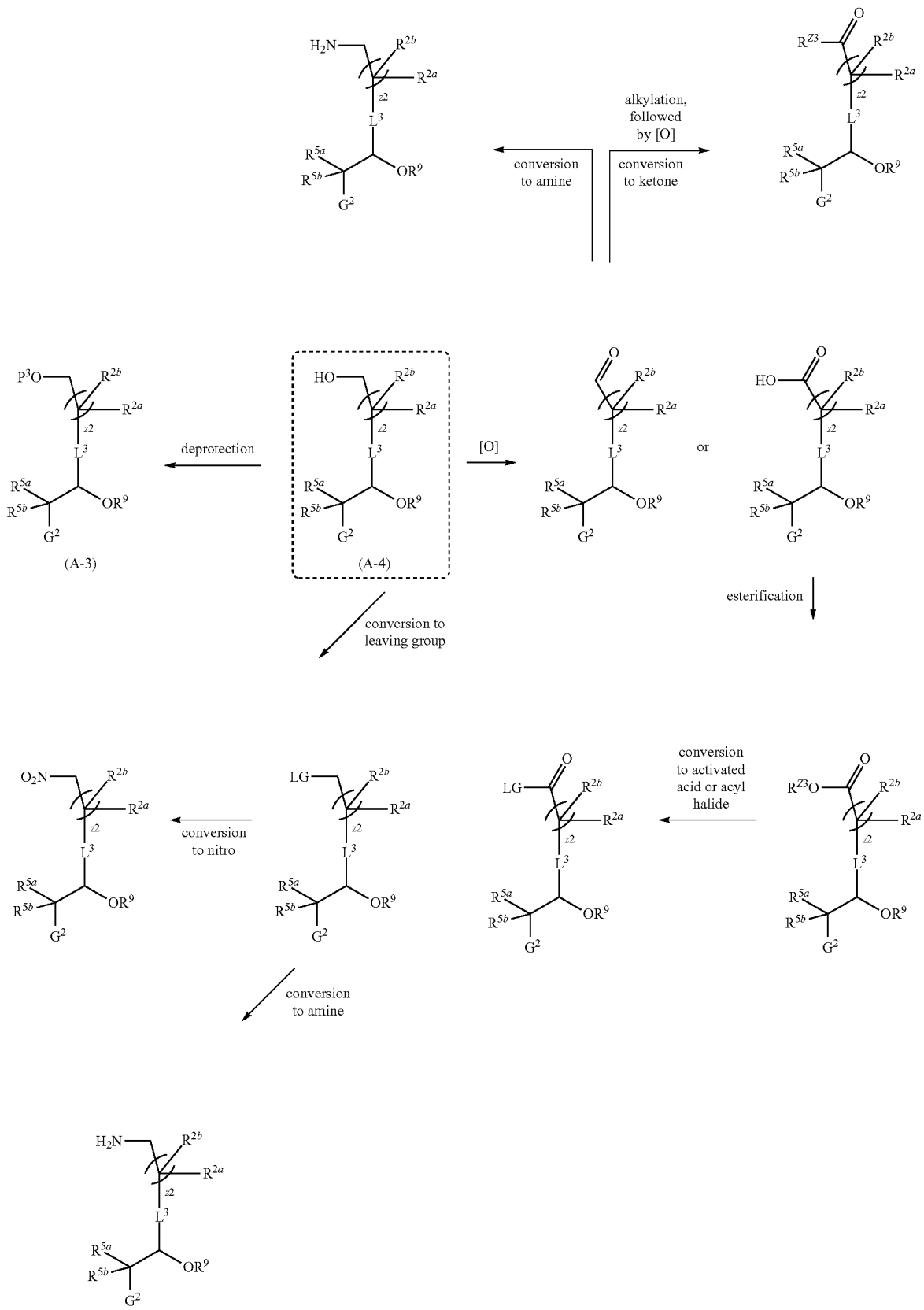

As an alternative to the aldehyde (A-1), further contemplated is an aldehyde of Formula (A-5), or salt thereof, which may be converted to various compounds similar to the synthetic manipulations as described in the proceeding Schemes. See, e.g., Scheme E-4.

Scheme E-4.

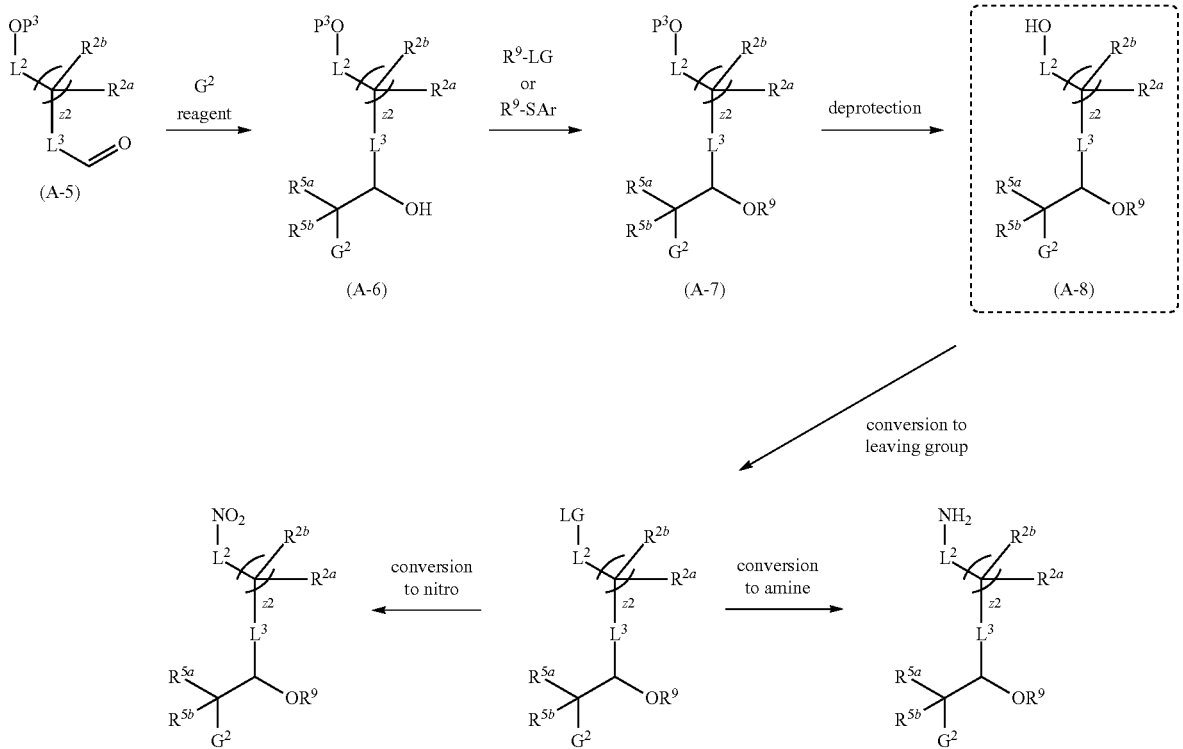

Furthermore, as an alternative to the aldehyde (A-1) and (A-5), further contemplated is an alkenyl compound of Formula (A-9), or salt thereof, which may be converted to various compounds similar to the synthetic manipulations as described in the proceeding Schemes. See, e.g., Scheme E-5.

Scheme E-5.

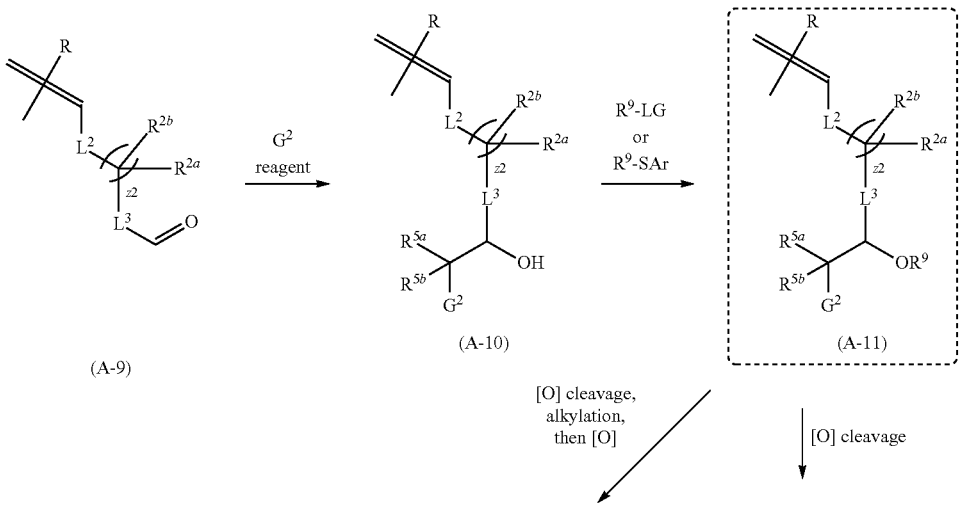

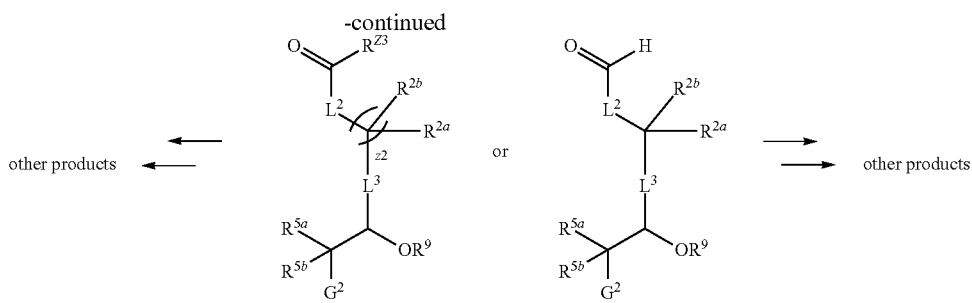

Aldehydes or ketones such as those described in Scheme E-5 can be modified to produce substituted amines such as those described in Scheme E-6. Formation of the chiral t-butyl sulfinimide followed by nucleophilic addition of $R^{Z4}$ (e.g., Grignard or organolithium reagents) produces intermediates such as C-37 or C-38 in either stereochemical configuration. Deprotection of the chiral auxiliary leads to desired amines C-39 and C-40, which are used for subsequent macrocyclization reactions.

Scheme E-6.

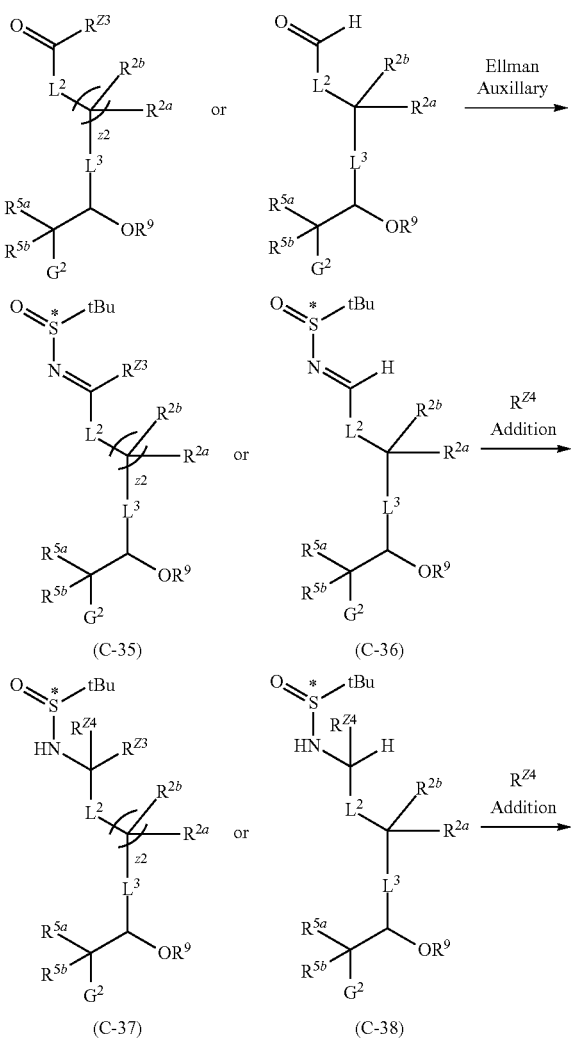

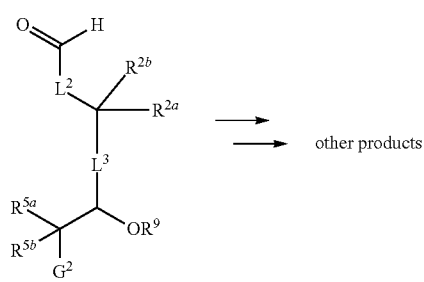

Aldehydes such as those described in Scheme E-5 can be further modified under conditions depicted in Scheme E-7 to arrive at other useful intermediates for derivitization or macrocyclization. Phosphonium salts or phosphonate ester derivatives such as those of formula C-42, wherein $R^{P1}$, $R^{P2}$, and $R^{P3}$ are each independently optionally substituted alkyl, optionally substituted alkenyl, optionally substituted alkynyl, optionally substituted carbocyclyl, optionally substituted heterocyclyl, optionally substituted aryl, or optionally substituted heteroaryl, can be used to homologate through alkene formation with a corresponding carbonyl containing organic compound.

Scheme E-7.

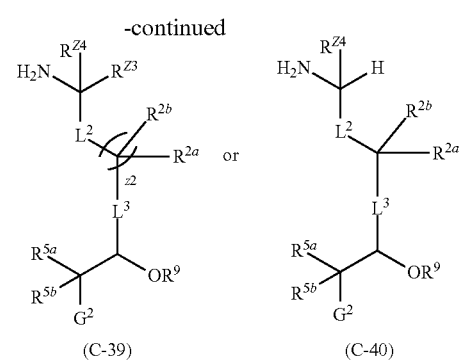

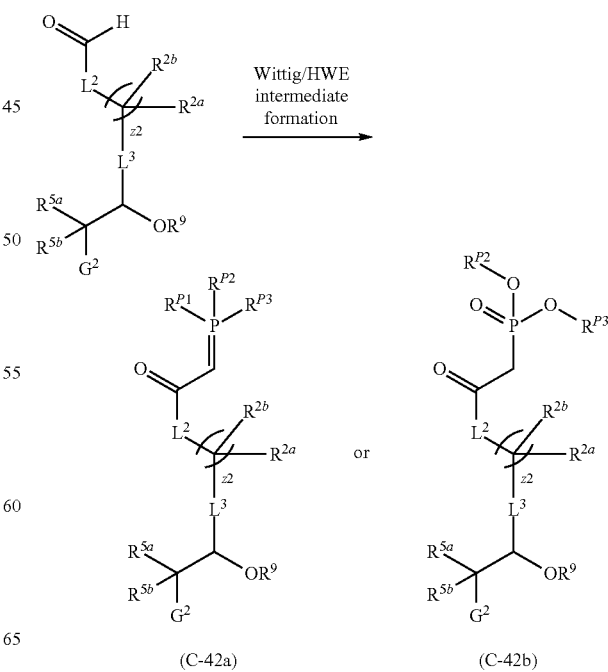

Expansion of the eastern half of the macrocycle in order to access larger ring sizes (e.g. 16-membered rings) can be accomplished as pictured herein (Scheme E-8). Treatment of the aldehydes with alkoxy phosphonium salt or phosphonate ester reagents provides vinyl ethers C-12 or C-13. Hydrolysis under acidic conditions affords the homologated aldehyde precursors C-14 Or C-15.

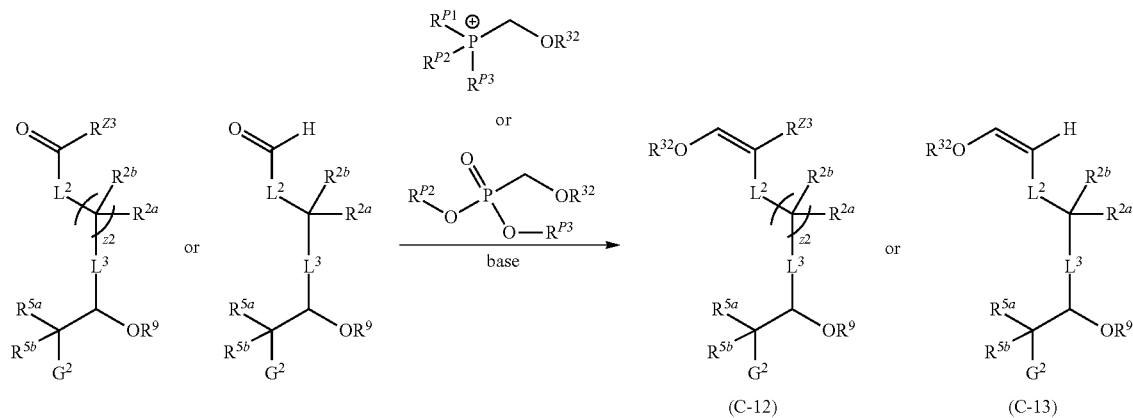

In certain embodiments wherein $L^2$ is $CH_2$, halogenation of eastern half aldehyde intermediates can be accomplished using a two-step sequence outlined in Scheme E-9. Enol ethers C-16 or C-17, wherein PG is an oxygen protecting group as defined herein, can be prepared using a base and an oxygen protecting group reagent (e.g., trimethylsilyl triflate or trimethylsilyl chloride). The intermediate silyl enol ethers can be halogenated using an electrophilic halogen source. In certain embodiments, the electrophilic halogen is fluorine. In certain embodiments, the halogenating reagent is Select-Fluor.

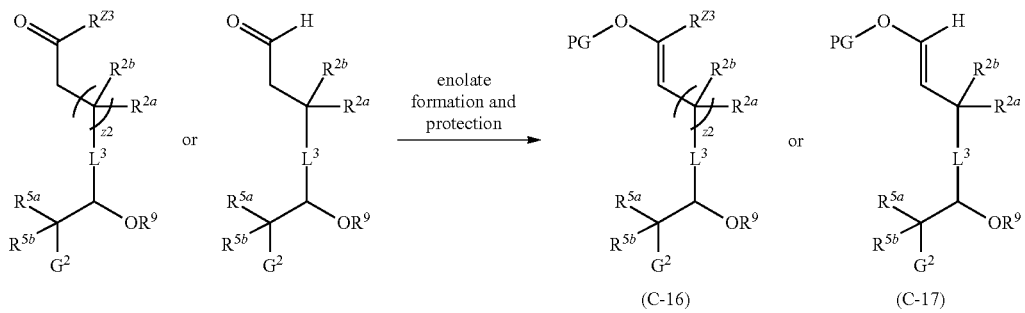

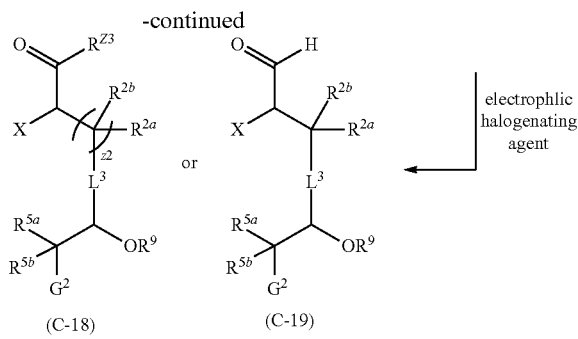

(C-18)   (C-19)

EXEMPLIFICATION

These and other aspects of the present invention will be further appreciated upon consideration of the following Examples, which are intended to illustrate certain particular embodiments of the invention but are not intended to limit its scope, as defined by the claims.

Macrolide Binding and Resistance

Figure 2:
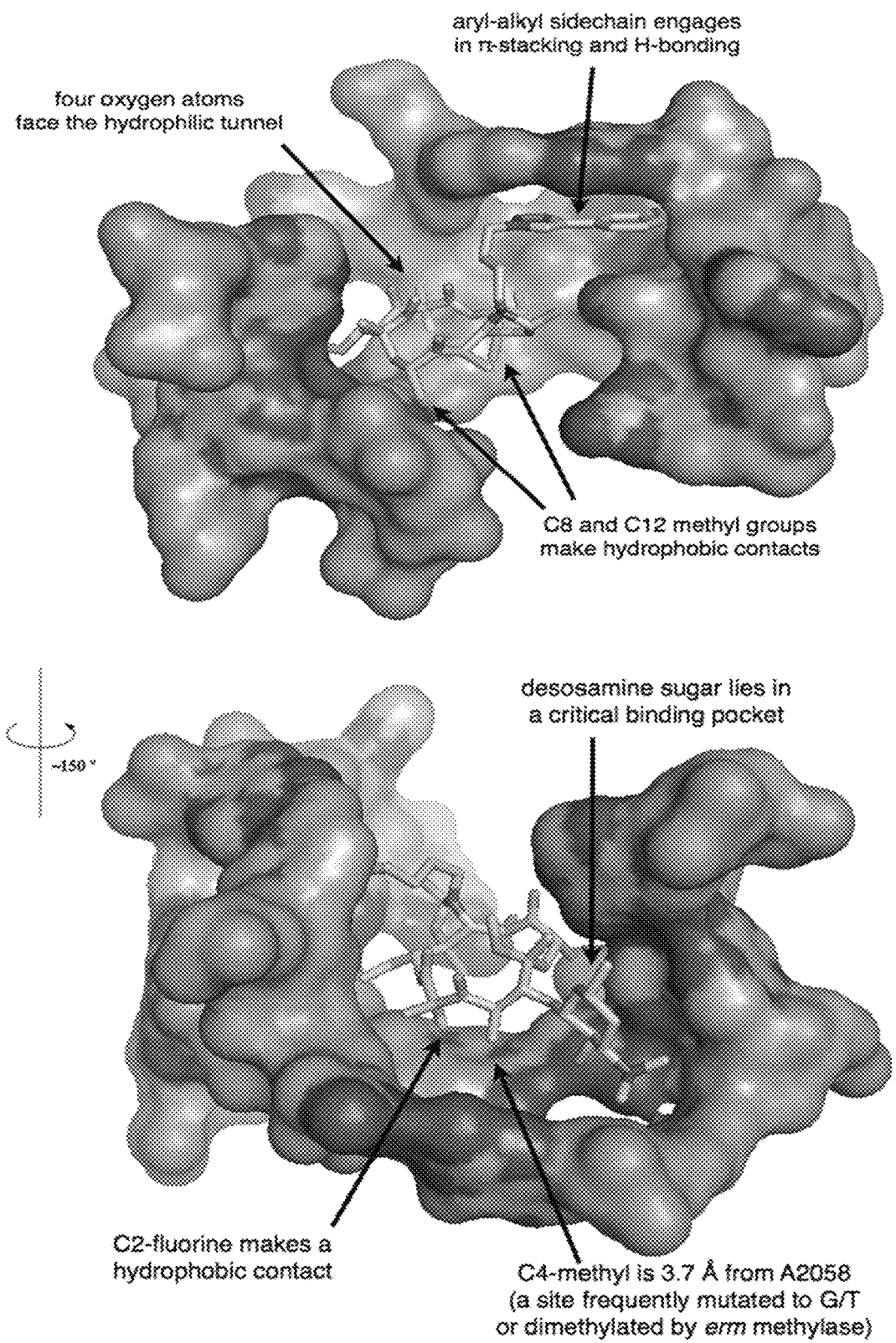
FIG. 2 depicts the crystal structure of solithromycin bound to E. coli. Residues in a 12-Å sphere generated using MacPyMol from PDB #3ORB. See, e.g., Llano-Sotelo Antimicrob. Agents Chemother. (2010) 54:4961-4970.

The macrolide antibiotics, as exemplified by the macrolides depicted in FIG. 1, inhibit peptide synthesis by hindering transit of the nascent peptide through the exit tunnel in the bacterial ribosome. All 13- to 16-membered macrolide antibiotics bind with almost identical macrolactone (or azalactone) conformations in which a hydrophobic face of the molecule (comprising several methyl groups and one ethyl group) is engaged with the wall of the peptidyl exit tunnel and a hydrophilic face of the molecule (comprising four C—O and C=O groups) is exposed to the hydrophobic interior of the tunnel (FIG. 2, 12 Å sphere around solithromycin depicted). See, e.g., Bulkley et al., Proc. Natl. Acad. Sci. U.S.A. 2010, 107, 17158-17163; Tu et al., Cell (Cambridge, Mass., U. S.) 2005, 121, 257-270; Hansen et al., J. Mol. Biol. 2003, 330, 1061-1075; Llano-Sotelo et al., Antimicrob. Agents Chemother. 2010, 54, 4961-4970. Critical hydrogen-bonding interactions occur between the desosamine sugar and the ribosome, which is consistent with the view that this residue, which is present in all macrolides approved by the FDA for human use (but is modified in tylosin, a veterinary antibiotic) is important in binding. The sidechains of telithromycin and solithromycin are believed to engage in pi-stacking interactions with the A752-U2609 base pair, enhancing binding to the ribosome. See, e.g., Mankin, Curr. Opin. Microbiol. 2008, 11, 414-421; Douthwaite et al., Mol. Microbiol. 2000, 36, 183-192; Hansen et al., Mol. Microbiol. 1999, 31, 623-631. The 3-aminophenyl substituent of solithromycin has been shown by X-ray crystallography to make contacts with A752 and G748 through hydrogen bonding, which may account in part for the higher binding affinity of solithromycin relative to telithromycin. See, e.g., Llano-Sotelo et al., Antimicrob. Agents Chemother. 2010, 54, 4961-4970. The fluorine atom at position C2 of solithromycin makes a hydrophobic contact with C2611, and is believed to account for the 4- to 16-fold increase in activity versus the non-fluorinated molecule against panels of Gram-positive bacteria. See, e.g., Llano-Sotelo et al., Antimicrob. Agents Chemother. 2010, 54, 4961-4970.

Modification of the macrolide binding pocket is one of the primary forms of resistance among pathogenic bacteria. This can take the form of a base modification (e.g., A2058 dimethylation by erm genes), a base mutation (e.g., A2058G, A2059G, C2611G), or a more subtle alteration of the binding pocket caused by distal mutations in the ribosome (e.g., LA ribosomal peptide modification). See, e.g., Leclercq et al., Antimicrob. Agents Chemother. 1991, 35, 1273-1276; Leclercq et al., Antimicrob. Agents Chemother. 1991, 35, 1267-1272; Weisblum, Antimicrob. Agents Chemother. 1995, 39, 577-585; Vester et al., Antimicrob. Agents Chemother. 2001, 45, 1-12; Tu et al., Cell (Cambridge, Mass., U. S.) 2005, 121, 257-270. Semi-synthetic modifications of macrolides, restricted to just a few positions, have led to greatly increased binding through additional contacts to the binding site. We believe that modifications to other positions yet unexplored provide great opportunity for further antibiotic development.

Inventive Convergent Synthetic Method

The past decade has seen remarkable advancements in our understanding of the ribosome, both in terms of its structure and function. High-resolution X-ray crystal structures of macrolide antibiotics bound to the ribosomes of several species of archaea and, recently, pathogenic bacteria have provided critical insights into the nature of macrolide binding. Highly detailed models of erythromycin and other macrolide antibiotics bound to bacterial ribosomes and, in particular, ribosomes of pathogenic organisms such as E. coli have been achieved by crystallographers only within the past three years. See, e.g., Dunkle et al., Proc. Natl. Acad. Sci. U.S.A. (2010) 707:17152-17157; Llano-Sotelo et al., Antimicrob. Agents Chemother. (2010) 54:4961-4970. Combined with a half century of biochemical and clinical data, the basis for rational drug design upon the macrolide scaffold is now extremely well-informed, making the design and synthesis of novel antibiotic candidates within this class especially timely, and we believe a great opportunity.

Although our understanding of the structural characteristics that contribute to macrolide binding has never been greater, much remains to be learned because the majority of positions of the macrolide scaffold have never been modified, a consequence of the inherent limitations of semi-synthesis. The inventive synthetic route to the macrolide scaffold allows for modification of the many positions that are not feasible using a semi-synthetic approach. We believe that interactions with the hydrophobic binding pocket can be enhanced by variations of alkyl substituents of the macrolactone; hydrophobic groups such as alkyl, fluoro, and/or fluoroalkyl are contemplated herein. Modification of the C4-position of macrolides might lead to enhanced binding to the modified ribosomes of resistant strains, and the inventive synthetic method enables facile variation of this position, as well as others. See, e.g., Tu et al., *Cell* (Cambridge, Mass., U. S.) (2005) 727:257-270; Hansen et al. *Mol. Cell* (2002) 70:117-128. The inventive synthetic method allows easy variation of the size and heteroatomic composition of the macrocycle. Variation of the desosamine residue is also easily achieved using the inventive synthetic method, permitting exploration of several analogs that could potentially overcome resistance associated with erm methylase, characterized by unfavorable interactions between the sugar and dimethylated A2058. See, e.g., Romero et al., *Tetrahedron Lett* (2005) 46:1483-1487; Liang et al., *Medicinal Chemistry Letters* (2005) 75:1307-1310.

Several guidelines have been followed in the inventive design of a fully synthetic route to macrolide antibiotics. First, the approach is by design component-based and convergent, so that a multiplicative expansion of analogs is possible with chemical variation of each component. Second, chemical transformations were selected to be scalable, so that sufficient amounts of any candidate antibiotic can be made available for MIC screening, animal testing, and ultimately even manufacturing.

A general thermally-induced macrolactonization of a dioxolenone or beta-keto ester is contemplated, proceeding through acylketene intermediate, delivering the macrolactone without the need for elaborate protecting groups or coupling reagents. The dioxolenone method was pioneered by Boeckman et al. for the preparation of medium-sized macrolactones. See, e.g., Boeckman, et al., *J. Am. Chem. Soc.* (1989) 777:8286-8288. The beta-keto ester method was explored by Witzeman in detail. See, e.g., Witzeman, et al., *J. Org. Chem.* (1991) 56:1713-1718.

Results discussed herein demonstrate that the macrolactonization using a dioxolenone or beta-keto ester works beautifully with diverse skeletal substitutions. The macrocyclization precursor is generated from two halves of approximately equal complexity (the western and eastern half) that in turn are derived from di verifiable building blocks. Our convergent building-block strategy enables the independent evolution (synthetic route, structural composition) of each component.

We have synthesized more than 50 novel 15-membered azalides antibiotic candidates from various combinations of 5 eastern halves and 6 western halves of the macrolide scaffold. All of these are novel chemical entities and none could have been prepared by semi-synthesis. Several of these candidates have been screened against a variety of pathogens such as *S. aureus, S. pneumoniae, E. coli,* and *H. influenzae,* among them a number of macrolide-resistant strains. Several of the new macrolides were found to have greater activity than azithromycin against both macrolide-susceptible and macrolide-resistant bacteria.

I. Synthesis of the Eastern Half

Example I-1. Synthesis of Allyl Enol Ether Starting Material

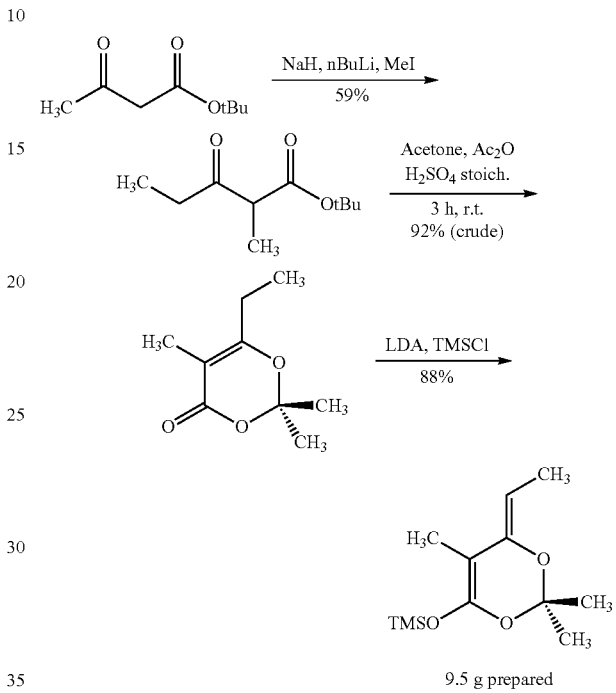

See Boeckman et al., *J. Am. Chem. Soc.* (1989) 111:8286-8288.

Example I-2. Formation of $Y^2$ Aldehyde from Alcohol C4 Desmethyl

A representative sample of eastern halves with a dioxolenone acyl-ketene precursor we have successfully synthesized is depicted herein. Each proceeds in 7 linear steps from the easily scaled coupling of an alkyl iodide (25 or 39) with methyl ketone 26. O-methylation afforded 28 in excellent yield. Oxidative cleavage exposed aldehyde 29, which underwent highly diastereoselective Mukaiyama aldol condensation with silyl enol ether 30 in the presence of magnesium bromide etherate to provide secondary carbinol 31 in excellent yield. Gratifyingly, glycosylation under Woodward conditions with thiopyrimidyl desosamine 32 in the presence of silver(I) triflate proceeded in good yield to deliver 33 as a single anomer. See, e.g., Woodward et al., *J. Am. Chem. Soc.* (1981) 703:3213-3215; Woodward et al., *J. Am. Chem. Soc.* (1981) 703:3210-3213; Woodward et al, *J. Am. Chem. Soc.* (1981) 703:3215-3217. Silyl deprotection and oxidation with Dess-Martin periodinane gave the complete C4-desmethyl eastern half aldehyde 34, in gram amounts in 7 steps and 55% overall yield from 25 and 26. Following metal-halogen exchange, use of Luche conditions ($CeCl_3$) provides the epimer at the C6 tertiary carbinol following addition to the ketone substrate.

Example I-3. Formation of Y² Aldehyde from Alcohol with C4 Desmethyl, Both C6 Epimers
(A)
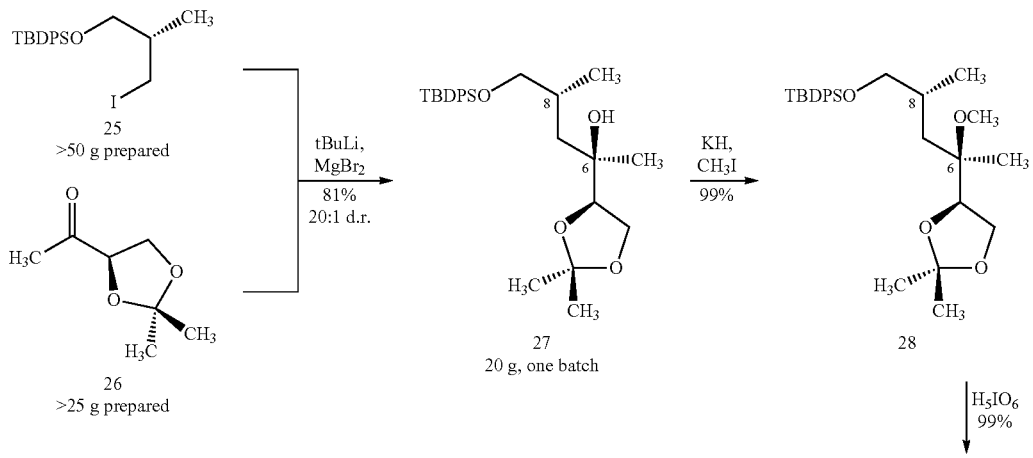
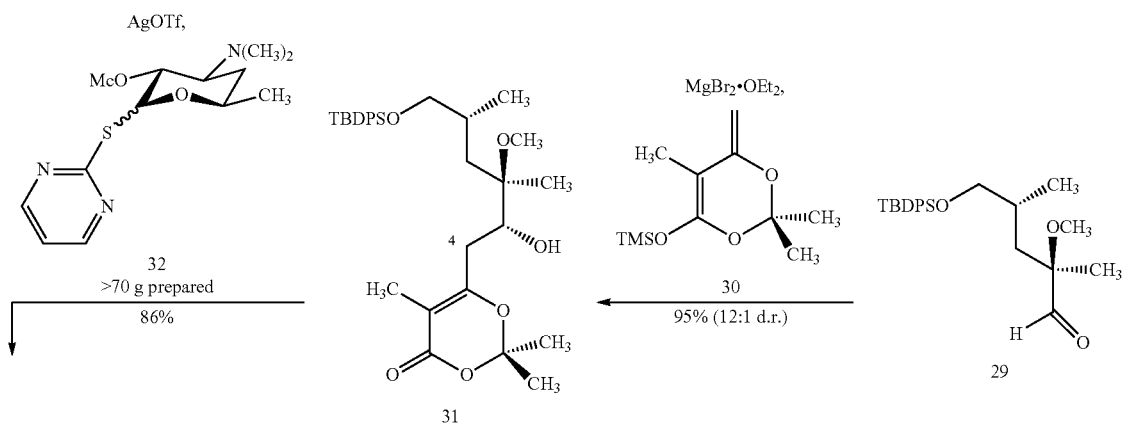
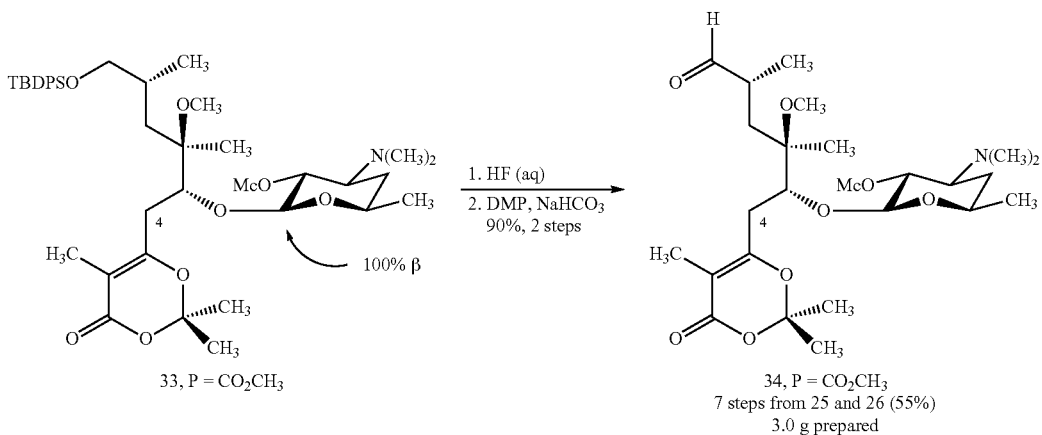

499 500
-continued
(B)
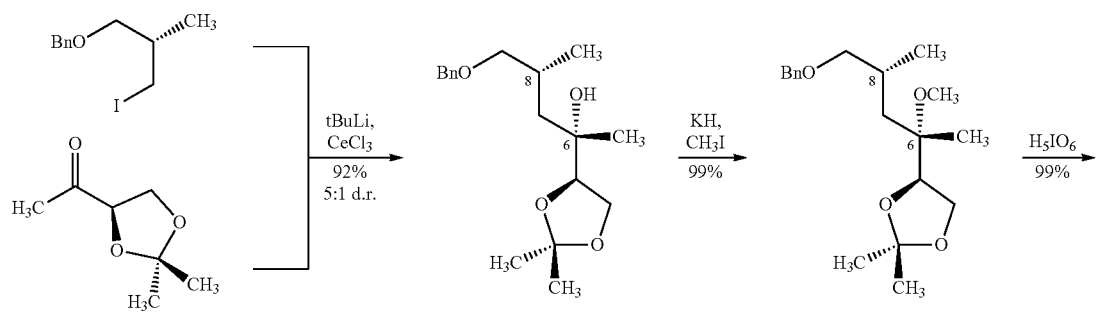
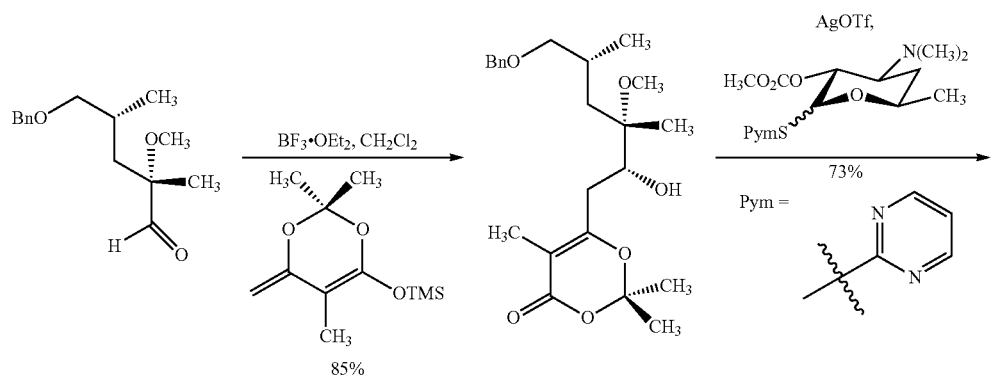
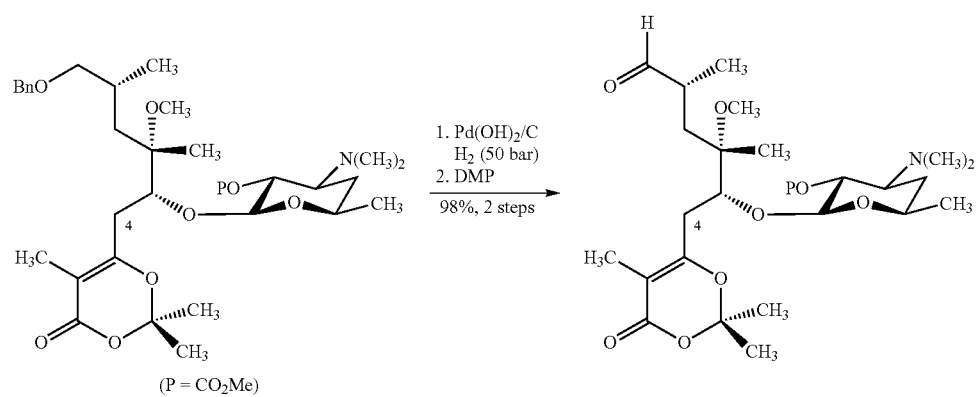

Example I-4. Formation of Y² Aldehyde from Alcohol with Either Epimeric C4 Methyl
As depicted below, eastern halves that incorporate C4 methyl group that is present in erythromycin can be accessed by using a methylated dioxolenone building block to provide both the natural and epimeric stereochemical configuration at C4.
(A)
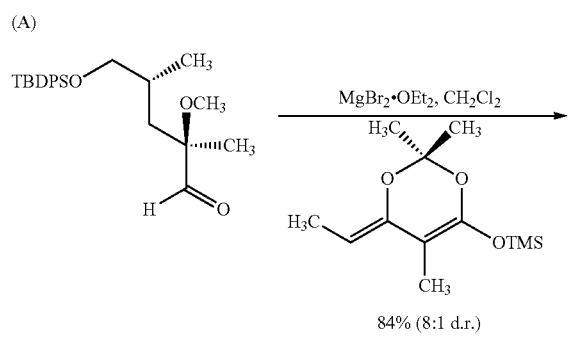
84% (8:1 d.r.)
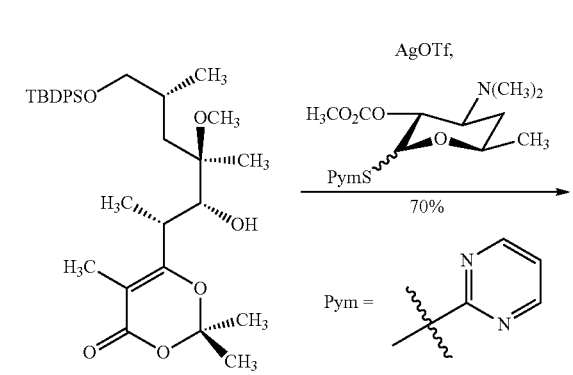
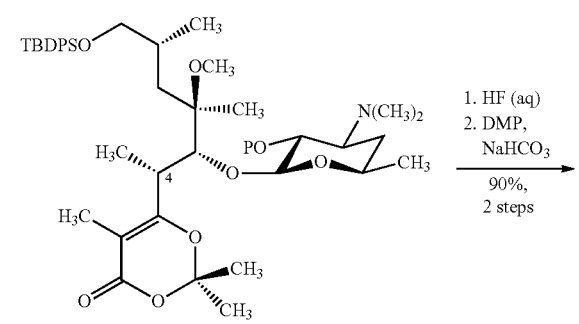
(P = CO₂Me)
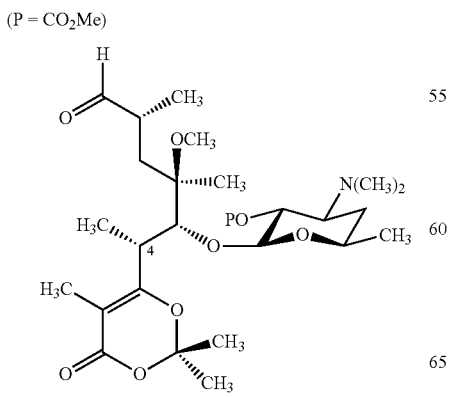
(B)
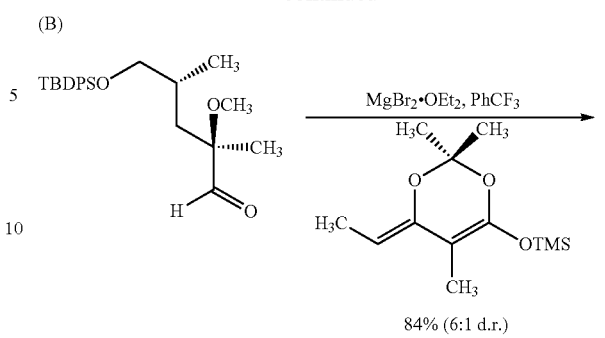
84% (6:1 d.r.)
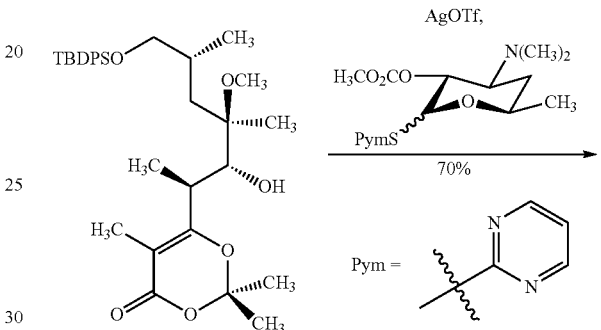
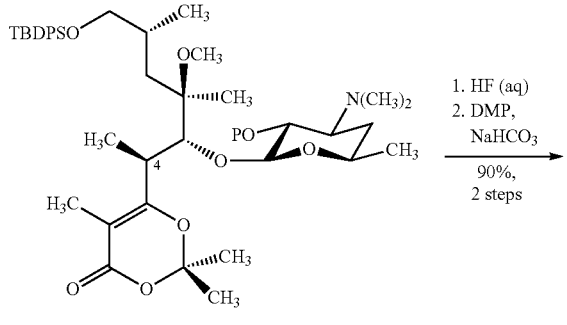
(P = CO₂Me)
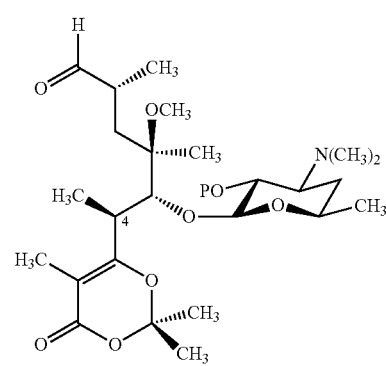

Example I-5. Formation of Y² Aldehyde from Alcohol with C6 Demethoxy and C4 Methyl
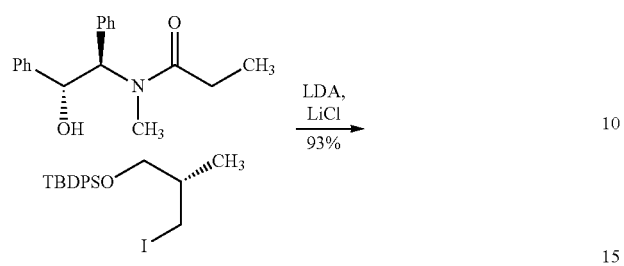
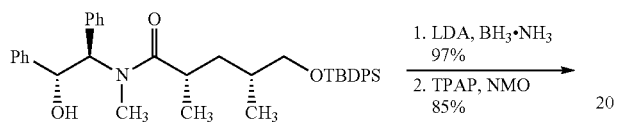
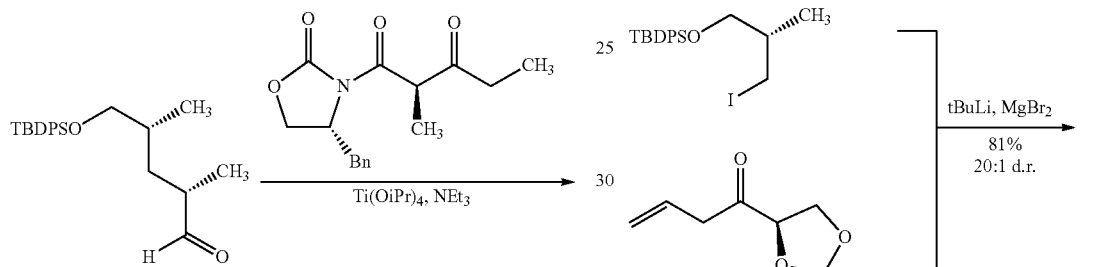
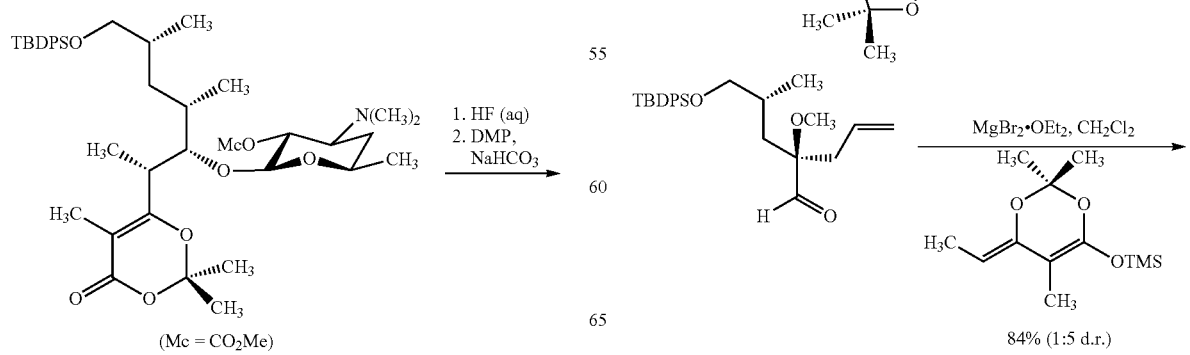
(Mc = CO₂Me)
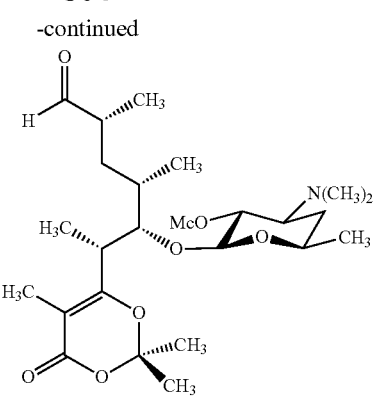
Example I-6. Formation of Y² Aldehyde from Alcohol with C6 Allyl and C4 Methyl
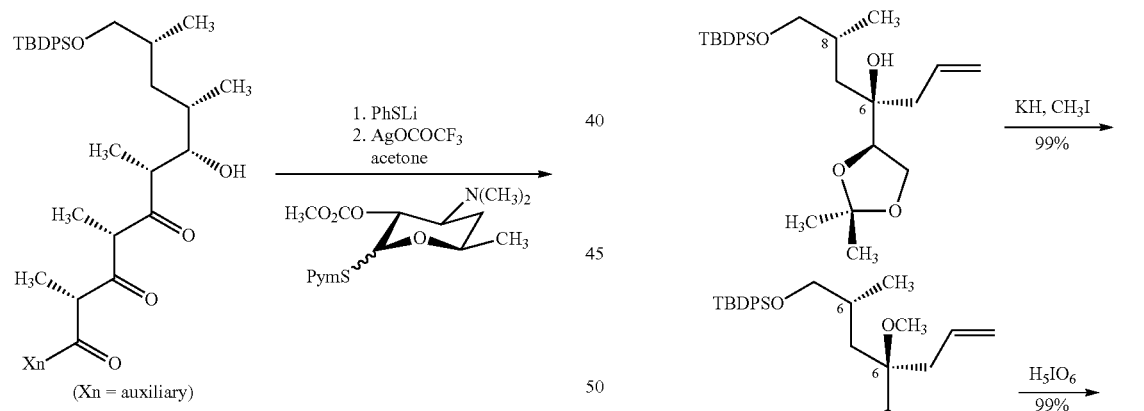

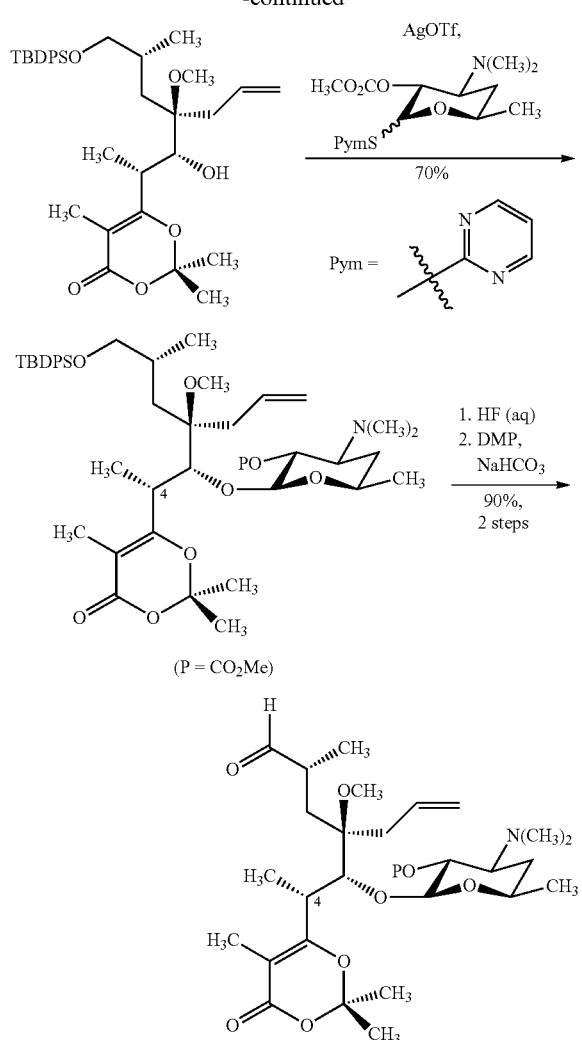
Example I-7. Formation of Y² Aldehyde from Alcohol with C6 Demethoxy Allyl
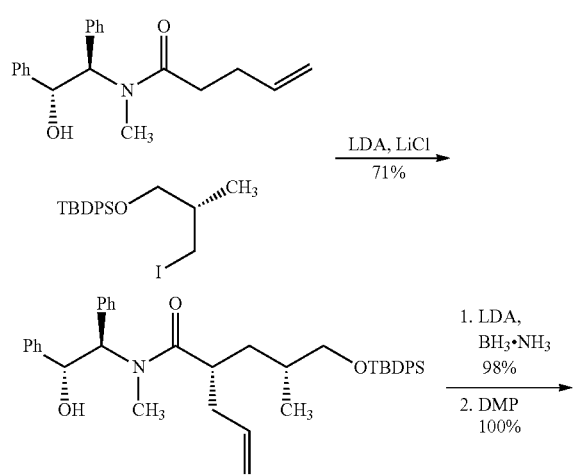
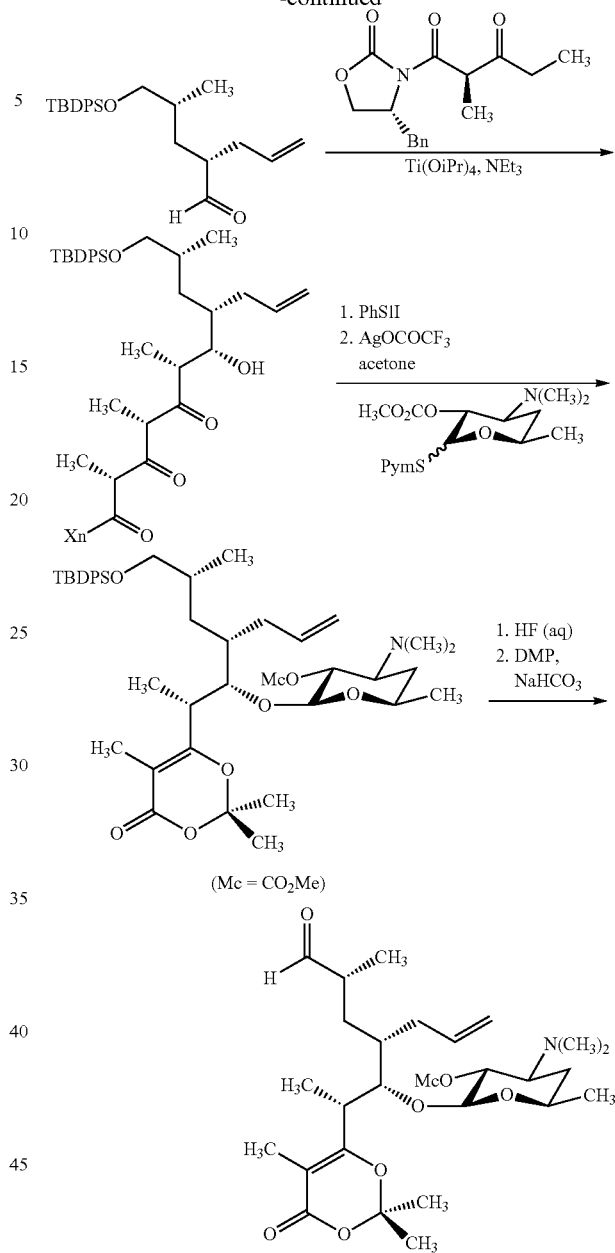
Example I-8. Formation of Y² Aldehyde with C6 O-Allyl from Tertiary Alcohol
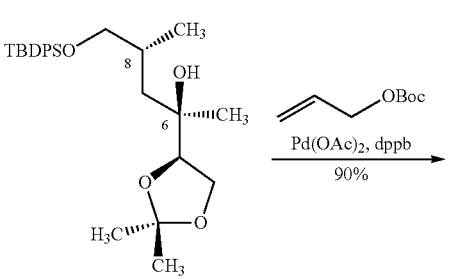

508
Example I-9. Formation of Y² Aldehyde with C6 O-Allyl C2 Desmethyl
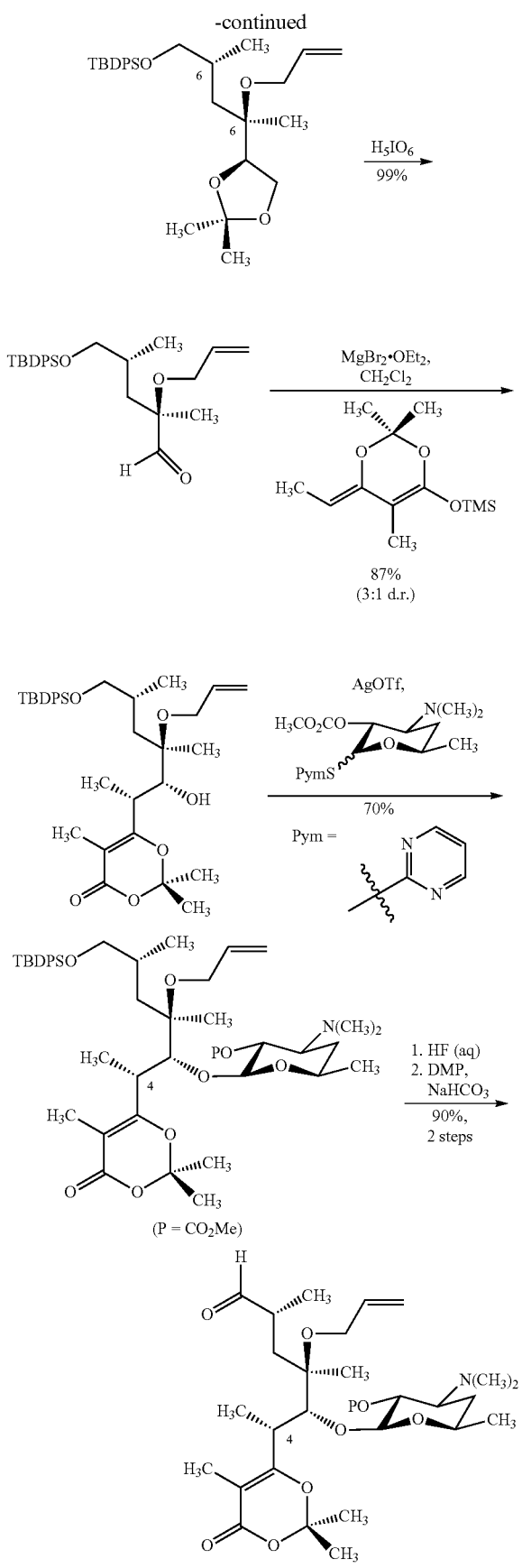
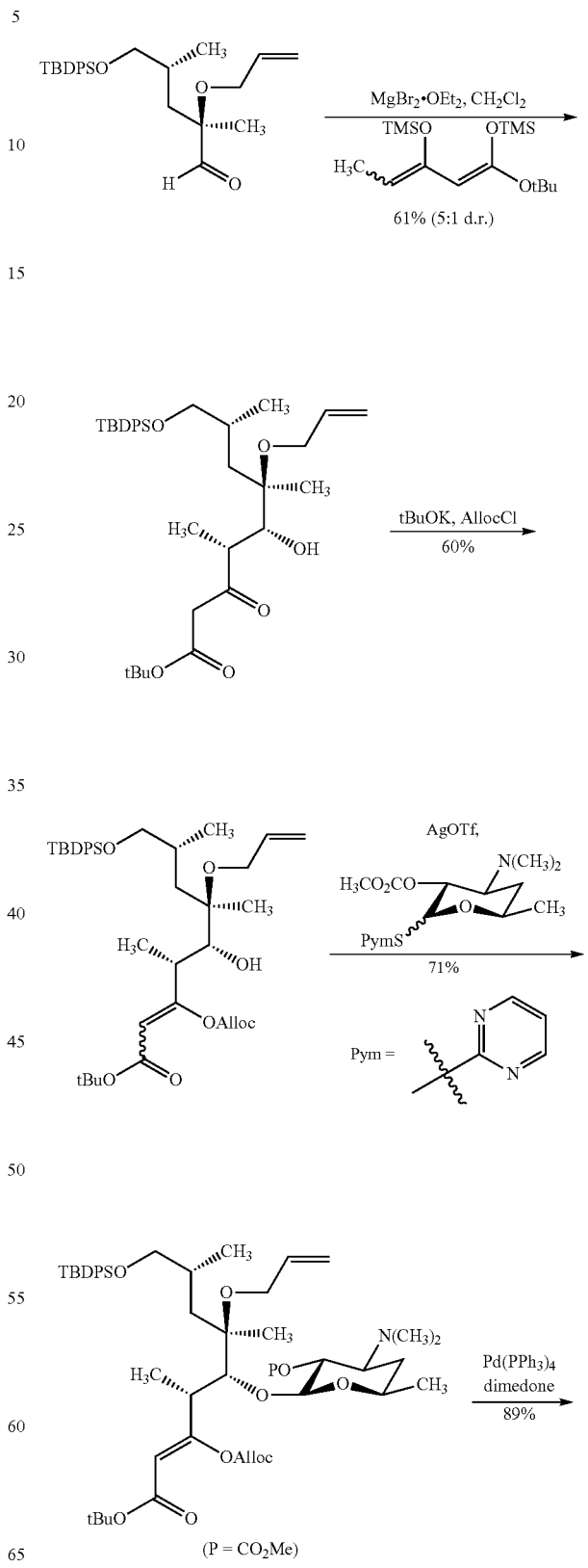

509
-continued
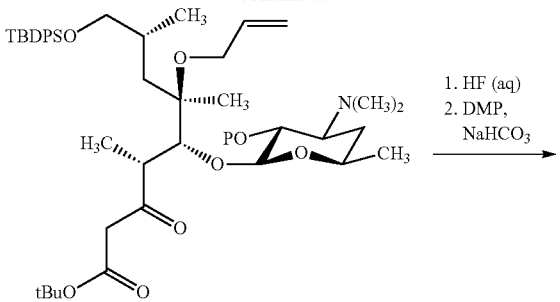
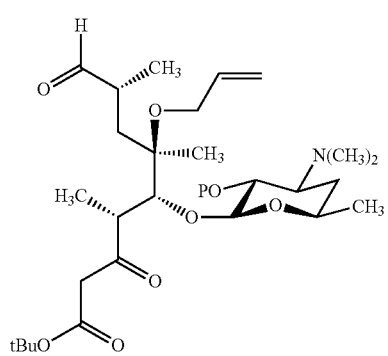
510
Example I-10. Formation of Y² Aldehyde from Alcohol
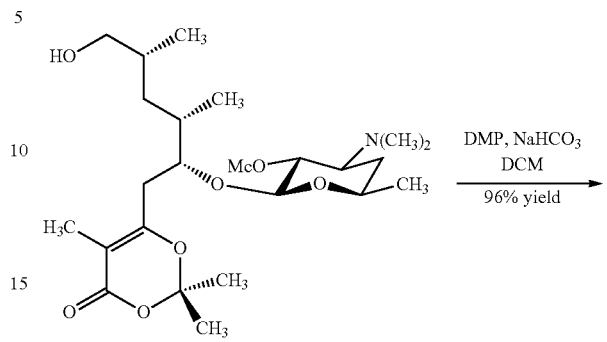
160 mg
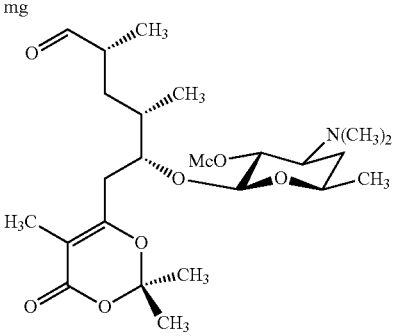
Example I-11. Formation of Y² Aldehyde from Alcohol C4 Dimethyl
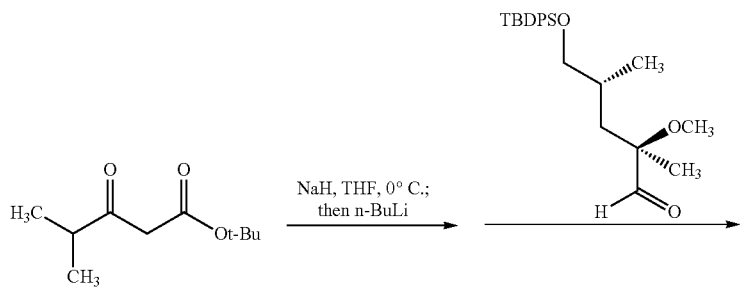
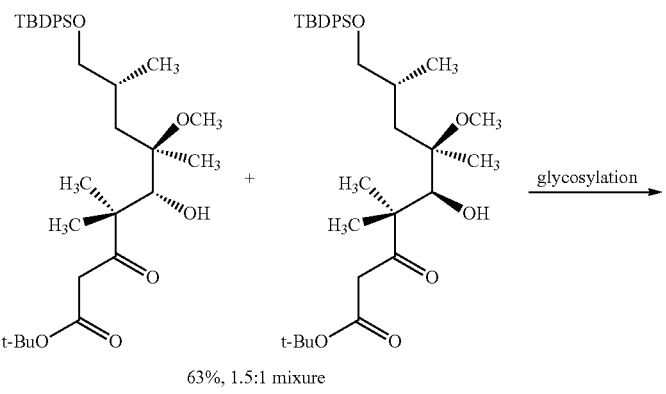
63%, 1.5:1 mixture

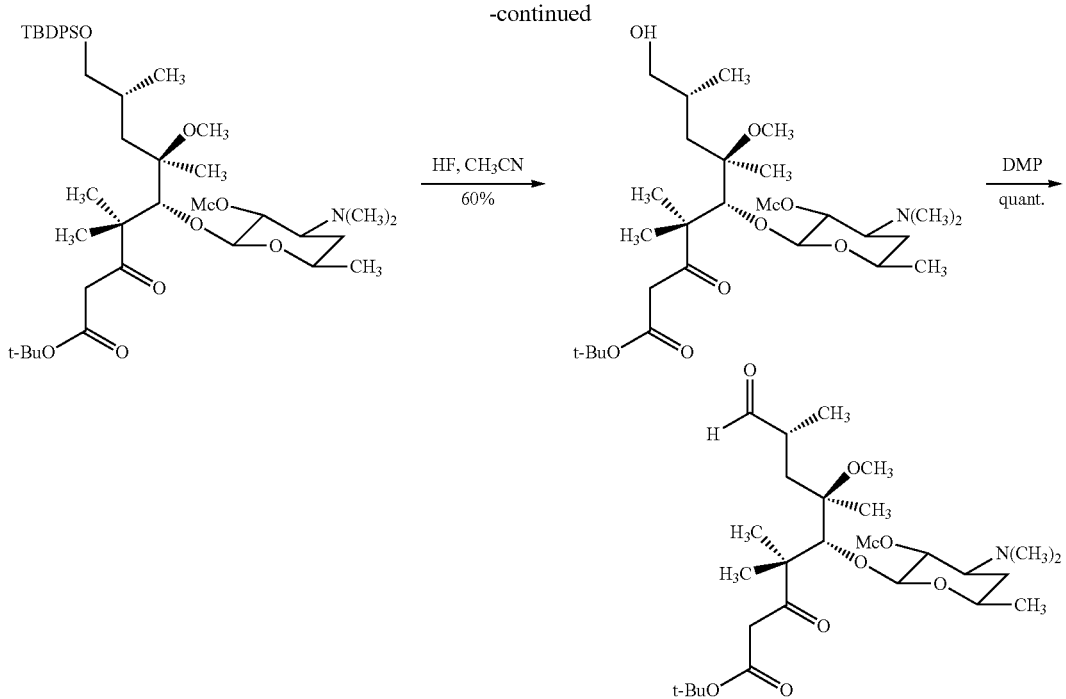
Example I-12. Formation of Y² Aldehyde from Alcohol C2 Desmethyl
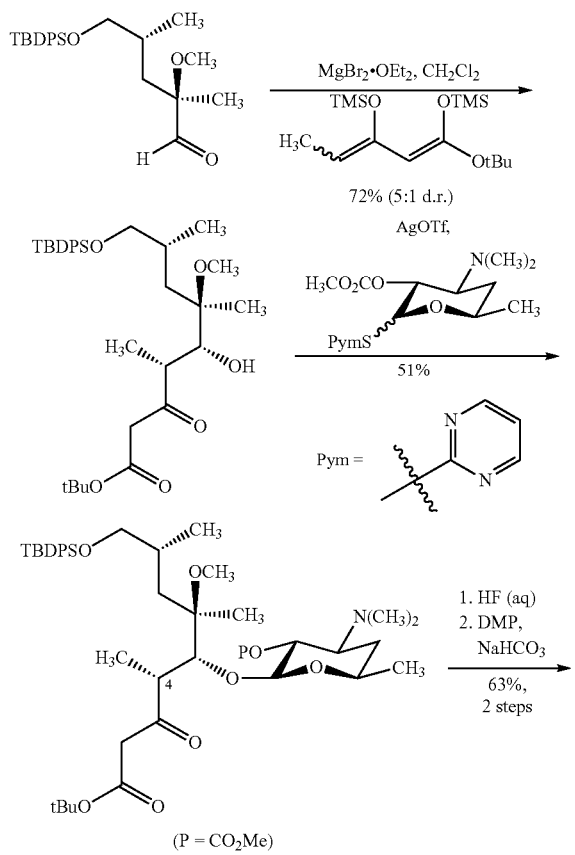
Example I-13. Formation of Y² Truncated Aldehyde with Elimination
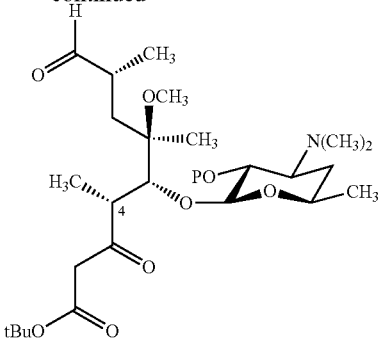
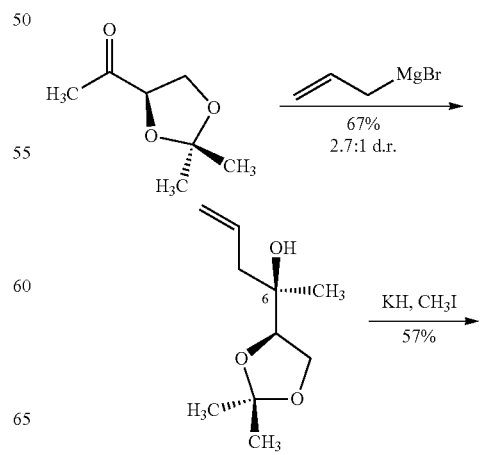

513
-continued
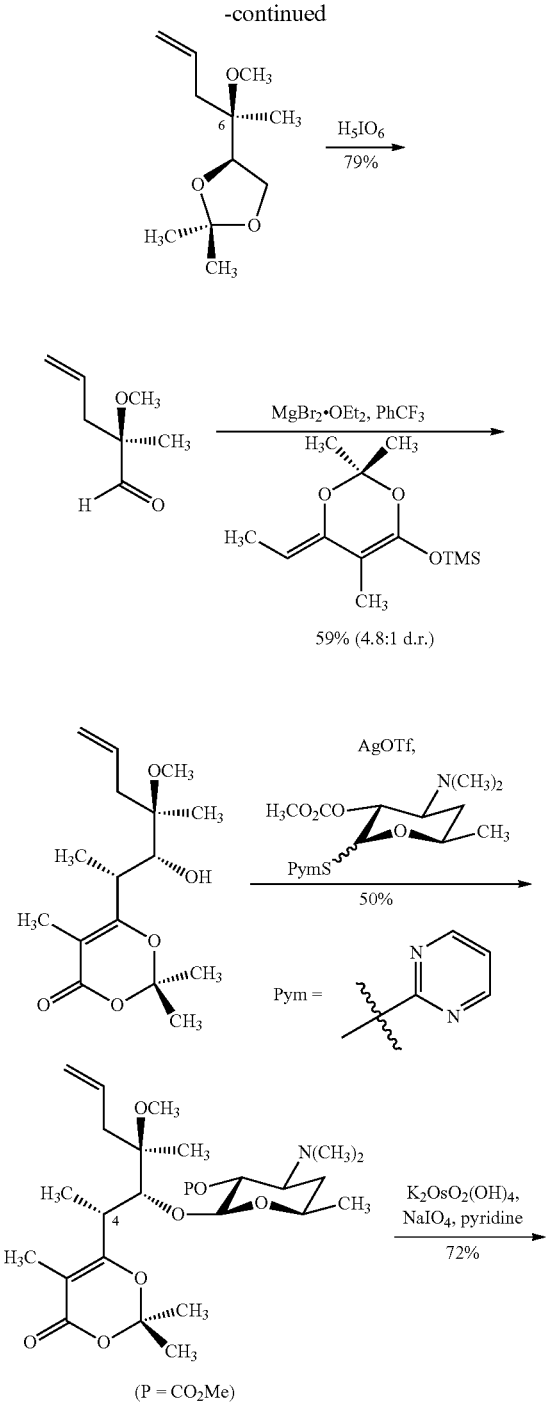
514
Example I-14. Formation of Y² Aldehyde from Oxidative Cleavage of Alkene
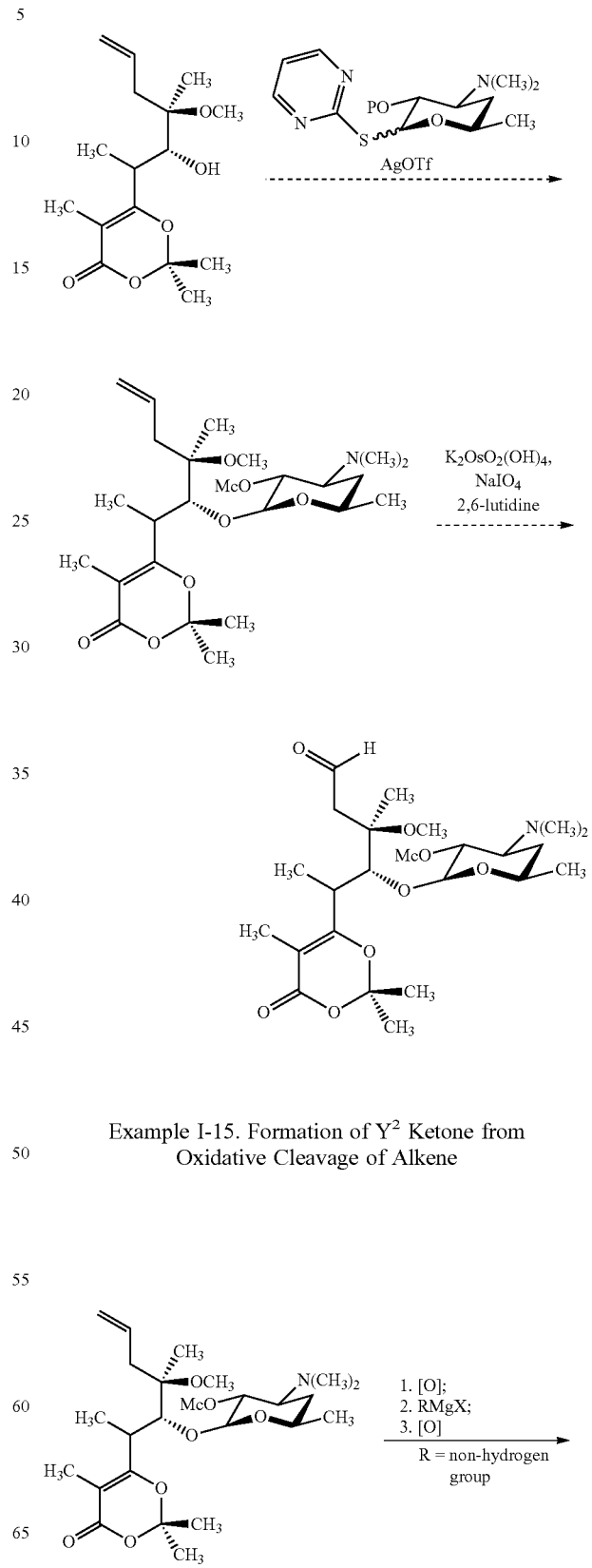
Example I-15. Formation of Y² Ketone from Oxidative Cleavage of Alkene

515
-continued
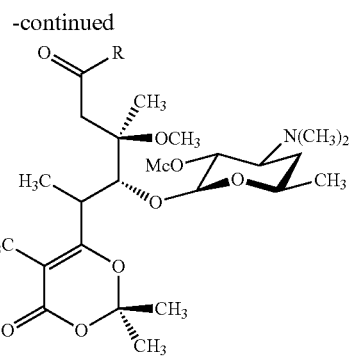
Example I-16. Formation of Y² Aldehyde from Oxidative Cleavage of Alkene
(A) Oxidative Cleavage
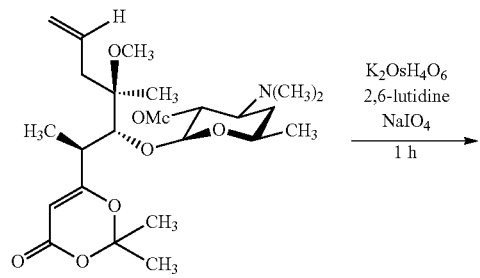
(B) Oxidative Cleavage and Elimination of OR³
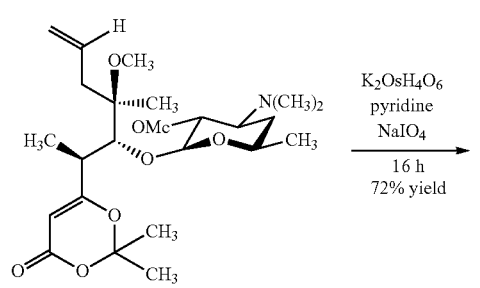
516
-continued
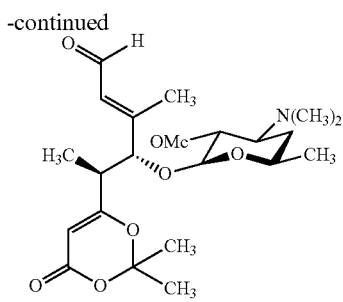
(C) Oxidative Cleavage of Diol
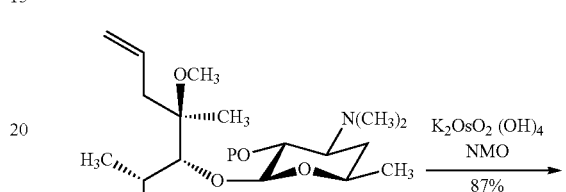
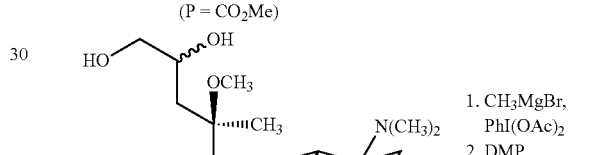
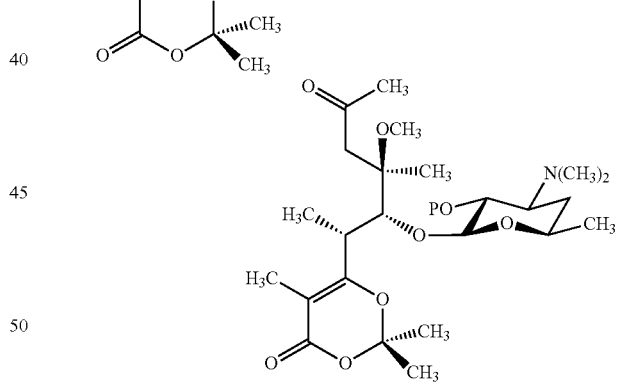
Example I-17. Formation of Y² Truncated Aldehyde with Vinyl Group Oxidation
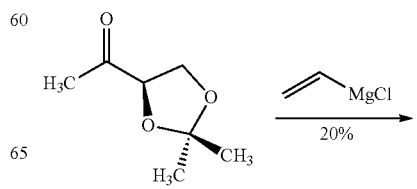

517
-continued
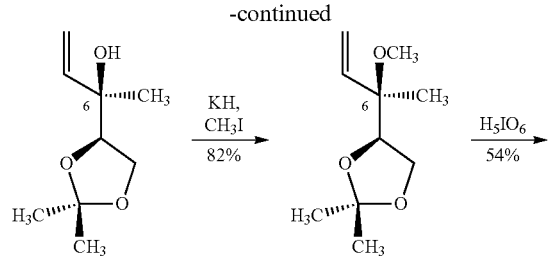
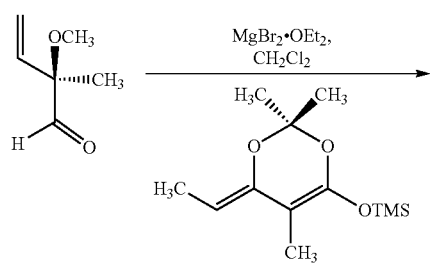
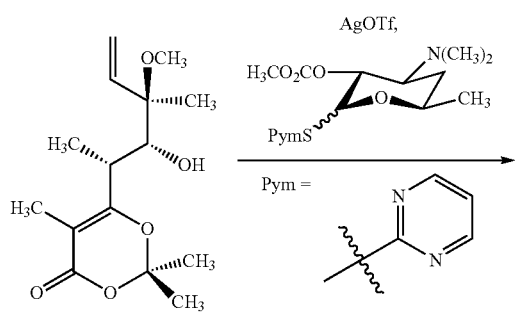
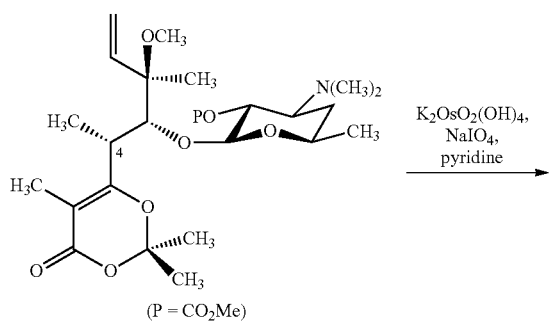
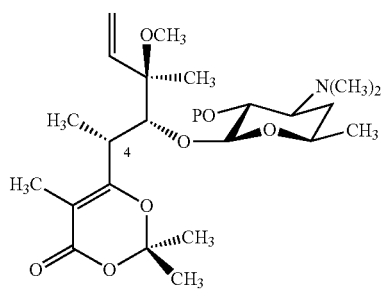
518
Example I-18. Formation of $Y^2$—$CH_2NO_2$ from an Iodo Intermediate
(A)
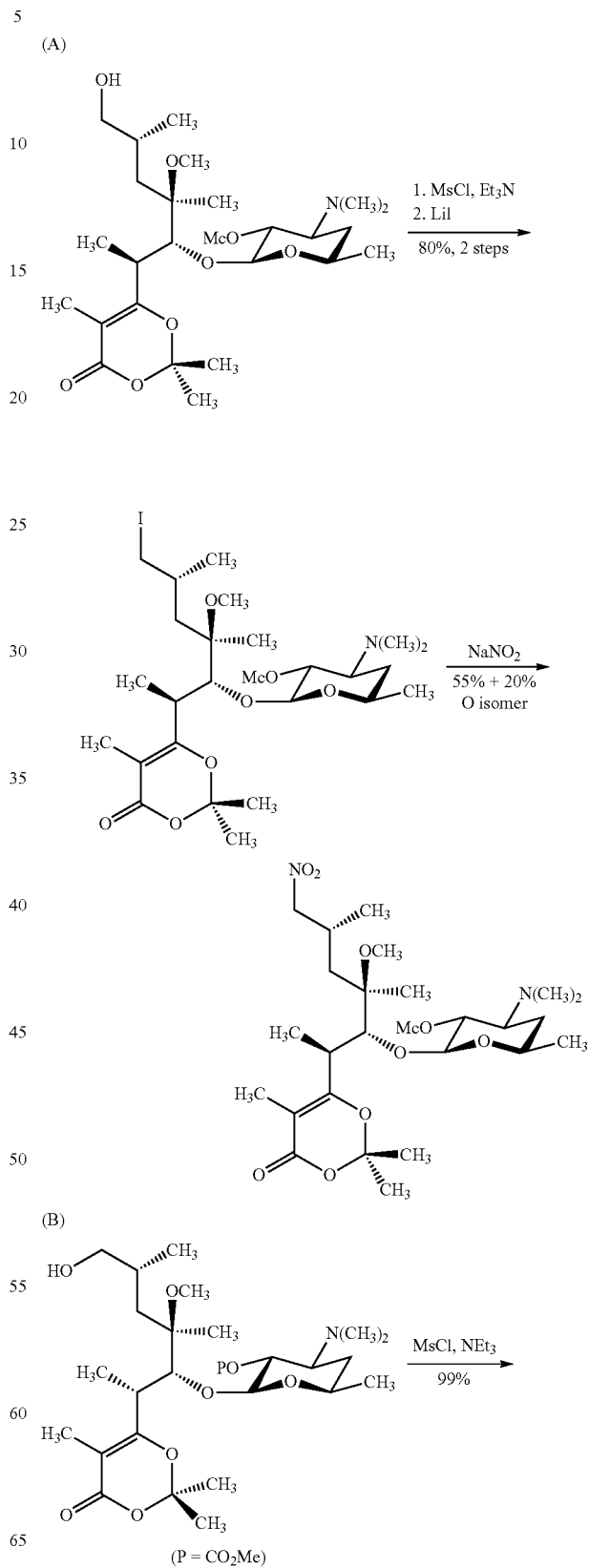
(B)

519
-continued
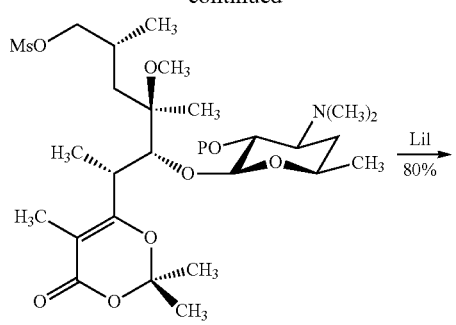
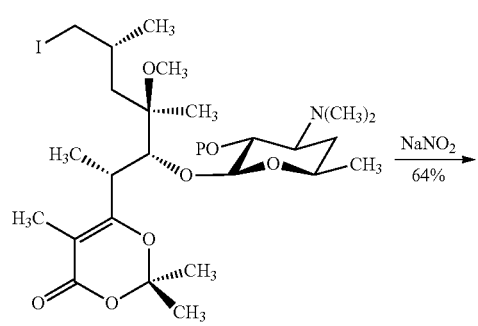
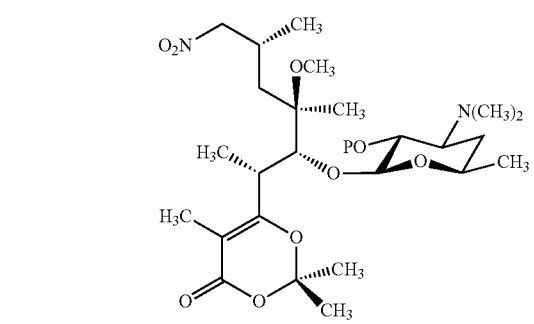
Example I-19. Formation of Y² Homologated Aldehyde
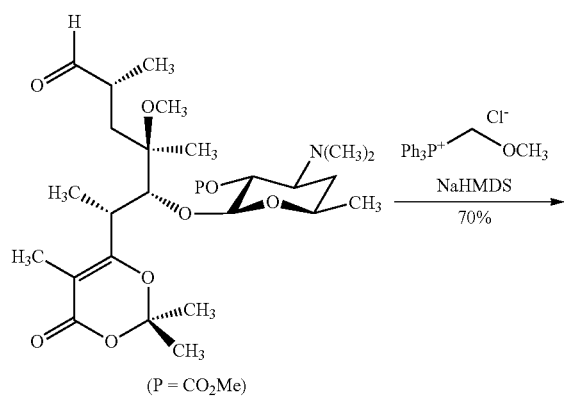
(P = CO₂Me)
520
-continued
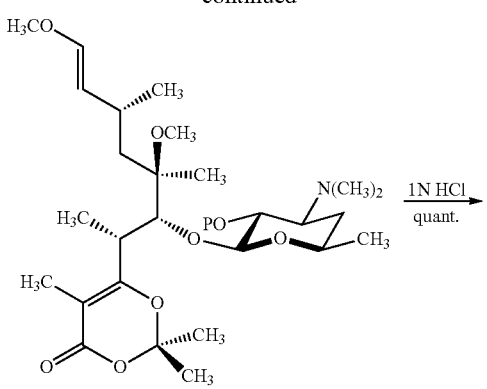
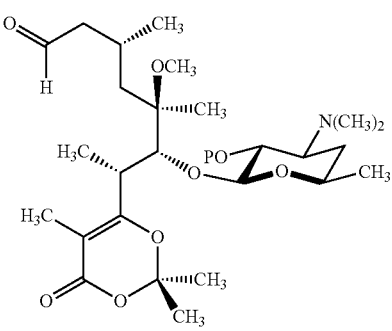
Example I-20. Oxidation to Y² Carboxylic Acid
(A)
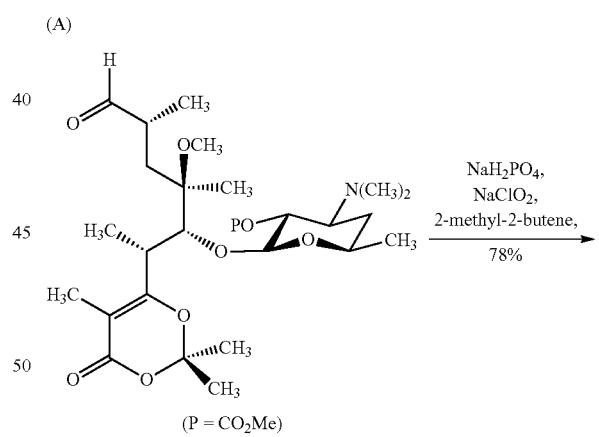
(P = CO₂Me)
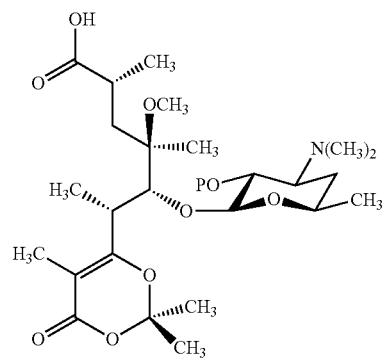

521
-continued
(B)
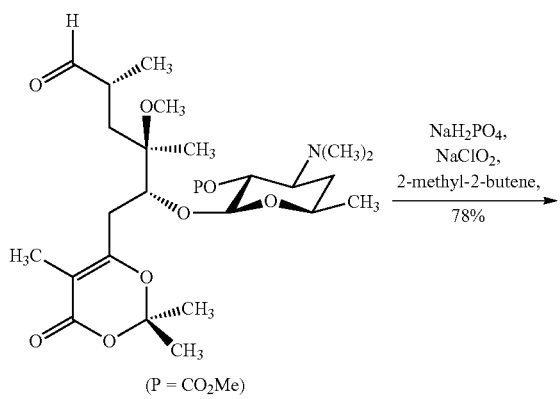
(P = CO₂Me)
Example I-21. Formation of Y² Amine
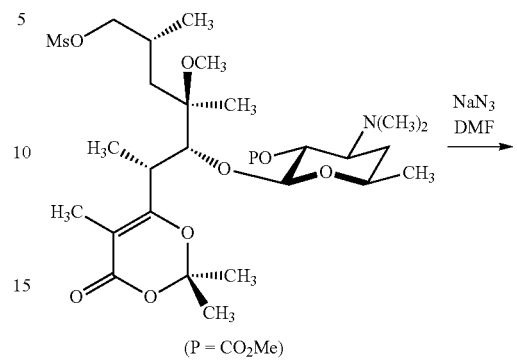
(P = CO₂Me)
(C)
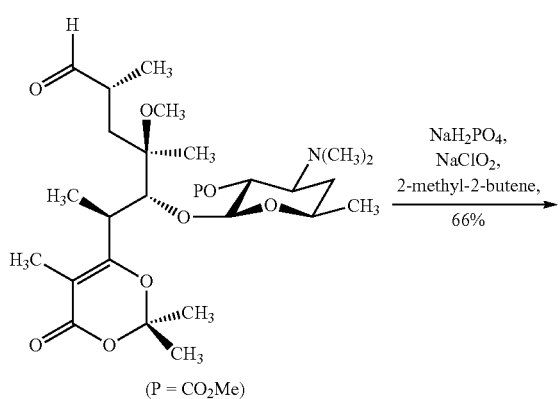
(P = CO₂Me)
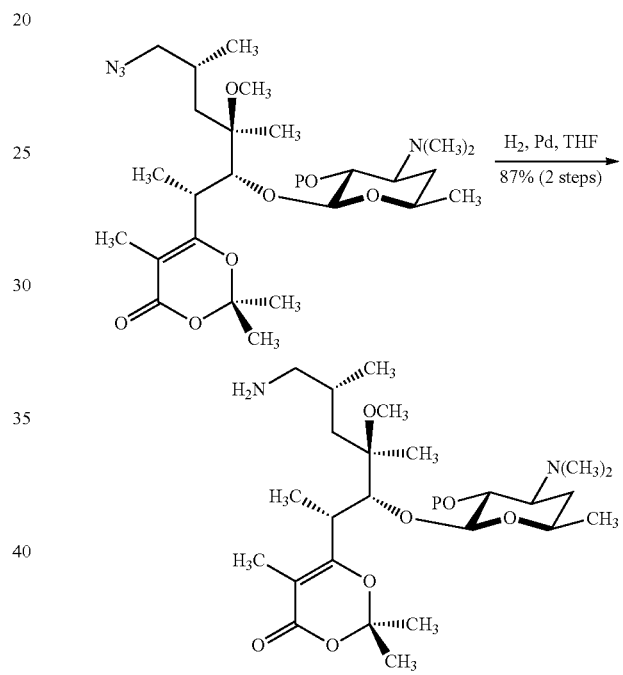
Example I-22. Additions to the Y² Aldehyde
(A)
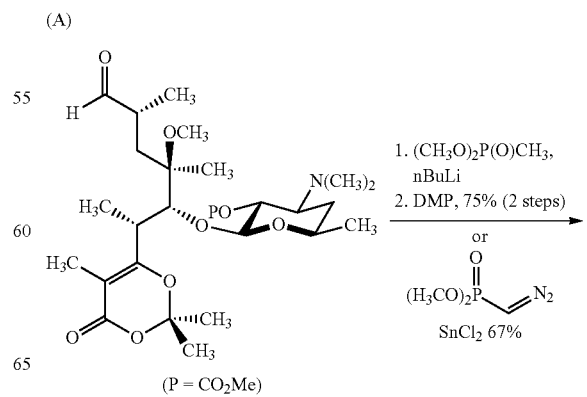
(P = CO₂Me)

523
-continued
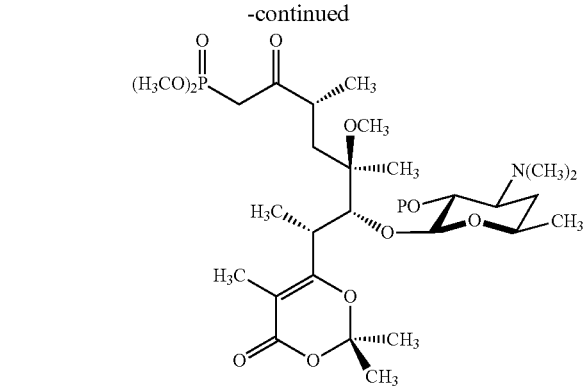
(B)
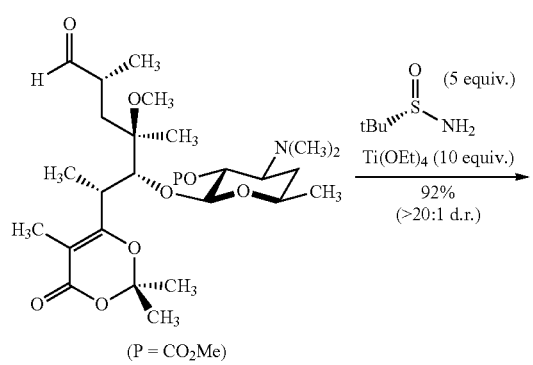
(P = CO₂Me)
524
Example I-23. Fluorination of the Y² Aldehyde
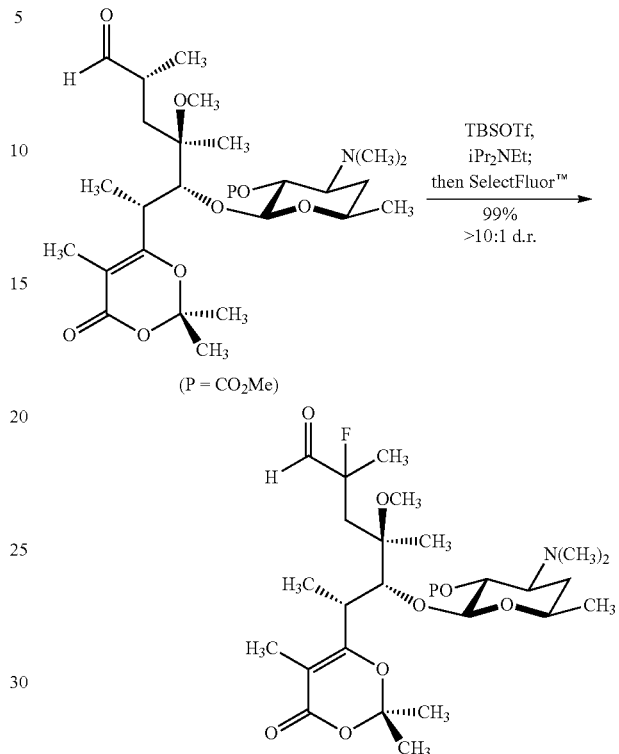
Example I-24. Cross Metathesis for Modification of the Y² Aldehyde
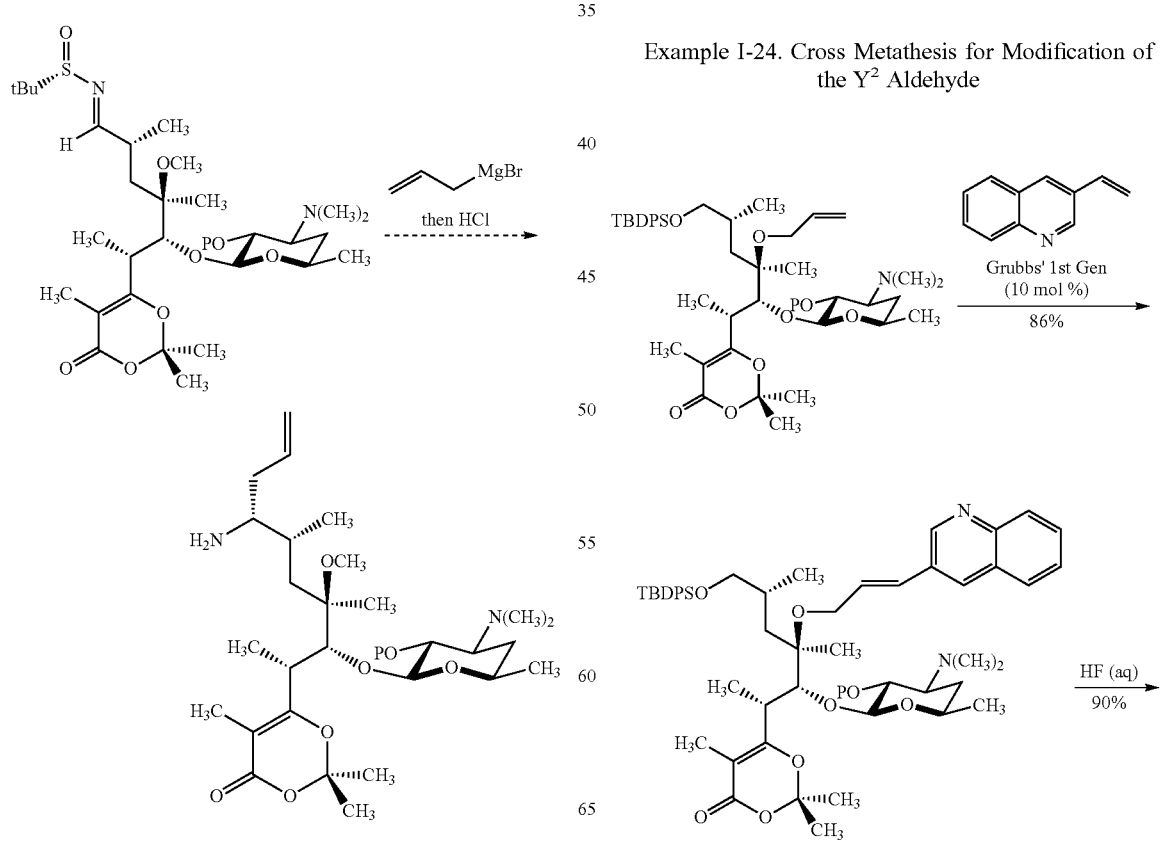

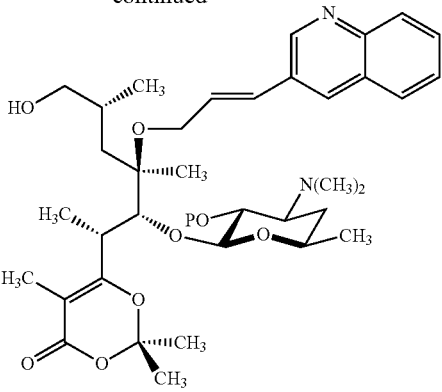

Exemplary Eastern Half Synthetic Procedures

Eastern Half with C2 Methyl Via Dioxolenone

Step 1

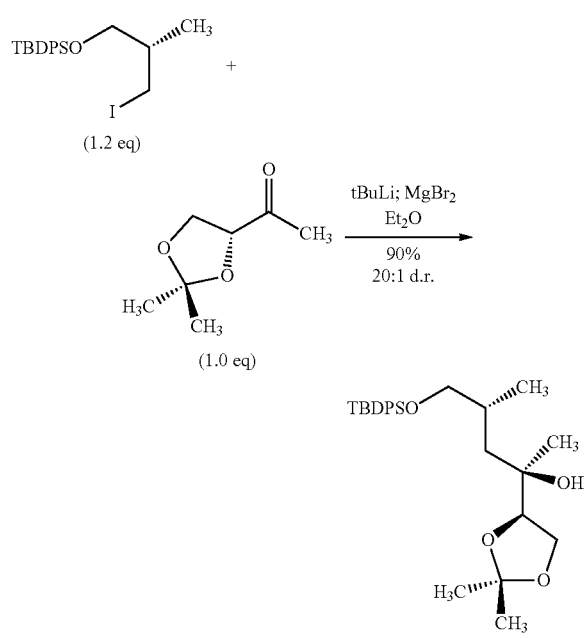

To a solution of (S)-tert-butyl(3-iodo-2-methylpropoxy)diphenylsilane (74.1 g, 169 mmol) in ether (512 mL) was added t-BuLi (1.52 M, 222 mL, 338 mmol) dropwise at −78° C. The resulting slightly cloudy suspension was stirred for 30 min. At this point, TLC (100% hexanes) indicated complete halogen-lithium exchange. A 1.5 M solution of MgBr$_2$ in 3:1 ethenbenzene (123 mL, 184 mmol) (Nakatsuka, M.; Ragan, J. A.; Sammakia, T.; Smith, D. B.; Uehling, D. E.; Schreiber, S. L. *J. Am. Chem. Soc.* 1990, 112, 5583-5601) was added dropwise. The resulting suspension was stirred for 30 min at −78° C. and briefly warmed to 0° C. (5 min) to give a clear solution. After cooling back to −78° C., a solution of (R)-1-(2,2-dimethyl-1,3-dioxolan-4-yl)ethanone (22.15 g, 154 mmol) (Leyes, A. E.; Poulter, C. D. *Org. Lett.* 1999, 1, 1067-1070) in ether (50 mL) was added dropwise to Grignard solution above via cannula. The resulting white mixture was stirred for 2 h at −78° C. TLC (30% ethyl acetate-hexanes) showed complete conversion. The reaction was quenched with half-saturated NH$_4$Cl solution (300 mL). The layers were partitioned, and the aqueous layer was extracted with ether (3×300 mL). The combined organic layers were washed with brine (500 mL), dried over sodium sulfate, filtered and concentrated. The crude product was purified by flash column chromatography (10-15% ether in hexanes) to give the product as a colorless oil (63.0 g, 90%). $^1$H NMR (500 MHz, CDCl$_3$) δ 7.73-7.66 (m, 4H), 7.48-7.36 (m, 6H), 4.03-3.86 (m, 3H), 3.55 (dd, J=9.8, 5.3 Hz, 1H), 3.44 (dd, J=9.8, 7.7 Hz, 1H), 3.09 (s, 1H), 2.07-1.96 (m, 1H), 1.86 (dd, J=14.5, 6.3 Hz, 1H), 1.42 (s, 3H), 1.39 (s, 3H), 1.33 (dd, J=14.4, 4.5 Hz, 1H), 1.14 (s, 3H), 1.08 (s, 9H), 0.91 (d, J=6.9 Hz, 3H). $^{13}$C NMR (126 MHz, CDCl$_3$) δ 135.66, 135.61, 133.31, 133.27, 129.68, 127.68, 127.65, 109.17, 82.02, 71.46, 70.08, 65.12, 43.02, 30.83, 26.87, 26.36, 25.39, 22.49, 19.45, 19.16. FTIR (neat), cm$^{-1}$: 3450 (br), 2957 (m), 1369 (s), 1211 (s), 1111 (s), 1066 (s), 823 (s), 738 (s), 702 (s); HRMS (ESI): Calcd for (C$_{27}$H$_{40}$O$_4$Si+H)$^+$: 457.2769. Found: 457.2775.

Step 2

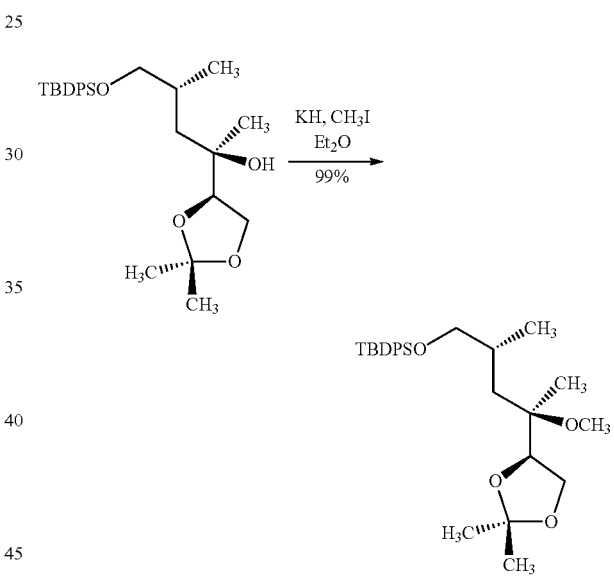

To a suspension of KH (35% dispersion in mineral oil, 6.67 g, 49.9 mmol) in ether (83 mL) was added an ether solution (83 mL) of (2R,4R)-5-((tert-butyldiphenylsilyl)oxy)-2-((R)-2,2-dimethyl-1,3-dioxolan-4-yl)-4-methylpentan-2-ol (19 g, 41.6 mmol) dropwise at 0° C. The transfer was quantitated with ether (2×5 mL). The resulting suspension was stirred for 1 h. Methyl iodide (freshly passed through basic alumina, 26.0 mL, 416 mmol) was added and the mixture was warmed to rt. After 2 h, TLC indicated complete reaction. The reaction mixture was slowly poured into 100 mL half-saturated NH$_4$Cl solution, and diluted with 100 mL ether. The layers were separated, and the aqueous layer was extracted with ether (2×50 mL). The combined organic layers were dried over MgSO$_4$, filtered and concentrated. The residue was purified by column chromatography (12% to 20% ether in hexanes) to give the product as a colorless oil. (19.5 g, 99%). $^1$H NMR (600 MHz, CDCl$_3$) δ 7.68-7.64 (m, 4H), 7.45-7.34 (m, 6H), 4.15 (t, J=7.2 Hz, 1H), 3.91 (dd, J=8.2, 6.9 Hz, 1H), 3.64 (t, J=7.9 Hz, 1H), 3.46 (dd, J=9.8, 6.2 Hz, 1H), 3.40 (dd, J=9.8, 6.5 Hz, 1H), 3.19 (s, 3H), 1.90-1.82 (m, 1H), 1.58 (dd, J=14.9, 4.0 Hz, 1H), 1.43 (s, 3H), 1.34 (s, 3H), 1.23 (dd, J=15.0, 7.8 Hz, 1H), 1.11 (s, 3H), 1.06 (d, J=2.8 Hz, 9H), 1.02 (d, J=6.7 Hz, 3H). $^{13}$C NMR (126 MHz, CDCl$_3$) δ 135.63, 135.59, 133.87, 129.56, 129.54, 127.59, 109.21, 80.14, 77.12, 69.60, 65.51, 49.92, 36.84, 31.28, 26.90, 26.23, 25.02, 19.26, 18.92, 18.50. FTIR (neat), cm$^{-1}$: 2957 (m), 1471 (s), 1369 (s), 1211 (s), 1155 (s), 1107 (s), 1066 (s), 823 (s), 738 (s), 700 (s); HRMS (ESI): Calcd for $(C_{28}H_{43}O_4Si+H)^+$: 471.2925. Found: 471.2944.

Step 3

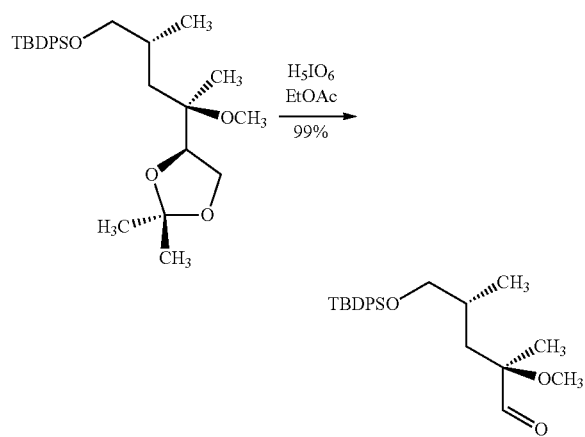

tert-butyl(((2R,4R)-4-((R)-2,2-dimethyl-1,3-dioxolan-4-yl)-4-methoxy-2-methylpentyl)oxy)diphenylsilane (19.5 g, 41.4 mmol) was dissolved in ethyl acetate (138 mL), and then periodic acid (18.89 g, 83 mmol) was added in one portion. The mixture was vigorously stirred for 1 h. The reaction was diluted with hexanes (138 mL). The suspension was passed through a short pad of silica, eluting with 50% ethyl acetate/hexanes (300 mL). The filtrate was concentrated to give the product as a colorless oil (16.8 g, 99%). $^1$H NMR (500 MHz, CDCl$_3$) δ 9.52 (s, 1H), 7.67 (dd, J=7.9, 1.5 Hz, 4H), 7.47-7.35 (m, 6H), 3.48 (dd, J=9.9, 5.7 Hz, 1H), 3.41 (dd, J=9.8, 6.2 Hz, 1H), 3.24 (s, 3H), 1.90-1.77 (m, 2H), 1.42 (dd, J=14.1, 6.6 Hz, 1H), 1.22 (s, 3H), 1.07 (s, 9H), 0.97 (d, J=6.7 Hz, 3H).

$^{13}$C NMR (126 MHz, CDCl$_3$) δ 204.68, 135.62, 135.60, 133.80, 133.79, 129.55, 127.59, 82.41, 68.97, 51.51, 37.91, 31.31, 26.88, 19.28, 18.58, 17.69. FTIR (neat), cm$^{-1}$: 2958 (m), 1735 (s), 1427 (s), 1105 (s), 1080 (s), 823 (s), 738 (s), 700 (s); HRMS (ESI): Calcd for $(C_{24}H_{34}O_3Si+H)^+$: 399.2350. Found: 399.2360.

Step 4

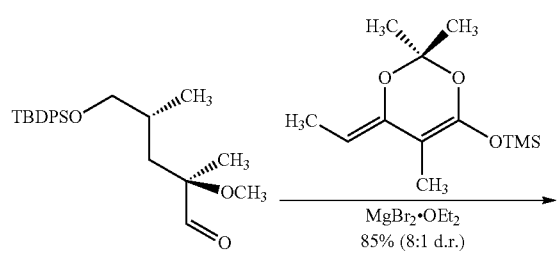

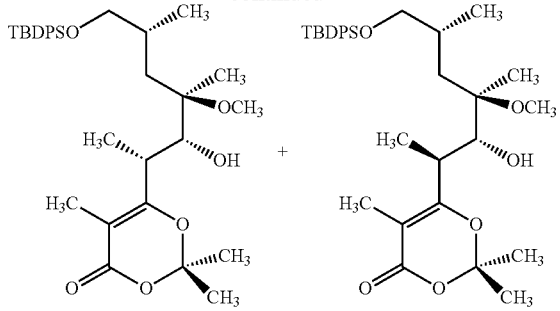

A solution of (2R, 4R)-5-((tert-butyldiphenylsilyl)oxy)-2-methoxy-2,4-dimethylpentanal (10.5 g, 26.3 mmol) in CH$_2$Cl$_2$ (105 mL) was cooled to -10° C. and treated with magnesium bromide diethyl etherate (20.41 g, 79 mmol). The mixture was stirred at this temperature for 10 min, and cooled to -78° C. (Z)-((4-ethylidene-2,2,5-trimethyl-4H-1,3-dioxin-6-yl)oxy)trimethylsilane (13.44 mL, 52.7 mmol) was added dropwise to the solution above. The mixture was stirred at -78° C. for 12 h, at which point TLC analysis (30% ethyl acetate/hexanes) indicated full conversion. The reaction was quenched by addition of ether (200 mL) and 1N HCl (100 mL). The layers were separated, and the aqueous layer was extracted with Et$_2$O (3×100 mL). The combined organic layers were washed with brine (2×100 mL) and dried over MgSO$_4$. The solution was filtered and concentrated in vacuo. Two columns were necessary to obtain pure syn diastereomer. The first column, eluting with 15:15:70 ether/ethyl acetate/hexanes gave product as an 8:1 diastereomeric mixture. The second column, eluting with 1-3% acetone in dichloromethane, gave the syn diastereomer (11.5 g, 77%), followed by anti diastereomer (1.2 g, 8%). Major isomer (syn): $^1$H NMR (500 MHz, CDCl$_3$) δ 7.73-7.62 (m, 4H), 7.48-7.34 (m, 6H), 3.72 (t, J=5.6 Hz, 1H), 3.47 (dd, J=9.8, 6.3 Hz, 1H), 3.43 (dd, J=9.8, 6.5 Hz, 1H), 2.96 (p, J=6.9 Hz, 1H), 2.42 (d, J=5.7 Hz, 1H), 1.85 (s, 3H), 1.83-1.77 (m, 1H), 1.74 (dd, J=14.3, 3.7 Hz, 1H), 1.66 (s, 3H), 1.65 (s, 3H), 1.33 (dd, J=14.2, 7.0 Hz, 1H), 1.21 (d, J=6.9 Hz, 3H), 1.11 (s, 3H), 1.07 (s, 9H), 1.00 (d, J=6.6 Hz, 3H). $^{13}$C NMR (126 MHz, CDCl$_3$) δ 168.22, 162.87, 135.59, 135.55, 133.76, 133.72, 129.60, 129.58, 127.61, 104.80, 99.04, 79.57, 73.86, 69.44, 49.08, 36.89, 35.98, 31.44, 26.87, 26.41, 23.62, 19.33, 19.26, 18.90, 14.14, 9.88. FTIR (neat), cm$^{-1}$: 3500 (br), 2931 (m), 1722 (s), 1637 (s), 1388 (s), 1356 (s), 1111 (s), 1072 (s), 702 (s), 613 (s); HRMS (ESI): Calcd for $(C_{33}H_{45}O_6Si+H)^+$: 569.3293. Found: 569.3304. Minor isomer (anti): $^1$H NMR (500 MHz, CDCl$_3$) δ 7.68 (d, J=6.5 Hz, 4H), 7.50-7.35 (m, 6H), 3.55-3.47 (m, 2H), 3.44 (dd, J=9.8, 6.6 Hz, 1H), 3.10 (s, 3H), 2.94-2.88 (m, 1H), 2.59 (d, J=7.5 Hz, 1H), 1.84 (s, 3H), 1.82-1.72 (m, 1H), 1.72-1.67 (m, 1H), 1.68 (s, 3H), 1.65 (s, 3H), 1.44 (dd, J=14.2, 7.1 Hz, 1H), 1.22 (d, J=7.0 Hz, 3H), 1.10 (s, 3H), 1.07 (s, 9H), 1.03 (d, J=6.7 Hz, 3H). $^{13}$C NMR (126 MHz, CDCl$_3$) δ 168.23, 162.88, 135.60, 135.57, 133.78, 133.74, 129.62, 129.59, 127.62, 104.82, 99.06, 79.58, 73.88, 69.45, 49.09, 36.90, 35.99, 31.46, 26.88, 26.43, 23.63, 19.34, 19.28, 18.91, 14.15, 9.89. FTIR (neat), cm$^{-1}$: 3483 (br), 2955 (m), 1720 (s), 1639 (s), 1466 (s), 1388 (s), 1359 (s), 1111 (s), 1074 (s), 702 (s), 615 (s); HRMS (ESI): Calcd for $(C_{33}H_{45}O_6Si+H)^+$: 569.3293. Found: 569.3292.

Step 5

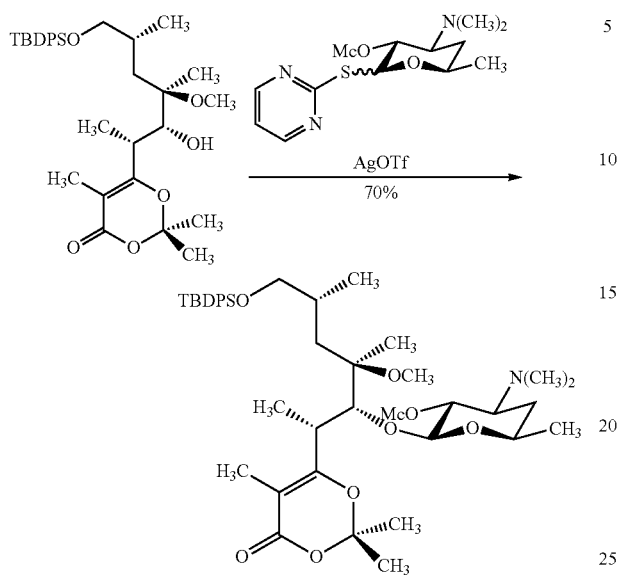

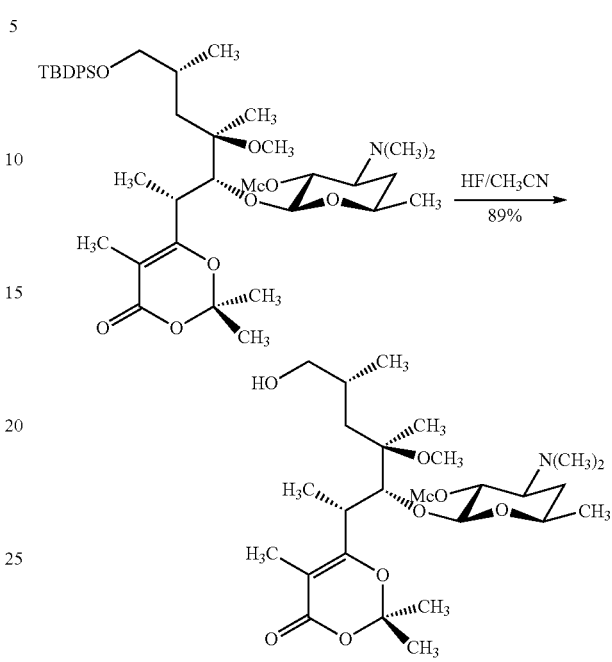

To a dry 200-mL flask was charged powdered dry 4 Å molecular sieves (10.0 g), toluene (41.8 mL) and CH$_2$Cl$_2$ (41.8 mL). In a separate flask, a mixture of 6-((2R,3R,4R,6R)-7-((tert-butyldiphenylsilyl)oxy)-3-hydroxy-4-methoxy-4,6-dimethylheptan-2-yl)-2,2,5-trimethyl-4H-1,3-dioxin-4-one (9.5 g, 16.70 mmol) and (2S,3R,4S,6R)-4-(dimethylamino)-6-methyl-2-(pyrimidin-2-ylthio)tetrahydro-2H-pyran-3-yl methyl carbonate (16.40 g, 50.1 mmol) (Velvadapu, V.; Andrade, R. B.; Carbohydr. Res. 2008, 343, 145-150) were azeotropically dried from benzene for 3 times. Then the residue was dissolved in CH$_2$Cl$_2$ (30 mL). This solution was added to the molecular sieves suspension above via cannula. The suspension was cooled to 0° C., and silver(I) trifluoromethanesulfonate (21.46 g, 84 mmol) was added in one portion. The mixture was stirred for 1 h at 0° C. At this point, TLC analysis (50% ethyl acetate in hexanes) indicated full consumption of starting material. The reaction was quenched with saturated aqueous NH$_4$Cl (10.0 mL), stirred for 5 min, and saturated aqueous NaHCO$_3$ (10 mL) was added. The mixture was filtered through a pad of Celite, rinsing with CH$_2$Cl$_2$ (100 mL), and the filtrate was washed with saturated aqueous NaHCO$_3$ (20 mL). The organic layer was dried over Na$_2$SO$_4$, filtered and concentrated. The crude product was purified by flash column chromatography (70% ethyl acetate in hexanes) to give the product as a white foam (9.0 g, 70%). $^1$H NMR (500 MHz, Benzene) δ 7.86-7.79 (m, 4H), 7.26-7.17 (m, 6H), 4.70 (dd, J=10.4, 7.5 Hz, 1H), 4.65 (d, J=7.5 Hz, 1H), 4.19 (t, J=8.0 Hz, 1H), 3.89 (dt, J=10.5, 5.3 Hz, 1H), 3.59 (dd, J=9.7, 7.5 Hz, 1H), 3.40 (s, 3H), 3.25-3.19 (m, 1H), 3.19-3.11 (m, 1H), 2.93 (s, 3H), 2.52 (td, J=12.1, 4.5 Hz, 1H), 2.09 (d, J=12.9 Hz, 6H), 2.03 (s, 3H), 1.85 (dd, J=14.3, 7.0 Hz, 1H), 1.62 (dt, J=18.6, 6.1 Hz, 1H), 1.45 (s, 3H), 1.34 (s, 3H), 1.28 (s, 3H), 1.22 (d, J=8.5 Hz, 3H), 1.20 (s, 9H), 1.18 (d, J=8.5 Hz, 3H), 1.06 (d, J=7.0 Hz, 3H). $^{13}$C NMR (126 MHz, CDCl$_3$) δ 167.94, 163.00, 155.17, 135.62, 134.26, 134.21, 129.38, 129.36, 127.47, 104.40, 99.83, 99.61, 79.02, 75.52, 69.16, 69.12, 63.11, 54.64, 49.40, 40.70, 36.40, 33.94, 31.12, 30.86, 26.87, 25.68, 24.38, 20.98, 20.20, 19.79, 19.34, 12.86, 9.77. FTIR (neat), cm$^{-1}$: 2935 (m), 1755 (s), 1724 (s), 1641 (s), 1456 (s), 1377 (s), 1265 (s), 1106 (s), 1053 (s), 704 (s), 613 (s); HRMS (ESI): Calcd for (C$_{43}$H$_{65}$NO$_{10}$Si+H)$^+$: 784.4451. Found: 784.4467.

In a plastic vial, TBDPS-OCH$_3$-EH (9.0 g, 11.48 mmol) was dissolved in CH$_3$CN (57.4 mL), and hydrofluoric acid (48% aq, 9.90 mL, 574 mmol) was added with a plastic syringe. The mixture was then stirred at room temperature for 12 h, at which point TLC analysis (10% methanol in ethyl acetate) indicated full consumption of starting material. The reaction solution was slowly added to an Erlenmyer containing saturated aqueous NaHCO$_3$ solution (300 mL). After gas evolution subsided, the mixture was extracted with ether (3×100 mL). The organic layers were combined, and extracted with 1 N HCl (3×25 mL). The ether layer was discarded. The acid layers were combined, to which solid NaHCO$_3$ was slowly added to adjust pH to 8. This aqueous solution was extracted with CH$_2$Cl$_2$ (3×100 mL). The combined CH$_2$Cl$_2$ layers were dried over Na$_2$SO$_4$, filtered and concentrated to give the product as a white foam (5.58 g, 89%). $^1$H NMR (500 MHz, Benzene) δ 4.85 (dd, J=10.5, 7.7 Hz, 1H), 4.69 (d, J=7.6 Hz, 1H), 3.96 (d, J=2.9 Hz, 1H), 3.61 (ddd, J=11.3, 7.2, 4.4 Hz, 1H), 3.49-3.36 (m, 2H), 3.33 (s, 3H), 3.15-3.01 (m, 1H), 2.97 (t, J=6.4 Hz, 1H), 2.73 (s, 3H), 2.56 (td, J=12.0, 4.3 Hz, 1H), 2.11 (s, 6H), 1.87 (s, 3H), 1.86-1.81 (m, 1H), 1.74 (dd, J=14.5, 3.1 Hz, 1H), 1.57 (dd, J=14.4, 9.1 Hz, 1H), 1.41 (s, 3H), 1.38 (s, 3H), 1.32 (s, 3H), 1.26 (dd, J=12.8, 2.9 Hz, 1H), 1.16 (d, J=7.3 Hz, 3H), 1.11-1.04 (m, 1H), 1.02 (d, J=6.1 Hz, 3H), 0.88 (d, J=6.8 Hz, 3H). $^{13}$C NMR (126 MHz, CDCl$_3$) δ 167.34, 162.79, 155.25, 104.54, 99.84, 79.79, 76.37, 75.48, 69.27, 68.42, 63.05, 54.71, 49.56, 40.69, 38.69, 33.83, 31.07, 30.83, 25.89, 24.19, 20.99, 19.92, 19.86, 13.00, 9.89. FTIR (neat), cm$^{-1}$: 3437 (br), 2939 (m), 1753 (s), 1724 (s), 1641 (s), 1454 (s), 1379 (s), 1267 (s), 1109 (s), 1053 (s), 732 (s); HRMS (ESI): Calcd for (C$_{27}$H$_{47}$NO$_{10}$+H)$^+$: 546.3272. Found: 546.3280.

Step 7

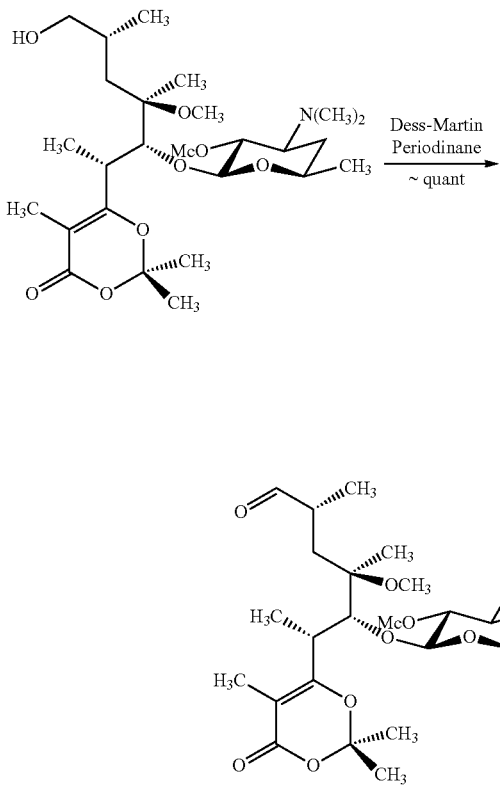

To a solution of the alcohol (2.1 g, 3.85 mmol) in CH₂Cl₂ (3.85 mL) was added Dess-Martin Periodinane (2.448 g, 5.77 mmol) and water (7.7 μL, 2 μL/mL CH₂Cl₂). The resulting milky suspension was stirred for 0.5 h at rt. The reaction was diluted with ether (50 mL), saturated aqueous Na₂S₂O₃ (20 mL), saturated aqueous NaHCO₃ (20 mL) and brine (20 mL). The resulting mixture was vigorously stirred for 30 min, and the layers were separated. The aqueous layer was extracted with ether (3×20 mL). The combined organic layers were washed with brine (10 mL), dried over MgSO₄, filtered and concentrated to give the product as a white foam (2.1 g, 100%). $^1$H NMR (500 MHz, CDCl₃) δ 9.36 (d, J=4.7 Hz, 1H), 4.62-4.51 (m, 2H), 3.86 (d, J=3.3 Hz, 1H), 3.78 (s, 3H), 3.51-3.40 (m, 1H), 3.37 (qd, J=7.3, 3.4 Hz, 1H), 2.97 (s, 3H), 2.81-2.69 (m, 1H), 2.47 (ddd, J=10.9, 7.7, 3.9 Hz, 1H), 2.31 (s, 6H), 1.86 (s, 3H), 1.81 (dd, J=14.0, 11.1 Hz, 1H), 1.77-1.73 (m, 1H), 1.68 (s, 3H), 1.66 (s, 3H), 1.58 (dd, J=14.1, 3.0 Hz, 1H), 1.43-1.30 (m, 1H), 1.26 (d, J=6.1 Hz, 3H), 1.25 (s, 3H), 1.07 (d, J=3.0 Hz, 3H), 1.06 (d, J=2.6 Hz, 3H). $^{13}$C NMR (126 MHz, Benzene) δ 202.57, 166.45, 161.71, 155.83, 104.17, 100.60, 100.46, 78.64, 78.26, 75.43, 69.23, 63.64, 54.18, 49.19, 42.02, 40.51, 37.52, 34.08, 30.22, 25.66, 24.02, 20.84, 20.33, 15.42, 13.14, 10.03. FTIR (neat), cm$^{-1}$: 2937 (m), 1753 (s), 1724 (s), 1643 (s), 1442 (s), 1377 (s), 1265 (s), 1109 (s), 1053 (s); HRMS (ESI): Calcd for (C₂₇H₄₅NO₁₀+H)⁺: 544.3116. Found: 544.3139.

Step 8

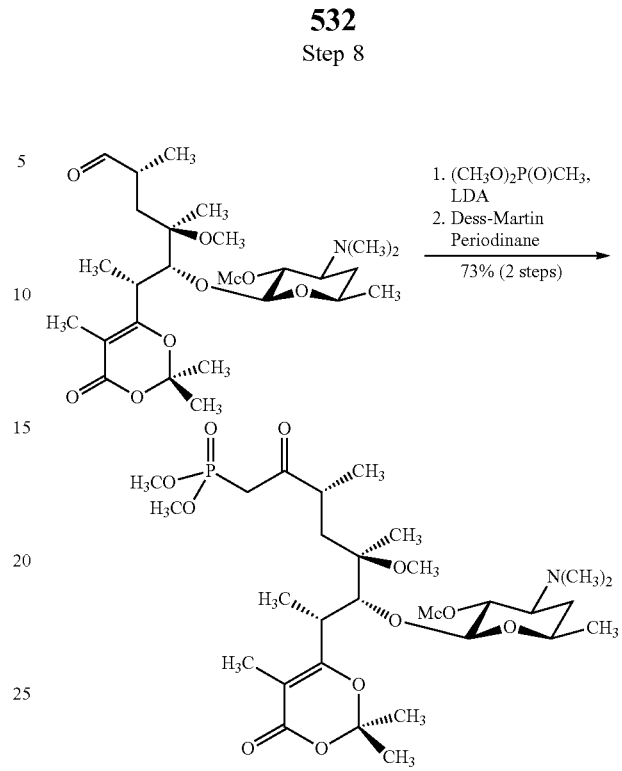

Lithium diisopropylamide (1.0 M solution in THF, freshly prepared from diisopropylamine and nBuLi, 2.415 mL, 2.415 mmol) was charged into a flamed-dried flask. THF (6.9 mL) was added to supplement the volume to 9.3 mL, and the solution was cooled to −78° C. A solution of dimethyl methylphosphonate (0.262 mL, 2.415 mmol) in THF (1 mL) was added dropwise. The resulting solution was stirred at −78° C. for 15 min. A solution of the aldehyde (1.01 g, 1.858 mmol) in THF (9.3 mL) was added dropwise via cannula, and the reaction was stirred for 30 min at −78° C. At this point, TLC (10% methanol in ethyl acetate) indicated full consumption of the aldehyde. The reaction was quenched by addition of saturated aqueous NH₄Cl solution (10 mL) at −78° C. and diluted with ethyl acetate (10 mL). The mixture was warmed to rt, and the layers were separated. The aqueous layer was extracted with ethyl acetate (2×20 mL). The combined organic layers were washed with brine, dried over Na₂SO₄, and concentrated. The crude material was dissolved in CH₂Cl₂ (5 mL), and Dess-Martin Periodinane (1.18 g, 2.79 mmol) was added in one batch, followed by water (10 μL, 2 μL/mL CH₂Cl₂). The reaction was stirred at rt for 1 h. At this point, TLC (10% methanol in ethyl acetate) indicated complete conversion to a less polar compound. To the reaction mixture was added Et₂O (20 mL), saturated aqueous NaHCO₃ (10 mL) and saturated aqueous Na₂S₂O₃ (10 mL). The mixture was vigorously for 30 min. The layers were separated and the aqueous layer was extracted with Et₂O (2×20 mL). The combined organic layers were washed with brine, dried over MgSO₄ and concentrated. The crude product was purified by flash column chromatography (2-3% methanol in CH₂Cl₂+ 0.2% saturated NH₄OH) to give the product as a white foam (0.90 g, 73%). $^1$H NMR (600 MHz, CDCl₃) δ 4.57-4.46 (m, 2H), 3.84 (d, J=3.3 Hz, 1H), 3.76 (t, J=3.7 Hz, 3H), 3.74 (d, J=2.7 Hz, 3H), 3.74 (s, 3H), 3.42 (dtd, J=11.9, 5.9, 4.3 Hz, 1H), 3.30-3.21 (m, 1H), 3.16 (dd, J=22.0, 14.7 Hz, 1H), 3.04 (dd, J=21.0, 14.7 Hz, 1H), 2.94 (s, 3H), 2.84-2.76 (m, 1H), 2.76-2.66 (m, 1H), 2.27 (s, 6H), 1.92 (dd, J=14.1, 10.5 Hz, 1H), 1.78 (s, 3H), 1.77-1.69 (m, 1H), 1.64 (d, J=12.4 Hz, 3H), 1.62 (s, 3H), 1.47-1.40 (m, 1H), 1.38-1.28 (m, 1H), 1.23 (s, 3H), 1.23 (d, J=6.3 Hz, 3H), 1.08 (d, J=6.9 Hz, 3H), 1.02 (d, J=7.4 Hz, 3H). $^{13}$C NMR (126 MHz, CDCl$_3$) δ 205.81 (d, J=6.2 Hz), 167.20, 162.75, 155.17, 104.39, 99.91, 99.84, 78.41, 76.52, 75.40, 69.23, 62.97, 54.66, 52.75, 52.74, 49.47, 42.19, 42.17, 40.62, 40.37, 39.31, 33.92, 30.75, 25.79, 24.17, 20.92, 19.78, 18.43, 13.04, 9.64. FTIR (neat), cm$^{-1}$: 2937 (m), 1753 (s), 1716 (s), 1643 (s), 1456 (s), 1377 (s), 1265 (s), 1109 (s), 1053 (s), 731 (s); HRMS (ESI): Calcd for $(C_{30}H_{52}NO_{13}P+H)^+$: 666.3249. Found: 666.3266.

Step 8a: Alternative Phosphonate Preparation

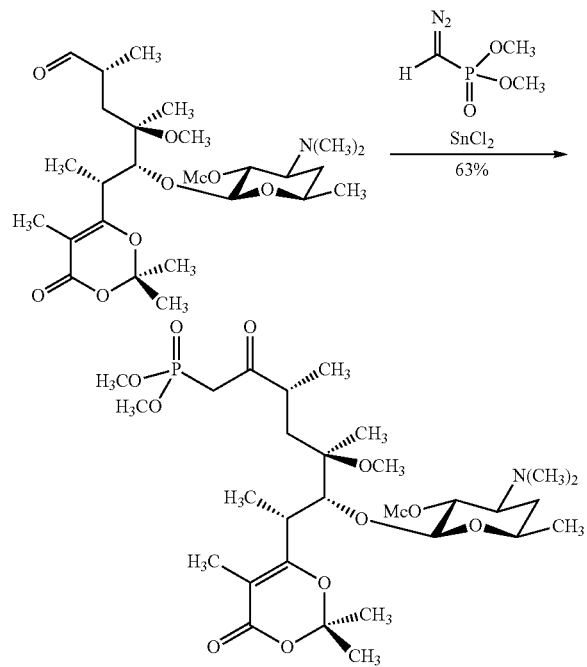

The aldehyde (100 mg, 0.184 mmol) was dissolved in CH$_2$Cl$_2$ (2.62 mL), and tin(II) chloride (6.98 mg, 0.037 mmol) was added. The solution was stirred at rt for 5 min, before dimethyl (diazomethyl)phosphonate (55.2 mg, 0.368 mmol) was added via syringe. The reaction was then warmed to 40° C. After 12 h, TLC (10% methanol in ethyl acetate) indicated full consumption of the aldehyde. The reaction was diluted with ethyl acetate (10 mL) and saturated aqueous NaHCO$_3$ (10 mL) and vigorously stirred. The layers were separated, and the aqueous layer was extracted with ethyl acetate (3×10 mL). The combined organic layers were dried over Na$_2$SO$_4$ and concentrated. The crude product was purified by flash column chromatography (2-3% methanol in CH$_2$Cl$_2$+0.2% saturated NH$_4$OH) to give the product as a white foam (75 mg, 63%).

Eastern Half without C2 Methyl Via β-Keto-t-Butyl Ester

Step 1

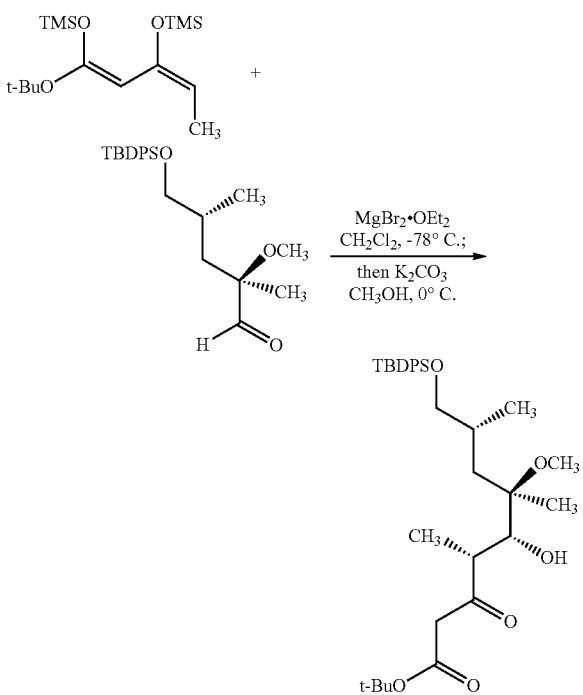

The aldehyde (575 mg, 1.443 mmol, 1 equiv) was dried by azeotropic distillation (benzene) and then dissolved in dichloromethane (11 mL). Magnesium bromide ethyl etherate (1.86 g, 7.21 mmol, 5.0 equiv) was added in one portion to this solution and the resulting mixture was cooled to −78° C. A solution of 1,3-bistrimethylsilyl dienol ether (1.37 g, 4.33 mmol, 3.0 equiv, for preparation see: Takai, K.; Nawate, Y.; Okabayashi, T.; Nakatsuji, H.; Iida, A.; Tanabe, Y. *Tetrahedron* 2009, 65, 5596-5607) in dichloromethane (1.5 mL) was added dropwise via syringe over 5 min to the aldehyde mixture at −78° C. The reaction mixture was stirred at this temperature for 3 h, then saturated aqueous ammonium chloride solution (12 mL) was added. The cooling bath was removed and the reaction flask was allowed to warm to 23° C. Water (40 mL) and dichloromethane (50 mL) were added and the phases were separated. The aqueous phase was extracted with dichloromethane (2×50 mL). The organic extracts were combined and the combined solution was dried over anhydrous sodium sulfate. The dried solution was filtered and the filtrate was concentrated. The crude aldol mixture was then dissolved in methanol (12 mL) and the resulting solution was cooled to 0° C. Potassium carbonate (20 mg, 0.1 equiv) was added in one portion to the crude product solution. After stirring at 0° C. for 6 min, aqueous potassium phosphate buffer solution (pH 7.0, 0.2 M, 25 mL) was added to the reaction solution. The cooling bath was removed and the reaction flask was allowed to warm to 23° C. Water (25 mL) and dichloromethane (60 mL) were added and the phases were separated. The aqueous phase was extracted with dichloromethane (2×60 mL). The organic extracts were combined and the combined solution was dried over anhydrous sodium sulfate. The dried solution was filtered and the filtrate was concentrated. The product was purified by flash-column chromatography (10% ethyl acetate-hexanes, grading to 12%), providing the aldol product in diastereomerically pure form (490 mg, 60%). A minor aldol diastereomer was isolated separately in diastereomerically pure form (97 mg, 12%). NB—clearly distinguishable peaks corresponding to the enol tautomer of aldol product (<10%) are reported with non-integer integrals. $^1$H NMR (500 MHz, CDCl$_3$) δ 7.67 (dd, 4H, J=7.8, 1.5 Hz), 7.42-7.36 (m, 6H), 4.96 (s, 0.07H), 3.86 (d, 1H, J=6.3 Hz), 3.53 (dd, 1H, J=9.8, 5.9 Hz), 3.41 (AB quartet, 2H), 3.40 (dd, 1H, J=9.8, 5.9 Hz), 3.12 (s, 0.21H), 3.00 (s, 3H), 2.86 (m, 1H), 2.24 (brs, 1H), 1.84-1.78 (m, 1H), 1.63 (dd, 1H, J=14.2, 4.9 Hz), 1.45 (s, 9H), 1.36 (dd, 1H, J=14.2, 6.3 Hz), 1.17 (d, 3H, J=7.3 Hz), 1.09 (s, 3H), 1.06 (s, 9H), 1.02 (d, 3H, J=6.3 Hz); $^{13}$C NMR (125 MHz, CDCl$_3$) δ 205.6, 166.6, 135.6, 135.6, 133.9, 129.5, 127.6, 81.5, 79.1, 75.1, 69.4, 49.9, 49.1, 47.0, 36.9, 31.5, 27.9, 26.9, 19.9, 19.2, 19.0, 12.9; FTIR (neat film), 3487 (w), 2932 (w), 1732 (m), 1707 (m), 1107 (s), 1071 (s), 700 (s) cm$^{-1}$; HRMS-ESI (m/z): [M+Na]$^+$ calcd for C$_{33}$H$_{50}$O$_6$SiNa, 593.3269. found, 593.3278.

Step 2 then was filtered through a thick pad of Celite. The Celite pad was washed with dichloromethane (100 mL) and the resulting filtrate was concentrated, providing an orange-brown foam. The crude product was purified by flash-column chromatography (40% ethyl acetate-hexanes, grading to 70%), affording the glycosylated product** as a white foam (1.09 g, 51%). $^1$H NMR (500 MHz, CDCl$_3$) δ 7.68 (d, 4H, J=6.3 Hz), 7.42-7.34 (m, 6H), 4.52 (dd, 1H, J=10.2, 7.8 Hz), 4.40 (d, 1H, J=7.8 Hz), 3.95 (d, 1H, J=7.8 Hz), 3.75 (s, 3H), 3.67 (dd, 1H, J=9.8, 4.4 Hz), 3.52-3.46 (m, 1H), 3.35-3.32 (m, 1H), 3.34 (AB quartet, 2H), 3.03-2.97 (m, 1H), 2.78 (s, 3H), 2.78-2.71 (m, 1H), 2.28 (s, 6H), 1.89-1.82 (m, 1H), 1.74 (brd, 1H), 1.43 (s, 9H), 1.35-1.30 (m, 2H), 1.26-1.23 (m, 1H), 1.22 (d, 3H, J=6.3 Hz), 1.14 (s, 3H), 1.12 (d, 3H, J=7.3 Hz), 1.06 (s, 9H), 1.04 (d, 3H, J=7.8 Hz); $^{13}$C NMR (125 MHz, CDCl$_3$) δ 204.6, 166.7, 155.1, 135.6, 134.2, 134.2, 129.4, 127.5, 101.2, 81.3, 80.8, 78.8, 75.5, 69.3, 69.0, 63.1, 54.7, 50.6, 49.4, 46.2, 40.7, 37.4, 31.4, 30.6, 28.0, 26.9, 20.9, 20.0, 19.6, 19.3, 13.7; FTIR (neat film), 2932 (w), 1755 (m), 1709 (w), 1263 (s), 1055 (s), 702 (s) cm$^{-1}$; HRMS-ESI (m/z): [M+H]$^+$ calcd for C$_{43}$H$_{68}$NO$_{10}$Si, 786.4607. found, 786.4619.

Step 3

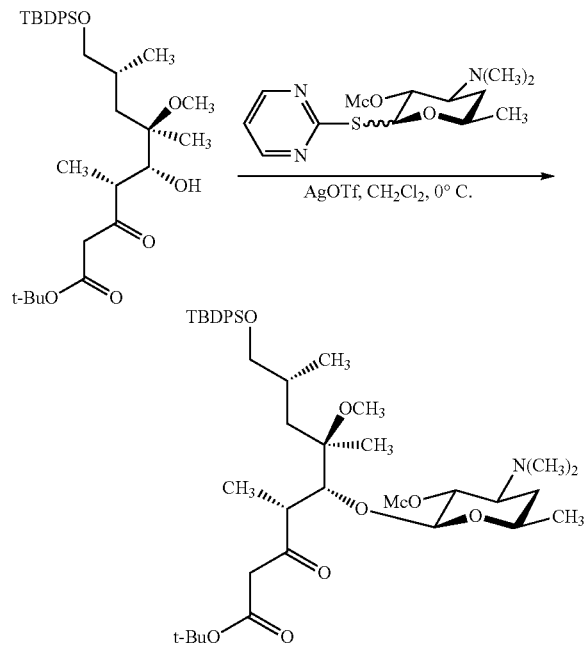

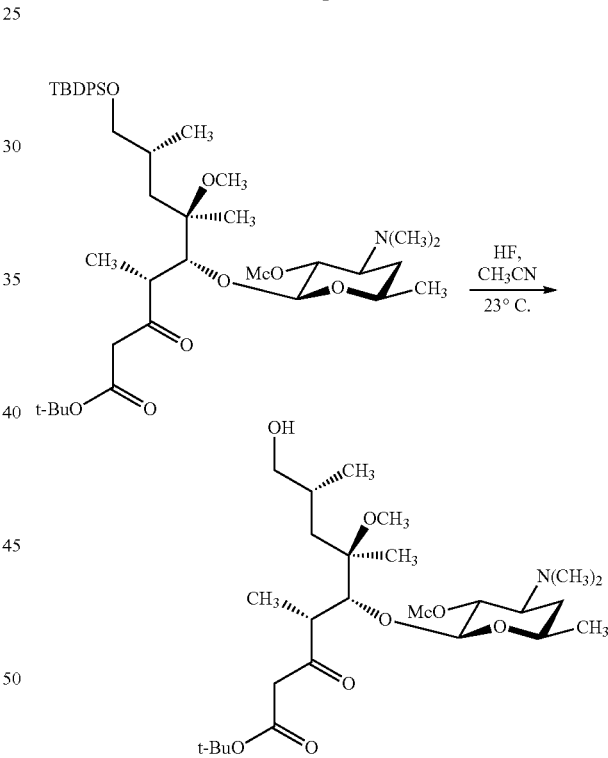

A mixture of the aldol product (1.55 g, 2.72 mmol, 1 equiv) and the 2-pyrimidinylthio glycoside (1.78 g, 5.43 mmol, 2.0 equiv) was dried by azeotropic distillation (benzene, 2×20 mL). The dried mixture was dissolved in dichloromethane (4.0 mL) and transferred via syringe to a flask containing a mixture of toluene (6.5 mL), dichloromethane (3.0 mL) and activated 4 Å molecular sieves (1.5 g). An additional portion of dichloromethane (1.0 mL) was used to ensure complete transfer into the reaction flask. The resulting mixture was stirred at 23° C. for 15 min, then was cooled to 0° C. Silver (I) trifluoromethanesulfonate (4.19 g, 16.3 mmol, 6.0 equiv) was added in one portion to the ice-cold, stirring reaction mixture. After stirring at 0° C. for 90 min, the reaction mixture was diluted with dichloromethane (10 mL) and then quenched by sequential dropwise addition of saturated aqueous ammonium chloride solution (1.5 mL) and saturated aqueous sodium bicarbonate solution (2.5 mL). The resulting mixture was allowed to warm to 23° C., Concentrated aqueous hydrofluoric acid solution (48%, 2.00 mL, 50.9 mmol, 40 equiv) was added dropwise via syringe to a solution of the glycosylated product (1.00 g, 1.27 mmol, 1 equiv) in acetonitrile (12 mL) in a polypropylene reaction vessel at 23° C. The reaction solution was stirred vigorously at 23° C. for 15 h, then was added dropwise via plastic pipette to an ice-cold solution of saturated aqueous sodium bicarbonate (60 mL). The resulting mixture was extracted with ethyl acetate (3×60 mL). The organic extracts were combined and the combined solution was dried over anhydrous sodium sulfate. The dried solution was filtered and the filtrate was concentrated. The crude product was purified by flash column chromatography (65% ethyl acetate-hexanes, grading to 75%), affording the deprotection product as a white foam (435 mg, 62%). $^1$H NMR (500 MHz, CDCl$_3$) δ 4.52 (dd, 1H, J=10.7, 7.8 Hz), 4.42 (d, 1H, J=7.8 Hz), 4.09 (d, 1H, J=7.8 Hz), 3.76 (s, 3H), 3.57-3.48 (m, 2H), 3.43 (s, 2H), 3.29-3.23 (m, 2H), 3.10-3.05 (m, 1H), 2.98 (s, 3H), 2.75-2.70 (m, 1H), 2.26 (s, 6H), 1.85-1.80 (brm, 1H), 1.73 (dd, 1H, J=12.7, 2.4 Hz), 1.55-1.45 (m, 2H), 1.45 (s, 9H), 1.35-1.28 (m, 1H), 1.27 (s, 3H), 1.22 (d, 3H, J=5.9 Hz), 1.14 (d, 3H, J=7.3 Hz), 0.92 (d, 3H, J=6.8 Hz); $^{13}$C NMR (125 MHz, CDCl$_3$) δ 204.5, 166.5, 155.2, 101.2, 81.6, 79.7, 79.5, 75.5, 69.1, 68.2, 62.9, 54.7, 50.4, 49.7, 46.1, 40.6, 38.7, 31.1, 30.6, 27.9, 20.9, 20.0, 19.7, 13.8; FTIR (neat film), 2936 (w), 1751 (m), 1709 (m), 1263 (s), 1051 (s) cm$^{-1}$; HRMS-ESI (m/z): [M+H]$^+$ calcd for C$_{27}$H$_{50}$NO$_{10}$, 548.3429. found, 548.3435.

Step 4

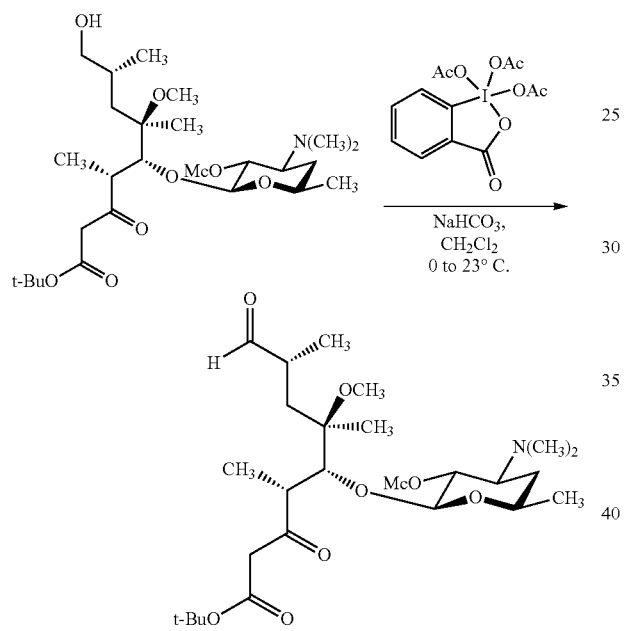

Sodium bicarbonate (557 mg, 6.63 mmol, 10 equiv) and Dess-Martin periodinane (618 mg, 1.46 mmol, 2.2 equiv) were added sequentially to a stirring solution of the alcohol (363 mg, 0.663 mmol, 1 equiv) in dichloromethane (10 mL) and water (20 μL) at 0° C. The resulting mixture was allowed to warm to 23° C. After stirring at this temperature for 1 h, the reaction mixture was diluted with diethyl ether (30 mL). Saturated aqueous sodium thiosulfate solution (15 mL), saturated aqueous sodium bicarbonate solution (7 mL) and saturated aqueous sodium chloride solution (7 ml) were added in sequence, and the resulting mixture was stirred vigorously for 10 min. The phases were then separated and the aqueous phase was extracted with diethyl ethyl (3×30 mL). The organic extracts were combined and the combined solution was washed sequentially with saturated aqueous sodium thiosulfate solution (2×20 mL) and saturated aqueous sodium chloride solution (20 mL). The resulting organic solution was then dried over anhydrous sodium sulfate. The dried solution was filtered and the filtrate was concentrated. The resulting yellow solid was used directly in the next step (reductive amination) without further purification (crude aldehyde>90% pure by $^1$H NMR analysis). $^1$H NMR (500 MHz, CDCl$_3$) δ 9.33 (d, 1H, J=4.9 Hz), 4.52 (dd, 1H, J=10.7, 7.8 Hz), 4.43 (d, 1H, J=7.8 Hz), 4.01 (d, 1H, J=8.8 Hz), 3.78 (s, 3H), 3.52-3.46 (m, 1H), 3.41 (AB quartet, 2H), 3.10-3.05 (m, 1H), 2.83 (s, 3H), 2.77-2.71 (m, 1H), 2.48-2.43 (m, 1H), 2.30-2.27 (m, 1H), 2.27 (s, 6H), 1.91 (dd, 1H, J=14.6, 11.2 Hz), 1.76-1.72 (m, 1H), 1.60 (dd, 1H, J=14.6, 3.4 Hz), 1.47 (s, 9H), 1.37-1.28 (m, 2H), 1.25 (s, 3H), 1.22 (d, 3H, J=5.9 Hz), 1.16 (d, 3H, J=7.3 Hz), 1.06 (d, 3H, J=6.8 Hz); $^{13}$C NMR (125 MHz, CDCl$_3$) δ 204.4, 204.1, 166.6, 155.2, 101.3, 81.5, 81.1, 78.3, 75.4, 69.1, 63.0, 54.7, 50.6, 49.5, 46.0, 41.9, 40.5, 38.0, 30.5, 27.9, 20.8, 19.9, 15.5, 13.8; FTIR (neat film), 2974 (w), 1753 (m), 1724 (m), 1711 (m), 1263 (s), 1053 (m) cm$^{-1}$; HRMS-ESI (m/z): [M+Na]$^+$ calcd for C$_{27}$H$_{47}$NNaO$_{10}$, 568.3092. found, 568.3094.

Synthesis of C6 Allyl Derivatives

Step 1

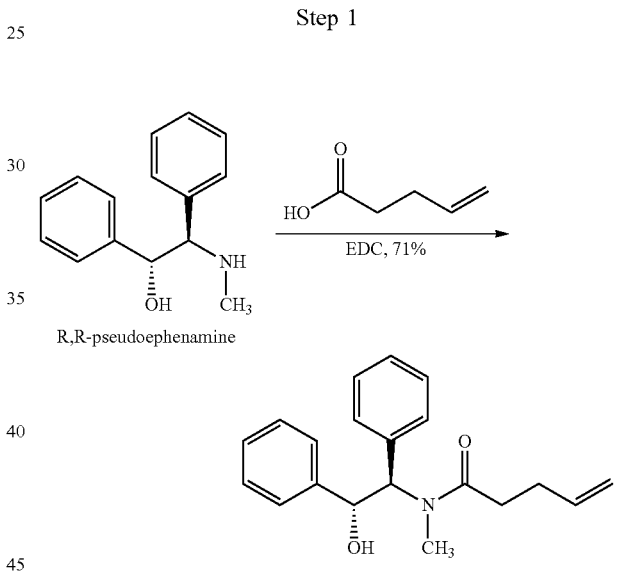

To a solution of Hunig's Base (10.48 ml, 60.0 mmol) in DMF (22 mL) cooled in an ice-water bath was added pent-4-enoic acid (2.041 ml, 20.00 mmol), HOBT (3.06 g, 20.00 mmol), and EDC (4.22 g, 22.00 mmol) sequentially. The solution was stirred at 0° C. for 5 minutes, and remains a light orange slurry throughout this time. (R,R)-pseudoephenamine (5 g, 22.00 mmol) (freshly crushed) was added in one portion, and the vessel was allowed to warm to 23° C. After 5 minutes, some product was visible by TLC (10% MeOH/DCM, +1% NH$_4$OH). After 20 minutes, the solution was completely homogeneous. After 1 h, conversion was >50%. At 19 h, progress had not changed. The mixture was diluted with water (200 mL) and extracted with ethyl acetate (3×75 mL). The organic layers were combined and the resulting light yellow solution was washed with water (2×100 mL), sat aq NaCl (1×75 mL), dried through a pad of sodium sulfate, and concentrated. The product was purified by flash chromatography (30% to 50% ethyl acetate to hexane) affording N-((1R,2R)-2-hydroxy-1,2-diphenyl-ethyl)-N-methylpent-4-enamide (5.32 g, 17.19 mmol, 86% yield).

Step 2

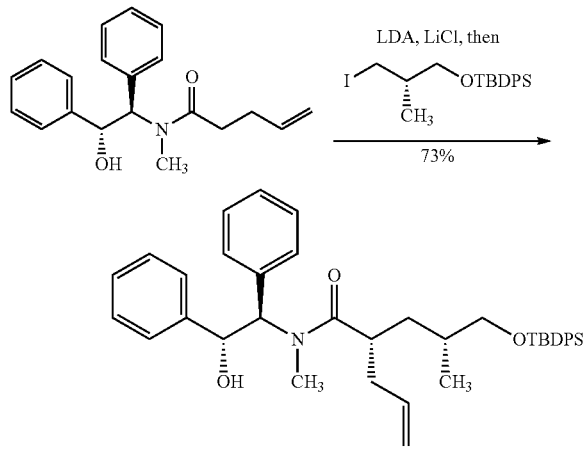

Lithium chloride (3.29 g, 78 mmol) was added to a 200-mL round-bottom flask equipped with a stir bar, and the whole was exposed to a gentle flame under vacuum (0.1 mmHg) for 2 minutes. The vessel and its contents were allowed to cool to 23° C., and THF (25 mL) and diisopropylamine (4.16 ml, 29.2 mmol) were added. The vessel was cooled to −78° C., and BuLi (12.06 ml, 28.6 mmol) was added dropwise. The solution was allowed to warm to 0° C., was stirred for 5 minutes at this temperature, and was re-cooled to −78° C. A solution of (R,R)-pseudoephenamine pent-4-enamide (4 g, 12.93 mmol) in tetrahydrofuran (20 mL+5 mL wash) was added dropwise via cannula, and the mixture was stirred for 30 min at −78° C., was allowed to warm to 23° C. and was stirred for 5 minutes at this temperature. A solution of (S)-tert-butyl(3-iodo-2-methylpropoxy)diphenylsilane (6.80 g, 15.51 mmol) in THF (10 mL) was added, and the transfer was quantitated with THF (2×2.5 mL). After 3 h, conversion was <50%. After 41 h, half-sat. aq. ammonium chloride (200 mL) was added, and the mixture was extracted with ethyl acetate (3×100 mL). The combined organic layers were washed with brine (100 mL), dried through a pad of sodium sulfate, and concentrated. The product was purified by column chromatography (20% to 25% ethyl acetate to hexanes) affording (S)-2-((R)-3-((tert-butyldiphenylsilyl)oxy)-2-methylpropyl)-N-((1R,2R)-2-hydroxy-1,2-diphenylethyl)-N-methylpent-4-enamide (5.86 g, 9.45 mmol, 73.1% yield).

Step 3

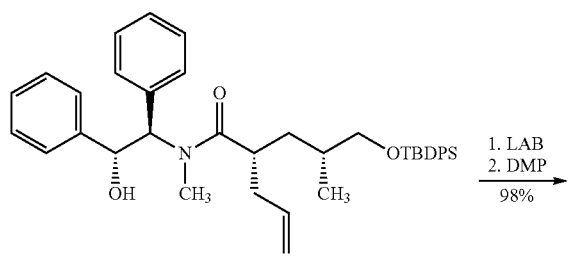

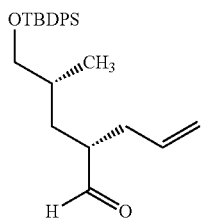

BuLi (12.61 ml, 29.9 mmol) was added by syringe to a stirring solution of diisopropylamine (4.59 ml, 32.2 mmol) in THF (32 mL) at −78° C. The vessel was transferred to an ice-water bath and was allowed to warm to 0° C. Borane-ammonia complex (1.051 g, 30.6 mmol) was added as a single portion, and a vigorous evolution of gas was observed. The mixture was stirred for 3 minutes at 0° C., and was then allowed to warm to 23° C., and was stirred for 15 minutes at this temperature. The vessel was re-cooled to 0° C., and a solution of (S)-2-((R)-3-((tert-butyldiphenylsilyl)oxy)-2-methylpropyl)-N-((1R,2R)-2-hydroxy-1,2-diphenylethyl)-N-methylpent-4-enamide (4.75 g, 7.66 mmol) in THF (32 mL+5 mL wash) was added by cannula. The reaction vessel was then allowed to warm to 23° C. (11:50 AM). After 3 h, the starting material had been completely consumed. The vessel was cooled in an ice-water bath, and 3 M hydrochloric acid (90 mL) was added carefully with vigorous stirring. The mixture was stirred at 0-10° C. for 30 minutes, and was then extracted with ether (4×100 mL). The combined ether extracts were washed with 3 M HCl (100 mL), 2 M NaOH (100 mL), sat aq NaCl (100 mL). The washed organic solution was dried over sodium sulfate and filtered, and the filtrate was concentrated. The first acidic, aqueous layer was treated with 2 M NaOH (~200 mL) until pH 14, and the resulting suspension was extracted with dichloromethane (2×150 mL) to recover pseudoephenamine ((1R,2R)-2-(methylamino)-1,2-diphenylethanol (1.61 g, 7.08 mmol, 92% yield). The crude product was purified by column chromatography (25% ether to hexanes) affording (S)-2-((R)-3-((tert-butyldiphenylsilyl)oxy)-2-methylpropyl)pent-4-en-1-ol (2.99 g, 7.54 mmol, 98% yield).

To a solution of (S)-2-((R)-3-((tert-butyldiphenylsilyl)oxy)-2-methylpropyl)pent-4-en-1-ol (1 g, 2.52 mmol) in dichloromethane (25 mL, 0.1 M) was added water (0.045 ml, 2.52 mmol), and the mixture was stirred vigorously. The vessel was immersed in a 23° C. water bath, and DMP (2.139 g, 5.04 mmol) was added. After 10 minutes, sat. aq. sodium bicarbonate (15 mL) and sat. aq. sodium thiosulfate (15 mL) were added to the reaction mixture, and the resulting biphasic, cloudy solution was stirred rapidly until each layer was homogeneous (~30 minutes). The layers were separated, and the aqueous layer was extracted with dichloromethane (2×20 mL). The combined organic layers were filtered through sodium sulfate, and the filtrate was concentrated. The crude product was purified by column chromatography (5% ether to hexanes) affording the product (~850 mg).

Step 4

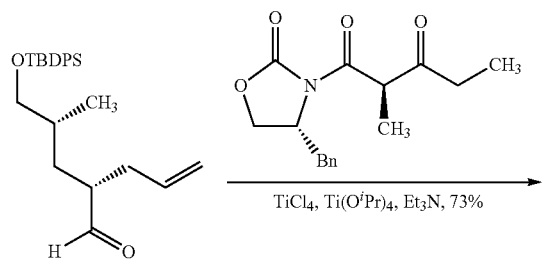

Dichloromethane (3.5 mL, starting concentration of keto-imide 0.2 M, final concentration 0.1 M) was added to a flame-dried 25-mL round-bottom flask equipped with a magnetic stir bar. The vessel was cooled to 0° C., and TiCl$_4$ (535 μl, 0.535 mmol) (DCM solution) was added, followed by titanium (IV) tetraisopropoxide (52.1 μl, 0.178 mmol). The mixture was stirred for 15 minutes at this temperature, at which time a solution of (R)-1-((R)-4-benzyl-2-oxooxa-zolidin-3-yl)-2-methylpentane-1,3-dione (200 mg, 0.691 mmol) in DCM (1.2 mL+0.6 mL wash) was added. To the resulting yellow solution was added triethylamine (103 μl, 0.737 mmol), resulting in a dark red solution. Stirring was continued at 0° C. for 1 h, at which point the vessel was cooled in a dry ice/acetone bath to −78° C., and a solution of (S)-2-((R)-3-((tert-butyldiphenylsilyl)oxy)-2-methylpro-pyl)pent-4-enal (182 mg, 0.461 mmol) in DCM (1.2 mL+0.6 mL wash) was added dropwise. After 2 h, sat. aq. ammonium chloride was added (10 mL), and the mixture was allowed to warm to ambient temp with vigorous stirring. The layers were separated and the aqueous layer was extracted with DCM (2×10 mL). The organic layers were combined and the resulting solution was filtered through a pad of sodium sulfate, and the creamy filtrate was concentrated. The crude product was purified by column chromatography (33% to 40% ether to hexanes first column, DCM then 5% ether to DCM second column) affording the product (2R,4R,5S,6S)-1-((R)-4-benzyl-2-oxooxazolidin-3-yl)-6-((R)-3-((tert-butyldiphenylsilyl)oxy)-2-methylpropyl)-5-hydroxy-2,4-dimethylnon-8-ene-1,3-dione (229 mg, >10:1 dr, 0.335 mmol, 72.7% yield).

Step 5

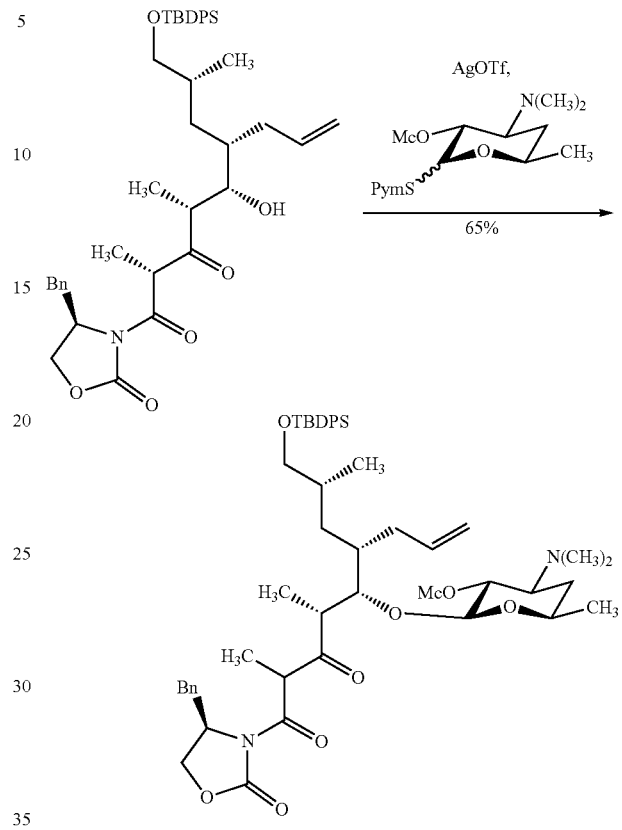

A solution of (2R,4R,5S,6S)-1-((R)-4-benzyl-2-oxooxa-zolidin-3-yl)-6-((R)-3-((tert-butyldiphenylsilyl)oxy)-2-methylpropyl)-5-hydroxy-2,4-dimethylnon-8-ene-1,3-dione (50 mg, 0.073 mmol) in benzene (2.5 mL) was added to a 10-mL round-bottom flask containing activated desosamine (47.9 mg, 0.146 mmol), and the resulting solution was evaporated under reduced pressure. The residue was exposed to high vacuum (0.1 Torr) for 10 minutes, and the vessel was back-filled with argon, equipped with a stir bar and a septum. 4 Å molecular sieves were added, followed by toluene (244 μl) and CH$_2$Cl$_2$ (244 μl). The solution was cooled to 0° C., and silver(I) trifluoromethanesulfonate (65.7 mg, 0.256 mmol) was added as a single portion. The resulting suspension changes visibly from a grainy precipitate to a fine powdery precipitate within the first 5 minutes. After 1.5 h, dichloromethane (2 mL) was added, followed by sat. aq. NH$_4$Cl (2 mL). The layers were mixed vigorously for 5 minutes, and sat. aq. sodium bicarbonate (5 mL) was added, and the layers were mixed vigorously. The resulting emulsion was filtered through a sintered-glass funnel, and the resulting biphasic mixture was mixed vigorously and separated. The aqueous layer was extracted with dichloromethane (5 mL), and the organic phases were combined, and the resulting solution was dried through a pad of sodium sulfate. The filtrate was concentrated under reduced pressure. The crude product was purified by column chromatography (100% ethyl acetate) to afford the product (2S,3R,4S,6R)-2-(((4S,5S,6R,8R)-9-((R)-4-benzyl-2-oxooxazolidin-3-yl)-4-((R)-3-((tert-butyldiphenylsilyl)oxy)-2-methylpropyl)-6,8-dimethyl-7,9-dioxonon-1-en-5- yl)oxy)-4-(dimethylamino)-6-methyltetrahydro-2H-pyran-3-yl methyl carbonate (43 mg, 0.048 mmol, 65.4% yield).

Step 6

Step 7

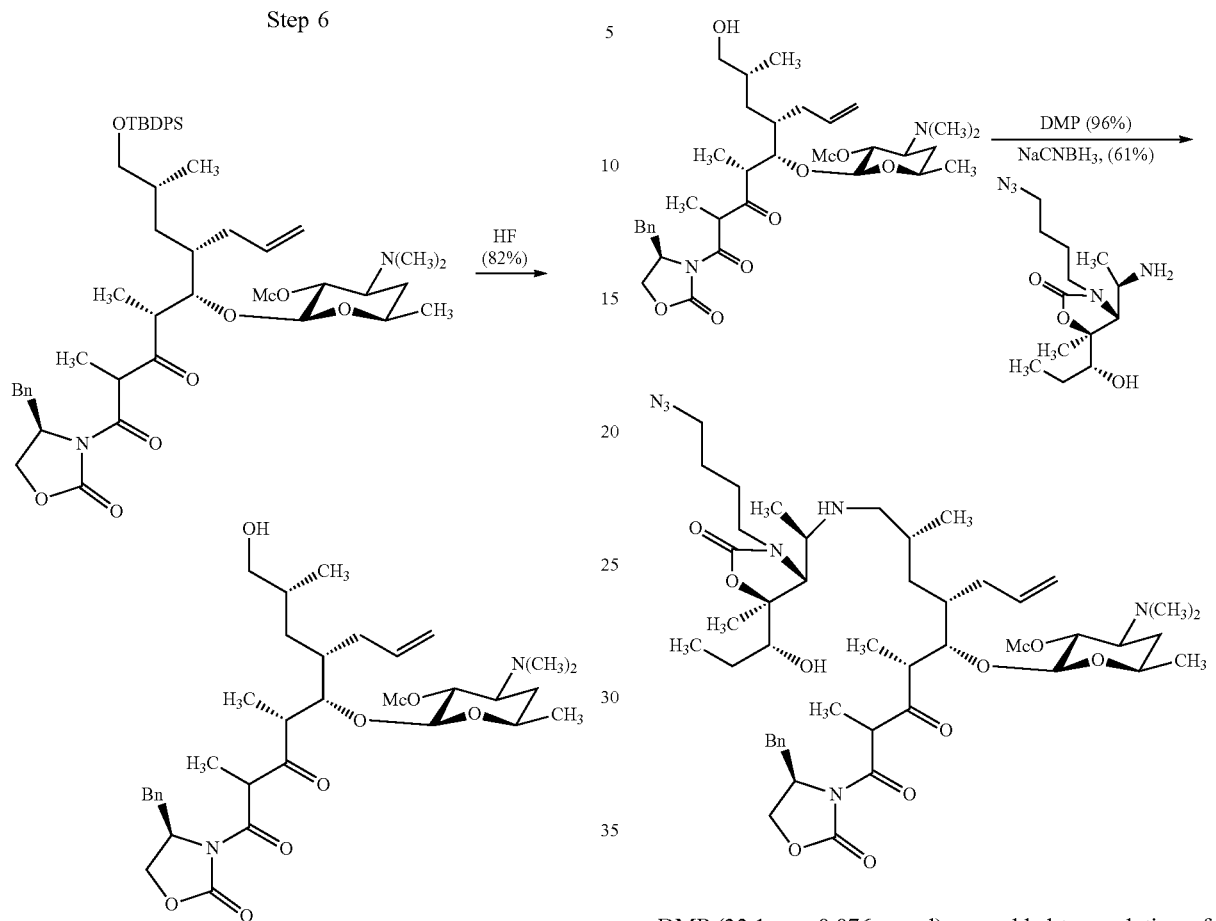

HF (80 µl, 2.224 mmol) (48% aqueous) was added to a solution of (2S,3R,4S,6R)-2-(((4S,5S,6R,8R)-9-((R)-4-benzyl-2-oxooxazolidin-3-yl)-4-((R)-3-((tert-butyldiphenylsilyl)oxy)-2-methylpropyl)-6,8-dimethyl-7,9-dioxonon-1-en-5-yl)oxy)-4-(dimethylamino)-6-methyltetrahydro-2H-pyran-3-yl methyl carbonate (40 mg, 0.044 mmol) in acetonitrile (445 µl) in a teflon tube at room temperature. After 20 h, the mixture was quenched carefully with sat. aq. sodium bicarbonate (3 mL), and was stirred vigorously until all bubbling ceased. The suspension was extracted with ether (3×2 mL). The organic layers were combined, and the resulting organic solution was extracted with 1 M HCl (2×1 mL). The acidic aqueous layer was basified with sat. aq. sodium bicarbonate (~5 mL), and the resulting suspension was extracted with dichloromethane (3×2 mL). The dichloromethane extracts were combined and the resulting clear, colorless solution was filtered through a pad of sodium sulfate. The filtrate was concentrated under reduced pressure to provide the product (2S,3R,4S,6R)-2-(((4S,5S,6R,8R)-9-((R)-4-benzyl-2-oxooxazolidin-3-yl)-4-((R)-3-hydroxy-2-methylpropyl)-6,8-dimethyl-7,9-dioxonon-1-en-5-yl)oxy)-4-(dimethylamino)-6-methyltetrahydro-2H-pyran-3-yl methyl carbonate as a colorless oil (24 mg, 0.036 mmol, 82% yield).

DMP (32.1 mg, 0.076 mmol) was added to a solution of (2S,3R,4S,6R)-2-(((4S,5S,6R,8R)-9-((R)-4-benzyl-2-oxooxazolidin-3-yl)-4-((R)-3-hydroxy-2-methylpropyl)-6,8-dimethyl-7,9-dioxonon-1-en-5-yl)oxy)-4-(dimethylamino)-6-methyltetrahydro-2H-pyran-3-yl methyl carbonate (25 mg, 0.038 mmol) in water-saturated dichloromethane (0.5 mL) in a 5-mL round-bottom flask that was immersed in a room-temperature water bath. After 15 minutes, DCM (1 mL), sat. aq. sodium bicarbonate (1 mL), and sat. sodium thiosulfate (1 mL) were added, and the solution was stirred vigorously for 10 minutes. The layers were separated, and the aqueous layer was extracted with dichloromethane (2×1 mL). The organic layers were combined and the resulting solution was filtered through a pad of sodium sulfate. The filtrate was concentrated.

To a solution of the western half amine (10.45 mg, 0.035 mmol) and sodium cyanoborohydride (5.49 mg, 0.087 mmol) in 9:1 methanol:acetic acid (0.3 mL) at −15° C. was added a solution of the crude aldehyde (23 mg, 0.035 mmol) in 9:1 methanol acetic acid (0.2 mL+0.1 mL wash). After 15 minutes, a second portion of sodium cyanoborohydride (5.49 mg, 0.087 mmol) was added. After 1 h, the mixture was transferred to a 0° C. ice bath. After 4 h, the mixture was slowly warmed to ambient temperature over night. The crude product was purified by column chromatography (2% to 3% to 4% to 5% MeOH to DCM with 0.2% to 0.5% NH₄OH additive) affording the desired product (20 mg, 0.021 mmol, 60.8% yield).

Synthesis of Eastern Half Building Blocks

(Z)-((4-ethylidene-2,2,5-trimethyl-4H-1,3-dioxin-6-yl)oxy)trimethylsilane

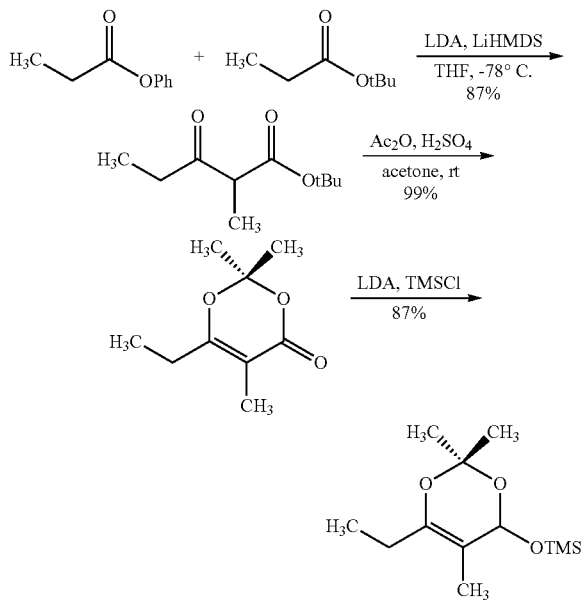

Step 1: Phenyl Propionate

Phenol (25 g, 266 mmol) and propionyl chloride (70 mL, 797 mmol) were added to a solution of trifluoromethanesulfonic acid (5.88 mL, 66.4 mmol) in acetonitrile (1 L) at 0° C. The resulting mixture was stirred at rt for 2 h. An ice water (1 L) and diethyl ether (500 mL) were added to the mixture. The organic layer was separated and the organic layer was washed with 1 M hydrogen chloride (1 L), saturated sodium bicarbonate aqueous solution (1 L), brine (1 L), dried over sodium sulfate and concentrated under reduced pressure. The residue was passed through a column of silica (n-pentane/diethyl ether, 10:1) to provide phenyl propionate (35.9 g, 90%) as a colorless oil. $^1$H NMR (CDCl$_3$, 600 MHz) δ=7.38 (t, 2H, J=7.8 Hz, CH of Ph), 7.22 (t, 1H, J=7.8 Hz, CH of Ph), 7.08 (d, 2H, J=7.8 Hz, CH of Ph), 2.60 (q, 2H, J=7.6 Hz, CH$_2$), 1.27 (t, 3H, J=7.6 Hz, CH$_3$).

Step 2: tert-Butyl 2-methyl-3-oxopentanoate

A 2.58 M solution of n-butyllithium in hexane (71.0 mL, 183 mmol) and a 2.41 M solution of n-butyllithium in hexane (33.2 mL, 80 mmol) was added dropwise to a solution of hexamethyldisilazane (58.4 mL, 275 mmol) in THF (160 mL) at 0° C. and the mixture was stirred at 0° C. for 45 min to prepare lithium hexamethyldisilazide (as a hexane and THF solution). A 2.42 M solution of n-butyllithium in hexane (69.0 mL, 167 mmol) and a 2.41 M solution of n-butyllithium in hexane (37.8 mL, 91 mmol) were added dropwise to a solution of diisopropylamine (36.3 mL, 258 mmol) in THF (160 mL) at −78° C. The resulting mixture was warmed to 0° C., stirred for 10 min and recooled to −78° C. A solution of tert-butyl propionate (32.5 g, 250 mmol) in THF (90 mL+35 mL×2 wash) was added to the above lithiumdiisopropylamide solution. The resulting mixture was stirred at −78° C. for 15 min. A freshly prepared solution of lithium hexamethyldisilazide in hexane and THF (323 mL, 30 mL×2 wash with THF) was added and then after 5 min a solution of phenyl propionate (39.4 g, 263 mmol) in THF (50 mL+25 mL×2 wash) was added to the reaction mixture at −78° C. The resulting mixture was stirred at −78° C. After 1 h, saturated ammonium chloride aqueous solution (150 mL) at −78° C. Diethyl ether (300 mL) and water (600 mL) were added to the mixture at rt. The organic layer was separated and washed with saturated sodium bicarbonate aqueous solution (2×300 mL), brine (300 mL) and dried over sodium sulfate. The aqueous layer was extracted with diethyl ether (2×300 mL). The combined organic layers were washed with a saturated NaHCO$_3$ aqueous solution (2×300 mL), brine (300 mL) and dried over sodium sulfate. The organic extracts were concentrated under reduced pressure. The residue was passed through a column of silica (n-pentane/diethyl ether, 40:1-2:1) to provide a mixture of phenyl propionate, tert-butyl 2-methyl-3-oxopentanoate and phenol. 1 M sodium hydroxide aqueous solution (500 mL) was added to a solution of the mixture in diethyl ether (250 mL) and the resulting solution was stirred at rt for 1.5 h. The organic layer was separated and washed with 1 M sodium hydroxide aqueous solution (250 mL), water (250 mL), brine (250 mL) and dried over sodium sulfate. The organic extract was concentrated under reduced pressure to provide tert-butyl 2-methyl-3-oxopentanoate (40.4 g, 87%) as a colorless oil. $^1$H NMR (CDCl$_3$, 600 MHz) δ=3.42 (q, 2H, J=7.3 Hz, CH$_2$ of Et), 2.64-2.46 (m, 1H, CH), 1.45 (s, 9H, (CH$_3$)$_3$), 1.29 (d, J=6.6 Hz, CH$_3$ of Me), 1.08 (t, 3H, J=7.3 Hz, CH$_3$ of Et).

Step 3: 6-Ethyl-2,2,5-trimethyl-4H-1,3-dioxin-4-one

Acetic anhydride (55.3 mL, 586 mmol) and sulfuric acid (10.4 mL, 195 mmol) were added to a mixture of tert-butyl 2-methyl-3-oxopentanoate (36.4 g, 195 mmol) and acetone (28.7 mL, 391 mmol) at 0° C. and the resulting mixture was stirred at rt for 5 h. The reaction mixture was diluted in diethyl ether (1 L) and saturated sodium bicarbonate aqueous solution (1.6 L). The mixture was stirred at rt for 2 h. The organic layer was separated and washed with saturated sodium bicarbonate aqueous solution (1 L×2), brine (1 L) and dried over sodium sulfate and concentrated under reduced pressure to provide 6-ethyl-2,2,5-trimethyl-4H-1,3-dioxin-4-one (32.8 g, 99%) as a colorless oil. The product was purified by distillation under reduced pressure (70° C., 520 mTorr). $^1$H NMR (CDCl$_3$, 600 MHz) δ=2.30 (q, 2H, J=7.6 Hz, CH$_2$ of Et), 1.82 (s, 3H, CH$_3$ of 5-Me), 1.65 (s, 6H, (CH$_3$)$_2$ of 2-Me), 1.12 (t, 3H, J=7.6 Hz, CH$_3$ of Et).

(Z)-((4-ethylidene-2,2,5-trimethyl-4H-1,3-dioxin-6-yl)oxy)trimethylsilane

To a solution of diisopropylamine (25.1 mL, 176 mmol) in THF (210 mL) at −78° C. was added nBuLi (76 mL, 2.32 M in hexanes, 176 mmol) dropwise. The resulting solution was warmed to 0° C. and stirred for 15 min. The solution was cooled to −78° C., and a solution of 6-ethyl-2,2,5-trimethyl-4H-1,3-dioxin-4-one in THF (50 mL+6 mL-rinse) was added dropwise via cannula. After stirring for 1 h at −78° C., freshly distilled TMSCl was added dropwise and the mixture was stirred for 3 h at −78° C. The mixture was warmed to r.t. and the solvent was removed under reduced pressure. The residue was diluted with dry pentane (100 mL) and filtered. The filtrate was concentrated. Crude material was purified by vacuum distillation. (~200 mTorr, 63-67° C.). $^1$H NMR (500 MHz, CDCl$_3$) δ 4.40 (q, J=6.9 Hz, 1H), 1.66 (d, J=6.9 Hz, 3H), 1.63 (s, 3H), 1.52 (s, 6H), 0.24 (s, 9H).

(S)-tert-Butyldiphenylsiloxy-3-iodo-2-methylpropane

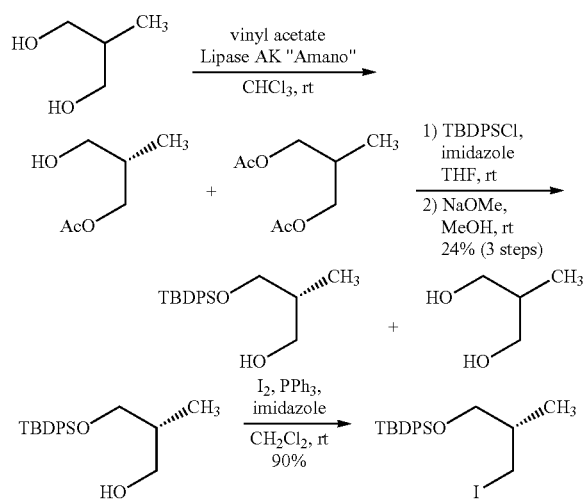

Step 1:
(R)-3-tert-Butyldiphenylsiloxy-2-methylpropan-1-ol

Vinyl acetate (286 mL, 3.11 mol) and lipase-AK "Amano" (17.1 g) were added to a solution of 2-methyl-1,3-propanediol (70 g, 777 mmol) in chloroform (1.5 L). The resulting mixture was stirred at rt for 20 h. The lipase was removed by filtration and washed with ethyl acetate. Then the filtrate was concentrated to provide a mixture of (S)-3-hydroxy-2-methylpropyl acetate (>99% ee) and 1,3-diacetoxy-2-methylpropane. The mixture was used in the next reaction step without separation. tert-Butyldiphenylsilyl-chloride (79 mL, 303 mmol) was added dropwise to a mixture of (S)-3-hydroxy-2-methylpropyl acetate and 1,3-diacetoxy-2-methylpropane (140 g, crude) and imidazole (41.3 g) in THF (620 mL). The resulting mixture was stirred at rt for 21 h. The reaction mixture was diluted with diethyl ether (1 L) and washed water (2×1 L) and brine. The organic layer was dried over sodium sulfate and concentrated under reduced pressure. A 25% solution of sodium methoxide in methanol (61 mL) was added to a solution of a mixture of (R)-3-tert-butyldiphenylsiloxy-2-methylpropyl acetate and 1,3-diacetoxy-2-methylpropane (194 mg, crude) in methanol (1 L) at 0° C. The resulting mixture was stirred at rt for 24 h. The reaction mixture was diluted with diethyl ether (1 L) and n-pentane (1 L), washed with saturated ammonium chloride aqueous solution (1 L), water (2×1 L) and brine (1 L). The organic layer was dried over sodium sulfate and concentrated under reduced pressure. The residue was passed through a column of silica (n-hexane/diethyl ether, 40:1~20:1~4:1) to provide (R)-3-tert-butyldiphenylsiloxy-2-methylpropan-1-ol (60.9 g) as a colorless oil. $^1$H NMR (CDCl$_3$, 400 MHz) δ=7.69-7.67 (m, 4H, CH of Ph), 7.46-7.38 (m, 6H, CH of Ph), 3.75-3.57 (m, 4H, CH$_2$OTBDPS, CH$_2$OH), 2.03-1.96 (m, 1H, CH$_2$CH(CH$_3$)CH$_2$), 1.06 (s, 9H, (CH$_3$)$_3$), 0.83 (d, 3H, J=10.8 Hz, CH$_2$CH(CH$_3$)CH$_2$)

Step 2: (S)-tert-Butyldiphenylsiloxy-3-iodo-2-methylpropane

Imidazole (12.4 g, 183 mmol, 2 equiv) and iodine (23.2 g, 91 mmol, 1 equiv) were added to a stirred solution of triphenylphosphine (24.0 g, 91 mmol, 1 equiv) in dichloromethane (180 mL). A solution of (R)-3-tert-butyldiphenylsiloxy-2-methylpropan-1-ol (30.0 g, 91 mmol) in dichloromethane (60 mL) was added to the reaction mixture at 0° C. The resulting mixture was stirred at rt for 5 h. A small amount of iodine was added to "titrate" triphenylphosphine, until the color of the reaction mixture is slightly yellow. The solvent was removed under reduced pressure. Silica gel (75 g) and hexane (300 mL) were added to the residue. The suspension was stirred for 20 min to absorb triphenylphosphine oxide and salts on silica. Then the mixture was filtered through a short pad of silica (n-hexane/diethyl ether, 95:5) to provide (S)-tert-butyldiphenylsiloxy-3-iodo-2-methylpropane (35.9 g, 90%) as a colorless oil. $^1$H NMR (CDCl$_3$, 400 MHz) δ=7.69-7.65 (m, 4H, CH of Ph), 7.46-7.36 (m, 6H, CH of Ph), 3.61-3.31 (m, 4H, CH$_2$O, CH$_2$I), 1.78-1.68 (m, 1H, CH$_2$CH(CH$_3$)CH$_2$), 1.06 (s, 9H, (CH$_3$)$_3$), 0.96 (d, 3H, J=10.2 Hz, CH$_2$CH(CH$_3$)CH$_2$).

II. Synthesis of the Western Half

Example II-1. Formation of Y$^1$ Amino

Our current route to the western half of hybrid "azaketolides" proceeds in just 7 linear steps from the striking (and novel) aldol coupling of pseudoephenamine glycinamide (7) and α-siloxyketone 18, affording the α-amino-β-hydroxyamide 19 as a single diastereomer in almost quantitative yield. This product maps perfectly to positions C10-O14 of azalides. This method provides a powerful construction of 1,2-amino alcohol derivatives with stereochemical homology to threonine, albeit with potential for broad modification of the alkyl side chain (methyl in threonine).

Exposure of aldol product 19 to phosgene in the presence of Hünig's base provided cyclic carbamate 20. Methyllithium-induced auxiliary cleavage furnished methyl ketone 21 (the auxiliary can be recovered at this stage). It is important to note that access to novel C10 substitution is available by employing various organolithium nucleophiles (e.g., using aryl organolithium, branched alkyl organolithium and, heteroaryl organolithium nucleophiles). This position bears a methyl group in erythromycin (1), and cannot be modified readily by semi-synthetic methods. Introduction of an azido-alkyl sidechain (comprised of 3-5 methylene units) proceeded smoothly in two steps to provide the diversifiable intermediates 23a-c, which were subjected to reductive amination conditions (ammonium acetate, sodium cyanoborohydride) in 72-73% yields along with ~15% of the minor diastereomers (not depicted). Cleavage of the silyl ether provided the western halves 24a-c, which contain four contiguous stereocenters of the macrolide skeleton, in a total of 7 steps and 31-43% yield (multigram scale) from 7 and 18.

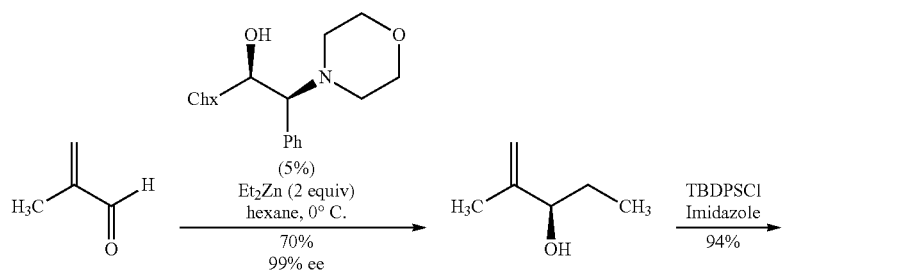
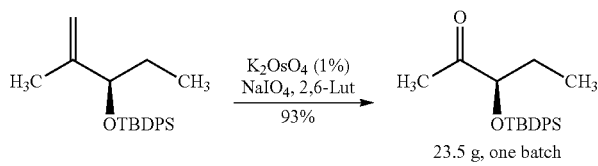
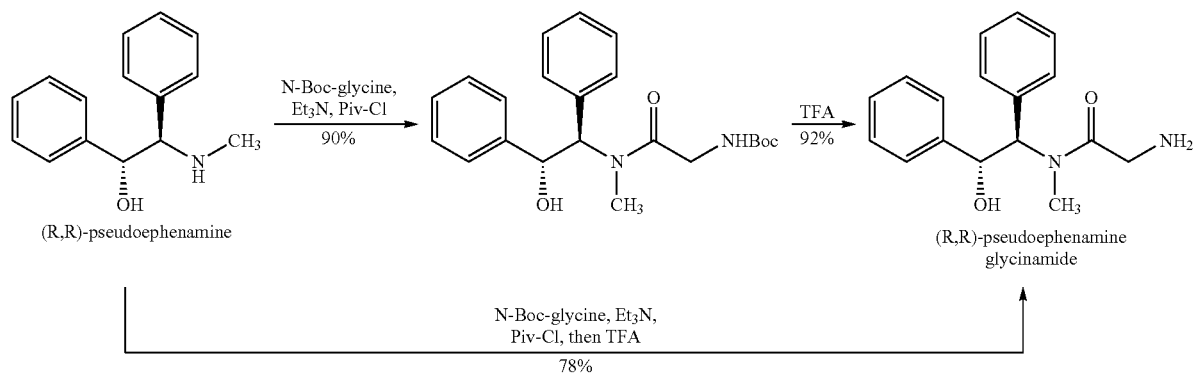
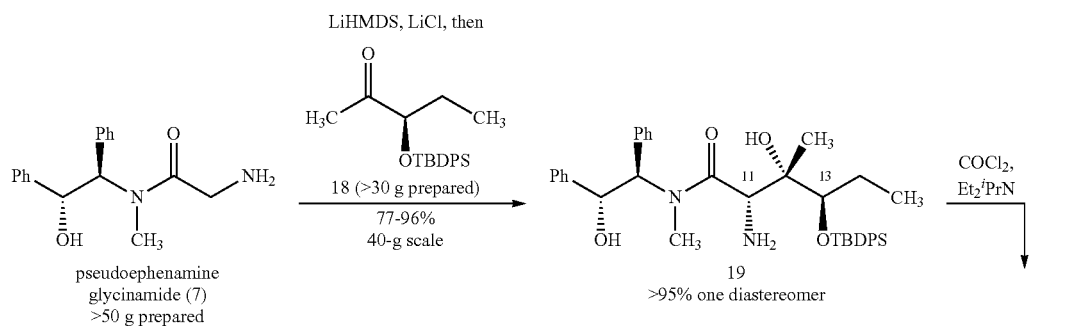
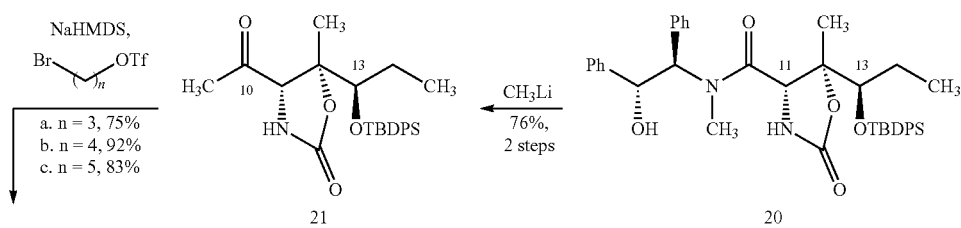

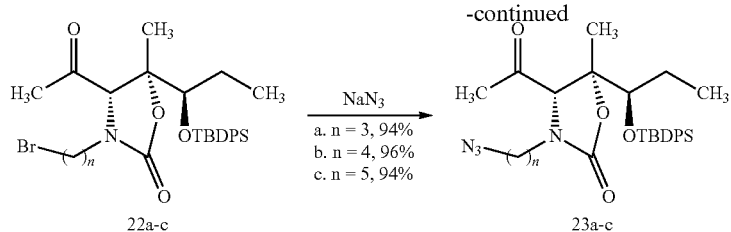
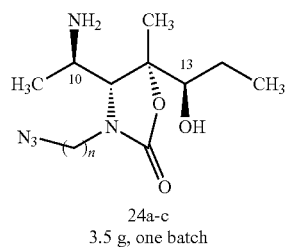
Example II-2. Alkylation Prior to Auxiliary Cleavage; Formation of $Y^1$ Alcohol and Ketone
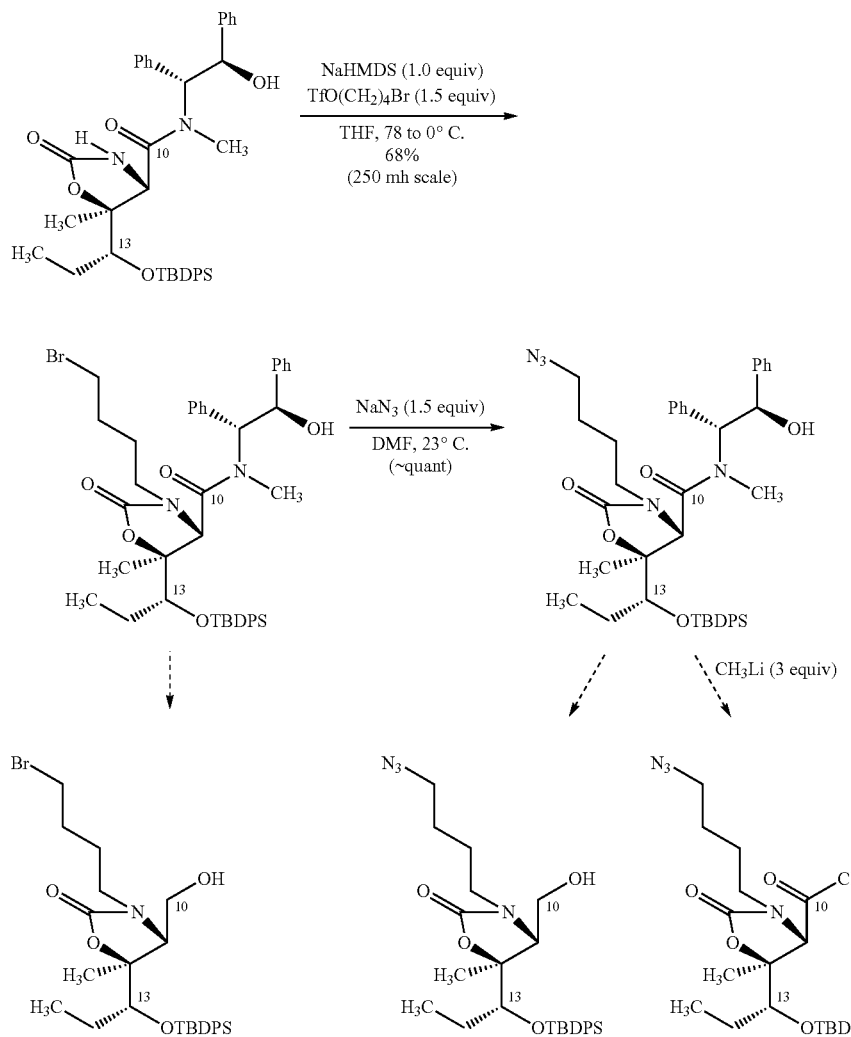

Example II-3. Formation of Y¹ Amino and Ketone
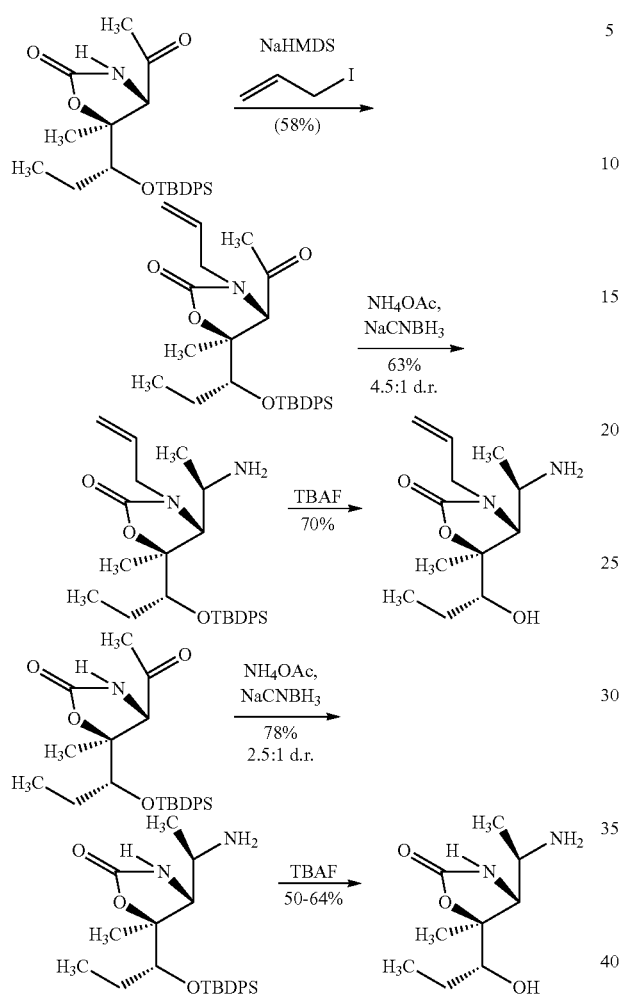
Example II-4. Formation of Y¹ Acid
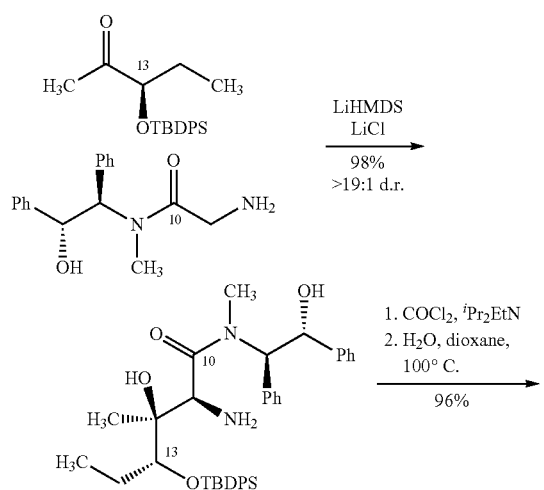
-continued
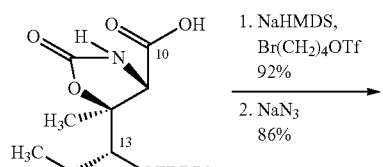
Example II-5. Formation of Y¹ Ketone
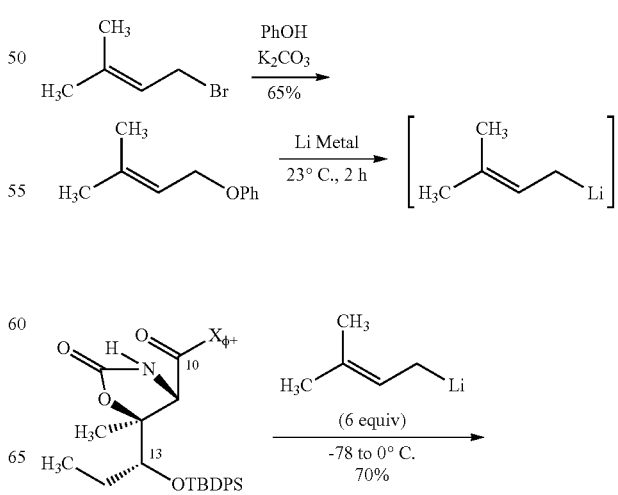

555
-continued
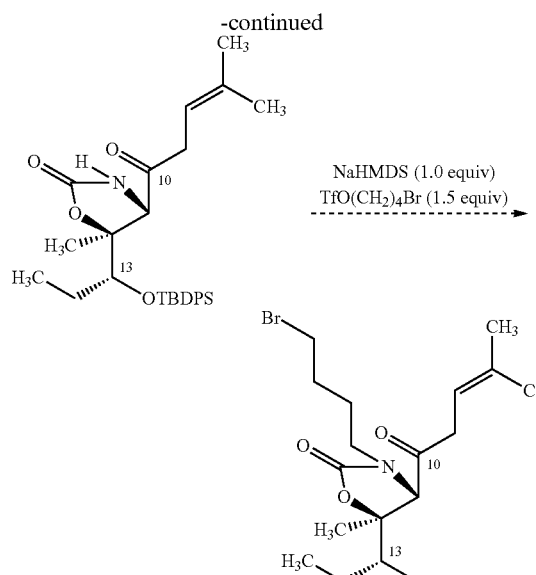
$X_{\phi+}$ is (R,R)-pseudoephenamine
Example II-6. Formation of $Y^1$ Leaving Group (LG)
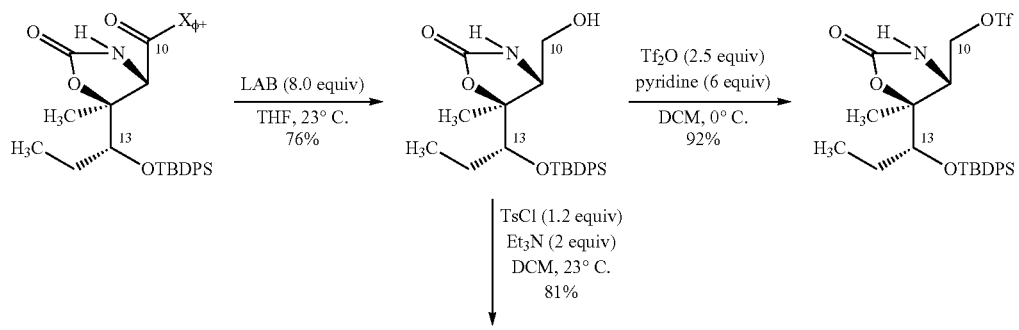
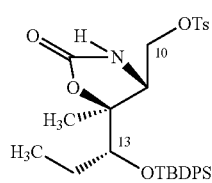
$X_{\phi+}$ is (R,R)-pseudoephenamine
556
Example II-7. Pre-Alkylation of Aldol Product Followed by Carbamate Formation
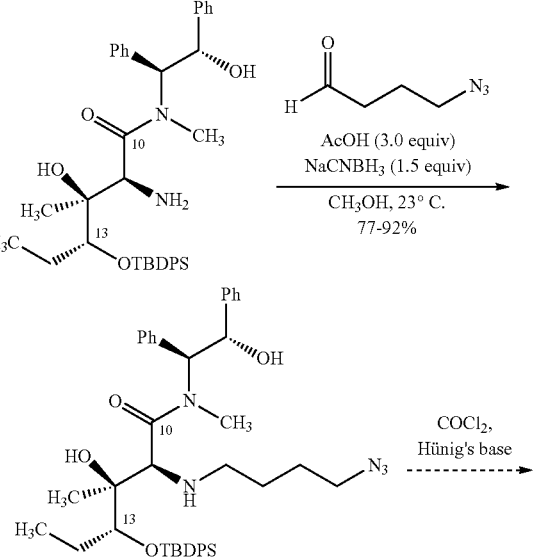

557
-continued
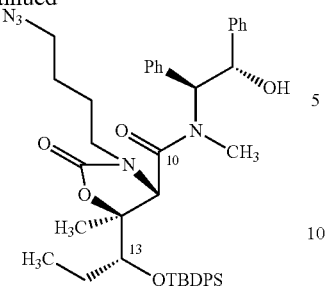
Example II-8. Alkylation Prior to Auxiliary Cleavage
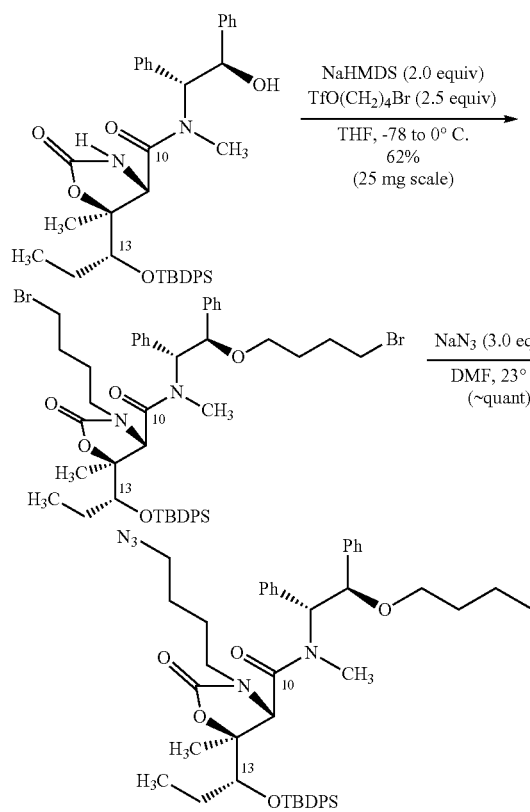
Example II-9. Diallylbromide Alkylation to Form Alkene Linkers to Azide
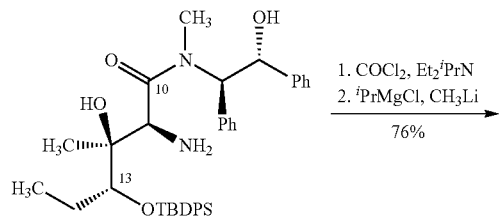
558
-continued
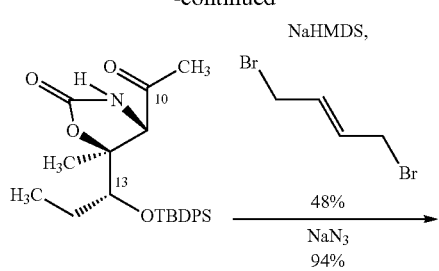
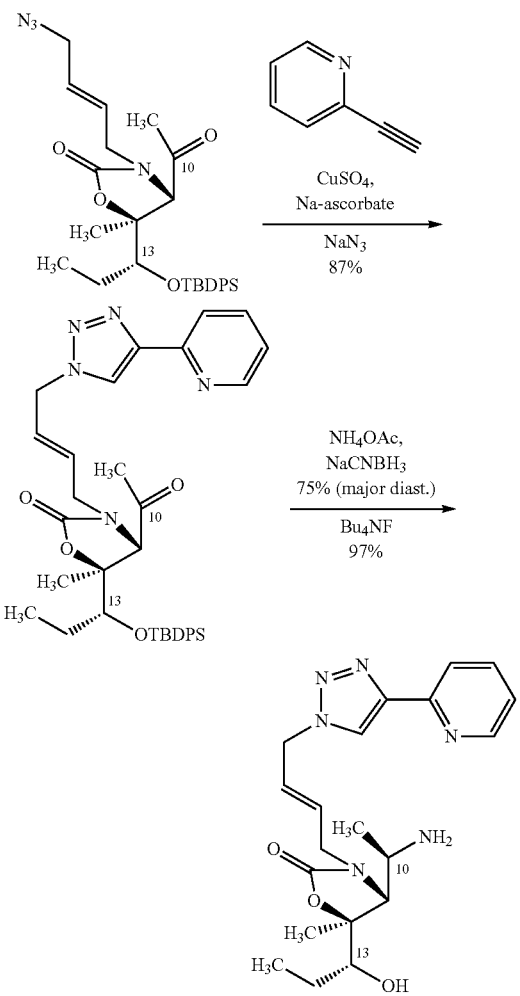
Example II-10. Formation of the $Y^1$ Amine with C10 Allyl
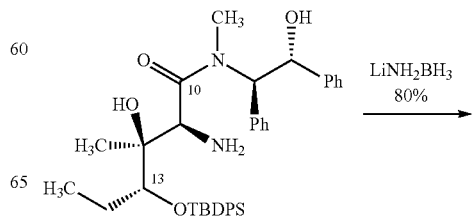

559
-continued
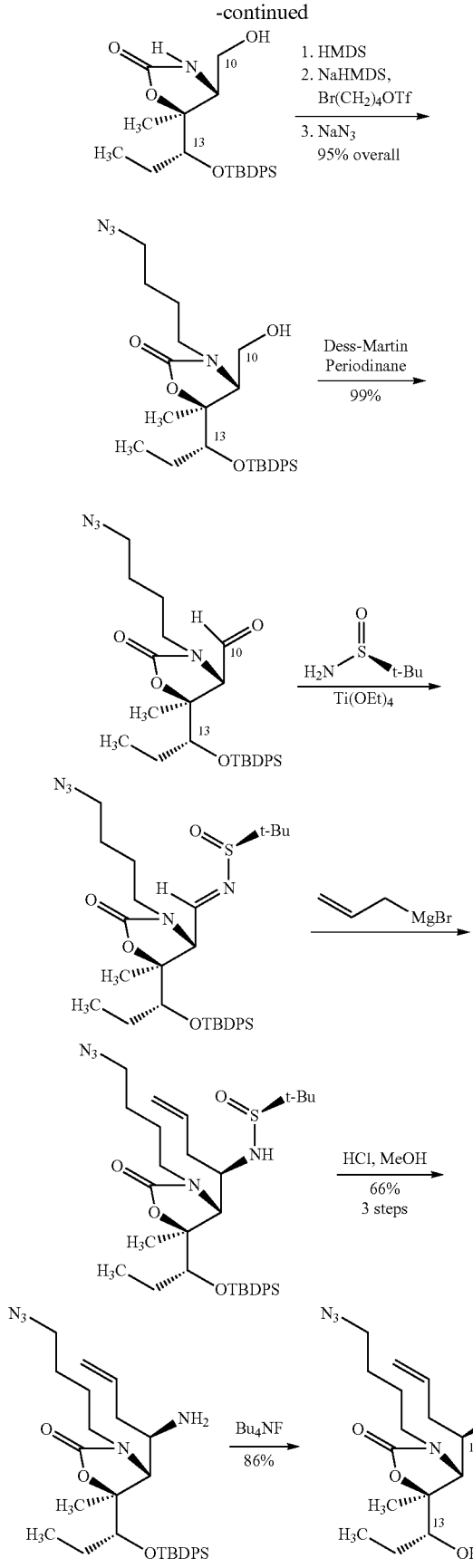
560
Example II-11. Formation of the Y¹ Amine with C10 Benzyl
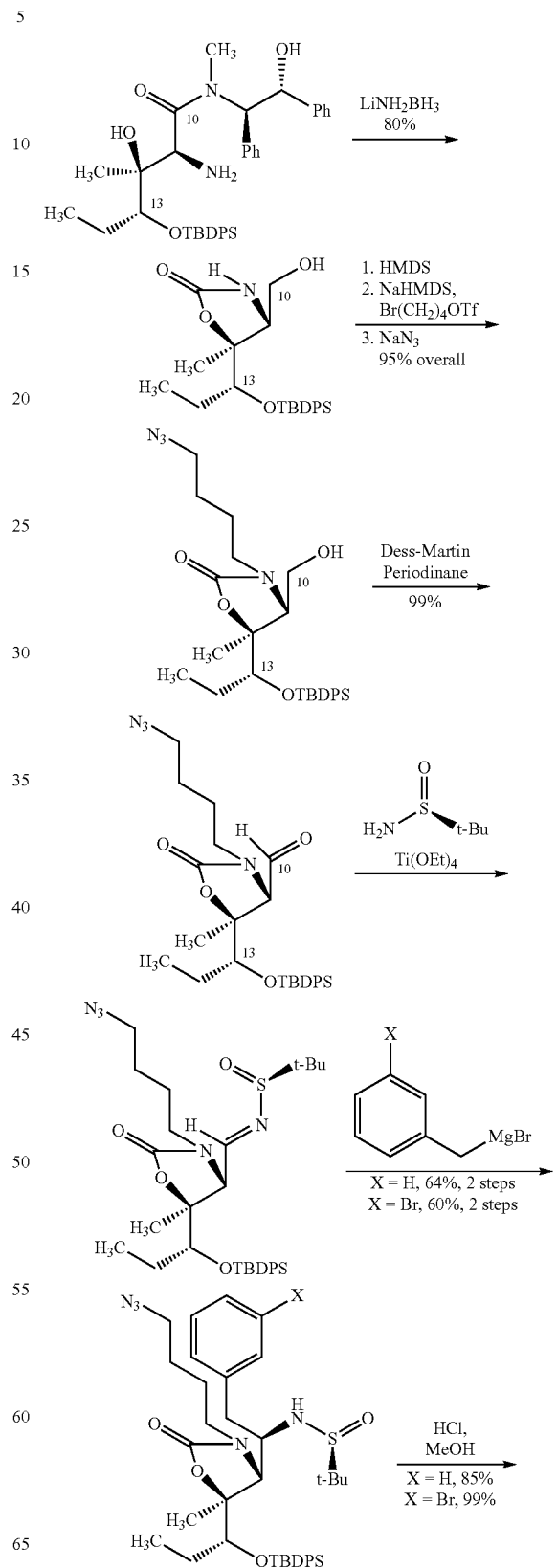

-continued
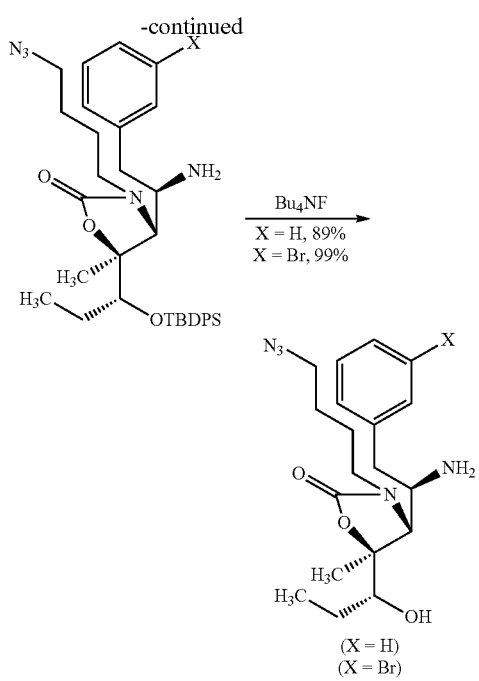
Example II-12. Formation of the Y¹ Amine with C10 Cyclopropyl
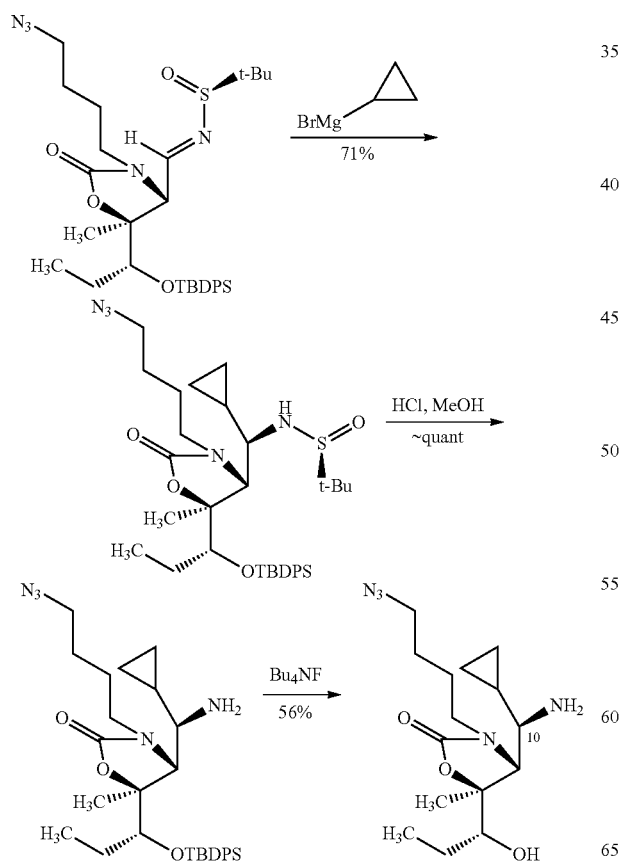
Example II-13. Formation of the Y¹ Amine with C10 Vinyl
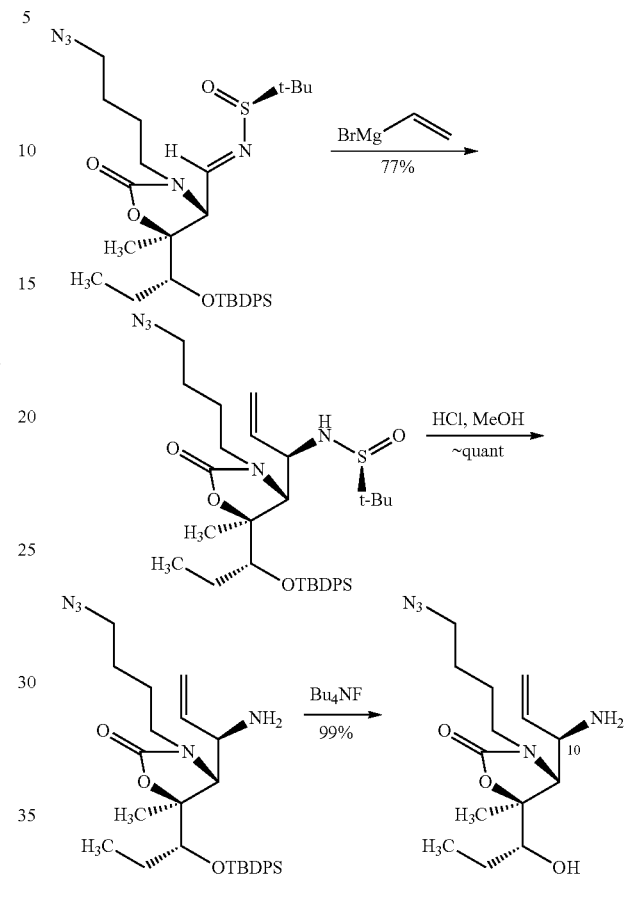
Example II-14. Formation of the Y¹ Amine with C10 CH Group
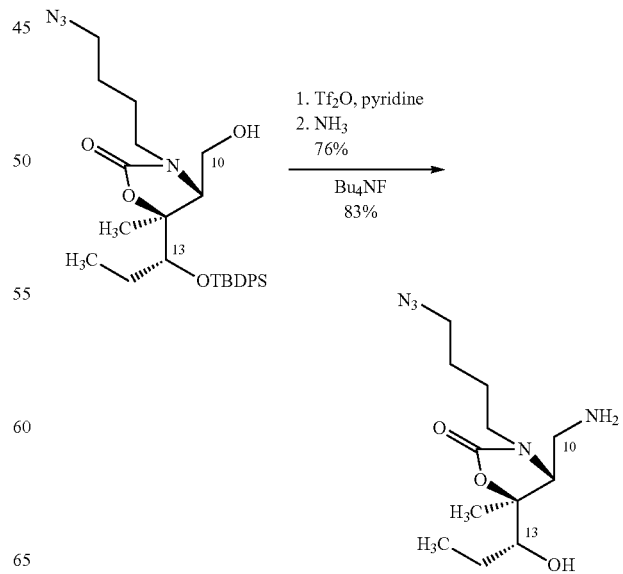

Example II-15. Formation of the Y¹ Homologated Aldehyde Precursor

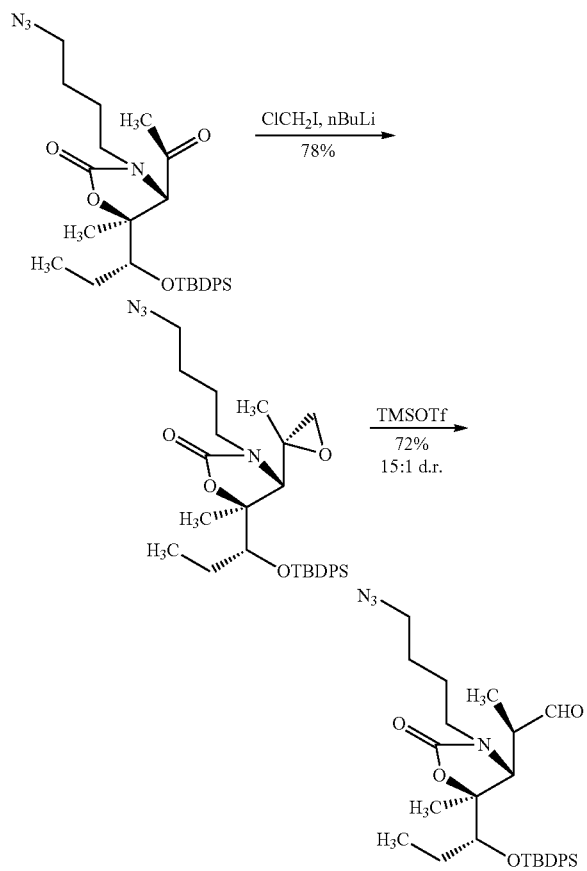

Example II-16. Formation of the Y¹ Aldehyde Precursor to the HWE or Wittig Reaction

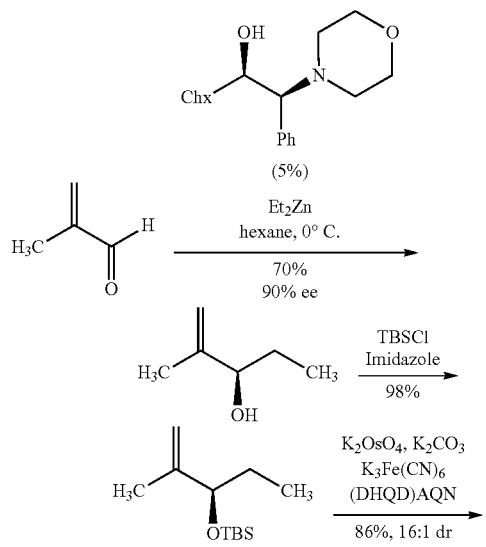

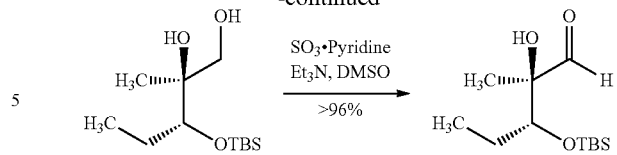

Example II-17. Formation of the Y¹ Vinyl Iodide Precursor

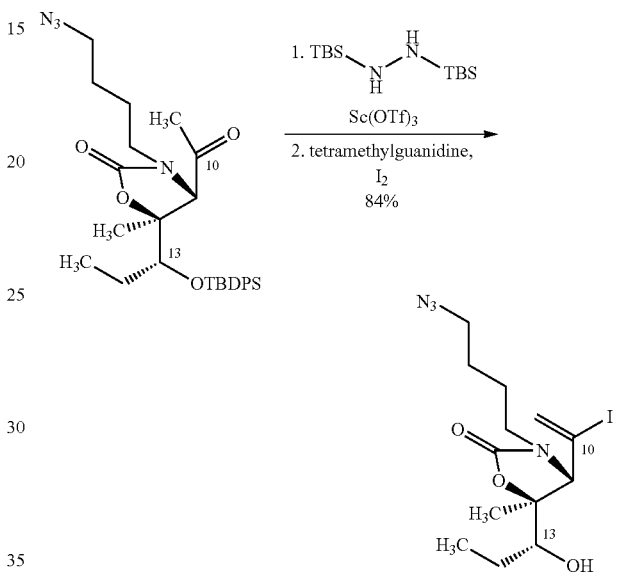

Exemplary Western Half Synthetic Procedures

Step 1

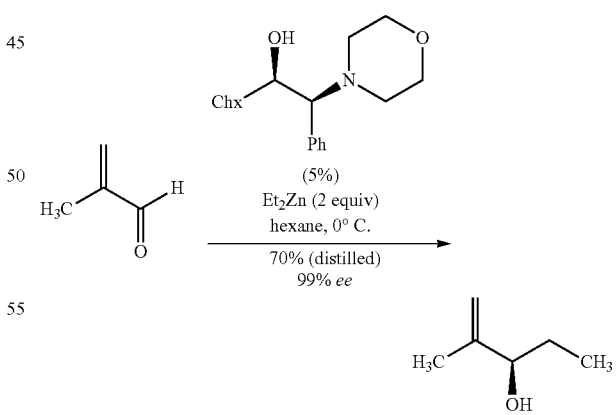

To a suspension of (1R,2S)-1-cyclohexyl-2-morpholino-2-phenylethanol (2.065 g, 7.13 mmol, prepared according to the procedure published by W. A. Nugent: *Org. Lett.* 2002, 4, 2133-2136) in n-hexane (100 mL) in a 1-L round-bottom flask under argon cooled with an ice water bath was added diethylzinc (285 ml, 285 mmol, Aldrich 1.0 M solution in hexanes) via cannula by applying a mild vacuum to the receiving flask. Large amounts of white smoke are present in the receiving flask during the transfer. The solution was allowed to stir for 30 minutes at this temperature, then methacrolein (11.81 ml, 143 mmol, freshly distilled prior to use to remove polymers and stabilizers) was added dropwise over 15 minutes, resulting in a pale-yellow, homogeneous solution. TLC (20% EA/H, compare to product, stain with KMnO$_4$) five minutes after the addition showed only the desired product and catalyst—however, it should be noted that methacrolein boils at 69° C., and monitoring for its disappearance is very difficult. After 15 minutes, the color had faded and the solution was clear and colorless. After 3 hours, 2 M HCl was added carefully, and a white precipitate crashes out, but re-dissolves as the solution reaches pH 1 (~500 mL HCl). The biphasic mixture was transferred to a separatory funnel and the layers were separated. The aqueous layer was further extracted with diethyl ether (2×250 mL), and the combined organic layers were washed with brine (300 mL) dried over sodium sulfate, filtered, and the filtrate was concentrated under reduced pressure (~40 Torr) at 0° C. The resulting clear oil was transferred to a 100-mL round-bottom flask, and the transfer was quantitated with ether (2×5 mL). The solvent was distilled off at atmospheric pressure through a short-path distillation head using a 90° C. oil bath. The vessel was cooled and the pressure was reduced to ~40 Torr. Once bubbling has stopped, the system was backfilled with air, the receiving flask was exchanged for a new one, and the pressure was once again reduced to 40 Torr. The receiving flask was immersed in a 0° C. ice bath, and the distillation was resumed using a 90° C. oil bath. The product distills as a clear liquid with a steady boiling point of 67° C. at ~40 Torr. Yield: 10.04 g (70%). The ee was not determined at this stage, but was measured for a later intermediate. The $^1$H-NMR and $^{13}$C-NMR data matched literature values: Paterson, I.; Perkins, M. V. Tetrahedron 1996, 52, 1811-1834; Cossy, J.; Bauer, D.; Bellosta, V. Tetrahedron 2002, 58, 5909-5922. The acidic aqueous layers from the extraction were combined and the resulting solution was basified with 2 M NaOH until the pH was 14, and a white solid precipitated. The resulting suspension was extracted with dichloromethane (3×100 mL). The organic layer was dried over sodium sulfate and concentrated. The residue was recrystallized from hexane to provide (1R,2S)-1-cyclohexyl-2-morpholino-2-phenylethanol (1.44 g, 4.98 mmol, 69.7% recovery).

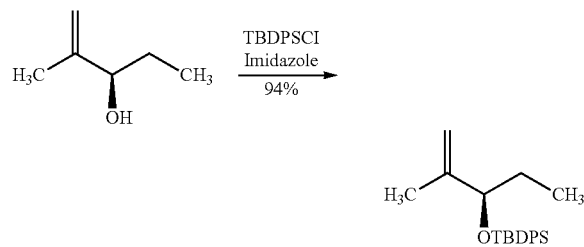

Step 2

To a solution of (R)-2-methylpent-1-en-3-ol (8 g, 80 mmol) in DMF (160 mL) was added imidazole (10.88 g, 160 mmol) followed by TBDPS-Cl (26.7 ml, 104 mmol) dropwise. The reaction solution was stirred at 23° C. for 18 hours, after which time TLC (20% EA/H) indicated that the starting material was consumed. The reaction solution was partitioned between hexanes (200 mL) and water (750 mL), and after vigorous mixing, the layers were separated. The aqueous layer was further extracted with hexanes (2×200 mL), and the combined organic layers were washed with water (2×300 mL). The washed solution was loaded onto a silica gel pad (4" diameter, 5" length) which was slurry-packed with hexanes. The pad was eluted in 500 mL fractions with hexanes (4000 mL total), and the fractions containing product (5-8) were combined and concentrated under reduced pressure, providing (R)-tert-butyl((2-methylpent-1-en-3-yl)oxy)diphenylsilane (25.33 g, 74.8 mmol, 94% yield) as a colorless oil. TLC (hexanes): R$_f$=0.24 (UV, KMnO$_4$), $^1$H NMR (500 MHz, CDCl$_3$), δ: 7.73-7.65 (m, 4H), 7.46-7.33 (m, 6H), 4.78-4.74 (m, 2H), 4.06 (dd, J=6.8, 5.6 Hz, 1H), 1.69 (s, 3H), 1.53-1.45 (m, 2H), 1.09 (s, 9H), 0.68 (t, J=7.5 Hz, 3H). $^{13}$C NMR (125 MHz, CDCl$_3$), δ: 146.0, 136.0, 135.9, 134.8, 134.2, 129.4, 129.4, 127.4, 127.3, 111.6, 78.4, 28.0, 27.0, 19.4, 17.2, 9.0. FTIR (neat), cm$^{-1}$: 2963, 2932, 1728, 1427, 1109, 1063, 714. HRMS could not be acquired due to poor ionization on ESI-TOF.

Step 3

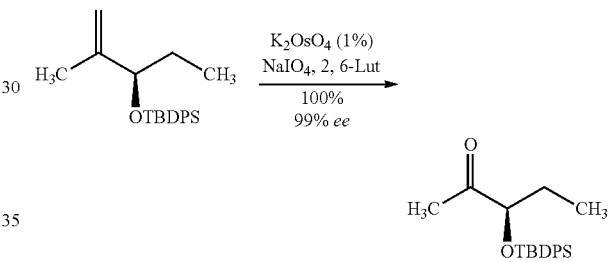

(R)-tert-butyl((2-methylpent-1-en-3-yl)oxy)diphenylsilane (13.65 g, 40.3 mmol) was suspended in THF (112 mL) and water (56 mL), resulting in a white slurry. 2,6-Lutidine (9.39 ml, 81 mmol) was added, followed by sodium periodate (34.5 g, 161 mmol) and potassium osmate dihydrate (0.149 g, 0.403 mmol), and the solution was vigorously stirred. After 26 h, the thick white slurry was diluted with water (400 mL) and extracted with hexanes (3×125 mL). The combined organic layers were washed with sodium thiosulfate (2×250 mL) and saturated copper sulfate (2×250 mL), and the washed solution was filtered through a pad of sodium sulfate. The filtrate was concentrated to provide (R)-3-((tert-butyldiphenylsilyl)oxy)pentan-2-one as a colorless oil (13.75 g, 100%). TLC (5% ether in hexanes): R$_f$=0.16 (UV, KMnO$_4$). $^1$H NMR (500 MHz, CDCl$_3$), δ: 7.67-7.60 (m, 4H), 7.48-7.41 (m, 2H), 7.41-7.34 (m, 4H), 4.09 (dd, J=6.5, 5.2 Hz, 1H), 2.08 (s, 3H), 1.71-1.52 (m, 2H), 1.13 (s, 9H), 0.82 (t, J=7.5 Hz, 3H). $^{13}$C NMR (125 MHz, CDCl$_3$), δ: 211.3, 135.8, 135.8, 133.5, 133.1, 129.9, 129.9, 127.7, 127.6, 80.2, 27.7, 27.00, 25.8, 19.3, 8.7. FTIR (neat), cm$^{-1}$: 2965, 2934, 2859, 1717, 1427, 1111, 1018, 713. HRMS (ESI): Calculated for (C$_{21}$H$_{28}$O$_2$Si+Na)$^+$: 363.1751. found: 363.1763. The ee of the product was determined to be 99% by analysis on a chiral stationary phase OD-H column using pure hexanes as eluent with detection at 168-218 nm at a flow rate of 1.0 mL/min.

Step 4

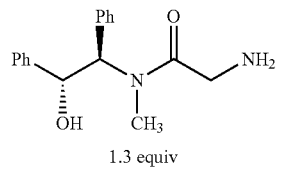
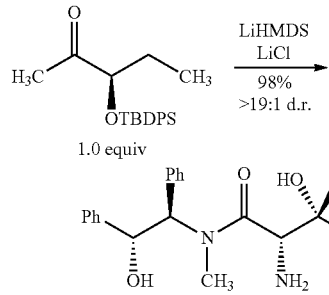

To a solution of hexamethyldisilazine (30.2 ml, 144 mmol) in THF (54 mL) at 0° C. was added butyllithium (2.62 M solution in hexanes, 52.3 ml, 137 mmol) dropwise over 10 minutes. The resulting solution of lithium hexamethyldisilazane was stirred for 30 minutes at this temperature before use. Lithium chloride (29.8 g, 703 mmol) was added to a 2-L round-bottom flask with a very large football stirbar and flame dried gently under high vacuum for 2 minutes. After the flask cooled to room temperature, (R,R)-pseudoephenamine glycinamide (20 g, 70.3 mmol) was added, and the flask was evacuated and backfilled with argon. Dry THF (833 mL) was added, and the resulting suspension was stirred for 5 minutes (the glycinamide dissolves, but some lithium chloride does not) and then the flask was cooled to 0° C. The solution of lithium hexamethyldisilazide was then added via cannula over 10 minutes, resulting in a light yellow solution. The solution was allowed to stir for 30 minutes at this temperature. A solution of (R)-3-((tert-butyldiphenylsilyl)oxy)pentan-2-one (18.42 g, 54.1 mmol) in THF (80 mL+20 mL rinse) was then transferred with a cannula over 10 minutes to the stirred solution of the glycinamide enolate. After the transfer, the solution thickened slightly. After 30 minutes, the yellow solution was diluted with water (750 mL) and the mixture was transferred to a separatory funnel. The layers were separated, and the aqueous layer was extracted with ethyl acetate (2×500 mL). The combined organic layers were washed with water (500 mL) and brine (500 mL), and the washed solution was dried with sodium sulfate, filtered through a fritted glass funnel, and the filtrate was concentrated. The residue was purified by chromatography on silica gel (2% MeOH/dichloromethane, 0.2% ammonium hydroxide), providing the product as a white foam (32.97 g, 98%). Mp=56-60° C. TLC (5% methanol-dichloromethane+0.5% saturated aqueous ammonium hydroxide solution): $R_f$=0.30 (UV, PMA). $^1$H NMR (15:1 ratio of rotamers; major rotamer reported, 500 MHz, CDCl$_3$), δ: 7.77 (d, 2H, J=6.8 Hz), 7.70 (d, 2H, J=6.8 Hz), 7.42-7.35 (m, 8H), 7.27-7.18 (m, 8H), 6.03 (d, 1H, J=8.8 Hz), 5.31 (d, 1H, J=8.8 Hz), 4.91 (br s, 1H), 3.92 (s, 1H), 3.84 (dd, 1H, J=5.9, 4.9 Hz), 2.94 (s, 3H), 1.79-1.74 (m, 1H), 1.41-1.36 (m, 1H), 1.10 (s, 3H), 0.98 (s, 9H). 0.58 (t, 3H, J=7.8 Hz). $^{13}$C NMR (125 MHz, CDCl$_3$), δ: 177.8, 141.1, 136.6, 135.9, 135.7, 134.4, 133.1, 129.8, 129.5, 128.5, 128.5, 128.4, 127.8, 127.7, 127.7, 127.4, 127.1, 76.4, 76.1, 72.7, 62.5, 52.6, 32.6, 27.0, 25.0, 19.5, 19.3, 12.1. FTIR (neat), cm$^{-1}$: 3372 (br), 3071 (m), 2934 (s), 2857 (s), 1608 (s), 1105 (m), 909 (s), 698 (s); HRMS (ESI): Calcd for (C$_{38}$H$_{48}$N$_2$O$_4$Si+Na)$^+$: 647.3276. Found: 647.3278.

Step 5

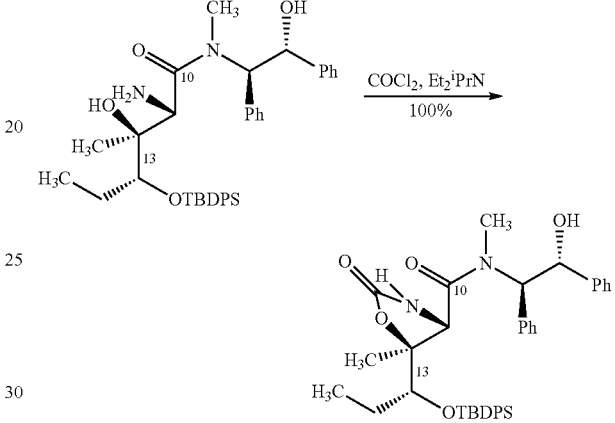

Diisopropylethylamine (23.7 mL, 136 mmol, 3 equiv) was added to a solution of the starting aldol adduct (28.3 g, 45.3 mmol, 1 equiv) in dichloromethane (850 mL) in a 2-L round-bottom flask. The reaction vessel was cooled to −78° C. in a dry ice-acetone cooling bath and a solution of phosgene in toluene (15% w/w, 37.2 mL, 52.1 mmol, 1.15 equiv) was added dropwise. Reaction progress was monitored by the consumption of starting material by TLC (5% methanol in dichloromethane+1% saturated aqueous ammonium hydroxide solution). After 30 min, half-saturated ammonium chloride solution (800 mL) was added, and the reaction vessel was allowed to warm to 23° C. with vigorous stirring. The layers were separated, and the aqueous layer was extracted with dichloromethane (2×250 mL). The combined organic layers were washed sequentially with 1 M aqueous hydrochloric acid solution (2×500 mL) and brine (500 mL). The washed organic phase was dried with sodium sulfate and the dried organic phase was filtered. The filtrate was concentrated to provide the carbamate product as a white solid (29.5 g, 100%). M.p.: 128-130° C. TLC (5% methanol-dichloromethane): $R_f$=0.28 (UV, PMA). $^1$H NMR (500 MHz, CDCl$_3$), δ: 7.71-7.66 (m, 4H), 7.43-7.32 (m, 8H), 7.23-7.14 (m, 8H), 6.13 (d, 1H, J=10.1 Hz), 6.02 (br s, 1H), 5.25 (d, 1H, J=10.1 Hz), 4.74 (s, 1H), 4.16 (br s, 1H), 3.81 (dd, 1H, J=6.4, 4.1 Hz), 2.83 (s, 3H), 1.65-1.58 (m, 1H), 1.56-1.51 (m, 1H), 1.15 (s, 3H), 1.03 (s, 9H). 0.60 (t, 3H, J=7.3 Hz). $^{13}$C NMR (125 MHz, CDCl$_3$), δ: 171.1, 159.4, 141.0, 136.1, 135.8, 135.7, 133.8, 132.4, 129.9, 129.7, 129.1, 128.3, 127.8, 127.7, 127.5, 87.2, 78.3, 71.9, 63.0, 57.7, 30.7, 27.0, 25.7, 19.6, 16.9, 11.3. FTIR (neat), cm$^{-1}$: 3341 (br), 3070, 2940, 2859, 1759, 1633, 1103, 700; HRMS (ESI): Calcd for (C$_{39}$H$_{46}$N2O$_5$Si+H)$^+$: 651.3249. Found: 651.3244.

Step 6

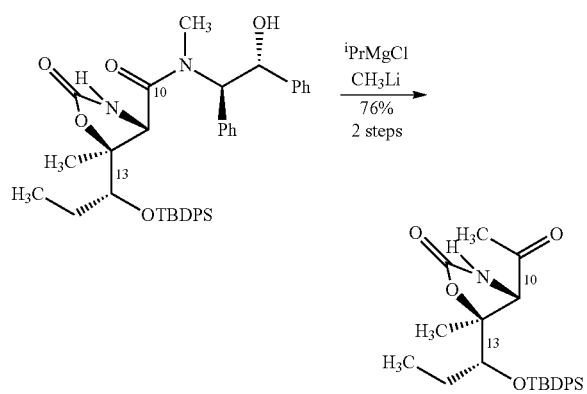

The aldol carbamate (29.5 g, 45.3 mmol) was azeotroped from 1,4-dioxane (100 mL), then from dichloromethane/hexanes (1:1, 400 mL), to produce a puffy white solid, which was exposed to high vacuum for 14 h. The vessel was backfilled with argon, and a stirbar was added followed by tetrahydrofuran (280 mL, final concentration 0.1 M), and the solution was stirred until complete dissolution followed by cooling to −78° C. Isopropylmagnesium chloride (56.6 ml, 113 mmol) was transferred to the reaction mixture via cannula over 5 minutes, resulting in a yellow/gray solution. After 5 minutes, methyllithium (57.5 ml, 90.5 mmol) (57.5 mL) was added, and the reaction vessel was removed from the bath and allowed to warm to 0° C. (~20 minutes), at which point a second portion of methyllithium (57.5 ml, 90.5 mmol, 1.57 M) was added, and the solution was allowed to warm to 23° C. TLC after 5 minutes (5% MeOH/DCM, 0.5% NH$_4$OH) indicated very low conversion to the desired product. After 2 hours, a white precipitate had appeared, and TLC indicated >50% conversion. After 24 h total, the reaction solution was transferred by cannula into a vigorously stirred 1 M solution of hydrochloric acid (750 mL). The layers were separated, and the aqueous layer was extracted with diethyl ether (2×250 mL). The combined organic extracts were washed with water (500 mL) and brine (250 mL). The washed solution was dried over sodium sulfate and filtered, and the filtrate was concentrated. The residue was purified by flash column chromatography (25% to 33% ethyl acetate in hexanes) to provide the methyl ketone as a white foam (15.1 g, 76%). TLC (33% ethyl acetate in hexanes): R$_f$=0.22 (UV, PMA), $^1$H NMR (500 MHz, CDCl$_3$), δ: 7.77-7.68 (m, 4H), 7.47-7.35 (m, 6H), 7.20 (s, 1H), 4.53 (s, 1H), 3.71 (t, J=5.2 Hz, 1H), 2.31 (s, 3H), 1.62 (ddd, J=14.9, 7.5, 5.7 Hz, 1H), 1.45 (ddd, J=14.8, 7.5, 4.8 Hz, 1H), 1.30 (s, 3H), 1.05 (s, 9H), 0.52 (t, J=7.5 Hz, 3H). $^{13}$C NMR (125 MHz, CDCl$_3$), δ: 207.6, 159.1, 136.0, 135.7, 133.9, 132.3, 129.9, 129.7, 127.7, 127.5, 87.6, 79.0, 64.4, 28.8, 26.9, 25.4, 19.5, 18.3, 11.3. FTIR (neat), cm$^{-1}$: 3308 (br), 2963, 2934, 2859, 1757, 1720, 1109, 714. HRMS (ESI): Calculated for (C$_{25}$H$_{33}$NO$_4$Si+H)$^+$: 440.2252. found: 440.2253.

Recovery of (R,R)-pseudoephenamine. The water and hydrochloric acid layers from the extraction were combined and adjusted to pH 14 with 3 M NaOH (500 mL), and the resulting slurry was extracted with ethyl acetate (3×250 mL). The combined organic extracts were dried over sodium sulfate and concentrated. The resulting crystalline solid is slightly yellow, and ~90% purity by NMR, and matched literature data (*Angew. Chem. Int. Ed.* 2012, 51, 4568-4571).

Step 7

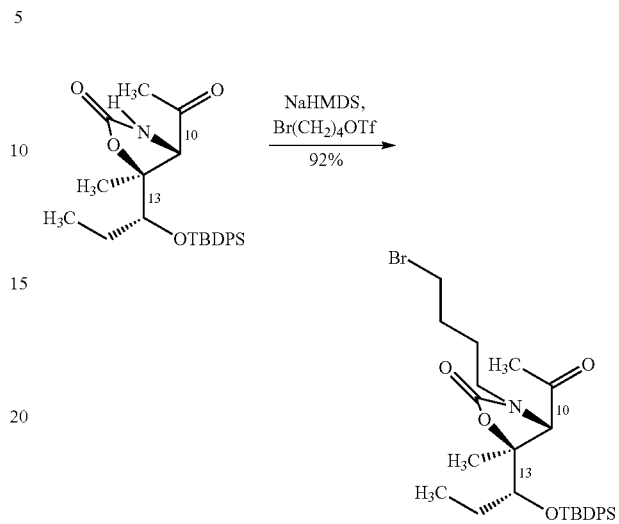

(4S,5S)-4-acetyl-5-((R)-1-((tert-butyldiphenylsilyl)oxy)propyl)-5-methyloxazolidin-2-one (11.55 g, 26.3 mmol) was azeotroped from benzene (200 mL), and exposed to high vacuum (~0.1 Torr) for 1 hour in a 500-mL round-bottom flask. The flask was backfilled with argon, and tetrahydrofuran (125 mL) was added. After the solid had completely dissolved, the mixture was cooled to −78° C. NaHMDS (26.3 ml, 26.3 mmol) (1.0 M solution) was added dropwise, resulting in a yellow solution that was stirred for 30 minutes at −78° C. 4-bromobutyl trifluoromethanesulfonate (11.23 g, 39.4 mmol) was added as a solution in diethyl ether (20 mL). After 5 min, the vessel was allowed to warm to 0° C. over 15 minutes. After another 15 minutes at 0° C., the starting material was completely consumed by TLC (33% EtOAc in hexanes), and the reaction solution was poured into half-saturated ammonium chloride (500 mL). The mixture was extracted with ether (3×150 mL), and the organic extracts were washed with brine (150 mL), dried over sodium sulfate, and filtered. The filtrate was concentrated, and the residue was purified by column chromatography on silica gel (15% to 25% ethyl acetate in hexanes) to provide a viscous colorless oil, which was further dried under high vacuum (~0.1 Torr) over 36 h with stirring. Yield: 13.83 g (92%). TLC (33% EtOAc in hexanes): R$_f$=0.46 (UV, PMA), $^1$H NMR (500 MHz, CDCl$_3$), δ: 7.73 (dt, J=6.7, 1.5 Hz, 2H), 7.67 (dt, J=6.7, 1.5 Hz, 2H), 7.49-7.37 (m, 6H), 4.41 (s, 1H), 3.61 (dd, J=6.2, 4.6 Hz, 1H), 3.47 (ddd, J=14.1, 9.4, 6.7 Hz, 1H), 3.34 (t, J=6.5 Hz, 2H), 2.81 (ddd, J=14.3, 9.3, 5.3 Hz, 1H), 2.22 (s, 3H), 1.77 (dq, J=8.8, 6.1 Hz, 2H), 1.68 (ddd, J=14.0, 7.5, 6.2 Hz, 1H), 1.58-1.41 (m, 2H), 1.34 (s, 3H), 1.08 (s, 9H), 0.55 (t, J=7.6 Hz, 3H). $^{13}$C NMR (125 MHz, CDCl$_3$), δ: 205.9, 156.9, 136.1, 135.7, 133.8, 132.3, 130.2, 129.9, 127.9, 127.6, 83.5, 78.5, 68.6, 42.7, 32.7, 29.5, 28.8, 27.0, 26.0, 25.7, 19.5, 16.7, 11.4. FTIR (neat), cm$^{-1}$: 2936, 2861, 2359, 1759, 1720, 1427, 1111, 705. HRMS (ESI): Calculated for (C$_{29}$H$_{40}$BrNO$_4$Si+H)$^+$: 574.1983. found: 574.1989.

Several other electrophiles may be used in the previous procedure in place of 4-bromobutyl trifluoromethanesulfonate. For example, the following electrophiles have been successfully implemented: 5-bromopentyl trifluoromethanesulfonate, 2-bromopropyl trifluoromethanesulfonate, (E)-4-bromobut-2-en-1-yl trifluoromethanesulfonate, and 4-bromobut-2-yn-1-yl trifluoromethanesulfonate.

Step 8

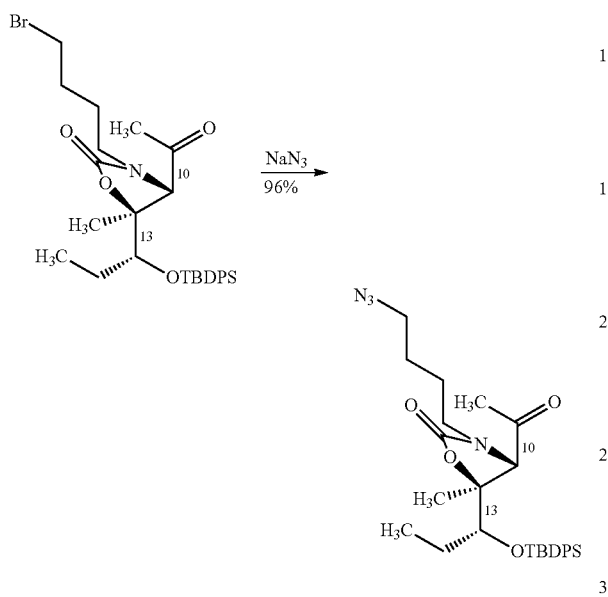

Sodium azide (1.721 g, 26.5 mmol) was added to a solution of (4S,5S)-4-acetyl-3-(4-bromobutyl)-5-((R)-1-((tert-butyldiphenylsilyl)oxy)propyl)-5-methyloxazolidin-2-one (13.83 g, 24.07 mmol) in dimethylformamide (73 mL), and the mixture was stirred rapidly under air. The reaction progress was monitored with thin layer chromatography (5% ethyl acetate in dichloromethane as eluent, brief exposure of each TLC plate to high vacuum to reduce DMF streaking prior to elution). After 2.5 hours, the starting material was completely consumed. The reaction solution was diluted with water (750 mL) and brine (75 mL) and the resulting slurry was extracted with diethyl ether (3×200 mL). The organic layers were combined and washed with water (2×300 mL), brine (1×300 mL) and dried with sodium sulfate. The dried solution was filtered, and the filtrate was concentrated. The residue was purified by column chromatography (25% ethyl acetate in hexanes) to provide the product as a colorless, viscous oil (12.4 g, 96%). TLC (33% EtOAc in hexanes): $R_f$=0.44 (UV, PMA), $^1$H NMR (500 MHz, CDCl$_3$), δ: 7.75-7.70 (m, 2H), 7.68-7.65 (m, 2H), 7.49-7.43 (m, 2H), 7.43-7.38 (m, 4H), 4.38 (s, 1H), 3.61 (dd, J=6.2, 4.6 Hz, 1H), 3.45 (ddd, J=13.9, 9.1, 6.6 Hz, 1H), 3.23 (t, J=6.7 Hz, 2H), 2.81 (ddd, J=14.1, 9.1, 5.3 Hz, 1H), 2.21 (s, 3H), 1.74-1.64 (m, 1H), 1.54-1.35 (m, 4H), 1.34 (s, 3H), 1.08 (s, 9H), 0.55 (t, J=7.6 Hz, 3H). $^{13}$C NMR (125 MHz, CDCl$_3$), δ: 205.9, 156.9, 136.0, 135.7, 133.8, 132.3, 130.1, 129.9, 127.9, 127.6, 83.5, 78.5, 68.7, 50.7, 43.1, 28.7, 26.9, 26.0, 25.7, 24.7, 19.5, 16.7, 11.4. FTIR (neat), cm$^{-1}$: 3707, 2938, 2864, 2097, 1761, 1720, 1111, 1056, 1040, 704. HRMS (ESI): Calculated for $(C_{29}H_{40}N_4O_4Si+H)^+$: 537.2892. found: 537.2898.

Step 9

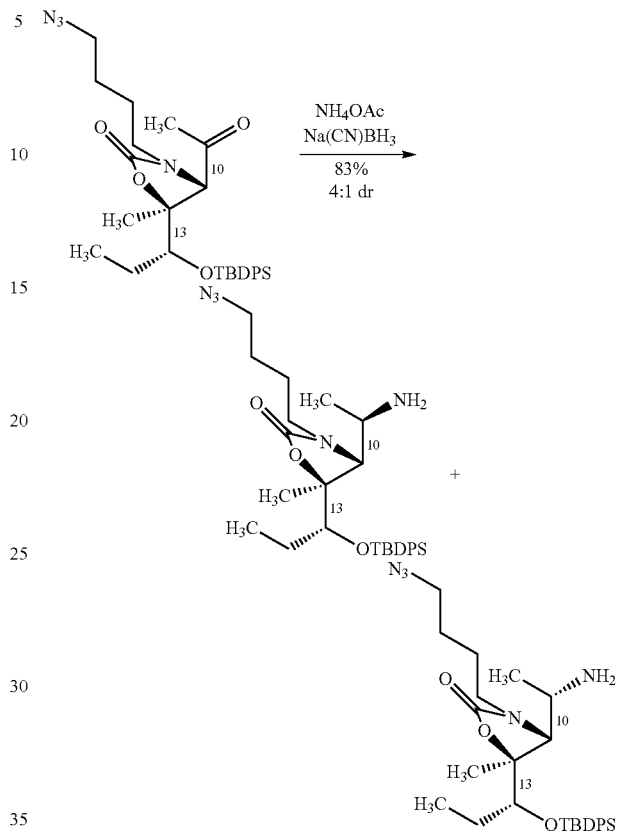

To (4S,5S)-4-acetyl-3-(4-azidobutyl)-5-((R)-1-((tert-butyldiphenylsilyl)oxy)propyl)-5-methyloxazolidin-2-one (10.5 g, 19.56 mmol) was added ammonium acetate (15.08 g, 196 mmol) and 4 Å molecular sieves (1:1 to starting material, w/w) followed by methanol (100 mL, 0.2 M). Sodium cyanoborohydride (2.459 g, 39.1 mmol) was added as a solid, and the mixture was stirred at 50° C. in a 200-mL round-bottom flask under argon. After 48 h, the stir bar was removed the mixture was evaporated to give a slurry. The slurry was diluted with ethyl acetate (200 mL) and filtered through a sintered glass funnel. The filtrate was washed with 1 M sodium hydroxide (200 mL), and the aqueous layer was extracted with ethyl acetate (2×100 mL). The combined organic layers were washed with brine (200 mL) and were dried with sodium sulfate. The dried solution as filtered, and the filtrate was concentrated. The residue was purified by column chromatography (2% methanol in dichloromethane+ 0.2% NH$_4$OH), to provide the two products in separate fractions. (4R,5S)-4-((R)-1-aminoethyl)-3-(4-azidobutyl)-5-((R)-1-((tert-butyldiphenylsilyl)oxy)propyl)-5-methyloxazolidin-2-one (major diastereomer, 6.9 g, 66%). Appearance: colorless oil. TLC (10% MeOH in dichloromethane, +1% NH$_4$OH): $R_f$=0.66 (UV, PMA). $^1$H NMR (500 MHz, CDCl$_3$), δ: 7.72-7.67 (m, 2H), 7.67-7.62 (m, 2H), 7.50-7.35 (m, 6H), 3.50 (s, 1H), 3.47 (t, J=5.6 Hz, 1H), 3.38-3.30 (m, 3H), 3.25-3.16 (m, 2H), 1.87-1.74 (m, 1H), 1.47 (s, 3H), 1.55-1.32 (m, 4H), 1.33-1.22 (m, 1H), 1.08-1.03 (m, 12H), 0.93 (br s, 2H), 0.68 (t, J=7.6 Hz, 3H). $^{13}$C NMR (125 MHz, CDCl$_3$), δ: 157.1, 135.9, 135.8, 133.5, 133.1, 130.0, 129.9, 127.8, 127.6, 83.5, 78.8, 65.4, 50.7, 47.7, 43.3, 27.0, 26.0, 25.3, 24.2, 19.5, 17.3, 14.0, 11.7. FTIR (neat), cm$^{-1}$: 2279, 3318, 2934, 2860, 2095, 1748, 1427, 1240, 1109, 1057, 702. HRMS (ESI): Calculated for $(C_{29}H_{43}N_5O_3Si+H)^+$: 538.3208. found: 538.3215. (4R,5S)-4-((S)-1-aminoethyl)-3-(4-azidobutyl)-5-((R)-1-((tert-butyldiphenylsilyl)oxy)propyl)-5-methyloxazolidin-2-one (minor diastereomer, 1.75 g, 17%). Appearance: colorless oil. TLC (10% MeOH in dichloromethane, +1% NH$_4$OH): R$_f$=0.63 (UV, PMA). $^1$H NMR (500 MHz, CDCl$_3$), δ: 7.69-7.65 (m, 2H), 7.64-7.60 (m, 2H), 7.49-7.35 (m, 6H), 3.50 (d, J=1.1 Hz, 1H), 3.47 (t, J=5.3 Hz, 1H), 3.41-3.31 (m, 1H), 3.24-3.18 (m, 3H), 2.97-2.88 (m, 1H), 1.84-1.74 (m, 1H), 1.56 (s, 3H), 1.53-1.38 (m, 4H), 1.36-1.27 (m, 1H), 1.14 (d, J=7.0 Hz, 3H), 1.04 (s, 9H), 0.66 (t, J=7.6 Hz, 3H). $^{13}$C NMR (125 MHz, CDCl$_3$), δ: 157.39, 135.93, 135.73, 133.74, 132.76, 130.01, 129.81, 127.82, 127.46, 84.63, 78.58, 65.09, 50.62, 46.91, 44.01, 26.94, 25.96, 25.37, 24.27, 23.54, 19.38, 14.12, 11.74. FTIR (neat), cm$^{-1}$: 3696, 2936, 2862, 2097, 1748, 1427, 1267, 1111, 1055, 1034, 704. HRMS (ESI): Calculated for $(C_{29}H_{43}N_5O_3Si+H)^+$: 538.3208. found: 538.3221.

Step 10

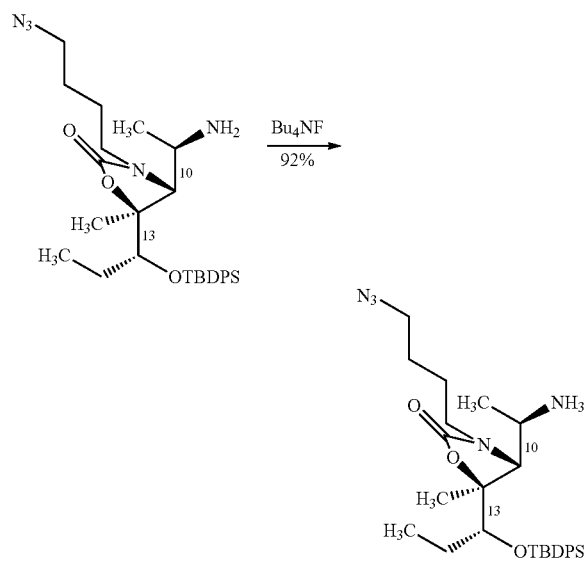

Tetrabutylammonium fluoride solution (1 M in tetrahydrofuran, 15.4 mL, 15.4 mmol) was added to a solution of (4R,5S)-4-((R)-1-aminoethyl)-3-(4-azidobutyl)-5-((R)-1-hydroxypropyl)-5-methyloxazolidin-2-one (6.9 g, 12.83 mmol) in tetrahydrofuran (64 mL) at 23° C. After 16 h, the starting material was completely consumed by TLC (5% MeOH/DCM, +0.5% NH$_4$OH). The stir bar was removed and the solution was concentrated. The residue was purified by column chromatography (5% to 7.5% methanol in dichloromethane, +0.5% NH$_4$OH) to provide the product as a clear, viscous oil (3.53 g, 92%). TLC (10% MeOH in dichloromethane, +1% NH$_4$OH): R$_f$=0.49 (PMA). $^1$H NMR (500 MHz, CDCl$_3$), δ: 3.63 (d, J=2.9 Hz, 1H), 3.52 (ddd, J=14.1, 8.8, 6.7 Hz, 1H), 3.36-3.21 (m, 5H), 2.26 (br s, 3H), 1.75-1.66 (m, 1H), 1.65-1.50 (m, 4H), 1.32 (s, 3H), 1.31-1.23 (m, 1H), 1.15 (d, J=6.5 Hz, 3H), 0.99 (t, J=7.4 Hz, 3H). $^{13}$C NMR (125 MHz, CDCl$_3$), δ: 157.94, 83.83, 77.77, 63.92, 50.87, 47.02, 43.26, 25.94, 23.90, 23.34, 19.10, 15.99, 10.88. FTIR (neat), cm$^{-1}$: 3680, 3370 (br), 2967, 2938, 2874, 2097, 1720, 1454, 1263, 1053, 1034. HRMS (ESI): Calculated for $(C_{13}H_{25}N_5O_3+Na)^+$: 322.1850. found: 322.1863.

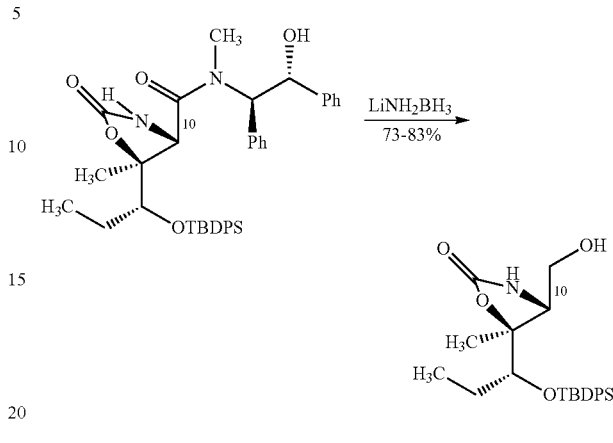

Step 6a

To a solution of diisopropylamine (10.51 ml, 73.7 mmol) in THF (90 mL) at −78° C. was added BuLi (2.50 M solution in hexanes, 28.8 ml, 71.9 mmol) dropwise. The reaction solution was warmed to 0° C. by transferring the vessel to an ice water bath, and ammonia-borane complex (2.276 g, 73.7 mmol) was added in a single portion. After the bubbling subsided, the solution was allowed to warm to 23° C., and was stirred for 15 minutes at this temperature before being re-cooled to 0° C. A solution of (4S,5S)-5-((R)-1-((tert-butyldiphenylsilyl)oxy)propyl)-N-((1R,2R)-2-hydroxy-1,2-diphenylethyl)-N,5-dimethyl-2-oxooxazolidine-4-carboxamide (6 g, 9.22 mmol) in THF (30 mL) was added by cannula, and the transfer was quantitated with 2×3.0 mL rinses of THF. After 10 minutes at 0° C., the vessel was allowed to warm to 23° C. After 1.5 hours, TLC (10% MeOH/DCM, 1% NH$_4$OH, run twice if necessary) indicated complete consumption of starting material. The mixture was cooled in an ice water bath, and 4 M HCl (100 mL) was added very carefully (CAUTION: gas evolution!). The mixture was allowed to warm to ambient temperature and was stirred vigorously for 30 minutes (gas evolution continued for 10-20 minutes), and was extracted with diethyl ether (3×75 mL). The combined organic layers were washed with 2 M HCl (20 mL), sodium bicarbonate (100 mL), sat. aq. NaCl (100 mL), dried through a pad of sodium sulfate, and concentrated. The residue was purified by column chromatography (50% to 100% EtOAc in hexanes) to provide the product as a white solid (2.88 g, 73%). TLC (50% EtOAc in hexanes): R$_f$=0.1 (UV, PMA). $^1$H NMR (500 MHz, CDCl$_3$), δ: 7.77-7.70 (m, 4H), 7.47-7.37 (m, 6H), 6.82 (s, 1H), 4.07 (dd, J=6.6, 4.1 Hz, 2H), 3.77-3.67 (m, 3H), 1.63-1.54 (m, 1H), 1.49-1.37 (m, 1H), 1.40 (s, 3H), 1.07 (s, 9H), 0.59 (t, J=7.5 Hz, 3H). $^{13}$C NMR (125 MHz, CDCl$_3$), δ: 159.4, 135.9, 135.7, 133.9, 132.5, 129.8, 129.6, 127.6, 127.4, 86.8, 78.9, 62.0, 58.3, 26.9, 25.3, 19.5, 15.8, 11.2. FTIR (neat), cm$^{-1}$: 3333 (br), 2936, 2959, 1744, 1427, 1109, 702. HRMS (ESI): Calculated for $(C_{24}H_{33}NO_4Si+H)^+$: 428.2252; found: 428.2250.

Recovery of pseudoephenamine: The aqueous layer from the extraction was basified with 6 M NaOH (to pH 14) and extracted with DCM (3×50 mL). The organic layers were dried over sodium sulfate and filtered, and the filtrate was concentrated. The resulting crystalline solid is slightly yellow, and ~90% pseudoephenamine by NMR (1.88 g, 90%). The $^1$H NMR spectra matched literature data (*Angew. Chem. Int. Ed.* 2012, 51, 4568-4571).

Step 7a

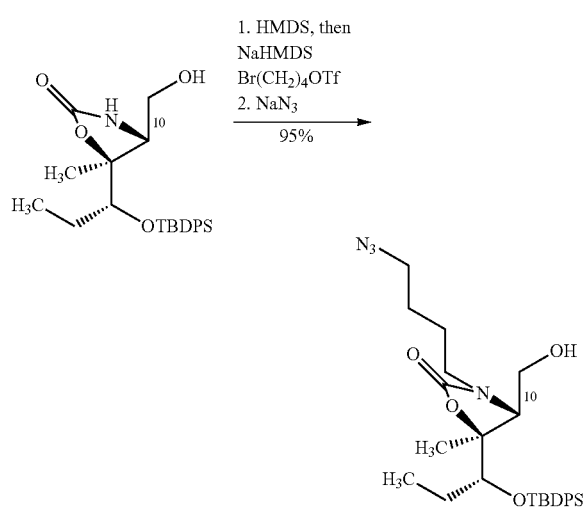

To a solution of (4R,5S)-5-((R)-1-((tert-butyldiphenylsilyl)oxy)propyl)-4-(hydroxymethyl)-5-methyloxazolidin-2-one (2.85 g, 6.66 mmol) in dichloromethane (12 mL) was added HMDS (4.19 ml, 19.99 mmol). The suspension was stirred at ambient temperature. Over an hour, the white precipitate gradually dissolved, resulting in a colorless, homogeneous solution. After 3 hours, the solvent was evaporated and the clear, colorless oil was exposed to high vacuum. Within an hour, the residue had solidified, and the solid was powdered with a spatula, and exposed to high vacuum for 18 h. The dried solid was then dissolved in tetrahydrofuran (25 mL), and the resulting solution was cooled to −78° C. NaHMDS (1 M solution in THF, 5.25 ml, 5.25 mmol) was added dropwise. The solution was stirred for 30 minutes at this temperature and a solution of 4-bromobutyl trifluoromethanesulfonate (2.139 g, 7.50 mmol) in diethyl ether (5 mL) was added. The vessel was transferred to an ice water bath. 3 minutes after reaching 0° C., TLC indicated complete conversion to a less polar spot (20% EA/H). Saturated aqueous ammonium chloride (50 mL) was added, and the mixture was stirred at 0° C. for 5 minutes. The layers were separated, and the aqueous layer was extracted with diethyl ether (2×20 mL). The combined organic layers were washed with water (30 mL), brine (30 mL), dried through a pad of sodium sulfate, and concentrated. The residue was dissolved in DMF (15 mL), and sodium azide (0.975 g, 15.00 mmol) was added in a single portion. After 2.5 hours, the mixture was diluted with water (200 mL) and the resulting suspension was extracted with diethyl ether (3×50 mL). The combined organic extracts were washed with water (100 mL), brine (100 mL), dried through a pad of sodium sulfate and concentrated. The residue was purified by column chromatography (50% EtOAc in hexanes) to provide (4R,5S)-3-(4-azidobutyl)-5-((R)-1-((tert-butyldiphenylsilyl)oxy)propyl)-4-(hydroxymethyl)-5-methyloxazolidin-2-one as a white solid (2.5 g, 95%). TLC (50% EtOAc in hexanes): $R_f$=0.41 (UV, PMA). $^1$H NMR (500 MHz, CDCl$_3$), δ: 7.72-7.64 (m, 4H), 7.47-7.35 (m, 6H), 3.84-3.71 (m, 3H), 3.59 (t, J=5.3 Hz, 1H), 3.36 (dt, J=14.4, 7.5 Hz, 1H), 3.23 (t, J=5.8 Hz, 2H), 3.16-3.04 (m, 2H), 1.74-1.62 (m, 1H), 1.57-1.35 (m, 5H), 1.46 (s, 3H), 1.04 (s, 9H), 0.59 (t, J=7.5 Hz, 3H). $^{13}$C NMR (125 MHz, CDCl$_3$), δ: 157.5, 135.9, 135.6, 133.8, 132.5, 129.8, 129.6, 127.6, 127.3, 83.7, 78.9, 60.9, 59.8, 50.7, 41.9, 26.8, 25.9, 25.3, 24.6, 19.3, 15.3, 11.4. FTIR (neat), cm$^{-1}$: 3425 (br), 2936, 2877, 2097, 1726, 1111, 1057, 702. HRMS (ESI): Calculated for $(C_{28}H_{40}N_4O_4Si+H)^+$: 525.2892. found: 525.2896.

Step 8a

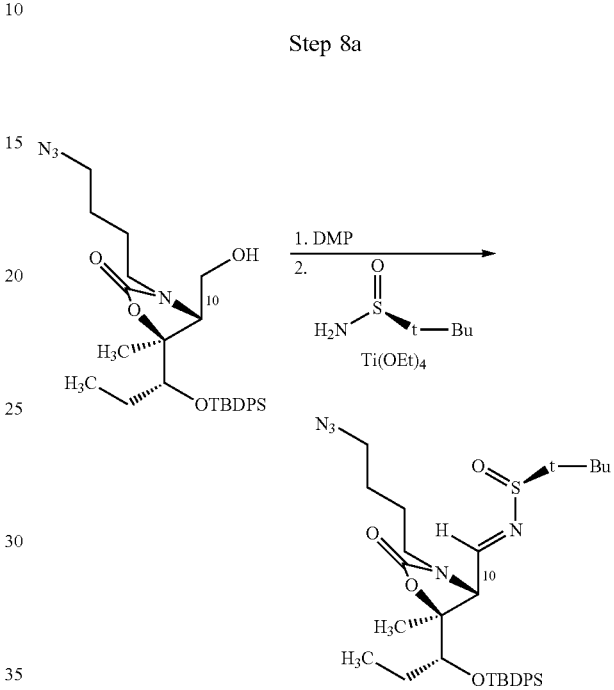

To a solution of (4R,5S)-3-(4-azidobutyl)-5-((R)-1-((tert-butyldiphenylsilyl)oxy)propyl)-4-(hydroxymethyl)-5-methyloxazolidin-2-one (510 mg, 0.972 mmol) in dichloromethane saturated with water (9 mL) in a 23° C. water bath was added Dess-Martin periodinane (824 mg, 1.944 mmol). After 45 minutes, TLC indicated complete conversion to a less polar spot (50% EtOAc in hexanes). The reaction mixture was diluted with diethyl ether (30 mL) and the resulting slurry washed with a 10% aqueous sodium bicarbonate and sat thiosulfate (1:1 by volume, 30 mL). The aqueous layer was extracted with diethyl ether (2×15 mL), and the combined organic layers were washed with sodium bicarbonate (2×10 mL), dried through a pad of sodium sulfate, and concentrated to provide the crude aldehyde, which was used without further purification. The crude aldehyde was dissolved in THF (5.0 mL) and the vessel was placed in a room-temperature water bath. tetraethoxytitanium (0.509 ml, 1.944 mmol) was added dropwise over 2 minutes followed by solid (S)-2-methylpropane-2-sulfinamide (0.118 g, 0.972 mmol). After 17 h, the mixture was transferred to a 50 mL reaction vessel containing saturated aqueous sodium chloride (5 mL), resulting in a thick white slurry. The transfer was quantitated with ethyl acetate (2×5 mL), and the slurry was stirred vigorously for 15 minutes. The layers were separated, and the organic layer was filtered through celite. The cake was washed with ethyl acetate (2×5 mL), and the filtrate was washed with sat. aq. NaCl (10 mL). The organic layer was dried through a pad of sodium sulfate and concentrated. Crude NMR revealed ~95% conversion to the desired sulfinimine, which was carried on crude without further purification. This intermediate can be used as an electrophile for several Grignard reagents or similar nucleophiles. Alternatively, (S)-2-methylpropane-2-sulfinamide can be used to make the opposite (R)-sulfinimine, which can be trifluoromethylated.

Step 9a: Addition of Allylmagnesium Bromide and Cleavage of the Auxiliary

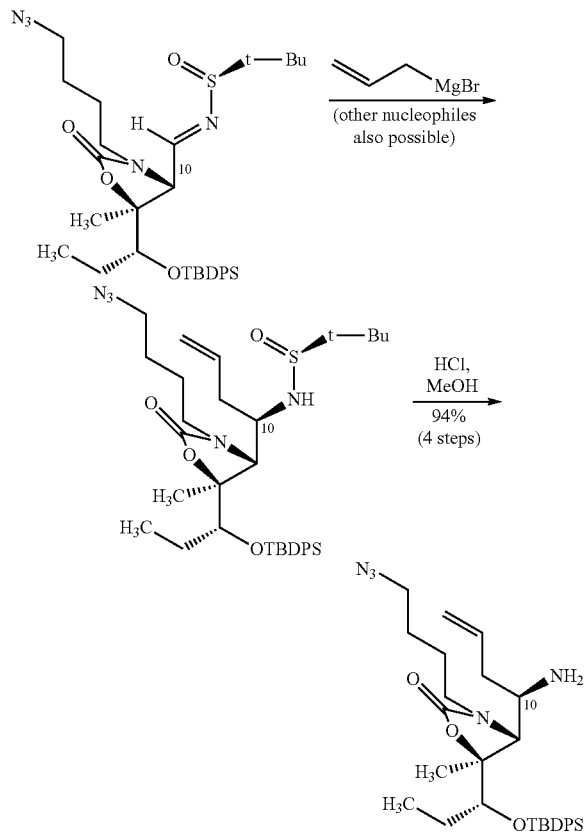

A solution of (S,E)-N-(((4R,5S)-3-(4-azidobutyl)-5-((R)-1-((tert-butyldiphenylsilyl)oxy)propyl)-5-methyl-2-oxooxazolidin-4-yl)methylene)-2-methylpropane-2-sulfinamide (1.0 g, 1.60 mmol) in dichloromethane (16 mL) was cooled to −78° C. in an acetone/dry ice bath. Allylmagnesium bromide (1.0 M solution in ether, 3.20 mL, 3.20 mmol) was added, and the reaction mixture was stirred at this temperature for 2 h. Half-saturated aqueous ammonium chloride (30 mL) was added, and the mixture was stirred vigorously and allowed to warm to ambient temperature. Ethyl acetate (30 mL) was added, and the layers were mixed vigorously and separated. The aqueous layer was extracted with ethyl acetate (2×20 mL), and the combined organic layers were washed with brine (40 mL), dried through a pad of sodium sulfate, and concentrated. The clear, oily residue was dissolved in methanol (8 mL) was added hydrochloric acid (4.0 M solution in dioxane, 1.6 mL, 6.39 mmol). After 45 minutes, the mixture was concentrated, and the residue was dissolved in ethyl acetate (20 mL) and washed with 2 M sodium hydroxide (20 mL). The aqueous layer was extracted with ethyl acetate (1×20 mL), and the combined organic layers were washed with sat aq NaCl (20 mL), passed through a pad of sodium sulfate and concentrated. The residue was purified by column chromatography on silica gel (2% MeOH in dichloromethane+0.2% NH$_4$OH) to provide (4R,5S)-4-((R)-1-aminobut-3-en-1-yl)-3-(4-azidobutyl)-5-((R)-1-((tert-butyldiphenylsilyl)oxy)propyl)-5-methyloxazolidin-2-one as a colorless oil (843 mg, 94%). TLC (EtOAc): R$_f$=0.55 (UV, PMA). $^1$H NMR (500 MHz, CDCl$_3$), δ: 7.69-7.66 (m, 2H), 7.65-7.61 (m, 2H), 7.48-7.35 (m, 7H), 5.71 (ddt, J=16.9, 10.2, 6.9 Hz, 1H), 5.14 (d, J=10.4 Hz, 1H), 5.11 (d, J=17.0 Hz, 1H), 3.57 (s, 1H), 3.50 (t, J=5.3 Hz, 1H), 3.37 (ddd, J=14.0, 9.8, 6.0 Hz, 1H), 3.26-3.19 (m, 2H), 2.99 (dd, J=10.0, 4.2 Hz, 1H), 2.90 (ddd, J=14.2, 10.1, 4.5 Hz, 1H), 2.20-2.02 (m, 2H), 1.84-1.73 (m, 1H), 1.59 (s, 3H), 1.53-1.37 (m, 4H), 1.35-1.29 (m, 1H), 1.16 (br s, 2H), 1.04 (s, 9H), 0.66 (t, J=7.5 Hz, 3H). $^{13}$C NMR (125 MHz, CDCl$_3$), δ: 157.4, 135.9, 135.7, 135.2, 133.7, 132.8, 130.0, 129.8, 127.8, 127.5, 118.0, 84.7, 78.8, 64.1, 51.3, 50.6, 43.9, 42.3, 27.0, 26.0, 25.5, 24.4, 19.4, 14.2, 11.8. FTIR (neat), cm$^{-1}$: 3364, 2938, 2877, 2097, 1724, 1267, 1111, 1059. HRMS (ESI): Calculated for (C$_{31}$H$_{45}$N$_5$O$_3$+Na)$^+$: 586.3184. found: 586.3179. Other Grignard reagents that have been successfully implemented include benzylmagnesium bromide, 3-bromobenzylmagnesium bromide, vinylmagnesium bromide, and cyclopropylmagnesium chloride.

Step 10a

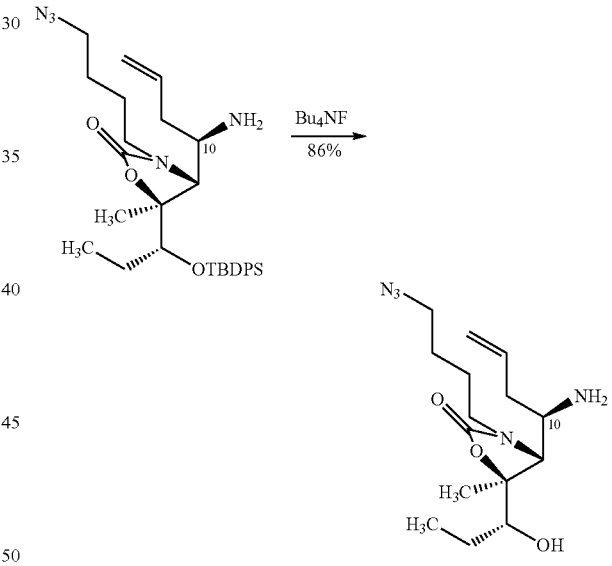

To a solution of (4R,5S)-4-((R)-1-aminobut-3-en-1-yl)-3-(4-azidobutyl)-5-((R)-1-((tert-butyldiphenylsilyl)oxy)propyl)-5-methyloxazolidin-2-one (843 mg, 1.495 mmol) in THF (7.5 mL) was added tetrabutylammonium fluoride (2.24 mL, 2.243 mmol). After 18 h, the mixture was concentrated and purified by column chromatography on silica gel (2 to 4% MeOH in dichloromethane+0.2% NH$_4$OH) to provide the product as a light yellow oil. TLC (EtOAc): R$_f$=0.20 (PMA). $^1$H NMR (500 MHz, CDCl$_3$), δ: 5.82-5.69 (m, 1H), 5.18-5.10 (m, 2H), 3.76 (d, J=1.9 Hz, 1H), 3.67-3.57 (m, 1H), 3.39 (dt, J=10.5, 1.8 Hz, 1H), 3.31 (t, J=6.5 Hz, 2H), 3.15-3.06 (m, 1H), 3.03-2.97 (m, 1H), 2.42-2.33 (m, 1H), 2.24-2.13 (m, 1H), 1.75-1.67 (m, 1H), 1.66-1.53 (m, 4H), 1.43 (s, 3H), 1.35-1.22 (m, 1H), 1.05-0.96 (m, 3H). $^{13}$C NMR (125 MHz, CDCl$_3$), δ: 158.1, 135.1, 118.3, 84.6, 78.1, 61.6, 50.9, 50.6, 43.6, 41.5, 26.0, 24.0, 23.4, 16.4, 10.9.

FTIR (neat), cm⁻¹: 3412 (br), 2972, 2942, 2876, 2098, 1724, 1456, 1261, 1047, 918. HRMS (ESI): Calculated for $(C_{15}H_{27}N_5O_3+Na)^+$: 348.2006. found: 348.2019.

Step 9b: Trifluoromethylation of (R)-Sulfinimine

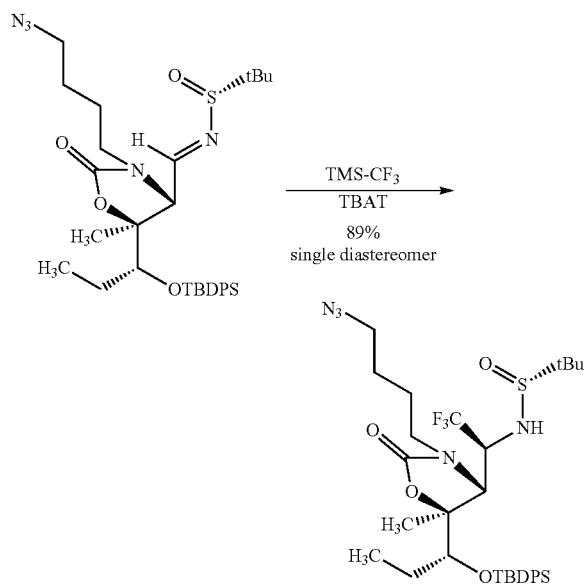

To a flame dried, 25-mL round-bottom flask was added (R,E)-N-(((4R,5S)-3-(4-azidobutyl)-5-((R)-1-((tert-butyldiphenylsilyl)oxy)propyl)-5-methyl-2-oxooxazolidin-4-yl)methylene)-2-methylpropane-2-sulfinamide (100 mg, 0.160 mmol, 1 equiv), tetrabultylammonium difluorotriphenylsilicate (95 mg, 0.176 mmol, 1.1 equiv), and 3 mL THF. The clear, slightly yellow solution was cooled to −50° C. in an acetone bath cooled with dry ice. At this point, a white precipitate formed. To this suspension was then added trifluoromethyltrimethylsilane (28.4 µL, 0.192 mmol, 1.2 eq) as a solution in 1 mL THF. After 1 h, the solution became clear again; however, TLC (30% EtOAc/hexanes) indicated only 50% conversion. The reaction was allowed to warm to room temperature and another portion of tetrabultylammonium difluorotriphenylsilicate (95 mg, 0.176 mmol, 1.1 eq) was added. The solution was then re-cooled to −50° C. and another portion of trifluoromethyltrimethylsilane (28.4 uL, 0.192 mmol, 1.2 eq) as a solution in 1 mL THF was added. After another 30 min., sat. aq. NH₄Cl (7 mL) was added. The slurry was allowed to warm to 23° C. with vigorous stirring, ethyl acetate (10 mL) was added, and the layers were separated. The aqueous layer was further extracted with ethyl acetate (2×10 mL) and the combined organic layers were filtered through a pad of sodium sulfate and the filtrate was concentrated. The residue was purified by column chromatography on silica gel (8 to 10 to 30% acetone/hexanes gradient elution), affording (R)—N—((S)-1-((4R,5S)-3-(4-azidobutyl)-5-((R)-1-((tert-butyldiphenylsilyl)oxy)propyl)-5-methyl-2-oxooxazolidin-4-yl)-2,2,2-trifluoroethyl)-2-methylpropane-2-sulfinamide as a white foam (99 mg, 0.142 mmol, single diastereomer, 89%). TLC (30% EtOAc in hexanes): Rf=0.1 (UV, CAM). ¹H NMR (399 MHz, CDCl₃) δ: 7.67 (d, J=6.63 Hz, 2H), 7.61 (d, J=6.63 Hz, 2H), 7.53-7.34 (m, 6H), 4.09 (s, 1H), 4.06-3.95 (m, 1H), 3.53-3.44 (m, 2H), 3.40-3.28 (m, 1H), 3.21 (t, J=6.63 Hz, 2H), 2.83-2.71 (m, 1H), 1.81-1.68 (m, 1H), 1.55 (s, 3H), 1.52-1.47 (m, 1H), 1.46-1.38 (m, 3H), 1.31 (d, J=5.85 Hz, 1H), 1.24 (s, 9H), 1.03 (s, 9H), 0.61 (t, J=7.61 Hz, 3H); ¹³C NMR (100 MHz, CDCl₃) δ: 157.01, 135.88 (2C), 135.68 (2C), 133.62, 132.10, 130.31, 129.94, 128.00 (2C), 127.55 (2C), 124.44 (d, J=285.25 Hz), 84.86, 78.24, 59.23, 58.25 (d, J=29.91 Hz), 57.85, 50.54, 43.33, 26.81 (3C), 25.91, 25.62, 24.39, 22.55 (3C), 19.26, 14.13, 11.79. ¹⁹F NMR (376 MHz, CDCl₃) δ: −70.13 (d, J=7.89 Hz, 3F); FTIR (neat) 2934, 2860, 2097, 1759, 1463, 1113, 704, 449 cm⁻¹; HRMS (ESI): Calculated for $(C_{33}H_{48}F_3N_5O_4SSi+H)^+$: 696.3221. found: 696.3226.

Step 10b: Coupling of the Halves-C10-Trifluoromethylation

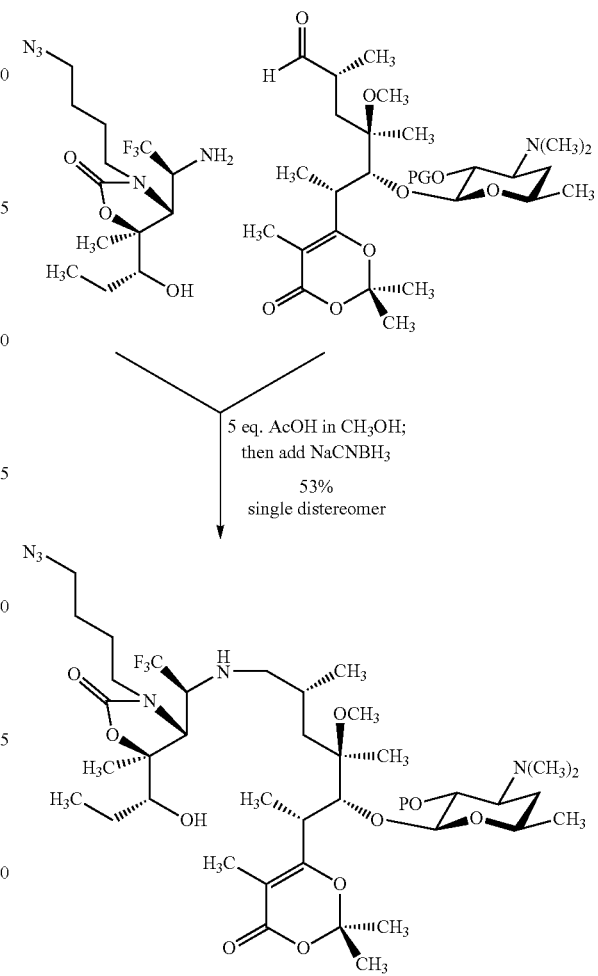

To a flame dried, 5-mL round-bottom flask was added (4R,5S)-4-((S)-1-amino-2,2,2-trifluoroethyl)-3-(4-azidobutyl)-5-((R)-1-hydroxypropyl)-5-methyloxazolidin-2-one (32 mg, 0.091 mmol, 1 eq.) and 500 µL anhydrous methanol. Glacial acetic acid (25.9 µl, 0.453 mmol, 5 equiv) was added followed by (2S,3R,4S,6R)-4-(dimethylamino)-2-(((2R,3R,4R,6R)-4-methoxy-4,6-dimethyl-7-oxo-2-(2,2,5-trimethyl-4-oxo-4H-1,3-dioxin-6-yl)heptan-3-yl)oxy)-6-methyltetrahydro-2H-pyran-3-yl methyl carbonate (49.2 mg, 0.091 mmol, 1 equiv) as a solid. The solution was allowed to stir under argon at 23° C. for 2 hours. Sodium cyanoborohydride (17.07 mg, 0.272 mmol, 3 equiv) was added to the solution. After 30 min., sat. aq. sodium bicarbonate (1 mL) was added. Dichloromethane (2 mL) was added and the layers were stirred vigorously. The layers were then separated and the aqueous layer was further extracted with dichloromethane (2×3 mL). The combined organic layers were washed with sat. aq. NaCl (5 mL) and then dried through a pad of sodium sulfate, filtered, and the filtrate was concentrated. The residue was purified by column chromatography on silica gel (90% ethyl acetate/hexanes/1% triethylamine additive) to afford (2S,3R,4S,6R)-2-(((2R,3R,4R,6R)-7-(((S)-1-((4R,5S)-3-(4-azidobutyl)-5-((R)-1-hydroxypropyl)-5-methyl-2-oxooxazolidin-4-yl)-2,2,2-trifluoroethyl)amino)-4-methoxy-4,6-dimethyl-2-(2,2,5-trimethyl-4-oxo-4H-1,3-dioxin-6-yl)heptan-3-yl)oxy)-4-(dimethylamino)-6-methyltetrahydro-2H-pyran-3-yl methyl carbonate as a clear, colorless oil (42 mg, 0.048 mmol, single diastereomer, 53%). $^1$H NMR (600 MHz, CDCl$_3$) δ: 4.61-4.53 (m, 2H), 4.13 (s, 1H), 3.85 (d, J=2.93 Hz, 1H), 3.76 (s, 3H), 3.68-3.59 (m, 1H), 3.50-3.41 (m, 2H), 3.34 (qd, J=7.63, 2.93 Hz, 1H), 3.31-3.27 (m, 2H), 3.12 (quin, J=8.20 Hz, 1H), 3.05 (s, 3H), 3.02 (dd, J=8.80, 5.28 Hz, 1H), 2.88 (dt, J=10.42, 5.06 Hz, 1H), 2.73 (t, J=10.56 Hz, 1H), 2.45 (ddd, J=10.56, 8.22, 6.46 Hz, 1H), 2.30 (s, 6H), 2.18 (d, J=4.11 Hz, 1H), 1.86 (s, 3H), 1.78-1.72 (m, 2H), 1.67 (s, 3H), 1.65 (s, 3H), 1.63-1.52 (m, 6H), 1.43 (s, 3H), 1.39-1.28 (m, 4H), 1.25 (d, J=5.87 Hz, 3H), 1.23 (s, 3H), 1.03 (t, J=7.60 Hz, 3H), 1.02 (d, J=7.60 Hz, 3H), 0.95 (d, J=6.46 Hz, 3H); $^{13}$C NMR (100 MHz, CDCl$_3$) δ: 167.84, 162.97, 157.93, 155.25, 126.69 (d, J=286.3), 104.51, 99.85, 99.53, 83.86, 79.16, 77.95, 76.71, 75.52, 69.19, 63.03, 59.63 (q, J=25.9 Hz), 56.13, 55.21, 54.70, 50.93, 49.50, 43.10, 40.68 (2C), 39.08, 33.76, 30.83, 29.41, 25.97, 25.75, 24.28, 23.64, 23.28, 21.21, 20.98, 20.20, 16.27, 12.81, 10.82, 9.86; $^{19}$F NMR (376 MHz, CDCl$_3$) δ: −70.36 (d, J=7.89 Hz, 3F); FUR (neat): 2959, 2864, 2361, 2342, 2099, 1751, 1269 cm$^{-1}$; HRMS (ESI): calculated for (C$_{40}$H$_{67}$F$_3$N$_6$O$_{12}$+H)$^+$: 881.4842; found: 881.4872.

III. Coupling Western and Eastern Halves and Macrocyclization

Reductive Amination

Example III-1A. Coupling by Reductive Amination

With efficient routes to three western halves (24a-c) and four eastern halves (34, 37, 38, 42) secured, coupling of the two halves and macrocyclization became the next and most important challenges to be addressed. While reductive amination conditions are generally robust and dependable, macrocyclization reactions are known to be capricious and highly substrate dependent. See, e.g., Paterson et al., Tetrahedron (1985) 41:3569-3624; Nakata, T; Masamune, S, et al., J. Am. Chem Soc. (1981) 103:1568. The appeal of the acylketene approach was high: it provides the macrolactone from a stable precursor under reagent-free, thermal conditions with no byproducts (except acetone). See, e.g., Boeckman et al., J. Am. Chem. Soc. (1989) 111:8286-8288; Reber et al., Chem. Soc. Rev. (2009) 38:3022-3034.

With efficient routes to three western halves (24a-c) and four eastern halves (34, 37, 38, 42) secured, coupling of the two halves and macrocyclization became the next and most important challenges to be addressed. While reductive amination conditions are generally robust and dependable, macrocyclization reactions are known to be capricious and highly substrate dependent. See, e.g., Paterson et al., Tetrahedron (1985) 41:3569-3624; Nakata, T; Masamune, S, et al., J. Am. Chem Soc. (1981) 103:1568. The appeal of the acylketene approach was high: it provides the macrolactone from a stable precursor under reagent-free, thermal conditions with no byproducts (except acetone). See, e.g., Boeckman et al., J. Am. Chem. Soc. (1989) 111:8286-8288; Reber et al., Chem. Soc. Rev. (2009) 38:3022-3034.

The preparation of the first fully synthetic aza-ketolide antibiotics by this de novo strategy is outlined below, using the western half 24b and the C4-natural eastern half 37 as just one of several different possible combinations of fully synthetic eastern and western halves. Reductive amination to couple 24b and 37 proceeded smoothly to provide 43. Much to our delight, when 43 was heated in toluene, macrocyclization occurred to deliver 44 in 80% yield as a single C2-stereoisomer. With the macrocycle in hand, removal of the methyl carbonate protecting group with methanol followed by copper-catalyzed azide-alkyne coupling provided a series of aryl analogs 45. Alternatively, the macrocycle 44 could be fluorinated at C2 with N-fluorosulfonimide and/or N-methylated with formic acid and formaldehyde to deliver any combination of C2-H/F and N9a-H/CH$_3$ (46-49). Each of these intermediates was further diversified by copper(I)-catalyzed coupling to afford a variety of aryl alkynes 50-52.

Scheme III-A.

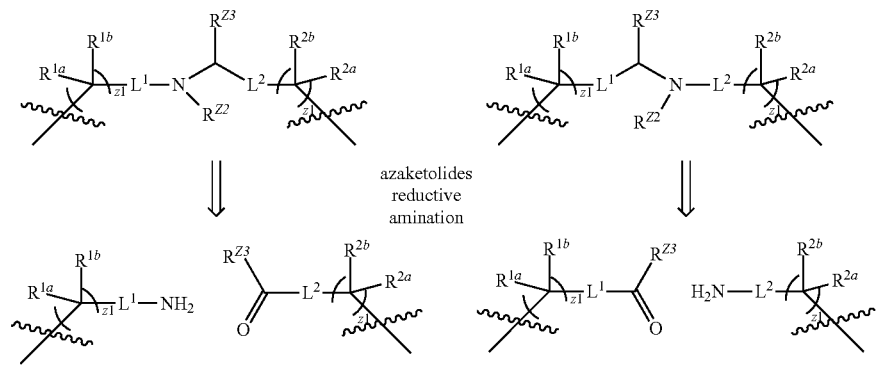

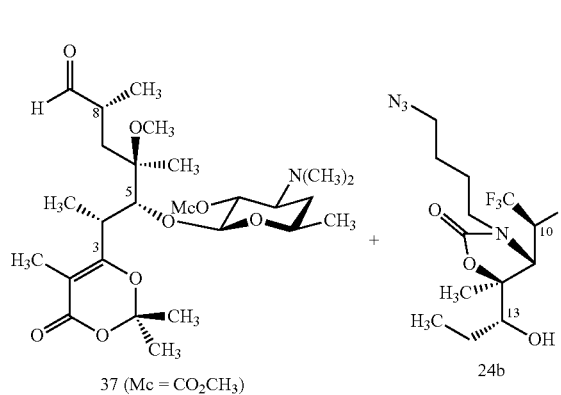
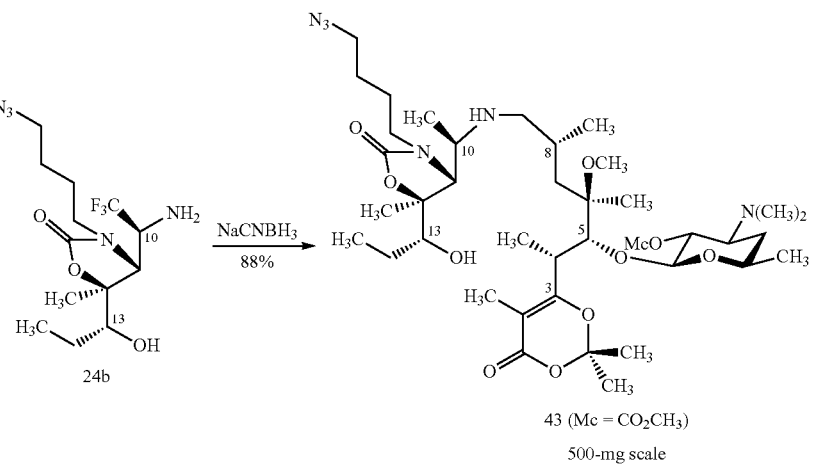
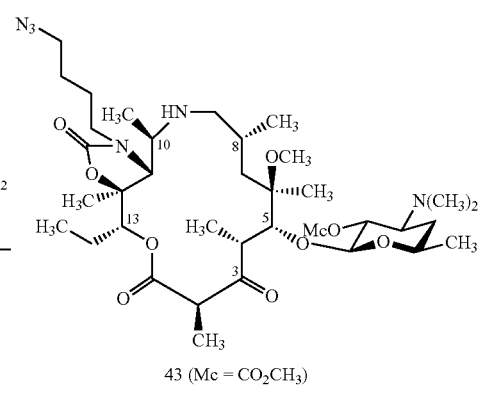
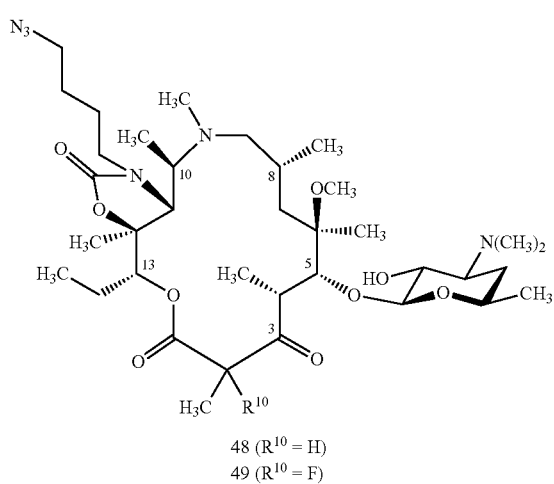

Example III-2A. Coupling by Reductive Amination
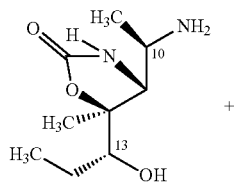
+
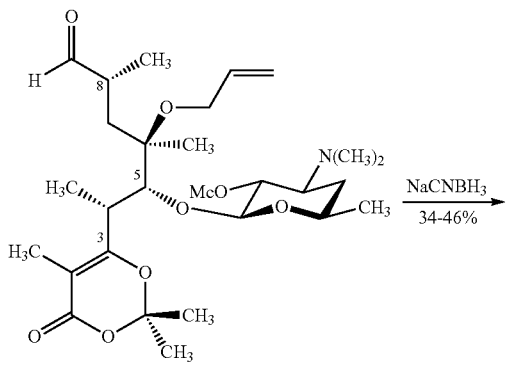
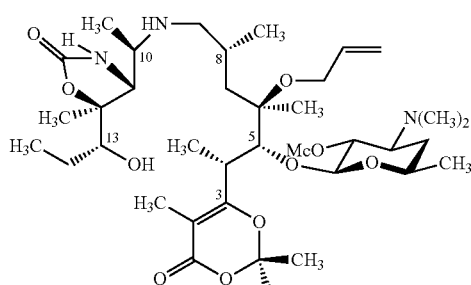
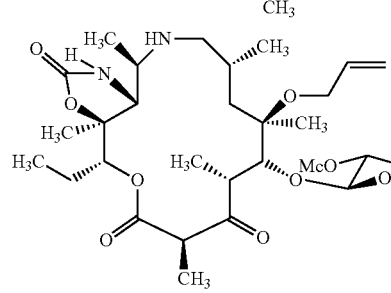
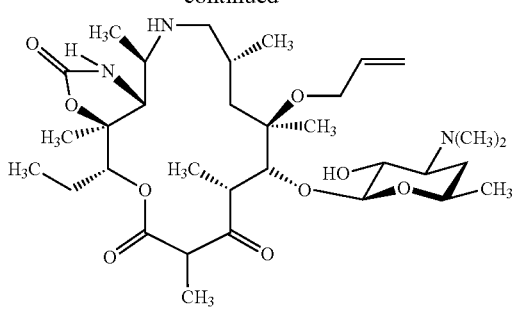
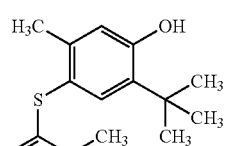
Kishi's radical inhibitor
Mc = methyl carbonate, -C(O)OCH₃
Example III-3A. Coupling by Reductive Amination
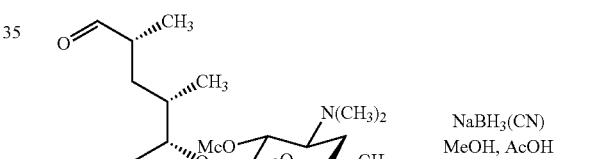
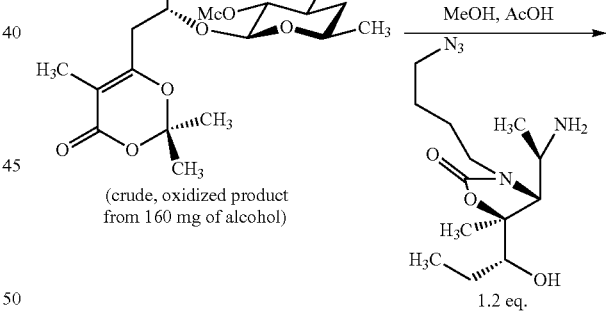
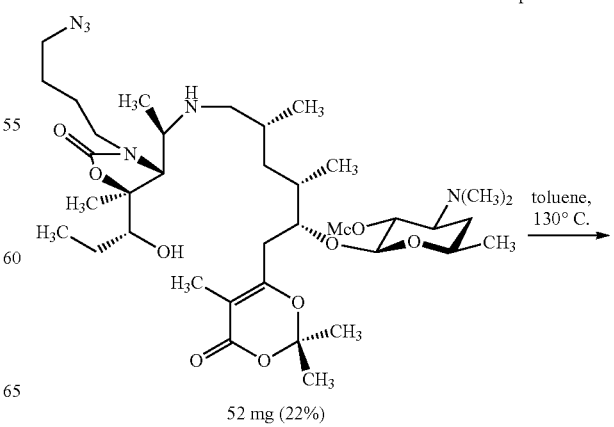
52 mg (22%)

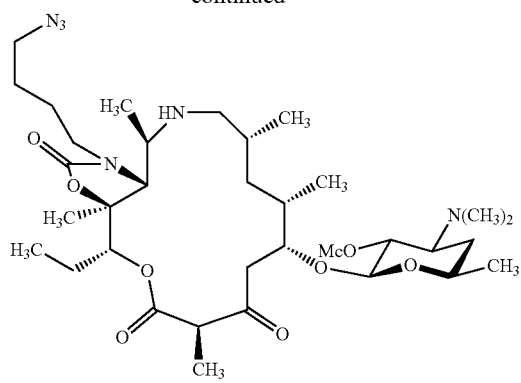
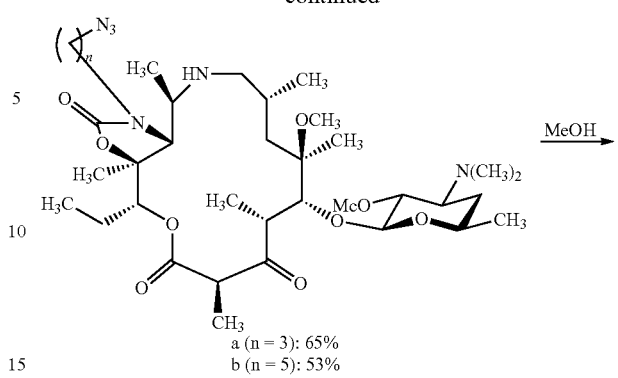
Example III-4A. Coupling by Reductive Amination
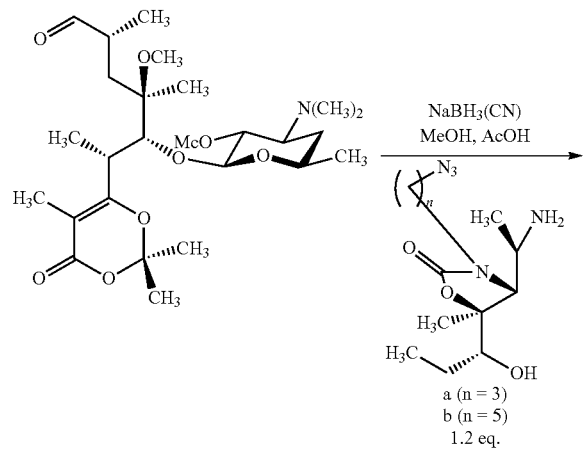
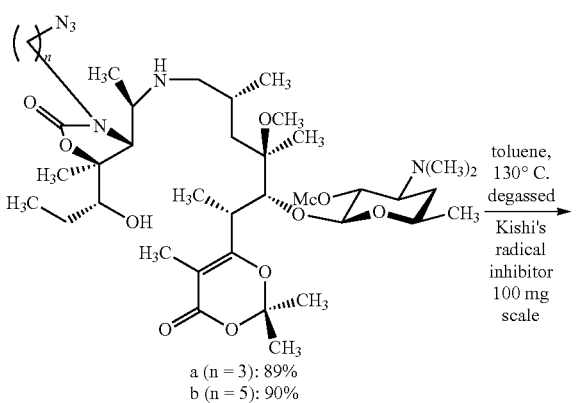
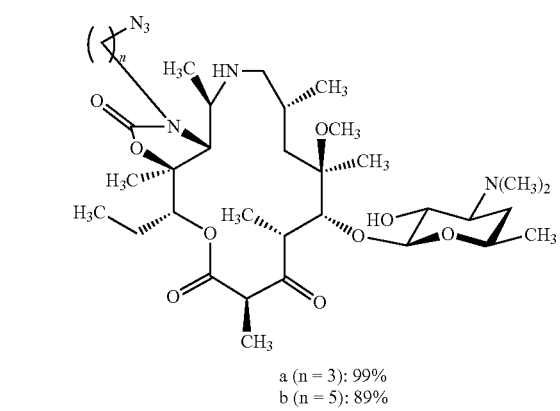
Example III-5A. Coupling by Reductive Amination
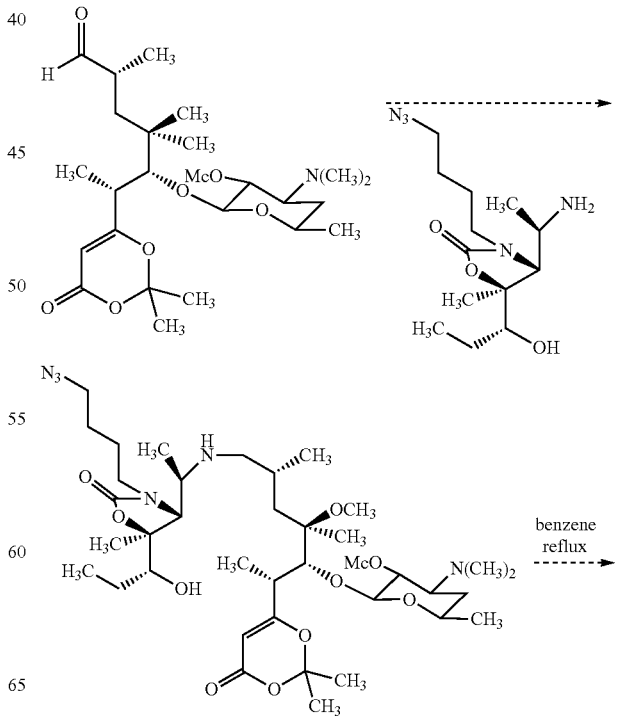

589
-continued
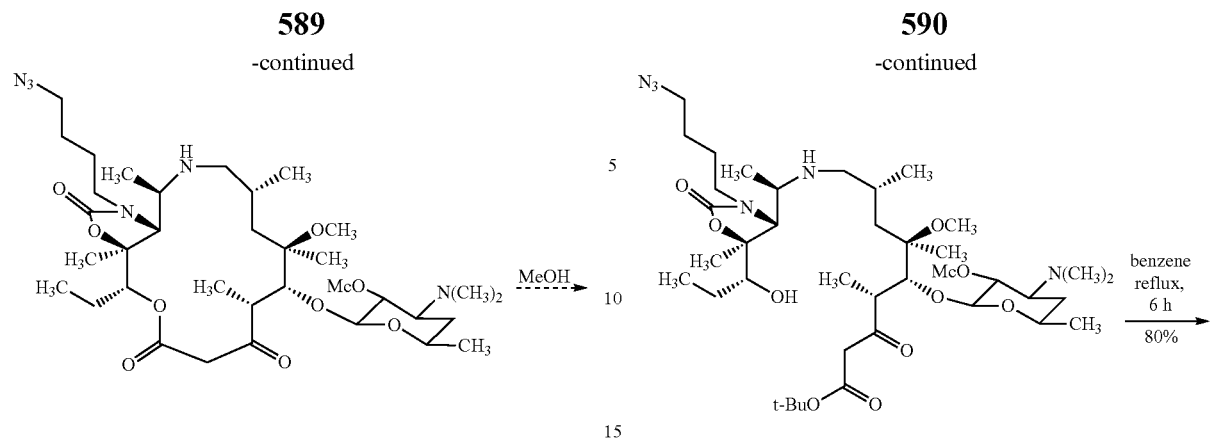
590
-continued
Example III-6A. Coupling by Reductive Amination
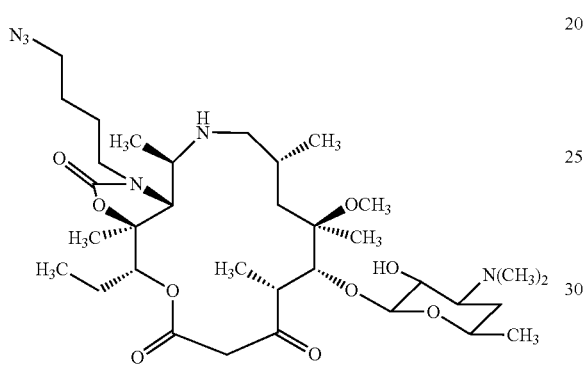
Example III-7A. Coupling by Reductive Amination
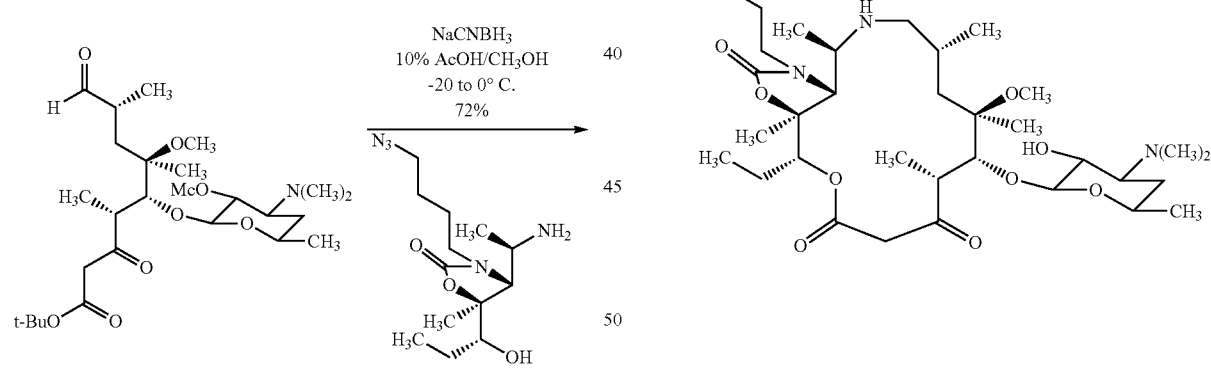
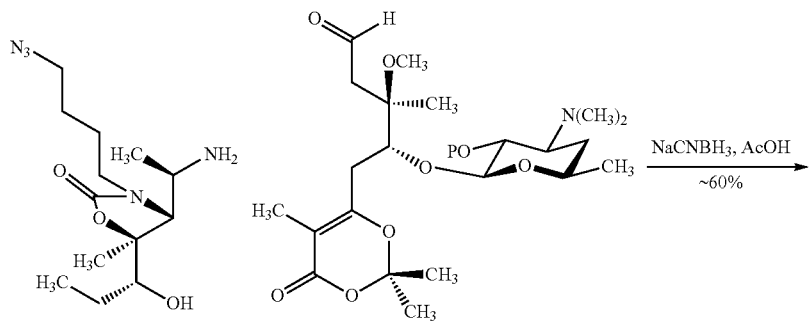

591
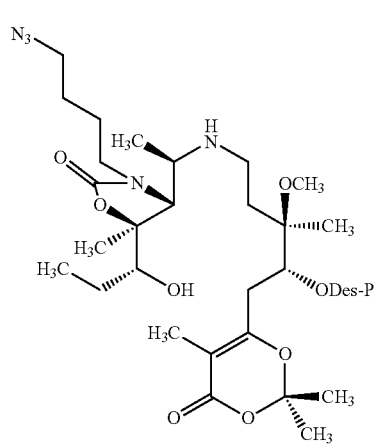
+
-continued
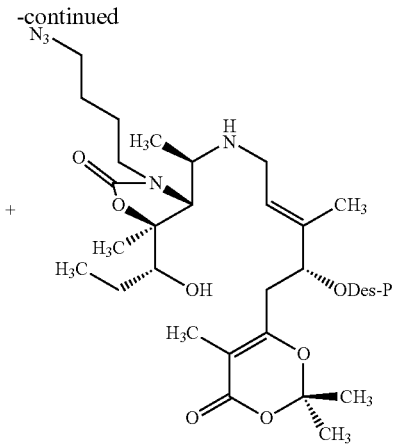
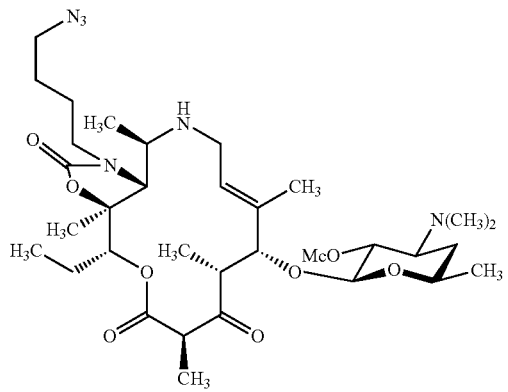
592
Example III-8A. Coupling by Reductive Amination
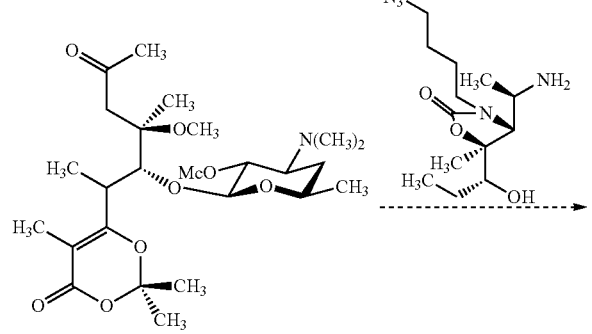 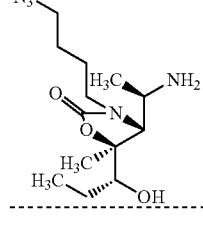
-continued
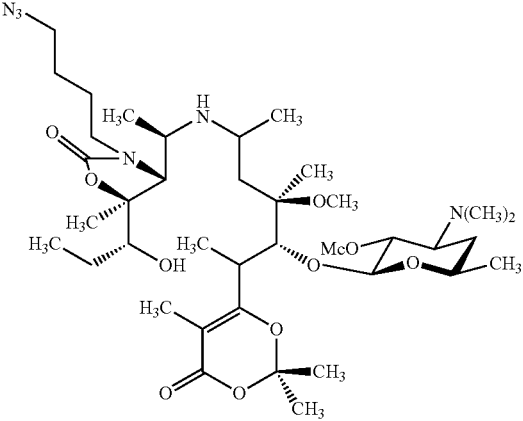

593
Example III-9A. Coupling by Reductive Amination
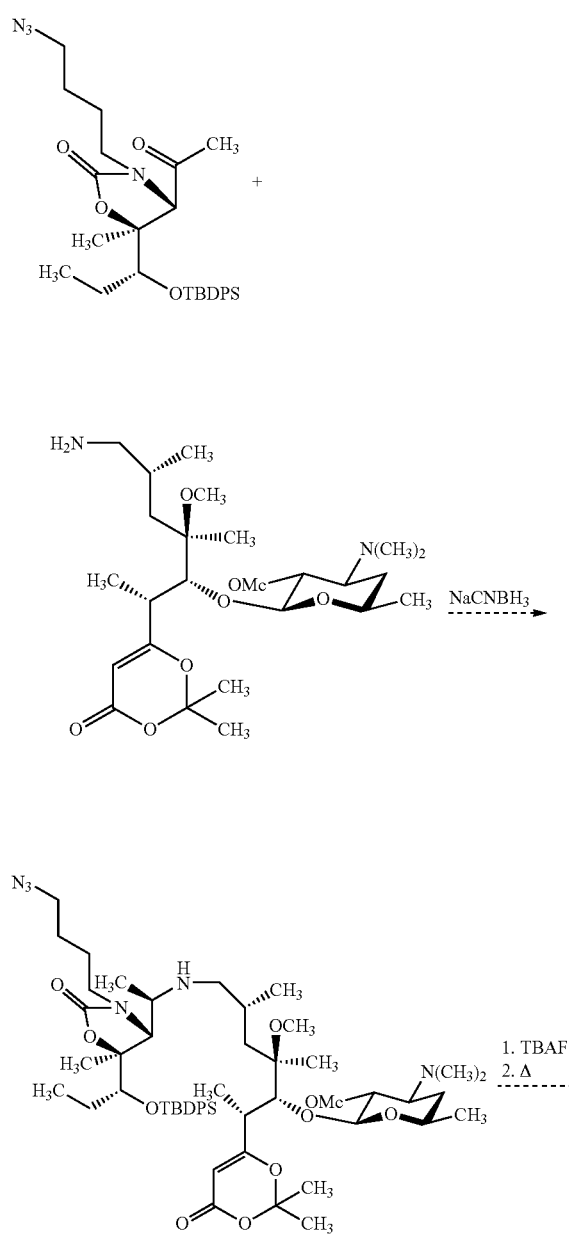
594
Example III-10A. Coupling by Reductive Amination
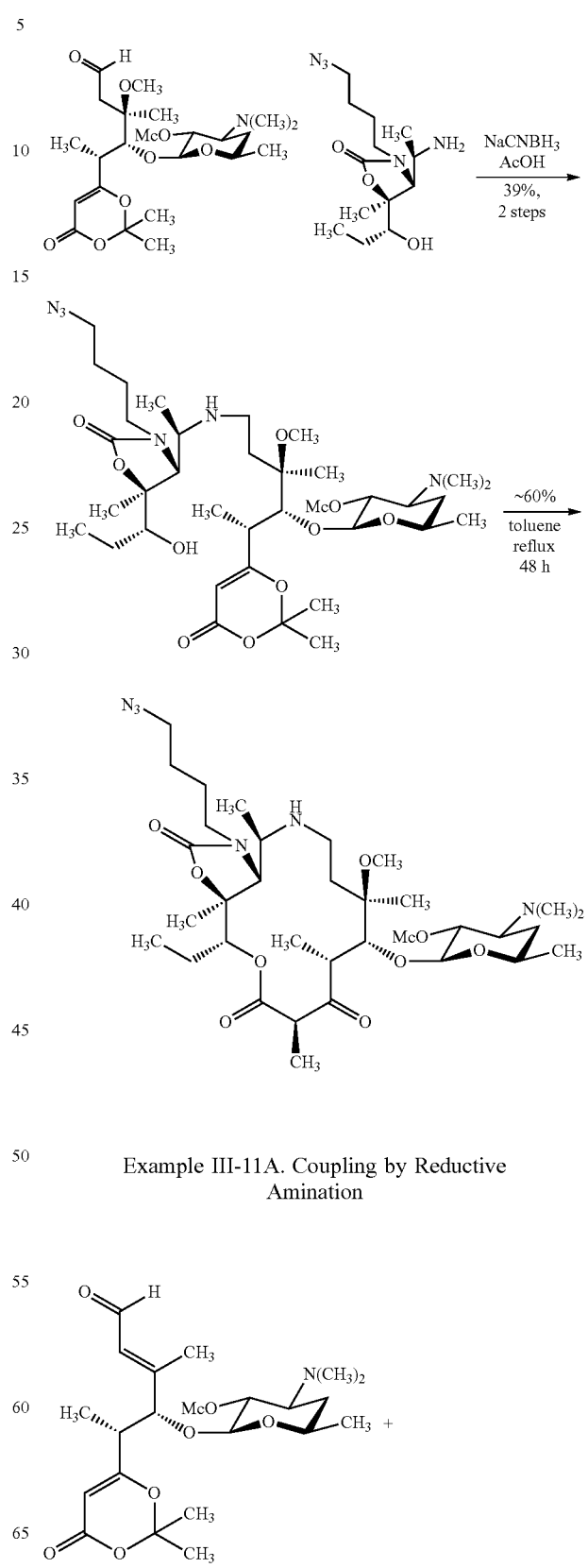
Example III-11A. Coupling by Reductive Amination

595
-continued
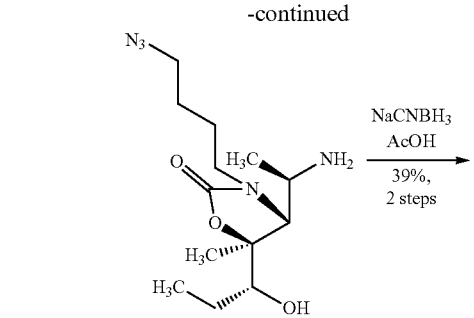
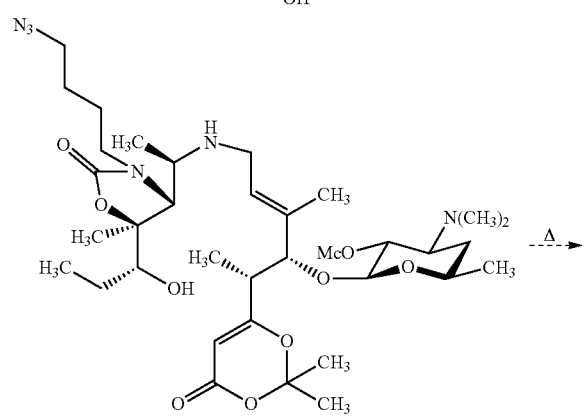
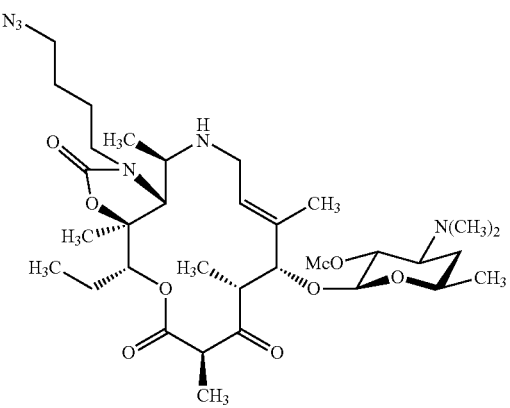
Example III-12A. Coupling by Reductive Amination
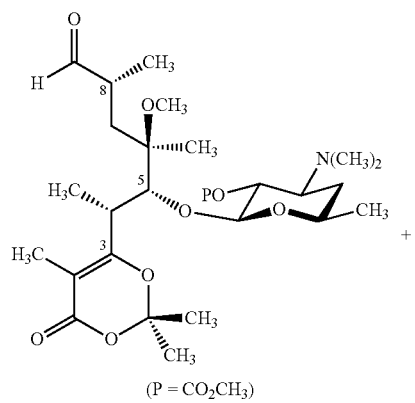
(P = CO₂CH₃)
596
-continued
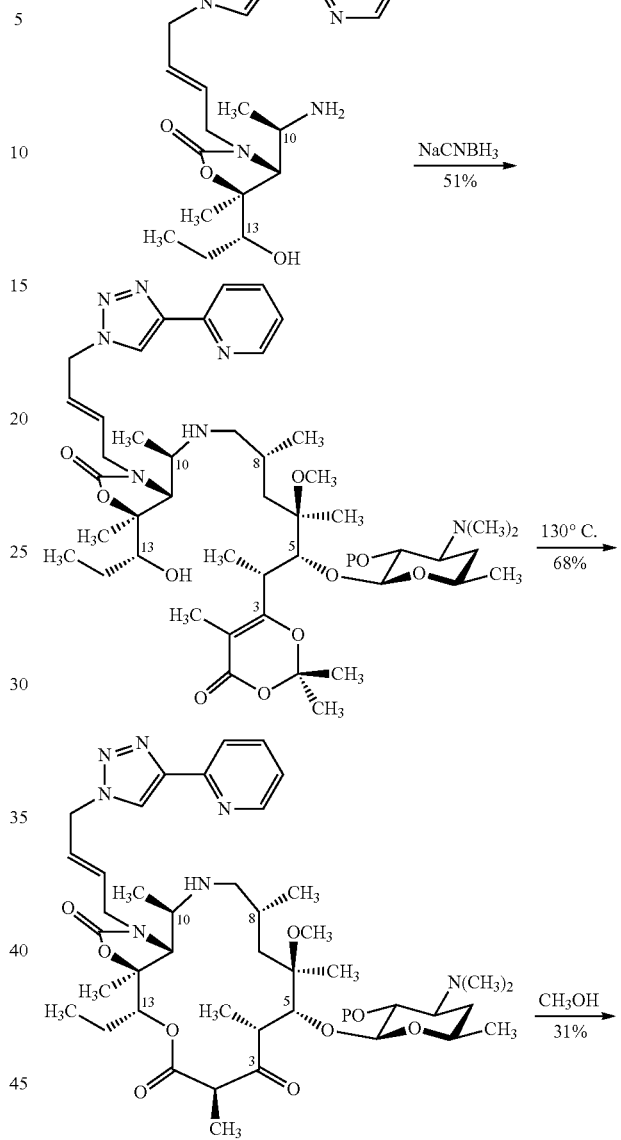
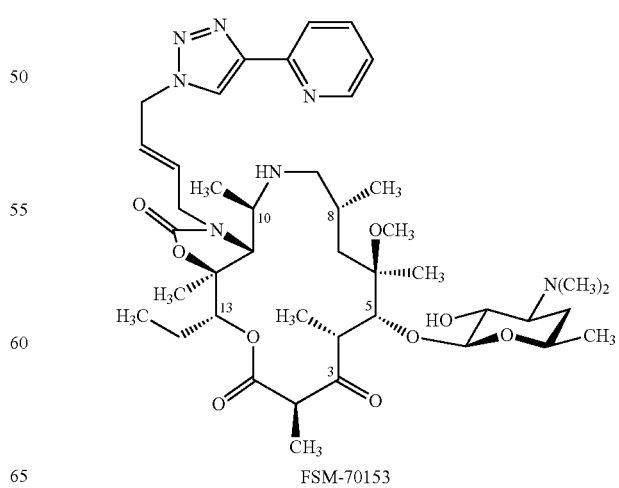
FSM-70153

597 598
Example III-13A. Coupling by Reductive Amination
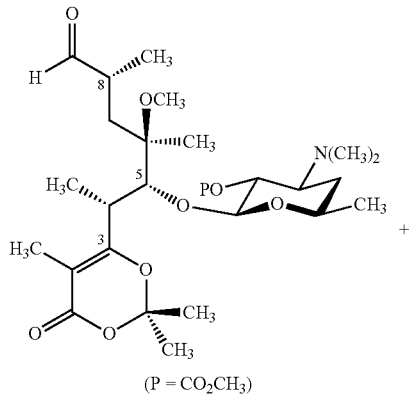
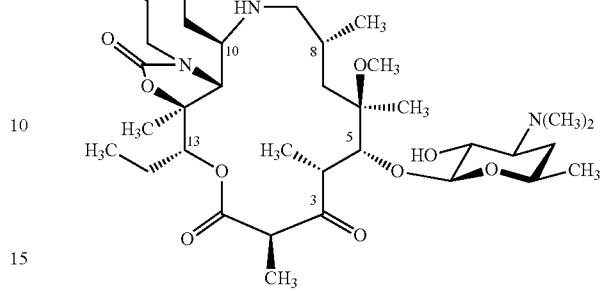
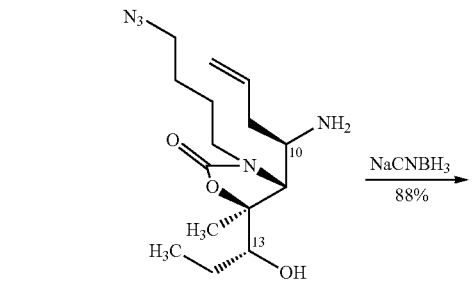
Example III-14A. Coupling by Reductive Amination
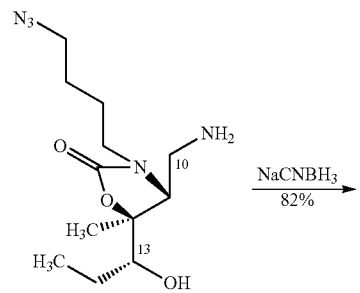
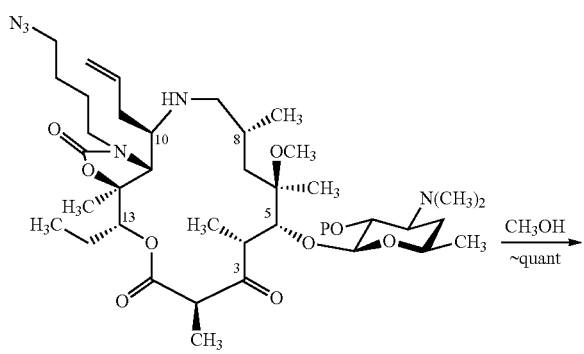
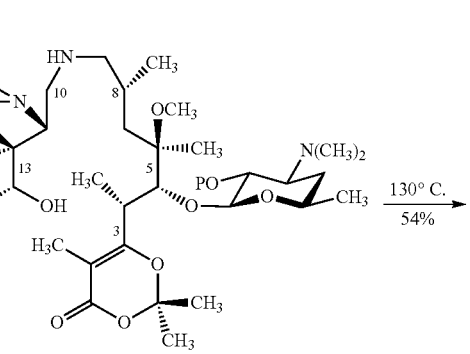

599
-continued
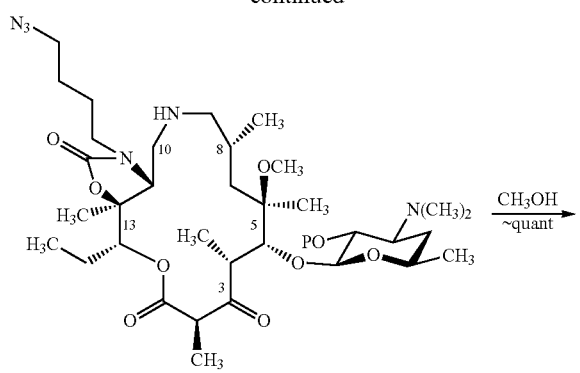
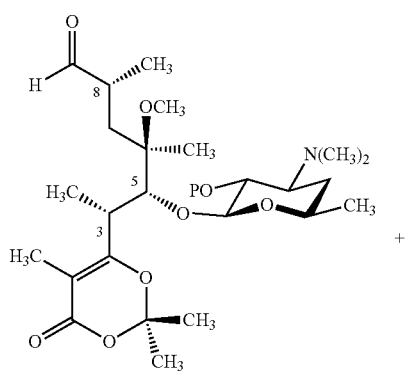
Example III-15A. Coupling by Reductive Amination
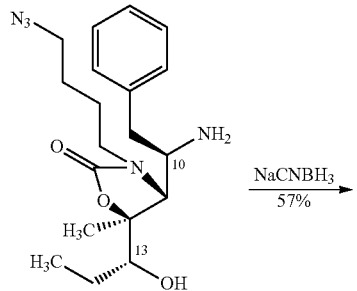
(P = CO₂CH₃)
600
-continued
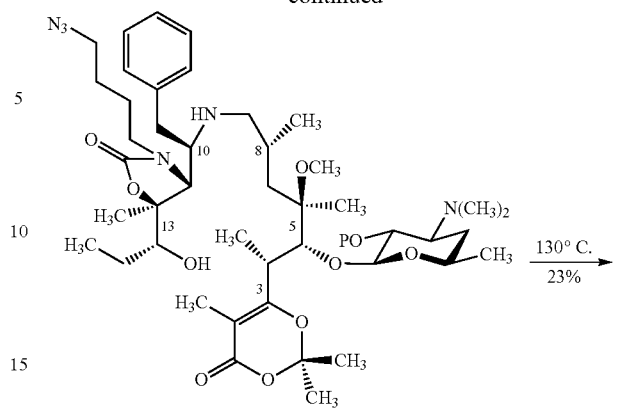
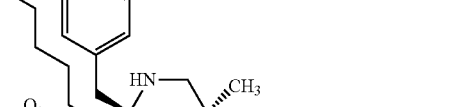
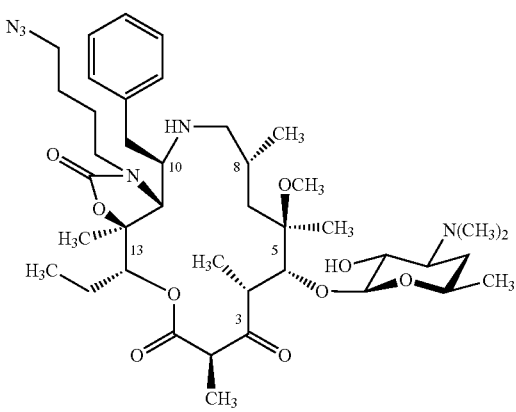

601
Example III-16A. Coupling by Reductive Amination
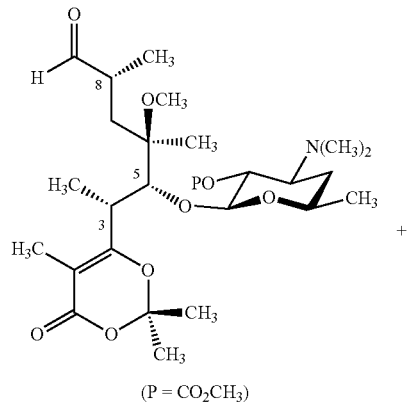
(P = CO₂CH₃)
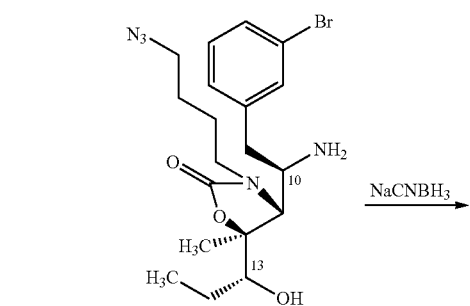
NaCNBH₃
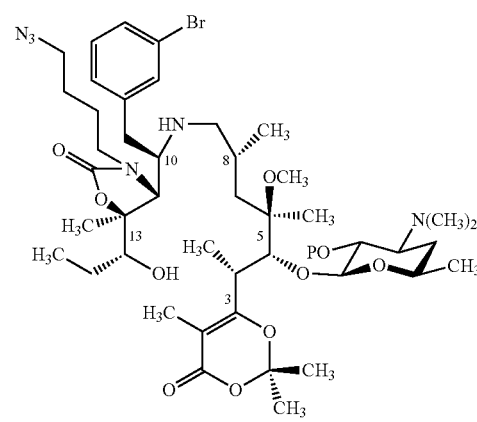
130° C.
36%,
2 steps
→
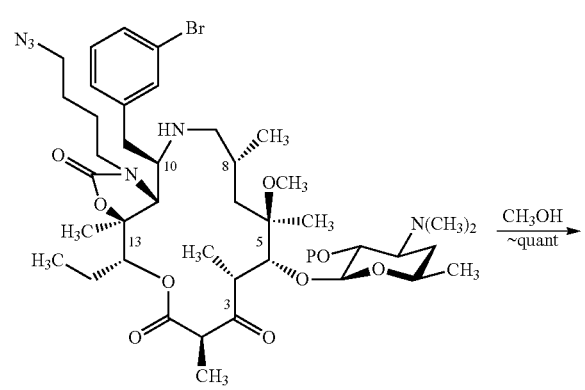
CH₃OH
~quant
→
602
-continued
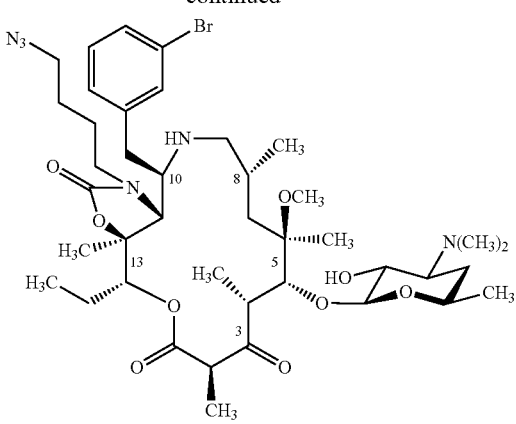
Example III-17A. Coupling by Reductive Amination
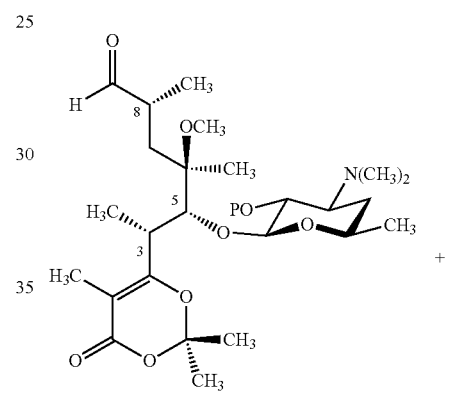
(P = CO₂CH₃)
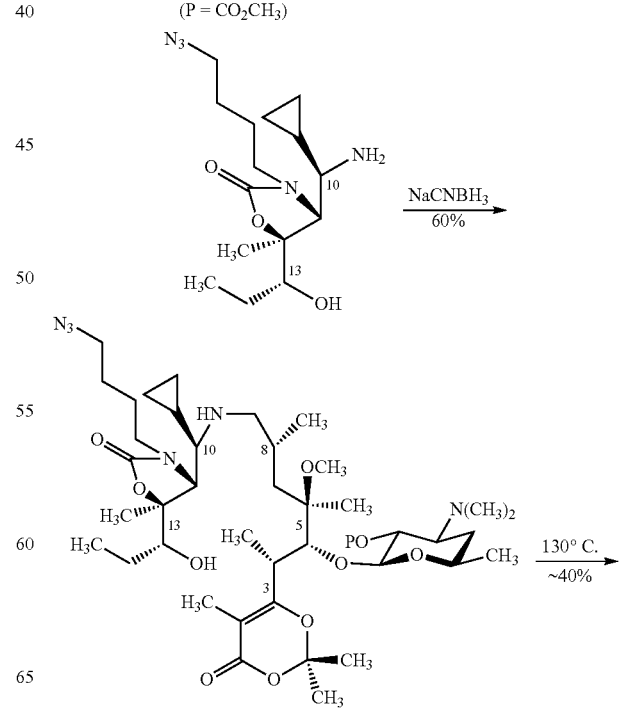
NaCNBH₃
60%
→
130° C.
~40%
→

603
-continued
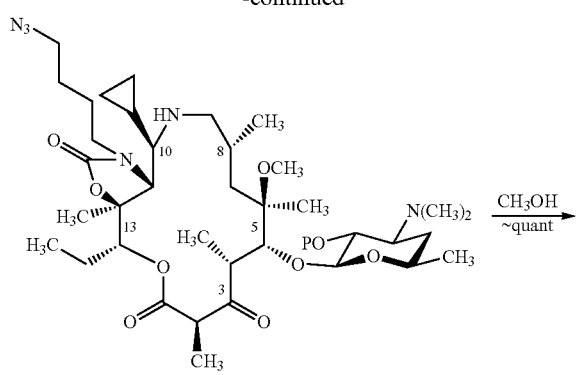
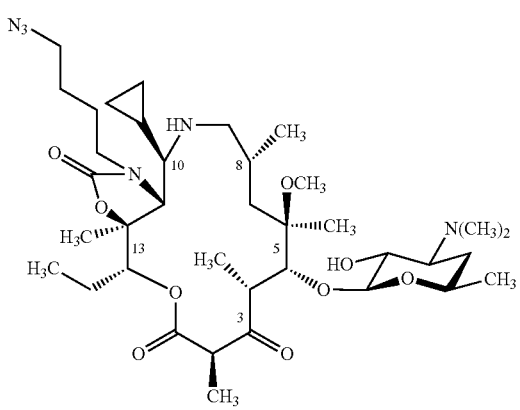
Example III-18A. Coupling by Reductive Amination
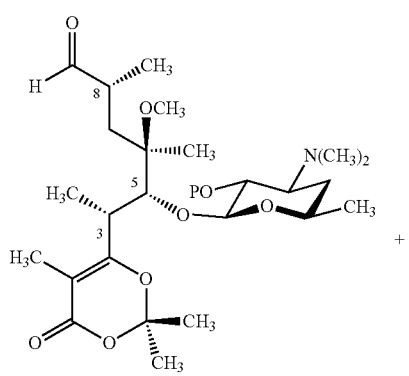
(P = CO₂CH₃)
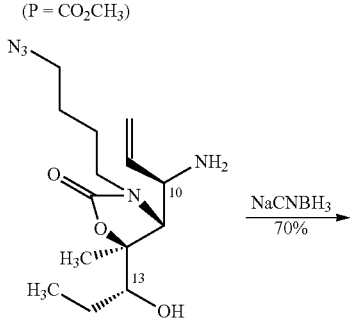
604
-continued
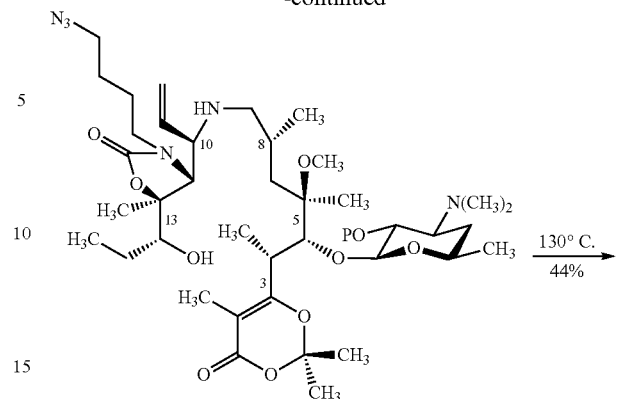
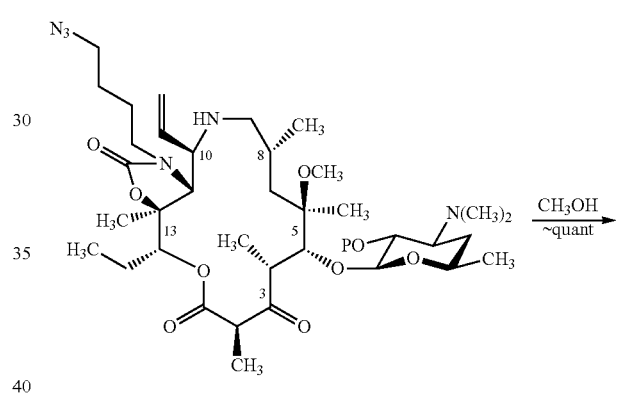
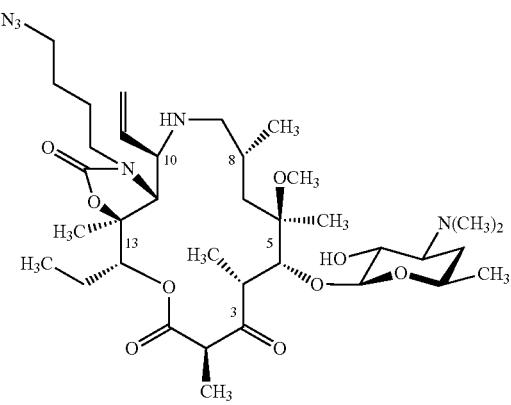

Example III-19A. Coupling by Reductive Amination
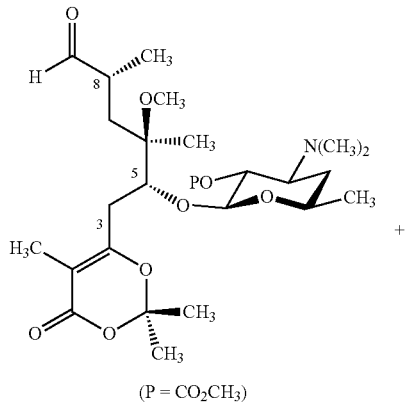
(P = CO$_2$CH$_3$)
+
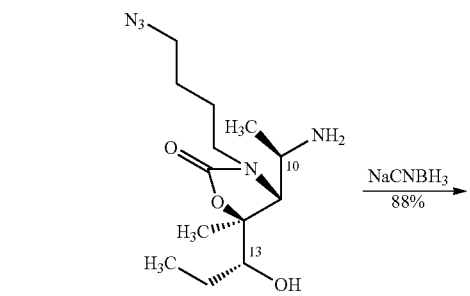 $\xrightarrow{\text{NaCNBH}_3}{88\%}$
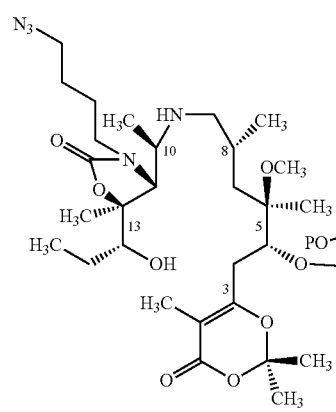 $\xrightarrow[92\%]{110°\text{ C.}}$
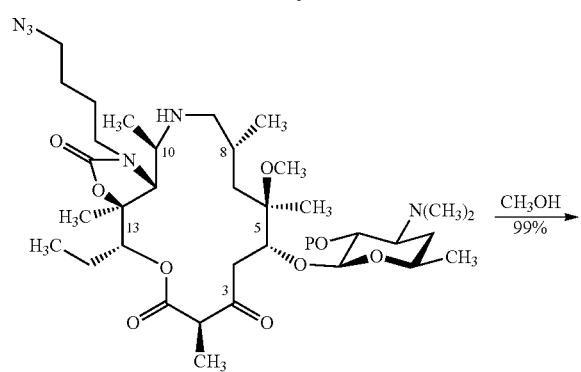 $\xrightarrow[99\%]{\text{CH}_3\text{OH}}$
-continued
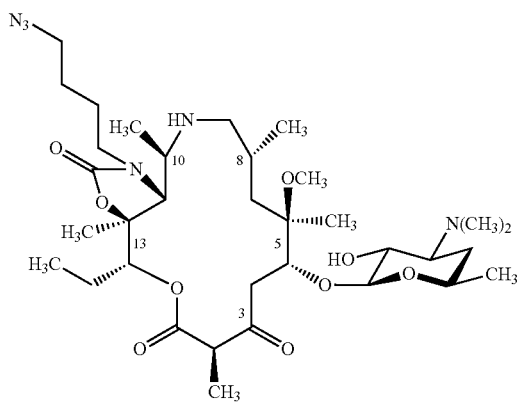
Example III-20A. Coupling by Reductive Amination
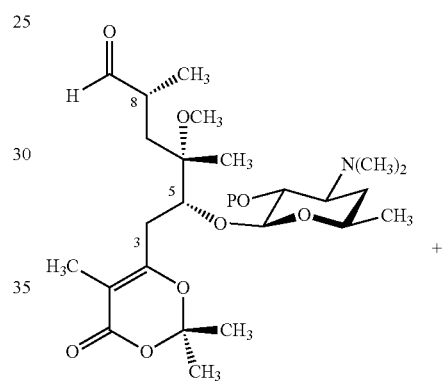
(P = CO$_2$CH$_3$)
+
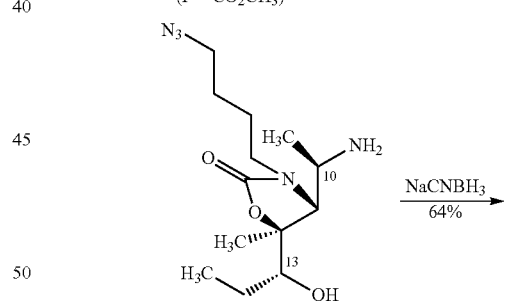 $\xrightarrow{\text{NaCNBH}_3}{64\%}$
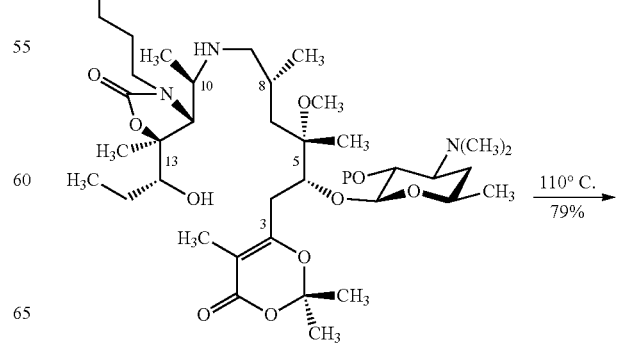 $\xrightarrow[79\%]{110°\text{ C.}}$

607
-continued
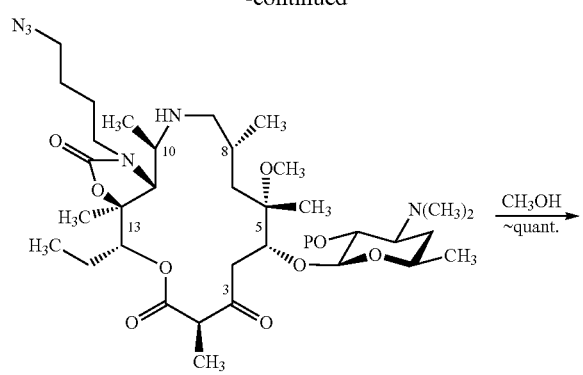
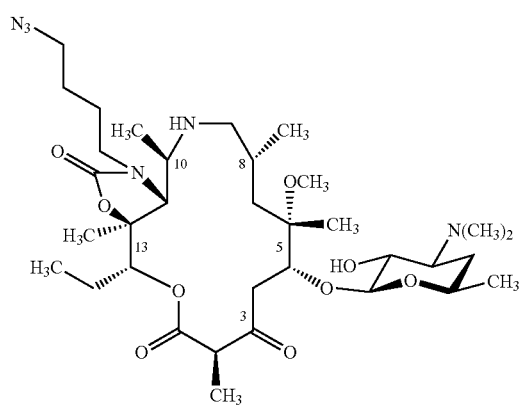
Example III-21A. Coupling by Reductive Amination
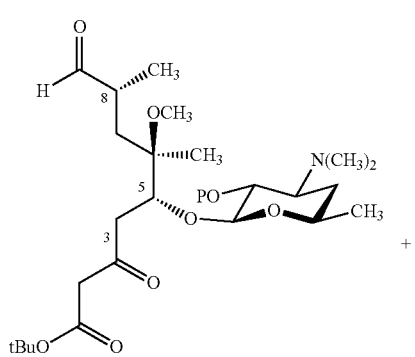
(P = CO₂CH₃)
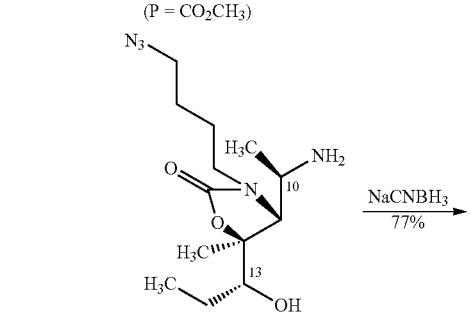
608
-continued
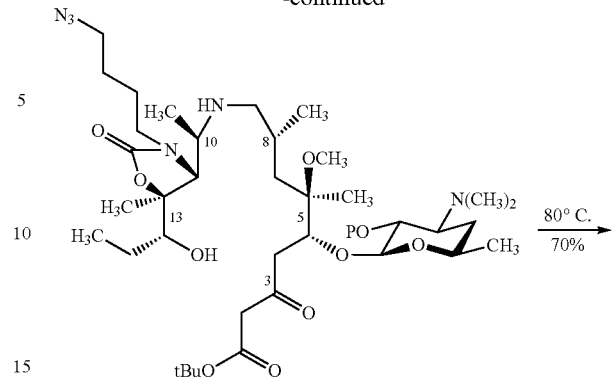
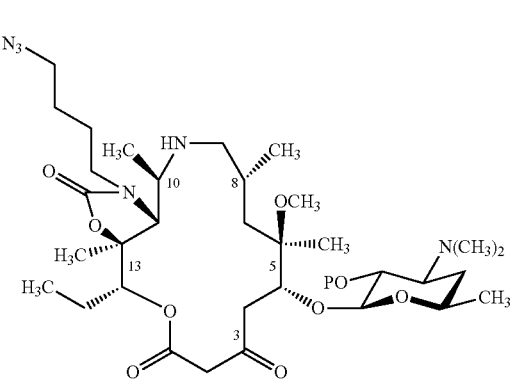
Example III-22A. Coupling by Reductive Amination
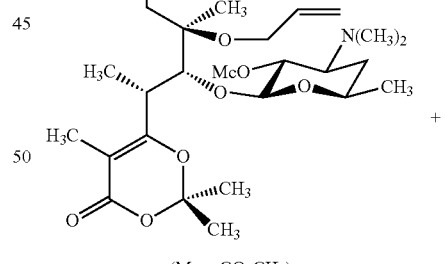
(Mc = CO₂CH₃)
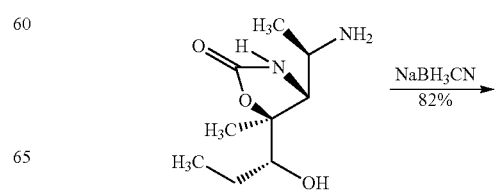

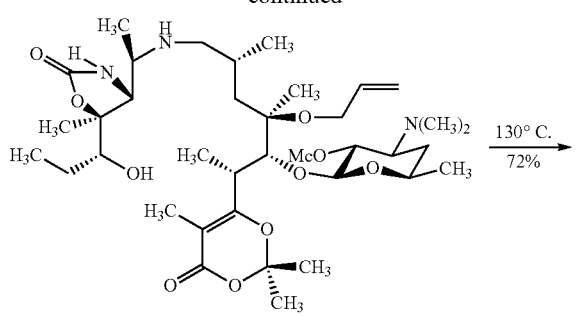
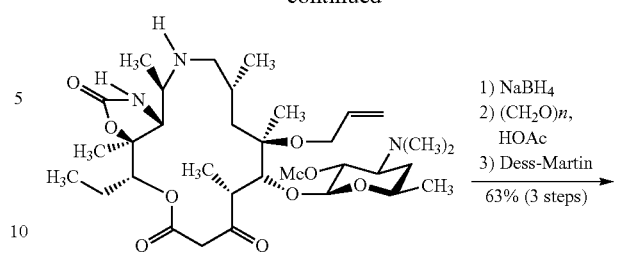
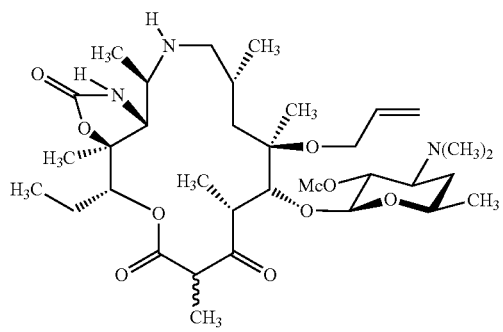
3:1 inseparable mixture
Example III-23A. Coupling by Reductive Amination
Example III-24A. Coupling by Reductive Amination
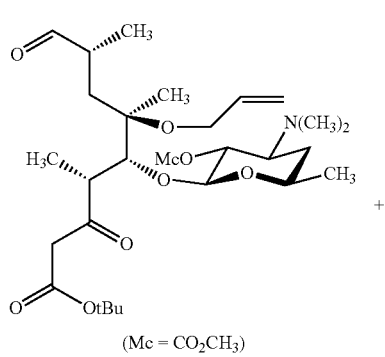
(Mc = CO₂CH₃)
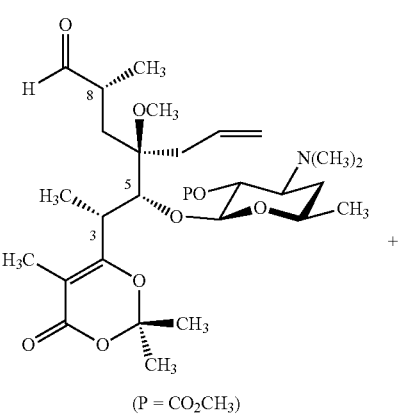
(P = CO₂CH₃)
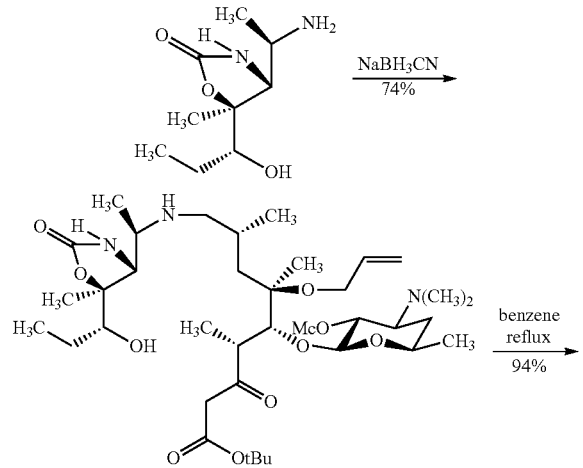
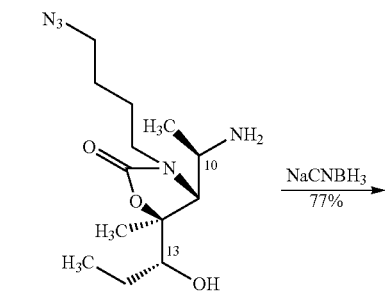

611
-continued
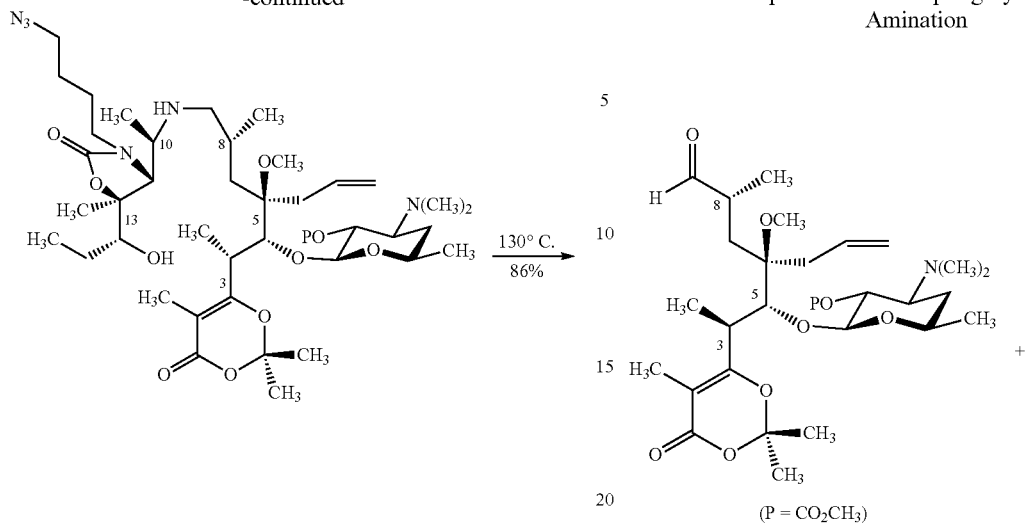
612
Example III-25A. Coupling by Reductive Amination
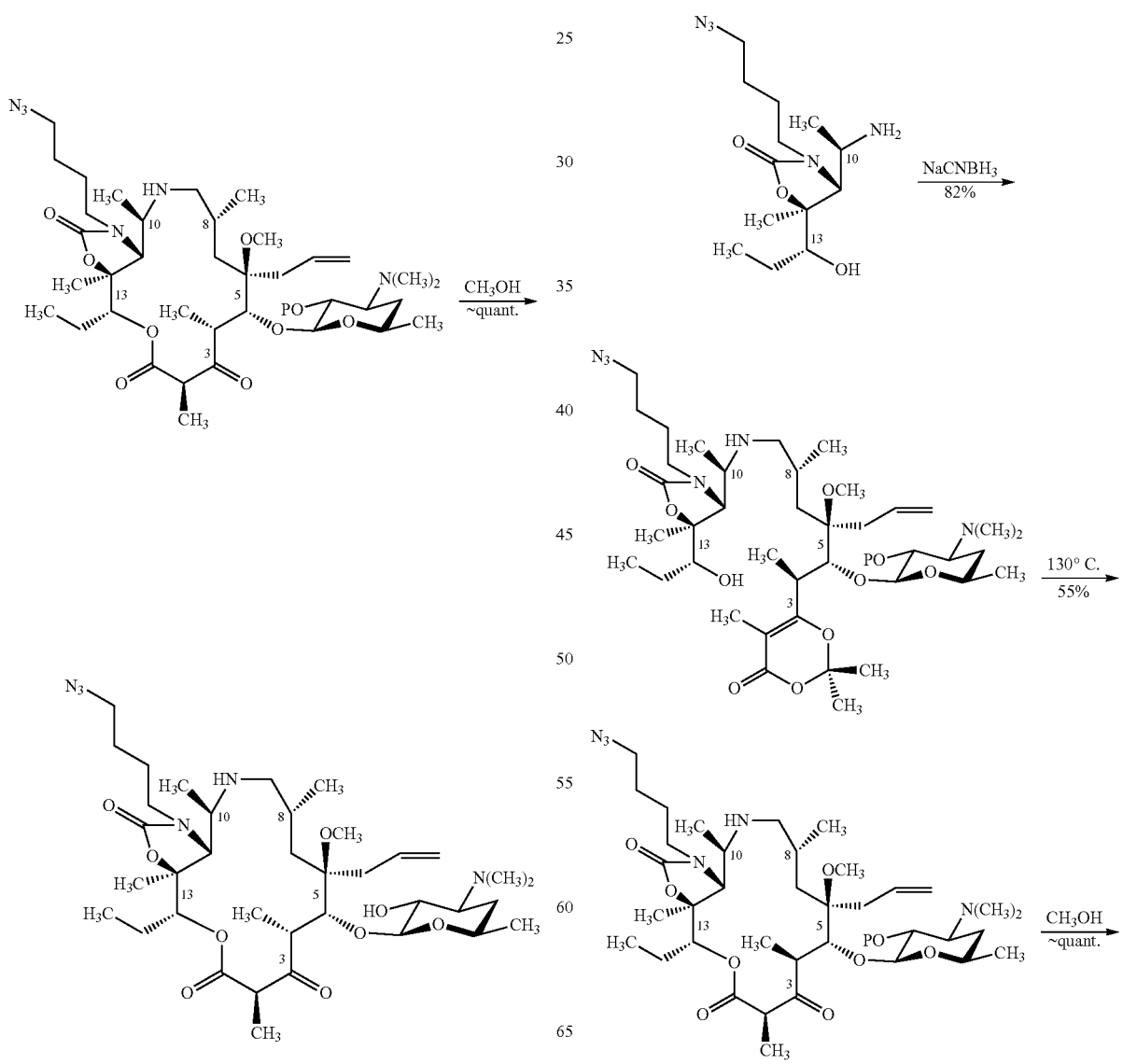

613
-continued
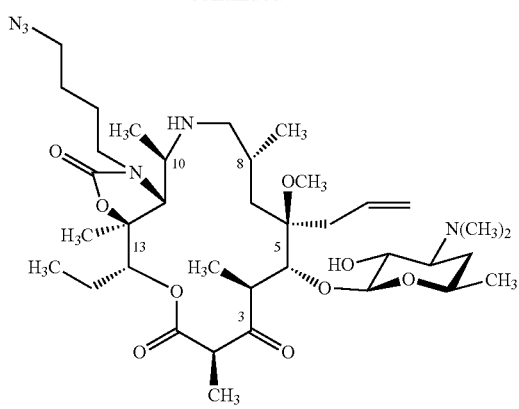
Example III-26A. Coupling by Reductive Amination
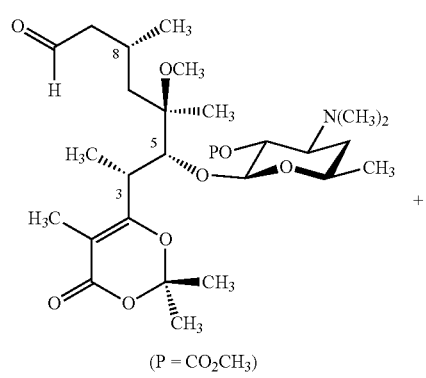
(P = CO₂CH₃)
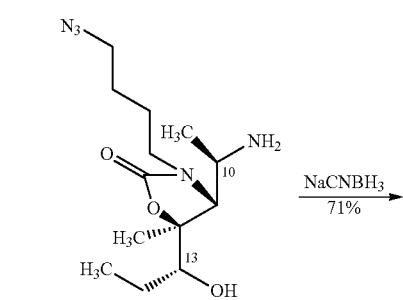
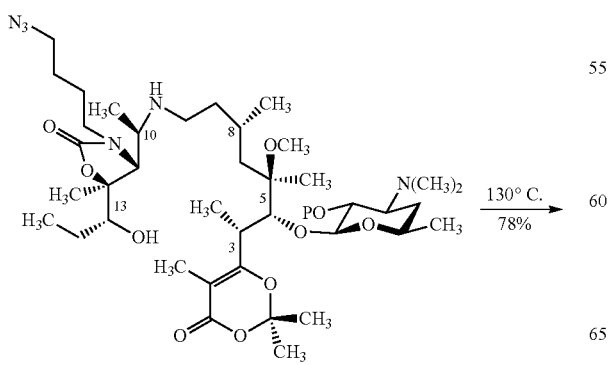
614
-continued
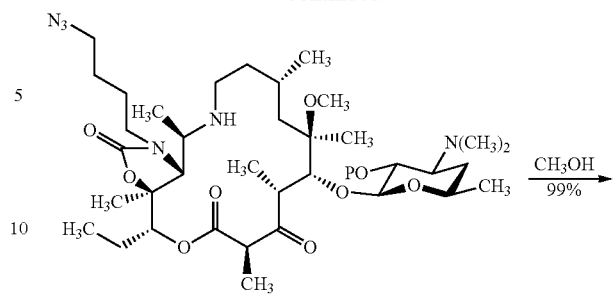
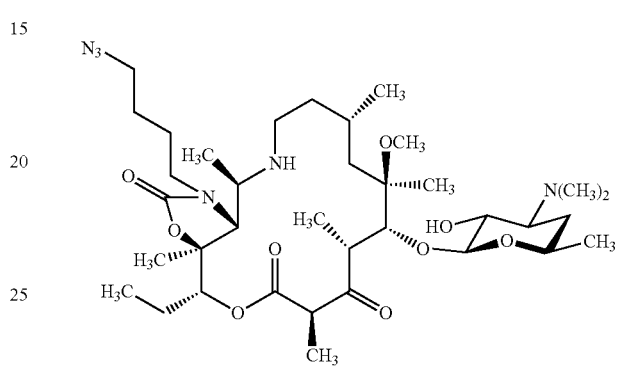
Example III-27A. Coupling by Reductive Amination
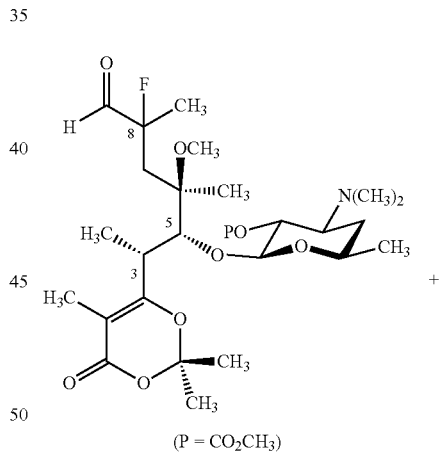
(P = CO₂CH₃)
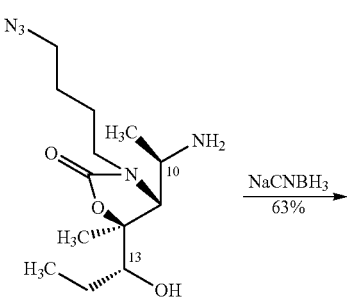

615
-continued
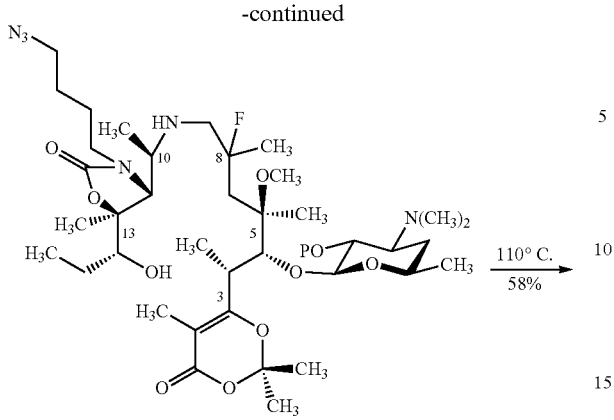
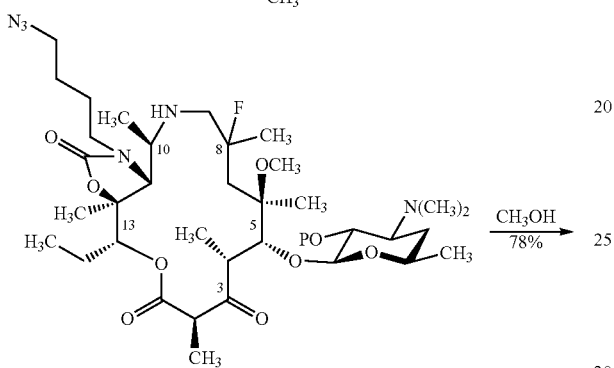
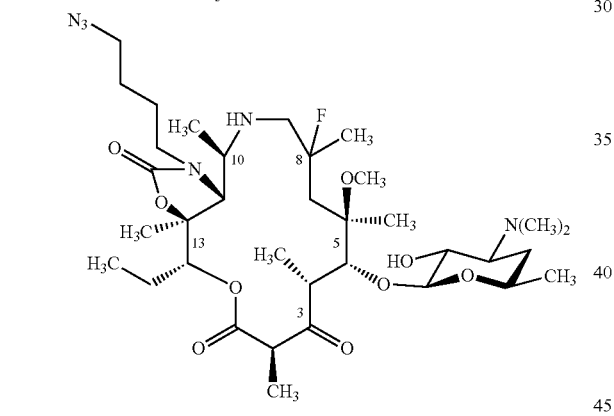
Example III-28A. Coupling by Reductive Amination
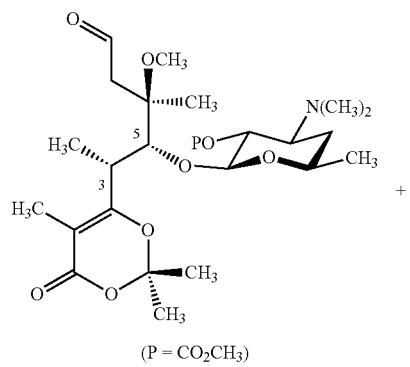
(P = CO₂CH₃)
616
-continued
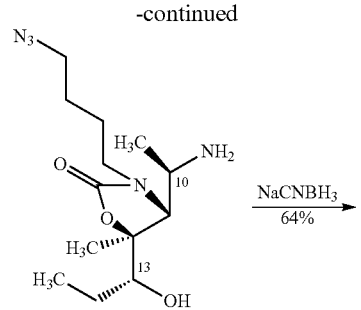
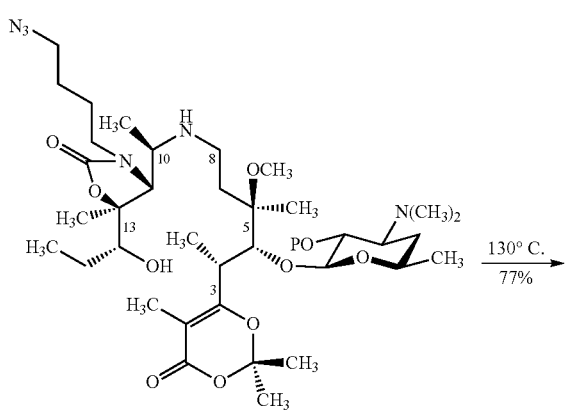
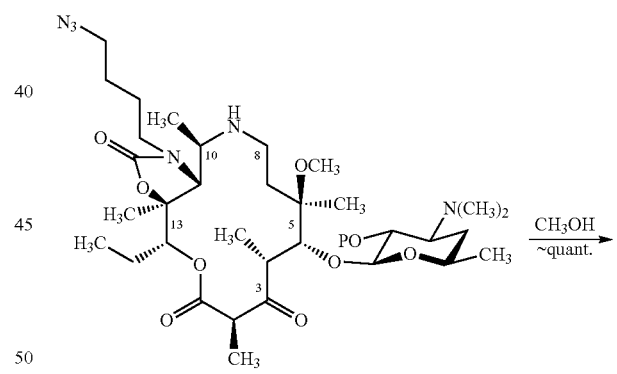
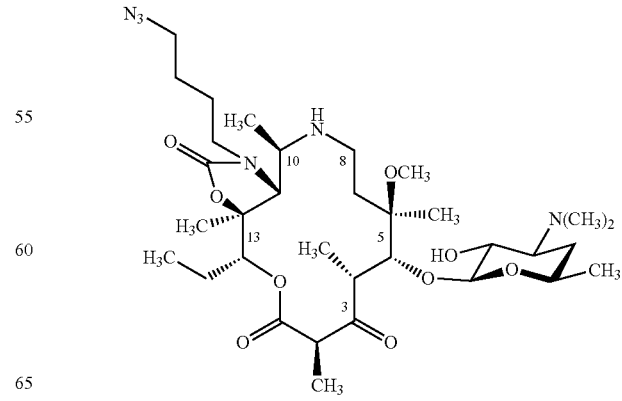

Example III-29A. Coupling by Reductive Amination
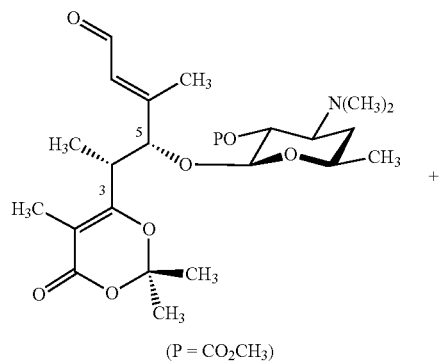
(P = CO₂CH₃)
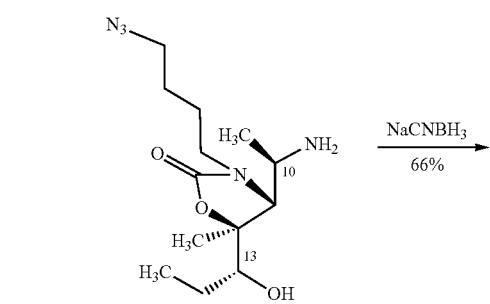
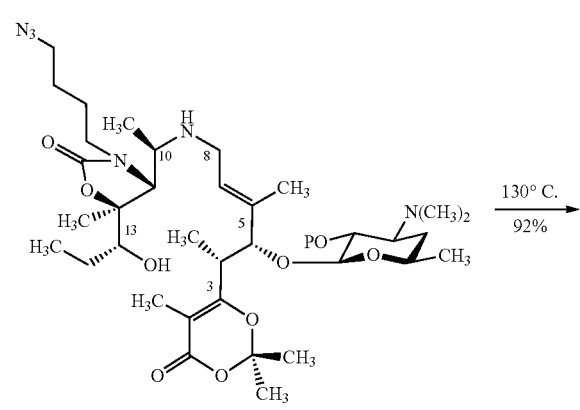
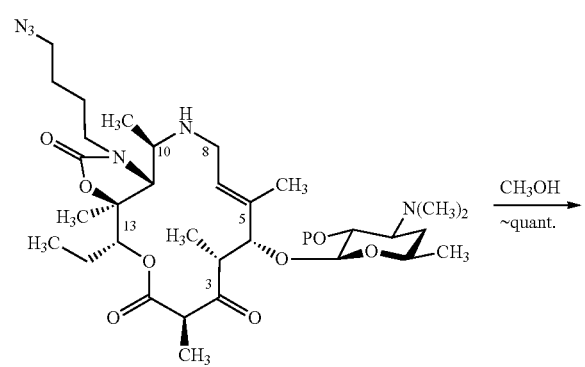
-continued
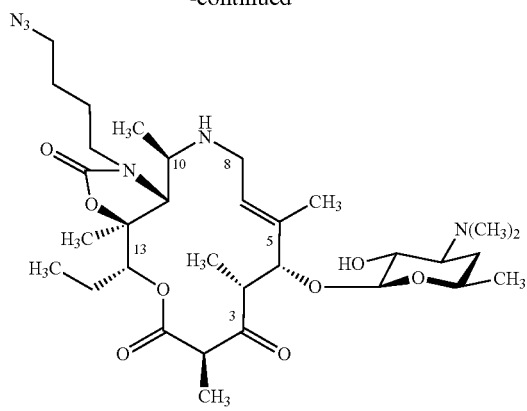
Example III-30A. Coupling by Reductive Amination
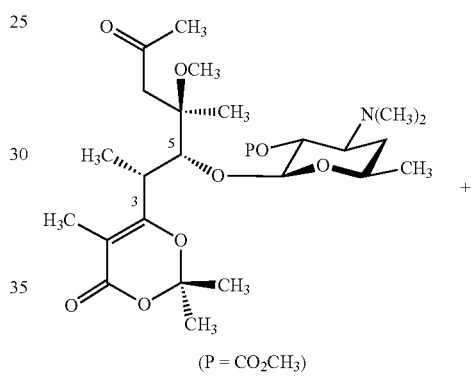
(P = CO₂CH₃)
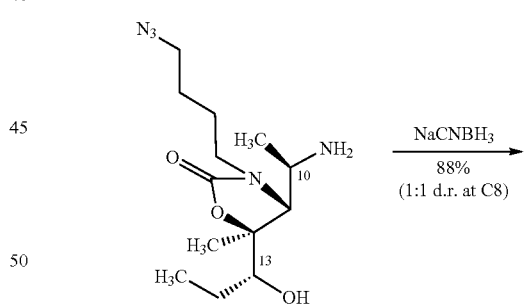
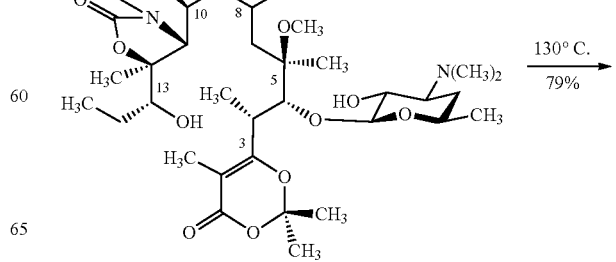

619
-continued
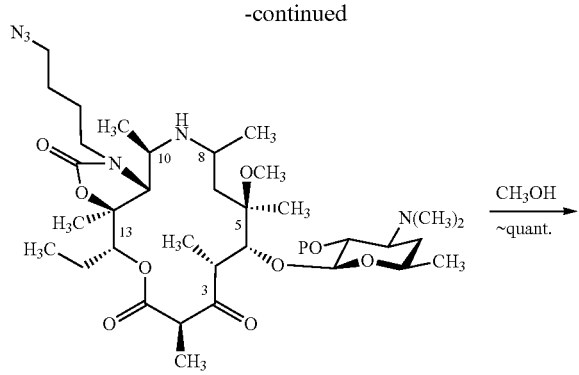
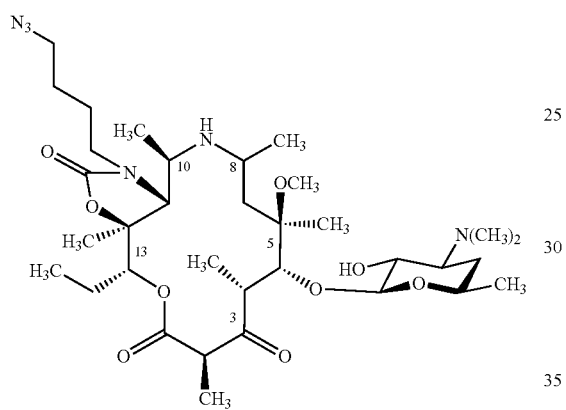
Example III-31A. Coupling by Reductive Amination
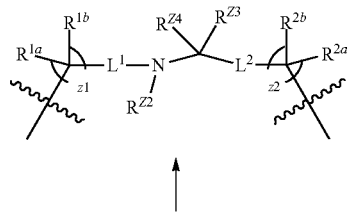
620
-continued
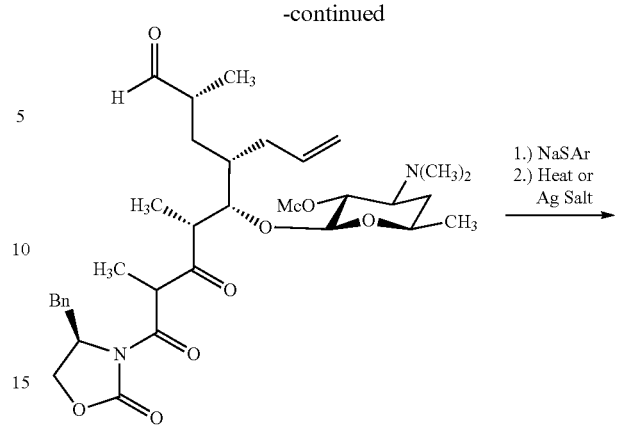
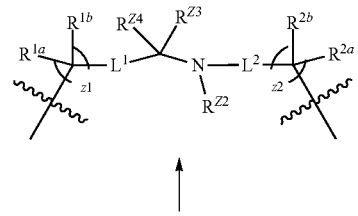
Imine Formation
Scheme III-B.
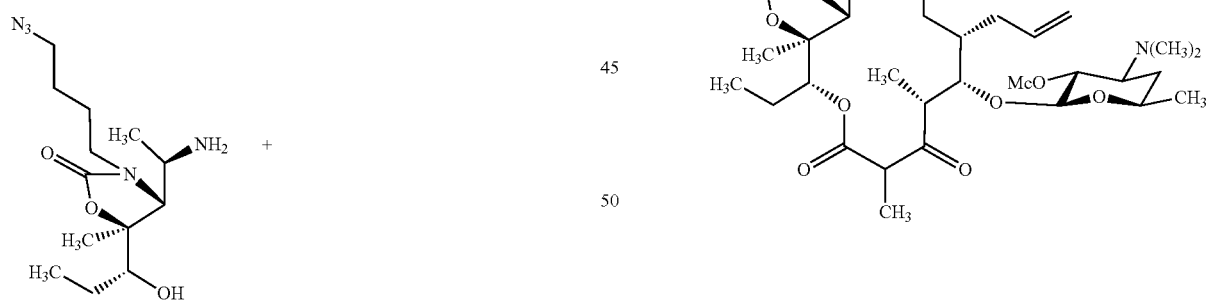

621
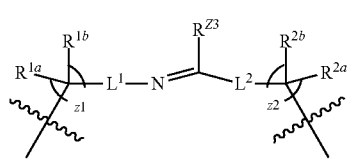
-continued
azaketolides
imine formation,
and optional alkylation
622
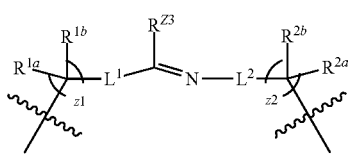
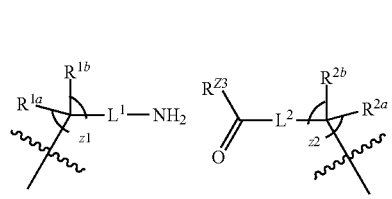
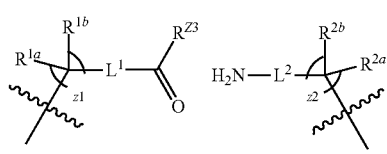
Example III-1B. Coupling by Imine Formation,
Followed by Alkylation of the Imine
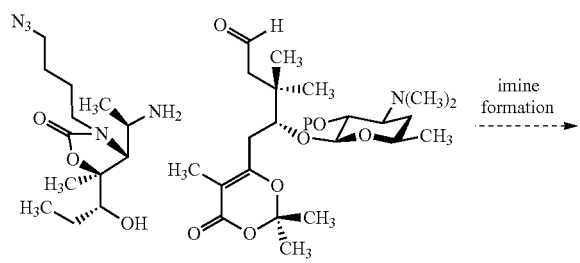
-continued
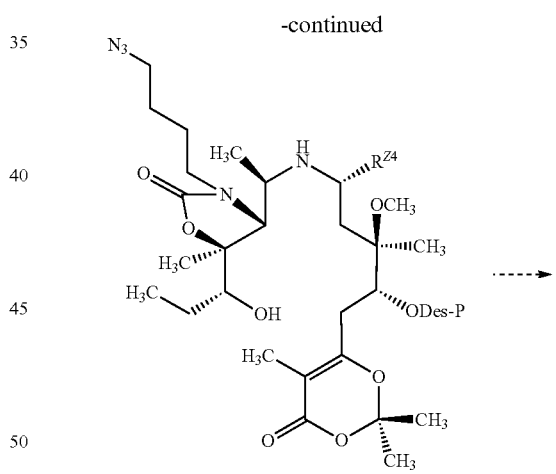
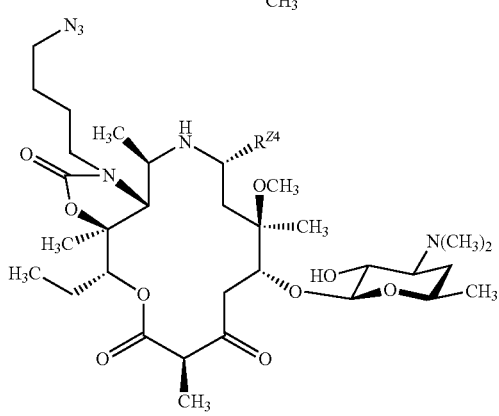

Nucleophilic Displacement
Scheme III-C.
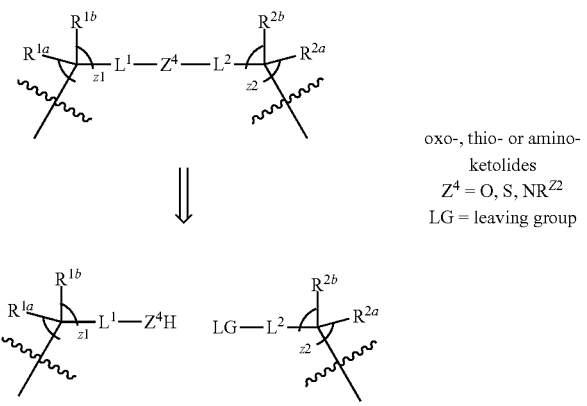
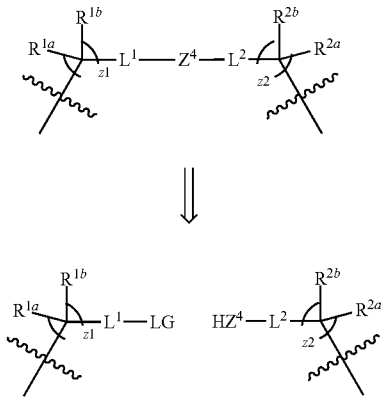
oxo-, thio- or amino-ketolides
$Z^4$ = O, S, $NR^{Z2}$
LG = leaving group
Example III-1C. Coupling by Nucleophilic Displacement
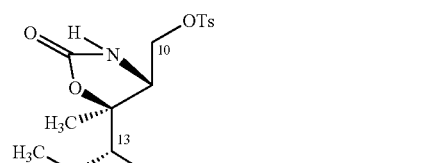
or
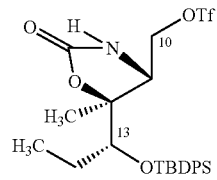
+
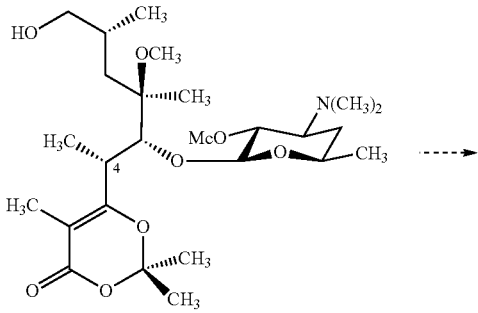
$\xrightarrow{\Delta}$
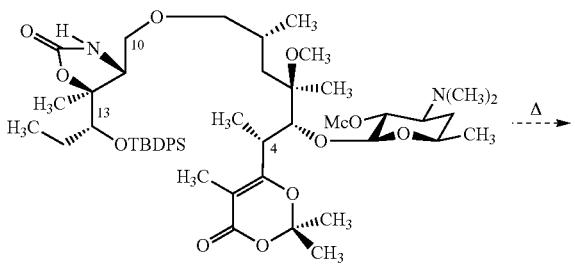
-continued
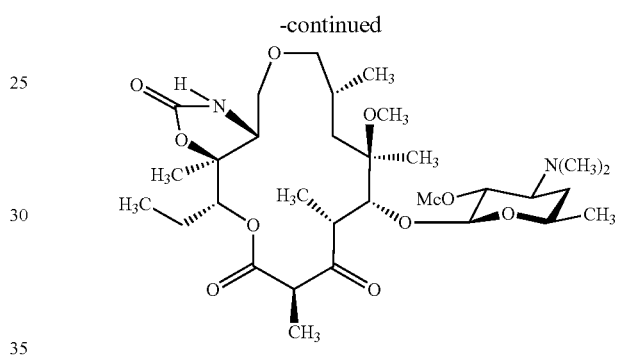
Example III-2C. Coupling by Nucleophilic Displacement
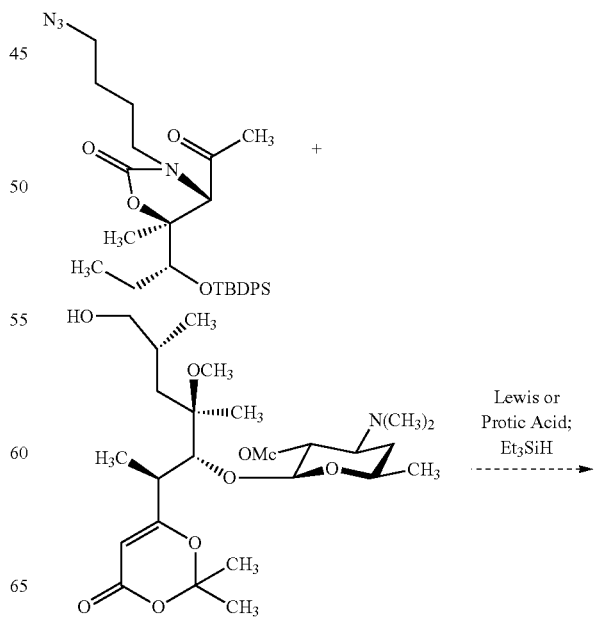
$\xrightarrow{\text{Lewis or Protic Acid;}}_{\text{Et}_3\text{SiH}}$

625
-continued
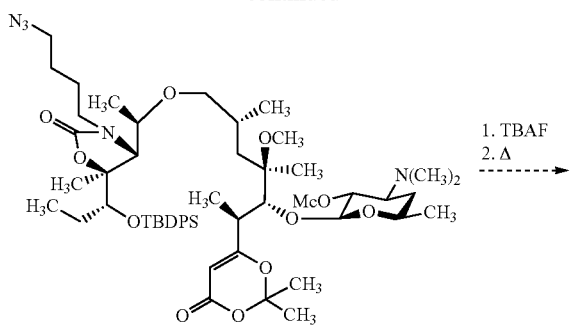
626
-continued
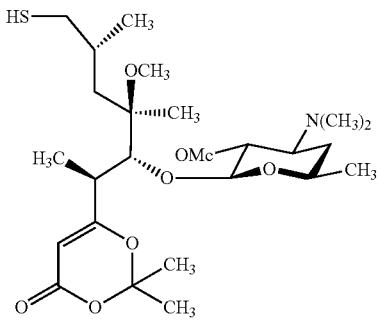
1. TBAF
2. Δ
Lewis or
Protic Acid;
Et₃SiH
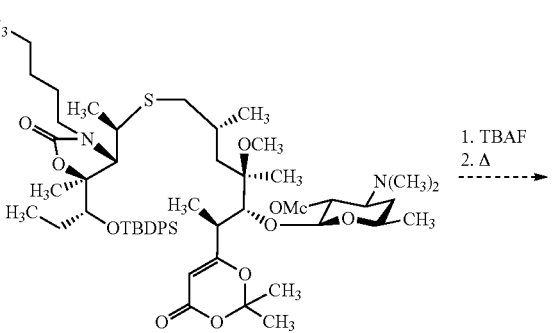
1. TBAF
2. Δ
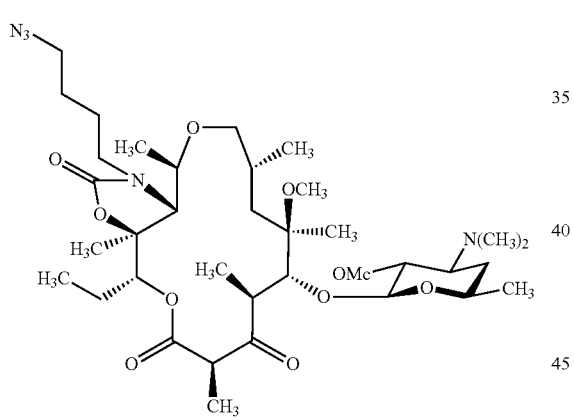
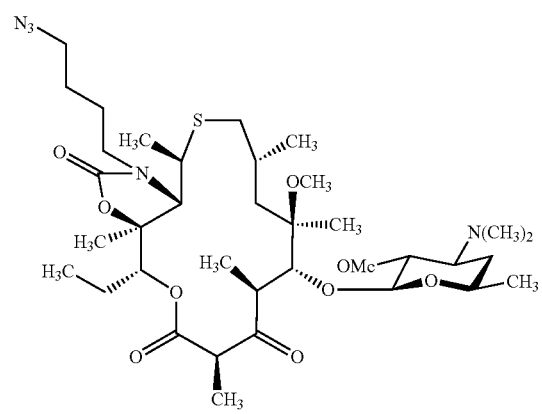
Example III-3C. Coupling by Nucleophilic Displacement
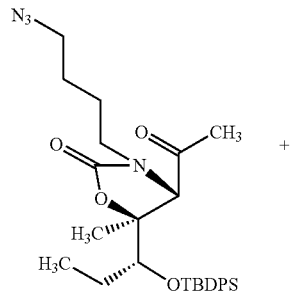 +

627
628
Nucleophilic 1,2-Addition
Scheme III-D.
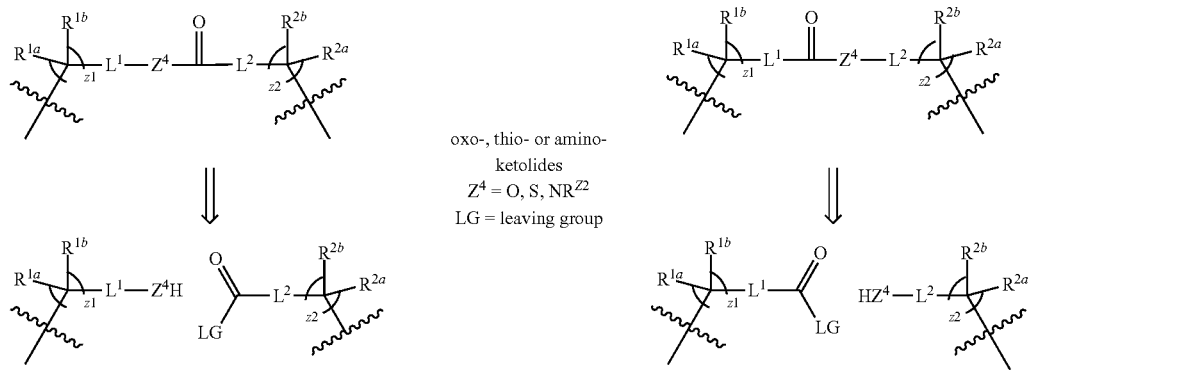
oxo-, thio- or amino-ketolides
$Z^4$ = O, S, $NR^{Z2}$
LG = leaving group
Example III-1D. Coupling by Ester Formation
-continued
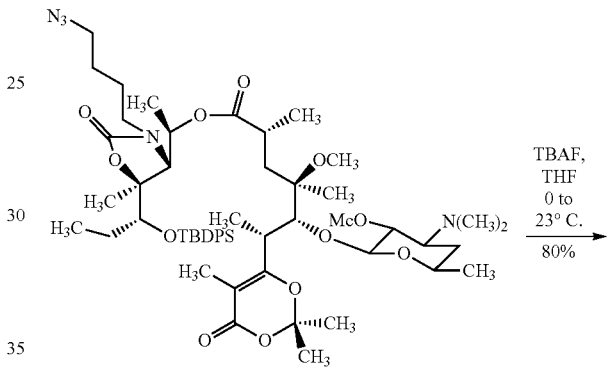
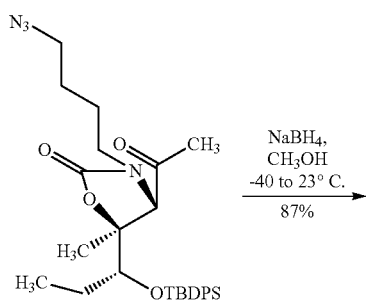
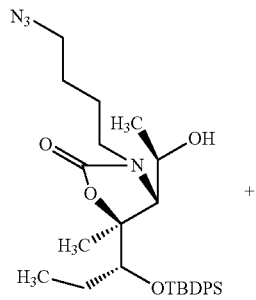
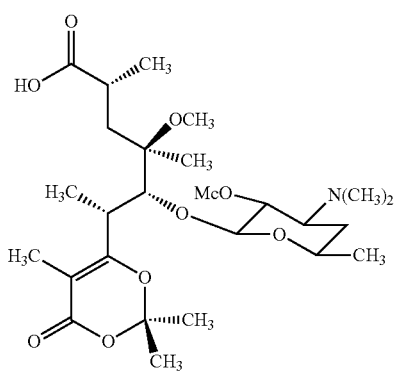
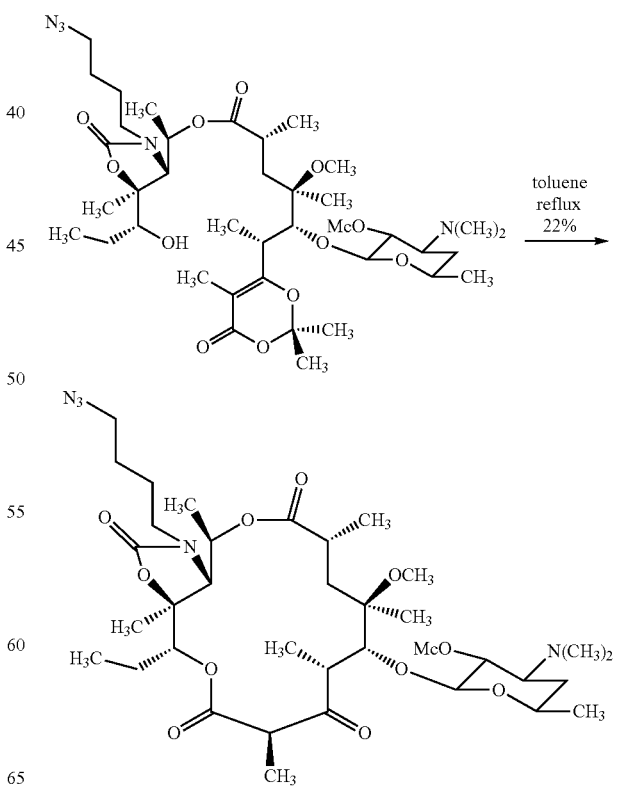

Example III-2D. Coupling by Ester Formation
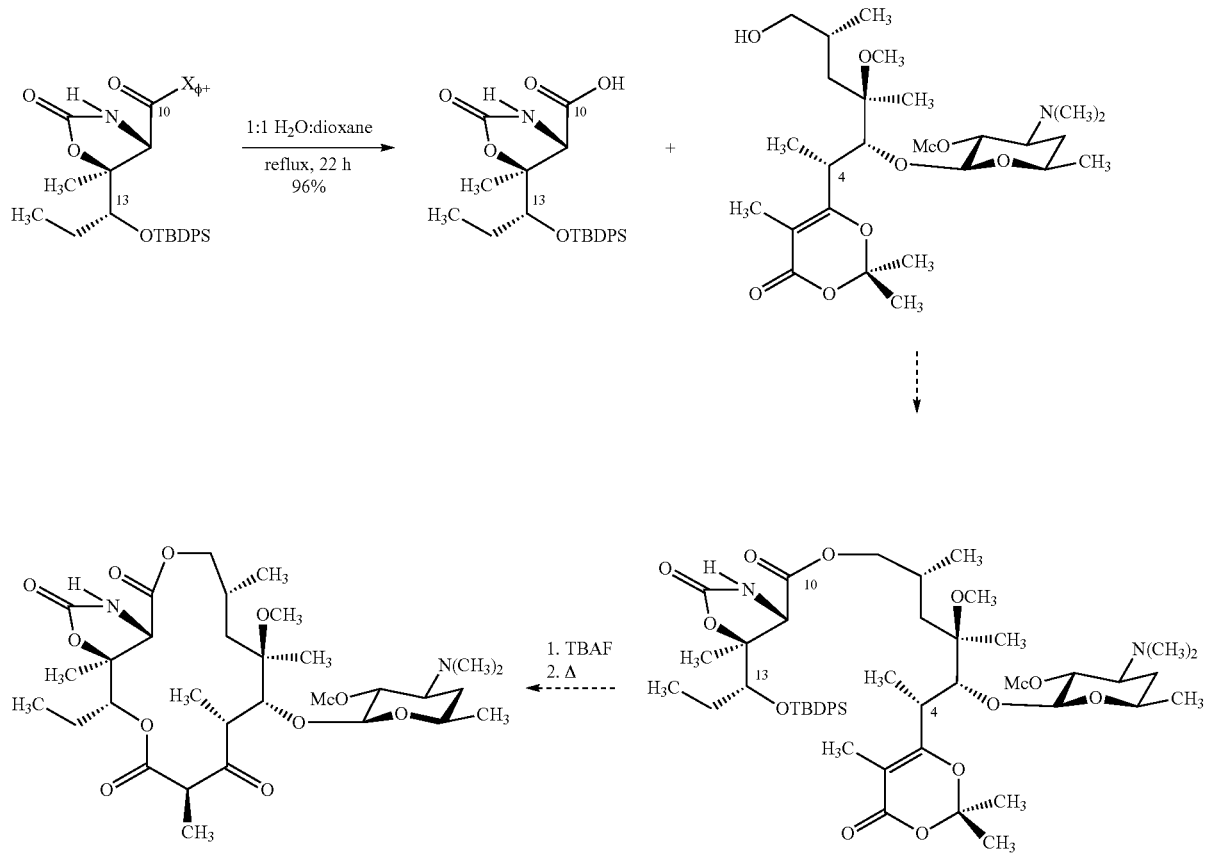
Example III-3D. Coupling by Amide Formation
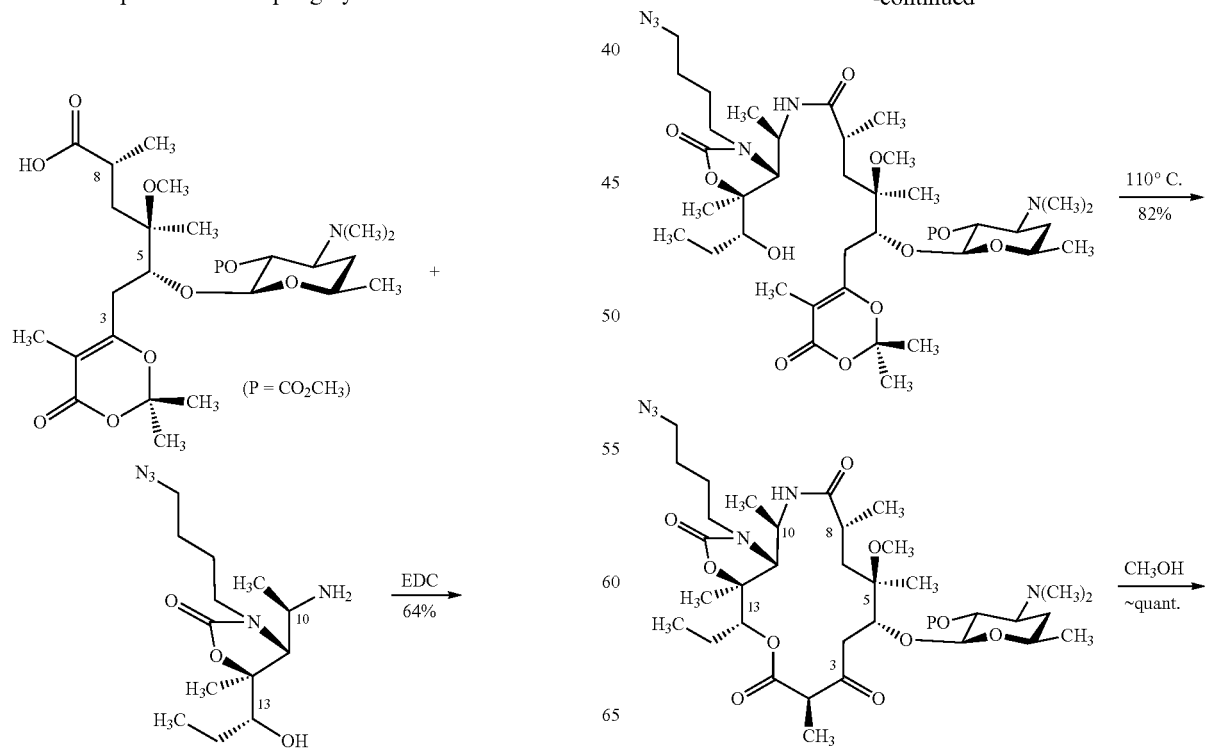

631
-continued
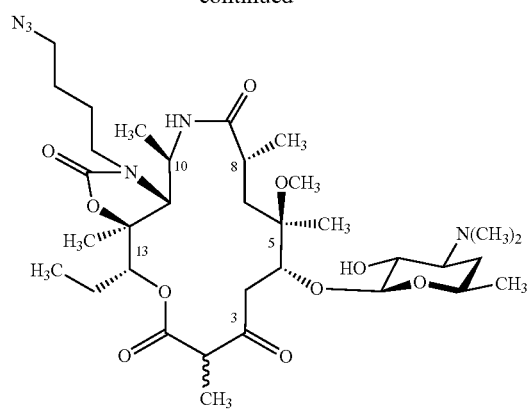
Example III-4D. Coupling by Amide Formation
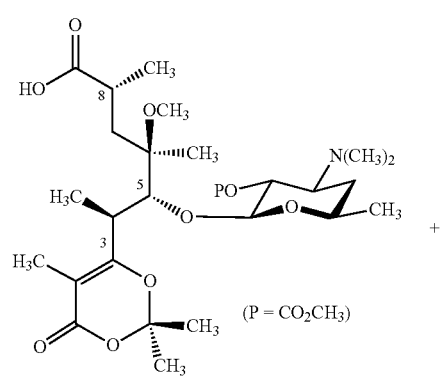
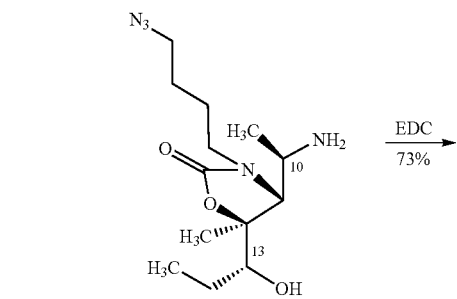
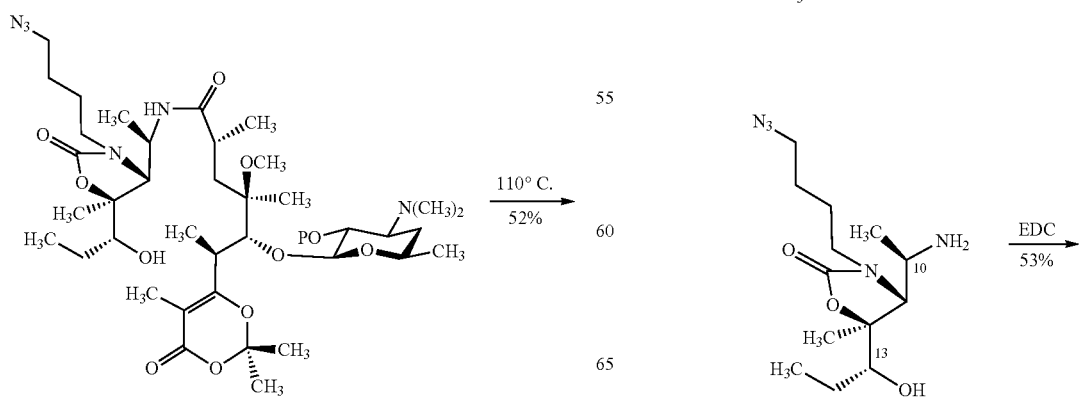
632
-continued
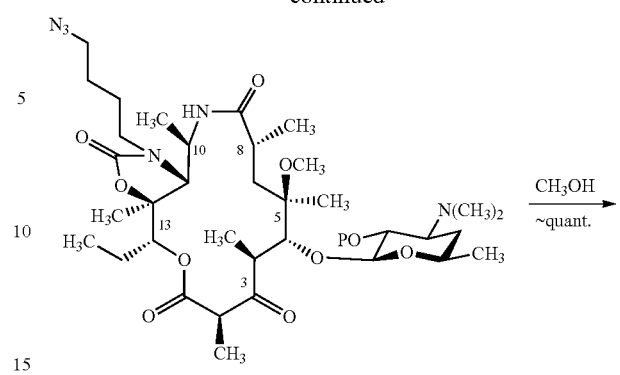
Example III-5D. Coupling by Amide Formation
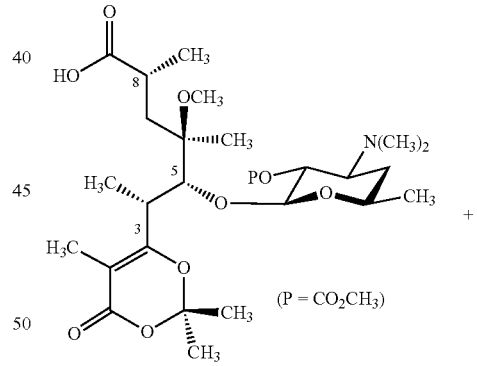

633
-continued
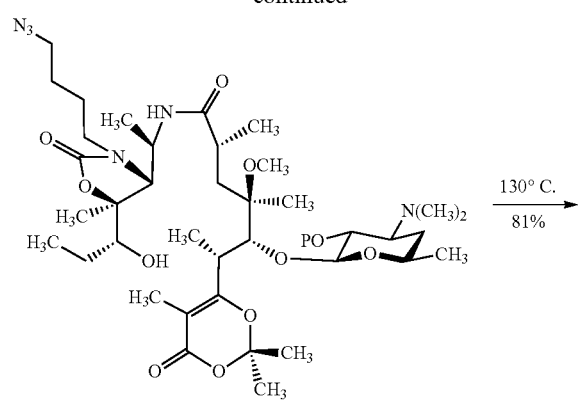
634
-continued
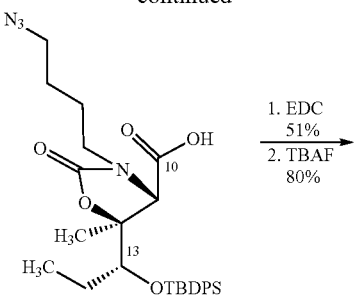
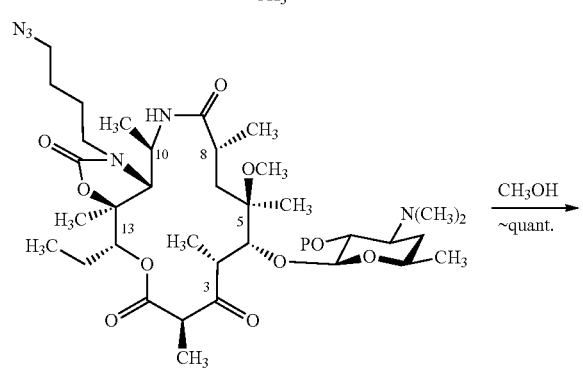
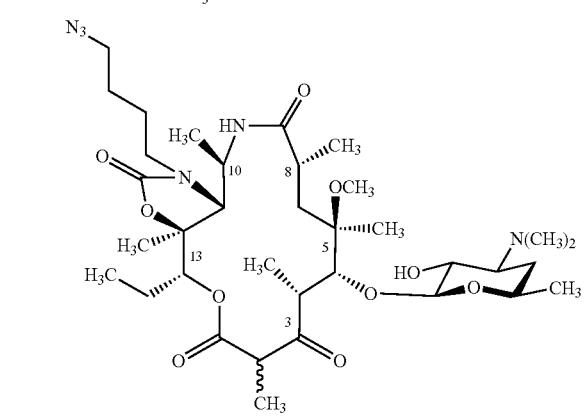
Example III-6D. Coupling by Amide Formation
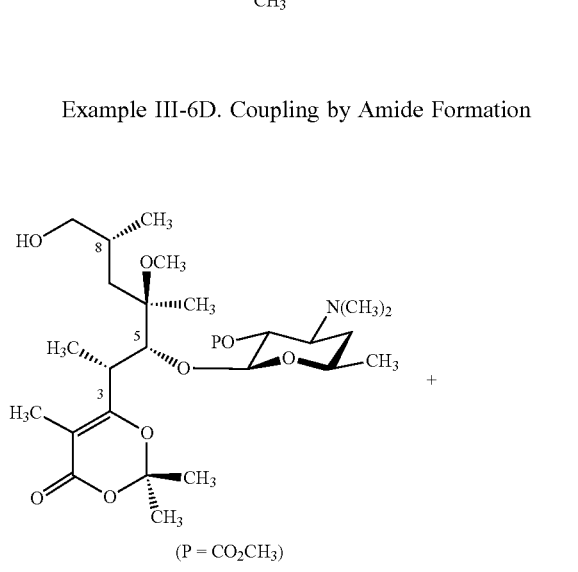
(P = CO₂CH₃)
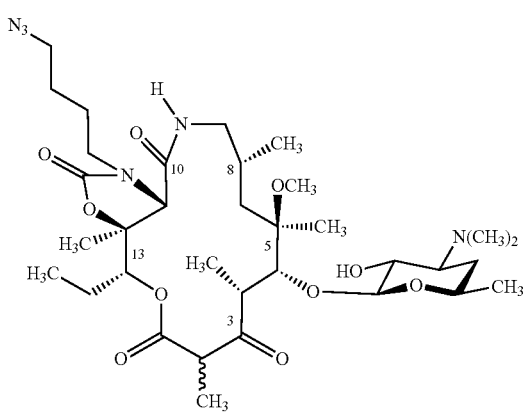

635
Nitro Aldol
Scheme III-E.
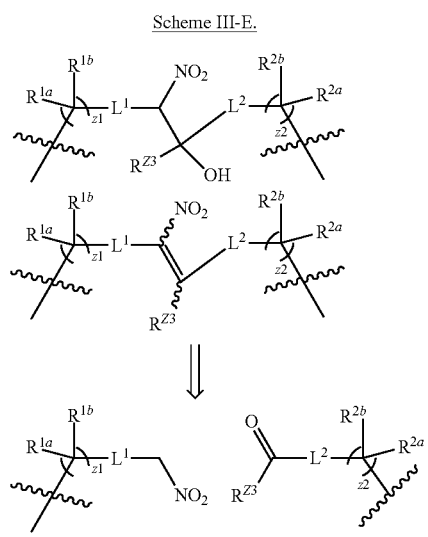
636
-continued
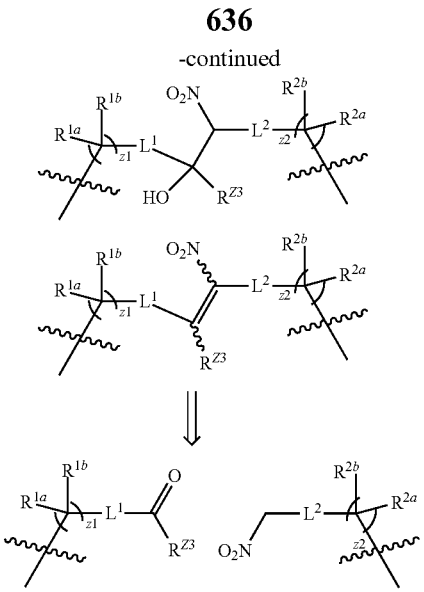
Example III-1E
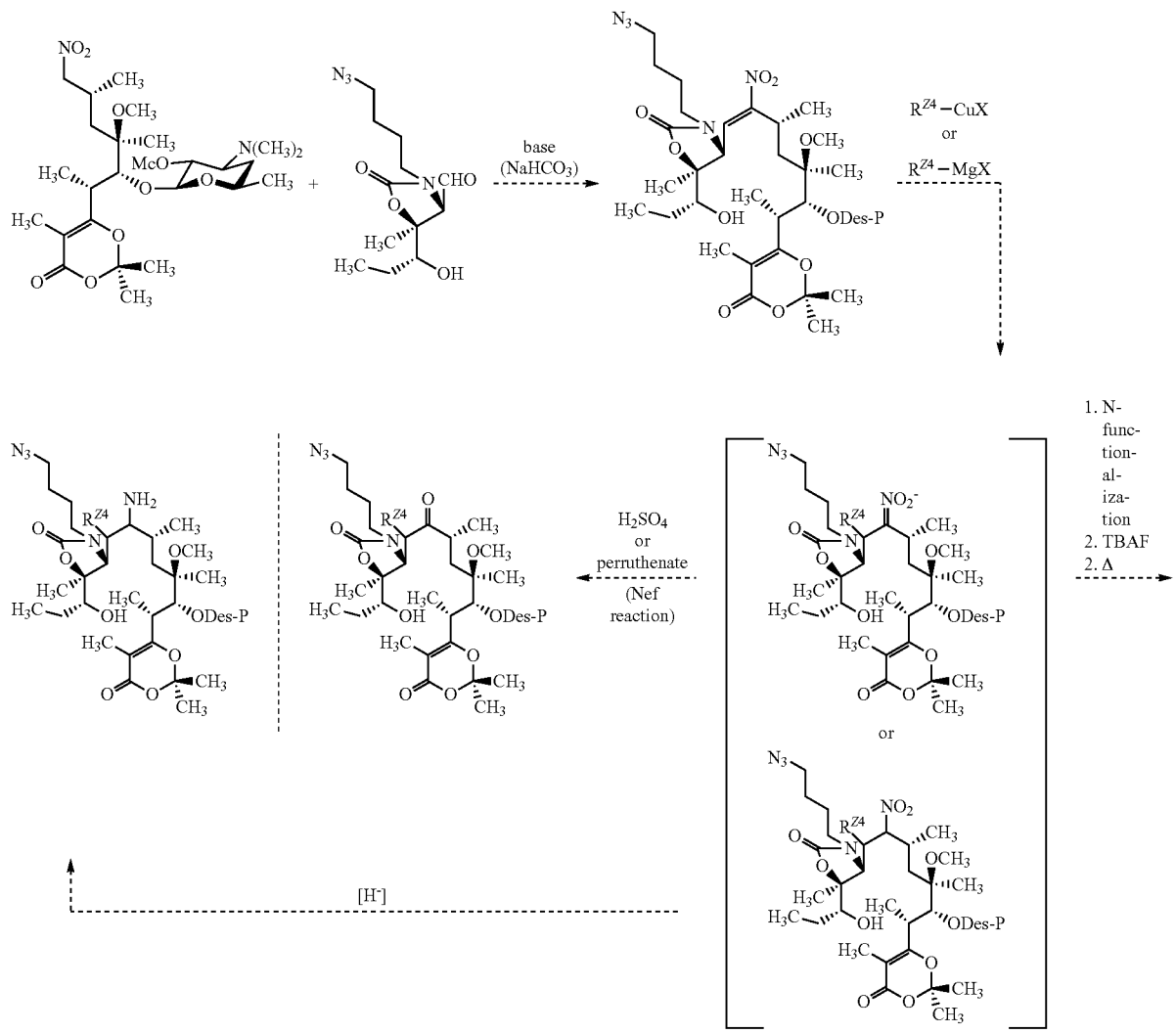

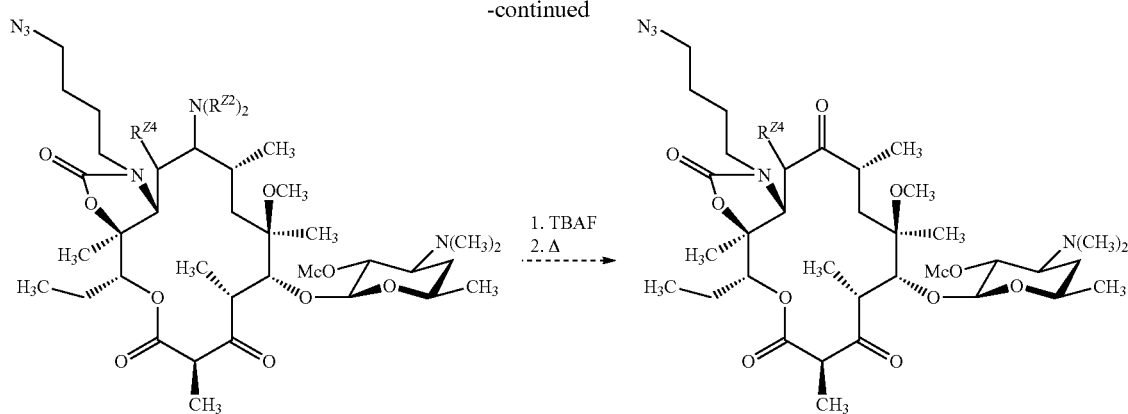
Wittig or Horner-Wadsworth-Emmons
Example III-1F
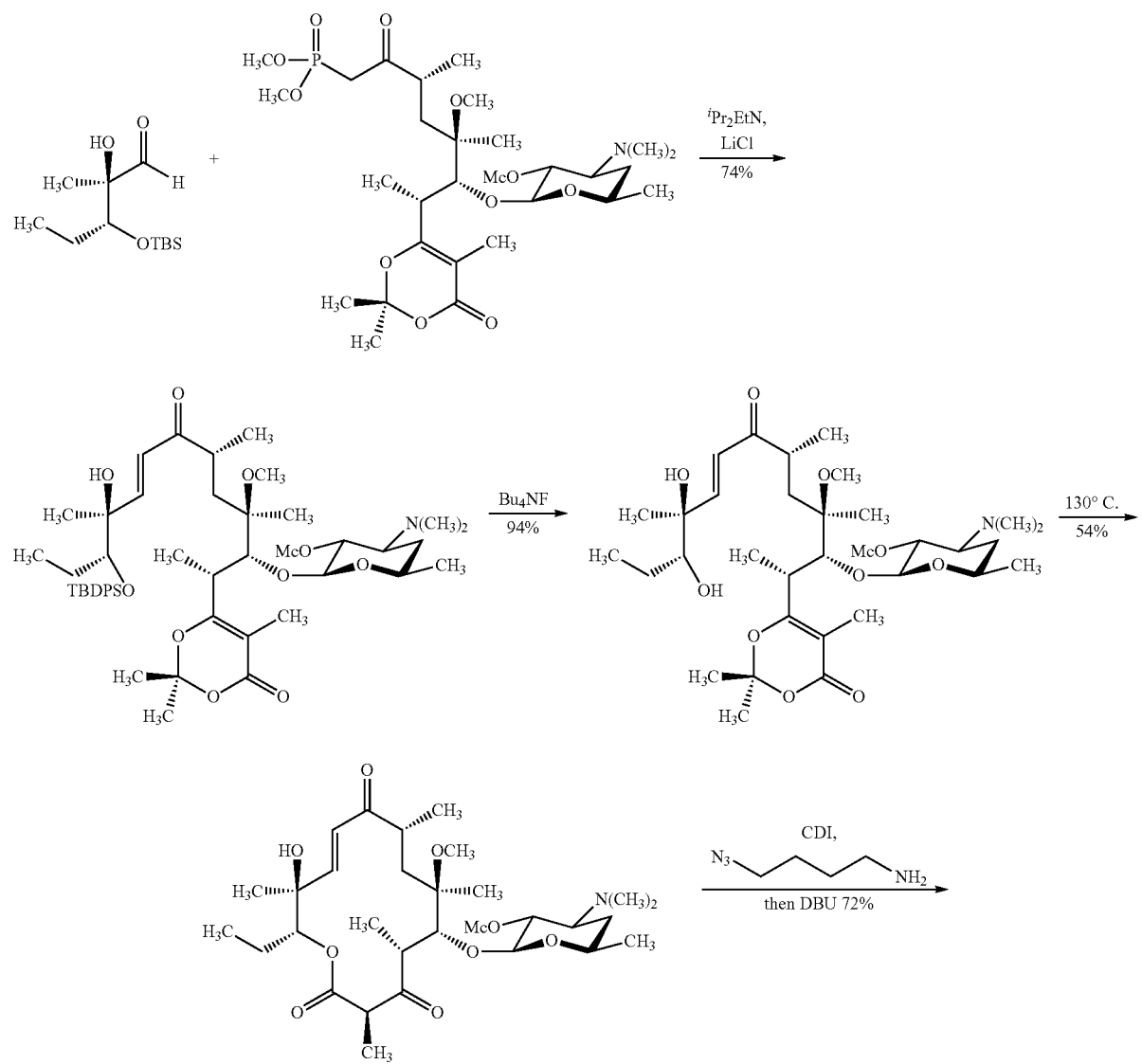

639
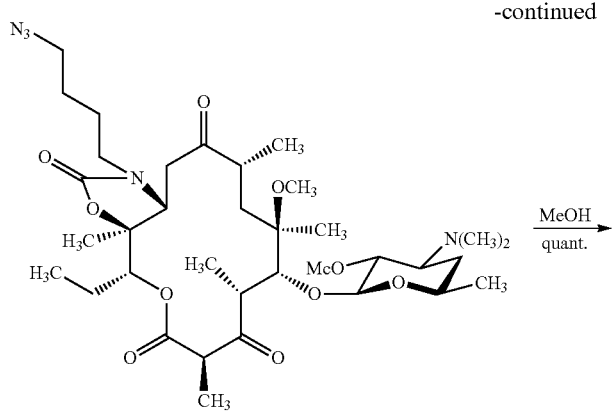
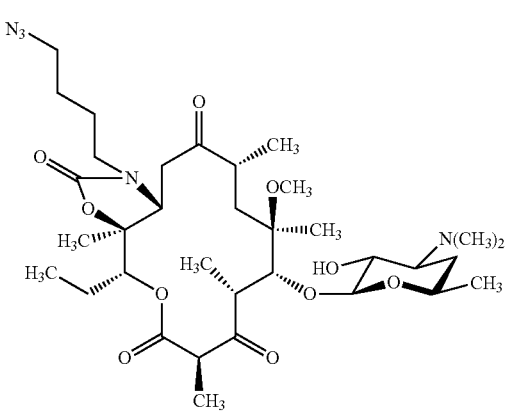
Example III-2F
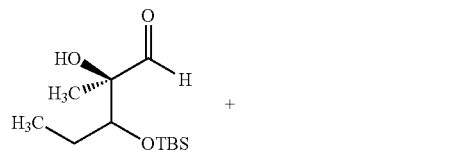
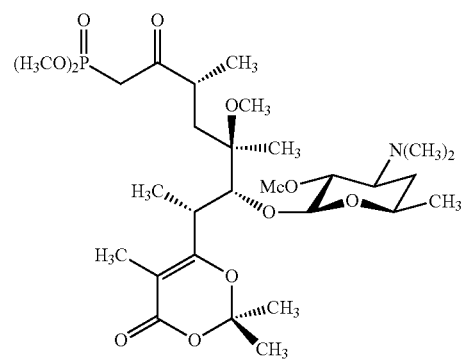
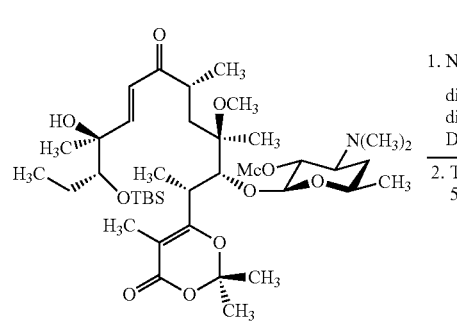
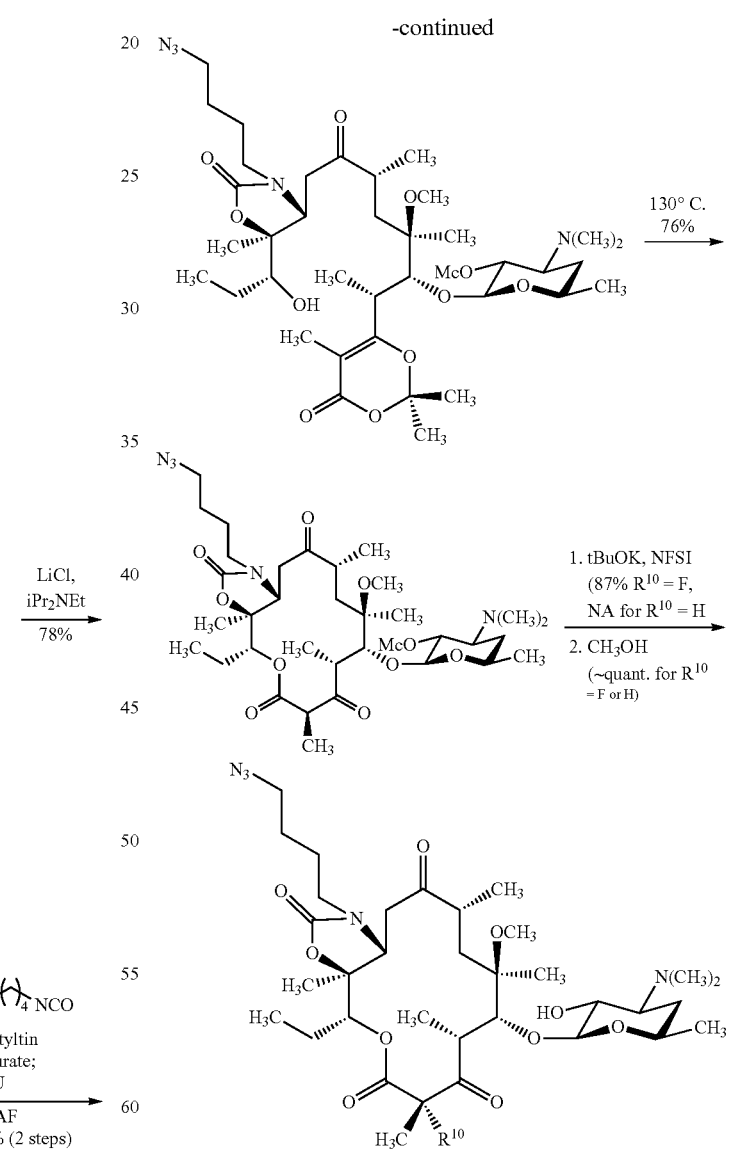
IV. Modifications after Macrocyclization
By strategically placing three diversity-generating transformations (C2 fluorination/alkylation, N-alkylation, azide-alkyne coupling) at the end of our route it is possible to rapidly expand the platform beyond variations incorporated in eastern and western halves.
Example IV-1. Alkylation/Coupling to the Amino Tether at C11
(A)
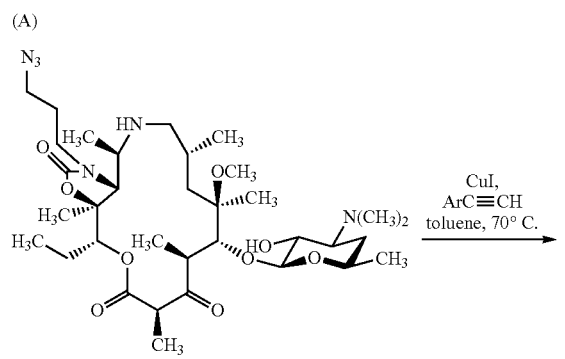
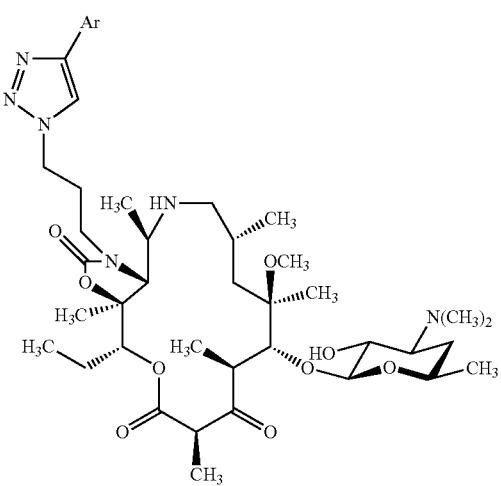
4a (3-aminilino) 61%
4b (2-pyrido) quant
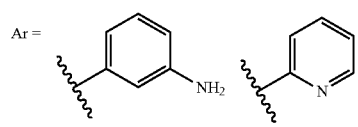
(B)
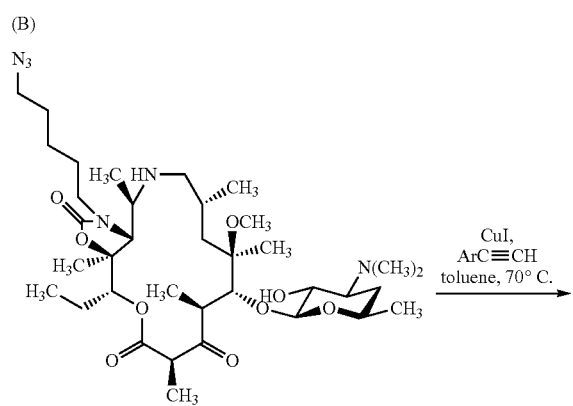
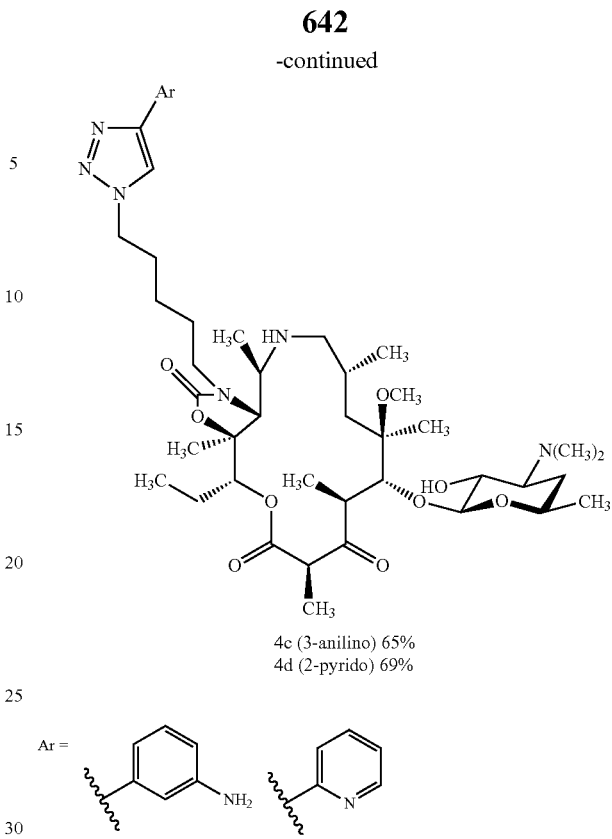
4c (3-anilino) 65%
4d (2-pyrido) 69%
Ar =
(C)
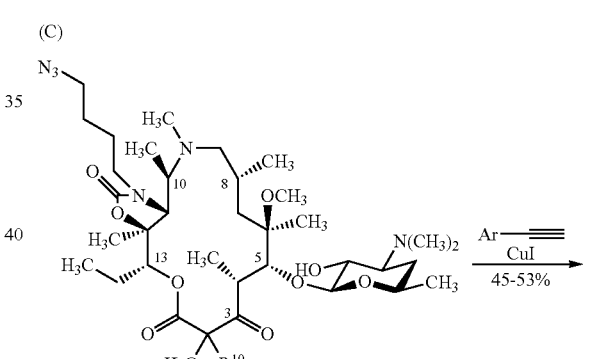
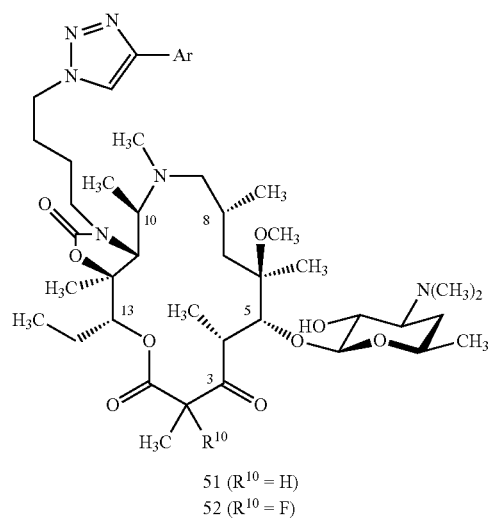
51 ($R^{10}$ = H)
52 ($R^{10}$ = F)

643
-continued
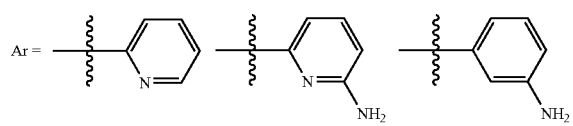
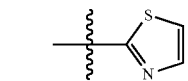
(D)
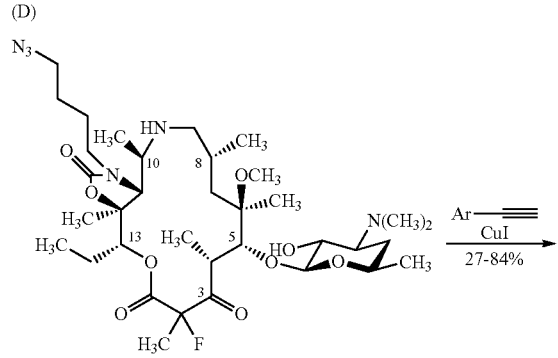
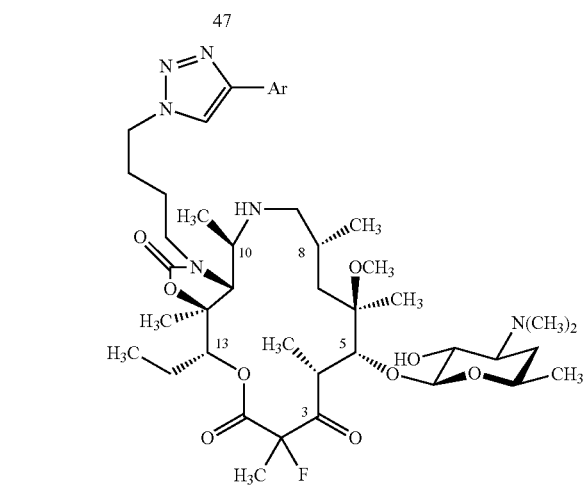
644
-continued
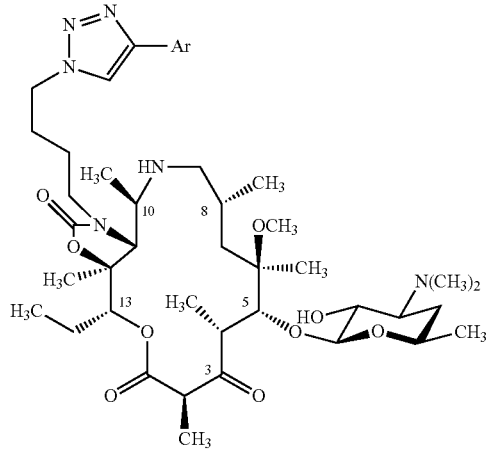
45
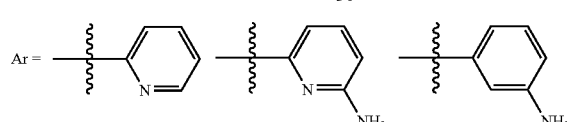
(F)
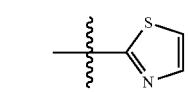
(E)
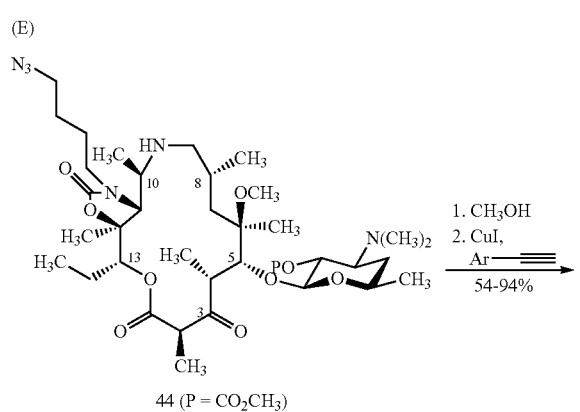
44 (P = CO₂CH₃)
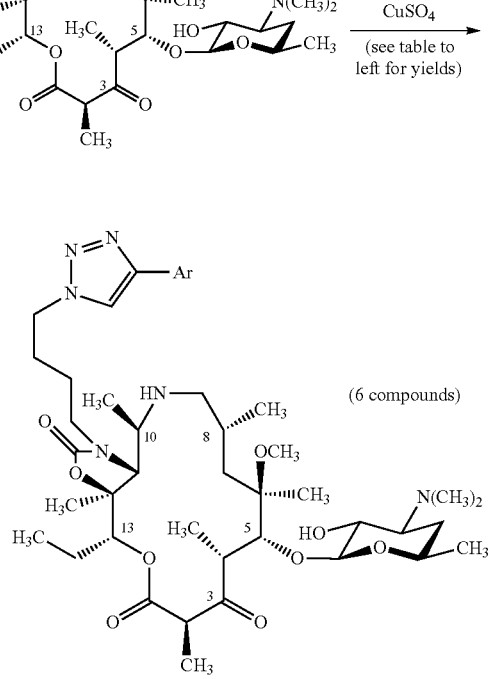
(6 compounds)

645
-continued
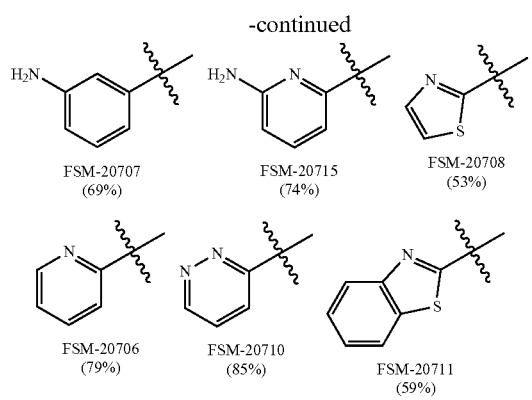
FSM-20707 (69%)  FSM-20715 (74%)  FSM-20708 (53%)
FSM-20706 (79%)  FSM-20710 (85%)  FSM-20711 (59%)
(G)
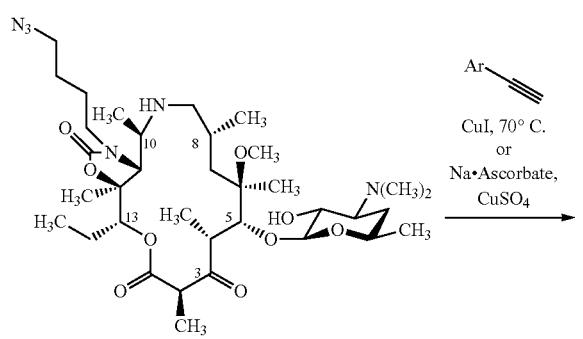
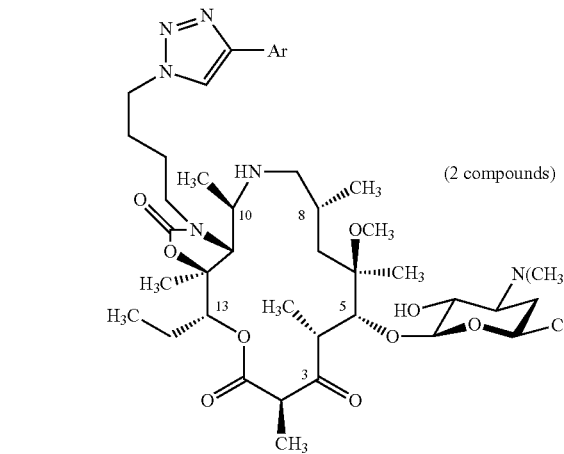
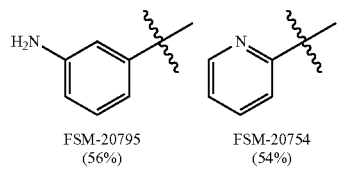
FSM-20795 (56%)  FSM-20754 (54%)
(H)
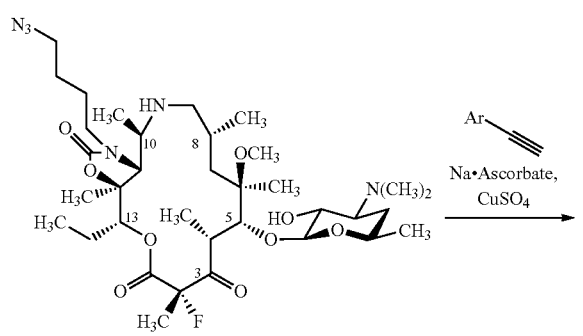
646
-continued
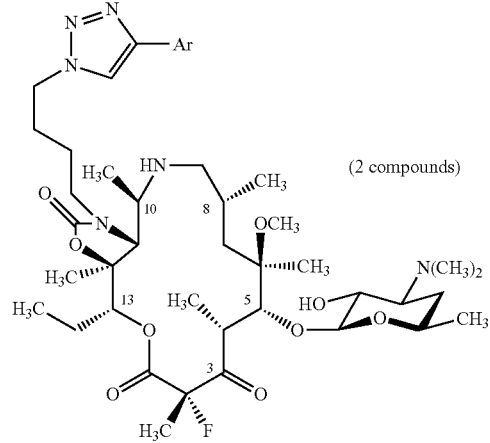
(2 compounds)
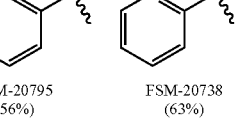
FSM-20795 (56%)  FSM-20738 (63%)
(I)
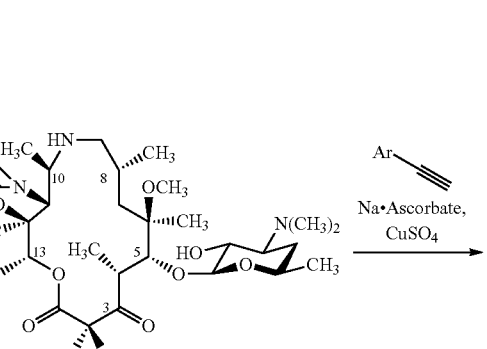
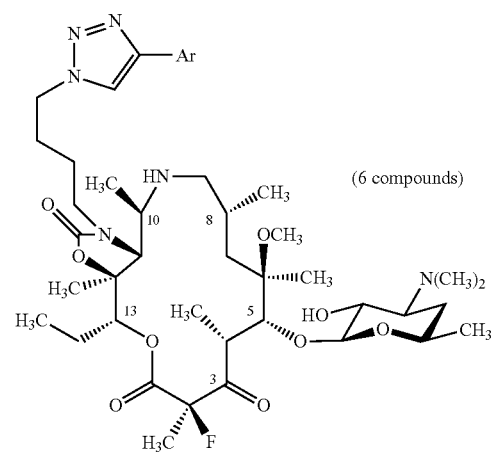
(6 compounds)

647
-continued
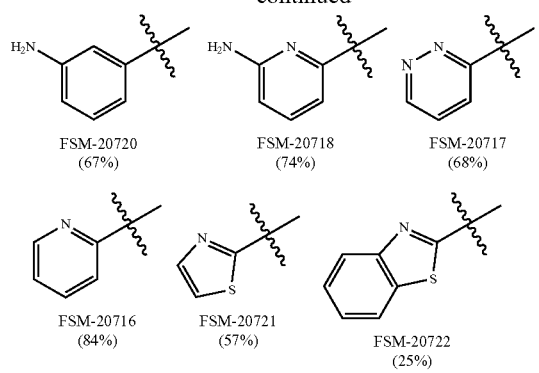
FSM-20720 (67%)  FSM-20718 (74%)  FSM-20717 (68%)
FSM-20716 (84%)  FSM-20721 (57%)  FSM-20722 (25%)
(J)
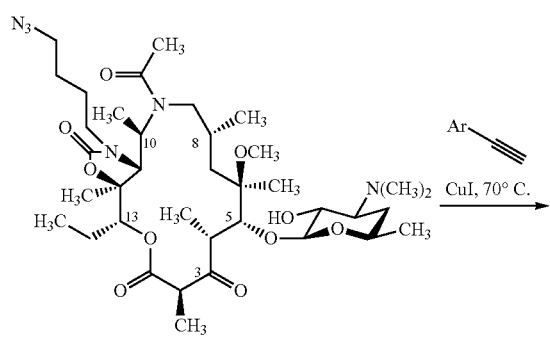
(4 compounds)
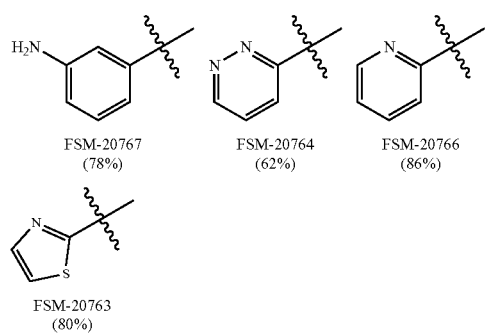
FSM-20767 (78%)  FSM-20764 (62%)  FSM-20766 (86%)
FSM-20763 (80%)
648
-continued
(K)
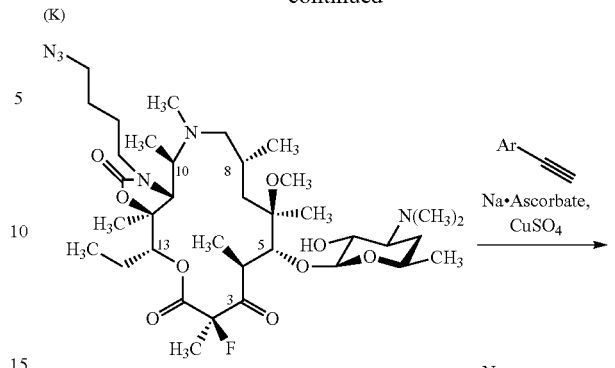
FSM-20703 (78% yield)
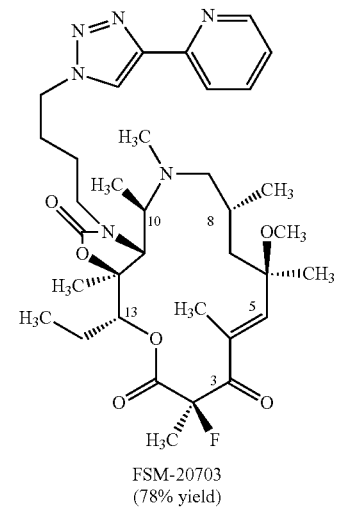
FSM-20706 (45% yield) (2 compounds)
(L)
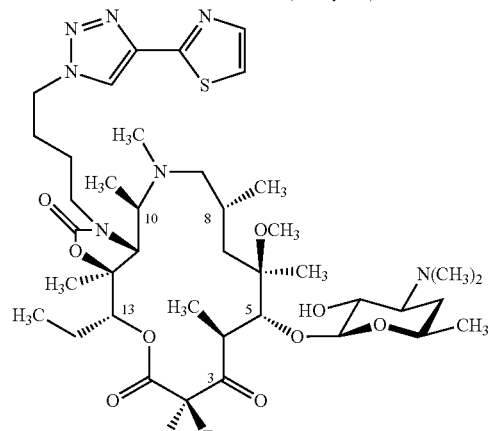

649
-continued
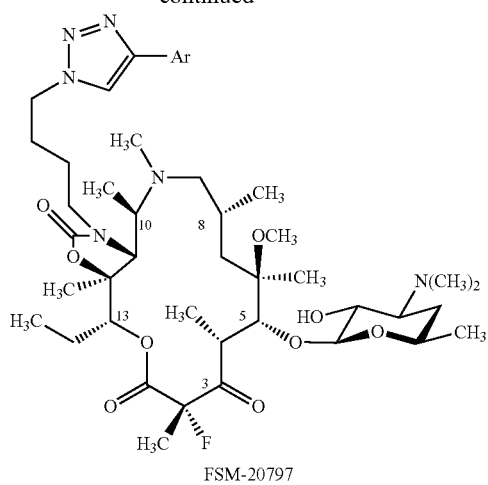
FSM-20797
(M)
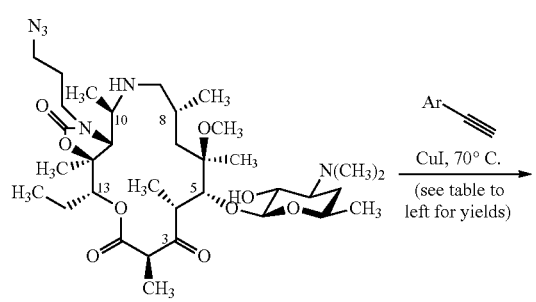
(2 compounds)
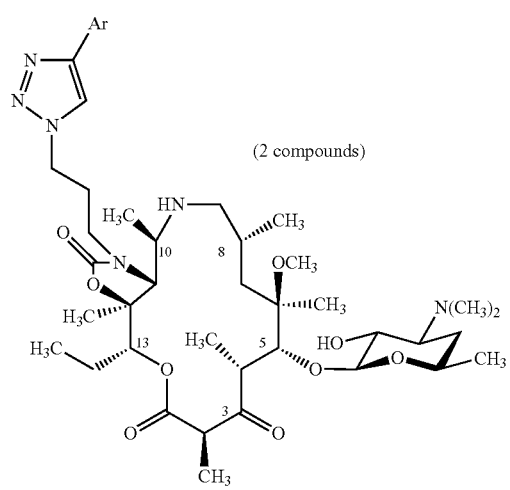
FSM-40347 (61%)   FSM-40348 (~quant)
650
-continued
(N)
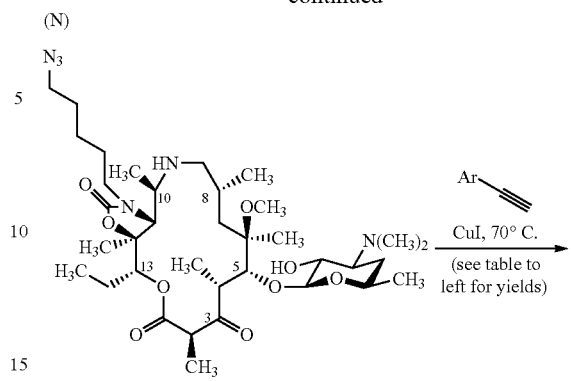
Ar—≡
CuI, 70° C.
(see table to left for yields)
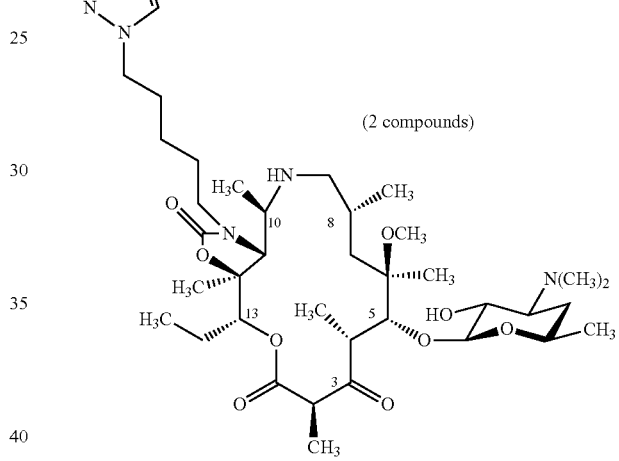
(2 compounds)
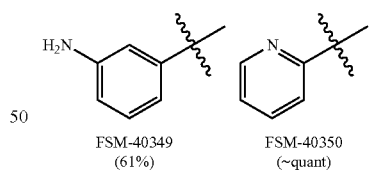
FSM-40349 (61%)   FSM-40350 (~quant)
(O)
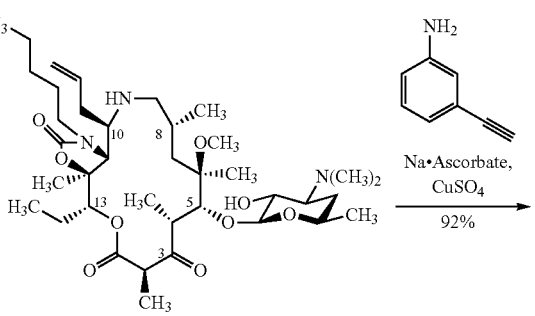
NH₂
≡
Na·Ascorbate, CuSO₄
92%

651
-continued
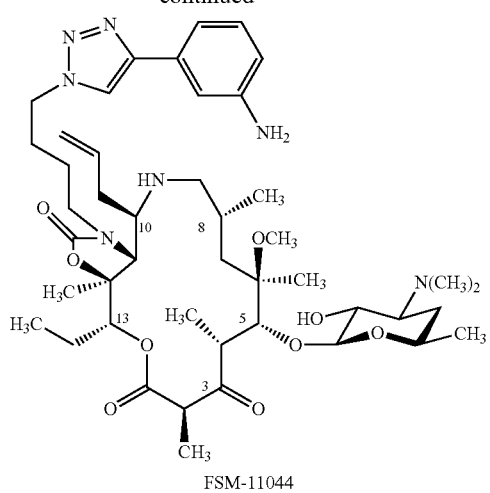
FSM-11044
(P)
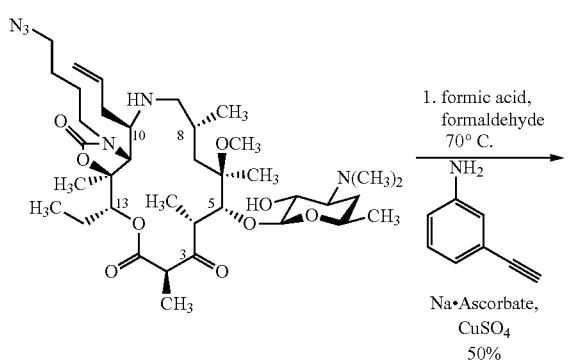
FSM-11094
(Q)
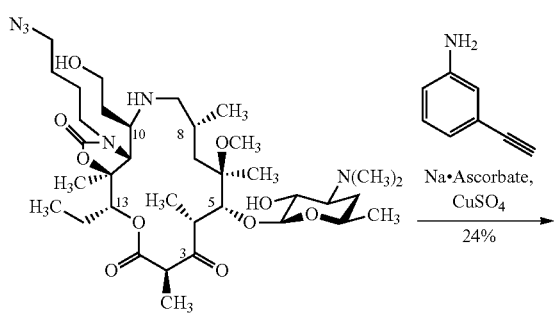
652
-continued
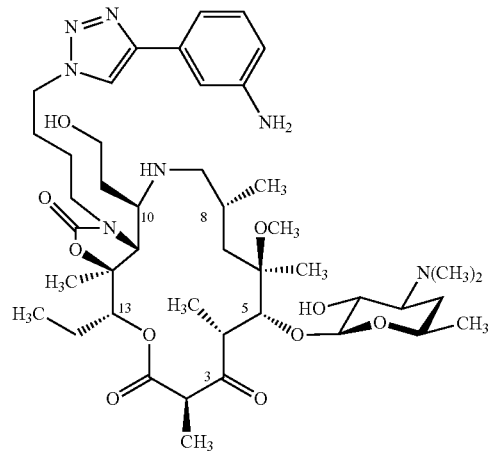
FSM-11056
(R)
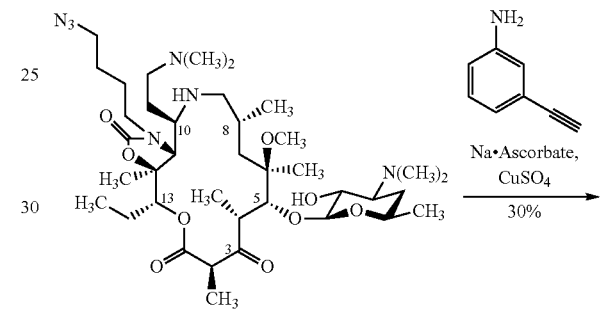
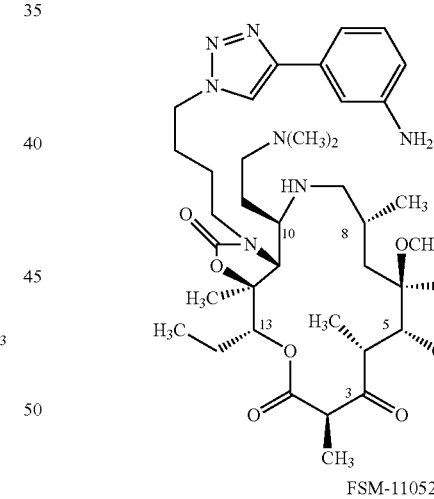
FSM-11052
(S)
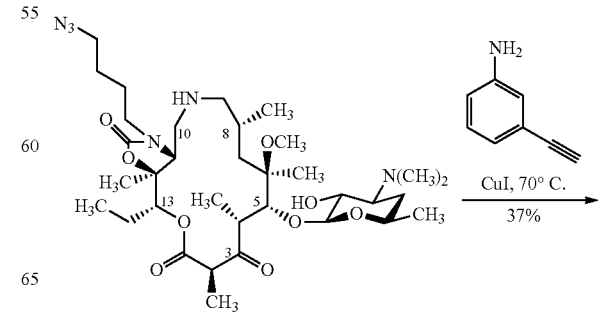

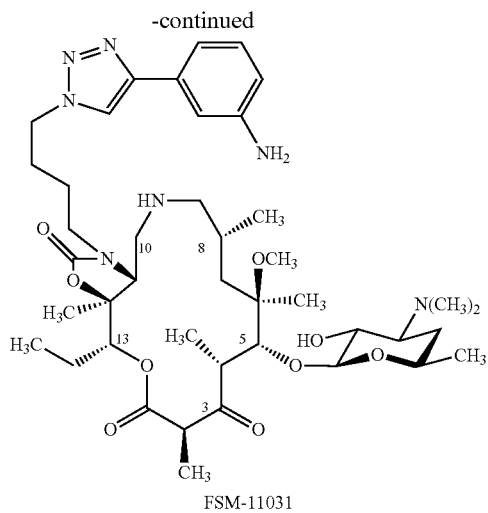
FSM-11031
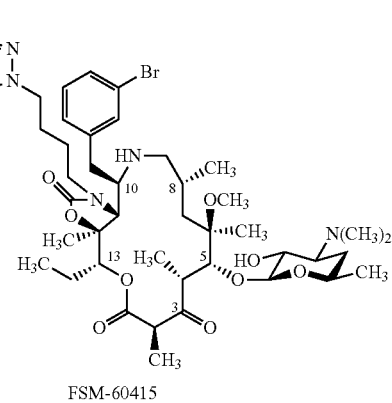
FSM-60415
(T)
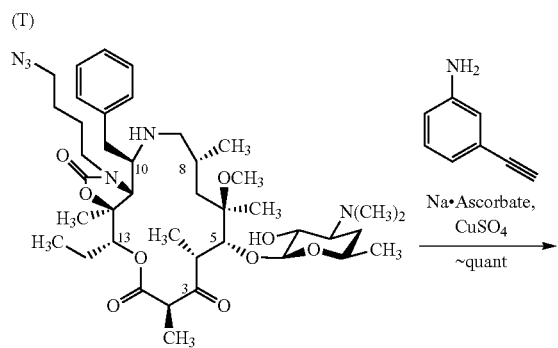
(V)
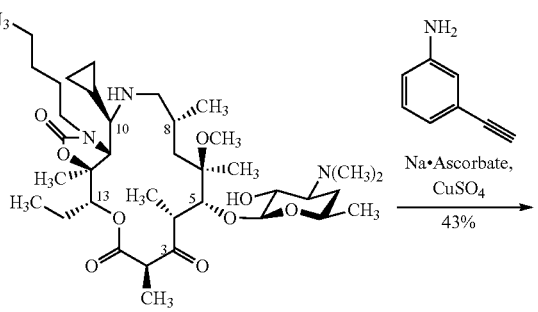
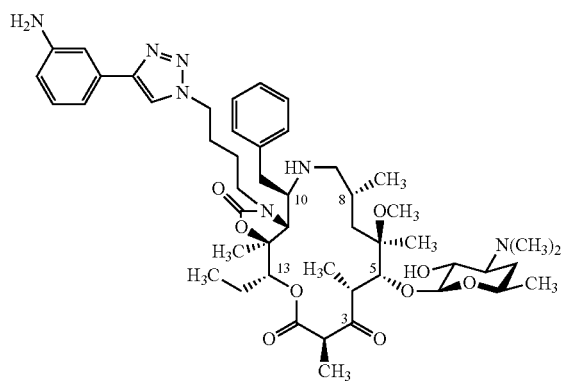
FSM-60353
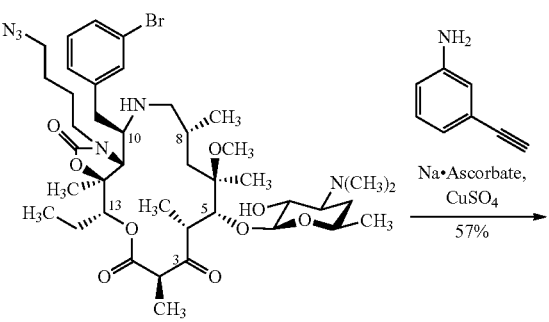
(U)
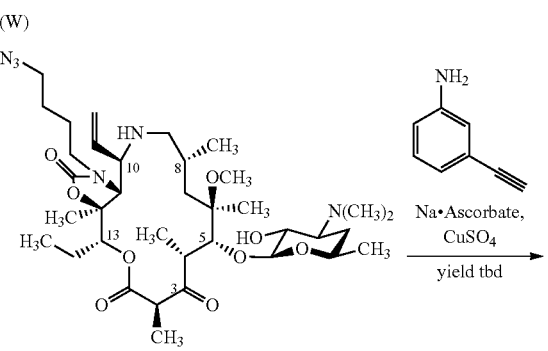
(W)

655
-continued
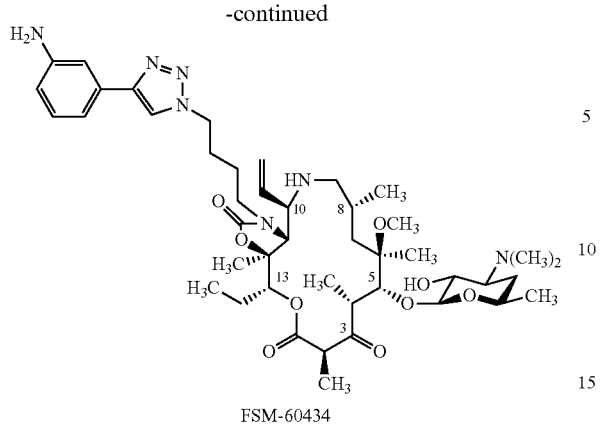
FSM-60434
(X)
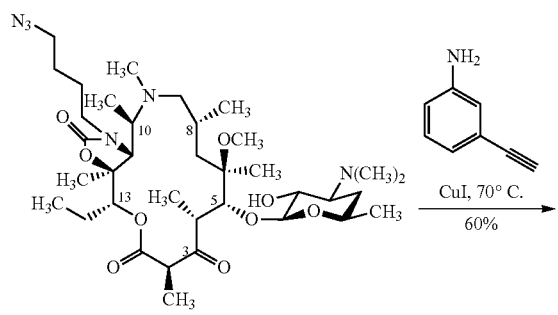
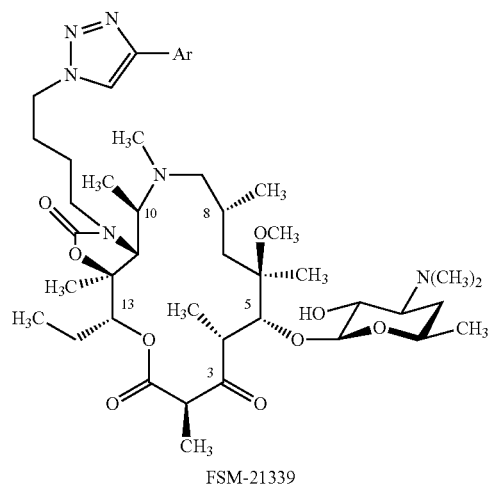
FSM-21339
(Y)
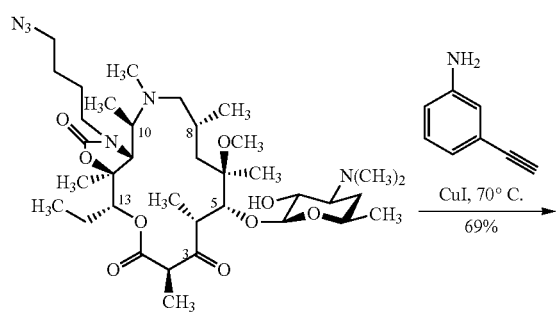
656
-continued
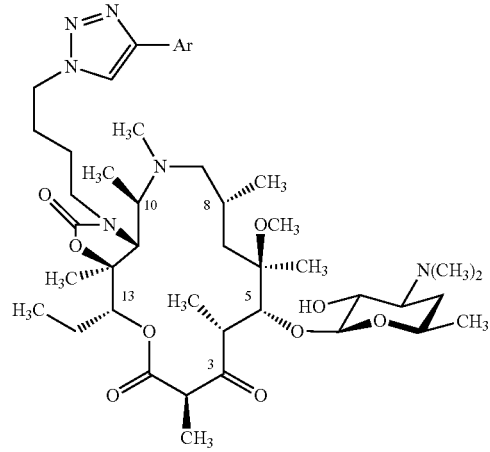
FSM-21335
(Z)
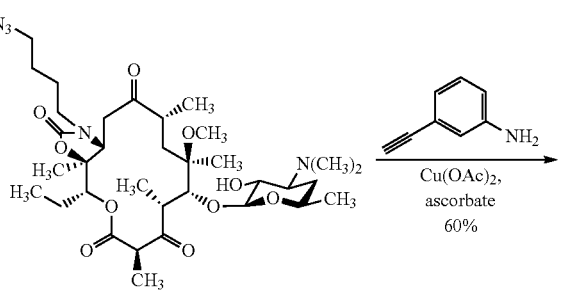
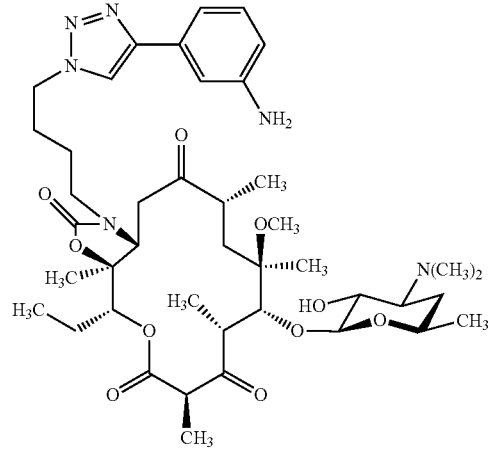
FSM-21535
(AA)
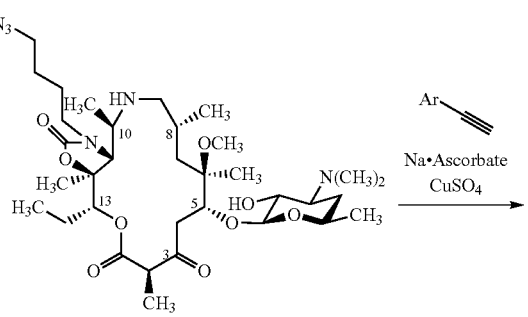

657
-continued
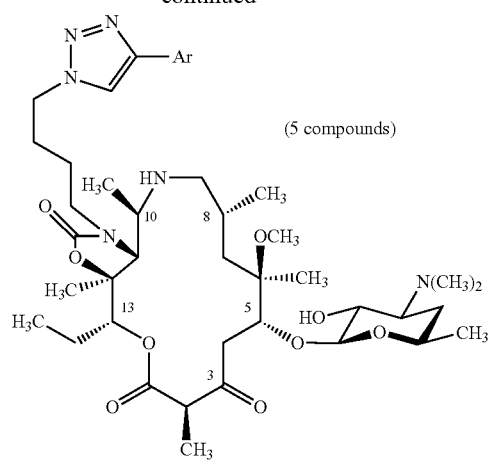
(5 compounds)
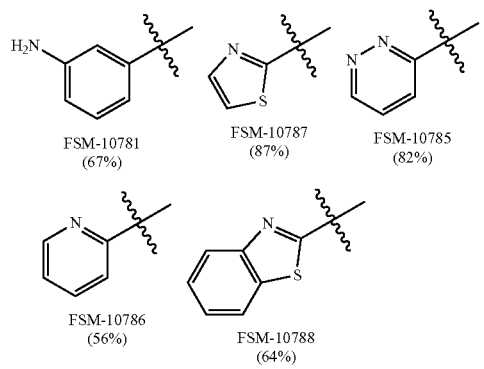
(BB)
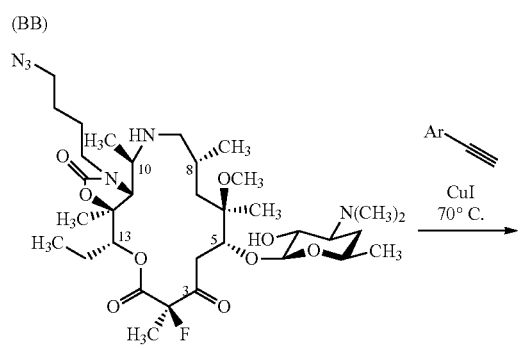
658
-continued
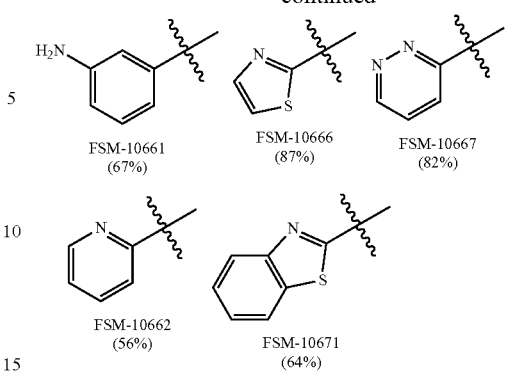
(CC)
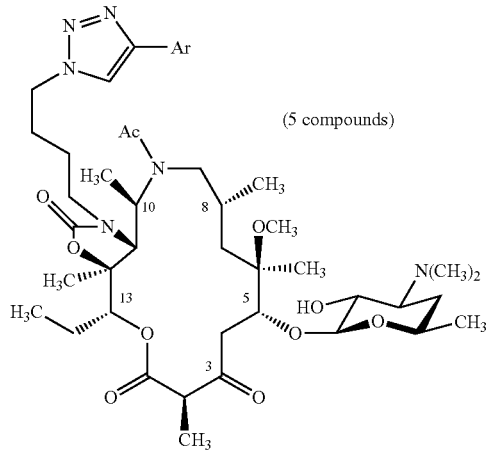
(5 compounds)
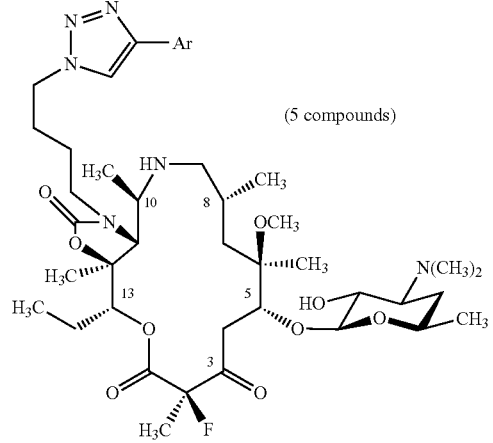

-continued
(DD)
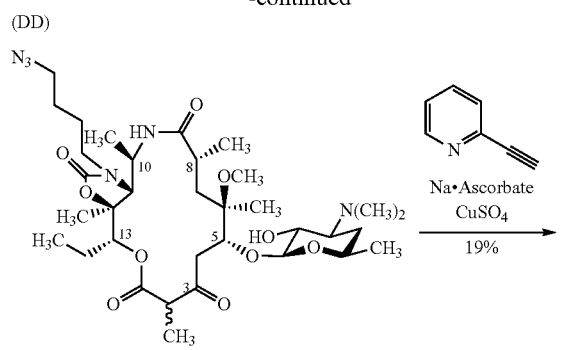
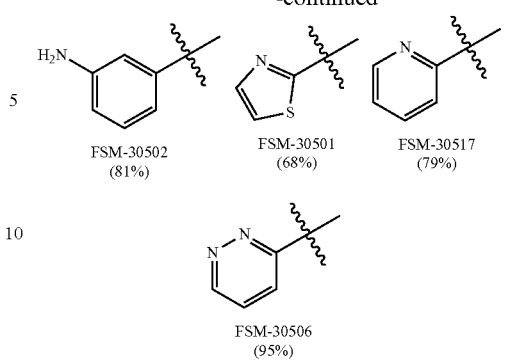
FSM-30502 (81%)  FSM-30501 (68%)  FSM-30517 (79%)
FSM-30506 (95%)
FSM-20739
(FF)
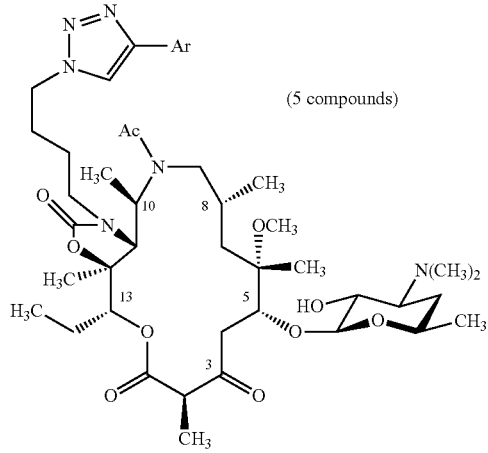
(EE)
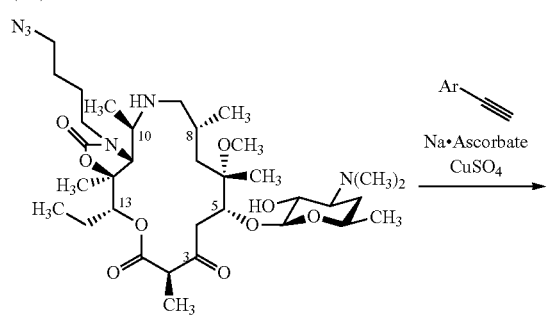
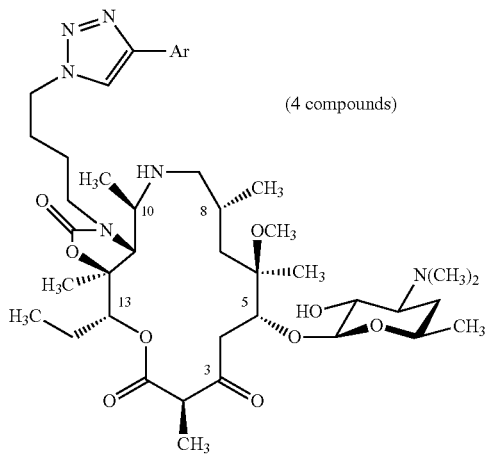
(4 compounds)
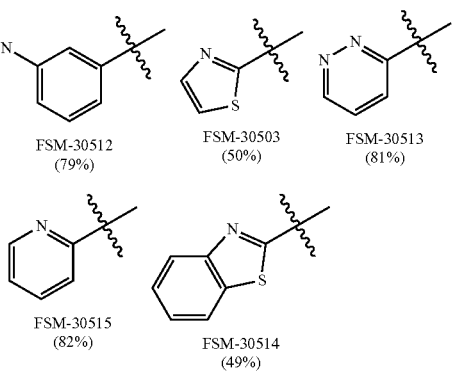
FSM-30512 (79%)  FSM-30503 (50%)  FSM-30513 (81%)
FSM-30515 (82%)  FSM-30514 (49%)

-continued
(GG)
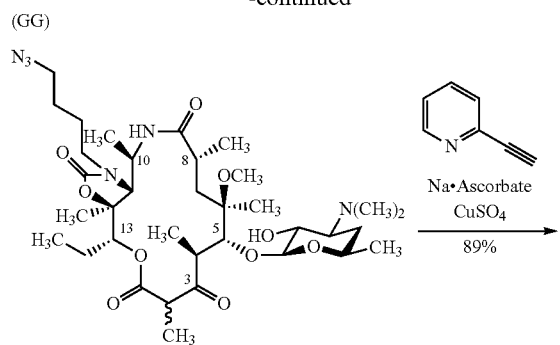
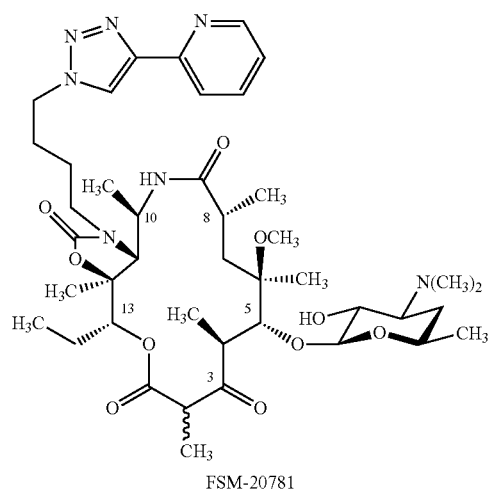
FSM-20781
(HH)
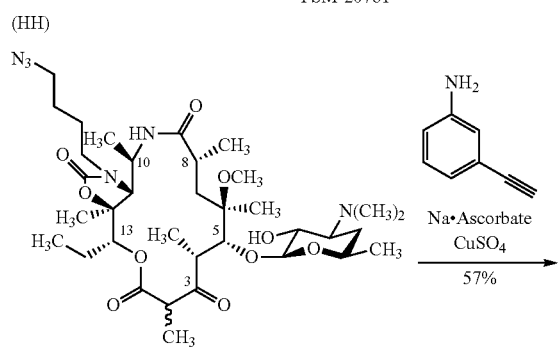
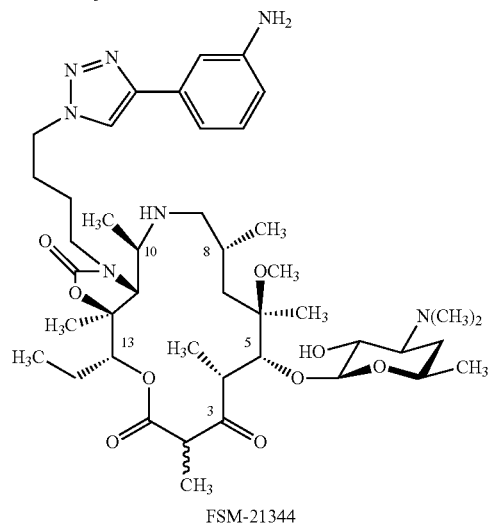
FSM-21344
-continued
(II)
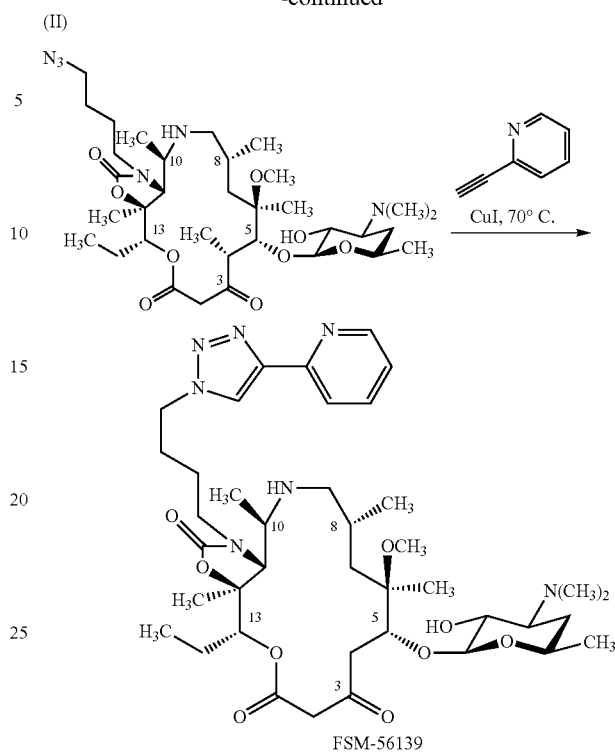
FSM-56139
(JJ)
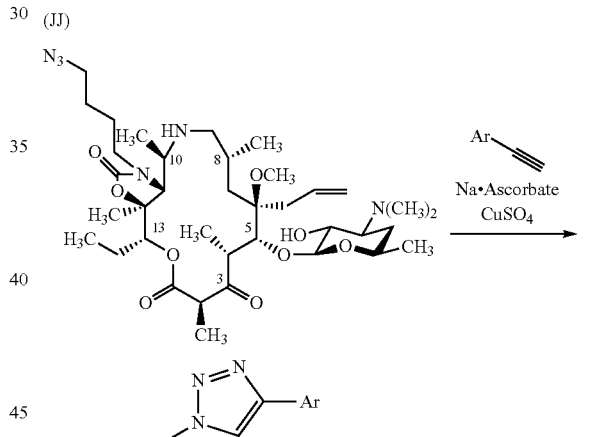
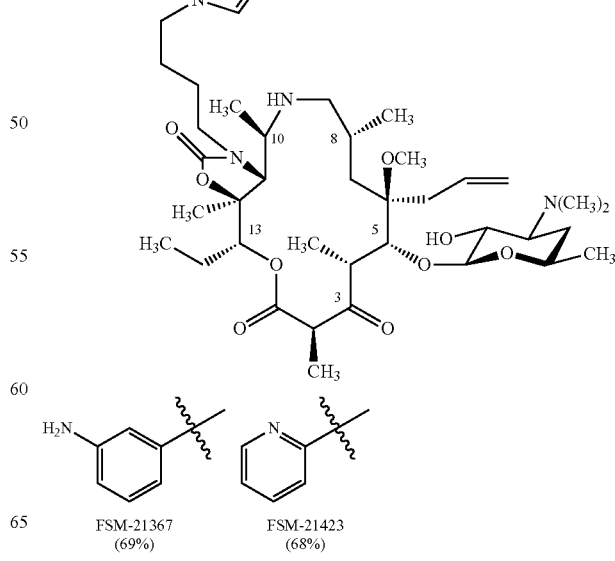
FSM-21367 (69%)    FSM-21423 (68%)

663
-continued
(KK)
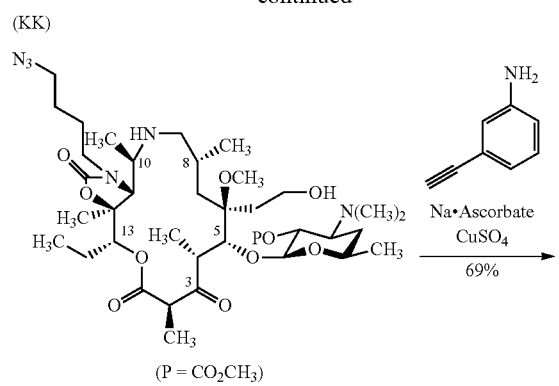
FSM-21368
(74%)
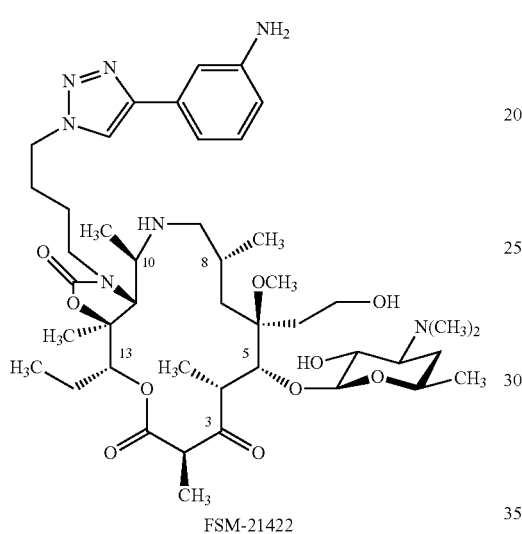
FSM-21422
(LL)
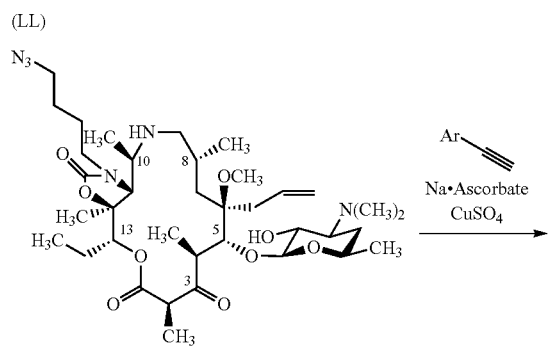
664
-continued
(MM)
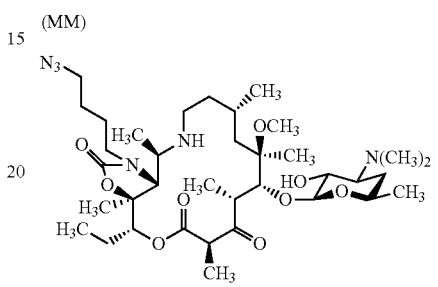
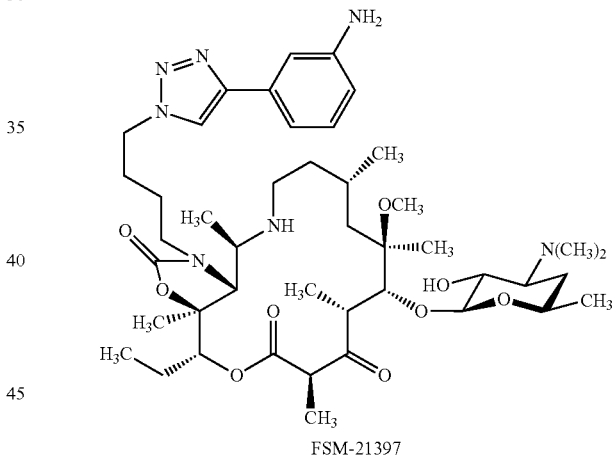
FSM-21397
(NN)
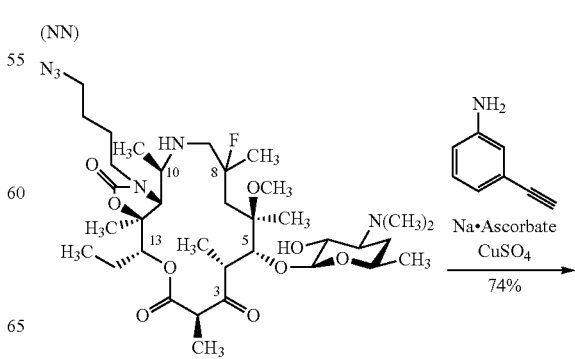
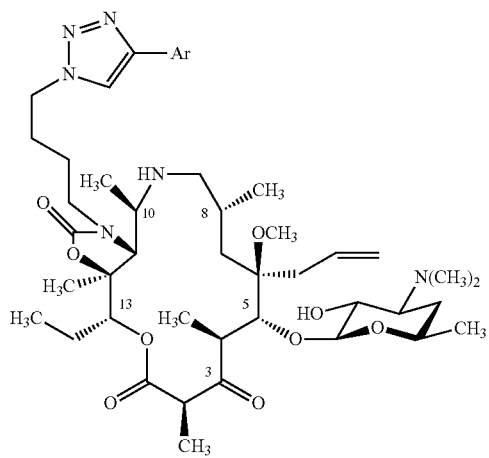

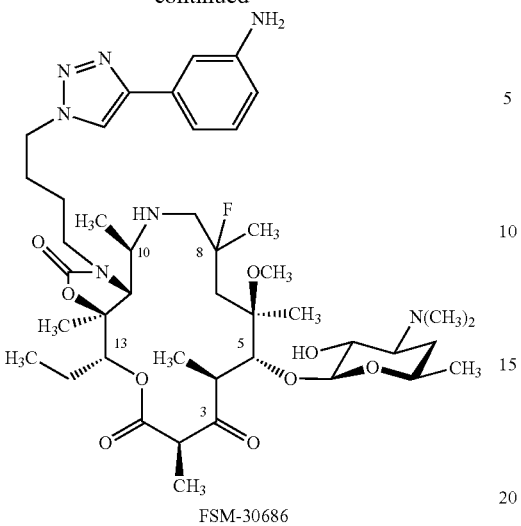
FSM-30686
(OO)
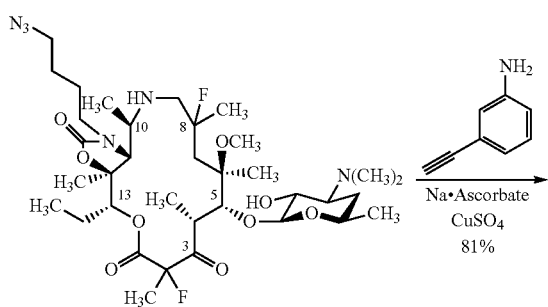
FSM-30704
(PP)
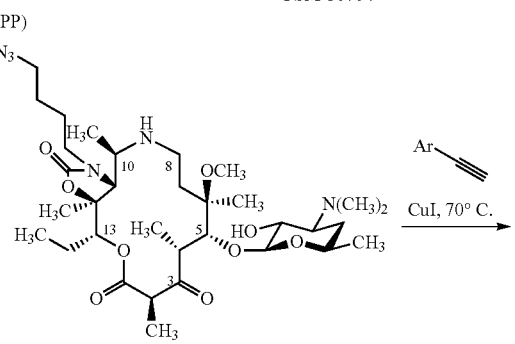
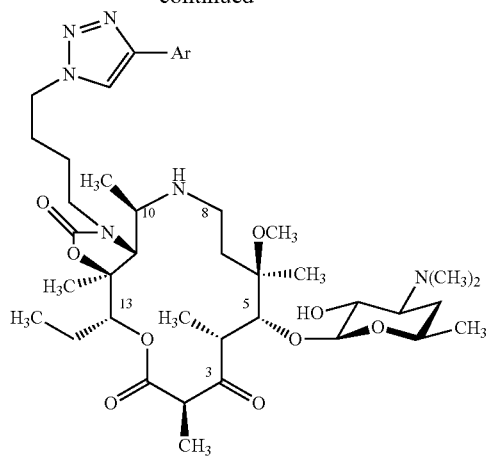
FSM-30622
(54%)
(QQ)
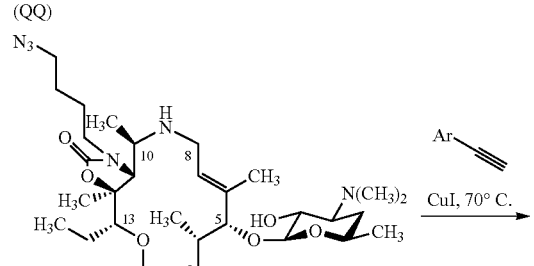
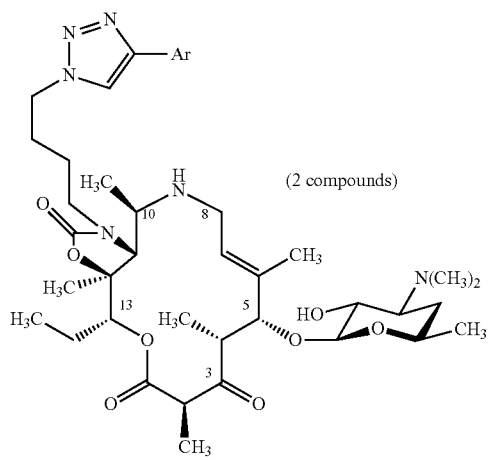
(2 compounds)
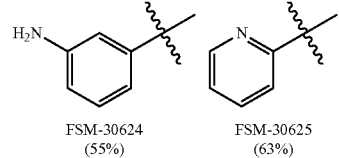
FSM-30624  FSM-30625
(55%)    (63%)

667
-continued
(RR)
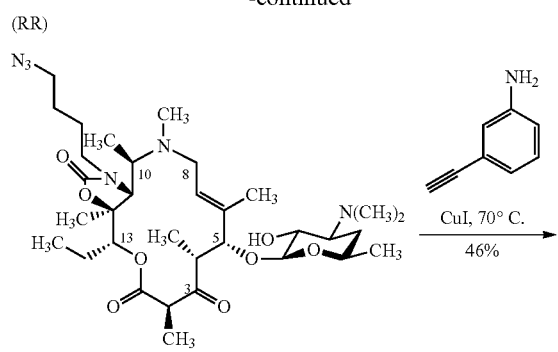
668
-continued
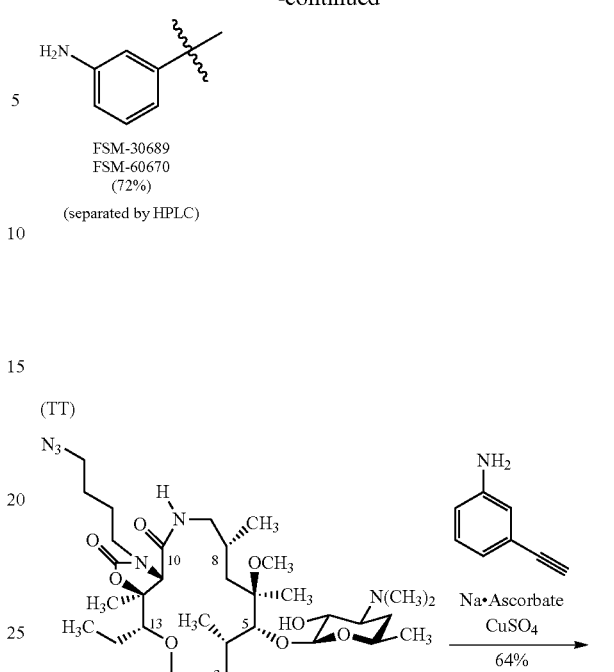
FSM-30689
FSM-60670
(72%)
(separated by HPLC)
(SS)
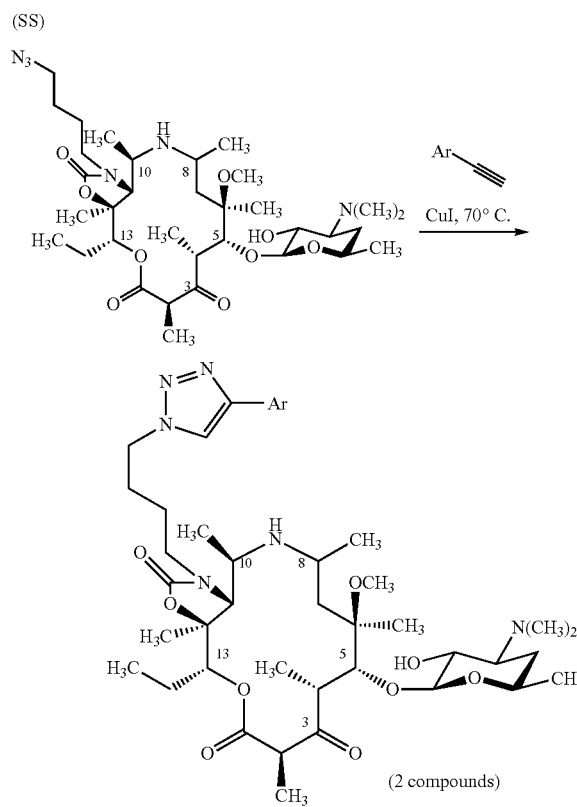
(2 compounds)
(TT)
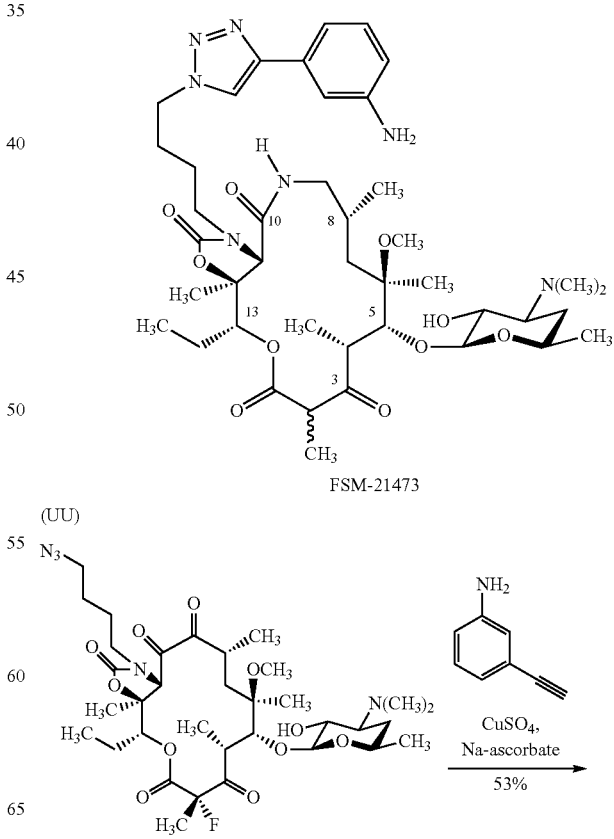

669
-continued
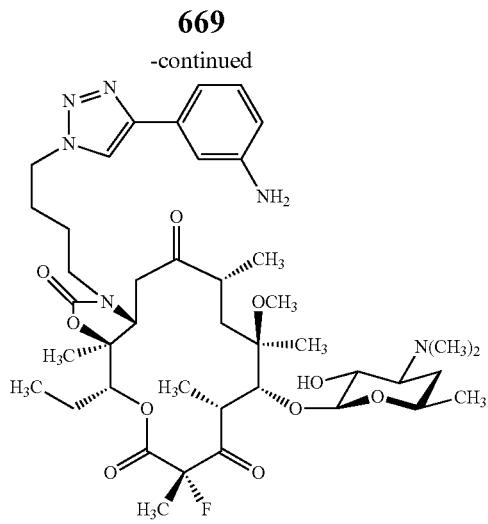
Example IV-2. Protection of the Secondary Amine
(A) CHO Protection
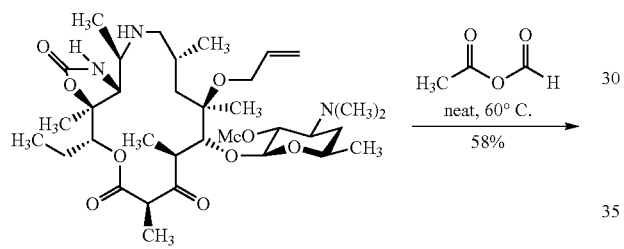
(B) Boc-Protection
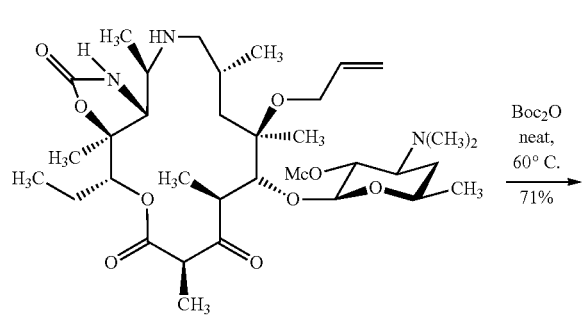
670
-continued
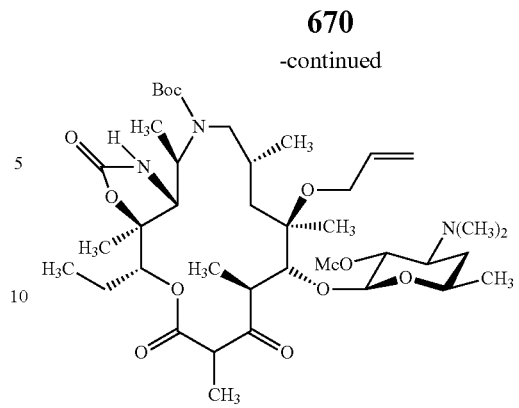
(C) Me-Protection
(c-1)
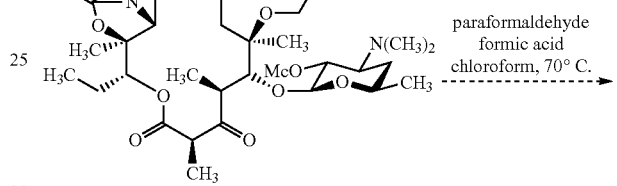
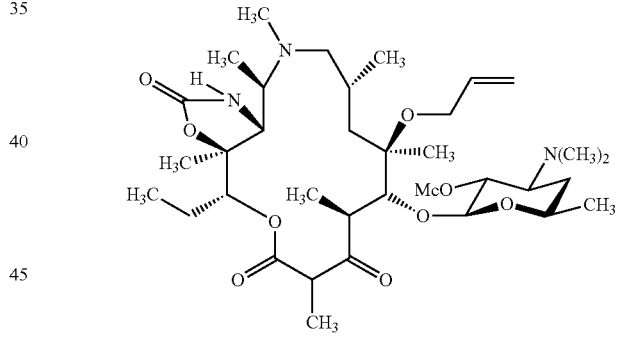
(c-2)
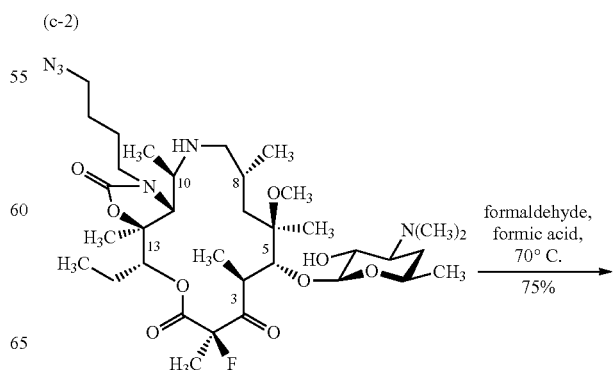

671
-continued
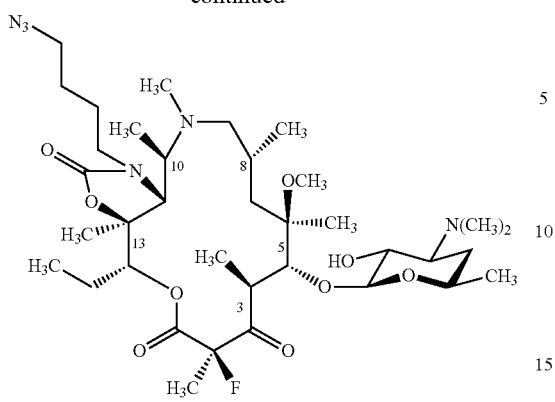
(c-3)
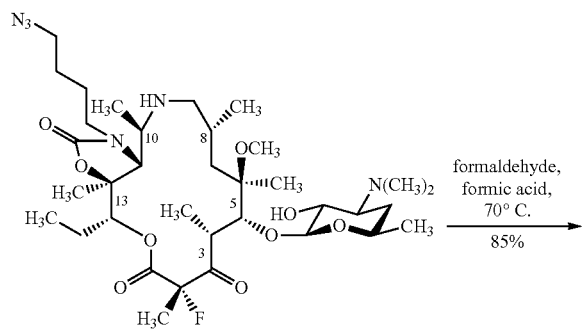
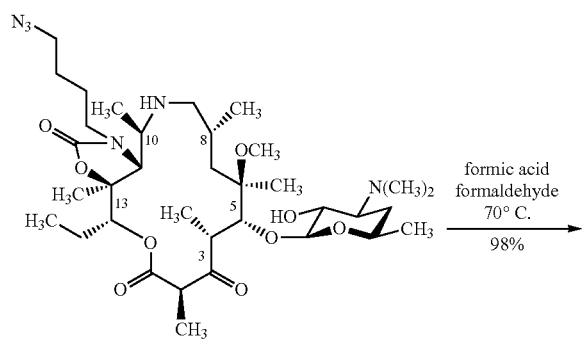
(c-3)
672
-continued
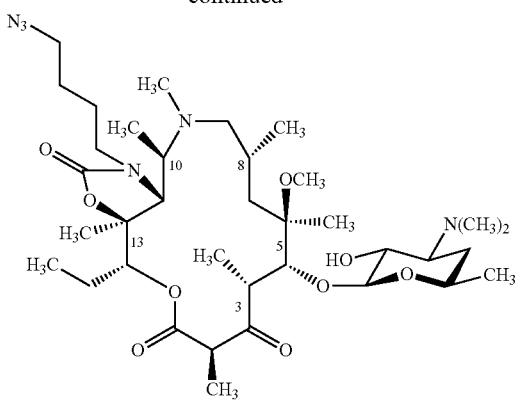
(c-4)
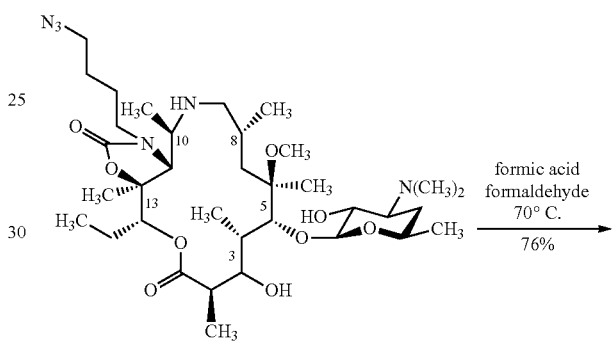
(c-5)
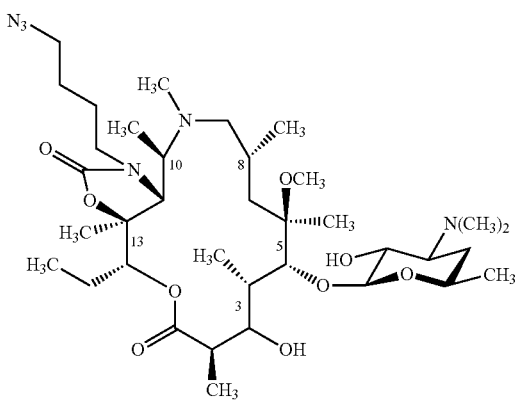
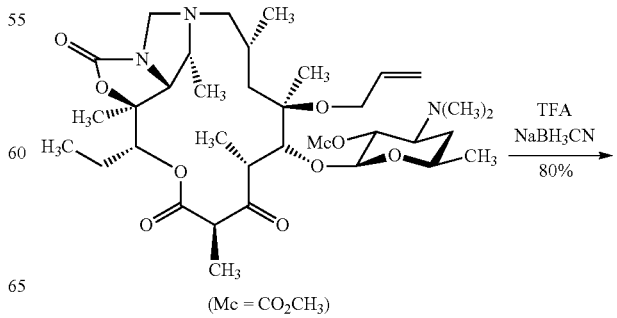
(Mc = CO₂CH₃)

673
-continued
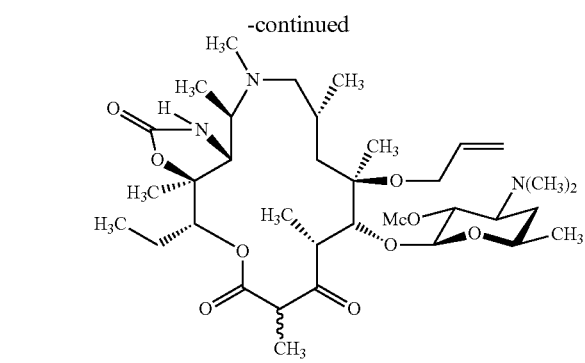
(c-6)
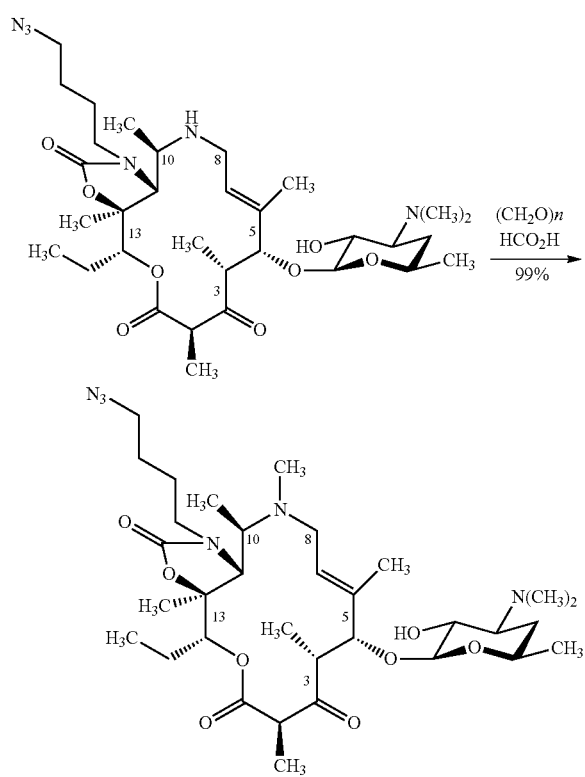
(D) N-Acetylation
(d-1)
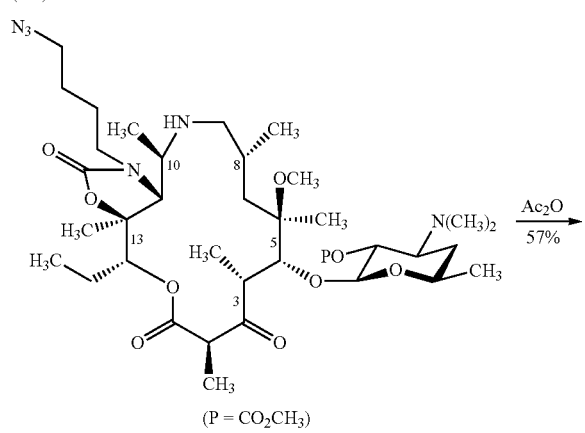
(P = CO₂CH₃)
674
-continued
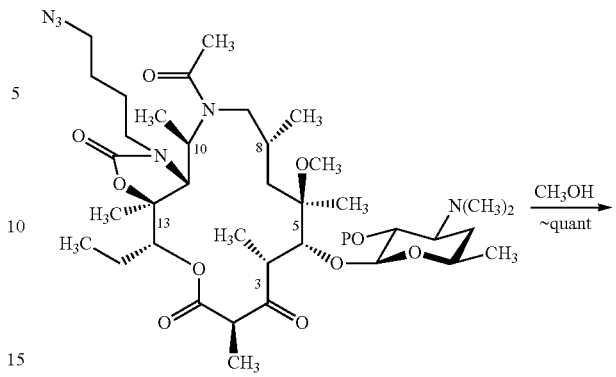
$\xrightarrow{\text{CH}_3\text{OH}}{\sim\text{quant}}$
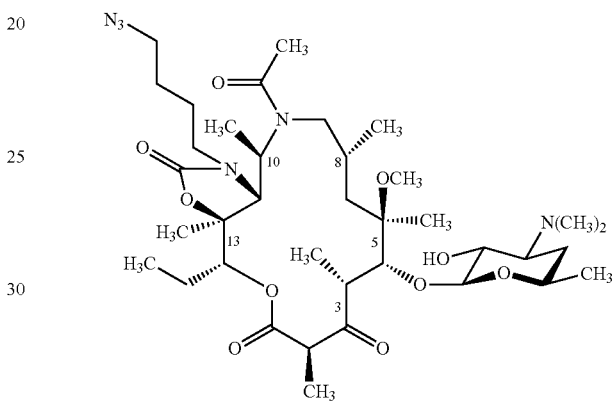
(d-2)
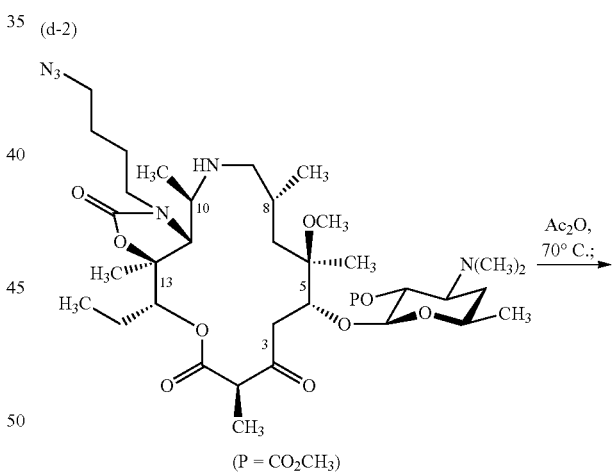
(P = CO₂CH₃)
$\xrightarrow[70^\circ\text{C.;}]{\text{Ac}_2\text{O},}$
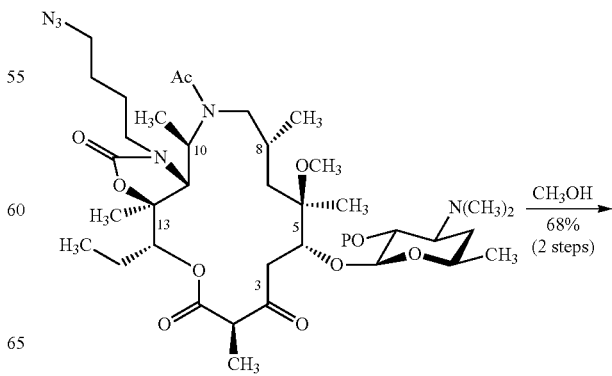
$\xrightarrow[\text{(2 steps)}]{\text{CH}_3\text{OH}}{68\%}$ 675
-continued
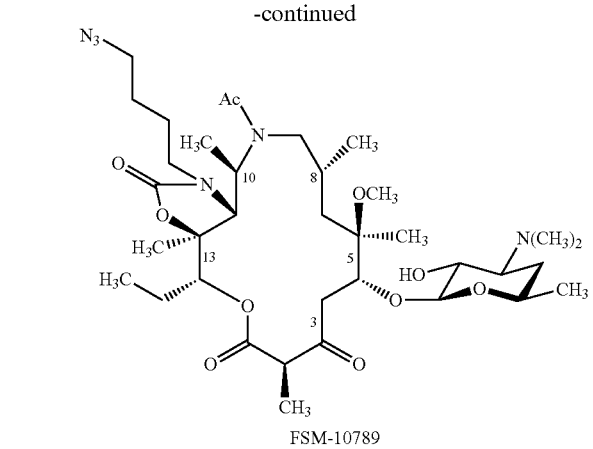
FSM-10789
(d-3)
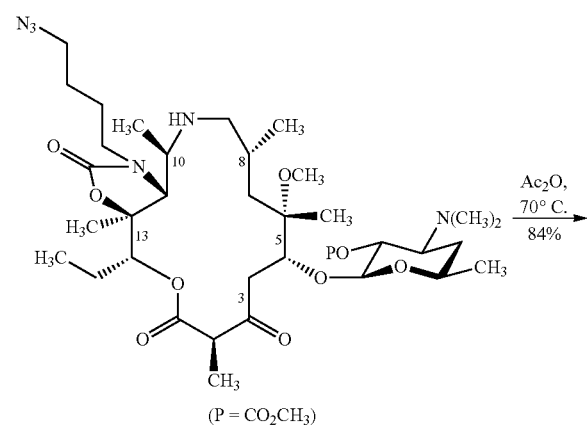
(P = CO$_2$CH$_3$)
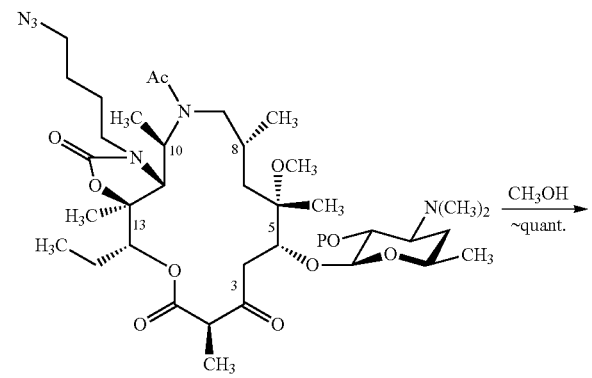
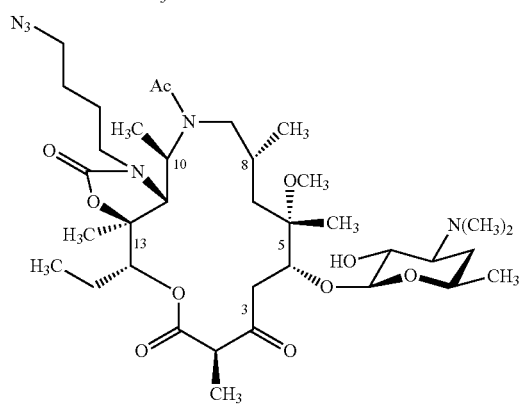
676
(E) Formyl Protection as Aminal
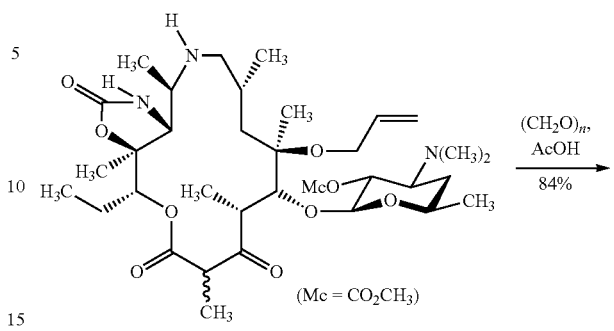
(Mc = CO$_2$CH$_3$)
3:1 inseparable mixture
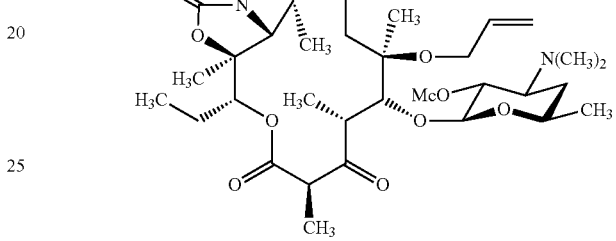
Example IV-3. Alkylation/Coupling to the C6 OR$^3$ Substituent, and Deprotection
(A)
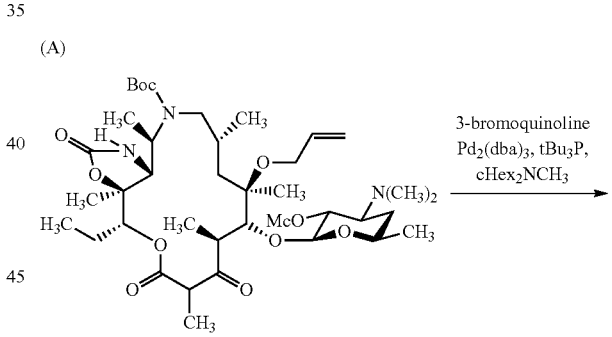
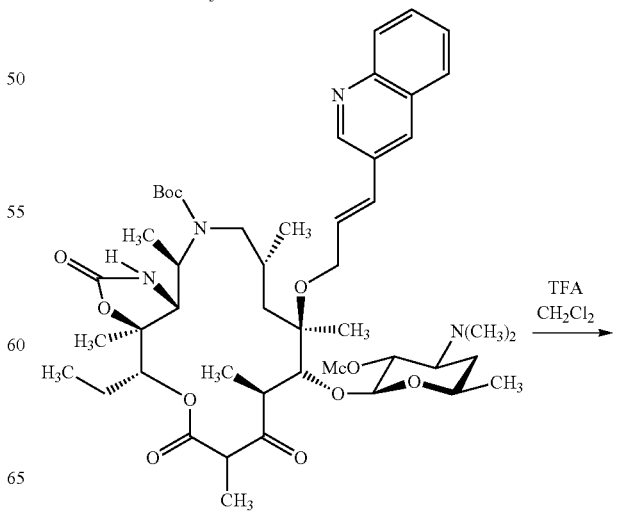

677
-continued

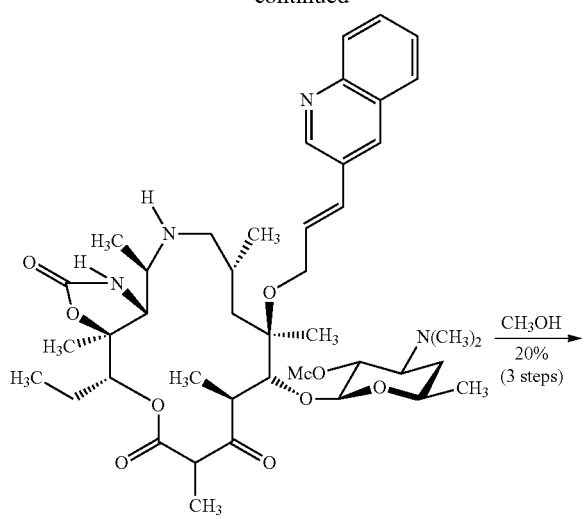

$\xrightarrow[\text{20%}]{\text{CH}_3\text{OH}}$
(3 steps)

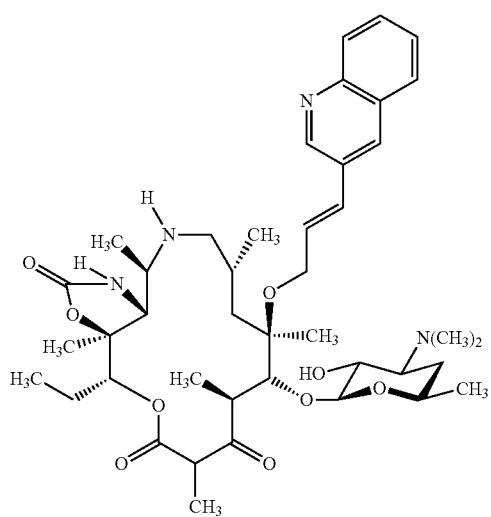

(B)

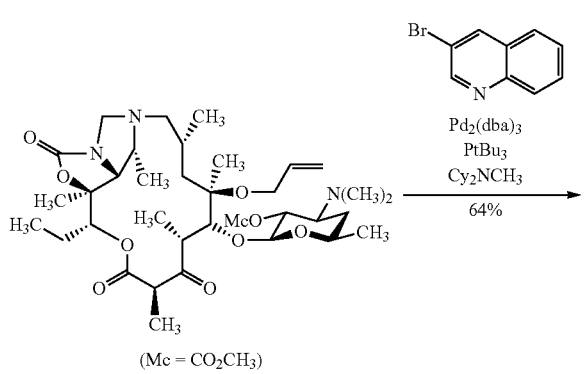

$\xrightarrow[\text{64%}]{\substack{\text{Pd}_2(\text{dba})_3 \\ \text{PtBu}_3 \\ \text{Cy}_2\text{NCH}_3}}$ (Mc = CO$_2$CH$_3$)

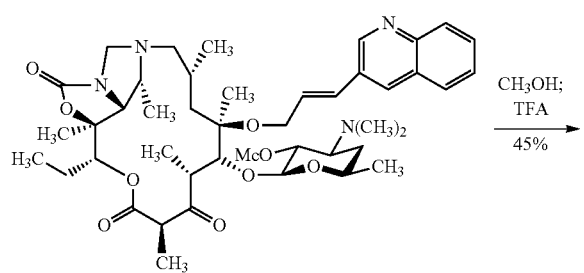

$\xrightarrow[\text{45%}]{\substack{\text{CH}_3\text{OH}; \\ \text{TFA}}}$

678
-continued

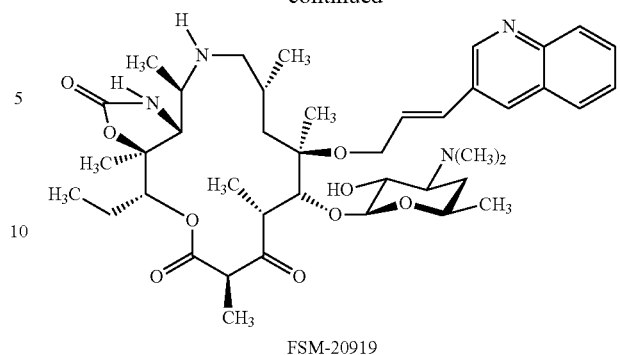

FSM-20919

(C)

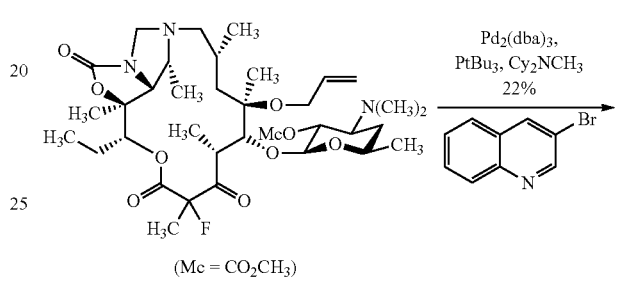

$\xrightarrow[\text{22%}]{\substack{\text{Pd}_2(\text{dba})_3, \\ \text{PtBu}_3, \text{Cy}_2\text{NCH}_3}}$ (Mc = CO$_2$CH$_3$)

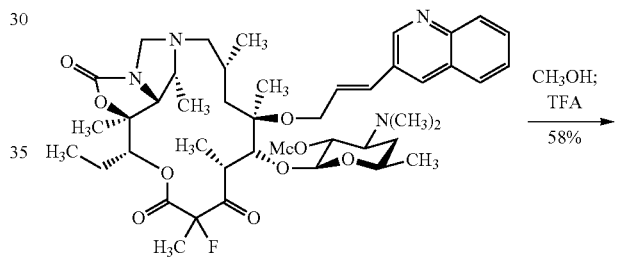

$\xrightarrow[\text{58%}]{\substack{\text{CH}_3\text{OH}; \\ \text{TFA}}}$

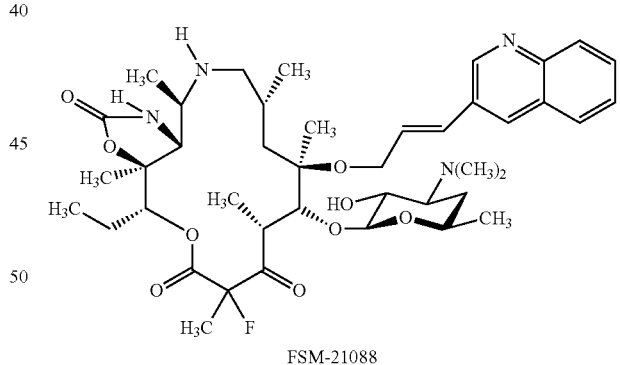

FSM-21088

(D)

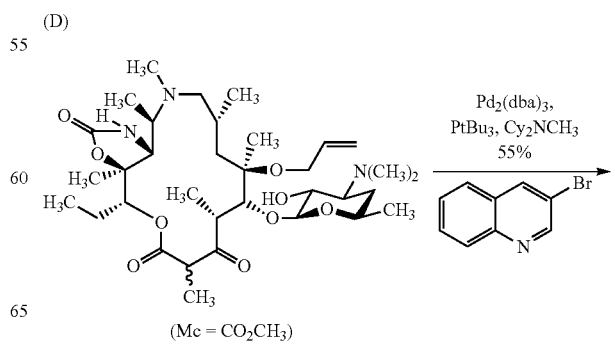

$\xrightarrow[\text{55%}]{\substack{\text{Pd}_2(\text{dba})_3, \\ \text{PtBu}_3, \text{Cy}_2\text{NCH}_3}}$ (Mc = CO$_2$CH$_3$)

679
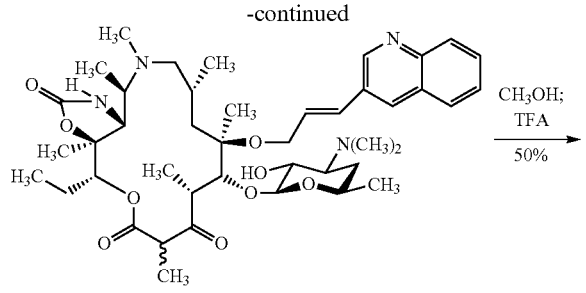
680
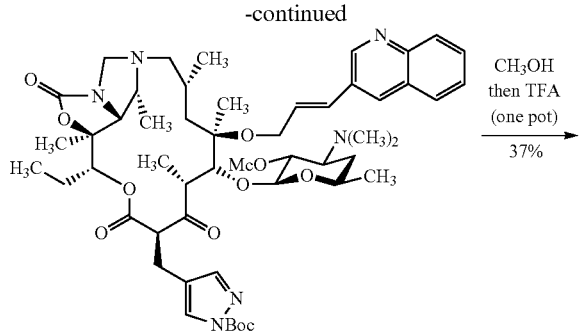
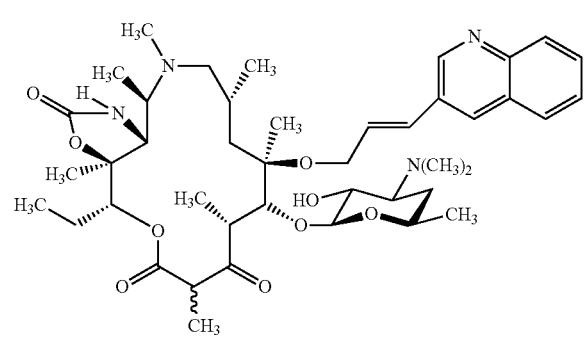
FSM-21118
(E)
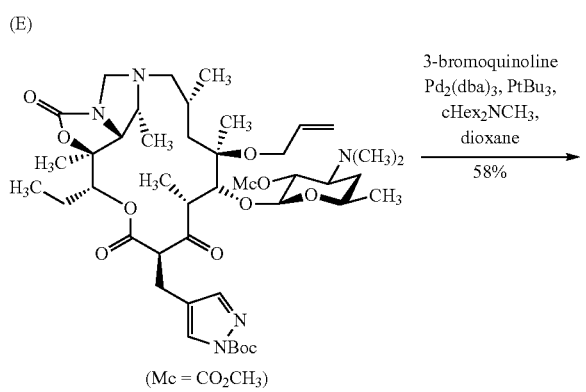
(Mc = CO₂CH₃)
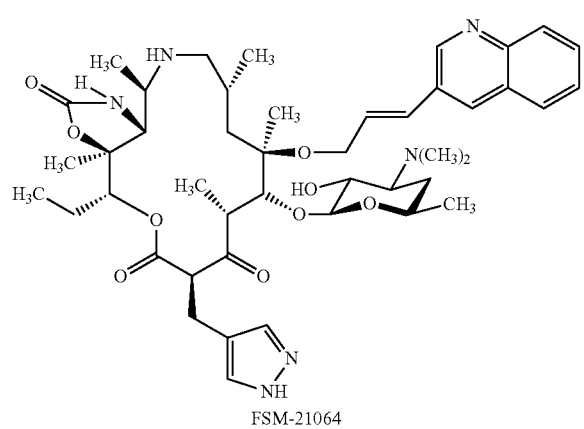
FSM-21064
Example IV-4. Double Bond Functionalization
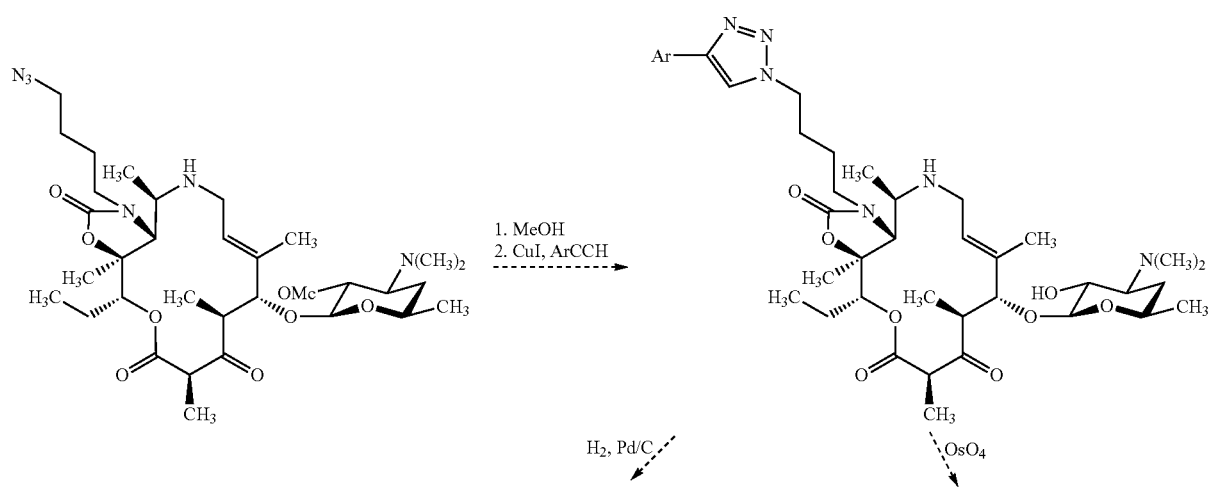

681
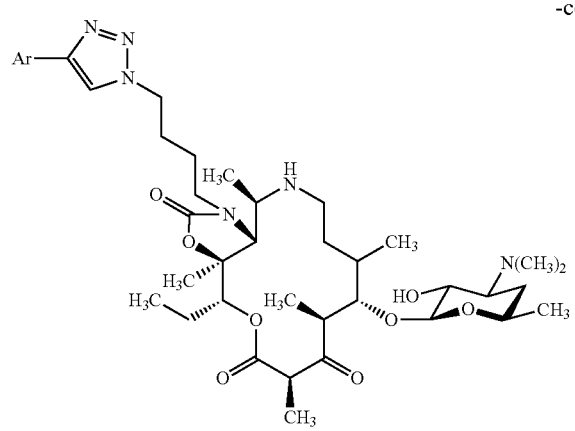
-continued
682
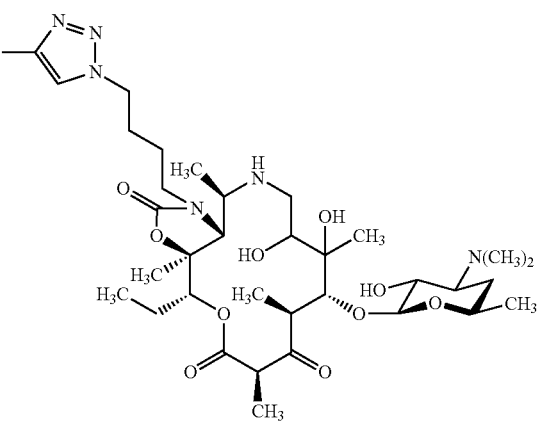
Example IV-5. Functionalization Through C2 Anion Formation
(A)
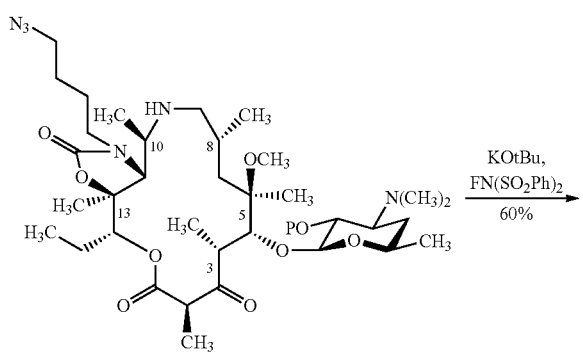
-continued
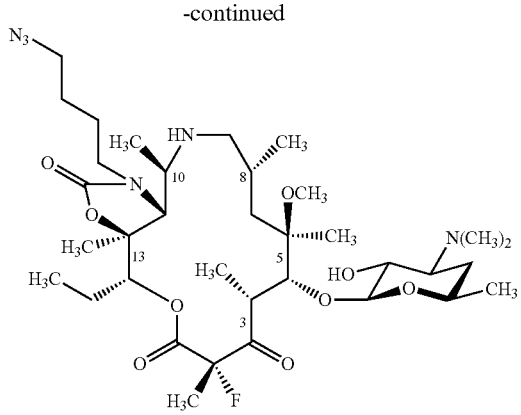
(B)
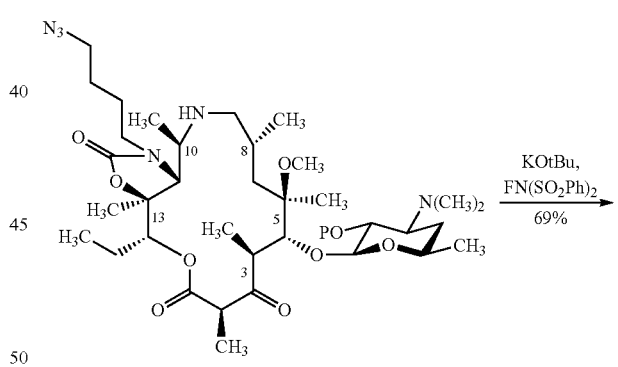
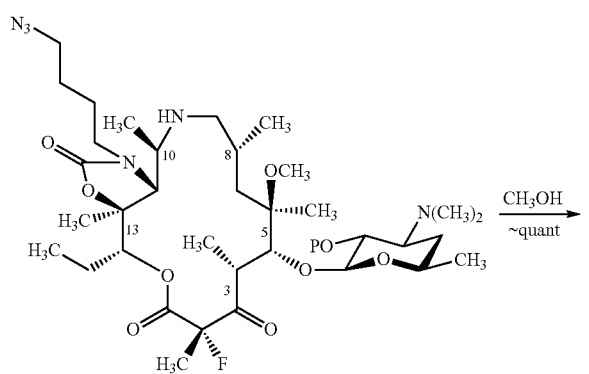
(stereochemistry unconfirmed)

683
-continued
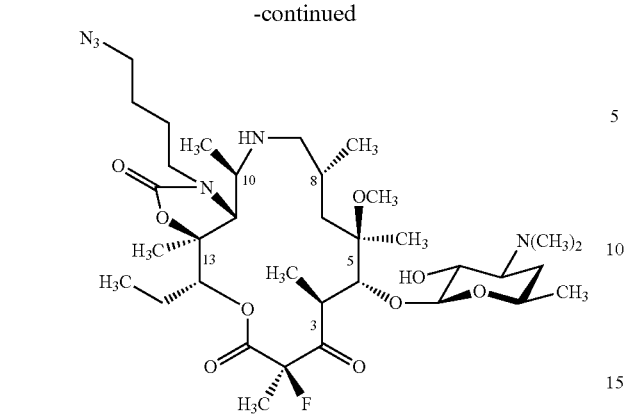
(C)
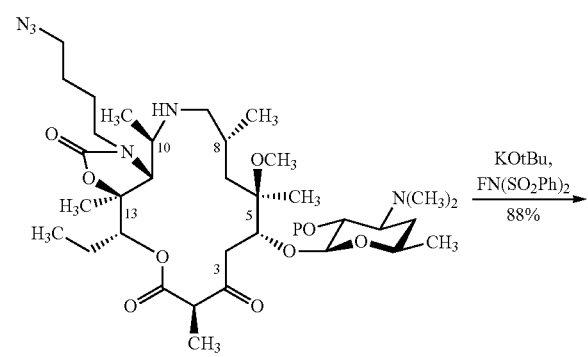
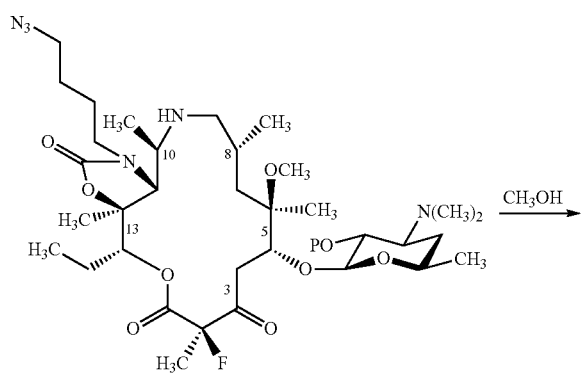
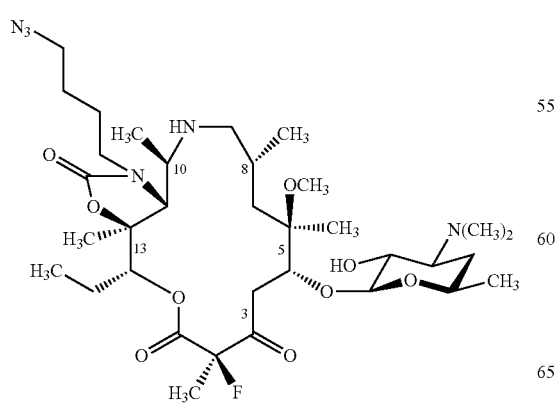
684
-continued
(D)
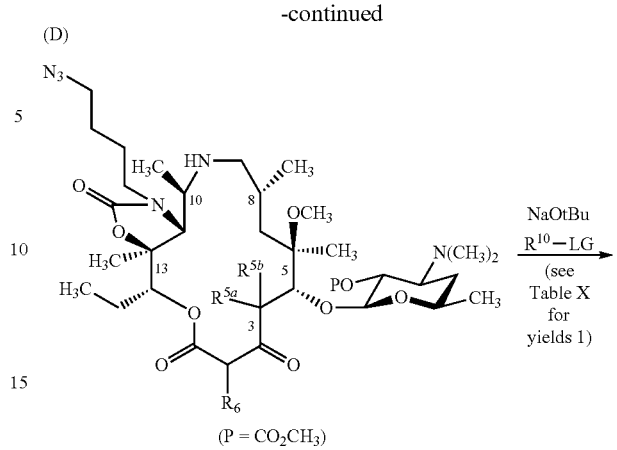
(P = CO₂CH₃)
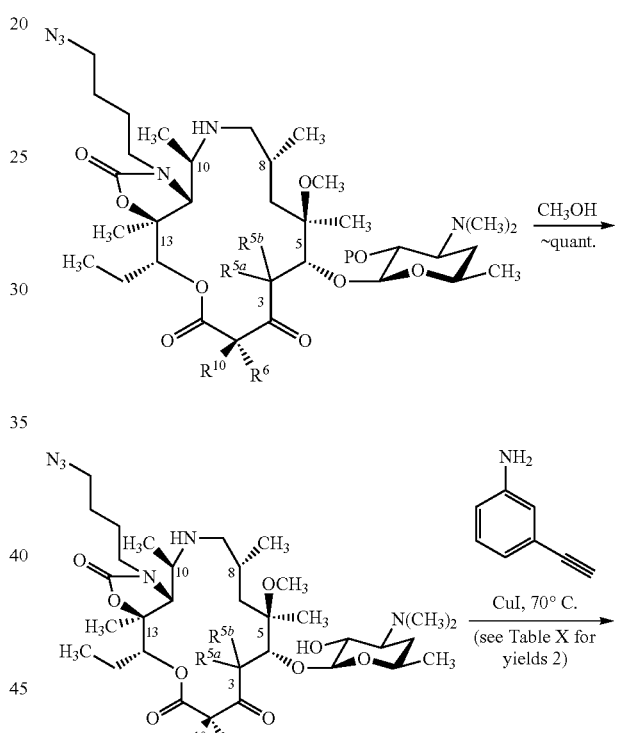
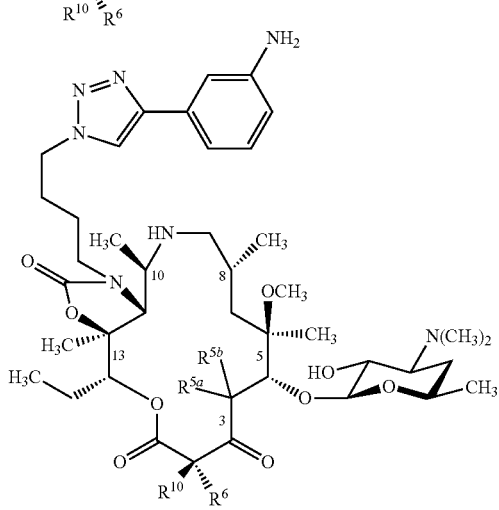

TABLE X

| Entry | R¹⁰-LG | R¹⁰, R⁶ | R⁵ᵃ, R⁵ᵇ | Yield 1 | Yield 2 | Cpmd. ID |
|---|---|---|---|---|---|---|
| 1 | None | H, H | Me, H | N/A | 41% | FSM-56133 |
| 2 | allyl iodide | allyl, H | Me, H | 62% | 32% | FSM-56156 |
| 3 | allyl iodide | allyl, H | H, H | — | — | — |
| 4 | benzyl bromide | benzyl, H | Me, H | 16% | 37% | FSM-56158 |
| 5 | benzyl bromide | benzyl, H | H, H | — | — | — |
| 6 | NCCH₂Br | NCCH₂, H | Me, H | 15% | 43% | FSM-56160 |
| 7 | NCCH₂Br | NCCH₂, H | H, H | — | — | — |
| 8 | tBuO₂C-CH₂-Br | tBuO₂C-CH₂, H | Me, H | 57% | 73% | FSM-56178 |
| 9 | tBuO₂C-CH₂-Br | tBuO₂C-CH₂, H | H, H | — | — | — |
| 11* | tBuO₂C-CH₂-Br | HO₂C-CH₂, H | Me, H | 57% | 73% | FSM-56178 |
| 12* | tBuO₂C-CH₂-Br | HO₂C-CH₂, H | H, H | — | — | — |
| 13* | 4-(bromomethyl)-1-Boc-pyrazole | 4-methyl-pyrazole-NH, H | Me, H | 36% | 20% | FSM-56192 |
| 14* | 4-(bromomethyl)-1-Boc-pyrazole | 4-methyl-pyrazole-NH, H | H, H | — | — | — |
| 15 | 5-(bromomethyl)thiazole | 5-methyl-thiazole, H | Me, H | 15 | 62% | FSM-56216 |

TABLE X-continued
| Entry | R[10]-LG | R[10], R[6] | R[5a], R[5b] | Yield 1 | Yield 2 | Cpmd. ID |
|---|---|---|---|---|---|---|
| 16 | 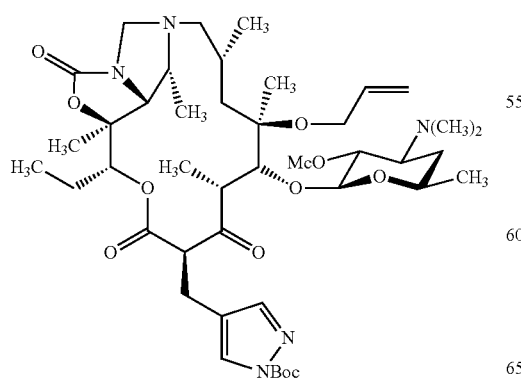 | 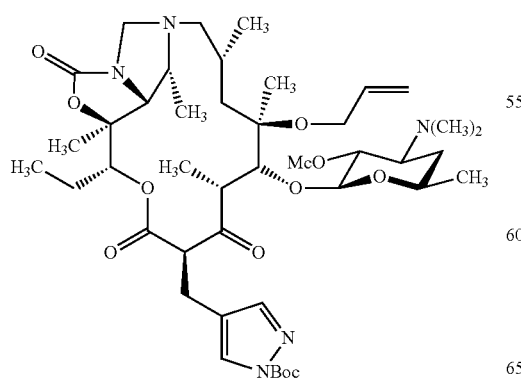 H | H, H | — | — | — |
*Additional deprotection step required at the end of the sequence
(E)
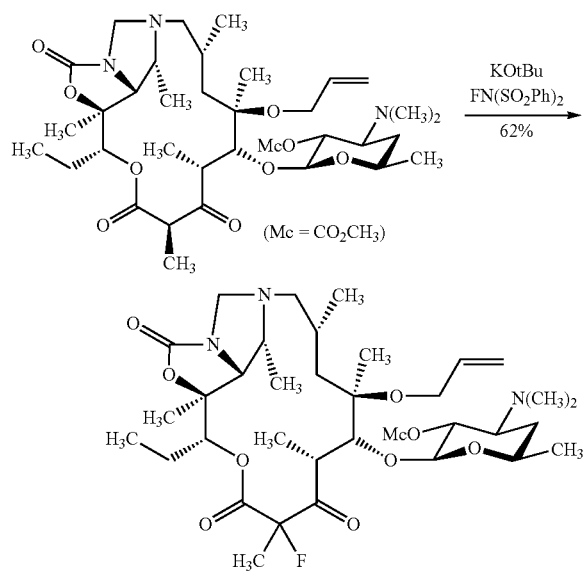
(F)
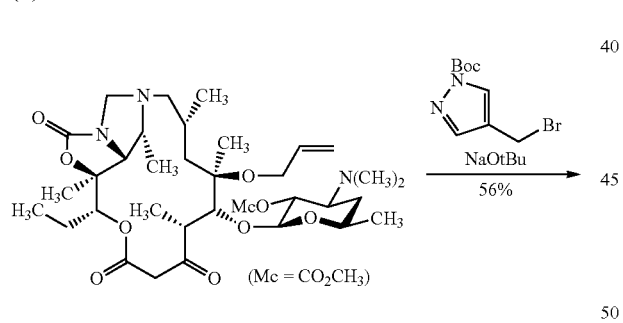
(G)
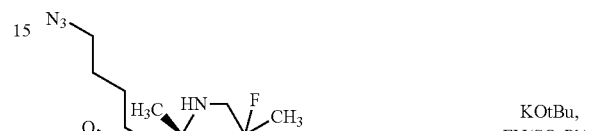
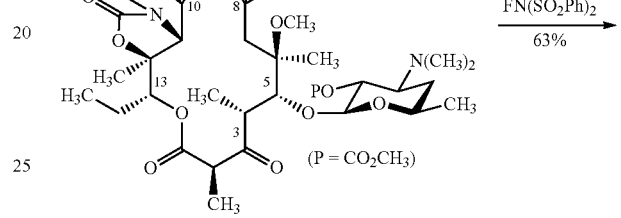
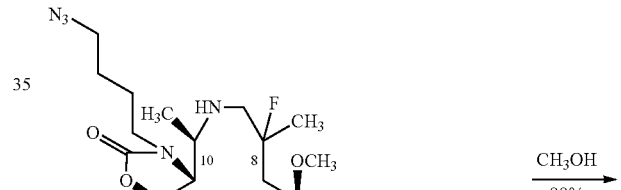
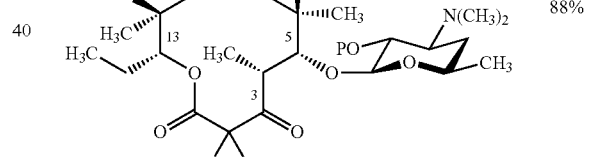
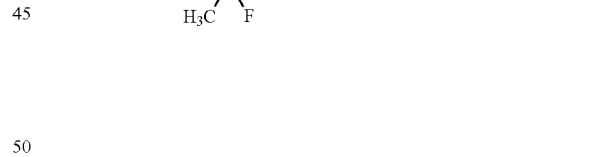
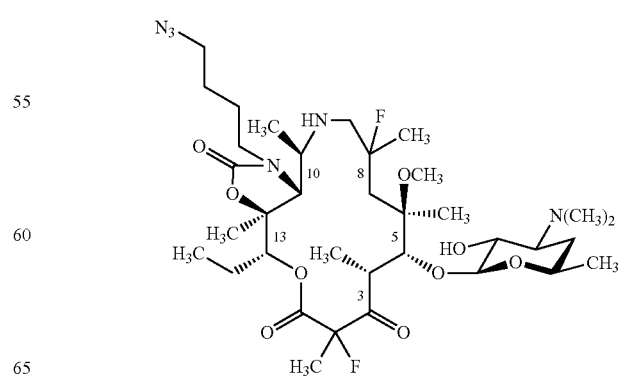

Example IV-6. Modifications at C10
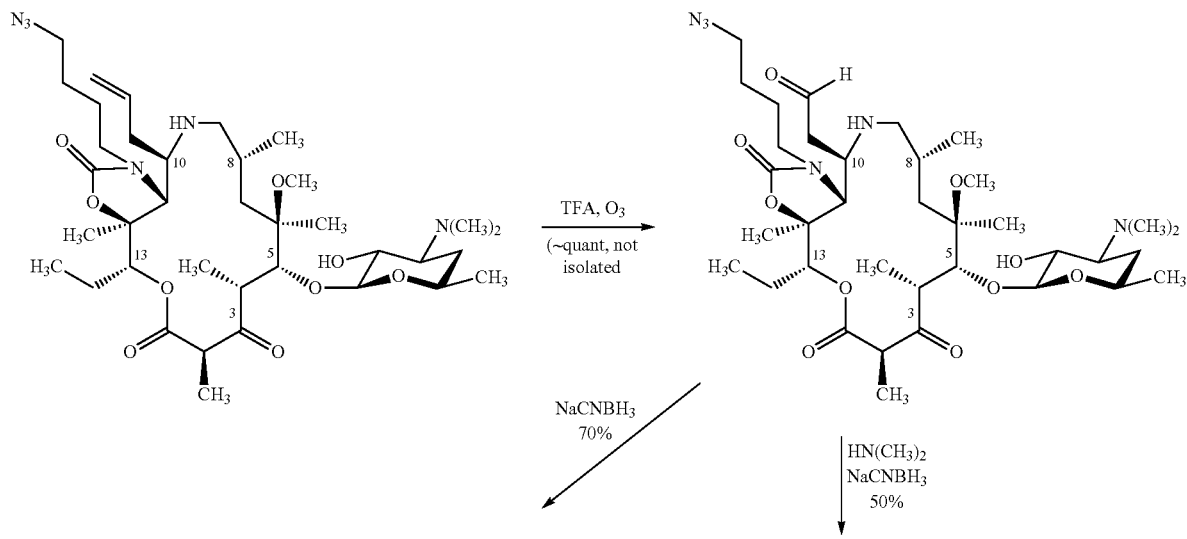
Example IV-7. Modifications at C3
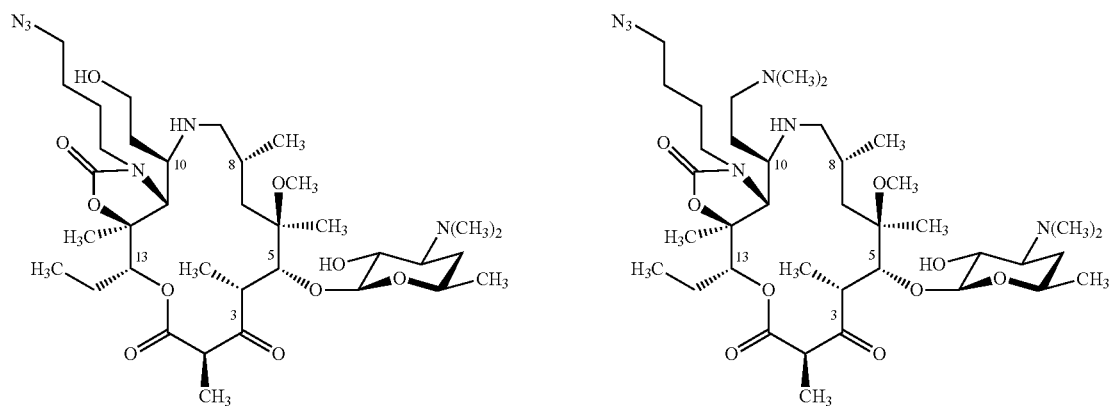
-continued
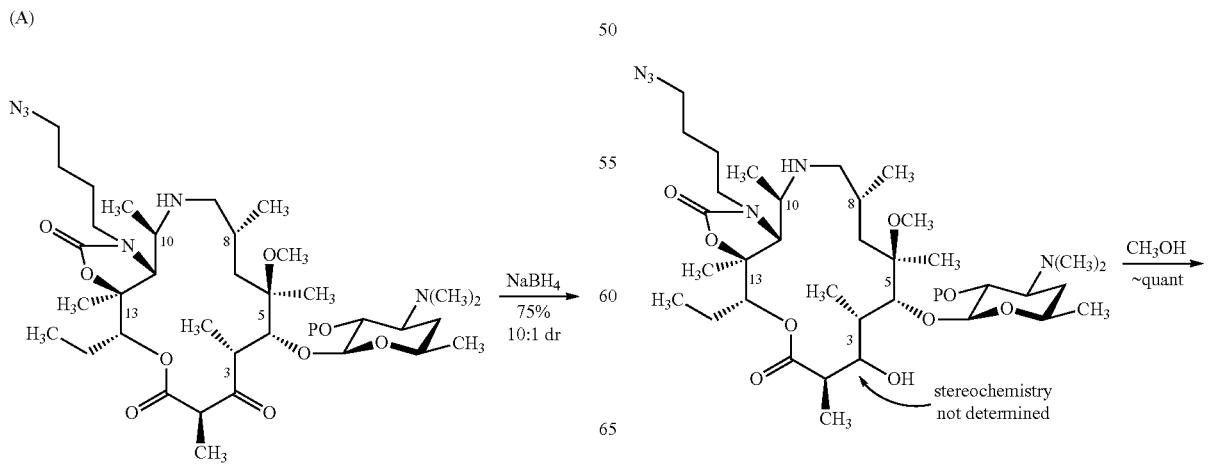

691
-continued
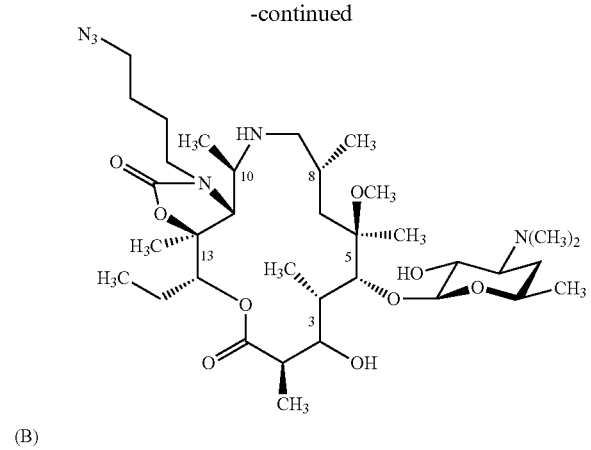
(B)
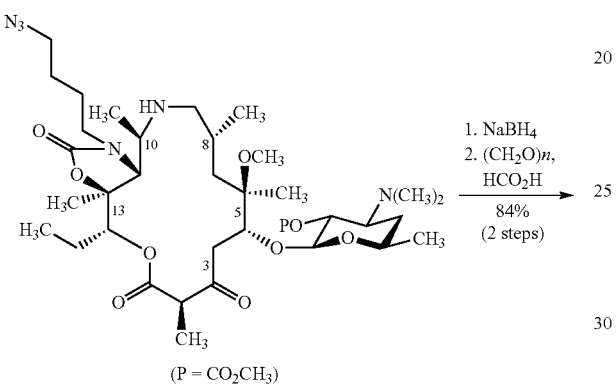
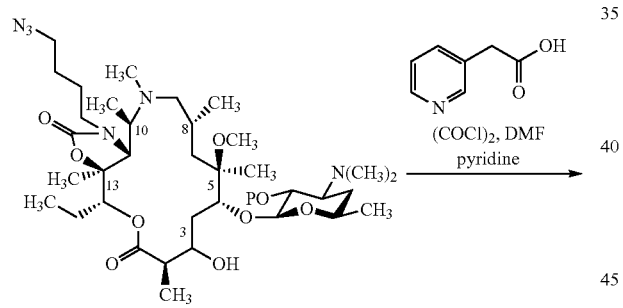
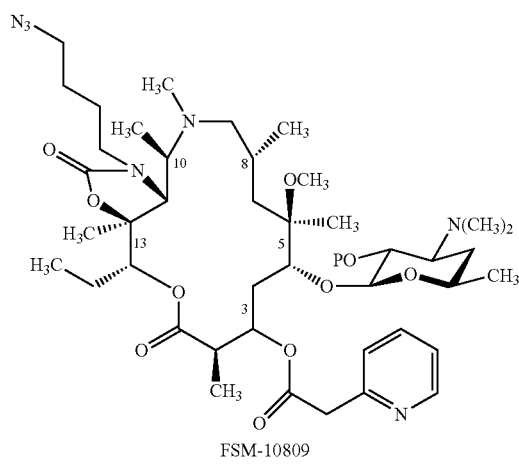
FSM-10809
692
Example IV-8. Modifications at C6
(A)
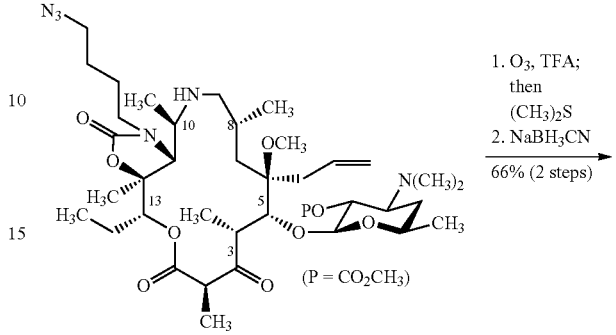
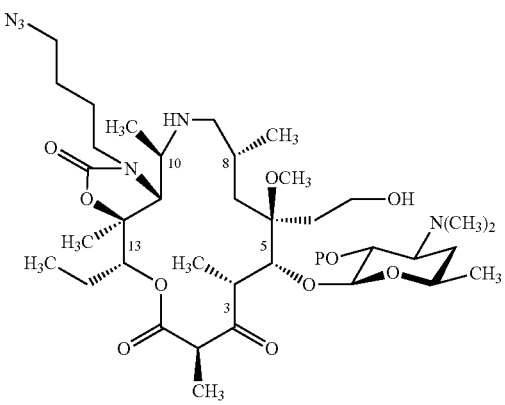
(B)
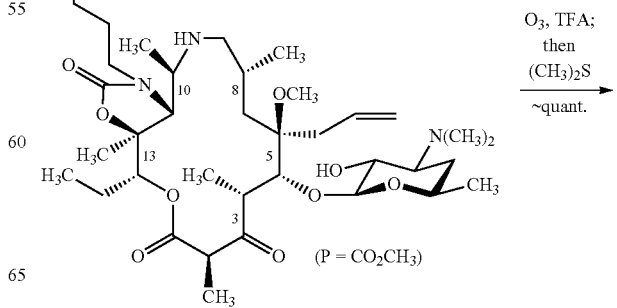

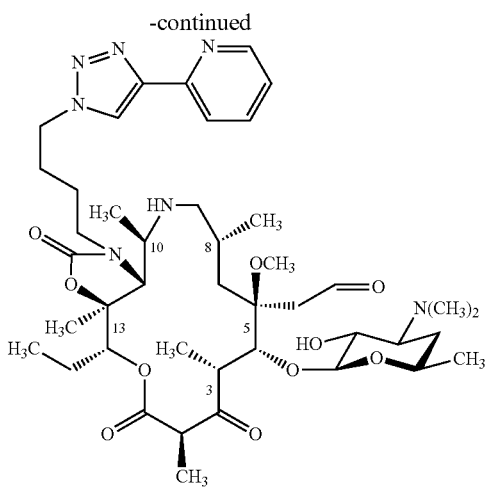

FSM-21428

Exemplary Synthetic Procedures for Coupling and Macrolide Formation

Part 3: Convergent Coupling, Macrocyclization, and Synthesis of Fully Synthetic Macrolides Part 3a: Azaketolides with a C2 Methyl Group Step 1

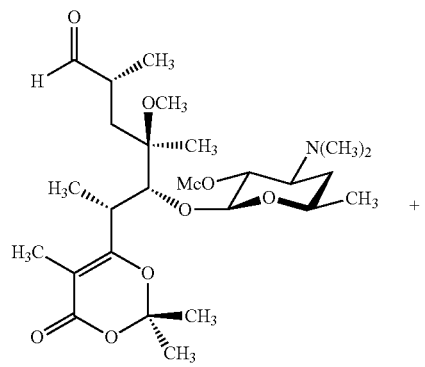

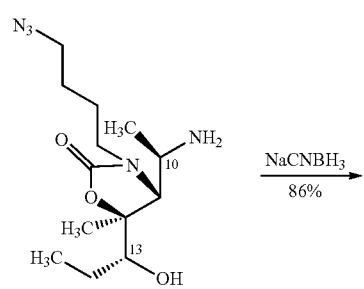

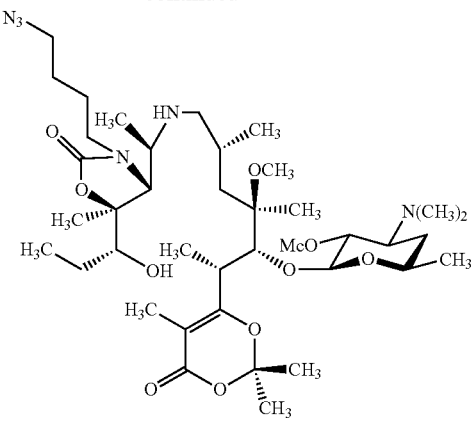

The amine (264 mg, 0.883 mmol) was dissolved in 9:1 methanol:acetic acid (3.0 mL), and the solution was cooled to −15° C. (ice/salt). Sodium cyanoborohydride (111 mg, 1.766 mmol) was added. The aldehyde (480 mg, 0.883 mmol) was added as a solution in 1.0 mL of 9:1 methanol: acetic acid. The transfer was quantitate with 2×0.5 mL of the same solvent. The reaction progress was monitored by TLC (10% methanol in ethyl acetate). Upon full consumption of the aldehyde (~1 h), the reaction mixture was concentrated, and the residue was diluted with dichloromethane (10 mL) and washed with saturated aqueous $NaHCO_3$ solution (5 mL). The layers were separated, and the aqueous phase was extracted with dichloromethane (2×5 mL). The combined organic phases were washed with water (5 mL) and brine (10 mL), dried through a pad of sodium sulfate, and concentrated. The residue was purified by column chromatography (3-5% methanol in $CH_2Cl_2$) to give the product as a white foam (630 mg, 86%). $^1$H NMR (500 MHz, $CDCl_3$) δ 4.59-4.46 (m, 2H), 3.83 (d, J=4.6 Hz, 1H), 3.76 (s, 3H), 3.71 (d, J=2.8 Hz, 1H), 3.56-3.41 (m, 3H), 3.36 (dd, J=10.3, 1.8 Hz, 1H), 3.30 (t, J=6.5 Hz, 2H), 3.26 (dd, J=7.2, 4.7 Hz, 1H), 3.05 (s, 3H), 2.81-2.69 (m, 2H), 2.50 (d, J=5.3 Hz, 2H), 2.28 (s, 6H), 1.84 (d, J=8.0 Hz, 3H), 1.83-1.71 (m, 3H), 1.70-1.66 (m, 3H), 1.64 (s, 3H), 1.63-1.53 (m, 5H), 1.41-1.32 (m, 3H), 1.31 (s, 3H), 1.25 (d, J=6.2 Hz, 3H), 1.24 (s, 3H), 1.11 (d, J=6.4 Hz, 3H), 1.06 (d, J=7.2 Hz, 3H), 1.02 (t, J=7.4 Hz, 3H), 0.96 (d, J=6.7 Hz, 3H). $^{13}$C NMR (126 MHz, $CDCl_3$) δ 167.83, 163.15, 157.94, 155.14, 104.50, 100.30, 98.95, 83.32, 79.30, 78.01, 77.45, 75.47, 69.18, 63.06, 61.85, 54.66, 54.46, 54.29, 50.96, 49.67, 43.34, 40.62, 40.42, 37.78, 34.41, 30.65, 28.70, 26.08, 26.03, 24.04, 23.74, 23.53, 23.17, 21.13, 20.91, 19.87, 16.60, 15.64, 13.34, 10.97, 9.83. FTIR (neat), cm$^{-1}$: 3430 (br), 2937 (m), 2096 (s), 1749 (s), 1724 (s), 1641 (s), 1442 (s), 1265 (s), 1109 (s), 1051 (s), 995 (s), 734 (s); HRMS (ESI): Calcd for $(C_{40}H_{70}N_6O_{12}+H)^+$: 827.5124. Found: 827.5107.

Step 2

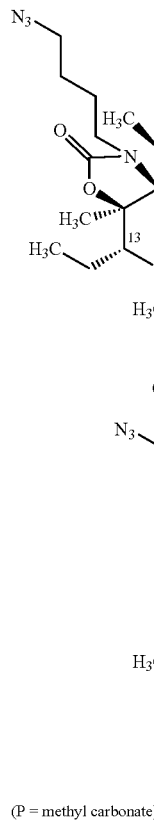

(P = methyl carbonate)

The coupled free alcohol (102 mg, 0.123 mmol) was azeotropically dried from benzene in a 100-mL flask. The flask was then fitted with a dry reflux condenser. Toluene (31 mL) was added through the condenser. The solution was degassed by bubbling argon through with a 22-gauge needle for 5 min. The top of the condenser was then fitted with a septum and argon line was attached. The solution was heated to reflux for 40 h. TLC analysis (10% methanol in ethyl acetate) indicated full conversion. The reaction mixture was cooled to room temperature and concentrated. The residue was purified by column chromatography (2-3% methanol in $CH_2Cl_2$) to give the product as a white foam (87 mg, 92%). Product exists as a 7:1 mixture of C2-epimers. The macrocyclization can also be performed in refluxing chlorobenzene, in which case reactions are generally complete within 16 h. $^1$H NMR (7:1 ratio of C2-epimers, major epimer reported, 500 MHz, $CDCl_3$) δ 4.94 (dd, J=10.9, 2.1 Hz, 1H), 4.55 (dd, J=10.5, 7.7 Hz, 1H), 4.51 (d, J=3.0 Hz, 1H), 4.46 (d, J=7.7 Hz, 1H), 3.83 (q, J=6.9 Hz, 1H), 3.76 (s, 3H), 3.68-3.55 (m, 3H), 3.40 (s, 1H), 3.37-3.24 (m, 2H), 3.03 (dd, J=7.9, 3.0 Hz, 1H), 3.00 (s, 3H), 2.84-2.70 (m, 3H), 2.28 (s, 6H), 2.02 (br, 1H), 2.00-1.90 (m, 1H), 1.81-1.52 (m, 9H), 1.45 (dd, J=14.5, 3.5 Hz, 1H), 1.41 (s, 3H), 1.38 (d, J=6.9 Hz, 3H), 1.28 (d, J=6.1 Hz, 3H), 1.25 (s, 3H), 1.18 (d, J=7.8 Hz, 3H), 1.08 (dd, J=14.7, 8.8 Hz, 1H), 0.97 (d, J=7.5 Hz, 3H), 0.95 (d, J=6.9 Hz, 3H), 0.87 (t, J=7.4 Hz, 3H). $^{13}$C NMR (126 MHz, $CDCl_3$) δ 205.59, 171.56, 156.82, 155.07, 100.29, 80.95, 78.36, 75.45, 74.60, 68.98, 65.37, 63.22, 59.10, 58.10, 54.68, 50.90, 49.92, 49.80, 44.94, 43.01, 40.73, 40.60, 30.44, 27.60, 26.18, 24.13, 21.78, 21.63, 21.01, 18.85, 14.20, 14.08, 14.02, 13.82, 10.31. FTIR (neat), cm$^{-1}$: 3300 (s), 2937 (m), 2096 (s), 1724 (s), 1643 (s), 1440 (s), 1377 (s), 1263 (s), 1109 (s), 1051 (s); HRMS (ESI): Calcd for $(C_{37}H_{64}N_6O_{11}+H)^+$: 769.4706. Found: 769.4721.

Step 3

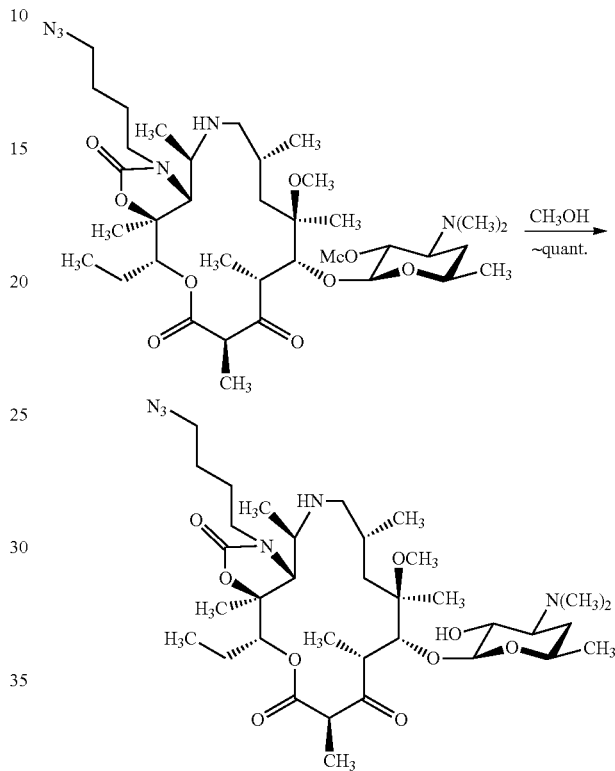

The macrolide (40 mg, 0.052 mmol) was dissolved in methanol (10 mL). The resulting solution was allowed to stand for 24 h at room temperature, at which point TLC (10% methanol in $CH_2Cl_2$+1% saturated $NH_4OH$) indicated full consumption of starting material. The solution was concentrated to give the product in pure form (37 mg, ~quant.). $^1$H NMR (11:1 ratio of C2-epimers, major epimer reported, 600 MHz, $CDCl_3$) δ 4.92 (dd, J=10.9, 2.2 Hz, 1H), 4.50 (d, J=3.7 Hz, 1H), 4.36 (d, J=7.4 Hz, 1H), 3.84 (q, J=6.9 Hz, 1H), 3.67-3.52 (m, 3H), 3.39 (s, 1H), 3.36-3.22 (m, 3H), 3.19 (dt, J=13.6, 6.8 Hz, 1H), 3.04 (ddd, J=15.2, 7.6, 3.6 Hz, 1H), 2.99 (d, J=7.4 Hz, 3H), 2.80-2.70 (m, 2H), 2.48 (ddd, J=12.3, 10.2, 3.9 Hz, 1H), 2.31-2.24 (m, 6H), 1.94 (tdd, J=15.0, 7.5, 2.2 Hz, 1H), 1.75 (t, J=10.4 Hz, 1H), 1.71-1.52 (m, 8H), 1.40 (s, 3H), 1.38 (d, J=7.0 Hz, 3H), 1.34 (d, J=7.8 Hz, 3H), 1.26 (s, 3H), 1.26 (d, J=5.3 Hz, 3H), 1.22-1.15 (m, 2H), 0.96 (d, J=6.1 Hz, 3H), 0.93 (d, J=7.0 Hz, 3H), 0.87 (t, J=7.4 Hz, 3H).

$^{13}$C NMR (126 MHz, $CDCl_3$) δ 205.83, 171.43, 156.85, 102.83, 81.00, 78.49, 78.34, 75.43, 70.17, 69.38, 65.94, 65.25, 59.17, 57.91, 50.93, 50.04, 49.88, 45.75, 43.04, 41.00, 40.26, 28.50, 27.79, 26.20, 24.13, 21.76, 21.67, 21.26, 18.98, 14.55, 14.42, 14.34, 14.12, 10.37.

FTIR (neat), cm$^{-1}$: 3470 (br), 3300 (s), 2941 (m), 2096 (s), 1739 (s), 1716 (s), 1070 (s), 729 (s); HRMS (ESI): Calcd for $(C_{35}H_{62}N_6O_9+H)^+$: 711.4651. Found: 711.4630.

Step 4

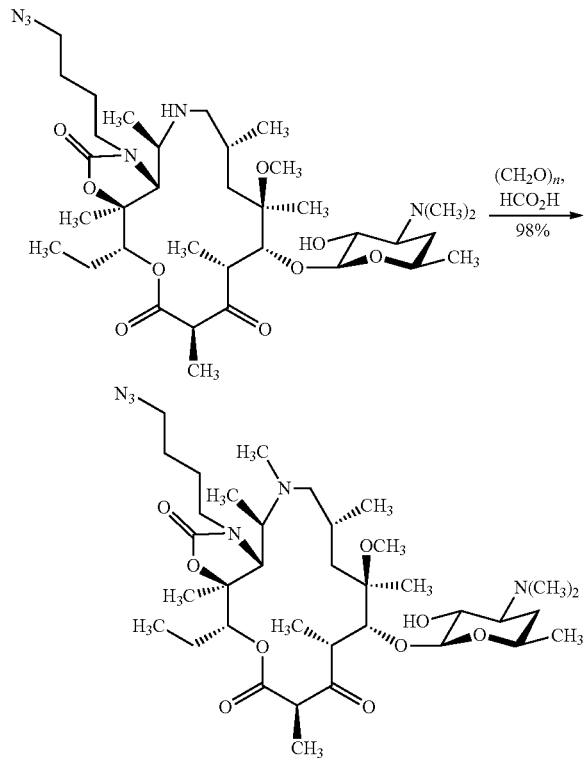

Step 3a

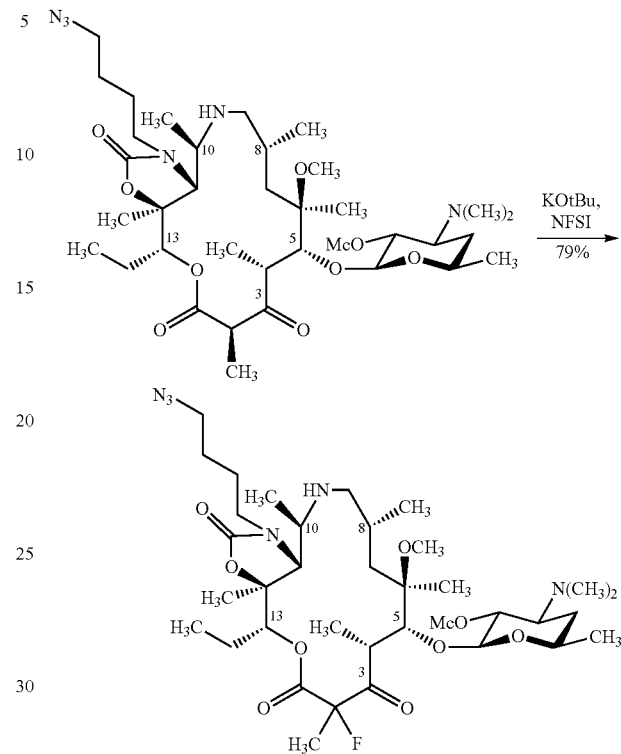

The macrolide (10 mg, 0.014 mmol) was dissolved in CDCl$_3$ (0.2 mL). Paraformaldehyde (2.53 mg, 0.084 mmol) and formic acid (5.40 µl, 0.141 mmol) were added. The mixture was heated in a 70° C. bath for 1.5 h. At this point, TLC (10% methanol in CH$_2$Cl$_2$+1% saturated NH$_4$OH) indicated full consumption of starting material. The reaction was diluted with CH$_2$Cl$_2$ (2 mL), and saturated aqueous NaHCO$_3$ (1 mL). The mixture was vigorously stirred and the layers were separated. The aqueous layer was extracted with CH$_2$Cl$_2$ (3×1 mL). The combined organic layers were dried over Na$_2$SO$_4$ and concentrated. The crude product was purified by column chromatography (3-4% methanol in CH$_2$Cl$_2$+0.3% saturated NH$_4$OH solution) to give the product in pure form (10 mg, 98%). The product exists as a 3:1 mixture of C2-epimers. $^1$H NMR (3:1 ratio of C2-epimers, major epimer is reported, 500 MHz, Benzene) δ 4.92 (dd, J=9.5, 2.9 Hz, 1H), 4.49 (d, J=7.3 Hz, 1H), 4.46 (d, J=6.9 Hz, 1H), 4.30-4.36 (m, 1H), 4.08 (d, J=10.4 Hz, 1H), 3.62 (ddd, J=14.4, 8.7, 7.2 Hz, 1H), 3.41-3.32 (m, 1H), 3.32-3.23 (m, 1H), 3.05 (s, 1H), 3.01-2.94 (m, 2H), 2.84 (d, J=7.6 Hz, 3H), 2.81-2.62 (m, 3H), 2.17-2.12 (m, 1H), 2.12-2.03 (m, 1H), 1.84 (s, 3H), 1.74 (s, 6H), 1.65 (d, J=6.7 Hz, 3H), 1.52 (d, J=6.8 Hz, 3H), 1.50 (s, 3H), 1.55-1.40 (m, 6H), 1.35 (s, 3H), 1.33-1.25 (m, 1H), 1.23-1.08 (m, 2H), 1.05 (d, J=6.1 Hz, 3H), 1.03-0.94 (m, 1H), 0.90 (d, J=6.1 Hz, 3H), 0.85 (t, J=7.5 Hz, 3H), 0.63 (d, J=7.0 Hz, 3H). FTIR (neat), cm$^{-1}$: 3470 (br), 2939 (m), 2096 (s), 1755 (s), 1716 (s), 1070 (s), 991 (s); HRMS (ESI): Calcd for (C$_{36}$H$_{64}$N$_6$O$_9$+H)$^+$: 725.4813. Found: 725.4799.

The macrolide (31 mg, 0.040 mmol) was dissolved in THF (1.0 mL). The solution was cooled to −78° C., and KOtBu (1.0 M solution in THF, 40.3 µL, 0.040 mmol) was added dropwise. The resulting mixture was stirred at −78° C. for 15 min, 0° C. for 1 min, and cooled to −78° C. A solution of N-fluorobenzenesulfonimide (12.71 mg, 0.040 mmol) in THF (0.5 mL) was added to the reaction mixture via syringe, quantitated with 0.1 mL THF. The reaction was stirred at −78° C. for 30 min. At this point, TLC analysis (10% methanol in ethyl acetate) indicated full conversion. The reaction was quenched by addition of saturated aqueous NaHCO$_3$ (1 mL), diluted with CH$_2$Cl$_2$ (10 mL), and stirred vigorously. The layers were separated, and the aqueous layer was extracted with CH$_2$Cl$_2$ (2×5 mL). The combined organic layers were washed with water (5 mL), dried over Na$_2$SO$_4$ and concentrated. The residue was purified by column chromatography (2-3% methanol in CH$_2$Cl$_2$) to give the product as a white foam (25 mg, 79%). $^1$H NMR (500 MHz, CDCl$_3$) δ 4.99 (d, J=10.6 Hz, 1H), 4.55 (dd, J=10.2, 7.7 Hz, 1H), 4.49 (d, J=7.4 Hz, 1H), 4.14 (d, J=8.1 Hz, 1H), 3.80 (s, 3H), 3.67-3.58 (m, 2H), 3.58-3.50 (m, 1H), 3.40-3.30 (m, 2H), 3.28 (s, 3H), 3.09 (br, 1H), 3.02-2.92 (m, 1H), 2.91-2.83 (m, 1H), 2.78 (td, J=12.1, 4.1 Hz, 1H), 2.72-2.63 (m, 1H), 2.30 (s, 6H), 2.05-1.91 (m, 2H), 1.85 (d, J=21.5 Hz, 3H), 1.81-1.51 (m, 8H), 1.47 (br s, 3H), 1.45-1.39 (m, 3H), 1.40-1.32 (m, 1H), 1.30 (s, 3H), 1.27 (d, J=6.1 Hz, 3H), 0.96 (d, J=5.3 Hz, 3H), 0.92 (d, J=7.2 Hz, 4H), 0.91 (t, J=7.3 Hz, 3H). HRMS (ESI): Calcd for (C$_{37}$H$_{63}$FN$_6$O$_{11}$+H)$^+$: 787.4617. Found: 787.4625.

Step 4a

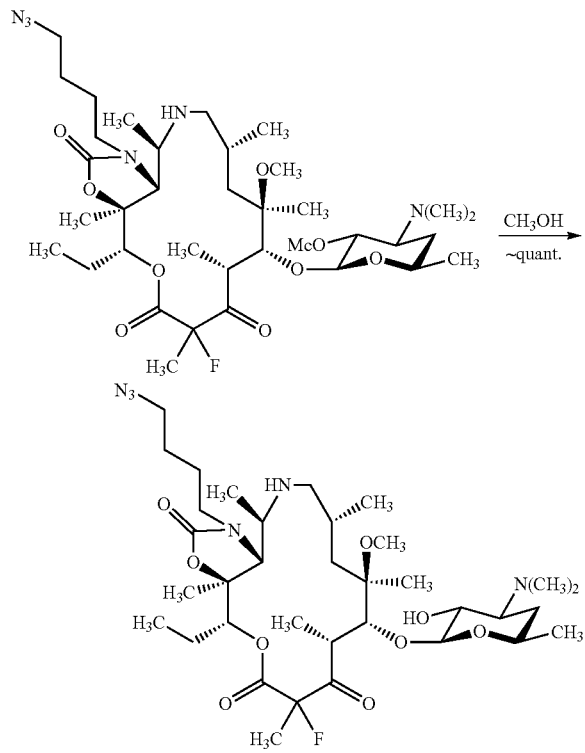

The macrolide (25 mg, 0.032 mmol) was dissolved in methanol (10 mL). The resulting solution was allowed to stand for 24 h at room temperature, at which point TLC (10% methanol in $CH_2Cl_2$+1% saturated $NH_4OH$) indicated full consumption of starting material. The solution was concentrated to give the product in pure form. $^1H$ NMR (500 MHz, $CDCl_3$) δ 4.95 (dd, J=10.9, 1.7 Hz, 1H), 4.40 (d, J=7.3 Hz, 1H), 4.15 (d, J=9.2 Hz, 1H), 3.66-3.50 (m, 4H), 3.38-3.30 (m, 2H), 3.28 (s, 3H), 3.20 (dd, J=10.2, 7.3 Hz, 1H), 3.13-3.06 (m, 1H), 3.03 (s, 1H), 2.95-2.89 (m, 1H), 2.72-2.62 (m, 1H), 2.49 (ddd, J=12.3, 10.4, 3.8 Hz, 1H), 2.28 (s, 6H), 2.00-1.90 (m, 2H), 1.85 (d, J=21.4 Hz, 3H), 1.73-1.57 (m, 9H), 1.55 (d, J=6.9 Hz, 3H), 1.49 (s, 3H), 1.32 (s, 3H), 1.26 (d, J=6.2 Hz, 3H), 1.24-1.21 (m, 1H), 0.95-0.85 (m, 9H).
HRMS (ESI): Calcd for $(C_{35}H_{61}FN_6O_9+H)^+$: 729.4557. Found: 729.4548.

Step 4b

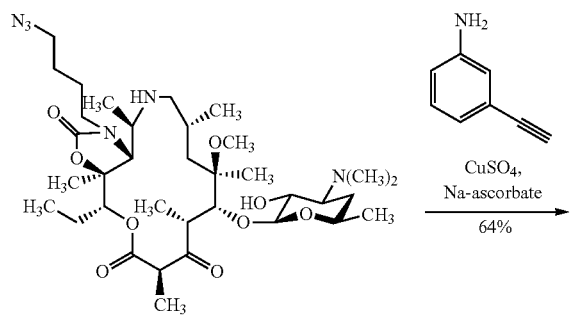

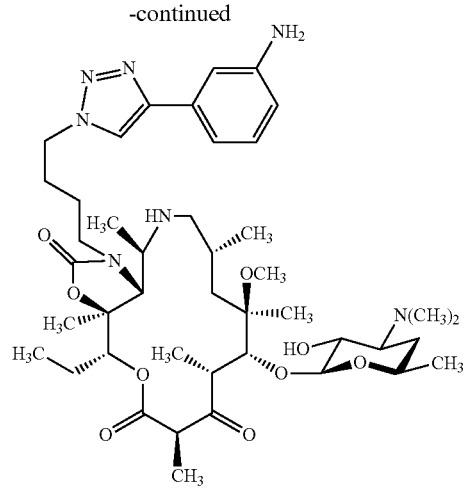

The macrolide (20 mg, 0.028 mmol) was dissolved in tBuOH/$H_2O$ (1:1, 0.2 mL). 3-ethynylaniline (9.89 mg, 0.084 mmol) was added, followed by sodium ascorbate (0.1 M in water, 56.3 μL, 5.63 μmol) and $CuSO_4$ (0.1 M in water, 11.25 μL, 1.125 mol). The mixture was stirred at rt under argon. After 16 h, LC-MS indicated complete conversion. 1 mL saturated aqueous $NaHCO_3$ was added, and the resulting solution was extracted with $CH_2Cl_2$ (3×5 mL). The combined organic layers were dried over $Na_2SO_4$ and concentrated. The residue was purified by flash column chromatography (2-3% methanol in $CH_2Cl_2$+0.2% saturated $NH_4OH$) to give the product as a slightly yellow solid (15 mg, 64%). $^1H$ NMR (500 MHz, $CDCl_3$) δ 7.81 (s, 1H), 7.25-7.12 (m, 3H), 6.68-6.62 (m, 1H), 4.96 (dd, J=10.8, 2.0 Hz, 1H), 4.52 (d, J=3.5 Hz, 1H), 4.49-4.40 (m, 2H), 4.38 (d, J=7.4 Hz, 1H), 3.89 (q, J=6.9 Hz, 1H), 3.77-3.58 (m, 4H), 3.42 (s, 1H), 3.24 (dd, J=10.0, 7.5 Hz, 1H), 3.05 (dt, J=11.0, 6.3 Hz, 1H), 2.96 (s, 3H), 2.84-2.71 (m, 2H), 2.59-2.48 (m, 1H), 2.32 (s, 6H), 2.09-1.92 (m, 3H), 1.82-1.48 (m, 7H), 1.44 (s, 3H), 1.42 (d, J=6.9 Hz, 3H), 1.37 (d, J=7.8 Hz, 3H), 1.29 (d, J=6.1 Hz, 3H), 1.26 (s, 3H), 1.18 (d, J=14.8 Hz, 1H), 0.99 (d, J=5.9 Hz, 3H), 0.94 (d, J=6.9 Hz, 3H), 0.89 (t, J=7.4 Hz, 3H). $^{13}C$ NMR (126 MHz, $CDCl_3$) δ 205.74, 171.70, 157.00, 147.81, 146.87, 131.63, 129.65, 119.60, 116.03, 114.73, 112.21, 102.85, 81.12, 78.49, 78.41, 75.29, 70.17, 69.43, 65.88, 65.49, 59.10, 57.89, 50.10, 49.88, 49.67, 45.73, 42.74, 40.91, 40.23, 28.40, 27.73, 27.52, 24.11, 21.73, 21.66, 21.25, 18.95, 14.54, 14.39, 14.32, 14.08, 10.44. FTIR (neat), $cm^{-1}$: 3452 (m), 2939 (m), 2096 (w), 1739 (s), 1456 (s), 1070 (s), 991 (s), 729 (s); HRMS (ESI): Calcd for $(C_{43}H_{69}N_7O_9+H)^+$: 828.5230. Found: 828.5216.

Part 3b: Azaketolides without a C2 Methyl Group: Macrocyclization and C2 Functionalization Step 1

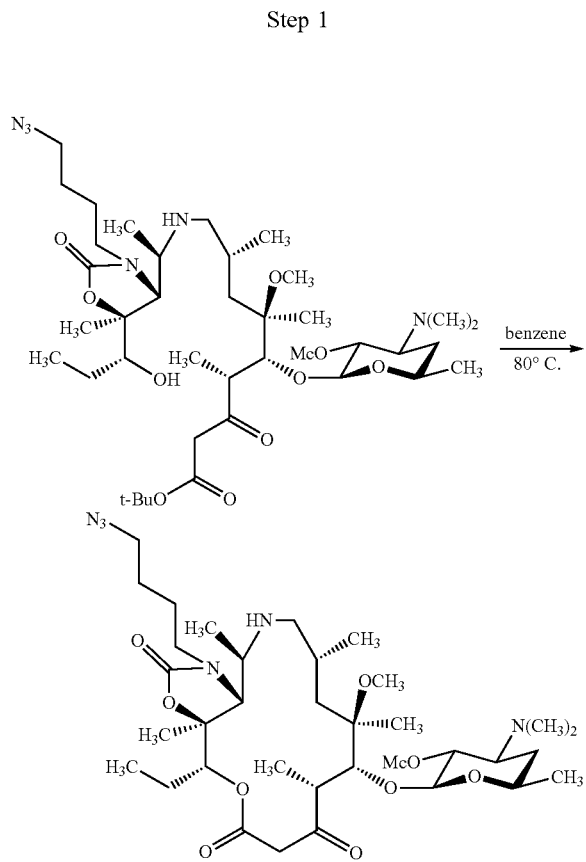

The macrocycle precursor alcohol (301 mg, 0.363 mmol, 1 equiv) was dried by azeotropic distillation (benzene, 20 mL). The dried substrate was dissolved in benzene (40 mL) and the resulting solution was degassed by bubbling through dry argon for 20 min using a long, large-bore metal needle. The needle was removed and the reaction flask was fitted with a reflux condenser. The reaction solution was heated at reflux for 12 h. The resulting solution was allowed to cool and then concentrated in vacuo, affording a pale yellow foam. The crude product was purified by flash-column chromatography (30% acetone-hexanes), providing the C2-desmethyl macrocycle as a white foam (230 mg, 84%). $^1$H NMR (500 MHz, CD$_3$OD) δ 4.93 (dd, 1H, J=10.7, 2.4 Hz), 4.54-4.49 (m, 2H), 4.15 (d, 1H, J=7.3 Hz), 3.76 (s, 3H), 3.66-3.61 (m, 1H), 3.57-3.51 (m, 2H), 3.39-3.29 (m, 3H), 3.16 (s, 3H), 2.99 (dd, 1H, J=11.2, 4.9 Hz), 2.92-2.85 (m, 2H), 2.61 (dd, 1H, J=10.3, 3.9 Hz), 2.29 (s, 6H), 1.96 (app t, 1H, J=10.2, 10.2 Hz), 1.87-1.80 (m, 2H), 1.68-1.57 (m, 7H), 1.48 (s, 3H), 1.38-1.32 (m, 2H), 1.29 (s, 3H), 1.28 (d, 3H, J=5.9 Hz), 1.23 (d, 3H, J=7.3 Hz), 0.96 (d, 3H, J=6.3 Hz), 0.95 (d, 3H, J=6.3 Hz), 0.91 (t, 3H, J=7.3 Hz); $^{13}$C NMR (125 MHz, CD$_3$OD) δ 204.0, 169.1, 159.0, 156.9, 103.0, 83.4, 80.5, 80.2, 79.1, 76.7, 70.3, 65.9, 63.9, 59.9, 57.6, 55.4, 52.0, 51.4, 44.0, 42.4, 40.7, 31.4, 29.3, 27.3, 25.2, 22.5, 22.5, 21.2, 20.0, 14.7, 14.4, 14.2; FTIR (neat film), 2938 (w), 2097 (w), 1751 (s), 1715 (m), 1263 (s), 1055 (s) cm$^{-1}$; HRMS-ESI (m/z): [M+Na]$^+$ calcd for C$_{36}$H$_{62}$N$_6$NaO$_{11}$, 777.4369. found, 777.4351.

Step 2

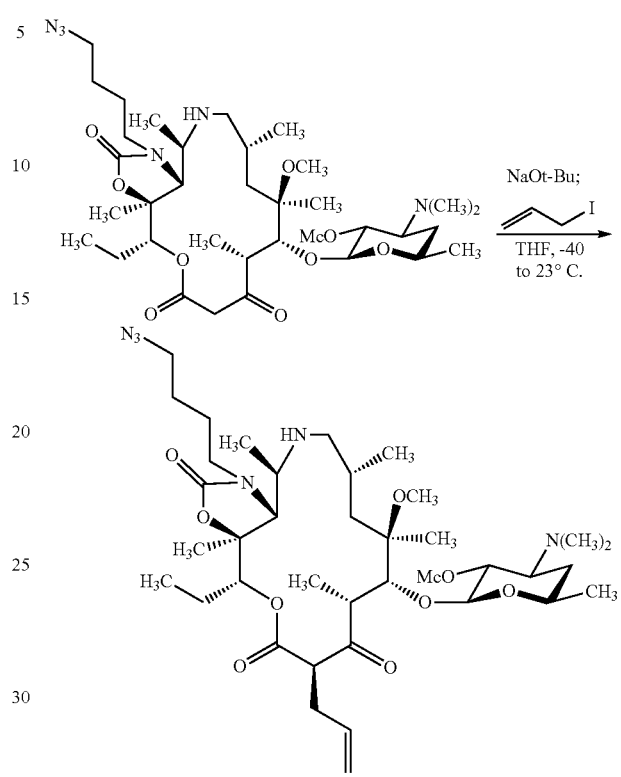

A solution of sodium tert-butoxide (2.0 M in tetrahydrofuran, 21.9 µL, 0.044 mmol, 1.1 equiv) was added dropwise via syringe to a solution of the C2-desmethyl macrocycle (30.0 mg, 0.040 mmol, 1 equiv) in tetrahydrofuran (0.25 mL) at −40° C. After stirring at this temperature for 30 min, allyl iodide (4.0 µL, 0.044 mmol, 1.1 equiv) was added to the reaction solution at −40° C. The resulting solution was allowed to warm slowly to 23° C. over 1.5 h, then was stirred at 23° C. for a further 3 h. The reaction mixture was quenched by addition of saturated aqueous ammonium chloride solution (0.5 mL). Dichloromethane (10 mL) and saturated aqueous sodium bicarbonate solution (5 mL) were added in sequence and the phases were separated. The aqueous phase was extracted with dichloromethane (2×10 mL). The organic extracts were combined and the combined solution was dried over anhydrous sodium sulfate. The dried solution was filtered and the filtrate was concentrated. The crude product was purified by flash-column chromatography (20% acetone-hexanes, grading to 25%), providing the C2-allyl macrocycle as a 5:1 mixture of C2 epimers (19.5 mg, 62%). NB—clearly distinguishable peaks corresponding to the minor C2 epimer are reported with non-integer integrals; integrals for all other multiplet peaks are rounded to the nearest integer. $^1$H NMR (500 MHz, CDCl$_3$) δ 5.78-5.70 (m, 1H), 5.14 (dd, 1H, J=17.1, 1.5 Hz), 5.08-5.06 (m, 1H), 4.93 (dd, 1H, J=9.8, 2.4 Hz), 4.56-4.52 (m, 2H), 4.41 (d, 1H, J=7.8 Hz), 4.18 (d, 0.2H, J=7.3 Hz), 3.91 (d, 0.2H, J=2.4 Hz), 3.81 (t, 1H, J=7.1 Hz), 3.78 (s, 0.6H), 3.77 (s, 3H), 3.71 (dd, 0.2H, J=8.8, 5.9 Hz), 3.66-3.56 (m, 4H), 3.41-3.25 (m, 5H), 3.00 (s, 3H), 3.00-2.95 (m, 1H), 2.82-2.70 (m, 5H), 2.50-2.43 (m, 1H), 2.29 (s, 1.2H), 2.28 (s, 6H), 1.99-1.94 (m, 1H), 1.78-1.61 (m, 9H), 1.58-1.52 (m, 2H), 1.46 (dd, 1H, J=14.6, 3.9 Hz), 1.41 (s, 3H), 1.35 (app t, 1H, J=12.7, 11.2 Hz), 1.29-1.25 (m, 11H), 1.18 (d, 3H, J=7.8 Hz), 1.12-1.07 (m, 2H), 0.96 (app t, 6H, J=7.3, 5.9 Hz), 0.90 (t, 3H, J=7.6 Hz), 0.84 (t, 0.6H, J=7.3 Hz); HRMS-ESI (m/z): [M+H]$^+$ calcd for $C_{39}H_{67}N_6O_{11}$, 795.4862. found, 795.4840.

Part 3c: Ketolides

Step 1

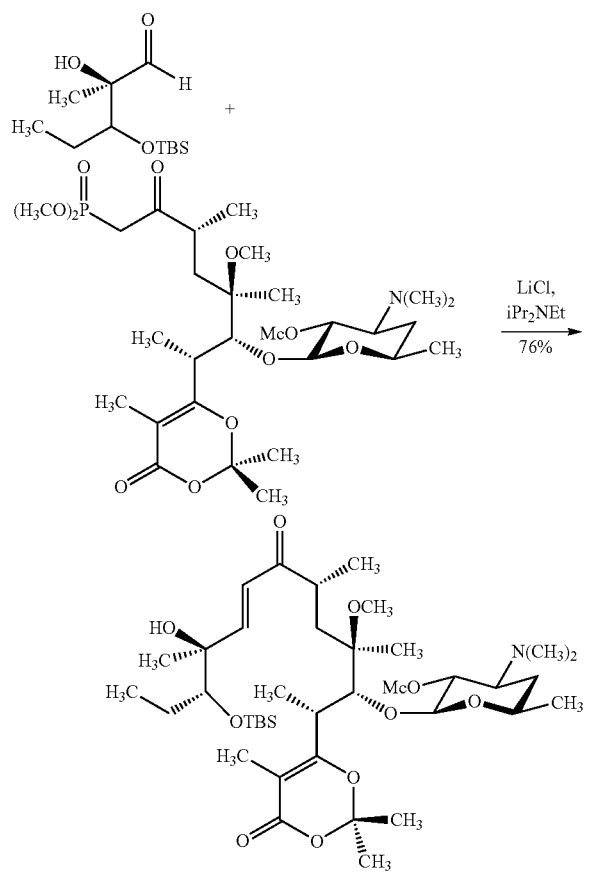

A 25-mL flask equipped with a stir bar was charged with anhydrous LiCl (0.153 g, 3.61 mmol). The vessel was heated with a gentle flame under vacuum (0.1 mmHg) for 2 min. The phosphonate (2.0 g, 3.00 mmol) was added as a solution in acetonitrile (15.02 mL), followed by diisopropylethylamine (0.630 mL, 3.61 mmol). The suspension was stirred at rt for 5 min. (2R,3R)-3-((tert-butyldimethylsilyl)oxy)-2-hydroxy-2-methylpentanal (0.740 g, 3.00 mmol) was added neat dropwise. The resulting suspension was then stirred at 30° C. After 12 h, TLC (10% methanol in ethyl acetate) indicated full consumption of the phosphonate. The reaction mixture was diluted with $CH_2Cl_2$ (30 mL), saturated aqueous $NaHCO_3$ (15 mL) and vigorously stirred. The layers were separated and the aqueous layer was extracted with $CH_2Cl_2$ (3×20 mL). The combined organic layers were dried over $Na_2SO_4$ and concentrated. The crude product was purified by flash column chromatography (2-3% methanol in $CH_2Cl_2$+0.2% saturated $NH_4OH$) to give the product as a white foam (1.80 g, 76%). $^1$H NMR (500 MHz, CDCl$_3$) δ 6.82 (d, J=15.6 Hz, 1H), 6.46 (d, J=15.6 Hz, 1H), 4.63-4.48 (m, 2H), 3.82 (d, J=3.4 Hz, 1H), 3.78 (s, 3H), 3.52 (dd, J=5.8, 4.6 Hz, 1H), 3.48-3.40 (m, 1H), 3.38-3.30 (m, 1H), 2.93 (s, 3H), 2.80-2.71 (m, 1H), 2.59 (s, 1H), 2.31 (s, 6H), 2.12 (dd, J=14.1, 10.2 Hz, 1H), 1.82 (s, 3H), 1.80-1.74 (m, 1H), 1.66 (s, 3H), 1.65 (s, 3H), 1.64-1.57 (m, 1H), 1.49-1.41 (m, 2H), 1.41-1.31 (m, 1H), 1.27 (s, 3H), 1.25 (d, J=6.2 Hz, 4H), 1.21 (s, 3H), 1.07 (d, J=3.5 Hz, 3H), 1.06 (d, J=3.0 Hz, 3H), 0.92 (s, 9H), 0.90 (t, J=2.8 Hz, 3H), 0.10 (d, J=1.9 Hz, 6H). $^{13}$C NMR (126 MHz, CDCl$_3$) δ 203.61, 167.58, 162.99, 155.24, 147.02, 125.97, 104.34, 99.94, 99.78, 79.32, 78.24, 77.40, 75.63, 75.49, 69.22, 63.04, 54.69, 49.40, 40.67, 39.82, 37.99, 34.12, 30.85, 26.16, 25.95, 25.89, 25.73, 24.32, 20.95, 20.09, 18.93, 18.20, 13.00, 10.75, 9.69, −3.88, −4.43. FTIR (neat), cm$^{-1}$: 3470 (br), 2937 (m), 1751 (s), 1716 (s), 1639 (s), 1267 (s), 1055 (s), 910 (s); HRMS (ESI): Calcd for $(C_{40}H_{71}NO_{12}Si+H)^+$: 786.4818. Found: 786.4824.

Step 2

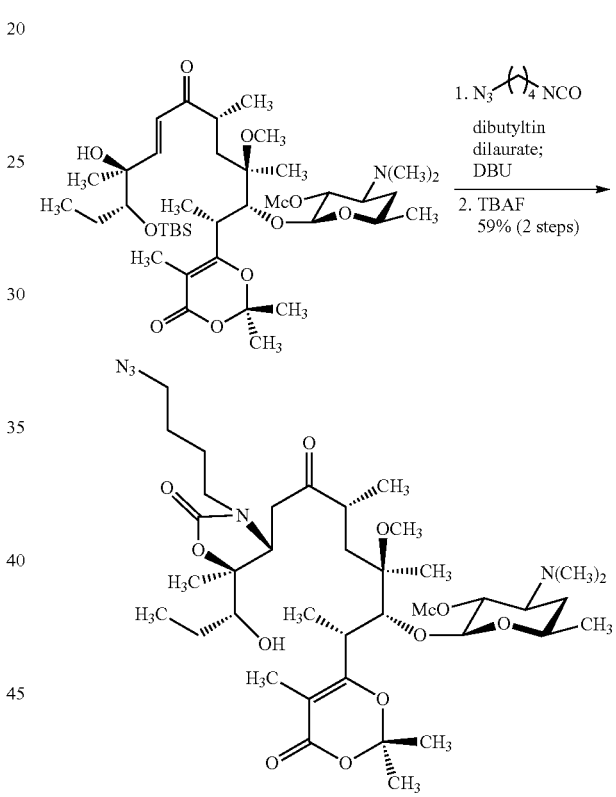

The unsaturated ketone (198 mg, 0.252 mmol) was dissolved in $CH_2Cl_2$ (2.5 mL). 1-azido-4-isocyanatobutane (176 mg, 1.259 mmol) was added, followed by dibutyltin dilaurate (150 μl, 0.252 mmol). The reaction was stirred at 80° C. After 6 h, LC-MS indicated full consumption of starting material. The solvent was removed and the residue was dissolved in DMF (2 mL). DBU (0.038 mL, 0.252 mmol) was added. The resulting solution was stirred at rt for 1 h, at which point LC-MS indicated full consumption of starting material. The reaction mixture was diluted with ether (10 mL) and water (5 mL), and stirred vigorously for 15 min. The layers were separated and the aqueous layer was extracted with ether (2×5 mL). The combined ether layers were washed with brine, dried over MgSO$_4$, filtered and concentrated to give the cyclized carbamate with ~10:1 d.r. at C11 (ratio determined by $^1$H NMR). The crude product was dissolved in THF (2 mL) and TBAF (1.0 M solution in THF, 0.378 mL, 0.378 mmol) was added. In 20 min, TLC (10% methanol in ethyl acetate) indicated full conversion to a slightly more polar compound. The reaction mixture was directly concentrated and purified by flash column chromatography (2-3% methanol in $CH_2Cl_2$+0.2% saturated $NH_4OH$) to give the product as a white foam (120 mg, 59%). $^1$H NMR (10:1 ratio of C11 epimers, major epimer is reported, 500 MHz, $CDCl_3$) δ 4.60-4.50 (m, 2H), 4.27 (t, J=5.9 Hz, 1H), 3.87 (d, J=3.5 Hz, 1H), 3.77 (s, 3H), 3.51 (d, J=10.5 Hz, 1H), 3.49-3.41 (m, 2H), 3.32 (t, J=6.5 Hz, 2H), 3.25 (qd, J=7.2, 3.4 Hz, 1H), 2.96 (s, 3H), 2.91-2.87 (m, 1H), 2.87-2.80 (m, 1H), 2.80-2.71 (m, 2H), 2.29 (s, 6H), 2.02 (dd, J=14.1, 10.7 Hz, 1H), 1.81 (s, 3H), 1.79-1.74 (m, 1H), 1.67 (d, J=6.3 Hz, 3H), 1.65 (s, 3H), 1.63-1.51 (m, 5H), 1.45 (dd, J=14.2, 1.9 Hz, 1H), 1.42-1.33 (m, 3H), 1.33-1.27 (m, 1H), 1.25 (d, J=6.0 Hz, 3H), 1.25 (s, 3H), 1.23 (s, 3H), 1.07 (d, J=7.0 Hz, 3H), 1.07 (d, J=7.4 Hz, 3H), 1.03 (t, J=7.4 Hz, 3H). $^{13}$C NMR (126 MHz, $CDCl_3$) δ 212.38, 167.16, 162.69, 156.89, 155.22, 104.51, 100.00, 99.58, 83.44, 78.67, 78.25, 75.41, 69.27, 62.94, 54.67, 54.45, 50.89, 49.62, 41.48, 41.29, 40.68, 40.61, 38.35, 34.02, 30.75, 25.94, 24.12, 23.99, 23.44, 20.92, 20.01, 19.06, 16.50, 13.08, 10.79, 9.72. FTIR (neat), cm$^{-1}$: 3443 (br), 2939 (m), 2096 (s), 1747 (s), 1720 (s), 1641 (s), 1265 (s), 1053 (s), 731 (s); HRMS (ESI): Calcd for $(C_{39}H_{65}N_5O_{13}+H)^+$: 812.4652. Found: 812.4666.

a freeze-pump-thaw cycle. The solution was then heated to reflux. After 16 h, the reaction was cooled and concentrated. The crude product was purified by flash column chromatography (2-3% methanol in $CH_2Cl_2$+0.2% saturated $NH_4OH$) to give the product as a white foam (78 mg, 76%). $^1$H NMR (500 MHz, $CDCl_3$) δ 4.94 (dd, J=9.1, 3.1 Hz, 1H), 4.49 (dd, J=10.4, 7.6 Hz, 1H), 4.39 (d, J=7.3 Hz, 1H), 3.97 (d, J=10.1 Hz, 1H), 3.84-3.81 (m, 1H), 3.79 (s, 3H), 3.71 (q, J=7.1 Hz, 1H), 3.55-3.42 (m, 2H), 3.37-3.25 (m, 2H), 3.10-3.00 (m, 1H), 3.00-2.89 (m, 1H), 2.76-2.66 (m, 1H), 2.66-2.57 (m, 1H), 2.53 (s, 3H), 2.39 (dd, J=18.0, 9.3 Hz, 1H), 2.26 (s, 6H), 2.01-1.88 (m, 1H), 1.78-1.66 (m, 4H), 1.66-1.47 (m, 5H), 1.43 (d, J=6.8 Hz, 3H), 1.36 (s, 3H), 1.30 (s, 3H), 1.28-1.24 (m, 1H), 1.22 (d, J=5.7 Hz, 3H), 1.16 (d, J=7.0 Hz, 6H), 0.89 (t, J=7.4 Hz, 3H). $^{13}$C NMR (126 MHz, $CDCl_3$) δ 209.98, 203.32, 168.76, 156.80, 155.18, 101.78, 81.62, 81.09, 79.65, 78.57, 75.56, 69.18, 63.24, 59.95, 54.80, 51.52, 51.02, 49.70, 48.45, 43.69, 42.92, 40.72, 40.61, 36.60, 30.17, 26.09, 25.22, 23.52, 20.85, 19.15, 18.20, 18.00, 15.35, 14.83, 10.47. FTIR (neat), cm$^{-1}$: 2939 (m), 2096 (s), 1751 (s), 1712 (s), 1265 (s), 1053 (s), 993 (s), 731 (s); HRMS (ESI): Calcd for $(C_{36}H_{59}N_5O_{12}+H)^+$: 754.4233. Found: 754.4257.

Step 3

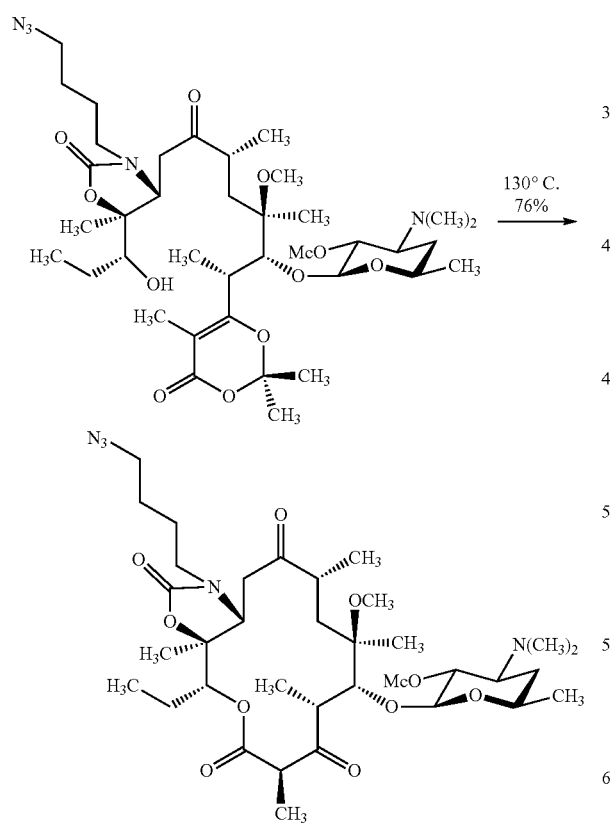

The cyclic carbamate (110 mg, 0.135 mmol) was azeotropically dried from benzene and dissolved in chlorobenzene (13.5 mL) in a 50-mL flask. The flask was fitted with a dry reflux condenser, and the equipment was degassed by Step 4

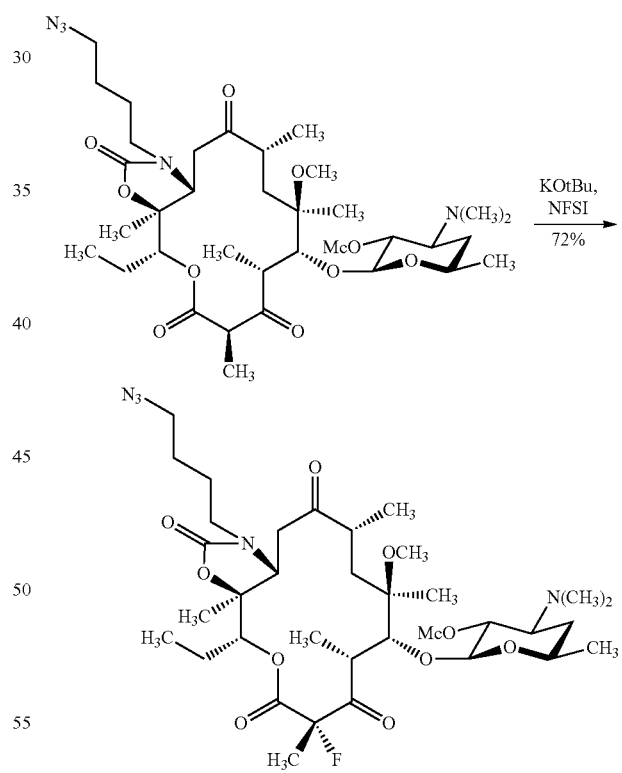

The macrocycle (30 mg, 0.040 mmol) was azeotropically dried from benzene and dissolved in THF (0.5 mL). The solution was cooled to −78° C. and KOtBu (1.0 M solution in THF, 0.044 mL, 0.044 mmol) was added dropwise. The resulting solution was stirred at −78° C. for 30 min, warmed to −20° C. for 5 min, and cooled back to −78° C. A solution of N-fluorobenzenesulfonimide (12.55 mg, 0.040 mmol) in THF (0.5 mL) was added via syringe to the enolate solution above. After 20 min, LC-MS showed full consumption of starting material. The reaction was quenched at −78° C. by adding saturated aqueous NaHCO₃ (1 mL), and ethyl acetate (5 mL). The mixture was vigorously stirred and the layers were separated. The aqueous layer was extracted with ethyl acetate (2×5 mL). The combined organic layers were washed with brine, dried over Na₂SO₄ and concentrated. The crude product was purified by flash column chromatography (2-3% methanol in CH₂Cl₂+0.2% saturated NH₄OH) to give the product (22 mg, 72%). ¹H NMR (500 MHz, CDCl₃) δ 4.94 (dd, J=8.2, 3.7 Hz, 1H), 4.50 (dd, J=10.5, 7.6 Hz, 1H), 4.42 (d, J=7.6 Hz, 1H), 3.85 (d, J=10.4 Hz, 1H), 3.81 (s, 3H), 3.83-3.79 (m, 1H), 3.62-3.57 (m, 1H), 3.55-3.37 (m, 2H), 3.36-3.24 (m, 2H), 3.06 (d, J=18.4 Hz, 1H), 2.76-2.67 (m, 2H), 2.65-2.56 (m, 1H), 2.43 (s, 3H), 2.42-2.33 (m, 1H), 2.26 (s, 6H), 2.06-1.90 (m, 2H), 1.75 (d, J=21.4 Hz, 3H), 1.70-1.48 (m, 7H), 1.38 (s, 3H), 1.28 (s, 3H), 1.27-1.24 (m, 1H), 1.22 (d, J=6.1 Hz, 3H), 1.18 (d, J=6.8 Hz, 6H), 0.95 (t, J=7.5 Hz, 3H). HRMS (ESI): Calcd for (C₃₆H₅₈FN₅O₁₂+H)⁺: 772.4139. Found: 772.4155.

Step 5

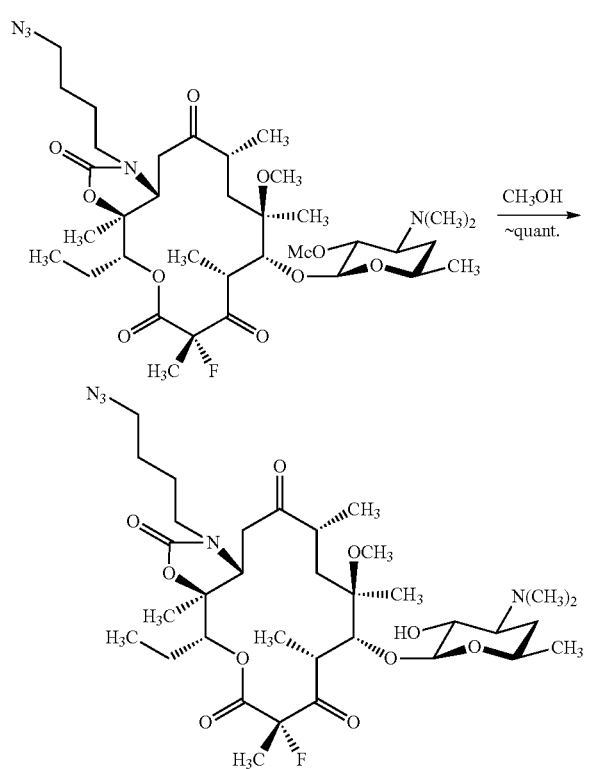

The desmethyl-C2-fluoro-macrocycle (8 mg, 10.36 μmol) was dissolved in methanol (1 mL) and was left standing for 24 h. At this point, LC-MS indicated full consumption of starting material. The reaction mixture was concentrated directly to give the product (7 mg, ~quant.). ¹H NMR (500 MHz, CDCl₃) δ 4.94 (dd, J=8.1, 3.8 Hz, 1H), 4.35 (d, J=7.3 Hz, 1H), 3.87 (d, J=9.9 Hz, 1H), 3.82 (d, J=9.7 Hz, 1H), 3.75-3.66 (m, 1H), 3.56-3.49 (m, 1H), 3.49-3.40 (m, 1H), 3.37-3.23 (m, 2H), 3.24-3.14 (m, 1H), 3.09 (d, J=18.8 Hz, 1H), 3.04 (dd, J=12.6, 4.1 Hz, 1H), 2.68-2.57 (m, 1H), 2.45 (s, 3H), 2.39 (dd, J=18.7, 9.9 Hz, 1H), 2.28 (s, 6H), 2.05-1.93 (m, 2H), 1.93-1.81 (m, 2H), 1.75 (d, J=21.4 Hz, 3H), 1.72-1.46 (m, 6H), 1.39 (s, 3H), 1.32 (d, J=7.0 Hz, 3H), 1.31 (s, 3H), 1.23 (d, J=6.1 Hz, 3H), 1.17 (d, J=6.9 Hz, 3H), 0.96 (t, J=7.6 Hz, 3H). HRMS (ESI): Calcd for (C₃₄H₅₆FN₅O₁₀+H)⁺: 714.4084; Found: 714.4101.

Step 6

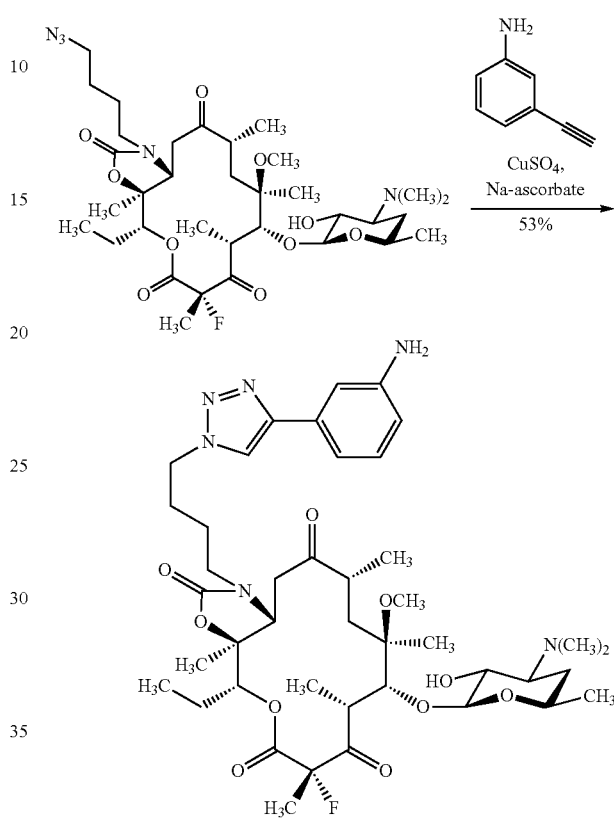

The C10-desmethyl-C2-fluoro-ketolide (7 mg, 9.81 μmol) was dissolved in tBuOH/H₂O (1:1, 0.2 mL). 3-Ethynylaniline (3.45 mg, 0.029 mmol) was added, followed by sodium ascorbate (0.1 M in water, 19.61 μl, 1.961 μmol) and CuSO₄ (0.1 M in water, 4.90 μl, 0.490 mol). The mixture was stirred at rt under argon. After 16 h, LC-MS indicated complete conversion, and 1 mL saturated aqueous NaHCO₃ was added, and the resulting solution was extracted with CH₂Cl₂ (3×5 mL). The combined organic layers were dried over Na₂SO₄ and concentrated. The residue was purified by flash column chromatography (2-3% methanol in CH₂Cl₂+0.2% saturated NH₄OH) to give the product as a slightly yellow solid (4.3 mg, 53%). ¹H NMR (500 MHz, CDCl₃) δ 7.81 (s, 1H), 7.26-7.13 (m, 3H), 6.68-6.61 (m, 1H), 4.96 (dd, J=8.1, 3.8 Hz, 1H), 4.45 (dd, J=7.4, 6.2 Hz, 2H), 4.36 (d, J=7.3 Hz, 1H), 3.86 (d, J=9.8 Hz, 1H), 3.81 (d, J=9.7 Hz, 1H), 3.76-3.63 (m, 1H), 3.59-3.48 (m, 2H), 3.20 (dd, J=10.2, 7.3 Hz, 1H), 3.09 (d, J=18.7 Hz, 1H), 3.06-2.99 (m, 1H), 2.63-2.55 (m, 1H), 2.55-2.45 (m, 1H), 2.42 (s, 3H), 2.34 (dd, J=18.7, 9.9 Hz, 1H), 2.29 (s, 6H), 2.09-1.81 (m, 5H), 1.77 (d, J=21.4 Hz, 3H), 1.74-1.54 (m, 4H), 1.40 (s, 3H), 1.33 (d, J=6.8 Hz, 3H), 1.29 (s, 3H), 1.28-1.26 (m, 1H), 1.25 (d, J=6.1 Hz, 3H), 1.11 (d, J=6.9 Hz, 3H), 0.98 (t, J=7.5 Hz, 3H). ¹³C NMR (126 MHz, CDCl₃) δ 210.78, 202.42 (d, J=29.1 Hz), 165.28 (d, J=23.4 Hz), 157.08, 147.79, 146.83, 131.61, 129.66, 119.72, 116.03, 114.78, 112.21, 104.30, 96.39 (d, J=207.0 Hz), 83.06, 81.30, 81.18, 79.02, 70.29, 69.55, 65.81, 60.66, 49.75, 48.90, 43.63, 42.68, 40.64, 40.22, 39.20, 36.22, 28.24, 27.48, 25.96 (d, J=23.2 Hz), 25.04, 23.87, 21.12, 18.79, 17.87, 16.10, 15.25, 10.67. FTIR (neat), cm$^{-1}$: 3381 (br), 2974 (s), 2098 (s), 1753 (s), 1712 (s), 1267 (s), 1053 (s), 731 (s); HRMS (ESI): Calcd for $(C_{42}H_{63}FN_6O_{10}+H)^+$: 831.4662. Found: 831.4668.

Characterization Data for Fully Synthetic Macrolides

TABLE Y1

| Compound and ID | NMR Data | MS Data |
|---|---|---|
| 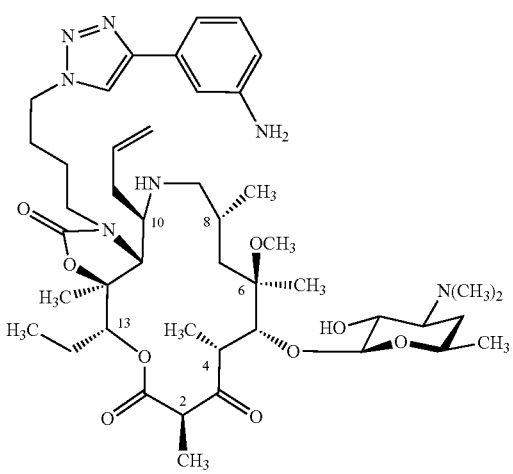<br>FSM-11044<br>Chemical Formula: $C_{45}H_{71}N_7O_9$ | $^1$H NMR for (500 MHz, CDCl$_3$) δ 7.82 (s, 1H), 7.32-7.28 (m, 1H), 7.21-7.18 (m, 2H), 6.68-6.61 (m, 1H), 5.75-5.63 (m, 1H), 5.04 (dd, J = 17.0, 1.6 Hz, 1H), 4.99 (dd, J = 10.0, 1.6 Hz, 1H), 4.86 (dd, J = 10.5, 2.3 Hz, 1H), 4.48-4.39 (m, 2H), 4.33 (d, J = 7.3 Hz, 1H), 4.03 (d, J = 9.5 Hz, 1H), 3.84 (q, J = 7.1 Hz, 1H), 3.78 (s, 1H), 3.57-3.48 (m, 2H), 3.39 (d, J = 4.0 Hz, 1H), 3.20 (dd, J = 10.1, 7.2 Hz, 1H), 3.13-3.04 (m, 1H), 2.97-2.86 (m, 1H), 2.78 (s, 3H), 2.72 (dt, J = 8.2, 4.3 Hz, 1H), 2.52 (dd, J = 11.6, 4.7 Hz, 1H), 2.49 (s, 1H), 2.46 (dd, J = 11.6, 4.3 Hz, 1H), 2.39-2.32 (m, 1H), 2.29 (s, 6H), 2.25-2.15 (m, 1H), 2.08-1.96 (m, 2H), 1.91 (ddd, J = 14.5, 7.5, 2.4 Hz, 1H), 1.77 (d, J = 6.6 Hz, 1H), 1.72-1.65 (m, 1H), 1.65-1.61 (m, 1H), 1.61 (s, 3H), 1.59-1.51 (m, 1H), 1.48 (d, J = 7.1 Hz, 3H), 1.47-1.41 (m, 1H), 1.31 (d, J = 7.1 Hz, 3H), 1.24 (s, 3H), 1.23 (d, J = 6.2 Hz, 3H), 1.25-1.17 (m, 2H), 0.92 (d, J = 6.7 Hz, 3H), 0.87 (t, J = 7.4 Hz, 3H). | HRMS (+H) calculated: 854.5386; found: 854.5373. |
| 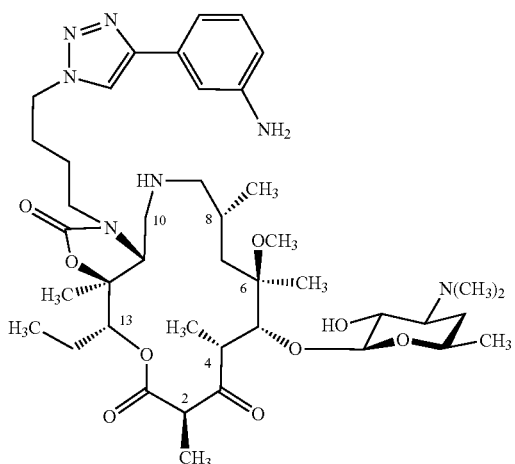<br>FSM-11031 | $^1$H NMR (500 MHz, CDCl$_3$) δ 7.80 (s, 1H), 7.27 (t, J = 2.0 Hz, 1H), 7.22-7.15 (m, 2H), 6.67-6.64 (m, 1H), 4.91 (dd, J = 10.4, 2.3 Hz, 1H), 4.47-4.41 (m, 2H), 4.35 (d, J = 7.3 Hz, 1H), 4.29-4.22 (m, 1H), 3.90-3.83 (m, 1H), 3.57-3.44 (m, 2H), 3.29-3.16 (m, 3H), 3.01-2.96 (m, 1H), 2.92 (s, 3H), 2.70-2.64 (m, 1H), 2.60-2.49 (m, 2H), 2.38-2.31 (m, 2H), 2.32 (s, 6H), 2.28 (d, J = 6.3 Hz, 1H), 2.08 (t, J = 9.7 Hz, 1H), 2.02-1.90 (m, 3H), 1.74-1.55 (m, 4H), 1.54-1.48 (m, 1H), 1.44 (d, J = 7.2 Hz, 3H), 1.42 (s, 3H), 1.37 (d, J = 7.2 Hz, 3H), 1.26-1.18 (m, 7H), 0.93 (d, J = 6.8 Hz, 3H), 0.89 (t, J = 7.4 Hz, 3H). | HRMS (+H) calculated: 814.5074; found: 814.5068. |

TABLE Y1-continued

| Compound and ID | NMR Data | MS Data |
|---|---|---|
| 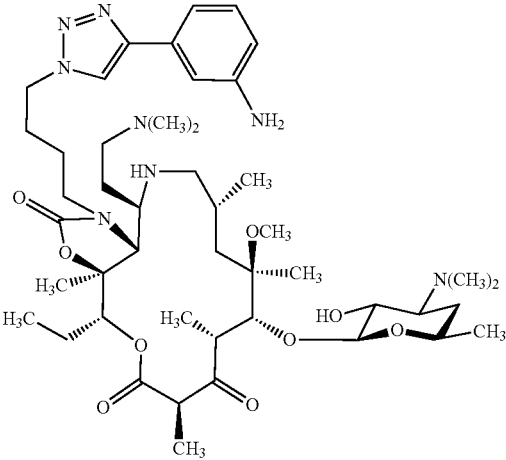<br>FSM-11052 | $^1$H NMR (500 MHz, CDCl$_3$) δ 7.84 (s, 1H), 7.32-7.29 (m, 1H), 7.22-7.18 (m, 2H), 6.66-6.63 (m, 1H), 4.86 (dd, J = 10.3, 2.3 Hz, 1H), 4.47-4.40 (m, 2H), 4.33 (d, J = 7.2 Hz, 1H), 4.03 (d, J = 9.5 Hz, 1H), 3.84 (q, J = 7.1 Hz, 1H), 3.56-3.46 (m, 2H), 3.38 (d, J = 4.0 Hz, 1H), 3.20 (dd, J = 10.0, 7.5 Hz, 1H), 3.09 (t, J = 8.2 Hz, 1H), 3.03-2.90 (m, 2H), 2.78 (s, 4H), 2.74 (s, 1H), 2.54 (dd, J = 11.7, 4.4 Hz, 1H), 2.48 (dd, J = 11.7, 4.4 Hz, 2H), 2.28 (s, 6H), 2.23 (s, 6H), 2.07-1.95 (m, 2H), 1.93-1.84 (m, 1H), 1.66 (d, J = 4.7 Hz, 10H), 1.60 (s, 3H), 1.48 (d, J = 7.1 Hz, 3H), 1.32 (d, J = 7.3 Hz, 3H), 1.26-1.21 (m, 6H), 0.94 (d, J = 6.8 Hz, 3H), 0.87 (t, J = 7.4 Hz, 3H). | HRMS (+H) calculated: 885.5808; found: 885.5780. |
| 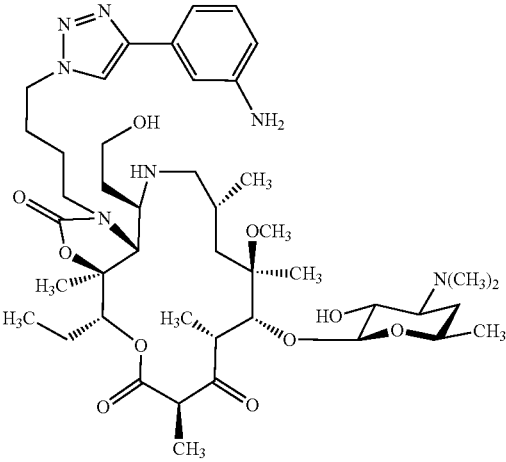<br>FSM-11056 | $^1$H NMR (500 MHz, CDCl$_3$) δ 7.82 (s, 1H), 7.31-7.29 (m, 1H), 7.21-7.17 (m, 2H), 6.65 (d, J = 5.0 Hz, 1H), 4.88 (dd, J = 10.3, 2.4 Hz, 1H), 4.44 (td, J = 7.0, 3.8 Hz, 2H), 4.33 (d, J = 7.2 Hz, 1H), 4.02 (d, J = 9.7 Hz, 1H), 3.83 (q, J = 7.1 Hz, 1H), 3.72 (t, J = 5.3 Hz, 1H), 3.52 (dq, J = 11.6, 5.8, 4.2 Hz, 2H), 3.40 (d, J = 3.9 Hz, 1H), 3.20 (dd, J = 10.2, 7.3 Hz, 1H), 3.08 (dd, J = 9.6, 7.1 Hz, 1H), 3.02-2.94 (m, 1H), 2.91 (dd, J = 8.9, 4.1 Hz, 1H), 2.76 (s, 3H), 2.66 (dd, J = 11.4, 4.1 Hz, 1H), 2.55 (dd, J = 11.4, 4.8 Hz, 1H), 2.49 (t, J = 11.0 Hz, 1H), 2.40-2.34 (m, 1H), 2.29 (s, 6H), 2.07-1.97 (m, 2H), 1.95-1.85 (m, 1H), 1.87-1.62 (m, 6H), 1.61 (s, 3H), 1.60-1.51 (m, 2H), 1.48 (d, J = 7.0 Hz, 3H), 1.40-1.34 (m, 1H), 1.31 (d, J = 7.1 Hz, 3H), 1.29-1.25 (m, 1H), 1.23 (s, 3H), 1.22 (d, J = 6.2 Hz, 3H), 0.96 (d, J = 6.7 Hz, 3H), 0.88 (t, J = 7.4 Hz, 3H). | HRMS (+H) calculated: 858.5335; found: 858.5315. |
| 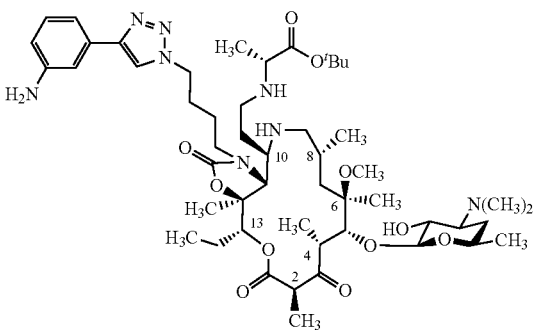<br>FSM-11238<br>Chemical Formula: C$_{51}$H$_{84}$N$_8$O$_{11}$ | $^1$H NMR (500 MHz, CDCl$_3$) δ 7.84 (s, 1H), 7.26 (s, 4H), 7.20-7.18 (m, 2H), 6.64 (dt, J = 6.3, 2.4 Hz, 1H), 4.85 (dd, J = 10.4, 2.4 Hz, 1H), 4.46-4.40 (m, 2H), 4.33 (d, J = 7.3 Hz, 1H), 4.02 (d, J = 9.4 Hz, 1H), 3.83 (q, J = 7.1 Hz, 1H), 3.60-3.47 (m, 2H), 3.37 (d, J = 3.9 Hz, 1H), 3.19 (dd, J = 10.2, 7.3 Hz, 1H), 3.14 (d, J = 7.0 Hz, 1H), 3.12-3.05 (m, 1H), 3.05-2.96 (m, 1H), 2.78 (s, 3H), 2.78-2.75 (m, 1H), 2.73-2.64 (m, 1H), 2.54-2.37 (m, 3H), 2.27 (s, 6H), 2.07-1.96 (m, 2H), 1.91 (ddd, J = 14.5, 7.5, 2.3 Hz, 1H), 1.77 (s, 1H), 1.72-1.60 (m, 3H), 1.58 (s, 3H), 1.56-1.53 (m, 1H), 1.48 (d, J = 7.2 Hz, 3H), 1.45 (s, 3H), 1.45 (s, 9H), 1.32 (d, J = 7.0 Hz, 3H), 1.23 (d, J = 5.1 Hz, 3H), 1.21 (s, 3H), 1.21 (d, J = 7.8 Hz, 3H), 0.93 (d, J = 6.8 Hz, 3H), 0.87 (t, J = 7.4 Hz, 3H). | HRMS (+H) calculated: 985.6332; found: 985.6355. |

TABLE Y1-continued

| Compound and ID | NMR Data | MS Data |
|---|---|---|
| 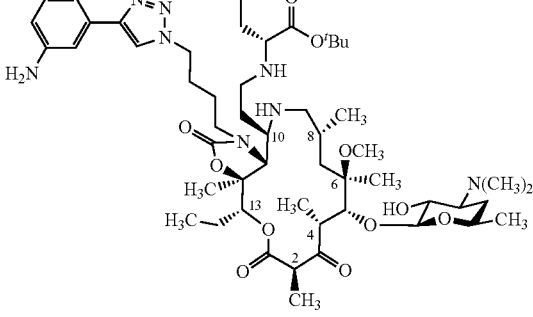<br>FSM-11252<br>Chemical Formula: $C_{56}H_{92}N_8O_{13}$ | $^1$H NMR (500 MHz, CDCl$_3$) δ 7.85 (s, 1H), 7.34-7.29 (m, 1H), 7.22-7.17 (m, 2H), 6.70-6.61 (m, 1H), 4.86 (dd, J = 10.4, 2.4 Hz, 1H), 4.44 (td, J = 8.9, 6.7, 2.6 Hz, 2H), 4.33 (d, J = 7.3 Hz, 1H), 4.02 (d, J = 9.5 Hz, 1H), 3.84 (q, J = 7.1 Hz, 1H), 3.62-3.46 (m, 2H), 3.40 (t, J = 6.5 Hz, 1H), 3.37 (d, J = 3.9 Hz, 1H), 3.24-3.15 (m, 3H), 3.14-3.04 (m, 1H), 3.04-2.96 (m, 1H), 2.82-2.73 (m, 1H), 2.77 (s, 3H), 2.72-2.64 (m, 1H), 2.58-2.41 (m, 4H), 2.27 (s, 6H), 2.08-1.96 (m, 2H), 1.94-1.86 (m, 1H), 1.80-1.73 (m, 1H), 1.71-1.62 (m, 3H), 1.58 (s, 3H), 1.57-1.52 (m, 1H), 1.48 (d, J = 7.1 Hz, 3H), 1.45 (d, J = 10.8 Hz, 3H), 1.45 (s, 9H), 1.42 (s, 9H), 1.36-1.34 (m, 1H), 1.31 (d, J = 7.0 Hz, 3H), 1.27-1.24 (m, 1H), 1.23 (s, 3H), 1.22 (d, J = 6.1 Hz, 3H), 0.92 (d, J = 6.7 Hz, 3H), 0.87 (t, J = 7.4 Hz, 3H). | HRMS (+H) calculated: 1085.6857; found: 1085.6875. |
| 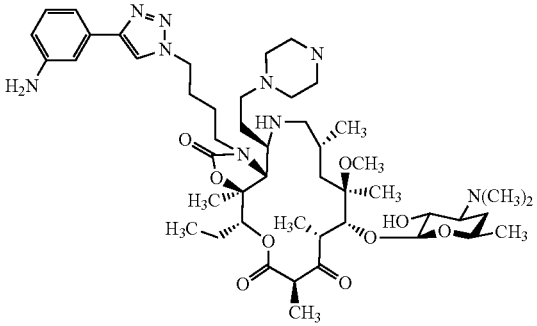<br>FSM-11253<br>Chemical Formula: $C_{48}H_{78}N_8O_{10}$ | $^1$H NMR (500 MHz, CDCl$_3$) δ 7.82 (s, 1H), 7.34-7.28 (m, 1H), 7.21-7.17 (m, 2H), 6.68-6.60 (m, 1H), 4.86 (dd, J = 10.3, 2.4 Hz, 1H), 4.47-4.41 (m, 2H), 4.33 (d, J = 7.4 Hz, 1H), 4.02 (d, J = 9.5 Hz, 1H), 3.83 (q, J = 7.1 Hz, 1H), 3.67 (t, J = 4.8 Hz, 4H), 3.58-3.48 (m, 2H), 3.39 (d, J = 3.9 Hz, 1H), 3.19 (dd, J = 10.4, 7.2 Hz, 1H), 3.13-3.04 (m, 1H), 2.99 (dt, J = 14.8, 5.9 Hz, 1H), 2.79 (s, 3H), 2.76-2.68 (m, 1H), 2.56-2.42 (m, 3H), 2.37 (dd, J = 11.5, 5.7 Hz, 4H), 2.27 (s, 6H), 2.08-1.96 (m, 2H), 1.94-1.84 (m, 1H), 1.82-1.75 (m, 1H), 1.72-1.61 (m, 4H), 1.59 (s, 3H), 1.56 (dd, J = 16.2, 9.8 Hz, 4H), 1.48 (d, J = 6.9 Hz, 3H), 1.46-1.41 (m, 1H), 1.40-1.33 (m, 1H), 1.32 (d, J = 6.9 Hz, 3H), 1.28-1.26 (m, 1H), 1.25 (s, 3H), 1.23 (d, J = 6.0 Hz, 3H), 0.94 (d, J = 6.7 Hz, 3H), 0.87 (t, J = 7.4 Hz, 3H). | HRMS (+H) calculated: 927.5914; found: 927.5939. |
| 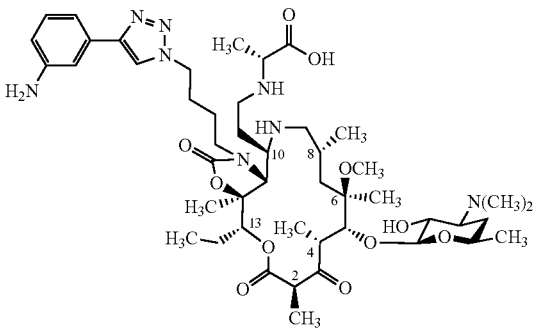<br>FSM-11258<br>Chemical Formula: $C_{47}H_{76}N_8O_{11}$ | $^1$H NMR (500 MHz, CD$_3$OD) δ 8.42 (s, 1H), 7.81-7.70 (m, 3H), 7.51 (t, J = 7.9 Hz, 1H), 7.22 (dd, J = 7.8, 1.9 Hz, 1H), 4.86 (dd, 1H, obscured by HDO peak), 4.58-4.49 (m, 2H), 4.44 (d, J = 6.5 Hz, 1H), 4.02 (d, J = 7.1 Hz, 1H), 4.00 (d, J = 9.6 Hz, 1H), 3.77-3.67 (m, 1H), 3.59 (d, J = 3.8 Hz, 1H), 3.59-3.51 (m, 1H), 3.47-3.41 (m, 2H), 3.25-3.19 (m, 1H), 3.14-3.05 (m, 1H), 2.88 (s, 3H), 2.79 (s, 3H), 2.78 (s, 3H), 2.69-2.59 (m, 1H), 2.16-2.09 (m, 1H), 2.07-2.00 (m, 4H), 1.98-1.90 (m, 2H), 1.89-1.80 (m, 1H), 1.69-1.67 (m, 1H), 1.67 (s, 3H), 1.65-1.57 (m, 3H), 1.56 (d, J = 7.0 Hz, 3H), 1.54-1.50 (m, 2H), 1.45 (d, J = 7.1 Hz, 3H), 1.32 (d, J = 6.1 Hz, 3H), 1.34-1.25 (m, 9H), 1.01 (d, J = 6.7 Hz, 3H), 0.89 (t, J = 7.4 Hz, 3H). | HRMS (+H) calculated: 929.5706; found: 929.5725. |
| 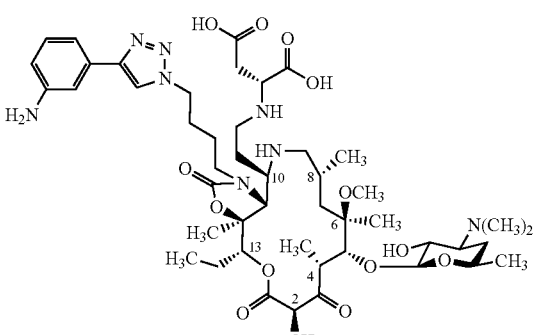<br>FSM-11259<br>Chemical Formula: $C_{48}H_{76}N_8O_{13}$ | $^1$H NMR (500 MHz, CD$_3$OD) δ 8.42 (s, 1H), 7.77 (t, J = 1.9 Hz, 1H), 7.75 (d, J = 7.8 Hz, 1H), 7.51 (t, J = 7.9 Hz, 1H), 7.22 (ddd, J = 8.1, 2.3, 1.0 Hz, 1H), 4.86 (dd, 1H, obscured by HDO peak), 4.58-4.49 (m, 2H), 4.44 (d, J = 6.5 Hz, 1H), 4.18 (dd, J = 6.4, 4.3 Hz, 1H), 4.02 (d, J = 7.1 Hz, 1H), 3.99 (d, J = 9.8 Hz, 1H), 3.77-3.67 (m, 1H), 3.60 (d, J = 3.8 Hz, 1H), 3.56 (dd, J = 15.2, 7.7 Hz, 1H), 3.48-3.40 (m, 2H), 3.30-3.17 (m, 1H), 3.14-2.96 (m, 2H), 2.88 (s, 3H), 2.78 (s, 6H), 2.66 (dd, J = 12.1, 6.8 Hz, 1H), 2.18-2.11 (m, 1H), 2.07-2.00 (m, 4H), 1.99-1.92 (m, 1H), 1.89-1.79 (m, 1H), 1.67 (s, 3H), 1.72-1.48 (m, 5H), 1.45 (d, J = 7.1 Hz, 3H), 1.42-1.33 (m, 2H), 1.32 (d, J = 6.1 Hz, 3H), 1.31-1.26 (m, 8H), 1.03 (d, J = 6.7 Hz, 3H), 0.89 (t, J = 7.4 Hz, 3H). | HRMS (+H) calculated: 973.5605; found: 973.5632. |

TABLE Y1-continued

| Compound and ID | NMR Data | MS Data |
|---|---|---|
| 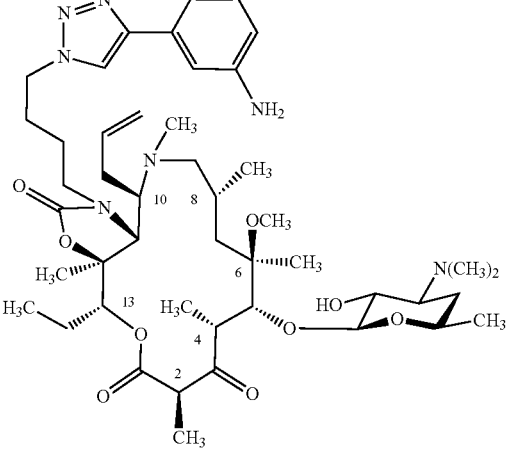<br>FSM-11094<br>Chemical Formula: $C_{46}H_{73}N_7O_9$ | $^1$H NMR (3:1 mixture of C2 epimers, major epimer reported, 500 MHz, CDCl$_3$) δ 7.83 (s, 1H), 7.22-7.17 (m, 2H), 6.70-6.60 (m, 1H), 5.72-5.62 (m, 1H), 5.06-5.01 (m, 1H), 5.00 (s, 1H), 4.75 (dd, J = 9.7, 2.6 Hz, 1H), 4.47-4.43 (m, 2H), 4.40 (d, J = 7.4 Hz, 1H), 4.36 (d, J = 6.8 Hz, 1H), 4.14-4.01 (m, 1H), 3.80 (q, J = 9.4 Hz, 1H), 3.60-3.44 (m, 2H), 3.28 (d, J = 3.5 Hz, 1H), 3.20 (t, J = 8.5 Hz, 1H), 3.07-2.89 (m, 2H), 2.86 (s, 3H), 2.76-2.67 (m, 1H), 2.62 (d, J = 14.3 Hz, 1H), 2.51 (s, 1H), 2.35 (s, 3H), 2.30 (s, 6H), 2.21-2.09 (m, 2H), 2.07-1.81 (m, 5H), 1.81-1.68 (m, 1H), 1.67 (s, 3H), 1.65-1.40 (m, 6H), 1.28 (s, 3H), 1.25-1.17 (m, 12H), 0.94 (t, J = 5.8 Hz, 3H). | HRMS (+H) calculated: 868.5548; found: 868.5544. |
| 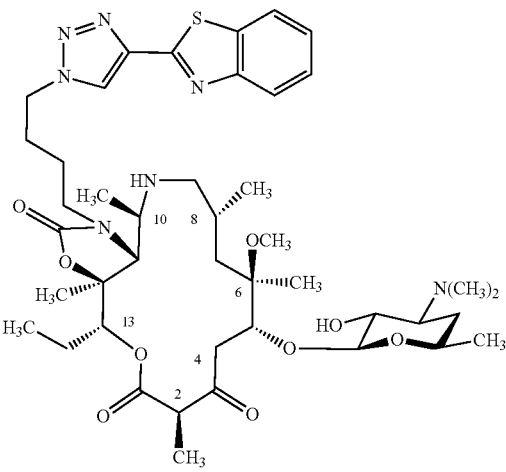<br>FSM-10788<br>Chemical Formula: $C_{43}H_{65}N_7O_9S$ | $^1$H NMR (500 MHz, CDCl$_3$) δ 8.26 (s, 1H), 8.02 (d, J = 8.2 Hz, 1H), 7.94 (d, J = 8.1 Hz, 1H), 7.49 (d, J = 7.5 Hz, 1H), 7.40 (t, J = 7.5 Hz, 1H), 4.95 (dd, J = 10.8, 2.2 Hz, 1H), 4.56 (dd, J = 5.3, 3.6 Hz, 1H), 4.52 (td, J = 7.4, 2.2 Hz, 2H), 4.28 (d, J = 7.4 Hz, 1H), 3.75-3.63 (m, 2H), 3.60 (q, J = 6.8 Hz, 1H), 3.60-3.50 (m, 1H), 3.30 (s, 1H), 3.17-3.08 (m, 2H), 3.07 (s, 3H), 2.81-2.73 (m, 2H), 2.67 (dd, J = 18.8, 5.4 Hz, 1H), 2.49-2.42 (m, 1H), 2.27 (s, 6H), 2.11-1.90 (m, 3H), 1.77-1.51 (m, 7H), 1.44 (d, J = 7.4 Hz, 1H), 1.42 (s, 3H), 1.36 (d, J = 6.9 Hz, 3H), 1.29 (s, 3H), 1.26 (d, J = 6.2 Hz, 3H), 1.24-1.20 (m, 1H), 0.98 (d, J = 6.1 Hz, 3H), 0.93 (d, J = 6.2 Hz, 3H), 0.89 (t, J = 7.4 Hz, 3H). | HRMS (+H) calculated: 856.4643; found: 856.4625. |
| 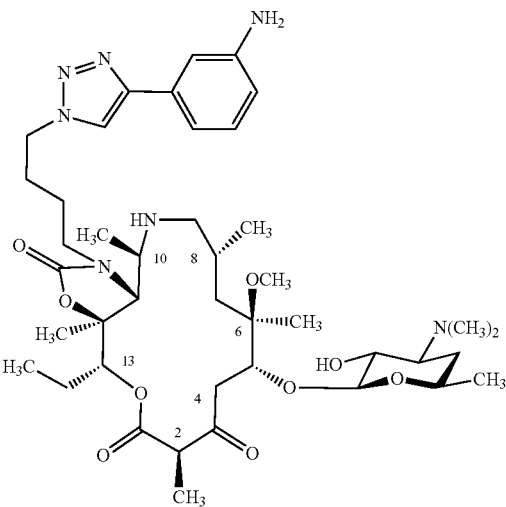<br>FSM-10781<br>Chemical Formula: $C_{42}H_{67}N_7O_9$ | $^1$H NMR (500 MHz, CDCl$_3$) δ 7.81 (s, 1H), 7.23 (t, J = 2.0 Hz, 1H), 7.17-7.12 (m, 1H), 6.65 (ddd, J = 7.8, 2.6, 1.1 Hz, 1H), 4.96 (dd, J = 10.8, 2.2 Hz, 1H), 4.54 (dd, J = 5.5, 3.5 Hz, 1H), 4.48-4.39 (m, 2H), 4.28 (d, J = 7.4 Hz, 1H), 3.78 (br s, 2H), 3.66 (t, J = 6.6 Hz, 2H), 3.63 (d, J = 6.9 Hz, 1H), 3.61-3.53 (m, 1H), 3.30 (s, 1H), 3.16-3.07 (m, 2H), 3.01 (s, 3H), 2.81-2.73 (m, 2H), 2.69 (dd, J = 18.8, 5.5 Hz, 1H), 2.48-2.42 (m, 1H), 2.27 (s, 1H), 2.26 (s, 6H), 2.07-1.89 (m, 3H), 1.76-1.58 (m, 8H), 1.55 (dd, J = 15.2, 3.7 Hz, 1H), 1.42 (s, 3H), 1.39 (d, J = 6.9 Hz, 3H), 1.31-1.28 (m, 1H), 1.27 (s, 3H), 1.26 (d, J = 6.2 Hz, 3H), 0.98 (d, 7= 6.1 Hz, 3H), 0.93 (d, J = 6.4 Hz, 3H), 0.87 (t, J = 7.4 Hz, 3H). | HRMS (+H) calculated: 814.5073; found: 814.5065. |

TABLE Y1-continued

| Compound and ID | NMR Data | MS Data |
|---|---|---|
| FSM-10794<br>Chemical Formula: $C_{42}H_{66}N_8O_{10}$ | $^1$H NMR (500 MHz, CDCl$_3$) δ 9.11 (dd, J = 5.0, 1.7 Hz, 1H), 8.35 (s, 1H), 8.35 (dd, J = 8.5, 1.7 Hz, 1H), 7.55 (dd, J = 8.6, 5.0 Hz, 1H), 4.95 (dd, J = 9.4, 2.8 Hz, 1H), 4.87-4.76 (m, 1H), 4.56-4.39 (m, 2H), 4.30 (dd, J = 10.9, 4.4 Hz, 1H), 4.24 (d, J = 7.3 Hz, 1H), 3.70 (q, J = 7.1 Hz, 1H), 3.66-3.52 (m, 2H), 3.53 (d, J = 10.9 Hz, 1H), 3.19-3.09 (m, 2H), 2.93 (br s, 1H), 2.91 (s, 3H), 2.80 (dd, J = 12.9, 11.1 Hz, 1H), 2.64 (dd, J = 12.9, 4.5 Hz, 1H), 2.50-2.43 (m, 1H), 2.28 (s, 6H), 2.17 (br s, 1H), 2.10 (s, 3H), 2.03-1.84 (m, 5H), 1.80-1.73 (m, 1H), 1.70 (d, J = 12.7 Hz, 1H), 1.58-1.46 (m, 2H), 1.43 (d, J = 7.3 Hz, 3H), 1.39 (s, 2H), 1.30 (s, 3H), 1.29-1.23 (m, 8H), 1.22 (s, 3H), 1.00 (d, J = 6.8 Hz, 3H), 0.90 (t, J = 7.5 Hz, 3H). | HRMS (+H) calculated: 843.4980; found: 843.4956. |
| FSM-10786<br>Chemical Formula: $C_{41}H_{65}N_7O_9$ | $^1$H NMR (500 MHz, CDCl$_3$) δ 8.56 (ddt, J = 4.9, 1.9, 1.0 Hz, 1H), 8.18-8.14 (m, 1H), 8.13 (s, 1H), 7.79-7.73 (m, 1H), 7.23-7.19 (m, 1H), 4.95 (dd, J = 10.8, 2.2 Hz, 1H), 4.55 (dd, J = 5.3, 3.7 Hz, 1H), 4.53-4.42 (m, 2H), 4.34-4.26 (m, 1H), 3.70-3.63 (m, 2H), 3.60 (q, J = 6.8 Hz, 1H), 3.59-3.54 (m, 1H), 3.30 (s, 1H), 3.17-3.08 (m, 2H), 3.05 (s, 3H), 2.82-2.73 (m, 2H), 2.66 (dd, J = 18.9, 5.4 Hz, 1H), 2.51-2.42 (m, 1H), 2.28 (s, 1H), 2.26 (s, 6H), 2.08-1.90 (m, 3H), 1.74-1.51 (m, 9H), 1.41 (s, 3H), 1.36 (dd, J = 7.0, 0.8 Hz, 3H), 1.28 (s, 3H), 1.27 (d, J = 6.2 Hz, 3H), 1.26-1.18 (m, 1H), 0.98 (d, J = 6.0 Hz, 3H), 0.92 (d, J = 6.2 Hz, 3H), 0.88 (t, J = 7.3 Hz, 3H). | HRMS (+H) calculated: 800.4917; found: 800.4913. |
| FSM-10789<br>Chemical Formula: $C_{36}H_{62}N_6O_{10}$ | $^1$H NMR (500 MHz, CDCl$_3$) δ 4.93 (dd, J = 9.2, 2.9 Hz, 1H), 4.80 (dd, J = 10.9, 7.1 Hz, 1H), 4.29 (dd, J = 11.0, 4.6 Hz, 1H), 4.22 (d, J = 7.3 Hz, 1H), 3.70 (q, J = 7.1 Hz, 1H), 3.63-3.53 (m, 2H), 3.51 (d, J = 11.1 Hz, 1H), 3.36-3.19 (m, 2H), 3.16-3.09 (m, 2H), 2.91 (s, 1H), 2.90 (s, 3H), 2.84-2.76 (m, 1H), 2.62 (dd, J = 13.0, 4.5 Hz, 1H), 2.48-2.39 (m, 1H), 2.25 (s, 6H), 2.16 (s, 1H), 2.09 (s, 3H), 1.93 (br s, 1H), 1.91-1.81 (m, 2H), 1.78-1.71 (m, 1H), 1.71-1.61 (m, 1H), 1.61-1.38 (m, 6H), 1.44 (d, J = 7.2 Hz, 3H), 1.40 (s, 1H), 1.29 (s, 3H), 1.27 (d, J = 6.6 Hz, 3H), 1.24 (d, J = 5.8 Hz, 3H), 1.20 (s, 3H), 1.00 (d, J = 6.9 Hz, 3H), 0.89 (t, J = 7.5 Hz, 3H). | HRMS (+H) calculated: 739.4606; found: 739.4598. |

TABLE Y1-continued

| Compound and ID | NMR Data | MS Data |
|---|---|---|
| 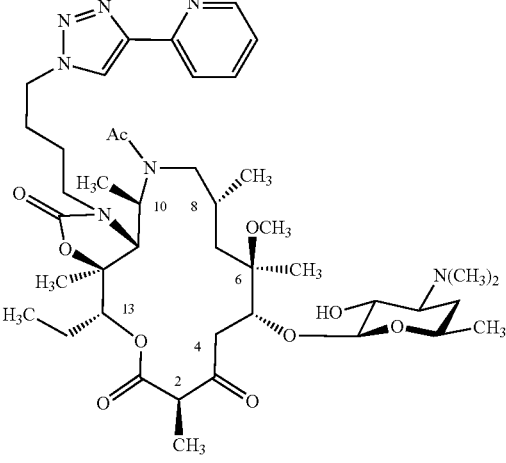<br>FSM-10792<br>Chemical Formula: $C_{43}H_{67}N_7O_{10}$ | $^1$H NMR (500 MHz, CDCl$_3$) δ 8.57 (d, J = 4.9 Hz, 1H), 8.15 (d, J = 7.9 Hz, 1H), 8.10 (s, 1H), 7.76 (td, J = 7.5, 1.6 Hz, 1H), 7.21 (ddd, J = 7.7, 4.7, 1.3 Hz, 1H), 4.96 (dd, J = 9.4, 2.8 Hz, 1H), 4.86-4.77 (m, 1H), 4.47-4.38 (m, 2H), 4.30 (dd, J = 10.6, 4.6 Hz, 1H), 4.24 (d, J = 7.3 Hz, 1H), 3.71 (q, J = 7.0 Hz, 1H), 3.66-3.55 (m, 2H), 3.53 (d, J = 11.0 Hz, 1H), 3.21-3.09 (m, 3H), 2.94 (br s, 1H), 2.92 (s, 3H), 2.80 (dd, J = 13.2, 11.0 Hz, 1H), 2.64 (dd, J = 13.0, 4.5 Hz, 1H), 2.47 (t, J = 11.7 Hz, 1H), 2.28 (s, 6H), 2.17 (br s, 1H), 2.10 (s, 3H), 2.01-1.86 (m, 4H), 1.86-1.72 (m, 1H), 1.70 (d, J = 13.0 Hz, 1H), 1.65-1.47 (m, 3H), 1.44 (d, J = 7.3 Hz, 3H), 1.42-1.35 (m, 2H), 1.30 (s, 3H), 1.25 (dd, J = 7.8, 5.7 Hz, 6H), 1.22 (s, 3H), 1.00 (d, J = 6.8 Hz, 3H), 0.91 (t, J = 7.5 Hz, 3H). | HRMS (+H) calculated: 842.5022; found: 842.5016. |
| 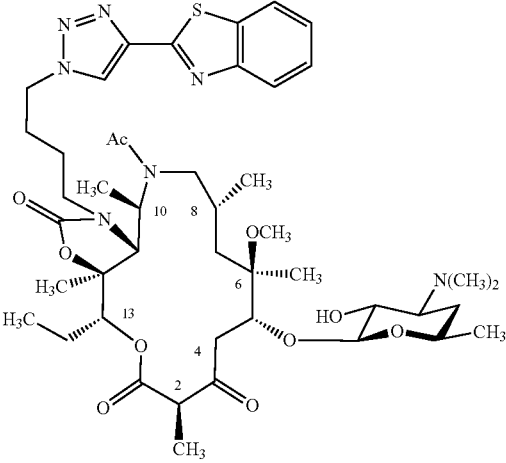<br>FSM-10791<br>Chemical Formula: $C_{45}H_{67}N_7O_{10}S$ | $^1$H NMR (500 MHz, CDCl$_3$) δ 8.23 (s, 1H), 8.02 (d, J = 8.1 Hz, 1H), 7.94 (d, J = 8.0 Hz, 1H), 7.50 (t, J = 7.5 Hz, 1H), 7.41 (t, J = 7.7 Hz, 1H), 4.96 (dd, J = 9.4, 2.7 Hz, 1H), 4.86-4.77 (m, 1H), 4.48 (q, J = 7.9, 6.4 Hz, 2H), 4.31 (dd, J = 10.9, 4.6 Hz, 1H), 4.24 (d, J = 7.3 Hz, 1H), 3.71 (q, J = 7.2 Hz, 1H), 3.67-3.48 (m, 2H), 3.54 (d, J = 11.1 Hz, 1H), 3.19-3.10 (m, 2H), 2.97 (s, 1H), 2.95 (s, 1H), 2.93 (s, 3H), 2.80 (dd, J = 12.9, 11.2 Hz, 1H), 2.65 (dd, J = 13.0, 4.7 Hz, 1H), 2.47 (t, J = 11.2 Hz, 1H), 2.28 (s, 6H), 2.17 (s, 1H), 2.11 (s, 3H), 2.04-1.85 (m, 5H), 1.82-1.75 (m, 1H), 1.70 (d, J = 12.8 Hz, 1H), 1.59-1.47 (m, 2H), 1.44 (d, J = 7.2 Hz, 3H), 1.42-1.35 (m, 2H), 1.31 (s, 3H), 1.29-1.24 (m, 6H), 1.22 (s, 3H), 1.01 (d, J = 6.8 Hz, 3H), 0.91 (t, J = 7.5 Hz, 3H). | HRMS (+H) calculated: 898.4748; found: 898.4727. |
| 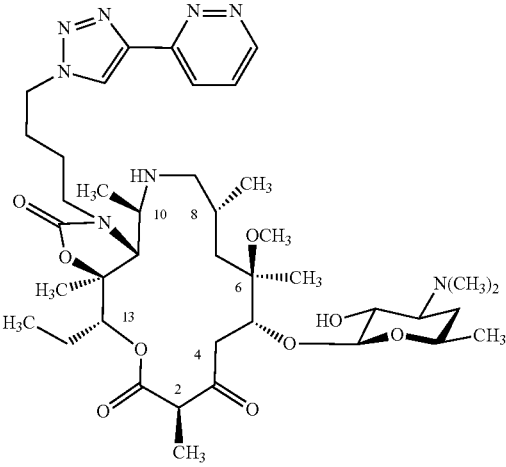<br>FSM-10785<br>Chemical Formula: $C_{40}H_{64}N_8O_9$ | $^1$H NMR (500 MHz, CDCl$_3$) δ 9.11 (dd, J = 4.9, 1.7 Hz, 1H), 8.37 (s, 1H), 8.32 (dd, J = 8.5, 1.7 Hz, 1H), 7.55 (dd, J = 8.6, 4.9 Hz, 1H), 4.94 (dd, J = 10.8, 2.2 Hz, 1H), 4.58-4.46 (m, 3H), 4.29 (d, J = 7.4 Hz, 1H), 3.70-3.63 (m, 2H), 3.60 (q, J = 6.9 Hz, 1H), 3.57-3.53 (m, 1H), 3.39 (br s, 1H), 3.29 (s, 3H), 3.19-3.08 (m, 2H), 3.07 (s, 3H), 2.82-2.73 (m, 2H), 2.67 (dd, J = 18.9, 5.4 Hz, 1H), 2.48 (t, J = 11.1 Hz, 1H), 2.30 (s, 1H), 2.28 (s, 6H), 2.09-1.89 (m, 3H), 1.75-1.52 (m, 8H), 1.41 (s, 3H), 1.35 (d, J = 6.9 Hz, 3H), 1.29 (s, 3H), 1.27 (d, J = 6.2 Hz, 3H), 1.25-1.20 (m, 1H), 0.98 (d, J = 6.1 Hz, 3H), 0.93 (d, J = 6.3 Hz, 3H), 0.88 (t, J = 7.4 Hz, 3H). | HRMS (+H) calculated: 801.4869; found: 801.4860. |

TABLE Y1-continued

| Compound and ID | NMR Data | MS Data |
|---|---|---|
| 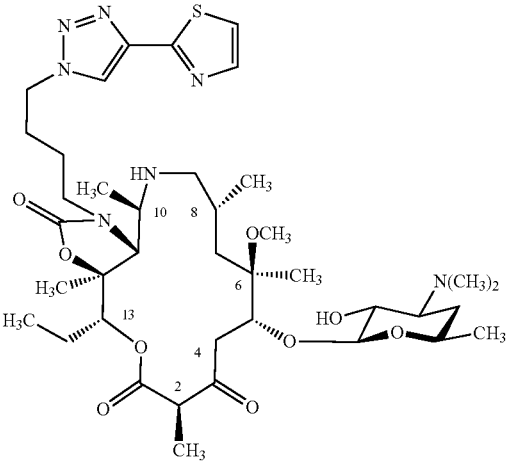<br>FSM-10787<br>Chemical Formula: C$_{39}$H$_{63}$N$_{9}$O$_{9}$S | $^1$H NMR (500 MHz, CDCl$_3$) δ 8.08 (s, 1H), 7.83 (d, J = 3.3 Hz, 1H), 7.34 (d, J = 3.2 Hz, 1H), 4.94 (d, J = 10.5 Hz, 1H), 4.55 (t, J = 4.5 Hz, 1H), 4.51-4.45 (m, 2H), 4.29 (d, J = 6.5 Hz, 1H), 3.69-3.63 (m, 2H), 3.60 (q, J = 6.9 Hz, 1H), 3.57-3.54 (m, 1H), 3.29 (s, 1H), 3.18-3.08 (m, 2H), 3.05 (s, 3H), 2.83-2.73 (m, 2H), 2.67 (dd, J = 18.9, 5.4 Hz, 1H), 2.50-2.42 (m, 1H), 2.28 (s, 1H), 2.27 (s, 6H), 2.07-1.90 (m, 3H), 1.76-1.51 (m, 9H), 1.41 (s, 3H), 1.36 (d, J = 7.0 Hz, 4H), 1.29 (s, 3H), 1.27 (d, J = 6.2 Hz, 3H), 0.98 (d, J = 6.0 Hz, 3H), 0.93 (d, J = 6.0 Hz, 3H), 0.88 (t, J = 7.1 Hz, 3H). | HRMS (+H) calculated: 806.4481; found: 806.4472. |
| 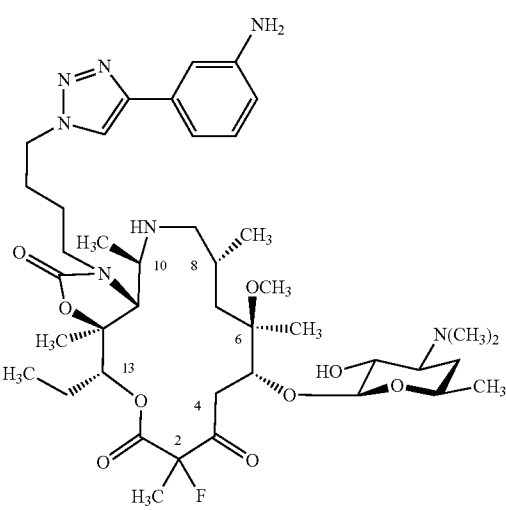<br>FSM-10661<br>Chemical Formula: C$_{42}$H$_{66}$FN$_{7}$O$_{9}$ | $^1$H NMR (500 MHz, CDCl$_3$) δ 7.80 (s, 1H), 7.20-7.14 (m, 3H), 6.66-6.63 (m, 1H), 4.97 (dd, J = 10.9, 2.1 Hz, 1H), 4.50-4.40 (m, 2H), 4.34 (dd, J = 8.9, 6.2 Hz, 1H), 4.29 (d, J = 7.3 Hz, 1H), 3.74 (br s, 2H), 3.65-3.54 (m, 3H), 3.22-3.11 (m, 2H), 3.17 (s, 3H), 3.00-2.94 (m, 1H), 2.92 (s, 1H), 2.69-2.61 (m, 2H), 2.50 (ddd, J = 12.2, 10.1, 3.9 Hz, 1H), 2.28 (s, 6H), 1.97 (ddd, J = 14.2, 7.5, 2.4 Hz, 3H), 1.79-1.72 (m, 2H), 1.78 (d, J = 21.7 Hz, 3H), 1.73-1.52 (m, 6H), 1.51 (s, 3H), 1.47 (dd, J = 14.8, 3.3 Hz, 1H), 1.31-1.24 (m, 2H), 1.26 (d, J = 6.3 Hz, 3H), 1.25 (s, 3H), 0.95-0.89 (m, 9H). | HRMS (+H) calculated: 832.4979; found: 832.4947. |
| 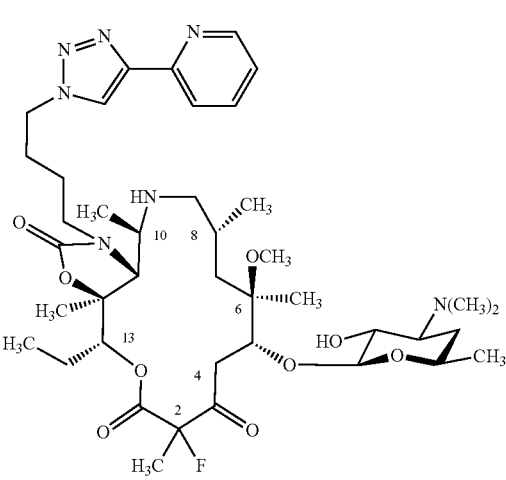<br>FSM-10662<br>Chemical Formula: C$_{41}$H$_{64}$FN$_{7}$O$_{9}$<br>Exact Mass: 817.4750 | $^1$H NMR (500 MHz, CDCl$_3$) δ 8.57 (ddd, J = 4.8, 1.8, 1.0 Hz, 1H), 8.15 (dt, J = 8.0, 1.1 Hz, 1H), 8.14 (s, 1H), 7.76 (td, J = 7.7, 1.8 Hz, 1H), 7.21 (ddd, J = 7.6, 4.9, 1.2 Hz, 1H), 4.97 (dd, J = 10.9, 2.1 Hz, 1H), 4.48 (t, J = 7.0 Hz, 2H), 4.35 (dd, J = 8.8, 6.5 Hz, 1H), 4.30 (d, J = 7.3 Hz, 1H), 3.68-3.52 (m, 3H), 3.21 (d, J = 0.7 Hz, 3H), 3.21-3.13 (m, 3H), 2.97 (q, J = 6.2 Hz, 1H), 2.92 (br s, 1H), 2.69-2.58 (m, 2H), 2.50 (ddd, J = 12.2, 10.1, 3.9 Hz, 1H), 2.29 (s, 6H), 2.05-1.92 (m, 3H), 1.77 (d, J = 21.7 Hz, 3H), 1.84-1.52 (m, 8H), 1.51 (s, 3H), 1.47 (dd, J = 14.8, 3.1 Hz, 1H), 1.33-1.26 (m, 1H), 1.28 (d, J = 6.1 Hz, 3H), 1.26 (s, 3H), 0.95-0.89 (m, 9H). | HRMS (+Na) calculated: 840.4642; found: 840.4597. |

TABLE Y1-continued

| Compound and ID | NMR Data | MS Data |
|---|---|---|
| 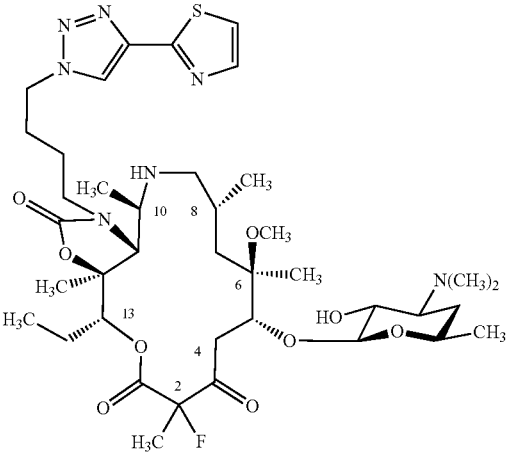<br>FSM-10666<br>Chemical Formula: $C_{39}H_{62}FN_7O_9S$ | $^1$H NMR (500 MHz, CDCl$_3$) δ 8.08 (s, 1H), 7.82 (d, J = 3.2 Hz, 1H), 7.33 (d, J = 3.3 Hz, 1H), 4.95 (dd, J = 10.9, 2.1 Hz, 1H), 4.48 (t, J = 7.3 Hz, 3H), 4.35 (dd, J = 9.0, 6.1 Hz, 1H), 4.29 (d, J = 7.3 Hz, 1H), 3.67-3.53 (m, 3H), 3.20 (s, 3H), 3.19-3.12 (m, 2H), 2.97 (q, J = 5.8 Hz, 1H), 2.91 (br s, 1H), 2.70-2.59 (m, 2H), 2.50 (ddd, J = 12.3, 10.2, 3.9 Hz, 1H), 2.28 (s, 6H), 2.25 (s, 1H), 2.06-1.88 (m, 3H), 1.76 (d, J = 21.7 Hz, 3H), 1.84-1.52 (m, 7H), 1.50 (s, 3H), 1.47 (dd, J = 15.0, 3.4 Hz, 1H), 1.31-1.25 (m, 1H), 1.27 (d, J = 6.2 Hz, 3H), 1.26 (s, 3H), 0.95-0.88 (m, 9H). | HRMS (+H) calculated: 824.4392; found: 824.4377. |
| 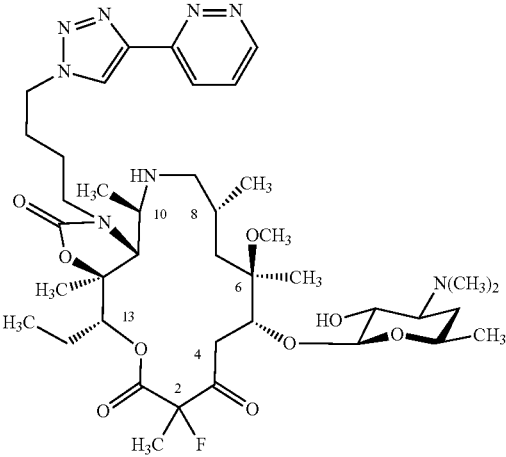<br>FSM-10667<br>Chemical Formula: $C_{40}H_{63}FN_8O_9$ | $^1$H NMR (500 MHz, CDCl$_3$) δ 9.11 (dd, J = 4.9, 1.7 Hz, 1H), 8.38 (s, 1H), 8.34-8.30 (m, 1H), 7.57-7.52 (m, 1H), 4.96 (dd, J = 10.9, 2.1 Hz, 1H), 4.54-4.49 (m, 2H), 4.35 (dd, J = 8.6, 6.7 Hz, 1H), 4.30 (d, J = 7.3 Hz, 1H), 3.70-3.53 (m, 3H), 3.36 (br s, 1H), 3.22 (s, 3H), 3.17 (ddd, J = 15.9, 11.4, 6.7 Hz, 2H), 2.98 (q, J = 6.2 Hz, 1H), 2.92 (s, 1H), 2.69-2.58 (m, 2H), 2.50 (ddd, J = 12.2, 10.1, 3.9 Hz, 1H), 2.28 (s, 6H), 2.25 (s, 1H), 2.08-1.85 (m, 4H), 1.76 (d, J = 21.7 Hz, 3H), 1.85-1.52 (m, 6H), 1.50 (s, 3H), 1.47 (dd, J = 14.8, 3.3 Hz, 1H), 1.30-1.22 (m, 7H), 0.96-0.88 (m, 9H). | HRMS (+H) calculated: 819.4775; found: 819.4738. |
| 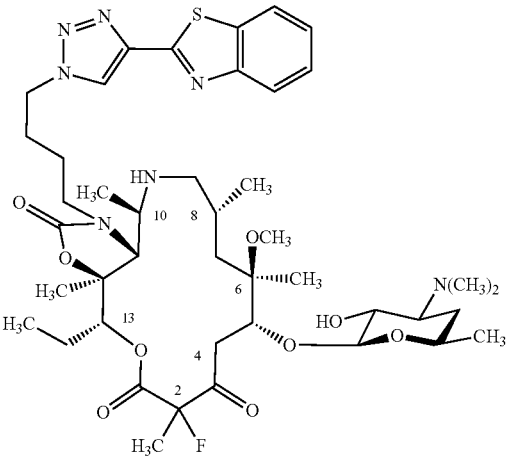<br>FSM-10671<br>Chemical Formula: $C_{43}H_{64}FN_7O_9S$ | $^1$H NMR (500 MHz, CDCl$_3$) δ 8.26 (s, 1H), 8.02 (dt, J = 8.2, 0.9 Hz, 1H), 7.94 (dt, J = 7.8, 1.1 Hz, 1H), 7.49 (ddd, J = 8.3, 7.2, 1.3 Hz, 1H), 7.40 (ddd, J = 8.2, 7.2, 1.2 Hz, 1H), 4.96 (dd, J = 10.9, 2.1 Hz, 1H), 4.52 (t, J = 7.3 Hz, 2H), 4.35 (dd, J = 8.6, 6.9 Hz, 1H), 4.29 (d, J = 7.3 Hz, 1H), 3.70-3.52 (m, 3H), 3.37 (br s, 1H), 3.22 (d, J = 0.8 Hz, 3H), 3.17 (ddd, J = 16.3, 11.3, 6.7 Hz, 2H), 2.98 (q, J = 6.3 Hz, 1H), 2.92 (s, 1H), 2.72-2.58 (m, 2H), 2.50 (ddd, J = 12.3, 10.1, 3.8 Hz, 1H), 2.38 (dd, J = 8.1, 1.9 Hz, 1H), 2.28 (s, 6H), 2.26 (s, 1H), 2.08-1.87 (m, 3H), 1.75 (d, J = 21.7 Hz, 3H), 1.84-1.52 (m, 6H), 1.51 (s, 3H), 1.49-1.45 (m, 1H), 1.27 (d, J = 6.2 Hz, 3H), 1.26 (s, 3H), 1.30-1.21 (m, 1H), 0.92 (dd, J = 6.8, 4.1 Hz, 9H). | (Product not stable, HRMS not obtained) |

TABLE Y1-continued

| Compound and ID | NMR Data | MS Data |
|---|---|---|
| 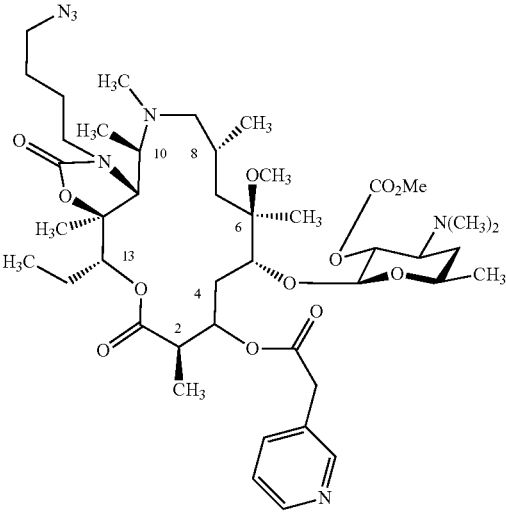<br>FSM-10809<br>Chemical Formula: $C_{44}H_{71}N_7O_{12}$ | — | HRMS (+H) calculated: 890.5233; found: 890.5251. |
| 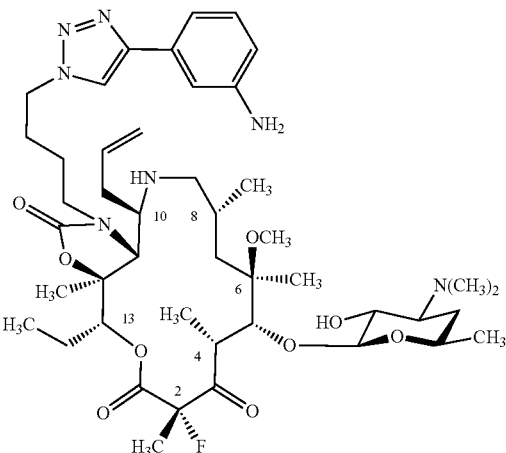<br>FSM-11203<br>Chemical Formula: $C_{45}H_{70}FN_7O_9$ | $^1$H NMR (500 MHz, CDCl$_3$) δ 7.82 (s, 1H), 7.28-7.26 (m, 1H), 7.20-7.16 (m, 2H), 6.65 (dt, J = 7.0, 2.4 Hz, 1H), 5.78-5.60 (m, 1H), 5.03 (dd, J = 16.9, 1.6 Hz, 1H), 4.99 (d, J = 10.2 Hz, 1H), 4.93 (d, J = 10.2 Hz, 1H), 4.50-4.42 (m, 2H), 4.40 (d, J = 7.4 Hz, 1H), 4.05 (d, J = 8.4 Hz, 1H), 3.75 (s, 2H), 3.59-3.47 (m, 2H), 3.36-3.26 (m, 1H), 3.25 (d, J = 4.0 Hz, 1H), 3.19 (dd, J = 9.9, 7.5 Hz, 1H), 3.06 (s, 3H), 2.98-2.88 (m, 1H), 2.78 (s, 1H), 2.73-2.63 (m, 1H), 2.55-2.46 (m, 1H), 2.45-2.38 (m, 1H), 2.27 (s, 6H), 2.26-2.19 (m, 1H), 2.11-1.88 (m, 3H), 1.83 (d, J = 21.8 Hz, 3H), 1.74-1.53 (m, 6H), 1.65 (s, 3H), 1.53-1.41 (m, 4H), 1.36-1.23 (m, 3H), 1.28 (s, 3H), 1.24 (d, J = 6.2 Hz, 3H), 0.91 (d, J = 6.4 Hz, 3H), 0.88 (t, J = 7.4 Hz, 3H). | HRMS (+H) calculated: 872.5292; found: 872.5315. |
| 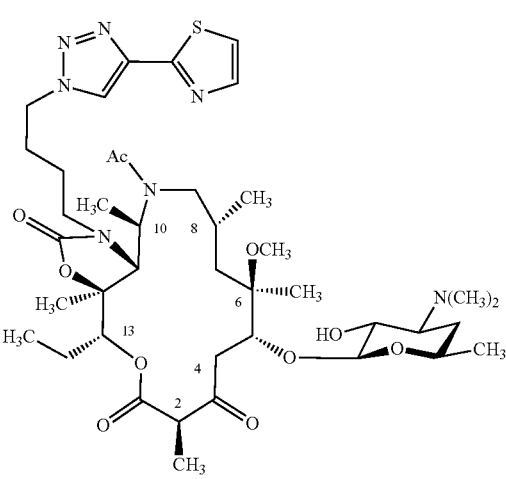<br>FSM-10790<br>Chemical Formula: $C_{41}H_{65}N_7O_{10}S$ | $^1$H NMR (500 MHz, CDCl$_3$) δ 8.05 (s, 1H), 7.84 (d, J = 3.4 Hz, 1H), 7.35 (d, J = 3.1 Hz, 1H), 4.95 (dd, J = 9.3, 2.7 Hz, 1H), 4.85-4.78 (m, 1H), 4.48-4.40 (m, 2H), 4.31 (dd, J = 10.8, 4.5 Hz, 1H), 4.24 (d, J = 7.3 Hz, 1H), 3.71 (q, J = 7.4 Hz, 1H), 3.67-3.56 (m, 2H), 3.54 (d, J = 11.0 Hz, 1H), 3.42 (br s, 1H), 3.21-3.09 (m, 2H), 2.95 (s, 1H), 2.92 (s, 3H), 2.80 (dd, J = 12.4, 11.1 Hz, 2H), 2.65 (dd, J = 13.0, 4.7 Hz, 1H), 2.47 (t, J = 11.2 Hz, 1H), 2.28 (s, 6H), 2.17 (s, 1H), 2.10 (s, 3H), 2.02-1.84 (m, 4H), 1.82-1.75 (m, 1H), 1.70 (d, J = 12.5 Hz, 1H), 1.59-1.47 (m, 2H), 1.44 (d, J = 7.3 Hz, 3H), 1.43-1.36 (m, 2H), 1.30 (s, 3H), 1.28-1.23 (m, 6H), 1.22 (s, 3H), 1.01 (d, J = 6.8 Hz, 3H), 0.91 (t, J = 7.5 Hz, 3H). | HRMS (+H) calculated: 848.4586; found: 848.4586. |

TABLE Y1-continued

| Compound and ID | NMR Data | MS Data |
|---|---|---|
| 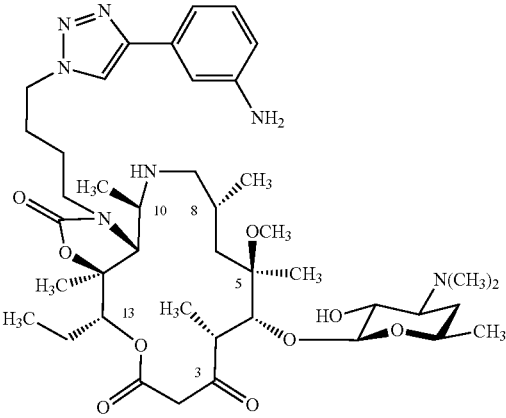<br>FSM-56133 | ¹H NMR (500 MHz, CD₃OD) δ 8.22 (s, 1H), 7.16 (s, 1H), 7.15-7.09 (m, 2H), 6.71-6.68 (m, 1H), 4.91 (dd, 1H, J = 10.3, 2.0 Hz), 4.53-4.47 (m, 2H), 4.35 (d, 1H, J = 7.3 Hz), 4.08 (d, 1H, J = 6.8 Hz), 3.61-3.54 (m, 3H), 3.25 (dd, 1H, J = 10.3, 7.3 Hz), 3.07 (s, 3H), 3.03-2.99 (m, 1H), 2.93 (app t, 1H, J = 7.3 Hz), 2.65-2.57 (m, 2H), 2.32 (s, 6H), 2.04-1.90 (m, 4H), 1.82 (ddd, 1H, J = 14.2, 7.3, 2.4 Hz), 1.77-1.71 (m, 2H), 1.70-1.55 (m, 5H), 1.49 (s, 3H), 1.43-1.39 (m, 1H), 1.32 (d, 3H, J = 7.3 Hz), 1.28-1.22 (m, 8H), 0.95-0.89 (m, 9H). | HRMS-ESI (m/z): [M + H]⁺ calcd for C₄₂H₆₈N₇O₉, 814.5073; found, 814.5077. |
| 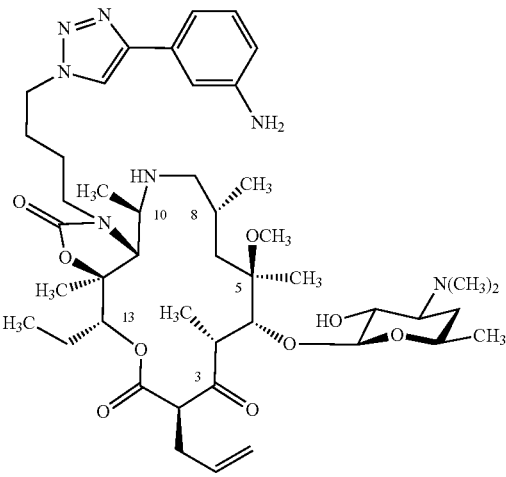<br>FSM-56156 | NB-clearly distinguishable peaks corresponding to the minor C2 epimer are reported with non-integer integrals; integrals for all other multiplet peaks are rounded to the nearest integer. ¹H NMR (500 MHz, CDCl₃) δ 7.82 (s, 0.2H), 7.78 (s, 1H), 7.27-7.24 (m, 1H), 7.22-7.13 (m, 2H), 6.66-6.63 (m, 1H), 5.78-5.70 (m, 1H), 5.58-5.50 (m, 0.2H), 5.14 (dd, 1H, J = 17.1, 1.5 Hz), 5.07 (d, 1H, J = 10.3 Hz), 4.93 (dd, 1H, J = 9.8, 2.0 Hz), 4.53 (d, 1H, J = 3.9 Hz), 4.50-4.41 (m, 2H), 4.32 (d, 1H, J = 7.3 Hz), 4.03 (brd, 0.2H, J = 7.0 Hz), 3.94 (brs, 0.2H), 3.86 (app t, 1H, J = 7.3, 6.8 Hz), 3.74-3.59 (m, 6H), 3.35 (s, 1H), 3.27-3.20 (m, 2H), 3.00-2.94 (m, 1H), 2.95 (s, 3H), 2.84-2.72 (m, 4H), 2.55 (brs, 1H), 2.50-2.45 (m, 1H), 2.32 (brs, 7H), 2.05-1.94 (m, 4H), 1.76-1.55 (m, 9H), 1.43 (s, 3H), 1.35 (d, 3H, J = 7.8 Hz), 1.32-1.20 (m, 15H), 1.20-1.14 (m, 2H), 0.97 (d, 3H, J = 5.9 Hz), 0.93-0.83 (m, 9H). | HRMS-ESI (m/z): [M + H]⁺ calcd for C₄₅H₇₂N₇O₉, 854.5386; found, 854.5376. |
| 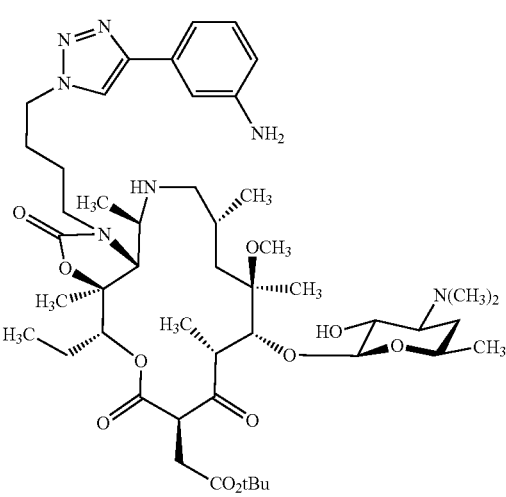<br>FSM-56178 | ¹H NMR (500 MHz, CDCl₃) δ 7.83 (s, 1H), 7.78 (s, 1H), 7.23-7.12 (m, 6H), 6.66-6.63 (m, 2H), 4.95 (dd, 1H, J = 10.3, 2.0 Hz), 4.87 (d, 1H, J = 10.7 Hz), 4.61 (d, 1H, J = 2.0 Hz), 4.48-4.33 (m, 6H), 4.26 (d, 1H, J = 7.3 Hz), 4.14 (d, 1H, J = 7.3 Hz), 4.06 (d, 1H, J = 5.4 Hz), 3.82-3.62 (m, 7H), 3.57-3.46 (m, 3H), 3.43-3.36 (m, 2H), 3.33 (s, 1H), 3.24 (d, 1H, J = 4.4 Hz), 3.21-3.15 (m, 2H), 3.11 (s, 3H), 3.06-2.99 (m, 2H), 2.92 (s, 3H), 2.86-2.70 (m, 6H), 2.53 (dd, 1H, J = 17.1, 5.4 Hz), 2.45-2.36 (m, 2H), 2.30-2.26 (m, 1H), 2.26 (s, 12H), 2.04-1.93 (m, 6H), 1.93-1.85 (m, 1H), 1.82-1.76 (m, 1H), 1.70-1.53 (m, 14H), 1.45 (s, 3H), 1.44 (s, 9H), 1.43 (s, 3H), 1.42 (s, 9H), 1.40 (s, 3H), 1.37-1.33 (m, 2H), 1.30 (s, 3H), 1.29-1.21 (m, 16H), 1.18-1.14 (m, 2H), 1.05 (d, 3H, J = 5.9 Hz), 0.96 (d, 3H, J = 6.3 Hz), 0.93 (d, 3H, J = 6.8 Hz), 0.92 (d, 3H, J = 6.3 Hz), 0.86 (app td, 6H). | HRMS-ESI (m/z): [M + H]⁺ calcd for C₄₈H₇₈N₇O₁₁, 928.5754; found, 928.5726. |

TABLE Y1-continued

| Compound and ID | NMR Data | MS Data |
|---|---|---|
| 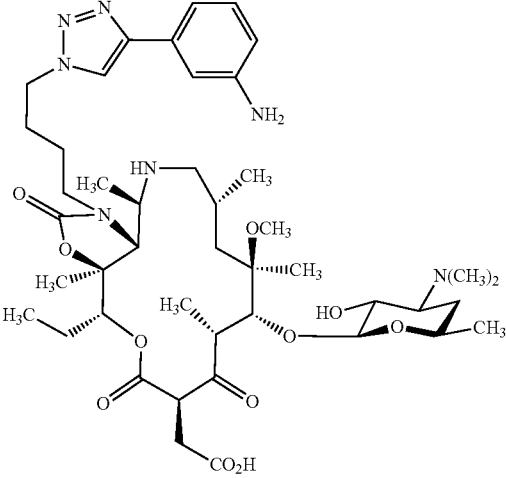<br>FSM-56185 | NB-clearly distinguishable peaks corresponding to the minor C2 epimer are reported with non-integer integrals; integrals for all other multiplet peaks are rounded to the nearest integer. $^1$H NMR (500 MHz, CD$_3$OD) δ 8.42 (s, 0.2H), 8.40 (s, 1H), 7.83-7.80 (m, 2H), 7.59 (app t, 1H, J = 8.3, 7.8 Hz), 7.33 (dd, 1H, J = 8.3, 2.5 Hz), 7.30-7.27 (m, 0.2H), 4.61 (d, 1H, J = 2.4 Hz), 4.58-4.46 (m, 2H), 4.43 (dd, 1H, J = 9.8, 4.4 Hz), 4.40 (d, 1H, J = 6.8 Hz), 4.13 (d, 0.2H, J = 6.8 Hz), 3.82-3.75 (m, 2H), 3.65 (q, 1H, J = 13.2, 6.8 Hz), 3.53 (s, 1H), 3.48-3.38 (m, 4H), 3.05 (s, 3H), 3.05-2.99 (m, 1H), 2.97-2.89 (m, 3H), 2.87 (s, 3H), 2.78 (s, 3H), 2.70 (t, 1H, J = 11.7 Hz), 2.53 (dd, 1H, J = 17.1, 4.4 Hz), 2.08-1.96 (m, 5H), 1.90-1.84 (m, 2H), 1.80-1.66 (m, 4H), 1.63-1.53 (m, 2H), 1.53 (s, 3H), 1.40-1.36 (m, 12H), 1.32 (d, 3H, J = 6.8 Hz), 1.31-1.27 (m, 2H), 1.07 (d, 3H, J = 7.4 Hz), 0.89 (t, 3H, J = 7.3 Hz), 0.84 (t, 0.6H, J = 7.3 Hz). | HRMS-ESI (m/z): [M + H]$^+$ calcd for C$_{44}$H$_{70}$N$_7$O$_{11}$, 872.5128; found, 872.5073. |
| 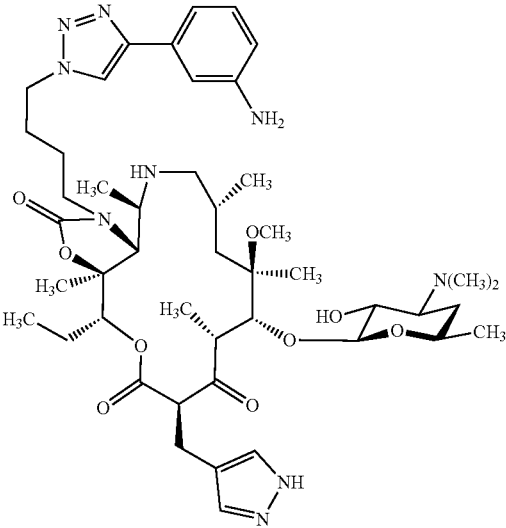<br>FSM-56192 | NB-clearly distinguishable peaks corresponding to the minor C2 epimer are reported with non-integer integrals; integrals for all other multiplet peaks are rounded to the nearest integer. $^1$H NMR (500 MHz, CDCl$_3$) δ 7.80 (s, 0.17H), 7.78 (s, 1H), 7.41 (s, 0.34H), 7.37 (s, 2H), 7.24-7.18 (m, 3H), 6.67 (dt, 1H, J = 6.8, 2.0 Hz), 4.86 (dd, 1H, J = 9.8, 2.9 Hz), 4.73 (dd, 0.17H), 4.57 (d, 1H, J = 3.9 Hz), 4.48-4.43 (m, 2H), 4.29 (d, 1H, J = 7.3 Hz), 4.05 (d, 0.17H, 7.3 Hz), 4.00 (dd, 1H, J = 8.3, 6.3 Hz), 3.77-3.58 (m, 4H), 3.43-3.37 (brm, 1H), 3.34 (s, 1H), 3.22-3.17 (m, 2H), 3.11 (s, 0.5H), 3.02-2.98 (m, 1H), 2.98 (s, 3H), 2.92 (dd, 1H, J = 15.1, 8.8 Hz), 2.83 (d, 0.17H, J = 4.9 Hz), 2.78-2.72 (brm, 2H), 2.50-2.42 (m, 1H), 2.27 (s, 6H), 2.26 (s, 1H), 2.05-1.97 (m, 2H), 1.88-1.80 (m, 2H), 1.73-1.54 (m, 10H), 1.39 (s, 3H), 1.39-1.36 (m, 1H), 1.35-1.29 (m, 3H), 1.29-1.25 (m, 12H), 1.25-1.21 (m, 3H), 1.19-1.13 (m, 3H), 0.95 (d, 3H, J = 6.3 Hz), 0.92 (d, 3H, J = 6.8 Hz), 0.90-0.82 (m, 2H), 0.47 (t, 3H, J = 7.3 Hz). | HRMS-ESI (m/z): [M + H]$^+$ calcd for C$_{46}$H$_{72}$N$_9$O$_9$, 894.5448; found, 894.5385. |
| 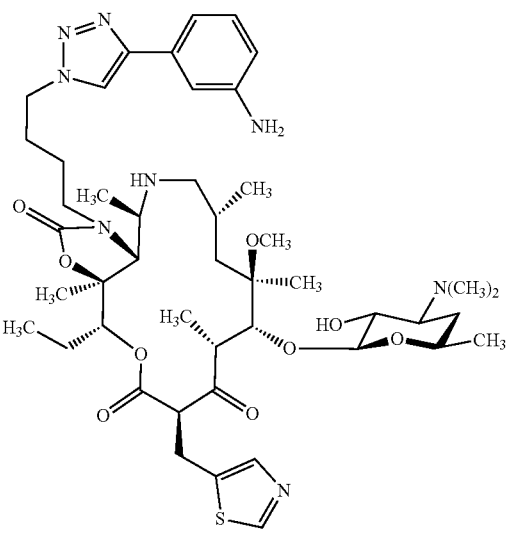<br>FSM-56216 | $^1$H NMR (500 MHz, CD$_3$OD) δ 8.88 (s, 1H), 7.69 (s, 1H), 4.63 (d, 1H, J = 3.4 Hz), 4.53 (dd, 1H, J = 10.7, 7.3 Hz), 4.40 (d, 1H, J = 7.3 Hz), 4.37 (dd, 1H, J = 8.3, 6.4 Hz), 3.77-3.74 (m, 1H), 3.74 (s, 3H), 3.66-3.61 (m, 1H), 3.61-3.52 (m, 3H), 3.37 (s, 1H), 3.37-3.30 (m, 2H), 3.07-3.03 (m, 1H), 3.03 (s, 3H), 2.88-2.82 (m, 2H), 2.75 (dd, 1H, J = 10.8, 3.4 Hz), 2.28 (s, 6H), 1.88-1.74 (m, 3H), 1.70-1.58 (m, 5H), 1.48-1.44 (m, 1H), 1.44 (s, 3H), 1.42-1.37 (m, 1H), 1.34-1.24 (m, 9H), 1.18 (d, 3H, J = 7.8 Hz), 1.16-1.06 (m, 2H), 0.95 (app t, 6H, J = 8.3, 7.3 Hz), 0.92-0.83 (m, 3H), 0.54 (t, 3H, J = 7.8 Hz). | HRMS-ESI (m/z): [M + H]$^+$ calcd for C$_{40}$H$_{66}$N$_7$O$_{11}$S, 852.4536; found, 852.4544. |

TABLE Y1-continued

| Compound and ID | NMR Data | MS Data |
|---|---|---|
| 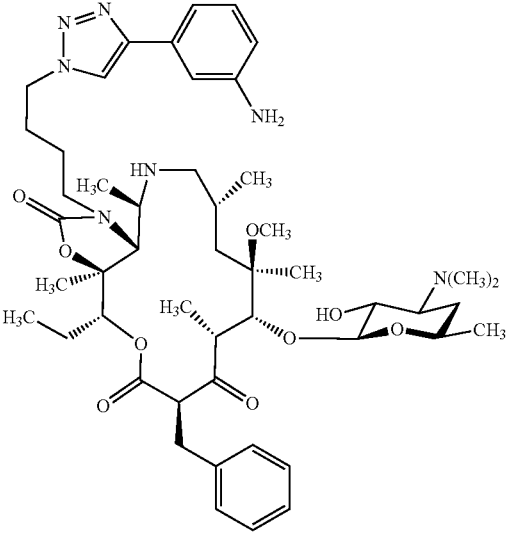<br>FSM-56158 | ¹H NMR (5:1 mixture of C2 epimers, major epimer is reported, 500 MHz, CDCl₃) δ 7.79 (s, 1H), 7.29-7.12 (m, 8H), 6.66 (d, J = 6.6 Hz, 1H), 4.81 (dd, J = 8.9, 3.1 Hz, 1H), 4.55 (d, J = 4.1 Hz, 1H), 4.45 (dd, J = 14.2, 7.1 Hz, 2H), 4.28 (d, J = 7.3 Hz, 2H), 4.10 (dd, J = 8.6, 6.4 Hz, 1H), 3.81-3.47 (m, 2H), 3.37 (dd, J = 14.1, 6.3 Hz, 1H), 3.32 (s, 1H), 3.23-3.16 (m, 1H), 3.14-3.02 (m, 2H), 2.97 (s, 3H), 2.77-2.68 (m, 2H), 2.52-2.40 (m, 1H), 2.28 (s, 6H), 2.09-1.90 (m, 2H), 1.84-1.43 (m, 9H), 1.36 (s, 3H), 1.27 (d, J = 6.2 Hz, 3H), 1.25 (s, 3H), 1.21 (d, J = 7.7 Hz, 3H), 1.14 (d, J = 18.0 Hz, 1H), 0.95 (d, J = 6.0 Hz, 3H), 0.92 (d, J = 6.6 Hz, 3H), 0.90-0.79 (m, 2H), 0.41 (t, J = 7.4 Hz, 3H). | HRMS (ESI): Calcd for (C₄₉H₇₃N₇O₉ + H)⁺: 904.5543; Found: 904.5577. |
| 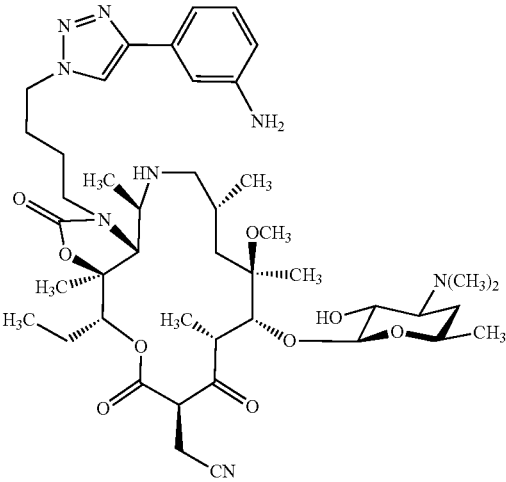<br>FSM-56160 | ¹H NMR (3:2 mixture of C2 epimers, protons are reported as seen, 500 MHz, CDCl₃) δ 7.85 (s, 1H), 7.75 (s, 1H), 7.24-7.08 (m, 6H), 6.66 (d, J = 6.1 Hz, 2H), 5.00 (d, J = 8.0 Hz, 1H), 4.80 (d, J = 8.0 Hz, 1H), 4.70-4.59 (m, 1H), 4.56 (d, J = 2.6 Hz, 1H), 4.53-4.32 (m, 5H), 4.32-4.25 (m, 2H), 4.11 (dd, J = 8.2, 5.8 Hz, 2H), 3.84-3.42 (m, 14H), 3.25 (s, 2H), 3.24-3.15 (m, 2H), 3.08-2.98 (m, 2H), 2.96 (s, 3H), 2.94-2.92 (m, 2H), 2.90 (s, 3H), 2.89-2.81 (m, 3H), 2.76 (t, J = 8.4 Hz, 4H), 2.61 (dd, J = 17.2, 8.3 Hz, 3H), 2.32 (s, 12H), 2.10-1.81 (m, 8H), 1.81-1.53 (m, 16H), 1.50 (s, 3H), 1.44 (s, 3H), 1.41 (d, J = 7.8 Hz, 3H), 1.35-1.16 (m, 15H), 1.00-0.91 (m, 18H). | HRMS (ESI): Calcd for (C₄₄H₆₆N₈O₉ + H)⁺: 853.5182 Found: 853.5168. |

- ($C_{49}H_{73}N_7O_9$ + H)⁺
- ($C_{44}H_{66}N_8O_9$ + H)⁺

TABLE Y1-continued

| Compound and ID | NMR Data | MS Data |
|---|---|---|
| 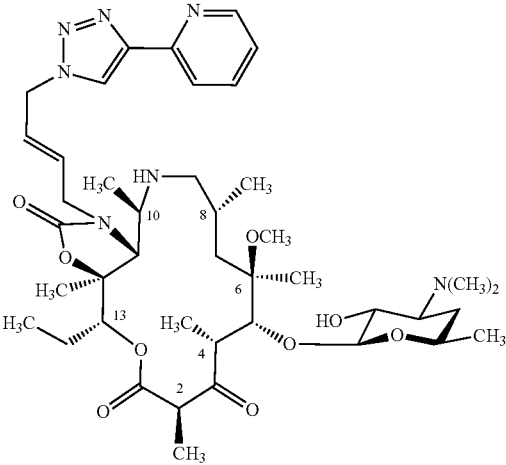<br>FSM-70153<br>Chemical Formula: $C_{42}H_{65}N_7O_9$ | $^1$H NMR (600 MHz, CDCl$_3$) δ 8.59-8.55 (m, 1H), 8.16 (s, 1H), 8.13 (d, J = 7.9 Hz, 1H), 7.76 (td, J = 7.7, 1.9 Hz, 1H), 7.20 (ddd, J = 7.5, 4.9, 1.1 Hz, 1H), 6.03-5.95 (m, 1H), 5.94-5.86 (m, 1H), 5.03 (t, J = 6.2 Hz, 2H), 4.95 (dd, J = 11.0, 2.2 Hz, 1H), 4.47 (d, J = 3.5 Hz, 1H), 4.37 (d, J = 7.5 Hz, 1H), 4.34 (dd, J = 16.2, 5.8 Hz, 1H), 4.23-4.17 (m, 1H), 3.84 (q, J = 6.8 Hz, 1H), 3.66-3.59 (m, 1H), 3.39 (s, 1H), 3.19 (dd, J = 10.2, 7.4 Hz, 1H), 3.11 (d, J = 0.8 Hz, 1H), 3.04-2.98 (m, 1H), 2.94 (d, J = 0.9 Hz, 3H), 2.80-2.75 (m, 1H), 2.73 (dd, J = 10.0,3.1 Hz, 1H), 2.52-2.45 (m, 2H), 2.26 (s, 6H), 1.99-1.92 (m, 1H), 1.77-1.52 (m, 5H), 1.42 (s, 3H), 1.39-1.35 (m, 3H), 1.34 (d, J = 7.8 Hz, 3H), 1.27 (d, J = 6.2 Hz, 3H), 1.24 (s, 3H), 1.23-1.19 (m, 1H), 1.18-1.14 (m, 1H), 0.97 (d, J = 6.1 Hz, 3H), 0.91 (d, J = 6.9 Hz, 3H), 0.87 (t, J = 7.2 Hz, 3H). | HRMS (M + Na)$^+$ Calculated: 834.4736 found: 834.4706. |
| 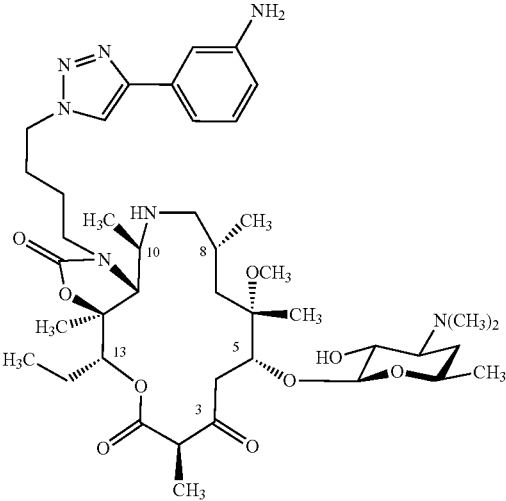<br>FSM-30502 | $^1$H NMR (500 MHz, CDCl$_3$) δ 7.86 (s, 1H), 7.29 (br s, 1H), 7.20-7.13 (m, 2H), 6.64-6.61 (m, 1H), 4.76 (dd, 1H, J = 8.7, 3.8 Hz), 4.54-4.41 (m, 2H), 4.39 (dd, 1H, J = 7.3, 3.6 Hz), 4.24 (d, 1H, J = 7.4 Hz), 3.70-3.61 (m, 2H), 3.60-3.51 (m, 2H), 3.46-3.38 (m, 1H), 3.32 (d, 1H, J = 3.1 Hz), 3.21 (s, 3H), 3.15 (app dd, 2H, J = 9.5, 6.7 Hz), 3.04 (dd, 1H, J = 16.5, 7.5 Hz), 2.72-2.64 (m, 1H), 2.59 (dd, 1H, J = 16.5, 3.5 Hz), 2.51 (dd, 1H, J = 10.8, 3.3 Hz), 2.27 (s, 6H), 2.05-1.77 (m, 6H), 1.74-1.55 (m, 4H), 1.53 (d, 2H, J = 5.8 Hz), 1.33 (s, 3H), 1.30 (d, 3H, J = 7.4 Hz), 1.23-1.18 (m, 6H), 0.99-0.93 (m, 9H). | HRMS (ESI): Calcd for $(C_{42}H_{67}N_7O_9 + H)^+$ 814.5073, found: 814.5098. |
| 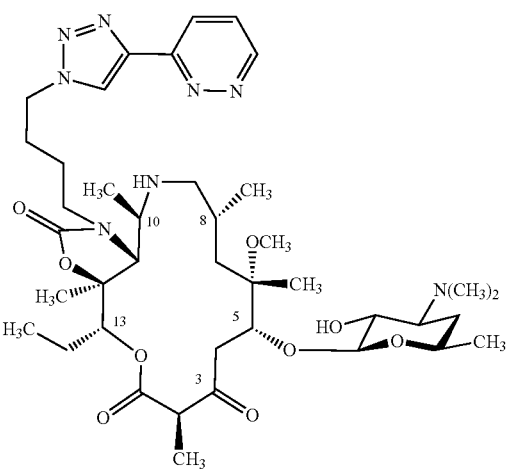<br>FSM-30506 | $^1$H NMR (500 MHz, CDCl$_3$) δ 9.10 (dd, 1H, J = 4.9, 1.7 Hz), 8.47 (s, 1H), 8.33 (dd, 1H, J = 8.5, 1.7 Hz), 7.54 (dd, 1H, J = 8.5, 5.0 Hz), 4.79 (dd, 1H, J = 9.1, 3.4 Hz), 4.55 (td, 2H, J = 7.5, 2.0 Hz), 4.43 (dd, 1H, J = 7.2, 3.8 Hz), 4.19 (d, 1H, J = 7.4 Hz), 3.70-3.58 (m, 3H), 3.53-3.42 (m, 2H), 3.31 (d, 1H, J = 3.4 Hz), 3.23 (s, 3H), 3.13 (dd, 1H, J = 10.2, 7.4 Hz), 3.08 (dd, 1H, J = 16.7, 7.3 Hz), 2.72-2.64 (m, 2H), 2.54 (dd, 1H, J = 10.7, 3.1 Hz), 2.48-2.42 (m, 1H), 2.24 (s, 6H), 2.12-1.84 (m, 6H), 1.74-1.51 (m, 6H), 1.37 (d, 3H, J = 7.4 Hz), 1.34 (s, 3H), 1.21 (s, 3H), 1.20 (d, 3H, J = 6.2 Hz), 1.00 (d, 3H, J = 6.4 Hz), 0.97-0.92 (m, 6H). | HRMS (ESI): Calcd for $(C_{40}H_{64}N_8O_9 + H)^+$ 801.4669, found: 801.4903. |

TABLE Y1-continued

| Compound and ID | NMR Data | MS Data |
|---|---|---|
| 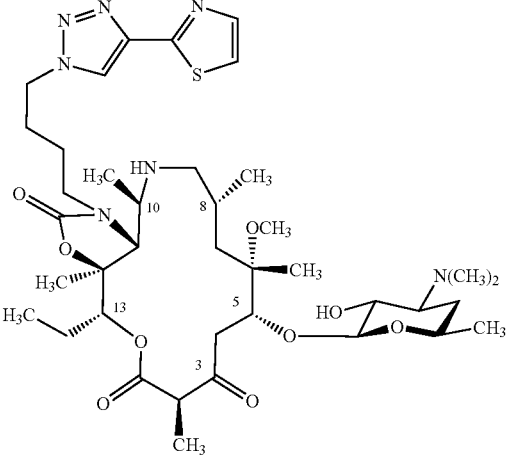 FSM-30501 | $^1$H NMR (500 MHz, CDCl$_3$) δ 8.18 (s, 1H), 7.82 (d, 1H, J = 3.2 Hz), 7.33 (d, 1H, J = 3.2 Hz), 4.78 (dd, 1H, J = 9.0, 3.6 Hz), 4.52 (td, 2H, J = 7.3, 3.4 Hz), 4.42 (dd, 1H, J = 7.4, 3.6 Hz), 4.16 (d, 1H, J = 7.4 Hz), 3.70-3.56 (m, 3H), 3.51-3.43 (m, 2H), 3.34 (d, 1H, J = 3.0 Hz), 3.22 (s, 3H), 3.12 (dd, 1H, J = 10.2, 7.4 Hz), 3.06 (dd, 1H, J = 16.5, 7.5 Hz), 2.72-2.67 (m, 1H), 2.64 (dd, 1H, J = 16.5, 3.4 Hz), 2.53 (dd, 1H, J = 10.7, 3.0 Hz), 2.48-2.42 (m, 1H), 2.25 (s, 6H), 2.09-1.75 (m, 6H), 1.73-1.55 (m, 4H), 1.53 (d, 2H, J = 5.8 Hz), 1.39 (d, 3H, J = 7.4 Hz), 1.34 (s, 3H), 1.21 (s, 3H), 1.19 (d, 3H, J = 6.2 Hz), 0.98 (d, 3H, J = 6.4 Hz), 0.97-0.92 (m, 6H). | HRMS (ESI): Calcd for (C$_{39}$H$_{63}$N$_7$O$_9$S + H)$^+$ 806.4481, found: 806.4477. |
| 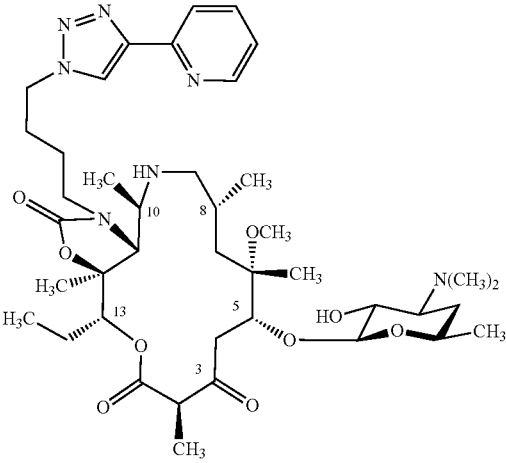 FSM-30517 | $^1$H NMR (500 MHz, CDCl$_3$) δ 8.57 (d, 1H, J = 4.8 Hz), 8.20 (s, 1H), 8.14 (d, 1H, J = 7.9 Hz), 7.75 (td, 1H, J = 7.7, 1.7 Hz), 7.20 (ddd, 1H, J = 7.5, 4.9, 1.0 Hz), 4.79 (dd, 1H, J = 9.0, 3.5 Hz), 4.52 (td, 2H, J = 7.4, 2.4 Hz), 4.42 (dd, 1H, J = 7.1, 3.8 Hz), 4.18 (d, 1H, J = 7.4 Hz), 3.69-3.54 (m, 3H), 3.51-3.41 (m, 2H), 3.32 (d, 1H, J = 3.4 Hz), 3.22 (s, 3H), 3.12 (dd, 1H, J = 10.2, 7.5 Hz), 3.07 (dd, 1H, J = 16.7, 7.2 Hz), 2.70-2.64 (m, 2H), 2.53 (dd, 1H, J = 10.7, 3.2 Hz), 2.46-2.40 (m, 1H), 2.23 (s, 6H), 2.09-1.78 (m, 6H), 1.73-1.51 (m, 6H), 1.36 (d, 3H, J = 7.4 Hz), 1.34 (s, 3H), 1.21 (s, 3H), 1.19 (d, 3H; J = 6.1 Hz), 0.99 (d, 3H; J = 6.4 Hz), 0.97-0.93 (m, 6H). | HRMS (ESI): Calcd for (C$_{41}$H$_{65}$N$_7$O$_9$ + H)$^+$ 800.4917, found: 800.4923. |
| 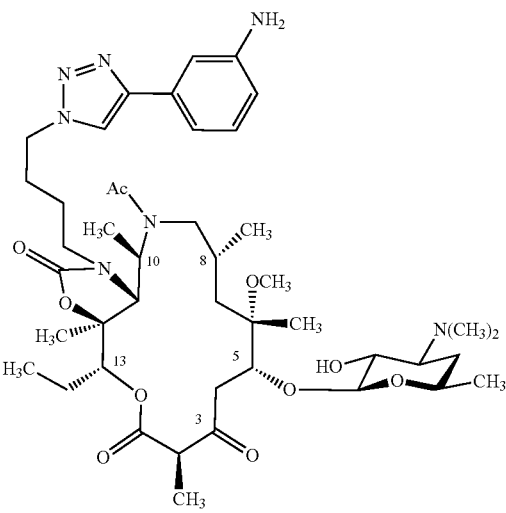 FSM-30512 | NB: Spectrum is a mixture of rotamers. Reported as it appears. $^1$H NMR (500 MHz, CDCl$_3$) δ 7.79 (s, 1H), 7.78 (s, 1H), 7.31 (s, 1H), 7.30 (s, 1H), 7.17 (td, J = 7.8, 3.1 Hz, 2H), 7.11 (d, J = 7.5 Hz, 2H), 6.67-6.61 (m, 2H), 4.88 (ddd, J = 12.3, 8.1, 4.5 Hz, 2H), 4.48-4.28 (m, 6H), 4.10 (d, J = 9.6 Hz, 1H), 4.02 (d, J = 10.7 Hz, 1H), 3.87 (t, J = 8.2 Hz, 1H), 3.74 (t, J = 13.3 Hz, 1H), 3.65 (dq, J = 14.0, 7.9, 7.4 Hz, 5H), 3.54-3.47 (m, 1H), 3.22 (dd, J = 13.1, 7.5 Hz, 8H), 2.87 (t, J = 13.7 Hz, 1H), 2.70 (s, 0H), 2.61 (d, J = 11.4 Hz, 1H), 2.36-2.24 (m, 14H), 2.15 (s, 3H), 2.04 (s, 3H), 2.02-1.50 (m, 11H), 1.43 (d, J = 6.7 Hz, 4H), 1.31-1.11 (m, 28H), 0.95 (td, J = 7.1, 4.2 Hz, 12H), 0.84 (d, J = 6.5 Hz, 3H). | HRMS (ESI): [M + H]$^+$ Calculated: 856.5179, found: 856.5156. |

TABLE Y1-continued

| Compound and ID | NMR Data | MS Data |
|---|---|---|
| 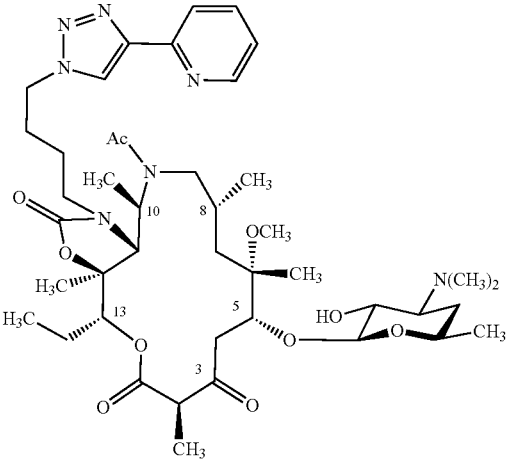<br>FSM-30515 | NB: Spectrum is a mixture of rotamers. Reported as it appears. $^1$H NMR (500 MHz, CDCl$_3$) δ 8.57 (d, J = 4.9 Hz, 2H), 8.18-8.12 (m, 4H), 7.80-7.72 (m, 2H), 7.24-7.20 (m, 2H), 4.97-4.82 (m, 4H), 4.49-4.35 (m, 6H), 4.30 (t, J = 8.8 Hz, 2H), 4.15-4.02 (m, 2H), 3.88 (t, J = 8.2 Hz, 1H), 3.79-3.53 (m, 5H), 3.27-3.16 (m, 8H), 2.93-2.84 (m, 1H), 2.55 (d, J = 13.0 Hz, 2H), 2.25 (d, J = 1.7 Hz, 12H), 2.15 (s, 3H), 2.04 (s, 3H), 2.01-1.77 (m, 7H), 1.71-1.51 (m, 6H), 1.43 (d, J = 6.7 Hz, 3H), 1.38 (s, 3H), 1.37 (s, 3H), 1.31-1.18 (m, 26H), 1.16 (s, 3H), 0.95 (td, J = 7.5, 3.4 Hz, 9H), 0.84 (d, J = 6.5 Hz, 3H). | HRMS (ESI): [M + H]$^+$ Calculated: 842.5022, found: 842.5042. |
| 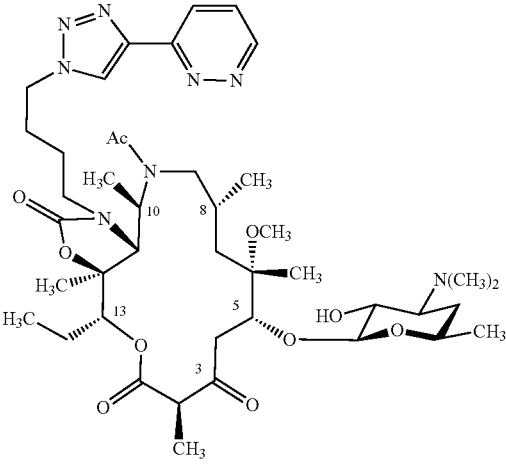<br>FSM-30513 | NB: Spectrum is a mixture of rotamers. Reported as it appears. $^1$H NMR (500 MHz, CDCl$_3$) δ 9.13-9.10 (m, 2H), 8.43 (s, 1H), 8.42 (s, 1H), 8.33 (d, J = 8.4 Hz, 2H), 7.58-7.53 (m, 2H), 4.95-4.82 (m, 3H), 4.55-4.34 (m, 6H), 4.28 (dd, J = 13.4, 7.3 Hz, 2H), 4.11 (d, J = 9.6 Hz, 1H), 4.03 (d, J = 10.6 Hz, 1H), 3.88 (t, J = 8.2 Hz, 1H), 3.78-3.53 (m, 5H), 3.23 (s, 3H), 3.20 (s, 3H), 3.20-3.06 (m, 2H), 2.94-2.85 (m, 1H), 2.56-2.49 (m, 2H), 2.26 (d, J = 1.9 Hz, 12H), 2.15 (s, 3H), 2.04 (s, 3H), 2.02-1.76 (m, 8H), 1.71-1.49 (m, 6H), 1.44 (d, J = 6.7 Hz, 3H), 1.39 (t, J = 6.9 Hz, 6H), 1.32-1.15 (m, 28H), 0.98-0.91 (m, 9H), 0.84 (d, J = 6.5 Hz, 3H). | HRMS (ESI): Calcd for (C$_{42}$H$_{66}$N$_8$O$_{10}$ + H)$^+$ 843.4975, found: 843.5001. |
| 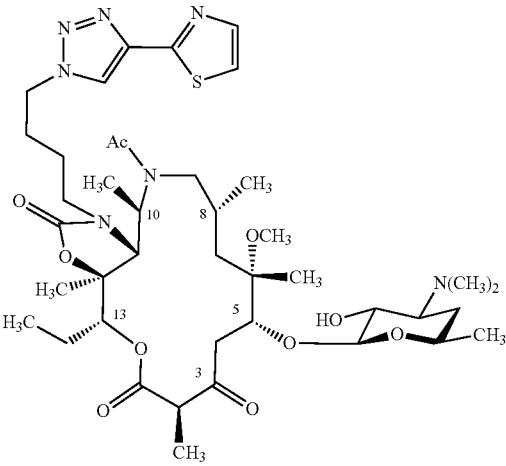<br>FSM-30503 | NB: Spectrum is a mixture of rotamers. Reported as it appears. $^1$H NMR (500 MHz, CDCl$_3$) δ 8.15-8.11 (m, 1H), 7.85-7.83 (m, 1H), 7.35 (td, J = 5.3, 4.3, 3.1 Hz, 1H), 4.94-4.83 (m, 2H), 4.51-4.35 (m, 3H), 4.27 (dd, J = 14.3, 7.3 Hz, 1H), 4.10 (d, J = 9.6 Hz, 1H), 4.03 (d, J = 10.8 Hz, 1H), 3.87 (t, J = 8.2 Hz, 1H), 3.79-3.52 (m, 4H), 3.23 (s, 2H), 3.20 (s, 2H), 2.93-2.84 (m, 1H), 2.60-2.49 (m, 2H), 2.26 (s, 6H), 2.15 (s, 2H), 2.04 (s, 1H), 2.02-1.75 (m, 4H), 1.73-1.49 (m, 3H), 1.48-1.37 (m, 6H), 1.31-1.24 (m, 5H), 1.23-1.13 (m, 9H), 0.95 (td, J = 7.6, 3.2 Hz, 6H), 0.84 (d, J = 6.5 Hz, 2H). | HRMS (ESI): Calcd for (C$_{41}$H$_{65}$N$_7$O$_{10}$S + H)$^+$ 848.4586, found: 848.4595. |

TABLE Y1-continued

| Compound and ID | NMR Data | MS Data |
|---|---|---|
| 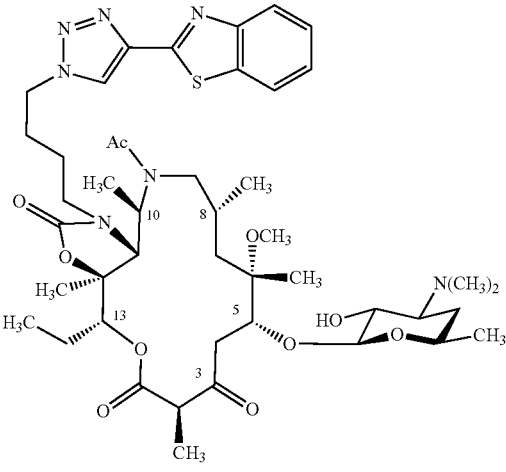  FSM-30514 | NB: Spectrum is a mixture of rotamers. Reported as it appears. $^1$H NMR (500 MHz, CDCl$_3$) δ 8.29 (d, J = 3.0 Hz, 2H), 8.02 (dd, J = 8.2, 1.0 Hz, 2H), 7.94 (d, J = 8.1 Hz, 2H), 7.50 (t, J = 7.7 Hz, 2H), 7.41 (t, J = 7.5 Hz, 3H), 4.89 (d, J = 24.5 Hz, 4H), 4.53-4.34 (m, 7H), 4.32 (d, J = 7.9 Hz, 1H), 4.11 (d, J = 9.6 Hz, 1H), 4.03 (d, J = 10.8 Hz, 1H), 3.88 (t, J = 8.2 Hz, 1H), 3.79-3.53 (m, 7H), 3.23 (s, 3H), 3.20 (s, 3H), 3.15 (s, 2H), 2.93-2.84 (m, 1H), 2.69-2.49 (m, 2H), 2.40 (s, 1H), 2.28 (s, 12H), 2.15 (s, 3H), 2.04 (s, 3H), 2.01-1.51 (m, 6H), 1.44 (d, J = 6.7 Hz, 3H), 1.38 (d, J = 7.1 Hz, 6H), 1.31-1.13 (m, 28H), 0.96 (dt, J = 10.6, 5.2 Hz, 9H), 0.84 (d, J = 6.5 Hz, 3H). | HRMS (ESI): Calcd for (C$_{45}$H$_{67}$N$_7$O$_{10}$S + H)$^+$ 898.4743, found: 898.4757. |
| 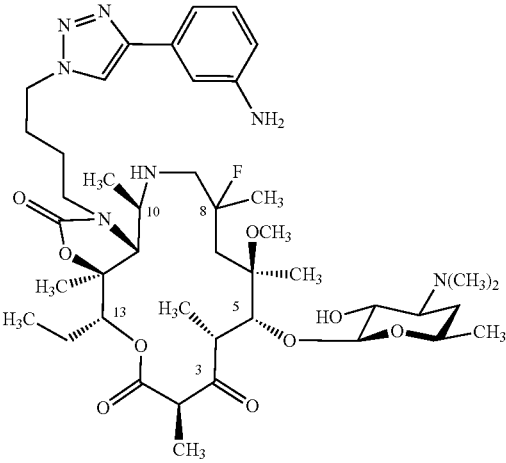  FSM-30686 | $^1$H NMR (500 MHz, CDCl$_3$) δ 7.83 (s, 1H), 7.30-7.25 (m, 1H), 7.22-7.12 (m, 2H), 6.64 (ddd, J = 7.4, 2.5, 1.6 Hz, 1H), 4.88 (dd, J = 10.7, 2.4 Hz, 1H), 4.43 (td, J = 7.9, 7.4, 1.7 Hz, 2H), 4.33 (dd, J = 20.5, 7.4 Hz, 1H), 4.26 (d, J = 6.8 Hz, 1H), 3.80 (q, J = 7.0 Hz, 1H), 3.71-3.60 (m, 1H), 3.58-3.49 (m, 1H), 3.48 (q, J = 7.1 Hz, 1H), 3.41 (d, J = 2.8 Hz, 1H), 3.25-3.17 (m, 1H), 3.07-3.00 (m, 1H), 2.98 (s, 3H), 2.91-2.81 (m, 1H), 2.28 (s, 3H), 2.26 (s, 3H), 2.05-1.89 (m, 5H), 1.80-1.53 (m, 5H), 1.50-1.30 (m, 19H), 1.06 (t, J = 6.3 Hz, 3H), 0.87 (ddt, J = 10.5, 7.3, 3.3 Hz, 7H). | HRMS (ESI): [M + H]$^+$ Calculated: 846.5135, found: 846.5166. |
| 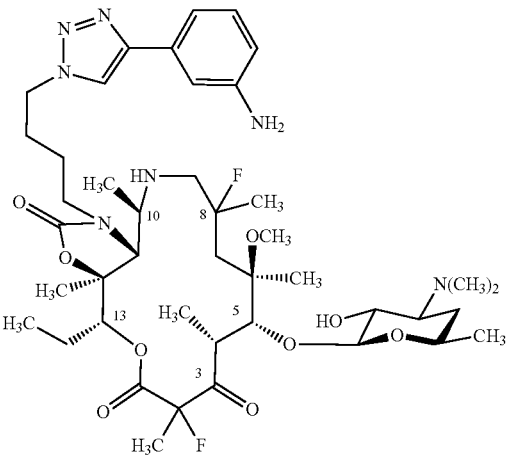  FSM-30704 | $^1$H NMR (500 MHz, CDCl$_3$) δ 7.83 (s, 1H), 7.28-7.27 (m, 1H), 7.19-7.14 (m, 2H), 6.64 (dt, J = 7.1, 2.2 Hz, 1H), 5.02 (dd, J = 10.5, 2.2 Hz, 1H), 4.45 (t, J = 7.4 Hz, 2H), 4.35 (d, J = 7.3 Hz, 1H), 4.13 (d, J = 8.0 Hz, 1H), 3.77-3.57 (m, 2H), 3.55-3.49 (m, 1H), 3.38 (s, 1H), 3.20 (s, 3H), 3.18-3.10 (m, 1H), 2.99-2.87 (m, 2H), 2.53-2.44 (m, 1H), 2.36 (s, 1H), 2.28 (s, 6H), 2.05-1.93 (m, 4H), 1.82 (d, J = 21.7 Hz, 3H), 1.78-1.56 (m, 6H), 1.45 (d, J = 7.4 Hz, 3H), 1.44 (s, 3H), 1.41 (s, 3H), 1.35 (d, J = 22.0 Hz, 3H), 1.25 (s, 3H), 1.24 (d, J = 6.2 Hz, 3H), 1.01 (d, J = 6.2 Hz, 3H), 0.91 (t, J = 7.4 Hz, 3H). | HRMS (ESI): [M + H]$^+$ Calculated: 814.5041, found: 814.5061. |

TABLE Y1-continued

| Compound and ID | NMR Data | MS Data |
|---|---|---|
| 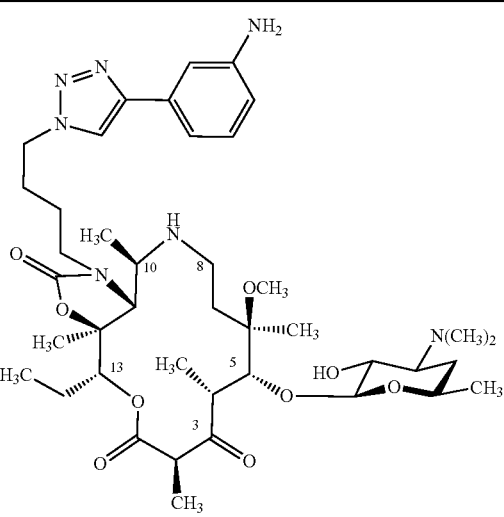 FSM-30622 | ¹H NMR (500 MHz, CDCl₃) δ 7.81 (s, 1H), 7.26-7.24 (br s, 1H), 7.20-7.11 (m, 2H), 6.64 (ddd, 1H, J = 7.6, 2.3, 1.2 Hz), 4.89 (dd, 1H, J = 10.5, 1.9 Hz), 4.47-4.40 (m, 2H), 4.27 (brd, 1H, J = 2.7 Hz), 4.26-4.19 (m, 1H), 3.68-3.61 (m, 1H), 3.48-3.40 (m, 1H), 3.40-3.33 (m, 1H), 3.27-3.23 (m, 2H), 3.19 (br d, 1H, J = 3.3 Hz), 3.12 (s, 3H), 2.92-2.85 (m, 1H), 2.82-2.74 (m, 2H), 2.53-2.47 (m, 1H), 2.46-2.38 (m, 1H), 2.29 (s, 6H), 2.05-1.86 (m, 6H), 1.70-1.60 (m, 4H), 1.42 (s, 3H), 1.39 (d, 3H, J = 7.0 Hz), 1.35-1.32 (m, 1H), 1.26-1.23 (m, 6H), 1.21 (d, 3H, J = 6.2 Hz), 1.07 (d, 3H, J = 6.5 Hz), 0.88 (t, 3H, J = 7.4 Hz). | HRMS (ESI): Calcd for (C₄₁H₆₅N₇O₉ + Na)⁺ 822.4736, found: 822.4735. |
| 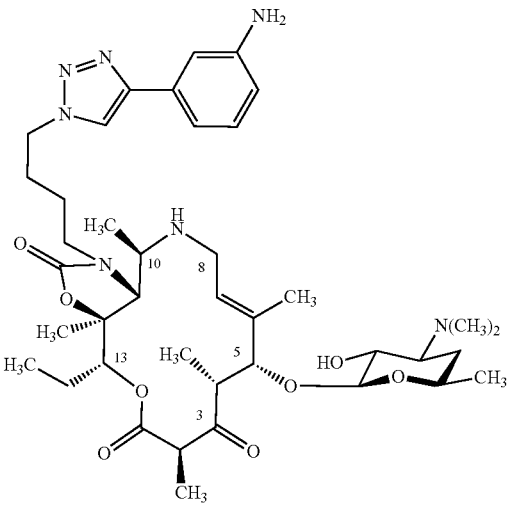 FSM-30624 | ¹H NMR (major isomer, 500 MHz, CDCl₃) δ 7.85 (s, 1H), 7.32-7.29 (m, 1H), 7.21-7.12 (m, 2H), 6.65 (ddd, 1H, J = 7.8, 2.4, 1.1 Hz), 5.45 (br t, 1H, J = 4.9 Hz), 4.83 (dd, 1H, J = 10.9, 2.3 Hz), 4.56-4.48 (m, 1H), 4.48-4.39 (m, 1H), 4.25 (d, 1H, J = 9.8 Hz), 4.05 (d, 1H, J = 7.4 Hz), 3.77 (q, 1H, J = 7.0 Hz), 3.70-3.62 (m, 1H), 3.45 (s, 1H), 3.43-3.21 (m, 5H), 3.10-3.02 (m, 1H), 2.83 (q, 1H, J = 6.0 Hz), 2.48 (ddd, 1H, J = 12.2, 10.3, 4.0 Hz), 2.27 (s, 6H), 2.04-1.87 (m, 4H), 1.75-1.55 (m, 5H), 1.58 (s, 3H), 1.47 (s, 3H), 1.36 (d, 3H, J = 7.0 Hz), 1.23-1.21 (m, 6H), 1.05 (d, 3H, J = 6.3 Hz), 0.85 (t, 3H, J = 7.4 Hz). | HRMS (ESI): Calcd for (C₄₀H₆₁N₇O₈ + H)⁺ 768.4654, found: 768.4654. |
| 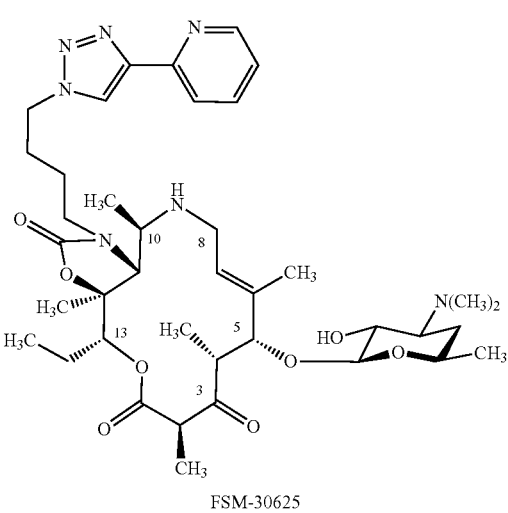 FSM-30625 | ¹H NMR (major isomer, 500 MHz, CDCl₃) δ 8.57 (ddd, 1H, J = 4.8, 1.7, 0.9 Hz), 8.21 (s, 1H), 8.17-8.14 (m, 1H), 7.77 (td, 1H, J = 7.8, 1.7 Hz), 7.21 (ddd, 1H, J = 7.5, 4.9, 1.0 Hz), 5.43 (br t, 1H, J = 4.8 Hz), 4.87 (dd, 1H, J = 10.8, 2.2 Hz), 4.56-4.45 (m, 2H), 4.28 (d, 1H, J = 9.4 Hz), 4.10 (d, 1H, J = 7.4 Hz), 3.83 (q, 1H, J = 7.0 Hz), 3.69-3.59 (m, 1H), 3.53 (s, 1H), 3.48-3.16 (m, 6H), 2.85 (q, 1H, J = 6.0 Hz), 2.63-2.51 (m, 1H), 2.33 (s, 6H), 2.10-1.87 (m, 4H), 1.79-1.66 (m, 4H), 1.64 (s, 3H), 1.62-1.59 (m, 1H), 1.48 (s, 3H), 1.37 (d, 3H, J = 7.0 Hz), 1.25 (d, 3H, J = 6.8 Hz), 1.24 (d, 3H, J = 6.1 Hz), 1.06 (d, 3H, J = 6.2 Hz), 0.86 (t, 3H, J = 7.4 Hz). | HRMS (ESI): Calcd for (C₃₉H₅₉N₇O₈ + H)⁺ 754.4498, found: 754.4525. |

TABLE Y1-continued

| Compound and ID | NMR Data | MS Data |
|---|---|---|
| 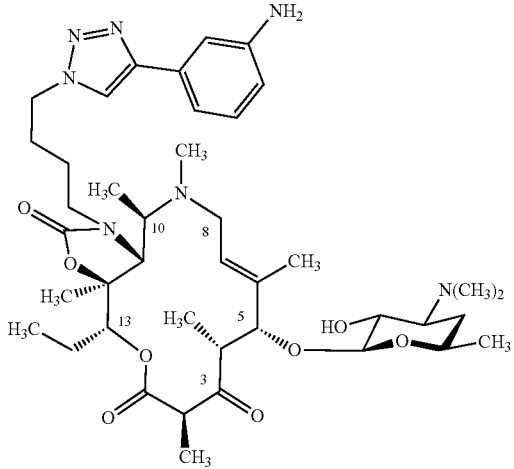<br>FSM-30633 | ¹H NMR (major isomer, 500 MHz, CDCl₃) δ 7.80 (s, 1H), 7.29-7.27 (m, 1H), 7.20-7.14 (m, 2H), 6.65 (ddd, 1H, J = 7.7, 2.3, 1.1 Hz), 5.38 (br s, 1H), 4.80 (dd, 1H, J = 10.3, 2.7 Hz), 4.54-4.37 (m, 2H), 4.17 (d, 1H, J = 10.4 Hz), 4.03 (d, 1H; J = 7.4 Hz), 3.67-3.58 (m, 2H), 3.49-3.32 (m, 4H), 3.30-3.24 (m, 1H), 3.19-3.04 (m, 2H), 2.78-2.70 (m, 1H), 2.53-2.47 (m, 1H), 2.29 (s, 6H), 2.26 (s, 3H), 2.06-1.87 (m, 4H), 1.76-1.57 (m, 5H), 1.62 (s, 3H), 1.46 (s, 3H), 1.33 (d, 3H, J = 7.1 Hz), 1.27-1.19 (m, 6H), 1.02 (d, 3H, J = 6.1 Hz), 0.87 (t, 3H, J = 7.4 Hz). | HRMS (ESI): Calcd for (C₄₁H₆₃N₇O₈ + H)⁺ 782.4811, found: 782.4808. |
| 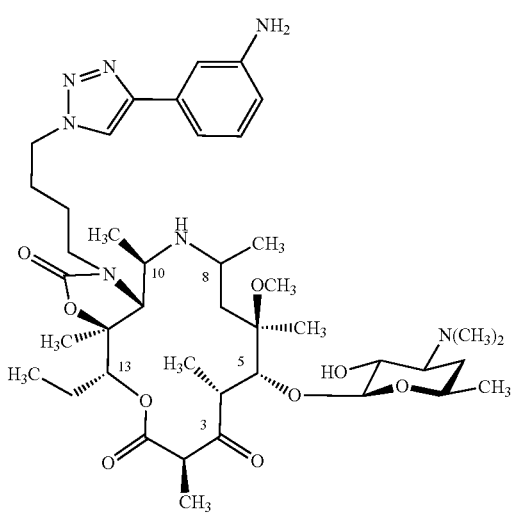<br>FSM-30689<br>(C8 epimer of FSM-30690) | NB: Spectrum is a mixture of C2 epimers. Reported as it appears. ¹H NMR (500 MHz, CDCl₃) δ 7.83 (s, 1H), 7.80 (s, 1H), 7.28-7.27 (m, 1H), 7.25-7.24 (m, 1H), 7.21-7.11 (m, 4H), 6.67-6.62 (m, 2H), 4.92-4.86 (m, 2H), 4.58 (d, J = 1.7 Hz, 1H), 4.46 (dt, J = 14.4, 7.1 Hz, 4H), 4.34 (d, J = 7.3 Hz, 1H), 4.30 (d, J = 7.4 Hz, 1H), 4.16 (q, J = 6.7 Hz, 1H), 4.07 (d, J = 5.7 Hz, 1H), 3.95 (q, J = 7.1 Hz, 1H), 3.68-3.53 (m, 3H), 3.45 (dh, J = 9.4, 4.3, 3.1 Hz, 3H), 3.32 (d, J = 2.4 Hz, 1H), 3.29-3.23 (m, 1H), 3.14 (s, 3H), 3.02 (s, 3H), 2.91-2.83 (m, 3H), 2.70-2.66 (m, 1H), 2.65-2.60 (m, 1H), 2.33 (s, 12H), 2.06-1.85 (m, 5H), 1.76-1.51 (m, 6H), 1.47 (d, J = 7.4 Hz, 3H), 1.42 (d, J = 7.2 Hz, 3H), 1.39 (s, 3H), 1.33 (d, J = 6.7 Hz, 3H), 1.28-1.22 (m, 21H), 1.18 (s, 3H), 1.15 (d, J = 6.1 Hz, 3H), 1.12 (s, 3H), 1.05 (d, J = 6.6 Hz, 3H), 0.97 (d, J = 6.6 Hz, 3H), 0.91-0.86 (m, 6H). | HRMS (ESI): [M + H]⁺ Calculated: 814.5073, found: 814.5104. |
| 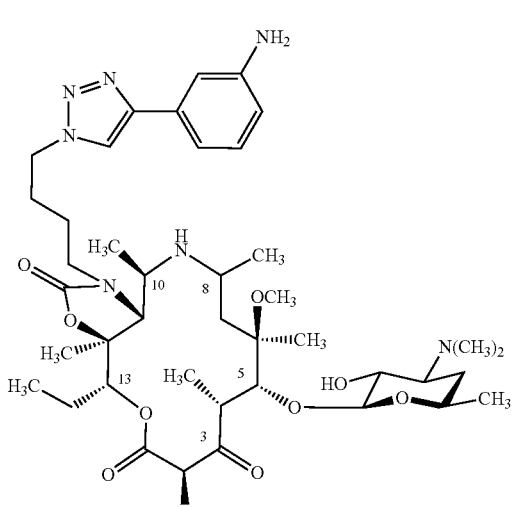<br>FSM-30689<br>(C8 epimer of FSM-30689) | NB: Spectrum is a mixture of C2 epimers. Reported as it appears. ¹H NMR (500 MHz, CDCl₃) δ 7.85 (s, 1H), 7.85-7.78 (m, 1H), 7.21-7.11 (m, 4H), 6.68-6.63 (m, 2H), 4.92-4.87 (m, 0H), 4.85 (dd, J = 10.1, 2.6 Hz, 1H), 4.52-4.41 (m, 5H), 4.35 (dd, J = 11.4, 7.3 Hz, 2H), 4.14 (br s, J = 16.3 Hz, 1H), 3.98 (d, J = 7.4 Hz, 2H), 3.66 (tt, J = 12.2, 7.5 Hz, 2H), 3.58 (s, 2H), 3.39-3.30 (m, 1H), 3.22-3.17 (m, 1H), 3.02 (s, 5H), 2.97-2.83 (m, 1H), 2.53-2.37 (m, 2H), 2.27 (s, 10H), 2.07-1.86 (m, 8H), 1.75-1.53 (m, 5H), 1.46 (s, 5H), 1.40 (d, J = 7.1 Hz, 4H), 1.30-1.17 (m, 24H), 1.09 (d, J = 6.6 Hz, 4H), 1.04 (d, J = 6.3 Hz, 5H), 0.91 (t, J = 7.5 Hz, 4H), 0.88-0.83 (m, 1H). | HRMS (ESI): [M + H]⁺ Calculated: 814.5073, found: 814.5095. |

TABLE Y1-continued

| Compound and ID | NMR Data | MS Data |
|---|---|---|
| 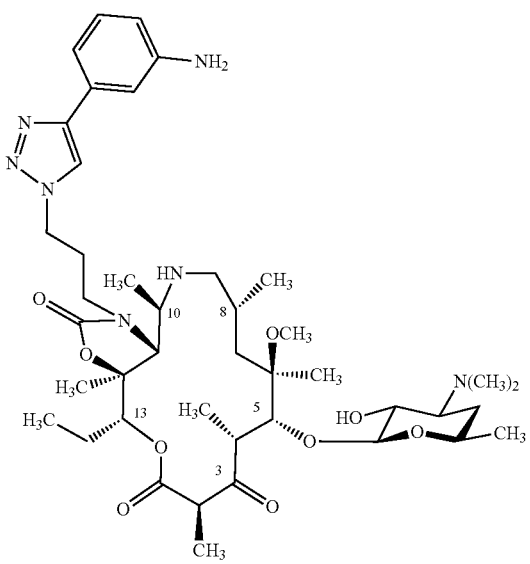<br>FSM-40347 | $^1$H NMR (500 MHz, CDCl$_3$), δ 0.85-0.93 (m, 6H), 0.98 (d, J = 6.04 Hz, 3H), 1.15 (dd, J = 14.65, 1.83 Hz, 1H), 1.21 (s, 3H), 1.22-1.30 (m, 7H), 1.35 (d, J = 7.75 Hz, 3H), 1.42 (d, J = 6.96 Hz, 3H), 1.44 (s, 3H), 1.49-1.78 (m, 7H), 1.98 (ddd, J = 14.45, 7.49, 1.98 Hz, 1H), 2.16-2.33 (m, 1H), 2.28 (s, 6H), 2.44-2.54 (m, 1H), 2.69 (d, J = 7.57 Hz, 1H), 2.74-2.80 (m, 1H), 2.88 (s, 3H), 3.03 (dd, J = 7.81, 3.66 Hz, 1H), 3.16-3.23 (m, 1H), 3.55-3.68 (m, 2H), 3.69-3.90 (m, 3H), 4.34 (d, J = 7.39 Hz, 1H), 4.38-4.53 (m, 3H), 4.95 (dd, J = 10.89, 1.98 Hz, 1H), 6.64 (dt, J = 6.45, 2.39 Hz, 1H), 7.14-7.22 (m, 2H), 7.22-7.25 (m, 1H), 8.07 (s, 1H). | HRMS: Calcd for C$_{42}$H$_{68}$N$_7$O$_9$ (M + H)$^+$: 814.5073, Found: 814.5035. |
| 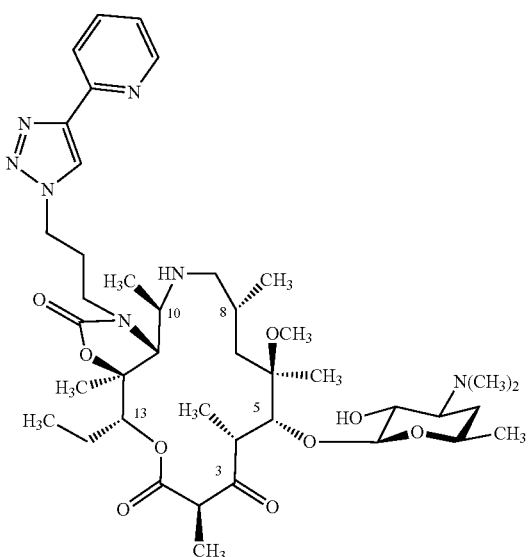<br>FSM-40348 | $^1$H NMR (500 MHz, CDCl$_3$), δ 0.84 (d, J = 6.84 Hz, 3H), 0.91 (t, J = 7.32 Hz, 3H), 0.98 (d, J = 6.10 Hz, 3H), 1.09-1.17 (m, 1H), 1.20 (s, 3H), 1.21-1.29 (m, 7H), 1.34 (d, J = 7.75 Hz, 3H), 1.41 (d, J = 6.90 Hz, 3H), 1.43 (s, 3H), 1.48-1.76 (m, 6H), 1.98 (ddd, J = 14.42, 7.49, 2.08 Hz, 1H), 2.23-2.37 (m, 3H), 2.29 (s, 6H), 2.51 (d, J = 9.83 Hz, 1H), 2.67 (dd, J = 9.86, 2.96 Hz, 1H), 2.76 (q, J = 5.94 Hz, 1H), 2.92 (s, 3H), 2.99-3.07 (m, 1H), 3.20 (dd, J = 10.16, 7.48 Hz, 1H), 3.57-3.67 (m, 2H), 3.79-3.87 (m, 2H), 4.37 (d, J = 7.39 Hz, 1H), 4.43-4.59 (m, 3H), 4.95 (dd, J = 10.77, 1.98 Hz, 1H), 7.21 (ddd, J = 7.49, 4.93, 1.07 Hz, 1H), 7.76 (td, J = 7.74, 1.74 Hz, 1H), 8.15 (d, J = 7.93 Hz, 1H), 8.28-8.30 (m, 1H), 8.58 (dd, J = 3.97, 0.79 Hz, 1H). | HRMS: Calcd for C$_{44}$H$_{66}$N$_7$O$_9$ (M + H)$^+$: 800.4917, Found: 800.4891. |

TABLE Y1-continued

| Compound and ID | NMR Data | MS Data |
| --- | --- | --- |
| 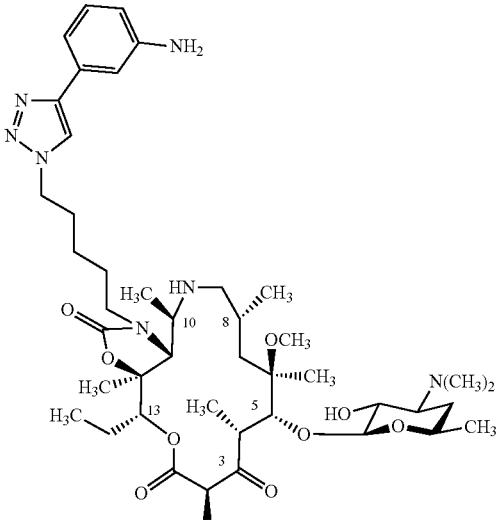 FSM-40349 | $^1$H NMR (500 MHz, CDCl$_3$), δ 0.84 (t, J = 7.35 Hz, 3H), 0.91 (d, J = 6.90 Hz, 3H), 0.96 (d, J = 6.10 Hz, 3H), 1.13-1.19 (m, 1H), 1.22-1.30 (m, 11H), 1.35 (d, J = 7.75 Hz, 3H), 1.39 (d, J = 6.90 Hz, 3H), 1.40 (s, 3H), 1.52-1.59 (m, 2H), 1.64-1.77 (m, 5H), 1.87-2.04 (m, 4H), 2.27 (s, 6H), 2.49 (t, J = 9.25 Hz, 1H), 2.69-2.80 (m, 2H), 2.95 (s, 3H), 3.03 (dd, J = 7.81, 3.66 Hz, 1H), 3.20 (dd, J = 10.10, 7.48 Hz, 1H), 3.52-3.65 (m, 4H), 3.70-3.81 (m, 2H), 3.85 (q, J = 6.90 Hz, 1H), 4.32-4.43 (m, 3H), 4.49 (d, J = 3.60 Hz, 1H), 4.92 (dd, J = 10.83, 1.92 Hz, 1H), 6.62-6.67 (m, 1H), 7.13-7.22 (m, 2H), 7.75 (s, 1H). | HRMS: Calcd for C$_{44}$H$_{72}$N$_7$O$_9$ (M + H)$^+$: 842.5386, Found: 842.5352. |
| 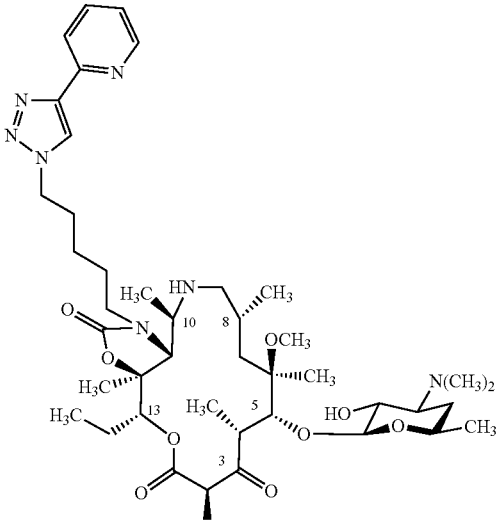 FSM-40350 | $^1$H NMR (500 MHz, CDCl$_3$), δ 0.88 (t, J = 7.35 Hz, 3H), 0.92 (d, J = 6.84 Hz, 3H), 0.97 (d, J = 5.98 Hz, 3H), 1.18 (dd, J = 14.71, 1.77 Hz, 1H), 1.21-1.31 (m, 10H), 1.36 (d, J = 7.81 Hz, 3H), 1.40 (d, J = 6.96 Hz, 3H), 1.42 (s, 3H), 1.43-1.48 (m, 2H), 1.51-1.66 (m, 3H), 1.66-1.78 (m, 4H), 1.91-2.09 (m, 3H), 2.30 (s, 6H), 2.51 (t, J = 8.94 Hz, 1H), 2.71-2.82 (m, 2H), 2.97 (s, 3H), 3.05 (dd, J = 7.78, 3.51 Hz, 1H), 3.22 (dd, J = 10.04, 7.54 Hz, 1H), 3.55-3.68 (m, 3H), 3.86 (q, J = 6.90 Hz, 1H), 4.36-4.44 (m, 3H), 4.51 (d, J = 3.48 Hz, 1H), 4.91-4.98 (m, 1H), 7.23 (ddd, J = 7.39, 4.76, 0.92 Hz, 1H), 7.74-7.81 (m, 1H), 8.13 (s, 1H), 8.15-8.20 (m, 1H), 8.59 (dd, J = 4.09, 0.73 Hz, 1H). | HRMS: Calcd for C$_{43}$H$_{70}$N$_7$O$_9$ (M + H)$^+$: 828.5235, Found: 828.5204. |
| 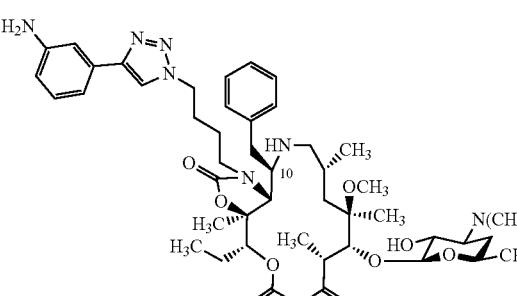 FSM-60353 | $^1$H NMR (500 MHz, CDCl$_3$) δ 7.80 (s, 1H), 7.31-7.28 (m, 1H), 7.27 (s, 1H), 7.26 (s, 1H), 7.21-7.16 (m, 3H), 7.12 (d, J = 7.81 Hz, 2H), 6.65 (td, J = 4.39, 2.44 Hz, 1H), 4.88 (dd, J = 9.77, 1.95 Hz, 1H), 4.39 (t, J = 7.08 Hz, 2H), 4.32 (d, J = 7.32 Hz, 1H), 4.02 (d, J = 9.77 Hz, 1H), 3.85 (q, J = 6.80, 1H), 3.81-3.75 (br s, 2H), 3.58-3.46 (m, 2H), 3.43 (d, J = 3.91 Hz, 1H), 3.30 (m, 1H), 3.22-3.15 (m, 1H), 3.13-3.05 (m, 1H), 2.94-2.88 (m, 2H), 2.85 (d, J = 4.88 Hz, 1H), 2.80-2.77 (m, 1H), 2.75 (s, 3H), 2.73-2.71 (m, 1H), 2.64 (dt, J = 14.65, 6.35 Hz, 1H), 2.49 (t, J = 9.28 Hz, 1H), 2.36 (d, J = 7.81 Hz, 1H), 2.29 (s, 6H), 2.02-1.90 (m, 4H), 1.73-1.71 (m, 3H), 1.70-1.65 (m, 2H), 1.59 (m, 4H), 1.49 (d, J = 7.32 Hz, 3H), 1.46-1.37 (m, 3H), 1.31 (d, J = 6.84 Hz, 3H), 1.27-1.25 (m, 1H), 1.23 (s, 3H), 0.88 (t, J = 7.57 Hz, 3H), 0.82 (d, J = 6.35 Hz, 3H). | HRMS (C$_{49}$H$_{73}$N$_7$O$_9$ + H)$^+$ calculated: 903.5548; found: 903.5515. |

TABLE Y1-continued

| Compound and ID | NMR Data | MS Data |
|---|---|---|
| 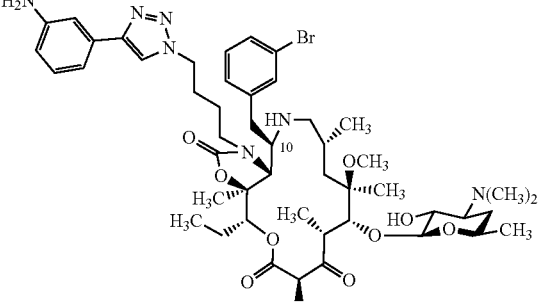<br>FSM-60415 | $^1$H NMR (600 MHz, CDCl$_3$) δ 7.82 (s, 1H), 7.34 (d, J = 7.63 Hz, 1H), 7.30 (s, 2H), 7.19 (d, J = 4.70 Hz, 2H), 7.14 (t, J = 8.22 Hz, 1H), 7.05 (d, J = 7.63 Hz, 1H), 6.68-6.62 (m, 1H), 4.88 (dd, J = 11.15, 2.35 Hz, 1H), 4.41 (td, J = 7.04, 3.40 Hz, 1H), 4.31 (d, J = 7.63 Hz, 1H), 4.11 (q, J = 7.00 Hz, 1H), 4.02 (d, J = 9.39 Hz, 1H), 3.85 (q, J = 7.00 Hz, 1H), 3.81-3.70 (br s, 2H), 3.55-3.48 (m, 1H), 3.42 (d, J = 3.52 Hz, 1H), 3.36 (m, 1H), 3.18 (dd, J = 8.80, 7.63 Hz, 1H), 3.10 (t, J = 7.63 Hz, 1H), 2.86 (dt, J = 7.04, 4.00 Hz, 1H), 2.79 (d, J = 7.04 Hz, 1H), 2.74 (s, 3H), 2.73-2.66 (m, 2H), 2.46 (t, J = 10.00 Hz, 1H), 2.30-2.29 (m, 1H), 2.29 (s, 6H), 2.19 (dd, J = 11.03, 4.10 Hz, 1H), 2.04 (s, 1H), 2.03-1.90 (m, 4H), 1.71 (s, 3H), 1.69-1.52 (m, 10H), 1.49 (d, J = 7.04 Hz, 3H), 1.39-1.34 (m, 1H), 1.30 (d, J = 7.04 Hz, 3H), 1.24-1.22 (m, 3H), 0.88 (t, J = 7.34 Hz, 3H), 0.84 (d, J = 6.46 Hz, 3H). | HRMS (C$_{49}$H$_{72}$BrN$_7$O$_9$ + H)$^+$ calculated: 982.4648 found: 982.4633. |
| 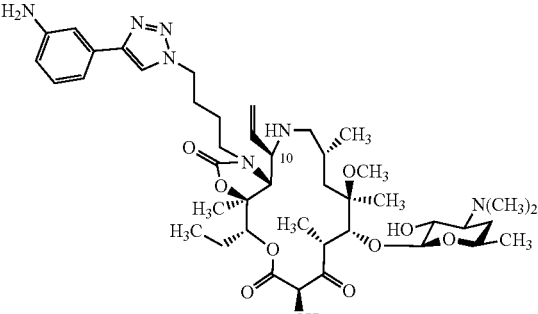<br>FSM-60434 | $^1$H NMR (600 MHz, CDCl$_3$) δ 7.83 (s, 1H), 7.31-7.29 (m, 1H), 7.20 (d, J = 4.70 Hz, 2H), 6.67-6.63 (m, 1H), 5.82-5.74 (m, 1H), 5.22 (ddd, J = 20.12, 13.23, 1.17 Hz, 2H), 4.85 (d, J = 10.56 Hz, 1H), 4.44 (m, 2H), 4.33 (d, J = 7.63 Hz, 1H), 4.09 (d, J = 9.39 Hz, 1H), 3.88 (q, J = 7.04 Hz, 1H), 3.83-3.75 (br s, 2H), 3.60 (quin, J = 7.04 Hz, 1H), 3.56-3.47 (m, 2H), 3.40 (d, J = 4.11 Hz, 1H), 3.23-3.16 (m, 2H), 3.15-3.11 (m, 1H), 3.05-2.98 (m, 1H), 2.81 (s, 3H), 2.46 (dd, J = 10.56, 2.35 Hz, 2H), 2.37 (dd, J = 12.33, 5.28 Hz, 2H), 2.28 (s, 6H), 2.17 (d, J = 1.17 Hz, 1H), 2.07-1.99 (m, 2H), 1.92-1.85 (m, 1H), 1.68 (dd, J = 14.38, 7.34 Hz, 3H), 1.59 (s, 3H), 1.49 (d, J = 7.04 Hz, 3H), 1.32 (d, J = 7.04 Hz, 3H), 1.25 (d, J = 1.17 Hz, 3H), 1.24 (d, J = 5.87 Hz, 3H), 0.95 (d, J = 6.46 Hz, 3H), 0.86 (t, J = 7.34 Hz, 3H). | HRMS (C$_{44}$H$_{69}$N$_7$O$_9$ + H)$^+$ calculated: 840.5230 found: 840.5250. |
| 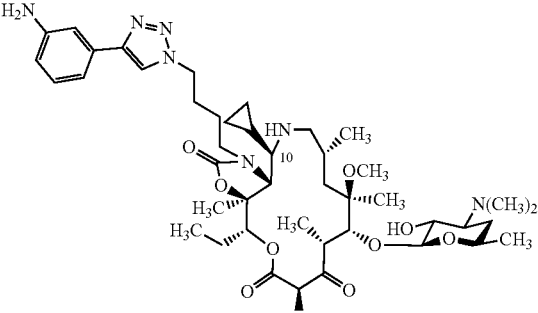<br>FSM-60432 | $^1$H NMR (600 MHz, D$_3$COD) δ 8.23-8.21 (s, 1H), 7.20-7.14 (m, 2H), 7.12-7.07 (m, 1H), 6.73-6.69 (m, 1H), 4.97 (dd, J = 11.15, 2.35 Hz, 1H), 4.58-4.47 (m, 2H), 4.45 (d, J = 4.70 Hz, 1H), 4.29 (d, J = 7.04 Hz, 1H) 4.06-4.01 (m, 1H), 3.65 (d, J = 5.28 Hz, 1H), 3.60 (d, J = 5.28 Hz, 1H), 3.57 (d, J = 4.70 Hz, 1H), 3.52 (d, J = 5.87 Hz, 1H), 3.50 (d, J = 5.87 Hz, 1H), 3.29-3.24 (m, 2H), 3.09-3.03 (m, 1H), 2.92 (s, 3H), 2.81-2.74 (m, 1H) 2.69-2.55 (m, 2H), 2.33 (s, 6H), 2.23-2.12 (m, 1H), 2.09-1.96 (m, 2H), 1.92-1.82 (m, 1H), 1.80-1.61 (m, 8H), 1.52 (dd, J = 16.43, 3.52 Hz, 2H), 1.47-1.43 (m, 3H), 1.36 (d, J = 7.04 Hz, 3H), 1.33 (d, J = 7.63 Hz, 3H), 1.31-1.27 (m, 5H), 1.26-1.24 (m, 3H), 1.18 (d, J = 6.46 Hz, 1H), 0.97 (d, J = 12.33 Hz, 3H), 0.89 (t, J = 7.00 Hz, 3H), 0.67-0.59 (m, 1H), 0.58-0.52 (m, 1H), 0.49-0.44 (m, 1H), 0.43-0.38 (m, 1H), 0.32-0.25 (m, 1H). | HRMS (C$_{45}$H$_{71}$N$_7$O$_9$ + H)$^+$ calculated: 843.5386 found: 854.5411. |
| 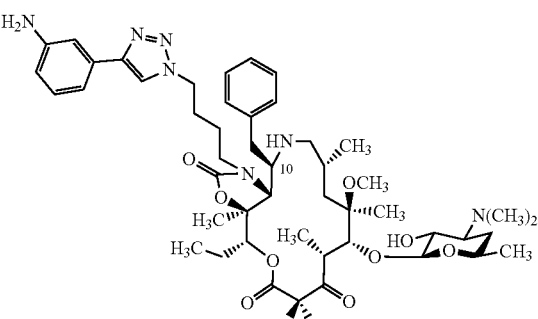<br>FSM-60506 | $^1$H NMR (600 MHz, CDCl$_3$) δ 7.80 (s, 1H), 7.28 (s, 1H), 7.26-7.24 (m, 2H), 7.21-7.15 (m, 3H), 7.13 (d, J = 7.04 Hz, 2H), 6.65 (dt, J = 7.04, 2.35 Hz, 1H), 4.97 (dd, J = 11.15, 1.17 Hz, 1H), 4.47-4.37 (m, 3H), 4.32 (t, J = 7.04 Hz, 1H), 4.01 (dd, J = 9.39, 1.76 Hz, 1H), 3.74 (m, 2H), 3.55-3.47 (m, 1H) 3.38-3.28 (br s, 2H), 3.27 (d, J = 3.52 Hz, 1H), 3.19 (dd, J = 9.40, 8.22 Hz, 1H), 3.02 (s, 3H), 2.80 (d, J = 9.98 Hz, 1H), 2.78 (d, J = 6.46 Hz, 1H), 2.76 (d, J = 7.63 Hz, 1H), 2.73-2.67 (m, 2H), 2.29 (s, 6H), 2.17 (dd, J = 11.74, 2.35 Hz, 1H), 2.08-1.92 (m, 5H), 1.83 (d, J = 21.13 Hz, 3H), 1.76 (s, 3H), 1.71-1.56 (m, 7H), 1.50 (d, J = 7.04 Hz, 3H), 1.31 (t, J = 6.46 Hz, 1H), 1.28 (d, J = 5.28 Hz, 1H), 1.27-1.24 (m, 3H), 1.23 (d, J = 6.46 Hz, 3H), 0.90 (t, J = 7.63 Hz, 3H), 0.81 (d, J = 6.46 Hz, 3H). | HRMS (C$_{49}$H$_{72}$FN$_7$O$_9$ + H)$^+$ calculated: 922.5448 found: 922.5471. |

TABLE Y1-continued

| Compound and ID | NMR Data | MS Data |
|---|---|---|
| 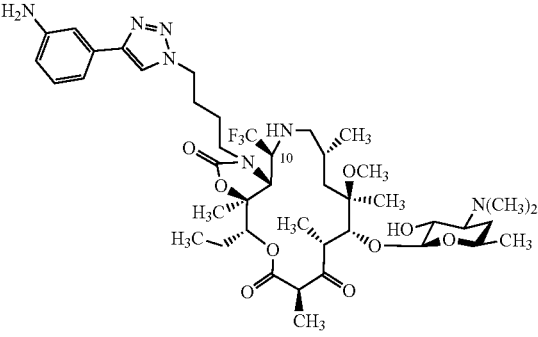<br>FSM-60546 | $^1$H NMR (600 MHz, CDCl$_3$) δ 7.81 (s, 1H), 7.30-7.28 (m, 1H), 7.21-7.17 (m, 2H), 6.67-6.62 (m, 1H), 4.88 (dd, J = 9.39, 2.35 Hz, 1H), 4.51-4.39 (m, 1H), 4.34 (d, J = 7.04 Hz, 1H), 4.06 (d, J = 9.39 Hz, 1H), 3.87 (q, J = 7.00, 1H), 3.80-3.74 (m, 1H), 3.66-3.58 (m, 1H), 3.57-3.47 (m, 2H), 3.41-3.24 (br s, 2H), 3.19 (t, J = 8.20 Hz, 1H), 3.12 (t, J = 8.80 Hz, 1H), 3.03-2.98 (m, 2H), 2.84-2.76 (m, 3H), 2.66 (d, J = 11.15 Hz, 1H), 2.62-2.56 (m, 1H), 2.46 (t, J = 8.80 Hz, 1H), 2.27 (s, 6H), 2.09-1.98 (m, 2H), 1.96-1.89 (m, 1H), 1.77-1.72 (m, 2H), 1.71-1.64 (m, 5H), 1.60 (s, 3H), 1.58-1.55 (m, 2H), 1.52 (d, J = 5.28 Hz, 1H), 1.48 (d, J = 7.04 Hz, 3H), 1.31 (d, J = 7.04 Hz, 3H), 1.26 (s, 3H), 1.24 (d, J = 5.87 Hz, 3H), 0.95 (d, J = 7.04 Hz, 3H), 0.87 (t, J = 7.34 Hz, 3H). | HRMS (C$_{43}$H$_{66}$F$_3$N$_7$O$_9$ + H)$^+$ calculated: 882.4947 found: 882.4967. |
| 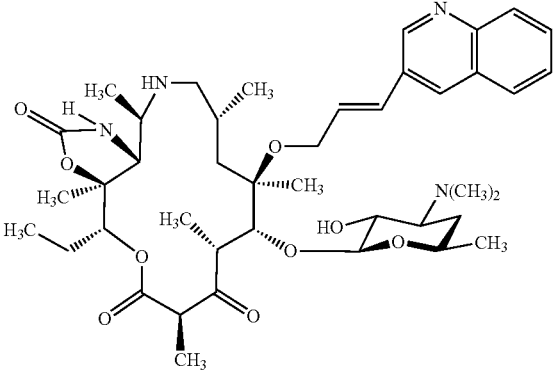<br>FSM-20919 | $^1$H NMR (500 MHz, CDCl$_3$) δ 9.00 (d, J = 2.1 Hz, 1H), 8.16 (d, J = 1.9 Hz, 1H), 8.07 (d, J = 8.4 Hz, 1H), 7.81 (d, J = 8.1 Hz, 1H), 7.68-7.62 (m, 1H), 7.52 (t, J = 7.5 Hz, 1H), 6.73 (d, J = 16.0 Hz, 1H), 6.43 (dt, J = 15.9, 6.6 Hz, 1H), 5.10 (dd, J = 10.5, 2.3 Hz, 1H), 5.06 (s, 1H), 4.63 (d, J = 1.9 Hz, 1H), 4.43 (d, J = 7.4 Hz, 1H), 4.07 (dd, J = 11.5, 6.7 Hz, 1H), 3.99 (q, J = 6.8 Hz, 1H), 3.91 (dd, J = 11.5, 6.5 Hz, 1H), 3.67-3.59 (m, 1H), 3.21 (dd, J = 10.0, 7.5 Hz, 1H), 3.13 (dt, J = 5.6, 4.0 Hz, 1H), 2.80 (d, J = 7.5 Hz, 1H), 2.70-2.60 (m, 1H), 2.54-2.43 (m, 1H), 2.31 (s, 6H), 1.99-1.87 (m, 1H), 1.81-1.71 (m, 2H), 1.69-1.64 (m, 1H), 1.64-1.57 (m, 2H), 1.46 (s, 3H), 1.43 (d, J = 6.9 Hz, 6H), 1.41 (s, 3H), 1.36-1.31 (m, 1H), 1.26 (d, J = 5.6Hz, 3H), 1.24-1.21 (m, 1H), 1.07 (dd, J = 10.5, 6.2 Hz, 1H), 0.96 (d, J = 6.0 Hz, 3H), 0.91 (t, J = 7.5 Hz, 3H). | HRMS (ESI): Calcd for (C$_{42}$H$_{62}$N$_4$O$_9$ + H)$^+$: 767.4589; Found: 767.4594. |
| 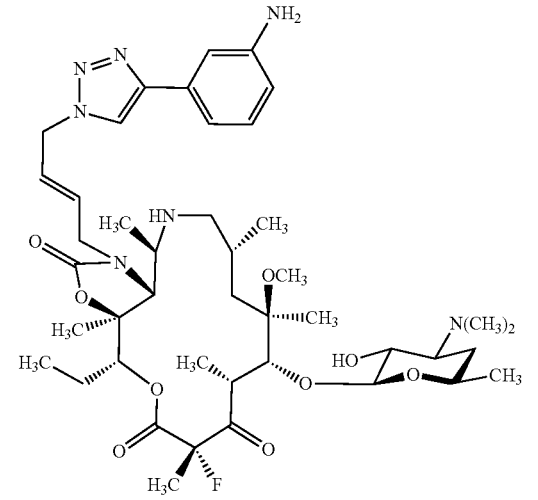<br>FSM-20795 | $^1$H NMR (500 MHz, CDCl$_3$) δ 7.81 (s, 1H), 7.22-7.12 (m, 3H), 6.68-6.61 (m, 1H), 4.95 (d, J = 9.3 Hz, 1H), 4.45 (t, J = 7.3 Hz, 2H), 4.39 (d, J = 7.3 Hz, 1H), 4.13 (d, J = 9.1 Hz, 1H), 3.81-3.58 (m, 4H), 3.58-3.48 (m, 1H), 3.22 (s, 3H), 3.21-3.16 (m, 1H), 3.13-3.06 (m, 1H), 3.03 (s, 1H), 2.93 (br, J = 18.2 Hz, 1H), 2.64 (br, J = 21.5 Hz, 1H), 2.54-2.45 (m, 1H), 2.28 (s, 6H), 2.08-1.91 (m, 3H), 1.86 (d, J = 21.4 Hz, 3H), 1.80-1.58 (m, 8H), 1.55 (d, J = 7.2 Hz, 3H), 1.50 (s, 3H), 1.27 (s, 3H), 1.25 (d, J = 6.1 Hz, 3H), 1.21 (d, J = 12.2 Hz, 1H), 0.97-0.87 (m, 9H). | HRMS (ESI): Calcd for (C$_{43}$H$_{68}$FN$_7$O$_9$ + H)$^+$: 846.5141; Found: 846.5114. |

TABLE Y1-continued

| Compound and ID | NMR Data | MS Data |
|---|---|---|
| 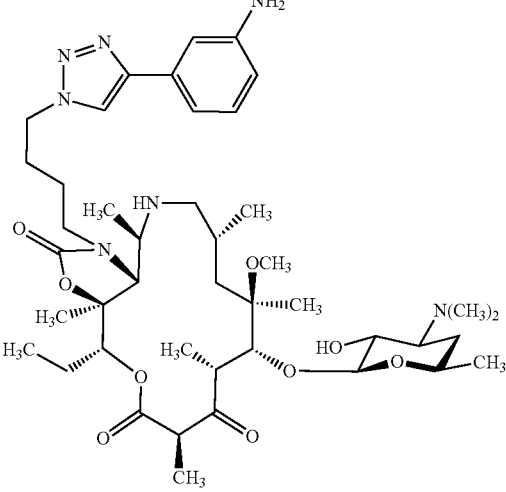 FSM-20707 | ¹H NMR (500 MHz, CDCl₃) δ 7.81 (s, 1H), 7.25-7.12 (m, 3H), 6.68-6.62 (m, 1H), 4.96 (dd, J = 10.8, 2.0 Hz, 1H), 4.52 (d, J = 3.5 Hz, 1H), 4.49-4.40 (m, 2H), 4.38 (d, J = 7.4 Hz, 1H), 3.89 (q, J = 6.9 Hz, 1H), 3.77-3.58 (m, 3H), 3.42 (s, 1H), 3.24 (dd, J = 10.0, 7.5 Hz, 1H), 3.05 (dt, J = 11.0, 6.3 Hz, 1H), 2.96 (s, 3H), 2.84-2.71 (m, 2H), 2.59-2.48 (m, 1H), 2.32 (s, 6H), 2.09-1.92 (m, 4H), 1.82-1.48 (m, 7H), 1.44 (s, 3H), 1.42 (d, J = 6.9 Hz, 3H), 1.37 (d, J = 7.8 Hz, 3H), 1.29 (d, J = 6.1 Hz, 3H), 1.26 (s, 3H), 1.18 (d, J = 14.8 Hz, 1H), 0.99 (d, J = 5.9 Hz, 3H), 0.94 (d, J = 6.9 Hz, 3H), 0.89 (t, J = 7.4 Hz, 3H). | HRMS (ESI): Calcd for (C₄₃H₆₉N₇O₉ + H)⁺: 828.5230; Found: 828.5216. |
| 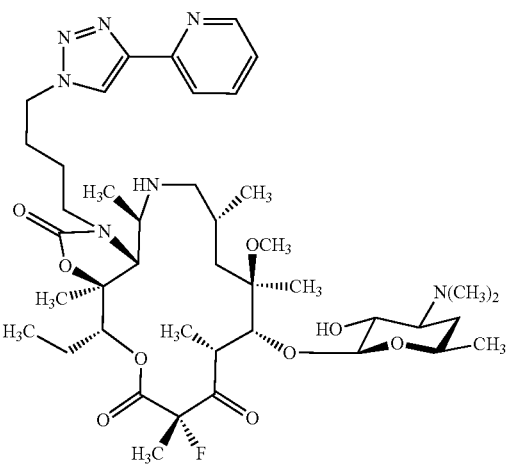 FSM-20738 | ¹H NMR (500 MHz, CDCl₃) δ 8.64-8.52 (m, 1H), 8.21-8.12 (m, 2H), 7.77 (td, J = 7.8, 1.7 Hz, 1H), 7.26-7.18 (m, 1H), 4.97 (d, J = 9.3 Hz, 1H), 4.49 (dd, J = 16.5, 9.4 Hz, 2H), 4.46-4.39 (m, 1H), 4.15 (d, J = 9.4 Hz, 1H), 3.73-3.60 (m, 2H), 3.60-3.48 (m, 1H), 3.26 (s, 3H), 3.25-3.21 (m, 1H), 3.16-3.00 (m, 2H), 2.99 (s, 1H), 2.98-2.87 (m, 1H), 2.66 (br, 1H), 2.61-2.50 (m, 1H), 2.33 (s, 6H), 2.14-1.92 (m, 3H), 1.87 (d, J = 21.2 Hz, 3H), 1.80-1.60 (m, 8H), 1.56 (d, J = 6.8 Hz, 3H), 1.51 (s, 3H), 1.29 (d, J = 6.1 Hz, 3H), 1.27 (s, 3H), 1.25-1.23 (m, 1H), 0.98-0.88 (m, 9H). | HRMS (ESI): Calcd for (C₄₂H₆₆FN₇O₉ + H)⁺: 832.4984; Found: 832.4998. |
| 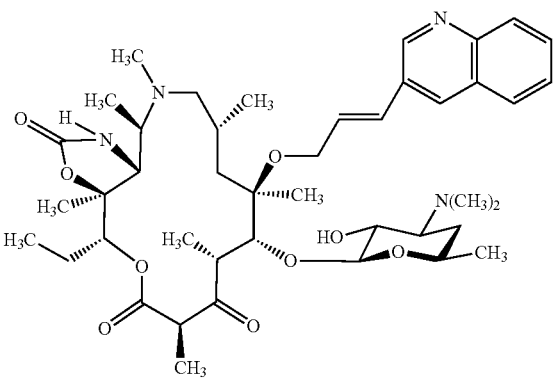 FSM-21118 | ¹H NMR (600 MHz, CDCl₃, 1:1 mixture of C2-epimers, NMR shifts are reported collectively) δ 8.99 (d, J = 2.1 Hz, 1H), 8.92 (d, J = 2.2 Hz, 1H), 8.08-8.02 (m, 2H), 7.97 (d, J = 2.0 Hz, 1H), 7.81-7.76 (m, 2H), 7.71-7.63 (m, 2H), 6.64 (t, J = 16.6 Hz, 2H), 6.52 (t, J = 6.0 Hz, 1H), 6.49 (t, J = 5.9 Hz, 1H), 6.31 (dd, J = 6.5, 5.0 Hz, 1H), 6.28 (dd, J = 6.5, 5.0 Hz, 1H), 5.24 (s, 1H), 5.14 (s, 1H), 4.85 (t, J = 5.3 Hz, 1H), 4.81 (dd, J = 8.3, 3.7 Hz, 1H), 4.48-4.41 (m, 2H), 4.22 (q, J = 6.8 Hz, 1H), 4.13-4.06 (m, 3H), 4.06-3.99 (m, 1H), 3.93-3.88 (m, 2H), 3.87 (d, J = 10.1 Hz, 1H), 3.67-3.59 (m, 4H), 3.56 (dd, J = 12.1, 7.6 Hz, 2H), 3.39 (br, 1H), 3.29 (d, J = 9.6 Hz, 2H), 3.25-3.17 (m, 1H), 3.01-2.90 (m, 2H), 2.84-2.74 (m, 2H), 2.70-2.61 (m, 2H), 2.49 (dd, J = 11.2, 3.9 Hz, 2H), 2.40 (s, 12H), 2.29 (dd, J = 11.7, 2.8 Hz, 2H), 2.12-2.02 (m, 6H), 2.00 (s, 3H), 1.97 (s, 3H), 1.84-1.71 (m, 3H), 1.70-1.63 (m, 4H), 1.63 (s, 3H), 1.61-1.60 (m, 3H), 1.42 (s, 3H), 1.36-1.33 (m, 9H), 1.27 (d, J = 4.6 Hz, 3H), 1.26 (d, J = 4.6 Hz, 3H), 1.19 (d, J = 6.8 Hz, 3H), 1.15 (d, J = 6.8 Hz, 3H), 1.03-0.97 (m, 12H), 0.94 (d, J = 6.5 Hz, 3H). | HRMS (ESI): Calcd for (C₄₃H₆₄N₄O₉ + H)⁺: 781.4746; Found: 781.4767. |

TABLE Y1-continued

| Compound and ID | NMR Data | MS Data |
|---|---|---|
| 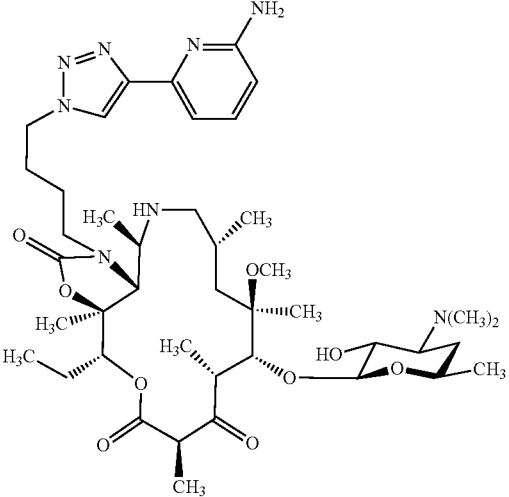<br>FSM-20715 | $^1$H NMR (500 MHz, CDCl$_3$) δ 8.04 (s, 1H), 7.55-7.44 (m, 2H), 6.45 (d, J = 7.8 Hz, 1H), 4.95 (d, J = 10.9 Hz, 1H), 4.56-4.42 (m, 4H), 4.39 (t, J = 7.8 Hz, 1H), 3.87 (q, J = 6.8 Hz, 1H), 3.76-3.58 (m, 3H), 3.42 (s, 1H), 3.26-3.19 (m, 1H), 3.06 (dt, J = 11.4, 7.2 Hz, 1H), 2.99 (s, 3H), 2.84-2.67 (m, 2H), 2.56-2.46 (m, 1H), 2.28 (s, 6H), 2.09-1.93 (m, 4H), 1.83-1.49 (m, 7H), 1.43 (s, 3H), 1.41 (d, J = 6.8 Hz, 3H), 1.37 (d, J = 7.7 Hz, 3H), 1.29 (d, J = 6.1 Hz, 3H), 1.27 (s, 3H), 1.18 (d, J = 14.7 Hz, 1H), 0.98 (d, J = 6.0 Hz, 3H), 0.93 (d, J = 6.8 Hz, 3H), 0.90 (t, J = 7.3 Hz, 3H). | HRMS (ESI): Calcd for (C$_{42}$H$_{68}$N$_8$O$_9$ + H)$^+$: 829.5188; Found: 829.5199. |
| 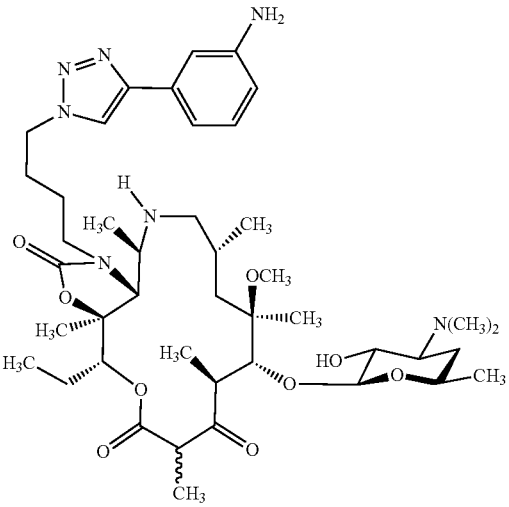<br>FSM-20789 | Note: The compound exists as a ~1:1 mixture of C2-epimers. Due to extensive overlapping, $^1$H NMR peaks are not discriminated and are reported collectively. $^1$H NMR (500 MHz, CDCl$_3$) δ 7.81 (s, 1H), 7.80 (s, 1H), 7.27-7.10 (m, 6H), 6.66 (d, J = 7.8 Hz, 2H), 4.96 (d, J = 9.2 Hz, 1H), 4.54-4.40 (m, 4H), 4.38 (d, J = 7.4 Hz, 1H), 3.98-3.92 (m, 1H), 3.89 (q, J = 6.9 Hz, 1H), 3.84-3.55 (m, 8H), 3.52 (s, 1H), 3.41 (s, 1H), 3.30-3.21 (m, 2H), 3.16 (s, 3H), 3.09-2.99 (m, 4H), 2.96 (s, 3H), 2.87-2.71 (m, 4H), 2.58-2.45 (m, 2H), 2.30 (s, 12H), 2.12-1.85 (m, 9H), 1.79-1.51 (m, 14H), 1.48 (d, J = 7.4 Hz, 3H), 1.44 (s, 3H), 1.43-1.41 (m, 3H), 1.39 (s, 3H), 1.37 (d, J = 7.8 Hz, 3H), 1.35 (d, J = 6.7 Hz, 3H), 1.29 (s, 3H), 1.26 (s, 3H), 1.25-1.22 (m, 5H), 1.21-1.14 (m, 4H), 1.07 (d, J = 6.3 Hz, 3H), 0.99 (d, J = 6.0 Hz, 3H), 0.95 (d, J = 6.8 Hz, 3H), 0.94 (d, J = 6.9 Hz, 3H), 0.89 (t, J = 7.2 Hz, 3H), 0.89 (t, J = 7.2, 2.4 Hz, 3H). | HRMS (ESI): Calcd for (C$_{43}$H$_{69}$N$_7$O$_9$ + H)$^+$: 828.5230; Found: 828.5228. |
| 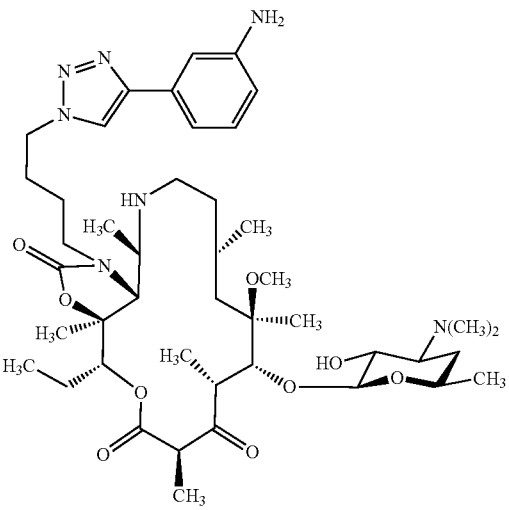<br>FSM-21397 | Note: The compound exists as a ~6:2:1 mixture of C2-epimers/C2-C3 enol. NMR data of major isomer is reported. $^1$H NMR (500 MHz, CDCl$_3$) δ 7.79 (s, 1H), 7.23-7.09 (m, 3H), 6.67 (t, J = 10.1 Hz, 1H), 4.95 (dd, J = 10.2, 1.9 Hz, 1H), 4.46-4.39 (m, 2H), 4.13 (d, J = 7.1 Hz, 1H), 3.79 (dd, J = 14.7, 7.3 Hz, 1H), 3.69-3.46 (m, 4H), 3.38 (s, 1H), 3.20 (dd, J = 10.1, 7.4 Hz, 2H), 3.08-3.03 (m, 1H), 2.92 (s, 3H), 2.81-2.72 (m, 1H), 2.56-2.44 (m, 2H), 2.29 (d, J = 2.5 Hz, 6H), 2.05-1.84 (m, 3H), 1.75-1.53 (m, 8H), 1.54-1.47 (m, 3H), 1.41 (s, 3H), 1.35 (d, J = 7.3 Hz, 3H), 1.31-1.20 (m, 8H), 1.05 (t, J = 6.5 Hz, 3H), 1.02-0.96 (m, 2H), 0.94 (d, J = 6.9 Hz, 3H), 0.90 (t, J = 7.4 Hz, 3H). $^{13}$C NMR (126 MHz, CDCl$_3$) δ 205.32, 170.11, 157.14, 147.82, 146.86, 131.64, 129.66, 119.63, 116.06, 114.75, 112.32, 103.61, 81.15, 79.66, 79.11, 70.28, 69.47, 65.83, 62.64, 55.58, 50.15, 49.74, 49.62, 46.49, 43.96, 42.84, 40.23, 37.42, 34.79, 28.26, 27.53, 26.03, 23.97, 22.64, 21.83, 21.22, 19.86, 16.05, 15.58, 14.16, 10.67. | HRMS (ESI): Calcd for (C$_{44}$H$_{71}$N$_7$O$_9$ + H)$^+$: 842.5386; Found: 842.5397. |

TABLE Y1-continued

| Compound and ID | NMR Data | MS Data |
|---|---|---|
| 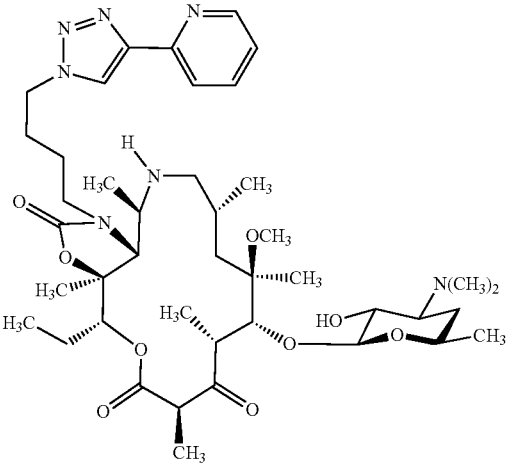<br>FSM-20706 | ¹H NMR (600 MHz, CDCl₃) δ 8.66-8.59 (m, 1H), 8.20 (d, J = 8.0 Hz, 1H), 8.19 (s, 1H), 7.82 (td, J = 7.7, 1.7 Hz, 1H), 7.29-7.23 (m, 1H), 4.99 (dd, J = 10.9, 2.0 Hz, 1H), 4.55 (d, J = 3.4 Hz, 1H), 4.52 (dd, J = 14.3, 7.0 Hz, 2H), 4.44 (d, J = 7.4 Hz, 1H), 3.90 (q, J = 6.9 Hz, 1H), 3.82-3.74 (m, 1H), 3.69 (dt, J = 6.0, 5.0 Hz, 2H), 3.55 (s, 1H), 3.46 (s, 1H), 3.33-3.24 (m, 1H), 3.13-3.07 (m, 1H), 3.04 (s, 3H), 2.80 (dd, J = 15.6, 9.2 Hz, 2H), 2.66-2.56 (m, 1H), 2.38 (s, 6H), 2.16-1.93 (m, 4H), 1.88-1.54 (m, 7H), 1.47 (s, 3H), 1.44 (d, J = 6.9 Hz, 3H), 1.40 (d, J = 7.8 Hz, 3H), 1.34 (d, J = 6.1 Hz, 3H), 1.31 (d, J = 8.4 Hz, 3H), 1.23 (dd, J = 9.8, 4.8 Hz, 1H), 1.03 (d, J = 5.6 Hz, 3H), 0.97 (d, J = 6.9 Hz, 3H), 0.94 (t, J = 7.4 Hz, 3H). ¹³C NMR (126 MHz, CDCl₃) δ 205.73, 171.64, 156.96, 150.40, 149.36, 148.38, 136.75, 122.67, 122.07, 121.89, 120.14, 102.75, 81.10, 78.50, 78.39, 75.38, 70.14, 69.33, 66.02, 65.28, 59.07, 57.89, 50.14, 49.88, 49.84, 45.69, 42.74, 40.93, 40.29, 28.67, 27.75, 27.62, 24.02, 21.74, 21.66, 21.25, 18.98, 14.46, 14.41, 14.33, 14.08, 10.42. | HRMS (ESI): Calcd for (C₄₂H₆₇N₇O₉ + H)⁺: 814.5075; Found: 814.5082. |
| 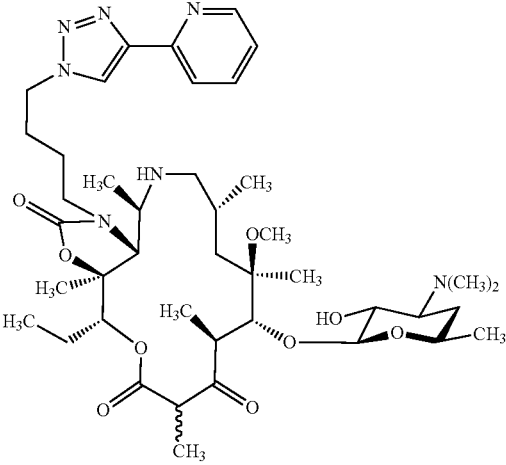<br>FSM-20754 | Note: The compound exists as a~1:1 mixture of C2-epimers. Due to extensive overlapping, ¹H NMR peaks are not discriminated and are reported collectively. ¹H NMR (500 MHz, CDCl₃) δ 8.58 (s, 2H), 8.21-8.03 (m, 4H), 7.82-7.73 (m, 2H), 7.24-7.17 (m, 2H), 4.95 (d, J = 8.8 Hz, 2H), 4.56-4.44 (m, 6H), 4.39 (d, J = 7.4 Hz, 1H), 4.09 (d, J = 6.7 Hz, 1H), 3.94 (d, J = 7.6 Hz, 1H), 3.86 (q, J = 6.9 Hz, 1H), 3.71 (d, J = 7.6 Hz, 3H), 3.66 (dd, J = 14.1, 7.2 Hz, 3H), 3.53 (s, 1H), 3.42 (s, 1H), 3.32-3.18 (m, 2H), 3.17 (s, 3H), 3.10-3.01 (m, 2H), 3.00 (s, 3H), 2.84 (d, J = 6.1 Hz, 1H), 2.81-2.69 (m, 3H), 2.59-2.41 (m, 2H), 2.31 (s, 12H), 2.04-1.81 (m, 8H), 1.81-1.50 (m, 14H), 1.43 (s, 3H), 1.42 (d, J = 7.3 Hz, 3H), 1.40 (d, J = 6.4 Hz, 3H), 1.39 (s, 3H), 1.36 (d, J = 7.7 Hz, 3H), 1.30 (d, J = 5.0 Hz, 3H), 1.29 (s, 3H), 1.28 (s, 3H), 1.26 (d, J = 2.4 Hz, 3H), 1.24 (d, J = 6.1 Hz, 3H), 1.19 (d, J = 14.6 Hz, 2H), 1.07 (d, J = 6.4 Hz, 3H), 0.98 (d, J = 6.0 Hz, 3H), 0.96-0.87 (m, 12H). | HRMS (ESI): Calcd for (C₄₂H₆₇N₇O₉ + H)⁺: 814.5073; Found: 814.5086. |
| 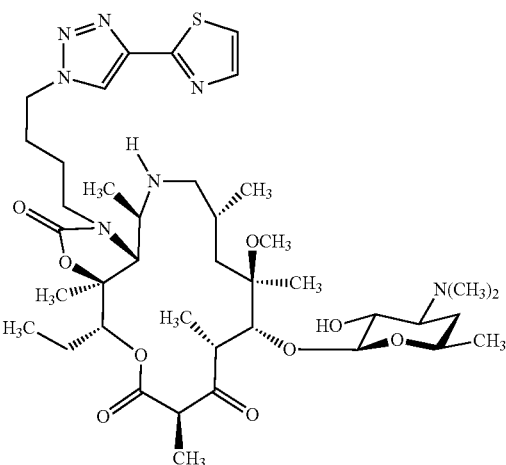<br>FSM-20708 | ¹H NMR (500 MHz, CDCl₃) δ 8.09 (s, 1H), 7.85 (d, J = 3.2 Hz, 1H), 7.36 (d, J = 3.2 Hz, 1H), 4.94 (dd, J = 10.9, 2.0 Hz, 1H), 4.58-4.44 (m, 3H), 4.40 (d, J = 7.4 Hz, 1H), 3.86 (q, J = 6.9 Hz, 1H), 3.77-3.69 (m, 1H), 3.69-3.61 (m, 2H), 3.61-3.52 (m, 1H), 3.40 (s, 1H), 3.31-3.24 (m, 1H), 3.09-3.00 (m, 1H), 2.99 (s, 2H), 2.83-2.67 (m, 2H), 2.67-2.54 (m, 1H), 2.37 (s, 6H), 2.13-1.87 (m, 4H), 1.87-1.48 (m, 7H), 1.43 (s, 3H), 1.39 (d, J = 6.9 Hz, 3H), 1.35 (d, J = 7.8 Hz, 3H), 1.30 (d, J = 6.1 Hz, 3H), 1.27 (s, 3H), 1.18 (d, J = 14.2 Hz, 1H), 0.99 (d, J = 5.2 Hz, 3H), 0.94 (d, J = 6.9 Hz, 3H), 0.90 (t, J = 7.4 Hz, 3H). | HRMS (ESI): Calcd for (C₄₀H₆₅N₇O₉ + H)⁺: 820.4643; Found: 814.4650. |

TABLE Y1-continued

| Compound and ID | NMR Data | MS Data |
|---|---|---|
| 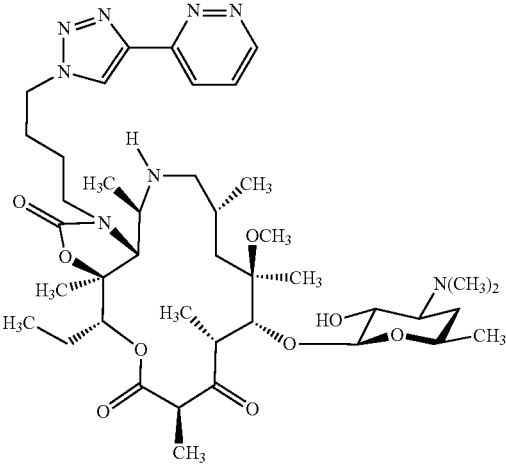<br>FSM-20710 | $^1$H NMR (600 MHz, CDCl$_3$) δ 9.17 (dd, J = 4.9, 1.6 Hz, 1H), 8.42 (s, 1H), 8.38 (dt, J = 8.5, 2.4 Hz, 1H), 7.61 (dd, J = 8.5, 4.9 Hz, 1H), 4.99 (dd, J = 10.9, 2.0 Hz, 1H), 4.65-4.49 (m, 3H), 4.43 (d, J = 7.4 Hz, 1H), 3.90 (q, J = 6.9 Hz, 1H), 3.83-3.74 (m, 1H), 3.74-3.63 (m, 2H), 3.57 (br s, 1H), 3.45 (s, 1H), 3.28 (dd, J = 22.9, 13.3 Hz, 1H), 3.13-3.06 (m, 1H), 3.05 (s, 3H), 2.86-2.75 (m, 2H), 2.67-2.55 (m, 1H), 2.39 (s, 6H), 2.15-2.07 (m, 2H), 2.07-1.97 (m, 2H), 1.87-1.55 (m, 8H), 1.47 (s, 3H), 1.43 (d, J = 6.9 Hz, 3H), 1.40 (d, J = 7.8 Hz, 3H), 1.34 (d, J = 6.1 Hz, 3H), 1.32 (s, 3H), 1.23 (d, J = 13.4 Hz, 1H), 1.03 (d, J = 5.6 Hz, 3H), 0.98 (d, J = 7.0 Hz, 3H), 0.94 (t, J = 7.4 Hz, 3H). | HRMS (ESI): Calcd for (C$_{41}$H$_{66}$N$_8$O$_9$ + H)$^+$: 815.5031; Found: 815.5052. |
| 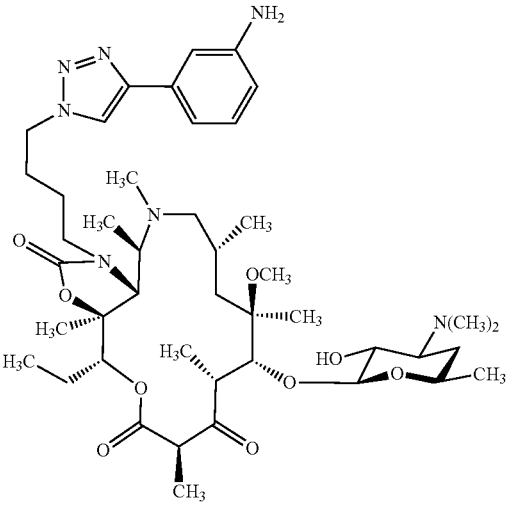<br>FSM-21339 | $^1$H NMR (500 MHz, CDCl$_3$) δ 7.82 (s, 1H), 7.25-7.22 (m, 1H), 7.20-7.12 (m, 2H), 4.73 (dd, J = 9.8, 2.3 Hz, 1H), 4.44 (t, J = 7.1 Hz, 2H), 4.39 (d, J = 7.3 Hz, 1H), 4.33 (q, J = 6.8 Hz, 1H), 4.10-3.94 (m, 1H), 3.79 (d, J = 10.4 Hz, 1H), 3.74-3.60 (m, 1H), 3.60-3.44 (m, 1H), 3.25-3.13 (m, 1H), 3.12-3.01 (m, 2H), 2.99 (d, J = 8.9 Hz, 1H), 2.86 (s, 3H), 2.65 (d, J = 14.0 Hz, 1H), 2.57-2.45 (m, 1H), 2.42 (dd, J = 11.4, 3.9 Hz, 1H), 2.29 (s, 6H), 2.05-1.95 (m, 4H), 1.93 (s, 3H), 1.86-1.75 (m, 2H), 1.73-1.59 (m, 5H), 1.28 (s, 3H), 1.25 (s, 3H), 1.23 (d, J = 6.1 Hz, 3H), 1.19 (d, J = 6.8 Hz, 3H), 1.16 (d, J = 6.8 Hz, 3H), 1.08 (d, J = 13.9, 9.3 Hz, 1H), 0.99 (d, J = 6.7 Hz, 3H), 0.94-0.89 (m, 6H). $^{13}$C NMR (126 MHz, CDCl$_3$) δ 204.82, 170.00, 157.06, 147.92, 146.80, 131.53, 129.68, 119.85, 116.08, 114.82, 112.22, 104.43, 83.56, 83.04, 79.52, 79.28, 70.27, 69.45, 65.86, 63.97, 61.77, 60.10, 53.44, 50.23, 49.60, 44.80, 44.16, 40.29, 36.17, 32.38, 28.47, 27.58, 25.12, 23.90, 22.12, 21.34, 21.14, 15.51, 14.27, 11.15, 11.01, 9.44. | HRMS (ESI): Calcd for (C$_{44}$H$_{71}$N$_7$O$_9$ + H)$^+$: 842.5386; Found: 842.5386. |
| 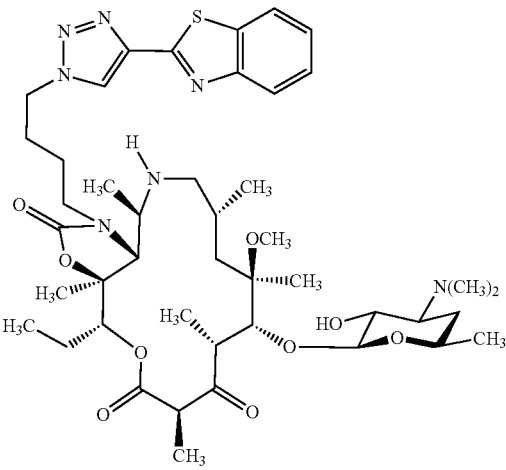<br>FSM-20711 | $^1$H NMR (600 MHz, CDCl$_3$) δ 8.32 (d, J = 9.4 Hz, 1H), 8.08 (d, J = 8.0 Hz, 1H), 8.00 (d, J = 7.6 Hz, 1H), 7.58-7.52 (m, 1H), 7.49-7.42 (m, 1H), 4.99 (dd, J = 10.9, 2.0 Hz, 1H), 4.67-4.51 (m, 3H), 4.44 (d, J = 7.4 Hz, 1H), 3.90 (q, J = 6.9 Hz, 1H), 3.84-3.75 (m, 1H), 3.75-3.64 (m, 3H), 3.46 (s, 1H), 3.38-3.30 (m, 1H), 3.09 (d, J = 5.1 Hz, 1H), 3.05 (s, 3H), 2.78-2.89 (m, 2H), 2.75-2.62 (m, 1H), 2.46 (s, 6H), 1.95-2.16 (m4H), 1.92-1.54 (m, 7H), 1.48 (s, 3H), 1.43 (d, J = 6.9 Hz, 3H), 1.40 (d, J = 7.8 Hz, 3H), 1.34 (d, J = 6.1 Hz, 3H), 1.31 (s, 3H), 1.23 (d, J = 11.5 Hz, 1H), 1.03 (br s, 3H), 0.98 (d, J = 6.6 Hz, 3H), 0.95 (t, J = 7.4 Hz, 3H). | HRMS (ESI): Calcd for (C$_{44}$H$_{67}$N$_7$O$_9$S + H)$^+$: 870.4799; Found: 870.4827. |

TABLE Y1-continued

| Compound and ID | NMR Data | MS Data |
|---|---|---|
| 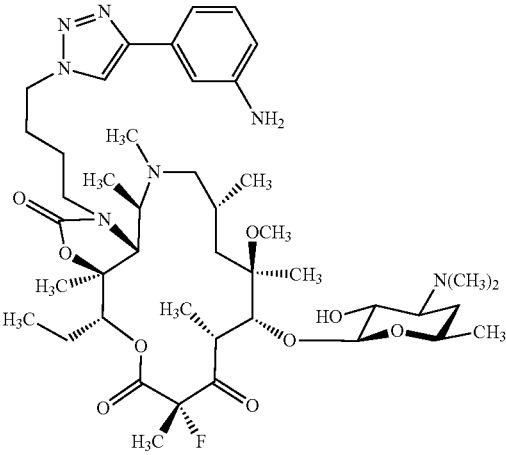 FSM-20797 | $^1$H NMR (500 MHz, CDCl$_3$) δ 7.82 (s, 1H), 7.19 (dt, J = 15.2, 7.6 Hz, 3H), 6.69-6.62 (m, 1H), 4.95 (dd, J = 8.4, 3.3 Hz, 1H), 4.58-4.41 (m, 2H), 4.37 (d, J = 7.2 Hz, 1H), 4.17 (d, J = 7.7 Hz, 1H), 3.67-3.40 (m, 4H), 3.40-3.31 (m, 1H), 3.31-3.23 (m, 1H), 3.10-3.05 (m, 1H), 3.07 (s, 3H), 2.85-2.78 (m, 2H), 2.75 (s, 1H), 2.49 (s, 6H), 2.31-2.20 (m, 1H), 2.12 (s, 3H), 2.08-1.91 (m, 3H), 1.79 (d, J = 22.1 Hz, 3H), 1.76-1.53 (m, 8H), 1.48 (s, 3H), 1.36 (d, J = 6.8 Hz, 3H), 1.28 (s, 3H), 1.27 (d, J = 6.2 Hz, 3H), 1.24-1.18 (m, 1H), 1.02 (d, J = 6.7 Hz, 3H), 1.00-0.94 (m, 6H). | HRMS (ESI): Calcd for (C$_{44}$H$_{70}$FN$_7$O$_9$ + H)$^+$: 860.5297; Found: 860.5283. |
| 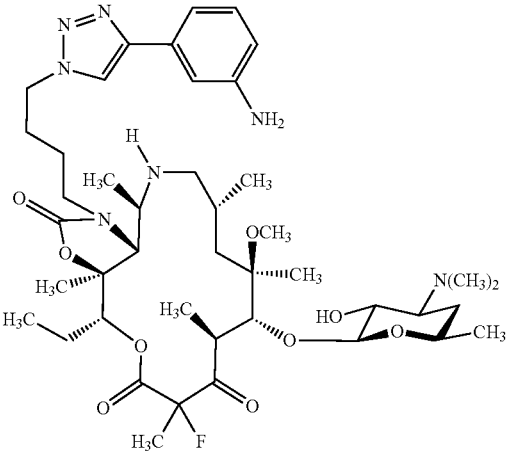 FSM-20720 | $^1$H NMR (500 MHz, CDCl$_3$) δ 7.85 (s, 1H), 7.30-7.28 (m, 1H), 7.24-7.12 (m, 2H), 6.71-6.57 (m, 1H), 5.02 (dd, J = 11.0, 1.7 Hz, 1H), 4.48 (t, J = 7.0 Hz, 2H), 4.31 (t, J = 7.3 Hz, 2H), 3.74 (s, 2H), 3.60 (ddd, J = 10.7, 6.1, 1.8 Hz, 4H), 3.26 (dd, J = 9.9, 7.3 Hz, 1H), 3.22 (s, 3H), 3.09 (n, J = 16.3 Hz, 2H), 2.65 (br, 1H), 2.55 (t, J = 9.4 Hz, 1H), 2.32 (s, 6H), 2.11-1.81 (m, 5H), 1.76 (d, J = 21.6 Hz, 3H), 1.74-1.61 (m, 6H), 1.56 (s, 3H), 1.38 (d, J = 7.2 Hz, 3H), 1.34-1.30 (m, 1H), 1.28 (d, J = 6.1 Hz, 3H), 1.24 (s, 3H), 0.99-0.86 (m, 9H). | HRMS (ESI): Calcd for (C$_{43}$H$_{68}$FN$_7$O$_9$ + H)$^+$: 843.5141; Found: 846.5134. |
| 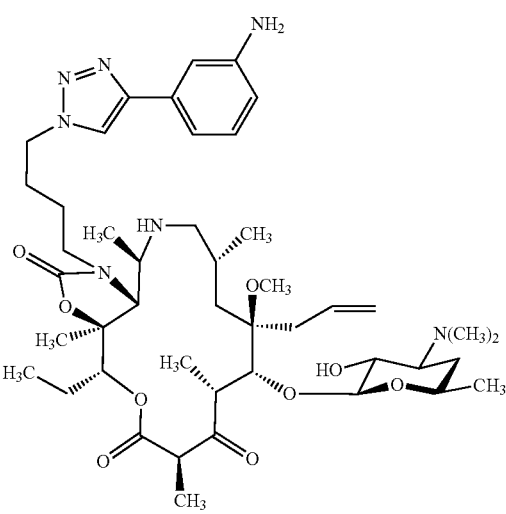 FSM-21367 | $^1$H NMR (500 MHz, CDCl$_3$) δ 7.78 (d, J = 8.9 Hz, 1H), 7.26-7.11 (m, 2H), 6.66 (dd, J = 7.3, 1.9 Hz, 1H), 6.06-5.92 (m, 1H), 5.09 (dd, J = 17.1, 1.7 Hz, 1H), 4.98 (dt, J = 10.9, 3.9 Hz, 2H), 4.66 (d, J = 3.4 Hz, 1H), 4.49-4.41 (m, 2H), 4.33 (d, J = 7.4 Hz, 1H), 3.88 (q, J = 6.9 Hz, 1H), 3.86-3.72 (m, 2H), 3.72-3.51 (m, 2H), 3.46 (s, 1H), 3.21 (dd, J = 9.7, 6.9 Hz, 1H), 3.08-3.05 (m, 1H), 3.04 (s, 3H), 2.81-2.76 (m, 1H), 2.59 (dd, J = 15.1, 5.8 Hz, 2H), 2.54-2.43 (m, 1H), 2.28 (s, 6H), 2.07-1.89 (m, 3H), 1.88-1.54 (m, 10H), 1.44 (s, 2H), 1.42 (t, J = 7.0 Hz, 3H), 1.39 (d, J = 7.8 Hz, 3H), 1.29 (d, J = 6.1 Hz, 3H), 1.23 (dd, J = 11.2, 5.0 Hz, 1H), 1.01 (d, J = 6.1 Hz, 3H), 0.91-0.86 (m, 6H). $^{13}$C NMR (126 MHz, CDCl$_3$) δ 205.74, 171.90, 157.03, 147.81, 146.85, 134.96, 131.65, 129.67, 119.58, 116.60, 116.06, 114.76, 112.24, 102.68, 81.09, 79.49, 78.40, 75.26, 70.20, 69.55, 65.90, 64.36, 59.19, 57.38, 50.37, 49.75, 49.66, 46.01, 42.73, 40.56, 40.25, 40.05, 28.32, 27.55, 27.22, 24.06, 21.65, 21.28, 21.18, 14.74, 14.53, 14.34, 14.03, 10.48. | HRMS (ESI): Calcd for (C$_{45}$H$_{71}$N$_7$O$_9$ + H)$^+$: 854.5386; Found: 854.5394. |

| Compound and ID | NMR Data | MS Data |
|---|---|---|
| 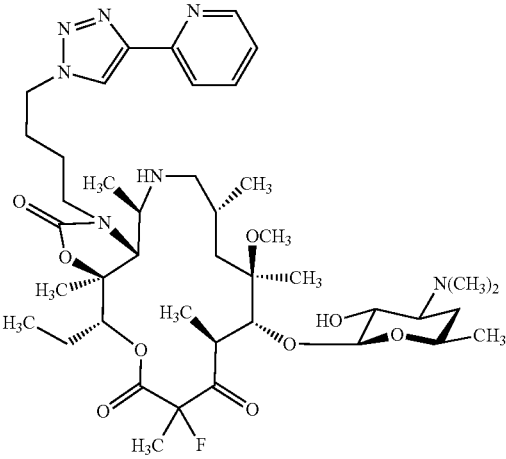

FSM-20716 | $^1$H NMR (500 MHz, CDCl$_3$) δ 8.58 (d, J = 4.3 Hz, 1H), 8.17 (d, J = 7.2 Hz, 2H), 7.77 (td, J = 7.8, 1.5 Hz, 1H), 7.22 (dd, J = 6.6, 5.1 Hz, 1H), 5.02 (d, J = 10.0 Hz, 1H), 4.50 (t, J = 7.2 Hz, 2H), 4.32 (d, J = 7.2 Hz, 2H), 3.77-3.42 (m, 4H), 3.29-3.25 (m, 1H), 3.25 (s, 3H), 3.16-2.94 (m, 2H), 2.63 (br, 1H), 2.57-2.47 (m, 1H), 2.31 (s, 6H), 2.15-1.81 (m, 5H), 1.75 (d, J = 21.6 Hz, 3H), 1.76-1.58 (m, 6H), 1.55 (s, 3H), 1.54-1.42 (m, 1H), 1.38 (d, J = 7.2 Hz, 3H), 1.30 (d, J = 6.2 Hz, 3H), 1.25 (s, 3H), 0.98-0.87 (m, 9H). | HRMS (ESI): Calcd for (C$_{42}$H$_{66}$FN$_7$O$_9$ + H)$^+$: 832.4984; Found: 832.5006. |
| 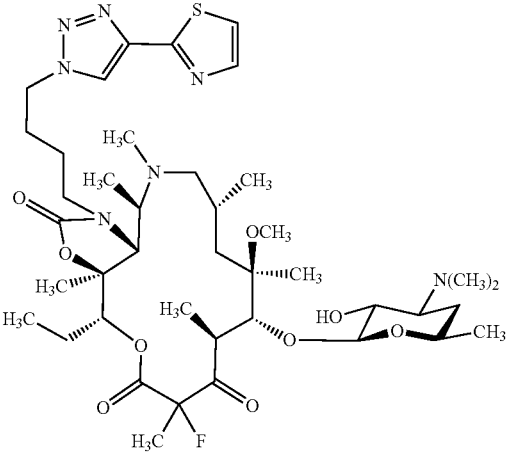

FSM-20705 | $^1$H NMR (500 MHz, CDCl$_3$) δ 8.10 (s, 1H), 7.85 (d, J = 3.2 Hz, 1H), 7.36 (d, J = 3.3 Hz, 1H), 4.83 (dd, J = 8.0, 3.8 Hz, 1H), 4.59-4.40 (m, 3H), 4.35 (d, J = 7.3 Hz, 1H), 3.85 (d, J = 3.2 Hz, 1H), 3.76-3.47 (m, 4H), 3.44-3.39 (m, 1H), 3.37 (d, J = 2.1 Hz, 1H), 3.28-3.16 (m, 1H), 3.11 (s, 3H), 2.74-2.63 (m, 1H), 2.41 (s, 6H), 2.31-2.28 (m, 1H), 2.10 (s, 3H), 2.04-1.92 (m, 3H), 1.72 (d, J = 21.5 Hz, 3H), 1.68-1.51 (m, 8H), 1.47 (s, 3H), 1.34 (d, J = 7.2 Hz, 3H), 1.29 (s, 3H), 1.25 (d, J = 6.1 Hz, 3H), 1.21 (dd, J = 14.7, 5.2 Hz, 1H), 1.02-0.96 (m, 6H), 0.94 (d, J = 6.6 Hz, 3H). | HRMS (ESI): Calcd for (C$_{41}$H$_{66}$FN$_7$O$_9$S + H)$^+$: 852.4705; Found: 852.4725. |
| 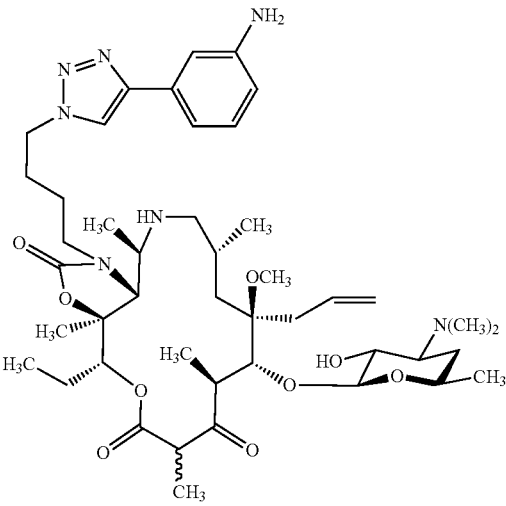

FSM-21368 | Note: The compound exists as a~1:1 mixture of C2-epimers. Due to extensive overlapping, $^1$H NMR peaks are not discriminated and are reported collectively. $^1$H NMR (500 MHz, CDCl$_3$) δ 7.79 (d, J = 2.6 Hz, 1H), 7.78 (d, J = 4.4 Hz, 1H), 7.26-7.12 (m, 6H), 6.71-6.60 (m, 2H), 5.99 (td, J = 17.3, 7.2 Hz, 1H), 5.82 (ddd, J = 17.1, 11.8, 7.7 Hz, 1H), 5.11 (dd, J = 19.2, 13.9 Hz, 4H), 4.98 (td, J = 10.7, 1.9 Hz, 2H), 4.67 (d, J = 3.4 Hz, 1H), 4.55-4.40 (m, 3H), 4.34 (t, J = 12.1 Hz, 1H), 4.08 (d, J = 9.3 Hz, 1H), 4.05-3.93 (m, 2H), 3.93-3.82 (m, 1H), 3.82-3.53 (m, 7H), 3.54-3.49 (m, 1H), 3.48 (s, 1H), 3.46 (s, 1H), 3.25-3.21 (m, 1H), 3.19 (s, 3H), 3.16-3.08 (m, 1H), 3.04 (s, 3H), 2.98 (dd, J = 10.2, 7.2 Hz, 1H), 2.84 (t, J = 6.6 Hz, 1H), 2.79 (dt, J = 12.5, 6.2 Hz, 1H), 2.66-2.54 (m, 4H), 2.54-2.29 (m, 2H), 2.28 (s, 6H), 2.26 (s, 6H), 2.10-1.85 (m, 6H), 1.85-1.48 (m, 20H), 1.44 (d, J = 3.9 Hz, 3H), 1.42 (s, 3H), 1.41 (d, J = 6.9 Hz, 3H), 1.40 (d, J = 1.2 Hz, 3H), 1.39 (d, J = 8.0 Hz, 3H), 1.38 (s, 3H), 1.29 (d, J = 6.1 Hz, 3H), 1.27-1.25 (m, 1H), 1.23 (d, J = 6.1 Hz, 3H), 1.21-1.15 (m, 1H), 1.07 (d, J = 6.6 Hz, 3H), 1.01 (d, J = 6.2 Hz, 3H), 0.94-0.85 (m, 12H). | HRMS (ESI): Calcd for (C$_{45}$H$_{71}$N$_7$O$_9$ + H)$^+$: 854.5386; Found: 854.5399. |

TABLE Y1-continued

| Compound and ID | NMR Data | MS Data |
|---|---|---|
| 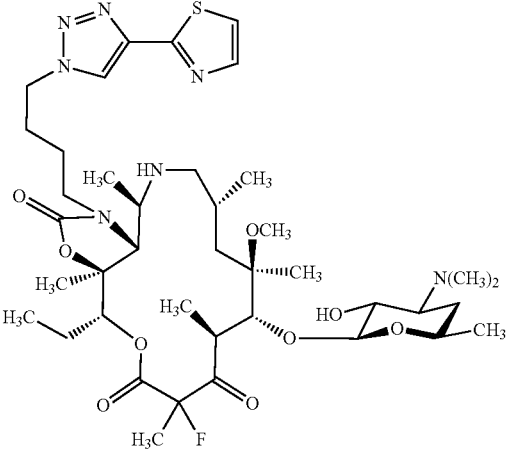<br>FSM-20721 | $^1$H NMR (500 MHz, CDCl$_3$) δ 8.10 (s, 1H), 7.84 (d, J = 3.2 Hz, 1H), 7.35 (d, J = 3.1 Hz, 1H), 5.01 (d, J = 10.0 Hz, 1H), 4.51 (t, J = 6.9 Hz, 2H), 4.32 (dd, J = 7.0, 3.3 Hz, 3H), 3.64 (ddd, J = 17.9, 16.2, 7.9 Hz, 4H), 3.30-3.26 (m, 2H), 3.22 (s, 3H), 3.17-2.91 (m, 2H), 2.61 (br, 1H), 2.55 (t, J = 9.6 Hz, 1H), 2.33 (s, 6H), 2.13-1.83 (m, 6H), 1.75 (d, J = 21.6 Hz, 3H), 1.70-1.58 (m, 5H), 1.55 (s, 3H), 1.38 (d, J = 7.2 Hz, 3H), 1.31 (d, J = 6.2 Hz, 3H), 1.26 (s, 3H), 1.22-1.17 (m, 1H), 0.97-0.89 (m, 9H). | HRMS (ESI): Calcd for (C$_{40}$H$_{64}$FN$_7$O$_9$ + H)$^+$: 838.4549; Found: 838.4555. |
| 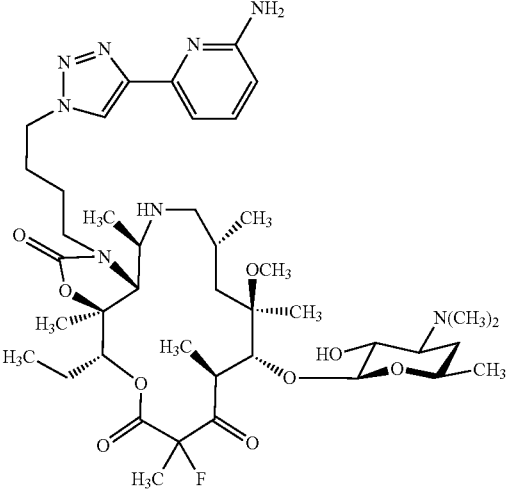<br>FSM-20718 | $^1$H NMR (500 MHz, CDCl$_3$) δ 8.03 (d, J = 19.8 Hz, 1H), 7.54-7.44 (m, 2H), 6.43 (dd, J = 7.5, 1.4 Hz, 1H), 5.01 (dd, J = 11.0, 1.8 Hz, 1H), 4.46 (t, J = 7.3 Hz, 2H), 4.43 (s, 2H), 4.31 (d, J = 7.3 Hz, 2H), 3.77-3.47 (m, 4H), 3.28-3.22 (m, 1H), 3.24 (s, 3H), 3.17-2.98 (m, 2H), 2.64 (br, 1H), 2.58-2.44 (m, 1H), 2.30 (s, 6H), 2.12-1.79 (m, 7H), 1.74 (d, J = 21.6 Hz, 3H), 1.69-1.57 (m, 4H), 1.54 (s, 3H), 1.37 (d, J = 7.2 Hz, 3H), 1.28 (d, J = 6.2 Hz, 3H), 1.24 (s, 3H), 0.98-0.88 (m, 9H). | HRMS (ESI): Calcd for (C$_{42}$H$_{67}$FN$_8$O$_9$ + H)$^+$: 847.5083; Found: 847.5121. |
| 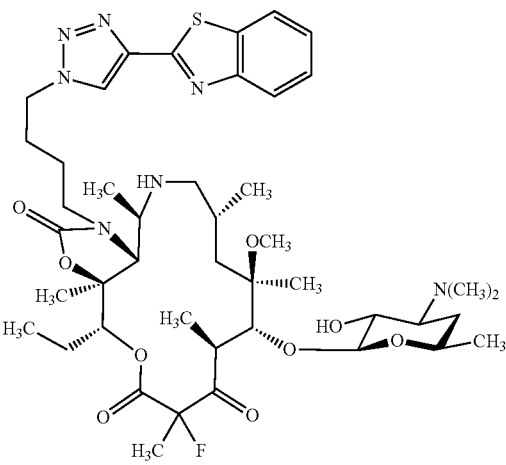<br>FSM-20722 | $^1$H NMR (500 MHz, CDCl$_3$) δ 8.38-8.21 (m, 1H), 8.03 (d, J = 8.1 Hz, 1H), 7.95 (d, J = 7.8 Hz, 1H), 7.50 (t, J = 7.8 Hz, 1H), 7.41 (t, J = 7.3 Hz, 1H), 5.02 (d, J = 10.4 Hz, 1H), 4.56 (t, J = 6.7 Hz, 2H), 4.37-4.25 (m, 2H), 3.59 (dt, J = 47.0, 23.5 Hz, 5H), 3.27 (s, 3H), 3.17-2.95 (m, 2H), 2.62-2.51 (m, 1H), 2.35 (s, 6H), 2.20-1.83 (m, 5H), 1.74 (d, J = 21.6 Hz, 3H), 1.65 (ddd, J = 14.4, 11.1, 7.2 Hz, 6H), 1.56 (s, 3H), 1.38 (d, J = 7.2 Hz, 3H), 1.29 (d, J = 6.1 Hz, 3H), 1.27 (s, 3H), 1.22-1.17 (m, 1H), 0.98-0.91 (m, 9H). | HRMS (ESI): Calcd for (C$_{44}$H$_{66}$FN$_7$O$_9$S + H)$^+$: 888.4705; Found: 888.4728. |

TABLE Y1-continued

| Compound and ID | NMR Data | MS Data |
|---|---|---|
| 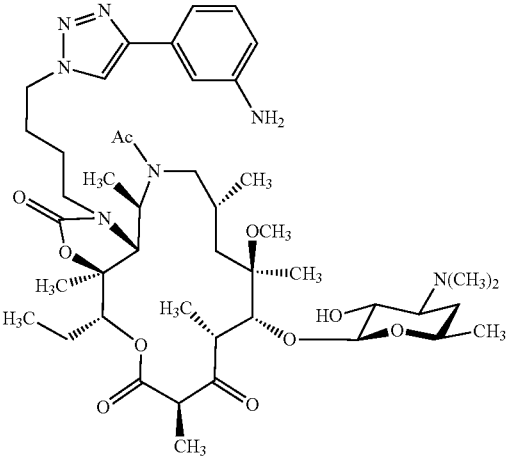FSM-20767 | Note: The ¹H NMR of this compound is complicated due to presence of both N9a amide rotamers and C2 epimers. | HRMS (ESI): Calcd for (C₄₅H₇₁N₇O₁₀ + 2H)²⁺: 435.7709; Found: 435.7708. |
| 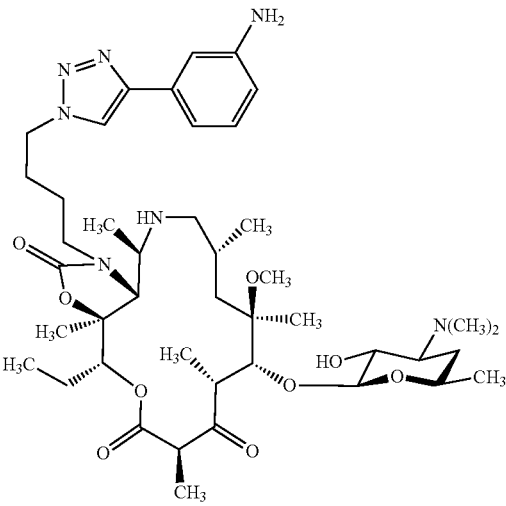FSM-21340 | ¹H NMR (600 MHz, CDCl₃) δ 7.76 (s, 1H), 7.25 (s, 1H), 7.17 (t, J = 7.7 Hz, 1H), 7.12 (d, J = 7.5 Hz, 1H), 6.66-6.59 (m, 1H), 4.98 (dd, J = 10.9, 1.6 Hz, 1H), 4.50 (s, 1H), 4.45 (tt, J = 13.8, 7.0 Hz, 2H), 4.24 (d, J = 7.3 Hz, 1H), 3.80-3.71 (m, 1H), 3.65 (dt, J = 20.7, 10.1 Hz, 1H), 3.55 (dt, J = 10.6, 6.0 Hz, 1H), 3.42 (br, 2H), 3.36 (s, 1H), 3.21 (dd, J = 9.5, 6.8 Hz, 1H), 3.18 (s, 3H), 2.94 (dt, J = 7.0, 5.3 Hz, 2H), 2.82 (d, J = 8.3 Hz, 1H), 2.68 (dd, J = 12.0, 5.9 Hz, 1H), 2.55-2.44 (m, 1H), 2.31-2.23 (m, 6H), 2.10-1.87 (m, 4H), 1.80-1.64 (m, 4H), 1.64-1.49 (m, 3H), 1.46 (dd, J = 14.4, 3.9 Hz, 1H), 1.37 (d, J = 5.4 Hz, 3H), 1.37 (s, 3H), 1.29 (d, J = 16.3 Hz, 1H), 1.26 (s, 3H), 1.24 (d, J = 6.2 Hz, 4H), 1.02 (d, J = 6.8 Hz, 3H), 0.95 (d, J = 6.0 Hz, 3H), 0.91 (d, J = 6.8 Hz, 3H), 0.84 (t, J = 7.3 Hz, 3H). ¹³C NMR (126 MHz, CDCl₃) δ 178.07, 157.09, 147.81, 146.83, 131.62, 129.65, 119.62, 116.01, 114.75, 112.24, 105.35, 81.37, 78.89, 77.76, 77.63, 70.42, 69.52, 65.84, 65.31, 59.50, 58.61, 50.27, 49.65, 42.61, 41.33, 40.84, 40.30, 38.31, 28.44, 27.61, 27.34, 24.08, 21.57, 21.53, 21.24, 18.86, 16.34, 14.17, 13.73, 13.16, 10.39. | HRMS (ESI): Calcd for (C₄₃H₇₁N₇O₉ + H)⁺: 830.5386; Found: 830.5401. |
| 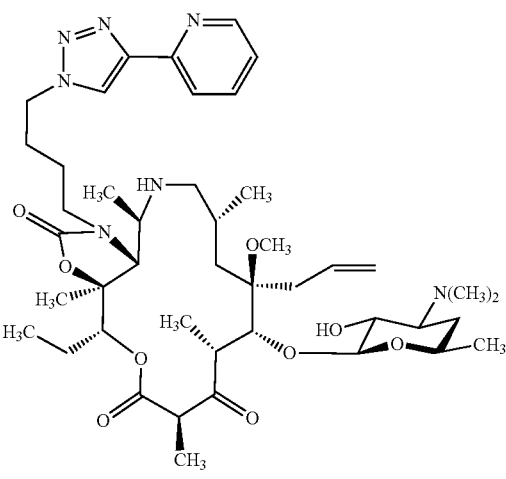FSM-21423 | ¹H NMR (500 MHz, CDCl₃) δ 8.62-8.53 (m, 1H), 8.17 (d, J = 7.2 Hz, 1H), 8.16 (s, 1H), 7.78 (td, J = 7.7, 1.8 Hz, 1H), 7.23 (ddd, J = 7.5, 4.9, 1.1 Hz, 1H), 5.99 (dq, J = 10.2, 7.1 Hz, 1H), 5.13-5.03 (m, 1H), 5.01-4.91 (m, 1H), 4.66 (d, J = 3.5 Hz, 1H), 4.58-4.40 (m, 3H), 4.34 (d, J = 7.4 Hz, 1H), 3.85 (q, J = 6.9 Hz, 1H), 3.80-3.69 (m, 1H), 3.69-3.59 (m, 3H), 3.47 (s, 1H), 3.21 (dd, J = 10.2, 7.5 Hz, 1H), 3.07 (s, 3H), 2.78 (q, J = 6.1 Hz, 1H), 2.61 (d, J = 7.2 Hz, 1H), 2.57 (dd, J = 10.3, 5.0 Hz, 1H), 2.53-2.42 (m, 1H), 2.29 (s, 6H), 2.14-1.90 (m, 4H), 1.88-1.67 (m, 9H), 1.43 (s, 3H), 1.41 (d, J = 7.0 Hz, 3H), 1.38 (d, J = 7.8 Hz, 3H), 1.30 (d, J = 6.1 Hz, 3H), 1.26-1.19 (m, 1H), 1.01 (d, J = 6.1 Hz, 3H), 0.92-0.87 (m, 6H). | HRMS (ESI): Calcd for (C₄₄H₆₉N₇O₉ + H)⁺: 840.5230; Found: 840.5233. |

TABLE Y1-continued

| Compound and ID | NMR Data | MS Data |
|---|---|---|
| 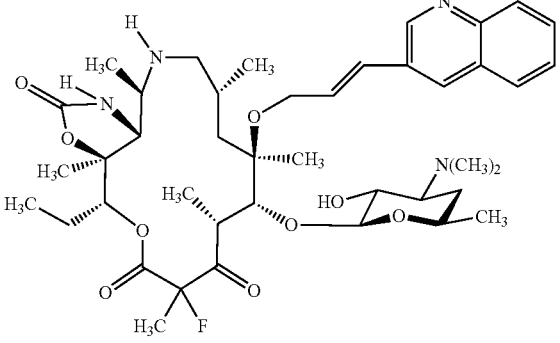<br>FSM-21088 | $^1$H NMR (600 MHz, CDCl$_3$) δ 9.03 (d, J = 2.1 Hz, 1H), 8.10 (s, 1H), 8.07 (d, J = 8.4 Hz, 1H), 7.83 (d, J = 8.0 Hz, 1H), 7.70-7.64 (m, 1H), 7.54 (t, J = 7.5 Hz, 1H), 6.73-6.65 (m, 2H), 5.12 (dd, J = 10.7, 2.0 Hz, 1H), 4.40 (d, J = 7.3 Hz, 1H), 4.27-4.10 (m, 2H), 3.84-3.73 (m, 2H), 3.69 (dd, J = 11.3, 5.6 Hz, 1H), 3.40 (s, 2H), 3.19 (dd, J = 10.0, 7.5 Hz, 1H), 3.13 (s, 1H), 2.95-2.89 (m, 1H), 2.87-2.81 (m, 1H), 2.51-2.40 (m, 1H), 2.25 (s, 6H), 2.04-1.93 (m, 3H), 1.89 (d, J = 22.5 Hz, 3H), 1.82 (d, J = 9.6 Hz, 2H), 1.66-1.56 (m, 2H), 1.52 (s, 3H), 1.45 (s, 3H), 1.31-1.27 (m, 1H), 1.22 (d, J = 7.9 Hz, 6H), 1.12-1.03 (br, 3H), 1.00 (d, J = 6.7 Hz, 3H), 0.91 (t, J = 7.4 Hz, 3H). | HRMS (ESI): Calcd for (C$_{42}$H$_{61}$FN$_4$O$_9$ + H)$^+$: 785.4495; Found: 785.4519. |
| 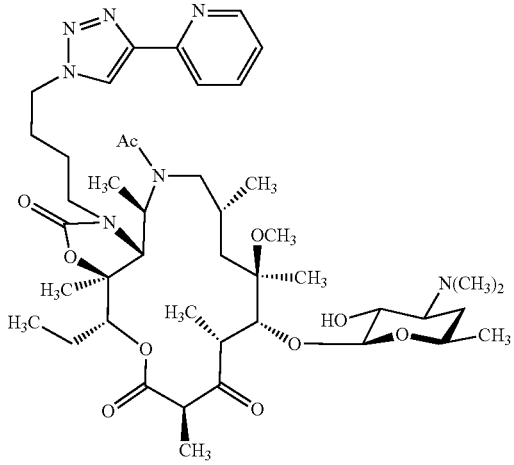<br>FSM-20766 | $^1$H NMR (8:1 mixture of rotamers, major rotajor reported, 500 MHz, CDCl$_3$) δ 8.62 (d, J = 4.2 Hz, 1H), 8.34 (br, 1H), 7.97 (br, J = 28.9 Hz, 1H), 7.28 (br, 1H), 4.93 (dd, J = 14.7, 5.6 Hz, 2H), 4.87-4.72 (m, 1H), 4.56-4.37 (m, 3H), 3.95 (d, J = 10.4 Hz, 1H), 3.68 (q, J = 7.1 Hz, 1H), 3.65-3.52 (m, 2H), 3.49 (d, J = 11.0 Hz, 1H), 3.38 (dt, J = 14.0, 8.1 Hz, 1H), 3.21-3.07 (m, 1H), 3.07-2.96 (m, 1H), 2.85 (s, 3H), 2.58-2.46 (m, 1H), 2.32 (s, 6H), 2.13 (s, 3H), 2.04-1.83 (m, 7H), 1.83-1.68 (m, 2H), 1.53 (dd, J = 16.8, 8.2 Hz, 1H), 1.46 (d, J = 6.9 Hz, 3H), 1.40 (d, J = 7.0 Hz, 1H), 1.37-1.24 (m, 13H), 1.22 (s, 3H), 1.02 (d, J = 6.8 Hz, 3H), 0.92 (t, J = 7.4 Hz, 3H). | HRMS (ESI): Calcd for (C$_{44}$H$_{69}$N$_7$O$_{10}$ + 2H)$^{2+}$: 428.7631; Found: 428.7632. |
| 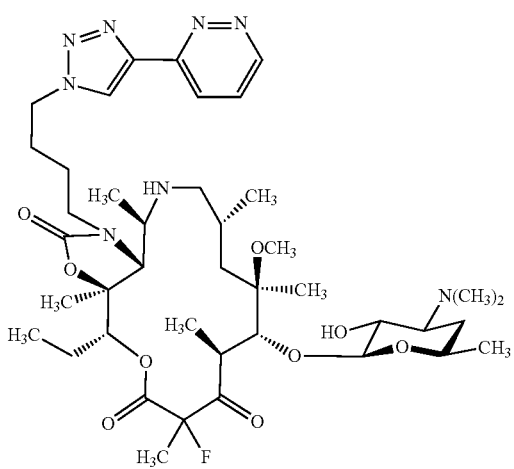<br>FSM-20717 | $^1$H NMR (500 MHz, CDCl$_3$) δ 9.16-9.06 (m, 1H), 8.41 (s, 1H), 8.36-8.27 (m, 1H), 7.56 (dd, J = 8.5, 4.9 Hz, 1H), 5.01 (d, J = 10.8 Hz, 1H), 4.54 (t, J = 7.2 Hz, 2H), 4.33 (d, J = 7.2 Hz, 2H), 3.79-3.47 (m, 4H), 3.29-3.24 (m, 1H), 3.26 (s, 3H), 3.15-3.06 (m, 2H), 3.06-2.95 (m, 1H), 2.63 (br, 1H), 2.58-2.49 (m, 1H), 2.32 (s, 6H), 2.13-1.84 (m, 6H), 1.75 (d, J = 21.7 Hz, 3H), 1.70-1.58 (m, 5H), 1.55 (s, 3H), 1.38 (d, J = 7.2 Hz, 3H), 1.30 (d, J = 6.2 Hz, 3H), 1.26 (s, 3H), 1.23-1.19 (m, 1H), 0.98-0.87 (m, 9H). | HRMS (ESI): Calcd for (C$_{41}$H$_{65}$FN$_8$O$_9$ + H)$^+$: 833.4931; Found: 833.4965. |

TABLE Y1-continued

| Compound and ID | NMR Data | MS Data |
|---|---|---|
| 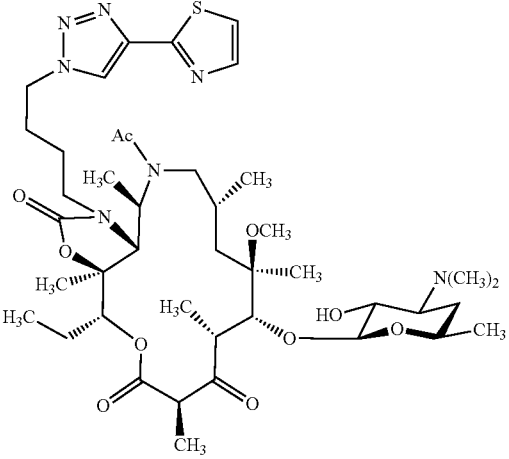 FSM-20763 | $^1$H NMR (500 MHz, CDCl$_3$) δ 8.07 (s, 1H), 7.85 (d, J = 3.2 Hz, 1H), 7.36 (d, J = 3.3 Hz, 1H), 4.97 (dd, J = 9.4, 2.6 Hz, 1H), 4.89-4.67 (m, 1H), 4.52-4.43 (m, 2H), 4.40 (d, J = 7.3 Hz, 1H), 3.96 (d, J = 10.4 Hz, 1H), 3.69 (q, J = 7.3 Hz, 1H), 3.66-3.54 (m, 2H), 3.52 (d, J = 11.1 Hz, 1H), 3.21 (dd, J = 10.0, 7.4 Hz, 1H), 3.14 (d, J = 7.6 Hz, 1H), 3.08-2.98 (m, 1H), 2.98-2.90 (m, 1H), 2.87 (s, 3H), 2.58-2.46 (m, 1H), 2.32 (s, 6H), 2.12 (s, 3H), 2.03-1.84 (m, 6H), 1.84-1.75 (m, 1H), 1.72 (d, J = 12.5 Hz, 1H), 1.67-1.60 (m, 1H), 1.60-1.53 (m, 1H), 1.50 (d, J = 7.2 Hz, 3H), 1.46-1.39 (m, 1H), 1.37 (d, J = 6.6 Hz, 3H), 1.32 (s, 3H), 1.30-1.28 (m, 1H), 1.27 (d, J = 4.5 Hz, 3H), 1.27 (s, 3H), 1.25 (d, J = 8.0 Hz, 3H), 1.01 (d, J = 6.9 Hz, 3H), 0.92 (t, J = 7.5 Hz, 3H). | HRMS (ESI): Calcd for (C$_{42}$H$_{67}$N$_7$O$_{10}$S + H)$^+$: 862.4748; Found: 862.4740. |
| 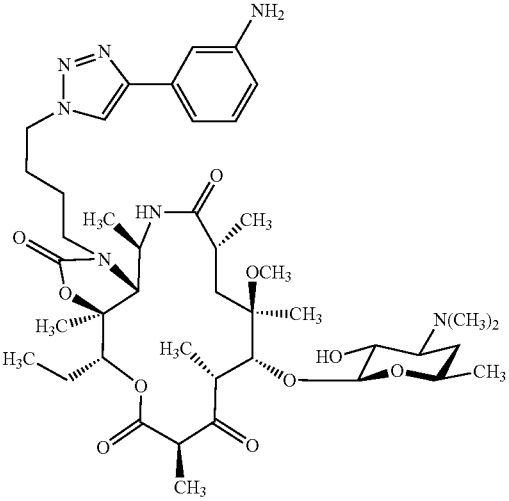 FSM-21344 | $^1$H NMR (600 MHz, CDCl$_3$) δ 7.78 (s, 1H), 7.24-7.11 (m, 3H), 6.66 (ddd, J = 7.7, 2.2, 1.0 Hz, 1H), 6.46 (d, J = 7.6 Hz, 1H), 4.83 (dd, J = 10.7, 2.0 Hz, 1H), 4.47-4.35 (m, 3H), 4.33 (d, J = 7.3 Hz, 1H), 4.09-4.05 (m, 2H), 3.53 (dtd, J = 10.4, 6.0, 4.3 Hz, 1H), 3.48-3.41 (m, 1H), 3.41-3.34 (m, 1H), 3.21 (d, J = 1.5 Hz, 1H), 3.20-3.15 (m, 1H), 2.84 (s, 3H), 2.82-2.73 (m, 1H), 2.55-2.43 (m, 1H), 2.43-2.33 (m, 1H), 2.26 (s, 6H), 2.01-1.88 (m, 2H), 1.88-1.79 (m, 2H), 1.79-1.68 (m, 3H), 1.68-1.62 (m, 1H), 1.62-1.51 (m, 2H), 1.49 (d, J = 7.4 Hz, 3H), 1.45 (s, 3H), 1.32 (d, J = 7.1 Hz, 3H), 1.30-1.26 (m, 1H), 1.23 (s, 3H), 1.21 (d, J = 6.2 Hz, 3H), 1.14 (d, J = 7.1 Hz, 3H), 1.00 (d, J = 7.1 Hz, 3H), 0.86 (t, J = 7.4 Hz, 3H). | HRMS (ESI): Calcd for (C$_{43}$H$_{67}$N$_7$O$_{10}$ + H)$^+$: 842.5022; Found: 842.5032. |
| 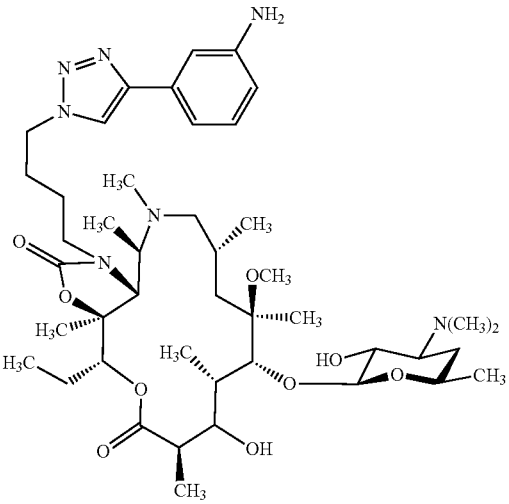 FSM-21335 | $^1$H NMR (600 MHz, CDCl$_3$) δ 7.85 (s, 1H), 7.28-7.27 (m, 1H), 7.20-7.11 (m, 2H), 6.64 (ddd, J = 7.6, 2.3, 1.3 Hz, 1H), 4.87 (dd, J = 10.4, 2.2 Hz, 1H), 4.63 (d, J = 7.5 Hz, 1H), 4.50-4.45 (m, 2H), 4.25 (d, J = 2.2 Hz, 1H), 3.80-3.71 (m, 1H), 3.71-3.61 (m, 1H), 3.61-3.56 (m, 1H), 3.55 (dd, J = 10.9, 6.1 Hz, 1H), 3.30-3.20 (m, 1H), 3.18 (s, 3H), 2.99-2.93 (m, 1H), 2.93-2.85 (m, 1H), 2.59-2.46 (m, 1H), 2.32 (s, 6H), 2.18-2.08 (m, 1H), 2.06 (s, 4H), 2.04-1.71 (m, 12H), 1.43 (s, 3H), 1.35-1.28 (m, 6H), 1.27 (d, J = 6.2 Hz, 3H), 1.26-1.24 (m, 1H), 1.02 (d, J = 6.7 Hz, 4H), 0.95 (d, J = 6.6 Hz, 3H), 0.93 (d, J = 6.9 Hz, 3H), 0.85 (t, J = 7.4 Hz, 3H). | HRMS (ESI): Calcd for (C$_{44}$H$_{73}$N$_7$O$_9$ + H)$^+$: 844.5548; Found: 844.5548. |

TABLE Y1-continued

| Compound and ID | NMR Data | MS Data |
| --- | --- | --- |
| 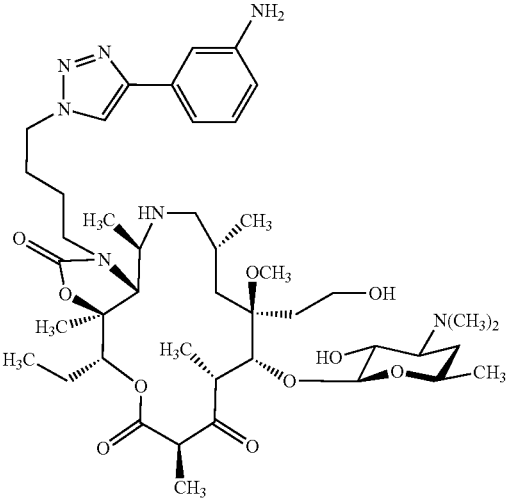<br>FSM-21442 | $^1$H NMR (500 MHz, CDCl$_3$) δ 7.79 (s, 1H), 7.26-7.11 (m, 3H), 6.67 (dd, J = 7.8, 1.3 Hz, 1H), 4.96 (dd, J = 10.8, 2.0 Hz, 1H), 4.80 (d, J = 2.9 Hz, 1H), 4.57-4.42 (m, 3H), 4.38 (d, J = 7.5 Hz, 1H), 3.94-3.79 (m, 2H), 3.79-3.60 (m, 3H), 3.43 (s, 1H), 3.22 (dd, J = 10.1, 7.5 Hz, 2H), 3.13-3.06 (m, 1H), 3.00 (s, 3H), 2.86-2.73 (m, 1H), 2.68 (d, J = 6.3 Hz, 1H), 2.59-2.43 (m, 1H), 2.29 (s, 6H), 2.13-1.84 (m, 5H), 1.81-1.50 (m, 8H), 1.44 (s, 3H), 1.41 (d, J = 6.8 Hz, 3H), 1.40 (d, J = 7.7 Hz, 3H), 1.34 (d, J = 6.2 Hz, 3H), 1.32-1.29 (m, 1H), 1.00 (d, J = 6.1 Hz, 3H), 0.92 (d, J = 5.5 Hz, 3H), 0.89 (t, J = 7.4 Hz, 3H). | HRMS (ESI): Calcd for (C$_{44}$H$_{71}$N$_7$O$_{10}$ + H)$^+$: 858.5335; Found: 858.5299. |
| 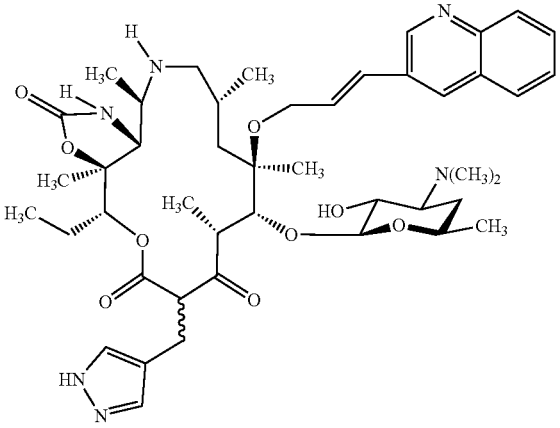<br>FSM-21264 | Note: The compound exists as a~3:1 mixture of C2-epimers. Major isomer is reported where possible for $^1$H NMR; otherwise reported peaks are reported collectively.<br>$^1$H NMR (500 MHz, CDCl$_3$) δ 9.02 (s, 1H), 8.22 (s, 1H), 8.06 (d, J = 8.6 Hz, 1H), 7.82 (d, J = 8.3 Hz, 1H), 7.66 (t, J = 7.0 Hz, 1H), 7.57-7.47 (m, 1H), 7.43 (s, 2H), 6.71 (d, J = 15.7 Hz, 1H), 6.48-6.31 (m, 1H), 4.90-4.78 (m, 1H), 4.74 (d, J = 2.1 Hz, 1H), 4.30 (d, J = 7.4 Hz, 1H), 4.16-4.12 (m, 1H), 4.11-4.05 (m, 1H), 3.91 (dd, J = 11.0, 6.8 Hz, 1H), 3.62 (dd, J = 9.2, 6.0 Hz, 1H), 3.27 (s, 1H), 3.23-3.09 (m, 1H), 3.10-3.04 (m, 1H), 2.89-2.79 (m, 1H), 2.70-2.63 (m, 1H), 2.54-2.47 (m, 1H), 2.29 (s, 6H), 1.99-1.87 (m, 1H), 1.81-1.71 (m, 2H), 1.69-1.64 (m, 1H), 1.64-1.57 (m, 2H), 1.47 (s, 3H), 1.41 (s, 3H), 1.40 (d, J = 4.3 Hz, 3H), 1.38 (d, J = 7.8 Hz, 7H), 1.36-1.31 (m, 1H), 1.28 (d, J = 6.1 Hz, 3H), 0.99 (d, J = 6.1 Hz, 3H), 0.55 (t, J = 7.4 Hz, 3H). | HRMS (ESI): Calcd for (C$_{45}$H$_{64}$NO$_9$ + 2H)$^{2+}$: 417.2440; Found: 417.2435. |
| 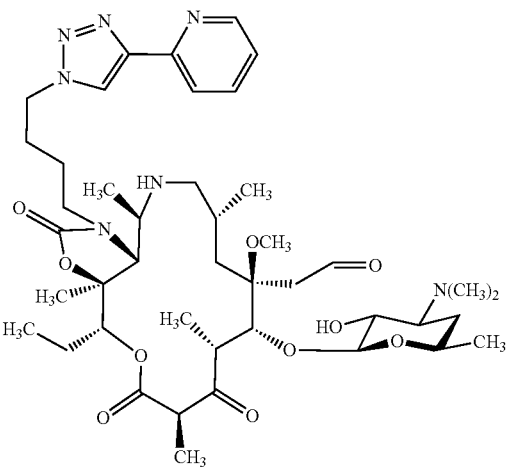<br>FSM-21428 | $^1$H NMR (500 MHz, CDCl$_3$) δ 9.96 (t, J = 2.5 Hz, 1H), 8.58 (d, J = 4.9 Hz, 1H), 8.23-8.09 (m, 2H), 7.78 (td, J = 7.7, 1.8 Hz, 1H), 7.23 (ddd, J = 6.4, 5.9, 2.7 Hz, 1H), 4.95 (dd, J = 10.8, 1.9 Hz, 1H), 4.86 (d, J = 3.0 Hz, 1H), 4.59-4.45 (m, 3H), 4.41 (d, J = 7.4 Hz, 1H), 4.00 (dd, J = 5.8, 3.8 Hz, 1H), 3.88 (q, J = 6.9 Hz, 1H), 3.75-3.61 (m, 3H), 3.42 (s, 1H), 3.18-3.10 (m, 1H), 3.07 (s, 3H), 2.88 (d, J = 14.1 Hz, 1H), 2.83-2.76 (m, 1H), 2.73 (dd, J = 10.4, 3.8 Hz, 1H), 2.60 (dd, J = 15.7, 2.6 Hz, 1H), 2.55-2.46 (m, 1H), 2.29 (s, 6H), 1.98 (ddd, J = 43.8, 25.1, 7.0 Hz, 3H), 1.90-1.52 (m, 8H), 1.44 (s, 3H), 1.41 (d, J = 6.8 Hz, 3H), 1.40 (d, J = 7.7 Hz, 3H), 1.34 (d, J = 6.2 Hz, 3H), 1.32-1.29 (m, 1H), 1.00 (d, J = 6.1 Hz, 3H), 0.92 (d, J = 5.5 Hz, 3H), 0.89 (t, J = 7.4 Hz, 3H). | HRMS (ESI): Calcd for (C$_{43}$H$_{67}$N$_7$O$_{10}$ + H)$^+$: 842.5028; Found: 842.4984. |

TABLE Y1-continued

| Compound and ID | NMR Data | MS Data |
|---|---|---|
| 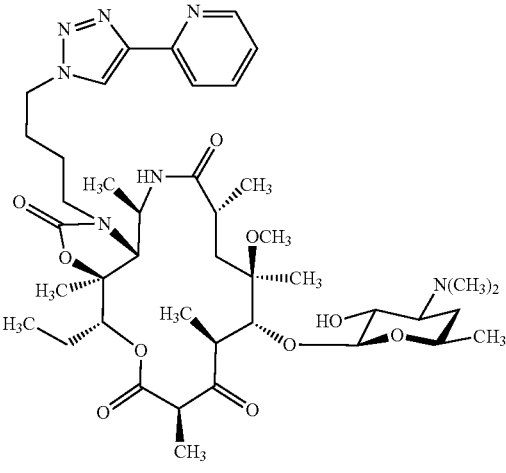<br>FSM-20781 | $^1$H NMR (500 MHz, Benzene) δ 8.48-8.42 (m, 1H), 8.33 (d, J = 7.9 Hz, 1H), 7.84 (s, 1H), 7.14-7.09 (m, 1H), 6.63-6.54 (m, 1H), 6.31 (d, J = 8.8 Hz, 1H), 5.12 (dd, J = 10.6, 2.2 Hz, 1H), 4.58-4.47 (m, 1H), 4.31 (d, J = 7.2 Hz, 1H), 4.07 (d, J = 7.4 Hz, 1H), 3.80-3.71 (m, 1H), 3.71-3.61 (m, 1H), 3.61-3.49 (m, 1H), 3.45-3.37 (m, 1H), 3.31 (s, 1H), 3.23 (d, J = 4.9 Hz, 1H), 3.16-2.99 (m, 2H), 2.90 (s, 3H), 2.80 (d, J = 13.0 Hz, 1H), 2.62-2.45 (m, 2H), 2.18-2.06 (m, 1H), 1.82 (s, 6H), 1.60 (d, J = 6.9 Hz, 3H), 1.69-1.49 (m, 8H), 1.46 (d, J = 6.7 Hz, 3H), 1.43 (s, 3H), 1.41-1.35 (m, 1H), 1.34 (s, 3H), 1.32 (d, J = 7.3 Hz, 3H), 1.01 (d, J = 6.1 Hz, 3H), 0.81 (d, J = 6.5 Hz, 3H), 0.84-0.77 (m, 1H), 0.71 (t, J = 7.4 Hz, 3H). | HRMS (ESI): Calcd for (C$_{42}$H$_{65}$N$_7$O$_{10}$ + H)$^+$: 828.4871; Found: 828.4888. |
| 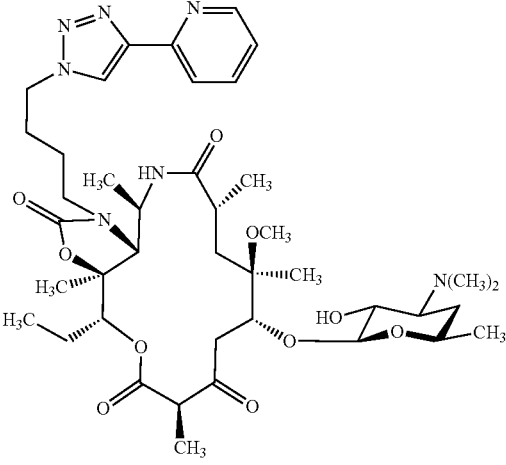<br>FSM-20739 | $^1$H NMR (500 MHz, CDCl$_3$) δ 8.60 (d, J = 4.2 Hz, 1H), 8.20 (s, 1H), 8.15 (d, J = 7.9 Hz, 1H), 7.80 (td, J = 7.7, 1.7 Hz, 1H), 7.26 (dd, J = 4.7, 2.9 Hz, 1H), 6.36 (br, 1H), 4.86-4.71 (m, 1H), 4.57-4.49 (m, 2H), 4.35 (dd, J = 12.1, 6.0 Hz, 2H), 3.86-3.77 (m, 1H), 3.63-3.50 (m, 2H), 3.36 (s, 1H), 3.32-3.23 (m, 1H), 3.03 (s, 3H), 3.01-2.91 (m, 1H), 2.68 (dd, J = 17.7, 4.9 Hz, 1H), 2.63-2.48 (m, 1H), 2.40-2.36 (m, 1H), 2.32 (s, 6H), 2.08 (dd, J = 12.6, 5.5 Hz, 1H), 2.04-1.95 (m, 1H), 1.94-1.77 (m, 2H), 1.72-1.51 (m, 7H), 1.47 (s, 3H), 1.40 (d, J = 7.2 Hz, 3H), 1.25 (d, J = 6.1 Hz, 3H), 1.23 (s, 3H), 1.19 (d, J = 7.3 Hz, 3H), 1.17-1.12 (m, 1H), 1.07 (d, J = 7.1 Hz, 3H), 0.92 (t, J = 7.3 Hz, 3H). | HRMS (ESI): Calcd for (C$_{41}$H$_{63}$N$_7$O$_{10}$ + H)$^+$: 814.4715; Found: 814.4720. |
| 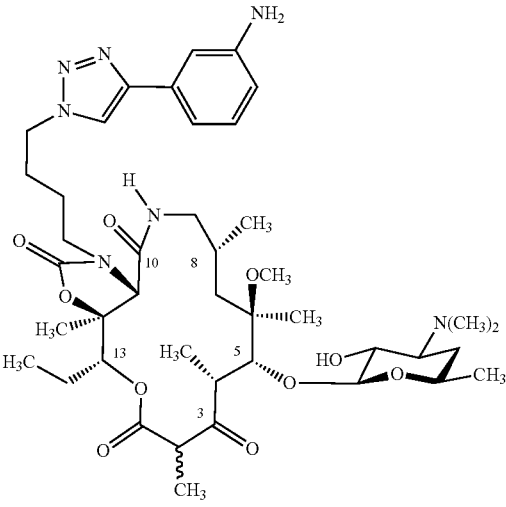<br>FSM-21473 | $^1$H NMR (3:1 mixture of C2-epimers, major epimer reported, 500 MHz, CDCl$_3$) δ 7.81 (s, 1H), 7.56 (s, 1H), 7.27-7.17 (m, 3H), 6.69-6.54 (m, 1H), 4.90 (dd, J = 10.7, 2.2 Hz, 1H), 4.43 (t, J = 7.0 Hz, 2H), 4.37 (d, J = 7.1 Hz, 1H), 4.33 (d, J = 7.3 Hz, 1H), 3.92 (q, J = 6.9 Hz, 1H), 3.82 (s, 1H), 3.64-3.48 (m, 2H), 3.33-3.18 (m, 2H), 3.15-3.01 (m, 2H), 2.96 (s, 3H), 2.84-2.72 (m, 1H), 2.56-2.44 (m, 1H), 2.30 (s, 6H), 2.14-1.90 (m, 3H), 1.89-1.49 (m, 8H), 1.46 (d, J = 7.0 Hz, 3H), 1.43 (d, J = 4.6 Hz, 3H), 1.36 (d, J = 7.7 Hz, 3H), 1.32 (s, 3H), 1.27 (d, J = 6.1 Hz, 3H), 1.26-1.20 (m, 1H), 0.96 (d, J = 7.0 Hz, 3H), 0.92 (t, J = 7.4 Hz, 3H). | HRMS (ESI): Calcd for (C$_{42}$H$_{65}$N$_7$O$_{10}$ + H)$^+$: 828.4866; Found: 828.4844. |

TABLE Y1-continued

| Compound and ID | NMR Data | MS Data |
|---|---|---|
| 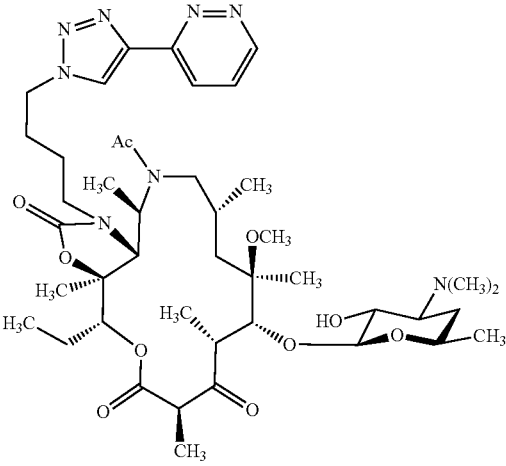<br>FSM-20764 | $^1$H NMR (8:1 mixture of rotamers, major rotajor reported, 500 MHz, CDCl$_3$) δ 9.13 (dd, J = 4.8, 1.6 Hz, 1H), 8.42-8.29 (m, 2H), 7.62-7.53 (m, 1H), 4.96 (dd, J = 9.4, 2.4 Hz, 1H), 4.82 (dd, J = 10.8, 6.9 Hz, 1H), 4.57-4.35 (m, 4H), 3.96 (d, J = 10.4 Hz, 1H), 3.69 (q, J = 7.2 Hz, 1H), 3.67-3.54 (m, 2H), 3.50 (d, J = 11.0 Hz, 1H), 3.19-3.08 (m, 2H), 3.07-2.98 (m, 1H), 2.98-2.87 (m, 1H), 2.85 (s, 3H), 2.73 (s, 6H), 2.13 (s, 3H), 1.94 (ddt, J = 72.1, 68.1, 40.1 Hz, 11H), 1.47 (d, J = 7.2 Hz, 3H), 1.45-1.38 (m, 1H), 1.34 (d, J = 6.7 Hz, 3H), 1.31 (d, J = 6.2 Hz, 3H), 1.29 (s, 3H), 1.27 (d, J = 6.2 Hz, 3H), 1.23 (s, 3H), 1.02 (d, J = 6.8 Hz, 3H), 0.91 (t, J = 7.5 Hz, 3H). | HRMS (ESI): Calcd for (C$_{43}$H$_{68}$N$_8$O$_{10}$ + 2H)$^{2+}$: 429.2607; Found: 429.2604. |
| 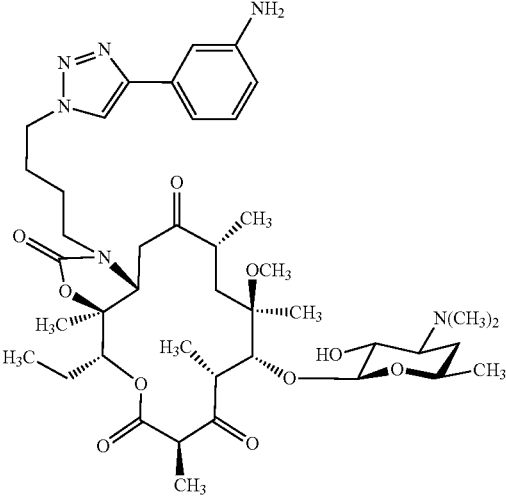<br>FSM-21535 | $^1$H NMR (500 MHz, CDCl$_3$) δ 7.81 (s, 1H), 7.24-7.09 (m, 3H), 6.66 (d, J = 6.2 Hz, 1H), 4.97 (d, J = 9.0 Hz, 1H), 4.45 (t, J = 6.7 Hz, 2H), 4.32 (d, J = 7.2 Hz, 1H), 3.98 (d, J = 10.3 Hz, 1H), 3.85 (d, J = 9.3 Hz, 1H), 3.81-3.68 (m, 1H), 3.62-3.49 (m, 2H), 3.24-3.14 (m, 1H), 3.14-2.89 (m, 3H), 2.67-2.55 (m, 1H), 2.52 (s, 3H), 2.37 (dd, J = 18.6, 9.2 Hz, 1H), 2.30 (s, 6H), 2.02-1.63 (m, 9H), 1.45 (d, J = 7.0 Hz, 3H), 1.37 (s, 3H), 1.31 (s, 3H), 1.28 (d, J = 10.9 Hz, 3H), 1.25 (d, J = 5.6 Hz, 3H), 1.23-1.20 (m, 1H), 1.10 (d, J = 6.8 Hz, 4H), 0.92 (t, J = 7.4 Hz, 3H). | HRMS (ESI): Calcd for (C$_{42}$H$_{64}$N$_6$O$_{10}$ + H)$^+$: 813.4762; Found: 813.4757 |
| 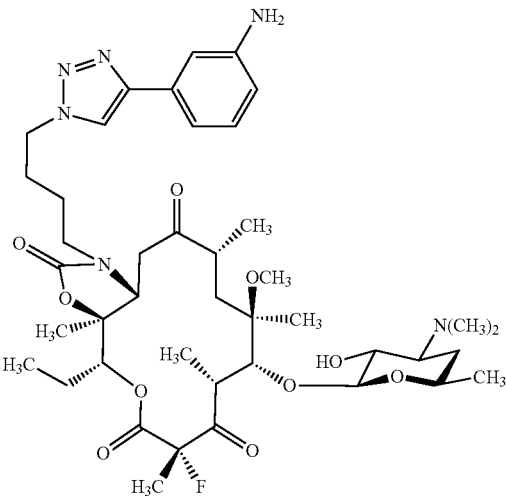<br>FSM-21598 | $^1$H NMR (500 MHz, CDCl$_3$) δ 7.81 (s, 1H), 7.26-7.13 (m, 3H), 6.68-6.61 (m, 1H), 4.96 (dd, J = 8.1, 3.8 Hz, 1H), 4.45 (dd, J = 7.4, 6.2 Hz, 2H), 4.36 (d, J = 7.3 Hz, 1H), 3.86 (d, J = 9.8 Hz, 1H), 3.81 (d, J = 9.7 Hz, 1H), 3.76-3.63 (m, 1H), 3.59-3.48 (m, 2H), 3.20 (dd, J = 10.2, 7.3 Hz, 1H), 3.09 (d, J = 18.7 Hz, 1H), 3.06-2.99 (m, 1H), 2.63-2.55 (m, 1H), 2.55-2.45 (m, 1H), 2.42 (s, 3H), 2.34 (dd, J = 18.7, 9.9 Hz, 1H), 2.29 (s, 6H), 2.09-1.81 (m, 5H), 1.77 (d, J = 21.4 Hz, 3H), 1.74-1.54 (m, 4H), 1.40 (s, 3H), 1.33 (d, J = 6.8 Hz, 3H), 1.29 (s, 3H), 1.28-1.26 (m, 1H), 1.25 (d, J = 6.1 Hz, 3H), 1.11 (d, J = 6.9 Hz, 3H), 0.98 (t, J = 7.5 Hz, 3H). $^{13}$C NMR (126 MHz, CDCl$_3$) δ 210.78, 202.42 (d, J = 29.1 Hz), 165.28 (d, J = 23.4 Hz), 157.08, 147.79, 146.83, 131.61, 129.66, 119.72, 116.03, 114.78, 112.21, 104.30, 96.39 (d, J = 207.0 Hz), 83.06, 81.30, 81.18, 79.02, 70.29, 69.55, 65.81, 60.66, 49.75, 48.90, 43.63, 42.68, 40.64, 40.22, 39.20, 36.22, 28.24, 27.48, 25.96 (d, J = 23.2 Hz), 25.04, 23.87, 21.12, 18.79, 17.87, 16.10, 15.25, 10.67. | FTIR (neat), cm$^{-1}$: 3381(br), 2974 (s), 2098 (s), 1753 (s), 1712 (s), 1267 (s), 1053 (s), 731 (s); HRMS (ESI): Calcd for (C$_{42}$H$_{63}$FN$_6$O$_{10}$ + H)$^+$: 831.4662; Found: 831.4668. |

TABLE Y1-continued

| Compound and ID | NMR Data | MS Data |
|---|---|---|
| 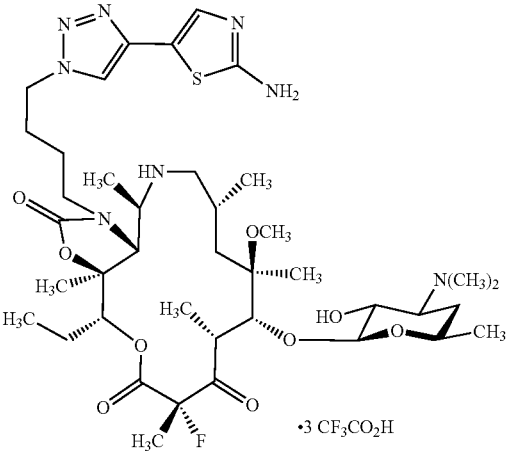<br>FSM-21760 | $^1$H NMR (500 MHz, CD$_3$OD) δ 8.31 (s, 1H), 7.50 (s, 1H), 4.99 (dd, J = 10.7, 2.1 Hz, 1H), 4.61 (d, J = 6.6 Hz, 1H), 4.60-4.43 (m, 2H), 4.21 (d, J = 10.1 Hz, 1H), 3.85-3.69 (m, 2H), 3.64 (q, J = 6.6 Hz, 1H), 3.53-3.44 (m, 2H), 3.35 (d, J = 9.4 Hz, 1H), 3.25 (s, 3H), 3.21 (s, 1H), 3.20-3.12 (m, 1H), 2.91 (s, 3H), 2.82 (s, 3H), 2.68 (t, J = 11.7 Hz, 1H), 2.16 (dd, J = 15.7, 6.0 Hz, 1H), 2.08 (d, J = 12.8 Hz, 1H), 2.05-1.99 (m, 4H), 1.96 (d, J = 21.6 Hz, 3H), 1.93-1.86 (m, 2H), 1.81-1.70 (m, 3H), 1.66 (d, J = 6.9 Hz, 3H), 1.61 (s, 3H), 1.59-1.53 (m, 1H), 1.43 (s, 3H), 1.38 (d, J = 6.1 Hz, 3H), 1.28 (d, J = 6.7 Hz, 3H), 1.07 (d, J = 7.1 Hz, 3H), 0.98 (t, J = 7.4 Hz, 3H). | HRMS (ESI): Calcd for (C$_{40}$H$_{65}$FN$_8$O$_9$S + H)$^+$: 853.4652; Found: 853.4658. |
| 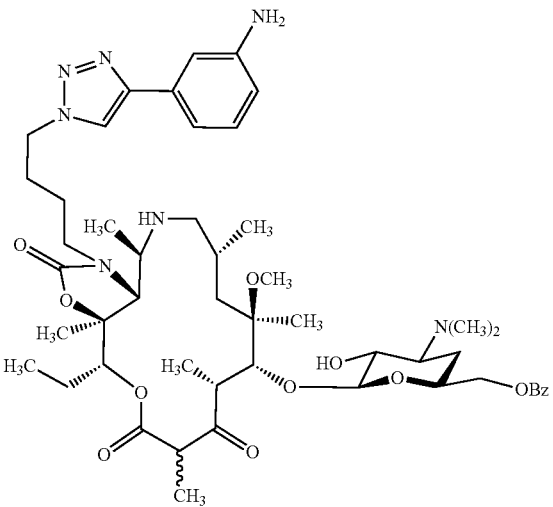<br>FSM-21797 | This compounds exists as a 2:1 mixture of C2-epimers. Protons are reported as seen. $^1$H NMR (500 MHz, CDCl$_3$) δ 8.06 (d, J = 7.3 Hz, 2H), 8.03 (d, J = 7.2 Hz, 2H), 7.88 (s, 1H), 7.83 (d, J = 9.2 Hz, 1H), 7.61-7.52 (m, 2H), 7.44 (dt, J = 22.5, 8.0 Hz, 4H), 7.26-7.12 (m, 6H), 6.68-6.61 (m, 2H), 4.94-4.77 (m, 2H), 4.72-4.52 (m, 2H), 4.52-4.35 (m, 6H), 4.27-4.14 (m, 2H), 4.14-3.51 (m, 12H), 3.23 (s, 2H), 3.09 (t, J = 39.7 Hz, 2H), 2.78 (dd, J = 21.3, 15.0 Hz, 2H), 2.74-2.53 (m, 4H), 2.52 (s, 6H), 2.51 (s, 6H), 2.08-1.82 (m, 8H), 1.82-1.50 (m, 8H), 1.50-1.41 (m, 6H), 1.38 (s, 6H), 1.32-1.29 (m, 2H), 1.29-1.23 (m, 6H), 1.21 (s, 1H), 1.20 (s, 1H), 1.02 (d, J = 3.2 Hz, 3H), 1.01 (d, J = 3.4 Hz, 3H), 0.96 (d, J = 6.7 Hz, 3H), 0.94 (d, J = 6.5 Hz, 3H), 0.86 (t, J = 5.6 Hz, 6H). | HRMS (ESI): Calcd for (C$_{50}$H$_{73}$N$_7$O$_{12}$ + H)$^+$: 964.5390; Found: 964.5407. |
| 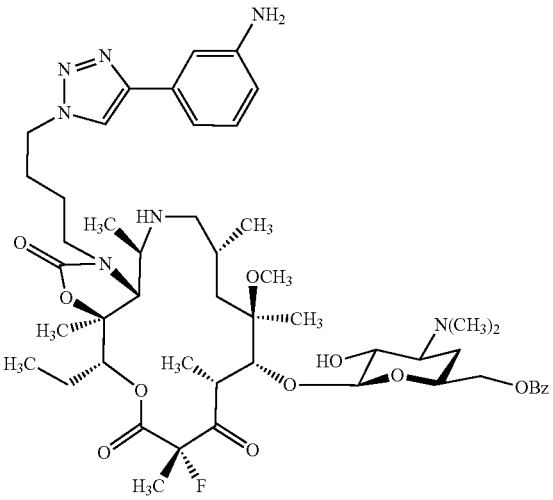<br>FSM-21798 | $^1$H NMR (500 MHz, CDCl$_3$) δ 8.08 (d, J = 7.3 Hz, 2H), 7.82 (d, J = 4.0 Hz, 1H), 7.58 (t, J = 7.4 Hz, 1H), 7.47 (t, J = 7.8 Hz, 2H), 7.25-7.09 (m, 3H), 6.65 (dd, J = 7.4, 2.2 Hz, 1H), 4.92 (d, J = 9.0 Hz, 1H), 4.86 (d, J = 6.8 Hz, 1H), 4.69 (dd, J = 12.0, 7.4 Hz, 1H), 4.46 (t, J = 7.2 Hz, 2H), 4.39 (dd, J = 11.9, 4.1 Hz, 1H), 4.28-4.22 (m, 1H), 4.14 (d, J = 8.1 Hz, 1H), 4.06 (s, 1H), 3.90 (dd, J = 10.0, 6.7 Hz, 1H), 3.82-3.73 (m, 2H), 3.64 (d, J = 6.7 Hz, 2H), 3.20 (s, 3H), 3.04 (s, 1H), 2.93-2.85 (m, 2H), 2.68-2.59 (m, 2H), 2.55 (s, 6H), 2.12-1.77 (m, 5H), 1.71 (d, J = 21.5 Hz, 3H), 1.68-1.53 (m, 5H), 1.48 (s, 3H), 1.43 (d, J = 14.9 Hz, 1H), 1.37 (d, J = 7.0 Hz, 3H), 1.33 (s, 3H), 1.30-1.21 (m, 1H), 0.95 (d, J = 6.9 Hz, 6H), 0.90 (t, J = 7.3 Hz, 3H). | HRMS (ESI): Calcd for (C$_{50}$H$_{72}$FN$_7$O$_{12}$ + H)$^+$: 982.5296; Found: 982.5294. |

| Compound and ID | NMR Data | MS Data |
|---|---|---|
| 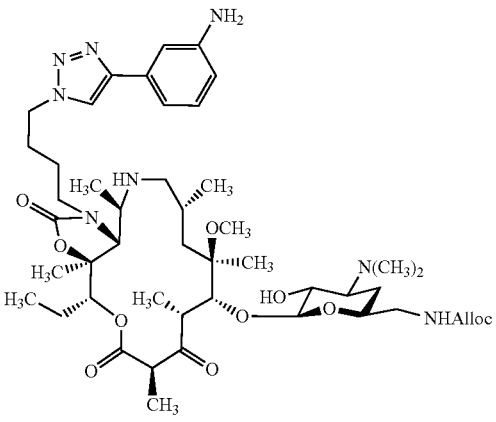<br>FSM-21795 | $^1$H NMR (500 MHz, CDCl$_3$) δ 7.81 (s, 1H), 7.25-7.06 (m, 3H), 6.73-6.62 (m, 1H), 5.98-5.86 (m, 1H), 5.33-5.25 (m, 1H), 5.25-5.14 (m, 1H), 5.05 (t, J = 5.6 Hz, 1H), 4.97 (dd, J = 10.8, 1.8 Hz, 1H), 4.59 (d, J = 10.1 Hz, 2H), 4.52 (t, J = 4.1 Hz, 1H), 4.50-4.42 (m, 2H), 4.40 (d, J = 7.4 Hz, 1H), 3.89 (q, J = 6.8 Hz, 1H), 3.78-3.58 (m, 3H), 3.46 (dd, J = 8.9, 4.7 Hz, 1H), 3.42 (s, 1H), 3.37-3.28 (m, 1H), 3.21 (dd, J = 10.1, 7.5 Hz, 1H), 3.11-2.98 (m, 1H), 2.95 (s, 3H), 2.77 (dt, J = 9.8, 4.3 Hz, 2H), 2.60-2.45 (m, 1H), 2.28 (s, 6H), 2.13-1.83 (m, 4H), 1.83-1.51 (m, 7H), 1.44 (s, 3H), 1.41 (d, J = 6.9 Hz, 3H), 1.38 (d, J = 7.8 Hz, 3H), 1.25 (s, 3H), 1.19 (d, J = 12.9 Hz, 1H), 0.99 (d, J = 6.1 Hz, 3H), 0.94 (d, J = 6.9 Hz, 3H), 0.89 (t, J = 7.4 Hz, 3H). | — |
| 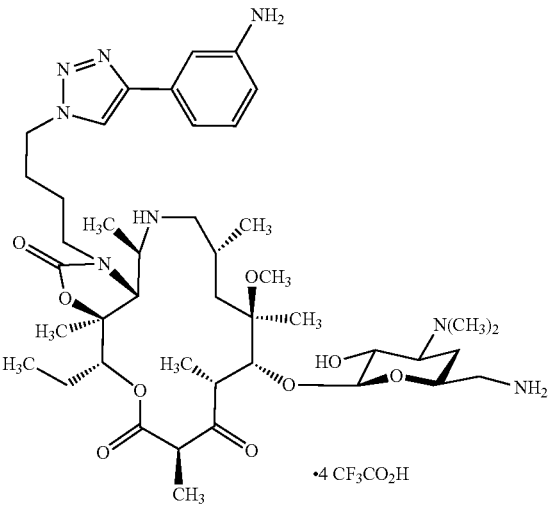<br>FSM-21700 | $^1$H NMR (500 MHz, CD$_3$OD) δ 8.43 (s, 1H), 7.84 (d, J = 6.8 Hz, 2H), 7.60 (t, J = 8.2 Hz, 1H), 7.34 (d, J = 8.4 Hz, 1H), 4.94 (dd, J = 10.6, 1.9 Hz, 1H), 4.62 (d, J = 3.2 Hz, 1H), 4.61-4.45 (m, 3H), 4.18 (q, J = 6.9 Hz, 1H), 4.01 (dd, J = 10.3, 8.6 Hz, 1H), 3.80 (dt, J = 15.2, 7.8 Hz, 1H), 3.67 (q, J = 6.1 Hz, 1H), 3.63 (s, 1H), 3.60-3.52 (m, 2H), 3.44 (dd, J = 11.9, 3.1 Hz, 1H), 3.23 (dd, J = 13.4, 8.1 Hz, 1H), 3.19 (s, 3H), 3.17-3.00 (m, 2H), 2.91 (s, 3H), 2.84 (s, 3H), 2.77 (t, J = 11.8 Hz, 1H), 2.25-1.97 (m, 3H), 1.97-1.59 (m, 8H), 1.55 (s, 3H), 1.44 (s, 3H), 1.38 (d, J = 7.6 Hz, 3H), 1.35 (d, J = 6.5 Hz, 3H), 1.33 (d, J = 4.7 Hz, 3H), 1.29-1.25 (m, 1H), 1.10 (d, J = 7.1 Hz, 3H), 0.91 (t, J = 7.7 Hz, 3H). | HRMS (ESI): Calcd for (C$_{43}$H$_{70}$N$_8$O$_9$ + H)$^+$: 843.5339; Found: 843.5353. |

V. Sugar Modifications

Some macrolides with modified desosamine residues exhibit potent activity against several key erythromycin-resistant pathogens. However, modification of the desosamine residue is impractical with semi-synthetic approaches. A fully synthetic approach to the macrolide scaffold allows for any sugar to be appended without a change in linear step count. Efforts for the synthesis of modified desosamine glycosyl donors and key intermediates for the synthesis of the eastern half applicable to the practical synthesis of novel macrolides antibiotic candidates was carried out.

Example V-1. Synthesis of 6-Allyloxycarbonylamino-D-Desosamine Donor 1v

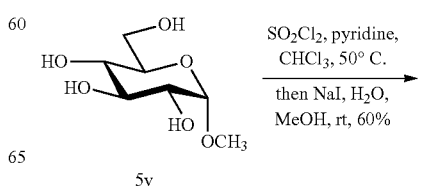

783

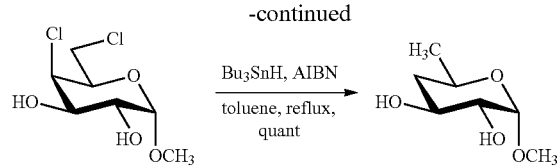
6v → 7v

Bu₃SnH, AIBN
toluene, reflux,
quant

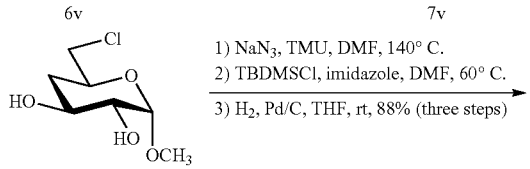
8v

1) NaN₃, TMU, DMF, 140° C.
2) TBDMSCl, imidazole, DMF, 60° C.
3) H₂, Pd/C, THF, rt, 88% (three steps)

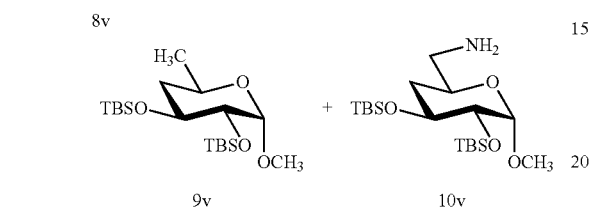
9v    10v 10v
1) Allyl chloroformate, Et₃N, MeCN, MeOH, rt
2) TBAF, THF, rt, 94% (two steps)

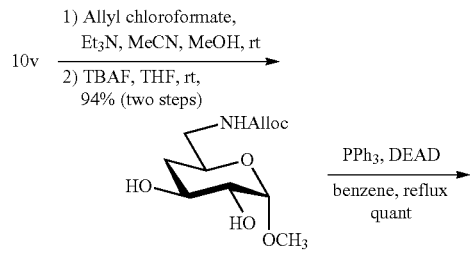
11v

PPh₃, DEAD
benzene, reflux
quant

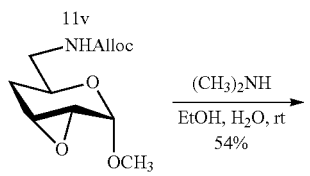
12v (CH₃)₂NH
EtOH, H₂O, rt
54%

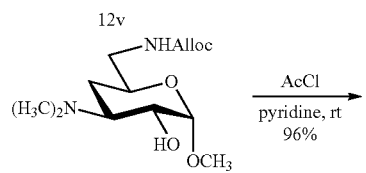
13v

AcCl
pyridine, rt
96%

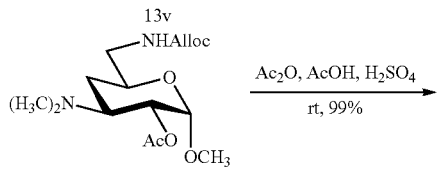
14v

Ac₂O, AcOH, H₂SO₄
rt, 99%

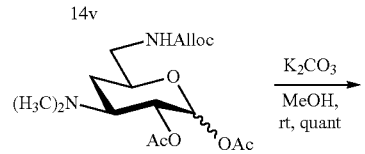
15v

K₂CO₃
MeOH,
rt, quant

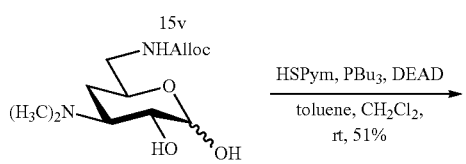
16v

HSPym, PBu₃, DEAD
toluene, CH₂Cl₂,
rt, 51%

784

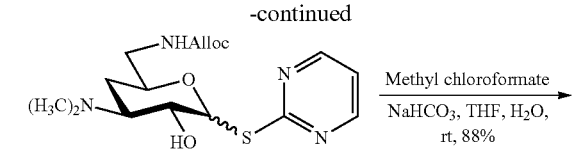
17v

Methyl chloroformate
NaHCO₃, THF, H₂O,
rt, 88%

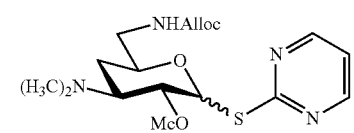
1v

Example V-2. Synthesis of 4,6-Dihydroxy-D-Desosamine Donor 2v

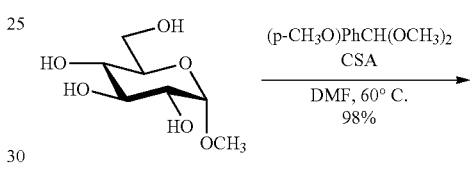
5v (p-CH₃O)PhCH(OCH₃)₂
CSA
DMF, 60° C.
98%

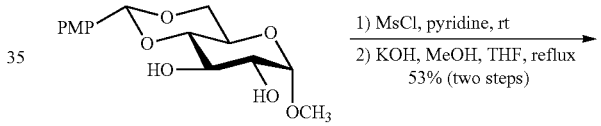
18v

1) MsCl, pyridine, rt
2) KOH, MeOH, THF, reflux
53% (two steps)

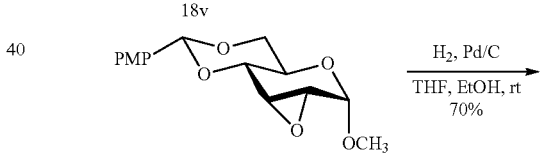
19v

H₂, Pd/C
THF, EtOH, rt
70%

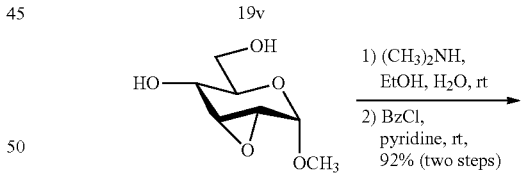
20v 1) (CH₃)₂NH, EtOH, H₂O, rt
2) BzCl, pyridine, rt,
92% (two steps)

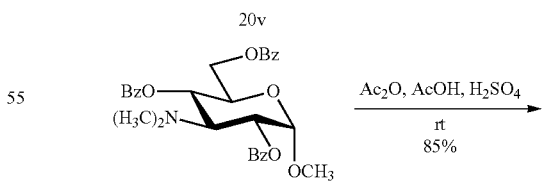
21v

Ac₂O, AcOH, H₂SO₄
rt
85%

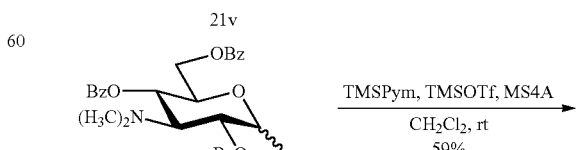
22v

TMSPym, TMSOTf, MS4A
CH₂Cl₂, rt
59%

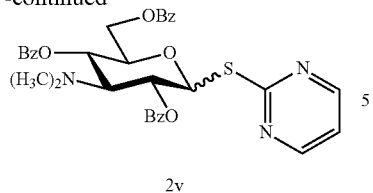

2v

Exemplary Synthetic Methods for Sugars

Synthesis of D-Desosamine Donor 1v

Step 1: Methyl 4,6-dideoxy-4,6-dichloro-α-D-galactopyranoside[2]

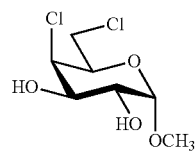

6v

Sulfuryl chloride (16.7 mL, 206 mmol, 8.0 equiv) was added dropwise over 1 h to a solution of methyl α-D-glucopyranoside (5.0 g, 25.7 mmol) in pyridine (30 mL) and chloroform (30 mL) at −78° C. The yellow suspension was stirred at −78° C. for 2 h and warmed to rt. The reaction mixture was heated to 50° C. and stirred for 40 h. After cooling to rt, the solution was diluted with methanol (15 mL) and water (15 mL) and subsequently neutralized by slow addition of solid sodium carbonate. A solution of sodium iodide (1.9 g, 12.7 mmol) in water (5 mL) and methanol (5 mL) was added to the reaction mixture, and the mixture was stirred an additional 10 min. The resulting mixture was filtered to remove insoluble matter and washed with chloroform (50 mL). The filtrate was separated into two layers and the aqueous layer was extracted with five 25-mL portions of chloroform. The combined organic layers were concentrated under reduced pressure. The residue was recrystallized from chloroform to provide methyl 4,6-dideoxy-4,6-dichloro-α-D-galactopyranoside (3.55 g, 60%) as a colorless solid. $^1$H NMR (CDCl$_3$, 500 MHz) δ=4.85 (d, 1H, J=3.8 Hz, H-1), 4.53 (d, 1H, J=3.1 Hz, H-4), 4.14 (t, 1H, J=6.5 Hz, H-5), 3.99 (dd, 1H, J=9.8 Hz, 3.1 Hz, H-3), 3.85 (dd, 1H, J=9.8 Hz, 3.8 Hz, H-2), 3.67 (d, 2H, J=6.5 Hz, H-6), 3.48 (s, 3H, OCH$_3$); $^{13}$C NMR (CDCl$_3$, 100 MHz) δ=99.4, 70.0, 69.4, 62.6, 55.9, 42.8; HRMS (ESI) Calcd for C$_7$H$_{12}$Cl$_2$NaO$_4$ [M+Na]$^+$: 253.0010. Found: 253.0020.

Step 2: Methyl 4,6-dideoxy-α-D-glucopyranoside[2], Methyl 6-chloro-4,6-dideoxy-α-D-glucopyranoside

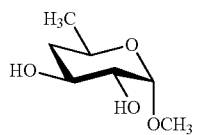

7v

+

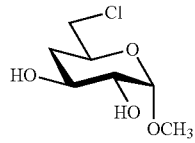

8v

Tributyltin hydride (98.0 mL, 364 mmol, 4.8 equiv) was added dropwise to a solution of methyl 4,6-dideoxy-4,6-dichloro-α-D-glucopyranoside (17.5 g, 76 mmol) and 2,2'-azobis(2-methylpropionitrile) (373 mg, 2.27 mmol, 0.03 equiv) in toluene (613 mL). The reaction mixture was refluxed for 12 h. After cooling to rt, the solution was diluted with acetonitrile and washed with five 250-mL portions of n-hexane. The combined organic layers were concentrated under reduced pressure. The residue was dissolved in water and washed with five 250-mL portions of diethyl ether. The combined organic layers were concentrated under reduced pressure. The residue was passed through a column of silica (dichloromethane/acetone, 10:1~3:1) to provide a mixture of methyl 4,6-dideoxy-α-D-glucopyranoside and methyl 6-chloro-4,6-dideoxy-α-D-glucopyranoside (13.2 g, quant, 30:70) as a colorless solid. The mixture was used in the next reaction step without separation. methyl 4,6-dideoxy-α-D-glucopyranoside: $^1$H NMR (CDCl$_3$, 400 MHz) δ=4.72 (d, 1H, J=3.6 Hz, H-1), 3.91-3.78 (m, 2H, H-3, H-5), 3.38 (s, 3H, OCH$_3$), 3.42-3.35 (m, 1H, H-2), 1.96 (ddd, J=12.3 Hz, 4.8 Hz, 1.6 Hz, H-4$_α$), 1.34 (q, 1H, J=12.3 Hz, H-4p), 1.19 (d, 3H, J=6.8 Hz, H-6); $^{13}$C NMR (CDCl$_3$, 100 MHz) δ=99.9, 74.4, 68.7, 64.1, 55.1, 39.9, 20.8; HRMS (ESI) Calcd for C$_7$H$_{14}$NaO$_4$ [M+Na]$^+$: 185.0790. Found: 185.0767. methyl 6-chloro-4,6-dideoxy-α-D-glucopyranoside: $^1$H NMR (CDCl$_3$, 400 MHz) δ=4.80 (d, 1H, J=3.6 Hz, H-1), 3.97-3.83 (m, 2H, H-3, H-5), 3.53 (d, 2H, J=5.2 Hz, H-6), 3.40 (s, 3H, OCH$_3$), 3.42-3.39 (m, 1H, H-2), 2.05 (dd, J=12.1 Hz, 3.6 Hz, H-4$_α$), 1.47 (q, 1H, J=12.1 Hz, H-4$_β$); $^{13}$C NMR (CDCl$_3$, 100 MHz) δ=99.8, 74.1, 68.2, 67.9, 55.3, 46.5, 35.7; HRMS (ESI) Calcd for C$_7$H$_{13}$ClNaO$_4$ [M+Na]$^+$: 219.0400. Found: 219.0397.

Step 3: Methyl 6-allyloxycarbonyloxyamino-4,6-dideoxy-α-D-glucopyranoside

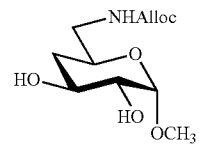

11v

Sodium azide (26.0 g, 400 mmol, 5.0 equiv of methyl 6-chloro-4,6-dideoxy-α-D-glucopyranoside) and tetramethylurea (3.95 mL, 33.6 mmol) was added to a solution of a mixture of methyl 4,6-dideoxy-α-D-glucopyranoside and methyl 6-chloro-4,6-dideoxy-α-D-glucopyranoside (22.2 g, 1:2) in DMF (750 mL). The reaction mixture was stirred at 140° C. for 18 h. After cooling to rt, the suspension was filtered, and the filtrate was concentrated under reduced pressure. The residue was passed through a column of silica (n-hexane/ethyl acetate, 1:1~0:1, dichloromethane/acetone, 3:1) to provide a mixture of methyl 4,6-dideoxy-α-D-glucopyranoside and methyl 6-azido-4,6-dideoxy-α-D-glucopyranoside (22.8 g, quant). tert-Butyldimethylsilylchloride (71.9 g, 477 mmol, 4.0 equiv) was added dropwise to a solution of a mixture of methyl 4,6-dideoxy-α-D-glucopyranoside and methyl 6-azido-4,6-dideoxy-α-D-glucopyranoside (22.8 g) and imidazole (64.9 g, 954 mmol, 8.0 equiv) in DMF (186 mL). The reaction mixture was stirred at 60° C. for 10 h. After cooling to rt, the solution was diluted with ethyl acetate and washed with five 200-mL portions of water. The combined organic layers were washed with brine and dried over sodium sulfate, and concentrated under reduced pressure. The residue was passed through a column of silica (n-hexane/ethyl acetate, 200:1~80:1) to provide a mixture of methyl 2,3-di(O-tert-butyldimethylsilyl)-4,6-dideoxy-α-D-glucopyranoside and methyl 6-azido-2,3-di(O-tert-butyldimethylsilyl)-4,6-dideoxy-α-D-glucopyranoside (49.9 g, quant).

To a 2 L-round-bottom flask with a stir bar were added a mixture of methyl 2,3-di(O-tert-butyldimethylsilyl)-4,6-dideoxy-α-D-glucopyranoside and methyl 6-azido-2,3-di(O-tert-butyldimethylsilyl)-4,6-dideoxy-α-D-glucopyranoside (49.9 g), 10% Pd/C (6.9 g, 20 wt % of methyl 6-azido-4,6-dideoxy-α-D-glucopyranoside) and THF (470 mL) and the system was sealed with a septum. The air inside was replaced with hydrogen (balloon) by five vacuum/argon cycles and the mixture was stirred at rt for 18 h. The reaction mixture was filtered through a Celite pad and washed with THF. The filtrate was concentrated under reduced pressure. The residue was passed through a column of silica (n-hexane/ethyl acetate, 40:1~2:1, ethyl acetate/methanol, 2:1) to provide methyl 2,3-di(O-tert-butyldimethylsilyl)-4,6-dideoxy-α-D-glucopyranoside (15.5 g, quant) and methyl 6-amino-2,3-di(O-tert-butyldimethylsilyl)-4,6-dideoxy-α-D-glucopyranoside (28.2 g, 88%).

Allyl chloroformate (11.1 mL, 104 mmol, 1.5 equiv) was added dropwise to a solution of methyl 6-amino-2,3-di(O-tert-butyldimethylsilyl)-4,6-dideoxy-α-D-glucopyranoside (28.2 g, 69.5 mmol) and triethylamine (14.5 mL, 104 mmol, 1.5 equiv) in acetonitrile (250 mL) and methanol (250 mL) at 0° C. The reaction mixture was stirred at rt for 10 h. Triethylamine (4.8 mL, 35 mmol, 0.5 equiv) and allyl chloroformate (3.7 mL, 35 mmol, 0.5 equiv) was added dropwise to the reaction mixture at 0° C. The reaction mixture was stirred at rt for 2 h. After the solvent was removed under reduced pressure, the residue was diluted with dichloromethane and water. The resulting mixture was separated into two layers and the aqueous layer was extracted with three 50-mL portions of dichloromethane. The combined organic layers were washed with brine and dried over sodium sulfate, and concentrated under reduced pressure. The residue was passed through a column of silica (n-hexane/ethyl acetate, 25:1~5:1) to provide methyl 6-allyloxycarbonylamino-2,3-di(O-tert-butyldimethylsilyl)-4,6-dideoxy-α-D-glucopyranoside (34.0 g, quant) as a colorless oil.

To a 1 L-round-bottom flask with a stir bar were added methyl 6-allyloxycarbonylamino-2,3-bis-(O-tert-butyldimethylsilyl)-4,6-dideoxy-α-D-glucopyranoside (34.0 g) and a 1.0 M solution of tetrabutylammoniumfluoride in THF (200 mL, 200 mmol, 2.9 equiv). The resulting mixture was stirred at rt for 12 h. calcium carbonate (45.0 g), DOWEX 50WX8-400 (135 g, without purification and activation) and methanol (324 mL) was added the reaction mixture and the suspension was stirred at rt for 2 h. The reaction mixture was filtered through a Celite pad and washed with methanol. The filtrate was concentrated under reduced pressure. The residue was passed through a column of silica (dichloromethane/acetone, 5:1~2:1) to provide methyl 6-allyloxycarbonylamino-4,6-dideoxy-α-D-glucopyranoside (17.1 g, 94%) as a colorless solid.

mp: 115-117° C.; $^1$H NMR (CDCl$_3$, 400 MHz) δ=5.95-5.85 (m, 1H, OCH$_2$CH=CH$_2$), 5.29 (d, 1H, J=17.2 Hz, OCH$_2$CH=CH$_{2\alpha}$), 5.20 (d, 1H, J=10.4 Hz, OCH$_2$CH=CH$_{2\beta}$), 4.75 (d, 1H, J=3.2 Hz, H-1), 4.56 (d, 2H, J=4.8 Hz, OCH$_2$CH=CH$_2$), 3.87-3.80 (m, 2H, H-2, H-5), 3.43-3.32 (m, 2H, H-3, H-6$_\alpha$), 3.37 (s, 3H, OCH$_3$), 3.19-3.12 (m, 1H, H-6$_\beta$), 1.97-1.93 (m, 1H, H-4$_\alpha$), 1.38 (q, 1H, J=12.0 Hz, H-4$_\beta$); $^{13}$C NMR (CDCl$_3$, 100 MHz) δ=156.3, 132.7, 117.7, 99.7, 74.3, 68.4, 67.1, 65.6, 55.2, 44.7, 35.1; HRMS (ESI) Calcd for C$_{11}$H$_{19}$NNaO$_6$ [M+Na]$^+$: 284.1110. Found: 284.1146.

Step 4: Methyl 6-allyloxycarbonylamino-α-D-desosamine

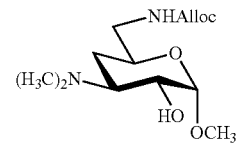

13v

A 40% solution of diethyl azodicarboxylate in toluene (42.3 mL, 98 mmol, 1.5 equiv) was added dropwise to a solution of methyl 6-allyloxycarbonylamino-4,6-dideoxy-α-D-glucopyranoside (17.1 g, 65.6 mmol), triphenylphosphine (25.8 g, 98 mmol, 1.5 equiv), MS4A (17.3 g) in benzene (650 mL). The reaction mixture was refluxed for 18 h. After cooling to rt, the solution was concentrated under reduced pressure. The residue was passed through a column of silica (n-hexane/diethyl ether, 5:1~0:1) to provide methyl 2,3-anhydro-4,6-dideoxy-α-D-allopyranoside (35.0 g, crude).

A 40% solution of dimethylamine in water (270 mL, 2.41 mol, 36.7 equiv) was added to a solution of methyl 2,3-anhydro-4,6-dideoxy-α-D-allopyranoside (35.0 g, crude) in ethanol (310 mL). The reaction mixture was stirred at rt for 40 h. After the solvent was removed under reduced pressure, the residue was dissolved in ethanol (310 mL) and 40% solution of dimethylamine in water (270 mL, 2.41 mol, 36.7 equiv) was added to the reaction mixture. The reaction mixture was stirred at rt for 40 h. After the solvent was removed under reduced pressure, the residue was passed through a column of silica (dichloromethane/acetone, 20:1, dichloromethane/methanol, 20:1~5:1) to provide methyl 6-allyloxycarbonylamino-α-D-desosaminide (10.2 g, 54%) as a colorless oil.

$^1$H NMR (CDCl$_3$, 400 MHz) δ=5.95-5.88 (m, 1H, OCH$_2$CH=CH$_2$), 5.30 (d, 1H, J=17.2 Hz, OCH$_2$CH=CH$_{2\alpha}$), 5.22 (d, 1H, J=10.4 Hz, OCH$_2$CH=CH$_{2\beta}$), 4.86 (d, 1H, J=3.2 Hz, H-1), 4.58 (d, 2H, J=3.6 Hz, OCH$_2$CH=CH$_2$), 3.88-3.85 (m, 1H, H-5), 3.61 (dd, 1H, J=7.0 Hz, 2.2 Hz, H-2), 3.44-3.34 (m, 4H, H-6$_a$, OCH$_3$), 3.20-3.11 (m, 2H, H-3, H-6$_\beta$), 2.42 (s, 6H, N(CH$_3$)$_2$), 1.84 (d, 1H, J=8.2 Hz, H-4$_\alpha$), 1.36 (q, 1H, J=8.2 Hz, H-4$_\beta$); $^{13}$C NMR (CDCl$_3$, 100 MHz) δ=156.2, 132.6, 117.7, 99.3, 68.3, 67.7, 65.3, 59.8, 54.8, 44.8, 39.6, 24.3; HRMS (ESI) Calcd for C$_{13}$H$_{25}$N$_2$O$_5$ [M+H]$^+$: 289.1763. Found: 289.1764.

Step 5: Methyl 2-O-acetyl-6-allyloxycarbonylamino-α-D-desosaminide

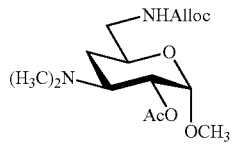

14v

Acetyl chloride (192 μL, 2.71 mmol, 5.0 equiv) were added to a solution of methyl 6-allyloxycarbonylamino-a-d-desosaminide (156 mg, 541 μmol) pyridine (1.2 mL). The resulting mixture was stirred at rt for 48 h. A saturated aqueous NaHCO$_3$ (12 mL) and ethyl acetate (6 mL) were added and the resulting mixture was stirred at rt for 1 h. The mixture was separated into two layers and the aqueous layer was extracted with three 10-mL portions of ethyl acetate. The combined organic layers were washed with brine and dried over sodium sulfate, and concentrated under reduced pressure. The residue was passed through a column of silica (dichloromethane/methanol, 1:0~20:1-10:1) to provide methyl 2-O-acetyl-6-allyloxycarbonylamino-a-d-desosaminide (171 mg, 96%) as a pale yellow oil. $^1$H NMR (acetone-d$_6$, 600 MHz) δ=5.95-5.89 (m, 1H, OCH$_2$CH=CH$_2$), 5.28 (dd, 1H, J=17.7 Hz, 1.4 Hz, OCH$_2$CH=CH$_{2\alpha}$), 5.14 (dd, 1H, J=10.8 Hz, 1.4 Hz, OCH$_2$CH=CH$_{2\beta}$), 4.80 (dd, 1H, J=10.5 Hz, 3.8 Hz, H-2), 4.73 (d, 1H, J=3.8 Hz, H-1), 4.51 (d, 2H, J=2.4 Hz, OCH$_2$CH=CH$_2$), 3.87-3.83 (m, 1H, H-5), 3.31 (s, 3H, OCH$_3$), 3.28-3.08 (m, 3H, H-3, H-6$_\alpha$, H-6$_\beta$), 2.23 (s, 6H, N(CH$_3$)$_2$), 2.00 (s, 3H, COCH$_3$), 1.82 (ddd, 1H, J=12.7 Hz, 4.2 Hz, 2.4 Hz, H-4$_\alpha$), 1.40 (q, 1H, J=12.7 Hz, H-4$_\beta$); $^{13}$C NMR (acetone-d$_6$, 100 MHz) δ=170.5, 157.1, 134.7, 116.9, 98.6, 71.3, 68.0, 65.4, 58.3, 54.9, 45.8, 40.7, 28.4, 21.0; HRMS (ESI) Calcd for C$_{15}$H$_{27}$N$_2$O$_6$ [M+H]$^+$: 331.1869. Found: 331.1864.

Step 6: 6-Allyloxycarbonylamino-1,2-O-diacetyl-D-desosamine

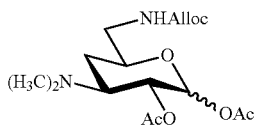

15v

Methyl 2-O-acetyl-6-allyloxycarbonylamino-α-D-desosaminide (736 mg, 2.23 mmol) was dissolved in a solution of acetic anhydride, acetic acid and sulfuric acid (8:2:0.1, prepared the day before) (37 mL) at 0° C. The mixture was stirred at 0° C. for 30 min and then at rt for 24 h. After addition of sodium acetate (296 mg) and water (37 mL), the reaction mixture was stirred at rt for 3 h to decompose the excess of acetic anhydride. After the solvent was removed under reduced pressure, the residue was diluted with ethyl acetate. A saturated sodium bicarbonate aqueous solution (40 mL) was added to the mixture and the organic layer was separated. The aqueous layer was extracted with ethyl acetate (3×40 mL). The combined organic layers were washed with brine (40 mL) and dried over sodium sulfate and concentrated under reduced pressure to provide 6-allyloxycarbonylamino-1,2-O-diacetyl-D-desosamine (α:β=5:1, 787 mg, 99%) as a pale yellow oil. $^1$H NMR (acetone-d$_6$, 600 MHz) major (α): δ=6.14 (d, 1H, J=4.2 Hz, H-1), 6.04-5.98 (m, 1H, OCH$_2$CH=CH$_2$), 5.42-5.39 (m, 1H, OCH$_2$CH=CH$_{2\alpha}$), 5.28-5.26 (m, 1H, OCH$_2$CH=CH$_{2\beta}$), 4.94 (dd, 1H, J=10.8 Hz, 3.6 Hz, H-2), 4.72-4.71 (m, 2H, OCH$_2$CH=CH$_2$), 4.16-4.11 (m, 1H, H-5), 3.93-3.78 (m, 2H, H-6$_\alpha$, H-6$_\beta$), 3.11 (dt, 1H, J=11.8 Hz, 4.0 Hz, H-3), 2.42 (s, 6H, N(CH$_3$)$_2$), 2.26 (s, 3H, COCH$_3$), 2.06 (s, 3H, COCH$_3$), 1.89-1.86 (m, 1H, H-4$_\alpha$), 1.47 (q, 1H, J=12.4 Hz, H-4$_\beta$); minor (β): δ=6.04-5.98 (m, 1H, OCH$_2$CH=CH$_2$), 5.50 (d, 1H, J=8.4 Hz, H-1), 5.42-5.39 (m, 1H, OCH$_2$CH=CH$_{2\alpha}$), 5.28-5.26 (m, 1H, OCH$_2$CH=CH$_{2\beta}$), 4.82 (dd, 1H, J=10.8 Hz, 8.4 Hz, H-2), 4.70-4.68 (m, 2H, OCH$_2$CH=CH$_2$), 4.16-4.11 (m, 1H, H-5), 3.98-3.82 (m, 2H, H-6$_\alpha$, H-6$_\beta$), 2.91-2.87 (m, 1H, H-3), 2.41 (s, 6H, N(CH$_3$)$_2$), 2.24 (s, 3H, COCH$_3$), 1.97 (s, 3H, COCH$_3$), 1.86-1.83 (m, 1H, H-4$_\alpha$), 1.42 (q, 1H, J=12.4 Hz, H-4$_\beta$); $^{13}$C NMR (acetone-d$_6$, 100 MHz) major (α): δ=170.3, 169.7, 155.0, 133.0, 118.5, 90.9, 69.9, 69.6, 67.8, 58.4, 47.8, 40.7, 28.4, 26.5, 20.8; HRMS (ESI) Calcd for C$_{16}$H$_{27}$N$_2$O$_7$ [M+H]$^+$: 359.1818. Found: 359.1824.

Step 7: 6-Allyloxycarbonylamino-D-desosamine

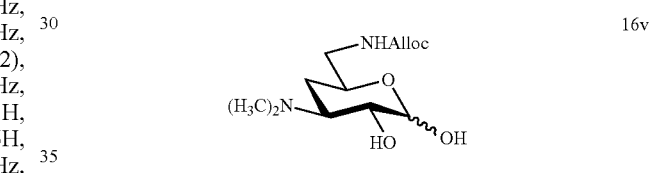

16v

Potassium carbonate (46.1 mg, 334 μmol, 1.2 equiv) was added to a solution of 6-allyloxycarbonylamino-1,2-O-diacetyl-D-desosamine (99.7 mg, 278 μmol) in methanol (4.7 mL) at 0° C. The mixture was stirred at 0° C. for 28 h. The reaction mixture was acidified (pH=ca. 6) with 1 M HCl and concentrated under reduced pressure. A saturated NaHCO$_3$ aqueous solution was added to the residue and it was basified (pH=ca. 9). The mixture was concentrated and the resulting insoluble matter was removed by filtration and washed with ethanol. The filtrate was concentrated and azeotroped with ethanol several times and dichloromethane several times. The residue was dissolved with dichloromethane and insoluble matter was removed by filtration and washed with dichloromethane. The filtrate was concentrated under reduced pressure to provide 6-allyloxycarbonylamino-D-desosamine (75.8 mg, quant) as a pale reddish foam. HRMS (ESI) Calcd for C$_{12}$H$_{23}$N$_2$O$_5$ [M+H]$^+$: 275.1607. Found: 275.1609.

Step 8: 6-Allyloxycarbonylamino-1-(2-pyrimidinethio)-D-desosamine

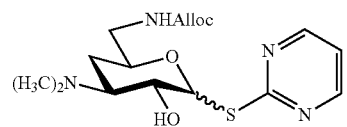

17v

A 40% solution of diethyl azodicarboxylate in toluene (2.50 mL, 5.73 mmol, 1.2 equiv) was added dropwise to a solution of tributylphosphine (1.41 mL, 5.73 mmol, 1.2 equiv) in toluene (43 mL) at −15° C. over 10 min. After stirring for 20 min, a suspension of 6-allyloxycarbonylamino-D-desosamine (1.31 g, 4.78 mmol) in dichloromethane (7.2 mL+3.6 mL×2 wash) was added to the mixture at the same temperature. After stirring for 45 min, 2-mercaptopyrimidine (643 mg, 5.73 mmol) was added. The resulting mixture was stirred at rt for 24 h. The reaction mixture was concentrated under reduced pressure. The residue was passed through a column of silica (dichloromethane/methanol, 20:1-5:1) to provide 6-allyloxycarbonylamino-1-(2-pyrimidinethio)-D-desosamine (α:β=1:7, 905 mg, 51%) as a pale yellow foam.

$^1$H NMR (CDCl$_3$, 600 MHz) major (β): δ=8.51 (d, 2H, J=4.8 Hz, CH of Pym), 6.99 (t, 1H, J=4.8 Hz, CH of Pym), 5.92-5.85 (m, 1H, OCH$_2$CH=CH$_2$), 5.52 (d, 1H, J=9.5 Hz, H-1), 5.26 (d, 1H, J=17.4 Hz, OCH$_2$CH=CH$_{2\alpha}$), 5.18 (d, 1H, J=10.2 Hz, OCH$_2$CH=CH$_{2\beta}$), 4.56-4.51 (m, 2H, OCH$_2$CH=CH$_2$), 3.72-3.69 (m, 1H, H-5), 3.53-3.45 (m, 2H, H-6$_a$, H-2), 3.12-3.08 (m, 1H, H-6$_\beta$), 2.73-2.67 (m, 1H, H-3), 2.31 (s, 6H, N(CH$_3$)$_2$), 1.81-1.78 (m, 1H, H-4$_\alpha$), 1.41 (q, 1H, J=12.2 Hz, H-4$_\beta$); minor (α): δ=8.54 (d, 2H, J=4.8 Hz, CH of Pym), 7.00 (t, 1H, J=4.8 Hz, CH of Pym), 6.68 (d, 1H, J=5.4 Hz, H-1), 5.92-5.85 (m, 1H, OCH$_2$CH=CH$_2$), 5.26 (d, 1H, J=17.4 Hz, OCH$_2$CH=CH$_{2\alpha}$), 5.18 (d, 1H, J=10.2 Hz, OCH$_2$CH=CH$_{2\beta}$), 4.48 (d, 2H, J=3.6 Hz, OCH$_2$CH=CH$_2$), 3.91 (dd, 1H, J=5.4 Hz, 4.5 Hz, H-2), 3.40-3.36 (m, 1H, H-6$_\alpha$), 3.22-3.17 (m, 1H, H-6$_\beta$), 2.77-2.73 (m, 1H, H-3), 2.30 (s, 6H, N(CH$_3$)$_2$), 1.81-1.78 (m, 1H, H-4$_\alpha$), 1.45-1.36 (m, 1H, H-4$_\beta$); $^{13}$C NMR (CDCl$_3$, 100 MHz) major (β): δ=170.5, 157.4, 156.3, 132.8, 117.4, 117.2, 84.9, 76.9, 67.9, 67.4, 65.5, 45.1, 40.3, 24.0; HRMS (ESI) Calcd for C$_{16}$H$_{25}$N$_4$O$_4$S [M+H]$^+$: 369.1597. Found: 369.1552.

Step 9: 6-Allyloxycarbonylamino-2-O-methoxycarbonyl-1-(2-pyrimidinethio)-D-desosamine

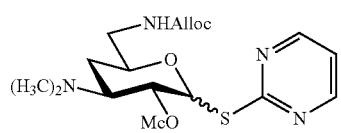

1v

Methyl chloroformate (92 μL, 1.19 mmol, 3.0 equiv) was added dropwise to a solution of 1-(2-pyrimidinethio)-6-allyloxycarbonylamino-D-desosamine (146 mg, 396 μmol) in THF (1.1 mL) and saturated sodium carbonate aqueous solution (1.1 mL). The reaction mixture was stirred at rt for 3 h. The mixture was diluted with acetone and concentrated under reduced pressure to reduce water in the mixture. The residue was passed through a column of silica (n-hexane/ethyl acetate/triethylamine, 5:4:1) to provide 6-allyloxycarbonylamino-2-O-methoxycarbonyl-1-(2-pyrimidinethio)-D-desosamine (149 mg, 88%) as a colorless foam. $^1$H NMR (CDCl$_3$, 500 MHz) major (β): δ=8.52 (d, 2H, J=5.0 Hz, CH of Pym), 7.01 (t, 1H, J=5.0 Hz, CH of Pym), 5.94-5.86 (m, 1H, OCH$_2$CH=CH$_2$), 5.60 (d, 1H, J=5.3 Hz, H-1), 5.28 (d, 1H, J=17.0 Hz, OCH$_2$CH=CH$_{2\alpha}$), 5.20 (d, 1H, J=10.0 Hz, OCH$_2$CH=CH$_{2\beta}$), 4.84 (t, J=5.3 Hz, H-2), 4.59-4.52 (m, 2H, OCH$_2$CH=CH$_2$), 3.79 (s, 3H, OCOCH$_3$), 3.73-3.69 (m, 1H, H-5), 3.52-3.47 (m, 1H, H-6$_\alpha$), 3.14-3.09 (m, 1H, H-6$_\beta$), 2.97-2.92 (m, 1H, H-3), 2.32 (s, 6H, N(CH$_3$)$_2$), 1.89-1.85 (m, 1H, H-4$_\alpha$), 1.53 (q, 1H, J=12.3 Hz, H-4$_\beta$); minor (α): δ=8.54 (d, 2H, J=5.0 Hz, CH of Pym), 7.01 (t, 1H, J=5.0 Hz, CH of Pym), 6.72 (d, 1H, J=5.2 Hz, H-1), 5.94-5.86 (m, 1H, OCH$_2$CH=CH$_2$), 5.28 (d, 1H, J=17.0 Hz, OCH$_2$CH=CH$_{2\alpha}$), 5.19-5.17 (m, 1H, OCH$_2$CH=CH$_{2\beta}$), 5.05 (dd, 1H, J=10.8 Hz, 5.2 Hz, H-2), 4.51-4.49 (m, 2H, OCH$_2$CH=CH$_2$), 3.81-3.76 (m, 1H, H-5), 3.75 (s, 3H, OCOCH$_3$), 3.47-3.39 (m, 1H, H-6$_\alpha$), 3.23-3.18 (m, 1H, H-6$_\beta$), 3.06-3.00 (m, 1H, H-3), 2.32 (s, 6H, N(CH$_3$)$_2$), 1.89-1.85 (m, 1H, H-4$_\alpha$), 1.53 (q, 1H, J=12.3 Hz, H-4$_\beta$); $^{13}$C NMR (CDCl$_3$, 125 MHz) major (β): δ=170.1, 157.4, 156.3, 155.0, 132.9, 117.4, 117.3, 83.1, 76.6, 72.0, 65.5, 64.7, 55.1, 44.9, 40.6, 26.1; HRMS (ESI) Calcd for C$_{18}$H$_{27}$N$_4$O$_6$S [M+H]$^+$: 427.1651. Found: 427.1645.

Synthesis of D-Desosamine Donor 2v

Step 1: Methyl 4,6-O-(4-methoxy)benzylidene-α-D-glucopyranoside

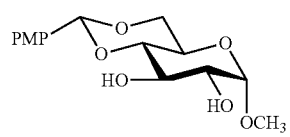

18v p-Anisaldehyde dimethylacetal (50 mL, 294 mmol, 1.14 equiv) was added to a suspension of a mixture of methyl α-D-glucopyranoside (50 g, 257 mmol) and D-camphorsulfonic acid (1.79 g, 7.72 mmol, 0.03 equiv) in DMF (250 mL). The reaction mixture was stirred at 60° C. for 21 h. After cooling to rt, the solution was concentrated under reduced pressure. A saturated sodium bicarbonate aqueous solution (500 mL) was added to the residue and the resulting mixture was stirred for 1 h. The precipitate was filtered and washed with cold aqueous saturated sodium bicarbonate solution (500 mL) to provide methyl 4,6-O-(4-methoxy)benzylidene-α-D-galactopyranoside (78.5 g, 98%) as a colorless solid. mp: 192-194° C.; $^1$H NMR (CD$_3$OD, 600 MHz) δ=7.40 (d, 2H, J=8.4 Hz, CH of Ar), 6.88 (d, 2H, J=8.4 Hz, CH of Ar), 5.51 (s, 1H, ArCH), 4.71 (d, 1H, J=3.8 Hz, H-1), 4.18 (dd, 1H, J=8.1 Hz, 3.3 Hz, H-6$_\alpha$), 3.81-3.78 (m, 1H, H-4), 3.78 (s, 3H, OCH$_3$ of An), 3.74-3.68 (m, 2H, H-3, H-6$_\beta$), 3.50 (dd, 1H, J=9.3 Hz, 3.8 Hz, H-2), 3.43-3.40 (m, 1H, H-5), 3.42 (s, 3H, OCH$_3$); $^{13}$C NMR (CD$_3$OD, 125 MHz) δ=161.6, 131.5, 128.8, 114.3, 103.0, 102.0, 82.9, 74.1, 72.0, 70.0, 63.9, 55.8, 55.7; HRMS (ESI) Calcd for C$_{15}$H$_{21}$O$_7$ [M+H]$^+$: 313.1287. Found: 313.1308.

Step 2: Methyl 2,3-anhydro-4,6-O-(4-methoxy)benzylidene-α-D-allopyranoside

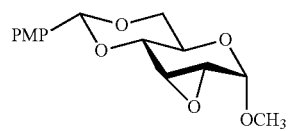

19v

Methanesulfonyl chloride (2.23 mL, 28.8 mmol, 3.0 equiv) was added dropwise to a solution of methyl 4,6-O-(4-methoxy)benzylidene-α-D-glucopyranoside (3.0 g, 9.61 mmol) in pyridine (20 mL). The reaction mixture was stirred at rt for 21 h. The reaction mixture was diluted with ethyl acetate and washed with 100-mL portions of water. The organic layer was washed with brine and dried over sodium sulfate, and concentrated under reduced pressure. The residue was used in the next reaction step without further purification. Potassium hydroxide (1.62 g, 28.8 mmol, 3.0 equiv) was added to a suspension of the residue in methanol (48 mL) and THF (32 mL). The reaction mixture was refluxed for 45 h. Then water was added, the reaction mixture was diluted with ethyl acetate and washed with 20 mL-portions of water. The combined organic layers were washed with brine and dried over sodium sulfate, and concentrated under reduced pressure. The residue was recrystallized from ethyl acetate to provide methyl 2,3-anhydro-4,6-O-(4-methoxy)benzylidene-α-D-allopyranoside (1.50 g, 53%) as a colorless solid. mp: 193-195° C.; $^1$H NMR (CDCl$_3$, 400 MHz) δ=7.42 (d, 2H, J=8.6 Hz, CH of Ar), 6.91 (d, 2H, J=8.6 Hz, CH of Ar), 5.53 (s, 1H, ArCH), 4.90 (s, 1H, H-1), 4.24 (dd, 1H, J=16.0 Hz, 10.4 Hz, H-4), 3.81 (s, 3H, OCH$_3$ of An), 3.75-3.64 (m, 3H, H-5, H-6), 3.52 (s, 3H, OCH$_3$), 3.47 (d, 1H, J=3.0 Hz, H-2), 3.17 (d, 1H, J=3.0 Hz, H-3); $^{13}$C NMR (CDCl$_3$, 100 MHz) δ=160.2, 129.6, 127.6, 113.7, 102.7, 95.3, 77.8, 68.9, 60.0, 55.9, 55.3, 53.1, 50.8; HRMS (ESI) Calcd for C$_{15}$H$_{19}$O$_6$ [M+H]$^+$: 295.1182. Found: 295.1184.

Step 3: Methyl 2,3-anhydro-α-D-allopyranoside$^8$

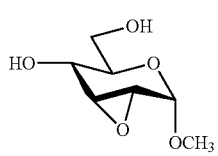

20v

To a 25 mL-round-bottom flask with a stir bar were added methyl 2,3-anhydro-4,6-O-(4-methoxy)-benzylidene-α-D-allopyranoside (4.0 g, 13.6 mmol), 5% Pd/C (1.6 g, 40 wt % of methyl 6-azido-4,6-dideoxy-α-D-glucopyranoside), ethanol (30 mL) and THF (90 mL). The system was sealed with a septum. The air inside was replaced with hydrogen (balloon) by five vacuum/argon cycles and the mixture was stirred at rt 18 h. The reaction mixture was filtered through a Celite pad and washed with THF and ethanol. The filtrate was concentrated under reduced pressure. The residue was dissolved in acetone and a precipitate was collected by filtration to afford methyl α-D-glucopyranoside (563 mg, 21%). The filtrate was concentrated under reduced pressure. The residue was passed through a column of silica dichloromethane/acetone, 20:1-3:1) to provide methyl 2,3-anhydro-α-D-allopyranoside (1.67 g, 70%) as a colorless solid. $^1$H NMR (CDCl$_3$, 300 MHz) δ=4.91 (s, 1H, H-1), 3.88 (s, 1H, H-4), 3.84-3.74 (m, 2H, H-6), 3.58-3.52 (m, 1H, H-5), 3.46 (s, 3H, OCH$_3$), 3.31 (d, 1H, J=3.8 Hz, H-2), 3.13 (d, 1H, J=3.8 Hz, H-3); $^{13}$C NMR (CDCl$_3$, 100 MHz) δ=96.0, 68.9, 62.6, 62.2, 55.7, 55.5, 49.9; HRMS (ESI) Calcd for C$_7$H$_{12}$NaO$_5$ [M+Na]$^+$: 199.0582. Found: 199.0580.

Step 4: Methyl 6-hydroxy-2,4,6-tri-O-benzoyl-α-D-mycaminoside

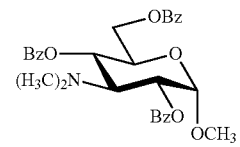

21v

A 40% solution of dimethylamine in water (32.9 mL, 292 mmol, 36.7 equiv) was added to a solution of methyl 2,3-anhydro-α-D-allopyranoside (1.40 g, 7.95 mmol) in ethanol (37.4 mL). The reaction mixture was stirred at rt for 310 h. The mixture was evaporated under reduced pressure and azeotroped with benzene three times to provide methyl 6-hydroxy-α-D-mycaminoside (1.76 g, crude).

Benzoyl chloride (4.62 mL, 39.8 mmol) were added to a solution of methyl 6-hydroxy-α-D-mycaminoside (1.76 g, crude) in pyridine (17 mL). The resulting mixture was stirred at rt for 38 h. A saturated sodium bicarbonate aqueous solution (170 mL) and ethyl acetate (85 mL) were added and the resulting mixture was stirred at rt for 1 h. The mixture was separated into two layers and the aqueous layer was extracted with three 10-mL portions of ethyl acetate. The combined organic layers were washed with brine and dried over sodium sulfate, and concentrated under reduced pressure. The residue was passed through a column of silica dichloromethane/methanol, 1:0-50:1) to provide methyl 6-hydroxy-2,4,6-tri-O-benzoyl-α-D-mycaminoside (3.92 g, 92%) as a pale reddish foam.

$^1$H NMR (CDCl$_3$, 600 MHz) δ=8.12-8.09 (m, 6H, CH of Ph), 7.62-7.57 (m, 3H, CH of Ph), 7.50-7.45 (m, 6H, CH of Ph), 5.73 (d, 1H, J=2.7 Hz, H-2), 5.71 (dd, J=6.6 Hz, 3.0 Hz, H-4), 4.90 (d, 1H, J=2.7 Hz, H-1), 4.75 (dd, 1H, J=11.6 Hz, 5.7 Hz, H-6$_α$), 4.65 (dd, 1H, J=11.6 Hz, 4.2 Hz, H-6$_β$), 4.33-4.31 (m, 1H, H-5), 3.41 (s, 3H, OCH$_3$), 3.38 (dd, 1H, J=9.3 Hz, 3.0 Hz, H-3), 2.45 (s, 6H, N(CH$_3$)$_2$); $^{13}$C NMR (CDCl$_3$, 100 MHz) δ=166.2, 165.9, 165.6, 133.4, 133.2, 133.2, 129.9, 129.8, 129.7, 129.7, 129.7, 128.6, 128.5, 128.4, 102.8, 72.9, 71.2, 69.8, 64.3, 61.1, 55.9, 42.6; HRMS (ESI) Calcd for C$_{30}$H$_{32}$NO$_8$ [M+H]$^+$: 532.2128. Found: 532.2146.

Step 5: 1-O-Acetyl-6-hydroxy-2,4,6-tri-O-benzoyl-D-mycaminose

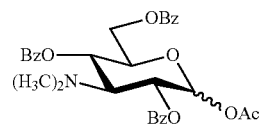

22v

Methyl 6-hydroxy-2,4,6-tri-O-benzoyl-α-D-mycaminoside (1.31 g, 2.46 mmol) was dissolved in a solution of acetic anhydride, acetic acid and sulfuric acid (8:2:0.1, prepared the day before) (41 mL) at 0° C. The mixture was stirred at 0° C. for 30 min and then at rt for 24 h. After addition of sodium acetate (327 mg) and water (41 mL), the reaction mixture was stirred at rt for 3 h to decompose the excess of acetic anhydride. After the solvent was removed under reduced pressure, the residue was diluted with ethyl acetate. A saturated NaHCO$_3$ aqueous solution (50 mL) was added to the mixture and the organic layer was separated. The aqueous layer was extracted with ethyl acetate (3×50 mL). The combined organic layers were washed with brine (50 mL) and dried over sodium sulfate and concentrated under reduced pressure to provide 1-O-acetyl-6-hydroxy-2,4,6-tri-O-benzoyl-D-mycaminose (α:β=2:3, 1.17 g, 85%) as a pale reddish foam. HRMS (ESI) Calcd for C$_{31}$H$_{32}$NO$_9$ [M+H]$^+$: 562.2077. Found: 562.2083.

Step 6: 6-Hydroxy-1-(2-pyrimidinethio)-2,4,6-tri-O-benzoyl-β-D-mycaminose

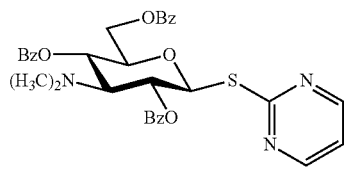

A solution of trimethylsilyl trifluoromethanesulfonate (145 µL, 800 µmol) and triethylamine (112 µL, 800 µmol) in benzene (0.4 mL+0.5 mL×2 wash) was added dropwise to a suspension of 2-mercaptopyrimidine (72 mg, 640 µmol) in benzene (5 mL). The mixture was stirred at rt for 1 h and heated at 50° C. After stirring at 50° C. for 24 h, cooled to rt. The reaction mixture was concentrated under reduced pressure. MS4A (200 mg) and dichloromethane (1.2 mL) were added to the residue. 1-O-acetyl-6-hydroxy-2,4,6-tri-O-benzoyl-D-mycaminose (36 mg, 64 µmol) was added to the mixture at 0° C. and the resulting mixture was stirred at –78° C. for 10 min. Trimethylsilyl trifluoromethanesulfonate (58 µL, 320 µmol) was added dropwise to the mixture at –78° C. and the resulting mixture was stirred at –78° C. After 30 min, the reaction mixture was warmed and stirred at 0° C. After 30 min, the reaction mixture was warmed to rt and stirred at rt for 40 h. A saturated NaHCO$_3$ aqueous solution (5 mL) was added to the mixture.

The resulting mixture was filtered through a MONSTR-PETTE fitted with cotton and washed with ethyl acetate (10 mL). The organic layer was washed with saturated NaHCO$_3$ aqueous solution (2×5 mL) and dried over sodium sulfate and concentrated under reduced pressure. The residue was passed through a column of silica (n-hexane/ethyl acetate, 3:1~2:1) to provide 6-hydroxy-1-(2-pyrimidinethio)-2,4,6-tri-O-benzoyl-β-D-mycaminose (23 mg, 59%) as a pale yellow foam. $^1$H NMR (CDCl$_3$, 600 MHz) δ=8.51 (d, 2H, J=4.8 Hz, CH of Pym), 8.15 (dd, 2H, J=7.9 Hz, 1.3 Hz, CH of Ph), 8.05 (dd, 2H, J=7.9 Hz, 1.3 Hz, CH of Ph), 8.02 (dd, 2H, J=7.9 Hz, 1.3 Hz, CH of Ph), 7.62-7.58 (m, 2H, CH of Ph), 7.57-7.53 (m, 1H, CH of Ph), 7.46 (dt, 4H, J=7.9 Hz, 3.0 Hz, CH of Ph), 7.39 (t, 2H, J=7.9 Hz, CH of Ph), 6.96 (t, 1H, J=4.8 Hz, CH of Pym), 6.70 (d, 1H, J=2.8 Hz, H-1), 6.01 (dd, J=6.8 Hz, 2.8 Hz, H-4), 5.91 (dd, 1H, J=6.3 Hz, 2.8 Hz, H-2), 4.86-4.83 (m, 1H, H-5), 4.65 (t, 2H, J=3.8 Hz, H-6), 3.36-3.35 (m, 1H, H-3), 2.54 (s, 6H, N(CH$_3$)$_2$); $^{13}$C NMR (CDCl$_3$, 100 MHz) δ=166.1, 165.5, 165.3, 157.5, 133.5, 133.4, 133.0, 130.0, 129.8, 129.8, 129.7, 128.7, 128.5, 128.3, 117.2, 81.6, 71.7, 69.9, 63.8, 62.3, 43.9; HRMS (ESI) Calcd for C$_{33}$H$_{32}$N$_3$O$_7$S [M+H]$^+$: 614.1961. Found: 614.2010.

REFERENCES FOR SUGAR SYNTHESIS

1. Velvadapu, V.; Andrade, R. B. *Carbohydr. Res.* 2008, 343, 145-150.
2. van Summeren, R. P.; Feringa, B. L.; Minnaard, A. J. *Org. Biomol. Chem.* 2005, 3, 2524-2533.
3. Oh, H.-S.; Xuan, R.; Kang, H.-Y. *Org. Biomol. Chem.* 2009, 7, 4458-4463.
4. Wang, L.-X; Lee, Y. C. *J. Chem. Soc., Perkin Trans. 1* 1996, 581-591.
5. Rodriguez-Perez, T.; Lavandera, I.; Fernandez, S.; Sanghvi, Y. S.; Ferrero, M.; Gotor, V. *Eur. J. Org. Chem.* 2007, 2769-2778.
6. Peri, F.; Marinzi, C.; Barath, M.; Granucci, F.; Urbano, M.; Nicotra, F. *Bioorg. Med. Chem.* 2006, 14, 190-199.
7. Walvoort, M. T. C.; Moggre, G.-J.; Lodder, G.; Overkleeft, H. S.; Codee, J. D. C.; van der Marel, G. A. *J. Org. Chem.* 2011, 76, 7301-7315.
8. Rehnberg, N.; Magnusson, G. *J. Org. Chem.* 1990, 55, 5467-5476.

General Aldol Method

Figure 3:
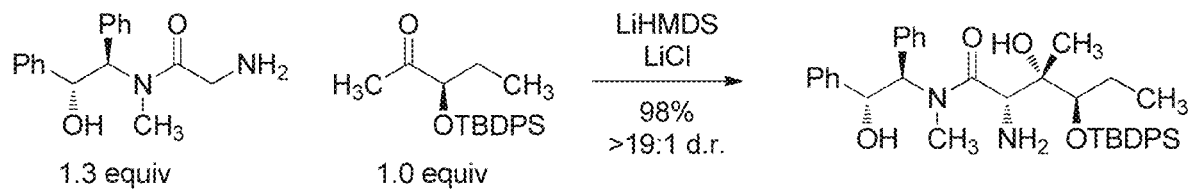
FIG. 3 depicts the Zimmerman Traxler and Felkin-Ahn model of an aldol reaction between pseudoephanamine glycinamide and a ketone.
Figure 3:
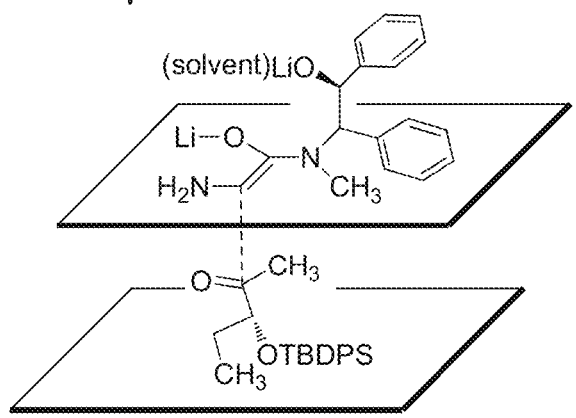
Figure 3:
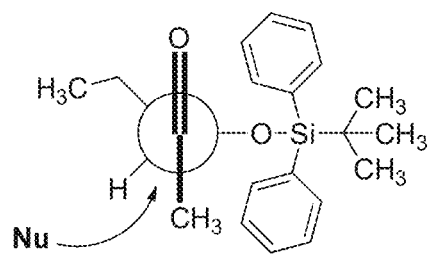

As generally described herein, in the construction of the western half, it was discovered that pseudoephanamine glycinamide undergoes highly selective addition to aldehydes and ketones to generate products with high diastereoselectivity in a single step (wherein R$^{29}$ is a sterically larger group than R$^8$). FIG. 3 depicts the Zimmerman Traxler and Felkin-Ahn model of this observed diastereoselectivity for entry 5 provided in the below Table Z1. Table Z2 shows further examples of the diastereoselective aldol method, wherein diastereomeric ratio is represented as the ratio of the major isomer (pictured) to the sum of all other minor diastereomers.

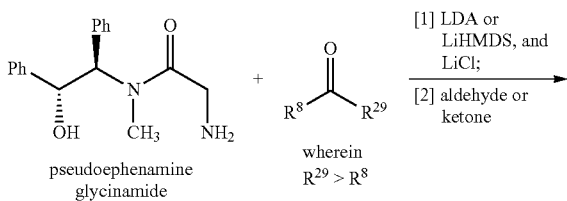

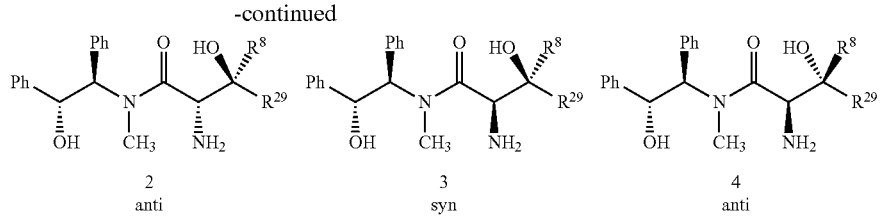
TABLE Z1
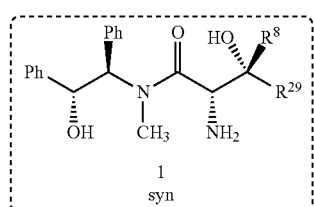
| Entry | (ketone/aldehyde) | Product |
|---|---|---|
| 1 | benzaldehyde | 89% yield, >10:1:0:0 |
| 2 | pivaldehyde | 95% yield, 17:1:1:0 |
| 3 | butyraldehyde | 88% yield, 12:2:1:0 |
| 4 | 3-methyl-2-butanone | 95% yield, 7:1:0:0 |
| 5 | (S)-3-(OTBDPS)-2-butanone | 96% yield, >19:1:0:0 |

TABLE Z2

| Entry | $R^8\underset{\underset{O}{\|}}{\overset{}{C}}R^{29}$ | Product |
|---|---|---|
| 1 | (S)-2,2-dimethyl-1,3-dioxolane-4-carbaldehyde | 66% yield, 89:11 |
| 2 | 4-nitrobenzaldehyde | 78% yield, 84:16 |
| 3 | furan-2-carbaldehyde | 63% yield, 79:21 |
| 4 | 4-(methylsulfonyl)benzaldehyde | 63% yield, 81:19 |
| 5 | 3-(triisopropylsilyl)propiolaldehyde | 75% yield, 83:17 |
| 6 | (E)-2-methyl-3-phenylacrylaldehyde | 78% yield, 79:21 |
| 7 | 3-methylbutan-2-one | 82% yield, 94:6 |

TABLE Z2-continued

| Entry | R[8]C(O)R[29] | Product |
|---|---|---|
| 8 | H₃C–CH=CH–Ph |  55% yield 77:23 |
| 9 | Et–C(O)–Et | 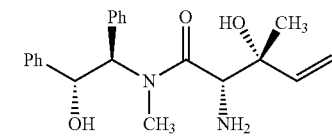 81% yield 95:5 |
| 10 | FH₂C–C(O)–CH₂F | 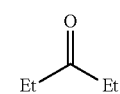 70% yield 94:6 |
| 11 | H₃C–C(O)–Ph | 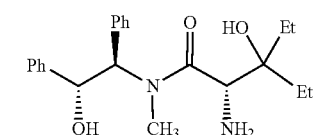 81% yield 88:12 |

Scheme EX-1 shows examples of hydrolysis of the chiral auxillary from intermediate aldol products. Scheme EX-2 shows an example of an alternative route for hydrolysis of the chiral auxillary. Scheme EX-3 shows an example of nitrogen group protection following the hydrolysis of the chiral auxillary.

Scheme EX-1

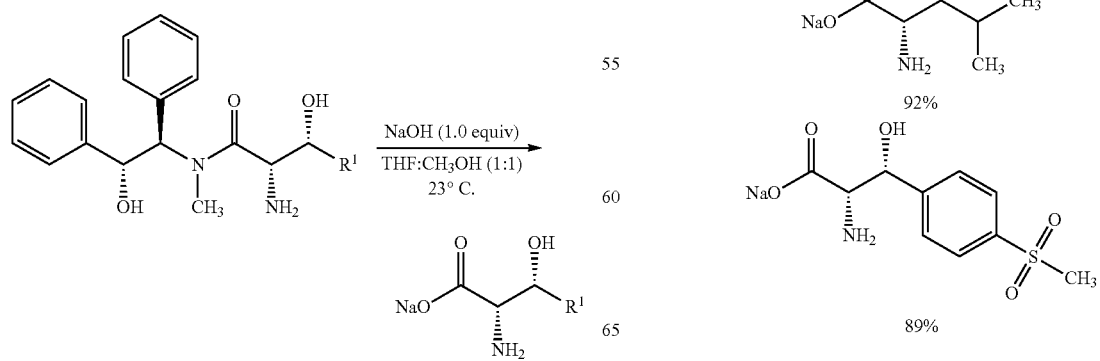

Scheme EX-2

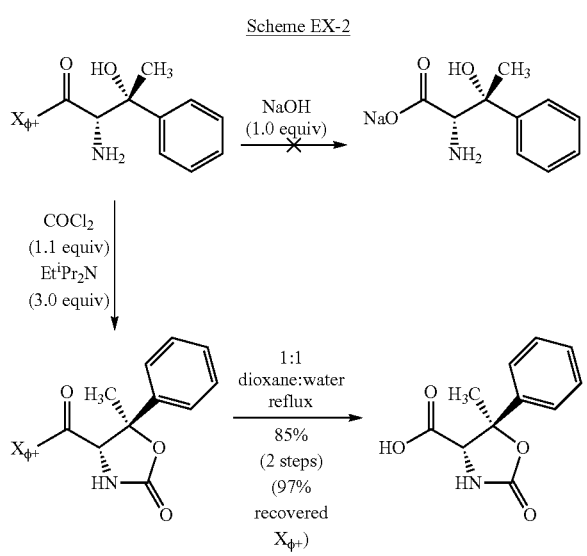

Scheme EX-3

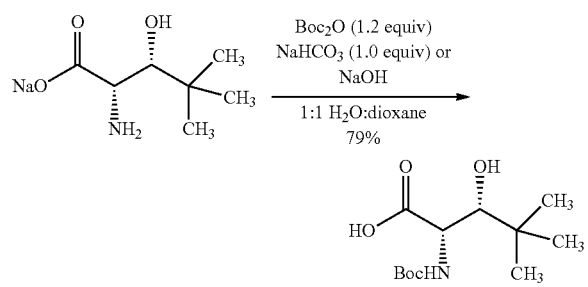

Biological Screening

We have collected MIC data for a total of 50 novel macrolides that this platform has produced against over 21 unique strains of *B. subtilis, E. coli, S. aureus, S. pneumoniae*, and *H. influenzae*, including several multidrug-resistant strains, with a special focus on macrolide resistant mechanisms (vide supra). Azithromycin was included as a control macrolide. CLSI standard procedures for broth dilution MIC determination were used. A sampling of some of the more interesting analogs we have produced to date is shown in Tables M1-M8. Certain analogs show greater activity than azithromycin in all strains of bacteria, especially against *S. aureus* and *S. pneumoniae* with efflux (mef, msr) and methylase (erm) genotypes, which are the two most prevalent forms of resistance to macrolides in the United States and Europe (ermA/B=ribosomal methylation, mefA, msrA=macrolide efflux). These genotypes can be constitutive or inducible. The finding that C4-epi (unnatural) isomers of the "azaketolide" macrolide class have enhanced activities relative to C4 natural isomers is very exciting.

In the future, all fully synthetic macrolides will be evaluated in a two-tier system, involving an initial in house screen against macrolide susceptible strains of *S. aureus* and *S. pneumoniae*. Macrolides found to possess threshold activity (MICs of 4 μg/mL or lower) against these bacterial strains will then be submitted for second-tier analysis against a full panel (16 strains, Gram-positive and Gram-negative organisms, including macrolide-resistant strains). After further rounds of optimization (synthesis, MIC determination), macrolides showing highly promising anti-microbial activity, especially against resistant strains, may be subject to further evaluation in rodent models of infection.

TABLE M1

| | | | MIC (μg/mL) of macrolides against *S. aureus* strains | | | | | |
|---|---|---|---|---|---|---|---|---|
| Entry | Macrolides | SA101 *S. aureus* ATCC29213 | SA183 *S. aureus* ermA positive msrA unknown | SA418 *S. aureus* ermA negative msrA positive | SA506 *S. aureus* ermA positive msrA unknown | SA557 *S. aureus* ermA unknown msrA positive | SA1707 *S. aureus* ermA negative msrA positive | SA1708 *S. aureus* ermA positive msrA negative |
| | Azithromycin | 1-2 | >32 | >32 | >32 | >32 | >32 | >32 |
| | Clindamycin | 0.125 | >32 | 0.0625-0125 | >32 | 0.125 | 0.0625-0.125 | 0.25 |
| | Erythromycin | 0.5 | | | | | | |
| | Spiramycin | 8 | | | | | | |
| 1. | FSM-10661 | >32 | | | | | | |
| 2. | FSM-10662 | >32 | | | | | | |
| 3. | FSM-10666 | >32 | | | | | | |
| 4. | FSM-10667 | >32 | | | | | | |
| 5. | FSM-10668 | >32 | | | | | | |
| 6. | FSM-10671 | >32 | | | | | | |
| 7. | FSM-10717 | 16 | | | | | | |
| 8. | FSM-10781 | >32 | | | | | | |
| 9. | FSM-10785 | >32 | | | | | | |
| 10. | FSM-10786 | >32 | | | | | | |
| 11. | FSM-10787 | >32 | | | | | | |
| 12. | FSM-10788 | >32 | | | | | | |
| 13. | FSM-10789 | >32 | | | | | | |
| 14. | FSM-10790 | >32 | | | | | | |
| 15. | FSM-10791 | >32 | | | | | | |
| 16. | FSM-10792 | >32 | | | | | | |
| 17. | FSM-10794 | >32 | | | | | | |

TABLE M1-continued

MIC (μg/mL) of macrolides against S. aureus strains

| Entry | Macrolides | SA101 S. aureus ATCC29213 | SA183 S. aureus ermA positive msrA unknown | SA418 S. aureus ermA negative msrA positive | SA506 S. aureus ermA positive msrA unknown | SA557 S. aureus ermA unknown msrA positive | SA1707 S. aureus ermA negative msrA positive | SA1708 S. aureus ermA positive msrA negative |
|---|---|---|---|---|---|---|---|---|
| 18. | FSM-10809 | >32 | >32 | >32 | >32 | >32 | >32 | >32 |
| 19. | FSM-20703 | >16 | | | | | | |
| 20. | FSM-20705 | 8 | | | | | | |
| 21. | FSM-20705 | 8 | >32 | 16 | >32 | 8 | 32 | 16 |
| 22. | FSM-20706 | 2 | >32 | 2 | >32 | 2 | 4 | 4 |
| 23. | FSM-20707 | 0.5->32 | >32 | 1 | >32 | 0.5-1 | 0.5-2 | 1-2 |
| 24. | FSM-20708 | 2 | | | | | | |
| 25. | FSM-20710 | 2 | | | | | | |
| 26. | FSM-20711 | 2 | | | | | | |
| 27. | FSM-20715 | 1-2 | >32 | 2 | >32 | 1 | 2 | 2 |
| 28. | FSM-20716 | 8 | >32 | 16 | >32 | 16 | 16 | 32 |
| 29. | FSM-20717 | 16 | | | | | | |
| 30. | FSM-20718 | 8 | >32 | 16 | >32 | 8 | 32 | 16 |
| 31. | FSM-20720 | 4-8 | >32 | 8 | >32 | 8 | 16 | 16 |
| 32. | FSM-20721 | 8 | >32 | 16 | >32 | 16 | 16 | 16 |
| 33. | FSM-20722 | 8 | | | | | | |
| 34. | FSM-20738 | 0.5-1 | >32 | 1 | >32 | 1 | 1 | 2 |
| 35. | FSM-20739 | >32 | >32 | >32 | >32 | >32 | >32 | >32 |
| 36. | FSM-20754 | 2 | >32 | 4 | >32 | 4 | 4 | 4 |
| 37. | FSM-20763 | 16 | | | | | | |
| 38. | FSM-20766 | 16 | | | | | | |
| 39. | FSM-20767 | 16 | | | | | | |
| 40. | FSM-20781 | >32 | >32 | >32 | >32 | >32 | >32 | >32 |
| 41. | FSM-20789 | 2 | >32 | 4 | >32 | 2 | 4 | 2 |
| 42. | FSM-20795 | 0.25-0.5 | >32 | 0.5-1 | >32 | 0.25-0.5 | 0.5-1 | 0.5 |
| 43. | FSM-20797 | 4 | >32 | 4 | >32 | 8 | 8 | 8 |
| 44. | FSM-30501 | >32 | | | | | | |
| 45. | FSM-30502 | >32 | | | | | | |
| 46. | FSM-30503 | >32 | | | | | | |
| 47. | FSM-30506 | >32 | | | | | | |
| 48. | FSM-30512 | >32 | | | | | | |
| 49. | FSM-30513 | >32 | | | | | | |
| 50. | FSM-30514 | >32 | | | | | | |
| 51. | FSM-30515 | >32 | | | | | | |
| 52. | FSM-30517 | >32 | | | | | | |

TABLE M2

MIC (μg/mL) of macrolides against S. pneumoniae strains

| Entry | Macrolides | Spn106 S. pneumonia ATCC49619 | Spn160 S. pneumoniae ermB unknown mefA positive | Spn1509 S. pneumoniae ermB positive mefA negative | Spn1533 S. pneumoniae ermB positive mefA positive | Spn1537 S. pneumoniae ermB positive mefA positive |
|---|---|---|---|---|---|---|
| | Azithromycin | 0.0625 | 2 | >32 | >32 | >32 |
| | Clindamycin | 0.0312 | ≤0.0156-0.0312 | 16-32 | >32 | >32 |
| 1. | FSM-10809 | >32 | >32 | >32 | >32 | >32 |
| 2. | FSM-20705 | 0.125-0.25 | 0.5-1 | 4-16 | >32 | >32 |
| 3. | FSM-20706 | ≤0.0156-0.0312 | 0.0625-0.125 | 0.5-2 | 32->32 | >32 |
| 4. | FSM-20707 | ≤0.0156-0.0312 | 0.0625-0.125 | 0.25-2 | 8->32 | 32 |
| 5. | FSM-20715 | ≤0.0156-0.0312 | 0.125-0.25 | 0.5-2 | >32 | >32 |
| 6. | FSM-20716 | 0.25 | 0.5 | 8 | >32 | >32 |
| 7. | FSM-20718 | ≤0.0156-0.25 | 0.25-1 | 0.5-4 | >32 | >32 |
| 8. | FSM-20720 | 0.125 | 0.5 | 2 | >32 | >32 |
| 9. | FSM-20721 | 0.125-0.25 | 0.5-1 | 8-16 | >32 | >32 |
| 10. | FSM-20738 | ≤0.0156-0.25 | 0.0625-1 | 0.5-8 | 32->32 | >32 |
| 11. | FSM-20739 | 32 | >32 | >32 | >32 | >32 |
| 12. | FSM-20754 | 0.0625 | 0.25 | 4 | >32 | >32 |
| 13. | FSM-20781 | 8 | >32 | >32 | >32 | >32 |
| 14. | FSM-20789 | 0.0625 | 0.25 | 1 | >32 | >32 |
| 15. | FSM-20795 | ≤0.0156 | 0.0312 | 0.125-0.25 | 16 | 32 |
| 16. | FSM-20797 | ≤0.0156 | 0.125 | 4 | >32 | >32 |

TABLE M3

MIC (µg/mL) of macrolides against *S. pneumoniae* and *H. influenzae* strains

| Entry | Macrolides | Spn1427 *S. pneumoniae* ermB positive mefA negative | HI175 *H. influenzae* ATCC49247 | HI281 *H. influenzae* |
|---|---|---|---|---|
|  | Azithromycin | >32 | 2 | 4 |
|  | Clindamycin | >32 | 16->32 | 16->32 |
| 1. | FSM-10809 | >32 | 32 | 8 |
| 2. | FSM-20705 | 32->32 | 16-32 | >32 |
| 3. | FSM-20706 | >32 | 0.5-2 | 4 |
| 4. | FSM-20707 | 2->32 | 1-2 | 4 |
| 5. | FSM-20715 | 4->32 | 2 | 4 |
| 6. | FSM-20716 | >32 | 8 | >32 |
| 7. | FSM-20718 | 4-32 | 2-16 | 4->32 |
| 8. | FSM-20720 | 8 | 4 | 32 |
| 9. | FSM-20721 | >32 | 8-32 | 32->32 |
| 10. | FSM-20738 | >32 | 0.5-8 | 4-32 |
| 11. | FSM-20739 | >32 | >32 | 32 |
| 12. | FSM-20754 | >32 | 2 | 8 |
| 13. | FSM-20781 | >32 | >32 | 32 |
| 14. | FSM-20789 | 8 | 4 | 8 |
| 15. | FSM-20795 | 1-2 | 1-2 | 4-8 |
| 16. | FSM-20797 | 32 | 8 | 32 |

TABLE M4

MIC (µg/mL) of macrolides against *E. coli* and *B. subtilis* strains

| Entry | Macrolides | EC107 *E. coli* ATCC25922 | EC878 *E. coli* tolC | EC882 *E. coli* imp | BS1723 *B. subtilis* BS168 WT wild type | BS1725 *B. subtilis* ermC (−ery) | BS1725 *B. subtilis* ermC (+ery) |
|---|---|---|---|---|---|---|---|
|  | Azithromycin | 4 | 0.5 | 0.0625 | 0.5 | >32 | >32 |
|  | Clindamycin | >32 | 2 | 2 | 1 | 2 | 4 |
|  | Erythromycin | >32 | 2 | 2 | 0.125 | >32 | >32 |
|  | Spiramycin | >32 | 16 | 1 | 2 | 2 | 16 |
| 1. | FSM-10661 | >32 | 16 | 2 | >32 | >32 | >32 |
| 2. | FSM-10662 | >32 | 16 | 4 | >32 | >32 | >32 |
| 3. | FSM-10666 | >32 | 16 | 4 | >32 | >32 | >32 |
| 4. | FSM-10667 | >32 | 16 | 4 | >32 | >32 | >32 |
| 5. | FSM-10668 | >32 | >32 | >32 | >32 | >32 | >32 |
| 6. | FSM-10671 | >32 | 32 | 8 | >32 | >32 | >32 |
| 7. | FSM-10781 | 16 | 1 | 0.25 | >32 | >32 | >32 |
| 8. | FSM-10785 | >32 | 2 | 1 | >32 | >32 | >32 |
| 9. | FSM-10786 | >32 | 2 | 0.25 | >32 | >32 | >32 |
| 10. | FSM-10787 | 32 | 2 | 0.125 | >32 | >32 | >32 |
| 11. | FSM-10788 | >32 | 1 | 0.0625 | >32 | >32 | >32 |
| 12. | FSM-10789 | >32 | 4 | 8 | >32 | >32 | >32 |
| 13. | FSM-10790 | >32 | 4 | 1 | >32 | >32 | >32 |
| 14. | FSM-10791 | >32 | 2 | 0.5 | >32 | >32 | >32 |
| 15. | FSM-10792 | >32 | 4 | 1 | >32 | >32 | >32 |
| 16. | FSM-10794 | >32 | 8 | 16 | >32 | >32 | >32 |
| 17. | FSM-20703 | >16 | >16 | 16 | >16 | >16 | >16 |
| 18. | FSM-20705 | >32 | 2 | 0.25 | 8 | 8 | >32 |
| 19. | FSM-20706 | 8 | 0.5 | 0.0625 | 1 | 1 | 16 |
| 20. | FSM-20707 | 8 | 0.5 | 0.0625 | 0.5 | 0.5 | 8 |
| 21. | FSM-20708 | 8 | 1 | 0.0625 | 1 | 1 | 16 |
| 22. | FSM-20710 | 8 | 1 | 0.0625 | 2 | 2 | 32 |
| 23. | FSM-20711 | 16 | 0.5 | 0.0312 | 2 | 2 | 32 |
| 24. | FSM-20715 | 4 | 0.5 | 0.0312 | 1 | 1 | 16 |
| 25. | FSM-20716 | >32 | 1 | 0.25 | 8 | 4 | >32 |
| 26. | FSM-20717 | >32 | 1 | 1 | 16 | 8 | >32 |
| 27. | FSM-20718 | >32 | 1 | 0.125 | 8 | 8 | >32 |
| 28. | FSM-20720 | >32 | 1 | 1 | 4 | 4 | >32 |
| 29. | FSM-20721 | >32 | 1 | 0.25 | 8 | 8 | >32 |
| 30. | FSM-20722 | >32 | 1 | 0.5 | 16 | 16 | >32 |
| 31. | FSM-20738 | 8 | 1 | 0.0625 | 0.25 | 0.25 | 4 |
| 32. | FSM-20754 | 16 | 0.5 | 0.125 | 2 | 2 | 32 |
| 33. | FSM-20763 | >32 | 4 | 2 | 16 | 16 | >32 |
| 34. | FSM-20766 | >32 | 4 | 1 | 32 | 32 | >32 |
| 35. | FSM-20767 | >32 | 4 | 1 | 16 | 8 | >32 |
| 36. | FSM-30501 | >32 | >32 | >32 | >32 | >32 | >32 |
| 37. | FSM-30502 | >32 | >32 | >32 | >32 | >32 | >32 |
| 38. | FSM-30503 | >32 | >32 | >32 | >32 | >32 | >32 |
| 39. | FSM-30506 | >32 | >32 | >32 | >32 | >32 | >32 |
| 40. | FSM-30512 | >32 | >32 | >32 | >32 | >32 | >32 |
| 41. | FSM-30513 | >32 | >32 | >32 | >32 | >32 | >32 |
| 42. | FSM-30514 | >32 | >32 | >32 | >32 | >32 | >32 |
| 43. | FSM-30515 | >32 | >32 | >32 | >32 | >32 | >32 |
| 44. | FSM-30517 | >32 | >32 | >32 | >32 | >32 | >32 |

TABLE M5

MIC (μg/mL) of macrolides against *S. aureus* (Newman, clinical isolate) and *E. coli* (MC4100) strains (round 1)

| Entry | Macrolides | *S. aureus* | *E. coli* |
|---|---|---|---|
| 1. | FSM-40347 | 2 | 8 |
| 2 | FSM-40348 | 8 | >32 |
| 3. | FSM-40349 | 2 | 16 |
| 4. | FSM-40350 | 2 | 16 |
| 5. | FSM-20919 | 0.25 | 2 |
| 6. | FSM-20738 (control) | 1 | 8 |

TABLE M6

MIC (μg/mL) of macrolides against *S. aureus* (Neuman, clinical isolate) and *E. coli* (MC4100) strains (round 2)

| Entry | Macrolides | *S. aureus* | *E. coli* |
|---|---|---|---|
| 1. | azithromycin | 1 | 8 |
| 2. | FSM-20707 | 0.5 | 4 |
| 3. | FSM-20919 | 0.5 | 2 |
| 4. | FSM-56133 | 4 | 8 |
| 5. | FSM-56139 | 16 | 32 |
| 6. | FSM-56156 | 2 | 4 |
| 7. | FSM-56158 | 8 | 32 |
| 8. | FSM-30622 | >32 | >32 |
| 9. | FSM-30624 | >32 | >32 |
| 10. | FSM-30625 | >32 | >32 |
| 11. | FSM-30633 | >32 | >32 |

TABLE M7

MIC (μg/mL) of macrolides against *E. coli*, *S. aureus*, and *S. pneumoniae* strains

| Entry | Macrolides | *E. coli* (ATCC 25922) | *S. aureus* (ATCC 29213) | *S. aureus* (USA300) | *S. aureus* (183) | *S. aureus* (506) | *S. aureus* (1708) | *S. pneumoniae* (49619) | *S. pneumonae* (160) |
|---|---|---|---|---|---|---|---|---|---|
| | Azithromycin | 8 | 2 | >32 | >32 | >32 | >32 | 0.125 | 2 |
| | Azithromycin | 8 | 2 | >32 | >32 | >32 | >32 | 0.125 | 2 |
| | Azithromycin | 8 | 1 | >32 | >32 | >32 | >32 | 0.125 | 2 |
| | Erythromycin | >32 | 0.5 | >32 | >32 | >32 | >32 | ≤0.0625 | 2 |
| | Erythromycin | >32 | 0.5 | >32 | >32 | >32 | >32 | ≤0.0625 | 2 |
| | Erythromycin | >32 | 0.25 | >32 | >32 | >32 | >32 | ≤0.0625 | 2 |
| | Minocycline | 1 | 0.25 | 0.25 | 16 | 2 | 0.5 | 0.25 | 8 |
| 1. | FSC-11074 | 8 | 8 | 4 | 8 | 16 | 16 | 4 | 32 |
| 2. | FSC-11077 | >32 | 32 | 16 | 32 | 32 | 32 | 4 | >32 |
| 3. | FSC-11083 | >32 | >32 | 32 | >32 | >32 | >32 | 16 | >32 |
| 4. | FSM-10781 | 32 | >32 | >32 | | >32 | >32 | 8 | 2 |
| 5. | FSM-11031 | 16 | 2 | 4 | >32 | >32 | 1 | 0.25 | 0.25 |
| 6. | FSM-11044 | 32 | 1 | 1 | >32 | >32 | 1 | 0.125 | 0.125 |
| 7. | FSM-11052 | >32 | 8 | 32 | >32 | >32 | 4 | 0.125 | 0.5 |
| 8. | FSM-11056 | >32 | 8 | 32 | >32 | >32 | 8 | 0.125 | 1 |
| 9. | FSM-11094 | >32 | 8 | 8 | >32 | >32 | 16 | 2 | 1 |
| 10. | FSM-20706 | 8 | 2 | 2 | | >32 | 1 | ≤0.0625 | 0.125 |
| 11. | FSM-20707 | 4 | 1 | 4 | >32 | >32 | 1 | ≤0.0625 | 0.125 |
| 12. | FSM-20708 | 4 | 2 | 2 | | >32 | 2 | 0.5 | 0.125 |
| 13. | FSM-20710 | 8 | 2 | 4 | >32 | >32 | 2 | 0.5 | 0.5 |
| 14. | FSM-20711 | 16 | 4 | 4 | >32 | >32 | 4 | 0.5 | 0.125 |
| 15. | FSM-20715 | 8 | 1 | 2 | >32 | >32 | 2 | 0.125 | 0.25 |
| 16. | FSM-20720 | >32 | 4 | 8 | | >32 | 8 | 1 | 0.5 |
| 17. | FSM-20738 | 8 | 0.5 | 1 | | >32 | 0.5 | ≤0.0625 | ≤0.0625 |
| 18. | FSM-20767 | >32 | 16 | 32 | | >32 | 32 | 0.5 | 2 |
| 19. | FSM-20789 | 16 | 2 | 4 | | >32 | 2 | 0.125 | 0.5 |
| 20. | FSM-20795 | 4 | 0.5 | 1 | >32 | >32 | 0.25 | ≤0.0625 | ≤0.0625 |
| 21. | FSM-20795 | 4 | 0.5 | 1 | >32 | >32 | 0.5 | ≤0.0625 | ≤0.0625 |
| 22. | FSM-20797 | 32 | 8 | 8 | | >32 | 8 | 0.5 | 0.25 |
| 23. | FSM-20919 | 4 | 0.25 | 0.5 | >32 | >32 | 0.25 | ≤0.0625 | ≤0.0625 |
| 24. | FSM-21079 | >32 | >32 | >32 | >32 | >32 | >32 | 8 | 2 |
| 25. | FSM-21088 | >32 | 16 | 16 | >32 | >32 | 8 | 2 | 0.5 |
| 26. | FSM-21118 | 8 | 1 | 2 | >32 | >32 | 1 | 0.125 | ≤0.0625 |
| 27. | FSM-21120 | >32 | 32 | >32 | >32 | >32 | >32 | 4 | 2 |
| 28. | FSM-21264 | >32 | >32 | >32 | >32 | >32 | >32 | 2 | 4 |
| 29. | FSM-21335 | 32 | >32 | 32 | >32 | >32 | >32 | 1 | 0.25 |
| 30. | FSM-21339 | 16 | 2 | 2 | >32 | >32 | 4 | ≤0.0625 | 0.125 |
| 31. | FSM-21340 | 4 | 16 | 16 | >32 | >32 | >32 | 0.5 | 0.5 |
| 32. | FSM-21344 | >32 | >32 | >32 | >32 | >32 | >32 | 0.5 | 8 |
| 33. | FSM-21367 | 4 | 8 | 8 | >32 | >32 | 16 | 0.25 | 0.125 |
| 34. | FSM-21368 | 8 | 8 | 8 | >32 | >32 | 16 | 1 | 0.25 |
| 35. | FSM-21397 | 16 | 2 | 2 | >32 | >32 | 2 | 0.125 | 0.25 |
| 36. | FSM-21422 | 32 | >32 | >32 | >32 | >32 | >32 | 1 | 4 |
| 37. | FSM-21423 | 32 | 16 | 16 | >32 | >32 | 32 | 1 | 0.25 |
| 38. | FSM-21428 | >32 | >32 | >32 | >32 | >32 | >32 | 4 | 4 |
| 39. | FSM-30502 | >32 | >32 | >32 | | >32 | >32 | >32 | >32 |
| 40. | FSM-30622 | >32 | >32 | >32 | | >32 | >32 | >32 | >32 |
| 41. | FSM-30633 | >32 | >32 | >32 | | >32 | >32 | >32 | >32 |
| 42. | FSM-30686 | 32 | 8 | 8 | >32 | >32 | 4 | 0.25 | 0.5 |
| 43. | FSM-30689 | >32 | >32 | >32 | >32 | >32 | >32 | 8 | 16 |
| 44. | FSM-30690 | >32 | >32 | >32 | >32 | >32 | >32 | >32 | >32 |
| 45. | FSM-30704 | 32 | 2 | 4 | >32 | >32 | 2 | 0.25 | 0.25 |
| 46. | FSM-40347 | 8 | 4 | 4 | | >32 | 4 | 0.25 | 0.125 |

TABLE M7-continued

MIC (μg/mL) of macrolides against *E. coli*, *S. aureus*, and *S. pneumoniae* strains

| Entry | Macrolides | *E. coli* (ATCC 25922) | *S. aureus* (ATCC 29213) | *S. aureus* (USA300) | *S. aureus* (183) | *S. aureus* (506) | *S. aureus* (1708) | *S. pneumoniae* (49619) | *S. pneumonae* (160) |
|---|---|---|---|---|---|---|---|---|---|
| 47. | FSM-40349 | 8 | 1 | 2 |  | >32 | 1 | ≤0.0625 | 0.125 |
| 48. | FSM-56133 | 8 | 4 | 8 |  | >32 | 4 | 1 | 0.5 |
| 49. | FSM-56156 | 16 | 4 | 8 |  | >32 | 4 | 1 | 0.25 |
| 50. | FSM-56160 | >32 | >32 | >32 | >32 | >32 | >32 | 16 | 2 |
| 51. | FSM-56178 | >32 | >32 | >32 | >32 | >32 | >32 | >32 | 8 |
| 52. | FSM-56185 | >32 | >32 | >32 | >32 | >32 | >32 | >32 | >32 |
| 53. | FSM-56192 | >32 | >32 | >32 | >32 | >32 | >32 | 2 | 8 |
| 54. | FSM-56216 | 32 | 32 | 32 | >32 | >32 | 16 | 1 | 2 |
| 55. | FSM-60353 | 32 | 0.5 | 0.5 | >32 | >32 | 0.5 | ≤0.0625 | ≤0.0625 |
| 56. | FSM-60415 | >32 | 2 | 2 | >32 | >32 | 2 | 0.5 | 0.5 |
| 57. | FSM-70153 | 4 | 1 | 2 | >32 | >32 | 4 | ≤0.0625 | 0.125 |
| 58. | FST-14005 | >32 | >32 | >32 | >32 | >32 | >32 | >32 | >32 |
| 59. | FST-14006 | 32 | 4 | 16 | 16 | 16 | 8 | 2 | 32 |

TABLE M8

MIC (μg/mL) of macrolides against *S. pneumoniae*, *E. faecalis*, *A. baumannii*, *K. pneumoniae*, and *H. influenzae* strains

| Entry | Macrolides | *S. pneumoniae* (1509) | *S. pneumoniae* (1533) | *S. pneumoniae* (1537) | *E. faecalis* (29212) | *A. baumannii* (BAA747-1) | *K. pneumoniae* (10031) | *H. influenzae* (49766) | *H. influenzae* (49247) |
|---|---|---|---|---|---|---|---|---|---|
|  | Azithromycin | >32 | >32 | >32 | 8 | 8 | 2 | 2 | 0.25 |
|  | Azithromycin | >32 | >32 | >32 | 8 | 4 | 2 | 2 | 0.25 |
|  | Azithromycin | >32 | >32 | >32 | 16 | 2 | 2 | 2 | 0.25 |
|  | Erythromycin | >32 | >32 | >32 | 2 | 32 | 8 | 8 | 2 |
|  | Erythromycin | >32 | >32 | >32 | 2 | 32 | 8 | 8 | 2 |
|  | Erythromycin | >32 | >32 | >32 | 2 | >32 | 8 | 8 | 2 |
|  | Minocycline | 16 | 8 | 8 | 8 | 0.5 | 0.5 | 8 | 4 |
| 1. | FSC-11074 | 32 | 4 | 4 | 16 | >32 | 2 | 0.5 | 0.25 |
| 2. | FSC-11077 | >32 | 4 | 4 | 16 | >32 | 16 | 2 | 1 |
| 3. | FSC-11083 | >32 | 16 | 16 | 32 | >32 | 16 | 4 | 4 |
| 4. | FSM-10781 | >32 | >32 | >32 | 8 | 32 | 8 | 8 | 1 |
| 5. | FSM-11031 | 1 | >32 | >32 | 0.25 | 16 | 4 | 4 | 2 |
| 6. | FSM-11044 | 1 | >32 | >32 | 0.25 | 32 | 8 | 8 | 2 |
| 7. | FSM-11052 | 0.5 | >32 | >32 | 2 | >32 | 16 | 32 | 8 |
| 8. | FSM-11056 | 0.5 | >32 | >32 | 2 | >32 | 16 | 16 | 4 |
| 9. | FSM-11094 | >32 | >32 | >32 | 4 | >32 | 16 | 16 | 8 |
| 10. | FSM-20706 | 4 | >32 | >32 | 0.25 | 32 | 4 | 2 | 0.5 |
| 11. | FSM-20707 | 1 | >32 | >32 | 0.25 | 8 | 2 | 2 | 0.5 |
| 12. | FSM-20708 | 4 | >32 | >32 | 0.5 | 16 | 2 | 2 | 0.25 |
| 13. | FSM-20710 | 16 | >32 | >32 | 0.5 | 16 | 4 | 2 | 0.5 |
| 14. | FSM-20711 | >32 | >32 | >32 | 1 | >32 | 4 | 8 | 1 |
| 15. | FSM-20715 | 2 | >32 | >32 | 0.25 | 8 | 2 | 2 | 0.5 |
| 16. | FSM-20720 | 8 | >32 | >32 | 2 | >32 | 8 | 32 | 8 |
| 17. | FSM-20738 | 2 | >32 | >32 | 0.125 | 32 | 4 | 4 | 0.5 |
| 18. | FSM-20767 | >32 | >32 | >32 | 4 | >32 | 32 | 16 | 8 |
| 19. | FSM-20789 | 4 | >32 | >32 | 0.5 | 32 | 4 | 8 | 2 |
| 20. | FSM-20795 | 0.5 | >32 | >32 | 0.125 | 16 | 2 | 4 | 0.5 |
| 21. | FSM-20795 | 1 | >32 | >32 | 0.125 | 16 | 2 | 4 | 0.5 |
| 22. | FSM-20797 | 16 | >32 | >32 | 1 | >32 | 8 | 16 | 4 |
| 23. | FSM-20919 | 0.5 | 32 | 32 | 0.5 | 16 | 16 | 4 | 1 |
| 24. | FSM-21079 | >32 | >32 | >32 | 16 | >32 | >32 | >32 | >32 |
| 25. | FSM-21088 | >32 | >32 | >32 | 8 | >32 | >32 | >32 | 8 |
| 26. | FSM-21118 | 1 | >32 | 32 | 0.5 | 32 | 2 | 8 | 2 |
| 27. | FSM-21120 | >32 | >32 | >32 | 16 | >32 | >32 | >32 | >32 |
| 28. | FSM-21264 | >32 | >32 | >32 | >32 | >32 | >32 | >32 | 8 |
| 29. | FSM-21335 | >32 | >32 | >32 | 16 | >32 | 4 | 32 | 4 |
| 30. | FSM-21339 | 1 | >32 | >32 | 0.5 | 32 | 4 | 8 | 2 |
| 31. | FSM-21340 | >32 | >32 | >32 | 8 | 8 | 2 | 4 | 1 |
| 32. | FSM-21344 | 4 | >32 | >32 | 16 | >32 | 16 | 32 | 8 |
| 33. | FSM-21367 | 8 | >32 | >32 | 2 | 16 | 4 | 4 | 1 |
| 34. | FSM-21368 | 8 | >32 | >32 | 2 | 16 | 4 | 8 | 2 |
| 35. | FSM-21397 | 4 | >32 | >32 | 0.5 | 16 | 4 | 4 | 2 |
| 36. | FSM-21422 | >32 | >32 | >32 | 16 | >32 | 8 | 16 | 8 |
| 37. | FSM-21423 | >32 | >32 | >32 | 4 | >32 | 8 | 16 | 2 |
| 38. | FSM-21428 | >32 | >32 | >32 | 16 | >32 | >32 | >32 | 32 |
| 39. | FSM-30502 | >32 | >32 | >32 | >32 | >32 | >32 | >32 | 16 |
| 40. | FSM-30622 | >32 | >32 | >32 | >32 | >32 | >32 | >32 | >32 |
| 41. | FSM-30633 | >32 | >32 | >32 | >32 | >32 | >32 | >32 | 32 |
| 42. | FSM-30686 | 4 | >32 | >32 | 0.5 | >32 | 8 | 8 | 2 |
| 43. | FSM-30689 | 16 | >32 | >32 | 32 | >32 | >32 | >32 | 16 |
| 44. | FSM-30690 | >32 | >32 | >32 | >32 | >32 | >32 | >32 | >32 |

TABLE M8-continued

MIC (μg/mL) of macrolides against *S. pneumoniae, E. faecalis, A. baumannii, K. pneumoniae,* and *H. influenzae* strains

| Entry | Macrolides | S. pneumoniae (1509) | S. pneumoniae (1533) | S. pneumoniae (1537) | E. faecalis (29212) | A. baumannii (BAA747-1) | K. pneumoniae (10031) | H. influenzae (49766) | H. influenzae (49247) |
|---|---|---|---|---|---|---|---|---|---|
| 45. | FSM-30704 | 1 | >32 | >32 | 0.5 | >32 | 16 | 8 | 2 |
| 46. | FSM-40347 | 32 | >32 | >32 | 0.25 | 8 | 2 | 4 | 0.5 |
| 47. | FSM-40349 | 2 | >32 | >32 | 0.125 | 32 | 2 | 2 | 0.5 |
| 48. | FSM-56133 | >32 | >32 | >32 | 0.5 | 32 | 2 | 4 | 1 |
| 49. | FSM-56156 | 8 | >32 | >32 | 1 | 32 | 4 | 8 | 2 |
| 50. | FSM-56160 | >32 | >32 | >32 | 8 | >32 | 8 | 32 | 8 |
| 51. | FSM-56178 | >32 | >32 | >32 | >32 | >32 | >32 | >32 | >32 |
| 52. | FSM-56185 | >32 | >32 | >32 | >32 | >32 | >32 | >32 | >32 |
| 53. | FSM-56192 | >32 | >32 | >32 | 32 | >32 | 16 | 32 | 8 |
| 54. | FSM-56216 | 32 | >32 | >32 | 8 | >32 | 8 | 16 | 4 |
| 55. | FSM-60353 | 1 | 32 | 32 | 0.25 | 32 | 8 | 8 | 2 |
| 56. | FSM-60415 | 4 | 32 | 32 | 2 | >32 | >32 | 32 | 8 |
| 57. | FSM-70153 | 4 | >32 | >32 | 0.25 | 16 | 2 | 2 | 0.5 |
| 58. | FST-14005 | >32 | >32 | >32 | >32 | >32 | >32 | >32 | >32 |
| 59. | FST-14006 | 16 | 16 | 16 | 32 | 4 | 4 | 4 | 2 |

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of formula:

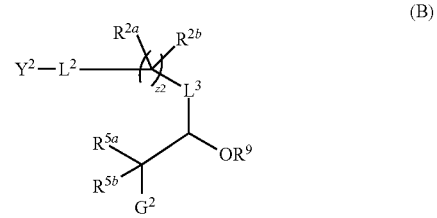

(B)

or a salt thereof;
wherein:
Y$^2$ is —Z$^4$H, —CH$_2$NO$_2$, a leaving group (LG), —C(=O)R$^{Z3}$, —C(=O)OR$^{Z3}$, —C(=O)LG, —C(=O)—CH=P(R$^{P1}$)(R$^{P2}$)(R$^{P3}$), or —C(=O)—CH$_2$—P(O)(OR$^{P2}$)(OR$^{P3}$);
Z$^4$ is —O—, —S—, or —NR$^{Z2}$—;
R$^{P1}$, R$^{P2}$, and R$^{P3}$ are each independently optionally substituted alkyl, optionally substituted alkenyl, optionally substituted alkynyl, optionally substituted carbocyclyl, optionally substituted heterocyclyl, optionally substituted aryl, or optionally substituted heteroaryl;

$L^2$ is a bond or —CH$_2$—;

z2 is 0, 1, or 2;

each instance of $R^{2a}$ and $R^{2b}$ is independently hydrogen, halogen, carbonyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or wherein $R^{2a}$ and $R^{2b}$ can be taken together to form

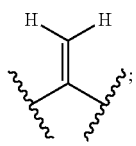

$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, amino, substituted amino, —C(=O)R$^{Z8}$, —C(=O)OR$^{Z8}$, —C(=O)N(R$^{Z8}$)$_2$, or a nitrogen protecting group;

$R^{Z3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$L^3$ is a group of formula:

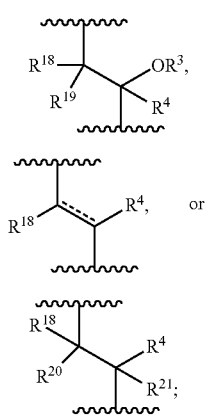

===== represents a single or double bond;

$R^3$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^{Z8}$, —C(=O)OR$^{Z8}$, —C(=O)N(R$^{Z8}$)$_2$, an oxygen protecting group, or a group of formula:

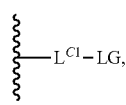

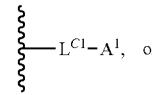

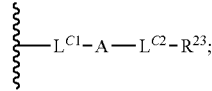

$R^4$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{18}$ and $R^{19}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{20}$ and $R^{21}$ is independently hydrogen, optionally substituted alkyl, optionally substituted alkenyl, optionally substituted alkynyl, optionally substituted carbocyclyl, optionally substituted aryl, optionally substituted heteroaryl, hydroxyl, substituted hydroxyl, thiol, substituted thiol, amino, substituted amino, halogen, or carbonyl, or $R^{20}$ and $R^{21}$ are joined to form an optionally substituted cyclopropyl or an oxiranyl ring;

each instance of $R^{5a}$ and $R^{5b}$ is independently hydrogen, halogen, silyl, optionally substituted alkyl, optionally substituted carbocyclyl, or optionally substituted heterocyclyl;

$R^9$ is optionally substituted alkenyl, optionally substituted alkynyl, optionally substituted carbocyclyl, optionally substituted aryl, optionally substituted heteroaryl, —C(=O)R$^{Z8}$, —C(=O)OR$^{Z8}$, —C(=O)N(R$^{Z8}$)$_2$, or a carbohydrate;

$G^2$ is a group of formula:

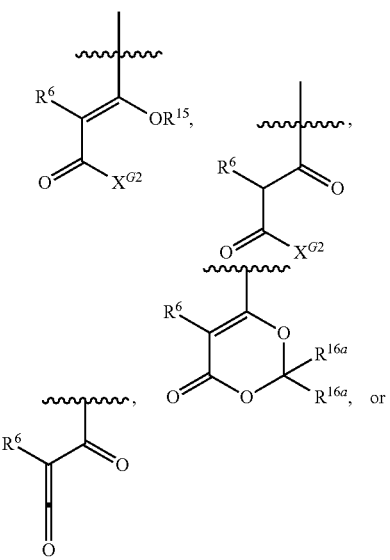

-continued

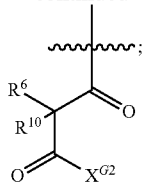

R[6] is hydrogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl, hydroxyl, substituted hydroxyl, thiol, substituted thiol, amino, substituted amino, carbonyl, silyl, or halogen;

R[10] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, hydroxyl, substituted hydroxyl, thiol, substituted thiol, amino, substituted amino, carbonyl, silyl, or halogen;

each instance of X[G2] is —OR[15], —SR[15], or —N(R[15])$_2$;

each instance of R[15] is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R[15] groups can be taken together to form an optionally substituted heteroaryl or heterocyclic ring;

each instance of R[16a] is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of L[C1] and L[C2] is independently a bond, optionally substituted alkylene, optionally substituted alkenylene, optionally substituted alkynylene, optionally substituted heteroalkylene, optionally substituted heteroalkenylene, optionally substituted heteroalkynylene, or combinations thereof;

each instance of A[1] is independently a leaving group (LG), —SH, —OH, —NH$_2$, —NH—NH$_2$, —N$_3$, —O—NH$_2$, —C(=O)R[X1],

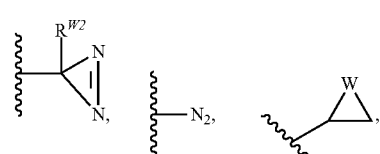

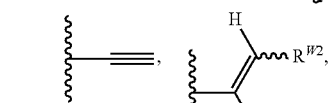

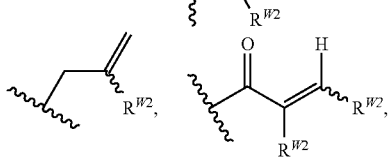

-continued

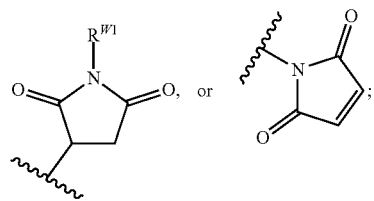

A is —NH—, —NH—NH—, —NH—O—, —O—NH—, —S—, —O—,

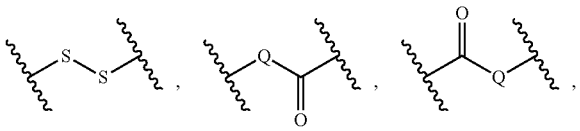

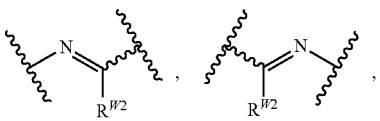

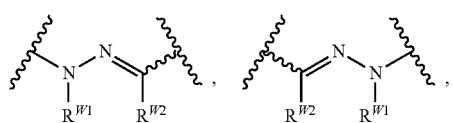

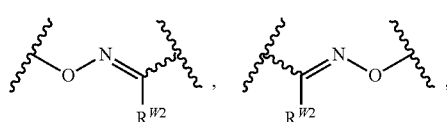

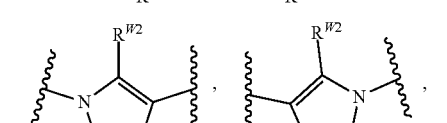

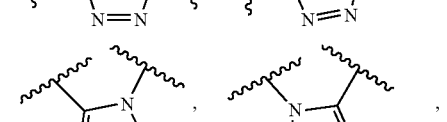

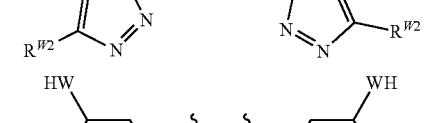

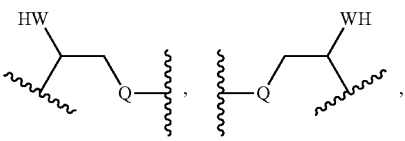

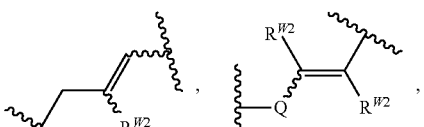

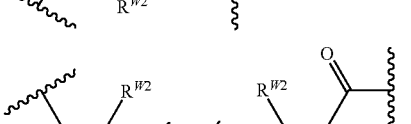

819
-continued

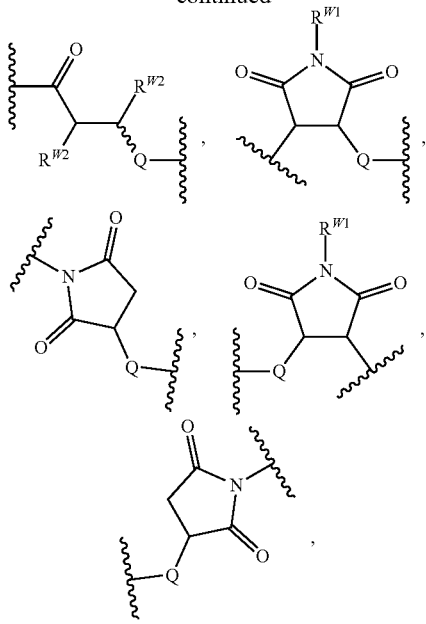

optionally substituted carbocyclyl, optionally substituted heterocyclyl, optionally substituted aryl, or optionally substituted heteroaryl;

Q is —NH—, —NH—NH—, —O—NH—, —NH—O—, —S—, or —O—;

W is O, S, or $NR^{W1}$;

$R^{W1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{W2}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{W2}$ groups are joined to form an optionally substituted cyclic moiety;

$R^{X1}$ is hydrogen, halogen, or —$OR^{X2}$, wherein $R^{X2}$ is hydrogen, optionally substituted alkyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{23}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups are joined to form an optionally substituted heterocyclyl or optionally substituted heteroaryl ring; and LG is a leaving group.

2. The compound of claim 1, wherein the compound is of formula:

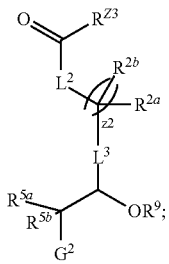

or a salt thereof.

3. The compound of claim 1, wherein the compound is of formula:

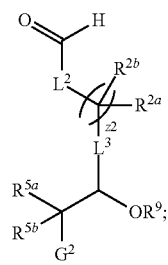

or a salt thereof.

4. The compound of claim 1, wherein the compound is of formula:

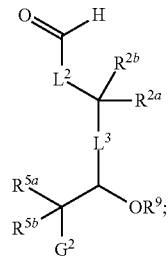

or a salt thereof.

5. The compound of claim 1, or a salt thereof, wherein $Y^2$ is a leaving group (LG), —C(=O)$R^{Z3}$, —C(=O)O$R^{Z3}$, —C(=O)LG, —C(=O)—CH=P($R^{P1}$)($R^{P2}$)($R^{P3}$), or —C(=O)—CH$_2$—P(O)(O$R^{P2}$)(O$R^{P1}$).

6. The compound of claim 1, or a salt thereof, wherein $Y^2$ is —C(=O)$R^{Z3}$.

7. The compound of claim 1, or a salt thereof, wherein $Y^2$ is —C(=O)$R^{Z3}$; and $R^{Z3}$ is hydrogen.

8. The compound of claim 1, or a salt thereof, wherein $L^3$ is a group of formula:

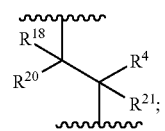

and $R^{21}$ is hydrogen.

9. The compound of claim 1, or a salt thereof, wherein $L^3$ is a group of formula:

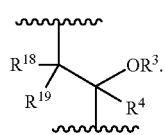

(L³-i)

10. The compound of claim 1, or a salt thereof, wherein $R^9$ is a group of formula:

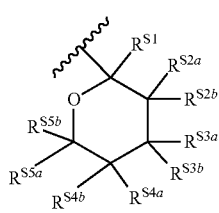

(s-1)

wherein:
each of $R^{S1}$, $R^{S2a}$, $R^{S2b}$, $R^{S3a}$, $R^{S3b}$, $R^{S4a}$, $R^{S4b}$, $R^{S5a}$, and $R^{S5b}$ is independently hydrogen, optionally substituted alkyl, —$OR^{SO}$, or —$N(R^{SN})_2$, or wherein $R^{S2a}$ or $R^{S2b}$ may be taken together with $R^{S3a}$ or $R^{S3b}$ to form an optionally substituted fused heterocyclic ring;
each instance of $R^{SO}$ is independently hydrogen, optionally substituted alkyl, optionally substituted alkenyl, optionally substituted heterocyclyl, or an oxygen protecting group; and
each instance of $R^{SN}$ is independently hydrogen, optionally substituted alkyl, or a nitrogen protecting group; or optionally two $R^{SN}$ are taken with the intervening atoms to form a heterocyclic ring.

11. The compound of claim 10, or a salt thereof, wherein $R^9$ is a group of formula:

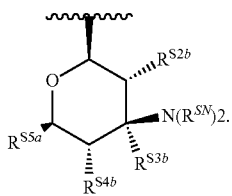

(s-2a)

12. The compound of claim 10, or a salt thereof, wherein $R^9$ is a group of formula:

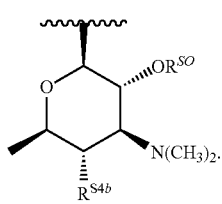

(s-2a-i)

13. The compound of claim 1, or a salt thereof, wherein $G^2$ is a group of formula:

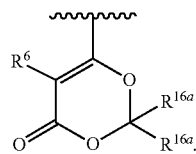

14. The compound of claim 1, or a salt thereof, wherein each instance of $R^{16a}$ is independently optionally substituted alkyl.

15. The compound of claim 1, wherein the compound is of formula:

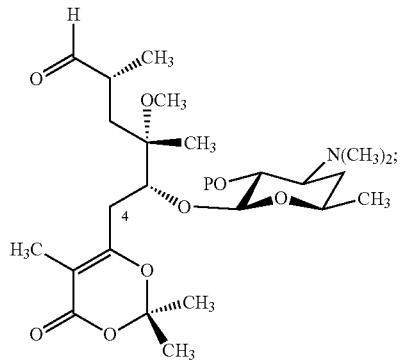

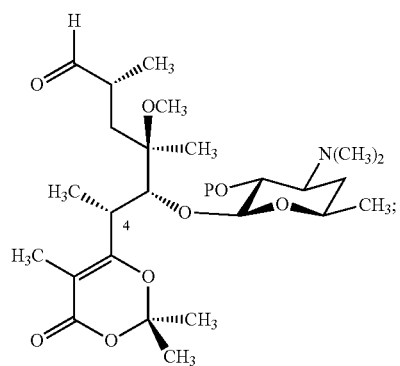

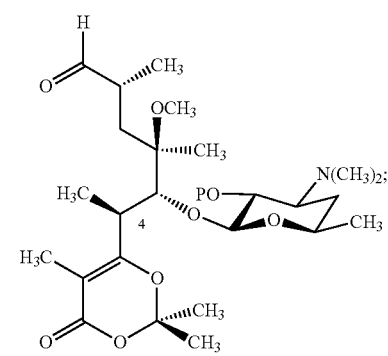

823
-continued
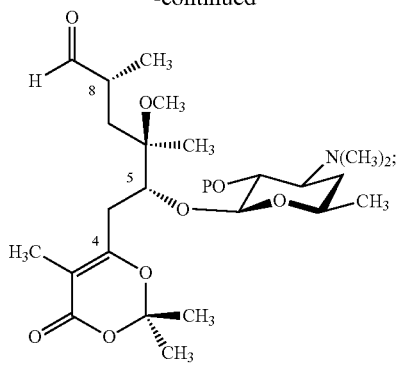
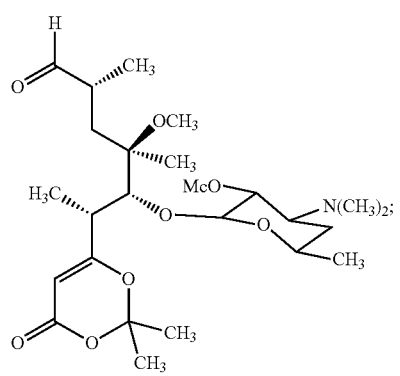
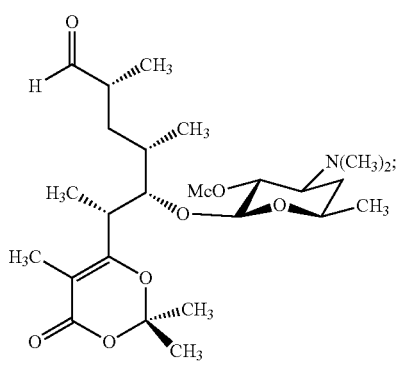
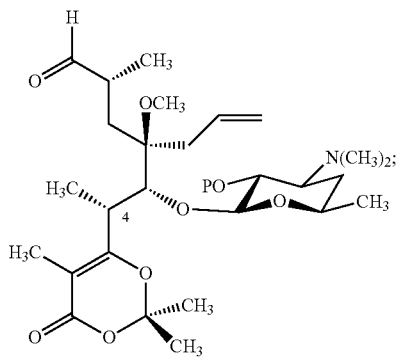
824
-continued
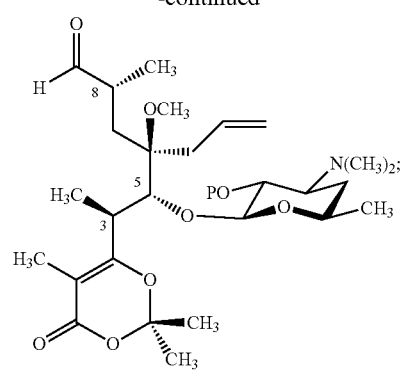
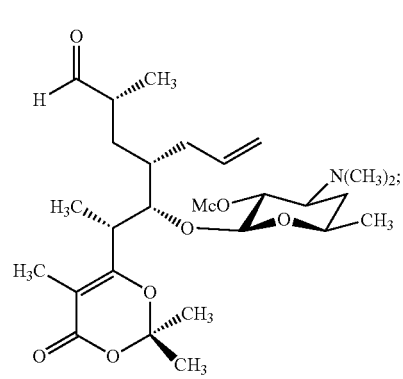
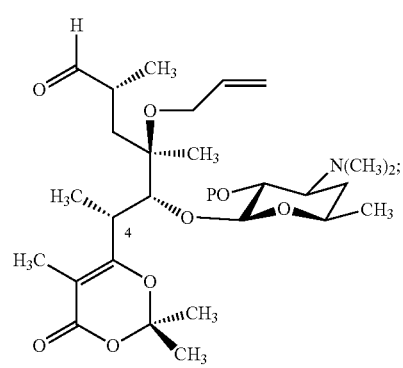
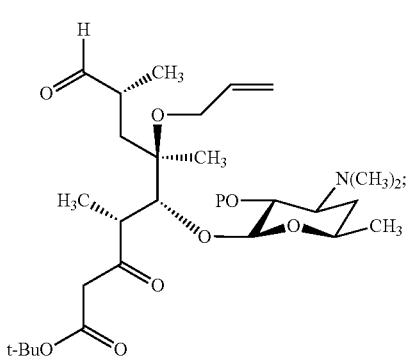

825
-continued
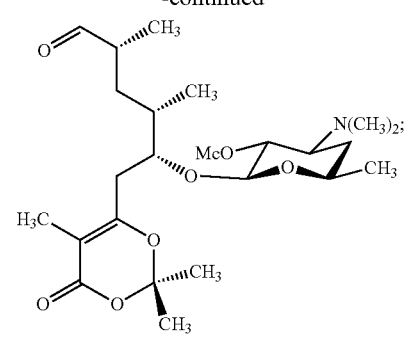
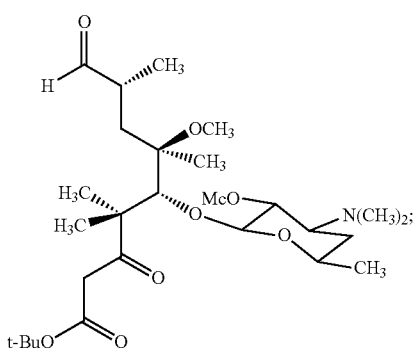
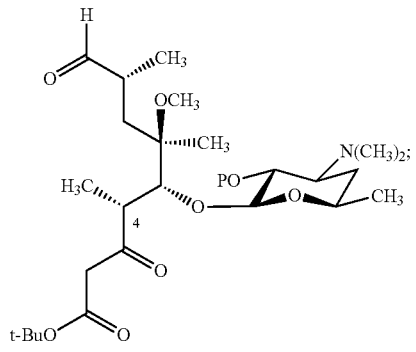
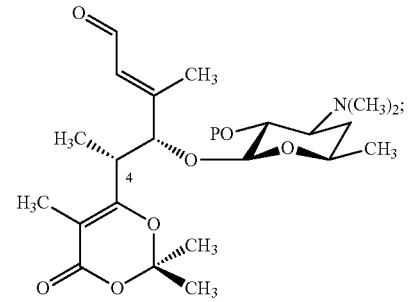
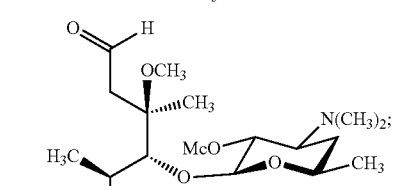
826
-continued
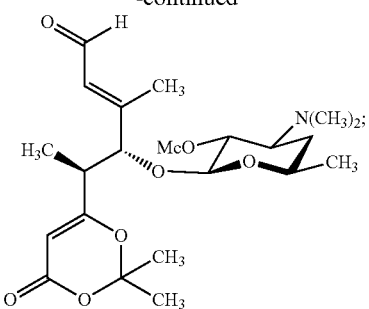
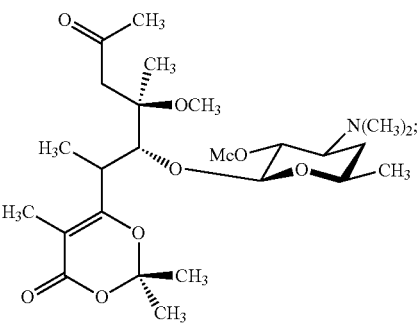
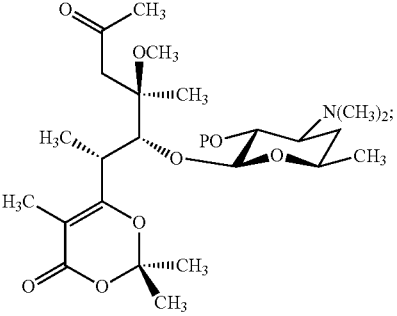
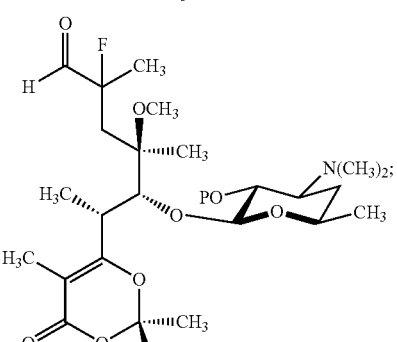
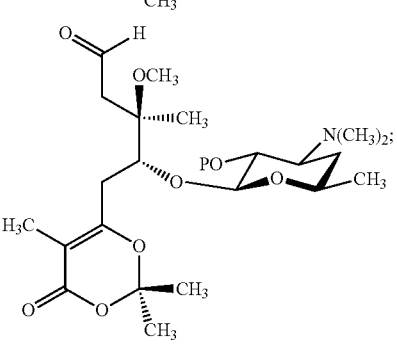

827
-continued

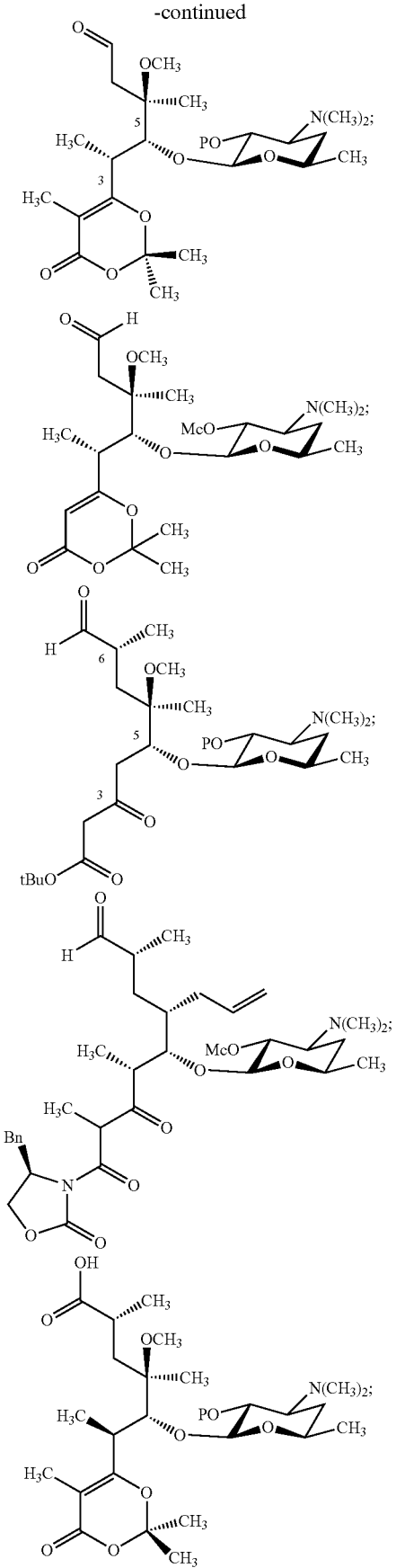

828
-continued

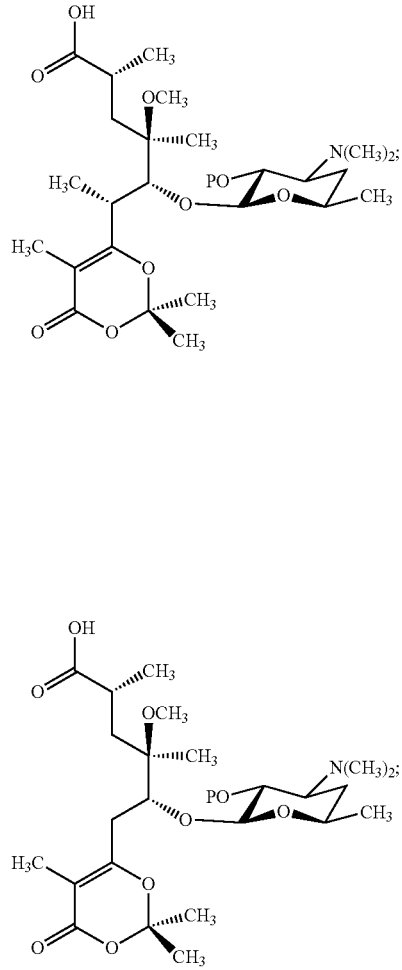

or a salt thereof, wherein P is an oxygen protecting group; and Mc is —C(=O)OCH$_3$.

16. The compound of claim 1, wherein the compound is of formula:

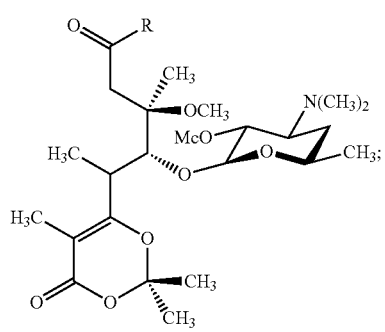

or a salt thereof, wherein R is optionally substituted alkyl, optionally substituted alkenyl, optionally substituted alkynyl, optionally substituted carbocyclyl, optionally substituted heterocyclyl, optionally substituted aryl, or optionally substituted heteroaryl; and Mc is —C(=O)OCH$_3$.

17. The compound of claim 1, wherein the compound is of formula:
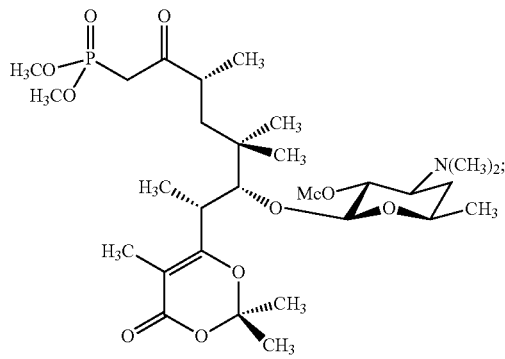
or a salt thereof, wherein Mc is —C(=O)OCH₃.
18. The compound of claim 1, wherein the compound is of formula:
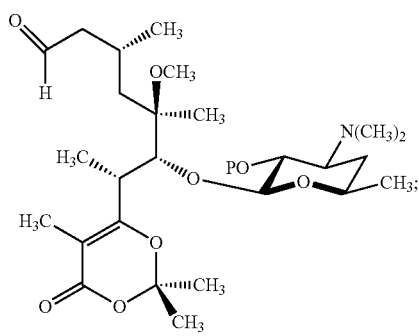
or a salt thereof, wherein P is an oxygen protecting group.
19. The compound of claim 1, wherein the compound is of formula:
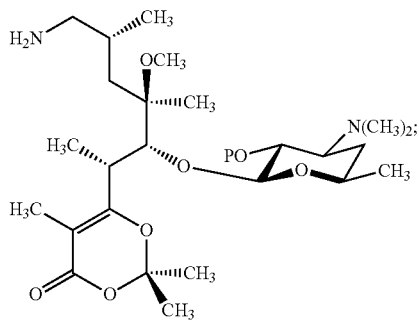
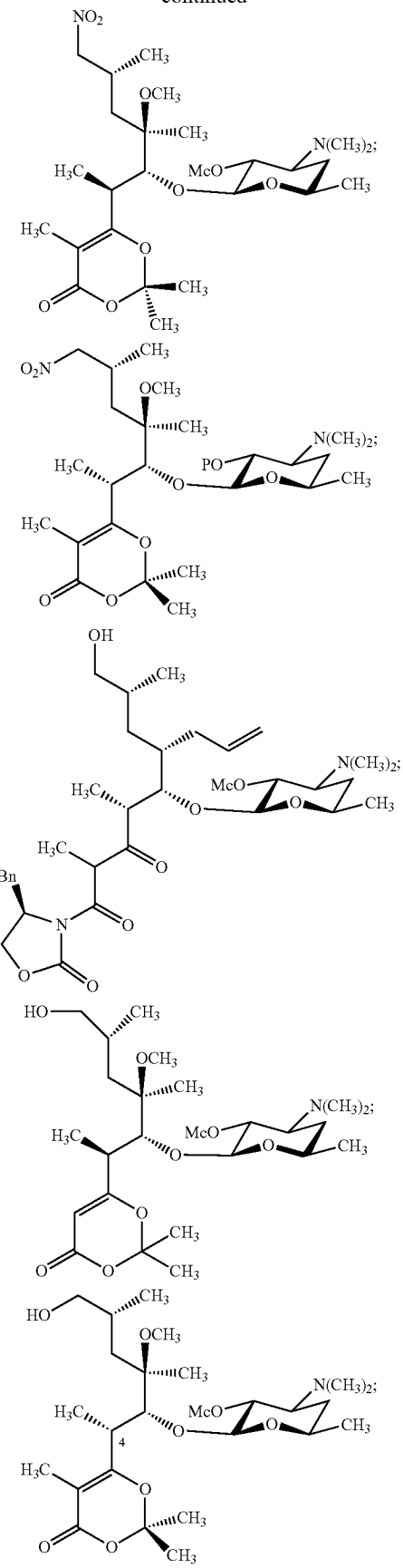

-continued

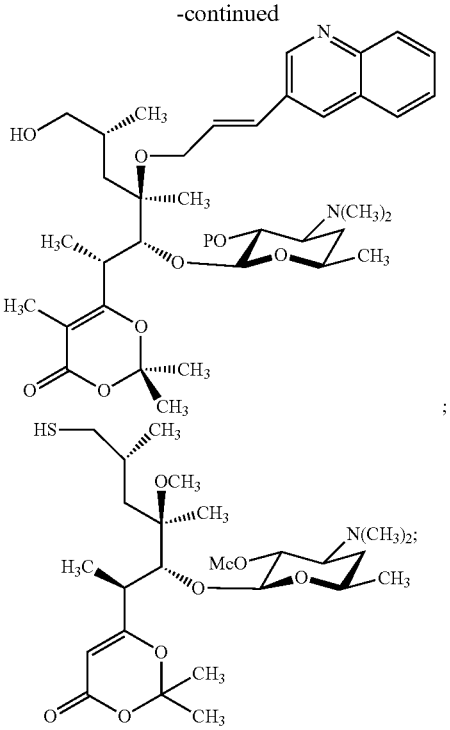

or a salt thereof, wherein P is an oxygen protecting group, and Mc is —C(=O)OCH$_3$.

20. The compound of claim 1, or a salt thereof, wherein oxygen protecting group is methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, or tosylate (Ts).

* * * * *

UNITED STATES PATENT AND TRADEMARK OFFICE
CERTIFICATE OF CORRECTION

| | | |
|---|---|---|
| PATENT NO. | : 11,634,449 B2 | Page 1 of 2 |
| APPLICATION NO. | : 17/112743 | |
| DATED | : April 25, 2023 | |
| INVENTOR(S) | : Andrew G. Myers et al. | |

It is certified that error appears in the above-identified patent and that said Letters Patent is hereby corrected as shown below:

In the Claims

In Claim 1, at Column 818, Lines 1-10, the formula:

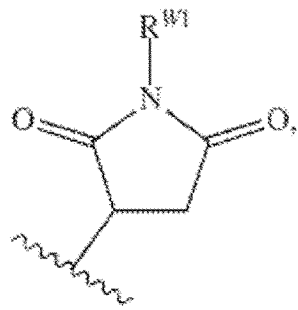

Should be replaced with:

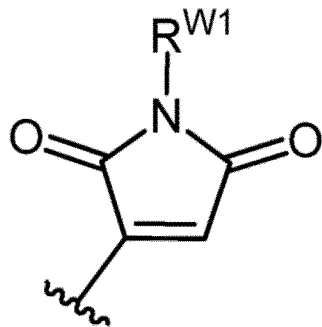

In Claim 5, at Column 820, Lines 49-52: "The compound of claim 1, or a salt thereof, wherein $Y^2$ is a leaving group (LG), $-C(=O)R^{Z3}$, $-C(=O)OR^{Z3}$, $-C(=O)LG$, $-C(=O)-CH=P(R^{P1})(R^{P2})(R^{P3})$, or $-C(=O)-CH_2-P(O)(OR^{P2})(OR^{P1})$."

Should be replaced with: -- The compound of claim 1, or a salt thereof, wherein $Y^2$ is a leaving group (LG), $-C(=O)R^{Z3}$, $-C(=O)OR^{Z3}$, $-C(=O)LG$, $-C(=O)-CH=P(R^{P1})(R^{P2})(R^{P3})$, or $-C(=O)-CH_2-P(O)(OR^{P2})(OR^{P3})$. --.

Signed and Sealed this
Fifth Day of September, 2023

Katherine Kelly Vidal
*Director of the United States Patent and Trademark Office*

CERTIFICATE OF CORRECTION (continued)
U.S. Pat. No. 11,634,449 B2

In Claim 11, at Column 821, Lines 45-52, the formula:

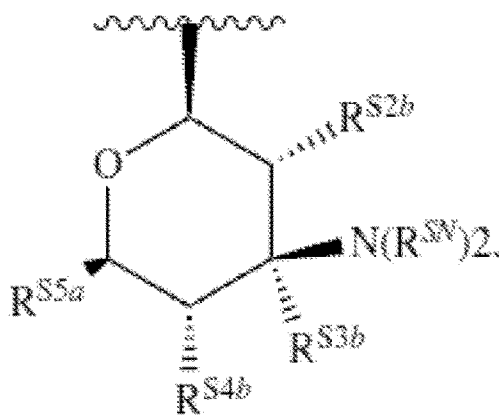

Should be replaced with:

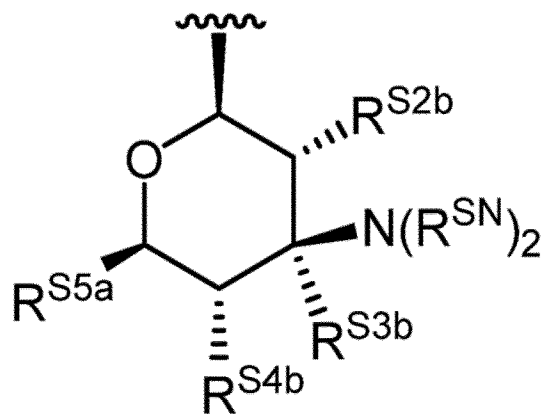

.